(12) United States Patent
Currie et al.

(10) Patent No.: US 9,376,441 B2
(45) Date of Patent: Jun. 28, 2016

(54) SUBSTITUTED PYRROLIDINES AS SYK INHIBITORS

(71) Applicant: Gilead Sciences, Inc., Foster City, CA (US)

(72) Inventors: Kevin S. Currie, North Branford, CT (US); Zhimin Du, Belmont, CA (US); Julie Farand, San Mateo, CA (US); Juan A. Guerrero, Concord, CA (US); Ashley A. Katana, San Mateo, CA (US); Darryl Kato, San Francisco, CA (US); Scott E. Lazerwith, San Francisco, CA (US); Jiayao Li, Foster City, CA (US); John O. Link, San Francisco, CA (US); Nicholas Mai, San Jose, CA (US); Gregory Notte, San Mateo, CA (US); Hyung-jung Pyun, Fremont, CA (US); Michael Sangi, San Mateo, CA (US); Aaron C. Schmitt, Hamden, CT (US); Adam J. Schrier, Redwood City, CA (US); Kirk L. Stevens, Bothell, WA (US); Chandrasekar Venkataramani, Redwood City, CA (US); William J. Watkins, Saratoga, CA (US); Zheng-Yu Yang, Palo Alto, CA (US); Jeff Zablocki, Los Altos, CA (US); Sheila Zipfel, San Mateo, CA (US); Jennifer R. Lo, Branford, CT (US); Seung H. Lee, Branford, CT (US); Zhongdong Zhao, Guilford, CT (US); Jeffrey Kropf, Branford, CT (US); Jianjun Xu, Madison, CT (US); Peter Blomgren, North Branford, CT (US); Scott A. Mitchell, East Haven, CT (US); JinMing Xiong, Guilford, CT (US); Jayaraman Chandrasekhar, Trumbull, CT (US)

(73) Assignee: Gilead Sciences, Inc., Foster City, AR (US)

( * ) Notice: Subject to any disclaimer, the term of this patent is extended or adjusted under 35 U.S.C. 154(b) by 23 days.

(21) Appl. No.: 14/448,160

(22) Filed: Jul. 31, 2014

(65) Prior Publication Data
US 2015/0038488 A1    Feb. 5, 2015

Related U.S. Application Data

(60) Provisional application No. 62/025,304, filed on Jul. 16, 2014, provisional application No. 61/860,870, filed on Jul. 31, 2013.

(51) Int. Cl.
*A61K 31/4015*    (2006.01)
*C07D 207/12*    (2006.01)
(Continued)

(52) U.S. Cl.
CPC ............ *C07D 487/04* (2013.01); *C07D 401/14* (2013.01); *C07D 403/12* (2013.01); *C07D 407/14* (2013.01); *C07D 417/04* (2013.01);
(Continued)

(58) Field of Classification Search
CPC ........................ A61K 31/4015; C07D 207/12
USPC ........... 514/424; 544/350, 372; 546/112, 121; 548/152, 306.1, 543
See application file for complete search history.

(56) References Cited

U.S. PATENT DOCUMENTS 8,450,321 B2    5/2013    Mitchell et al.
8,455,493 B2    6/2013    Mitchell et al.
(Continued)

FOREIGN PATENT DOCUMENTS

WO    WO-2009/102468 A1    8/2009
WO    WO-2010/027500 A1    3/2010
WO    WO 2015/017610    *    2/2015

OTHER PUBLICATIONS

Jordan, V. C. Nature Reviews: Drug Discovery, 2, 2003, 205.*
(Continued)

*Primary Examiner* — Douglas M Willis

(57) ABSTRACT

The present disclosure relates to compounds that are Syk inhibitors and to their use in the treatment of various disease states, including cancer and inflammatory conditions. In particular embodiments, the structure of the compounds is given by Formula I:

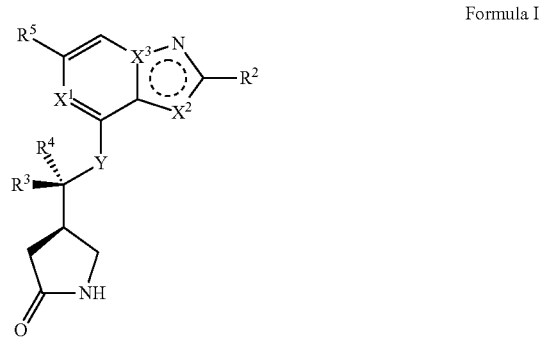

Formula I wherein $X^1$, $X^2$, $X^3$, $R^2$, $R^3$, $R^4$, $R^5$, and Y are as described herein. The present disclosure further provides pharmaceutical compositions that include a compound of Formula I, or pharmaceutically acceptable salts thereof, and methods of using these compounds and compositions to treat conditions mediated by Syk.

20 Claims, No Drawings

(51) Int. Cl.
  *C07D 487/04* (2006.01)
  *C07D 401/14* (2006.01)
  *C07D 403/12* (2006.01)
  *C07D 417/04* (2006.01)
  *C07D 417/12* (2006.01)
  *C07D 471/04* (2006.01)
  *C07D 407/14* (2006.01)
  *C07D 417/14* (2006.01)

(52) U.S. Cl.
  CPC ............ *C07D 417/12* (2013.01); *C07D 417/14* (2013.01); *C07D 471/04* (2013.01)

(56) References Cited

U.S. PATENT DOCUMENTS

| | | |
|---|---|---|
| 8,748,607 B2 | 6/2014 | Mitchell et al. |
| 8,765,761 B2 | 7/2014 | Mitchell et al. |
| 9,120,811 B2 | 9/2015 | Mitchell et al. |
| 9,212,191 B2 | 12/2015 | Mitchell et al. |

OTHER PUBLICATIONS

Hackam, et al. JAMA, 296(14), 2006, 1731-1732.*
International Search Report mailed Nov. 27, 2014, for PCT Application No. PCT/US2014/049032, filed on Jul. 31, 2014, 3 pages.

* cited by examiner

SUBSTITUTED PYRROLIDINES AS SYK INHIBITORS

FIELD

The present disclosure relates to novel compounds and to their use in the treatment of various diseases, including cancer and inflammatory conditions. The disclosure also relates to methods for preparation of the compounds and to pharmaceutical compositions comprising such compounds.

BACKGROUND

Protein kinases, the largest family of human enzymes, encompass well over 500 proteins. Spleen Tyrosine Kinase (Syk) is a member of the Syk family of tyrosine kinases, and is a regulator of early B-cell development as well as mature B-cell activation, signaling, and survival.

Syk is a non-receptor tyrosine kinase that plays critical roles in immunoreceptor- and integrin-mediated signaling in a variety of cell types, including B cells, macrophages, monocytes, mast cells, eosinophils, basophils, neutrophils, dendritic cells, T cells, natural killer cells, platelets, and osteoclasts. Immunoreceptors as described here include classical immunoreceptors and immunoreceptor-like molecules. Classical immunoreceptors include B-cell and T-cell antigen receptors as well as various immunoglobulin receptors (Fc receptors). Immunoreceptor-like molecules are either structurally related to immunoreceptors or participate in similar signal transduction pathways and are primarily involved in non-adaptive immune functions, including neutrophil activation, natural killer cell recognition, and osteoclast activity. Integrins are cell surface receptors that play key roles in the control of leukocyte adhesion and activation in both innate and adaptive immunity.

Ligand binding leads to activation of both immunoreceptors and integrins, which results in Src family kinases being activated, and phosphorylation of immunoreceptor tyrosine-based activation motifs (ITAMs) in the cytoplasmic face of receptor-associated transmembrane adaptors. Syk binds to the phosphorylated ITAM motifs of the adaptors, leading to activation of Syk and subsequent phosphorylation and activation of downstream signaling pathways.

Syk is essential for B-cell activation through B-cell receptor (BCR) signaling. Syk becomes activated upon binding to phosphoryated BCR and thus initiates the early signaling events following BCR activation. B-cell signaling through BCR can lead to a wide range of biological outputs, which in turn depend on the developmental stage of the B-cell. The magnitude and duration of BCR signals must be precisely regulated. Aberrant BCR-mediated signaling can cause disregulated B-cell activation and/or the formation of pathogenic auto-antibodies leading to multiple autoimmune and/or inflammatory diseases. Mice lacking Syk show impaired maturation of B-cells, diminished immunoglobulin production, compromised T-cell-independent immune responses and marked attenuation of the sustained calcium sign upon BCR stimulation.

A large body of evidence supports the role of B-cells and the humoral immune system in the pathogenesis of autoimmune and/or inflammatory diseases. Protein-based therapeutics (such as Rituxan) developed to deplete B-cells represent an approach to the treatment of a number of autoimmune and inflammatory diseases. Auto-antibodies and their resulting immune complexes are known to play pathogenic roles in autoimmune disease and/or inflammatory disease. The pathogenic response to these antibodies is dependent on signaling through Fc Receptors, which is, in turn, dependent upon Syk. Because of Syk's role in B-cell activation, as well as FcR dependent signaling, inhibitors of Syk can be useful as inhibitors of B-cell mediated pathogenic activity, including autoantibody production. Therefore, inhibition of Syk enzymatic activity in cells is proposed as a treatment for autoimmune disease through its effects on autoantibody production.

Syk also plays a key role in FCεRI mediated mast cell degranulation and eosinophil activation. Thus, Syk is implicated in allergic disorders including asthma. Syk binds to the phosphorylated gamma chain of FCεRI via its SH2 domains and is essential for downstream signaling. Syk deficient mast cells demonstrate defective degranulation, arachidonic acid and cytokine secretion. This also has been shown for pharmacologic agents that inhibit Syk activity in mast cells. Treatment with Syk antisense oligonucleotides inhibits antigen-induced infiltration of eosinophils and neutrophils in an animal model of asthma. Syk deficient eosinophils also show impaired activation in response to FCεRI stimulation. Therefore, small molecule inhibitors of Syk will be useful for treatment of allergy-induced inflammatory diseases including asthma.

Syk is also expressed in mast cells and monocytes and has been shown to be important for the function of these cells. For example, Syk deficiency in mice is associated with impaired IgE-mediated mast cell activation, which is marked diminution of TNF-alpha and other inflammatory cytokine release. Syk kinase inhibitors have also been shown to inhibit mast cell degranulation in cell based assays. Additionally, Syk inhibitors have been shown to inhibit antigen-induced passive cutaneous anaphylaxsis, bronchoconstriction and bronchial edema in rats.

Thus, the inhibition of Syk activity can be useful for the treatment of allergic disorders, autoimmune diseases and inflammatory diseases such as: SLE, rheumatoid arthritis, multiple vasculitides, idiopathic thrombocytopenic purpura (ITP), myasthenia gravis, allergic rhinitis, chronic obstructive pulmonary disease (COPD), adult respiratory distress syndrome (ARDs) and asthma. In addition, Syk has been reported to play an important role in ligand-independent tonic signaling through the B-cell receptor, known to be an important survival signal in B-cells. Thus, inhibition of Syk activity may also be useful in treating certain types of cancer, including B-cell lymphoma and leukemia.

SUMMARY

Accordingly, the present disclosure provides novel compounds that function as Syk inhibitors. In one embodiment, the disclosure provides compounds of Formula I:

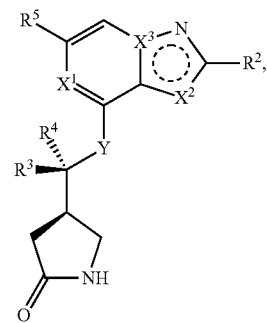

Formula I wherein:

$X^1$ is CH or N;

$X^2$ is $CR^{1a}$, $NR^{1b}$ or S;

$X^3$ is C or N;

wherein, $X^1$, $X^2$ and $X^3$ are arranged in such a way to form a heteroaromatic ring system, and $R^{1a}$ is hydrogen, halo, haloalkyl, cyano, $C_{1-6}$ alkyl, $C_{1-6}$ alkoxy, $C_{3-6}$ cycloalkoxy, $C_{3-12}$) cycloalkyl, $C_{2-12}$ heterocyclyl, $C_{6-12}$ aryl, $C_{2-12}$ heteroaryl, or —$N(R^{20})(R^{22})$, wherein the $C_{1-6}$ alkyl, $C_{3-12}$ cycloalkyl, $C_{2-12}$heterocyclyl, $C_{6-12}$ aryl, or $C_{2-12}$heteroaryl moieties may be optionally substituted with one, two, or three substituents independently selected from fluoro, $CFH_2$, $CF_2H$, $CF_3$, $C_{1-6}$ alkyl, $C_{1-6}$ alkoxy, $C_{3-6}$ cycloalkoxy, $C_{3-12}$ cycloalkyl, and —$N(R^{20})(R^{22})$, $R^{1b}$ is hydrogen, haloalkyl, $C_{1-6}$ alkyl, $C_{3-12}$ cycloalkyl, $C_{2-12}$ heterocyclyl, $C_{6-12}$ aryl, or $C_{2-12}$ heteroaryl, wherein the $C_{1-6}$ alkyl, $C_{3-12}$ cycloalkyl, $C_{2-12}$heterocyclyl, $C_{6-12}$ aryl, or $C_{2-12}$heteroaryl moieties may be optionally substituted with one, two, or three substituents independently selected from fluoro, $CFH_2$, $CF_2H$, $CF_3$, and $C_{1-6}$ alkyl, $C_{1-6}$ alkoxy, $C_{3-6}$ cycloalkoxy, $C_{3-12}$ cycloalkyl, and —$N(R^{20})(R^{22})$, provided that either (a) or (b) applies:

a) when $X^3$ is N then $X^2$ is $CR^{1a}$, or b) when $X^2$ is S then $X^1$ is CH and $X^3$ is C;

Y is O or NH;

$R^2$ is hydrogen, $C_{1-6}$ alkyl, $C_{3-12}$ cycloalkyl, $C_{2-12}$ heterocyclyl, $C_{1-6}$ alkoxy, or —$N(R^{20})(R^{22})$;

wherein the $C_{1-6}$ alkyl, $C_{3-12}$ cycloalkyl, $C_{2-12}$heterocyclyl, or $C_{1-6}$ alkoxy moieties may be optionally substituted with one, two, or three substituents independently selected from fluoro, $CFH_2$, $CF_2H$, $CF_3$, $C_{1-6}$ alkyl, and $C_{1-6}$ alkoxy;

each $R^3$ and $R^4$ is independently hydrogen, $C_{1-6}$ alkyl, $C_{3-8}$ cycloalkyl, $C_{2-8}$ heterocyclyl, and $C_{2-6}$ alkenyl, wherein the $C_{1-6}$ alkyl, $C_{3-8}$ cycloalkyl, $C_{2-8}$ heterocyclyl, and $C_{2-6}$ alkenyl moieties may be optionally substituted with one, two, or three substituents independently selected from halogen, $C_{1-6}$ alkyl, $C_{3-6}$ cycloalkyl, $C_{6-12}$ aryl, $C_{2-8}$ heterocyclyl, $C_{2-12}$ heteroaryl, —$OR^{20}$, or —$N(R^{20})(R^{22})$;

$R^5$ is monocyclic or bicyclic $C_{6-12}$ aryl, monocyclic or bicyclic $C_{3-12}$ cycloalkyl, monocyclic or bicyclic $C_{2-8}$ heterocyclyl, or monocyclic or bicyclic $C_{2-12}$ heteroaryl having one, two, three, or four heteroatoms individually selected from O, N, and S;

wherein the monocyclic or bicyclic $C_{6-12}$ aryl, monocyclic or bicyclic $C_{3-12}$ cycloalkyl, monocyclic or bicyclic $C_{2-8}$ heterocyclyl, or monocyclic or bicyclic $C_{2-12}$ heteroaryl moiety may be optionally substituted with one, two, or three substituents independently selected from the group consisting of $C_{1-6}$ alkyl, $C_{2-6}$ alkynyl, $C_{1-6}$ alkoxy, halo, —$NO_2$, —$CFH_2$, —$CF_3$, —$CF_2H$, —$OCF_3$, $C_{3-6}$ cycloalkyl, $C_{2-8}$ heterocyclyl, $C_{6-12}$ aryl, $C_{2-12}$ heteroaryl, —$S(O)_2R^{20}$, —$S(O)_2$—$N(R^{20})(R^{22})$, —$N(R^{20})(R^{22})$, —$N(R^{20})$—$S(O)_2$—$R^{20}$, —$N(R^{20})$—$C(O)$—$R^{22}$, —$C(O)$—$R^{20}$, —$C(O)$—$OR^{20}$, —$C(O)$—$N(R^{20})(R^{22})$, —CN, oxo, and —$O$—$R^{20}$;

wherein the $C_{1-6}$ alkyl, $C_{2-6}$ alkynyl, $C_{1-6}$ alkoxy, $C_{3-8}$ cycloalkyl, $C_{2-8}$ heterocyclyl, $C_{6-12}$ aryl, or $C_{2-12}$ heteroaryl moiety may be optionally further substituted with one, two, or three substituents independently selected from the group consisting of halo, —$NO_2$, —$CFH_2$, —$CF_3$, —$CF_2H$, —$OCF_3$, $C_{1-6}$ alkyl, $C_{3-6}$ cycloalkyl, $C_{6-12}$ aryl, $C_{2-8}$ heterocyclyl, $C_{2-6}$ heteroaryl, —$N(R^{20})(R^{22})$, —$C(O)$—$R^{20}$, —$C(O)$—$OR^{20}$, —$C(O)$—$N(R^{20})(R^{22})$, —CN, —$S(O)_2R^{20}$, —$S(O)_2$—$N(R^{20})(R^{22})$, —$S(O)_2$—$R^{20}$—$N(R^{20})(R^{22})$, oxo, and —$O$—$R^{20}$;

wherein the $C_{1-6}$ alkyl, $C_{3-6}$ cycloalkyl, $C_{2-8}$ heterocyclyl, $C_{6-12}$ aryl, and $C_{2-6}$ heteroaryl may be further optionally substituted with one, two, or three substituents independently selected from the group consisting of $C_{1-6}$ alkyl, $C_{3-6}$ cycloalkyl, $C_{6-12}$ aryl, $C_{2-6}$ heteroaryl, $C_{2-8}$ heterocyclyl, halo, —$NO_2$, —$CFH_2$, —$CF_2H$, —$CF_3$, —$OCF_3$, —$N(R^{20})(R^{22})$, —$C(O)$—$R^{20}$, —$C(O)$—$OR^{20}$, —$C(O)$—$N(R^{20})(R^{22})$, —CN, —$S(O)_2$—$R^{20}$, $S(O)_2$—$N(R^{20})(R^{22})$, —$S(O)_2$—$R^{20}$, —$N(R^{20})(R^{22})$, oxo, and —$O$—$R^{20}$; and each $R^{20}$ and $R^{22}$ is independently hydrogen, $C_{1-6}$ alkyl, $C_{2-6}$ alkenyl, $C_{2-6}$ alkynyl, $C_{3-6}$ cycloalkyl, $C_{2-8}$ heterocyclyl, $C_{6-12}$ aryl, or $C_{2-12}$ heteroaryl;

wherein each $C_{1-6}$ alkyl, $C_{2-6}$ alkenyl, $C_{2-6}$ alkynyl, $C_{3-6}$ cycloalkyl, $C_{2-8}$ heterocyclyl, $C_{6-12}$ aryl and $C_{2-12}$ heteroaryl are optionally substituted with one, two or three substituents independently selected from the group consisting of hydroxyl, halo, $C_{1-6}$ alkyl, acylamino, oxo, —$NO_2$, —$S(O)_2R^{26}$, —CN, $C_{1-6}$ alkoxy, $C_{3-6}$ cycloalkoxy, —$CFH_2$, —$CF_3$, —$CF_2H$, —$OCF_3$, —$OCH_2CF_3$, —$C(O)$—$NH_2$, $C_{6-12}$ aryl, $C_{3-6}$ cycloalkyl, $C_{2-8}$ heterocyclyl, and $C_{2-6}$ heteroaryl; and wherein $R^{26}$ is $C_{1-6}$ alkyl, $C_{2-6}$ alkenyl, $C_{2-6}$ alkynyl, $C_{3-6}$ cycloalkyl, $C_{2-8}$ heterocyclyl, $C_{6-12}$ aryl, $C_{2-6}$ heteroaryl, acylamino, $NH_2$, —$CFH_2$, —$CF_3$, —$CF_2H$;

or a pharmaceutically acceptable salt, ester, stereoisomer, mixture of stereoisomers or tautomer thereof.

Some embodiments provide a method of using the compounds of Formula I, or additional Formula(s) described throughout (such as Formula II, III, IV, V, or VI described below), in the treatment of a disease or condition in a patient that is amenable to treatment by a Syk inhibitor. Such diseases and conditions include inflammatory disorders, allergic disorders, autoimmune diseases, or a cancer. Conditions that may be treated with the compounds disclosed herein include, but are not limited to, lymphoma, multiple myeloma, and leukemia. Additional diseases or conditions that may be treated include, but are not limited to acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), non-Hodgkin's lymphoma (NHL), mantle cell lymphoma (MCL), follicular lymphoma, Waldestrom's macroglobulinemia (WM), T-cell lymphoma, B-cell lymphoma, diffuse large B-cell lymphoma (DLBCL), pancreatic cancer, bladder cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancer, CNS cancer, brain cancer, bone cancer, soft tissue sarcoma, non-small cell lung cancer, small-cell lung cancer, colon cancer, systemic lupus erythematosus (SLE), myestenia gravis, rheumatoid arthritis (RA), acute disseminated encephalomyelitis, idiopathic thrombocytopenic purpura, multiple sclerosis (MS), Sjoegren's syndrome, autoimmune hemolytic anemia, asthma, rheumatoid arthritis, multiple sclerosis, or lupus, psoriasis, ulcerative colitis, Crohn's disease, irritable bowel syndrome, dermatomyositis, multiple sclerosis.

In certain embodiments, the disclosure provides pharmaceutical compositions comprising a therapeutically effective amount of a compound of Formula I or additional Formulas described throughout (such as Formula II, III, IV, V, or VI described below), or a pharmaceutically acceptable salt, ester, stereoisomer, mixture of stereoisomers or tautomer thereof, and at least one pharmaceutically acceptable excipient.

Also provided are methods of treating a disease or condition selected from an inflammatory disorder, an allergic disorder, an autoimmune disease, or a cancer in a patient in need thereof, comprising administering to the patient a therapeutic effective amount of a compound of Formula I or additional Formulas described throughout (such as Formula II, III, IV, V, or VI described below), or a pharmaceutically acceptable salt, ester, stereoisomer, mixture of stereoisomers or tautomer thereof, or a pharmaceutical composition thereof.

Also provided is a kit that includes a compound of Formula I or additional Formulas described throughout (such as Formula II, III, IV, V, or VI described below), or a pharmaceutically acceptable salt, ester, stereoisomer, mixture of stereoisomers or tautomer thereof; and a label and/or instructions for use of the compound in the treatment of a disease or condition mediated by Syk activity.

Also provided are articles of manufacture that include a compound of Formula I or additional Formulas described throughout (such as Formula II, III, IV, V, or VI described below), or a pharmaceutically acceptable salt, prodrug, or solvate thereof; and a container. In one embodiment, the container may be a vial, jar, ampoule, preloaded syringe, or an intravenous bag.

The inventions of this disclosure are described throughout. In addition, specific embodiments of the invention are as disclosed herein.

DETAILED DESCRIPTION

Definitions

Also provided herein are separate embodiments, each comprising a compound of Formula Ia, Formula Ib, or Formula Ic, or a pharmaceutically acceptable salt thereof:

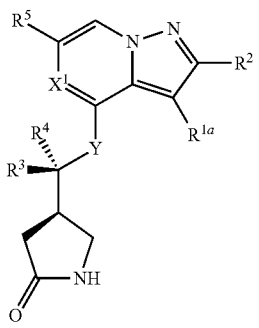

Formula Ia

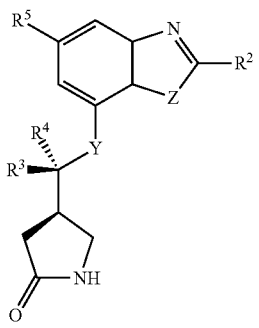

Formula Ib

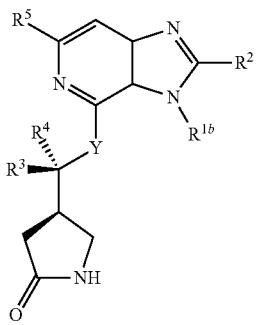

Formula Ic wherein, in each instance, the variables Y, $R^{1a}$, $R^{1b}$, $R^1$, $R^2$, $R^3$, $R^4$, $R^5$, and $X^1$ are as defined above for Formula I, Z is selected from a) sulfur or b) nitrogen substituted by R.

Also provided are separate embodiments, each comprising a compound of Formula II, Formula III, Formula IV, Formula V, or Formula VI, or a pharmaceutically acceptable salt thereof:

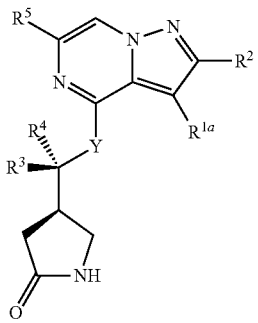

Formula II

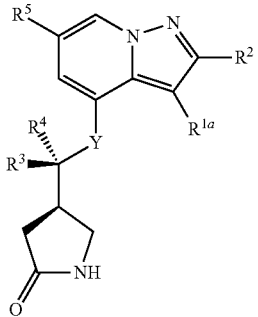

Formula III

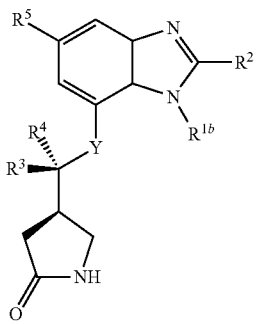

Formula IV

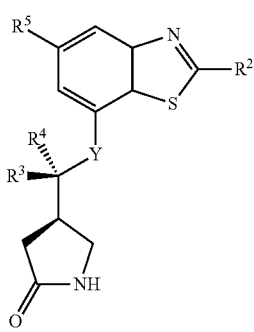

Formula V

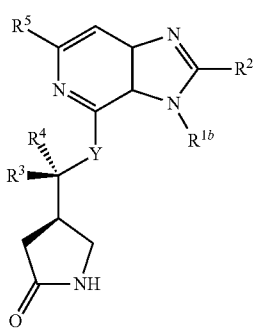

Formula VI wherein, in each instance, the variables Y, $R^{1a}$, $R^{1b}$, $R^1$, $R^2$, $R^3$, $R^4$, K and $R^5$ are as defined above for Formula I.

Within each of the embodiments described above comprising a compound of Formula I, Formula Ia, Formula Ib, Formula Ic, Formula II, Formula III, Formula IV, Formula V, or Formula VI, or a pharmaceutically acceptable salt thereof, there is a further, separate embodiment wherein Y is O and all other variables are as defined above for Formula I. Within each of the embodiments described above comprising a compound of Formula I, Formula Ia, Formula Ib, Formula Ic, Formula II, Formula III, Formula IV, Formula V, or Formula VI, or a pharmaceutically acceptable salt thereof, there is also a further, separate embodiment wherein Y is O, $R^2$ is H or methyl, and all other variables are as defined above for Formula I. Within each of the embodiments described above comprising a compound of Formula I, Formula Ia, Formula Ib, Formula Ic, Formula II, Formula III, Formula IV, Formula V, or Formula VI, or Formula VI, or a pharmaceutically acceptable salt thereof, there is also a further, separate embodiment wherein Y is O, $R^2$ is H, $R^3$ is $C_{1-6}$ alkyl, $R^4$ is H or methyl, and all other variables are as defined above for Formula I. Within each of the embodiments described above comprising a compound of Formula I, Formula Ia, Formula Ib, Formula Ic, Formula II, Formula III, Formula IV, Formula V, or Formula VI, or a pharmaceutically acceptable salt thereof, there is another further, separate embodiment wherein Y is O, $R^2$ is H, $R^3$ is methyl, $R^4$ is H, and all other variables are as defined above for Formula I.

As used in the present disclosure, the following words and phrases are generally intended to have the meanings as set forth below, except to the extent that the context in which they are used indicates otherwise.

"Alkyl" refers to a monoradical unbranched or branched saturated hydrocarbon chain. In some embodiments, alkyl as used herein has 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. When an alkyl residue having a specific number of carbons is named, all geometric isomers having that number of carbons may be encompassed; thus, for example, "butyl" can include n-butyl, sec-butyl, isobutyl and t-butyl; "propyl" can include n-propyl and isopropyl. In some embodiments, "lower alkyl" refers to alkyl groups having 1 to 6 carbons (i.e., $C_{1-6}$ alkyl).

The term "substituted alkyl" refers to:

1) an alkyl group as defined above, having 1, 2, 3, 4 or 5 substituents, (in some embodiments, 1, 2 or 3 substituents) selected from the group consisting of alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)-heterocyclyl, —S(O)-aryl, —S(O)-heteroaryl, —S(O)$_2$-alkyl, —S(O)$_2$—$C_{3-6}$ cycloalkyl, —S(O)$_2$—$C_{2-8}$ heterocyclyl, —S(O)$_2$-heterocyclyl, —S(O)$_2$-aryl and —S(O)$_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, haloalkyl, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2; or 2) an alkyl group as defined above that is interrupted by 1-10 atoms (e.g. 1, 2, 3, 4 or 5 atoms) independently chosen from oxygen, sulfur and NR$^a$, where R$^a$ is chosen from hydrogen, alkyl, cycloalkyl, alkenyl, cycloalkenyl, alkynyl, aryl, heteroaryl and heterocyclyl. All substituents may be optionally further substituted by alkyl, alkenyl, alkynyl, carboxy, carboxyalkyl, aminocarbonyl, hydroxy, alkoxy, halogen, haloalkyl, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2; or 3) an alkyl group as defined above that has both 1, 2, 3, 4 or 5 substituents as defined above and is also interrupted by 1-10 atoms (e.g. 1, 2, 3, 4 or 5 atoms) as defined above.

The term "lower alkyl" refers to a monoradical branched or unbranched saturated hydrocarbon chain having 1, 2, 3, 4, 5 or 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents (in some embodiments, 1, 2 or 3 substituents), as defined for substituted alkyl or a lower alkyl group as defined above that is interrupted by 1, 2, 3, 4 or 5 atoms as defined for substituted alkyl or a lower alkyl group as defined above that has both 1, 2, 3, 4 or 5 substituents as defined above and is also interrupted by 1, 2, 3, 4 or 5 atoms as defined above.

The term "alkylene" refers to a diradical of a branched or unbranched saturated hydrocarbon chain, in some embodiments, having from 1 to 20 carbon atoms (e.g. 1-10 carbon atoms or 1, 2, 3, 4, 5 or 6 carbon atoms). This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—), and the like.

The term "lower alkylene" refers to a diradical of a branched or unbranched saturated hydrocarbon chain, in some embodiments, having 1, 2, 3, 4, 5 or 6 carbon atoms.

The term "substituted alkylene" refers to an alkylene group as defined above having 1 to 5 substituents (in some embodiments, 1, 2 or 3 substituents) as defined for substituted alkyl.

The term "alkenyl" refers to a monoradical of a branched or unbranched unsaturated hydrocarbon group having from 2 to 20 carbon atoms (in some embodiments, from 2 to 10 carbon atoms, e.g. 2 to 6 carbon atoms) and having from 1 to 6 carbon-carbon double bonds, e.g. 1, 2 or 3 carbon-carbon double bonds. In some embodiments, alkenyl groups include ethenyl (or vinyl, i.e. —CH═CH$_2$), 1-propylene (or allyl, i.e. —CH$_2$CH═CH$_2$), isopropylene (—C(CH$_3$)═CH$_2$), and the like.

The term "lower alkenyl" refers to alkenyl as defined above having from 2 to 6 carbon atoms.

The term "substituted alkenyl" refers to an alkenyl group as defined above having 1 to 5 substituents (in some embodiments, 1, 2 or 3 substituents) as defined for substituted alkyl.

The term "alkenylene" refers to a diradical of a branched or unbranched unsaturated hydrocarbon group having from 2 to 20 carbon atoms (in some embodiments, from 2 to 10 carbon atoms, e.g. 2 to 6 carbon atoms) and having from 1 to 6 carbon-carbon double bonds, e.g. 1, 2 or 3 carbon-carbon double bonds.

The term "alkynyl" refers to a monoradical of an unsaturated hydrocarbon, in some embodiments, having from 2 to 20 carbon atoms (in some embodiments, from 2 to 10 carbon atoms, e.g. 2 to 6 carbon atoms) and having from 1 to 6 carbon-carbon triple bonds e.g. 1, 2 or 3 carbon-carbon triple bonds. In some embodiments, alkynyl groups include ethynyl (—C≡CH), propargyl (or propynyl, i.e. —C≡CCH$_3$), and the like.

The term "substituted alkynyl" refers to an alkynyl group as defined above having 1 to 5 substituents (in some embodiments, 1, 2 or 3 substituents) as defined for substituted alkyl.

The term "alkynylene" refers to a diradical of an unsaturated hydrocarbon, in some embodiments, having from 2 to 20 carbon atoms (in some embodiments, from 2 to 10 carbon atoms, e.g. 2 to 6 carbon atoms) and having from 1 to 6 carbon-carbon triple bonds e.g. 1, 2 or 3 carbon-carbon triple bonds.

The term "hydroxy" or "hydroxyl" refers to a group —OH.

The term "alkoxy" refers to the group R—O—, where R is alkyl or —Y—Z, in which Y is alkylene and Z is alkenyl or alkynyl, where alkyl, alkenyl and alkynyl are as defined herein. In some embodiments, alkoxy groups are alkyl-O— and includes, by way of example, methoxy, ethoxy, n-propoxy, iso-propoxy, n-butoxy, tert-butoxy, sec-butoxy, n-pentoxy, n-hexyloxy, 1,2-dimethylbutoxy, and the like.

The term "lower alkoxy" refers to the group R—O— in which R is optionally substituted lower alkyl. This term is exemplified by groups such as methoxy, ethoxy, n-propoxy, iso-propoxy, n-butoxy, iso-butoxy, t-butoxy, n-hexyloxy, and the like.

The term "substituted alkoxy" refers to the group R—O—, where R is substituted alkyl or —Y—Z, in which Y is substituted alkylene and Z is substituted alkenyl or substituted alkynyl, where substituted alkyl, substituted alkenyl and substituted alkynyl are as defined herein.

The term "cycloalkyl" refers to a saturated or partially unsaturated cyclic alkyl group. In some embodiments, cycloalkyl as used herein has from 3 to 20 ring carbon atoms (i.e., C$_{3-20}$ cycloalkyl), or 3 to 12 ring carbon atoms (i.e., C$_{3-12}$ cycloalkyl), or 3 to 8 ring carbon atoms (i.e., C$_{3-8}$ cycloalkyl). Examples of cycloalkyl groups include cyclopropyl, cyclobutyl, cyclopentyl, cyclohexyl and cyclohexenyl.

The term "substituted cycloalkyl" refer to cycloalkyl or cycloalkenyl groups having 1, 2, 3, 4 or 5 substituents (in some embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, haloalkyl, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)-heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl. The term "substituted cycloalkyl" also includes cycloalkyl groups wherein one or more of the annular carbon atoms of the cycloalkyl group has an oxo group bonded thereto. In addition, a substituent on the cycloalkyl or cycloalkenyl may be attached to the same carbon atom as, or is geminal to, the attachment of the substituted cycloalkyl or cycloalkenyl to the 6,7-ring system. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, haloalkyl, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "cycloalkoxy" refers to the group cycloalkyl-O—.

The term "substituted cycloalkoxy" refers to the group substituted cycloalkyl-O—.

The term "cycloalkenyloxy" refers to the group cycloalkenyl-O—.

The term "substituted cycloalkenyloxy" refers to the group substituted cycloalkenyl-O—.

The term "aryl" refers to a carbocyclic group having at least one aromatic ring. Aryl groups may have a single ring (e.g., phenyl), multiple rings (e.g., biphenyl), or multiple fused rings (e.g., naphthyl, fluorenyl, and anthryl). In certain embodiments, aryl as used herein has 6 to 20 ring carbon atoms (i.e., C$_{6-20}$ aryl), 6 to 12 carbon ring atoms (i.e., C$_{6-12}$ aryl), or 6 to 8 carbon ring atoms (i.e., C$_{6-8}$ aryl). Aryl, however, does not encompass or overlap in any way with heteroaryl or heterocyclyl, separately defined below. In certain embodiments, if one or more aryl groups are fused with a heteroaryl ring, the resulting ring system is heteroaryl. Similarly, if one or more aryl groups are fused with a heterocyclic ring, the resulting ring system is heterocyclic.

Unless otherwise constrained by the definition for the aryl substituent, such aryl groups can optionally be substituted with 1, 2, 3, 4 or 5 substituents (in some embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, haloalkyl, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)-heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, haloalkyl, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "heterocyclyl", "heterocycle," or "heterocyclic" refers to a cyclic alkyl group, with one or more ring heteroatoms independently selected from nitrogen, oxygen and sulfur. In some embodiments, the heterocyclyl as used herein has 2 to 20 ring carbon atoms (i.e., C$_{2-20}$ heterocyclyl), 2 to 12 ring carbon atoms (i.e., C$_{2-12}$ heterocyclyl), or 2 to 8 ring carbon atoms (i.e., C$_{2-8}$ heterocyclyl); and 1 to 5 ring heteroatoms, 1 to 4 ring heteroatoms, 1 to 3 ring heteroatoms, 1 or 2 ring heteroatoms, or 1 ring heteroatom independently selected from nitrogen, sulfur or oxygen. In one example, a heterocyclic group has 2 to 8 ring carbon atoms, with 1 to 3 ring heteroatoms independently selected from nitrogen, oxygen and sulfur. Examples of heterocyclic groups may include pyrrolidinyl, piperidinyl, piperazinyl, oxetanyl, dioxolanyl, azetidinyl, and morpholinyl. The heterocycle may have more than one ring that may be fused, spiro or bridged.

Unless otherwise constrained by the definition for the heterocyclic substituent, such heterocyclic groups can be optionally substituted with 1 to 5 substituents (in some embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, haloalkyl, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)-heterocyclyl, —S(O)-aryl, —S(O)-heteroaryl, —S(O)$_2$-alkyl, —S(O)$_2$—C$_{3-6}$cycloalkyl, —S(O)$_2$—C$_{2-8}$heterocyclyl, —S(O)$_2$-aryl and —S(O)$_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, haloalkyl, amino, substituted amino, cyano, cycloalkyl, heterocyclyl, aryl, heteroaryl, and —S(O)R$^a$, in which R$^a$ is alkyl, aryl or heteroaryl and n is 0, 1 or 2. Examples of heterocyclics include tetrahydrofuranyl, morpholino, piperidinyl, and the like.

The term "heterocyclooxy" refers to the group —O-heterocyclyl.

The term "heteroaryl" refers to a carbocyclic group having at least one aromatic ring with one or more ring heteroatoms independently selected from nitrogen, oxygen, and sulfur. Heteroaryl groups may have multiple rings, or multiple fused rings. In some embodiments, heteroaryl is an aromatic, monocyclic or bicyclic ring containing one or more heteroatoms independently selected from nitrogen, oxygen and sulfur with the remaining ring atoms being carbon. In certain embodiments, heteroaryl as used herein has 2 to 20 ring carbon atoms (i.e., C$_{2-20}$ heteroaryl), 2 to 12 ring carbon atoms (i.e., C$_{2-12}$ heteroaryl), or 2 to 8 carbon ring atoms (i.e., C$_{2-8}$ heteroaryl); and 1 to 5 heteroatoms, 1 to 4 heteroatoms, 1 to 3 ring heteroatoms, 1 or 2 ring heteroatoms, or 1 ring heteroatom independently selected from nitrogen, oxygen, and sulfur. In one example, a heteroaryl has 3 to 8 ring carbon atoms, with 1 to 3 ring heteroatoms independently selected from nitrogen, oxygen and sulfur. Examples of heteroaryl groups include pyridyl, pyridazinyl, pyrimidinyl, benzothiazolyl, and pyrazolyl. Heteroaryl does not encompass or overlap with aryl or heterocyclyl as defined above. In certain embodiments, if one or more heteroaryl groups are fused with a heterocyclyl ring, the resulting ring system is heteroaryl.

Unless otherwise constrained by the definition for the heteroaryl substituent, such heteroaryl groups can be optionally substituted with 1 to 5 substituents (in some embodiments, 1, 2 or 3 substituents) selected from the group consisting alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, haloalkyl, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)-heterocyclyl, —S(O)-aryl, —S(O)-heteroaryl, —S(O)$_2$-alkyl, —S(O)$_2$—C$_{3-6}$ cycloalkyl, —S(O)$_2$—C$_{2-8}$ heterocyclyl, —S(O)$_2$-aryl and —S(O)$_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, haloalkyl, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2. Such heteroaryl groups can have a single ring (e.g., pyridyl or furyl) or multiple condensed rings (e.g., indolizinyl, benzothiazole or benzothienyl). Examples of nitrogen heterocyclyls and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

The term "heteroaryloxy" refers to the group heteroaryl-O—.

The term "amino" refers to the group —NH$_2$.

The term "substituted amino" refers to the group —NRR where each R is independently selected from the group consisting of hydrogen, alkyl, cycloalkyl, aryl, heteroaryl and heterocyclyl provided that both R groups are not hydrogen or a group —Y—Z, in which Y is optionally substituted alkylene and Z is alkenyl, cycloalkenyl or alkynyl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, haloalkyl, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "alkyl amine" refers to R—NH$_2$ in which R is optionally substituted alkyl.

The term "dialkyl amine" refers to R—NHR in which each R is independently an optionally substituted alkyl.

The term "trialkyl amine" refers to NR$_3$ in which each R is independently an optionally substituted alkyl.

The term "cyano" refers to the group —CN.

The term "azido" refers to a group

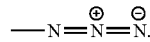

The term "keto" or "oxo" refers to a group =O.

The term "carboxy" refers to a group —C(O)—OH.

The term "ester" or "carboxyester" refers to the group —C(O)OR, where R is alkyl, cycloalkyl, aryl, heteroaryl or heterocyclyl, which may be optionally further substituted by alkyl, alkoxy, halogen, haloalkyl, amino, substituted amino, cyano or —S(O)$_n$R$^a$, in which R$^a$ is alkyl, aryl or heteroaryl and n is 0, 1 or 2.

The term "acyl" denotes the group —C(O)R, in which R is hydrogen, alkyl, cycloalkyl, heterocyclyl, aryl or heteroaryl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, haloalkyl, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "carboxyalkyl" refers to the groups —C(O)O-alkyl or —C(O)O-cycloalkyl, where alkyl and cycloalkyl are as defined herein, and may be optionally further substituted by alkyl, alkenyl, alkynyl, carboxy, carboxyalkyl, aminocarbonyl, hydroxy, alkoxy, halogen, haloalkyl, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "aminocarbonyl" refers to the group —C(O)NRR where each R is independently hydrogen, alkyl, cycloalkyl, aryl, heteroaryl, or heterocyclyl, or where both R groups are joined to form a heterocyclic group (e.g., morpholino). Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, haloalkyl, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "acyloxy" refers to the group —OC(O)—R, in which R is alkyl, cycloalkyl, heterocyclyl, aryl or heteroaryl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, haloalkyl, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "acylamino" refers to the group —NRC(O)R where each R is independently hydrogen, alkyl, cycloalkyl, aryl, heteroaryl or heterocyclyl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, haloalkyl, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "alkoxycarbonylamino" refers to the group —N(R$^d$)C(O)OR in which R is alkyl and R$^d$ is hydrogen or alkyl. Unless otherwise constrained by the definition, each alkyl may optionally be further substituted by 1, 2 or 3 substituents selected from the group consisting of alkyl, alkenyl, alkynyl, carboxy, carboxyalkyl, aminocarbonyl, hydroxy, alkoxy, halogen, haloalkyl, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "aminocarbonylamino" refers to the group —NR$^c$C(O)NRR, wherein R$^c$ is hydrogen or alkyl and each R is hydrogen, alkyl, cycloalkyl, aryl, heteroaryl or heterocyclyl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, haloalkyl, amino, substituted amino, cyano, cycloalkyl, heterocyclyl, aryl, heteroaryl, and —S(O)$_1$R$^a$, in which R$^a$ is alkyl, aryl or heteroaryl and n is 0, 1 or 2.

The term "thiol" refers to the group —SH.

The term "thiocarbonyl" refers to a group =S.

The term "alkylthio" refers to the group —S-alkyl.

The term "substituted alkylthio" refers to the group —S-substituted alkyl.

The term "heterocyclylthio" refers to the group —S-heterocyclyl.

The term "arylthio" refers to the group —S-aryl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, cycloalkyl, heterocyclyl, aryl or heteroaryl. "Substituted sulfoxide" refers to a group —S(O)R, in which R is substituted alkyl, substituted cycloalkyl, substituted heterocyclyl, substituted aryl or substituted heteroaryl, as defined herein.

The term "sulfone" refers to a group —S(O)$_2$R, in which R is alkyl, cycloalkyl, heterocyclyl, aryl or heteroaryl. "Substituted sulfone" refers to a group —S(O)$_2$R, in which R is substituted alkyl, substituted cycloalkyl, substituted heterocyclyl, substituted aryl or substituted heteroaryl, as defined herein.

The term "aminosulfonyl" refers to the group —S(O)$_2$NRR, wherein each R is independently hydrogen, alkyl, cycloalkyl, aryl, heteroaryl or heterocyclyl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, haloalkyl, amino, substituted amino, cyano, cycloalkyl, heterocyclyl, aryl, heteroaryl, and —S(O)$_1$R$^a$, in which R$^a$ is alkyl, aryl or heteroaryl and n is 0, 1 or 2.

The term "hydroxyamino" refers to the group —NHOH.

The term "alkoxyamino" refers to the group —NHOR in which R is optionally substituted alkyl.

The term "halogen" or "halo" refers to fluoro, bromo, chloro and iodo and the term "halogen" includes fluorine, chlorine, bromine, and iodine. "Haloalkyl" refers to an unbranched or branched chain alkyl group as defined above, wherein one or more hydrogen atoms are replaced by a halogen. For example, where a residue is substituted with more than one halogen, it may be referred to by using a prefix corresponding to the number of halogen moieties attached. For example, dihaloaryl, dihaloalkyl, and trihaloaryl refer to aryl and alkyl substituted with two ("di") or three ("tri") halo groups, which may be, but are not necessarily, the same halogen; thus, for example, 4-chloro-3-fluorophenyl is within the scope of dihaloaryl. A haloalkyl group in which each H of the alkyl chain is replaced with a halogen is referred to as a "perhaloalkyl." The term "haloalkyl" includes "perhaloalkyl" groups. One example of a perhaloalkyl group is trifluoromethyl (—CF$_3$). "Fluoroalkyl" and "perfluoroalkyl" groups are, respectively, "haloalkyl" and "perhaloalkyl" groups in which each halogen is fluorine and includes, as examples, fluoromethyl, fluoroethyl, fluoropropyl, difluoromethyl, difluoroethyl, difluoropropyl, trifluoromethyl, trifluoroethyl, and trifluoropropyl groups.

The term "$C_{1-3}$ haloalkyl" refers to an alkyl group having from 1 to 3 carbon atoms covalently bonded to from 1 to 7, or from 1 to 6, or from 1 to 3, halogen(s), where alkyl and halogen are defined herein. In some embodiments, $C_{1-3}$ haloalkyl includes, by way of example, trifluoromethyl, difluoromethyl, fluoromethyl, 2,2,2-trifluoroethyl, 2,2-difluoroethyl, 2-fluoroethyl, 3,3,3-trifluoropropyl, 3,3-difluoropropyl, 3-fluoropropyl.

"Optional" or "optionally" means that the subsequently described event or circumstance may or may not occur, and that the description includes instances where said event or circumstance occurs and instances in which it does not.

A "substituted" group includes embodiments in which a monoradical substituent is bound to a single atom of the substituted group (e.g. forming a branch), and also includes embodiments in which the substituent may be a diradical bridging group bound to two adjacent atoms of the substituted group, thereby forming a fused ring on the substituted group.

Where a given group (moiety) is described herein as being attached to a second group and the site of attachment is not explicit, the given group may be attached at any available site of the given group to any available site of the second group. For example, a "lower alkyl-substituted phenyl", where the attachment sites are not explicit, may have any available site of the lower alkyl group attached to any available site of the phenyl group. In this regard, an "available site" is a site of the group at which a hydrogen of the group may be replaced with a substituent.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. Also not included are infinite numbers of substituents, whether the substituents are the same or different. In such cases, the maximum number of such substituents is three. Each of the above definitions is thus constrained by a limitation that, for example, substituted aryl groups are limited to -substituted aryl-(substituted aryl)-substituted aryl.

A compound of a given formula (e.g. the compound of Formula I, which also includes compounds of all other Formulas herein) is intended to encompass the compounds of the disclosure, and the pharmaceutically acceptable salts, pharmaceutically acceptable esters, isomers, tautomers, solvates, isotopes, hydrates, polymorphs, and prodrugs of such compounds. Additionally, the compounds of the disclosure may possess one or more asymmetric centers, and can be produced as a racemic mixture or as individual enantiomers or diastereoisomers. The number of stereoisomers present in any given compound of a given formula depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis or by resolution of the compound by conventional means. The individual stereoisomers (including individual enantiomers and diastereoisomers) as well as racemic and non-racemic mixtures of stereoisomers are encompassed within the scope of the present disclosure, all of which are intended to be depicted by the structures of this specification unless otherwise specifically indicated.

"Isomers" are different compounds that have the same molecular formula. Isomers include stereoisomers, enantiomers and diastereomers.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn Ingold Prelog R S system. When the compound is a pure enantiomer the stereochemistry at each chiral carbon may be specified by either R or S. Resolved compounds whose absolute configuration is unknown are designated (+) or (−) depending on the direction (dextro- or laevorotary) that they rotate the plane of polarized light at the wavelength of the sodium D line.

Some of the compounds exist as tautomeric isomers. Tautomeric isomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers. Non-limiting examples of amide-comprising and imidic acid-comprising tautomers are shown below:

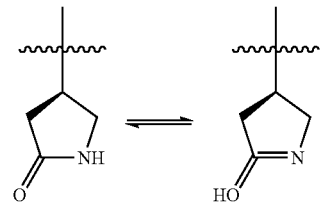

The term "therapeutically effective amount" refers to an amount that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "polymorph" refers to different crystal structures of a crystalline compound. The different polymorphs may result from differences in crystal packing (packing polymorphism) or differences in packing between different conformers of the same molecule (conformational polymorphism).

The term "solvate" refers to a complex formed by the combining of a compound of Formula I, II, III, IV, V, or VI and a solvent.

The term "hydrate" refers to the complex formed by the combining of a compound of Formula I, II, III, IV, V, or VI and water.

The term "prodrug" refers to compounds of Formula I, II, III, IV, V, or VI that include chemical groups which, in vivo, can be converted and/or can be split off from the remainder of the molecule to provide for the active drug, a pharmaceutically acceptable salt thereof or a biologically active metabolite thereof.

Any formula or structure given herein, including Formula I, II, III, IV, V, or VI compounds, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compounds described herein, including those of Formulas I, II, III, IV, V, or VI.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

The disclosure also included compounds of Formula I, II, III, IV, V, or VI in which from 1 to n hydrogens attached to a carbon atom is/are replaced by deuterium, in which n is the number of hydrogens in the molecule. Such compounds exhibit increased resistance to metabolism and are thus useful for increasing the half life of any compound of Formula I, II, III, IV, V, or VI when administered to a mammal. See, for example, Foster, "Deuterium Isotope Effects in Studies of Drug Metabolism", Trends Pharmacol. Sci. 5(12):524-527 (1984). Such compounds are synthesized by means well known in the art, for example by employing starting materials in which one or more hydrogens have been replaced by deuterium.

The term "inhibition" indicates a significant decrease in the baseline activity of a biological activity or process. "Inhibition of Syk activity" refers to a decrease in Syk activity as a direct or indirect response to the presence of a compound of Formula I, II, III, IV, V, or VI, or a pharmaceutically acceptable salt thereof, relative to the activity of Syk in the absence of the a compound. The decrease in activity may be due to the direct interaction of the compound with Syk, or due to the interaction of the chemical entity(ies) described herein with one or more other factors that in turn affect Syk activity. For example, the presence of the chemical entity(ies) may decrease Syk activity by directly binding to the Syk, by causing (directly or indirectly) another factor to decrease Syk activity, or by (directly or indirectly) decreasing the amount of Syk present in the cell or organism.

Inhibition of Syk activity also refers to observable inhibition of Syk activity in a standard biochemical assay for Syk activity, such as the ATP hydrolysis assay described below. In some embodiments, the chemical entity described herein has an IC50 value less than or equal to 1 micromolar. In some embodiments, the chemical entity has an IC50 value less than or equal to less than 100 nanomolar. In some embodiments, the chemical entity has an IC50 value less than or equal to 10 nanomolar.

"Inhibition of B-cell activity" refers to a decrease in B-cell activity as a direct or indirect response to the presence of a compound of Formula I, II, III, IV, V, or VI, or a pharmaceutically acceptable salt thereof, relative to the activity of B-cells in the absence of the a compound. The decrease in activity may be due to the direct interaction of the compound with Syk or with one or more other factors that in turn affect B-cell activity.

Inhibition of B-cell activity also refers to observable inhibition of CD86 expression in a standard assay such as the assay described below. In some embodiments, the chemical entity described herein has an IC50 value less than or equal to 10 micromolar. In some embodiments, the chemical entity has an IC50 value less than or equal to less than 1 micromolar. In some embodiments, the chemical entity has an IC50 value less than or equal to 500 nanomolar.

"B cell activity" also includes activation, redistribution, reorganization, or capping of one or more various B cell membrane receptors, or membrane-bound immunoglobulins, e.g., IgM, IgG, and IgD. Most B cells also have membrane receptors for Fc portion of IgG in the form of either antigen-antibody complexes or aggregated IgG. B cells also carry membrane receptors for the activated components of complement, e.g., C3b, C3d, C4, and C1q. These various membrane receptors and membrane-bound immunoglobulins have membrane mobility and can undergo redistribution and capping that can initiate signal transduction.

B cell activity also includes the synthesis or production of antibodies or immunoglobulins. Immunoglobulins are synthesized by the B cell series and have common structural features and structural units. Five immunoglobulin classes, i.e., IgG, IgA, IgM, IgD, and IgE, are recognized on the basis of structural differences of their heavy chains including the amino acid sequence and length of the polypeptide chain. Antibodies to a given antigen may be detected in all or several classes of immunoglobulins or may be restricted to a single class or subclass of immunoglobulin. Autoantibodies or autoimmune antibodies may likewise belong to one or several classes of immunoglobulins. For example, rheumatoid factors (antibodies to IgG) are most often recognized as an IgM immunoglobulin, but can also consist of IgG or IgA.

In addition, B cell activity also is intended to include a series of events leading to B cell clonal expansion (proliferation) from precursor B lymphocytes and differentiation into antibody-synthesizing plasma cells which takes place in conjunction with antigen-binding and with cytokine signals from other cells.

"Inhibition of B-cell proliferation" refers to inhibition of proliferation of abnormal B-cells, such as cancerous B-cells, e.g. lymphoma B-cells and/or inhibition of normal, non-diseased B-cells. The term "inhibition of B-cell proliferation" indicates any significant decrease in the number of B-cells, either in vitro or in vivo. Thus an inhibition of B-cell proliferation in vitro would be any significant decrease in the number of B-cells in an in vitro sample contacted with a compound of Formula I, II, III, IV, V, or VI, or a pharmaceutically acceptable salt thereof as compared to a matched sample not contacted with the chemical entity(ies).

Inhibition of B-cell proliferation also refers to observable inhibition of B-cell proliferation in a standard thymidine incorporation assay for B-cell proliferation, such as the assay described herein. In some embodiments, the chemical entity has an IC50 value less than or equal to 10 micromolar. In some embodiments, the chemical entity has an IC50 value less than or equal to less than 1 micromolar. In some embodiments, the chemical entity has an IC50 value less than or equal to 500 nanomolar.

An "allergy" or "allergic disorder" refers to acquired hypersensitivity to a substance (allergen). Allergic conditions include eczema, allergic rhinitis or coryza, hay fever, bronchial asthma, urticaria (hives) and food allergies, and other atopic conditions. Food allergies include pollen allergies, dairy allergies, including milk allergies, soy allergies, egg allergies, wheat allergies, nut allergies, including allergies to peanuts and tree nuts (walnuts, almonds, hazelnuts, cashews, pistachios, pecans, Brazil nuts, beechnuts, butternuts, chestnuts, Chinquapin nut, hickory nuts, etc) and seafood allergies.

"Asthma" refers to a disorder of the respiratory system characterized by inflammation, narrowing of the airways and increased reactivity of the airways to inhaled agents. Asthma is frequently, although not exclusively associated with atopic or allergic symptoms.

By "significant" is meant any detectable change that is statistically significant in a standard parametric test of statistical significance such as Student's T-test, where p<0.05.

A "disease responsive to inhibition of Syk activity" is a disease in which inhibiting Syk kinase provides a therapeutic benefit such as an amelioration of symptoms, decrease in disease progression, prevention or delay of disease onset, or inhibition of aberrant activity of certain cell-types (monocytes, B-cells, and mast cells).

"Patient" refers to an animal, such as a mammal, that has been or will be the object of treatment, observation or experiment. The methods described herein may be useful in both human therapy and veterinary applications. In some embodiments, the patient is a mammal; in some embodiments the patient is human; and in some embodiments the patient is chosen from cats and dogs.

The term "treatment" or "treating" means administration of a compound of the invention, by or at the direction of a competent caregiver, to a mammal having a disease for purposes including:
(i) preventing the disease, that is, causing the clinical symptoms of the disease not to develop;
(ii) inhibiting the disease, that is, arresting the development of clinical symptoms; and/or
(iii) relieving the disease, that is, causing the regression of clinical symptoms.

In many cases, the compounds of this disclosure are capable of forming acid and/or base salts by virtue of the presence of amino and/or carboxyl groups or groups similar thereto.

The term "pharmaceutically acceptable salt" of a given compound refers to salts that retain the biological effectiveness and properties of the given compound, and which are not biologically or otherwise undesirable. Pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Amines are of general structure $N(R^{30})(R^{31})(R^{32})$, wherein mono-substituted amines have 2 of the three substituents on nitrogen ($R^{30}$, $R^{31}$ and $R^{32}$) as hydrogen, di-substituted amines have 1 of the three substituents on nitrogen ($R^{30}$, $R^{31}$ and $R^{32}$) as hydrogen, whereas tri-substituted amines have none of the three substituents on nitrogen ($R^{30}$, $R^{31}$ and $R^{32}$) as hydrogen. $R^{30}$, $R^{31}$ and $R^{32}$ are selected from a variety of substituents such as hydrogen, optionally substituted alkyl, aryl, heteroayl, cycloalkyl, cycloalkenyl, heterocyclyl and the like. The above-mentioned amines refer to the compounds wherein either one, two or three substituents on the nitrogen are as listed in the name. For example, the term "cycloalkenyl amine" refers to cycloalkenyl-$NH_2$, wherein "cycloalkenyl" is as defined herein. The term "diheteroarylamine" refers to NH(heteroaryl)$_2$, wherein "heteroaryl" is as defined herein and so on.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Nomenclature

Names of compounds of the present disclosure are provided using ACD/Name software for naming chemical compounds (Advanced Chemistry Development, Inc., Toronto, Canada). Other compounds or radicals may be named with common names or systematic or non-systematic names. The naming and numbering of the compounds of the disclosure is illustrated with a representative compound of Formula I:

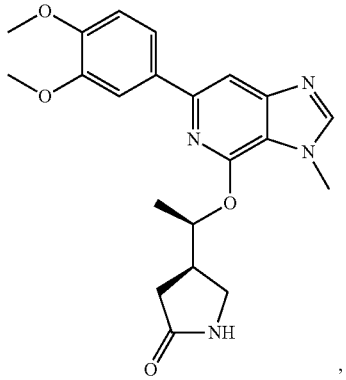 [SMILES: COc1ccc(-c2cc3ncn(C)c3c(O[C@H](C)[C@H]3CNC(=O)C3)n2)cc1OC]

also referred to as (R)-4-((R)-1-(6-(3,4-dimethoxyphenyl)-3-methyl-3H-imidazo[4,5-c]pyridin-4-yloxy)ethyl)pyrrolidin-2-one.

Compounds

For each of the embodiments identified by Formula I, Formula Ia, Formula Ib, Formula Ic, Formula II, Formula III, Formula IV, Formula V, and Formula VI, there is another embodiment comprising a compound of each formula, or a pharmaceutically acceptable salt thereof, respectively, wherein $R^5$ is a moiety selected from the group of phenyl, pyrazolyl, pyridinyl, pyrazolo[1,5-a]pyridinyl, benzo[d][1,3]dioxolyl, benzomorpholinyl, thiazolyl, cyclohex-1-enyl, pyridine-2(1H)-one-yl, dihydrobenzo[f][1,4]oxazepine-5(2H)-one-yl, benzothiazolyl, thieno[3,2-c]pyrazolyl, ethynyl, indazolyl, pyrimidinyl, imidazolyl, indolinyl, pyrazinyl, pyridazine, pyrido[3,2-b][1,4]oxazinyl, 2,3-dihydro-[1,4]dioxino[2,3-b]pyridinyl, quinazolin-4(3H)-one-yl, pyrrolo[2,3-b]pyridine-2(3H)-one-yl, pyrrolo[3,2-c]pyridine-2(3H)-one-yl, 3,4-dihydroquinolin-2(1H)-one-yl, indoline-2-one, pyrazolo[3,4-b]pyridinyl, 2,3-dihydrobenzofuranyl, 2H-benzo[b][1,4]oxazin-3(4H)-one-yl, 3,4-dihydroquinolin-2(1H)-one-yl, pyrido[3,2-b][1,4]oxazin-3(4H)-one-yl, benzimidazolyl, imidazo[1,2-a]pyridinyl, imidazo[1,2-a]pyridinyl, isoindoline-1-one-yl, benzomorpholin-3-one-yl, benzomorpholin-2-one-yl, benzimidazolin-2-one-yl, 2,3-dihydro-1H-pyrido[2,3-b][1,4]oxazinyl, pyrido[2,3-b][1,4]oxazin-2(3H)-one-yl, spiro[azetidine-3,3'-indolin]-2'-one-yl, benzo[d][1,3]oxazin-2(4H)-one-yl, spiro[indoline-3,4'-piperidin]-2-one-yl, 3,4-dihydrospiro[benzo[b][1,4]oxazine-2,1'-cyclopropane]-yl, indolyl, benzoxazolin-2-one-yl, pyrrolo[3,2-b]pyridine-2(3H)-one-yl, thiophenyl, 3,4-dihydro-pyrido[3,2-b][1,4]oxazinyl, 1,3,4-thiadiazolyl, indolinyl, isothiazolyl, 1,2,3-triazolyl, 1,2,3,4-tetrahydroquinaline and thieno[2,3-c]pyridinyl; with each of the R5 moieties being substituted by 0, 1, 2, or 3 substituents selected from $C_{1-6}$ alkyl, $C_{2-6}$ alkynyl, $C_{1-6}$ alkoxy, halo, $-NO_2$, $-CFH_2$, $-CF_3$, $-CF_2H$, $-OCF_3$, $C_{3-8}$ cycloalkyl, $C_{2-8}$ heterocyclyl, $C_{6-12}$ aryl, $C_{2-12}$ heteroaryl, $-S(O)_2R^{20}$, $-S(O)_2-N(R^{20})(R^{22})$, $-N(R^{20})(R^{22})$, $-N(R^{20})N(R^{20})-C(O)-R^{22}$, $-C(O)-R^{20}$, $-C(O)-OR^{20}$, $-C(O)-N(R^{20})(R^{22})$, $-CN$, oxo, and $-O-R^{20}$;

wherein the $C_{1-6}$ alkyl, $C_{2-6}$ alkynyl, $C_{1-6}$ alkoxy, $C_{3-8}$ cycloalkyl, $C_{2-8}$ heterocyclyl, $C_{6-12}$ aryl, or $C_{2-12}$ heteroaryl moiety may be optionally further substituted with one, two, or three substituents independently selected from the group consisting of halo, $-NO_2$, $-CFH_2$, $-CF_3$, $-CF_2H$, $-OCF_3$, $C_{1-6}$ alkyl, $C_{3-6}$ cycloalkyl, $C_{6-12}$ aryl, $C_{2-8}$ heterocyclyl, $C_{2-6}$ heteroaryl, $-N(R^{20})(R^{22})$, $-C(O)R^{20}$, $-C(O)-OR^{20}$, $-C(O)-N(R^{20})(R^{22})$, $-CN$, $-S(O)_2R^{20}$, $-S(O)_2-N(R^{20})(R^{22})$, $-S(O)_2-R^{20}-N(R^{20})(R^{22})$, oxo, and $-O-R^{20}$;

wherein the $C_{1-6}$ alkyl, $C_{3-6}$ cycloalkyl, $C_{2-8}$ heterocyclyl, $C_{6-12}$ aryl, and $C_{2-6}$ heteroaryl may be further optionally substituted with one, two, or three substituents independently selected from the group consisting of $C_{1-6}$ alkyl, $C_{3-6}$ cycloalkyl, $C_{6-12}$ aryl, $C_{2-6}$ heteroaryl, $C_{2-8}$ heterocyclyl, halo, $-NO_2$, $-CFH_2$, $-CF_2H$, $-CF_3$, $-OCF_3$, $-N(R^{20})(R^{22})$, $C(O)-R^{20}$, $-C(O)-OR^{20}$, $-C(O)-N(R^{20})(R^{22})$, $-CN$, $-S(O)_2R^{20}$, $-S(O)_2-N(R^{20})(R^{22})$, $-S(O)_2-R^{20}-N(R^{20})(R^{22})$, oxo, and $-O-R^{20}$; and each $R^{20}$ and $R^{22}$ is independently hydrogen, $C_{1-6}$ alkyl, $C_{2-6}$ alkenyl, $C_{2-6}$ alkynyl, $C_{3-6}$ cycloalkyl, $C_{2-8}$ heterocyclyl, $C_{6-12}$ aryl, or $C_{2-12}$ heteroaryl; wherein each $C_{1-6}$ alkyl, $C_{2-6}$ alkenyl, $C_{2-6}$ alkynyl, $C_{3-6}$ cycloalkyl, $C_{2-8}$ heterocyclyl, $C_{6-12}$ aryl and $C_{2-12}$ heteroaryl are optionally substituted with one, two or three substituents independently selected from the group consisting of hydroxyl, halo, $C_{1-6}$ alkyl, acylamino, oxo, $-NO_2$, $-S(O)_2R^{26}$, $-CN$, $C_{1-6}$ alkoxy, $C_{3-6}$ cycloalkoxy, $-CFH_2$, $-CF_3$, $-CF_2H$, $-OCF_3$, $-OCH_2CF_3$, $-C(O)-NH_2$, $C_{6-12}$ aryl, $C_{3-6}$ cycloalkyl, $C_{2-8}$ heterocyclyl, and $C_{2-6}$ heteroaryl; and wherein $R^{26}$ is $C_{1-6}$ alkyl, $C_{2-6}$ alkenyl, $C_{2-6}$ alkynyl, $C_{3-6}$ cycloalkyl, $C_{2-8}$ heterocyclyl, $C_{6-12}$ aryl, $C_{2-6}$ heteroaryl, acylamino, $NH_2$, $-CFH_2$, $-CF_3$, $-CF_2H$.

In some embodiments, $X^1$ is CH. In other embodiments, $X^1$ is N.

In some embodiments, $X^2$ is $CR^{1a}$. In certain embodiments, $R^{1a}$ is hydrogen, halo, $C_{1-6}$ alkyl, or $C_{3-6}$ cycloalkyl. In certain embodiments, $R^{1a}$ is hydrogen, methyl, chloro, $-CF_3$, $-CF_2H$, $-CFH_2$, or cyclopropyl. In other embodiments, $R^{1a}$ is hydrogen, chloro, methyl, ethyl, propyl, butyl, or cyclopropyl. In certain embodiments, $R^{1a}$ is hydrogen, methyl, or chloro. In other embodiments, $R^{1a}$ is $-CF_3$, $-CF_2H$, $-CFH_2$, or cyclopropyl. In certain embodiments, $R^{1a}$ is haloalkyl. In one embodiment, $R^{1a}$ is $-CF_3$. In some embodiments, $R^{1a}$ is $C_{3-6}$ cycloalkyl. In one embodiment, $R^{1a}$ is cyclopropyl.

In other embodiments, $X^2$ is $NR^{1b}$. In certain embodiments, $R^{1b}$ is hydrogen, methyl, ethyl, propyl (e.g., isopropyl), cyclopropyl, $CHF_2$, $CH_2CF_3$,

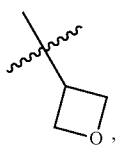 [SMILES: *C1COC1]

CH$_2$CH$_2$F, or cyclobutyl. In certain embodiments, R$^{1b}$ is haloalkyl. In one embodiment, R$^{1b}$ is —CF$_3$.

In yet other embodiments, X$^2$ is S.

In some embodiments, X$^3$ is C. In other embodiments, X$^3$ is N.

In certain embodiments, X$^1$, X$^2$ and X$^3$ are to form:

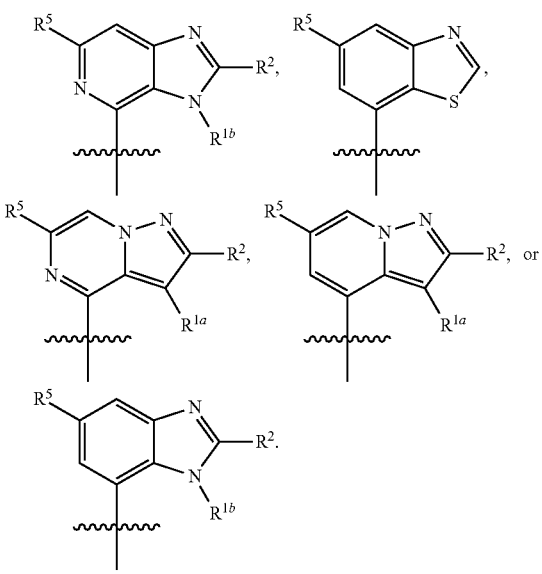

In one variation, X$^1$, X$^2$ and X$^3$ are arranged and substituted in such a way to form a heteroaromatic ring system with 10π electrons.

It is intended and understood that each and every variation of X$^1$, X$^2$ and X$^3$ may be combined with each other, and with each and every variation of R$^2$, R$^3$, R$^4$, R$^5$, and Y, as if each and every combination is individually described.

In some embodiments, R$^2$ is hydrogen. In other embodiments, R$^2$ is C$_{1-6}$ alkyl. In one variation, embodiments, R$^2$ is C$_{1-4}$ alkyl. In another variation, R$^2$ is methyl.

It is intended and understood that each and every variation of R$^2$ may be combined with each and every variation of X$^1$, X$^2$, X$^3$, R$^3$, R$^4$, and R$^5$, as if each and every combination is individually described.

In some embodiments, each R$^3$ and R$^4$ is independently C$_{1-4}$ alkyl optionally substituted with 1 to 3 members independently selected from halogen and C$_{1-4}$ alkoxy and R$^4$ is hydrogen. In certain embodiments, R$^3$ is C$_{1-4}$ alkyl optionally substituted with 1 to 3 members independently selected from halogen and C$_{1-4}$ alkoxy, and R$^4$ is hydrogen. In other embodiments, R$^4$ is C$_{1-4}$ alkyl optionally substituted with 1 to 3 members independently selected from halogen and C$_{1-4}$ alkoxy and R$^3$ is hydrogen.

For each of the embodiments identified by Formula I, Formula 1a, Formula 1b, Formula Ic, Formula II, Formula III, Formula IV, Formula V, and Formula VI, there additional separate embodiments comprising a compound of each formula, or a pharmaceutically acceptable salt thereof, respectively, wherein, as separate embodiments for each formula:

a) R$^3$ and R$^4$ are each independently hydrogen or C$_{1-6}$ alkyl;
b) R$^3$ is hydrogen;
c) R$^4$ is hydrogen or C$_{1-6}$ alkyl;
d) R$^3$ is hydrogen and R$^4$ is C$_{1-6}$ alkyl;
e) each R$^3$ and R$^4$ is independently hydrogen, methyl,

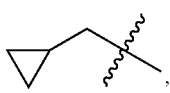

CH$_2$CH$_2$F,

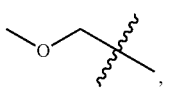

CHF$_2$,

ethyl, or CH$_2$CHF$_2$;

f) R$^3$ is hydrogen, and R$^4$ is methyl,

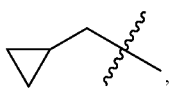

CH$_2$CH$_2$F,

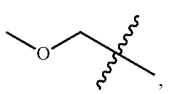 [SMILES: *COC]

CHF$_2$

ethyl, or CH$_2$CHF$_2$; and g) R$^3$ is hydrogen, and R$^4$ is methyl.

In each of the embodiments a)-g), above, all other variables are as otherwise defined for Formulas I through VI, respectively.

It is intended and understood that each and every variation of R$^3$ and R$^4$ may be combined with each and every variation of X$^1$, X$^2$, X$^3$, R$^2$, and R$^5$, as if each and every combination is individually described.

For each of the embodiments identified by Formula I, Formula 1a, Formula 1b, Formula Ic, Formula II, Formula III, Formula IV, Formula V, and Formula VI, there is another embodiment comprising a compound of each formula, or a pharmaceutically acceptable salt thereof, respectively, wherein $R^5$ is a cyclic ring selected from the group consisting of phenyl, pyridinyl, pyrimidinyl, indazolyl, indolyl, benzoimidazolyl, benzothiazolyl, benzoxazolyl, benzotriazolyl, dihydrobenzoxazinyl, dihydroindolyl, benzodioxolyl, thiazolyl, pyrazolopyrindinyl, cyclohexenyl, cyclohexanyl, tetrahydrobenzoxazepanyl, oxazepanyl, piperazinyl, thienopyrazolyl, pyrazinyl, pyridzainyl, triazinyl, indolinyl, pyrazolyl, imidazolylmorpholinyl, thiomorpholinyl, thiomorpholinyl sulfone, piperidinyl, thiophenyl, quinolinyl, quinoxalinyl, quinazolinyl, or naphthalenyl. In one variation, the cyclic ring may be optionally substituted with one, two, or three substituents independently selected from the group consisting of halo, $C_{1-6}$ alkyl, $C_{1-6}$ alkoxy, $C_{2-6}$ alkynyl, $C_{3-8}$ cycloalkyl, $C_{2-8}$ heterocyclyl, $C_{6-12}$ aryl, $C_{2-12}$ heteroaryl, —S(O)$_2$—R$^{26}$, —S(O)$_2$—N(R$^{20}$)(R$^{22}$), —N(R$^{20}$)(R$^{22}$), —NO$_2$, —N(R$^{20}$)—S(O)$_2$—R$^{20}$, —N(R$^{20}$)—C(O)R$^{22}$, —C(O) R$^{20}$, —C(O)—OR$^{20}$, —C(O)—N(R$^{20}$)(R$^{22}$), CN, oxo, and —O—R$^{20}$, wherein the alkyl, cycloalkyl, heterocyclyl, aryl, or heteroaryl moieties may be further optionally substituted with one, two or three substituents independently selected from the group consisting of halo, $C_{1-6}$ alkyl, $C_{3-6}$ cycloalkyl, $C_{6-12}$ aryl, $C_{2-8}$ heterocyclyl, $C_{2-6}$ heteroaryl, —S(O)$_2$—R$^{20}$, —S(O)$_2$—N(R$^{20}$((R$^{22}$), —NO$_2$, —N(R$^{20}$)(R$^{22}$), —C(O)—R$^{20}$, —C(O)—OR$^{20}$, —C(O)—N(R$^{20}$)(R$^{22}$), —CN, oxo, and —O—R$^{20}$; wherein each R$^{20}$ and R$^{22}$ is independently selected from the group consisting of hydrogen, $C_{1-6}$ alkyl, $C_{2-6}$ alkenyl, $C_{2-6}$ alkynyl, $C_{3-6}$ cycloalkyl, $C_{2-8}$ heterocyclyl, $C_{6-12}$ aryl, and $C_{2-6}$ heteroaryl.

It should be understood that the cyclic ring may be monocyclic or bicyclic. In certain embodiments, the cyclic ring may have more than one ring that may be fused, spiro or bridged. For example, in certain embodiments, $R^5$ is a monocyclic or bicyclic $C_{2-8}$ heterocyclyl. In one embodiment, $R^5$ is a $C_{2-8}$ heterocyclyl with more than one ring that may be fused, spiro or bridged.

For each of the embodiments identified by Formula I, Formula 1a, Formula 1b, Formula Ic, Formula II, Formula III, Formula IV, Formula V, and Formula VI, there is another embodiment comprising a compound of each formula, or a pharmaceutically acceptable salt thereof, respectively, wherein $R^5$ is phenyl, pyridinyl, pyrazolyl, indazolyl, benzothiazolyl, dihydrobenzoxazinyl, benzodioxolyl, thiazolyl, pyrazolopyrindinyl, cyclohexenyl, tetrahydrobenzoxazepanyl, and thienopyrazolyl;

wherein the phenyl, pyridinyl, pyrazolyl, indazolyl, benzothiazolyl, dihydrobenzoxazinyl, benzodioxolyl, thiazolyl, pyrazolopyrindinyl, cyclohexenyl, tetrahydrobenzoxazepanyl, and thienopyrazolyl moieties may be optionally substituted with one, two, or three substituents independently selected from the group consisting of halo, $C_{1-6}$ alkyl, $C_{1-6}$ alkoxy, $C_{2-6}$ alkynyl, $C_{3-8}$ cycloalkyl, $C_{2-8}$ heterocyclyl, $C_{6-12}$ aryl, $C_{2-6}$) heteroaryl, —S(O)$_2$—R$^{20}$, —S(O)$_2$—N(R$^{20}$)(R$^{22}$), —N(R$^{20}$)(R$^{22}$), —NO$_2$, —CF$_3$, —OCF$_3$, —N(R$^{20}$)—S(O)$_2$—R$^{20}$, —N(R$^{20}$)—C(O)—R$^{22}$, —C(O)—R$^{20}$, —C(O)—OR$^{20}$, —C(O)—N(R$^{20}$)(R$^{22}$), —CN, oxo, and —O—R$^{20}$;

wherein the alkyl, cycloalkyl, heterocyclyl, aryl, or heteroaryl moieties may be further optionally substituted with one, two or three substituents independently selected from the group consisting of halo, $C_{1-6}$ alkyl, $C_{3-6}$ cycloalkyl, $C_{6-12}$ aryl, $C_{2-8}$ heterocyclyl, $C_{2-6}$heteroaryl, —S(O)$_2$—R$^{20}$, —S(O)$_2$—N(R$^{20}$)(R$^{22}$) NO$_2$, CF$_3$, —OCF$_3$, —N(R$^{20}$)(R$^{22}$), —C(O)—R$^{20}$, —C(O)—OR$^{20}$, —C(O)—N(R$^{20}$)(R$^{22}$), —CN, and —O—R$^{20}$; wherein each R$^{20}$ and R$^{22}$ is independently selected from the group consisting of hydrogen, $C_{1-6}$ alkyl, $C_{2-6}$ alkenyl, $C_{2-6}$ alkynyl, $C_{3-6}$ cycloalkyl, $C_{2-8}$ heterocyclyl, $C_{6-12}$ aryl, and $C_{2-6}$ heteroaryl.

For each of the embodiments identified by Formula I, Formula 1a, Formula 1b, Formula Ic, Formula II, Formula III, Formula IV, Formula V, and Formula VI, there is another embodiment comprising a compound of each formula, or a pharmaceutically acceptable salt thereof, respectively, wherein $R^5$ is phenyl, pyridinyl, pyrazolyl, indazolyl, benzothiazolyl, dihydrobenzoxazinyl, benzodioxolyl, thiazolyl, pyrazolopyrindinyl, cyclohexenyl, tetrahydrobenzoxazepanyl, and thienopyrazolyl;

wherein the phenyl, pyridinyl, pyrazolyl, indazolyl, benzothiazolyl, dihydrobenzoxazinyl, benzodioxolyl, thiazolyl, pyrazolopyrindinyl, cyclohexenyl, tetrahydrobenzoxazepanyl, and thienopyrazolyl moieties may be optionally substituted with one, two, or three substituents independently selected from the group consisting of halo, —CF$_3$, —CHF$_2$, —OCF$_3$, $C_{1-6}$ alkyl, $C_{3-6}$ cycloalkyl, $C_{2-8}$ heterocyclyl, —S(O)$_2$—R$^{20}$, —S(O)$_2$—NR$^{20}$R$^{22}$, —N(R$^{20}$)(R$^{22}$), —C(O)—OR$^{20}$, —CN, oxo, and —O—R$^{20}$;

wherein the $C_{1-6}$ alkyl, $C_{3-8}$ cycloalkyl, $C_{2-8}$ heterocyclyl moieties may be optionally further substituted with one, two or three substituents independently selected from the group consisting of halo, —CF$_3$, —CHF$_2$, —OCF$_3$, $C_{1-6}$ alkyl, $C_{3-8}$ cycloalkyl, $C_{2-8}$ heterocyclyl, —N(R$^{20}$)(R$^{22}$), —C(O)R$^{20}$, —C(O)—OR$^{20}$, —C(O)—N(R$^{20}$)(R$^{22}$), —CN, —O—R$^{20}$, —S(O)$_2$—R$^{20}$, —S(O)$_2$—NR$^{20}$R$^{22}$, and oxo;

wherein each R$^{20}$ and R$^{22}$ is independently selected from the group consisting of hydrogen, $C_{1-6}$ alkyl, $C_{1-6}$ alkoxy, $C_{2-6}$ alkenyl, $C_{2-6}$ alkynyl, $C_{3-8}$ cycloalkyl, $C_{2-8}$ heterocyclyl, $C_{6-12}$ aryl, and $C_{2-6}$ heteroaryl.

For each of the embodiments identified by Formula I, Formula 1a, Formula 1b, Formula Ic, Formula II, Formula III, Formula IV, Formula V, and Formula VI, there is another embodiment comprising a compound of each formula, or a pharmaceutically acceptable salt thereof, respectively, wherein $R^5$ is selected from the groups:

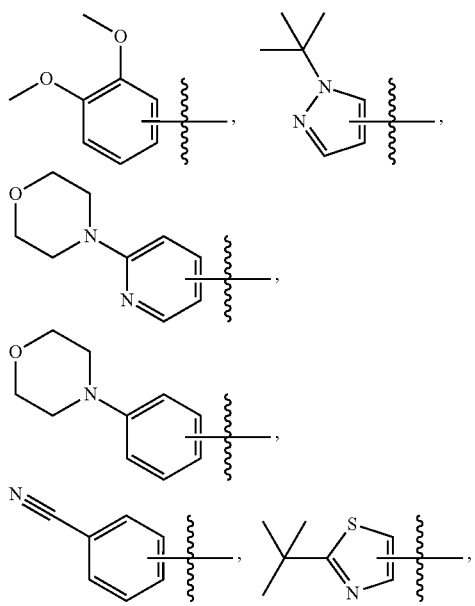

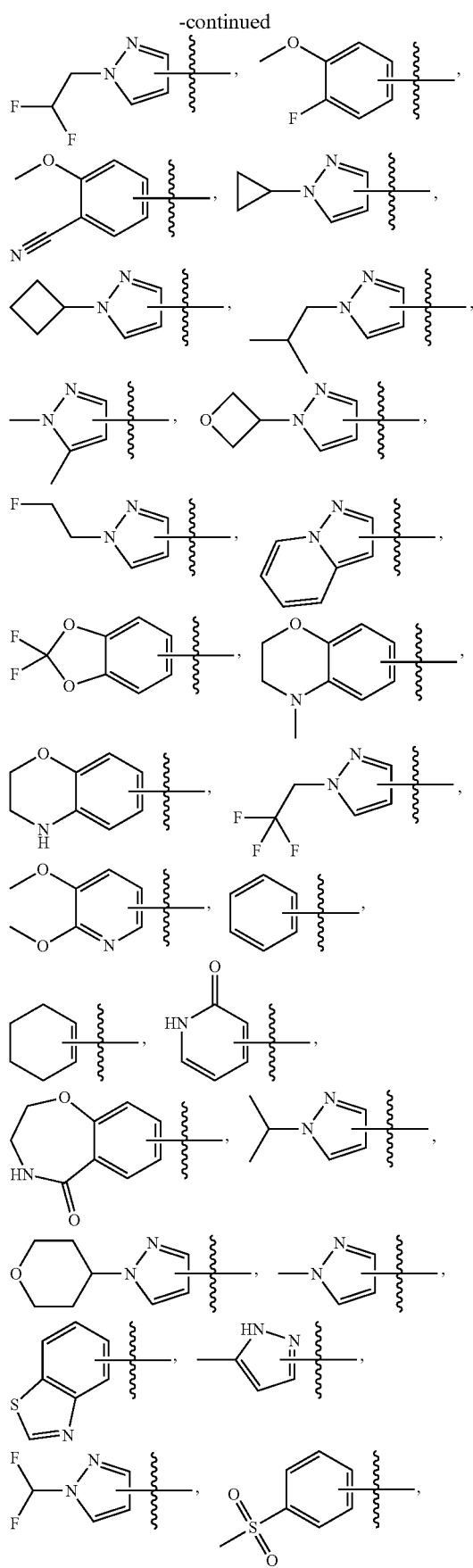
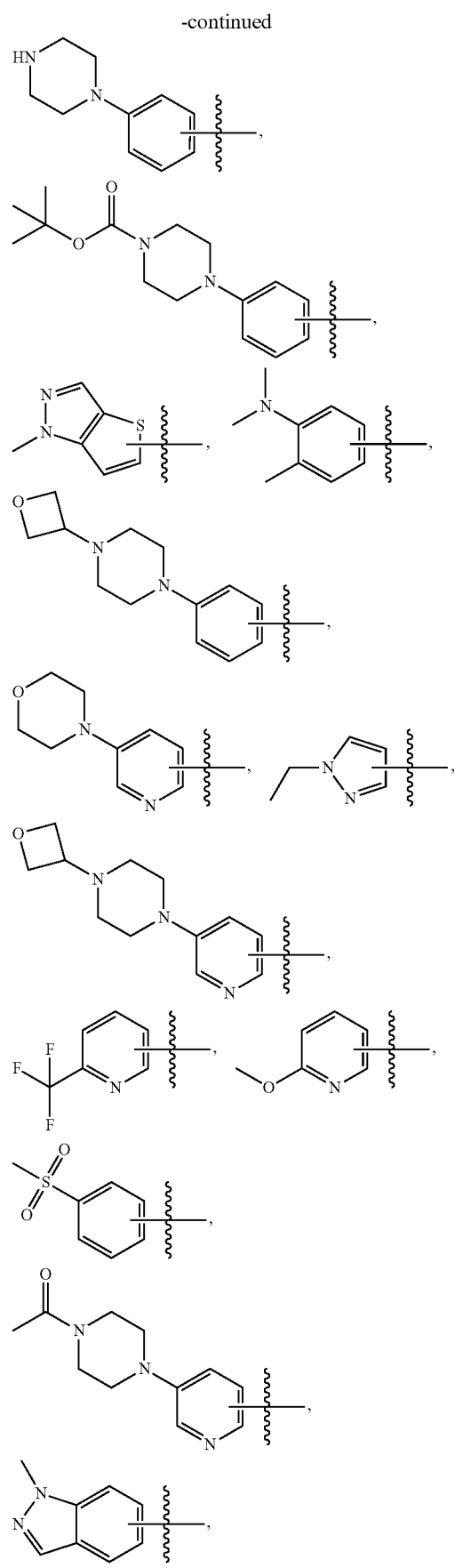

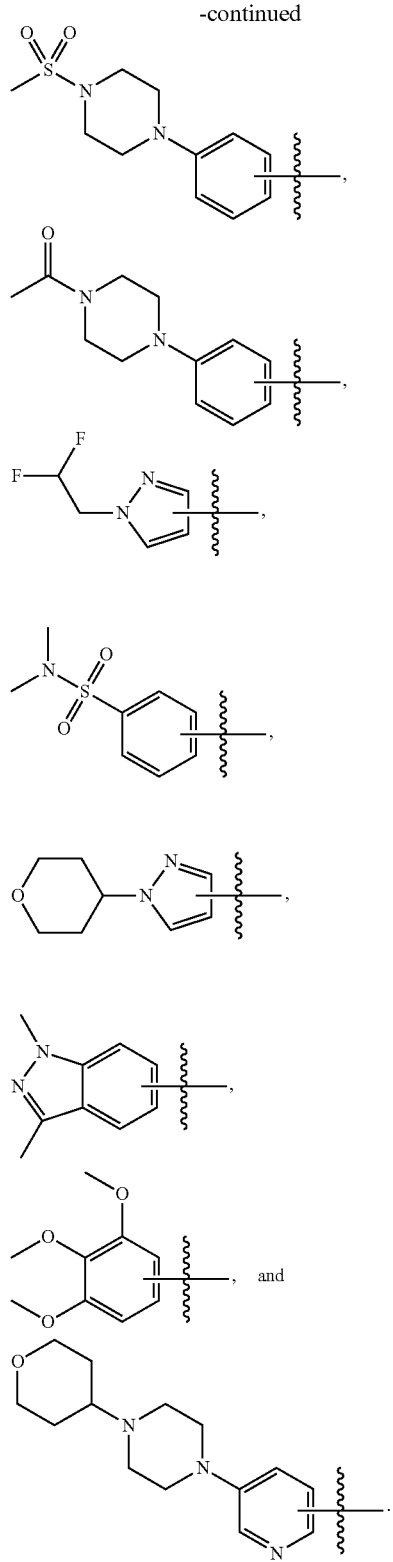
For each of the embodiments identified by Formula I, Formula Ia, Formula Ib, Formula Ic, Formula II, Formula III, Formula IV, Formula V, and Formula VI, there is another embodiment comprising a compound of each formula, or a pharmaceutically acceptable salt thereof, respectively, wherein $R^5$ is selected from the group of:

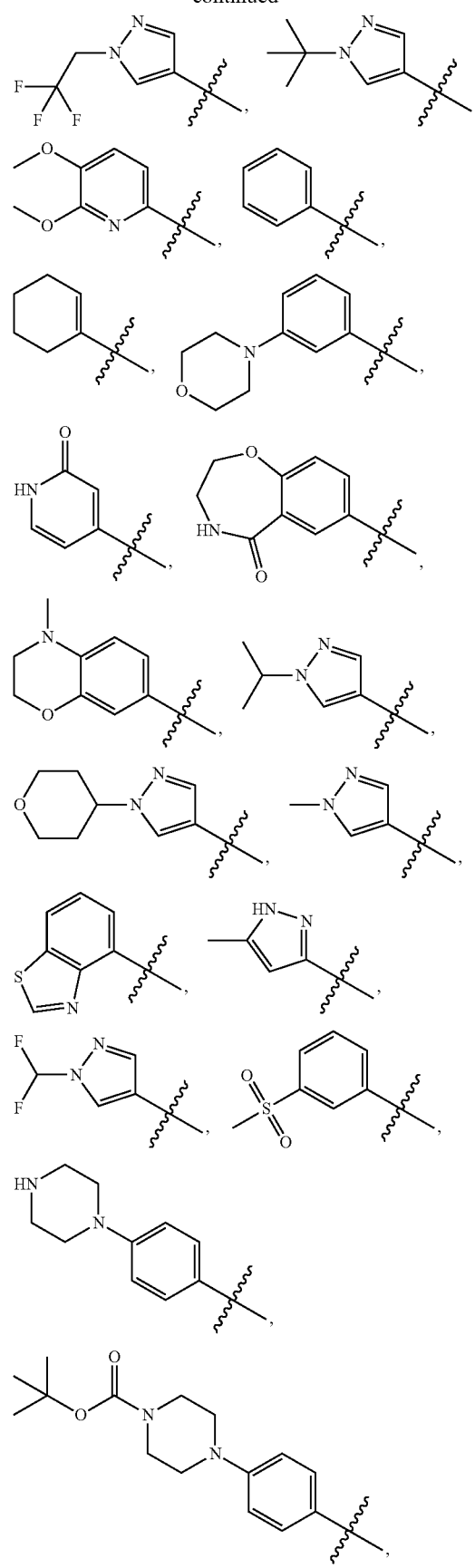
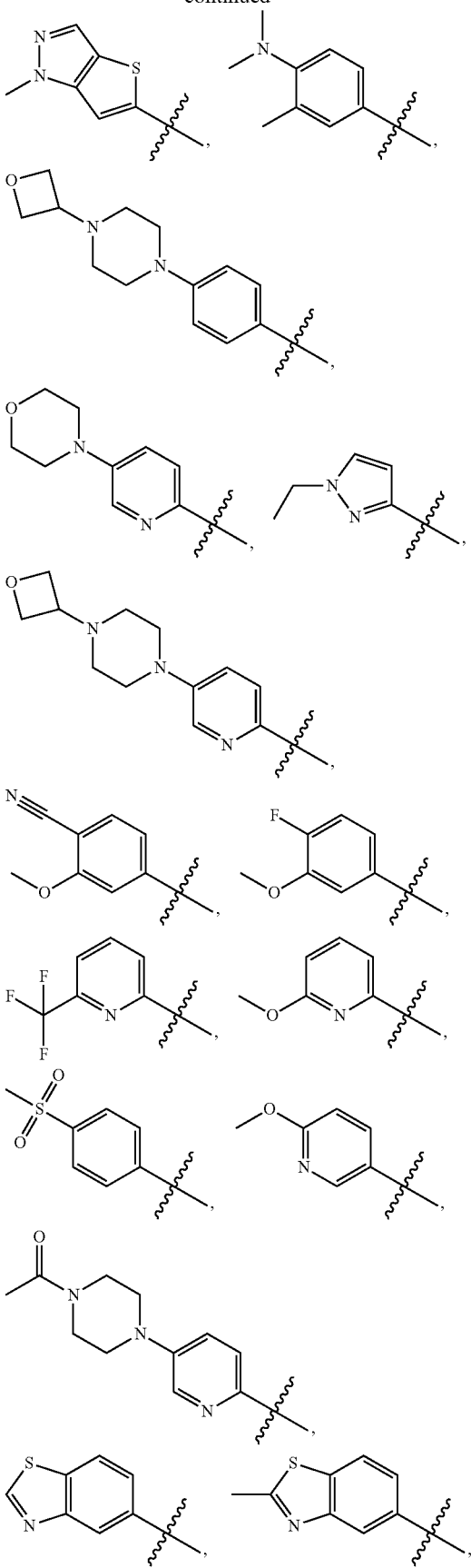

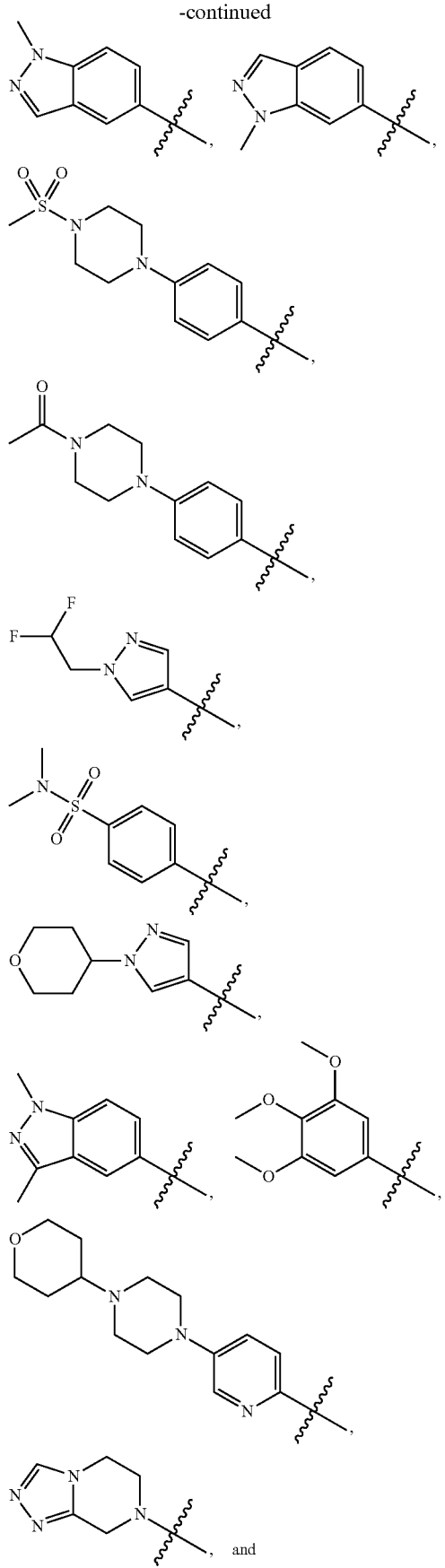
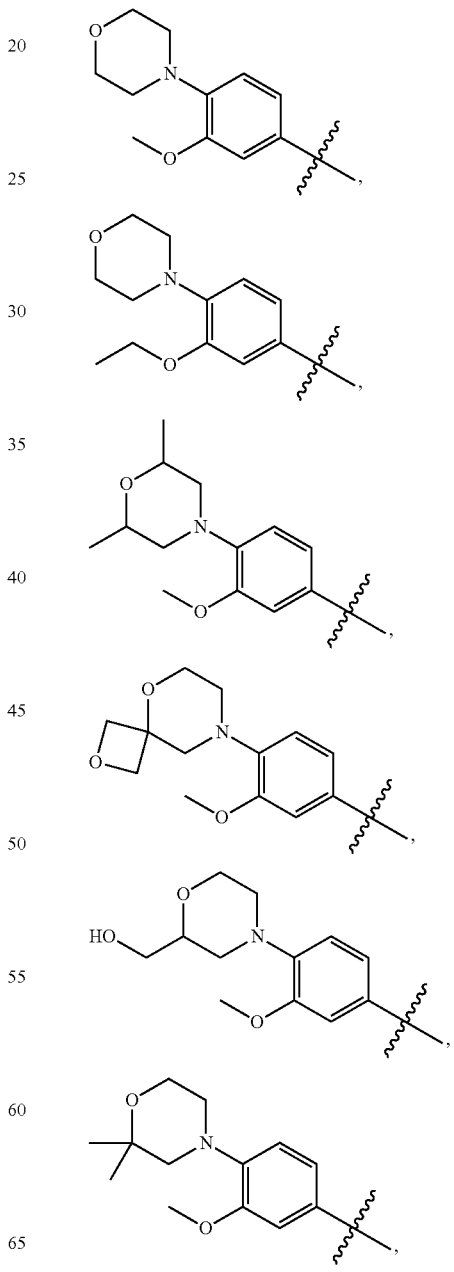
For each of the embodiments identified by Formula I, Formula Ia, Formula Ib, Formula Ic, Formula II, Formula III, Formula IV, Formula V, and Formula VI, there is another embodiment comprising a compound of each formula, or a pharmaceutically acceptable salt thereof, respectively, wherein $R^5$ is selected form the group of:

35
-continued
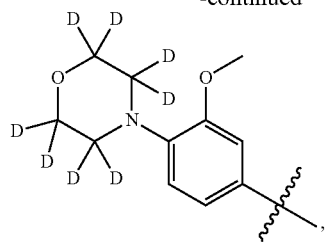
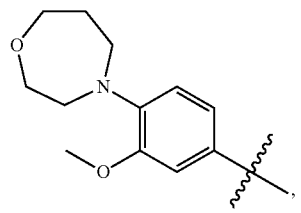
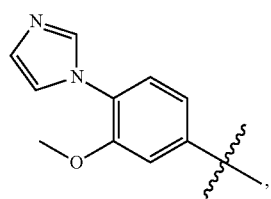
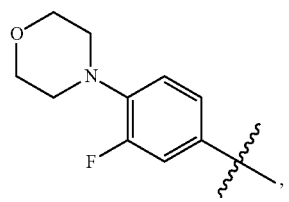
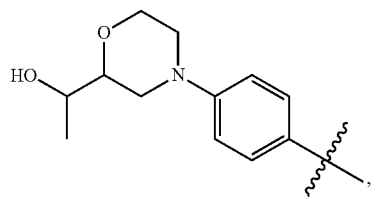
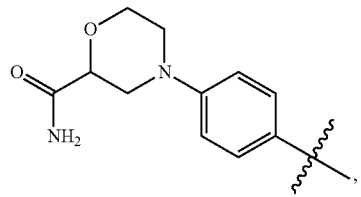
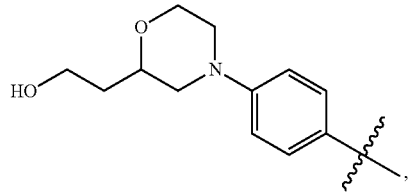
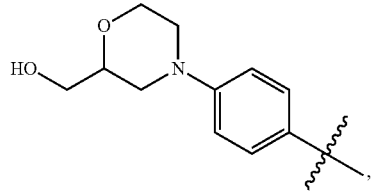
36
-continued
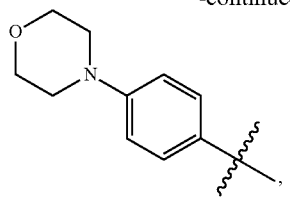
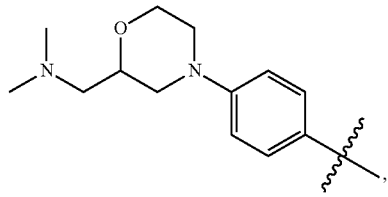
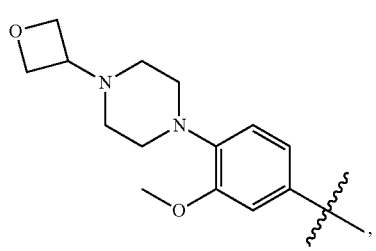
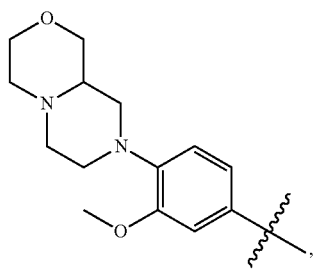
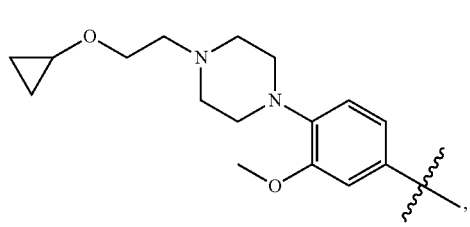
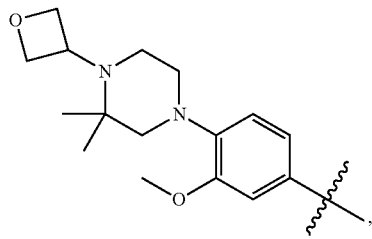
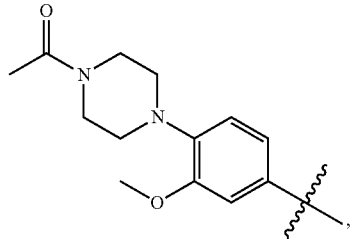

37
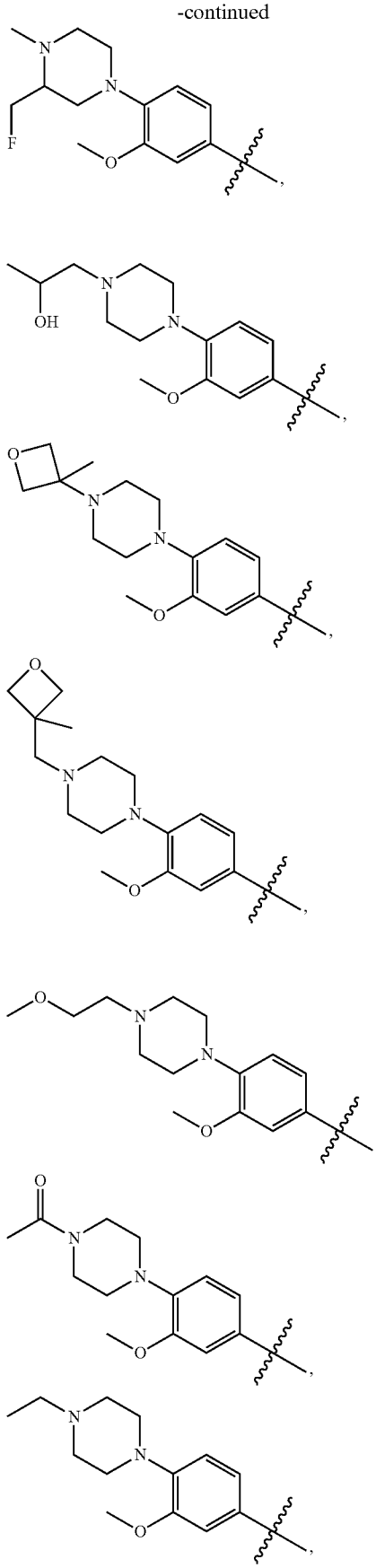
38
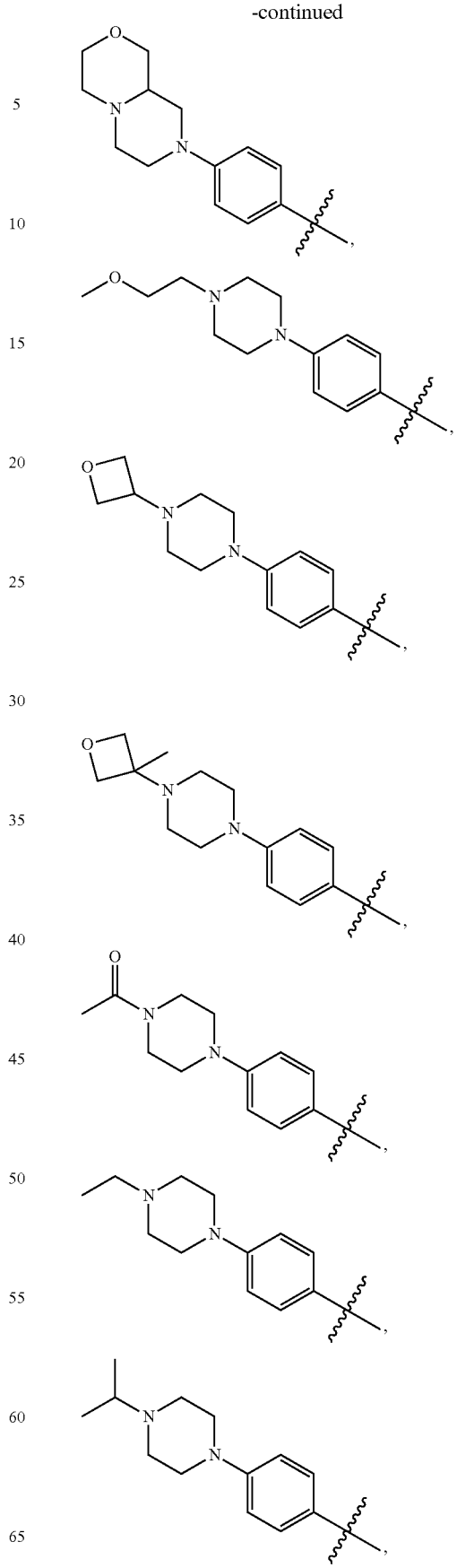

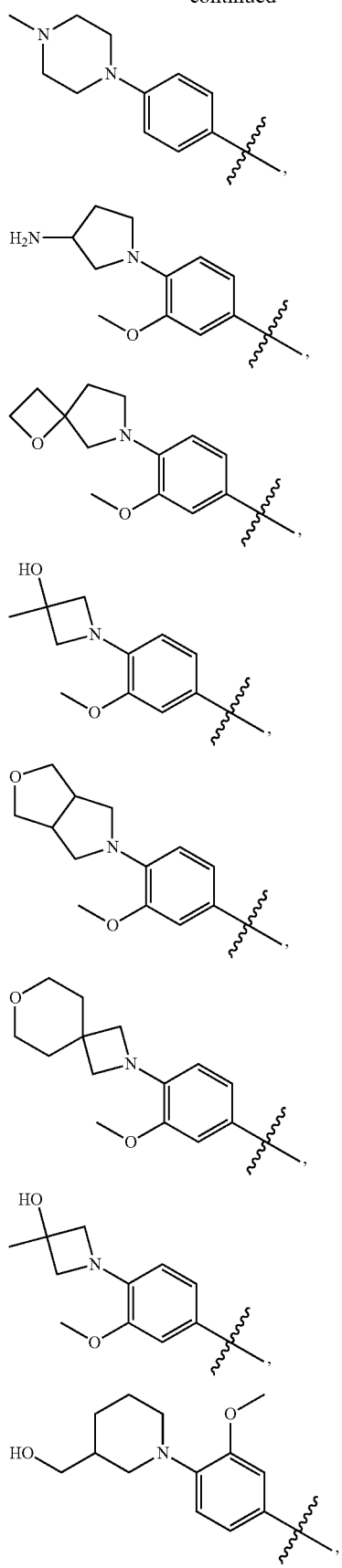
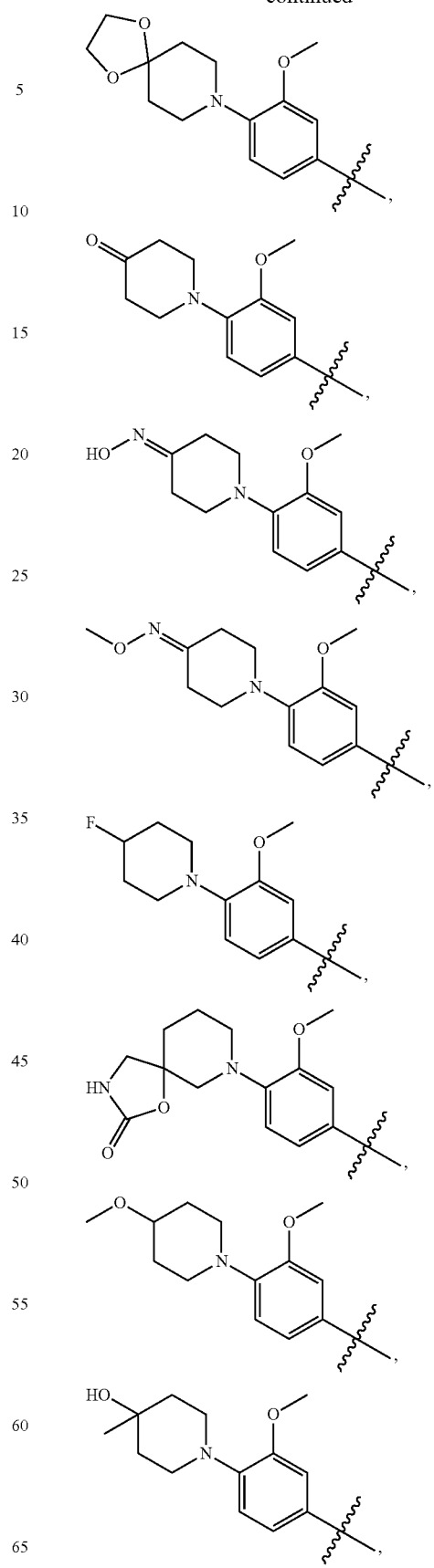

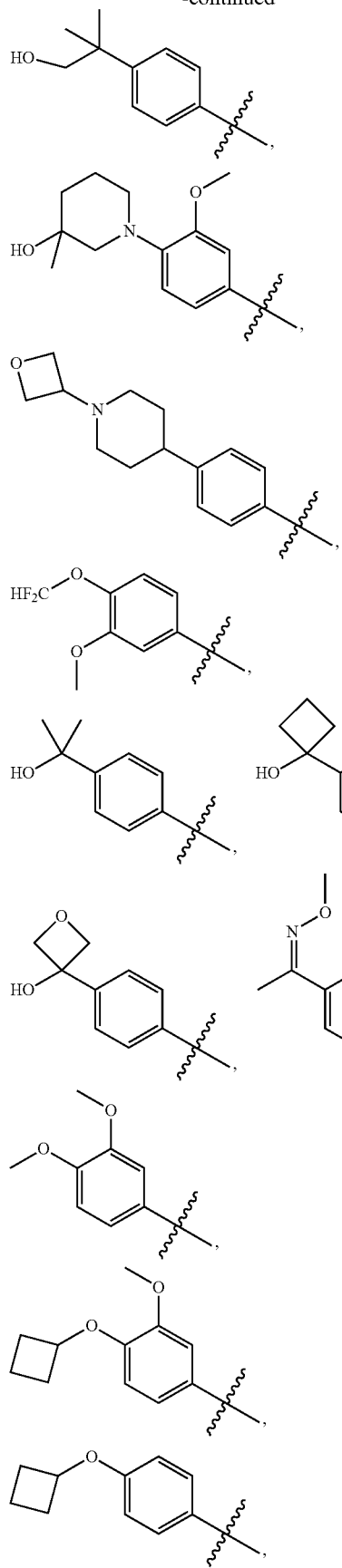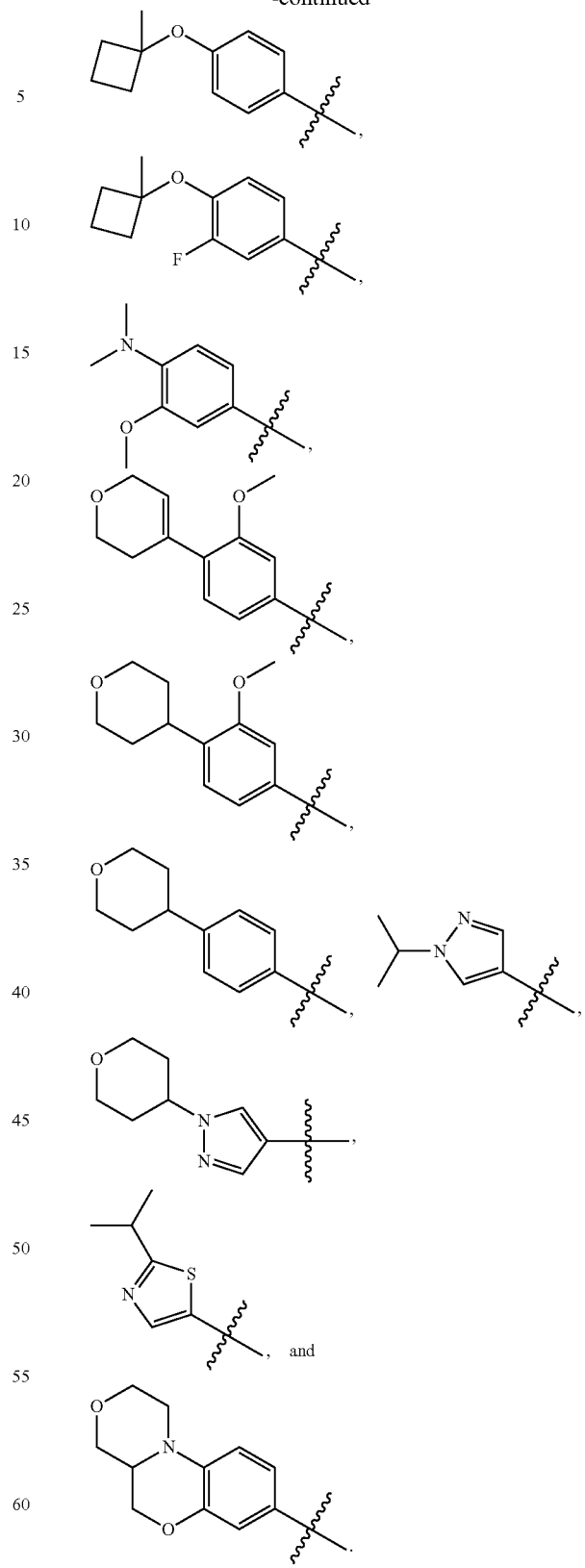
For each of the embodiments identified by Formula I, Formula Ia, Formula Ib, Formula Ic, Formula II, Formula III, Formula IV, Formula V, and Formula VI, there is another embodiment comprising a compound of each formula, or a pharmaceutically acceptable salt thereof, respectively, wherein $R^5$ is selected from the group of:

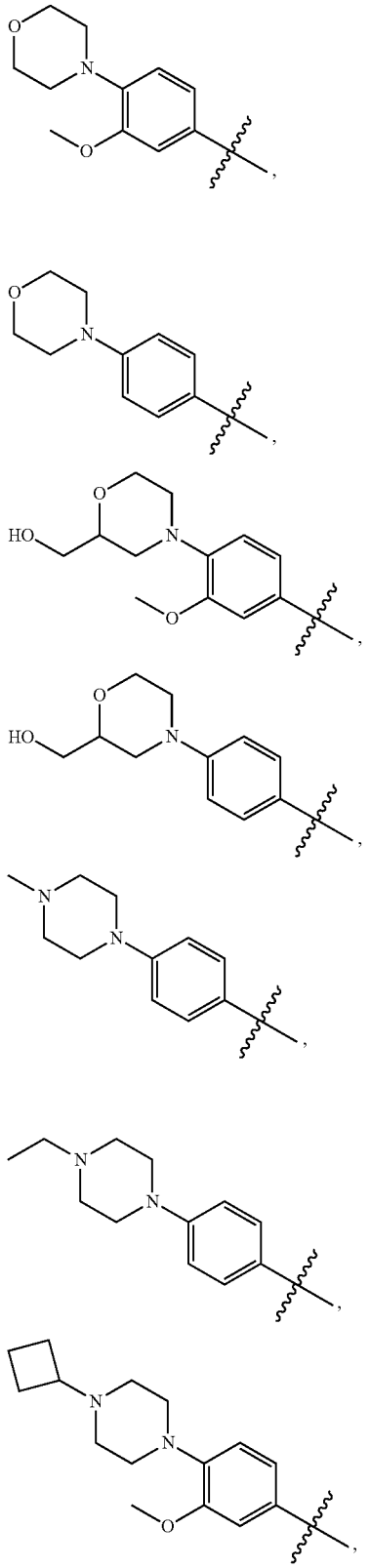

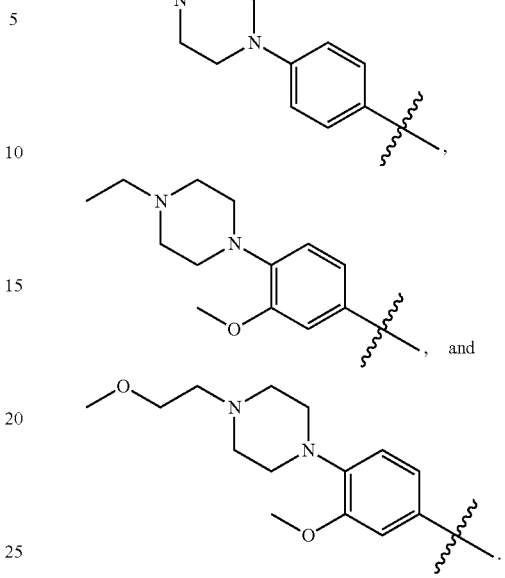

For each of the embodiments identified by Formula I, Formula 1a, Formula 1b, Formula Ic, Formula II, Formula III, Formula IV, Formula V, and Formula VI, there is yet another embodiment comprising a compound of each formula, or a pharmaceutically acceptable salt thereof, respectively, wherein $R^5$ is selected from

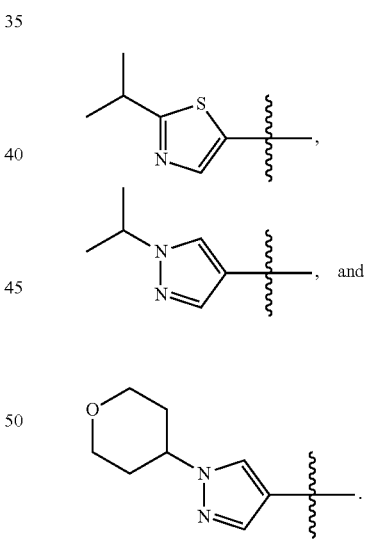

It is intended and understood that each and every variation of $R^5$ may be combined with each and every variation of $X^1$, $X^2$, $X^3$, $R^2$, $R^3$, $R^4$, and Y as if each and every combination is individually described.

In some embodiments, Y is O. In other embodiments, Y is NH.

It should be understood that the embodiments and structures as described herein with respect to Formula I are suitable for compounds of any formulae detailed herein, including II, III, IV, V and VI where applicable.

In other aspects, provided is a compound of Formula II:

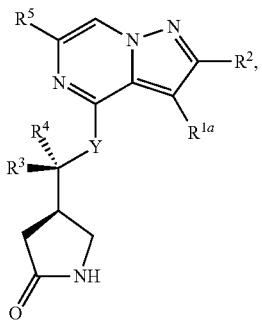

Formula II wherein $R^{1a}$, $R^2$, $R^3$, $R^4$, $R^5$ and Y are as specified above for Formula I, or a pharmaceutically acceptable salt, ester, stereoisomer, mixture of stereoisomers or tautomer thereof.

One embodiment comprises a compound of Formula II, or a pharmaceutically acceptable salt thereof, wherein:

Y is oxygen;

$R^{1a}$ is hydrogen, halo, haloalkyl, CN, $C_{1-6}$ alkyl, $C_{3-6}$ cycloalkyl, —$CH_2$—$C_{3-6}$ cycloalkyl, or $C_{2-5}$ heterocyclyl;

$R^2$ is hydrogen or $C_{1-6}$ alkyl, wherein the $C_{1-6}$ alkyl group is substituted by 0, 1, 2, or 3 fluorine atoms or 0 or 1 substituents selected from hydroxy or $C_{1-6}$ alkoxy;

$R^3$ is H, $C_{1-6}$ alkyl, $C_{2-3}$ alkenyl, or $C_{2-3}$ alkynyl, wherein the $C_{1-6}$ alkyl group is substituted by 0, 1, 2, or 3 fluorine atoms or 0 or 1 substituents selected from hydroxy or $C_{1-6}$ alkoxy;

$R^4$ is hydrogen; and $R^5$ is a moiety selected from the group of phenyl, pyrazolyl, pyridinyl, pyrazolo[1,5-a]pyridinyl, benzo[d][1,3]dioxolyl, benzomorpholinyl, thiazolyl, cyclohex-1-enyl, pyridine-2(1H)-one-yl, dihydrobenzo[f][1,4]oxazepine-5(2H)-one-yl, benzothiazolyl, thieno[3,2-c]pyrazolyl, ethynyl, indazolyl, pyrimidinyl, imidazolyl, indolinyl, pyrazinyl, pyridazine, pyrido[3,2-b][1,4]oxazinyl, 2,3-dihydro-[1,4]dioxino[2,3-b]pyridinyl, quinazolin-4(3H)-one-yl, pyrrolo[2,3-b]pyridine-2(3H)-one-yl, pyrrolo[3,2-c]pyridine-2(3H)-one-yl, 3,4-dihydroquinolin-2(1H)-one-yl, indoline-2-one, pyrazolo[3,4-b]pyridinyl, 2,3-dihydrobenzofuranyl, 2H-benzo[b][1,4]oxazin-3(4H)-one-yl, 3,4-dihydroquinolin-2(1H)-one-yl, pyrido[3,2-b][1,4]oxazin-3(4H)-one-yl, benzimidazolyl, imidazo[1,2-a]pyridinyl, imidazo[1,2-a]pyridinyl, isoindoline-1-one-yl, benzomorpholin-3-one-yl, benzomorpholin-2-one-yl, benzimidazolin-2-one-yl, 2,3-dihydro-1H-pyrido[2,3-b][1,4]oxazinyl, pyrido[2,3-b][1,4]oxazin-2(3H)-one-yl, spiro[azetidine-3,3'-indolin]-2'-one-yl, benzo[d][1,3]oxazin-2(4H)-one-yl, spiro[indoline-3,4'-piperidin]-2-one-yl, 3,4-dihydrospiro[benzo[b][1,4]oxazine-2,1'-cyclopropane]-yl, indolyl, benzoxazolin-2-one-yl, pyrrolo[3,2-b]pyridine-2(3H)-one-yl, thiophenyl, 3,4-dihydro-pyrido[3,2-b][1,4]oxazinyl, 1,3,4-thiadiazolyl, indolinyl, isothiazolyl, 1,2,3-triazolyl, 1,2,3,4-tetrahydroquinolinyl, and thieno[2,3-c]pyridinyl;

wherein each of the $R^5$ moieties may be independently, optionally substituted with one, two or three substituents independently selected from the group consisting of halo, $C_{1-6}$ alkyl, $C_{1-6}$ alkoxy, $C_{2-6}$ alkenyl, $C_{2-6}$ alkynyl, $C_{3-8}$ cycloalkyl, $C_{2-8}$ heterocyclyl, —$S(O)_2$—$R^{20}$, —$S(O)_2$—$NR^{20}R^{22}$, —$NO_2$, —$N(R^{20})(R^{22})$, —$C(O)$—$OR^{20}$, —CN, oxo, and —O—$R^{20}$;

wherein each alkyl, alkoxy, alkenyl, alkynyl, cycloalkyl, or heterocyclyl moiety may be further optionally substituted with one, two or three substituents independently selected from the group consisting of halo, CN, $C_{1-6}$ alkyl, $C_{3-6}$ cycloalkyl, $C_{6-12}$ aryl, $C_{2-8}$ heterocyclyl, $C_{2-6}$heteroaryl, —$S(O)_2$—$R^{20}$, —$NO_2$, —$N(R^{20})(R^{22})$, —$C(O)$—$R^{20}$, —$C(O)$—$OR^{20}$, $C(O)$—$N(R^{20})(R^{22})$, —CN, oxo, and —O—$R^{20}$; and wherein each $R^{20}$ and $R^{22}$ is independently selected from the group consisting of hydrogen, $C_{1-6}$ alkyl, $C_{2-6}$ alkenyl, $C_{2-6}$ alkynyl, $C_{3-8}$ cycloalkyl, $C_{2-8}$ heterocyclyl, $C_{6-12}$ aryl, and $C_{2-6}$heteroaryl.

An embodiment comprises a compound of Formula II, or a pharmaceutically acceptable salt thereof, wherein:

Y is oxygen;

$R^{1a}$ is hydrogen, CN, chloro, methyl, ethyl, propyl, or butyl;

$R^2$ is hydrogen or methyl;

$R^3$ is methyl, ethyl, propyl, or butyl;

$R^4$ is hydrogen; and $R^5$ is phenyl or pyrazolyl, wherein the phenyl or pyrazolyl moieties may be optionally substituted with one or two substituents of fluoro, chloro, bromo, cyano, methyl, ethyl, propyl, butyl, methoxy, ethoxy, propoxy, cyclopropyl, cyclobutyl, fluoromethyl, fluoroethyl, fluoropropyl, difluoromethyl, difluoroethyl, difluoropropyl, trifluoromethyl, trifluoroethyl, trifluoropropyl, piperazinyl, or morpholino;

wherein the $R^5$ piperazinyl group can be further substituted by 0 or 1 group selected from $C_{2-5}$heterocyclyl, —$S(O)_2$-alkyl, —$S(O)_2$—$C_{3-6}$ cycloalkyl, —$S(O)_2$—$C_{2-8}$heterocyclyl, and —$C(O)$—$C_{1-6}$ alkyl.

In each of the embodiments above for Formula III there is a further embodiment in which $R^{1a}$ is hydrogen, halo, or $C_{1-6}$ alkyl and all other variables are as described for the particular embodiment. In each of the embodiments above for Formula III there is a further embodiment in which $R^{1a}$ is hydrogen, fluoro, chloro, $CF_3$, methyl, ethyl, or cyclopropyl and all other variables are as described for the particular embodiment. In each of the embodiments above for Formula III there is a further embodiment in which $R^{1a}$ is hydrogen, methyl, $CF_3$, or cyclopropyl and all other variables are as described for the particular embodiment.

Another embodiment comprises a compound of Formula II, or a pharmaceutically acceptable salt, ester, stereoisomer, mixture of stereoisomers or tautomer thereof, wherein Y is oxygen; $R^{1a}$ is selected from hydrogen, methyl, CN, bromo, and chloro; $R^2$ is hydrogen or methyl; $R^3$ is methyl; $R^4$ is hydrogen; and $R^5$ is selected from:

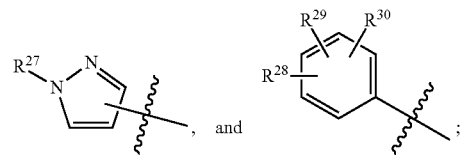

$R^{27}$ is H, $C_{1-4}$ alkyl, —$CH_2F$, $CHF_2$, or $CF_3$;

$R^{28}$, $R^{29}$, and $R^{30}$ are each independently selected from hydrogen, fluorine, cyano, and —O—$C_{1-3}$ alkyl;

or $R^{28}$ and $R^{29}$ are selected from hydrogen and —O—$C_{1-4}$ alkyl, and $R^{30}$ is morpholino or piperazinyl, wherein the piperazinyl group is substituted by 0 or 1 substituent selected from —$SO_2H$, —$SO_2(C_{1-3}$ alkyl), —$SO_2$—$C_{3-6}$ cycloalkyl, —$SO_2$—$C_{2-8}$ heterocyclyl, —$C(O)$—$C_{1-4}$ alkyl, $C_{3-6}$ cycloalkyl, and $C_{2-5}$heterocyclyl.

Yet another embodiment comprises a compound of Formula II, or a pharmaceutically acceptable salt, ester, stereoisomer, mixture of stereoisomers or tautomer thereof, wherein Y is oxygen; $R^{1a}$ is selected from hydrogen, methyl, and chloro; $R^2$ is hydrogen or methyl; $R^3$ is methyl; $R^4$ is hydrogen; and $R^5$ is:

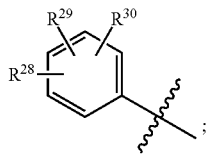

$R^{28}$, $R^{29}$, and $R^{30}$ are each independently selected from hydrogen and methoxy; or $R^{28}$ and $R^{29}$ are hydrogen and $R^{30}$ is morpholino.

A further embodiment comprises a compound of Formula IIa, or a pharmaceutically acceptable salt thereof:

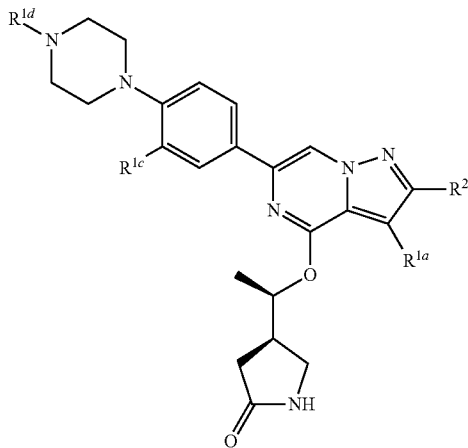

Formula IIa wherein:
$R^{1a}$ is selected from hydrogen, methyl, and CN;
$R^2$ is hydrogen or methyl;
$R^{1c}$ is hydrogen or methoxy; and
$R^{1d}$ is selected from hydrogen, $C_{1-4}$ alkyl, —C(O)—$C_{1-4}$ alkyl, —SO$_2$H, —S(O)$_2$-alkyl, —S(O)$_2$—$C_{3-6}$ cycloalkyl, —S(O)$_2$—$C_{2-8}$ heterocyclyl, —S(O)$_2$—$C_{3-6}$ cycloalkyl, —S(O)$_2$—$C_{2-8}$ heterocyclyl,
$C_{3-6}$ cycloalkyl, and $C_{2-6}$ heterocyclyl.

Another embodiment comprises a compound of Formula IIa, or a pharmaceutically acceptable salt thereof, as defined above, wherein $R^2$ is hydrogen. Still another embodiment comprises a compound of Formula IIa, or a pharmaceutically acceptable salt thereof, as defined above, wherein $R^2$ is hydrogen; $R^{1a}$ is selected from hydrogen and methyl; $R^{1c}$ is selected from hydrogen and methoxy; and $R^{1d}$ is selected from hydrogen, methyl, —C(O)—CH$_3$, —SO$_2$—CH$_3$, and a $C_{2-6}$ heterocyclyl ring selected from oxiranyl, oxetanyl, tetrahydrofuranyl, and tetrahydro-2H-pyranyl.

In one embodiment, the compound of Formula II is selected from:
(R)-4-((R)-1-((6-(3,4-dimethoxyphenyl)pyrazolo[1,5-a]pyrazin-4-yl)oxy)ethyl)pyrrolidin-2-one;
(R)-4-((R)-1-((6-(3,4-dimethoxyphenyl)-3-methylpyrazolo[1,5-a]pyrazin-4-yl)oxy)ethyl)pyrrolidin-2-one;
(R)-4-((R)-1-((3-methyl-6-(4-morpholinophenyl)pyrazolo[1,5-a]pyrazin-4-yl)oxy)ethyl)pyrrolidin-2-one;
(R)-4-((R)-1-((3-chloro-6-(3,4-dimethoxyphenyl)pyrazolo[1,5-a]pyrazin-4-yl)oxy)ethyl)pyrrolidin-2-one;
(R)-4-((R)-1-((6-(3,4-dimethoxyphenyl)-2-methylpyrazolo[1,5-a]pyrazin-4-yl)oxy)ethyl)pyrrolidin-2-one; and
(R)-4-((R)-1-((6-(1-(tert-butyl)-1H-pyrazol-4-yl)-3-methylpyrazolo[1,5-a]pyrazin-4-yl)oxy)ethyl)pyrrolidin-2-one;
or a pharmaceutically acceptable salt, ester, stereoisomer, mixture of stereoisomers or tautomer thereof.

In yet other aspects, provided is a compound of Formula III:

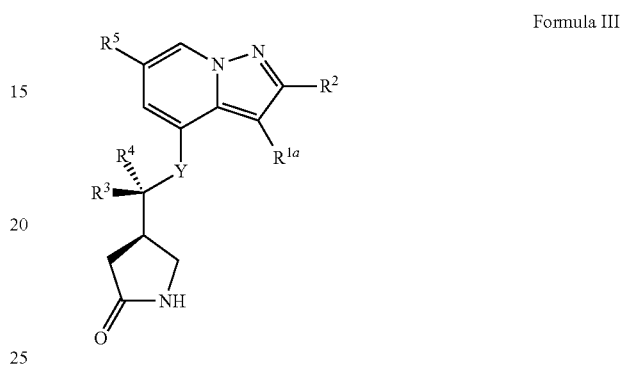

Formula III wherein $R^{1a}$, $R^2$, $R^3$, $R^4$ and $R^5$ are as specified above for Formula I, or a pharmaceutically acceptable salt, ester, stereoisomer, mixture of stereoisomers or tautomer thereof.

One embodiment comprises a compound of Formula III, or a pharmaceutically acceptable salt thereof, wherein:
Y is oxygen;
$R^{1a}$ is hydrogen, halo, haloalkyl, CN, $C_{1-6}$ alkyl, $C_{3-6}$ cycloalkyl, —CH$_2$—$C_{3-6}$ cycloalkyl, or $C_{2-5}$ heterocyclyl;
$R^2$ is hydrogen or $C_{1-6}$ alkyl, wherein the $C_{1-6}$ alkyl group is substituted by 0, 1, 2, or 3 fluorine atoms or 0 or 1 substituents selected from hydroxy or $C_{1-6}$ alkoxy;
$R^3$ is H, $C_{1-6}$ alkyl, $C_{2-3}$ alkenyl, or $C_{2-3}$ alkynyl, wherein the $C_{1-6}$ alkyl group is substituted by 0, 1, 2, or 3 fluorine atoms or 0 or 1 substituents selected from hydroxy or $C_{1-6}$ alkoxy;
$R^4$ is hydrogen; and
$R^5$ is a moiety selected from the group of phenyl, pyrazolyl, pyridinyl, pyrazolo[1,5-a]pyridinyl, benzo[d][1,3]dioxolyl, benzomorpholinyl, thiazolyl, cyclohex-1-enyl, pyridine-2(1H)-one-yl, dihydrobenzo[f][1,4]oxazepine-5(2H)-one-yl, benzothiazolyl, thieno[3,2-c]pyrazolyl, ethynyl, indazolyl, pyrimidinyl, imidazolyl, indolinyl, pyrazinyl, pyridazine, pyrido[3,2-b][1,4]oxazinyl, 2,3-dihydro-[1,4]dioxino[2,3-b]pyridinyl, quinazolin-4(3H)-one-yl, pyrrolo[2,3-b]pyridine-2(3H)-one-yl, pyrrolo[3,2-c]pyridine-2(3H)-one-yl, 3,4-dihydroquinolin-2(1H)-one-yl, indoline-2-one, pyrazolo[3,4-b]pyridinyl, 2,3-dihydrobenzofuranyl, 2H-benzo[b][1,4]oxazin-3(4H)-one-yl, 3,4-dihydroquinolin-2(1H)-one-yl, pyrido[3,2-b][1,4]oxazin-3(4H)-one-yl, benzimidazolyl, imidazo[1,2-a]pyridinyl, imidazo[1,2-a]pyridinyl, isoindoline-1-one-yl, benzomorpholin-3-one-yl, benzomorpholin-2-one-yl, benzimidazolin-2-one-yl, 2,3-dihydro-1H-pyrido[2,3-b][1,4]oxazinyl, pyrido[2,3-b][1,4]oxazin-2(3H)-one-yl, spiro[azetidine-3,3'-indolin]-2'-one-yl, benzo[d][1,3]oxazin-2(4H)-one-yl, spiro[indoline-3,4'-piperidin]-2-one-yl, 3,4-dihydrospiro[benzo[b][1,4]oxazine-2,1'-cyclopropane]-yl, indolyl, benzoxazolin-2-one-yl, pyrrolo[3,2-b]pyridine-2(3H)-one-yl, thiophenyl, 3,4-dihydro-pyrido[3,2-b][1,4]oxazinyl, 1,3,4-thiadiazolyl, indolinyl, isothiazolyl, 1,2,3-triazolyl, 1,2,3,4-tetrahydroquinolinyl, and thieno[2,3-c]pyridinyl;

wherein each of the $R^5$ moieties may be independently, optionally substituted with one, two or three substituents independently selected from the group consisting of halo, $C_{1-6}$ alkyl, $C_{1-6}$ alkoxy, $C_{2-6}$ alkenyl, $C_{2-6}$ alkynyl, $C_{3-8}$ cycloalkyl, $C_{2-8}$ heterocyclyl, $—S(O)_2—R^{20}$, $—S(O)_2—NR^{20}R^{22}$, $—NO_2$, $—N(R^{20})(R^{22})$, $—C(O)—OR^{20}$, $—CN$, oxo, and $—O—R^{20}$;

wherein each alkyl, alkoxy, alkenyl, alkynyl, cycloalkyl, or heterocyclyl moiety may be further optionally substituted with one, two or three substituents independently selected from the group consisting of halo, CN, $C_{1-6}$ alkyl, $C_{3-6}$ cycloalkyl, $C_{6-12}$ aryl, $C_{2-8}$ heterocyclyl, $C_{2-6}$ heteroaryl, $—S(O)_2—R^{20}$, $—NO_2$, $—N(R^{20})(R^{22})$, $—C(O)—R^{20}$, $—C(O)—OR^{20}$, $—C(O)—N(R^{20})(R^{22})$, $—CN$, oxo, and $—O—R^{20}$; and wherein each $R^{20}$ and $R^{22}$ is independently selected from the group consisting of hydrogen, $C_{1-6}$ alkyl, $C_{2-6}$ alkenyl, $C_{2-6}$ alkynyl, $C_{3-8}$ cycloalkyl, $C_{2-8}$ heterocyclyl, $C_{6-12}$ aryl, and $C_{2-6}$ heteroaryl.

Another embodiment comprises a compound of Formula III, or a pharmaceutically acceptable salt thereof, wherein:
Y is oxygen;
$R^{1a}$ is hydrogen, halo, haloalkyl, CN, $C_{1-6}$ alkyl, or $C_{3-6}$ cycloalkyl;
$R^2$ is hydrogen;
$R^3$ is $C_{1-6}$ alkyl;
$R^4$ is hydrogen; and
$R^5$ is phenyl, pyridinyl, pyrazolyl, indazolyl, thieno[3,2-c]pyrazolyl, pyrimidinyl, imidazolyl, and indoline-2-one-yl;
wherein $R^5$ the phenyl, pyridinyl, pyrazolyl, indazolyl, thieno[3,2-c]pyrazolyl, pyrimidinyl, imidazolyl, and indoline-2-one-yl moieties are independently substituted with zero, one, two, or three substituents independently selected from the group consisting of halo, $C_{1-6}$ alkyl, $C_{1-6}$ alkoxy, $C_{2-6}$ alkynyl, $C_{3-8}$ cycloalkyl, $C_{2-8}$ heterocyclyl, $—S(O)_2—R^{20}$, $—S(O)_2—NR^{20}R^{22}$, $—NO_2$, $—N(R^{20})(R^{22})$, $—C(O)—OR^{20}$, $—CN$, oxo, and $—O—R^{20}$;

wherein the alkyl, alkoxy, alkynyl, cycloalkyl, or heterocyclyl moieties are further optionally substituted with zero, one, two or three substituents independently selected from the group consisting of halo, $C_{1-6}$ alkyl, $C_{3-6}$ cycloalkyl, $C_{6-12}$ aryl, $C_{2-8}$ heterocyclyl, $C_{2-6}$ heteroaryl, $—NO_2$, $—S(O)_2—R^{20}$, $—N(R^{20})(R^{22})$, $—C(O)—R^{20}$, $—C(O)—OR^{20}$, $—C(O)—N(R^{20})(R^{22})$, $—CN$, and $—O—R^{20}$; and wherein each $R^{20}$ and $R^{22}$ is independently selected from the group consisting of hydrogen, $C_{1-6}$ alkyl, $C_{2-6}$ alkenyl, $C_{2-6}$ alkynyl, $C_{3-8}$ cycloalkyl, $C_{2-8}$ heterocyclyl, $C_{6-12}$ aryl, and $C_{2-6}$ heteroaryl.

Another embodiment comprises a compound of Formula III, or a pharmaceutically acceptable salt thereof, wherein:
Y is oxygen;
$R^{1a}$ is hydrogen, CN, Cl, methyl, ethyl, propyl, butyl, or $C_{3-6}$ cycloalkyl;
$R^2$ is hydrogen;
$R^3$ is methyl;
$R^4$ is hydrogen; and
$R^5$ is phenyl, pyridinyl, or pyrazolyl; wherein the phenyl, pyridinyl, or pyrazolyl moieties may be optionally substituted with one, two, or three members of methyl, ethyl, propyl, butyl, cyano, methoxy, ethoxy, propoxy, morpholinyl, piperazinyl, oxetanyl, $C_{1-4}$ fluoroalkyl, cyclopropyl, or cyclobutyl.

In each of the embodiments above for Formula III there is a further embodiment in which $R^{1a}$ is hydrogen, CN, halo, $C_{1-6}$ alkyl, or $C_{3-6}$ cycloalkyl and all other embodiments are as previously defined. In each of the embodiments above for Formula III there is a further embodiment in which $R^{1a}$ is hydrogen, methyl, chloro, $—CF_3$, $—CF_2H$, $—CFH_2$, or cyclopropyl and all other embodiments are as previously defined. In each of the embodiments above for Formula III there is a further embodiment in which $R^{1a}$ is hydrogen, CN, chloro, methyl, ethyl, propyl, butyl, or cyclopropyl and all other embodiments are as previously defined. In each of the embodiments above for Formula III there is a further embodiment in which $R^{1a}$ is hydrogen, methyl, or chloro and all other embodiments are as previously defined. In each of the embodiments above for Formula III there is a further embodiment in which $R^{1a}$ is $—CF_3$, $—CF_2H$, $—CFH_2$, or cyclopropyl and all other embodiments are as previously defined. In each of the embodiments above for Formula III there is a further embodiment in which $R^{1a}$ is haloalkyl and all other embodiments are as previously defined. In each of the embodiments above for Formula III there is a further embodiment in which $R^{1a}$ is $—CF_3$ and all other embodiments are as previously defined. In each of the embodiments above for Formula III there is a further embodiment in which $R^{1a}$ is $C_{3-6}$ cycloalkyl and all other embodiments are as previously defined. In each of the embodiments above for Formula III there is a further embodiment in which $R^{1a}$ is cyclopropyl and all other embodiments are as previously defined.

Another embodiment comprises a compound of Formula III, or a pharmaceutically acceptable salt, ester, stereoisomer, mixture of stereoisomers or tautomer thereof, wherein Y is oxygen; $R^{1a}$ is selected from hydrogen, methyl, chloro, and cyclopropyl; $R^2$ is hydrogen or methyl; $R^3$ is methyl; $R^4$ is hydrogen; and $R^5$ is selected from:

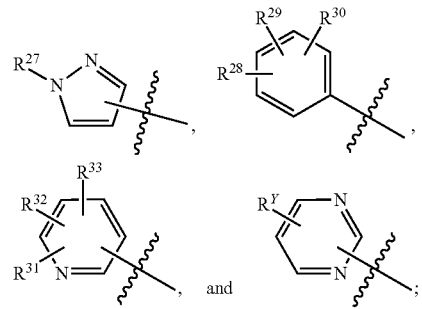

$R^{27}$ is selected from $C_{1-4}$ alkyl, $C_{1-4}$ haloalkyl, and $C_{2-6}$ heterocyclyl;

$R^{28}$, $R^{29}$, and $R^{30}$ are each independently selected from hydrogen and $—OC_{1-3}$ alkyl;

or $R^{28}$ and $R^{29}$ are hydrogen or $—OC_{1-3}$ alkyl, and $R^{30}$ is morpholino or piperazinyl, wherein the piperazinyl group is substituted by 0 or 1 substituent selected from $—SO_2H$, $—SO_2(C_{1-3}$ alkyl), $—SO_2—C_{3-6}$ cycloalkyl, $—SO_2—C_{2-8}$ heterocyclyl, $C_{1-4}$ alkyl, $—C(O)—C_{1-4}$ alkyl, $C_{3-6}$ cycloalkyl, and $C_{2-6}$ heterocyclyl;

and $R^{31}$, $R^{32}$, and $R^{33}$ are each independently selected from hydrogen, $C_{1-3}$ alkyl, and $—OC_{1-3}$ alkyl;

or $R^{31}$ and $R^{32}$ are hydrogen or $—OC_{1-3}$ alkyl, and $R^{33}$ is morpholino or piperazinyl, wherein the piperazinyl group is substituted by 0 or 1 substituent selected from $—SO_2H$, $SO_2(C_{1-3}$ alkyl), $C_{1-4}$ alkyl, $—C(O)—C_{1-4}$ alkyl, $C_{3-6}$ cycloalkyl, and $C_{2-6}$ heterocyclyl; and $R^Y$ is selected from H, $C_{1-4}$ alkyl, and $—OC_{1-3}$ alkyl.

A further embodiment comprises a compound of Formula III, or a pharmaceutically acceptable salt, ester, stereoisomer, mixture of stereoisomers or tautomer thereof, wherein Y is oxygen; $R^{1a}$ is selected from hydrogen, methyl, chloro, and cyclopropyl; $R^2$ is hydrogen; $R^3$ is methyl; $R^4$ is hydrogen; and $R^5$ is selected from:

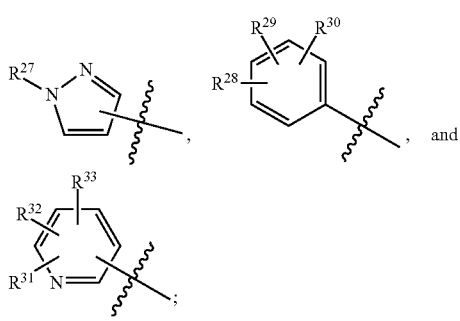

$R^{27}$ is selected from methyl, ethyl, propyl, butyl, fluoromethyl, fluoroethyl, fluoropropyl, difluoromethyl, difluoroethyl, difluoroproypl, trifluoromethyl, trifluoroethyl, and trifluoropropyl;

$R^{28}$, $R^{29}$, and $R^{30}$ are each independently selected from hydrogen and methoxy;

or $R^{28}$ and $R^{29}$ are hydrogen and $R^{30}$ is morpholino; and $R^{31}$, $R^{32}$, and $R^{33}$ are each independently selected from hydrogen and methoxy;

or $R^{31}$ and $R^{32}$ are each independently selected from hydrogen and methoxy, and $R^{33}$ is piperazinyl, wherein the piperazinyl group is substituted by 0 or 1 substituent selected from —SO$_2$H, —SO$_2$(C$_{1-3}$ alkyl), —SO$_2$—C$_{3-6}$ cycloalkyl, —SO$_2$—C$_{2-8}$ heterocyclyl, C$_{1-4}$ alkyl, C$_{3-6}$ cycloalkyl, and C$_{2-6}$ heterocyclyl.

A further embodiment comprises a compound of Formula IIIa, or a pharmaceutically acceptable salt thereof:

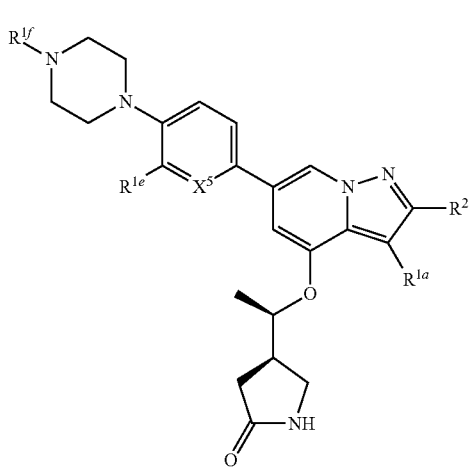

IIIa wherein:

$R^{1a}$ is selected from hydrogen, CN, methyl, chloro, and cyclopropyl;

$R^2$ is hydrogen or methyl;

$X^5$ is selected from carbon or nitrogen;

$R^{1e}$ is hydrogen or methoxy; and $R^{1f}$ is selected from hydrogen, —SO$_2$H, —SO$_2$(C$_{1-3}$ alkyl), C$_{1-4}$ alkyl, C$_{3-6}$ cycloalkyl, and C$_{2-6}$ heterocyclyl.

Another embodiment comprises a compound of Formula IIIa, or a pharmaceutically acceptable salt thereof, as defined above, wherein $R^2$ is hydrogen.

Another embodiment comprises a compound of Formula IIIa, or a pharmaceutically acceptable salt thereof, as defined above, wherein $R^2$ is hydrogen and $X^5$ is carbon.

Another embodiment comprises a compound of Formula IIIa, or a pharmaceutically acceptable salt thereof, as defined above, wherein $R^2$ is hydrogen and $X^5$ is nitrogen.

In one embodiment, the compound of Formula III is selected from:

(R)-4-((R)-1-((6-(3,4-dimethoxyphenyl)pyrazolo[1,5-a]pyridin-4-yl)oxy)ethyl)pyrrolidin-2-one;

(R)-4-((R)-1-((6-(4-morpholinophenyl)pyrazolo[1,5-a]pyridin-4-yl)oxy)ethyl)pyrrolidin-2-one;

(R)-4-((R)-1-((3-chloro-6-(3,4-dimethoxyphenyl)pyrazolo[1,5-a]pyridin-4-yl)oxy)ethyl)pyrrolidin-2-one;

(R)-4-((R)-1-((3-chloro-6-(4-morpholinophenyl)pyrazolo[1,5-a]pyridin-4-yl)oxy)ethyl)pyrrolidin-2-one;

(R)-4-((R)-1-((6-(3,4,5-trimethoxyphenyl)pyrazolo[1,5-a]pyridin-4-yl)oxy)ethyl)pyrrolidin-2-one;

(R)-4-((R)-1-((6-(5,6-dimethoxypyridin-2-yl)pyrazolo[1,5-a]pyridin-4-yl)oxy)ethyl)pyrrolidin-2-one;

(R)-4-((R)-1-((6-(1-(tert-butyl)-1H-pyrazol-4-yl)pyrazolo[1,5-a]pyridin-4-yl)oxy)ethyl)pyrrolidin-2-one;

(R)-4-((R)-1-((6-(1-(tert-butyl)-1H-pyrazol-4-yl)-3-methylpyrazolo[1,5-a]pyridin-4-yl)oxy)ethyl)pyrrolidin-2-one;

(R)-4-((R)-1-((6-(1-(tert-butyl)-1H-pyrazol-4-yl)-3-chloropyrazolo[1,5-a]pyridin-4-yl)oxy)ethyl)pyrrolidin-2-one; and (R)-4-((R)-1-((6-(1-(2,2-difluoroethyl)-1H-pyrazol-4-yl)pyrazolo[1,5-a]pyridin-4-yl)oxy)ethyl)pyrrolidin-2-one;

or a pharmaceutically acceptable salt, ester, stereoisomer, mixture of stereoisomers or tautomer thereof.

A further embodiment provides a compound of Formula IV, or a pharmaceutically acceptable salt thereof:

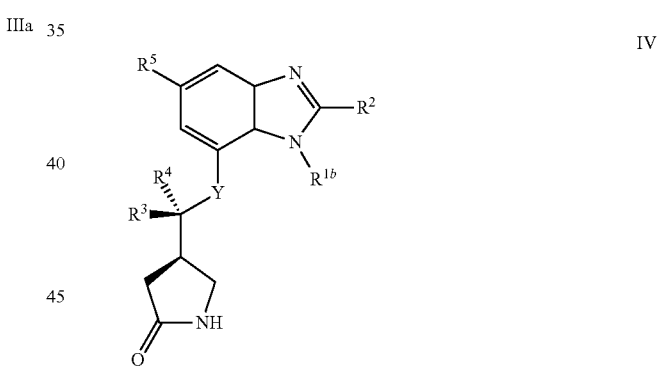

IV wherein $R^{1b}$, $R^2$, $R^3$, $R^4$, $R^5$ and Y are as specified above for Formula I, or a pharmaceutically acceptable salt, ester, stereoisomer, mixture of stereoisomers or tautomer thereof.

One embodiment comprises a compound of Formula IV, or a pharmaceutically acceptable salt thereof, wherein:

Y is oxygen;

$R^{1b}$ K is hydrogen, halo, C$_{1-6}$ alkyl, C$_{3-6}$ cycloalkyl, or C$_{2-8}$ heterocyclyl; wherein the alkyl, cycloalkyl or heterocyclyl groups may be substituted with zero, one, two, or three substituents selected from fluoro or C$_{1-6}$ alkyl;

$R^2$ is hydrogen or C$_{1-6}$ alkyl, wherein the C$_{1-6}$ alkyl group is substituted by 0, 1, 2, or 3 fluorine atoms or 0 or 1 substituents selected from hydroxy or C$_{1-6}$ alkoxy;

$R^3$ is H, C$_{1-6}$ alkyl, C$_{2-3}$ alkenyl, or C$_{2-3}$ alkynyl, wherein the C$_{1-6}$ alkyl group is substituted by 0, 1, 2, or 3 fluorine atoms or 0 or 1 substituents selected from hydroxy or C$_{1-6}$ alkoxy;

$R^4$ is hydrogen; and

R⁵ is a moiety selected from the group of phenyl, pyrazolyl, pyridinyl, pyrazolo[1,5-a]pyridinyl, benzo[d][1,3]dioxolyl, benzomorpholinyl, thiazolyl, cyclohex-1-enyl, pyridine-2 (1H)-one-yl, dihydrobenzo[f][1,4]oxazepine-5(2H)-one-yl, benzothiazolyl, thieno[3,2-c]pyrazolyl, ethynyl, indazolyl, pyrimidinyl, imidazolyl, indolinyl, pyrazinyl, pyridazine, pyrido[3,2-b][1,4]oxazinyl, 2,3-dihydro-[1,4]dioxino[2,3-b]pyridinyl, quinazolin-4(3H)-one-yl, pyrrolo[2,3-b]pyridine-2(3H)-one-yl, pyrrolo[3,2-c]pyridine-2(3H)-one-yl, 3,4-dihydroquinolin-2(1H)-one-yl, indoline-2-one, pyrazolo[3,4-b]pyridinyl, 2,3-dihydrobenzofuranyl, 2H-benzo[b][1,4]oxazin-3(4H)-one-yl, 3,4-dihydroquinolin-2(1H)-one-yl, pyrido[3,2-b][1,4]oxazin-3 (4H)-one-yl, benzimidazolyl, imidazo[1,2-a]pyridinyl, imidazo[1,2-a]pyridinyl, isoindoline-1-one-yl, benzomorpholin-3-one-yl, benzomorpholin-2-one-yl, benzimidazolin-2-one-yl, 2,3-dihydro-1H-pyrido[2,3-b][1,4]oxazinyl, pyrido[2,3-b][1,4]oxazin-2(3H)-one-yl, spiro[azetidine-3,3'-indolin]-2'-one-yl, benzo[d][1,3]oxazin-2(4H)-one-yl, spiro[indoline-3,4'-piperidin]-2-one-yl, 3,4-dihydrospiro[benzo[b][1,4]oxazine-2,1'-cyclopropane]-yl, indolyl, benzoxazolin-2-one-yl, pyrrolo[3,2-b]pyridine-2(3H)-one-yl, thiophenyl, 3,4-dihydro-pyrido[3,2-b][1,4]oxazinyl, 1,3,4-thiadiazolyl, indolinyl, isothiazolyl, 1,2,3-triazolyl, 1,2,3,4-tetrahydroquinolinyl, and thieno[2,3-c]pyridinyl;

wherein each of the R⁵ moieties may be independently, optionally substituted with one, two or three substituents independently selected from the group consisting of halo, $C_{1-6}$ alkyl, $C_{1-6}$ alkoxy, $C_{2-6}$ alkenyl, $C_{2-6}$ alkynyl, $C_{3-8}$ cycloalkyl, $C_{2-8}$ heterocyclyl, —S(O)₂—R²⁰, —S(O)₂—NR²⁰R²², —NO₂, —N(R²⁰)(R²²), —C(O)—OR²⁰, —CN, oxo, and —O—R²⁰;

wherein each alkyl, alkoxy, alkenyl, alkynyl, cycloalkyl, or heterocyclyl moiety may be further optionally substituted with one, two or three substituents independently selected from the group consisting of halo, CN, $C_{1-6}$ alkyl, $C_{3-6}$ cycloalkyl, $C_{6-12}$ aryl, $C_{2-8}$ heterocyclyl, $C_{2-6}$ heteroaryl, —S(O)₂—R²⁰, —NO₂, —N(R²⁰)(R²²), —C(O)—R²⁰, —C(O)—OR²⁰, —C(O)—N(R²⁰)(R²²), —CN, oxo, and —O—R²⁰; and wherein each R²⁰ and R²² is independently selected from the group consisting of hydrogen, $C_{1-6}$ alkyl, $C_{2-6}$ alkenyl, $C_{2-6}$ alkynyl, $C_{3-8}$ cycloalkyl, $C_{2-8}$ heterocyclyl, $C_{6-12}$ aryl, and $C_{2-6}$ heteroaryl.

Another embodiment comprises a compound of Formula IV, or a pharmaceutically acceptable salt thereof, wherein:
Y is oxygen;
$R^{1b}$ K is hydrogen, $C_{1-4}$ alkyl, or $C_{3-6}$ cycloalkyl, wherein the $C_{1-4}$ alkyl and cycloalkyl groups may be substituted with zero, one, two, or three substituents selected from fluoro or $C_{1-6}$ alkyl;
R² is hydrogen or methyl;
R³ is methyl, ethyl, propyl, or butyl;
R⁴ is hydrogen; and
R⁵ is a moiety selected from the group of phenyl, pyridinyl, pyrazolyl, 2,3-dihydro-[1,4]dioxino[2,3-b]pyridinyl, benzomorpholinyl, thiazolyl, indolinyl, 1,3,4-thiadiazolyl, pyrimidinyl, imidazolyl, pyrazinyl, pyridazinyl, 2,3-dihydro-[1,4]dioxino[2,3-b]pyridinyl, pyrrolo[2,3-b]pyridine-2(3H)-one-yl, pyrido[2,3-b][1,4]oxazin-2(3H)-one-yl, pyrido[3,2-b][1,4]oxazin-3(4H)-one-yl, 3,4-dihydro-pyrido[3,2-b][1,4]oxazinyl, benzimidazolyl, and 2,3-dihydro-1H-pyrido[2,3-b][1,4]oxazinyl; wherein the R⁵ moieties may be optionally substituted with one, two, or three substituents selected from the group of $C_{1-6}$ alkyl, cyano, methoxy, —NH₂, —NH($C_{1-3}$ alkyl), —N($C_{1-3}$ alkyl)₂, ethoxy, propoxy, morpholinyl, piperazinyl, oxetanyl, F, fluoromethyl, fluoroethyl, fluoropropyl, difluoromethyl, difluoroethyl, difluoroproypl, trifluoromethyl, trifluoroethyl, trifluoropropyl, cyclopropyl, and cyclobutyl;
wherein the R⁵$C_{1-6}$ alkyl substituent is substituted with 0 or 1 OH group; and
the R⁵ phenyl moiety is further substituted by 0 or 1 substituent selected from morpholino, or a group of the formula:

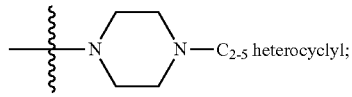

the R⁵ pyridazinyl moiety is further substituted by 0 or 1 substituent selected from morpholino, or a group of the formula:

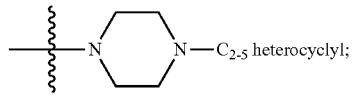

the R⁵ pyridinyl moiety is further substituted by 0 or 1 substituent selected from a) a piperazinyl moiety substituted by 0 or 1 substituent selected from —C(O)—$C_{1-3}$ alkyl, —S(O)₂-alkyl, —S(O)₂—$C_{3-6}$ cycloalkyl, and —S(O)₂—$C_{2-8}$ heterocyclyl; and
b) a piperidinyl moiety substituted by 0 or 1 substituent selected from $C_{2-5}$ heterocyclyl and 6-oxa-3-azabicyclo[3.1.1]heptanyl;
the R⁵ pyrazolyl moiety is further substituted by 0, 1, 2, or 3 substituents selected from a) $C_{2-5}$ heterocyclyl, b) $C_{1-6}$ alkyl substituted by 0, 1, or 2 substituents selected from OH, CN, F, —C(O)-morpholino, —CO₂H, —CO₂—$C_{1-3}$ alkyl, —C(O)NH₂, —C(O)NH($C_{1-3}$ alkyl), and —C(O)N($C_{1-3}$ alkyl)₂, and c) pyridinyl; and
the R⁵ thiazolyl moiety is further substituted by a) morpholino, b) $C_{2-5}$ heterocyclyl, or $C_{1-6}$ alkyl substituted by 0, 1, or 2 substituents selected from OH, CN, F, —C(O)-morpholino, —CO₂H, —CO₂—$C_{1-3}$ alkyl, —C(O)NH₂, —C(O)NH($C_{1-3}$ alkyl), and —C(O)N($C_{1-3}$ alkyl)₂.

In certain embodiments of Formula IV Y is oxygen; $R^{1b}$ is hydrogen, CN, Cl, or $C_{1-4}$ alkyl, or $C_{1-4}$fluoroalkyl; R² is hydrogen; R³ is $C_{1-4}$ alkyl; R⁴ is hydrogen; and R⁵ is phenyl, pyridinyl, pyrazolyl; wherein the phenyl, pyridinyl, or pyrazolyl moieties may be optionally substituted with one, two, or three members of methyl, ethyl, propyl, butyl, methoxy, ethoxy, propoxy, morpholinyl, piperazinyl, oxetanyl, fluoromethyl, fluoroethyl, fluoropropyl, difluoromethyl, difluoroethyl, difluoroproypl, trifluoromethyl, trifluoroethyl, trifluoropropyl, cyclopropyl, or cyclobutyl.

In each of the embodiments above for Formula IV there is a further embodiment in which $R^{1b}$ is hydrogen, CN, halo, $C_{1-6}$ alkyl, or $C_{3-6}$ cycloalkyl and all other variables are as described for the particular embodiment. In each of the embodiments above for Formula IV there is a further embodiment in which $R^{1b}$ is hydrogen, methyl, chloro, —CF₃, —CF₂H, —CFH₂, or cyclopropyl and all other variables are as described for the particular embodiment. In each of the embodiments above for Formula IV there is a further embodiment in which $R^{1b}$ K is hydrogen, CN, chloro, methyl, ethyl, propyl, butyl, or cyclopropyl and all other variables are as described for the particular embodiment. In each of the embodiments above for Formula IV there is a further embodiment in which $R^{1b}$ is hydrogen, methyl, or chloro and all other variables are as described for the particular embodiment. In each of the embodiments above for Formula IV there is a further embodiment in which $R^{1b}$ is —$CF_3$, —$CF_2H$, —$CFH_2$, or cyclopropyl and all other variables are as described for the particular embodiment. In certain embodiments, $R^{1b}$ is haloalkyl and all other variables are as described for the particular embodiment. In each of the embodiments above for Formula IV there is a further embodiment in which $R^{1b}$ is —$CF_3$. In some embodiments, $R^{1b}$ is $C_{3-6}$ cycloalkyl and all other variables are as described for the particular embodiment. In each of the embodiments above for Formula IV there is a further embodiment in which $R^{1b}$ is cyclopropyl, and all other variables are as described for the particular embodiment Another embodiment comprises a compound of Formula III, or a pharmaceutically acceptable salt, ester, stereoisomer, mixture of stereoisomers or tautomer thereof, wherein Y is oxygen; $R^{1a}$ is selected from hydrogen, methyl, and chloro; $R^2$ is hydrogen or methyl; $R^3$ is methyl; $R^4$ is hydrogen; and $R^5$ is selected from:

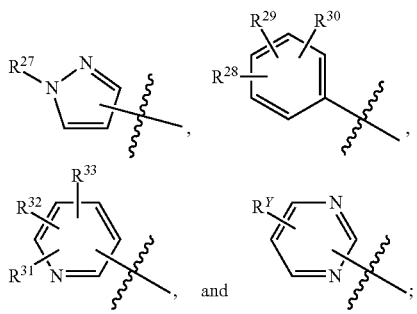

$R^{27}$ is selected from $C_{1-4}$ alkyl, fluoromethyl, fluoroethyl, fluoropropyl, difluoromethyl, difluoroethyl, difluoropropyl, trifluoromethyl, trifluoroethyl, trifluoropropyl, and $C_{2-6}$ heterocyclyl, wherein the $C_{1-4}$ alkyl is substituted by 0 or 1 substituent selected from OH, $CO_2H$, and $CO_2(C_{1-3}$ alkyl);

$R^{28}$, $R^{29}$, and $R^{30}$ are each independently selected from hydrogen, F, and —$OC_{1-3}$ alkyl;

or $R^{28}$ and $R^{29}$ are hydrogen or —$OC_{1-3}$ alkyl, and $R^{30}$ is morpholino or piperazinyl, wherein the piperazinyl group is substituted by 0 or 1 substituent selected from —$SO_2H$, $SO_2$($C_{1-3}$ alkyl), —$SO_2$—$C_{3-6}$ cycloalkyl, —$SO_2$—$C_{2-8}$ heterocyclyl, $C_{1-4}$ alkyl, —C(O)—$C_{1-4}$ alkyl, $C_{3-6}$ cycloalkyl, and $C_{2-6}$ heterocyclyl;

and $R^{31}$, $R^{32}$, and $R^{33}$ are each independently selected from hydrogen, $C_{1-3}$ alkyl, and —$OC_{1-3}$ alkyl;

or $R^{31}$ and $R^{32}$ are hydrogen or —$OC_{1-3}$ alkyl, and $R^{33}$ is morpholino or piperazinyl, wherein the piperazinyl group is substituted by 0 or 1 substituent selected from —$SO_2H$, —$SO_2(C_{1-3}$ alkyl), $C_{1-4}$ alkyl, —C(O)—$C_{1-4}$ alkyl, $C_{3-6}$ cycloalkyl, and $C_{2-6}$ heterocyclyl;

$R^Y$ is selected from H, $C_{1-4}$ alkyl, and —$OC_{1-3}$ alkyl; and $R^Z$ is selected from H and methyl.

A further embodiment comprises a compound of Formula IV, or a pharmaceutically acceptable salt, ester, stereoisomer, mixture of stereoisomers or tautomer thereof, wherein Y is oxygen; $R^{1b}$ is selected from hydrogen, methyl, and chloro; $R^2$ is hydrogen; $R^3$ is methyl; $R^4$ is hydrogen; and $R^5$ is selected from:

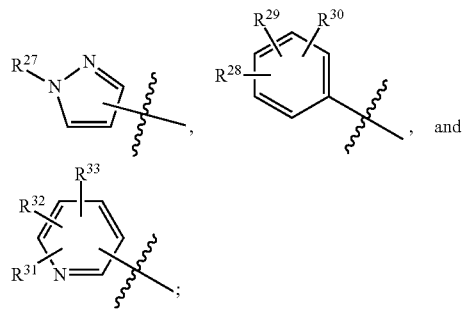

$R^{27}$ is selected from $C_{1-4}$ alkyl, fluoromethyl, fluoroethyl, fluoropropyl, difluoromethyl, difluoroethyl, difluoroproypl, trifluoromethyl, trifluoroethyl, and trifluoropropyl, wherein the $C_{1-4}$ alkyl is substituted by 0 or 1 substituent selected from OH, $CO_2H$, and $CO_2(C_{1-3}$ alkyl);

$R^{28}$, $R^{29}$, and $R^{30}$ are each independently selected from hydrogen, F, and methoxy;

or $R^{28}$ and $R^{29}$ are hydrogen and $R^{30}$ is morpholino or piperazinyl, wherein the piperazinyl group is substituted by 0 or 1 substituent selected from —$SO_2H$, —$SO_2(C_{1-3}$ alkyl), $C_{1-4}$ alkyl, —C(O)—$C_{1-4}$ alkyl, $C_{3-6}$ cycloalkyl, and $C_{2-6}$ heterocyclyl; and $R^{31}$, $R^{32}$, and $R^{33}$ are each independently selected from hydrogen and methoxy;

or $R^{31}$ and $R^{32}$ are each independently selected from hydrogen and methoxy, and $R^{33}$ is piperazinyl, wherein the piperazinyl group is substituted by 0 or 1 substituent selected from —$SO_2H$, —$SO_2(C_{1-3}$ alkyl), —$SO_2$—$C_{3-6}$ cycloalkyl, —$SO_2$—$C_{2-8}$ heterocyclyl, $C_{1-4}$ alkyl, $C_{3-6}$ cycloalkyl, and $C_{2-6}$ heterocyclyl;

In one embodiment, the compound of Formula IV is selected from:

(R)-4-((R)-1-((5-(1-(tert-butyl)-1H-pyrazol-4-yl)-1-methyl-1H-benzo[d]imidazol-7-yl)oxy)ethyl)pyrrolidin-2-one;

(R)-4-((R)-1-((1-methyl-5-(6-(trifluoromethyl)pyridin-2-yl)-1H-benzo[d]imidazol-7-yl)oxy)ethyl)pyrrolidin-2-one;

(R)-4-((R)-1-((5-(6-methoxypyridin-2-yl)-1-methyl-1H-benzo[d]imidazol-7-yl)oxy)ethyl)pyrrolidin-2-one;

(R)-4-((R)-1-((5-(5,6-dimethoxypyridin-2-yl)-1,2-dimethyl-1H-benzo[d]imidazol-7-yl)oxy)ethyl)pyrrolidin-2-one;

(R)-4-((R)-1-((5-(5,6-dimethoxypyridin-2-yl)-1-methyl-1H-benzo[d]imidazol-7-yl)oxy)ethyl)pyrrolidin-2-one; and (R)-4-((R)-1-((5-(3,4-dimethoxyphenyl)-1-methyl-1H-benzo[d]imidazol-7-yl)oxy)ethyl)pyrrolidin-2-one;

or a pharmaceutically acceptable salt, ester, stereoisomer, mixture of stereoisomers or tautomer thereof.

In yet other aspects, provided is a compound of Formula V:

Formula V

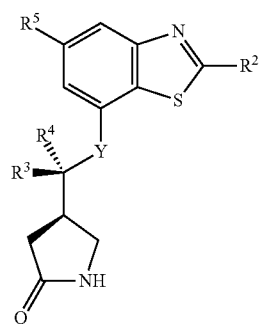

wherein $R^2$, $R^3$, $R^4$ and $R^5$ are as specified above for Formula I, or a pharmaceutically acceptable salt, ester, stereoisomer, mixture of stereoisomers or tautomer thereof.

One embodiment comprises a compound of Formula V, or a pharmaceutically acceptable salt thereof, wherein:
Y is oxygen;
$R^2$ is hydrogen or $C_{1-6}$ alkyl, wherein the $C_{1-6}$ alkyl group is substituted by 0, 1, 2, or 3 fluorine atoms or 0 or 1 substituents selected from hydroxy or $C_{1-6}$ alkoxy;
$R^3$ is H, $C_{1-6}$ alkyl, $C_{2-3}$ alkenyl, or $C_{2-3}$ alkynyl, wherein the $C_{1-6}$ alkyl group is substituted by 0, 1, 2, or 3 fluorine atoms or 0 or 1 substituents selected from hydroxy or $C_{1-6}$ alkoxy;
$R^4$ is hydrogen; and
$R^5$ is a moiety selected from the group of phenyl, pyrazolyl, pyridinyl, pyrazolo[1,5-a]pyridinyl, benzo[d][1,3]dioxolyl, benzomorpholinyl, thiazolyl, cyclohex-1-enyl, pyridine-2(1H)-one-yl, dihydrobenzo[f][1,4]oxazepine-5(2H)-one-yl, benzothiazolyl, thieno[3,2-c]pyrazolyl, ethynyl, indazolyl, pyrimidinyl, imidazolyl, indolinyl, pyrazinyl, pyridazine, pyrido[3,2-b][1,4]oxazinyl, 2,3-dihydro-[1,4]dioxino[2,3-b]pyridinyl, quinazolin-4(3H)-one-yl, pyrrolo[2,3-b]pyridine-2(3H)-one-yl, pyrrolo[3,2-c]pyridine-2(3H)-one-yl, 3,4-dihydroquinolin-2(1H)-one-yl, indoline-2-one, pyrazolo[3,4-b]pyridinyl, 2,3-dihydrobenzofuranyl, 2H-benzo[b][1,4]oxazin-3(4H)-one-yl, 3,4-dihydroquinolin-2(1H)-one-yl, pyrido[3,2-b][1,4]oxazin-3(4H)-one-yl, benzimidazolyl, imidazo[1,2-a]pyridinyl, imidazo[1,2-a]pyridinyl, isoindoline-1-one-yl, benzomorpholin-3-one-yl, benzomorpholin-2-one-yl, benzimidazolin-2-one-yl, 2,3-dihydro-1H-pyrido[2,3-b][1,4]oxazinyl, pyrido[2,3-b][1,4]oxazin-2(3H)-one-yl, spiro[azetidine-3,3'-indolin]-2'-one-yl, benzo[d][1,3]oxazin-2(4H)-one-yl, spiro[indoline-3,4'-piperidin]-2-one-yl, 3,4-dihydrospiro[benzo[b][1,4]oxazine-2,1'-cyclopropane]-yl, indolyl, benzoxazolin-2-one-yl, pyrrolo[3,2-b]pyridine-2(3H)-one-yl, thiophenyl, 3,4-dihydro-pyrido[3,2-b][1,4]oxazinyl, 1,3,4-thiadiazolyl, indolinyl, isothiazolyl, 1,2,3-triazolyl, 1,2,3,4-tetrahydroquinolinyl, and thieno[2,3-c]pyridinyl;
wherein each of the $R^5$ moieties may be independently, optionally substituted with one, two or three substituents independently selected from the group consisting of halo, $C_{1-6}$ alkyl, $C_{1-6}$ alkoxy, $C_{2-6}$ alkenyl, $C_{2-6}$ alkynyl, $C_{3-8}$ cycloalkyl, $C_{2-8}$heterocyclyl, —S(O)$_2$—R$^{20}$, —S(O)$_2$—NR$^{20}$R$^{22}$, —NO$_2$, —N(R$^{20}$)(R$^{22}$), —C(O)—OR$^{20}$, —CN, oxo, and —O—R$^{20}$;
wherein each alkyl, alkoxy, alkenyl, alkynyl, cycloalkyl, or heterocyclyl moiety may be further optionally substituted with one, two or three substituents independently selected from the group consisting of halo, CN, $C_{1-6}$ alkyl, $C_{3-6}$ cycloalkyl, $C_{6-12}$ aryl, $C_{2-8}$ heterocyclyl, $C_{2-6}$ heteroaryl, —S(O)$_2$—R$^{20}$, —NO$_2$, —N(R$^{20}$)(R$^{22}$), —C(O)—R$^{20}$, —C(O)—OR$^{20}$, —C(O)—N(R$^{20}$)(R$^{22}$), —CN, oxo, and —O—R$^{20}$; and
wherein each $R^{20}$ and $R^{22}$ is independently selected from the group consisting of hydrogen, $C_{1-6}$ alkyl, $C_{2-6}$ alkenyl, $C_{2-6}$ alkynyl, $C_{3-8}$ cycloalkyl, $C_{2-8}$ heterocyclyl, $C_{6-12}$ aryl, and $C_{2-6}$ heteroaryl.

Another embodiment comprises a compound of Formula V, or a pharmaceutically acceptable salt thereof, wherein: Y is oxygen; $R^2$ is hydrogen or methyl;
$R^3$ is H, $C_{1-6}$ alkyl, $C_{2-3}$ alkenyl, or $C_{2-3}$ alkynyl; $R^4$ is hydrogen;
$R^5$ is a moiety selected from the group of phenyl, pyridinyl, pyrazolyl, pyrazinyl, pyridazinyl, thiazolyl, benzothiazolyl, benzomorpholinyl, thieno[3,2-c]pyrazolyl, indazolyl, indoline-2-one-yl, quinazolin-4(3H)one-yl, pyrrolo[2,3-b]pyridine-2(3H)-one-yl, pyrrolo[3,2-c]pyridine-2(3H)-one-yl, 3,4-dihydroquinolin-2(1H)-one-yl, pyrazolo[3,4-b]pyridinyl, 2,3-dihydrobenzofuranyl, 3,4-dihydroquinolin-2(1H)-one-yl, and 3,4-dihydro-pyrido[3,2-b][1,4]oxazinyl; wherein each of the $R^5$ moieties is substituted with zero, one, two, or three members of $C_{1-6}$ alkyl, $C_{1-6}$ alkoxy, $C_{3-8}$ cycloalkyl, or $C_{2-8}$ heterocyclyl;
wherein the alkyl, alkoxy, cycloalkyl and heterocyclyl substituents on each $R^5$ moiety may be independently further substituted with zero or one substituent selected from halo, $C_{3-8}$ cycloalkyl, $C_{2-8}$ heterocyclyl, —C(O)O—R$^{20}$, —C(O)R$^{20}$, —NO$_2$, —N(R$^{20}$)(R$^{22}$), —S(O)$_2$—R$^{20}$, —S(O)$_2$—N(R$^{20}$)(R$^{22}$)—C(O)—N(R$^{20}$)(R$^{22}$), oxo, —CN, and —O—R$^{20}$; and
wherein each $R^{20}$ and $R^{22}$ is independently selected from the group consisting of hydrogen, $C_{1-6}$ alkyl, $C_{2-6}$ alkenyl, $C_{2-6}$ alkynyl, $C_{3-8}$ cycloalkyl, $C_{2-8}$ heterocyclyl, $C_{6-12}$ aryl, and $C_{2-6}$ heteroaryl.

An embodiment comprises a compound of Formula V, or a pharmaceutically acceptable salt thereof, wherein Y is oxygen; $R^2$ is hydrogen or methyl; $R^3$ is H or methyl; $R^4$ is hydrogen; and $R^5$ is a pyrazolyl, thiazolyl, or imidazolyl group, the pyrazolyl, thiazolyl, or imidazolyl group being unsubstituted or substituted with one substituent selected from $C_{1-6}$ alkyl and $C_{1-6}$ haloalkyl.

Another embodiment comprises a compound of Formula V, or a pharmaceutically acceptable salt thereof, wherein: Y is oxygen; $R^2$ is hydrogen or methyl; $R^3$ is H or methyl; $R^4$ is hydrogen; and $R^5$ is a pyrazolyl, thiazolyl, or imidazolyl group, the pyrazolyl, thiazolyl, or imidazolyl group being unsubstituted or substituted with one substituent selected from $C_{1-4}$ alkyl and $C_{1-4}$ fluoroalkyl.

Another embodiment comprises a compound of Formula V, or a pharmaceutically acceptable salt thereof, wherein: Y is oxygen; $R^2$ is hydrogen or methyl; $R^3$ is H or methyl; $R^4$ is hydrogen; and $R^5$ is a moiety selected from the group of benzothiazolyl, benzomorpholinyl, thieno[3,2-c]pyrazolyl, indazolyl, indoline-2-one-yl, quinazolin-4(3H)one-yl, pyrrolo[2,3-b]pyridine-2(3H)-one-yl, pyrrolo[3,2-c]pyridine-2(3H)-one-yl, 3,4-dihydroquinolin-2(1H)-one-yl, pyrazolo[3,4-b]pyridinyl, 2,3-dihydrobenzofuranyl, 3,4-dihydroquinolin-2(1H)-one-yl, and 3,4-dihydro-pyrido[3,2-b][1,4]oxazinyl; wherein each of the $R^5$ moieties is substituted with zero, one, two, or three members of $C_{1-6}$ alkyl, $C_{1-6}$ alkoxy, $C_{3-8}$ cycloalkyl, or $C_{2-8}$ heterocyclyl.

Another embodiment comprises a compound of Formula (Va), or a pharmaceutically acceptable salt thereof:

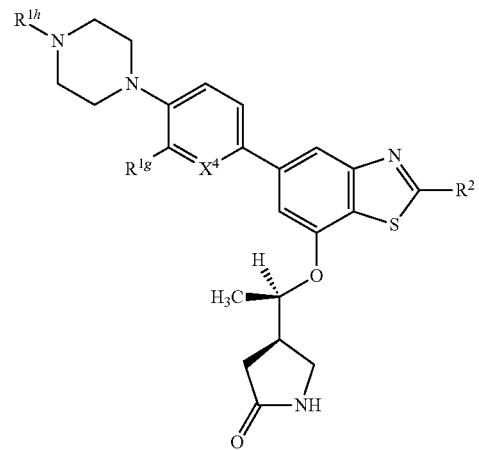

Formula (Va)

wherein:

R² is hydrogen or methyl;

X⁴ is carbon or nitrogen;

R¹ᵍ is hydrogen or methoxy; and

R¹ᵇ is selected from hydrogen, —SO₂(C₁₋₃ alkyl), —SO₂—C₃₋₆ cycloalkyl, —SO₂—C₂₋₈ heterocyclyl, —C(O)—C₁₋₆ alkyl, —C(O)—C₃₋₆ cycloalkyl, —CO₂H, —CO₂—C₁₋₆ alkyl, and a 4-, 5-, or 6-membered heterocyclyl group having one oxygen ring heteroatom.

A further embodiment comprises a compound of Formula (Va), as defined above, wherein R² is hydrogen, or a pharmaceutically acceptable salt thereof.

In one embodiment of Formula V, the compound is selected from:

(R)-4-((R)-1-((5-(1-cyclobutyl-1H-pyrazol-4-yl)benzo[d]thiazol-7-yl)oxy)ethyl)pyrrolidin-2-one;

(R)-4-((R)-1-((5-(1-(2,2-difluoroethyl)-1H-pyrazol-4-yl)benzo[d]thiazol-7-yl)oxy)ethyl)pyrrolidin-2-one;

(R)-4-((R)-1-((5-(1-isopropyl-1H-pyrazol-4-yl)benzo[d]thiazol-7-yl)oxy)ethyl)pyrrolidin-2-one;

(R)-4-((R)-1-((5-(1-(tert-butyl)-1H-pyrazol-4-yl)benzo[d]thiazol-7-yl)oxy)ethyl)pyrrolidin-2-one;

(R)-4-((R)-1-((5-(1-ethyl-1H-pyrazol-3-yl)benzo[d]thiazol-7-yl)oxy)ethyl)pyrrolidin-2-one;

(R)-4-((R)-1-((5-(1-(tert-butyl)-1H-pyrazol-4-yl)-2-methylbenzo[d]thiazol-7-yl)oxy)ethyl)pyrrolidin-2-one;

(R)-4-((R)-1-((5-(1-isopropyl-1H-pyrazol-3-yl)benzo[d]thiazol-7-yl)oxy)ethyl)pyrrolidin-2-one;

(R)-4-((R)-1-((5-(1-(tetrahydro-2H-pyran-4-yl)-1H-pyrazol-4-yl)benzo[d]thiazol-7-yl)oxy)ethyl)pyrrolidin-2-one;

(R)-4-((R)-1-((5-(5-morpholinopyridin-2-yl)benzo[d]thiazol-7-yl)oxy)ethyl)pyrrolidin-2-one;

tert-butyl 4-(6-(7-((R)-1-((R)-5-oxopyrrolidin-3-yl)ethoxy)benzo[d]thiazol-5-yl)pyridin-3-yl)piperazine-1-carboxylate;

(R)-4-((R)-1-((5-(5-(4-(oxetan-3-yl)piperazin-1-yl)pyridin-2-yl)benzo[d]thiazol-7-yl)oxy)ethyl)pyrrolidin-2-one;

(R)-4-((R)-1-((5-(5-(4-acetylpiperazin-1-yl)pyridin-2-yl)benzo[d]thiazol-7-yl)oxy)ethyl)pyrrolidin-2-one;

(R)-4-((R)-1-((5-(5-(4-(tetrahydro-2H-pyran-4-yl)piperazin-1-yl)pyridin-2-yl)benzo[d]thiazol-7-yl)oxy)ethyl)pyrrolidin-2-one;

(R)-4-((R)-1-((5-(5,6-dimethoxypyridin-2-yl)benzo[d]thiazol-7-yl)oxy)ethyl)pyrrolidin-2-one;

(R)-4-((R)-1-((5-(4-(4-(oxetan-3-yl)piperazin-1-yl)phenyl)benzo[d]thiazol-7-yl)oxy)ethyl)pyrrolidin-2-one;

(R)-4-((R)-1-((5-(4-morpholinophenyl)benzo[d]thiazol-7-yl)oxy)ethyl)pyrrolidin-2-one;

(R)-4-((R)-1-((5-(3,4-dimethoxyphenyl)benzo[d]thiazol-7-yl)oxy)ethyl)pyrrolidin-2-one;

(R)-4-((R)-1-((5-(3,4-dimethoxyphenyl)-2-methylbenzo[d]thiazol-7-yl)oxy)ethyl)pyrrolidin-2-one;

tert-butyl 4-(4-(7-((R)-1-((R)-5-oxopyrrolidin-3-yl)ethoxy)benzo[d]thiazol-5-yl)phenyl)piperazine-1-carboxylate;

(R)-4-((R)-1-([4,5'-bibenzo[d]thiazol]-7'-yloxy)ethyl)pyrrolidin-2-one;

(S)-4-((S)-1-((5-(2-(tert-butyl)thiazol-5-yl)benzo[d]thiazol-7-yl)oxy)ethyl)pyrrolidin-2-one; and (R)-4-((R)-1-((5-(1-methyl-1H-thieno[3,2-c]pyrazol-5-yl)benzo[d]thiazol-7-yl)oxy)ethyl)pyrrolidin-2-one;

or a pharmaceutically acceptable salt, ester, stereoisomer, mixture of stereoisomers or tautomer thereof.

In yet other aspects, provided is a compound of Formula VI:

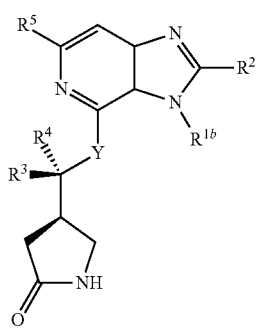

Formula VI wherein Y, R¹ᵇ, R², R³, R⁴ and R⁵ are as specified above for Formula I, or a pharmaceutically acceptable salt, ester, stereoisomer, mixture of stereoisomers or tautomer thereof.

One embodiment comprises a compound of Formula VI, or a pharmaceutically acceptable salt thereof, wherein:

Y is oxygen;

R² is hydrogen or C₁₋₆ alkyl, wherein the C₁₋₆ alkyl group is substituted by 0, 1, 2, or 3 fluorine atoms or 0 or 1 substituents selected from hydroxy or C₁₋₆ alkoxy;

R³ is H, C₁₋₆ alkyl, C₂₋₃ alkenyl, or C₂₋₃ alkynyl, wherein the C₁₋₆ alkyl group is substituted by 0, 1, 2, or 3 fluorine atoms or 0 or 1 substituents selected from hydroxy or C₁₋₆ alkoxy;

R⁴ is hydrogen; and

R⁵ is a moiety selected from the group of phenyl, pyrazolyl, pyridinyl, pyrazolo[1,5-a]pyridinyl, benzo[d][1,3]dioxolyl, benzomorpholinyl, thiazolyl, cyclohex-1-enyl, pyridine-2(1H)-one-yl, dihydrobenzo[f][1,4]oxazepine-5(2H)-one-yl, benzothiazolyl, thieno[3,2-c]pyrazolyl, ethynyl, indazolyl, pyrimidinyl, imidazolyl, indolinyl, pyrazinyl, pyridazine, pyrido[3,2-b][1,4]oxazinyl, 2,3-dihydro-[1,4]dioxino[2,3-b]pyridinyl, quinazolin-4(3H)-one-yl, pyrrolo[2,3-b]pyridine-2(3H)-one-yl, pyrrolo[3,2-c]pyridine-2(3H)-one-yl, 3,4-dihydroquinolin-2(1H)-one-yl, indoline-2-one, pyrazolo[3,4-b]pyridinyl, 2,3-dihydrobenzofuranyl, 2H-benzo[b][1,4]oxazin-3(4H)-one-yl, 3,4-dihydroquinolin-2(1H)-one-yl, pyrido[3,2-b][1,4]oxazin-3(4H)-one-yl, benzimidazolyl, imidazo[1,2-a]pyridinyl, imidazo[1,2-a]pyridinyl, isoindoline-1-one-yl, benzomorpholin-3-one-yl, benzomorpholin-2-one-yl, benzimidazolin-2-one-yl, 2,3-dihydro-1H-pyrido[2,3-b][1,4]oxazinyl, pyrido[2,3-b][1,4]oxazin-2(3H)-one-yl, spiro[azetidine-3,3'-indolin]-2'-one-yl, benzo[d][1,3]oxazin-2(4H)-one-yl, spiro[indoline-3,4'-piperidin]-2-one-yl, 3,4-dihydrospiro[benzo[b][1,4]oxazine-2,1'-cyclopropane]-yl, indolyl, benzoxazolin-2-one-yl, pyrrolo[3,2-b]pyridine-2(3H)-one-yl, thiophenyl, 3,4-dihydro-pyrido[3,2-b][1,4]oxazinyl, 1,3,4-thiadiazolyl, indolinyl, isothiazolyl, 1,2,3-triazolyl, 1,2,3,4-tetrahydroquinolinyl, and thieno[2,3-c]pyridinyl;

wherein each of the R⁵ moieties may be independently, optionally substituted with one, two or three substituents independently selected from the group consisting of halo, C₁₋₆ alkyl, C₁₋₆ alkoxy, C₂₋₆ alkenyl, C₂₋₆ alkynyl, C₃₋₈ cycloalkyl, C₂₋₈ heterocyclyl, —S(O)₂—R²⁰, —S(O)₂—NR²⁰R²², —NO₂, —N(R²⁰)(R²²), —C(O)—OR²⁰, —CN, oxo, and —O—R²⁰;

wherein each alkyl, alkoxy, alkenyl, alkynyl, cycloalkyl, or heterocyclyl moiety may be further optionally substituted with one, two or three substituents independently selected from the group consisting of halo, CN, $C_{1-6}$ alkyl, $C_{3-6}$ cycloalkyl, $C_{6-12}$ aryl, $C_{2-8}$ heterocyclyl, $C_{2-6}$ heteroaryl, —S(O)$_2$—R$^{20}$, —NO$_2$, —N(R$^{20}$)(R$^{22}$), —C(O)R$^{20}$, —C(O)—OR$^{20}$, —C(O)—N(R$^{20}$)(R$^{22}$), —CN, oxo, and —O—R$^{20}$; and wherein each R$^{20}$ and R$^{22}$ is independently selected from the group consisting of hydrogen, $C_{1-6}$ alkyl, $C_{2-6}$ alkenyl, $C_{2-6}$ alkynyl, $C_{3-8}$ cycloalkyl, $C_{2-8}$ heterocyclyl, $C_{6-12}$ aryl, and $C_{2-6}$ heteroaryl.

Another embodiment comprises a compound of Formula VI, or a pharmaceutically acceptable salt thereof, wherein:

Y is oxygen;

R$^2$ is hydrogen or $C_{1-6}$ alkyl, wherein the $C_{1-6}$ alkyl group is substituted by 0, 1, 2, or 3 fluorine atoms or 0 or 1 substituents selected from hydroxy or $C_{1-6}$ alkoxy;

R$^3$ is H, $C_{1-6}$ alkyl, $C_{2-3}$ alkenyl, or $C_{2-3}$ alkynyl, wherein the $C_{1-6}$ alkyl group is substituted by 0, 1, 2, or 3 fluorine atoms or 0 or 1 substituents selected from hydroxy or $C_{1-6}$ alkoxy;

R$^4$ is hydrogen; and

R$^5$ is a moiety selected from the group of phenyl, pyrazolyl, pyridinyl, pyrazolo[1,5-a]pyridinyl, benzo[d][1,3]dioxolyl, benzomorpholinyl, thiazolyl, cyclohex-1-enyl, pyridine-2(1H)-one-yl, dihydrobenzo[f][1,4]oxazepine-5(2H)-one-yl, thieno[3,2-c]pyrazolyl, ethynyl, indazolyl, indolinyl, 3,4-dihydroquinolin-2(1H)-one-yl, indoline-2-one, 2H-benzo[b][1,4]oxazin-3(4H)-one-yl, 3,4-dihydroquinolin-2(1H)-one-yl, imidazo[1,2-a]pyridinyl, imidazo[1,2-a]pyridinyl, isoindoline-1-one-yl, benzomorpholin-3-one-yl, benzomorpholin-2-one-yl, benzimidazolin-2-one-yl, 2,3-dihydro-1H-pyrido[2,3-b][1,4]oxazinyl, spiro[azetidine-3,3'-indolin]-2'-one-yl, benzo[d][1,3]oxazin-2(4H)-one-yl, spiro[indoline-3,4'-piperidin]-2-one-yl, 3,4-dihydrospiro[benzo[b][1,4]oxazine-2,1'-cyclopropane]-yl, indolyl, benzoxazolin-2-one-yl, pyrrolo[3,2-b]pyridine-2(3H)-one-yl, thiophenyl, indolinyl, isothiazolyl, and thieno[2,3-c]pyridinyl; wherein each of the R$^5$ moieties may be independently, optionally substituted with one, two or three substituents independently selected from the group consisting of halo, $C_{1-6}$ alkyl, $C_{1-6}$ alkoxy, $C_{2-6}$ alkenyl, $C_{2-6}$ alkynyl, $C_{3-8}$ cycloalkyl, $C_{2-8}$ heterocyclyl, —S(O)$_2$—R$^{20}$, —S(O)$_2$—NR$^{20}$R$^{22}$, —NO$_2$, —N(R$^{20}$)(R$^{22}$), —C(O)—OR$^{20}$, —CN, oxo, and —O—R$^{20}$;

wherein each alkyl, alkoxy, alkenyl, alkynyl, cycloalkyl, or heterocyclyl moiety may be further optionally substituted with one, two or three substituents independently selected from the group consisting of halo, CN, $C_{1-6}$ alkyl, $C_{3-6}$ cycloalkyl, $C_{6-12}$ aryl, $C_{2-8}$ heterocyclyl, $C_{2-6}$ heteroaryl, —S(O)$_2$—R$^{20}$, —NO$_2$, —N(R$^{20}$)(R$^{22}$), —C(O)—R$^{20}$, —C(O)—OR$^{20}$, —C(O)—N(R$^{20}$)(R$^{22}$), —CN, oxo, and —O—R$^{20}$; and wherein each R$^{20}$ and R$^{22}$ is independently selected from the group consisting of hydrogen, $C_{1-6}$ alkyl, $C_{2-6}$ alkenyl, $C_{2-6}$ alkynyl, $C_{3-8}$ cycloalkyl, $C_{2-8}$ heterocyclyl, $C_{6-12}$ aryl, and $C_{2-6}$ heteroaryl.

In one embodiment of Formula VI,

Y is oxygen;

R$^{1b}$ K is hydrogen, halo, $C_{1-6}$ alkyl, $C_{3-6}$ cycloalkyl, or $C_{2-8}$ heterocyclyl; wherein alkyl, cycloalkyl or heterocyclyl may be optionally substituted with fluoro or $C_{1-6}$ alkyl;

R$^2$ is hydrogen or $C_{1-6}$ alkyl;

R$^3$ is H, $C_{1-6}$ alkyl, $C_{2-3}$ alkenyl, or $C_{2-3}$ alkynyl, $C_{3-6}$ cycloalkyl, or $C_{1-6}$ alkoxy;

wherein alkyl, cycloalkyl or alkoxy may be optionally substituted with halo or $C_{1-6}$ alkyl.

R$^4$ is hydrogen;

R$^5$ is phenyl, pyridinyl, pyrazolyl, thiazolyl, indazolyl, cyclohexenyl, thienopyrazolyl, or pyrazolopyridinyl;

wherein the phenyl, pyridinyl, pyrazolyl, thiazolyl, indazolyl, cyclohexenyl, thienopyrazolyl, or pyrazolopyridinyl moiety may be optionally substituted with 1 to 3 members of halo, $C_{1-6}$alkyl, $C_{1-6}$ alkoxy, $C_{3-8}$ cycloalkyl, $C_{2-8}$ heterocyclyl, —C(O)O—R$^{20}$, —C(O)R$^{20}$, —NO$_2$, —N(R$^{20}$)(R$^{22}$), —S(O)$_2$—R$^{20}$, —S(O)$_2$—N(R$^{20}$)(R$^{22}$), —C(O)N(R$^{20}$)(R$^{22}$), —CN, oxo, and —O—R$^{20}$;

wherein the $C_{3-8}$ cycloalkyl or $C_{2-8}$ heterocyclyl moiety may be independently optionally further substituted with $C_{3-8}$ cycloalkyl, $C_{2-8}$ heterocyclyl, —C(O)O—R$^{20}$, —C(O)R$^{20}$, —NO$_2$, —N(R$^{20}$)(R$^{22}$), —S(O)$_2$—R$^{20}$, —S(O)$_2$—N(R$^{20}$)(R$^{22}$), —C(O)N(R$^{20}$)(R$^{22}$), —CN, oxo, and —O—R$^{20}$;

wherein each R$^{20}$ and R$^{22}$ is independently selected from the group consisting of hydrogen, $C_{1-6}$ alkyl, $C_{2-6}$ alkenyl, $C_{2-6}$ alkynyl, $C_{3-8}$ cycloalkyl, $C_{2-8}$ heterocyclyl, $C_{6-12}$ aryl, and $C_{2-6}$ heteroaryl.

In certain embodiments of Formula VI,

Y is oxygen;

R$^{1b}$ is hydrogen, methyl, ethyl, propyl, butyl, cyclopropyl, cyclobutyl, cyclopropylmethyl, cyclopropyethyl, fluoromethyl, difluoromethyl, trifluoromethyl, fluroethyl, difluoroethyl, trifluoroethyl, or oxetanyl;

R$^2$ is hydrogen, methyl, ethyl, propyl, butyl;

R$^3$ is propyl, butyl, cyclopropyl, cyclobutyl, cyclopropylmethyl, cyclopropyethyl, fluoromethyl, difluoromethyl, trifluoromethyl, fluroethyl, difluoroethyl, trifluoroethyl, methoxyethyl, or ethoxyethyl;

R$^4$ is hydrogen;

R$^5$ is phenyl, pyridinyl, pyrazolyl, thiazolyl, indazolyl, cyclohexenyl, thienopyrazolyl, or pyrazolopyridinyl;

wherein each of the moiety may be optionally substituted with 1 to 3 members of fluoro, chloro, bromo, butyl, isopropyl, methyl, methoxyethyl, ethoxyethyl, difluoromethyl, difluoroethyl, fluroethyl, trifluoroethyl, cyclobutyl, cyclopropyl, cyclopropylmethyl, piperazinyl, morpholinyl, oxetanyl, tetrahydropyranyl, —C(O)O—R$^{20}$, —C(O)R$^{20}$, —NO$_2$, —N(R$^{20}$)(R$^{22}$), —S(O)$_2$—R$^{20}$, —S(O)$_2$—N(R$^{20}$)(R$^{22}$), —C(O)—N(R$^{20}$)(R$^{22}$), —CN, oxo, and —O—R$^{20}$;

wherein piperazinyl or morpholinyl may be further optionally substituted with methyl, ethyl, propyl, methoxy, ethoxy, oxetanyl, tetrahydropyranyl, —C(O)O—R$^{20}$, —C(O)R$^{20}$, —NO$_2$, —N(R$^{20}$)(R$^{22}$), —S(O)$_2$—R$^{20}$, —S(O)$_2$—N(R$^{20}$)(R$^{22}$), —C(O)—N(R$^{20}$)(R$^{22}$), —CN, or oxo;

wherein each R$^{20}$ and R$^{22}$ is independently selected from the group consisting of hydrogen, $C_{1-6}$ alkyl, $C_{2-6}$ alkenyl, $C_{2-6}$ alkynyl, $C_{3-8}$ cycloalkyl, $C_{2-8}$ heterocyclyl, $C_{6-12}$ aryl, and $C_{2-6}$ heteroaryl.

In certain embodiments of Formula VI, R$^5$ is pyridinyl or pyrazolyl optionally substituted with 1 to 3 members independently selected from methyl, ethyl, propyl, isopropyl, butyl, tert-butyl, isobutyl CF$_3$, CF$_3$CH$_2$—, CF$_2$HCH$_2$—, CFH$_2$CH$_2$—, methoxy, ethoxy, morpholino, oxetanyl, furanyl, tetrahydropyranyl, cyclopropyl, cyclobutyl, cyclopentyl, and cyclohexyl.

In other embodiments of Formula VI, R$^5$ is phenyl optionally substituted with 1 to 3 members independently selected from halogen, cyano, methyl, ethyl, propyl, isopropyl, butyl, tert-butyl, isobutyl CF$_3$, CF$_3$CH$_2$—, CF$_2$HCH$_2$—, CFH$_2$CH$_2$—, methoxy, ethoxy, morpholino, oxetanyl, furanyl, tetrahydropyranyl, cyclopropyl, cyclobutyl, cyclopentyl, another embodiment provides a compound of the formula VIa, or a pharmaceutically acceptable salt thereof:

A

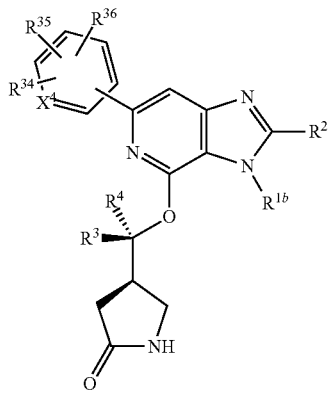

VIa wherein:
$R^{1b}$ is selected from hydrogen, halo, $C_{1-3}$ haloalkyl, $C_{1-6}$ alkyl, $C_{3-6}$ cycloalkyl, and $C_{2-5}$ heterocyclyl;
$R^2$ is H or $C_{1-3}$ alkyl;
$R^3$ is $C_{1-6}$ alkyl;
$R^4$ is H;
$X^4$ is carbon or nitrogen;
$R^{34}$, $R^{35}$, and $R^{36}$ are each, independently, selected from hydrogen, $C_{1-6}$ alkyl, —O—$C_{1-6}$ alkyl, —CN, halogen, —S(O)$_2$-alkyl, —S(O)$_2$—$C_{3-6}$ cycloalkyl, —S(O)$_2$—$C_{2-8}$ heterocyclyl, —NH$_2$, —NH($C_{1-6}$ alkyl), —N($C_{1-6}$ alkyl)$_2$, —SO$_2$NH$_2$, —SO$_2$NH($C_{1-6}$ alkyl), and —SO$_2$N($C_{1-6}$ alkyl)$_2$, wherein the $C_{1-6}$ alkyl and —O—$C_{1-6}$ alkyl groups are independently substituted by 0, 1, 2, or 3 substituents selected from OH, CN, and halo;
or $R^{34}$ and $R^{35}$ are selected from hydrogen and —O—$C_{1-3}$ alkyl, and $R^{36}$ is selected from:

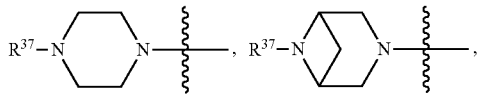

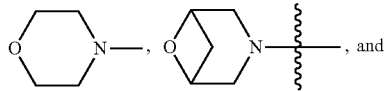, and

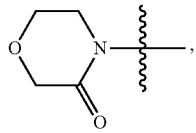

$R^{37}$ is selected from hydrogen, $C_{1-3}$ alkyl, —C(O)—$C_{1-3}$ alkyl, —CO$_2$—$C_{1-6}$ alkyl, —SO$_2$H, —S(O)$_2$-alkyl, —S(O)$_2$—$C_{3-6}$ cycloalkyl, —S(O)$_2$—$C_{2-8}$ heterocyclyl, $C_{1-3}$ haloalkyl, $C_{3-6}$ cycloalkyl, and $C_{2-5}$ heterocyclyl;
or, when $X^4$ is carbon, $R^{34}$ is hydrogen or —O—$C_{1-3}$ alkyl, and $R^{35}$ and $R^{36}$, together with the phenyl ring to which they are bound, form a group selected from:

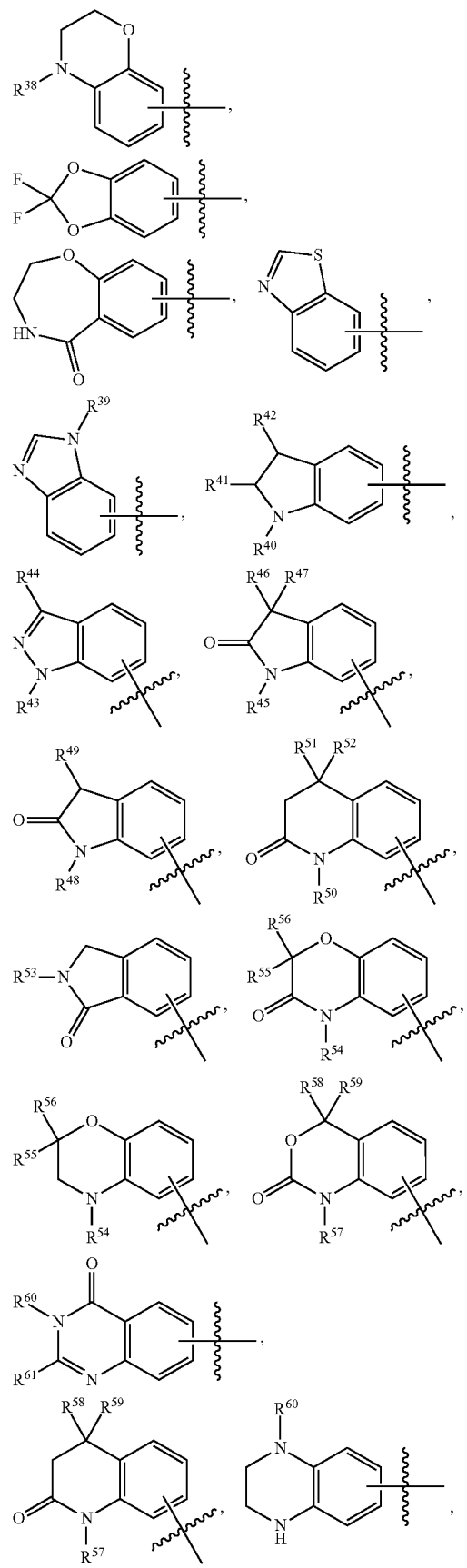

-continued

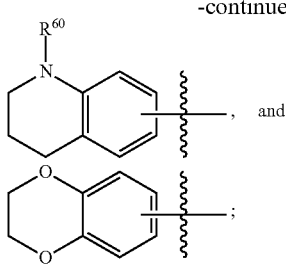, and $R^{41}$ and $R^{42}$ are each independently selected from H, oxo, and $C_{1-3}$ alkyl;

$R^{44}$ and $R^{61}$ are each independently selected from H and $C_{1-3}$ alkyl;

$R^{38}$, $R^{39}$, $R^{40}$, $R^{43}$, $R^{45}$, $R^{48}$, $R^{49}$, $R^{50}$, $R^{53}$, $R^{54}$, $R^{57}$, $R^{60}$, and $R^{60}$, are each independently selected from H, $C_{3-6}$ cycloalkyl, $C_{2-5}$ heterocyclyl, and $C_{1-4}$ alkyl, wherein the $C_{1-4}$ alkyl is optionally substituted by one, two, or three substituents selected from OH, halogen, —$NH_2$, —$NH(C_{1-3}$ alkyl), and —$N(C_{1-3}$ alkyl$)_2$;

$R^{46}$, $R^{47}$, $R^{51}$, $R^{52}$, $R^{55}$, $R^{56}$, $R^{58}$, and $R^{59}$ are independently selected from H, halo, $C_{1-3}$ alkyl, oxo, and =N—O—$C_{1-3}$ alkyl;

or, independently, each of the adjacent pairs of substituents $R^{46}$ and $R^{47}$, $R^{51}$ and $R^{52}$, $R^{55}$ and $R^{56}$, and $R^{58}$ and $R^{59}$, respectively:

a) together with the carbon atom to which they are bound, form a three-, four-, five-, or six-membered spirocycle optionally containing one or two ring heteroatoms selected from nitrogen and oxygen, wherein each spirocycle ring nitrogen atom is substituted with one substituent selected from hydrogen, $C_{1-3}$ alkyl, —C(O)—$C_{1-3}$ alkyl, $C_{1-3}$ haloalkyl, $C_{3-6}$ cycloalkyl, and $C_{2-5}$ heterocyclyl; or b) form an oxo or a $C_{1-3}$ alkyloxyimino group;

or, when $X^4$ is nitrogen, $R^{34}$ is hydrogen or —O—$C_{1-3}$ alkyl, and $R^{35}$ and $R^{36}$, together with the phenyl ring to which they are bound, form a group of the formula:

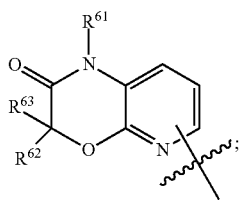

$R^{61}$ is selected from H, $C_{3-6}$ cycloalkyl, $C_{2-5}$ heterocyclyl, and $C_{1-4}$ alkyl, wherein the $C_{1-4}$ alkyl is optionally substituted by one, two, or three substituents selected from —OH, halogen, —$NH_2$, —$NH(C_{1-3}$ alkyl), and —$N(C_{1-3}$ alkyl$)_2$;

$R^{62}$ and $R^{63}$ are independently hydrogen or $C_{1-3}$ alkyl, or $R^{62}$ and $R^{63}$ together with the carbon atom to which they are bound:

a) form a three-, four-, five-, or six-membered spirocycle optionally containing one or two ring heteroatoms selected from nitrogen and oxygen, wherein each spirocycle ring nitrogen atom is substituted with one substituent selected from hydrogen, $C_{1-3}$ alkyl, $C_{3-6}$ cycloalkyl, and $C_{2-5}$ heterocyclyl; or b) form an oxo or a $C_{1-3}$ alkyloxyimino group.

Another embodiment comprises a compound of Formula VIa, or a pharmaceutically acceptable salt thereof, as defined above, wherein $R^{34}$, $R^{35}$, and $R^{36}$ are each, independently, selected from hydrogen, $C_{1-3}$ alkyl, and —O—$C_{1-3}$ alkyl.

Still another embodiment comprises a compound of Formula VIa, or a pharmaceutically acceptable salt thereof, as defined above, wherein $R^{34}$, $R^{35}$, and $R^{36}$ are each, independently, selected from hydrogen and —O—$C_{1-3}$ alkyl.

A further embodiment comprises a compound of Formula VIa, or a pharmaceutically acceptable salt thereof, as defined above, wherein $R^{34}$, $R^{35}$, and $R^{36}$ are each, independently, selected from hydrogen and —O—$CH_3$.

Another embodiment comprises a compound of Formula VIa, or a pharmaceutically acceptable salt thereof, as defined above, wherein $R^{34}$ and $R^{35}$ are —O—$CH_3$ and $R^{36}$ is selected from hydrogen and —O—$CH_3$.

Also provided is an embodiment comprising a compound of Formula VIa, or a pharmaceutically acceptable salt thereof, wherein:

$R^{1b}$ is selected from hydrogen, $C_{1-3}$ haloalkyl, $C_{1-3}$ alkyl, $C_{3-6}$ cycloalkyl, and $C_{2-5}$ heterocyclyl; $R^2$ is H or $CH_3$; $R^3$ is $CH_3$; $R^4$ is H;

$R^{34}$, $R^{35}$, and $R^{36}$ are each, independently, selected from hydrogen, $CH_3$, —O—$CH_3$, —CN, halogen, —$SO_2$—$CH_3$, —$NH_2$, —$NH(CH_3)$, and —$N(CH_3)_2$;

or $R^{34}$ and $R^{35}$ are independently hydrogen or —O—$CH_3$, and $R^{36}$ is selected from:

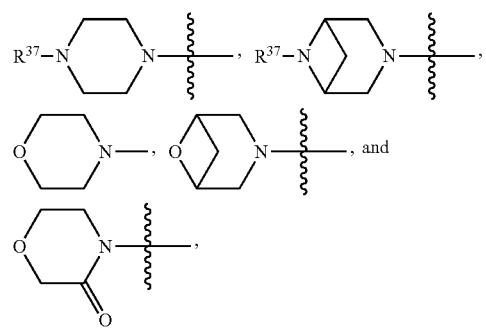

$R^{37}$ is selected from hydrogen, $CH_3$, —C(O)—$C_{1-3}$ alkyl, —$CO_2$—$C_{1-6}$ alkyl, —$SO_2H$, and —$SO_2$—$CH_3$;

or $R^{34}$ is hydrogen or —O—$CH_3$ and $R^{35}$ and $R^{36}$, together with the phenyl ring to which they are bound, form a group selected from:

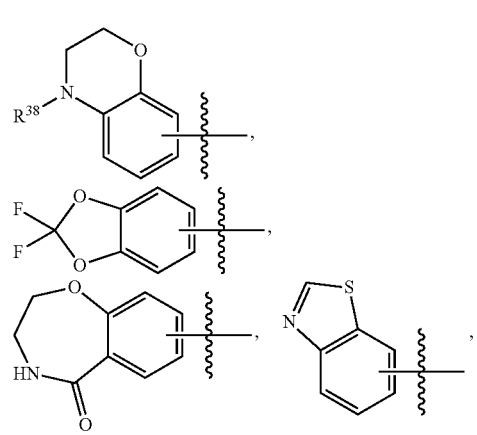

-continued

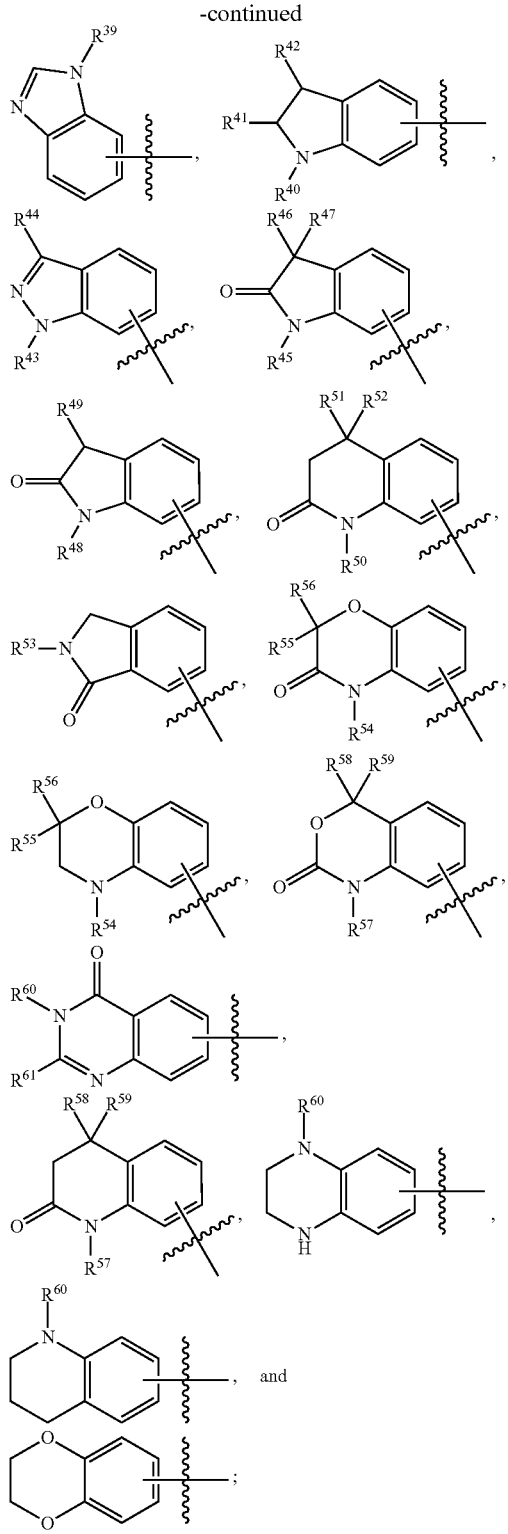

$R^{38}$ is selected from hydrogen and $CH_3$;

$R^{39}$ is selected from hydrogen and $CH_3$;

$R^{41}$, $R^{42}$, $R^{44}$, $R^{46}$, $R^{47}$, $R^{51}$, $R^{52}$, $R^{55}$, $R^{56}$, $R^{58}$, $R^{59}$, and $R^{61}$ are each independently selected from H and $C_{1-3}$ alkyl;

$R^{40}$, $R^{43}$, $R^{45}$, $R^{50}$, $R^{53}$, $R^{54}$, $R^{57}$, $R^{60}$, and $R^{60}$ are each independently selected from H, $C_{3-6}$ cycloalkyl, $C_{2-5}$ heterocyclyl, and $C_{1-4}$ alkyl, wherein the $C_{1-4}$ alkyl is optionally substituted by one, two, or three substituents selected from —OH, halogen, —$NH_2$, —$NH(C_{1-3}$ alkyl), and —$N(C_{1-3}$ alkyl)$_2$;

or, independently, each of the adjacent pairs of substituents $R^{46}$ and $R^{47}$, and $R^{51}$ and $R^{52}$, $R^{55}$ and $R^{56}$, and $R^{58}$ and $R^{59}$, respectively, together with the carbon atom to which they are bound, form a three-, four-, five-, or six-membered spirocycle optionally containing one ring nitrogen atom, wherein the spirocycle ring nitrogen atom is substituted with one substituent selected from hydrogen, $C_{1-3}$ alkyl, $C_{3-6}$ cycloalkyl, and $C_{2-5}$ heterocyclyl.

A further embodiment comprises a compound of Formula VIa, or a pharmaceutically acceptable salt thereof, wherein $R^{1b}$ is selected from hydrogen, $C_{1-3}$ haloalkyl, $C_{1-3}$ alkyl, $C_{3-6}$ cycloalkyl, and $C_{2-5}$ heterocyclyl; $R^2$ is H or $CH_3$; $R^3$ is $CH_3$; $R^4$ is H; $R^{34}$ and $R^{35}$ are —O—$CH_3$; and $R^{36}$ is selected from hydrogen and —O—$CH_3$.

Within each of the embodiments comprising a compound of Formula VIa, or a pharmaceutically acceptable salt thereof, there is a further embodiment wherein $X^4$ is carbon and all other variables are as described for the particular embodiment. Within each of the embodiments comprising a compound of Formula VIa, or a pharmaceutically acceptable salt thereof, there is still a further embodiment wherein $X^4$ is nitrogen and all other variables are as described for the particular embodiment.

Three additional embodiments independently comprise compounds of Formula VIb, VIc, and VId, or a pharmaceutically acceptable salt thereof:

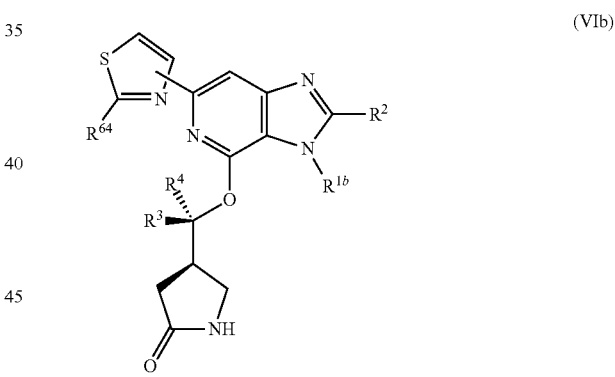

(VIb)

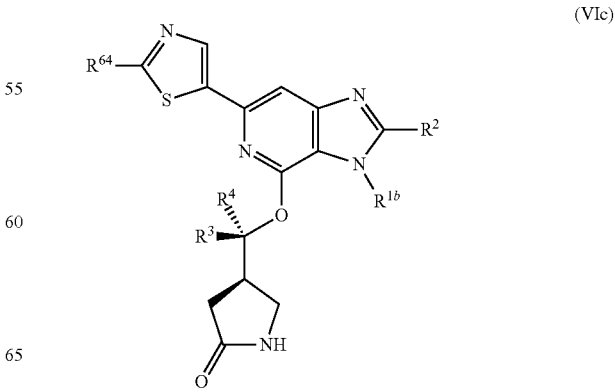

(VIc)

-continued

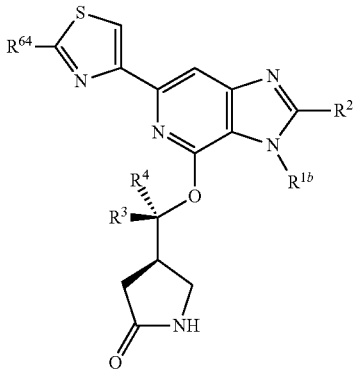

(VId)

wherein, in each embodiment:
$R^{1b}$ is selected from hydrogen, halo, $C_{1-3}$ haloalkyl, $C_{1-6}$ alkyl, $C_{3-6}$ cycloalkyl, and $C_{2-5}$ heterocyclyl;
$R^2$ is H or $C_{1-3}$ alkyl;
$R^3$ is $C_{1-6}$ alkyl;
$R^4$ is H; and
$R^{64}$ is hydrogen or $C_{1-6}$ alkyl.

Still three more embodiments independently comprise compounds of Formula VIb, Formula VIc, and Formula VId, or a pharmaceutically acceptable salt thereof, as defined above, wherein in each embodiment $R^{1b}$ is selected from $C_{1-3}$ haloalkyl and $C_{1-6}$ alkyl; $R^2$ is H; $R^3$ is —CH$_3$; $R^4$ is H; and $R^{64}$ is hydrogen or $C_{1-6}$ alkyl.

In one embodiment of Formula VI, the compound is selected from:
(R)-4-((R)-1-(6-(1-tert-butyl-1H-pyrazol-4-yl)-3-methyl-3H-imidazo[4,5-c]pyridin-4-yloxy)ethyl)pyrrolidin-2-one;
(R)-4-((R)-1-(6-(1-tert-butyl-1H-pyrazol-4-yl)-3-(difluoromethyl)-3H-imidazo[4,5-c]pyridin-4-yloxy)ethyl)pyrrolidin-2-one;
(R)-4-((S)-1-(6-(1-tert-butyl-1H-pyrazol-4-yl)-3-methyl-3H-imidazo[4,5-c]pyridin-4-yloxy)-2-fluoroethyl)pyrrolidin-2-one;
(R)-4-((S)-1-(6-(1-tert-butyl-1H-pyrazol-4-yl)-3-methyl-3H-imidazo[4,5-c]pyridin-4-yloxy)-2-methoxyethyl)pyrrolidin-2-one;
(R)-4-((R)-1-(6-(1-(2,2-difluoroethyl)-1H-pyrazol-4-yl)-3-methyl-3H-imidazo[4,5-c]pyridin-4-yloxy)ethyl)pyrrolidin-2-one;
(R)-4-((R)-1-(6-(1-cyclopropyl-1H-pyrazol-4-yl)-3-methyl-3H-imidazo[4,5-c]pyridin-4-yloxy)ethyl)pyrrolidin-2-one;
(R)-4-((R)-1-(6-(1-cyclobutyl-1H-pyrazol-4-yl)-3-methyl-3H-imidazo[4,5-c]pyridin-4-yloxy)ethyl)pyrrolidin-2-one;
(R)-4-((R)-1-(6-(1-isobutyl-1H-pyrazol-4-yl)-3-methyl-3H-imidazo[4,5-c]pyridin-4-yloxy)ethyl)pyrrolidin-2-one;
(R)-4-((R)-1-(6-(1,5-dimethyl-1H-pyrazol-4-yl)-3-methyl-3H-imidazo[4,5-c]pyridin-4-yloxy)ethyl)pyrrolidin-2-one;
(R)-4-((R)-1-(3-methyl-6-(1-(oxetan-3-yl)-1H-pyrazol-4-yl)-3H-imidazo[4,5-c]pyridin-4-yloxy)ethyl)pyrrolidin-2-one;
(R)-4-((R)-1-(6-(1-(2-fluoroethyl)-1H-pyrazol-4-yl)-3-methyl-3H-imidazo[4,5-c]pyridin-4-yloxy)ethyl)pyrrolidin-2-one;
(R)-4-((R)-1-(3-methyl-6-(1-(2,2,2-trifluoroethyl)-1H-pyrazol-4-yl)-3H-imidazo[4,5-c]pyridin-4-yloxy)ethyl)pyrrolidin-2-one;
(R)-4-((S)-1-(6-(1-tert-butyl-1H-pyrazol-4-yl)-3-methyl-3H-imidazo[4,5-c]pyridin-4-yloxy)-2,2-difluoroethyl)pyrrolidin-2-one;
(R)-4-((R)-1-(6-(1-isopropyl-1H-pyrazol-4-yl)-3-methyl-3H-imidazo[4,5-c]pyridin-4-yloxy)ethyl)pyrrolidin-2-one;
(R)-4-((R)-1-(3-methyl-6-(1-(tetrahydro-2H-pyran-4-yl)-1H-pyrazol-4-yl)-3H-imidazo[4,5-c]pyridin-4-yloxy)ethyl)pyrrolidin-2-one;
(R)-4-((R)-1-(3-methyl-6-(1-methyl-1H-pyrazol-4-yl)-3H-imidazo[4,5-c]pyridin-4-yloxy)ethyl)pyrrolidin-2-one;
(R)-4-((R)-1-(6-(1-tert-butyl-1H-pyrazol-4-yl)-3-methyl-3H-imidazo[4,5-c]pyridin-4-yloxy)-3-methoxypropyl)pyrrolidin-2-one;
(R)-4-((R)-1-(6-(1-tert-butyl-1H-pyrazol-4-yl)-3-methyl-3H-imidazo[4,5-c]pyridin-4-yloxy)propyl)pyrrolidin-2-one;
(R)-4-((R)-1-(3-methyl-6-(6-morpholinopyridin-3-yl)-3H-imidazo[4,5-c]pyridin-4-yloxy)ethyl)pyrrolidin-2-one; and
(R)-4-((R)-1-(6-(5,6-dimethoxypyridin-2-yl)-3-methyl-3H-imidazo[4,5-c]pyridin-4-yloxy)ethyl)pyrrolidin-2-one;
or a pharmaceutically acceptable salt, ester, stereoisomer, mixture of stereoisomers or tautomer thereof.

In another embodiment of Formula VI, the compound is selected from:
(R)-4-((R)-1-(6-(3,4-dimethoxyphenyl)-3-methyl-3H-imidazo[4,5-c]pyridin-4-yloxy)ethyl)pyrrolidin-2-one;
(R)-4-((R)-1-(6-(3,4-dimethoxyphenyl)-3-ethyl-3H-imidazo[4,5-c]pyridin-4-yloxy)ethyl)pyrrolidin-2-one;
(R)-4-((S)-1-(6-(3,4-dimethoxyphenyl)-3-methyl-3H-imidazo[4,5-c]pyridin-4-yloxy)ethyl)pyrrolidin-2-one;
(R)-4-((R)-1-(3-cyclopropyl-6-(3,4-dimethoxyphenyl)-3H-imidazo[4,5-c]pyridin-4-yloxy)ethyl)pyrrolidin-2-one;
(R)-4-((R)-1-(3-(difluoromethyl)-6-(3,4-dimethoxyphenyl)-3H-imidazo[4,5-c]pyridin-4-yloxy)ethyl)pyrrolidin-2-one;
(R)-4-((R)-1-(3-methyl-6-(3,4,5-trimethoxyphenyl)-3H-imidazo[4,5-c]pyridin-4-yloxy)ethyl)pyrrolidin-2-one;
(R)-4-((6-(3,4-dimethoxyphenyl)-3-methyl-3H-imidazo[4,5-c]pyridin-4-yloxy)methyl)pyrrolidin-2-one;
(R)-4-((R)-2-cyclopropyl-1-(6-(3,4-dimethoxyphenyl)-3-methyl-3H-imidazo[4,5-c]pyridin-4-yloxy)ethyl)pyrrolidin-2-one;
(R)-4-((R)-1-(3-methyl-6-(4-morpholinophenyl)-3H-imidazo[4,5-c]pyridin-4-yloxy)ethyl)pyrrolidin-2-one;
(R)-4-((R)-1-(6-(3,4-dimethoxyphenyl)-3H-imidazo[4,5-c]pyridin-4-yloxy)ethyl)pyrrolidin-2-one;
(R)-4-((R)-1-(6-(3,4-dimethoxyphenyl)-3-isopropyl-3H-imidazo[4,5-c]pyridin-4-yloxy)ethyl)pyrrolidin-2-one;
4-(3-methyl-4-((R)-1-((R)-5-oxopyrrolidin-3-yl)ethoxy)-3H-imidazo[4,5-c]pyridin-6-yl)benzonitrile;
(4R)-4-((1R)-1-(6-(3,4-dimethoxyphenyl)-2,3-dimethyl-3a,7a-dihydro-3H-imidazo[4,5-c]pyridin-4-yloxy)ethyl)pyrrolidin-2-one;
(R)-4-((R)-1-(6-(3,4-dimethoxyphenyl)-3-(2,2,2-trifluoroethyl)-3H-imidazo[4,5-c]pyridin-4-yloxy)ethyl)pyrrolidin-2-one;
(R)-4-((R)-1-(6-(3,4-dimethoxyphenyl)-3-(oxetan-3-yl)-3H-imidazo[4,5-c]pyridin-4-yloxy)ethyl)pyrrolidin-2-one;
(R)-4-((R)-1-(3-(2,2-difluoroethyl)-6-(3,4-dimethoxyphenyl)-3H-imidazo[4,5-c]pyridin-4-yloxy)ethyl)pyrrolidin-2-one;
(R)-4-((R)-1-(6-(3,4-dimethoxyphenyl)-3-(fluoromethyl)-3H-imidazo[4,5-c]pyridin-4-yloxy)ethyl)pyrrolidin-2-one;

(R)-4-((R)-1-(6-(3-fluoro-4-methoxyphenyl)-3-methyl-3H-imidazo[4,5-c]pyridin-4-yloxy)ethyl)pyrrolidin-2-one;

2-methoxy-5-(3-methyl-4-((R)-1-((R)-5-oxopyrrolidin-3-yl)ethoxy)-3H-imidazo[4,5-c]pyridin-6-yl)benzonitrile2-methoxy-5-(3-methyl-4-((R)-1-((R)-5-oxopyrrolidin-3-yl)ethoxy)-3H-imidazo[4,5-c]pyridin-6-yl)benzonitrile; and (R)-4-((R)-1-(3-methyl-6-phenyl-3H-imidazo[4,5-c]pyridin-4-yloxy)ethyl)pyrrolidin-2-one;

(R)-4-((R)-1-(3-methyl-6-(3-morpholinophenyl)-3H-imidazo[4,5-c]pyridin-4-yloxy)ethyl)pyrrolidin-2-one;

or a pharmaceutically acceptable salt, ester, stereoisomer, mixture of stereoisomers or tautomer thereof.

In yet another embodiment of Formula VI, the compound is selected from:

(R)-4-((R)-1-(6-(2-tert-butylthiazol-4-yl)-3-methyl-3H-imidazo[4,5-c]pyridin-4-yloxy)ethyl)pyrrolidin-2-one;

(R)-4-((R)-1-(3-methyl-6-(pyrazolo[1,5-a]pyridin-3-yl)-3H-imidazo[4,5-c]pyridin-4-yloxy)ethyl)pyrrolidin-2-one;

(R)-4-((R)-1-(6-(2,2-difluorobenzo[d][1,3]dioxol-5-yl)-3-methyl-3H-imidazo[4,5-c]pyridin-4-yloxy)ethyl)pyrrolidin-2-one;

(R)-4-((R)-1-(3-methyl-6-(4-methyl-3,4-dihydro-2H-benzo[b][1,4]oxazin-6-yl)-3H-imidazo[4,5-c]pyridin-4-yloxy)ethyl)pyrrolidin-2-one;

(R)-4-((R)-1-(6-(3,4-dihydro-2H-benzo[b][1,4]oxazin-6-yl)-3-methyl-3H-imidazo[4,5-c]pyridin-4-yloxy)ethyl)pyrrolidin-2-one;

(R)-4-((R)-1-(6-(2-tert-butylthiazol-5-yl)-3-methyl-3H-imidazo[4,5-c]pyridin-4-yloxy)ethyl)pyrrolidin-2-one;

(R)-4-((R)-1-(6-cyclohexenyl-3-methyl-3H-imidazo[4,5-c]pyridin-4-yloxy)ethyl)pyrrolidin-2-one;

4-(3-methyl-4-((R)-1-((R)-5-oxopyrrolidin-3-yl)ethoxy)-3H-imidazo[4,5-c]pyridin-6-yl)pyridin-2(1H)-one;

7-(3-methyl-4-((R)-1-((R)-5-oxopyrrolidin-3-yl)ethoxy)-3H-imidazo[4,5-c]pyridin-6-yl)-3,4-dihydrobenzo[f][1,4]oxazepin-5(2H)-one;

(R)-4-((R)-1-(3-methyl-6-(4-methyl-3,4-dihydro-2H-benzo[b][1,4]oxazin-7-yl)-3H-imidazo[4,5-c]pyridin-4-yloxy)ethyl)pyrrolidin-2-one (R)-4-((R)-1-((6-(benzo[d]thiazol-5-yl)-3-methyl-3H-imidazo[4,5-c]pyridin-4-yl)oxy)ethyl)pyrrolidin-2-one;

(R)-4-((R)-1-((3-methyl-6-(2-methylbenzo[d]thiazol-5-yl)-3H-imidazo[4,5-c]pyridin-4-yl)oxy)ethyl)pyrrolidin-2-one;

(R)-4-((R)-1-((3-methyl-6-(1-methyl-1H-indazol-5-yl)-3H-imidazo[4,5-c]pyridin-4-yl)oxy)ethyl)pyrrolidin-2-one;

(R)-4-((R)-1-((3-methyl-6-(1-methyl-1H-indazol-6-yl)-3H-imidazo[4,5-c]pyridin-4-yl)oxy)ethyl)pyrrolidin-2-one; and (R)-4-((R)-1-((6-(1,3-dimethyl-1H-indazol-5-yl)-3-methyl-3H-imidazo[4,5-c]pyridin-4-yl)oxy)ethyl)pyrrolidin-2-one;

or a pharmaceutically acceptable salt, ester, stereoisomer, mixture of stereoisomers or tautomer thereof.

In yet another embodiment of Formula VI, the compound is selected from:

(R)-4-((R)-1-((3-methyl-6-(4-(4-(methylsulfonyl)piperazin-1-yl)phenyl)-3H-imidazo[4,5-c]pyridin-4-yl)oxy)ethyl)pyrrolidin-2-one;

(R)-4-((R)-1-((6-(3,4-dimethoxyphenyl)-3-methyl-3H-imidazo[4,5-c]pyridin-4-yl)oxy)propyl)pyrrolidin-2-one;

(R)-4-((S)-1-((6-(3,4-dimethoxyphenyl)-3-methyl-3H-imidazo[4,5-c]pyridin-4-yl)oxy)-2,2,2-trifluoroethyl)pyrrolidin-2-one;

(R)-4-((R)-1-((3-methyl-6-(4-(4-(oxetan-3-yl)piperazin-1-yl)phenyl)-3H-imidazo[4,5-c]pyridin-4-yl)oxy)ethyl)pyrrolidin-2-one;

(R)-4-((R)-1-((6-(4-(4-acetylpiperazin-1-yl)phenyl)-3-methyl-3H-imidazo[4,5-c]pyridin-4-yl)oxy)ethyl)pyrrolidin-2-one;

(R)-7-((R)-1-((3-(difluoromethyl)-6-(3,4-dimethoxyphenyl)-3H-imidazo[4,5-c]pyridin-4-yl)oxy)ethyl)-5-azaspiro[2.4]heptan-4-one;

N,N-dimethyl-4-(3-methyl-4-((R)-1-((R)-5-oxopyrrolidin-3-yl)ethoxy)-3H-imidazo[4,5-c]pyridin-6-yl)benzenesulfonamide;

(R)-4-((R)-1-((3-(difluoromethyl)-6-(3,4-dimethoxyphenyl)-2-methyl-3H-imidazo[4,5-c]pyridin-4-yl)oxy)ethyl)pyrrolidin-2-one;

(R)-4-((R)-1-((3-cyclopropyl-6-(3,4-dimethoxyphenyl)-2-methyl-3H-imidazo[4,5-c]pyridin-4-yl)oxy)ethyl)pyrrolidin-2-one; and (R)-4-((R)-1-((6-(3,4-dimethoxyphenyl)-3-isopropyl-2-methyl-3H-imidazo[4,5-c]pyridin-4-yl)oxy)ethyl)pyrrolidin-2-one;

or a pharmaceutically acceptable salt, ester, stereoisomer, mixture of stereoisomers or tautomer thereof.

Three additional embodiments independently comprise compounds of Formula VIe, VIf, and VIg, or a pharmaceutically acceptable salt thereof:

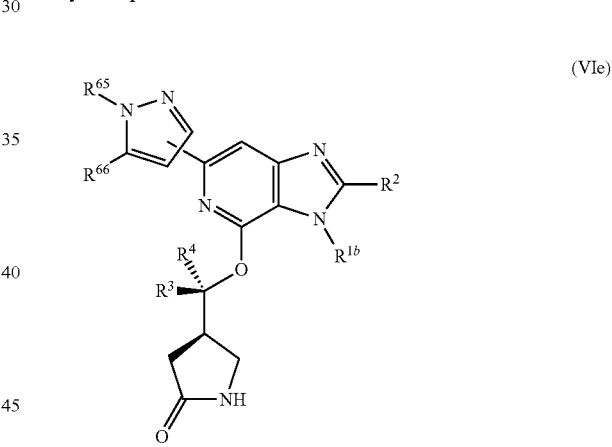

(VIe)

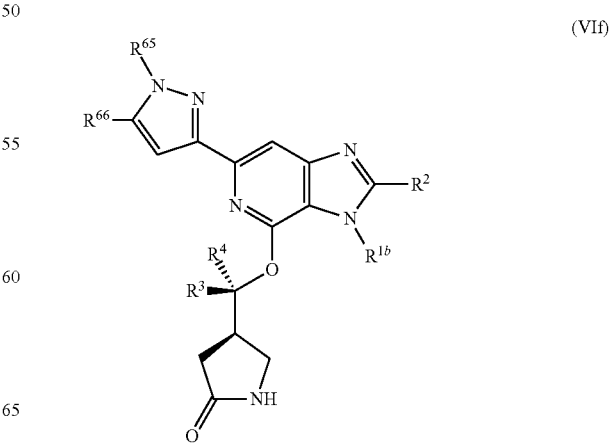

(VIf)

-continued (VIg)

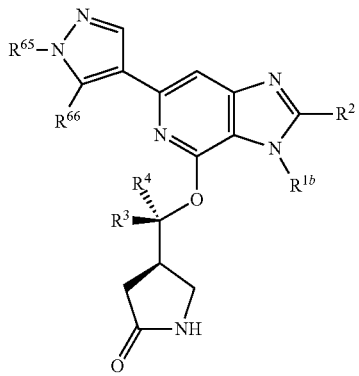

wherein:
$R^{1b}$ is selected from hydrogen, halo, $CH_2F$, $CHF_2$, $CF_3$, $C_{1-6}$ alkyl, $C_{3-6}$ cycloalkyl, and $C_{2-5}$ heterocyclyl;
$R^2$ is H or $C_{1-3}$ alkyl;
$R^3$ is selected from $C_{1-3}$ alkyl, $C_{2-3}$ alkenyl, —$CH_2$—O—$CH_3$, —$CH_2$—$CH_2$—O—$CH_3$, —$CH_2CH_2F$, —$CH_2CHF_2$, and —$CH_2CF_3$;
$R^4$ is H; and
$R^{65}$ is selected from hydrogen, $C_{1-6}$ alkyl, $C_{3-6}$ cycloalkyl, $C_{2-6}$ heterocyclyl, —$CH_2CH_2F$, —$CH_2CHF_2$, and —$CH_2CF_3$;
$R^{66}$ is selected from hydrogen and $C_{1-3}$ alkyl;
or $R^{65}$ and $R^{66}$, together with the pyrazole ring to which they are bound, form a group of the formula:

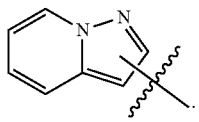

Still three more embodiments independently comprise compounds of Formula VIe, Formula VIf, and Formula VIg, or a pharmaceutically acceptable salt thereof, as defined above, wherein in each embodiment $R^{1b}$ is selected from methyl, $CH_2F$, $CHF_2$, and $CF_3$;
$R^2$ is H; $R^3$ is selected from methyl, ethyl, —$CH_2$—CH═$CH_2$, and —$CH_2$—$CH_2$—O—$CH_3$; $R^4$ is H; $R^{65}$ is selected from hydrogen, $C_{1-6}$ alkyl, $C_{3-6}$ cycloalkyl, —$CH_2CH_2F$, —$CH_2CHF_2$, —$CH_2CF_3$:

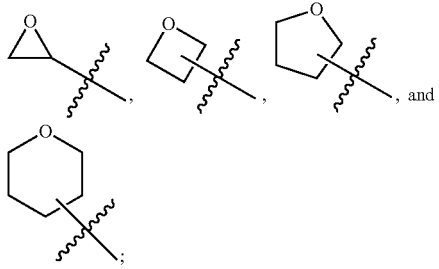

$R^{66}$ is selected from hydrogen and methyl;
or $R^{65}$ and $R^{66}$, together with the pyrazole ring to which they are bound, form a pyrazolo[1,5-a]pyridinyl group of the formula:

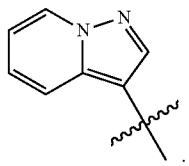 [SMILES: *c1cnn2ccccc12]

Another embodiment comprises a compound of Formula VIh, or a pharmaceutically acceptable salt thereof:

(VIh)

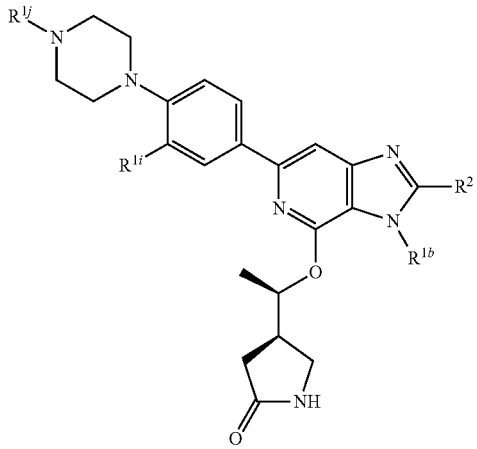

wherein:
$R^{1b}$ is selected from hydrogen, methyl, cyclopropyl, $CH_2F$, $CHF_2$, and $CF_3$;
$R^2$ is hydrogen or $C_{1-3}$ alkyl;
$R^{1i}$ is selected from H and methoxy; and
$R^{1j}$ is selected from H, $C_{1-4}$ alkyl, $C_{1-3}$ haloalkyl, —$SO_2H$, —$SO_2(C_{1-3}$ alkyl), $C_{1-4}$ alkyl, —C(O)—$C_{1-4}$ alkyl, $C_{3-6}$ cycloalkyl, and $C_{2-6}$ heterocyclyl.

Another embodiment comprises a compound of Formula VIh, or a pharmaceutically acceptable salt thereof, wherein $R^{1b}$ is selected from hydrogen, methyl, cyclopropyl, $CH_2F$, $CHF_2$, and $CF_3$; $R^2$ is hydrogen or methyl; $R^{1i}$ is selected from H and methoxy; and $R^{1j}$ is selected from H, $C_{1-4}$ alkyl, —$CH_2F$, —$CHF_2$, —$CF_3$, —$CH_2CH_2F$, —$CH_2CHF_2$, —$CH_2CF_3$, $SO_2H$, —$SO_2(C_{1-3}$ alkyl), $C_{1-4}$ alkyl, —C(O)—$C_{1-4}$ alkyl, and $C_{2-6}$ heterocyclyl group selected from oxiranyl, oxetanyl, tetrahydrofuranyl, and tetrahydro-2H-pyranyl.

Another embodiment comprises a compound of Formula VIi, or a pharmaceutically acceptable salt thereof:

(VIi)

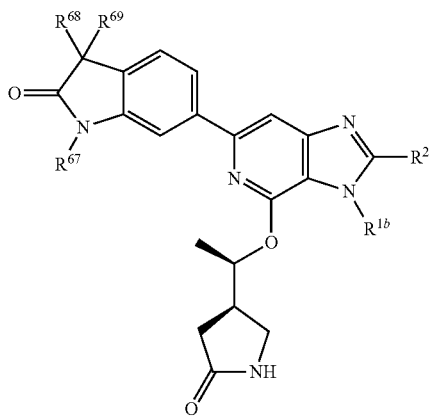

wherein:

$R^{1b}$ is selected from hydrogen, halo, $C_{1-3}$ haloalkyl, $C_{1-6}$ alkyl, $C_{3-6}$ cycloalkyl, and $C_{2-5}$ heterocyclyl;

$R^2$ is H or $C_{1-3}$ alkyl;

$R^3$ is $C_{1-6}$ alkyl;

$R^4$ is H;

$R^{67}$ is selected from H, $C_{3-6}$ cycloalkyl, $C_{2-5}$ heterocyclyl, and $C_{1-4}$ alkyl, wherein the $C_{1-4}$ alkyl is optionally substituted by one, two, or three substituents selected from —OH, halogen, —NH$_2$, —NH($C_{1-3}$ alkyl), and —N($C_{1-3}$ alkyl)$_2$;

$R^{68}$ and $R^{69}$ are each independently selected from H, halo, and $C_{1-3}$ alkyl;

or $R^{68}$ and $R^{69}$, together with the carbon atom to which they are bound, form a three-, four-, five-, or six-membered spirocycle containing zero, one, or two ring heteroatoms selected from nitrogen and oxygen, wherein each spirocycle ring nitrogen atom, when present, is substituted with one substituent selected from hydrogen, $C_{1-3}$ alkyl, —C(O)—$C_{1-3}$ alkyl, $C_{1-3}$ haloalkyl, $C_{3-6}$ cycloalkyl, and $C_{2-5}$ heterocyclyl; or $R^{68}$ and $R^{69}$ together form an oxo or a $C_{1-3}$ alkyloxyimino group.

A further embodiment comprises a compound of Formula Vii wherein $R^2$ is hydrogen and $R^{1b}$, $R^3$, $R^4$, R45, and R46 are as defined above, or a pharmaceutically acceptable salt thereof.

Another embodiment comprises a compound of Formula VIi, or a pharmaceutically acceptable salt thereof, wherein:

$R^{1b}$ is selected from $C_{3-6}$ cycloalkyl and $C_{1-3}$ haloalkyl;

$R^2$ is hydrogen;

$R^{67}$ is selected from H, $C_{3-6}$ cycloalkyl, $C_{2-5}$ heterocyclyl, and $C_{1-4}$ alkyl, wherein the $C_{1-4}$ alkyl is optionally substituted by one, two, or three substituents selected from —OH, fluorine, —NH$_2$, —NH($C_{1-3}$ alkyl), and —N($C_{1-3}$ alkyl)$_2$;

$R^{68}$ and $R^{69}$ are each independently selected from H, fluorine, and methyl;

or $R^{68}$ and $R^{69}$, together with the carbon atom to which they are bound, form a three-, four-, five-, or six-membered spirocycle containing:

a) zero ring heteroatoms; or b) one nitrogen heteroatom wherein the spirocycle ring nitrogen heteroatom is substituted with one substituent selected from hydrogen, $C_{1-3}$ alkyl, —C(O)—$C_{1-3}$ alkyl, $C_{1-3}$ haloalkyl, $C_{3-6}$ cycloalkyl, and $C_{2-5}$ heterocyclyl; or c) one or two oxygen heteroatoms; or $R^{68}$ and $R^{69}$ together form an oxo or a $C_{1-3}$ alkyloxyimino group.

Two separate embodiments independently comprise a compound of Formula VIj or Formula VIk, respectively, or a pharmaceutically acceptable salt thereof:

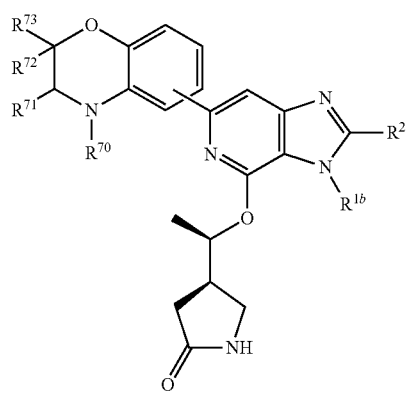

(VIj)

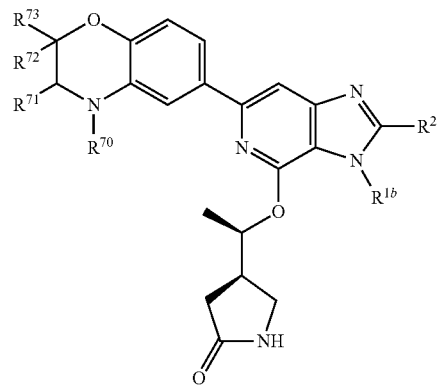

(VIk)

Wherein in each embodiment:

$R^{1b}$ is selected from hydrogen, halo, $C_{1-3}$ haloalkyl, $C_{1-6}$ alkyl, $C_{3-6}$ cycloalkyl, and $C_{2-5}$ heterocyclyl;

$R^2$ is H or $C_{1-3}$ alkyl;

$R^{70}$ is selected from H, $C_{3-6}$ cycloalkyl, $C_{2-5}$ heterocyclyl, and $C_{1-4}$ alkyl, wherein the $C_{1-4}$ alkyl is optionally substituted by one, two, or three substituents selected from —OH, halogen, —NH$_2$, —NH($C_{1-3}$ alkyl), and —N($C_{1-3}$ alkyl)$_2$;

$R^{71}$ is H or oxo; and $R^{72}$ and $R^{73}$ are each independently selected from H, halo, and $C_{1-3}$ alkyl;

or $R^{72}$ and $R^{73}$, together with the carbon atom to which they are bound, form a three-, four-, five-, or six-membered spirocycle containing zero, one, or two ring heteroatoms selected from nitrogen and oxygen, wherein each spirocycle ring nitrogen atom, when present, is substituted with one substituent selected from hydrogen, $C_{1-3}$ alkyl, —C(O)—$C_{1-3}$ alkyl, $C_{1-3}$ haloalkyl, $C_{3-6}$ cycloalkyl, and $C_{2-5}$ heterocyclyl; or $R^{72}$ and $R^{73}$ together form an oxo or a $C_{1-3}$ alkyloxyimino group.

Two further embodiments comprise a compound of Formula VIj or Formula VIk, respectively, wherein in each embodiment $R^2$ is hydrogen and $R^{1b}$, $R^{70}$, $R^{71}$, $R^{72}$, and $R^{73}$ are as defined above, or a pharmaceutically acceptable salt thereof.

Two further embodiments comprise a compound of Formula VIj or Formula VIk, respectively, wherein in each embodiment:

$R^{1b}$ is selected from $C_{1-3}$ fluoroalkyl, $C_{1-4}$ alkyl, and $C_{3-6}$ cycloalkyl;

$R^2$ is hydrogen;

$R^{70}$ is selected from H and $C_{1-4}$ alkyl;

$R^{71}$ is H or oxo; and $R^{72}$ and $R^{73}$ are each independently selected from H, fluoro, and $C_{1-3}$ alkyl;

or $R^{72}$ and $R^{73}$, together with the carbon atom to which they are bound, form a three-, four-, five-, or six-membered spirocycle containing zero heteroatoms.

Two further embodiments comprise a compound of Formula VIj or Formula VIk, respectively, wherein in each embodiment:

$R^{1b}$ is selected from $C_{1-3}$ fluoroalkyl, and $C_{3-6}$ cycloalkyl;

$R^2$ is hydrogen;

$R^{70}$ is selected from H and methyl;

$R^{71}$ is oxo; and $R^{72}$ and $R^{73}$ are each independently selected from H and methyl;

or R² and R⁷³, together with the carbon atom to which they are bound, form a three-, four-, five-, or six-membered spirocycle containing zero heteroatoms.

Representative compounds of the invention are listed in Table A below in its non-isomeric form. The compounds in Table A are named using ChemBioDraw Ultra 12.0 and it should be understood that other names be used to identify compounds of the same structure. Other compounds or radicals may be named with common names, or systematic or non-systematic names. The compounds may also be named using other nomenclature systems and symbols that are commonly recognized in the art of chemistry including, for example, Chemical Abstract Service (CAS) and International Union of Pure and Applied Chemistry (IUPAC). The naming and numbering of the compounds of the present disclosure is illustrated with representative compounds of Formulas I, II, III, IV, V or VI shown in Table A below.

TABLE A

| Representative Compounds | |
|---|---|
| Structure | Name |
| | (R)-4-((R)-1-(6-(3,4-dimethoxyphenyl)-3-methyl-3H-imidazo[4,5-c]pyridin-4-yloxy)ethyl)pyrrolidin-2-one |
| | (R)-4-((S)-1-(6-(3,4-dimethoxyphenyl)-3-methyl-3H-imidazo[4,5-c]pyridin-4-yloxy)ethyl)pyrrolidin-2-one |
| | (R)-4-((R)-1-(3-(difluoromethyl)-6-(3,4-dimethoxyphenyl)-3H-imidazo[4,5-c]pyridin-4-yloxy)ethyl)pyrrolidin-2-one |

TABLE A-continued

Representative Compounds

| Structure | Name |
|---|---|
| 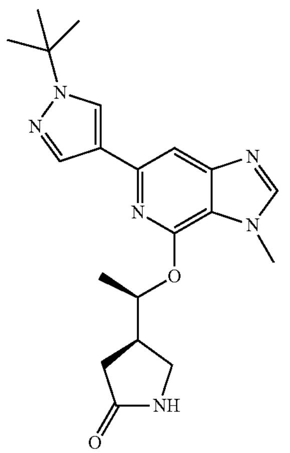 [SMILES: C[C@@H](Oc1nc(-c2cnn(C(C)(C)C)c2)cc2ncn(C)c12)[C@H]1CNC(=O)C1] | (R)-4-((R)-1-(6-(1-tert-butyl-1H-pyrazol-4-yl)-3-methyl-3H-imidazo[4,5-c]pyridin-4-yloxy)ethyl)pyrrolidin-2-one |
| 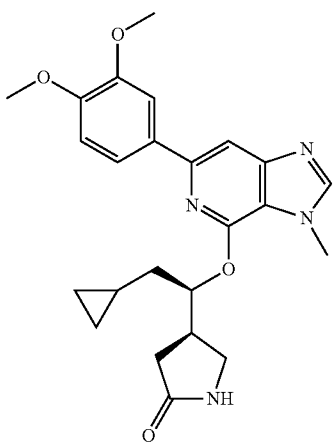 [SMILES: COc1ccc(-c2cc3ncn(C)c3c(O[C@H](CC3CC3)[C@H]3CNC(=O)C3)n2)cc1OC] | (R)-4-((R)-2-cyclopropyl-1-(6-(3,4-dimethoxyphenyl)-3-methyl-3H-imidazo[4,5-c]pyridin-4-yloxy)ethyl)pyrrolidin-2-one |
| 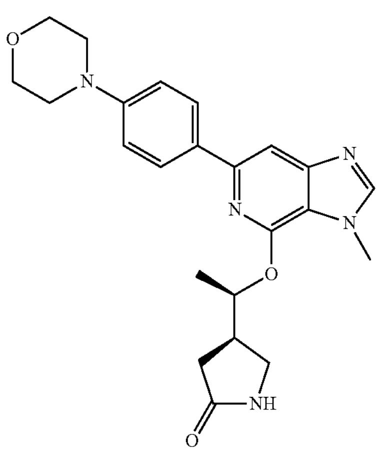 [SMILES: C[C@@H](Oc1nc(-c2ccc(N3CCOCC3)cc2)cc2ncn(C)c12)[C@H]1CNC(=O)C1] | (R)-4-((R)-1-(3-methyl-6-(4-morpholinophenyl)-3H-imidazo[4,5-c]pyridin-4-yloxy)ethyl)pyrrolidin-2-one |

TABLE A-continued

Representative Compounds

| Structure | Name |
|---|---|
| 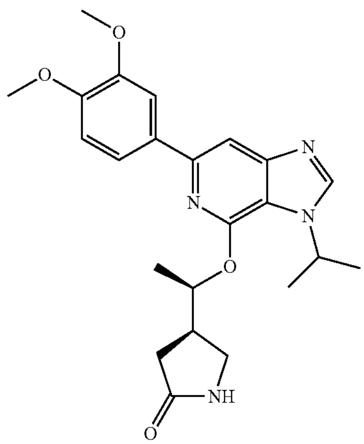 [SMILES: COc1ccc(-c2cc3ncn(C(C)C)c3c(O[C@H](C)[C@H]3CNC(=O)C3)n2)cc1OC] | (R)-4-((R)-1-(6-(3,4-dimethoxyphenyl)-3-isopropyl-3H-imidazo[4,5-c]pyridin-4-yloxy)ethyl)pyrrolidin-2-one |
| 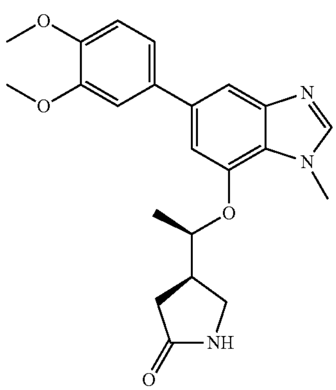 [SMILES: COc1ccc(-c2cc(O[C@H](C)[C@H]3CNC(=O)C3)c3c(c2)ncn3C)cc1OC] | (R)-4-((R)-1-(5-(3,4-dimethoxyphenyl)-1-methyl-1H-benzo[d]imidazol-7-yloxy)ethyl)pyrrolidin-2-one |
| 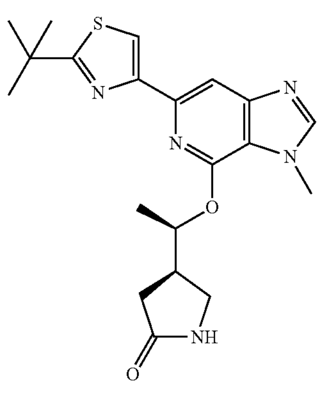 [SMILES: C[C@@H](Oc1nc(-c2csc(C(C)(C)C)n2)cc2ncn(C)c12)[C@H]1CNC(=O)C1] | (R)-4-((R)-1-(6-(2-tert-butylthiazol-4-yl)-3-methyl-3H-imidazo[4,5-c]pyridin-4-yloxy)ethyl)pyrrolidin-2-one |

TABLE A-continued

Representative Compounds

| Structure | Name |
|---|---|
| 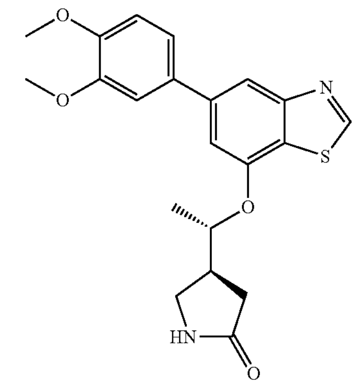 [SMILES: COc1ccc(-c2cc(O[C@@H](C)[C@@H]3CNC(=O)C3)c3scnc3c2)cc1OC] | (R)-4-((R)-1-((5-(3,4-dimethoxyphenyl)benzo[d]thiazol-7-yl)oxy)ethyl)pyrrolidin-2-one |
| 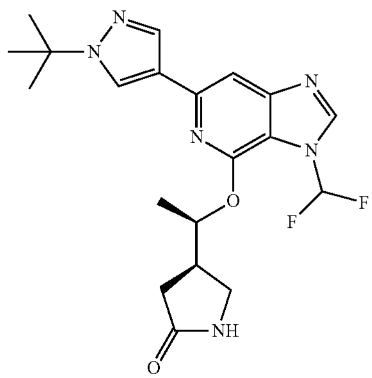 [SMILES: C[C@@H](Oc1nc(-c2cnn(C(C)(C)C)c2)cc2ncn(C(F)F)c12)[C@H]1CNC(=O)C1] | (R)-4-((R)-1-(6-(1-tert-butyl-1H-pyrazol-4-yl)-3-(difluoromethyl)-3H-imidazo[4,5-c]pyridin-4-yloxy)ethyl)pyrrolidin-2-one |
| 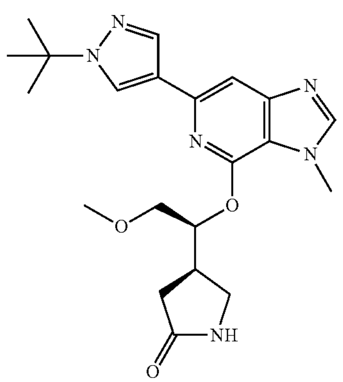 [SMILES: COC[C@@H](Oc1nc(-c2cnn(C(C)(C)C)c2)cc2ncn(C)c12)[C@H]1CNC(=O)C1] | (R)-4-((S)-1-(6-(1-tert-butyl-1H-pyrazol-4-yl)-3-methyl-3H-imidazo[4,5-c]pyridin-4-yloxy)-2-methoxyethyl)pyrrolidin-2-one |
| 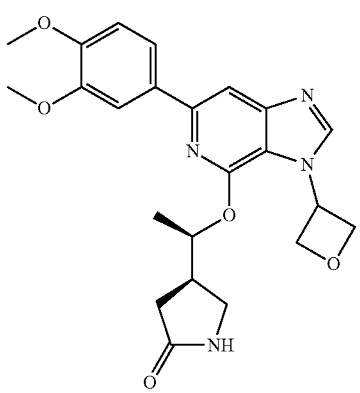 [SMILES: COc1ccc(-c2cc3ncn(C4COC4)c3c(O[C@H](C)[C@H]3CNC(=O)C3)n2)cc1OC] | (R)-4-((R)-1-(6-(3,4-dimethoxyphenyl)-3-(oxetan-3-yl)-3H-imidazo[4,5-c]pyridin-4-yloxy)ethyl)pyrrolidin-2-one |

TABLE A-continued

Representative Compounds

| Structure | Name |
|---|---|
| 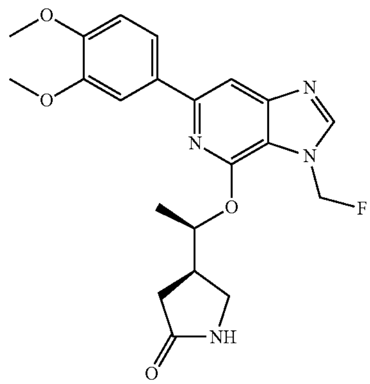 [SMILES: COc1ccc(-c2cc3ncn(CF)c3c(O[C@H](C)[C@H]3CNC(=O)C3)n2)cc1OC] | (R)-4-((R)-1-(6-(3,4-dimethoxyphenyl)-3-(fluoromethyl)-3H-imidazo[4,5-c]pyridin-4-yloxy)ethyl)pyrrolidin-2-one |
| 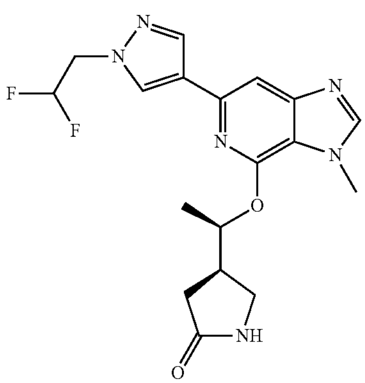 [SMILES: C[C@@H](Oc1nc(-c2cnn(CC(F)F)c2)cc2ncn(C)c12)[C@H]1CNC(=O)C1] | (R)-4-((R)-1-(6-(1-(2,2-difluoroethyl)-1H-pyrazol-4-yl)-3-methyl-3H-imidazo[4,5-c]pyridin-4-yloxy)ethyl)pyrrolidin-2-one |
| 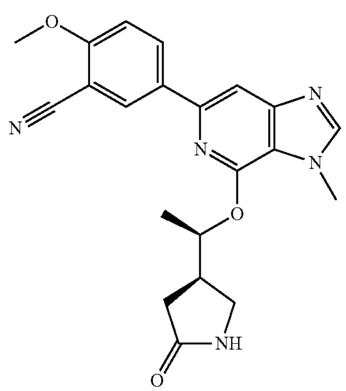 [SMILES: COc1ccc(-c2cc3ncn(C)c3c(O[C@H](C)[C@H]3CNC(=O)C3)n2)cc1C#N] | 2-methoxy-5-(3-methyl-4-((R)-1-((R)-5-oxopyrrolidin-3-yl)ethoxy)-3H-imidazo[4,5-c]pyridin-6-yl)benzonitrile2-methoxy-5-(3-methyl-4-((R)-1-((R)-5-oxopyrrolidin-3-yl)ethoxy)-3H-imidazo[4,5-c]pyridin-6-yl)benzonitrile |
| 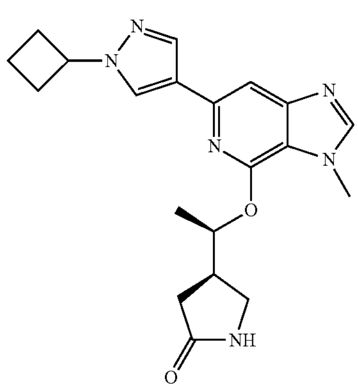 [SMILES: C[C@@H](Oc1nc(-c2cnn(C3CCC3)c2)cc2ncn(C)c12)[C@H]1CNC(=O)C1] | (R)-4-((R)-1-(6-(1-cyclobutyl-1H-pyrazol-4-yl)-3-methyl-3H-imidazo[4,5-c]pyridin-4-yloxy)ethyl)pyrrolidin-2-one |

TABLE A-continued

Representative Compounds

| Structure | Name |
|---|---|
| 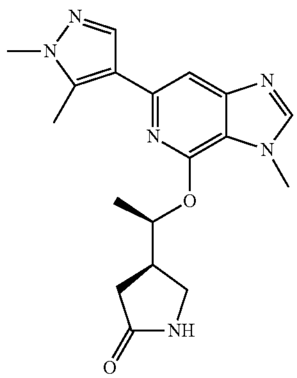 [SMILES: Cc1c(-c2cc3ncn(C)c3c(O[C@H](C)[C@H]3CNC(=O)C3)n2)cnn1C] | (R)-4-((R)-1-(6-(1,5-dimethyl-1H-pyrazol-4-yl)-3-methyl-3H-imidazo[4,5-c]pyridin-4-yloxy)ethyl)pyrrolidin-2-one |
| 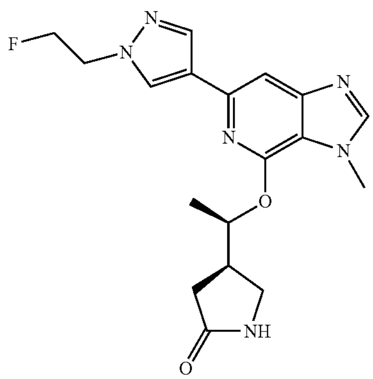 [SMILES: C[C@@H](Oc1nc(-c2cnn(CCF)c2)cc2ncn(C)c12)[C@H]1CNC(=O)C1] | (R)-4-((R)-1-(6-(1-(2-fluoroethyl)-1H-pyrazol-4-yl)-3-methyl-3H-imidazo[4,5-c]pyridin-4-yloxy)ethyl)pyrrolidin-2-one |
| 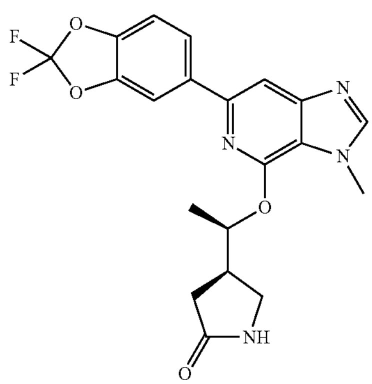 [SMILES: C[C@@H](Oc1nc(-c2ccc3c(c2)OC(F)(F)O3)cc2ncn(C)c12)[C@H]1CNC(=O)C1] | (R)-4-((R)-1-(6-(2,2-difluorobenzo[d][1,3]dioxol-5-yl)-3-methyl-3H-imidazo[4,5-c]pyridin-4-yloxy)ethyl)pyrrolidin-2-one |
| 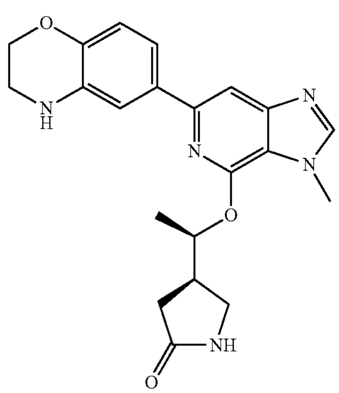 [SMILES: C[C@@H](Oc1nc(-c2ccc3c(c2)NCCO3)cc2ncn(C)c12)[C@H]1CNC(=O)C1] | (R)-4-((R)-1-(6-(3,4-dihydro-2H-benzo[b][1,4]oxazin-6-yl)-3-methyl-3H-imidazo[4,5-c]pyridin-4-yloxy)ethyl)pyrrolidin-2-one |

TABLE A-continued

Representative Compounds

| Structure | Name |
|---|---|
| 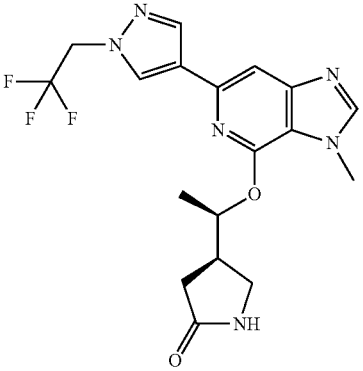 [SMILES: C[C@@H](Oc1nc(-c2cnn(CC(F)(F)F)c2)cc2ncn(C)c12)[C@H]1CNC(=O)C1] | (R)-4-((R)-1-(3-methyl-6-(1-(2,2,2-trifluoroethyl)-1H-pyrazol-4-yl)-3H-imidazo[4,5-c]pyridin-4-yloxy)ethyl)pyrrolidin-2-one |
| 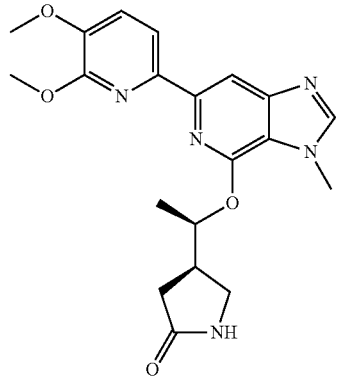 | (R)-4-((R)-1-(6-(5,6-dimethoxypyridin-2-yl)-3-methyl-3H-imidazo[4,5-c]pyridin-4-yloxy)ethyl)pyrrolidin-2-one |
| 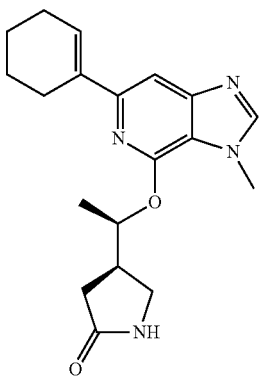 [SMILES: C[C@@H](Oc1nc(C2=CCCCC2)cc2ncn(C)c12)[C@H]1CNC(=O)C1] | (R)-4-((R)-1-(6-cyclohexenyl-3-methyl-3H-imidazo[4,5-c]pyridin-4-yloxy)ethyl)pyrrolidin-2-one |
| 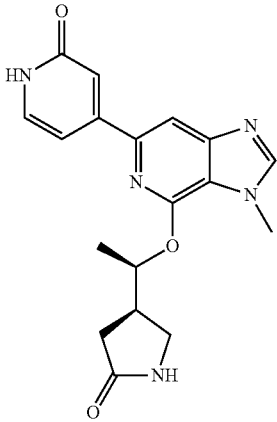 [SMILES: C[C@@H](Oc1nc(-c2cc[nH]c(=O)c2)cc2ncn(C)c12)[C@H]1CNC(=O)C1] | 4-(3-methyl-4-((R)-1-((R)-5-oxopyrrolidin-3-yl)ethoxy)-3H-imidazo[4,5-c]pyridin-6-yl)pyridin-2(1H)-one |

TABLE A-continued

Representative Compounds

| Structure | Name |
|---|---|
| 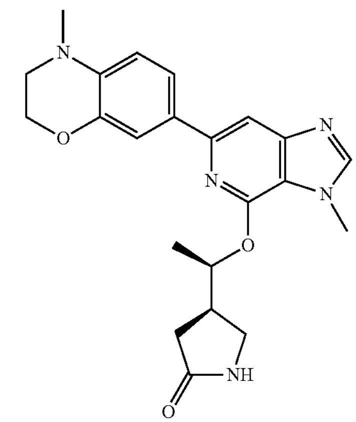 [SMILES: C[C@@H](Oc1nc(-c2ccc3c(c2)OCCN3C)cc2ncn(C)c12)[C@H]1CNC(=O)C1] | (R)-4-((R)-1-(3-methyl-6-(4-methyl-3,4-dihydro-2H-benzo[b][1,4]oxazin-7-yl)-3H-imidazo[4,5-c]pyridin-4-yloxy)ethyl)pyrrolidin-2-one |
| 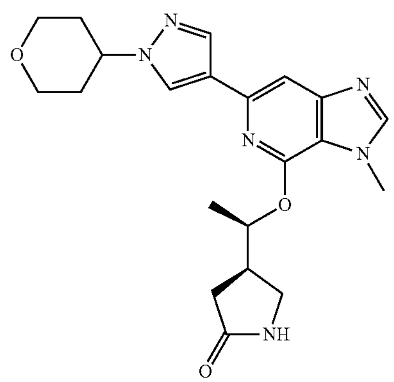 [SMILES: C[C@@H](Oc1nc(-c2cnn(C3CCOCC3)c2)cc2ncn(C)c12)[C@H]1CNC(=O)C1] | (R)-4-((R)-1-(3-methyl-6-(1-(tetrahydro-2H-pyran-4-yl)-1H-pyrazol-4-yl)-3H-imidazo[4,5-c]pyridin-4-yloxy)ethyl)pyrrolidin-2-one |
| 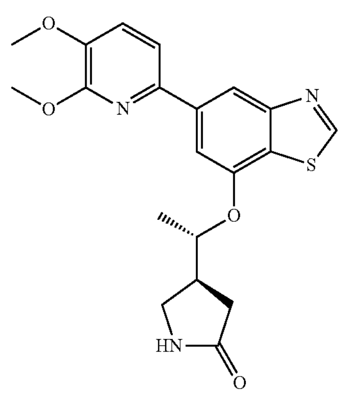 [SMILES: COc1ccc(-c2cc(O[C@@H](C)[C@@H]3CNC(=O)C3)c3scnc3c2)nc1OC] | (R)-4-((R)-1-((5-(5,6-dimethoxypyridin-2-yl)benzo[d]thiazol-7-yl)oxy)ethyl)pyrrolidin-2-one |
| 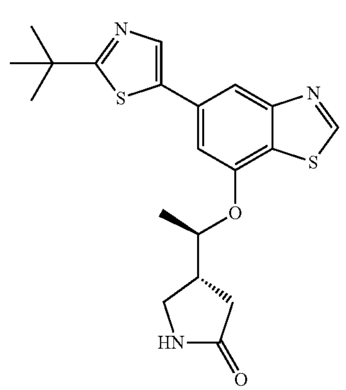 [SMILES: C[C@@H](Oc1cc(-c2cnc(C(C)(C)C)s2)cc2ncsc12)[C@H]1CNC(=O)C1] | (S)-4-((S)-1-((5-(2-(tert-butyl)thiazol-5-yl)benzo[d]thiazol-7-yl)oxy)ethyl)pyrrolidin-2-one |

TABLE A-continued

Representative Compounds

| Structure | Name |
|---|---|
| 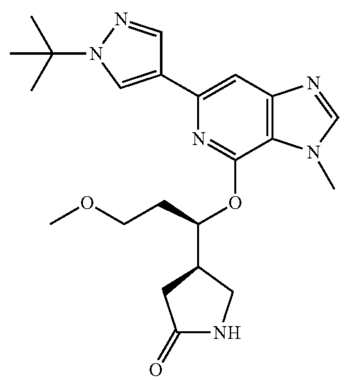 [SMILES: COCC[C@@H](Oc1nc(-c2cnn(C(C)(C)C)c2)cc2ncn(C)c12)[C@H]1CNC(=O)C1] | (R)-4-((R)-1-(6-(1-tert-butyl-1H-pyrazol-4-yl)-3-methyl-3H-imidazo[4,5-c]pyridin-4-yloxy)-3-methoxypropyl)pyrrolidin-2-one |
| 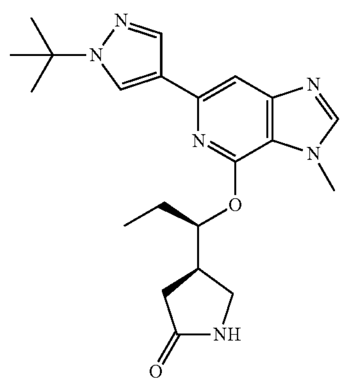 [SMILES: CC[C@@H](Oc1nc(-c2cnn(C(C)(C)C)c2)cc2ncn(C)c12)[C@H]1CNC(=O)C1] | (R)-4-((R)-1-(6-(1-tert-butyl-1H-pyrazol-4-yl)-3-methyl-3H-imidazo[4,5-c]pyridin-4-yloxy)propyl)pyrrolidin-2-one |
| 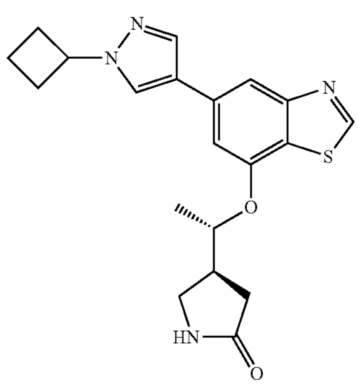 [SMILES: C[C@H](Oc1cc(-c2cnn(C3CCC3)c2)cc2ncsc12)[C@@H]1CNC(=O)C1] | (R)-4-((R)-1-((5-(1-cyclobutyl-1H-pyrazol-4-yl)benzo[d]thiazol-7-yl)oxy)ethyl)pyrrolidin-2-one |
| 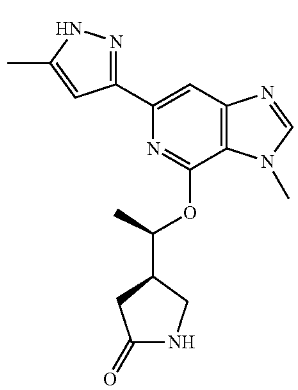 [SMILES: Cc1cc(-c2cc3ncn(C)c3c(O[C@H](C)[C@H]3CNC(=O)C3)n2)n[nH]1] | (R)-4-((R)-1-(3-methyl-6-(5-methyl-1H-pyrazol-3-yl)-3H-imidazo[4,5-c]pyridin-4-yloxy)ethyl)pyrrolidin-2-one |

TABLE A-continued

Representative Compounds

| Structure | Name |
|---|---|
| 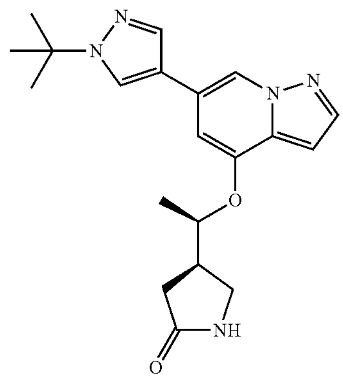 [SMILES: C[C@@H](Oc1cc(-c2cnn(C(C)(C)C)c2)cn2nccc12)[C@H]1CNC(=O)C1] | (R)-4-((R)-1-((6-(1-(tert-butyl)-1H-pyrazol-4-yl)pyrazolo[1,5-a]pyridin-4-yl)oxy)ethyl)pyrrolidin-2-one |
| 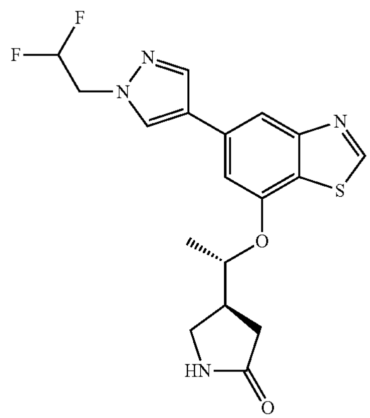 [SMILES: C[C@H](Oc1cc(-c2cnn(CC(F)F)c2)cc2ncsc12)[C@@H]1CNC(=O)C1] | (R)-4-((R)-1-((5-(1-(2,2-difluoroethyl)-1H-pyrazol-4-yl)benzo[d]thiazol-7-yl)oxy)ethyl)pyrrolidin-2-one |
| 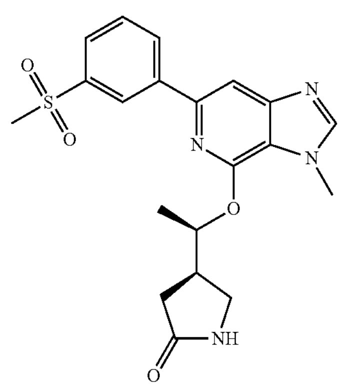 [SMILES: C[C@@H](Oc1nc(-c2cccc(S(C)(=O)=O)c2)cc2ncn(C)c12)[C@H]1CNC(=O)C1] | (R)-4-((R)-1-(3-methyl-6-(3-(methylsulfonyl)phenyl)-3H-imidazo[4,5-c]pyridin-4-yloxy)ethyl)pyrrolidin-2-one |
| 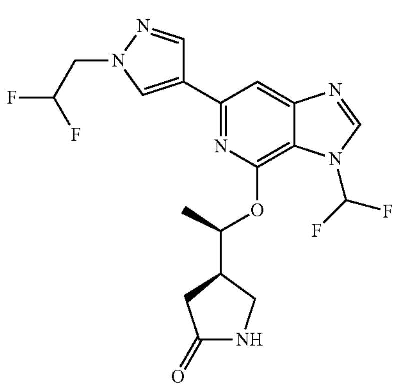 [SMILES: C[C@@H](Oc1nc(-c2cnn(CC(F)F)c2)cc2ncn(C(F)F)c12)[C@H]1CNC(=O)C1] | (R)-4-((R)-1-(6-(1-(2,2-difluoroethyl)-1H-pyrazol-4-yl)-3-(difluoromethyl)-3H-imidazo[4,5-c]pyridin-4-yloxy)ethyl)pyrrolidin-2-one |

TABLE A-continued

Representative Compounds

| Structure | Name |
|---|---|
| 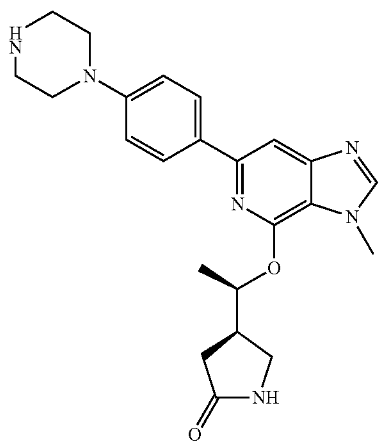 [SMILES: C[C@@H](Oc1nc(-c2ccc(N3CCNCC3)cc2)cc2ncn(C)c12)[C@H]1CNC(=O)C1] | (R)-4-((R)-1-(3-methyl-6-(4-(piperazin-1-yl)phenyl)-3H-imidazo[4,5-c]pyridin-4-yloxy)ethyl)pyrrolidin-2-one |
| 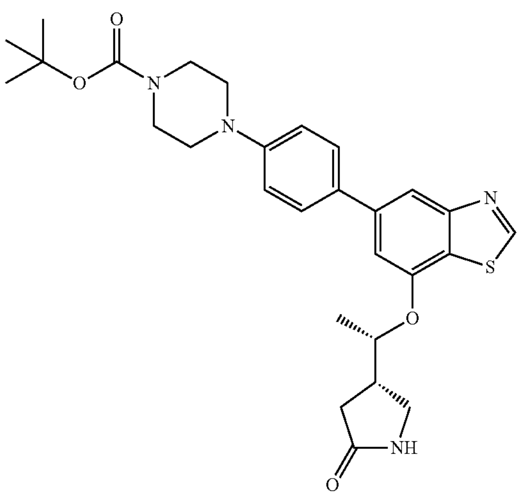 [SMILES: C[C@H](Oc1cc(-c2ccc(N3CCN(C(=O)OC(C)(C)C)CC3)cc2)cc2ncsc12)[C@@H]1CNC(=O)C1] | tert-butyl 4-(4-(7-((R)-1-((R)-5-oxopyrrolidin-3-yl)ethoxy)benzo[d]thiazol-5-yl)phenyl)piperazine-1-carboxylate |
| 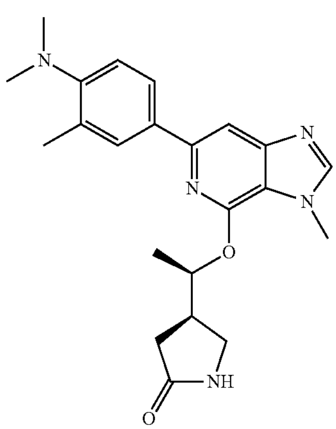 [SMILES: Cc1cc(-c2cc3ncn(C)c3c(O[C@H](C)[C@H]3CNC(=O)C3)n2)ccc1N(C)C] | (R)-4-((R)-1-(6-(4-(dimethylamino)-3-methylphenyl)-3-methyl-3H-imidazo[4,5-c]pyridin-4-yloxy)ethyl)pyrrolidin-2-one |

TABLE A-continued

Representative Compounds

| Structure | Name |
|---|---|
| 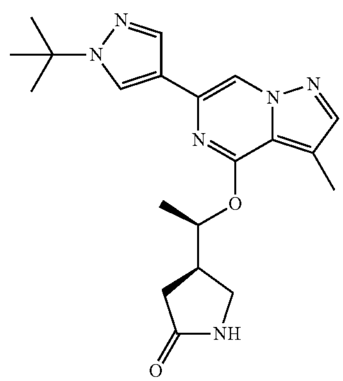 [SMILES: Cc1cnn2cc(-c3cnn(C(C)(C)C)c3)nc(O[C@H](C)[C@H]3CNC(=O)C3)c12] | (R)-4-((R)-1-((6-(1-(tert-butyl)-1H-pyrazol-4-yl)-3-methylpyrazolo[1,5-a]pyrazin-4-yl)oxy)ethyl)pyrrolidin-2-one |
| 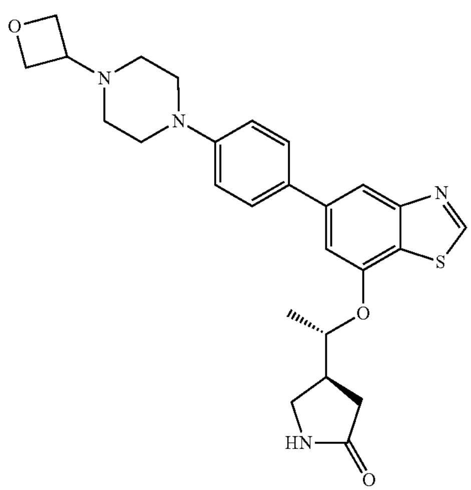 [SMILES: C[C@H](Oc1cc(-c2ccc(N3CCN(C4COC4)CC3)cc2)cc2ncsc12)[C@@H]1CNC(=O)C1] | (R)-4-((R)-1-((5-(4-(4-(oxetan-3-yl)piperazin-1-yl)phenyl)benzo[d]thiazol-7-y)oxy)ethyl)pyrrolidin-2-one |
| 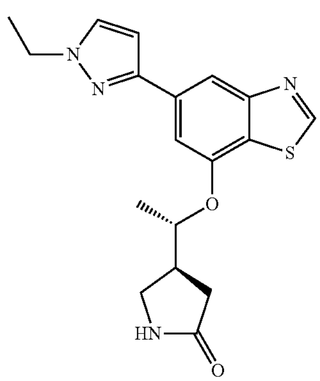 [SMILES: CCn1ccc(-c2cc(O[C@@H](C)[C@@H]3CNC(=O)C3)c3scnc3c2)n1] | (R)-4-((R)-1-((5-(1-ethyl-1H-pyrazol-3-yl)benzo[d]thiazol-7-yl)oxy)ethyl)pyrrolidin-2-one |

TABLE A-continued

Representative Compounds

| Structure | Name |
|---|---|
| 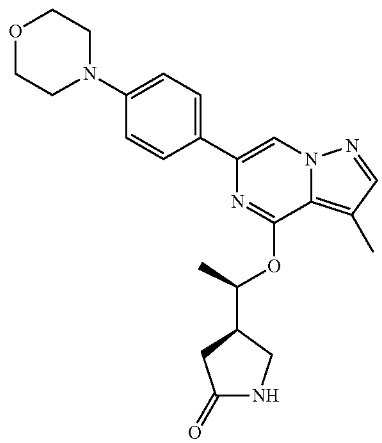 [SMILES: Cc1cnn2cc(-c3ccc(N4CCOCC4)cc3)nc(O[C@H](C)[C@H]3CNC(=O)C3)c12] | (R)-4-((R)-1-((3-methyl-6-(4-morpholinophenyl)pyrazolo[1,5-a]pyrazin-4-yl)oxy)ethyl)pyrrolidin-2-one |
| 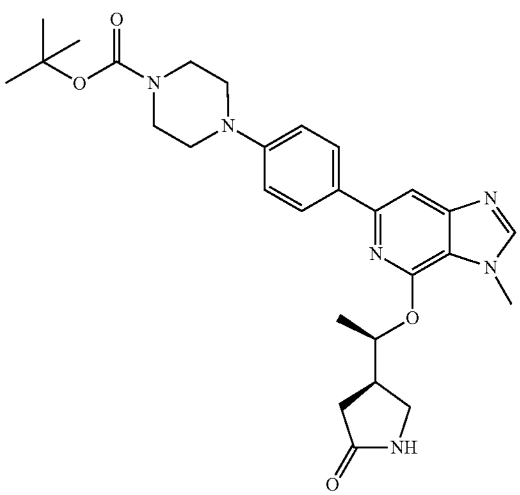 [SMILES: C[C@@H](Oc1nc(-c2ccc(N3CCN(C(=O)OC(C)(C)C)CC3)cc2)cc2ncn(C)c12)[C@H]1CNC(=O)C1] | tert-butyl 4-(4-(3-methyl-4-((R)-1-((R)-5-oxopyrrolidin-3-yl)ethoxy)-3H-imidazo[4,5-c]pyridin-6-yl)phenyl)piperazine-1-carboxylate |
| 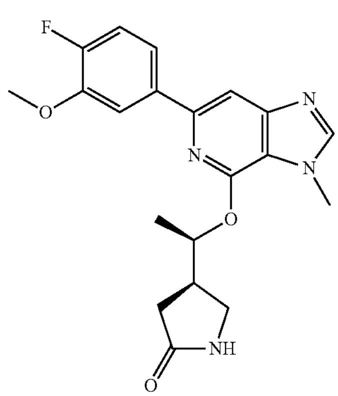 [SMILES: COc1cc(-c2cc3ncn(C)c3c(O[C@H](C)[C@H]3CNC(=O)C3)n2)ccc1F] | (R)-4-((R)-1-(6-(4-fluoro-3-methoxyphenyl)-3-methyl-3H-imidazo[4,5-c]pyridin-4-yloxy)ethyl)pyrrolidin-2-one |

TABLE A-continued

Representative Compounds

| Structure | Name |
|---|---|
| 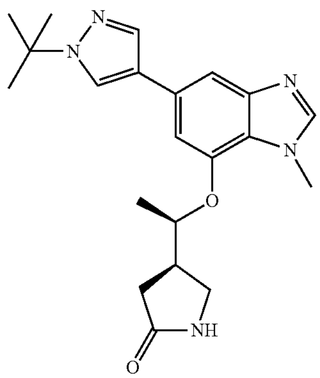 [SMILES: C[C@@H](Oc1cc(-c2cnn(C(C)(C)C)c2)cc2ncn(C)c12)[C@H]1CNC(=O)C1] | (R)-4-((R)-1-(5-(1-tert-butyl-1H-pyrazol-4-yl)-1-methyl-1H-benzo[d]imidazol-7-yloxy)ethyl)pyrrolidin-2-one |
| 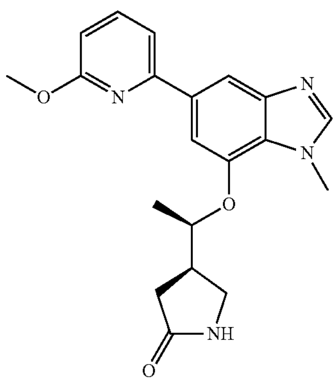 [SMILES: COc1cccc(-c2cc(O[C@H](C)[C@H]3CNC(=O)C3)c3c(c2)ncn3C)n1] | (R)-4-((R)-1-(5-(6-methoxypyridin-2-yl)-1-methyl-1H-benzo[d]imidazol-7-yloxy)ethyl)pyrrolidin-2-one |
| 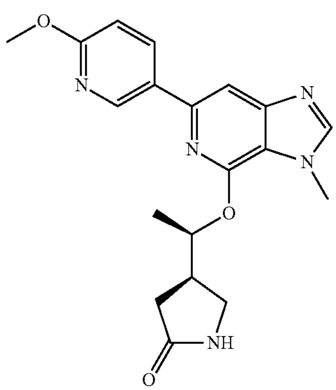 [SMILES: COc1ccc(-c2cc3ncn(C)c3c(O[C@H](C)[C@H]3CNC(=O)C3)n2)cn1] | (R)-4-((R)-1-(6-(6-methoxypyridin-3-yl)-3-methyl-3H-imidazo[4,5-c]pyridin-4-yloxy)ethyl)pyrrolidin-2-one |
| 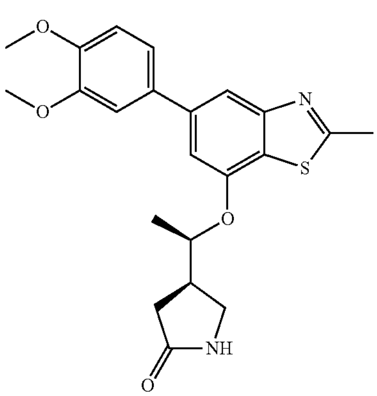 | (R)-4-((R)-1-((5-(3,4-dimethoxyphenyl)-2-methylbenzo[d]thiazol-7-yl)oxy)ethyl)pyrrolidin-2-one |

TABLE A-continued
Representative Compounds
| Structure | Name |
|---|---|
| 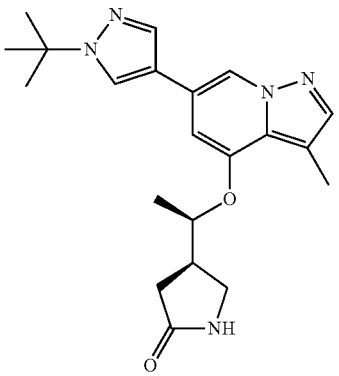 [SMILES: Cc1cnn2cc(-c3cnn(C(C)(C)C)c3)cc(O[C@H](C)[C@H]3CNC(=O)C3)c12] | (R)-4-((R)-1-((6-(1-(tert-butyl)-1H-pyrazol-4-yl)-3-methylpyrazolo[1,5-a]pyridin-4-yl)oxy)ethyl)pyrrolidin-2-one |
| 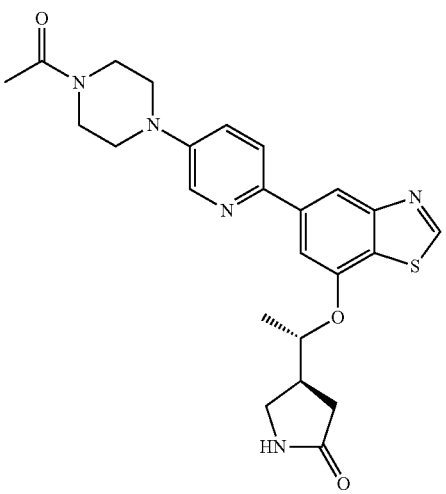 [SMILES: CC(=O)N1CCN(c2ccc(-c3cc(O[C@@H](C)[C@@H]4CNC(=O)C4)c4scnc4c3)nc2)CC1] | (R)-4-((R)-1-((5-(5-(4-acetylpiperazin-1-yl)pyridin-2-yl)benzo[d]thiazol-7-yl)oxy)ethyl)pyrrolidin-2-one |
| 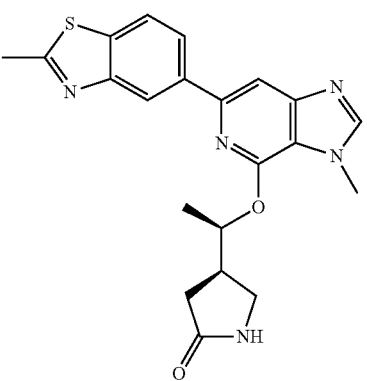 [SMILES: Cc1nc2cc(-c3cc4ncn(C)c4c(O[C@H](C)[C@H]4CNC(=O)C4)n3)ccc2s1] | (R)-4-((R)-1-((3-methyl-6-(2-methylbenzo[d]thiazol-5-yl)-3H-imidazo[4,5-c]pyridin-4-yl)oxy)ethyl)pyrrolidin-2-one |

TABLE A-continued

Representative Compounds

| Structure | Name |
|---|---|
| 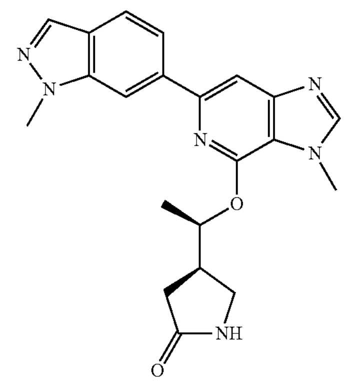 [SMILES: C[C@@H](Oc1nc(-c2ccc3cnn(C)c3c2)cc2ncn(C)c12)[C@H]1CNC(=O)C1] | (R)-4-((R)-1-((3-methyl-6-(1-methyl-1H-indazol-6-yl)-3H-imidazo[4,5-c]pyridin-4-yl)oxy)ethyl)pyrrolidin-2-one |
| 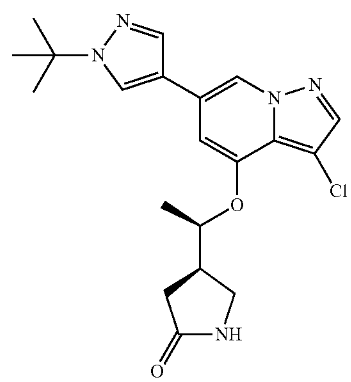 [SMILES: C[C@@H](Oc1cc(-c2cnn(C(C)(C)C)c2)cn2ncc(Cl)c12)[C@H]1CNC(=O)C1] | (R)-4-((R)-1-((6-(1-(tert-butyl)-1H-pyrazol-4-yl)-3-chloropyrazolo[1,5-a]pyridin-4-yl)oxy)ethyl)pyrrolidin-2-one |
| 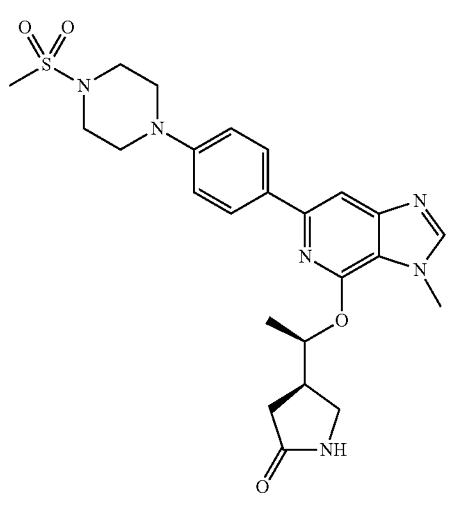 [SMILES: C[C@@H](Oc1nc(-c2ccc(N3CCN(S(C)(=O)=O)CC3)cc2)cc2ncn(C)c12)[C@H]1CNC(=O)C1] | (R)-4-((R)-1-((3-methyl-6-(4-(4-(methylsulfonyl)piperazin-1-yl)phenyl)-3H-imidazo[4,5-c]pyridin-4-yl)oxy)ethyl)pyrrolidin-2-one |

TABLE A-continued

Representative Compounds

| Structure | Name |
|---|---|
| 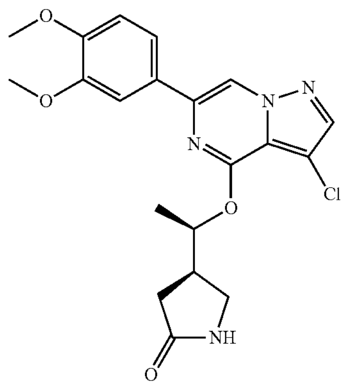 [SMILES: COc1ccc(-c2cn3ncc(Cl)c3c(O[C@H](C)[C@H]3CNC(=O)C3)n2)cc1OC] | (R)-4-((R)-1-((3-chloro-6-(3,4-dimethoxyphenyl)pyrazolo[1,5-a]pyrazin-4-yl)oxy)ethyl)pyrrolidin-2-one |
| 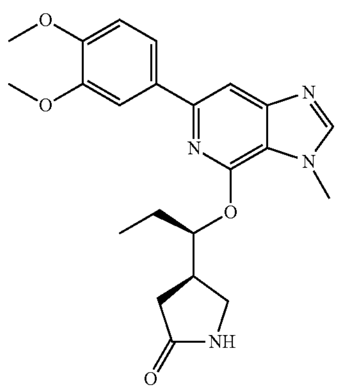 [SMILES: CC[C@@H](Oc1nc(-c2ccc(OC)c(OC)c2)cc2ncn(C)c12)[C@H]1CNC(=O)C1] | (R)-4-((R)-1-((6-(3,4-dimethoxyphenyl)-3-methyl-3H-imidazo[4,5-c]pyridin-4-yl)oxy)propyl)pyrrolidin-2-one |
| 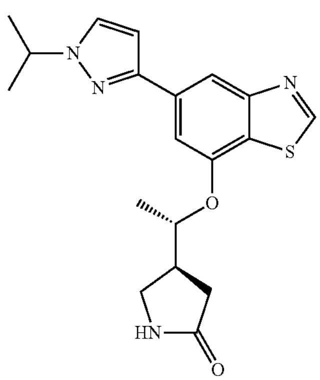 [SMILES: CC(C)n1ccc(-c2cc(O[C@@H](C)[C@@H]3CNC(=O)C3)c3scnc3c2)n1] | (R)-4-((R)-1-((5-(1-isopropyl-1H-pyrazol-3-yl)benzo[d]thiazol-7-yl)oxy)ethyl)pyrrolidin-2-one |

TABLE A-continued

Representative Compounds

| Structure | Name |
|---|---|
| 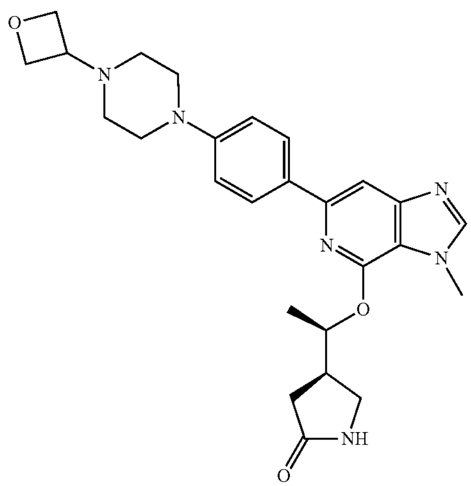 [SMILES: C[C@@H](Oc1nc(-c2ccc(N3CCN(C4COC4)CC3)cc2)cc2ncn(C)c12)[C@H]1CNC(=O)C1] | (R)-4-((R)-1-((3-methyl-6-(4-(4-(oxetan-3-yl)piperazin-1-yl)phenyl)-3H-imidazo[4,5-c]pyridin-4-yl)oxy)ethyl)pyrrolidin-2-one |
| 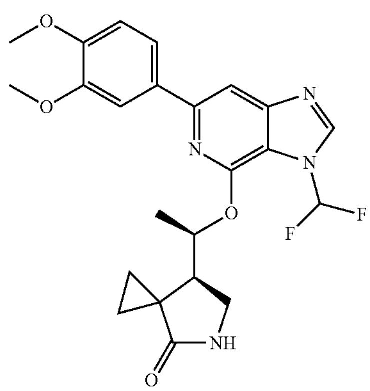 [SMILES: COc1ccc(-c2cc3ncn(C(F)F)c3c(O[C@H](C)[C@H]3CNC(=O)C34CC4)n2)cc1OC] | (R)-7-((R)-1-((3-(difluoromethyl)-6-(3,4-dimethoxyphenyl)-3H-imidazo[4,5-c]pyridin-4-yl)oxy)ethyl)-5-azaspiro[2.4]heptan-4-one |
| 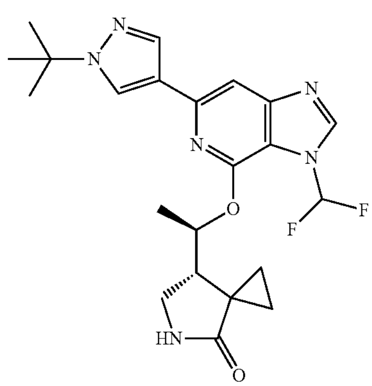 [SMILES: C[C@@H](Oc1nc(-c2cnn(C(C)(C)C)c2)cc2ncn(C(F)F)c12)[C@H]1CNC(=O)C12CC2] | (R)-7-((R)-1-((6-(1-(tert-butyl)-1H-pyrazol-4-yl)-3-(difluoromethyl)-3H-imidazo[4,5-c]pyridin-4-yl)oxy)ethyl)-5-azaspiro[2.4]heptan-4-one |

TABLE A-continued

Representative Compounds

| Structure | Name |
|---|---|
| 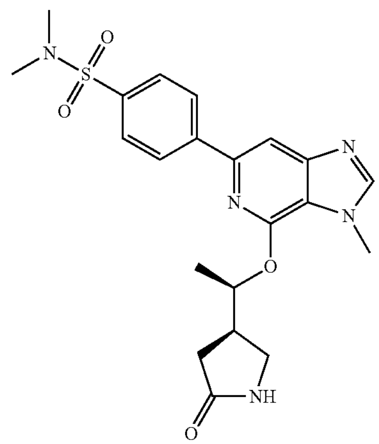 [SMILES: C[C@@H](Oc1nc(-c2ccc(S(=O)(=O)N(C)C)cc2)cc2ncn(C)c12)[C@H]1CNC(=O)C1] | N,N-dimethyl-4-(3-methyl-4-((R)-1-((R)-5-oxopyrrolidin-3-yl)ethoxy)-3H-imidazo[4,5-c]pyridin-6-yl)benzenesulfonamide |
| 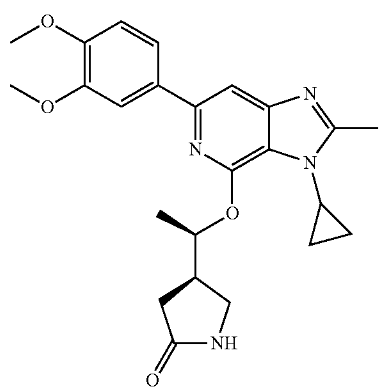 | (R)-4-((R)-1-((3-cyclopropyl-6-(3,4-dimethoxyphenyl)-2-methyl-3H-imidazo[4,5-c]pyridin-4-yl)oxy)ethyl)pyrrolidin-2-one |
| 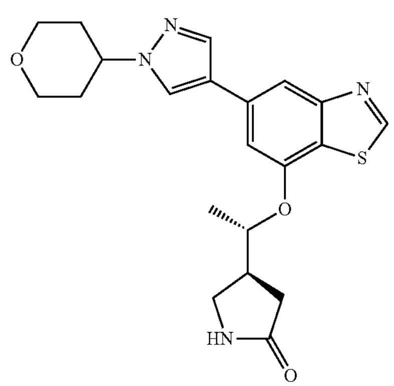 [SMILES: C[C@H](Oc1cc(-c2cnn(C3CCOCC3)c2)cc2ncsc12)[C@@H]1CNC(=O)C1] | (R)-4-((R)-1-((5-(1-(tetrahydro-2H-pyran-4-yl)-1H-pyrazol-4-yl)benzo[d]thiazol-7-yl)oxy)ethyl)pyrrolidin-2-one |

TABLE A-continued

Representative Compounds

| Structure | Name |
|---|---|
| 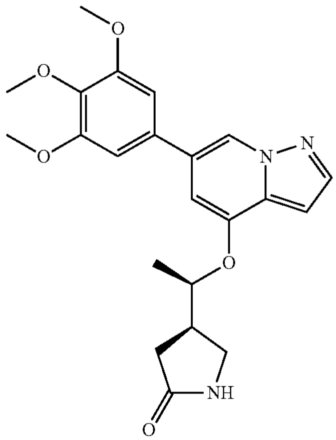 [SMILES: COc1cc(-c2cc(O[C@H](C)[C@H]3CNC(=O)C3)c3ccnn3c2)cc(OC)c1OC] | (R)-4-((R)-1-((6-(3,4,5-trimethoxyphenyl)pyrazolo[1,5-a]pyridin-4-yl)oxy)ethyl)pyrrolidin-2-one |
| 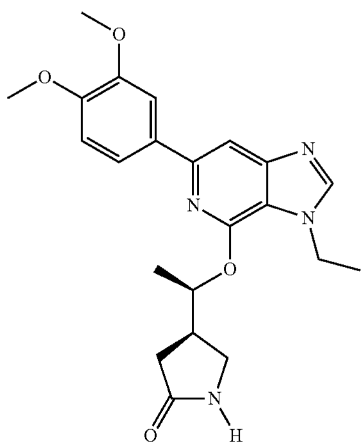 [SMILES: CCn1cnc2cc(-c3ccc(OC)c(OC)c3)nc(O[C@H](C)[C@H]3CNC(=O)C3)c21] | (R)-4-((R)-1-(6-(3,4-dimethoxyphenyl)-3-ethyl-3H-imidazo[4,5-c]pyridin-4-yloxy)ethyl)pyrrolidin-2-one |
| 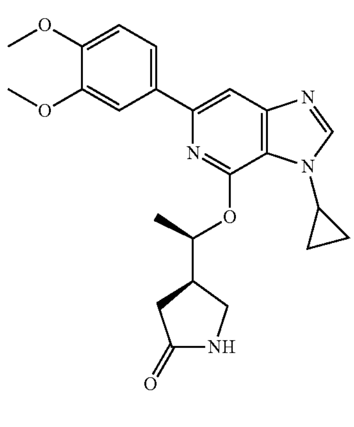 [SMILES: COc1ccc(-c2cc3ncn(C4CC4)c3c(O[C@H](C)[C@H]3CNC(=O)C3)n2)cc1OC] | (R)-4-((R)-1-(3-cyclopropyl-6-(3,4-dimethoxyphenyl)-3H-imidazo[4,5-c]pyridin-4-yloxy)ethyl)pyrrolidin-2-one |

TABLE A-continued

Representative Compounds

| Structure | Name |
|---|---|
| 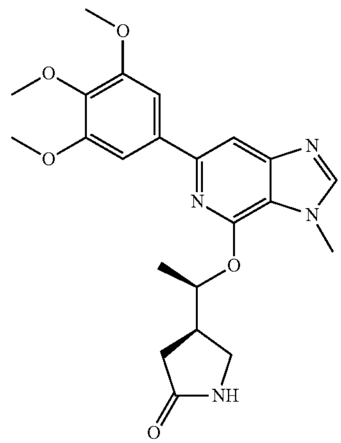 [SMILES: COc1cc(-c2cc3ncn(C)c3c(O[C@H](C)[C@H]3CNC(=O)C3)n2)cc(OC)c1OC] | (R)-4-((R)-1-(3-methyl-6-(3,4,5-trimethoxyphenyl)-3H-imidazo[4,5-c]pyridin-4-yloxy)ethyl)pyrrolidin-2-one |
| 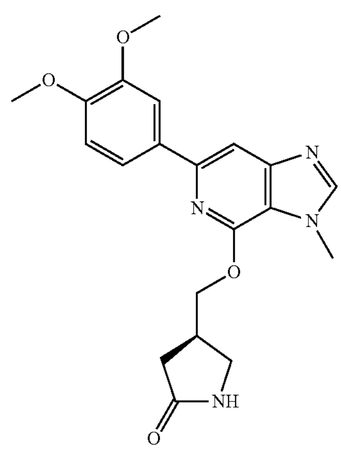 [SMILES: COc1ccc(-c2cc3ncn(C)c3c(OC[C@H]3CNC(=O)C3)n2)cc1OC] | (R)-4-((6-(3,4-dimethoxyphenyl)-3-methyl-3H-imidazo[4,5-c]pyridin-4-yloxy)methyl)pyrrolidin-2-one |
| 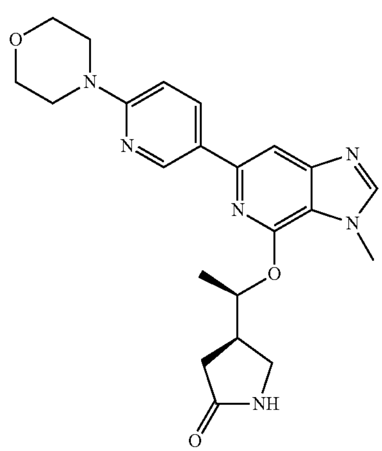 [SMILES: C[C@@H](Oc1nc(-c2ccc(N3CCOCC3)nc2)cc2ncn(C)c12)[C@H]1CNC(=O)C1] | (R)-4-((R)-1-(3-methyl-6-(6-morpholinopyridin-3-yl)-3H-imidazo[4,5-c]pyridin-4-yloxy)ethyl)pyrrolidin-2-one |

TABLE A-continued
Representative Compounds
| Structure | Name |
|---|---|
| 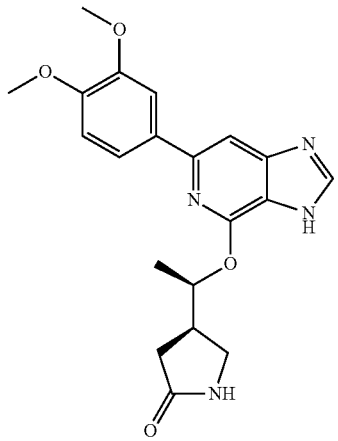 [SMILES: COc1ccc(-c2cc3nc[nH]c3c(O[C@H](C)[C@H]3CNC(=O)C3)n2)cc1OC] | (R)-4-((R)-1-(6-(3,4-dimethoxyphenyl)-3H-imidazo[4,5-c]pyridin-4-yloxy)ethyl)pyrrolidin-2-one |
| 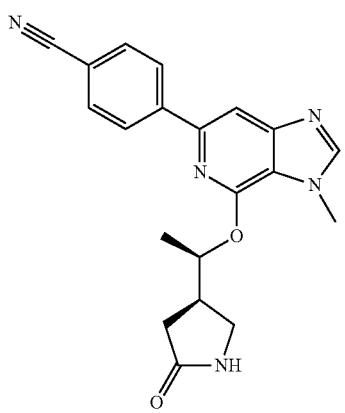 [SMILES: C[C@@H](Oc1nc(-c2ccc(C#N)cc2)cc2ncn(C)c12)[C@H]1CNC(=O)C1] | 4-(3-methyl-4-((R)-1-((R)-5-oxopyrrolidin-3-yl)ethoxy)-3H-imidazo[4,5-c]pyridin-6-yl)benzonitrile |
| 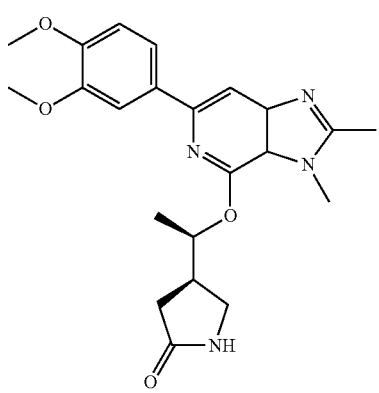 | (4R)-4-((1R)-1-(6-(3,4-dimethoxyphenyl)-2,3-dimethyl-3a,7a-dihydro-3H-imidazo[4,5-c]pyridin-4-yloxy)ethyl)pyrrolidin-2-one |

TABLE A-continued

Representative Compounds

| Structure | Name |
|---|---|
| 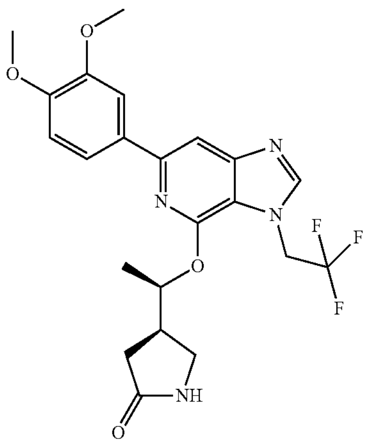 [SMILES: COc1ccc(-c2cc3ncn(CC(F)(F)F)c3c(O[C@H](C)[C@H]3CNC(=O)C3)n2)cc1OC] | (R)-4-((R)-1-(6-(3,4-dimethoxyphenyl)-3-(2,2,2-trifluoroethyl)-3H-imidazo[4,5-c]pyridin-4-yloxy)ethyl)pyrrolidin-2-one |
| 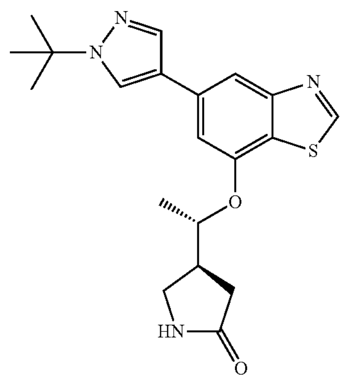 [SMILES: C[C@H](Oc1cc(-c2cnn(C(C)(C)C)c2)cc2ncsc12)[C@@H]1CNC(=O)C1] | (R)-4-((R)-1-((5-(1-(tert-butyl)-1H-pyrazol-4-yl)benzo[d]thiazol-7-yl)oxy)ethyl)pyrrolidin-2-one |
| 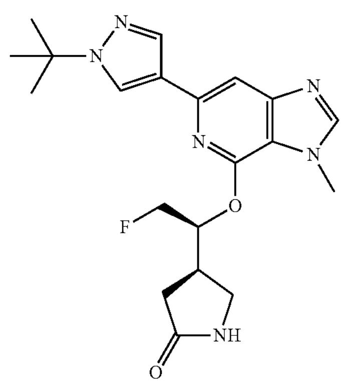 [SMILES: Cn1cnc2cc(-c3cnn(C(C)(C)C)c3)nc(O[C@H](CF)[C@H]3CNC(=O)C3)c21] | (R)-4-((S)-1-(6-(1-tert-butyl-1H-pyrazol-4-yl)-3-methyl-3H-imidazo[4,5-c]pyridin-4-yloxy)-2-fluoroethyl)pyrrolidin-2-one |
| 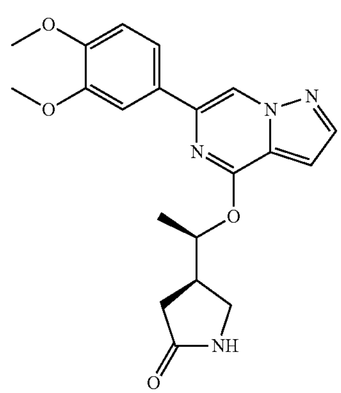 [SMILES: COc1ccc(-c2cn3nccc3c(O[C@H](C)[C@H]3CNC(=O)C3)n2)cc1OC] | (R)-4-((R)-1-((6-(3,4-dimethoxyphenyl)pyrazolo[1,5-a]pyrazin-4-yl)oxy)ethyl)pyrrolidin-2-one |

TABLE A-continued

Representative Compounds

| Structure | Name |
|---|---|
| 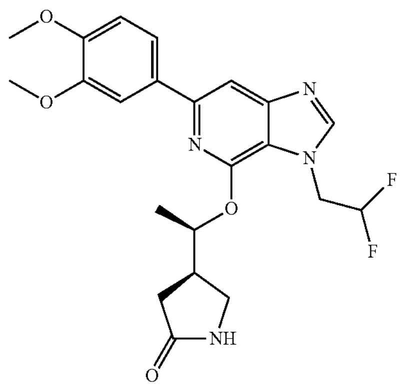 [SMILES: COc1ccc(-c2cc3ncn(CC(F)F)c3c(O[C@H](C)[C@H]3CNC(=O)C3)n2)cc1OC] | (R)-4-((R)-1-(3-(2,2-difluoroethyl)-6-(3,4-dimethoxyphenyl)-3H-imidazo[4,5-c]pyridin-4-yloxy)ethyl)pyrrolidin-2-one |
| 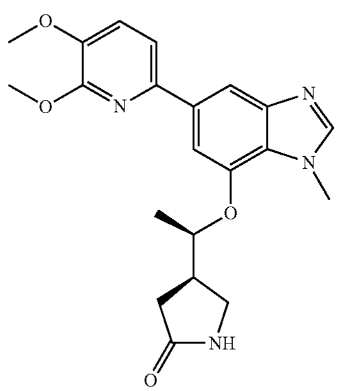 | (R)-4-((R)-1-(5-(5,6-dimethoxypyridin-2-yl)-1-methyl-1H-benzo[d]imidazol-7-yloxy)ethyl)pyrrolidin-2-one |
| 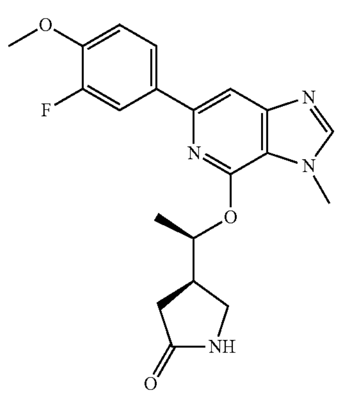 [SMILES: COc1ccc(-c2cc3ncn(C)c3c(O[C@H](C)[C@H]3CNC(=O)C3)n2)cc1F] | (R)-4-((R)-1-(6-(3-fluoro-4-methoxyphenyl)-3-methyl-3H-imidazo[4,5-c]pyridin-4-yloxy)ethyl)pyrrolidin-2-one |
| 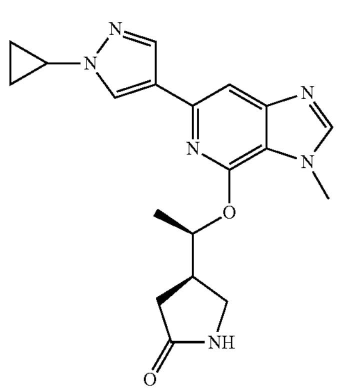 [SMILES: C[C@@H](Oc1nc(-c2cnn(C3CC3)c2)cc2ncn(C)c12)[C@H]1CNC(=O)C1] | (R)-4-((R)-1-(6-(1-cyclopropyl-1H-pyrazol-4-yl)-3-methyl-3H-imidazo[4,5-c]pyridin-4-yloxy)ethyl)pyrrolidin-2-one |

TABLE A-continued

Representative Compounds

| Structure | Name |
|---|---|
| 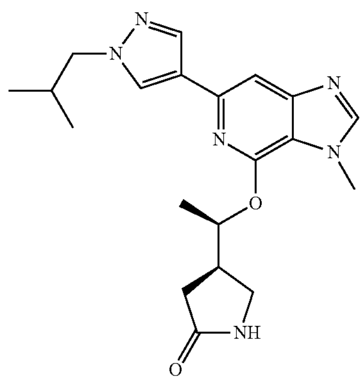 [SMILES: CC(C)Cn1cc(-c2cc3ncn(C)c3c(O[C@H](C)[C@H]3CNC(=O)C3)n2)cn1] | (R)-4-((R)-1-(6-(1-isobutyl-1H-pyrazol-4-yl)-3-methyl-3H-imidazo[4,5-c]pyridin-4-yloxy)ethyl)pyrrolidin-2-one |
| 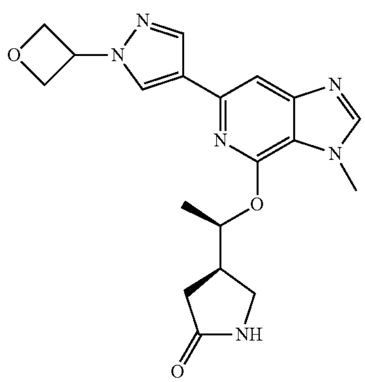 [SMILES: C[C@@H](Oc1nc(-c2cnn(C3COC3)c2)cc2ncn(C)c12)[C@H]1CNC(=O)C1] | (R)-4-((R)-1-(3-methyl-6-(1-(oxetan-3-yl)-1H-pyrazol-4-yl)-3H-imidazo[4,5-c]pyridin-4-yloxy)ethyl)pyrrolidin-2-one |
| | (R)-4-((R)-1-(3-methyl-6-(pyrazolo[1,5-a]pyridin-3-yl)-3H-imidazo[4,5-c]pyridin-4-yloxy)ethyl)pyrrolidin-2-one |
| 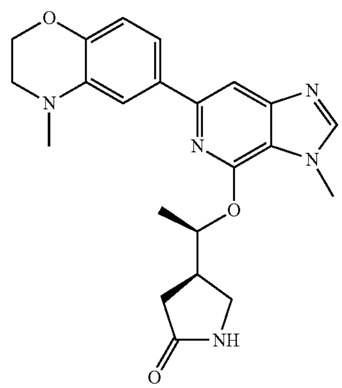 [SMILES: C[C@@H](Oc1nc(-c2ccc3c(c2)N(C)CCO3)cc2ncn(C)c12)[C@H]1CNC(=O)C1] | (R)-4-((R)-1-(3-methyl-6-(4-methyl-3,4-dihydro-2H-benzo[b][1,4]oxazin-6-yl)-3H-imidazo[4,5-c]pyridin-4-yloxy)ethyl)pyrrolidin-2-one |

TABLE A-continued

Representative Compounds

| Structure | Name |
|---|---|
| 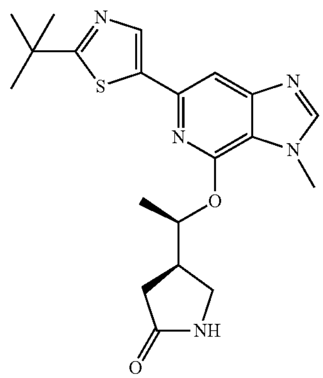 [SMILES: C[C@@H](Oc1nc(-c2cnc(C(C)(C)C)s2)cc2ncn(C)c12)[C@H]1CNC(=O)C1] | (R)-4-((R)-1-(6-(2-tert-butylthiazol-5-yl)-3-methyl-3H-imidazo[4,5-c]pyridin-4-yloxy)ethyl)pyrrolidin-2-one |
| 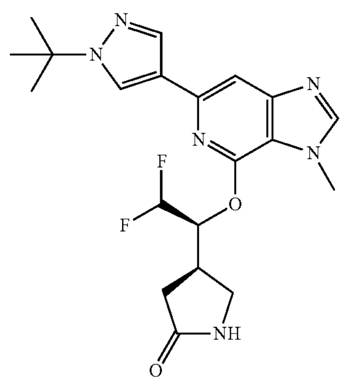 [SMILES: Cn1cnc2cc(-c3cnn(C(C)(C)C)c3)nc(O[C@H](C(F)F)[C@H]3CNC(=O)C3)c21] | (R)-4-((S)-1-(6-(1-tert-butyl-1H-pyrazol-4-yl)-3-methyl-3H-imidazo[4,5-c]pyridin-4-yloxy)-2,2-difluoroethyl)pyrrolidin-2-one |
| 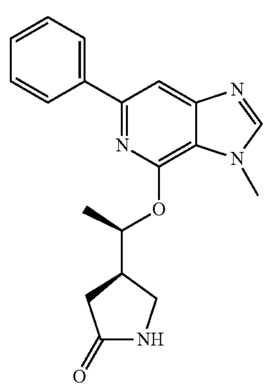 [SMILES: C[C@@H](Oc1nc(-c2ccccc2)cc2ncn(C)c12)[C@H]1CNC(=O)C1] | (R)-4-((R)-1-(3-methyl-6-phenyl-3H-imidazo[4,5-c]pyridin-4-yloxy)ethyl)pyrrolidin-2-one |
| 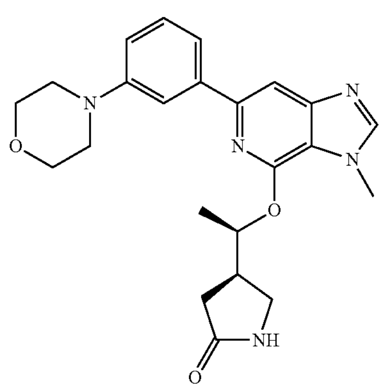 [SMILES: C[C@@H](Oc1nc(-c2cccc(N3CCOCC3)c2)cc2ncn(C)c12)[C@H]1CNC(=O)C1] | (R)-4-((R)-1-(3-methyl-6-(3-morpholinophenyl)-3H-imidazo[4,5-c]pyridin-4-yloxy)ethyl)pyrrolidin-2-one |

TABLE A-continued

Representative Compounds

| Structure | Name |
|---|---|
| 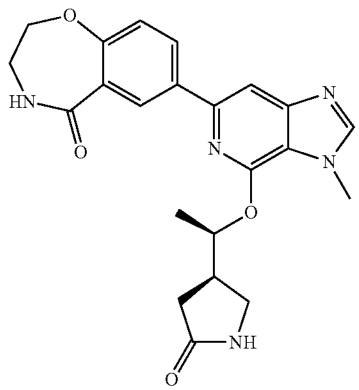 [SMILES: C[C@@H](Oc1nc(-c2ccc3c(c2)C(=O)NCCO3)cc2ncn(C)c12)[C@H]1CNC(=O)C1] | 7-(3-methyl-4-((R)-1-((R)-5-oxopyrrolidin-3-yl)ethoxy)-3H-imidazo[4,5-c]pyridin-6-yl)-3,4-dihydrobenzo[f][1,4]oxazepin-5(2H)-one |
| 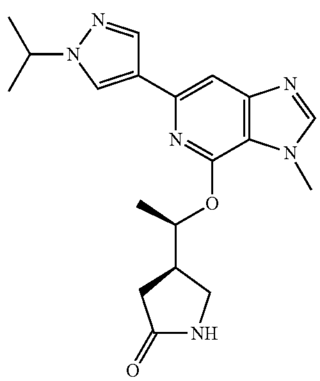 [SMILES: CC(C)n1cc(-c2cc3ncn(C)c3c(O[C@H](C)[C@H]3CNC(=O)C3)n2)cn1] | (R)-4-((R)-1-(6-(1-isopropyl-1H-pyrazol-4-yl)-3-methyl-3H-imidazo[4,5-c]pyridin-4-yloxy)ethyl)pyrrolidin-2-one |
| 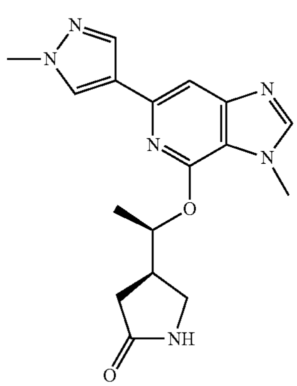 [SMILES: C[C@@H](Oc1nc(-c2cnn(C)c2)cc2ncn(C)c12)[C@H]1CNC(=O)C1] | (R)-4-((R)-1-(3-methyl-6-(1-methyl-1H-pyrazol-4-yl)-3H-imidazo[4,5-c]pyridin-4-yloxy)ethyl)pyrrolidin-2-one |

TABLE A-continued

Representative Compounds

| Structure | Name |
|---|---|
| 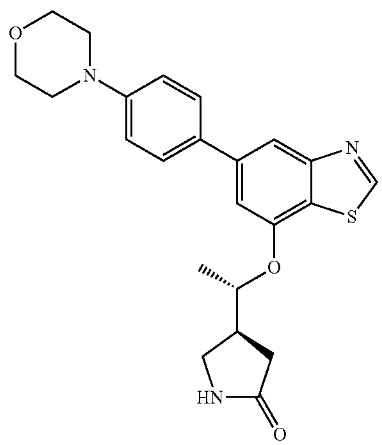 [SMILES: C[C@H](Oc1cc(-c2ccc(N3CCOCC3)cc2)cc2ncsc12)[C@@H]1CNC(=O)C1] | (R)-4-((R)-1-((5-(4-morpholinophenyl)benzo[d]thiazol-7-yl)oxy)ethyl)pyrrolidin-2-one |
| 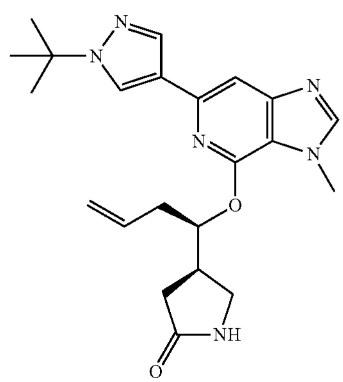 [SMILES: C=CC[C@@H](Oc1nc(-c2cnn(C(C)(C)C)c2)cc2ncn(C)c12)[C@H]1CNC(=O)C1] | (R)-4-((R)-1-((6-(1-(tert-butyl)-1H-pyrazol-4-yl)-3-methyl-3H-imidazo[4,5-c]pyridin-4-yl)oxy)but-3-en-1-yl)pyrrolidin-2-one |
| 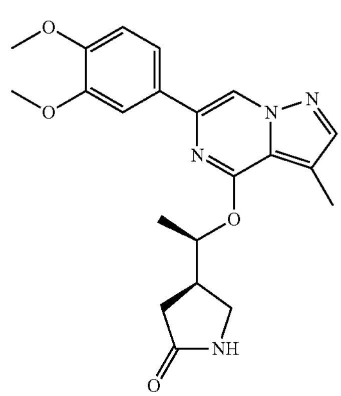 [SMILES: COc1ccc(-c2cn3ncc(C)c3c(O[C@H](C)[C@H]3CNC(=O)C3)n2)cc1OC] | (R)-4-((R)-1-((6-(3,4-dimethoxyphenyl)-3-methylpyrazolo[1,5-a]pyrazin-4-yl)oxy)ethyl)pyrrolidin-2-one |

TABLE A-continued

Representative Compounds

| Structure | Name |
|---|---|
| 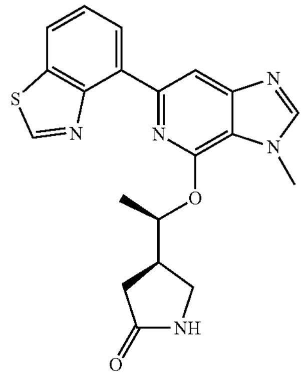 [SMILES: C[C@@H](Oc1nc(-c2cccc3scnc23)cc2ncn(C)c12)[C@H]1CNC(=O)C1] | (R)-4-((R)-1-(6-(benzo[d]thiazol-4-yl)-3-methyl-3H-imidazo[4,5-c]pyridin-4-yloxy)ethyl)pyrrolidin-2-one |
| 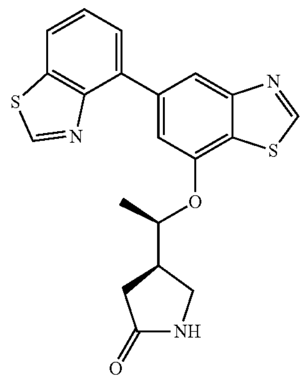 [SMILES: C[C@@H](Oc1cc(-c2cccc3scnc23)cc2ncsc12)[C@H]1CNC(=O)C1] | (R)-4-((R)-1-([4,5'-bibenzo[d]thiazol]-7'-yloxy)ethyl)pyrrolidin-2-one |
| 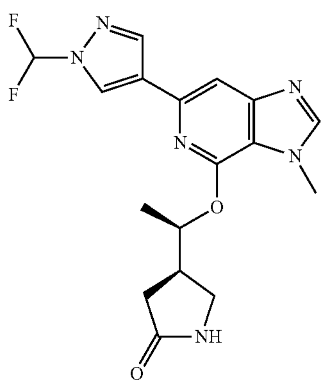 [SMILES: C[C@@H](Oc1nc(-c2cnn(C(F)F)c2)cc2ncn(C)c12)[C@H]1CNC(=O)C1] | (R)-4-((R)-1-(6-(1-(difluoromethyl)-1H-pyrazol-4-yl)-3-methyl-3H-imidazo[4,5-c]pyridin-4-yloxy)ethyl)pyrrolidin-2-one |
| 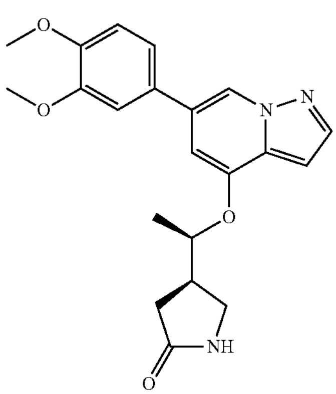 [SMILES: COc1ccc(-c2cc(O[C@H](C)[C@H]3CNC(=O)C3)c3ccnn3c2)cc1OC] | (R)-4-((R)-1-((6-(3,4-dimethoxyphenyl)pyrazolo[1,5-a]pyridin-4-yl)oxy)ethyl)pyrrolidin-2-one |

TABLE A-continued

Representative Compounds

| Structure | Name |
|---|---|
| 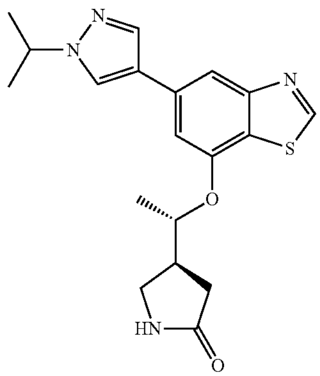 [SMILES: CC(C)n1cc(-c2cc(O[C@@H](C)[C@@H]3CNC(=O)C3)c3scnc3c2)cn1] | (R)-4-((R)-1-((5-(1-isopropyl-1H-pyrazol-4-yl)benzo[d]thiazol-7-yl)oxy)ethyl)pyrrolidin-2-one |
| 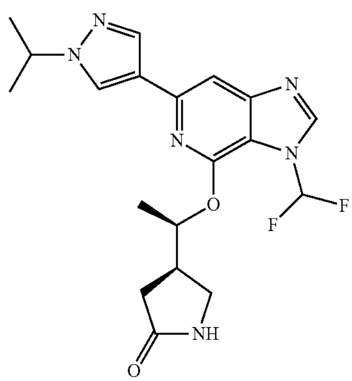 [SMILES: CC(C)n1cc(-c2cc3ncn(C(F)F)c3c(O[C@H](C)[C@H]3CNC(=O)C3)n2)cn1] | (R)-4-((R)-1-(3-(difluoromethyl)-6-(1-isopropyl-1H-pyrazol-4-yl)-3H-imidazo[4,5-c]pyridin-4-yloxy)ethyl)pyrrolidin-2-one |
| 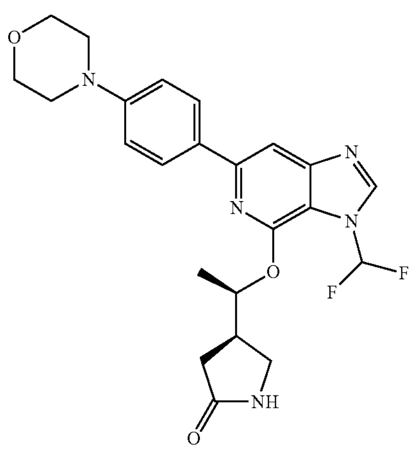 [SMILES: C[C@@H](Oc1nc(-c2ccc(N3CCOCC3)cc2)cc2ncn(C(F)F)c12)[C@H]1CNC(=O)C1] | (R)-4-((R)-1-(3-(difluoromethyl)-6-(4-morpholinophenyl)-3H-imidazo[4,5-c]pyridin-4-yloxy)ethyl)pyrrolidin-2-one |
| 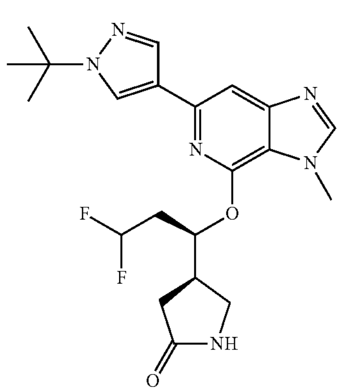 [SMILES: Cn1cnc2cc(-c3cnn(C(C)(C)C)c3)nc(O[C@H](CC(F)F)[C@H]3CNC(=O)C3)c21] | (R)-4-((R)-1-(6-(1-tert-butyl-1H-pyrazol-4-yl)-3-methyl-3H-imidazo[4,5-c]pyridin-4-yloxy)-3,3-difluoropropyl)pyrrolidin-2-one |

TABLE A-continued

Representative Compounds

| Structure | Name |
|---|---|
| 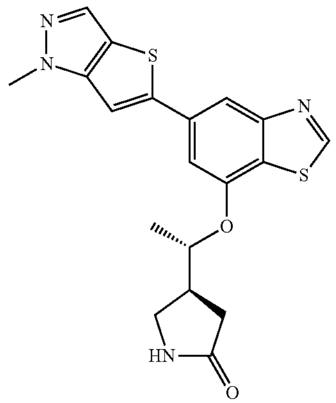 [SMILES: C[C@H](Oc1cc(-c2cc3c(cnn3C)s2)cc2ncsc12)[C@@H]1CNC(=O)C1] | (R)-4-((R)-1-((5-(1-methyl-1H-thieno[3,2-c]pyrazol-5-yl)benzo[d]thiazol-7-yl)oxy)ethyl)pyrrolidin-2-one |
| 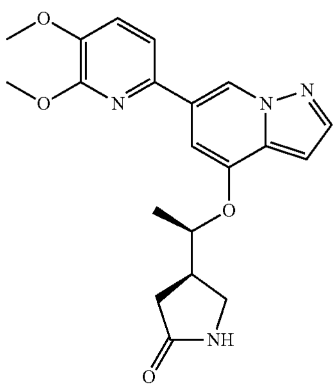 [SMILES: COc1ccc(-c2cc(O[C@H](C)[C@H]3CNC(=O)C3)c3ccnn3c2)nc1OC] | (R)-4-((R)-1-((6-(5,6-dimethoxypyridin-2-yl)pyrazolo[1,5-a]pyridin-4-yl)oxy)ethyl)pyrrolidin-2-one |
| 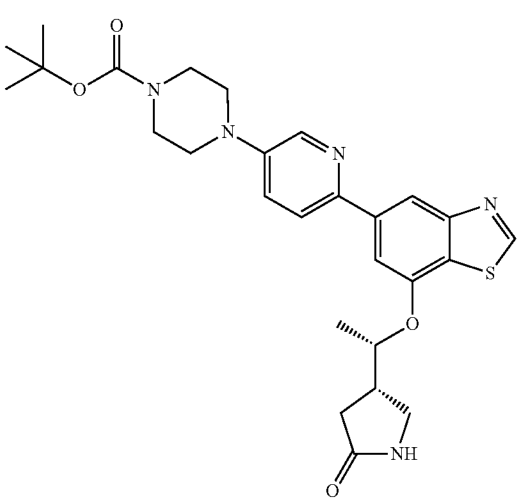 [SMILES: C[C@H](Oc1cc(-c2ccc(N3CCN(C(=O)OC(C)(C)C)CC3)cn2)cc2ncsc12)[C@@H]1CNC(=O)C1] | tert-butyl 4-(6-(7-((R)-1-((R)-5-oxopyrrolidin-3-yl)ethoxy)benzo[d]thiazol-5-yl)pyridin-3-yl)piperazine-1-carboxylate |

TABLE A-continued

Representative Compounds

| Structure | Name |
|---|---|
| 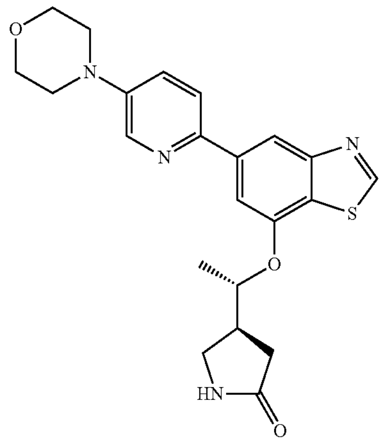 | (R)-4-((R)-1-((5-(5-morpholinopyridin-2-yl)benzo[d]thiazol-7-yl)oxy)ethyl)pyrrolidin-2-one |
| 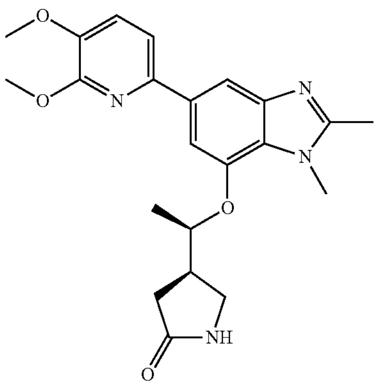 | (R)-4-((R)-1-(5-(5,6-dimethoxypyridin-2-yl)-1,2-dimethyl-1H-benzo[d]imidazol-7-yloxy)ethyl)pyrrolidin-2-one |
| 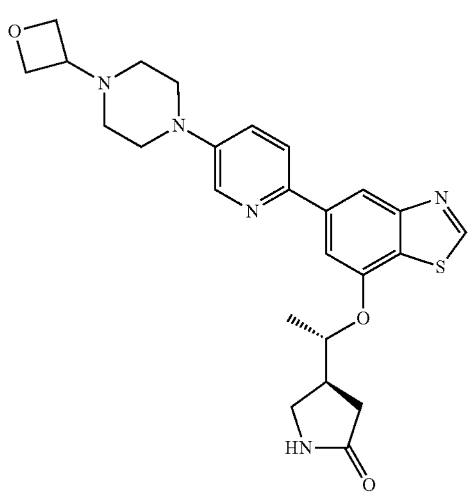 [SMILES: C[C@H](Oc1cc(-c2ccc(N3CCN(C4COC4)CC3)cn2)cc2ncsc12)[C@@H]1CNC(=O)C1] | (R)-4-((R)-1-((5-(5-(4-(oxetan-3-yl)piperazin-1-yl)pyridin-2-yl)benzo[d]thiazol-7-yl)oxy)ethyl)pyrrolidin-2-one |

TABLE A-continued
Representative Compounds
| Structure | Name |
|---|---|
| 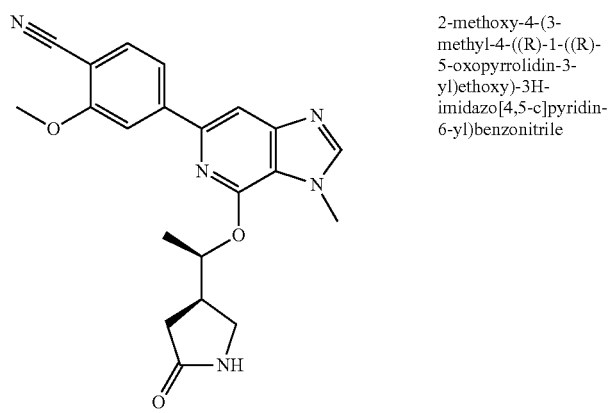 | 2-methoxy-4-(3-methyl-4-((R)-1-((R)-5-oxopyrrolidin-3-yl)ethoxy)-3H-imidazo[4,5-c]pyridin-6-yl)benzonitrile |
| 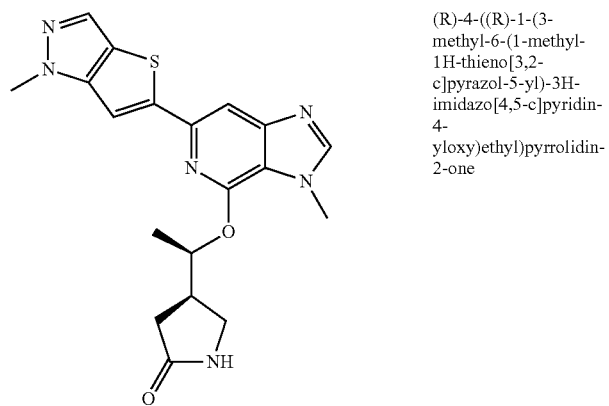 | (R)-4-((R)-1-(3-methyl-6-(1-methyl-1H-thieno[3,2-c]pyrazol-5-yl)-3H-imidazo[4,5-c]pyridin-4-yloxy)ethyl)pyrrolidin-2-one |
| 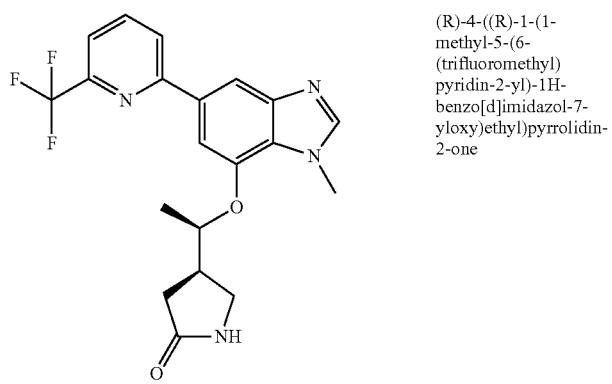 | (R)-4-((R)-1-(1-methyl-5-(6-(trifluoromethyl)pyridin-2-yl)-1H-benzo[d]imidazol-7-yloxy)ethyl)pyrrolidin-2-one |

TABLE A-continued

Representative Compounds

| Structure | Name |
|---|---|
| 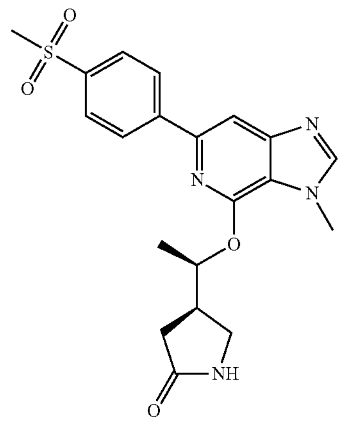 [SMILES: C[C@@H](Oc1nc(-c2ccc(S(C)(=O)=O)cc2)cc2ncn(C)c12)[C@H]1CNC(=O)C1] | (R)-4-((R)-1-(3-methyl-6-(4-(methylsulfonyl)phenyl)-3H-imidazo[4,5-c]pyridin-4-yloxy)ethyl)pyrrolidin-2-one |
| 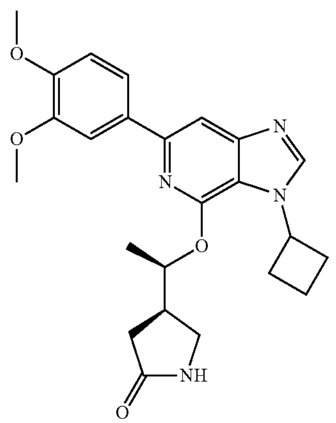 [SMILES: COc1ccc(-c2cc3ncn(C4CCC4)c3c(O[C@H](C)[C@H]3CNC(=O)C3)n2)cc1OC] | (R)-4-((R)-1-(3-cyclobutyl-6-(3,4-dimethoxyphenyl)-3H-imidazo[4,5-c]pyridin-4-yloxy)ethyl)pyrrolidin-2-one |
| 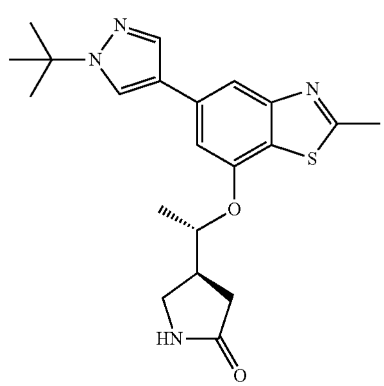 [SMILES: Cc1nc2cc(-c3cnn(C(C)(C)C)c3)cc(O[C@@H](C)[C@@H]3CNC(=O)C3)c2s1] | (R)-4-((R)-1-((5-(1-(tert-butyl)-1H-pyrazol-4-yl)-2-methylbenzo[d]thiazol-7-yl)oxy)ethyl)pyrrolidin-2-one |

TABLE A-continued

Representative Compounds

| Structure | Name |
|---|---|
| 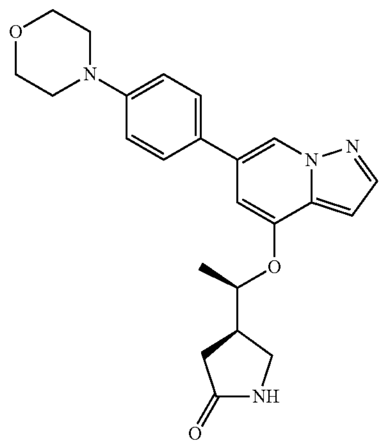 [SMILES: C[C@@H](Oc1cc(-c2ccc(N3CCOCC3)cc2)cn2nccc12)[C@H]1CNC(=O)C1] | (R)-4-((R)-1-((6-(4-morpholinophenyl)pyrazolo[1,5-a]pyridin-4-yl)oxy)ethyl)pyrrolidin-2-one |
| 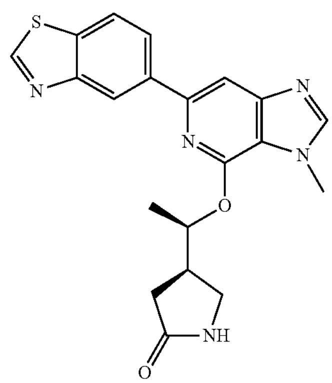 [SMILES: C[C@@H](Oc1nc(-c2ccc3scnc3c2)cc2ncn(C)c12)[C@H]1CNC(=O)C1] | (R)-4-((R)-1-((6-(benzo[d]thiazol-5-yl)-3-methyl-3H-imidazo[4,5-c]pyridin-4-yl)oxy)ethyl)pyrrolidin-2-one |
| 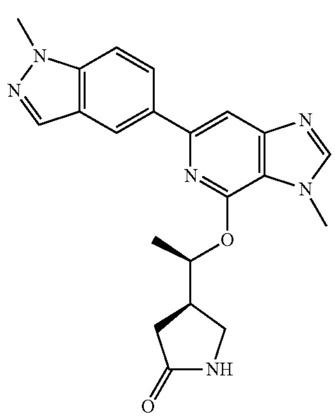 [SMILES: C[C@@H](Oc1nc(-c2ccc3c(cnn3C)c2)cc2ncn(C)c12)[C@H]1CNC(=O)C1] | (R)-4-((R)-1-((3-methyl-6-(1-methyl-1H-indazol-5-yl)-3H-imidazo[4,5-c]pyridin-4-yl)oxy)ethyl)pyrrolidin-2-one |

TABLE A-continued

Representative Compounds

| Structure | Name |
|---|---|
| 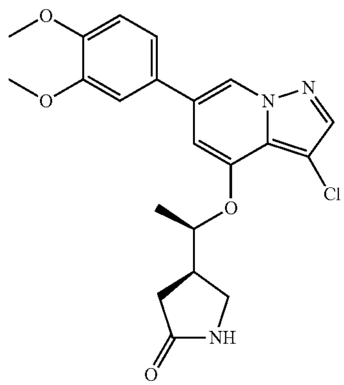 [SMILES: COc1ccc(-c2cc(O[C@H](C)[C@H]3CNC(=O)C3)c3c(Cl)cnn3c2)cc1OC] | (R)-4-((R)-1-((3-chloro-6-(3,4-dimethoxyphenyl)pyrazolo[1,5-a]pyridin-4-yl)oxy)ethyl)pyrrolidin-2-one |
| 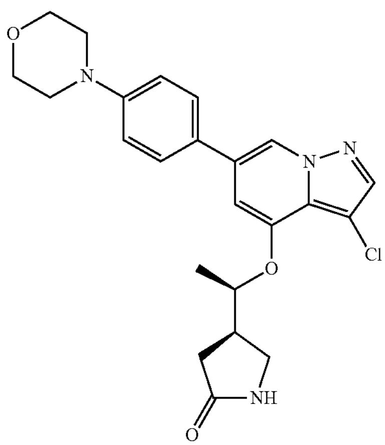 [SMILES: C[C@@H](Oc1cc(-c2ccc(N3CCOCC3)cc2)cn2ncc(Cl)c12)[C@H]1CNC(=O)C1] | (R)-4-((R)-1-((3-chloro-6-(4-morpholinophenyl)pyrazolo[1,5-a]pyridin-4-yl)oxy)ethyl)pyrrolidin-2-one |
| 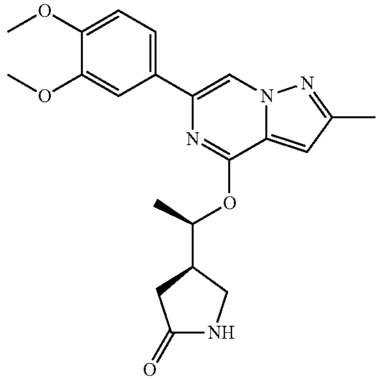 | (R)-4-((R)-1-((6-(3,4-dimethoxyphenyl)-2-methylpyrazolo[1,5-a]pyrazin-4-yl)oxy)ethyl)pyrrolidin-2-one |

TABLE A-continued

Representative Compounds

| Structure | Name |
|---|---|
| 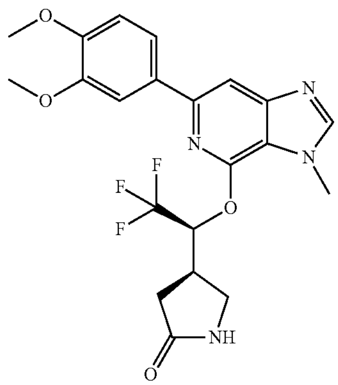 [SMILES: COc1ccc(-c2cc3ncn(C)c3c(O[C@@H]([C@H]3CNC(=O)C3)C(F)(F)F)n2)cc1OC] | (R)-4-((S)-1-((6-(3,4-dimethoxyphenyl)-3-methyl-3H-imidazo[4,5-c]pyridin-4-yl)oxy)-2,2,2-trifluoroethyl)pyrrolidin-2-one |
| 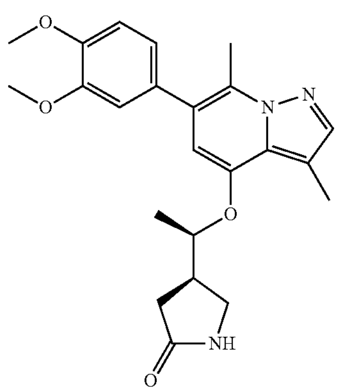 [SMILES: COc1ccc(-c2cc(O[C@H](C)[C@H]3CNC(=O)C3)c3c(C)cnn3c2C)cc1OC] | (R)-4-((R)-1-((6-(3,4-dimethoxyphenyl)-3,7-dimethylpyrazolo[1,5-a]pyridin-4-yl)oxy)ethyl)pyrrolidin-2-one |
| 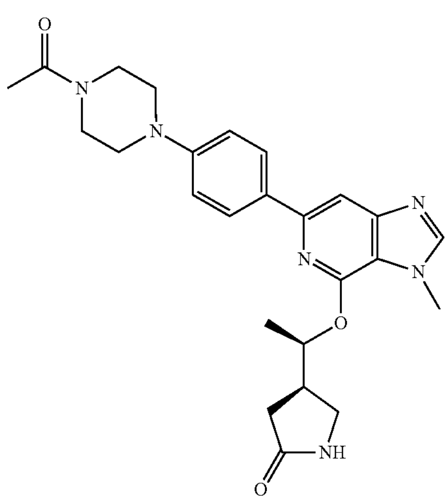 [SMILES: CC(=O)N1CCN(c2ccc(-c3cc4ncn(C)c4c(O[C@H](C)[C@H]4CNC(=O)C4)n3)cc2)CC1] | (R)-4-((R)-1-((6-(4-(4-acetylpiperazin-1-yl)phenyl)-3-methyl-3H-imidazo[4,5-c]pyridin-4-yl)oxy)ethyl)pyrrolidin-2-one |

TABLE A-continued

Representative Compounds

| Structure | Name |
|---|---|
| 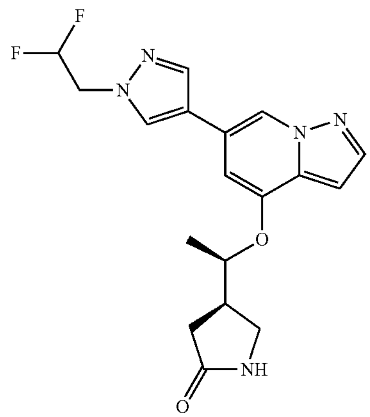 [SMILES: C[C@@H](Oc1cc(-c2cnn(CC(F)F)c2)cn2nccc12)[C@H]1CNC(=O)C1] | (R)-4-((R)-1-((6-(1-(2,2-difluoroethyl)-1H-pyrazol-4-yl)pyrazolo[1,5-a]pyridin-4-yl)oxy)ethyl)pyrrolidin-2-one |
| 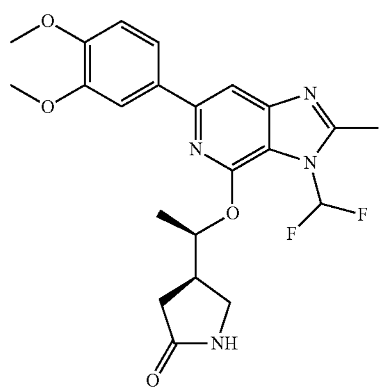 | (R)-4-((R)-1-((3-(difluoromethyl)-6-(3,4-dimethoxyphenyl)-2-methyl-3H-imidazo[4,5-c]pyridin-4-yl)oxy)ethyl)pyrrolidin-2-one |
| 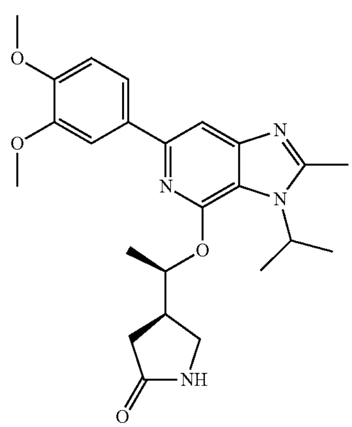 [SMILES: COc1ccc(-c2cc3nc(C)n(C(C)C)c3c(O[C@H](C)[C@H]3CNC(=O)C3)n2)cc1OC] | (R)-4-((R)-1-((6-(3,4-dimethoxyphenyl)-3-isopropyl-2-methyl-3H-imidazo[4,5-c]pyridin-4-yl)oxy)ethyl)pyrrolidin-2-one |

TABLE A-continued

Representative Compounds

| Structure | Name |
|---|---|
| 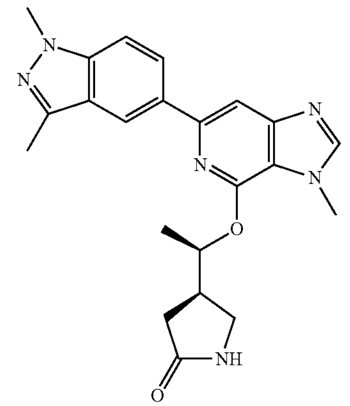 [SMILES: Cc1nn(C)c2ccc(-c3cc4ncn(C)c4c(O[C@H](C)[C@H]4CNC(=O)C4)n3)cc12] | (R)-4-((R)-1-((6-(1,3-dimethyl-1H-indazol-5-yl)-3-methyl-3H-imidazo[4,5-c]pyridin-4-yl)oxy)ethyl)pyrrolidin-2-one |
| 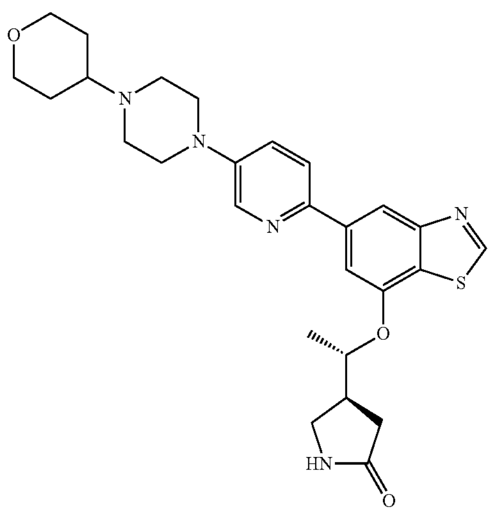 [SMILES: C[C@H](Oc1cc(-c2ccc(N3CCN(C4CCOCC4)CC3)cn2)cc2ncsc12)[C@@H]1CNC(=O)C1] | (R)-4-((R)-1-((5-(5-(4-(tetrahydro-2H-pyran-4-yl)piperazin-1-yl)pyridin-2-yl)benzo[d]thiazol-7-yl)oxy)ethyl)pyrrolidin-2-one |
| 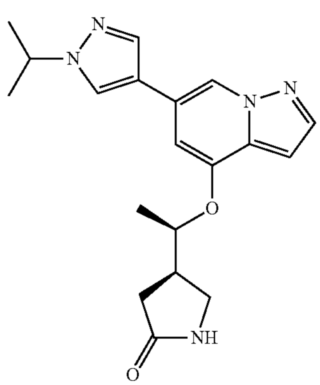 [SMILES: CC(C)n1cc(-c2cc(O[C@H](C)[C@H]3CNC(=O)C3)c3ccnn3c2)cn1] | (R)-4-((R)-1-((6-(1-isopropyl-1H-pyrazol-4-yl)pyrazolo[1,5-a]pyridin-4-yl)oxy)ethyl)pyrrolidin-2-one |

Methods of Use

Provided is a method of treating a patient, for example, a mammal, such as a human, having a disease responsive to inhibition of Syk activity, comprising administrating to the patient having such a disease, an effective amount of a compound of Formula I, II, III, IV, V, or VI, or a pharmaceutically acceptable salt thereof.

In some embodiments, the compounds of Formula I, II, III, IV, V, or VI, or a pharmaceutically acceptable salt thereof, may also inhibit other kinases, such that disease, disease symptoms, and conditions associated with these kinases is also treated.

Methods of treatment also include inhibiting Syk activity and/or inhibiting B-cell activity, by inhibiting ATP binding or hydrolysis by Syk or by some other mechanism, in vivo, in a patient suffering from a disease responsive to inhibition of Syk activity, by administering an effective concentration of a compound of Formula I, II, III, IV, V, or VI, or a pharmaceutically acceptable salt thereof. An example of an effective concentration would be that concentration sufficient to inhibit Syk activity in vitro. An effective concentration may be ascertained experimentally, for example by assaying blood concentration of the chemical entity, or theoretically, by calculating bioavailability.

In some embodiments, the condition responsive to inhibition of Syk activity and/or B-cell activity is cancer, an allergic disorder and/or an autoimmune and/or inflammatory disease, and/or an acute inflammatory reaction.

Also provided is a method of treating a patient having cancer, an allergic disorder and/or an autoimmune and/or inflammatory disease, and/or an acute inflammatory reaction, by administering an effective amount of a compound of Formula I, II, III, IV, V, or VI, or a pharmaceutically acceptable salt thereof.

In some embodiments, the conditions and diseases that can be affected using a compound of Formula I, II, III, IV, V, or VI, or a pharmaceutically acceptable salt thereof, include, but are not limited to: allergic disorders, including but not limited to eczema, allergic rhinitis or coryza, hay fever, bronchial asthma, urticaria (hives) and food allergies (including pollen allergies, dairy allergies, including milk allergies, soy allergies, egg allergies, wheat allergies, nut allergies, including allergies to peanuts and tree nuts, including walnuts, almonds, hazelnuts, cashews, pistachios, pecans, Brazil nuts, beechnuts, butternuts, chestnuts, Chinquapin nuts, hickory nuts, etc and seafood allergies), and other atopic conditions; autoimmune and/or inflammatory diseases, including but not limited to psoriasis, Crohn's disease, irritable bowel syndrome, Sjogren's disease, tissue graft rejection, and hyperacute rejection of transplanted organs, asthma, systemic lupus erythematosus (and associated glomerulonephritis), dermatomyositis, multiple sclerosis, scleroderma, vasculitis (ANCA-associated and other vasculitides), autoimmune hemolytic and thrombocytopenic states, Goodpasture's syndrome (and associated glomerulonephritis and pulmonary hemorrhage), atherosclerosis, rheumatoid arthritis, chronic Idiopathic thrombocytopenic purpura (ITP), Addison's disease, Parkinson's disease, Alzheimer's disease, diabetes, septic shock, myasthenia gravis, and the like; acute inflammatory reactions, including but not limited to skin sunburn, inflammatory pelvic disease, inflammatory bowel disease, urethritis, uveitis, sinusitis, pneumonitis, encephalitis, meningitis, myocarditis, nephritis, osteomyelitis, myositis, hepatitis, gastritis, enteritis, dermatitis, gingivitis, appendicitis, pancreatitis, and cholocystitis; polycystic kidney disease, and cancer, including but not limited to, B-cell lymphoma, lymphoma (including Hodgkin's and non-Hodgkins lymphoma), hairy cell leukemia, multiple myeloma, chronic and acute myelogenous leukemia, and chronic and acute lymphocytic leukemia.

Syk is a known inhibitor of apoptosis in lymphoma B-cells. Defective apoptosis contributes to the pathogenesis and drug resistance of human leukemias and lymphomas. Thus, further provided is a method of promoting or inducing apoptosis in cells expressing Syk comprising contacting the cell with a compound of Formula I, II, III, IV, V, or VI, or a pharmaceutically acceptable salt thereof.

In some embodiments, provided is a method of treating a patient having cancer by administering an effective amount of a compound of Formula I, II, III, IV, V, or VI, or a pharmaceutically acceptable salt thereof. In particular embodiments, the cancer is leukemia or lymphoma. In specific embodiments, the cancer is acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), indolent non-Hodgkin's lymphoma (iNHL), refractory iNHL, non-Hodgkin's lymphoma (NHL), mantle cell lymphoma (MCL), follicular lymphoma, Waldestrom's macroglobulinemia (WM), T-cell lymphoma, B-cell lymphoma, and diffuse large B-cell lymphoma (DLBCL). In one embodiment, the cancer is T-cell acute lymphoblastic leukemia (T-ALL), or B-cell acute lymphoblastic leukemia (B-ALL). The non-Hodgkin lymphoma encompasses the indolent B-cell diseases that include, for example, follicular lymphoma, lymphoplasmacytic lymphoma, Waldenstrom macroglobulinemia, and marginal zone lymphoma, as well as the aggressive lymphomas that include, for example, Burkitt lymphoma, diffuse large B-cell lymphoma (DLBCL) and mantle cell lymphoma (MCL). In one embodiment, the cancer is indolent non-Hodgkin's lymphoma (iNHL).

In some embodiments, provided is a method of treating a patient having a hematologic malignancy by administering an effective amount of a compound of Formula I, II, III, IV, V, or VI, or a pharmaceutically acceptable salt thereof. In specific embodiments, the hematologic malignancy is leukemia (e.g., chronic lymphocytic leukemia) or lymphoma (e.g., non-Hodgkin's lymphoma).

Dosage levels of the order, for example, of from 0.1 mg to 140 mg per kilogram of body weight per day can be useful in the treatment of the above-indicated conditions (0.5 mg to 7 g per patient per day). The amount of active ingredient that may be combined with the vehicle to produce a single dosage form will vary depending upon the host treated and the particular mode of administration. Dosage unit forms will generally contain from 1 mg to 500 mg of an active ingredient.

Frequency of dosage may also vary depending on the compound used and the particular disease treated. In some embodiments, for example, for the treatment of an allergic disorder and/or autoimmune and/or inflammatory disease, a dosage regimen of 4 times daily or less is used. In some embodiments, a dosage regimen of 1 or 2 times daily is used. It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease in the patient undergoing therapy.

A labeled form of a compound of Formula I, II, III, IV, V, or VI, or a pharmaceutically acceptable salt thereof, herein can be used as a diagnostic for identifying and/or obtaining compounds that have the function of modulating an activity of a kinase as described herein. The compounds of Formula I, II, III, IV, V, or VI, or a pharmaceutically acceptable salt thereof may additionally be used for validating, optimizing, and standardizing bioassays. By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

Pharmaceutical Compositions and Administration

Compounds of Formula I, II, III, IV, V, or VI, or a pharmaceutically acceptable salt thereof, are usually administered in the form of pharmaceutical compositions. This disclosure therefore provides pharmaceutical compositions that contain, as the active ingredient, one or more of the compounds described, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.)

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral, particularly by injection. The forms in which the novel compositions of the present disclosure may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present disclosure. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present disclosure in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Preferably, for parenteral administration, sterile injectable solutions are prepared containing a therapeutically effective amount, e.g., 0.1 to 700 mg, of a compound of Formula I, II, III, IV, V, or VI, or a pharmaceutically acceptable salt thereof. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

Oral administration is another route for administration of compounds of Formula I, II, III, IV, V, or VI, or a pharmaceutically acceptable salt thereof. Administration may be via capsule or enteric coated tablets, or the like. In making the pharmaceutical compositions that include a compound of Formula I, II, III, IV, V, or VI, or a pharmaceutically acceptable salt thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions of the disclosure can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present disclosure employs transdermal delivery devices ("patches"). Such transdermal patches may be used to provide continuous or discontinuous infusion of the compounds of the present disclosure in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. Preferably, for oral administration, each dosage unit contains from 1 mg to 2 g, or alternatively, or 100 mg to 500 mg, of a compound of Formula I, II, III, IV, V, or VI, or a pharmaceutically acceptable salt thereof, and for parenteral administration, preferably from 0.1 mg to 700 mg, or alternatively, 0.1 mg to 100 mg, of a compound a compound of Formula I, II, III, IV, V, or VI, or a pharmaceutically acceptable salt thereof. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present disclosure may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid or solid compositions comprising a compound of Formula I, II, III, IV, V, or VI, or a pharmaceutically acceptable salt thereof may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Combination Therapy

Also provided are methods of treatment in which a compound of Formula I, II, III, IV, V, or VI, or a pharmaceutically acceptable salt thereof, is the only active agent given to a patient and also includes methods of treatment in which a compound of Formula I, II, III, IV, V, or VI, or a pharmaceutically acceptable salt thereof, is given to a patient in combination with one or more additional active agents.

Thus in some embodiments, a method of treating cancer, an allergic disorder and/or an autoimmune and/or inflammatory disease, and/or an acute inflammatory reaction comprises administering to a patient in need thereof an effective amount of a compound of Formula I, II, III, IV, V, or VI, or a pharmaceutically acceptable salt thereof, together with a second active agent, which can be useful for treating a cancer, an allergic disorder and/or an autoimmune and/or inflammatory disease, and/or an acute inflammatory reaction. For example the second agent may be an anti-inflammatory agent. Treatment with the second active agent may be prior to, concomitant with, or following treatment with a compound of Formula I, II, III, IV, V, or VI, or a pharmaceutically acceptable salt thereof. In some embodiments, a compound of Formula I, II, III, IV, V, or VI, or a pharmaceutically acceptable salt thereof is combined with another active agent in a single dosage form. Suitable antitumor therapeutics that may be used in combination with a compound of Formula I, II, III, IV, V, or VI, or a pharmaceutically acceptable salt thereof include, but are not limited to, chemotherapeutic agents, for example mitomycin C, carboplatin, taxol, cisplatin, paclitaxel, etoposide, doxorubicin, or a combination comprising at least one of the foregoing chemotherapeutic agents. Radiotherapeutic antitumor agents may also be used, alone or in combination with chemotherapeutic agents.

Compounds of Formula I, II, III, IV, V, or VI, or a pharmaceutically acceptable salt thereof can be useful as chemosensitizing agents, and, thus, can be useful in combination with other chemotherapeutic drugs, in particular, drugs that induce apoptosis.

A method for increasing sensitivity of cancer cells to chemotherapy, comprising administering to a patient undergoing chemotherapy a chemotherapeutic agent together with a compound of Formula I, II, III, IV, V, or VI, or a pharmaceutically acceptable salt thereof in an amount sufficient to increase the sensitivity of cancer cells to the chemotherapeutic agent is also provided herein.

Examples of other chemotherapeutic drugs that can be used in combination with compounds of Formula I, II, III, IV, V, or VI, or a pharmaceutically acceptable salt thereof include topoisomerase I inhibitors (camptothesin or topotecan), topoisomerase II inhibitors (e.g. daunomycin and etoposide), alkylating agents (e.g. cyclophosphamide, melphalan and BCNU), tubulin directed agents (e.g. taxol and vinblastine), and biological agents (e.g. antibodies such as anti CD20 antibody, IDEC 8, immunotoxins, and cytokines).

In some embodiments, the compounds of Formula I, II, III, IV, V, or VI, or a pharmaceutically acceptable salt thereof are used in combination with Rituxan® (Rituximab) or other agents that work by selectively depleting CD20+ B-cells.

Included herein are methods of treatment in which a compound of Formula I, II, III, IV, V, or VI, or a pharmaceutically acceptable salt thereof is administered in combination with an anti-inflammatory agent. Anti-inflammatory agents include but are not limited to NSAIDs, non-specific and COX-2 specific cyclooxgenase enzyme inhibitors, gold compounds, corticosteroids, methotrexate, tumor necrosis factor receptor (TNF) receptors antagonists, immunosuppressants and methotrexate.

Examples of NSAIDs include, but are not limited to ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors (i.e., a compound that inhibits COX-2 with an IC50 that is at least 50-fold lower than the IC50 for COX-1) such as celecoxib, valdecoxib, lumiracoxib, etoricoxib and/or rofecoxib.

In a further embodiment, the anti-inflammatory agent is a salicylate. Salicylates include but are not limited to acetylsalicylic acid or aspirin, sodium salicylate, and choline and magnesium salicylates.

The anti-inflammatory agent may also be a corticosteroid. For example, the corticosteroid may be chosen from cortisone, dexamethasone, methylprednisolone, prednisolone, prednisolone sodium phosphate, and prednisone.

In some embodiments, the anti-inflammatory therapeutic agent is a gold compound such as gold sodium thiomalate or auranofin.

In some embodiments, the anti-inflammatory agent is a metabolic inhibitor such as a dihydrofolate reductase inhibitor, such as methotrexate or a dihydroorotate dehydrogenase inhibitor, such as leflunomide.

In some embodiments, the compounds of Formula I, II, III, IV, V, or VI, or a pharmaceutically acceptable salt thereof are used in combination with at least one anti-inflammatory compound is an anti-C5 monoclonal antibody (such as eculizumab or pexelizumab), a TNF antagonist, such as entanercept, or infliximab, which is an anti-TNF alpha monoclonal antibody.

In some embodiments, the compounds of Formula I, II, III, IV, V, or VI, or a pharmaceutically acceptable salt thereof are used in combination with at least one active agent is an immunosuppressant compound such as methotrexate, leflunomide, cyclosporine, tacrolimus, azathioprine, or mycophenolate mofetil.

In other embodiments, the compounds of Formula I, II, III, IV, V, or VI, or a pharmaceutically acceptable salt thereof are used in combination with one or more phosphatidylinositol 3-kinase (PI3K) inhibitors, including for example, Compounds A, B and C (whose structures are provided below), or a pharmaceutically acceptable salt thereof.

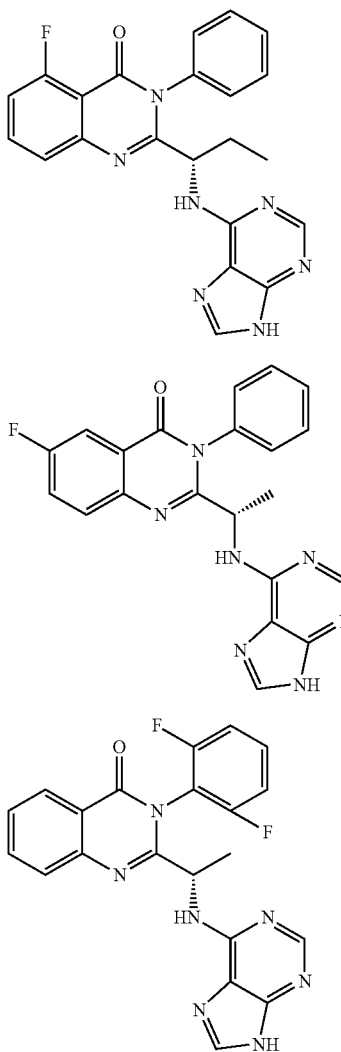

Compound A

Compound B

Compound C

In yet other embodiments, the compounds of Formula I, II, III, IV, V, or VI, or a pharmaceutically acceptable salt thereof are used in combination with one or more inhibitors of lysyl oxidase-like 2 (LOXL2) and a substance that bind to LOXL2, including for example, a humanized monoclonal antibody (mAb) with an immunoglobulin IgG4 isotype directed against human LOXL2.

Kits

Kits comprising a pharmaceutical composition comprising a compound of Formula I, II, III, IV, V, or VI, or a pharmaceutically acceptable salt thereof, and at least one pharmaceutically acceptable carrier is also provided. In some embodiments, the kit comprises instructions for use in the treatment of cancer or inflammatory conditions. In a particular variation, the instructions are directed to use of the pharmaceutical composition for the treatment of cancer, including for example, leukemia or lymphoma. In specific embodiments, the cancer is acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), indolent non-Hodgkin's lymphoma (iNHL), refractory iNHL, non-Hodgkin's lymphoma (NHL), mantle cell lymphoma (MCL), follicular lymphoma, Waldestrom's macroglobulinemia (WM), T-cell lymphoma, B-cell lymphoma, and diffuse large B-cell lymphoma (DLBCL). In one embodiment, the cancer is T-cell acute lymphoblastic leukemia (T-ALL), or B-cell acute lymphoblastic leukemia (B-ALL). The non-Hodgkin lymphoma encompasses the indolent B-cell diseases that include, for example, follicular lymphoma, lymphoplasmacytic lymphoma, Waldenstrom macroglobulinemia, and marginal zone lymphoma, as well as the aggressive lymphomas that include, for example, Burkitt lymphoma, diffuse large B-cell lymphoma (DLBCL) and mantle cell lymphoma (MCL). In one embodiment, the cancer is indolent non-Hodgkin's lymphoma (iNHL)

In a particular variation, the instructions are directed to use of the pharmaceutical composition for the treatment of an autoimmune disease. Specific embodiments of an autoimmune disease include asthma, rheumatoid arthritis, multiple sclerosis, and lupus.

Any pharmaceutical composition provided in the present disclosure may be used in the kits, the same as if each and every composition were specifically and individually listed for use a kit.

Articles of Manufacture

Articles of manufacture comprising a container in which a compound of Formula I, II, III, IV, V, or VI, or a pharmaceutically acceptable salt thereof, and at least one pharmaceutically acceptable carrier are contained are provided. The article of manufacture may be a bottle, vial, ampoule, single-use disposable applicator, or the like, containing the pharmaceutical composition provided in the present disclosure. The container may be formed from a variety of materials, such as glass or plastic and in one aspect also contains a label on, or associated with, the container which indicates directions for use in the treatment of cancer or inflammatory conditions.

It should be understood that the active ingredient may be packaged in any material capable of improving chemical and physical stability, such as an aluminum foil bag.

Unit dosage forms of the pharmaceutical composition comprising a compound of Formula I, II, III, IV, V, or VI, or a pharmaceutically acceptable salt thereof, and at least one pharmaceutically acceptable carrier are also provided.

Any pharmaceutical composition provided in the present disclosure may be used in the articles of manufacture, the same as if each and every composition were specifically and individually listed for use an article of manufacture.

Synthesis

The compounds of the disclosure may be prepared using methods disclosed herein and routine modifications thereof which will be apparent given the disclosure herein and methods well known in the art. Conventional and well-known synthetic methods may be used in addition to the teachings herein. The synthesis of typical compounds of Formula I, II, III, IV, V, or VI, or a pharmaceutically acceptable salt thereof, e.g. compounds having structures described by one or more of Formula I, II, III, IV, V, or VI, or other formulas or compounds disclosed herein, may be accomplished as described in the following examples. If available, reagents may be purchased commercially, e.g. from Sigma Aldrich or other chemical suppliers.

General Syntheses

Typical embodiments of compounds in accordance with the present disclosure may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments of the present disclosure, inspection of the structure of the compound to be synthesized will provide the identity of each substituent group. The identity of the final product will generally render apparent the identity of the necessary starting materials by a simple process of inspection, given the examples herein.

Synthetic Reaction Parameters

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) *Protecting Groups in Organic Synthesis*, 3rd Edition, Wiley, New York, and references cited therein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5$^{th}$ Edition, 2001), and Larock's Comprehensive Organic Transformations (VCH Publishers Inc., 1989).

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present disclosure are inert organic solvents, and the reactions are carried out under an inert gas, preferably nitrogen.

The term "q.s." means adding a quantity sufficient to achieve a stated function, e.g., to bring a solution to the desired volume (i.e., 100%).

The compounds of the present invention are prepared according to the general schemes provided below.

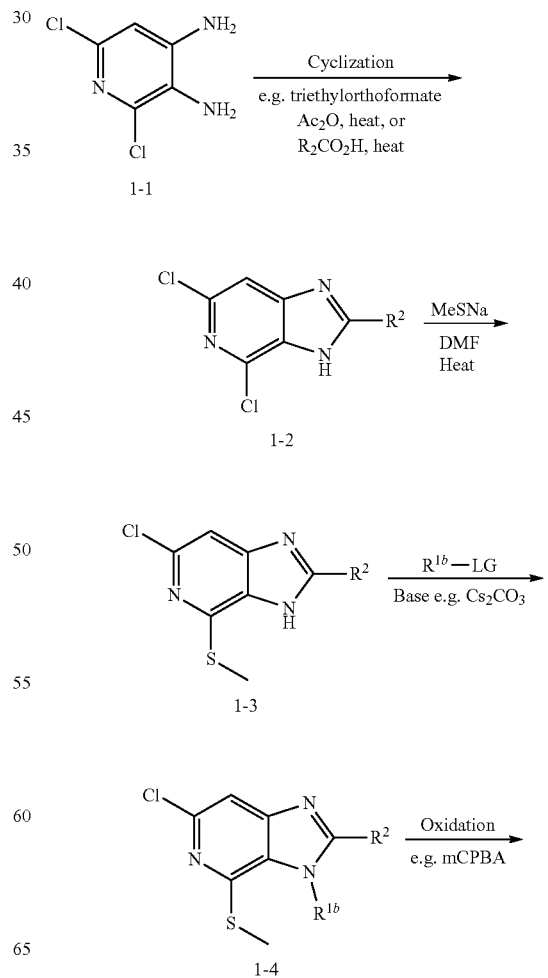

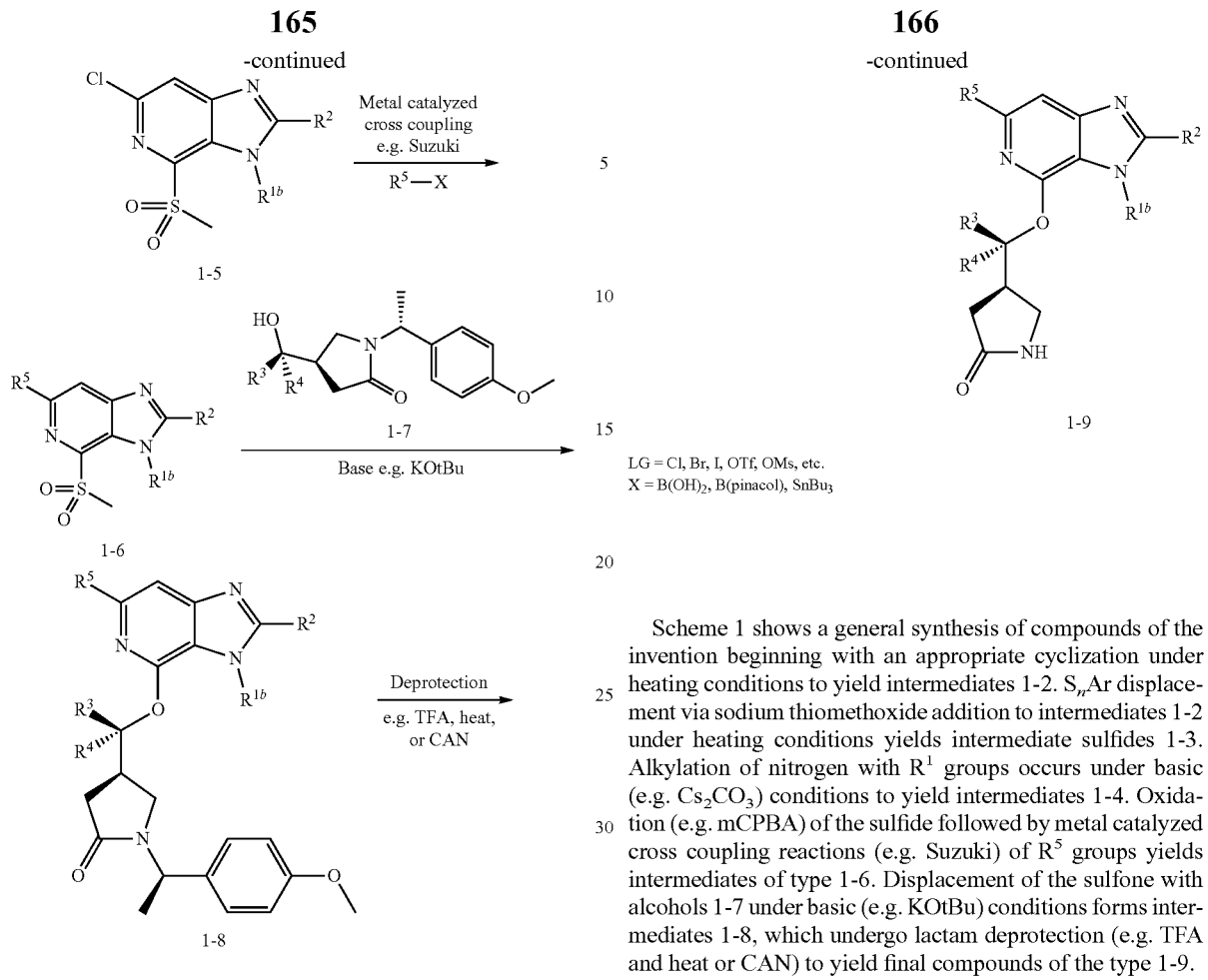

LG = Cl, Br, I, OTf, OMs, etc.
X = B(OH)$_2$, B(pinacol), SnBu$_3$

Scheme 1 shows a general synthesis of compounds of the invention beginning with an appropriate cyclization under heating conditions to yield intermediates 1-2. S$_n$Ar displacement via sodium thiomethoxide addition to intermediates 1-2 under heating conditions yields intermediate sulfides 1-3. Alkylation of nitrogen with R$^1$ groups occurs under basic (e.g. Cs$_2$CO$_3$) conditions to yield intermediates 1-4. Oxidation (e.g. mCPBA) of the sulfide followed by metal catalyzed cross coupling reactions (e.g. Suzuki) of R$^5$ groups yields intermediates of type 1-6. Displacement of the sulfone with alcohols 1-7 under basic (e.g. KOtBu) conditions forms intermediates 1-8, which undergo lactam deprotection (e.g. TFA and heat or CAN) to yield final compounds of the type 1-9.

General Scheme 2

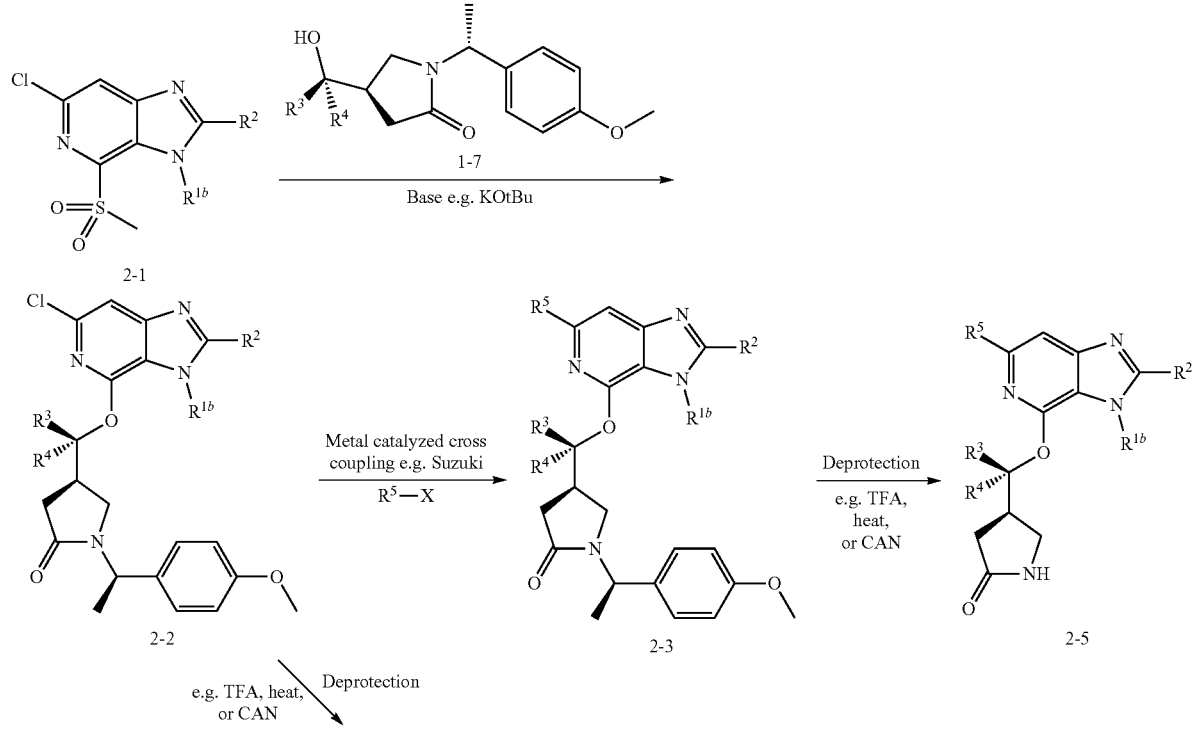

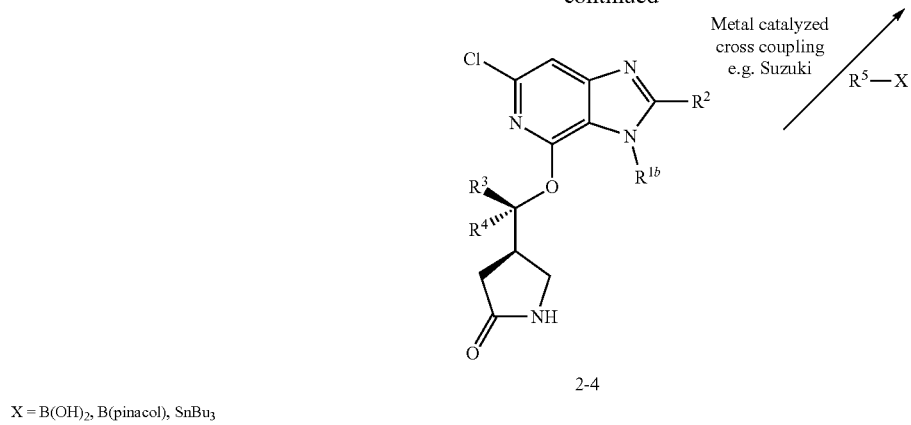

2-4

X = B(OH)₂, B(pinacol), SnBu₃

Scheme 2 describes a general synthesis of compounds of the invention. Sulfone 2-1 can undergo an S$_n$Ar reaction with alcohols 1-7 under basic (e.g. KOtBu) conditions to form intermediates 2-2. Chloride 2-2 reacts under metal catalyzed cross coupling reactions (e.g. Suzuki) of R⁵ groups to yield intermediates 2-3, which undergo lactam deprotection (e.g. TFA and heat or CAN) to yield final compounds of the type 2-5. Intermediates 2-3 can also first be deprotected (e.g. TFA and heat or CAN) to yield intermediates 2-4, which can then undergo metal catalyzed cross coupling reactions (e.g. Suzuki) of R⁵ groups to yield final compounds of type 2-5.

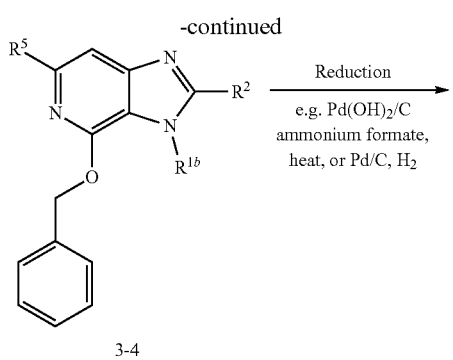

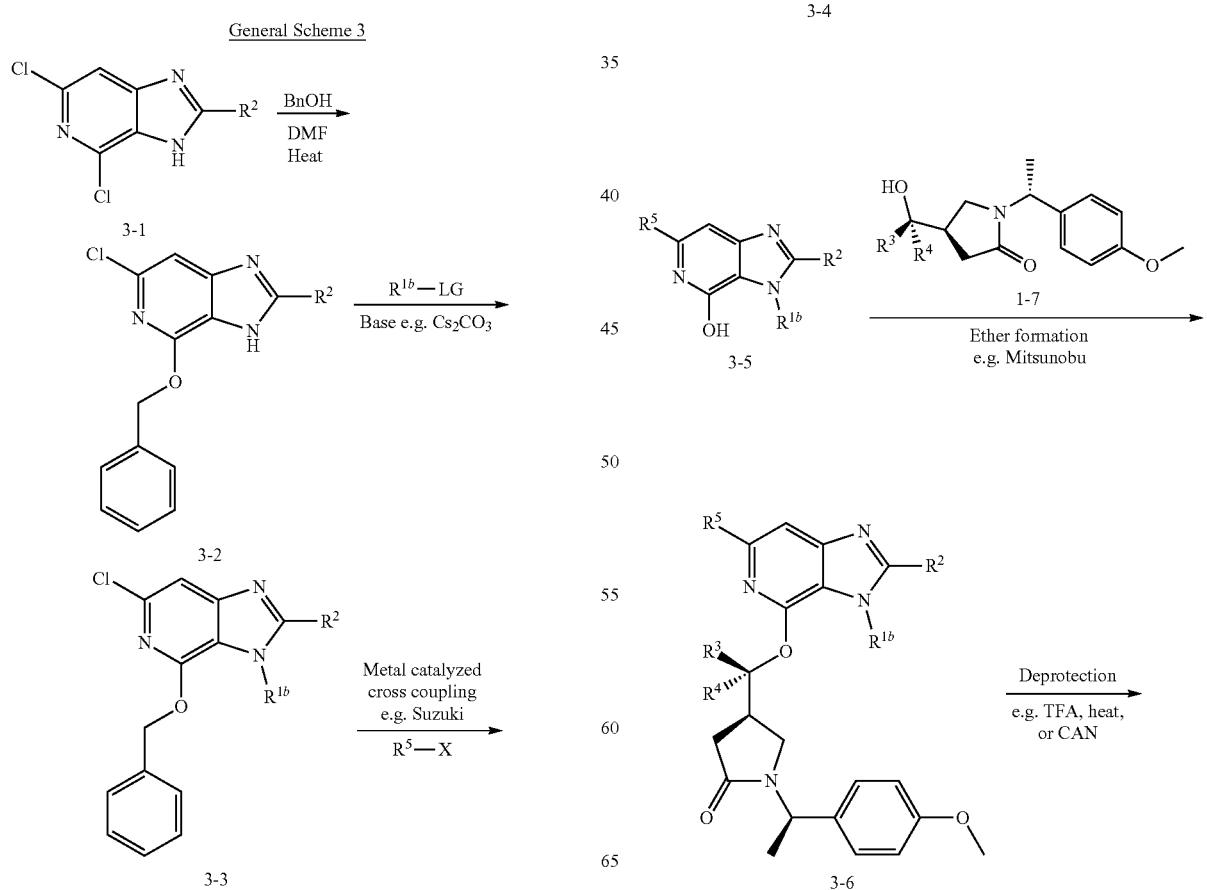

-continued

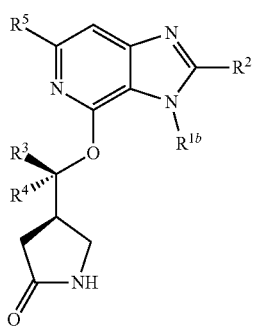
3-7

LG = Cl, Br, I, OTf, etc.
X = B(OH)₂, B(pinacol), SnBu₃

Scheme 3 describes an alternate synthesis of compounds of the invention wherein benzyl alcohol addition to 4,6-dichloro-3H-imidazo[4,5-c]pyridine 3-1 under heating conditions yields chloride 3-2. Alkylation of nitrogen with $R^1$ groups occurs under basic (e.g. $Cs_2CO_3$) conditions to yield intermediates 3-3. These can undergo metal catalyzed cross coupling reactions (e.g. Suzuki) of $R^5$ groups to yield intermediates 3-4, which can be reduced (e.g. Pd/C, ammonium formate, heat) to form intermediates 3-5. Etherification of 3-5 with 1-7 (e.g. Mitsunobu) yields intermediates 3-6, which undergo lactam deprotection (e.g. TFA and heat or CAN) to yield final compounds of the type 3-7.

General Scheme 4

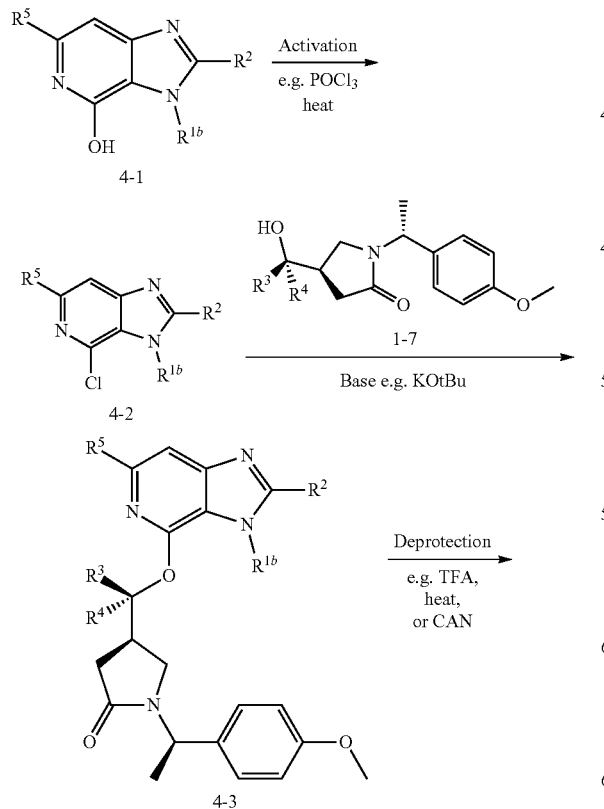

-continued

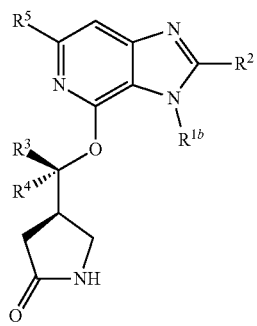
4-4

Scheme 4 describes a synthesis of compounds of the invention beginning with activation (e.g. $POCl_3$, heat) of intermediates 4-1 to form 4-2, which can undergo an $S_NAr$ reaction with alcohols 1-7 under basic (e.g. KOtBu) conditions to form intermediates 4-3. Lactam deprotection (e.g. TFA and heat or CAN) yields final compounds of the type 4-4.

General Scheme 5

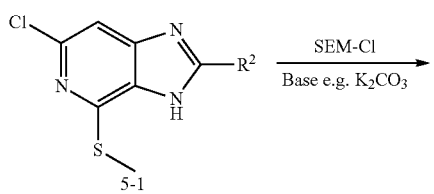
5-1

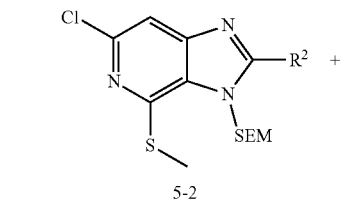
5-2

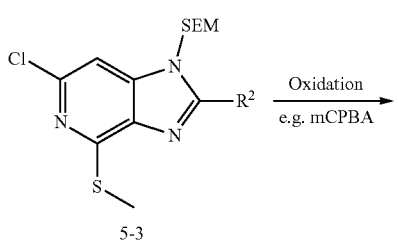
5-3

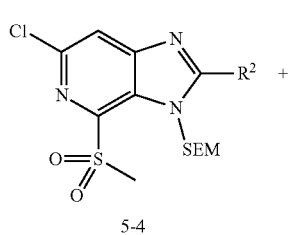
5-4

-continued
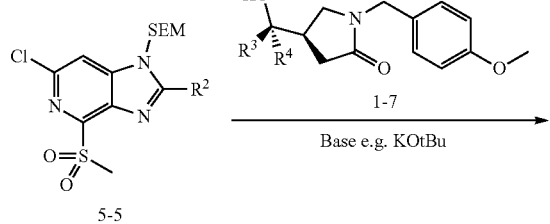
5-5
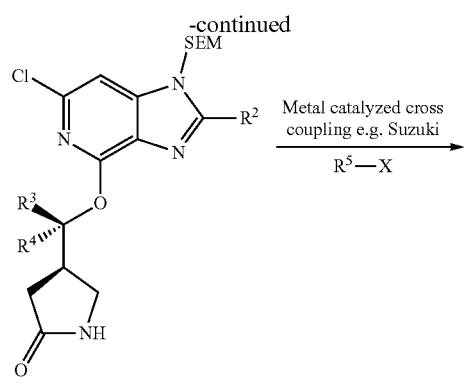
5-9
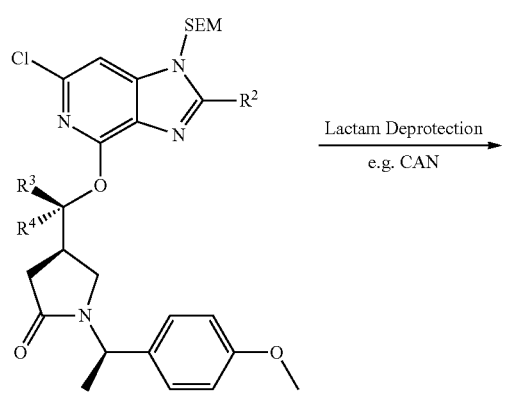
5-6
+
5-7
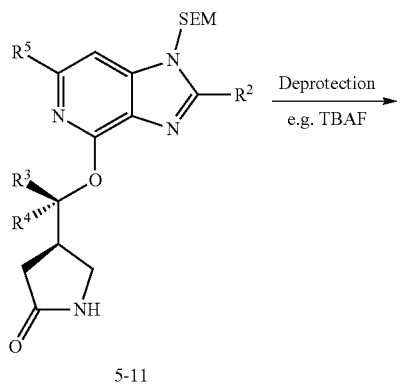
5-10
+
5-11
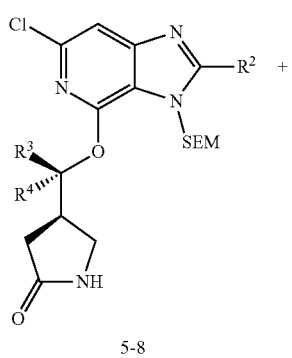
5-8
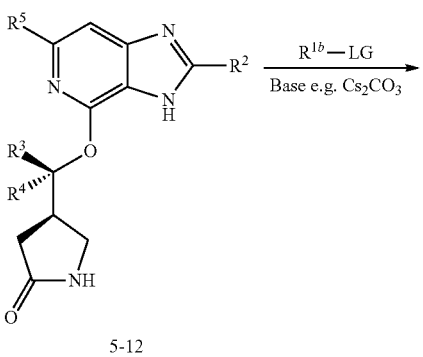
5-12

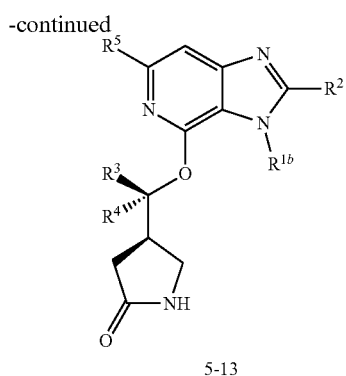

5-13

Scheme 5 describes a general synthesis of compounds of the invention beginning with protection (SEM-Cl, base e.g. $K_2CO_3$) of sulfide intermediate 5-1 yielding a mixture of intermediates 5-2 and 5-3. Oxidation (e.g. mCPBA) of the sulfide, followed by $S_nAr$ of the resulting intermediates 5-4 and 5-5 with alcohols 1-7 under basic (e.g. KOtBu) conditions forms a mixture of intermediates 5-6 and 5-7. Lactam deprotection (e.g. CAN), followed by installation of $R^5$ groups under metal catalyzed coupling conditions (e.g. Suzuki), gets to a mixture of intermediates 5-10 and 5-11. Deprotection of the SEM group (e.g. TFA/heat or TBAF), followed by alkylation of nitrogen with $R^1$ groups under basic conditions (e.g. $Cs_2CO_3$) yields final compounds of the type 5-13.

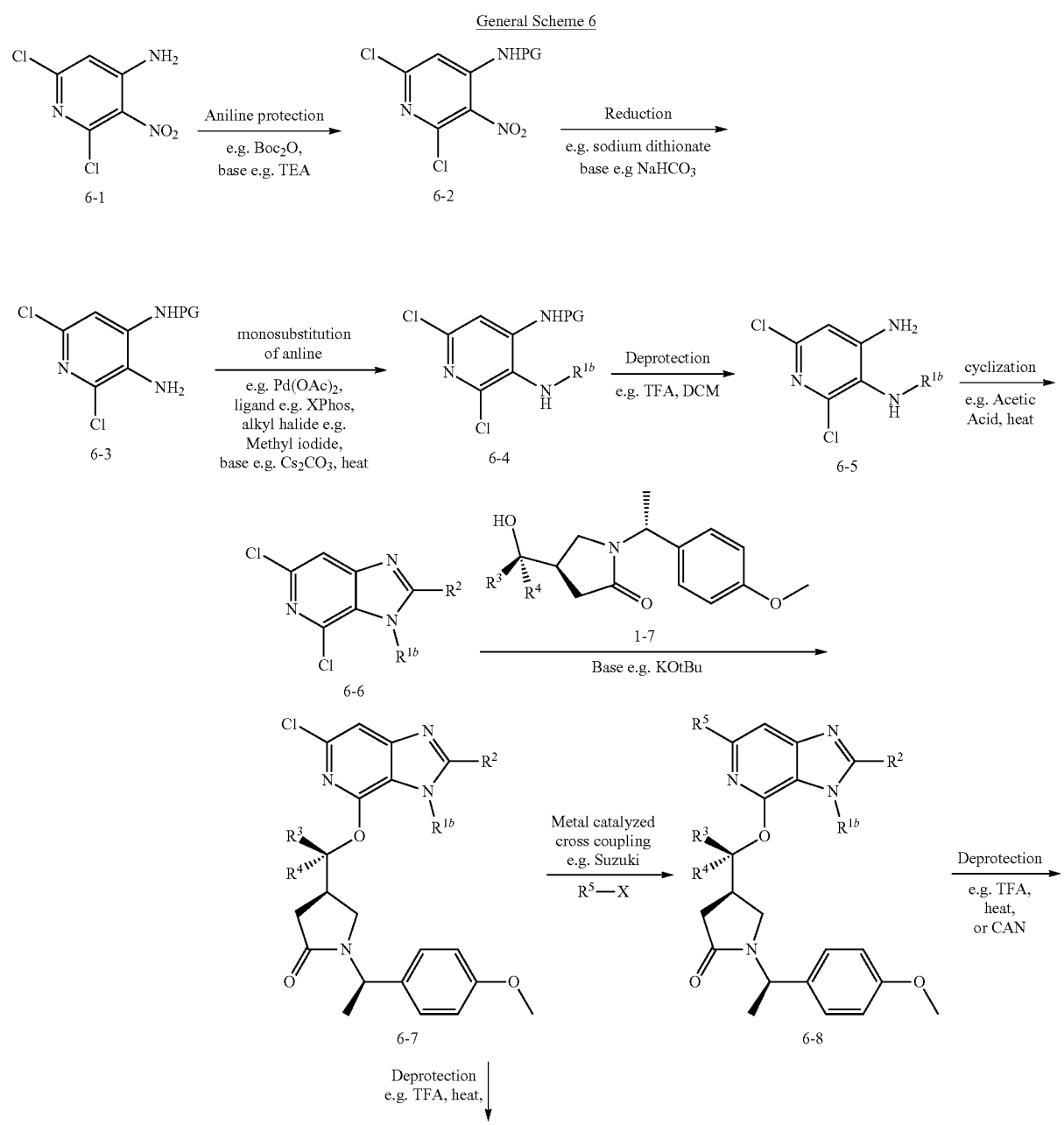

General Scheme 6

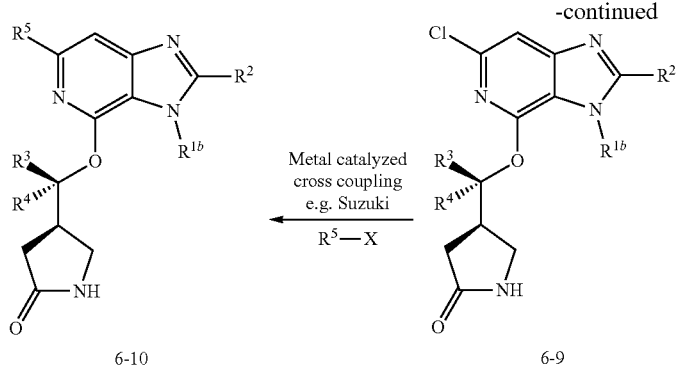

6-10           6-9

PG = Boc, CBz, etc.
X = B(OH)$_2$, B(pinacol), SnBu$_3$

Scheme 6 describes a general synthesis of final compounds of the invention beginning with aniline protection (e.g. Boc$_2$O and base e.g. TEA) of 2,6-dichloro-3-nitropyridin-4-amine 6-1 to yield intermediates 6-2. Nitro reduction (e.g. sodium dithionate and base e.g. NaHCO$_3$) forms diamines 6-3, which can be monoalkylated with R$^{1b}$ groups under coupling conditions (e.g. Pd(OAc)$_2$, XPhos, alkyl halide e.g. Methyl iodide, base e.g. Cs$_2$CO$_3$, and heat) to yield intermediates 6-4. Removal of the protecting group (e.g. TFA, DCM), followed by cyclization (e.g. acetic acid, heat) installs R$^2$ groups in intermediates 6-6. S$_n$Ar reactions with alcohols 1-7 under basic (e.g. KOtBu) conditions forms intermediates 6-7. Chloride 6-7 reacts under metal catalyzed cross coupling reactions (e.g. Suzuki) of R$^5$ groups to yield intermediates 6-8, which undergo lactam deprotection (e.g. TFA and heat or CAN) to yield final compounds of the type 6-10. Intermediates 6-7 can also first be deprotected (e.g. TFA and heat or CAN) to yield intermediates 6-9, which can undergo metal catalyzed cross coupling reactions (e.g. Suzuki) of R$^5$ groups to yield final compounds of type 6-10.

General Scheme 7

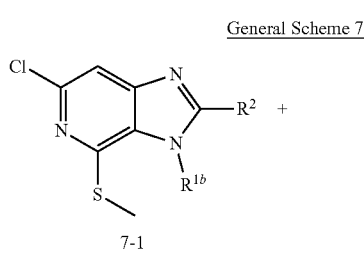

7-1

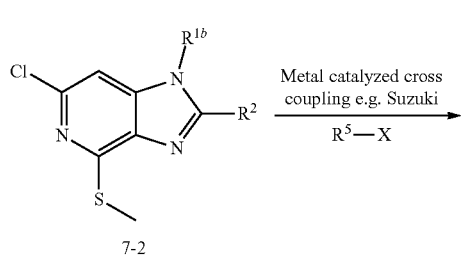

7-2

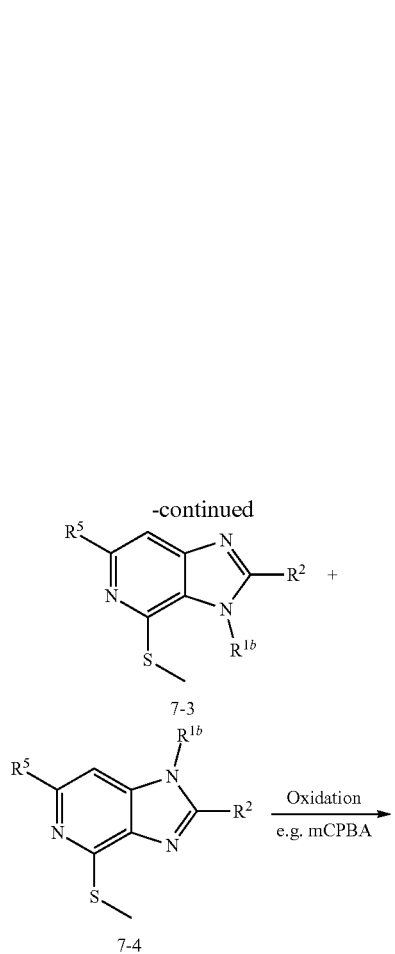

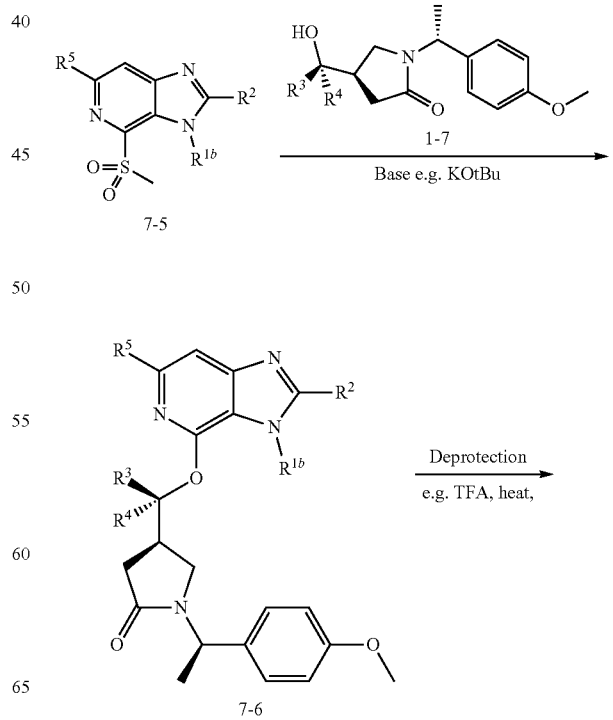

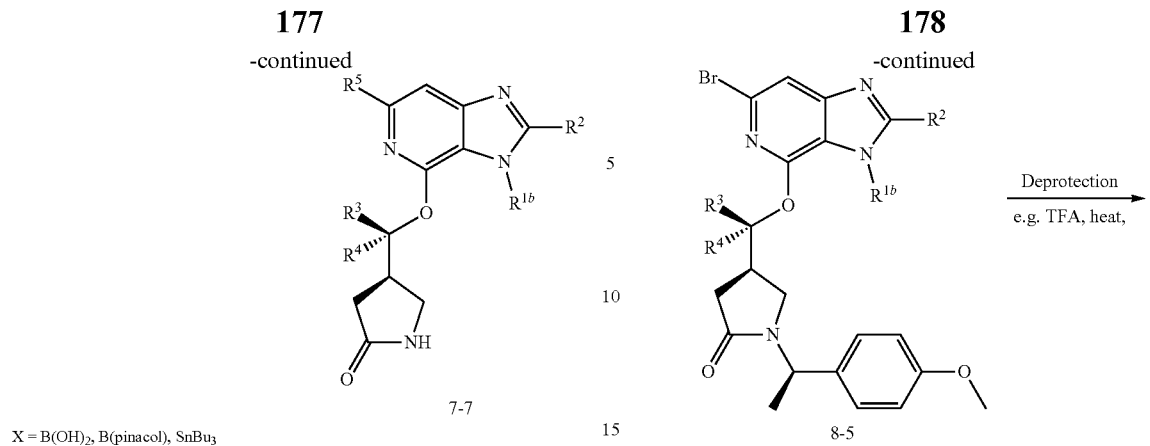

7-7

X = B(OH)₂, B(pinacol), SnBu₃

Scheme 7 shows a general synthesis of final compounds of the invention beginning with a mixture of intermediates 7-1 and 7-2. Installation of $R^5$ groups occurs under metal catalyzed coupling conditions (e.g. Suzuki) to form a mixture of intermediates 7-3 and 7-4. Oxidation (e.g. mCPBA) of this mixture, followed by isomer separation, can yield intermediates 7-5. $S_nAr$ reaction with alcohols 1-7 under basic (e.g. KOtBu) conditions, followed by deprotection (e.g. TFA and heat, or CAN) yields final compounds 7-7.

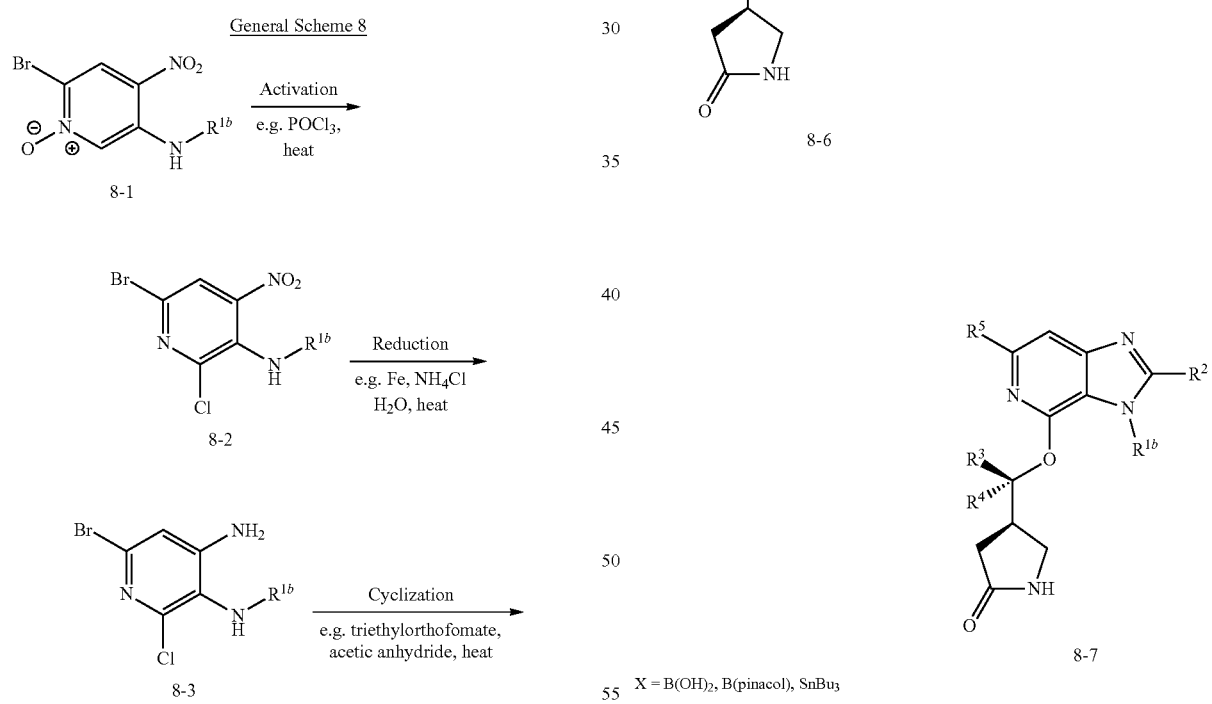

X = B(OH)₂, B(pinacol), SnBu₃

Scheme 8 describes an alternate synthesis of compounds of the invention wherein N-oxide 8-1 is activated (e.g. POCl₃ and heat) and subsequently reduced (e.g. Fe, NH₄Cl, H₂O, and heat) to yield intermediates 8-3. Cyclization (e.g. triethylorthoformate, acetic anhydride, and heat) occurs, followed by $S_nAr$ of the resulting intermediates 8-4 with alcohols 1-7 under basic (e.g. KOtBu) conditions forms intermediates 8-5. Deprotection (e.g. TFA and heat or CAN) yields intermediates 8-6, which can undergo metal catalyzed cross coupling reactions (e.g. Suzuki) of $R^5$ groups to yield final compounds of type 8-7.

General Scheme 9

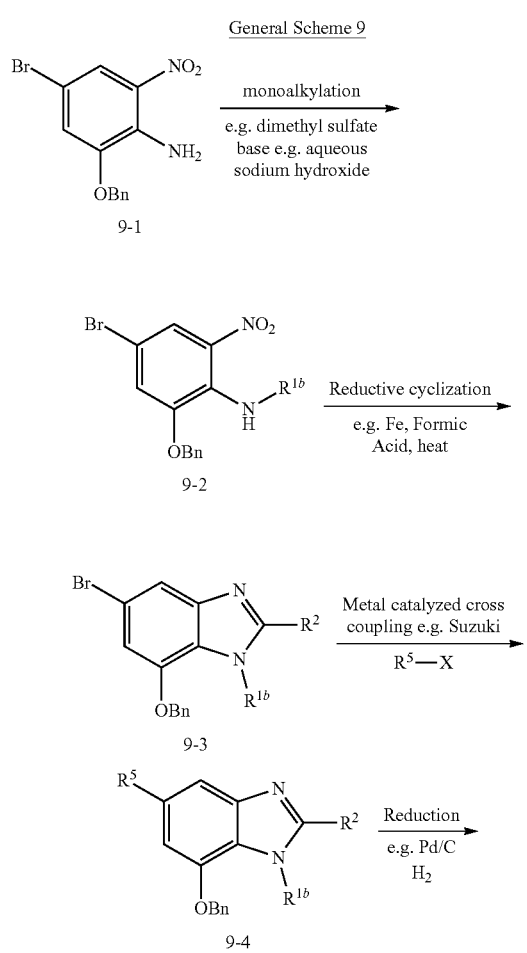

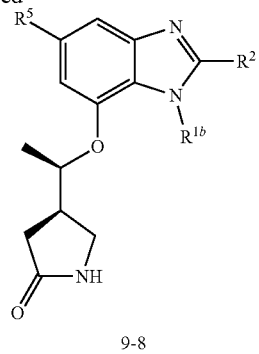

Ar = Ph, p-MethoxyPhenyl, etc.
X = B(OH)₂, B(pinacol), SnBu₃

Scheme 9 shows a general synthesis of compounds of the invention beginning with bromide 9-1. Monoalkylation of $R^{1b}$ groups (e.g. dimethyl sulfate and base e.g. aqueous sodium hydroxide) yields intermediates 9-2. A reductive cyclization (e.g. Fe, formic acid, and heat) forms intermediates 9-3. Installation of $R^5$ groups occurs under metal catalyzed coupling conditions (e.g. Suzuki) to get intermediates 9-4. Benzyl removal (e.g. Pd/C, H₂), followed by $S_n2$ displacement (base e.g. Cs₂CO₃ and heat) with 9-6 yields intermediates 9-7. Subsequent deprotection (e.g. TFA and heat or CAN) yields final compounds 9-8.

General Scheme 10

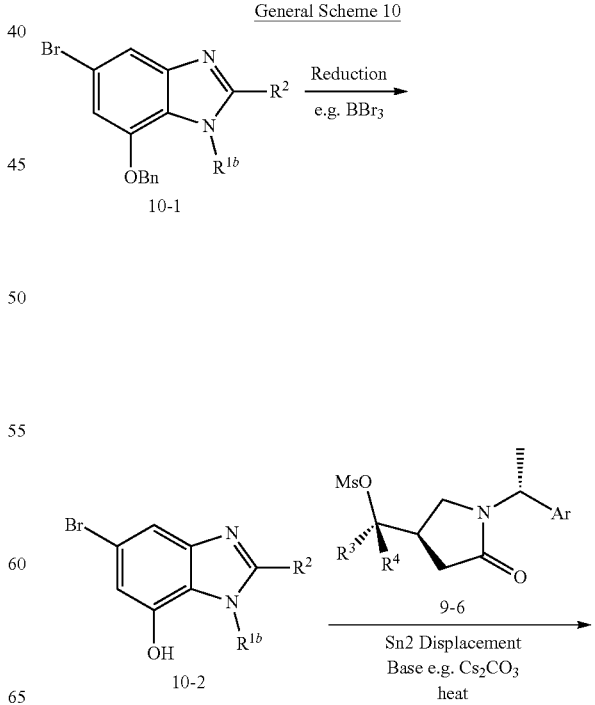

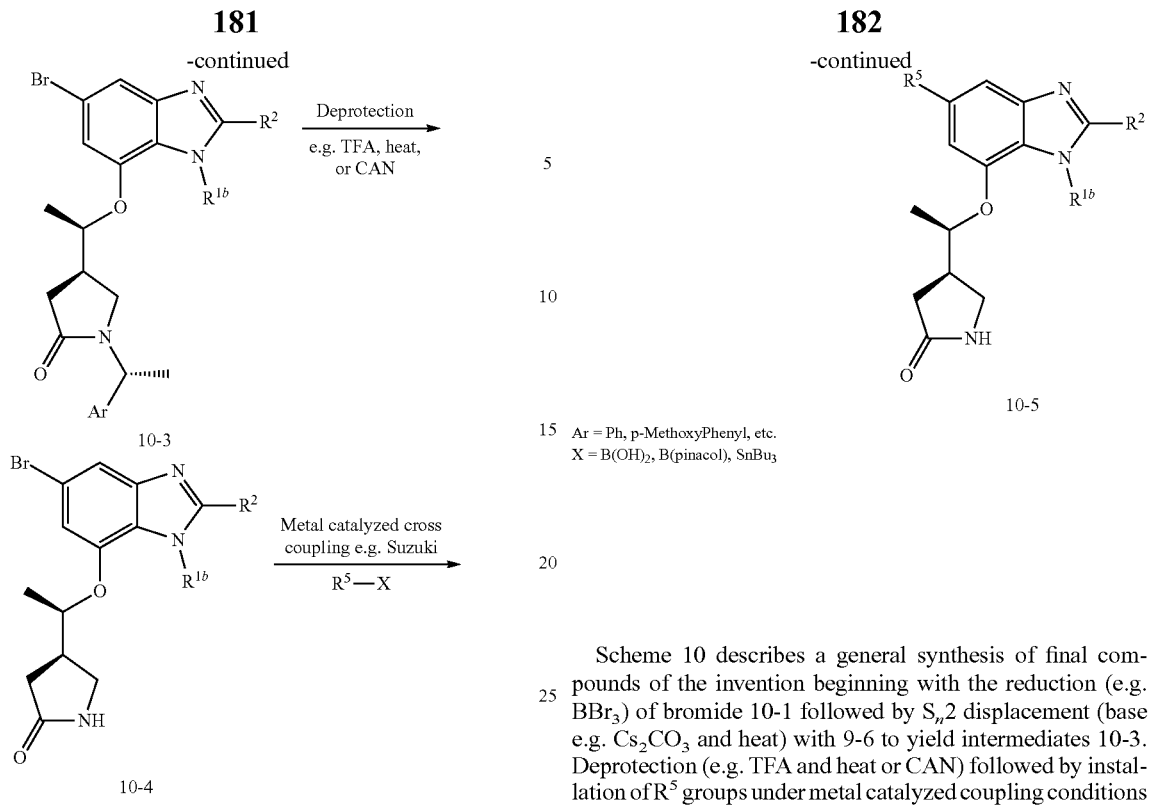

Scheme 10 describes a general synthesis of final compounds of the invention beginning with the reduction (e.g. $BBr_3$) of bromide 10-1 followed by $S_n2$ displacement (base e.g. $Cs_2CO_3$ and heat) with 9-6 to yield intermediates 10-3. Deprotection (e.g. TFA and heat or CAN) followed by installation of $R^5$ groups under metal catalyzed coupling conditions (e.g. Suzuki) yields final compounds 10-5

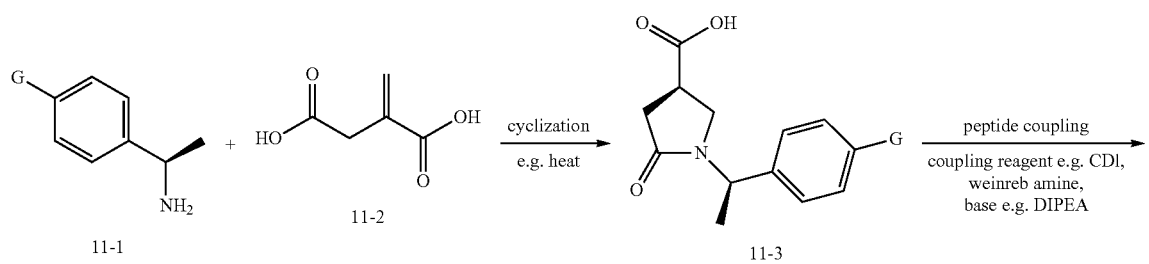

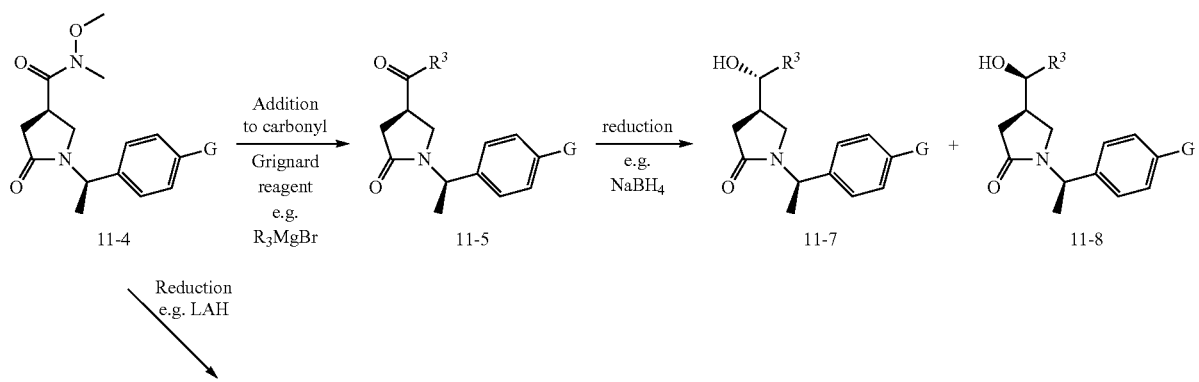

-continued

Nucleophillic Addition
to aldehyde
e.g. R₃MgBr, R₃Li, etc.

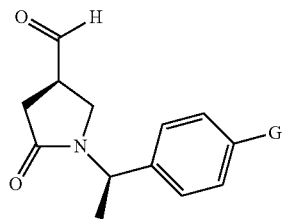

11-6

Scheme 11 describes a general synthesis of intermediates of type 11-7 and 11-8. A cyclization under heating conditions of 11-1 and itaconic acid, yields acids 11-3. Peptide coupling (e.g. CDI, Weinreb amine, and base e.g. DIPEA), followed by carbonyl addition (e.g. Grignard reagent addition) forms ketones of type 11-5. These can undergo reductions (e.g. NaBH₄) to yield chiral alcohols 11-7 and 11-8. Alternatively, reduction (e.g. LAH) of Weinreb amides 11-4 to their corresponding aldehydes 11-6, followed by nucleophilic addition (e.g. R₃MgBr) also yields chiral alcohols 11-7 and 11-8.

General Scheme 12

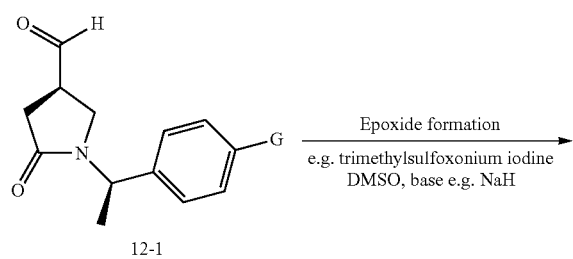

12-1

Epoxide formation
e.g. trimethylsulfoxonium iodine
DMSO, base e.g. NaH

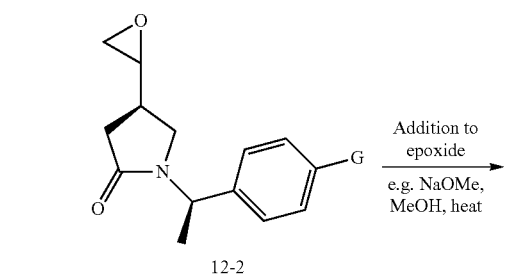

12-2

Addition to epoxide
e.g. NaOMe, MeOH, heat

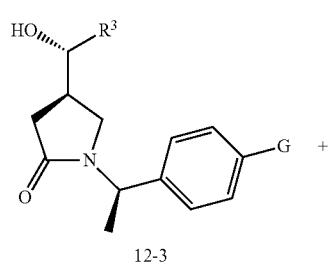

12-3

+

-continued

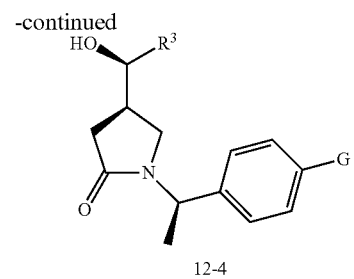

12-4

G = H, OMe

Scheme 12 describes a general synthesis of alcohol intermediates 12-3 and 12-4. Epoxidation (e.g. trimethylsulfoxonium iodide, DMSO, and base e.g. NaH) of aldehydes 12-1 forms epoxides 12-2, which can be reacted (e.g. NaOMe, MeOH, and heat) and opened to yield chiral alcohols 12-3 and 12-4.

General Scheme 13

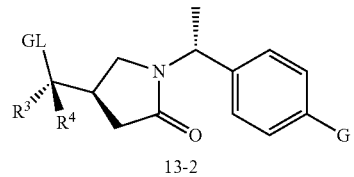

13-1

Alcohol activation
e.g. MsCl,
base e.g. TEA 13-2

LG = OMs, OTf, etc.
G = H, OMe

Scheme 13 describes a general synthesis of intermediates 13-2, which are products of the activation (e.g. MsCl and base e.g. TEA) of alcohols 13-1.

General Scheme 14

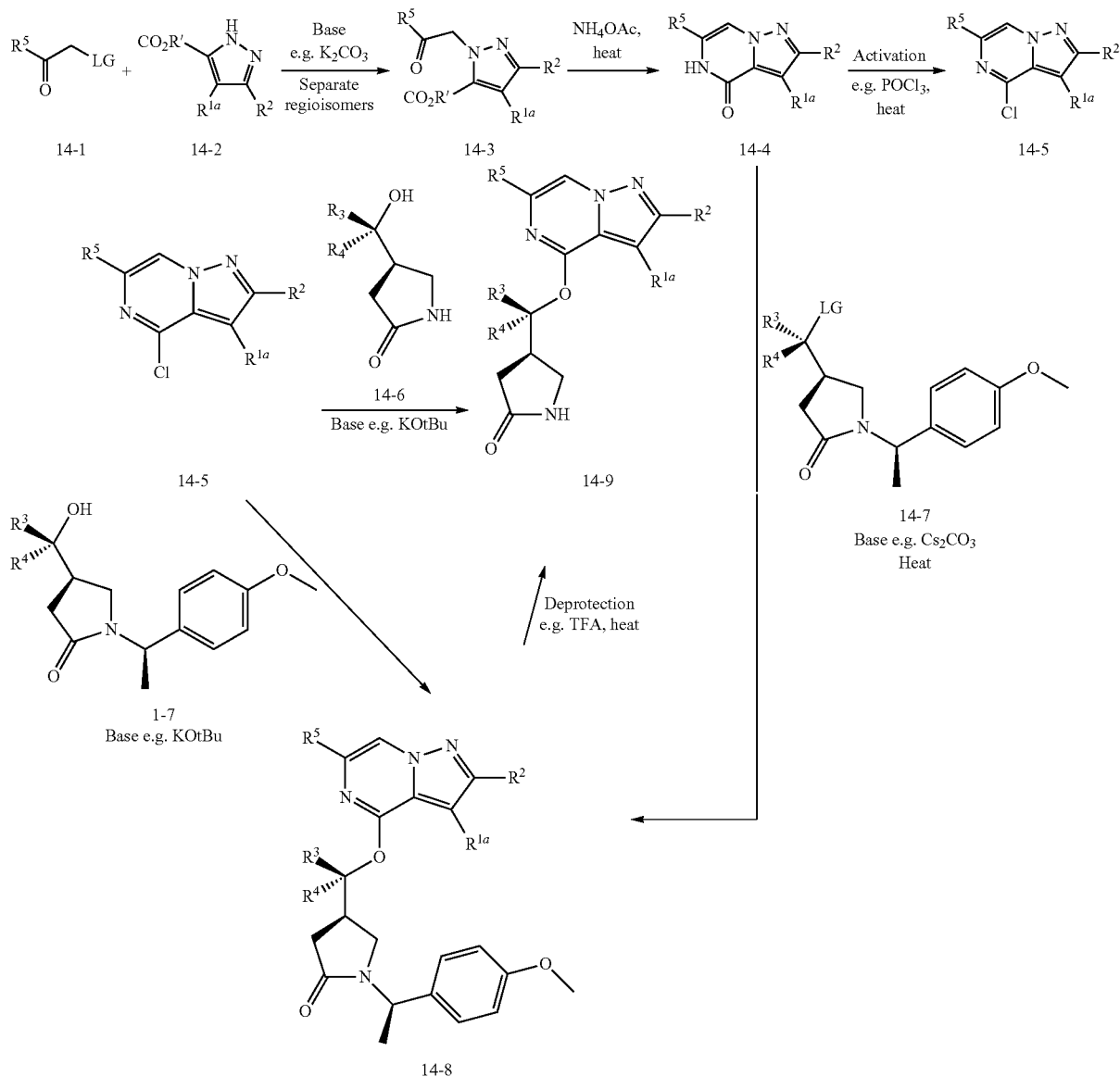

where:
LG = Br, Cl, I, OMs, OTs, etc.
R' = Me, Et

Scheme 14 shows a general synthesis of compounds of the invention beginning with reaction of intermediates 14-1 and 14-2 under basic (e.g. $K_2CO_3$) conditions to yield intermediate 14-3. Cyclization under heating conditions with ammonium acetate yields intermediate 14-4. Activation (e.g. $POCl_3$, heat) of intermediates 14-4 yield intermediates 14-5, which can be reacted with alcohols 14-6 under basic (e.g. KOtBu) conditions to yield final compounds of the type 14-9. Alternatively, intermediates 14-5 can be reacted with alcohols 1-7 under basic (e.g. KOtBu) conditions, followed by deprotection (e.g. TFA, heat) of intermediates 14-8 to yield final compounds of the type 14-9. In yet another alternative, intermediates 14-4 can be reacted with 14-7 under basic (e.g. $Cs_2CO_3$), heating conditions, followed by deprotection (e.g. TFA, heat) of intermediates 14-8 to yield final compounds of the type 14-9.

It will also be appreciated that the addition of any substituent may result in the production of a number of isomeric products any or all of which may be isolated and purified using conventional techniques.

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

| List of abbreviations and acronyms. | |
|---|---|
| Abbreviation | Meaning |
| ° C. | Degree Celcius |
| anal | Analytical |
| ATP | Adenosine-5'-triphosphate |
| ATX II | Anemonia sulcata toxin |
| AcOH | Acetic acid |
| ACN | Acetonitrile |
| CAN | Ceric ammonium nitrate |
| CDI | 1,1'-carbonyldiimidazole |
| CHO | Chinese hamster ovary |
| conc. | Concentrated |
| d | Doublet |
| DABCO | 1,4-Diazabicyclo[2.2.2]octane |
| DAST | (Diethylamino)sulfur trifluoride |
| dd | Doublet of doublets |
| DCE | 1,2-dichloroethane |
| DCM | Dichloromethane |
| DEAD | Diethyl azodicarboxylate |
| DIPEA | N,N-diisopropylethylamine |
| DMAP | 4-dimethylaminopyridine |
| DME | 1,2-dimethoxyethane |
| DMF | Dimethylformamide |
| DMSO | Dimethylsulfoxide |
| dppf | 1,1'-Bis(diphenylphosphino)ferrocene |
| EA | Ethyl alcohol |
| ECF | Extracellular fluid |
| EDTA | Ethylenediaminetetraacetic acid |
| EGTA | Ethylene glycol tetraacetic acid |
| equiv/eq | Equivalents |
| ESI | Electrospray ionization |
| Ac | Acetate |
| Et | Ethyl |
| g | Grams |
| HEPES | (4-(2-Hydroxyethyl)-1-piperazineethanesulfonic acid ) |
| HATU | 2-(7-Aza-1H-Benzotriazole -1-yl)-1,1,3,3-tetramethyluronium hexafluorophosphate |
| hERG | human Ether-á-go-go Related Gene |
| HMDS | hexamethyldisilazane(azide) |
| HPLC | High-performance liquid chromatography |
| h | Hours |
| Hz | Hertz |
| IC$_{50}$ | The half maximal inhibitory concentration |
| IMR-32 | Human neuroblastoma cell line |
| J | Coupling constant |
| Kg | Kilogram |
| kHz | Kilohertz |
| LAH | Lithium ammonium hydride |
| LCMS/LC-MS | Liquid chromatography-mass spectrometry |
| M | Molar |
| m | multiplet |
| m/z | mass-to-charge ratio |
| M+ | Mass peak |
| M + H | Mass peak plus hydrogen |
| mCPBA | 3-chloroperoxybenzoic acid |
| Me | Methyl |
| mg | Milligram |
| MHz | Megahertz |
| min/m | Minute |
| ml/mL | Milliliter |
| mM | Millimolar |
| mmol | Millimole |
| nmol | Nanomole |
| mOsmol | Milliosmole |
| MRM | Magnetic Resonance Microscopy |
| MS | Mass spectroscopy |
| ms | Millisecond |
| mV | Millivolt |
| mw | Microwave |
| N | Normal |
| mol | Mole |
| NMP | N-methylpyrrolidinone |
| NMR | Nuclear magnetic resonance |
| pA | Picoamps |
| Ph | Phenyl |
| ppm | Parts per million |
| prep | Preparative |
| q.s. | Quantity sufficient to achieve a stated function |
| Rf | Retention factor |

| List of abbreviations and acronyms. | |
|---|---|
| Abbreviation | Meaning |
| RP | Reverse phase |
| RT/rt | Room temperature |
| s | Second |
| s | Singlet |
| SEM | 2-(Trimethylsilyl)ethoxymethyl |
| t | Triplet |
| TB | Tonic Block |
| TEA | Triethylamine |
| TFA | Trifluoroacetic acid |
| THF | Tetrahydrofuran |
| TLC | Thin layer chromatography |
| TMS | trimethylsilyl |
| TTX | Tetrodotoxin |
| UDB | Use Dependent Block |
| WT | Wild type |
| δ | Chemical shift |
| µg | Microgram |
| µL/µl | Microliter |
| µM | Micromolar |
| µm | Micrometer |
| µmol | Micromole |

EXAMPLES

Preparation of Alcohol Intermediates for $S_NAr$ and Mitsunobu Reactions

Example 1.01

Preparation of (R)-1-((R)-1-(4-methoxyphenyl)ethyl)-5-oxopyrrolidine-3-carboxylic acid

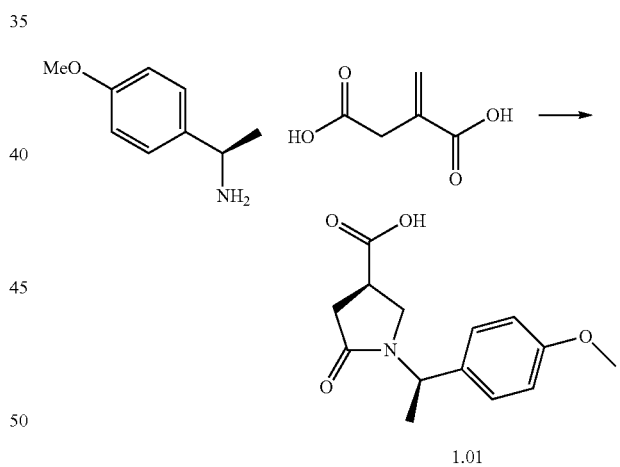

1.01

To a stirred solution of itaconic acid (35 g, 269 mmol) in NMP at 70° C. was added (R)-1-(4-methoxyphenyl)ethanamine (37 g, 245 mmol) via syringe. The mixture was heated at 80° C. for 1 hour and warmed to 120° C. for an additional 4 hours. The reaction was cooled to rt and poured into 550 mL of water with vigorous stirring. The mixture was aged for 1 hour over which time a slurry was formed. The solids were collected via filtration and washed with water. The solids were dried and transferred to a flask and recrystallized from iPrOH. Upon cooling and stirring, a thick slurry was obtained which was filtered to afford solids enriched in the major diastereomer. This material was again recrystallized from iPrOH to obtain (R)-1-((R)-1-(4-methoxyphenyl)ethyl)-5-oxopyrrolidine-3-carboxylic acid 1.01.

LCMS-ESI+ (m/z): [M+H]+ calcd for $C_{14}H_{17}NO_4$: 264.3; found 264.2.

Example 1.02

Preparation of (R)-N-methoxy-1-((R)-1-(4-methoxyphenyl)ethyl)-N-methyl-5-oxopyrrolidine-3-carboxamide

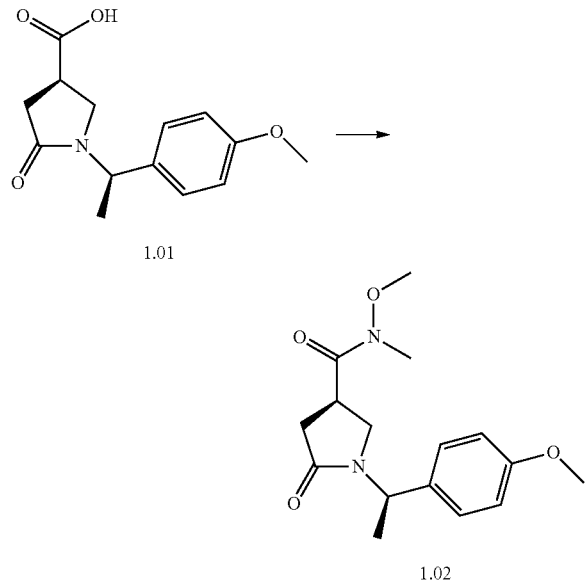

To a suspension of (R)-1-((R)-1-(4-methoxyphenyl)ethyl)-5-oxopyrrolidine-3-carboxylic acid 1.01 (1.0 g, 3.80 mmol) in 2-MeTHF (5 mL) was added CDI (925 mg, 5.70 mmol) and the mixture was stirred for 75 minutes over which time the reaction became homogenous. Diisopropylethyl amine (800 µL, 4.56 mmol) and N,O-dimethylhydroxylamine (445 mg, 4.56 mmol) were added and the reaction was stirred for 3 hours. 3M HCl (4 mL, 12 mmol) was added and the mixture was stirred for 5 minutes. The layers were separated, and the aqueous layer was extracted with EtOAc (2×20 mL). The combined organics were dried (MgSO4), filtered and concentrated to afford (R)-N-methoxy-1-((R)-1-(4-methoxyphenyl) ethyl)-N-methyl-5-oxopyrrolidine-3-carboxamide 1.02.

LCMS-ESI+ (m/z): [M+H]+ calcd for $C_{16}H_{22}N_2O_4$: 307.4; found 307.1.

Example 1.03

Preparation of (R)-4-acetyl-1-((R)-1-(4-methoxyphenyl)ethyl)pyrrolidin-2-one

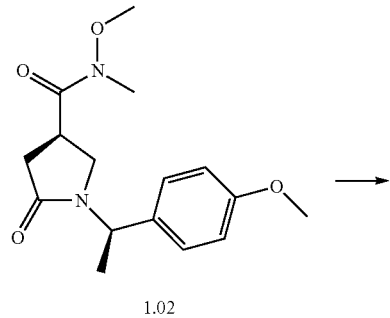

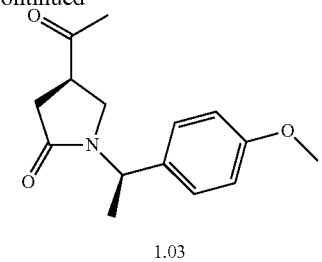

A solution of (R)-N-methoxy-1-((R)-1-(4-methoxyphenyl)ethyl)-N-methyl-5-oxopyrrolidine-3-carboxamide 1.02 (6.87 g, 22.4 mmol) in THF (70 mL) was cooled to an internal temperature of 19° C. under Ar. Methylmagnesium bromide (3 M in Et2O, 14.9 mL, 44.7 mmol) was added in portions over ca. 10 min to keep the internal temperature below 10° C. The resulting mixture was stirred for 1 h, by which time the internal temperature had reached −12° C., and was then warmed in an ice bath to 0° C. After an additional 50 min, the reaction was quenched with saturated aqueous NH4Cl (150 mL) and was diluted with EtOAc (150 mL) and water to dissolve solids. The phases were separated, and the aqueous phase was extracted with EtOAc (100 mL). The combined organic phase was dried over Na2SO4, filtered, and concentrated onto 25 g silica gel. The product was purified by silica gel chromatography (15% to 45% acetone in hexanes) to afford (R)-4-acetyl-1-((R)-1-(4-methoxyphenyl)ethyl)pyrrolidin-2-one 1.03.

LCMS-ESI+ (m/z): [M+H]+ calcd for $C_{15}H_{20}NO_3$: 262.1; found 262.2.

Example 1.04

Preparation of (R)-4-((R)-1-hydroxyethyl)-1-((R)-1-(4-methoxyphenyl)ethyl)pyrrolidin-2-one

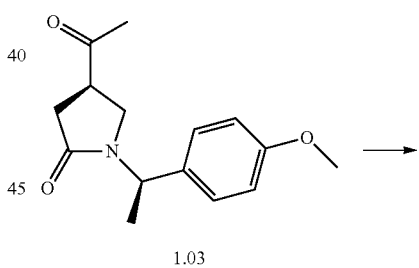

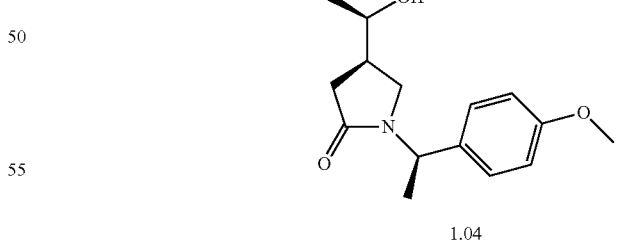

In a vial under Ar, [Rh(C5Me5)Cl2]2 (120 mg, 0.19 mmol) and (1S,2S)-(−)-N-p-Tosyl-1,2-diphenylethylenediamine (168 mg, 0.458 mmol) were taken up in MeCN (2 mL). Triethylamine (0.19 mL, 1.4 mmol) was added and the resulting mixture was stirred 45 min prior to use.

In a separate flask, a solution of (R)-4-acetyl-1-((R)-1-(4-methoxyphenyl)ethyl)pyrrolidin-2-one 1.03 (1.8 g, 6.9 mmol) in MeCN (34 mL) was cooled to an internal temperature of −10° C. under Ar in a jacketed 3-neck flask equipped with a thermocouple. Triethylamine (5.1 mL, 36 mmol) was added during the cooling ramp at 0° C. Formic acid (0.525 mL, 13.9 mmol) was added once the internal temperature reached −10° C. The aforementioned catalyst mixture was then added in one portion, washing with additional MeCN (2×1 mL). The resulting orange solution was stirred for 18 h at −10° C. and was then warmed to 0° C. After an additional 4.5 h, hydrochloric acid (3 M, 13 mL, 39 mmol) was added followed by EtOAc (50 mL) and brine (30 mL). The phases were separated, and the aqueous phase was extracted with EtOAc (50 mL). The combined organic phase was dried over Na$_2$SO$_4$, filtered, and concentrated. The product was purified by silica gel chromatography (35% to 50% acetone in hexanes) to afford (R)-4-((R)-1-hydroxyethyl)-1-((R)-1-(4-methoxyphenyl)ethyl)pyrrolidin-2-one 1.04.

LCMS-ESI$^+$ (m/z): [M+H]$^+$ calcd for C$_{15}$H$_{22}$NO$_3$: 264.2; found 264.2.

Example 1.05

Preparation of (R)-4-((S)-1-hydroxyethyl)-1-((R)-1-(4-methoxyphenyl)ethyl)pyrrolidin-2-one

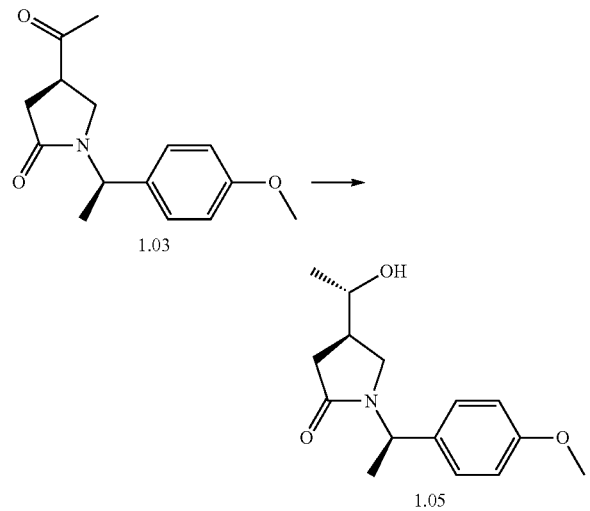

In a vial under N$_2$, [Rh(C$_5$Me$_5$)Cl$_2$]$_2$ (62 mg, 0.10 mmol) and (1R,2R)-(−)-N-p-Tosyl-1,2-diphenylethylenediamine (87 mg, 0.24 mmol) were taken up in MeCN (1 mL). Triethylamine (0.1 mL, 0.7 mmol) was added and the resulting mixture was stirred 40 min prior to use. Meanwhile, a solution of (R)-4-acetyl-1-((R)-1-(4-methoxyphenyl)ethyl)pyrrolidin-2-one 1.03 (1.06 g, 4.06 mmol) and triethylamine (3 mL, 21.3 mmol) in MeCN (20 mL) was cooled to an internal temperature of −10° C. under Ar in a jacketed 3-neck flask equipped with a thermocouple. Formic acid (0.525 mL, 13.9 mmol) was added during the cooling ramp once the internal temperature reached 0° C. Once the internal temperature reached −10° C., the aforementioned catalyst mixture was added in one portion, washing with additional MeCN (3×1 mL). The resulting orange solution was stirred for 48 h at −10° C. and was then warmed to r.t. Hydrochloric acid (3 M, 7.5 mL, 22.5 mmol) was added followed by dilution with EtOAc (50 mL) and brine (30 mL). The phases were separated, and the aqueous phase was extracted with EtOAc (50 mL). The combined organic phase was dried over Na$_2$SO$_4$, filtered, and concentrated onto 10 g silica gel. The product was purified by silica gel chromatography (35% to 50% acetone in hexanes) to afford (R)-4-((S)-1-hydroxyethyl)-1-((R)-1-(4-methoxyphenyl)ethyl)pyrrolidin-2-one 1.05.

LCMS-ESI$^+$ (m/z): [M+H]$^+$ calcd for C$_{15}$H$_{22}$NO$_3$: 264.2; found 264.2.

Example 1.06

Preparation of (R)-4-(hydroxymethyl)-1-((R)-1-(4-methoxyphenyl)ethyl)pyrrolidin-2-one

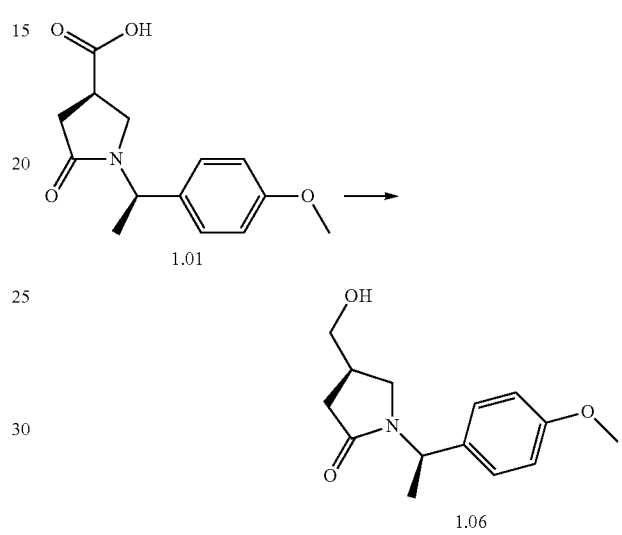

To a solution of (R)-1-((R)-1-(4-methoxyphenyl)ethyl)-5-oxopyrrolidine-3-carboxylic acid 1.01 (610 mg, 2.32 mmol) in THF (6 mL) at 0° C. was added BH$_3$-Me$_2$S (2M, 1.74 mL, 3.48 mmol) and the reaction was stirred for 3 hours. Water and EtOAc were added, the layers were separated and the aqueous layer was extracted with EtOAc (4×25 mL). The residue was purified by flash chromatography (EtOAc→15% MeOH in EtOAc) to afford (R)-4-(hydroxymethyl)-1-((R)-1-(4-methoxyphenyl)ethyl)pyrrolidin-2-one 1.06.

LCMS-ESI$^+$ (m/z): [M+H]$^+$ calcd for C$_{14}$H$_{19}$NO$_3$: 250.3; found 250.1.

Example 1.07

Preparation of (R)-1-((R)-1-(4-methoxyphenyl)ethyl)-5-oxopyrrolidine-3-carbaldehyde

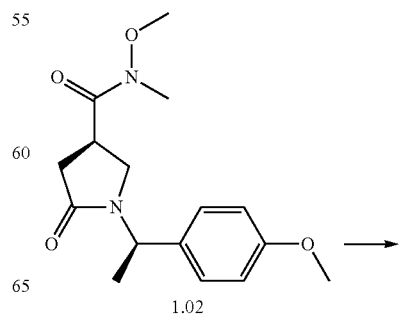

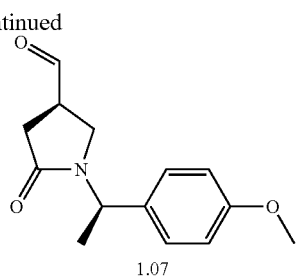
1.07

To a solution of (R)-N-methoxy-1-((R)-1-(4-methoxyphenyl)ethyl)-N-methyl-5-oxopyrrolidine-3-carboxamide 1.02 (260 mg, 0.85 mmol) in THF (6 mL) at 0° C. was added a solution of LAH in THF (1M, 430 μL, 0.43 mmol). The reaction was stirred for 1 hour and quenched by the addition of KHSO$_4$ (sat aq, 15 mL). The mixture was stirred for 5 minutes and Et$_2$O (20 mL) was added. The layers were separated and the aqueous layer was extracted with Et$_2$O (3×20 mL). The combined organics were dried (MgSO$_4$), filtered and concentrated to afford (R)-1-((R)-1-(4-methoxyphenyl)ethyl)-5-oxopyrrolidine-3-carbaldehyde 1.07.

LCMS-ESI$^+$ (m/z): [M+H]$^+$ calcd for C$_{14}$H$_{17}$NO$_3$: 248.3; found 248.0.

Example 1.08

Preparation of (R)-4-((R)-1-hydroxybut-3-enyl)-1-((R)-1-(4-methoxyphenyl)ethyl)pyrrolidin-2-one

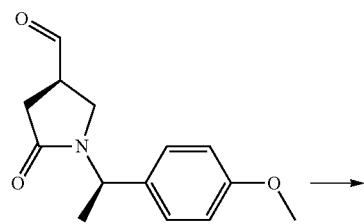

To a solution of (R)-1-((R)-1-(4-methoxyphenyl)ethyl)-5-oxopyrrolidine-3-carbaldehyde 1.07 (0.93 g, 3.76 mmol) at rt was added (S,S)-2-allyl-1,3-bis-(4-bromobenzyl)-2-chlorooctahydro-2-1H-1,3,2-benzodiazasilole (3.338 g, 6.02 mmol) followed by Sc(III) triflate (0.093 g, 0.188 mmol). The reaction was stirred at rt for 1.5 hr and the solvent was removed. To the residue was added Et$_2$O (80 mL) and 1M HCl (20 mL). The suspension was stirred for 1 hr and the solids were removed by filtration. The filter cake was washed with ether. The filtrate was transferred to a separatory funnel and the layers were separated. The aqueous layer was further extracted with Et$_2$O (3×40 mL). The combined organics were dried (MgSO$_4$), filtered and concentrated. The residue was purified by flash chromatography to afford (R)-4-((R)-1-hydroxybut-3-enyl)-1-((R)-1-(4-methoxyphenyl)ethyl)pyrrolidin-2-one 1.08.

LCMS-ESI$^+$ (m/z): [M+H]$^+$ calcd for C$_{17}$H$_{23}$NO$_3$: 290.4; found 290.0.

Example 1.09

Preparation of (R)-4-((R)-2-cyclopropyl-1-hydroxyethyl)-1-((R)-1-(4-methoxyphenyl)ethyl)pyrrolidin-2-one

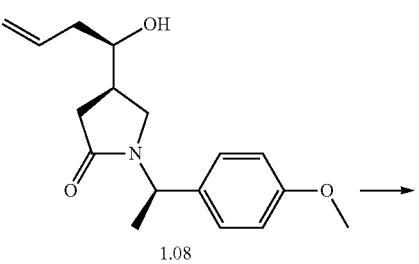

To a solution of (R)-4-((R)-1-hydroxybut-3-enyl)-1-4R)-1-(4-methoxyphenyl)ethyl)pyrrolidin-2-one 1.08 (145 mg, 0.50 mmol) at 0° C. was added 1M diethyl zinc (2.51 ml, 2.51 mmol). Diiodomethane (0.404 ml, 5.01 mmol) was added, and the mixture was stirred at rt for 60 min and quenched by the addition of sat NH$_4$Cl (10 mL). EtOAc was added, stirred 5 min and the layers were separated. The aqueous layer was extracted with EtOAc (2×10 mL) and the combined organics were dried (MgSO$_4$), filtered and concentrated. The residue was purified by flash chromatography (20-->100% EtOAc in hexanes) to afford (R)-4-((R)-2-cyclopropyl-1-hydroxyethyl)-1-((R)-1-(4-methoxyphenyl)ethyl)pyrrolidin-2-one 1.09.

LCMS-ESI$^+$ (m/z): [M+H]$^+$ calcd for C$_{18}$H$_{25}$NO$_3$: 304.4; found 304.2.

Example 1.10

Preparation of (4R)-4-(2-fluoro-1-hydroxy-2-(phenylsulfonyl)ethyl)-1-((R)-1-(4-methoxyphenyl)ethyl)pyrrolidin-2-one

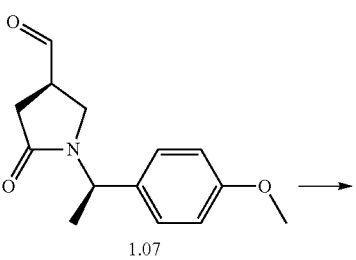

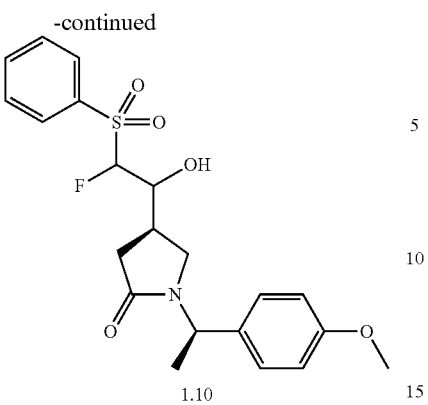

1.10

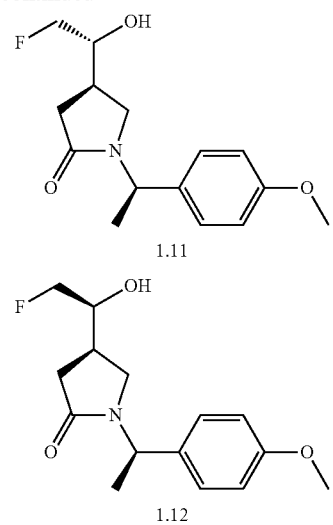

1.11

1.12

Diisopropyl amine (0.27 ml, 1.88 mmol) was added to THF (5 mL) and this solution was cooled to 0° C. n-butyllithium (1.06 mL, 1.70 mmol, 1.6M in hexanes) was added and the reaction was held at 0° C. for 15 min and cooled to −78° C. To solution this was added (fluoromethylsulfonyl)benzene (327 mg, 1.88 mmol) in THF (5 mL) and the reaction was stirred at −78° C. for 20 min. A solution of (R)-1-((R)-1-(4-methoxyphenyl)ethyl)-5-oxopyrrolidine-3-carbaldehyde 1.07 (400 mg, 1.62 mmol) in THF (5 mL) was added. The reaction was stirred at −78° C. for 1.5 h, at which time LC/MS analysis indicated complete reaction. The reaction was quenched at −78° C. by addition of sat' d NH$_4$Cl solution (10 mL) and extracted with EtOAc (2×20 mL). The combined organics were washed with water and brine. The organic layer was dried (MgSO$_4$), filtered and concentrated.

The residue is purified by flash chromatography to afford (4R)-4-(2-fluoro-1-hydroxy-2-(phenylsulfonyl)ethyl)-1-((R)-1-(4-methoxyphenyl)ethyl)pyrrolidin-2-one 1.10 as a mixture of diastereomers.

LCMS-ESI$^+$ (m/z): [M+H]$^+$ calcd for $C_{21}H_{24}FNO_5S$: 422.5; found 422.0.

(4R)-4-(2-fluoro-1-hydroxy-2-(phenylsulfonyl)ethyl)-1-((R)-1-(4-methoxyphenyl)ethyl)pyrrolidin-2-one 1.10 (170 mg, 0.403 mol) was dissolved in methanol (15 mL) and Na$_2$HPO$_4$ (430 mg, 2.42 mmol) was added. The reaction was cooled to −15° C. and sodium-mercury amalgam (10% Na, 556 mg) was added. The reaction was stirred at −15° C. for 2 h at which time LCMS analysis indicated complete reaction. Stirring was discontinued and the solids were allowed to settle. The MeOH layer was decanted off and filtered. The solids were washed with MeOH and the filtrate was concentrated. The two diastereomers were separated by RP-HPLC (C18 Gemini Column), and the stereochemistry of the later eluting diastereomer (R)-4-((S)-2-fluoro-1-hydroxyethyl)-1-((R)-1-(4-methoxyphenyl)ethyl)pyrrolidin-2-one 1.12 was assigned based on analogy to the assignment for (R)-4-((R)-1-hydroxybut-3-enyl)-1-((R)-1-(4-methoxyphenyl)ethyl)pyrrolidin-2-one 1.08.

LCMS-ESI$^+$ (m/z): [M+H]$^+$ calcd for $C_{15}H_{20}FNO_3$: 282.3; found 281.9.

The first eluting diastereomer was obtained and assigned as (R)-4-((R)-2-fluoro-1-hydroxyethyl)-1-((R)-1-(4-methoxyphenyl)ethyl)pyrrolidin-2-one 1.11.

Example 1.13

Preparation of (4R)-1-((R)-1-(4-methoxyphenyl) ethyl)-4-(oxiran-2-yl)pyrrolidin-2-one Example 1.12

Preparation of (R)-4-((S)-2-fluoro-1-hydroxyethyl)-1-((R)-1-(4-methoxyphenyl)ethyl)pyrrolidin-2-one

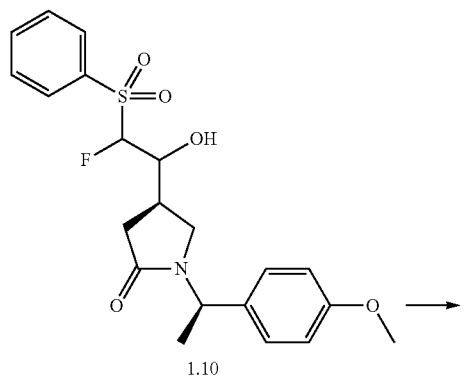

1.10

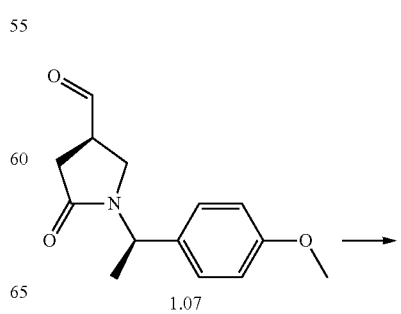

1.07

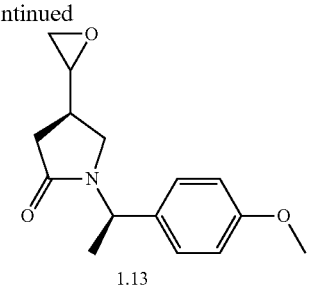

1.13

To suspension of trimethylsulfoxonium iodide (579 mg, 2.63 mmol) in DMSO (5 mL) was added NaH (60%, 116 mg, 2.89 mmol), and the reaction was stirred for 30 minutes. A solution of (R)-1-((R)-1-(4-methoxyphenyl)ethyl)-5-oxopyrrolidine-3-carbaldehyde 1.07 (650 mg, 2.63 mmol) in DMSO (5 mL) was added and the reaction was stirred for 30 minutes at 0° C. The reaction was poured into ice water (20 mL) and EtOAc (20 mL) was added. The aqueous layer was extracted with EtOAc (3×25 mL), and the combined organics were dried (MgSO$_4$), filtered and concentrated. Flash chromatography (50→100% EtOAc in hexanes) provided (4R)-1-((R)-1-(4-methoxyphenyl)ethyl)-4-(oxiran-2-yl)pyrrolidin-2-one 1.13.

LCMS-ESI$^+$ (m/z): [M+H]$^+$ calcd for C$_{15}$H$_{19}$NO$_3$: 262.3; found 261.9.

Example 1.14

Preparation of (4R)-4-(1-hydroxy-2-methoxyethyl)-1-((R)-1-(4-methoxyphenyl)ethyl)pyrrolidin-2-one

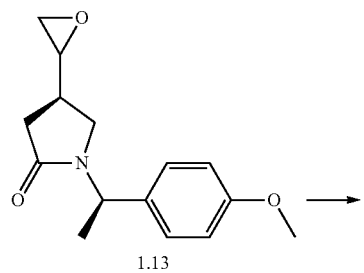

1.13

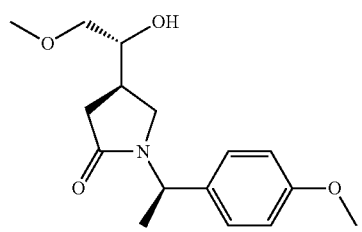

1.14

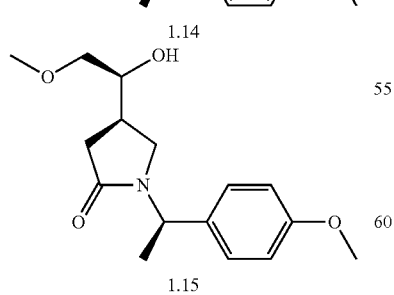

1.15

To a solution of (4R)-1-((R)-1-(4-methoxyphenyl)ethyl)-4-(oxiran-2-yl)pyrrolidin-2-one 1.13 (150 mg, 0.57 mmol) in MeOH (5 mL) was added NaOMe (125 mg, 25% in MeOH), and the solution was heated at 55° C. for 3 hours. The reaction was concentrated and purified by flash chromatography (EtOAc→10% MeOH in EtOAC) to afford the product as a mixture of diastereomers. The isolated mixture was purified by RP-HPLC (C18 Gemini Column) to afford the later eluting diastereomer, which was assigned as (R)-4-((S)-1-hydroxy-2-methoxyethyl)-1-((R)-1-(4-methoxyphenyl)ethyl)pyrrolidin-2-one 1.15.

LCMS-ESI$^+$ (m/z): [M+H]$^+$ calcd for C$_{16}$H$_{23}$NO$_4$: 294.4; found 294.0.

Example 1.17

Preparation of (S)-1-((R)-5-oxo-1-((R)-1-phenylethyl)pyrrolidin-3-yl)ethyl methanesulfonate

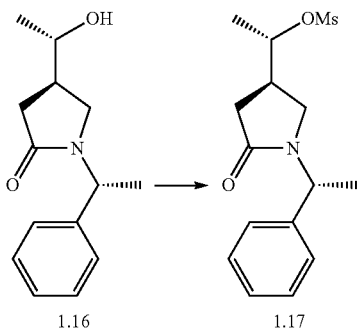 [SMILES: C[C@H](O)[C@@H]1CC(=O)N([C@H](C)c2ccccc2)C1 ; C[C@H](OS(C)(=O)=O)[C@@H]1CC(=O)N([C@H](C)c2ccccc2)C1]

1.16    1.17

To a solution of (R)-4-((S)-1-hydroxyethyl)-1-((R)-1-phenylethyl)pyrrolidin-2-one 1.16 (prepared in an analogous fashion to Example 1.05, but starting the sequence with (R)-1-phenylethanamine in place of (R)-1-(4-methoxyphenyl)ethanamine) (300 mg, 1.28 mmol) in DCM (6 mL) was added triethylamine (0.25 mL, 1.8 mmol) and the reaction mixture was cooled to 0° C. Then methanesulfonyl chloride (0.11 mL, 1.4 mmol) was added and stirred at the same temperature for 30 min. The reaction mixture was then diluted with DCM and washed successively with 1N HCl, brine and dried over anhydrous magnesium sulfate. The residue was purified by flash column chromatography (SiO$_2$, 80% EtOAc/hexanes to 100% EtOAc) to give (S)-1-((R)-5-oxo-1-((R)-1-phenylethyl)pyrrolidin-3-yl)ethyl methanesulfonate 1.17.

LC/MS found for C$_{15}$H$_{21}$NO$_4$S as (M+H)$^+$ 312.1.

Example 1.18

Preparation of (R)-4-((S)-1-hydroxyethyl)pyrrolidin-2-one

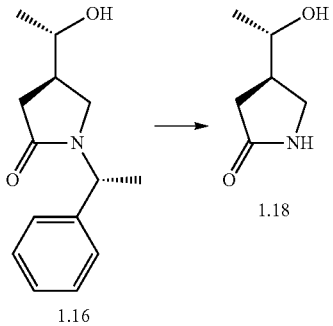

1.16    1.18

A solution of (R)-4-((S)-1-hydroxyethyl)-1-((R)-1-phenylethyl)pyrrolidin-2-one (500 mg, 2.1 mmol) in TFA (3.6 mL) was heated to 150° C. in a microwave reactor. After 90 min, the resulting mixture was diluted with DCM and concentrated in vacuo. The resulting residue was dissolved in DCM (15 mL) and water (20 mL). The phases were separated, and the organic phase was extracted with water (4×20 mL). The combined aqueous phase was concentrated in vacuo, and the resulting crude residue was purified by silica gel chromatography (10% to 30% MeOH in DCM) to afford (R)-4-((S)-1-hydroxyethyl)pyrrolidin-2-one 1.18.

LCMS-ESI$^+$ (m/z): [M+H]$^+$ calcd for $C_6H_{12}NO_2$: 130.1; found: 130.1.

Example 1.19

Preparation of (4R)-1-[(1R)-1-(4-methoxyphenyl)ethyl]-4-(prop-2-enoyl)pyrrolidin-2-one

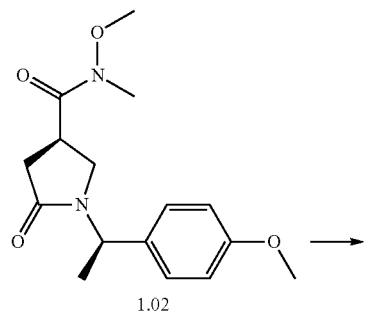

1.02

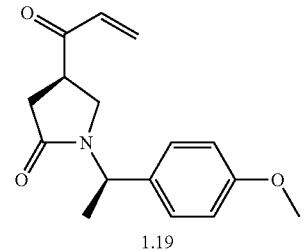

1.19

Into a 500-mL 3-necked round-bottom flask purged and maintained with an inert atmosphere of nitrogen was placed a solution of (3R)-N-methoxy-1-[(1R)-1-(4-methoxyphenyl)ethyl]-N-methyl-5-oxopyrrolidine-3-carboxamide 1.02 (15 g, 48.96 mmol, 1.00 equiv) in tetrahydrofuran (150 mL), followed by the addition of bromo(ethenyl)magnesium in THF (1 M) (147 mL, 3.00 equiv) dropwise with stirring at −66° C. The resulting solution was stirred at −66° C. for 3 h, poured into 250 mL of water/ice and diluted with 250 mL of ethyl acetate. The resulting solution was extracted with 3×300 mL of ethyl acetate. The organic layers were combined, washed with 3×300 mL of brine, dried over anhydrous sodium sulfate and concentrated under vacuum to afford (4R)-1-[(1R)-1-(4-methoxyphenyl)ethyl]-4-(prop-2-enoyl)pyrrolidin-2-one 1.19.

Example 1.20

Preparation of (R)-1-((R)-1-(4-methoxyphenyl)ethyl)-4-(3-methoxypropanoyl)pyrrolidin-2-one

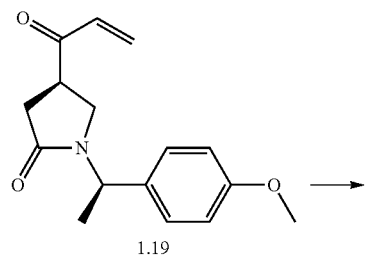

1.19

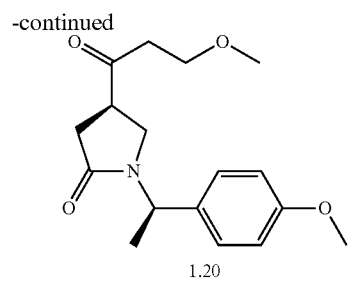

1.20

Into a 250-mL 3-necked round-bottom flask purged and maintained with an inert atmosphere of nitrogen was placed a solution of (4R)-1-[(1R)-1-(4-methoxyphenyl)ethyl]-4-(prop-2-enoyl)pyrrolidin-2-one 1.19 (12 g, 43.90 mmol, 1.00 equiv) in methanol (120 mL), followed by the addition of sulfuric acid (6.24 mL, 98%) dropwise with stirring at 0° C. The resulting solution was stirred overnight at room temperature, quenched by the addition of 100 mL of water/ice and extracted with 3×300 mL of ethyl acetate. The organic layers were combined, washed with 3×300 mL of brine, dried over anhydrous sodium sulfate and concentrated under vacuum to afford (R)-1-((R)-1-(4-methoxyphenyl)ethyl)-4-(3-methoxypropanoyl)pyrrolidin-2-one 1.20.

Example 1.21

Preparation of (R)-4-((R)-1-hydroxy-3-methoxypropyl)-1-4R)-1-(4-methoxyphenyl)ethyl)pyrrolidin-2-one

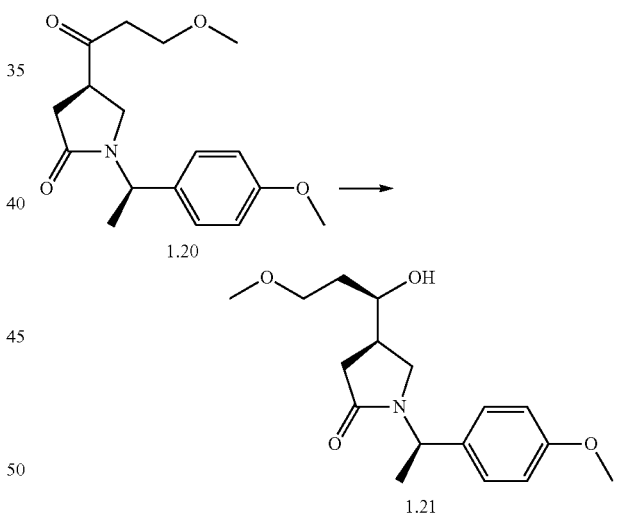

1.21

Into a 250-mL 3-necked round-bottom flask purged and maintained with an inert atmosphere of nitrogen was placed (R)-1-((R)-1-(4-methoxyphenyl)ethyl)-4-(3-methoxypropanoyl)pyrrolidin-2-one 1.20 (12 g, 39.30 mmol, 1.00 equiv), ethanol (100 mL), followed by the addition of NaBH$_4$ (3.35 g, 88.16 mmol, 2.50 equiv) in several batches with stifling at 0° C. The resulting solution was stirred at 0° C. for 2 h, quenched by the addition of 100 mL of water/ice and extracted with 3×300 mL of ethyl acetate. The organic layers were combined, washed with 3×300 mL of brine, dried over anhydrous sodium sulfate and concentrated under vacuum. The residue was applied onto a silica gel column eluting with dichloromethane: methanol (200:1-80:1) to afford (4R)-4-(1-hydroxypropyl)-1-((R)-1-(4-methoxyphenyl)ethyl)pyrrolidin- 2-one as a mixture of diastereomers. The diastereomers were separated by chiral HPLC (CHIRALPAK IC), and the later eluting diastereomer was collected to afford (R)-4-((R)-1-hydroxy-3-methoxypropyl)-1-((R)-1-(4-methoxyphenyl)ethyl)pyrrolidin-2-one 1.21. This compound is the later eluting diastereomer under RP-HPLC conditions (Gemini column, water/acetonitrile/TFA).

¹H NMR (300 MHz, CDCl₃): δ 1.49-1.52 (m, 3H), 1.59-1.72 (m, 2H), 2.29-2.34 (m, 1H), 2.48-2.51 (d, 2H, J=8.7 Hz), 2.95-3.01 (m, 1H), 3.16-3.19 (m, 1H), 3.37 (s, 3H), 3.52-3.59 (m, 1H), 3.63-3.69 (m, 1H), 3.75-3.82 (m, 4H), 5.43-5.48 (m, 1H), 6.86-6.90 (d, 2H), 7.22-7.25 (d, 2H).

Example 1.22

Preparation of (R)-1-((R)-1-(4-methoxyphenyl)ethyl)-4-propionylpyrrolidin-2-one

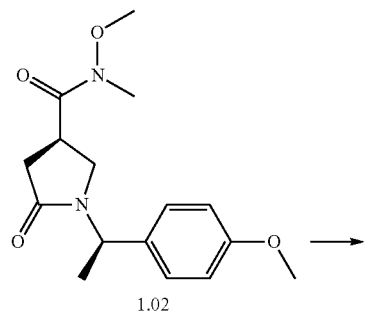

1.02

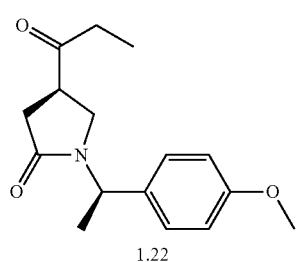

1.22

Into a 500-mL 3-necked round-bottom flask purged and maintained with an inert atmosphere of nitrogen was placed a solution of N-methoxy-1-[(1R)-1-(4-methoxyphenyl)ethyl]-N-methyl-5-oxopyrrolidine-3-carboxamide 1.02 (20 g, 65.28 mmol, 1.00 equiv) in tetrahydrofuran (200 mL), followed by the addition of bromo(ethyl)magnesium in THF (1 M) (44 mL) dropwise with stirring at −10° C. The resulting solution was stirred at −10° C. for 2 h, quenched by the addition of 200 mL of water/ice and extracted with 3×500 mL of ethyl acetate. The organic layers were combined, washed with 2×500 mL of hydrogen chloride (1 M) and 3×500 mL of brine, dried over anhydrous sodium sulfate and concentrated under vacuum. The residue was applied onto a silica gel column eluting with ethyl acetate: petroleum ether (1:5-1:1) to afford (R)-1-((R)-1-(4-methoxyphenyl)ethyl)-4-propionylpyrrolidin-2-one 1.22.

Example 1.23

Preparation of (R)-4-((R)-1-hydroxypropyl)-1-((R)-1-(4-methoxyphenyl)ethyl)pyrrolidin-2-one

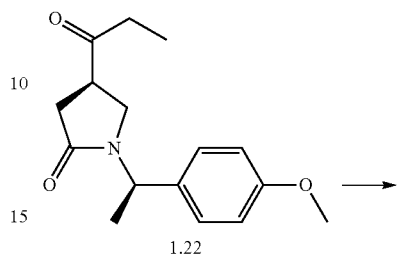

1.22

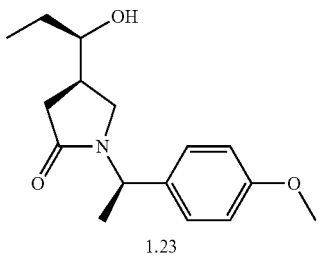

1.23

Into a 250-mL 3-necked round-bottom flask purged and maintained with an inert atmosphere of nitrogen was placed (4R)-1-[(1R)-1-(4-methoxyphenyl)ethyl]-4-propanoylpyrrolidin-2-one 1.22 (6 g, 21.79 mmol, 1.00 equiv), ethanol (60 mL), followed by the addition of NaBH₄ (1.85 g, 48.68 mmol, 2.50 equiv) in several batches with stifling at 0° C. The resulting solution was stirred at room temperature for 2 h, quenched by the addition of 100 mL of water/ice, extracted with 3×200 mL of ethyl acetate. The organic layers were combined, washed with 2×200 mL of brine, dried over anhydrous sodium sulfate and concentrated under vacuum. The residue was washed with 1×100 mL of ether and the solids were collected by filtration to afford (4R)-4-(1-hydroxypropyl)-1-[(1R)-1-(4-methoxyphenyl)ethyl]pyrrolidin-2-one as a mixture of diastereomers. The diastereomers were separated by chiral HPLC (CHIRALPAK AD), and the earlier eluting diastereomer was collected to afford (R)-4-((R)-1-hydroxypropyl)-1-((R)-1-(4-methoxyphenyl)ethyl)pyrrolidin-2-one 1.23. This compound is the later eluting diastereomer under RP-HPLC conditions (Gemini column, water/acetonitrile/TFA).

¹H NMR (300 MHz, CDCl₃): δ 0.9-1.0 (t, 3H), 1.37-1.52 (m, 5H), 2.28-2.38 (m, 1H), 2.47-2.50 (m, 2H), 2.97-3.03 (t, 1H), 3.14-3.20 (t, 1H), 3.46-3.52 (m, 1H), 3.82 (s, 3H), 5.43-5.50 (m, 1H), 6.87-6.90 (d, 2H, J=6.9 Hz), 7.23-7.26 (d, 2H, J=8.4 Hz).

Example 1.24

Preparation of 4-(2,2-difluoro-1-hydroxyethyl)-1-((R)-1-(4-methoxyphenyl)ethyl)pyrrolidin-2-one

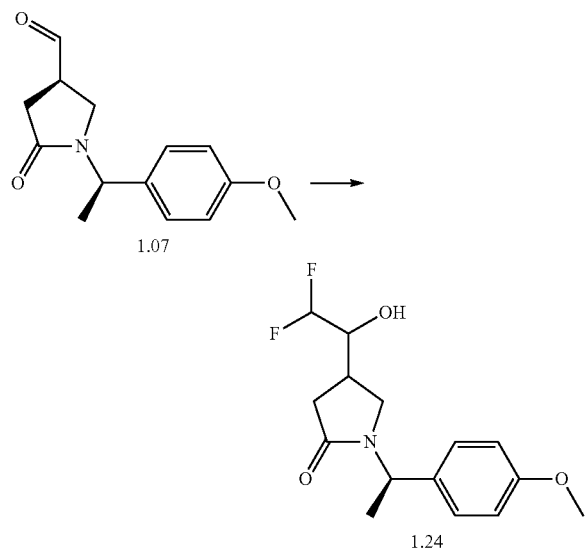

Under a nitrogen atmosphere, KF (0.28 g, 1.87 mmol) and 18-crown-6 (0.49 g, 1.87 mmol) were added to a solution of (3R)-1-[(1R)-1-(4-methoxyphenyl)ethyl]-5-oxopyrrolidine-3-carbaldehyde 1.07 (420 mg, 1.7 mmol) and (difluoromethyl)trimethylsilane (530 mg, 0.52 mmol, 68 uL), and the mixture was stirred at room temperature for 5 hours. 1M HCl was added, and the reaction was stirred for 15 minutes. EtOAc and water were added and the aqueous layer was extracted with EtOAc. The combined organics were dried (MgSO$_4$), filtered and concentrated. The residue was purified by flash chromatography (0→15% MeOH in EtOAc) to afford 4-(2,2-difluoro-1-hydroxyethyl)-1-((R)-1-(4-methoxyphenyl)ethyl)pyrrolidin-2-one 1.24 as a mixture of diastereomers, which were not separated at this stage.

LCMS-ESI$^+$ (m/z): [M+H]$^+$ calcd for C$_{15}$H$_{19}$F$_2$NO$_3$: 300.3; found 300.2.

Example 1.25

Preparation of (R)-4-((R)-1-(4-methoxybenzyloxy)but-3-enyl)-1-((R)-1-(4-methoxyphenyl)ethyl)pyrrolidin-2-one

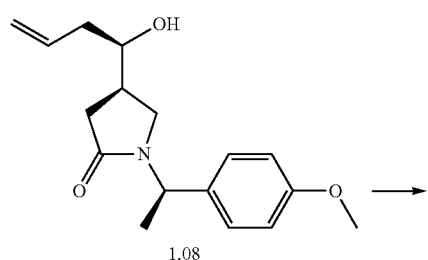

To a solution of the alcohol 1.08 (480 mg 1.7 mmol) in 8 mL of DMF at 0° C. was added NaH (166 mg, 60% dispersion in oil, 4.2 mmol) and their reaction was stirred for 30 minutes at 0° C. p-Methoxybenzyl chloride (0.36 mL, 2.7 mmol) was added and the resulting mixture stirred at room temperature for 3 hr. The reaction was quenched with water, and the mixture was extracted with EtOAc. The combined organics were dried (MgSO$_4$), filtered, and concentrated. The crude product was purified by flash chromatography (30-70% EtOAc in hexanes) to afford (R)-4-((R)-1-(4-methoxybenzyloxy)but-3-enyl)-1-((R)-1-(4-methoxyphenyl)ethyl)pyrrolidin-2-one 1.25.

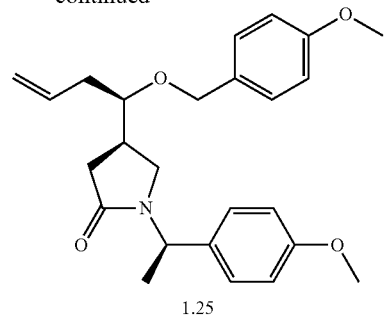

LCMS-ESI$^+$ (m/z): [M+H]$^+$ calcd for C$_{25}$H$_{11}$Na$_4$: 410.2; found 410.0.

Examples 1.26 and 1.27

Preparation of (R)-4-((R)-3,3-difluoro-1-(4-methoxybenzyloxy)propyl)-1-((R)-1-(4-methoxyphenyl)ethyl)pyrrolidin-2-one

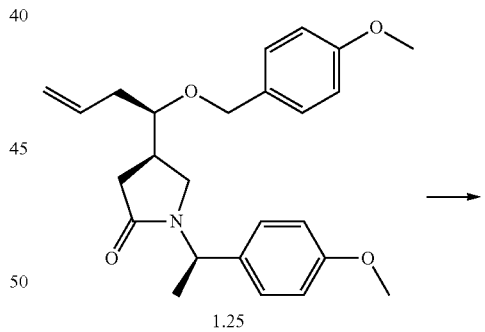

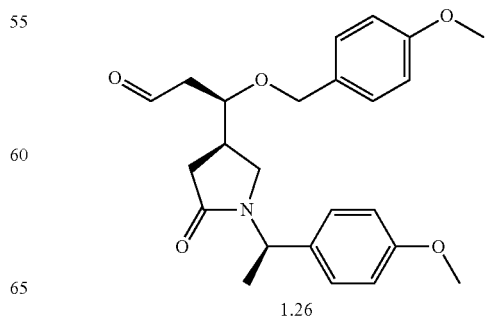

-continued

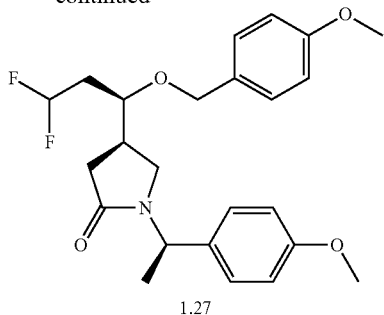

1.27

To a solution of 1.25 (250 mg, 0.61 mmol) in THF (9 ml) and water (3 mL) was added N-methyl morpholine oxide (93 mg, 0.79 mmol) and $OsO_4$ (0.194 ml, 0.031 mmol, 4 w % in water) and the reaction was protected from light and stirred overnight. To the mixture was added sodium bisulfite (127 mg, 1.22 mmol) and water (5 ml) and stirred 10 minutes. EtoAc was added, the layers were separated and the aqueous layer was extracted with EtOAc. The combined organic layers were dried over $MgSO_4$, filtered and concentrated. The residue was used directly in the next step.

To a solution of the crude diol (400 mg, 0.90 mmol) obtained as described above, in dioxane/water (3:1, 12 ml) at 0° C. was added 2,6 lutidine (193 mg, 1.80 mmol) and stirred 5 min. $NaIO_4$ (523 mg, 2.26 mmol) was added and the reaction was stirred at 0° C. for 1 hr and warmed to rt for 5 min. Water (5 mL), brine (5 mL) and EtOAc (20 mL) were added and the layers separated. The aqueous layer was extracted with EtoAc, and the combined organics were dried ($MgSO_4$), filtered and concentrated. The residue was purified via flash chromatography (50-100% EtOAc in hexanes) to provide (R)-3-(4-methoxybenzyloxy)-3-((R)-1-((R)-1-(4-methoxyphenyl)ethyl)-5-oxopyrrolidin-3-yl)propanal 1.26.

To a solution of 1.26 (50 mg, 0.12 mmol) in 1 ml DCM at 0° C. was added DAST (29 mg, 0.18 mmol) dropwise. The reaction was warmed to room temperature and stirred for 2 hours. The reaction was cooled to 0° C., and quenched by the dropwise addition of $NaHCO_3$(sat. aqueous). The layers were separated and the aqueous was extracted with methylene chloride and the combined organics were dried ($MgSO_4$), filtered and concentrated. The residue was purified by flash chromatography to afford (R)-4-((R)-3,3-difluoro-1-(4-methoxybenzyloxy)propyl)-1-((R)-1-(4-methoxyphenyl)ethyl)pyrrolidin-2-one 1.27.

LCMS-ESI$^+$ (m/z): [M+H]$^+$ calcd for $C_{16}H_{21}F_2NO_3$: 434.2; found 434.1.

Example 1.28

Preparation of (R)-4-((R)-3,3-difluoro-1-hydroxypropyl)pyrrolidin-2-one

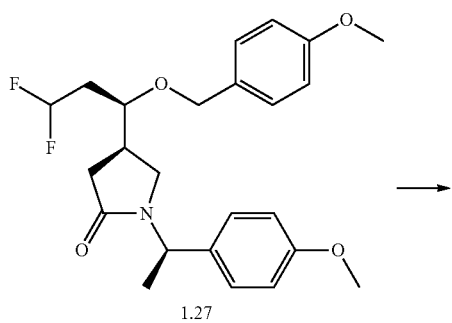

1.27

-continued

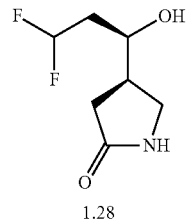

1.28

To a stirred solution of 1.27 (44 mg, 0.10 mmol) in acetonitrile/water (1:1, 2 mL) was added Ceric ammonium nitrate (233 mg, 0.43 mmol) and the reaction was stirred for 1 hr. The reaction mixture was concentrated and purified by flash chromatography (10-20% MeOH in $CH_2Cl_2$) to afford (R)-4-((R)-3,3-difluoro-1-hydroxypropyl)pyrrolidin-2-one 1.28.

LCMS-ESI$^+$ (m/z): [M+H]$^+$ calcd for $C_7H_{11}F_2NO_2$: 180.1; found 180.1.

Example 1.29

Preparation of (R)-1-((R)-1-(4-methoxyphenyl)ethyl)-4-48)-2,2,2-trifluoro-1-hydroxyethyl)pyrrolidin-2-one

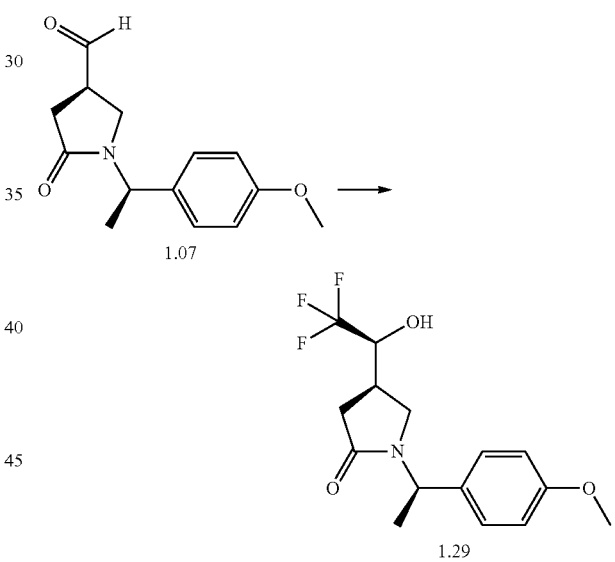

Into a 250-mL 3-necked round-bottom flask purged and maintained with an inert atmosphere of nitrogen was placed a solution of (3R)-1-[(1R)-1-(4-methoxyphenyl)ethyl]-5-oxopyrrolidine-3-carbaldehyde 1.07 (7 g, 28.31 mmol, 1.00 equiv) in toluene (100 mL), trimethyl(trifluoromethyl)silane (2.9 mL), followed by the addition of tetrabutylammonium fluoride (1 mol/L in tetrahydrofuran) (1.53 mL) dropwise with stirring at −60° C. The resulting solution was stirred overnight at room temperature, quenched by the addition of 100 mL of water/ice and extracted with 3×300 mL of ethyl acetate. The organic layers were combined, washed with 3×300 mL of brine, dried over anhydrous sodium sulfate and concentrated under vacuum. The residue was applied onto a silica gel column eluting with dichloromethane: methanol (200:1-80:1) to afford (4R)-1-[(1R)-1-(4-methoxyphenyl)ethyl]-4-(2,2,2-trifluoro-1-hydroxyethyl)pyrrolidin-2-one. The diastereomers were separated by chiral HPLC (CHIRALPAK IC), and the later eluting diastereomer was collected to afford (R)-1-((R)-1-(4-methoxyphenyl)ethyl)-4-((S)-2,2,2-trifluoro-1-hydroxyethyl)pyrrolidin-2-one 1.29. This compound is the earlier diastereomer under RP-HPLC conditions (Gemini column, water/acetonitrile/TFA).

(300 MHz, CDCl$_3$): δ 1.49-1.52 (m, 3H), 2.48-2.76 (m, 3H), 3.08-3.14 (m, 1H), 3.27-3.33 (m, 1H), 3.82 (s, 3H), 3.90-3.98 (m, 1H), 5.40-5.45 (m, 1H), 6.87-6.91 (d, 2H), 7.21-7.24 (d, 2H).

Example 1.30

Preparation of (S)-1-((R)-1-((R)-1-(4-methoxyphenyl)ethyl)-5-oxopyrrolidin-3-yl)ethyl methanesulfonate

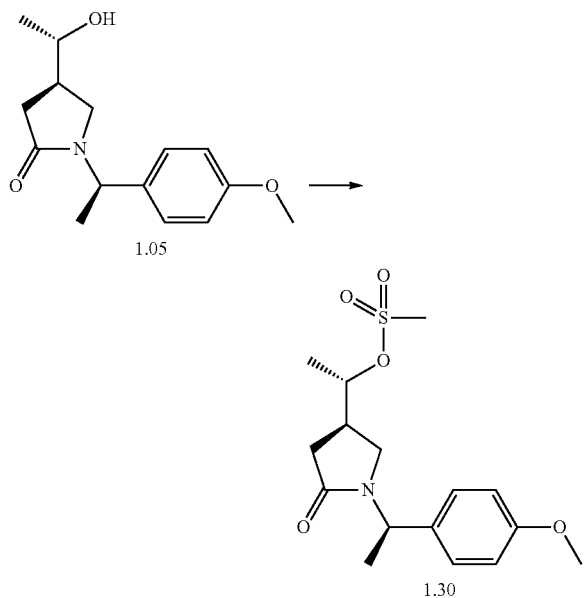

This intermediate was prepared in analogous fashion to example 1.17 using (R)-4-((S)-1-hydroxyethyl)-1-((R)-1-(4-methoxyphenyl)ethyl)pyrrolidin-2-one 1.05 as the starting material: LCMS-ESI$^+$ (m/z): [M+H]$^+$ calcd for C$_{15}$H$_{21}$NO$_3$: 264.2; found 264.1.

Preparation of Common Intermediates

Example 2.01

Preparation of 6-chloro-4-(methylthio)-3H-imidazo[4,5-c]pyridine

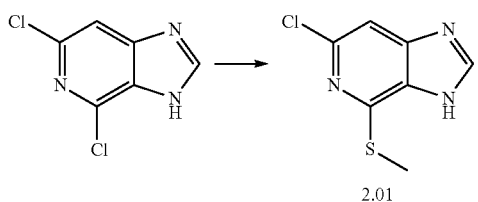

To a solution of 4,6-dichloro-3H-imidazo[4,5-c]pyridine (2.01 g, 10.7 mmol) in DMF (21 mL) at room temperature was added sodium methanethiolate (1.88 g, 26.8 mmol). Mixture was heated at 120° C. for eight hours. An additional 801 mg of sodium methanethiolate was added and mixture stirred at 120° C. for fifteen hours. After adding an additional 340 mg of sodium methanethiolate and heating at 120° C. for five hours, reaction mixture was cooled to room temperature and poured into 100 mL of water. This was then extracted with ethyl acetate (5×150 mL) and combined organic layers were washed with 50% Brine (100 mL), dried (Na$_2$SO$_4$), filtered, and concentrated under reduced pressure to yield 6-chloro-4-(methylthio)-3H-imidazo[4,5-c]pyridine 2.01, which was used in the next step without further purification.

$^1$H NMR (400 MHz, CD$_3$OD) δ 8.22 (s, 1H), 7.28 (s, 1H), 2.65 (s, 3H).

Example 2.02

Preparation of 6-chloro-3-methyl-4-(methylthio)-3H-imidazo[4,5-c]pyridine

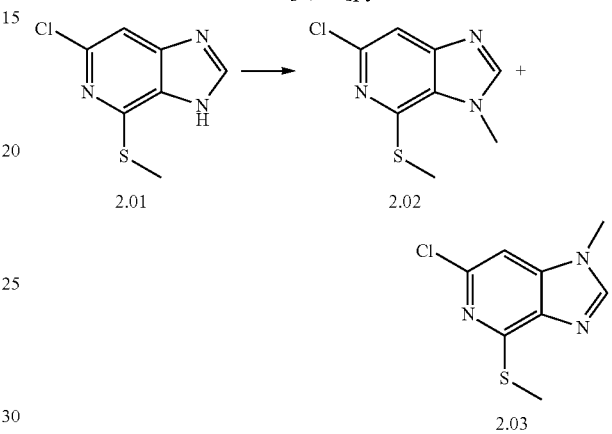

Iodomethane (0.52 mL, 8.36 mmol) was added to a solution of 6-chloro-4-(methylthio)-3H-imidazo[4,5-c]pyridine 2.01 (1.40 g, 7.04 mmol) and potassium carbonate (1.95 g, 14.1 mmol) in 46 mL of DMF at room temperature. After 90 minutes, reaction mixture was taken up in ethyl acetate (150 mL) and washed with 50% saturated NaHCO$_3$ $_{(aq)}$(2×100 mL). After separating layers, aqueous was extracted with ethyl acetate (100 mL). All combined organic layers were washed with 50% brine (100 mL), dried (Na$_2$SO$_4$), filtered, and concentrated under reduced pressure to yield a solid. This was purified via silica gel column chromatography (5-25% acetone in hexanes) to yield 6-chloro-3-methyl-4-(methylthio)-3H-imidazo[4,5-c]pyridine 2.02 (first eluting product).

LCMS-ESI$^+$ (m/z): [M+H]$^+$ calcd for C$_8$H$_8$ClN$_3$S: 214.01; found: 214.06.

Example 2.04

Preparation of 6-chloro-3-methyl-4-(methylsulfonyl)-3H-imidazo[4,5-c]pyridine

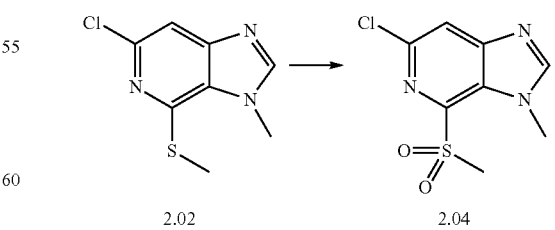

To a solution of 6-chloro-3-methyl-4-(methylthio)-3H-imidazo[4,5-c]pyridine 2.02 (450 mg, 2.11 mmol) in dichloromethane (16 mL) at 0° C., was added mCPBA (≤77%, 972 mg, 4.34 mmol) and mixture was warmed to room temperature. After 80 minutes, an additional 200 mg of mCPBA was added. After an additional twenty minutes, a solution of 50% saturated Na$_2$S$_2$O$_3$ $_{(aq)}$ (20 mL) was added and reaction mixture stirred at room temperature for fifteen minutes. Layers were separated and aqueous was extracted with ethyl acetate (4×15 mL). All organic layers were combined, washed with saturated NaHCO$_3$ $_{(aq)}$ (2×30 mL), dried (Na$_2$SO$_4$), filtered, and concentrated under reduced pressure to yield 6-chloro-3-methyl-4-(methylsulfonyl)-3H-imidazo[4,5-c]pyridine 2.04.

LCMS-ESI$^+$ (m/z): [M+H]$^+$ calcd for C$_8$H$_9$ClN$_3$O$_2$S: 246.00; found: 246.07.

Example 2.05

Preparation of (R)-4-((R)-1-(6-chloro-3-methyl-3H-imidazo[4,5-c]pyridin-4-yloxy)ethyl)-1-((R)-1-(4-methoxyphenyl)ethyl)pyrrolidin-2-one

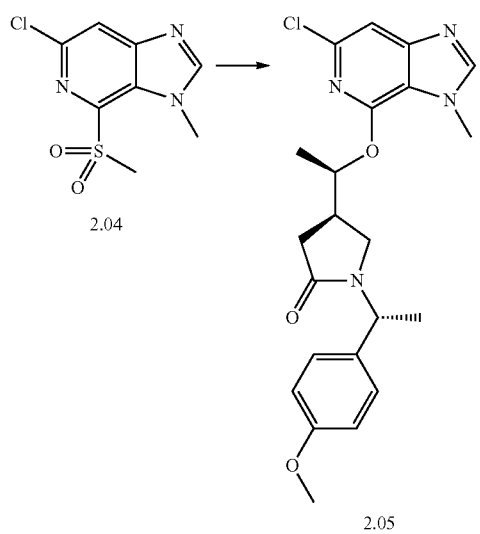 [SMILES: Cn1cnc2cc(Cl)nc(S(C)(=O)=O)c21 ; COc1ccc([C@@H](C)N2C[C@H]([C@@H](C)Oc3nc(Cl)cc4ncn(C)c34)CC2=O)cc1]

A solution of NaHMDS in THF (1.0 M, 1.05 mL, 1.05 mmol) was added to a solution of (R)-4-((R)-1-hydroxyethyl)-1-((R)-1-(4-methoxyphenyl)ethyl)pyrrolidin-2-one 1.04 (277 mg, 1.05 mmol) in DMF (14 mL) at room temperature. After 18 minutes, a suspension of 6-chloro-3-methyl-4-(methylsulfonyl)-3H-imidazo[4,5-c]pyridine 2.04 (237 mg, 0.967 mmol) in DMF (4 mL) was added and mixture stirred at room temperature. After 40 minutes, LC/MS indicated full conversion to desired product. Reaction mixture was quenched with 15 mL of water, poured into 30 mL of water and extracted with ethyl acetate (3×50 mL). Combined organics were washed with 50% Brine (2×50 mL), dried (Na$_2$SO$_4$), filtered, and concentrated under reduced pressure to a residue. This residue was purified by silica gel column chromatography (0-10% methanol in dichloromethane) to yield (R)-4-((R)-1-(6-chloro-3-methyl-3H-imidazo[4,5-c]pyridin-4-yloxy)ethyl)-1-((R)-1-(4-methoxyphenyl)ethyl)pyrrolidin-2-one 2.05.

LCMS-ESI$^+$ (m/z): [M+H]$^+$ calcd for C$_{22}$H$_{26}$ClN$_4$O$_3$: 429.16; found: 429.21.

Example 2.06

Preparation of (R)-4-((R)-1-(6-chloro-3-methyl-3H-imidazo[4,5-c]pyridin-4-yloxy)ethyl)pyrrolidin-2-one

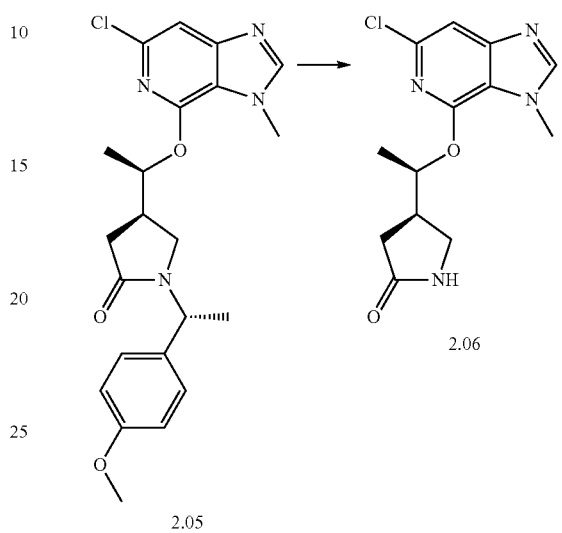

(R)-4-((R)-1-(6-chloro-3-methyl-3H-imidazo[4,5-c]pyridin-4-yloxy)ethyl)-1-((R)-1-(4-methoxyphenyl)ethyl)pyrrolidin-2-one 2.05 (32 mg, 0.075 mmol) was dissolved in trifluoroacetic acid (1.1 mL) at room temperature and mixture was heated between 55-60° C. overnight. After cooling to room temperature, mixture was concentrated under reduced pressure, taken up in ethyl acetate, washed with saturated NaHCO$_3$ $_{(aq)}$, and layers separated. Aqueous layer was extracted with ethyl acetate (3×) and combined organic layers were washed with 1:1 saturated NaHCO$_3$ $_{(aq)}$: brine, dried (Na$_2$SO$_4$), filtered, and concentrated under reduced pressure to yield (R)-4-((R)-1-(6-chloro-3-methyl-3H-imidazo[4,5-c]pyridin-4-yloxy)ethyl)pyrrolidin-2-one 2.06, which was used without further purification.

LCMS-ESI$^+$ (m/z): [M+H]$^+$ calcd for C$_{13}$H$_{16}$ClN$_4$O$_2$: 295.09; found: 295.05.

Examples 2.07 and 2.08

Preparation of 6-chloro-4-(methylthio)-3-((2-(trimethylsilyl)ethoxy)methyl)-3H-imidazo[4,5-c]pyridine and 6-chloro-4-(methylthio)-1-((2-(trimethylsilyl)ethoxy)methyl)-1H-imidazo[4,5-c]pyridine

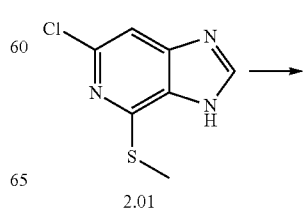

-continued

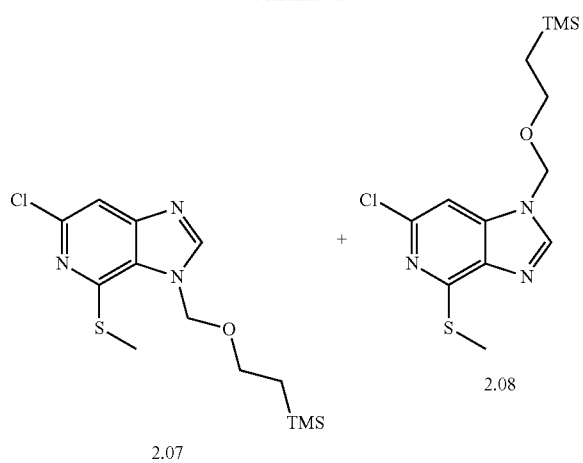

2.07    2.08

(2-(chloromethoxy)ethyl)trimethylsilane (251 mg, 1.51 mmol) was added to a solution of 6-chloro-4-(methylthio)-3H-imidazo[4,5-c]pyridine 2.01 (300 mg, 1.5 mmol) and potassium carbonate (1.224 g, 3.76 mmol) in 10 mL of DMF at room temperature. After 1 h, reaction mixture was taken up in ethyl acetate (150 mL) and was washed with saturated NaHCO$_3$ $_{(aq)}$ (2×100 mL) and brine. The combined organic layers were dried (MgSO$_4$), filtered, and concentrated under reduced pressure to afford a mixture of 2.07 and 2.08, which were used in the next step without further purification.

LCMS [M+H]$^+$: 329.97, and LCMS [M+H]$^+$: 329.9.

Example 2.09 and 2.10

Preparation of 6-chloro-4-(methylsulfonyl)-3-((2-(trimethylsilyl)ethoxy)methyl)-3H-imidazo[4,5-c]pyridine and 6-chloro-4-(methylsulfonyl)-1-((2-(trimethylsilyl)ethoxy)methyl)-1H-imidazo[4,5-c]pyridine

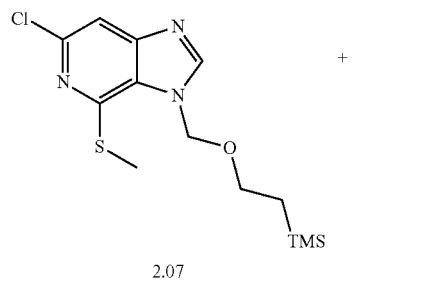

2.07

2.08

Into a solution of 6-chloro-4-(methylsulfonyl)-3-((2-(trimethylsilyl)ethoxy)methyl)-3H-imidazo[4,5-c]pyridine 2.07 and 6-chloro-4-(methylsulfonyl)-1-((2-(trimethylsilyl)ethoxy)methyl)-1H-imidazo[4,5-c]pyridine 2.08 (536 mg, 1.62 mmol) in dichloromethane (10 mL) at 0° C., was added mCPBA (<77%, 841 mg) and mixture was warmed to room temperature. After 2 h, a 20% solution of Na$_2$S$_2$O$_3$ $_{(aq)}$ (20 mL) was added and reaction mixture stirred at room temperature for 15 minutes. The mixture was taken up in ethyl acetate (150 mL) and washed with saturated NaHCO$_3$ $_{(aq)}$ and brine. The combined organic layers were dried (MgSO$_4$), filtered, and concentrated under reduced pressure, This residue was purified by silica gel column chromatography (eluted with 30% to 100% of ethyl acetate in hexane) to yield 6-chloro-4-(methylsulfonyl)-34(2-(trimethylsilyl)ethoxy)methyl)-3H-imidazo[4,5-c]pyridine 2.09 and 6-chloro-4-(methylsulfonyl)-1-((2-(trimethylsilyl)ethoxy)methyl)-1H-imidazo[4,5-c]pyridine 2.10.

6-chloro-4-(methylsulfonyl)-3-((2-(trimethylsilyl)ethoxy)methyl)-3H-imidazo[4,5-c]pyridine 2.09: LCMS [M+H]$^+$: 361.93. $^1$H NMR (400 MHz, CDCl$_3$) ppm: δ 8.396 (s, 1H), 7.956 (s, 1H), 6.003 (s, 2H), 3.66 (t, 2H), 3.528 (s, 3H), 0.984 (t, 2H), 0.00 (s, 9H).

6-chloro-4-(methylsulfonyl)-1-((2-(trimethylsilyl)ethoxy)methyl)-1H-imidazo[4,5-c]pyridine 2.10: LCMS [M+H]$^+$: 361.93. $^1$H NMR (400 MHz, CDCl$_3$) ppm: δ 8.232 (s, 1H), 7.754 (s, 1H), 5.601 (s, 2H), 3.550 (t, 2H), 3.495 (s, 3H), 0.948 (t, 2H), 0.00 (s, 9H).

Example 2.11

Preparation of (R)-4-((R)-1-(6-chloro-3-((2-(trimethylsilyl)ethoxy)methyl)-3H-imidazo[4,5-c]pyridin-4-yloxy)ethyl)-1-((R)-1-(4-methoxyphenyl)ethyl)pyrrolidin-2-one

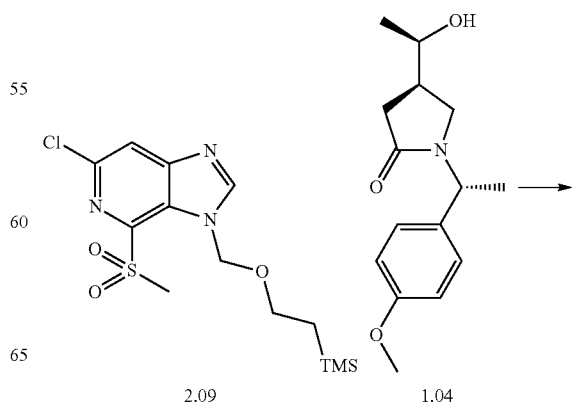

2.09    1.04

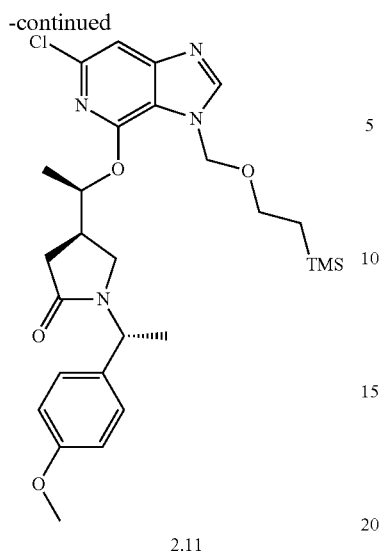

2.11

A solution of NaHMDS in THF (1M, 0.85 ml, 0.85 mmol) was added to a solution of (R)-4-((R)-1-hydroxyethyl)-1-((R)-1-(4-methoxyphenyl)ethyl)pyrrolidin-2-one 1.04 (205 mg, 0.78 mmol) in DMF (10 mL) at room temperature. After 5 minutes, a solution of 6-chloro-4-(methylsulfonyl)-3-((2-(trimethylsilyl)ethoxy)methyl)-3H-imidazo[4,5-c]pyridine 2.09 (256 mg, 0.707 mmol) in DMF (2 mL) was added and mixture stirred at room temperature. After 10 minutes, LC/MS indicated full conversion to desired product. Reaction mixture was quenched with 15 mL of water, poured into 30 mL of water, and extracted with ethyl acetate (100 mL). Organics were washed with Brine (2×50 mL), dried (MgSO₄), filtered, and concentrated under reduced pressure to yield (R)-4-((R)-1-(6-chloro-3-((2-(trimethylsilyl)ethoxy)methyl)-3H-imidazo[4,5-c]pyridin-4-yloxy)ethyl)-1-((R)-1-(4-methoxyphenyl)ethyl)pyrrolidin-2-one 2.11, which was used in the next step without further purification.

LCMS [M+H]⁺: 545.03.

Example 2.12

Preparation of (R)-4-((R)-1-(6-chloro-3-((2-(trimethylsilyl)ethoxy)methyl)-3H-imidazo[4,5-c]pyridin-4-yloxy)ethyl)pyrrolidin-2-one

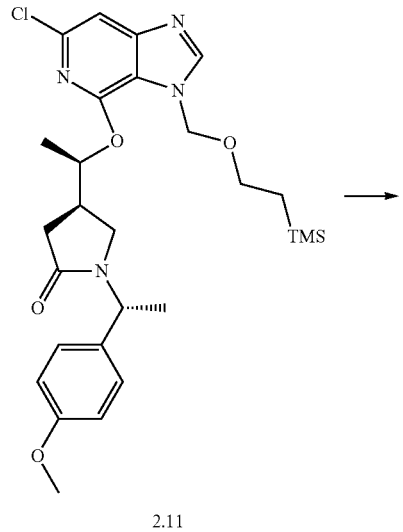

2.11

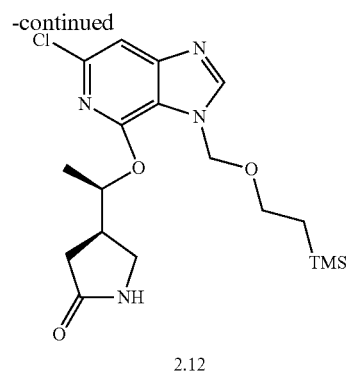

2.12

A solution of CAN (1.28 g, 2.34 mmol) in 10 mL of water was added to a solution of (R)-4-((R)-1-(6-chloro-3-((2-(trimethylsilyl)ethoxy)methyl)-3H-imidazo[4,5-c]pyridin-4-yloxy)ethyl)-1-((R)-1-(4-methoxyphenyl)ethyl)pyrrolidin-2-one 2.11 (425 mg, 0.78 mmol) in MeCN (10 mL) at room temperature. After 2 h, reaction mixture was poured into 30 mL of water and extracted with ethyl acetate (100 mL) and washed with brine (2×50 mL), dried (MgSO₄), filtered, and concentrated under reduced pressure to yield a residue. Residue was washed with hexane to yield (R)-4-((R)-1-(6-chloro-34(2-(trimethylsilyl)ethoxy)methyl)-3H-imidazo[4,5-c]pyridin-4-yloxy)ethyl)pyrrolidin-2-one 2.12, which was used without further purification.

LCMS [M+H]⁺: 410.83

Example 2.13 and 2.14

Preparation of 6-chloro-3-ethyl-4-(methylthio)-3H-imidazo[4,5-c]pyridine and 6-chloro-1-ethyl-4-(methylthio)-1H-imidazo[4,5-c]pyridine

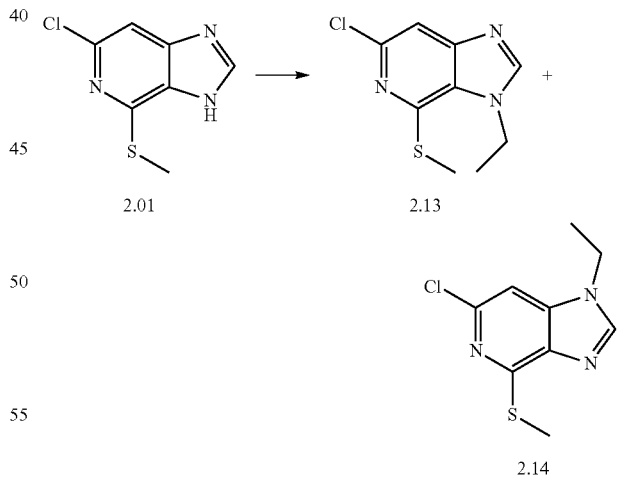

Iodoethane (0.474 g, 3.04 mmol) was added to a solution of 6-chloro-4-(methylthio)-3H-imidazo[4,5-c]pyridine 2.01 (0.506 g, 2.53 mmol) and potassium carbonate (0.56 g, 4 mmol) in 10 mL of DMF at room temperature. After 1 h, reaction mixture was taken up in ethyl acetate (150 mL) and washed with saturated NaHCO₃ (aq) (2×100 mL) and brine. The combined organic layers were dried (MgSO₄), filtered, and concentrated under reduced pressure to yield a mixture of 6-chloro-3-ethyl-4-(methylthio)-3H-imidazo[4,5-c]pyridine 2.13 and 6-chloro-1-ethyl-4-(methylthio)-1H-imidazo[4,5-c]pyridine 2.14.

6-chloro-3-ethyl-4-(methylthio)-3H-imidazo[4,5-c]pyridine 2.13:

LCMS [M+H]+: 228.01.

1H NMR (400 MHz, CDCl3) δ 7.93 (s, 1H), 7.39 (s, 1H), 4.5 (q, 2H), 2.71 (s, 3H), 1.53 (t, 3H).

6-chloro-1-ethyl-4-(methylthio)-1H-imidazo[4,5-c]pyridine 2.14:

LCMS [M+H]+: 228.01.

1H NMR (400 MHz, CDCl3) ppm: δ 7.844 (s, 1H), 7.049 (s, 1H), 4.14 (q, 2H), 2.674 (s, 3H), 1.498 (t, 3H).

Example 2.15 and 2.16

Preparation of 6-chloro-3-ethyl-4-(methylsulfonyl)-3H-imidazo[4,5-c]pyridine and 6-chloro-1-ethyl-4-(methylsulfonyl)-1H-imidazo[4,5-c]pyridine

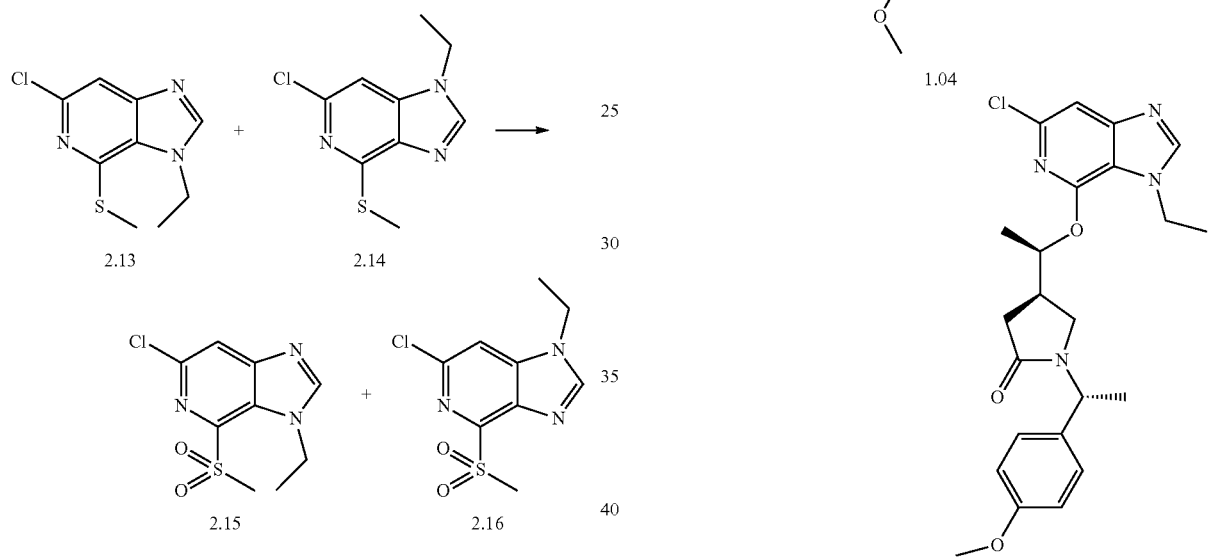

To a solution of 6-chloro-3-ethyl-4-(methylthio)-3H-imidazo[4,5-c]pyridine 2.13 and 6-chloro-1-ethyl-4-(methylthio)-1H-imidazo[4,5-c]pyridine 2.14 (306 mg, 1.34 mmol) in dichloromethane (10 mL) at 0° C., was added mCPBA (≤77%, 557 mg) and mixture was warmed to room temperature. After 2 h, a 20% solution of Na2S2O3 (aq) (20 mL) was added and reaction mixture was stirred at room temperature for 15 minutes. Then the mixture was taken up in ethyl acetate (150 mL) and washed with saturated NaHCO3 (aq) and brine. The combined organic layers were dried (MgSO4), filtered, and concentrated under reduced pressure. The resulting residue was purified by silica gel column chromatography (eluted with 0-20% methanol in ethyl acetate) to yield 6-chloro-3-ethyl-4-(methylsulfonyl)-3H-imidazo[4,5-c]pyridine 2.15 and 6-chloro-1-ethyl-4-(methylsulfonyl)-1H-imidazo[4,5-c]pyridine 2.16.

6-chloro-3-ethyl-4-(methylsulfonyl)-3H-imidazo[4,5-c]pyridine 2.15:

LCMS [M+H]+: 260.02.

1H NMR (400 MHz, CDCl3) ppm: δ 8.154 (s, 1H), 7.837 (s, 1H), 4.68 (q, 2H), 3.5 (s, 3H), 1.564 (t, 3H).

6-chloro-1-ethyl-4-(methylsulfonyl)-1H-imidazo[4,5-c]pyridine 2.16:

LCMS [M+H]+: 260.1.

1H NMR (400 MHz, CDCl3) ppm: δ 8.152 (s, 1H), 7.584 (s, 1H), 4.28 (q, 2H), 3.438 (s, 3H), 1.552 (t, 3H).

Example 2.17

Preparation of (R)-4-((R)-1-(6-chloro-3-ethyl-3H-imidazo[4,5-c]pyridin-4-yloxy)ethyl)-1-((R)-1-(4-methoxyphenyl)ethyl)pyrrolidin-2-one

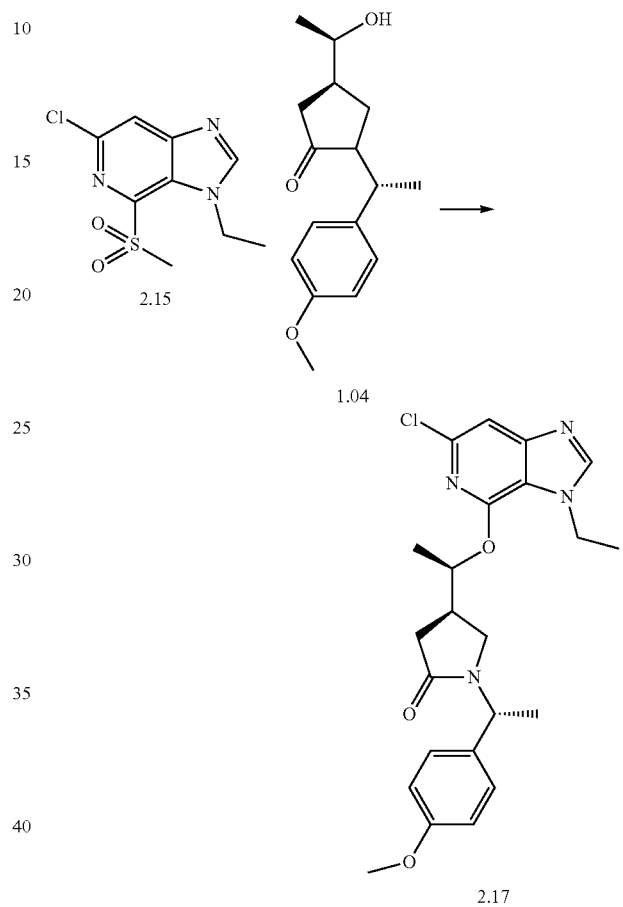

Following the procedure of Example 2.11, beginning with 6-chloro-3-ethyl-4-(methylsulfonyl)-3H-imidazo[4,5-c]pyridine 2.15 (65 mg, 0.25 mmol) and (R)-4-((R)-1-hydroxyethyl)-1-((R)-1-(4-methoxyphenyl)ethyl)pyrrolidin-2-one 1.04 (72 mg, 0.275 mmol), (R)-4-((R)-1-(6-chloro-3-ethyl-3H-imidazo[4,5-c]pyridin-4-yloxy)ethyl)-1-((R)-1-(4-methoxyphenyl)ethyl)pyrrolidin-2-one 2.17 was synthesized.

LCMS [M+H]+: 443.28.

Example 2.18 and 2.19

Preparation of 6-chloro-3-isopropyl-4-(methylthio)-3H-imidazo[4,5-c]pyridine and 6-chloro-1-isopropyl-4-(methylthio)-1H-imidazo[4,5-c]pyridine

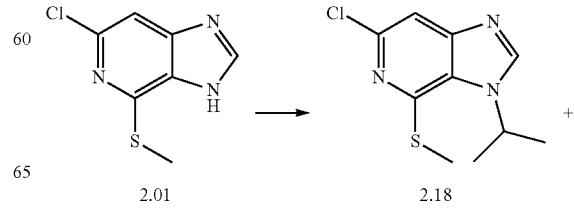

-continued

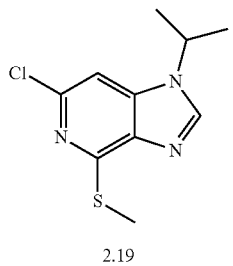

2.19

2-Iodopropane (255 mg, 1.5 mmol) was added to a solution of 6-chloro-4-(methylthio)-3H-imidazo[4,5-c]pyridine 2.01 (300 mg, 1.5 mmol) and cesium carbonate (1.23 g, 3.78 mmol) in 10 mL of DMF at room temperature. After 1 h, reaction mixture was taken up in ethyl acetate (150 mL) and washed with saturated NaHCO$_3$ $_{(aq)}$ (2×100 mL) and brine. The combined organic layers were dried (MgSO$_4$), filtered, and concentrated under reduced pressure to yield a mixture of 6-chloro-3-isopropyl-4-(methylthio)-3H-imidazo[4,5-c]pyridine 2.18 and 6-chloro-1-isopropyl-4-(methylthio)-1H-imidazo[4,5-c]pyridine 2.19.

6-chloro-3-isopropyl-4-(methylthio)-3H-imidazo[4,5-c]pyridine 2.18:

LCMS [M+H]$^+$: 241.96.

$^1$H NMR (400 MHz, CDCl$_3$): δ 8.1 (s, 1H), 7.4 (s, 1H), 5.23 (m, 1H), 2.712 (s, 3H), 1.62 (d, 6H).

6-chloro-1-isopropyl-4-(methylthio)-1H-imidazo[4,5-c]pyridine 2.19:

LCMS [M+H]$^+$: 242.06.

$^1$H NMR (400 MHz, CDCl$_3$) ppm: δ 7.91 (s, 1H), 7.073 (s, 1H), 4.52 (m, 1H), 2.676 (s, 3H), 1.588 (d, 6H).

Example 2.20

Preparation of 6-chloro-3-isopropyl-4-(methylsulfonyl)-3H-imidazo[4,5-c]pyridine

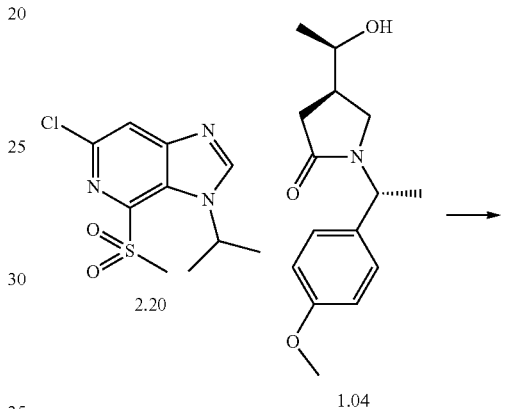

Following the procedure of Example 2.15, beginning with the mixture of 6-chloro-3-isopropyl-4-(methylthio)-3H-imidazo[4,5-c]pyridine 2.18 and 6-chloro-1-isopropyl-4-(methylthio)-1H-imidazo[4,5-c]pyridine 2.19 (355 mg, 1.5 mmol) from the previous step, 6-chloro-3-isopropyl-4-(methylsulfonyl)-3H-imidazo[4,5-c]pyridine 2.20 was synthesized.

LCMS [M+H]$^+$: 273.85.

$^1$H NMR (400 MHz, CDCl$_3$): δ 8.318 (s, 1H), 7.868 (s, 1H), 5.598 (m, 1H), 3.52 (s, 3H), 1.62 (d, 6H).

Example 2.22

Preparation of (R)-4-((R)-1-(6-chloro-3-isopropyl-3H-imidazo[4,5-c]pyridin-4-yloxy)ethyl)-1-((R)-1-(4-methoxyphenyl)ethyl)pyrrolidin-2-one

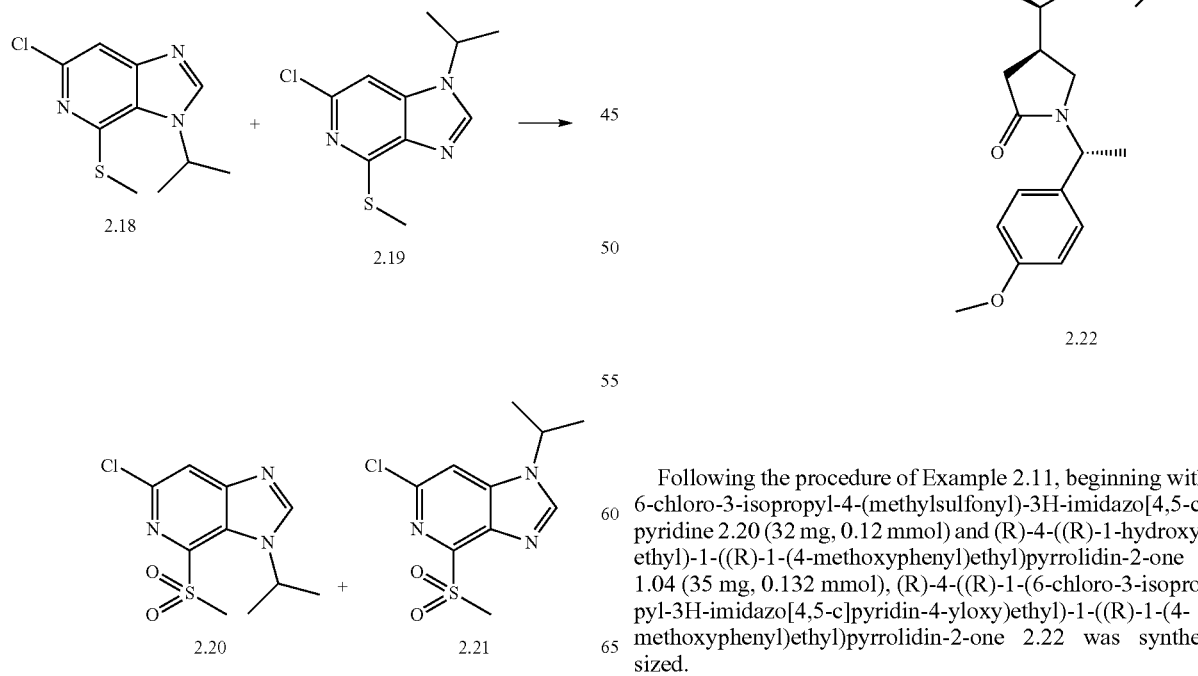

Following the procedure of Example 2.11, beginning with 6-chloro-3-isopropyl-4-(methylsulfonyl)-3H-imidazo[4,5-c]pyridine 2.20 (32 mg, 0.12 mmol) and (R)-4-((R)-1-hydroxyethyl)-1-((R)-1-(4-methoxyphenyl)ethyl)pyrrolidin-2-one 1.04 (35 mg, 0.132 mmol), (R)-4-((R)-1-(6-chloro-3-isopropyl-3H-imidazo[4,5-c]pyridin-4-yloxy)ethyl)-1-((R)-1-(4-methoxyphenyl)ethyl)pyrrolidin-2-one 2.22 was synthesized.

LCMS [M+H]$^+$: 457.28.

Example 2.23

Preparation of (R)-4-((R)-1-(6-chloro-3-isopropyl-3H-imidazo[4,5-c]pyridin-4-yloxy)ethyl)pyrrolidin-2-one

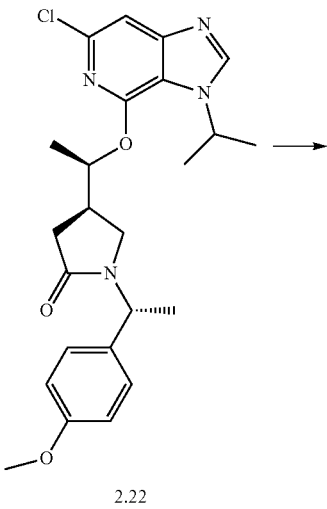

2.22

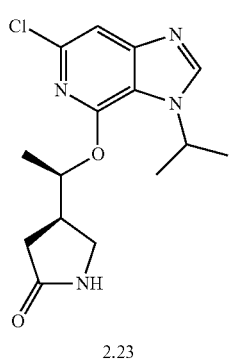

2.23

Following the procedure of Example 2.12, beginning with (R)-4-((R)-1-(6-chloro-3-isopropyl-3H-imidazo[4,5-c]pyridin-4-yloxy)ethyl)-1-((R)-1-(4-methoxyphenyl)ethyl)pyrrolidin-2-one 2.22 (50 mg, 0.109 mmol), (R)-4-((R)-1-(6-chloro-3-isopropyl-3H-imidazo[4,5-c]pyridin-4-yloxy)ethyl)pyrrolidin-2-one 2.23 was synthesized.

LCMS [M+H]$^+$: 323.03.

Example 2.24

Preparation of 4-(benzyloxy)-6-chloro-3H-imidazo[4,5-c]pyridine

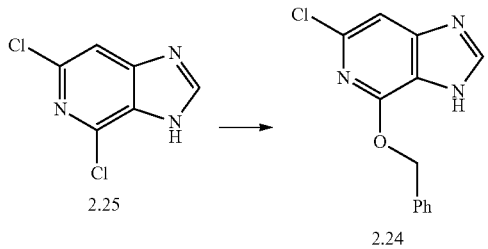 [SMILES: Clc1cc2nc[nH]c2c(Cl)n1 ; Clc1cc2nc[nH]c2c(OCc2ccccc2)n1]

To a solution of 4,6-dichloro-3H-imidazo[4,5-c]pyridine (2.00 g, 10.6 mmol) in BnOH (23 mL) was added powdered NaOH (1.28 g, 31.9 mmol) and the reaction was heated to 150° C. overnight. The benzyl alcohol was removed by vacuum distillation, and the residue was suspended in water (15 mL) and AcOH (3 mL) was added to bring the pH to ~7. The aqueous layer was extracted with CH$_2$Cl$_2$ (3×50 mL). The combined organics were dried (MgSO$_4$), filtered and concentrated. The residue was purified by flash chromatography (1:1 hex EtOAc-->EtOAc/10% MeOH) to afford 4-(benzyloxy)-6-chloro-3H-imidazo[4,5-c]pyridine 2.24.

LCMS-ESI$^+$ (m/z): [M+H]$^+$ calcd for C$_{13}$H$_{10}$ClN$_3$O: 260.1; found 260.1.

Example 2.25

Preparation of 4-(benzyloxy)-6-chloro-3-methyl-3H-imidazo[4,5-c]pyridine

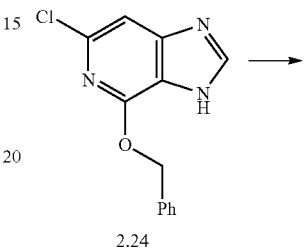

2.24

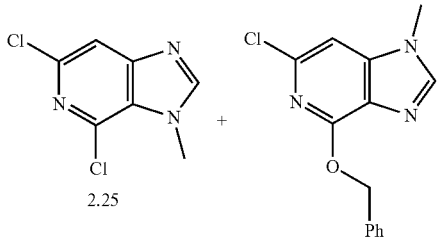

2.25

A mixture of 4-(benzyloxy)-6-chloro-3H-imidazo[4,5-c]pyridine 2.24 (1.00 g, 3.85 mmol) and K$_2$CO$_3$ (1.06 g, 7.70 mmol) were suspended in DMF and iodomethane (0.312 mL. 5.01 mmol) was added dropwise. The reaction was stirred for 2 hours and judged to be complete by LC and TLC. The reaction was concentrated, diluted with NaHCO$_3$ (30 mL) and EtOAc (50 mL), and the layers were separated. The aqueous layer was extracted with EtOAc (3×50 mL), dried, filtered, and concentrated under reduced pressure to afford a mixture of regioisomers. Purification via flash chromatography (2→5% THF in CH$_2$Cl$_2$) afforded 4-(benzyloxy)-6-chloro-3-methyl-3H-imidazo[4,5-c]pyridine 2.25 as the first eluting isomer.

LCMS-ESI$^+$ (m/z): [M+H]$^+$ calcd for C$_{14}$H$_{12}$ClN$_3$O: 274.1; found 274.0.

Example 2.26

Preparation of 4-(benzyloxy)-6-(3,4-dimethoxyphenyl)-3-methyl-3H-imidazo[4,5-c]pyridine

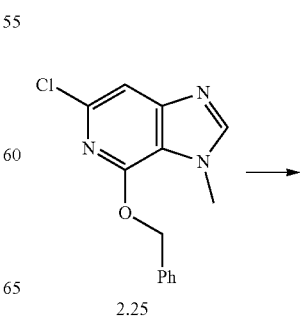

2.25

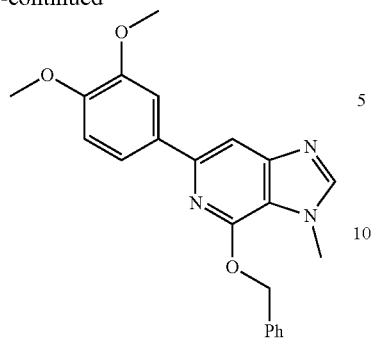

2.26

To a mixture of 4-(benzyloxy)-6-chloro-3-methyl-3H-imidazo[4,5-c]pyridine 2.25 (0.54 g, 1.97 mmol), $K_2CO_3$ (0.68 g, 4.93 mmol), Pd(dppf)Cl$_2$ (0.07 g, 0.1 mmol), and dimethoxy phenyl boronic acid (0.65 g, 3.55 mmol) under $N_2$ was added toluene, iPrOH, and water (2:1:1, 10 mL), and the reaction was heated to 100° C. for 5 hrs. The reaction was cooled and EtOAc (40 mL)/NaHCO$_3$ (20 mL) were added, the layers were separated and the aqueous was extracted with EtOAc (2×25 mL). The combined organics were washed with brine (50 mL), dried (MgSO$_4$), filtered and concentrated. The residue was purified by flash chromatography (EtOAc 0-->5% MeOH gradient) to afford 4-(benzyloxy)-6-(3,4-dimethoxyphenyl)-3-methyl-3H-imidazo[4,5-c]pyridine 2.26.

LCMS-ESI$^+$ (m/z): [M+H]$^+$ calcd for $C_{22}H_{21}N_3O_3$: 376.2; found 376.1.

Example 2.27

Preparation of 6-(3,4-dimethoxyphenyl)-3-methyl-3H-imidazo[4,5-c]pyridin-4-ol

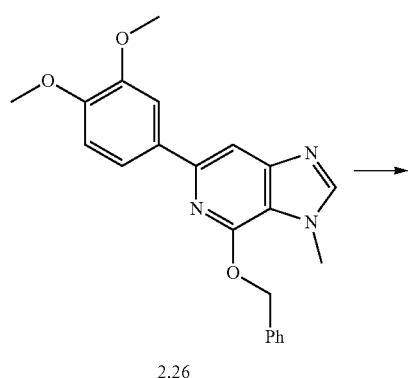

2.26

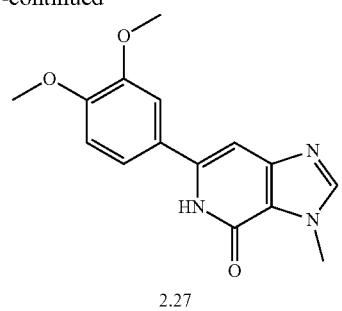

2.27

To a mixture of 4-(benzyloxy)-6-(3,4-dimethoxyphenyl)-3-methyl-3H-imidazo[4,5-c]pyridine 2.26 (290 mg, 0.772 mmol), Pd(OH)$_2$ (46 mg, 60 mg/mmol), and ammonium formate (975 mg, 15.5 mmol) under $N_2$ was added EtOH (12 mL) and DMF (4 mL) and the mixture was heated to 75° C. for 30 minutes. The reaction was cooled, filtered through celite and washed with EtOH/DCM. The filtrate was concentrated, dry loaded onto a column, and purified by flash chromatography (EtOAc→10% MeOH/EtOAc) to afford 6-(3,4-dimethoxyphenyl)-3-methyl-3H-imidazo[4,5-c]pyridin-4-ol 2.27.

LCMS-ESI$^+$ (m/z): [M+H]$^+$ calcd for $C_{15}H_{15}N_3O_3$: 286.1; found 286.1.

Example 2.28

Preparation of 4-(benzyloxy)-6-chloro-3-(difluoromethyl)-3H-imidazo[4,5-c]pyridine

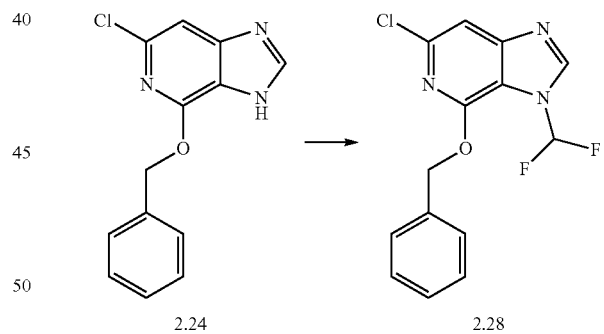

2.24      2.28

A mixture of 4-(benzyloxy)-6-chloro-3H-imidazo[4,5-c]pyridine 2.24 (252 mg, 0.97 mmol) and $K_2CO_3$ (570 mg, 4.1 mmol) in DMF (3 mL) was heated to 90° C. Chlorodifluoromethane was bubbled through the suspension at a rate of ca. 5 bubbles/sec. After 45 min, the bubbling of chlorodifluoromethane was ceased and the reaction mixture was cooled to r.t. The reaction was diluted with EtOAc (25 mL) and water (25 mL), and the phases were separated. The organic phase was washed with water (25 mL) and brine (25 mL), was dried over Na$_2$SO$_4$, and was filtered and concentrated to a crude residue. Purification by silica gel chromatography (10% to 20% to 40% EtOAc in hexanes) provided 4-(benzyloxy)-6-chloro-3-(difluoromethyl)-3H-imidazo[4,5-c]pyridine 2.28.

LCMS-ESI+ (m/z): [M+H]+ calcd for C$_{14}$H$_{11}$ClF$_2$N$_3$O: 310.1; found 310.2.

Example 2.29

Preparation of 3-(difluoromethyl)-6-(3,4-dimethoxyphenyl)-3H-imidazo[4,5-c]pyridin-4(5H)-one

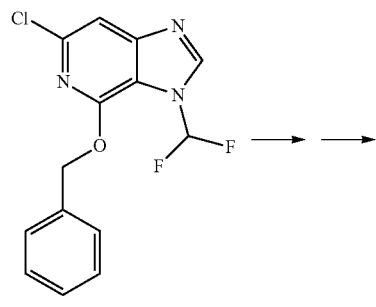

2.28

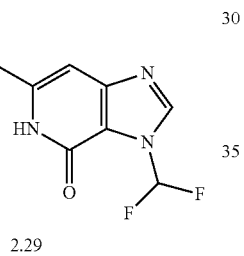

2.29

4-(benzyloxy)-6-chloro-3-(difluoromethyl)-3H-imidazo[4,5-c]pyridine 2.28 (113 mg, 0.365 mmol), 3,4-dimethoxyphenylboronic acid (107 mg, 0.588 mmol), bis(di-tert-butyl(4-dimethylaminophenyl)phosphine)dichloropalladium(II) (14.5 mg, 0.0205 mmol) and K$_2$CO$_3$ (164 mg, 1.19 mmol) were taken up in toluene (3 mL) and water (0.6 mL) under Ar. The stirred mixture was heated to 90° C. After 3.5 h, additional boronic acid (35 mg, 0.19 mmol), catalyst (4.5 mg, 0.0064 mmol), and K$_2$CO$_3$ (53 mg, 0.38 mmol) were added as a suspension in toluene (1 mL) and water (0.3 mL). After an additional 1 h, the reaction mixture was cooled to r.t. and was diluted with EtOAc (20 mL) and water (20 mL). The phases were separated, and the aqueous phase was extracted with EtOAc (20 mL). The organic phase was dried over Na$_2$SO$_4$, filtered, and concentrated onto silica gel. Purification by silica gel chromatography (20% to 50% acetone in hexanes) provided a residue that was dissolved in EtOH (3 mL) and DMF (2 mL). Ammonium formate (260 mg, 4.1 mmol) and Pd(OH)$_2$ on carbon (20 wt. % Pd, 40 mg) were added and the mixture was heated to 70° C. and stirred for 20 min. The mixture was diluted with DMF (5 mL) and filtered through Celite. The filtrate was concentrated in vacuo and the resulting crude solid was purified by silica gel chromatography (0% to 10% MeOH in DCM) to provide 3-(difluoromethyl)-6-(3,4-dimethoxyphenyl)-3H-imidazo[4,5-c]pyridin-4(5H)-one 2.29.

LCMS-ESI+ (m/z): [M+H]+ calcd for C$_{15}$H$_{14}$F$_2$N$_3$O$_3$: 322.1; found 321.8.

Example 2.30

Preparation of (R)-4-((R)-1-(3-(difluoromethyl)-6-(3,4-dimethoxyphenyl)-3H-imidazo[4,5-c]pyridin-4-yloxy)ethyl)-1-((R)-1-(4-methoxyphenyl)ethyl)pyrrolidin-2-one

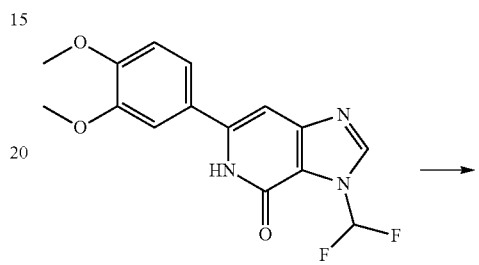

2.29

2.30

3-(difluoromethyl)-6-(3,4-dimethoxyphenyl)-3H-imidazo[4,5-c]pyridin-4(5H)-one 2.29 (49 mg, 0.153 mmol), lactam alcohol 1.05 (60 mg, 0.23 mmol), and PPh$_3$ (60 mg, 0.23 mmol) were taken up in THF (2 mL). To the resulting suspension was added DEAD (38 μL, 0.24 mmol) dropwise. The resulting clear colorless solution was heated to 40° C. and stirred 15 h. The solution was then diluted with DCM and concentrated directly onto silica gel. Purification by silica gel chromatography gave (R)-4-((R)-1-(3-(difluoromethyl)-6-(3,4-dimethoxyphenyl)-3H-imidazo[4,5-c]pyridin-4-yloxy)ethyl)-1-((R)-1-(4-methoxyphenyl)ethyl)pyrrolidin-2-one 2.30 that was used without further purification. LCMS-ESI⁺ (m/z): [M+H]⁺ calcd for $C_{30}H_{33}F_2N_4O_5$: 567.2; found 567.4.

Example 2.31

Preparation of 4-(benzyloxy)-6-(1-tert-butyl-1H-pyrazol-4-yl)-3-(difluoromethyl)-3H-imidazo[4,5-c]pyridine

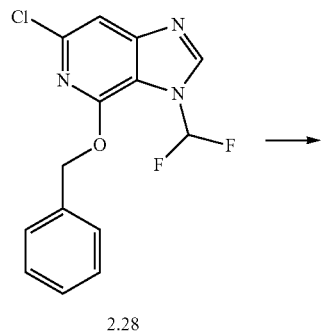

2.28

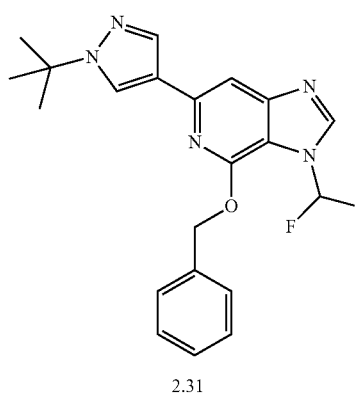

2.31

4-(benzyloxy)-6-chloro-3-(difluoromethyl)-3H-imidazo[4,5-c]pyridine 2.28 (109 mg, 0.352 mmol), 1-tert-butyl-4-(4,4,5,5-tetramethyl-1,3-dioxolan-2-yl)-1H-pyrazole (177 mg, 0.708 mmol), bis(di-tert-butyl(4-dimethylaminophenyl)phosphine)dichloropalladium(II) (17 mg, 0.024 mmol) and $K_3PO_4$ (235 mg, 1.11 mmol) were taken up in dioxane (3 mL) under Ar. Water (0.45 mL) was added and the stirred mixture was heated to 100° C. After 1.25 h, the reaction mixture was cooled to r.t. and was diluted with EtOAc (20 mL) and half-saturated brine (20 mL). The phases were separated, and the aqueous phase was extracted with EtOAc (20 mL). The organic phase was dried over $Na_2SO_4$, filtered, and concentrated onto silica gel. Purification by silica gel chromatography (15% to 50% EtOAc in hexanes) provided 4-(benzyloxy)-6-(1-tert-butyl-1H-pyrazol-4-yl)-3-(difluoromethyl)-3H-imidazo[4,5-c]pyridine 2.31.

LCMS-ESI⁺ (m/z): [M+H]⁺ calcd for $C_{21}H_{22}F_2N_5O$: 398.2; found 398.2.

Example 2.33

Preparation of 6-(1-tert-butyl-1H-pyrazol-4-yl)-3-(difluoromethyl)-3H-imidazo[4,5-c]pyridin-4(5H)-one

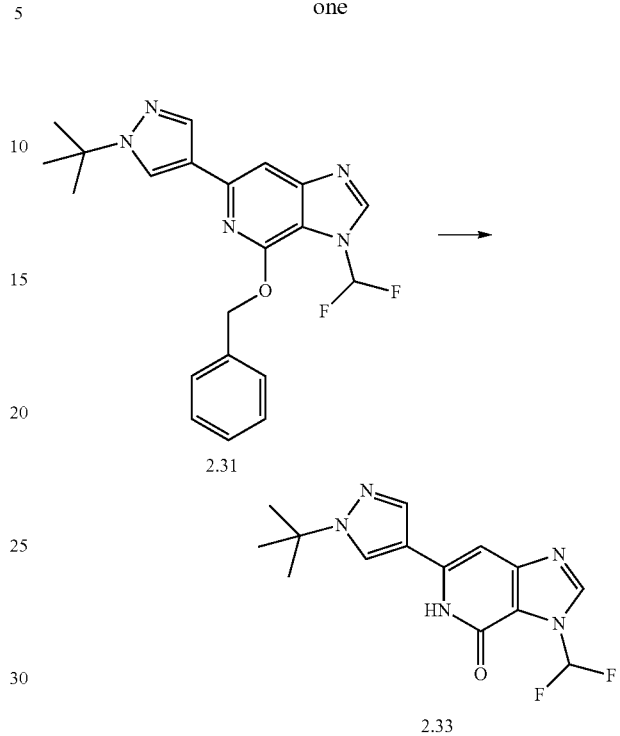

To a solution of 4-(benzyloxy)-6-(1-tert-butyl-1H-pyrazol-4-yl)-3-(difluoromethyl)-3H-imidazo[4,5-c]pyridine 2.31 (136 mg, 0.342 mmol) in EtOH (2 mL) and DMF (2 mL) was added ammonium formate (265 mg, 4.2 mmol) and Pd(OH)₂ on carbon (20 wt. % Pd, 58 mg). The mixture was heated to 55° C. and was stirred for 1 h. The mixture was diluted with DMF (5 mL) and filtered through Celite. The filtrate was concentrated in vacuo to provide 6-(1-tert-butyl-1H-pyrazol-4-yl)-3-(difluoromethyl)-3H-imidazo[4,5-c]pyridin-4(5H)-one 2.33, which was used without further purification.

LCMS-ESI⁺ (m/z): [M+H]⁺ calcd for $C_{14}H_{16}F_2N_5O$: 308.1; found 308.3.

Example 2.34

Preparation of (R)-4-((R)-1-(6-(1-tert-butyl-1H-pyrazol-4-yl)-3-(difluoromethyl)-3H-imidazo[4,5-c]pyridin-4-yloxy)ethyl)-1-((R)-1-(4-methoxyphenyl)ethyl)pyrrolidin-2-one

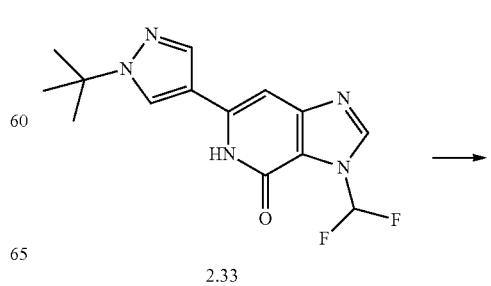

2.33

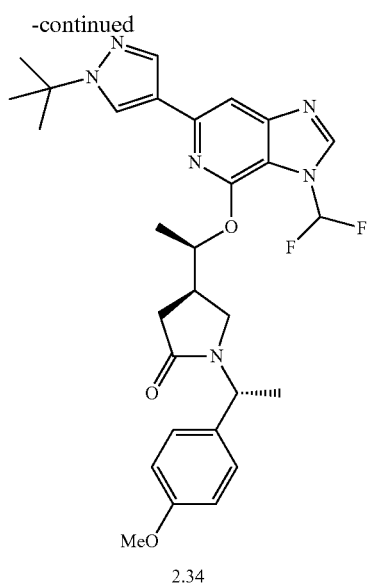

2.34

6-(1-tert-butyl-1H-pyrazol-4-yl)-3-(difluoromethyl)-3H-imidazo[4,5-c]pyridin-4(5H)-one 2.33 (33 mg, 0.107 mmol), lactam alcohol 1.05 (42 mg, 0.16 mmol), and PPh$_3$ (44 mg, 0.17 mmol) were taken up in THF (1 mL). To the resulting suspension was added DEAD (26 µL, 0.17 mmol) dropwise. The resulting cloudy solution was heated to 40° C. and stirred 1.25 h. The solution was then diluted with DCM and concentrated directly onto silica gel. Purification by silica gel chromatography (15% to 60% acetone in hexanes) afforded (R)-4-((R)-1-(6-(1-tert-butyl-1H-pyrazol-4-yl)-3-(difluoromethyl)-3H-imidazo[4,5-c]pyridin-4-yloxy)ethyl)-1-((R)-1-(4-methoxyphenyl)ethyl)pyrrolidin-2-one 2.34 that was used without further purification.

LCMS-ESI$^+$ (m/z): [M+H]$^+$ calcd for C$_{29}$H$_{35}$F$_2$N$_6$O$_3$: 553.3; found 553.2.

Example 2.35

Preparation of 4-(benzyloxy)-6-chloro-3-cyclopropyl-3H-imidazo[4,5-c]pyridine

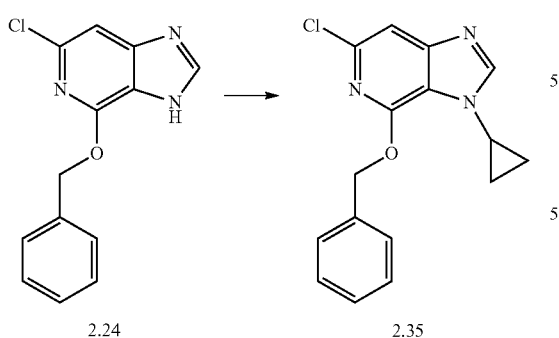

2.24      2.35

In a vial, Cu(OAc)$_2$ (356 mg, 1.96 mmol) and 2,2'-bipyridine (306 mg, 1.95 mmol) were suspended in 1,2-DCE (3 mL). The resulting suspension was heated to 70° C. and was stirred 5 min prior to use.

In a separate flask 4-(benzyloxy)-6-chloro-3H-imidazo[4,5-c]pyridine 2.24 (502 mg, 1.93 mmol), cyclopropane boronic acid (334 mg, 3.89 mmol) and Na$_2$CO$_3$ (415 mg, 3.9 mmol) were taken up in 1,2-DCE (13 mL). The aforementioned catalyst mixture was then added to this mixture, washing with 4×1 mL 1,2-DCE. The resulting mixture was heated to 70° C. and was stirred open to the air. After 7 h, additional Na$_2$CO$_3$ (215 mg, 2.03 mmol) and boronic acid (170 mg, 2.0 mmol) were added along with a heated suspension of Cu(OAc)$_2$ (182 mg, 1.0 mmol) and 2,2'-bipyridine (155 mg, 0.99 mmol) in 1,2-DCE (3 mL). After an additional 1.5 h, additional boronic acid (340 mg, 4.0 mmol) and Na$_2$CO$_3$ (415 mg, 3.9 mmol) were added and the reaction was capped and stirred overnight. After an additional 14.5 h, additional boronic acid (150 mg, 1.7 mmol) and Na$_2$CO$_3$ (215 mg, 2.03 mmol) were added and the mixture was stirred open to air. After an additional 1.5 h, the reaction mixture was cooled to r.t., was diluted with EtOAc (75 mL), and was filtered through Celite. The filtrate was washed with half-saturated aqueous NH$_4$Cl (75 mL), water (50 mL), and brine (50 mL). The organic phase was dried over Na$_2$SO$_4$, filtered, and concentrated. Purification by silica gel chromatography (0% to 5% THF in DCM) provided 4-(benzyloxy)-6-chloro-3-cyclopropyl-3H-imidazo[4,5-c]pyridine 2.35.

LCMS-ESI$^+$ (m/z): [M+H]$^+$ calcd for C$_{16}$H$_{15}$ClN$_3$O: 300.1; found 300.1.

Example 2.36

Preparation of 4-(benzyloxy)-3-cyclopropyl-6-(3,4-dimethoxyphenyl)-3H-imidazo[4,5-c]pyridine

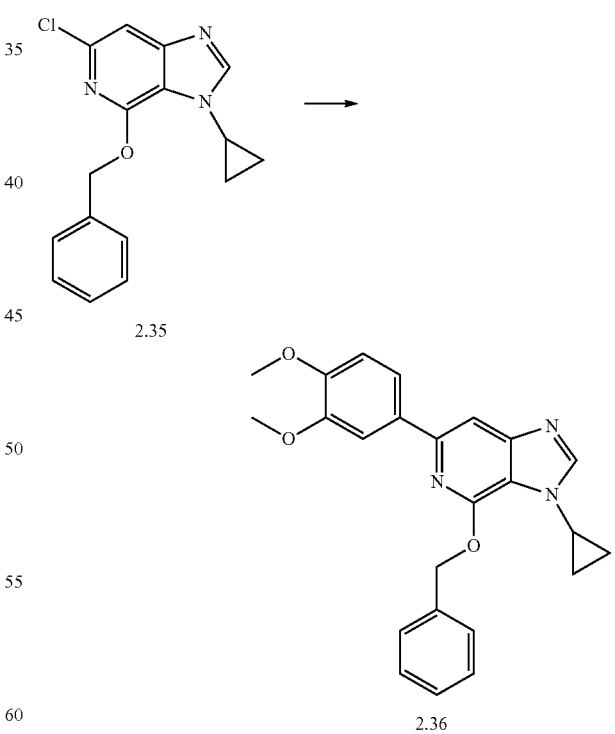

4-(benzyloxy)-6-chloro-3-cyclopropyl-3H-imidazo[4,5-c]pyridine 2.35 (306 mg, 1.02 mmol), 3,4-dimethoxyphenylboronic acid (297 mg, 1.63 mmol), bis(di-tert-butyl(4-dimethylaminophenyl)phosphine)dichloropalladium(II) (36 mg, 0.051 mmol) and K$_2$CO$_3$ (450 mg, 3.3 mmol) were taken up in toluene (8.3 mL) and water (1.7 mL) under Ar. The stirred mixture was heated to 90° C. After 4 h, the temperature was increased to 100° C.

After an additional 16 h, the reaction mixture was cooled to r.t. and diluted with EtOAc (30 mL) and water (30 mL). The phases were separated, and the organic phase was dried over Na$_2$SO$_4$, filtered, and concentrated onto silica gel. Purification by silica gel chromatography (35% to 65% acetone in hexanes) provided 4-(benzyloxy)-3-cyclopropyl-6-(3,4-dimethoxyphenyl)-3H-imidazo[4,5-c]pyridine 2.36.

LCMS-ESI$^+$ (m/z): [M+H]$^+$ calcd for C$_{24}$H$_{24}$N$_3$O$_3$: 402.2; found 401.8.

Example 2.37

Preparation of 3-cyclopropyl-6-(3,4-dimethoxyphenyl)-3H-imidazo[4,5-c]pyridin-4(5H)-one

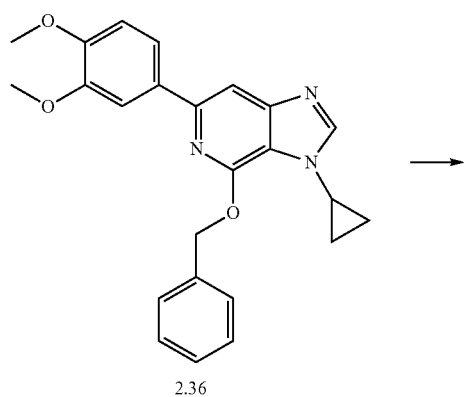

2.36

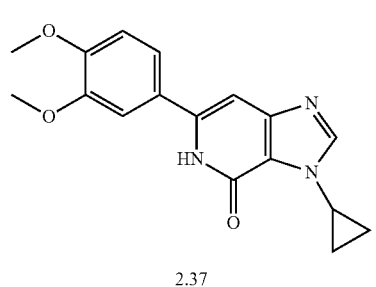

2.37

To a solution of 4-(benzyloxy)-3-cyclopropyl-6-(3,4-dimethoxyphenyl)-3H-imidazo[4,5-c]pyridine 2.36 (270 mg, 0.67 mmol) in EtOH (6.5 mL) and DMF (2.1 mL) was added ammonium formate (670 mg, 10.6 mmol) and Pd(OH)$_2$ on carbon (20 wt. % Pd, 70 mg). The mixture was heated to 65° C. and stirred for 40 min. The mixture was diluted with DMF (10 mL) and EtOH (10 mL) and was filtered through Celite. The filtrate was concentrated in vacuo and the resulting crude solid was purified by silica gel chromatography (0% to 15% MeOH in DCM) to provide 3-cyclopropyl-6-(3,4-dimethoxyphenyl)-3H-imidazo[4,5-c]pyridin-4(5H)-one 2.37.

LCMS-ESI$^+$ (m/z): [M+H]$^+$ calcd for C$_{17}$H$_{18}$N$_3$O$_3$: 312.1; found 312.2.

Example 2.38

Preparation of (R)-4-((R)-1-(3-cyclopropyl-6-(3,4-dimethoxyphenyl)-3H-imidazo[4,5-c]pyridin-4-yloxy)ethyl)-1-((R)-1-(4-methoxyphenyl)ethyl)pyrrolidin-2-one

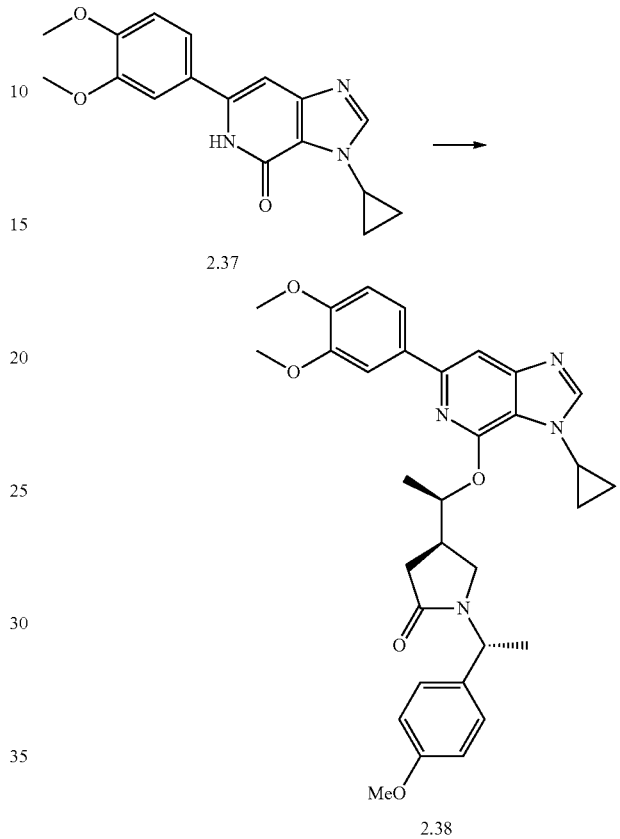

3-cyclopropyl-6-(3,4-dimethoxyphenyl)-3H-imidazo[4,5-c]pyridin-4 (5H)-one 2.37 (48.9 mg, 0.157 mmol), lactam alcohol 1.05 (63 mg, 0.24 mmol), and PPh$_3$ (63 mg, 0.24 mmol) were taken up in THF (1.6 mL). To the resulting suspension was added DEAD (38 μL, 0.24 mmol) dropwise. The resulting mixture was heated to 40° C. and stirred 15 h. The solution was then diluted with DCM and concentrated directly onto silica gel. Purification by silica gel chromatography (35% to 55% to 65% to 100% acetone in hexanes) gave (R)-4-((R)-1-(3-cyclopropyl-6-(3,4-dimethoxyphenyl)-3H-imidazo[4,5-c]pyridin-4-yloxy)ethyl)-1-((R)-1-(4-methoxyphenyl)ethyl)pyrrolidin-2-one 2.38.

LCMS-ESI$^+$ (m/z): [M+H]$^+$ calcd for C$_{32}$H$_{37}$N$_4$O$_5$: 557.3; found 557.4.

Example 2.41

Preparation of 6-(1-tert-butyl-1H-pyrazol-4-yl)-3-methyl-4-(methylsulfonyl)-3H-imidazo[4,5-c]pyridine

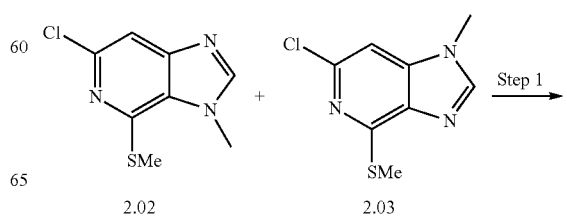

2.02     2.03

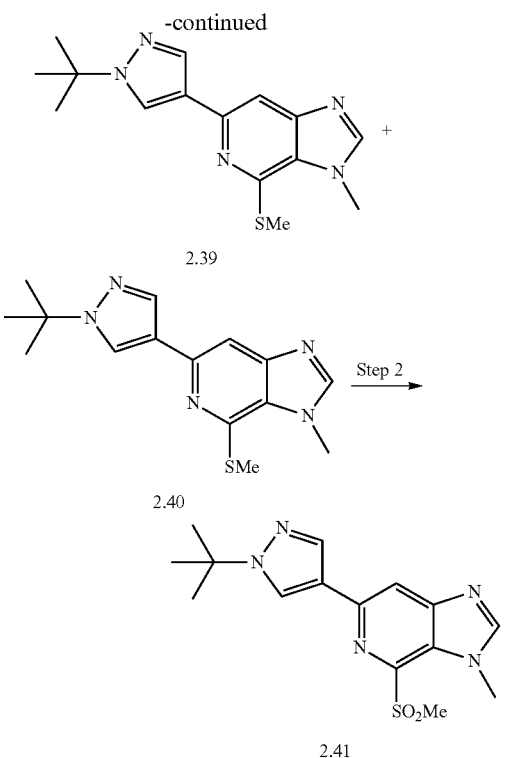

Step 1: To a mixture of 6-chloro-3-methyl-4-(methylthio)-3H-imidazo[4,5-c]pyridine 2.02 and 6-chloro-1-methyl-4-(methylthio)-1H-imidazo[4,5-c]pyridine 2.03 (prepared as previously described, ~1:2 mixture of regioisomers, 1.25 g, 5.85 mmol),1-tert-butyl-4-(4,4,5,5-tetramethyl-1,3-dioxolan-2-yl)-1H-pyrazole (2.20 g, 8.78 mmol), and Cs$_2$CO$_3$ (5.72 g, 17.6 mmol) was added DME (20 mL) and water (10 mL) and the solution was degassed for 10 min. [1,3-Bis(2,6-Diisopropylphenyl)imidazol-2-ylidene](3-chloropyridyl)palladium(II) dichloride (397 mg, 0.585 mmol) was added and the reaction was heated to 100 deg C. for 1 hour. Upon cooling, the aqueous layer was removed, EtOAc and water were added, and the layers separated. The organic layer was dried (MgSO$_4$), filtered and concentrated. The residue was purified by flash chromatography (EtOAc 0-->5% MeOH gradient) to afford 6-(1-tert-butyl-1H-pyrazol-4-yl)-3-methyl-4-(methylthio)-3H-imidazo[4,5-c]pyridine 2.39 and 6-(1-tert-butyl-1H-pyrazol-4-yl)-3-methyl-4-(methylthio)-3H-imidazo[4,5-c]pyridine 2.40, which were isolated as a mixture and carried directly into the next step.

LCMS-ESI$^+$ (m/z): [M+H]$^+$ calcd for C$_{15}$H$_{19}$N$_5$S: 302.1; found 302.2.

Step 2: To a stirred solution of 6-(1-tert-butyl-1H-pyrazol-4-yl)-3-methyl-4-(methylthio)-3H-imidazo[4,5-c]pyridine 2.39 and 6-(1-tert-butyl-1H-pyrazol-4-yl)-3-methyl-4-(methylthio)-3H-imidazo[4,5-c]pyridine 2.40 (1.44 g, 4.78 mmol) in DCM at 0° C. was added mCPBA (2.47 g, 14.3 mmol) and the reaction was stirred for 5 min at 0° C. and warmed to rt for 2 hours. Water (20 mL) and EtOAc (40 mL) were added and the layers were separated and the aqueous was extracted with EtOAc (3×40 mL). The combined organics were washed with saturated NaHCO$_3$ (2×50 mL), dried (MgSO$_4$), filtered and concentrated. The residue was purified by flash chomatrography to afford 6-(1-tert-butyl-1H-pyrazol-4-yl)-3-methyl-4-(methylsulfonyl)-3H-imidazo[4,5-c]pyridine 2.41.

LCMS-ESI$^+$ (m/z): [M+H]$^+$ calcd for C$_{15}$H$_{15}$N$_5$O$_2$S: 334.1; found 334.1.

Example 2.42

Preparation of tert-butyl 2,6-dichloro-3-nitropyridin-4-ylcarbamate

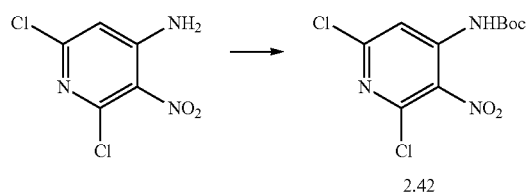 [SMILES: Nc1cc(Cl)nc(Cl)c1[N+](=O)[O-] ; CC(C)(C)OC(=O)Nc1cc(Cl)nc(Cl)c1[N+](=O)[O-]]

A mixture of 2,6-dichloro-3-nitropyridin-4-amine (3.0 g, 14.42 mmol), di-tert-butyl dicarbonate (3.98 g, 18.24 mmol), and 4-dimethylaminopyridine (DMAP) (0.19 g, 1.63 mmol) in THF (10 mL) was stirred at room temperature. After 1 hr, LC/MS indicated full conversion to desired product. Solvent was removed under reduced pressure. Solids re-dissolved and extracted with ethyl acetate and water. Organic layer was washed with brine, dried over MgSO$_4$, filtered, and concentrated under reduced pressure. Residues obtained were purified by column chromatography on silica gel (30% EtOAc-hexane) to give tert-butyl 2,6-dichloro-3-nitropyridin-4-ylcarbamate 2.42.

LCMS-ESI$^+$ (m/z): [M+H]$^+$ calcd for C$_{10}$H$_{11}$C$_{12}$N$_3$O$_4$: 308.01; found: 308.0.

Example 2.43

Preparation of tert-butyl 3-amino-2,6-dichloropyridin-4-ylcarbamate

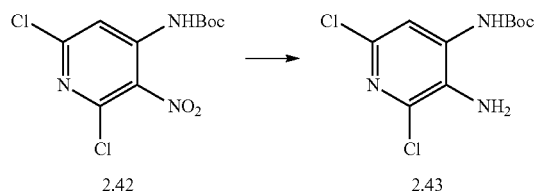 [SMILES: CC(C)(C)OC(=O)Nc1cc(Cl)nc(Cl)c1[N+](=O)[O-] ; CC(C)(C)OC(=O)Nc1cc(Cl)nc(Cl)c1N]

Tert-butyl 2,6-dichloro-3-nitropyridin-4-ylcarbamate 2.42 (2.0 g, 6.49 mmol) was dissolved in THF (10 mL) and cooled to 0° C. in ice-bath. To this solution sodium dithionite (3.39 g, 19.47 mmol), and NaHCO$_3$ (1.6 g) dissolved in 10 mL of water, were added and the mixture was stirred at 0° C. After 1 hr, LC/MS indicated full conversion to desired product, solvent was removed under reduced pressure. Solids re-dissolved and extracted with ethyl acetate and water. Organic layer was washed with brine, dried over MgSO$_4$, filtered, and concentrated under reduced pressure. Residue obtained was recrystallized from acetonitrile to obtain tert-butyl 3-amino-2,6-dichloropyridin-4-ylcarbamate 2.43 that was used for next step without further purification.

LCMS-ESI⁺ (m/z): [M+H]⁺ calc for $C_{10}H_{13}C_{12}N_3O_2$: 278.04; found: 278.1.

Example 2.44

Preparation of tert-butyl 2,6-dichloro-3-(methylamino)pyridin-4-ylcarbamate

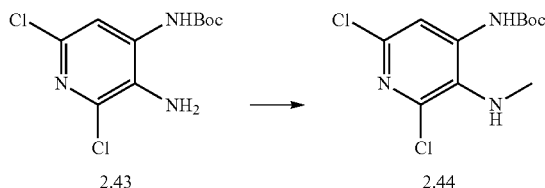 [SMILES: CC(C)(C)OC(=O)Nc1cc(Cl)nc(Cl)c1N ; CNc1c(NC(=O)OC(C)(C)C)cc(Cl)nc1Cl]

Palladium (II) acetate (0.21 g, 0.31 mmol) and 2-Dicyclohexylphosphino-2',4',6'-triisopropylbiphenyl (X-phos) (0.36 g, 0.75 mmol) were combined in toluene and heated at 120° C. for 3 min in microwave reactor. To this mixture tert-butyl 3-amino-2,6-dichloropyridin-4-ylcarbamate 2.43 (0.87 g, 3.12 mmol), $Cs_2CO_3$ (3.06 g, 9.38 mmol) and methyl iodide (0.196 mL, 3.12 mmol) were added and heated at 90° C. for 2 hr in a microwave reactor. After completion of the reaction, solvent was removed under reduced pressure. Solids were dissolved and extracted with ethyl acetate and water. Organic layer was washed with brine, dried over $MgSO_4$, filtered, and concentrated under reduced pressure. The residue obtained was heated in acetonitrile and solids were filtered out to obtain tert-butyl 2,6-dichloro-3-(methylamino)pyridin-4-ylcarbamate 2.44 that was used for next step without further purification.

LCMS-ESI⁺ (m/z): [M+H]⁺ calcd for $C_{11}H_{15}C_{12}N_3O_2$: 292.05; found: 292.1.

Example 2.45

Preparation of 2,6-dichloro-N3-methylpyridine-3,4-diamine

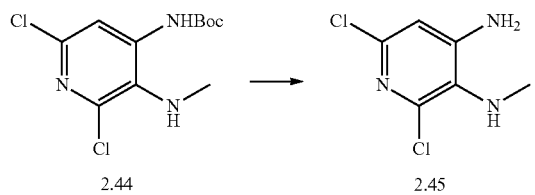 [SMILES: CNc1c(NC(=O)OC(C)(C)C)cc(Cl)nc1Cl ; CNc1c(N)cc(Cl)nc1Cl]

Tert-butyl 2,6-dichloro-3-(methylamino)pyridin-4-ylcarbamate 2.44 (0.60 g) was dissolved in a mixture of DCM/TFA 1:1 (5 mL) and stirred at room temperature. After 1 h, LC/MS indicated full conversion to desired product. Mixture was concentrated under reduced pressure, taken up in ethyl acetate, washed with 1N HCl and layers separated. Aqueous layer was extracted again with ethyl acetate and saturated $NaHCO_{3\,(aq)}$, and layers separated. Organic layer was washed with brine, dried over $MgSO_4$, filtered, and concentrated under reduced pressure to yield 2,6-dichloro-N3-methylpyridine-3,4-diamine 2.45 that was used for next step without further purification. LCMS-ESI⁺ (m/z): [M+H]⁺ calcd for $C_6H_7C_{12}N_3$: 192.0; found: 192.1.

Example 2.47

Preparation of 4,6-dichloro-2,3-dimethyl-3H-imidazo[4,5-c]pyridine

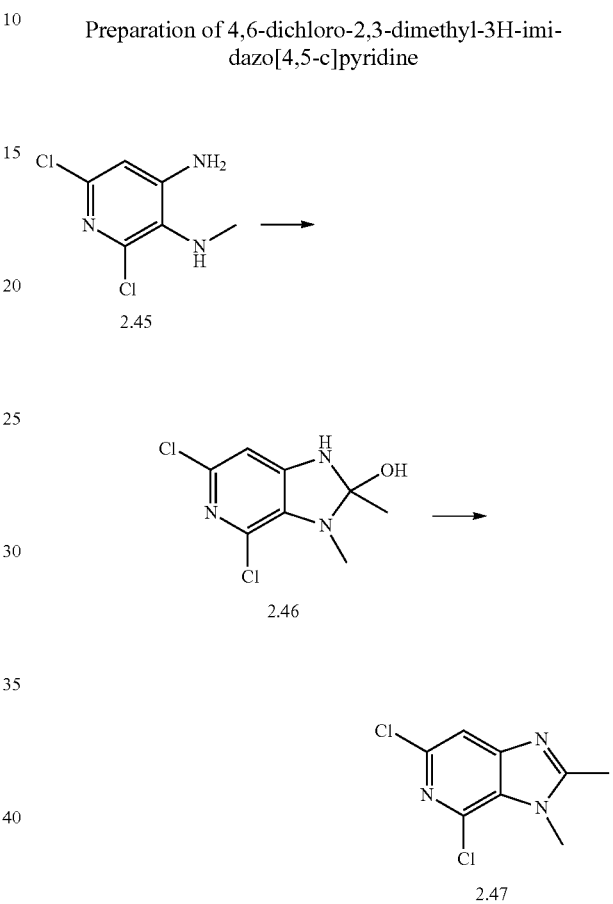

2,6-dichloro-N3-methylpyridine-3,4-diamine 2.45 (0.15 g, 0.78 mmol) was dissolved in AcOH (5 mL) and heated in a sealed tube at 100° C. After 48 hr, LC/MS indicated full conversion to desired intermediate 4,6-dichloro-2,3-dimethyl-2,3-dihydro-1H-imidazo[4,5-c]pyridin-2-ol 2.46. Reaction mixture was evaporated under reduced pressure and re-dissolved with MeOH (3 mL), 4-methylbenzenesulfonic acid (220 mg, 1.2 mmol) was added and mixture heated at 120° C. in a microwave reactor. After 20 min, LC/MS indicated full conversion to desired product. Solvent was removed under reduced pressure, and solids were diluted and extracted with ethyl acetate and water. The organic layer was washed with water and brine. Organic phase was then dried over $MgSO_4$, and evaporated under reduced pressure to obtain 4,6-dichloro-2,3-dimethyl-3H-imidazo[4,5-c]pyridine 2.47 that was used for next step without further purification.

LCMS-ESI⁺ (m/z): [M+H]⁺ calcd for $C_8H_7C_{12}N_3$: 216.0; found: 216.0.

Example 2.48

Preparation of (R)-4-((R)-1-(6-chloro-2,3-dimethyl-3H-imidazo[4,5-c]pyridin-4-yloxy)ethyl)-1-((R)-1-(4-methoxyphenyl)ethyl)pyrrolidin-2-one

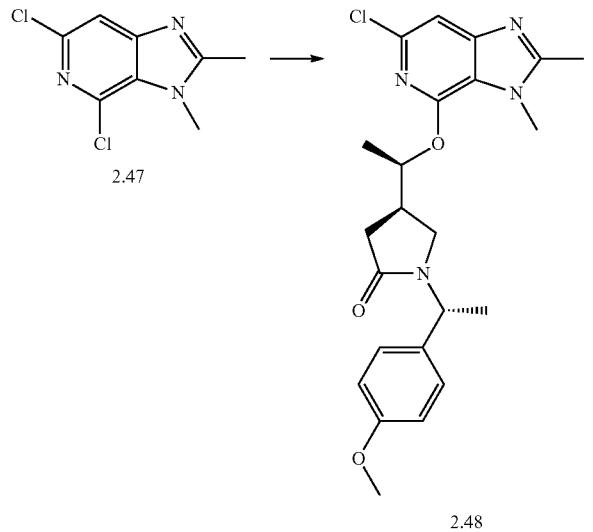 [SMILES: Cc1nc2cc(Cl)nc(Cl)c2n1C ; COc1ccc([C@@H](C)N2C[C@H]([C@@H](C)Oc3nc(Cl)cc4nc(C)n(C)c34)CC2=O)cc1]

A solution of tBuOK in THF (1.0 M, 0.92 mL, 0.92 mmol) was added to a solution of (R)-4-((R)-1-hydroxyethyl)-1-((R)-1-(4-methoxyphenyl)ethyl)pyrrolidin-2-one 1.04 (128 mg, 0.486 mmol) in THF (3 mL) at room temperature. After eighteen minutes, a suspension of 4,6-dichloro-2,3-dimethyl-3H-imidazo[4,5-c]pyridine 2.47 (0.1 g, 0.463 mmol) in THF (3 mL) was added and mixture stirred at 60° C. for fifteen minutes. LC/MS indicated full conversion to desired product. Reaction mixture was quenched with water, and extracted with ethyl acetate. Organic phase was dried over MgSO$_4$ and evaporated under reduced pressure to obtain (R)-4-((R)-1-(6-chloro-2,3-dimethyl-3H-imidazo[4,5-c]pyridin-4-yloxy)ethyl)-1-((R)-1-(4-methoxyphenyl)ethyl)pyrrolidin-2-one 2.48 that was used without further purification.

LCMS-ESI$^+$ (m/z): [M+H]$^+$ calcd for C$_{23}$H$_{27}$C$_1$N$_4$O$_3$: 443.18; found: 443.2.

Example 2.50

Preparation of 2-(benzyloxy)-4-bromo-N-methyl-6-nitroaniline

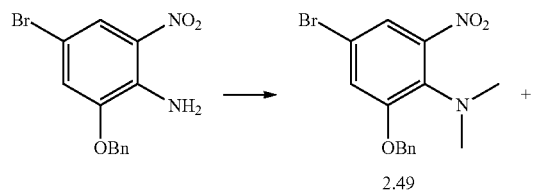

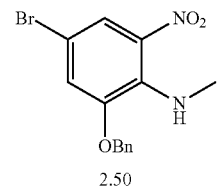

To a suspension of 2.7 g of 2-(benzyloxy)-4-bromo-6-nitroaniline in toluene (20 mL) at room temperature, 16 mL 50% sodium hydroxide solution, 0.30 g tetrabutylammonium hydrogen sulfate and 0.91 mL dimethyl sulfate were added and stirred at the rt. After 2 h, water was added to the reaction mixture. The organic layer was separated from aq layer was then extracted with EtOAc (3×). Combined organic layer were then washed successively with water and brine and dried over anhydrous magnesium sulfate. The residue was purified by flash column chromatography (SiO$_2$, 2% EtOAc/Hexanes to 30% EtOAc/hexanes) to give 2-(benzyloxy)-4-bromo-N,N-dimethyl-6-nitroaniline 2.49 (first to elute on the column) and 2-(benzyloxy)-4-bromo-N-methyl-6-nitroaniline 2.50.

LC/MS found for C$_{14}$H$_{13}$BrN$_2$O$_3$ as (M+H)$^+$ 339.1.

Example 2.51

Preparation of 7-(benzyloxy)-5-bromo-1-methyl-1H-benzo[d]imidazole

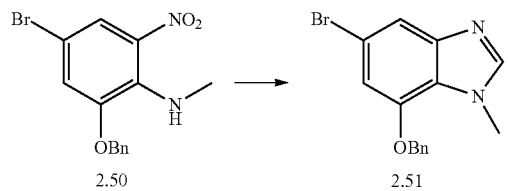 [SMILES: CNc1c(OCc2ccccc2)cc(Br)cc1[N+](=O)[O-] ; Cn1cnc2cc(Br)cc(OCc3ccccc3)c21]

To a solution of 2-(benzyloxy)-4-bromo-N-methyl-6-nitroaniline 2.50 (770 mg, 2.25 mmol) in ethanol (12 mL) and formic acid (15 mL) was added iron (630 mg, 11.27 mmol) and heated at 90° C. at 4 h and LCMS shows still lot of starting material present. 500 mg of iron was added and the mixture was heated at 90° C. overnight. The reaction mixture was concentrated, diluted with water and acidified to pH~7 with sat'd NaHCO$_3$ and then the aqueous layer was extracted with EtOAc (3×). Combined organic layer were then washed successively with water and brine and dried over anhydrous magnesium sulfate. The residue was purified by flash column chromatography (SiO$_2$, 100% EtOAc) to give 7-(benzyloxy)-5-bromo-1-methyl-1H-benzo[d]imidazole 2.51.

LC/MS found for C$_{15}$H$_{13}$BrN$_2$O as (M+H)$^+$ 319.1.

Example 2.52

Preparation of 7-(benzyloxy)-5-(3,4-dimethoxyphenyl)-1-methyl-1H-benzo[d]imidazole

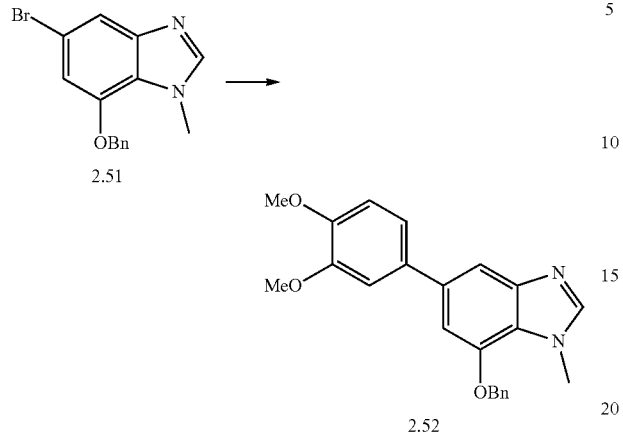

To a mixture 7-(benzyloxy)-5-bromo-1-methyl-1H-benzo[d]imidazole 2.51 (105 mg, 0.33 mmol), 3,4-dimethoxy phenyl boronic acid (72 mg, 0.39 mmol), $Cs_2CO_3$ (294 mg, 0.90 mmol) and PEPPSI"-IPr catalyst (10.2 mg, 0.015 mmol) was added DME and water (1:1, 3 mL) and the reaction was heated to 110° C. for 1 hr. The reaction mixture was concentrated and purified by flash chromatography ($SiO_2$, 0% MeOH/EtOAc to 20% MeOHEtOAc/MeOH) to afford 7-(benzyloxy)-5-(3,4-dimethoxyphenyl)-1-methyl-1H-benzo[d]imidazole 2.52.

LC/MS found for $C_{23}H_{22}N_2O_3$ as $(M+H)^+$ 375.1.

Example 2.53

Preparation of 5-(3,4-dimethoxyphenyl)-1-methyl-1H-benzo[d]imidazol-7-ol

To a solution of 7-(benzyloxy)-5-(3,4-dimethoxyphenyl)-1-methyl-1H-benzo[d]imidazole 2.52 (106 mg) in ethanol (4 mL) was added Pd/C (10% wet). The mixture was stirred at 1 atm $H_2$ overnight. LCMS showed some starting material was still remaining, another 50 mg of Pd/C (10% wet) was added and after 1 h under $H_2$ (balloon), the reaction mixture was diluted with ethanol and filtered through celite and washed with ethanol. The filtrate was then concentrated and purified by flash chromatography ($SiO_2$, 1% MeOH/EtOAc to 30% MeOH/EtOAc) to afford 5-(3,4-dimethoxyphenyl)-1-methyl-1H-benzo[d]imidazol-7-ol 2.53.

LC/MS found for $C_{16}H_{16}N_2O_3$ as $(M+H)^+$ 285.2.

Example 2.55

Preparation of (R)-4-((R)-1-(5-(3,4-dimethoxyphenyl)-1-methyl-1H-benzo[d]imidazol-7-yloxy)ethyl)-1-((R)-1-phenylethyl)pyrrolidin-2-one

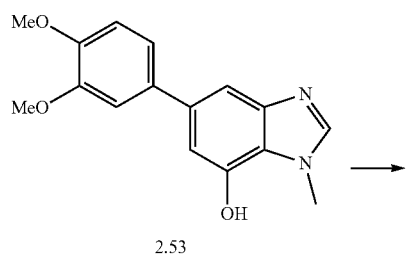

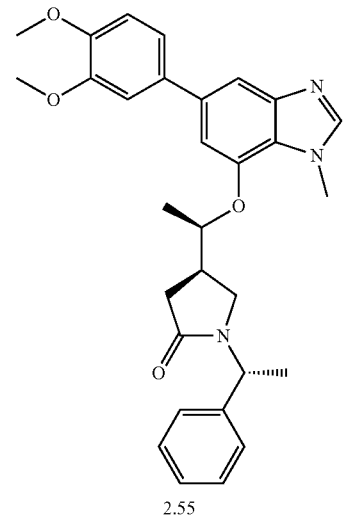

To a solution of 5-(3,4-dimethoxyphenyl)-1-methyl-1H-benzo[d]imidazol-7-ol 2.53 (42 mg, 0.148 mmol) in DMF (3 mL) was added (S)-1-((R)-5-oxo-1-((R)-1-phenylethyl)pyrrolidin-3-yl)ethyl methanesulfonate 1.17 (55 mg, 0.177 mmol) and $Cs_2CO_3$ (72 mg, 0.22 mmol) and the reaction mixture was heated at 90° C. for 2 h. The reaction mixture was concentrated and purified by flash chromatography ($SiO_2$, 2% MeOH/EtOAc 25% MeOH/EtOAc) to give (R)-4-((R)-1-(5-(3,4-dimethoxyphenyl)-1-methyl-1H-benzo[d]imidazol-7-yloxy)ethyl)-1-((R)-1-phenylethyl)pyrrolidin-2-one 2.55.

LC/MS found for $C_{30}H_{33}N_3O_4$ as $(M+H)^+$ 500.3.

Example 2.56

Preparation of 5-bromo-1-methyl-1H-benzo[d]imidazol-7-ol

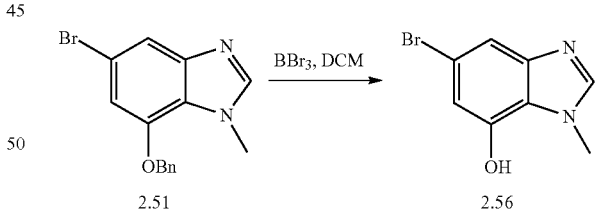

To a solution of 7-(benzyloxy)-5-bromo-1-methyl-1H-benzo[d]imidazole 2.51 (157 mg, 0.495 mmol) in DCM (3 mL) at 0° C. was added a solution of 1.0M $BBr_3$ in THF (1.1 equiv). After 1 h at 0° C., the reaction mixture was diluted with DCM and washed with sat'd $NaHCO_3$ and then the aqueous layer was then extracted with EtOAc (3×). Combined organic layers were washed successively with water and brine and dried over anhydrous magnesium sulfate. The residue was purified by flash column chromatography ($SiO_2$, 0% MeOH/EtOAc→10% MeOH/EtOAc) to give of 5-bromo-1-methyl-1H-benzo[d]imidazol-7-ol 2.56.

LC/MS found for $C_8H_7BrN_2O$ as $(M+H)^+$ 229.0.

Example 2.57

Preparation of (R)-4-((R)-1-(5-bromo-1-methyl-1H-benzo[d]imidazol-7-yloxy)ethyl)-1-((R)-1-phenylethyl)pyrrolidin-2-one

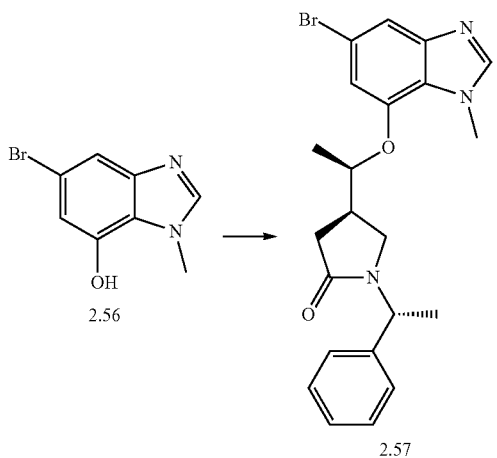 [SMILES: Cn1cnc2cc(Br)cc(O)c21 ; C[C@H](c1ccccc1)N1C[C@H]([C@@H](C)Oc2cc(Br)cc3ncn(C)c23)CC1=O]

To a solution of 5-bromo-1-methyl-1H-benzo[d]imidazol-7-ol 2.56 (15 mg, 0.066 mmol) in DMF (2 mL) was added (S)-1-((R)-5-oxo-1-((R)-1-phenylethyl)pyrrolidin-3-yl) ethyl methanesulfonate 1.17 (41 mg, 0.312 mmol) and $Cs_2CO_3$ (33 mg, 0.1 mmol) and the reaction mixture was heated at 90° C. for 1 h. The reaction mixture was then diluted with ethyl acetate, washed with water (3×), brine and dried over anhydrous magnesium sulfate. Filtration, followed by concentration gave (R)-4-((R)-1-(5-bromo-1-methyl-1H-benzo[d]imidazol-7-yloxy)ethyl)-1-((R)-1-phenylethyl)pyrrolidin-2-one 2.57, which was used for next step without further purification.

LC/MS found for $C_{22}H_{24}BrN_3O_2$ as $(M+H)^+$ 442.1.

Example 2.58

Preparation of (R)-4-((R)-1-(5-bromo-1-methyl-1H-benzo[d]imidazol-7-yloxy)ethyl)pyrrolidin-2-one

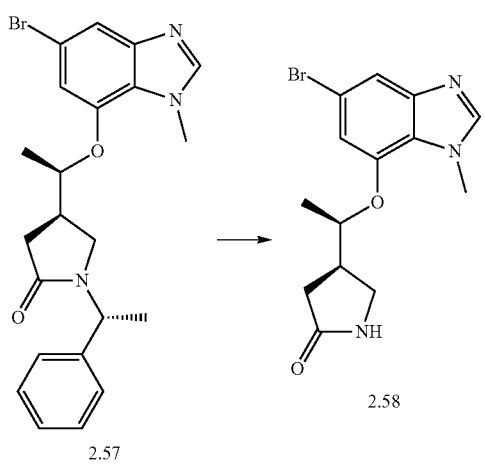 [SMILES: C[C@H](c1ccccc1)N1C[C@H]([C@@H](C)Oc2cc(Br)cc3ncn(C)c23)CC1=O ; C[C@@H](Oc1cc(Br)cc2ncn(C)c12)[C@H]1CNC(=O)C1]

(R)-4-((R)-1-(5-bromo-1-methyl-1H-benzo[d]imidazol-7-yloxy)ethyl)-1-((R)-1-phenylethyl)pyrrolidin-2-one 2.57 in TFA (2 mL) was heated in the microwave for 30 min at 140° C. The reaction mixture was then concentrated to give (R)-4-((R)-1-(5-bromo-1-methyl-1H-benzo[d]imidazol-7-yloxy) ethyl)pyrrolidin-2-one 2.58, which was used without further purification.

LC/MS found for $C_{14}H_{16}BrN_3O_2$ as $(M+H)^+$ 340.1.

Example 2.59

Preparation of 6-bromo-2-chloro-N-methyl-4-nitropyridin-3-amine

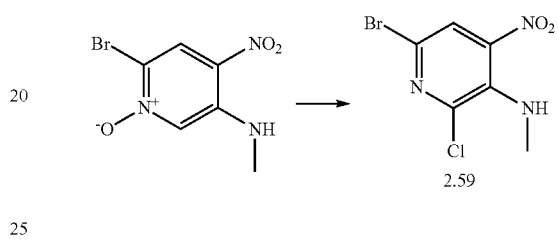

A suspension of 2-bromo-5-(methylamino)-4-nitropyridine 1-oxide (3.35 g, 13.51 mmol) in phosphorous oxychloride (35 mL, 374 mmol) was heated at 110° C. After 1 h, the reaction mixture was cooled to r.t. and evaporated to dryness in vacuo. The residue was partitioned between EtOAc (100 mL) and saturated sodium hydrogen carbonate, the layers were separated and the organic layer was washed with brine and dried over $MgSO_4$. The residue was purified by flash column chromatography ($SiO_2$, 0% EtOAc/Hexanes to 30% EtOAc/hexanes) to give 6-bromo-2-chloro-N-methyl-4-nitropyridin-3-amine 2.59.

LC/MS found for $C_6H_5BrClN_3O_2$ as $(M+H)^+$ 267.4.

Example 2.60

Preparation of 6-bromo-4-chloro-3-methyl-3H-imidazo[4,5-c]pyridine

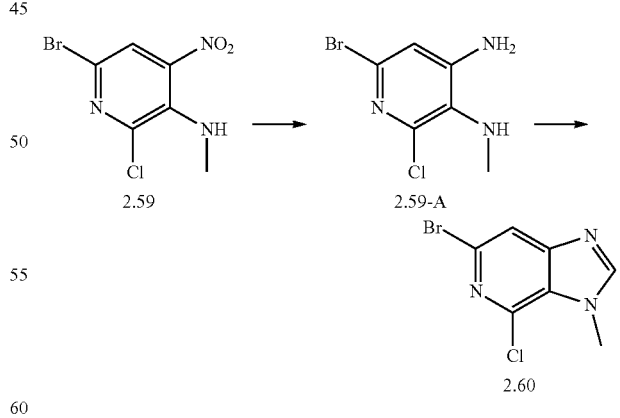

To a solution of 6-bromo-2-chloro-N-methyl-4-nitropyridin-3-amine 2.59 (1 g, 3.75 mmol) in ethanol (10 ml) was added Fe powder (1.05 g, 18.7 mmol) and a solution of ammonium chloride (1 g, 18.8 mmol) in water (3 mL). The mixture was heated in microwave at 140° C. for 30 min. The mixture was then diluted with EtOAc, filtered and evaporated to give 6-bromo-2-chloro-N3-methylpyridine-3,4-diamine 2.59-A, which was used in the next step without purification.

LC/MS found for $C_6H_7BrClN_3$ as $(M+H)^+$ 237.1.

The above crude diamine 2.59-A was dissolved in a mixture of triethylorthoformate:Acetic anhydride (1:1, 9 mL). The reaction mixture was heated to 155° C. for 1 h, cooled to rt and then evaporated. The residue was dissolved in 2.5M NaOH (20 mL) and heated at 50° C. 45 min. The resulting solution was cooled to rt, neutralized with AcOH, and cooled to 0° C. The precipitate was filtered to give 6-bromo-4-chloro-3-methyl-3H-imidazo[4,5-c]pyridine 2.60.

LC/MS found for $C_7H_5BrClN_3$ as $(M+H)^+$ 247.2.

Example 2.61

Preparation of (R)-4-((R)-1-(6-bromo-3-methyl-3H-imidazo[4,5-c]pyridin-4-yloxy)ethyl)-1-((R)-1-(4-methoxyphenyl)ethyl)pyrrolidin-2-one

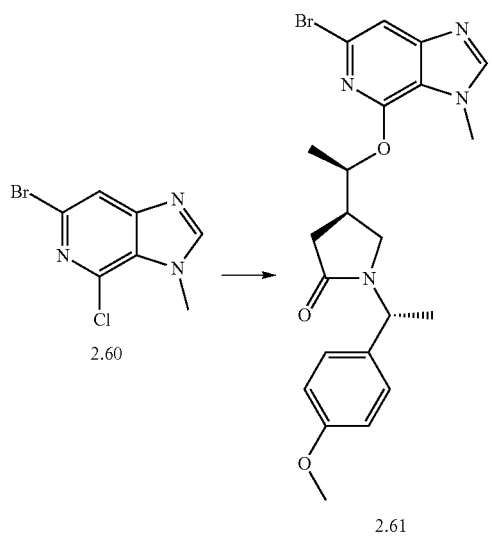 [SMILES: Cn1cnc2cc(Br)nc(Cl)c21 ; COc1ccc([C@@H](C)N2C[C@H]([C@@H](C)Oc3nc(Br)cc4ncn(C)c34)CC2=O)cc1]

2.61

To a solution of (R)-4-((R)-1-hydroxyethyl)-1-((R)-1-(4-methoxyphenyl)ethyl)pyrrolidin-2-one 1.04 (135 mg, 0.51 mmol) in dry THF (6 mL) was added potassium tert-butoxide (72 mg, 0.64 mmol) and the reaction mixture was stirred at rt for 5 min. Then 6-bromo-4-chloro-3-methyl-3H-imidazo[4,5-c]pyridine 2.60 (105 mg, 0.43 mmol) was added and reaction mixture was heated to 60° C. After 12 h, cooled to rt, quenched the reaction mixture with water (0.5 mL) and concentrated. The residue was purified by flash column chromatography (SiO$_2$, 0% MeOH/EtOAc to 20% EtOAc/hexanes) to give ((R)-4-((R)-1-(6-bromo-3-methyl-3H-imidazo[4,5-c]pyridin-4-yloxy)ethyl)-1-((R)-1-(4-methoxyphenyl)ethyl)pyrrolidin-2-one 2.61.

LC/MS found for $C_{22}H_{25}BrN_4O_3$ as $(M+H)^+$ 474.1.

Example 2.62

Preparation of (R)-4-((R)-1-(6-bromo-3-methyl-3H-imidazo[4,5-c]pyridin-4-yloxy)ethyl)pyrrolidin-2-one

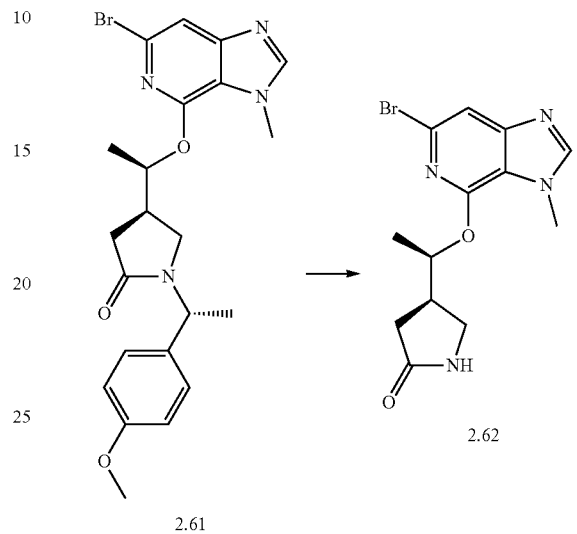

A solution of (R)-4-((R)-1-(6-bromo-3-methyl-3H-imidazo[4,5-c]pyridin-4-yloxy)ethyl)-1-((R)-1-(4-methoxyphenyl)ethyl)pyrrolidin-2-one 2.61 (256 mg, 0.54 mmol) in TFA (8 mL) was heated at 55° C. for 16 h, cooled to rt and then evaporated to give (R)-4-((R)-1-hydroxyethyl)-1-((R)-1-(4-methoxyphenyl)ethyl)pyrrolidin-2-one 2.62 as TFA salt, which was used without purification.

LC/MS found for $C_{13}H_{15}BrO_2N_4$ as $(M+H)^+$ 340.1.

Example 2.64

Preparation of (R)-4-((R)-1-(6-chloro-3-(difluoromethyl)-3H-imidazo[4,5-c]pyridin-4-yloxy)ethyl)pyrrolidin-2-one

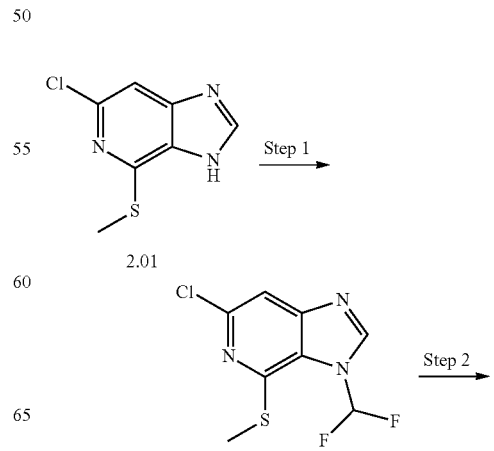

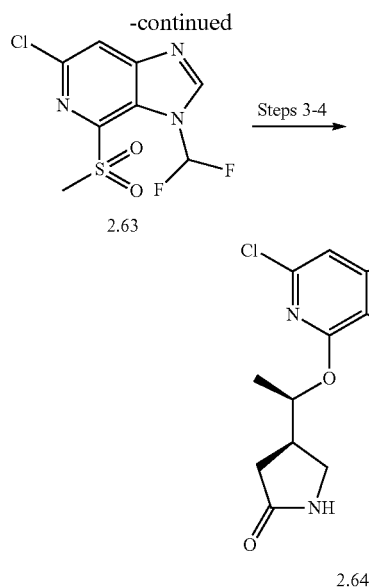

2.63

Steps 3-4

2.64

Step 1: A mixture of 6-chloro-4-(methylthio)-3H-imidazo[4,5-c]pyridine 2.01 (1.19 g, 5.96 mmol) and $K_2CO_3$ (3.3 g, 24 mmol) in DMF (20 mL) was heated to 90° C. Chlorodifluoromethane was bubbled through the stirred mixture at a rate of 5-10 bubbles/sec. After 15 min, the mixture was cooled to r.t., filtered, and concentrated in vacuo. The resulting residue was diluted with EtOAc (50 mL) and half-saturated brine (50 mL). The phases were separated, and the organic phase was dried over $Na_2SO_4$, filtered, and concentrated. The resulting residue was purified by silica gel chromatography (0-2.5% THF in DCM to afford 6-chloro-3-(difluoromethyl)-4-(methylthio)-3H-imidazo[4,5-c]pyridine as the early eluting isomer. LCMS-ESI$^+$ (m/z): [M+H]$^+$ calcd for $C_8H_7ClF_2N_3S$: 250.0; found: 250.1.

Step 2: To a solution of 6-chloro-3-(difluoromethyl)-4-(methylthio)-3H-imidazo[4,5-c]pyridine (431 mg, 1.73 mmol) in DCM (12 mL) was added m-CPBA (max. 77%, 1.1 g, 4.9 mmol). After stifling 4 h, saturated aqueous sodium thiosulfate (30 mL) was added and the biphasic mixture was stirred 15 min. The mixture was diluted with EtOAc (30 mL) and water (30 mL). The phases were separated, and the organic layer was washed with saturated $NaHCO_3$ (2×50 mL), dried over $Na_2SO_4$, filtered, and concentrated to afford 6-chloro-3-(difluoromethyl)-4-(methylsulfonyl)-3H-imidazo[4,5-c]pyridine 2.63 that was used without further purification. LCMS-ESI$^+$ (m/z): [M+H]$^+$ calcd for $C_8H_7ClF_2N_3O_2S$: 282.0; found: 282.0.

Step 3: Under Ar, NaHMDS (1.0 M in THF, 0.96 mL, 0.96 mmol) was added over 30 s to a solution of (R)-4-((R)-1-hydroxyethyl)-1-((R)-1-(4-methoxyphenyl)ethyl)pyrrolidin-2-one 1.04 (255 mg, 0.968 mmol) in DMF (3 mL). After stirring 10 min, the resulting mixture was added over ca. 45 s to a cooled (−20° C.) solution of 6-chloro-3-(difluoromethyl)-4-(methylsulfonyl)-3H-imidazo[4,5-c]pyridine (215 mg, 0.763 mmol) in DMF (3 mL). After stifling 15 min, the reaction was quenched with saturated $NH_4Cl$ (3 mL) and was diluted with EtOAc (20 mL) and water (20 mL). The phases were separated, and the organic layer was washed with water (30 mL) and brine (30 mL). The organic phase was dried over $Na_2SO_4$, filtered, and concentrated. The crude residue was purified by silica gel chromatography (20-45% acetone in hexanes) to provide (R)-4-((R)-1-(6-chloro-3-(difluoromethyl)-3H-imidazo[4,5-c]pyridin-4-yloxy)ethyl)-1-((R)-1-(4-methoxyphenyl)ethyl)pyrrolidin-2-one. LCMS-ESI$^+$ (m/z): [M+H]$^+$ calcd for $C_{22}H_{24}ClF_2N_4O_3$: 465.2; found: 464.9.

Step 4: (R)-4-((R)-1-(6-chloro-3-(difluoromethyl)-3H-imidazo[4,5-c]pyridin-4-yloxy)ethyl)-1-4R)-1-(4-methoxyphenyl)ethyl)pyrrolidin-2-one (460 mg, 0.99 mmol) was dissolved in TFA (15 mL) and the resulting solution was heated to 70° C. After 5.5 h, the temperature was reduced to 60° C. After an additional 15 h, the reaction mixture was concentrated in vacuo and was dissolved in EtOAc (75 mL). The resulting solution was washed with a 1:1 mixture of saturated $NaHCO_3$:brine (80 mL), and the aqueous phase was extracted with EtOAc (50 mL). The combined organic phase was dried over $Na_2SO_4$, filtered, and concentrated. Purification by silica gel chromatography (0-15% MeOH in DCM) provided (R)-4-((R)-1-(6-chloro-3-(difluoromethyl)-3H-imidazo[4,5-c]pyridin-4-yloxy)ethyl)pyrrolidin-2-one 2.64. LCMS-ESI$^+$ (m/z): [M+H]$^+$ calcd for $C_{13}H_{14}ClF_2N_4O_2$: 331.1; found: 331.1.

Example 2.65

Preparation of 6-(3,4-dimethoxyphenyl)-3-methyl-4-(methylsulfonyl)-3H-imidazo[4,5-c]pyridine

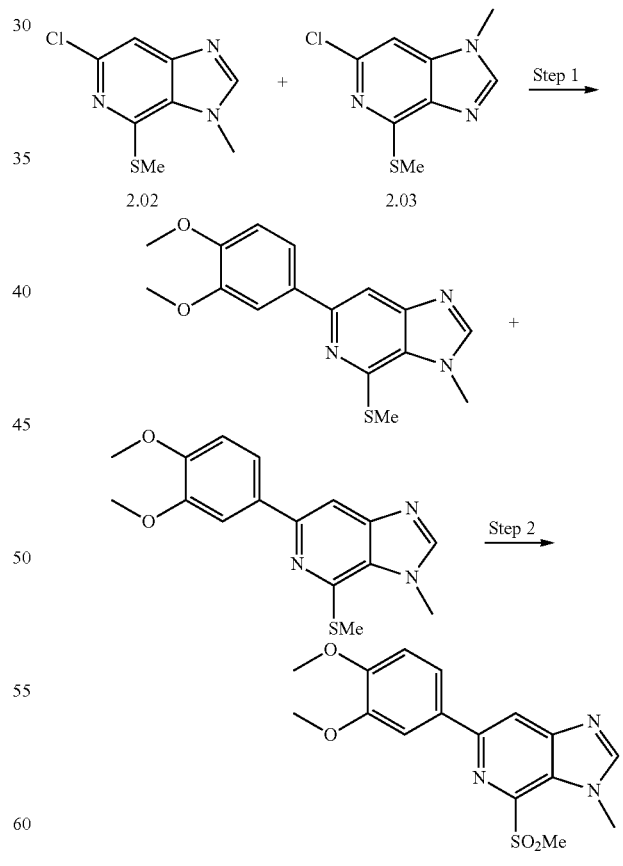

2.65

6-(3,4-dimethoxyphenyl)-3-methyl-4-(methylsulfonyl)-3H-imidazo[4,5-c]pyridine 2.65 was prepared in analogous fashion to example 2.41 using 3,4-dimethoxyphenylboronic.

LCMS-ESI+ (m/z): [M+H]+ calcd for $C_{16}H_{17}N_3O_4S$: 348.1; found 348.1.

Example 2.66

Preparation of (R)-4-((R)-1-(6-(3,4-dimethoxyphenyl)-2-methyl-3H-imidazo[4,5-c]pyridin-4-yloxy)ethyl)pyrrolidin-2-one

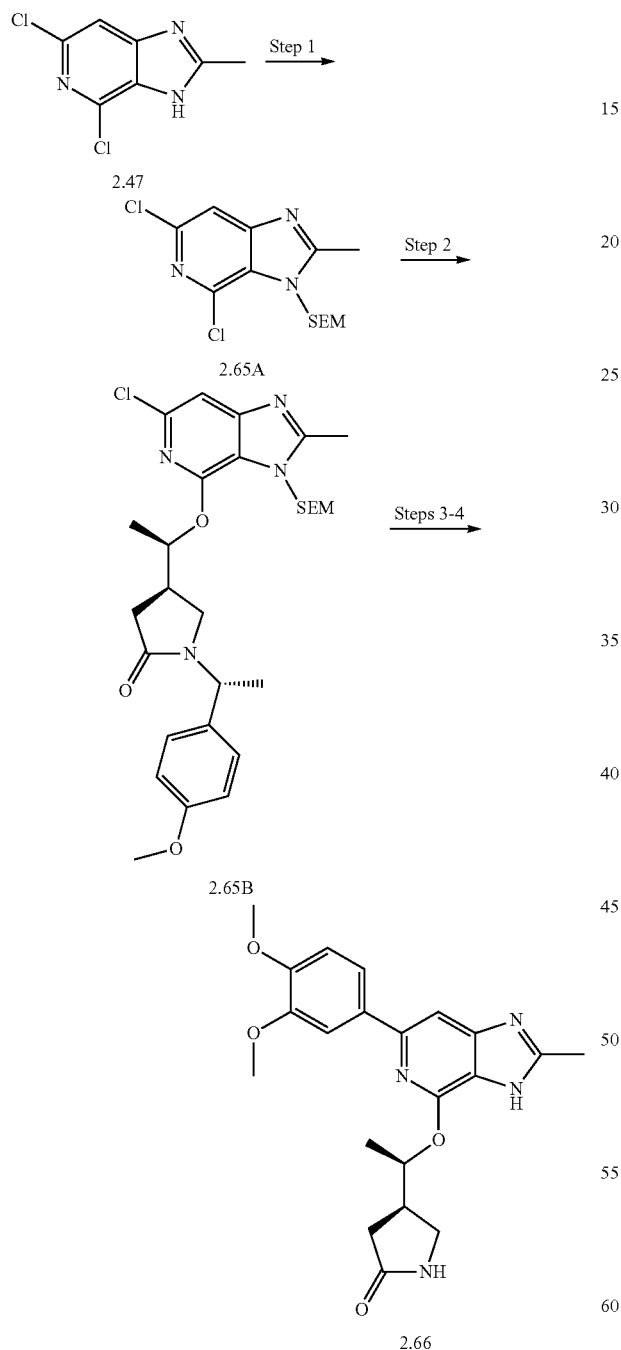

Step 1: (2-(chloromethoxy)ethyl)trimethylsilane (1.2 eq) was added to a solution of 4,6-dichloro-2-methyl-3H-imidazo[4,5-c]pyridine 2.47 (1 eq) and potassium carbonate (3.0 eq) in DMF at room temperature. After 1 h, reaction mixture was taken up in ethyl acetate and washed with saturated $NaHCO_3{}_{(aq)}$ and brine. The combined organic layers were dried ($MgSO_4$), filtered, and concentrated under reduced pressure to yield a mixture of crude 2.65A. [M+H]+ calcd $C_{13}H_{19}Cl_2N_3OSi$: 332.07; found 332.0.

Step 2: A solution of tBuOK in THF (1.0 M, 1.5 eq) was added to a solution of (R)-4-((R)-1-hydroxyethyl)-1-((R)-1-(4-methoxyphenyl)ethyl)pyrrolidin-2-one 1.04 (1 eq) in THF at room temperature. After eighteen minutes, a suspension of 4,6-dichloro-2-methyl-3-((2-(trimethylsilyl)ethoxy)methyl)-3H-imidazo[4,5-c]pyridine 2.65A (0.1 g, 0.9 eq) in THF was added and mixture stirred at 60° C. for 6 hours. LC/MS indicated full conversion to desired product. Reaction mixture was quenched with water and extracted with ethyl acetate. Organic phase was dried over $MgSO_4$, evaporated under reduced pressure. Residues were purified by normal phase chromatography (EtOAc/Hexanes 1:1) to yield 2.65B. [M+H]+ calcd $C_{28}H_{39}ClN_4O_4Si$: 559.24; found 559.2.

Step 3: To a (R)-4-((R)-1-(6-chloro-2-methyl-3-((2-(trimethylsilyl)ethoxy)methyl)-3H-imidazo[4,5-c]pyridin-4-yloxy)ethyl)-1-((R)-1-(4-methoxyphenyl)ethyl)pyrrolidin-2-one 2.65B (1 eq), 3,4-dimethoxy phenyl boronic acid (1.3 eq), $Cs_2CO_3$ (3.0 eq) and PEPPSI"-IPr catalyst (0.1 eq) was added 1-4 Dioxane and water (2:1) and the reaction was heated to 100° C. for 1 hr. The reaction mixture was concentrated and purified by normal phase chromatography (Hexanes:Acetone 1:1) to afford (R)-4-((R)-1-(6-(3,4-dimethoxyphenyl)-2-methyl-3-((2-(trimethylsilyl)ethoxy)methyl)-3H-imidazo[4,5-c]pyridin-4-yloxy)ethyl)-1-((R)-1-(4-methoxyphenyl)ethyl)pyrrolidin-2-one.[M+H]+ calcd $C_{36}H_{48}N_4O_6Si$: 661.33; found 661.3

Step 4: (R)-4-((R)-1-(6-(3,4-dimethoxyphenyl)-2-methyl-3-((2-(trimethylsilyl)ethoxy)methyl)-3H-imidazo[4,5-c]pyridin-4-yloxy)ethyl)-1-((R)-1-(4-methoxyphenyl)ethyl)pyrrolidin-2-one was dissolved in TFA. Reaction was heated to 60° C. After 6 h, reaction was cooled to r.t. and was concentrated in vacuo. The resulting residue was diluted with EtOAc, brine, and saturated $NaHCO_3$. The phases were separated, and the aqueous phase was extracted with EtOAc. The organic layer was dried over $MgSO_4$, filtered, and concentrated to afford (R)-4-((R)-1-(6-(3,4-dimethoxyphenyl)-2-methyl-3H-imidazo[4,5-c]pyridin-4-yloxy)ethyl)pyrrolidin-2-one 2.66 that was used without further purification. [M+H]+ calcd $C_{21}H_{24}N_4O_4$: 397.18; found 397.1.

Example 2.67

Preparation of 2-bromo-5-(cyclopropylamino)-4-nitropyridine 1-oxide

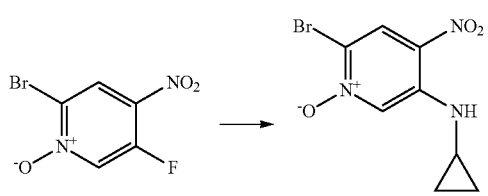

To a solution of 2-bromo-5-fluoro-4-nitropyridine 1-oxide (3000 mg, 12.66 mmol) in THF (10 mL) was added cyclopropylamine (868 mg, 15.1 mmol). Solution was stirred at room temperature for 1 h. Mixture was partitioned between EtOAc and saturated aqueous NaHCO₃. Organic layer was washed with brine and dried over MgSO₄ to provide 2-bromo-5-(cyclopropylamino)-4-nitropyridine 1-oxide 2.67. Residue was used for next step without further purification. LC/MS found for $C_8H_8BrN_3O_3$ as $(M+H)^+$ 275.9.

Example 2.68

Preparation of 6-bromo-2-chloro-N-cyclopropyl-4-nitropyridin-3-amine and 2,6-dichloro-N-cyclopropyl-4-nitropyridin-3-amine

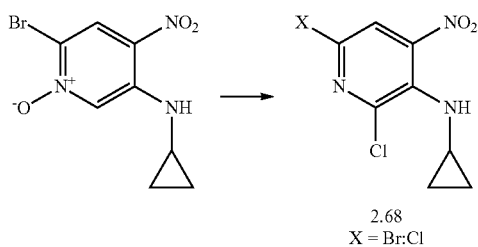

2.68
X = Br:Cl

A suspension of 2-bromo-5-(cyclopropylamino)-4-nitropyridine 1-oxide (2.0 g, 7.3 mmol) in phosphorous oxychloride (20 mL, 219 mmol) was heated at 60° C. After 10 min, the reaction mixture was cooled to room temperature and was quenched by addition to 300 mL of water at room temperature with vigorous stifling. Mixture was partitioned between EtOAc and an aqueous saturated solution of sodium hydrogen carbonate. Organic layer was washed with brine and dried over MgSO₄. Residue was purified by flash column chromatography (Hexanes/EtOAc 5:1) to give a ~2:1 mixture of 6-bromo-2-chloro-N-cyclopropyl-4-nitropyridin-3-amine and 2,6-dichloro-N-cyclopropyl-4-nitropyridin-3-amine (Mixture=2.68). LC/MS found for $C_8H_7BrClN_3O_2$ as $(M+H)^+$ 291.9 and $C_8H_7Cl_2N_3O_2$ as $(M+H)^+$ 250.0.

Example 2.69

Preparation of 6-bromo-4-chloro-3-cyclopropyl-3H-imidazo[4,5-c]pyridine and 4,6-dichloro-3-cyclopropyl-3H-imidazo[4,5-c]pyridine and 4,6-dichloro-3-cyclopropyl-3H-imidazo[4,5-c]pyridine

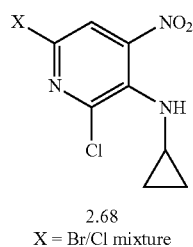

2.68
X = Br/Cl mixture

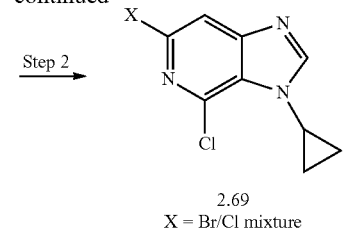

X = Br/Cl 2.69
X = Br/Cl mixture

Step 1: To a mixture of 6-bromo-2-chloro-N-cyclopropyl-4-nitropyridin-3-amine and 2,6-dichloro-N-cyclopropyl-4-nitropyridin-3-amine (mixture=2.68) (1.14 g, 3.93 mmol) in ethanol (10 mL) was added Fe powder (1.08 g, 19.5 mmol) and an aqueous solution of ammonium chloride (1.04 g, 19.49 mmol) (3 mL). The mixture was heated at 60° C. for 3 h. Mixture was diluted with EtOAc, filtered and evaporated to give a mixture of 6-bromo-2-chloro-N3-cyclopropylpyridine-3,4-diamine and 2,6-dichloro-N3-cyclopropylpyridine-3,4-diamine that was used in the next step without purification. LC/MS found for $C_8H_9BrClN_3$ as $(M+H)^+$ 261.9 and $C_8H_9Cl_2N_3$ as $(M+H)^+$ 220.0.

Step 2: Crude material from above was dissolved in triethyl orthoformate (10 mL) and heated at 140° C. for 5 h. Mixture was cooled to room temperature and was evaporated under reduced pressure. Mixture was partitioned between EtOAc and water; organic layer was washed with brine and dried over MgSO₄. Residue was purified by flash column chromatography (EtOAc/Acetone 2:1) to give a ~2:1 mixture of 6-bromo-4-chloro-3-cyclopropyl-3H-imidazo[4,5-c]pyridine and 4,6-dichloro-3-cyclopropyl-3H-imidazo[4,5-c]pyridine (Mixture=2.69). LC/MS found $C_9H_7BrClN_3$ as $(M+H)^+$ 271.9 and $C_9H_7Cl_2N_3$ as $(M+H)^+$ 230.0.

Example 2.70

Preparation of (R)-4-((R)-1-((6-bromo-3-cyclopropyl-3H-imidazo[4,5-c]pyridin-4-yl)oxy)ethyl)-1-4R)-1-(4-methoxyphenyl)ethyl)pyrrolidin-2-one and (R)-4-((R)-1-((6-chloro-3-cyclopropyl-3H-imidazo[4,5-c]pyridin-4-yl)oxy)ethyl)-1-((R)-1-(4-methoxyphenyl)ethyl)pyrrolidin-2-one

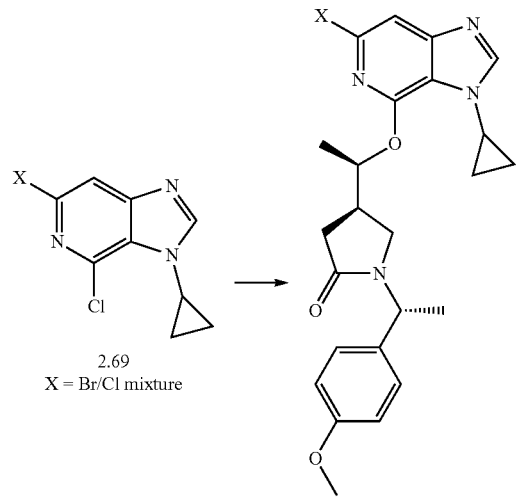

2.70
X = Br/Cl mixture

Following the procedure to synthesize example 2.65B, beginning with a mixture of 6-bromo-4-chloro-3-cyclopropyl-3H-imidazo[4,5-c]pyridine and 4,6-dichloro-3-cyclopropyl-3H-imidazo[4,5-c]pyridine 2.69 (0.85 mg, 3.1 mmol) along with (R)-4-((R)-1-hydroxyethyl)-1-((R)-1-(4-methoxyphenyl)ethyl)pyrrolidin-2-one 1.04 (987 mg, 3.75 mmol) a mixture of (R)-4-((R)-1-((6-bromo-3-cyclopropyl-3H-imidazo[4,5-c]pyridin-4-yl)oxy)ethyl)-1-((R)-1-(4-methoxyphenyl)ethyl)pyrrolidin-2-one and (R)-4-((R)-1-((6-chloro-3-cyclopropyl-3H-imidazo[4,5-c]pyridin-4-yl)oxy)ethyl)-1-((R)-1-(4-methoxyphenyl)ethyl)pyrrolidin-2-one (mixture=2.70) was prepared. LC/MS found $C_{24}H_{27}BrN_4O_3$ as (M+H)$^+$ 499.1 and $C_{24}H_{27}ClN_4O$ as (M+H)$^+$ 455.1.

Example 2.71

Preparation of (R)-4-((R)-1-((6-bromo-3-cyclopropyl-3H-imidazo[4,5-c]pyridin-4-yl)oxy)ethyl)pyrrolidin-2-one and (R)-4-((R)-1-((6-chloro-3-cyclopropyl-3H-imidazo[4,5-c]pyridin-4-yl)oxy)ethyl)pyrrolidin-2-one

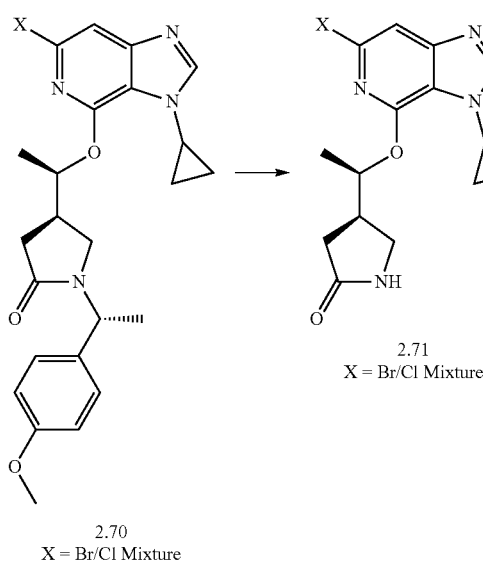

2.70
X = Br/Cl Mixture 2.71
X = Br/Cl Mixture

Mixture 2.70 of (R)-4-((R)-1-(6-bromo-3-cyclopropyl-3H-imidazo[4,5-c]pyridin-4-yloxy)ethyl)-1-((R)-1-(4-methoxyphenyl)ethyl)pyrrolidin-2-one and (R)-4-((R)-1-((6-chloro-3-cyclopropyl-3H-imidazo[4,5-c]pyridin-4-yl)oxy)ethyl)-1-((R)-1-(4-methoxyphenyl)ethyl)pyrrolidin-2-one (1.37 g, ~2.75 mmol) in trifluoroacetic acid (25 mL) was heated at 60° C. for 22 hours. After cooling to room temperature, reaction mixture was concentrated under reduced pressure and resulting oil was taken up in 125 mL of ethyl acetate and washed with 70 mL saturated NaHCO$_3$ $_{(aq)}$. Layers were separated and aqueous was extracted with ethyl acetate (5×90 mL), and combined organics were dried (Na$_2$SO$_4$), filtered, concentrated under reduced pressure. The resulting residue was purified via silica gel column chromatography (0-10% methanol in dichloromethane) to yield a mixture of (R)-4-((R)-1-((6-bromo-3-cyclopropyl-3H-imidazo[4,5-c]pyridin-4-yl)oxy)ethyl)pyrrolidin-2-one and (R)-4-((R)-1-((6-chloro-3-cyclopropyl-3H-imidazo[4,5-c]pyridin-4-yl)oxy)ethyl)pyrrolidin-2-one (mixture=2.71). LCMS-ESI$^+$ (m/z): [M+H]$^+$ calcd for $C_{15}H_{18}BrN_4O_2$: 365.05; found: 365.21. LCMS-ESI$^+$ (m/z): [M+H]$^+$ calcd for $C_{15}H_{18}ClN_4O_2$: 321.10; found: 321.19.

Example 2.72

Preparation of (R)-4-((R)-1-((6-bromo-3-(1-methylcyclopropyl)-3H-imidazo[4,5-c]pyridin-4-yl)oxy) ethyl)-1-((R)-1-(4-methoxyphenyl)ethyl)pyrrolidin-2-one and (R)-4-((R)-1-((6-chloro-3-(1-methylcyclopropyl)-3H-imidazo[4,5-c]pyridin-4-yl) oxy)ethyl)-1-4R)-1-(4-methoxyphenyl)ethyl) pyrrolidin-2-one

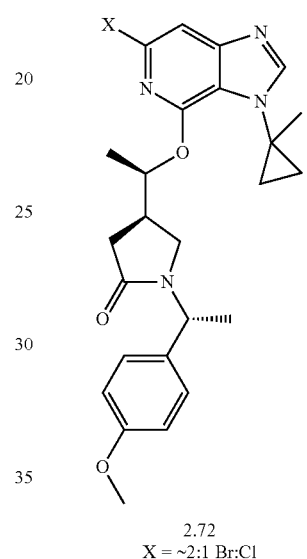

2.72
X = ~2:1 Br:Cl

Following the procedures described for intermediate mixtures 2.69 and 2.70 beginning with 2-bromo-5-fluoro-4-nitropyridine 1-oxide and 1-methylcyclopropanamine, a mixture of (R)-4-((R)-1-((6-bromo-3-(1-methylcyclopropyl)-3H-imidazo[4,5-c]pyridin-4-yl)oxy)ethyl)-1-((R)-1-(4-methoxyphenyl)ethyl)pyrrolidin-2-one and (R)-4-((R)-1-((6-chloro-3-(1-methylcyclopropyl)-3H-imidazo[4,5-c]pyridin-4-yl)oxy)ethyl)-1-((R)-1-(4-methoxyphenyl)ethyl)pyrrolidin-2-one (Mixture=2.72) was prepared. LCMS-ESI$^+$ (m/z): [M+H]$^+$ calcd for $C_{25}H_{29}BrN_4O_3$: 513.2; found: 513.1 and [M+H]$^+$ calcd for $C_{25}H_{30}ClN_4O_3$: 469.2; found: 469.1.

Example 2.73

Preparation of 5-bromo-1-cyclopropyl-1H-benzo[d]imidazol-7-ol

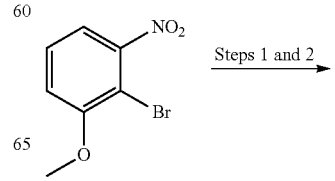

Steps 1 and 2

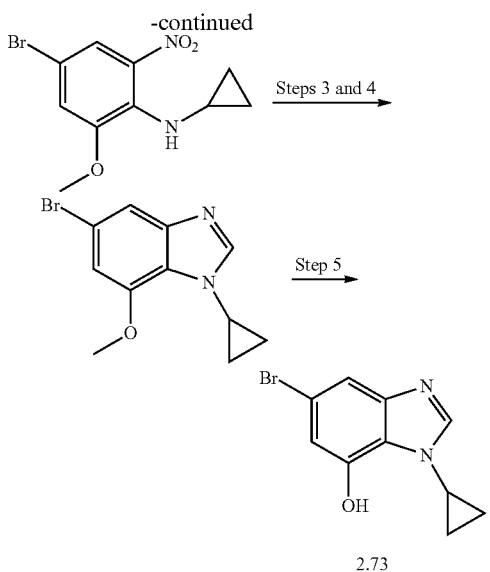

Step 1: 2-bromo-1-methoxy-3-nitrobenzene (10.6 g, 45.7 mmol) and cyclopropylamine (16 mL, 230 mmol) were dissolved in 1,4-dioxane (50 mL). The stirred mixture was heated mixture in sealed flask to 115 C. After 66 h, mixture was cooled to r.t. and was diluted with EtOAc (100 mL), water (100 mL) and brine (50 mL). The phases were separated and extracted with EtOAc (100 mL). The combined organic phase was dried over $Na_2SO_4$, filtered, and concentrated. The concentrate was purified by silica gel chromatography (0-20% EtOAc in hexanes) to afford N-cyclopropyl-2-methoxy-6-nitroaniline. LCMS-ESI$^+$ (m/z): [M+H]$^+$ calcd for $C_{10}H_{13}N_2O_3$: 209.09; found: 209.96.

Step 2: N-cyclopropyl-2-methoxy-6-nitroaniline (1.05 g, 5.04 mmol) was dissolved in MeOH (25 mL). Bromine (0.27 mL, 5.2 mmol) was added dropwise over 1 min, and the resulting mixture was stirred 1 h. Additional bromine (0.05 mL, 0.98 mmol) was then added and the resulting mixture was stirred for an additional 30 min. The mixture was then diluted with DCM (75 mL) and $H_2O$ (50 mL), and the aqueous phase was basified with saturated aqueous $NH_4OH$ (2 mL). The phases were separated, and the aqueous phase was extracted with DCM (30 mL). The combined organic phase was dried over $Na_2SO_4$, filtered, and concentrated. The resulting residue was purified by silica gel chromatography (0-25% EtOAc in hexanes) to afford 4-bromo-N-cyclopropyl-2-methoxy-6-nitroaniline. LCMS-ESI$^+$ (m/z): [M+H]$^+$ calcd for $C_{10}H_{12}BrN_2O_3$: 287.0; found: 286.9.

Step 3: 4-bromo-N-cyclopropyl-2-methoxy-6-nitroaniline (1.05 g, 3.66 mmol) and iron powder (1.43 g, 25.6 mmol) were suspended in ethanol (19 mL) and acetic acid (9.5 mL). The stirred mixture was heated to 60° C. for 1 h and was diluted with EtOH (20 mL EtOH). Celite (15 g) was added and the mixture was filtered through a pad of Celite with EtOH. The filtrated was concentrated in vacuo. The crude residue was taken up in and concentrated once from 30 mL EtOH to afford crude 4-bromo-N1-cyclopropyl-6-methoxy-benzene-1,2-diamine that was used immediately in the following step. LCMS-ESI$^+$ (m/z): [M+H]$^+$ calcd for $C_{10}H_{14}BrN_2O$: 257.03; found: 257.15.

Step 4: The crude product from above (ca. 3.66 mmol) was suspended in 1,2-dichloroethane (13 mL) under $N_2$. N,N-Dimethylformamide dimethyl acetal (0.82 mL, 6.19 mmol) was added and the resulting stirred mixture was heated to 50 C. After 1.5 h, the reaction mixture was diluted with DCM (30 mL) and filtered with DCM through a short pad of Celite. The filtrate was concentrated in vacuo and was adsorbed onto silica gel (~10 g). Purification by silica gel chromatography (5-30% acetone in hexanes) provided 5-bromo-1-cyclopropyl-7-methoxy-1H-benzo[d]imidazole. LCMS-ESI$^+$ (m/z): [M+H]$^+$ calcd for $C_{11}H_{12}BrN_2O$: 267.01; found: 267.25.

Step 5: 5-bromo-1-cyclopropyl-7-methoxy-1H-benzo[d]imidazole (0.54 g, 2.01 mmol) was dissolved in dichloromethane (12 mL) under $N_2$. A 1M $BBr_3$ solution in DCM (12 mL, 12 mmol) was added dropwise over 1 min. The resulting stirred suspension was heated to 35° C. After 5 h, the reaction mixture was cooled in an ice water bath. A 7M ammonia in MeOH solution (7.5 mL, 53 mmol) was then added over 2 min via syringe. The mixture was stirred 5 min and was removed from the ice bath. After an additional 10 min, the mixture was concentrated in vacuo, and the crude product was dissolved in MeOH (30 mL) and was concentrated in vacuo. The resulting crude solids were suspended in 20% MeOH in DCM (30 mL) and were filter through a short pad of silica, eluting with 20% MeOH in DCM. Filtrate was concentrated in vacuo, and the crude product was adsorbed onto silica gel. Purification by silica gel chromatography (0-20% MeOH in DCM) gave 5-bromo-1-cyclopropyl-1H-benzo[d]imidazol-7-ol (2.73). LCMS-ES r (m/z): [m+H]+ calcd for $C_{10}H_{10}BrN_2O$: 253.00; found: 253.14.

Example 2.74

Preparation of (R)-4-((R)-1-((5-bromo-1-cyclopropyl-1H-benzo[d]imidazol-7-yl)oxy)ethyl)-1-((R)-1-(4-methoxyphenyl)ethyl)pyrrolidin-2-one

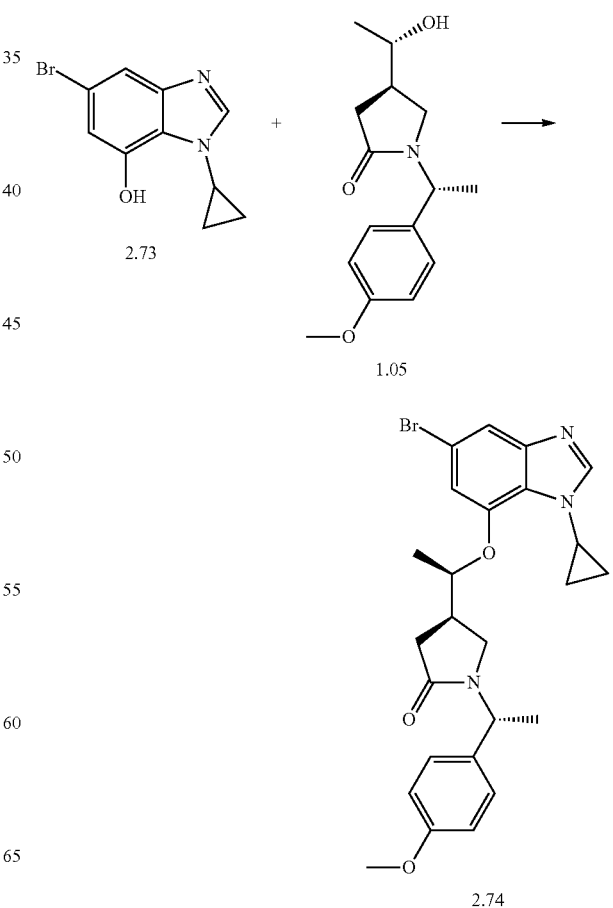

5-bromo-1-cyclopropyl-1H-benzo[d]imidazol-7-ol 2.73 (1.4 g, 5.53 mmol), (R)-4-((S)-1-hydroxyethyl)-1-((R)-1-(4-methoxyphenyl)ethyl)pyrrolidin-2-one 1.05 (2.04 g, 7.75 mmol), and triphenylphosphine (2.04 g, 7.78 mmol) were taken up in THF (30 mL). Diethyl azodicarboxylate (1.2 ml, 7.65 mmol) was added dropwise over 1 min, and the resulting stirred solution was heated to 40 C. After 1 h, add additional portions of intermediate 1.05 (0.27 g, 1.02 mmol), triphenylphosphine (0.27 g, 1.02 mmol), and diethyl azodicarboxylate (0.15 ml, 0.96 mmol) were added. The mixture was stirred an additional 1.5 h and was then concentrated directly onto silica gel. Purification by silica gel chromatography (20-100% acetone:hexanes) provided (R)-4-((R)-1-((5-bromo-1-cyclopropyl-1H-benzo[d]imidazol-7-yl)oxy)ethyl)-1-((R)-1-(4-methoxyphenyl)ethyl)pyrrolidin-2-one (2.74). LCMS-ESI$^+$ (m/z): [M+H]$^+$ calcd for C$_{25}$H$_{29}$BrN$_3$O$_3$: 498.14; found: 498.37.

Example 2.75

Preparation of (R)-4-((R)-1-((5-bromo-1-cyclopropyl-1H-benzo[d]imidazol-7-yl)oxy)ethyl)pyrrolidin-2-one

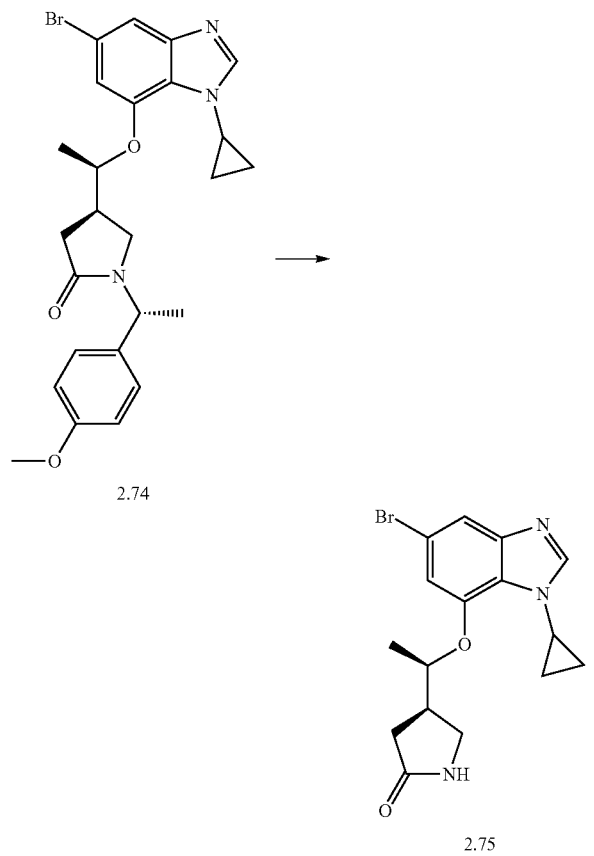

(R)-4-((R)-1-((5-bromo-1-cyclopropyl-1H-benzo[d]imidazol-7-yl)oxy)ethyl)-1-((R)-1-(4-methoxyphenyl)ethyl)pyrrolidin-2-one 2.74 (2.09 g, 4.19 mmol) was dissolved in TFA (42 mL, 550 mmol). The resulting solution was heated to 70° C. and was stirred for 19 h. The reaction mixture was concentrated and partitioned between EtOAc (100 mL) and saturated aqueous NaHCO$_3$ (75 mL). The phases were separated, and the aqueous phase was extracted with EtOAc (2×75 mL). The combined organic phase was dried over Na$_2$SO$_4$, filtered, and concentrated, and the crude concentrate was purified by silica gel chromatography (0-20% MeOH in DCM) to provide (R)-4-((R)-1-((5-bromo-1-cyclopropyl-1H-benzo[d]imidazol-7-yl)oxy)ethyl)pyrrolidin-2-one (2.75). LCMS-ESI$^+$ (m/z): [M+H]$^+$ calcd for C$_{16}$H$_{19}$BrN$_3$O$_2$: 364.07; found: 364.05.

Example 2.76

Preparation of (R)-4-((R)-1-((1-cyclopropyl-5-(4,4,5,5-tetramethyl-1,3,2-dioxaborolan-2-yl)-1H-benzo[d]imidazol-7-yl)oxy)ethyl)pyrrolidin-2-one

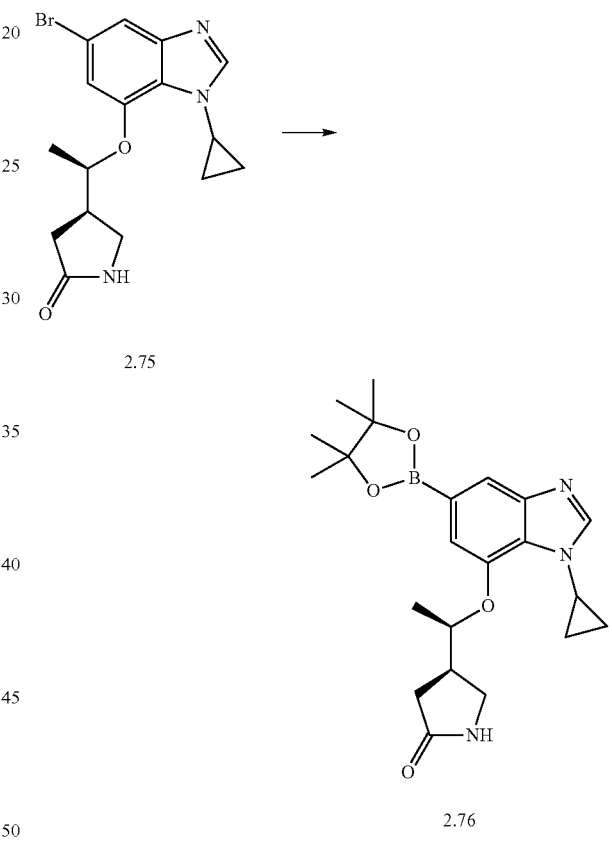

(R)-4-((R)-1-((5-bromo-1-cyclopropyl-1H-benzo[d]imidazol-7-yl)oxy)ethyl)pyrrolidin-2-one 2.75 (496 mg, 1.36 mmol), dichloro 1,1'-bis(diphenylphosphino)ferrocene palladium (II) dichloromethane (0.06 g, 0.07 mmol), 4,4,4',4',5,5,5',5'-octamethyl-2,2'-bi(1,3,2-dioxaborolane) (0.56 g, 2.19 mmol) and KOAc (0.41 g, 4.18 mmol) were taken up in 1,4-Dioxane (10 mL) under Ar. The stirred mixture was heated to 105° C. After 1.25 h, the mixture was diluted with EtOAc (50 mL), water (20 mL) and brine (20 mL), and the layers were separated. The aqueous phase was extracted with EtOAc (2×50 mL) and the combined organic phase was dried over Na$_2$SO$_4$, filtered, and concentrated. The crude concentrate was purified by silica gel (50-100% acetone in hexanes) to afford (R)-4-((R)-1-((1-cyclopropyl-5-(4,4,5,5-tetramethyl-1,3,2-dioxaborolan-2-yl)-1H-benzo[d]imidazol-7-yl)

oxy)ethyl)pyrrolidin-2-one (2.76). LCMS-ESI⁺ (m/z): [M+H]⁺ calcd for $C_{22}H_{31}BN_3O_4$: 412.24; found: 412.39.

Example 2.77

(R)-4-((R)-1-((5-(5,6-dimethoxypyridin-2-yl)-1-ethyl-1H-benzo[d]imidazol-7-yl)oxy)ethyl)pyrrolidin-2-one

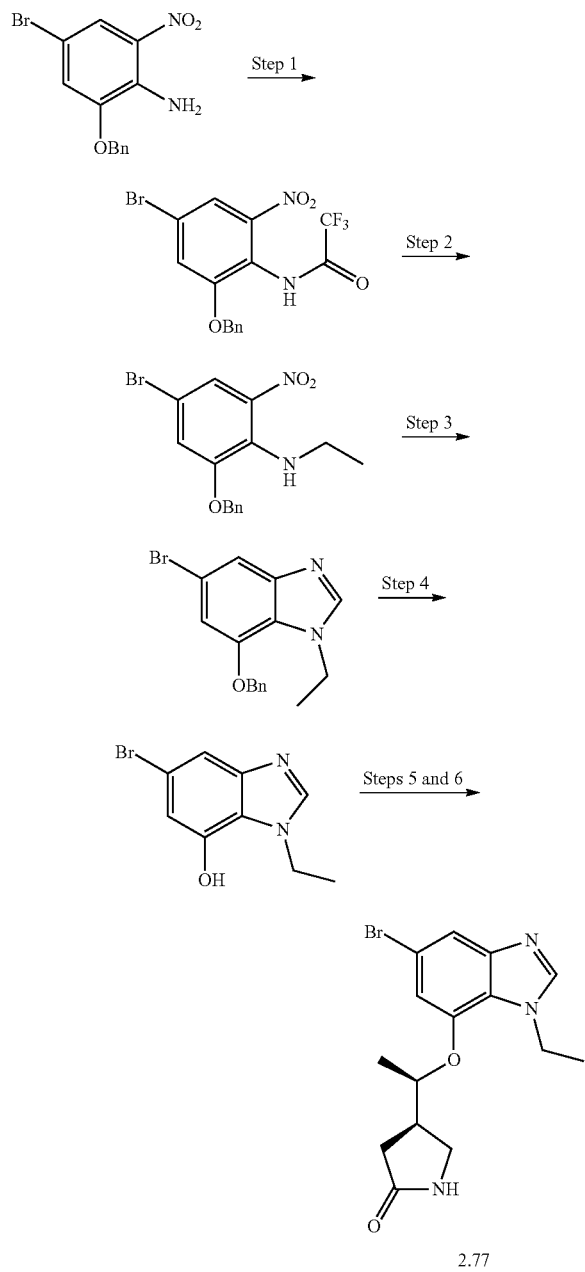

2.77

Step 1: 4,5-Dimethyl-2-nitrofluoroacetanilide: Trifluoroacetic acid anhydride (1.34 mL, 9.6 mmol) was added dropwise to a stirred solution of 2-(benzyloxy)-4-bromo-6-nitroaniline (1.56 g, 4.8 mmol) in methylene chloride (10 mL) at 0° C. Then triethylamine (1.4 mL, 10.1 mmol) was added slowly to the stirred solution. The reaction mixture was slowly warmed to room temperature and stirred for 1 h at room temperature. The reaction mixture was then diluted with DCM (100 mL) and washed with 2 M HCl, NaHCO₃, and brine. The organic layer was then dried (MgSO₄), filtered, evaporated, and dried to give 4,5-Dimethyl-2-nitrofluoroacetanilide which was used further without purification. LCMS-ESI⁺ (m/z): [M+Na]⁺ calcd for $C_{15}H_{10}BrF_3N_2O_4Na$: 441.0; found: 440.9.

Step 2: 2-(benzyloxy)-4-bromo-N-ethyl-6-nitroaniline: To a solution of 4,5-Dimethyl-2-nitrofluoroacetanilide (1.04 g, 2.5 mmol) in DMF (12 mL) was added K₂CO₃ (1.7 g, 12.5 mmol). After stirring at rt for 30 min, ethyl iodide (0.3 mL, 3.75 mmol) was added and the reaction mixture heated to reflux overnight. After 16 h, the reaction was cooled to rt and DMF was vacuum-evaporated, and the residue was dissolved in water and extracted with ethyl acetate (5×). The combined organic layers were dried with anhydrous MgSO4, filtered, and concentrated in vacuum to yield a yellow-red residue. The residue was subjected to flash chromatography using ethyl acetate/hexanes to give the title compound. LCMS-ESI⁺ (m/z): [M+H]⁺ calcd for $C_{15}H_{16}BrN_2O_3$: 351.0; found: 351.0.

Step 3: 7-(benzyloxy)-5-bromo-1-ethyl-1H-benzo[d]imidazole: To a solution of 2-(benzyloxy)-4-bromo-N-ethyl-6-nitroaniline (230 mg, 0.66 mmol) in ethanol (10 mL) and formic acid (10 mL) was added iron (731 mg, 13.1 mmol) and the reaction mixture was heated at 90° C. at 2 h. The reaction mixture was concentrated, diluted with water and brought to pH ~7 with sat'd NaHCO₃ and then the aqueous layer was extracted with EtOAc (3×). Combined organic layer was then washed successively with water and brine and dried over anhydrous magnesium sulfate, filtered, evaporated, and dried to give the title compound which was used further without purification. LCMS-ESI⁺ (m/z): [M+H]⁺ calcd for $C_{16}H_{16}BrN_2O$: 331.0; found: 331.0.

Step 4: 5-bromo-1-ethyl-1H-benzo[d]imidazol-7-ol: To a solution of 7-(benzyloxy)-5-bromo-1-ethyl-1H-benzo[d]imidazole (225 mg, 0.679 mmol) in DCM (8 mL) at 0° C. was added a solution of 1.0 M BBr₃ in THF (0.66 mL, 1.5 equiv). After 1 h at 0° C., methanol (1.5 mL), and diethylamine (1.3 mL) were added to the reaction mixture, which was then stirred at rt for 1 h. Reaction mixture was then concentrated and water was added, the solids formed were filtered, washed with water and dried to give the title compound which was used further without purification. LCMS-ESI⁺ (m/z): [M+H]⁺ calcd for $C_9H_{10}BrN_2O$: 241.0; found: 241.0.

Step 5: (S)-1-((R)-1-((R)-1-(4-methoxyphenyl)ethyl)-5-oxopyrrolidin-3-yl)ethyl methanesulfonate: To a solution of 5-bromo-1-ethyl-1H-benzo[d]imidazol-7-ol (126 mg, 0.523 mmol) in DMF (5 mL) was added ((S)-1-((R)-1-((R)-1-(4-methoxyphenyl)ethyl)-5-oxopyrrolidin-3-yl)ethyl methanesulfonate 1.30 (303 mg, 0.888 mmol) and Cs₂CO₃ (306 mg, 0.94 mmol) and the reaction mixture was heated at 90° C. for 4 h. The reaction mixture was then concentrated and the resulting residue was subjected to flash chromatography using 20% MeOH/ethyl acetate to give the title compound. LCMS-ESI⁺ (m/z): 487.1.

Step 6: (R)-4-((R)-1-((5-bromo-1-ethyl-1H-benzo[d]imidazol-7-yl)oxy)ethyl) pyrrolidin-2-one: (R)-4-((R)-1-((5-bromo-1-ethyl-1H-benzo[d]imidazol-7-yl)oxy)ethyl)-1-((R)-1-(4-methoxyphenyl)ethyl)pyrrolidin-2-one (155 mg, 0.319 mmol) in TFA (5 mL) was heated in at 55° C. for 16 h. The reaction mixture was then concentrated to give (R)-4-((R)-1-((5-bromo-1-ethyl-1H-benzo[d]imidazol-7-yl)oxy)ethyl)pyrrolidin-2-one 2.77 which was used for next step without further purification. LCMS-ESI⁺ (m/z): 353.0.

Example 2.78

Preparation of N-(6-bromo-2-chloro-3-(methylamino)pyridin-4-yl)propionamide

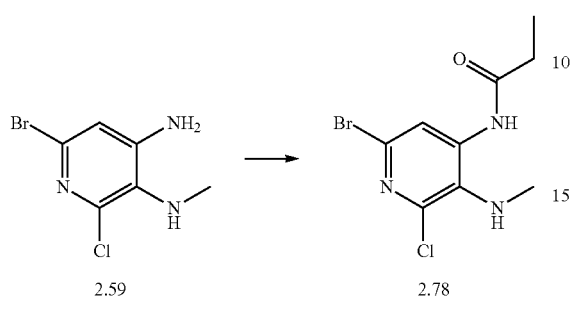

6-bromo-2-chloro-N3-methylpyridine-3,4-diamine 2.59 (410 mg, 2.74 mmol) was dissolved in pyridine (10 mL). Mixture was cooled down to 0° C. and then propanoyl chloride (207 mg) was added portion wise. Mixture was stirred at 0° C. for 1 h. Reaction mixture was poured into water and extracted with ethyl acetate. Organic phase was dried over $Mg_2SO_4$, filtered, and concentrated under reduced pressure. Resulting residues were purified by silica gel chromatography (5% MeOH in DCM) to provide N-(6-bromo-2-chloro-3-(methylamino)pyridin-4-yl)propionamide (2.78). LC/MS found for $C_9H_{11}BrClN_3O$ as $(M+H)^+$ 291.9.

Example 2.79

Preparation of 6-bromo-4-chloro-2-ethyl-3-methyl-3H-imidazo[4,5-c]pyridine

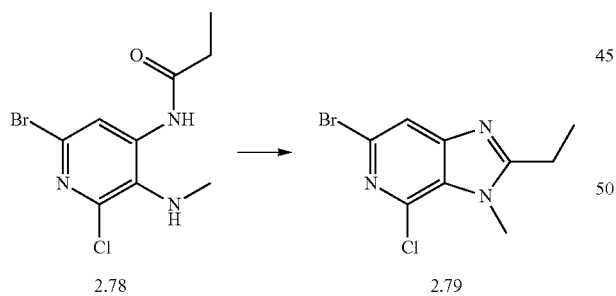

N-(6-bromo-2-chloro-3-(methylamino)pyridin-4-yl)propionamide 2.78 (213 mg, 0.73 mmol) was dissolved in a mixture of HCl (37% aqueous solution) and AcOH 1:5 (12 mL) and the mixture was heated in a sealed tube at 100° C. After 2 h, LC/MS indicated full conversion to desired product. Reaction mixture was evaporated under reduced pressure. Solids were suspended and stirred for 10 min in a basic aqueous solution of $NaHCO_3$ Solids were collected by filtration to isolate 6-bromo-4-chloro-2-ethyl-3-methyl-3H-imidazo[4,5-c]pyridine 2.79. LCMS found for $C_9H_9BrClN_3$ as $(M+H)^+$ 273.9.

Example 2.80

Preparation of (R)-4-((R)-1-((6-bromo-2-ethyl-3-methyl-3H-imidazo[4,5-c]pyridin-4-yl)oxy)ethyl)-1-48)-1-(4-methoxyphenyl)ethyl)pyrrolidin-2-one

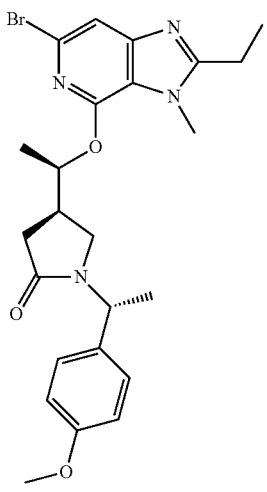

Following the procedure to synthesize example 2.65B, beginning with 6-bromo-4-chloro-2-ethyl-3-methyl-3H-imidazo[4,5-c]pyridine 2.79 (150 mg, 0.54 mmol) along with (R)-4-((R)-1-hydroxyethyl)-1-((R)-1-(4-methoxyphenyl)ethyl)pyrrolidin-2-one 1.04 (213 mg, 0.76 mmol) the compound (R)-4-((R)-1-((6-bromo-2-ethyl-3-methyl-3H-imidazo[4,5-c]pyridin-4-yl)oxy)ethyl)-1-((R)-1-(4-methoxyphenyl)ethyl)pyrrolidin-2-one 2.80 was prepared. LC/MS found for $C_{24}H_{29}BrN_4O_3$ as $(M+H)^+$ 501.1.

General Procedure A for Synthesis of Examples 3A.01-3A.13

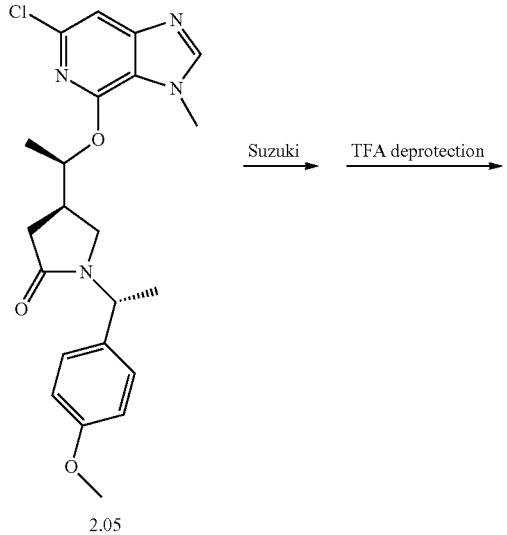

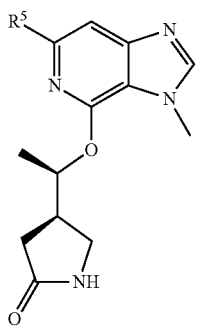

Examples 3A.01-3A.13

To an appropriate sized container charged with a magnetic stir bar, (R)-4-((R)-1-(6-chloro-3-methyl-3H-imidazo[4,5-c]pyridin-4-yloxy)ethyl)-1-((R)-1-(4-methoxyphenyl)ethyl)pyrrolidin-2-one 2.05 (1 equiv), boronic acid or ester (1.2 equiv), cesium carbonate (3 equiv), and PEPPSI-IPr catalyst (0.1 equiv) were added and reagents were taken up in 2:1 DME:water. After evacuating and backfilling with argon, mixture was heated at 100° C. for one hour. After cooling to room temperature, mixture is poured into water and extracted with ethyl acetate. Combined organics were dried, filtered, and concentrated under reduced pressure and resulting residues were used without further purification. Residues were dissolved in trifluoroacetic acid and mixture was heated at 55-60° C. overnight. After cooling to room temperature, mixture was concentrated under reduced pressure, taken up in ethyl acetate, washed with saturated NaHCO$_3$ $_{(aq)}$, and layers separated. Aqueous layer was extracted with ethyl acetate and combined organic layers were washed with 1:1 saturated NaHCO$_3$ $_{(aq)}$: brine, dried, filtered, and concentrated under reduced pressure to yield residues. Residues were purified by silica gel column chromatography or reverse phase HPLC to yield Examples 3A.01-3A.13.

Example 3A.01

Preparation of (R)-4-((R)-1-(3-methyl-6-(3,4,5-trimethoxyphenyl)-3H-imidazo[4,5-c]pyridin-4-yloxy)ethyl)pyrrolidin-2-one

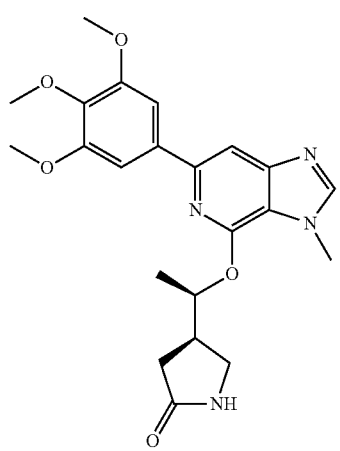

Example 3A.01

Following General Procedure A, beginning with (R)-4-((R)-1-(6-chloro-3-methyl-3H-imidazo[4,5-c]pyridin-4-yloxy)ethyl)-1-((R)-1-(4-methoxyphenyl)ethyl)pyrrolidin-2-one 2.05 (93 mg, 0.217 mmol) and 3,4,5-trimethoxyphenylboronic acid (52 mg, 0.245 mmol), (R)-4-((R)-1-(3-methyl-6-(3,4,5-trimethoxyphenyl)-3H-imidazo[4,5-c]pyridin-4-yloxy)ethyl)pyrrolidin-2-one 3A.01 was synthesized.

$^1$H NMR (400 MHz, CD$_3$OD) δ 8.15 (s, 1H), 7.68 (s, 1H), 7.38 (s, 2H), 5.71 (p, J=6 Hz, 1H), 4.06 (s, 3H), 3.94 (s, 6H), 3.81 (s, 3H), 3.63 (t, J=9.6 Hz, 1H), 3.40 (dd, J=10.2, 5.2 Hz, 1H), 3.02-2.95 (m, 1H), 2.64-2.50 (m, 2H), 1.53 (d, J=6.4 Hz, 3H).

LCMS-ESI$^+$ (m/z): [M+H]$^+$ calcd for C$_{22}$H$_{27}$N$_4$O$_5$: 427.19; found 427.18.

Example 3A.02

Preparation of (R)-4-((R)-1-(6-(1-tert-butyl-1H-pyrazol-4-yl)-3-methyl-3H-imidazo[4,5-c]pyridin-4-yloxy)ethyl)pyrrolidin-2-one

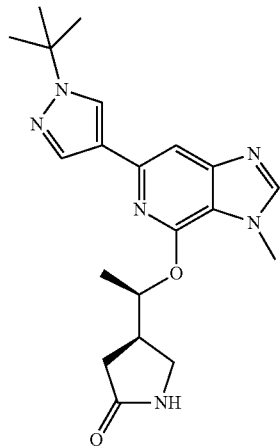

Example 3A.02

Following General Procedure A, beginning with (R)-4-((R)-1-(6-chloro-3-methyl-3H-imidazo[4,5-c]pyridin-4-yloxy)ethyl)-1-((R)-1-(4-methoxyphenyl)ethyl)pyrrolidin-2-one 2.05 (73 mg, 0.171 mmol) and 1-tert-butyl-pyrazole-4-boronic acid pinacol ester (51 mg, 0.204 mmol), (R)-4-((R)-1-(6-(1-tert-butyl-1H-pyrazol-4-yl)-3-methyl-3H-imidazo[4,5-c]pyridin-4-yloxy)ethyl)pyrrolidin-2-one 3A.02 was synthesized.

$^1$H NMR (400 MHz, CD$_3$OD) δ 8.20 (s, 1H), 8.08 (s, 1H), 7.98 (s, 1H), 7.43 (s, 1H), 5.73 (p, J=6 Hz, 1H), 4.03 (s, 3H), 3.62 (t, J=9.2 Hz, 1H), 3.40 (dd, J=10, 5.6 Hz, 1H), 2.99-2.89 (m, 1H), 2.63-2.47 (m, 2H), 1.63 (s, 9H), 1.48 (d, J=6.4 Hz, 3H).

LCMS-ESI$^+$ (m/z): [M+H]$^+$ calcd for C$_{20}$H$_{27}$N$_6$O$_2$: 383.21; found: 383.20.

Example 3A.03

Preparation of (R)-4-((R)-1-(6-(1-(2,2-difluoroethyl)-1H-pyrazol-4-yl)-3-methyl-3H-imidazo[4,5-c]pyridin-4-yloxy)ethyl)pyrrolidin-2-one

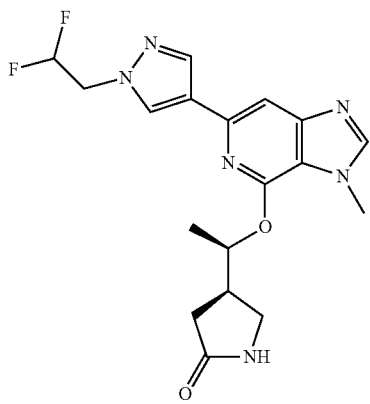

Example 3A.03

Following General Procedure A, beginning with (R)-4-((R)-1-(6-chloro-3-methyl-3H-imidazo[4,5-c]pyridin-4-yloxy)ethyl)-1-((R)-1-(4-methoxyphenyl)ethyl)pyrrolidin-2-one 2.05 (30 mg, 0.070 mmol) and 1-(2,2-difluoroethyl)-4-(4,4,5,5-tetramethyl-1,3,2-dioxaborolan-2-yl-1H pyrazole (21.7 mg, 0.084 mmol), (R)-4-((R)-1-(6-(1-(2,2-difluoroethyl)-1H-pyrazol-4-yl)-3-methyl-3H-imidazo[4,5-c]pyridin-4-yloxy)ethyl)pyrrolidin-2-one 3A.03 was synthesized following purification by reverse phase HPLC.

$^1$H NMR (400 MHz, DMSO-d6) δ 8.24 (s, 1H), 8.18 (s, 1H), 8.07 (d, J=0.7 Hz, 1H), 7.55 (s, 1H), 7.52 (s, 1H), 6.40 (tt, J=55.2, 3.9 Hz, 1H), 5.51 (p, J=6.0 Hz, 1H), 4.65 (td, J=15.1, 3.8 Hz, 2H), 3.94 (s, 3H), 3.42 (t, J=9.2 Hz, 1H), 3.17 (dd, J=9.7, 6.2 Hz, 1H), 2.90-2.72 (m, 1H), 2.44-2.18 (m, 2H), 1.39 (d, J=6.2 Hz, 3H).

LCMS-ESI$^+$ (m/z): [M+H]$^+$ calcd for $C_{18}H_{20}F_2N_6O_2$: 391.2; found: 391.2.

Example 3A.04

Preparation of (R)-4-((R)-1-(3-methyl-6-(6-morpholinopyridin-3-yl)-3H-imidazo[4,5-c]pyridin-4-yloxy)ethyl)pyrrolidin-2-one

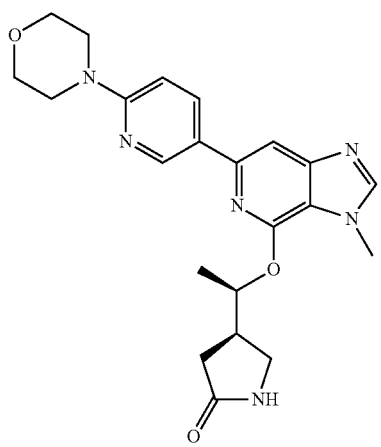

Example 3A.04

Following General Procedure A, beginning with (R)-4-((R)-1-(6-chloro-3-methyl-3H-imidazo[4,5-c]pyridin-4-yloxy)ethyl)-1-((R)-1-(4-methoxyphenyl)ethyl)pyrrolidin-2-one 2.05 (49 mg, 0.114 mmol) and 6-morpholinopyridin-3-ylboronic acid (28 mg, 0.135 mmol), (R)-4-((R)-1-(3-methyl-6-(6-morpholinopyridin-3-yl)-3H-imidazo[4,5-c]pyridin-4-yloxy)ethyl)pyrrolidin-2-one 3A.04 was synthesized.

$^1$H NMR (400 MHz, CD$_3$OD) δ 8.83 (d, J=2.4 Hz, 1H), 8.22 (dd, J=8.8 Hz, 2.4 Hz, 1H), 8.12 (s, 1H), 7.58 (s, 1H), 6.90 (d, J=8.8 Hz, 1H), 5.73 (p, J=6 Hz, 1H), 4.05 (s, 3H), 3.84-3.78 (m, 4H), 3.62 (t, J=9.4 Hz, 1H), 3.56-3.51 (m, 4H), 3.40 (dd, J=10.2, 5.6 Hz, 1H), 3.00-2.91 (m, 1H), 2.64-2.48 (m, 2H), 1.50 (d, J=6 Hz, 3H).

LCMS-ESI$^+$ (m/z): [M+H]$^+$ calcd for $C_{22}H_{27}N_6O_3$: 423.21; found: 423.20.

Example 3A.05

Preparation of (R)-4-((R)-1-(3-methyl-6-(4-morpholinophenyl)-3H-imidazo[4,5-c]pyridin-4-yloxy)ethyl)pyrrolidin-2-one

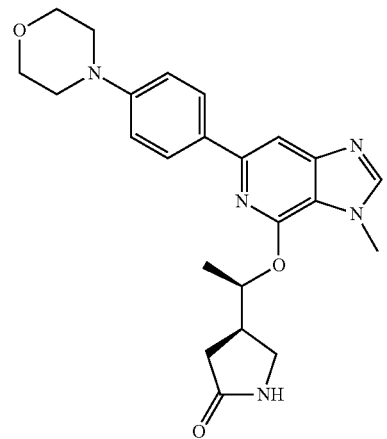

Example 3A.05

Following General Procedure A, beginning with (R)-4-((R)-1-(6-chloro-3-methyl-3H-imidazo[4,5-c]pyridin-4-yloxy)ethyl)-1-((R)-1-(4-methoxyphenyl)ethyl)pyrrolidin-2-one 2.05 (49 mg, 0.114 mmol) and 4-morpholinophenylboronic acid (28 mg, 0.135 mmol), (R)-4-((R)-1-(3-methyl-6-(4-morpholinophenyl)-3H-imidazo[4,5-c]pyridin-4-yloxy)ethyl)pyrrolidin-2-one 3A.05 was synthesized.

$^1$H NMR (400 MHz, CD$_3$OD) δ 8.10 (s, 1H), 7.95 (d, J=9.2 Hz, 2H), 7.57 (s, 1H), 7.03 (d, J=9.2 Hz, 2H), 5.76 (p, J=6 Hz, 1H), 4.04 (s, 3H), 3.87-3.81 (m, 4H), 3.62 (t, J=9.6 Hz, 1H), 3.38 (dd, J=10.2, 5.6 Hz, 1H), 3.24-3.16 (m, 4H) 3.00-2.91 (m, 1H), 2.64-2.48 (m, 2H), 1.50 (d, J=6 Hz, 3H).

LCMS-ESI$^+$ (m/z): [M+H]$^+$ calcd for $C_{23}H_{28}N_5O_3$: 422.21; found: 422.20.

Example 3A.06

Preparation of 4-(3-methyl-4-((R)-1-((R)-5-oxopyrrolidin-3-yl)ethoxy)-3H-imidazo[4,5-c]pyridin-6-yl)benzonitrile

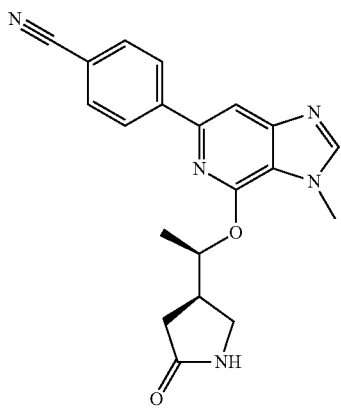

Example 3A.06

Following General Procedure A, beginning with (R)-4-((R)-1-(6-chloro-3-methyl-3H-imidazo[4,5-c]pyridin-4-yloxy)ethyl)-1-((R)-1-(4-methoxyphenyl)ethyl)pyrrolidin-2-one 2.05 (49 mg, 0.089 mmol) and 4-cyanophenylboronic acid (17 mg, 0.116 mmol), 4-(3-methyl-4-((R)-1-((R)-5-oxopyrrolidin-3-yl)ethoxy)-3H-imidazo[4,5-c]pyridin-6-yl)benzonitrile 3A.06 was synthesized.

$^1$H NMR (400 MHz, DMSO-$d_6$) δ 8.29 (d, J=7.6 Hz, 2H), 8.285 (s, 1H), 8.12 (s, 1H), 8.01 (s, 1H), 7.89 (d, J=7.6 Hz, 1H), 7.56 (s, 1H), 5.55 (p, J=6 Hz, 1H), 3.97 (s, 3H), 3.41 (t, J=9.2 Hz, 1H), 3.17 (dd, J=9.8, 6 Hz, 1H), 2.87-2.77 (m, 1H), 2.40-2.22 (m, 2H), 1.41 (d, J=6.4 Hz, 3H).

LCMS-ESI$^+$ (m/z): [M+H]$^+$ calcd for $C_{20}H_{20}N_5O_2$: 362.15; found: 362.12.

Example 3A.07

Preparation of (R)-4-((R)-1-(6-(2-tert-butylthiazol-4-yl)-3-methyl-3H-imidazo[4,5-c]pyridin-4-yloxy)ethyl)pyrrolidin-2-one

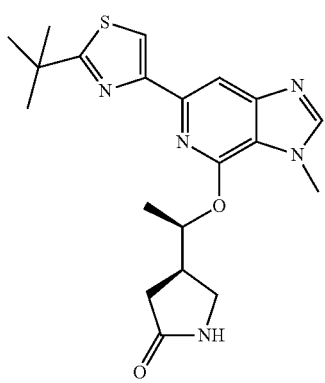

Example 3A.07

Following General Procedure A, beginning with (R)-4-((R)-1-(6-chloro-3-methyl-3H-imidazo[4,5-c]pyridin-4-yloxy)ethyl)-1-((R)-1-(4-methoxyphenyl)ethyl)pyrrolidin-2-one 2.05 (53 mg, 0.124 mmol) and 2-tBu-thiazole-4-boronic acid pinacol ester (39 mg, 0.146 mmol), (R)-4-((R)-1-(6-(2-tert-butylthiazol-4-yl)-3-methyl-3H-imidazo[4,5-c]pyridin-4-yloxy)ethyl)pyrrolidin-2-one 3A.07 was synthesized.

$^1$H NMR (400 MHz, CD$_3$OD) δ 8.13 (s, 1H), 7.97 (s, 1H), 7.84 (s, 1H), 5.75 (p, J=6 Hz, 1H), 4.05 (s, 3H), 3.66-3.57 (m, 1H), 3.40 (dd, J=10.2, 5.5 Hz, 1H), 3.01-2.91 (m, 1H), 2.64-2.46 (m, 2H), 1.50 (d, J=6 Hz, 3H), 1.49 (s, 9H).

LCMS-ESI$^+$ (m/z): [M+H]$^+$ calcd for $C_{20}H_{26}N_5O_2S$: 400.17; found: 400.17.

Example 3A.08

Preparation of (R)-4-((R)-1-(6-(2-tert-butylthiazol-5-yl)-3-methyl-3H-imidazo[4,5-c]pyridin-4-yloxy)ethyl)pyrrolidin-2-one

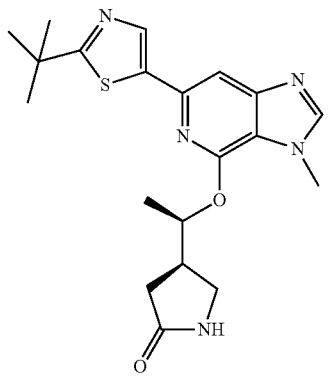

Example 3A.08

Following General Procedure A, beginning with (R)-4-((R)-1-(6-chloro-3-methyl-3H-imidazo[4,5-c]pyridin-4-yloxy)ethyl)-1-((R)-1-(4-methoxyphenyl)ethyl)pyrrolidin-2-one 2.05 (32 mg, 0.075 mmol) and 2-(tert-butyl)-thiazole-5-boronic acid pinacol ester (25 mg, 0.094 mmol), (R)-4-((R)-1-(6-(2-tert-butylthiazol-5-yl)-3-methyl-3H-imidazo[4,5-c]pyridin-4-yloxy)ethyl)pyrrolidin-2-one 3A.08 was synthesized.

$^1$H NMR (400 MHz, CD$_3$OD) δ 8.16 (s, 1H), 8.11 (s, 1H), 7.62 (s, 1H), 5.64 (dd, J=6.3 Hz, 1H), 4.05 (s, 3H), 3.62 (dd, J=10.2, 8.6 Hz, 1H), 3.38 (dd, J=10.2, 5.5 Hz, 1H), 3.03-2.90 (m, 1H), 2.64-2.42 (m, 2H), 1.50 (d, J=6.2 Hz, 3H), 1.47 (s, 9H).

LCMS-ESI$^+$ (m/z): [M+H]$^+$ calcd for $C_{20}H_{26}N_5O_2S$: 400.17; found: 400.21.

Example 3A.09

Preparation of (R)-4-((R)-1-(6-(1-isobutyl-1H-pyrazol-4-yl)-3-methyl-3H-imidazo[4,5-c]pyridin-4-yloxy)ethyl)pyrrolidin-2-one

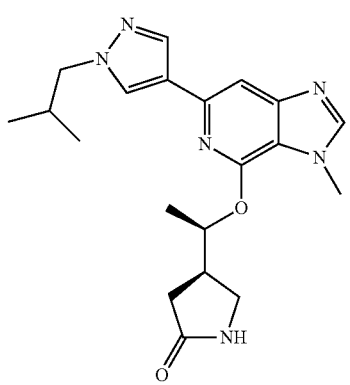

Example 3A.09

Following General Procedure A, beginning with (R)-4-((R)-1-(6-chloro-3-methyl-3H-imidazo[4,5-c]pyridin-4-yloxy)ethyl)-1-((R)-1-(4-methoxyphenyl)ethyl)pyrrolidin-2-one 2.05 (20 mg, 0.047 mmol) and 1-isobutylpyrazole-4-boronic acid pinacol ester (14 mg, 0.056 mmol), (R)-4-((R)-1-(6-(1-isobutyl-1H-pyrazol-4-yl)-3-methyl-3H-imidazo[4,5-c]pyridin-4-yloxy)ethyl)pyrrolidin-2-one 3A.09 was isolated as the trifluoroacetic acid salt, following prep HPLC (2-95% acetonitrile in water, 0.1% trifluoroacetic acid buffer).

¹H NMR (400 MHz, DMSO-d₆) δ 8.73 (s, 1H), 8.25 (s, 1H), 8.02 (s, 1H), 7.57 (s, 1H), 7.51 (s, 1H), 5.54 (p, J=6.1 Hz, 1H), 4.01 (s, 3H), 3.95 (d, J=7.2 Hz, 2H), 3.42 (t, J=9.1 Hz, 1H), 3.17 (dd, J=9.8, 6.2 Hz, 1H), 2.82 (h, J=7.5, 7.1 Hz, 1H), 2.42-2.21 (m, 2H), 2.20-2.10 (m, 1H), 1.40 (d, J=6.2 Hz, 3H), 0.87 (d, J=6.7 Hz, 6H).

LCMS-ESI⁺ (m/z): [M+H]⁺ calcd for $C_{20}H_{26}N_6O_2$: 383.2; found 383.2.

Example 3A.10

Preparation of (R)-4-((R)-1-(6-(1-cyclopropyl-1H-pyrazol-4-yl)-3-methyl-3H-imidazo[4,5-c]pyridin-4-yloxy)ethyl)pyrrolidin-2-one

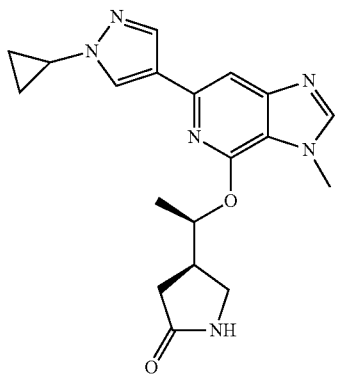

Example 3A.10

Following General Procedure A, beginning with (R)-4-((R)-1-(6-chloro-3-methyl-3H-imidazo[4,5-c]pyridin-4-yloxy)ethyl)-1-((R)-1-(4-methoxyphenyl)ethyl)pyrrolidin-2-one 2.05 (20 mg, 0.047 mmol) and 1-cyclopropyl-4-(4,4,5,5-tetramethyl-1,3,2-dioxaborolan-2-yl)-1H-pyrazole (13.1 mg, 0.056 mmol), (R)-4-((R)-1-(6-(1-cyclopropyl-1H-pyrazol-4-yl)-3-methyl-3H-imidazo[4,5-c]pyridin-4-yloxy)ethyl)pyrrolidin-2-one 3A.10 was synthesized.

¹H NMR (400 MHz, DMSO-d₆) δ 8.22 (s, 1H), 8.16 (s, 1H), 7.92 (d, J=0.8 Hz, 1H), 7.54 (s, 1H), 7.48 (s, 1H), 5.52 (p, J=5.8 Hz, 1H), 3.93 (s, 3H), 3.77-3.72 (m, 1H), 3.41 (t, J=9.1 Hz, 1H), 3.17 (dd, J=9.7, 6.1 Hz, 1H), 2.89-2.72 (m, 1H), 2.38-2.23 (m, 2H), 1.38 (d, J=6.2 Hz, 3H), 1.13-0.91 (m, 4H).

LCMS-ESI⁺ (m/z): [M+H]⁺ calcd for $C_{19}H_{22}N_6O_2$: 367.2; found 367.2.

Example 3A.11

Preparation of (R)-4-((R)-1-(6-(1,5-dimethyl-1H-pyrazol-4-yl)-3-methyl-3H-imidazo[4,5-c]pyridin-4-yloxy)ethyl)pyrrolidin-2-one

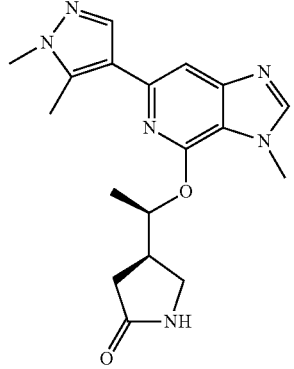

Example 3A.11

Following General Procedure A, beginning with (R)-4-((R)-1-(6-chloro-3-methyl-3H-imidazo[4,5-c]pyridin-4-yloxy)ethyl)-1-((R)-1-(4-methoxyphenyl)ethyl)pyrrolidin-2-one 2.05 (20 mg, 0.047 mmol) and 1,5-dimethyl-4-(4,4,5,5-tetramethyl-1,3,2-dioxaborolan-2-yl-1H pyrazole (12.4 mg, 0.056 mmol), (R)-4-((R)-1-(6-(1,5-dimethyl-1H-pyrazol-4-yl)-3-methyl-3H-imidazo[4,5-c]pyridin-4-yloxy)ethyl)pyrrolidin-2-one 3A.11 was isolated as the trifluoroacetic acid salt, following prep HPLC (2-95% acetonitrile in water, 0.1% trifluoroacetic acid buffer).

¹H NMR (400 MHz, DMSO-d₆) δ 8.49 (s, 1H), 7.86 (s, 1H), 7.57 (s, 1H), 7.42 (s, 1H), 5.44 (p, J=6.0 Hz, 1H), 3.98 (s, 3H), 3.77 (s, 3H), 3.41 (t, J=9.1 Hz, 1H), 3.14 (dd, J=9.8, 6.1 Hz, 1H), 2.93-2.73 (m, 1H), 2.59 (s, 3H), 2.42-2.17 (m, 2H), 1.38 (d, J=6.2 Hz, 3H).

LCMS-ESI⁺ (m/z): [M+H]⁺ calcd for $C_{18}H_{22}N_6O_2$: 355.2; found 355.2.

Example 3A.12

Preparation of (R)-4-((R)-1-(6-(1-cyclobutyl-1H-pyrazol-4-yl)-3-methyl-3H-imidazo[4,5-c]pyridin-4-yloxy)ethyl)pyrrolidin-2-one

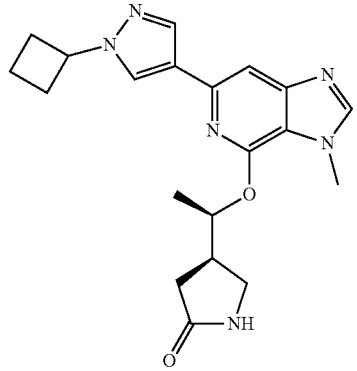

Example 3A.12

Following General Procedure A, beginning with (R)-4-((R)-1-(6-chloro-3-methyl-3H-imidazo[4,5-c]pyridin-4-yloxy)ethyl)-1-((R)-1-(4-methoxyphenyl)ethyl)pyrrolidin-2-one 2.05 (20 mg, 0.047 mmol) and 1-cyclobutyl-4-(4,4,5,5-tetramethyl-1,3,2-dioxaborolan-2-yl)-1H-pyrazole (14 mg, 0.056 mmol), (R)-4-((R)-1-(6-(1-cyclobutyl-1H-pyrazol-4-yl)-3-methyl-3H-imidazo[4,5-c]pyridin-4-yloxy)ethyl)pyrrolidin-2-one 3A.12 was isolated as the trifluoroacetic acid salt, following prep HPLC (2-95% acetonitrile in water, 0.1% trifluoroacetic acid buffer).

¹H NMR (400 MHz, DMSO-d₆) δ 8.54 (s, 1H), 8.31 (s, 1H), 8.02 (s, 1H), 7.56 (s, 1H), 7.52 (s, 1H), 5.55 (p, J=6.3 Hz, 1H), 4.86 (p, J=8.7 Hz, 1H), 3.98 (s, 3H), 3.42 (t, J=9.1 Hz, 1H), 3.17 (dd, J=9.8, 6.2 Hz, 1H), 2.86-2.77 (m, 1H), 2.59-2.18 (m, 6H), 1.90-1.71 (m, 2H), 1.39 (d, J=6.1 Hz, 3H).

LCMS-ESI⁺ (m/z): [M+H]⁺ calcd for $C_{20}H_{24}N_6O_2$: 381.2; found 381.3.

Example 3A.13

Preparation of (R)-4-((R)-1-(3-methyl-6-(4-(piperazin-1-yl)phenyl)-3H-imidazo[4,5-c]pyridin-4-yloxy)ethyl)pyrrolidin-2-one Example 3A.13

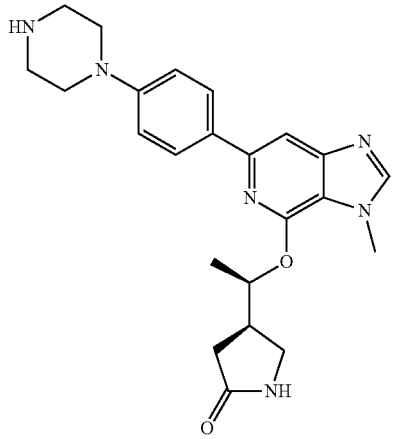

Following General Procedure A, beginning with (R)-4-((R)-1-(6-chloro-3-methyl-3H-imidazo[4,5-c]pyridin-4-yloxy)ethyl)-1-((R)-1-(4-methoxyphenyl)ethyl)pyrrolidin-2-one 2.05 (100 mg, 0.233 mmol) and 4-(4-BOC-piperazino)phenylboronic acid (93 mg, 0.303 mmol), the residue was purified via prep HPLC (2-95% acetonitrile in water, 0.1% trifluoroacteic acid buffer) to isolate (R)-4-((R)-1-(3-methyl-6-(4-(piperazin-1-yl)phenyl)-3H-imidazo[4,5-c]pyridin-4-yloxy)ethyl)pyrrolidin-2-one 3A.13 as the trifluoroacetic acid salt.

¹H NMR (400 MHz, DMSO-d6) δ 8.74 (s, 2H), 8.43 (s, 1H), 8.00 (d, J=8.8 Hz, 2H), 7.72 (s, 1H), 7.58 (s, 1H), 7.08 (d, J=8.9 Hz, 2H), 5.54 (p, J=6.5 Hz, 1H), 3.99 (s, 3H), 3.45-3.41 (m, 4H), 3.30-3.23 (m, 4H), 3.18 (dd, J=9.8, 6.2 Hz, 1H), 2.91-2.76 (m, 1H), 2.44-2.21 (m, 2H), 1.42 (d, J=6.2 Hz, 3H).

LCMS-ESI⁺ (m/z): [M+H]+ calcd for $C_{23}H_{28}N_6O_2$: 421.2; found: 421.1.

General Procedure B for Synthesis of Examples 3B.01-3B.31

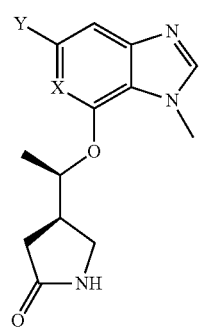

2.06, 2.58 or 2.62

X = CH or N
Y = Cl or Br

Suzuki

-continued

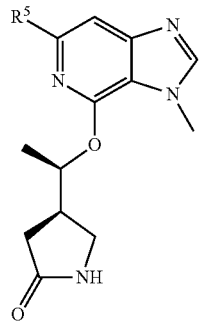

Examples 3B.01-3B.31

To an appropriate sized container charged with a magnetic stir bar, aryl halide 2.06, 2.58 or 2.62 (1 equiv), boronic acid or ester (1.2 equiv), cesium carbonate (3 equiv), and PEPPSI-IPr catalyst (0.1 equiv) were added and reagents were taken up in 2:1 DME:water. After evacuating and backfilling with argon, mixture was heated at 100° C. for one hour. After cooling to room temperature, mixture is poured into water and extracted with ethyl acetate. Combined organics were dried, filtered, and concentrated under reduced pressure and resulting residues were purified by silica gel column chromatography or reverse phase HPLC to yield Examples 3B.01-3B.31.

Example 3B.01

Preparation of (R)-4-((R)-1-(6-(3-fluoro-4-methoxyphenyl)-3-methyl-3H-imidazo[4,5-c]pyridin-4-yloxy)ethyl)pyrrolidin-2-one Example 3B.01

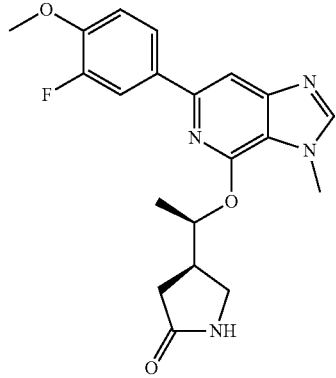

Following General Procedure B, beginning with (R)-4-((R)-1-(6-chloro-3-methyl-3H-imidazo[4,5-c]pyridin-4-yloxy)ethyl)pyrrolidin-2-one 2.06 (30 mg, 0.070 mmol) and 3-fluoro-4-methoxyphenylboronic acid (13 mg, 0.076 mmol), (R)-4-((R)-1-(6-(3-fluoro-4-methoxyphenyl)-3-methyl-3H-imidazo[4,5-c]pyridin-4-yloxy)ethyl)pyrrolidin-2-one 3B.01 was synthesized.

¹H NMR (400 MHz CD₃OD) δ 8.13 (s, 1H), 7.83 (d, J=2.4 Hz, 1H), 7.79 (d, J=2.8 Hz, 1H), 7.62 (s, 1H), 7.15 (t, J=9.2 Hz, 1H), 5.75 (p, J=6.4 Hz, 1H), 4.05 (s, 3H), 3.92 (s, 3H), 3.62 (dd, J=10.2, 8.7 Hz, 1H), 3.39 (dd, J=10.2, 5.6 Hz, 1H), 3.02-2.92 (m, 1H), 2.64-2.48 (m, 2H), 1.51 (d, J=6 Hz, 3H).

LCMS-ESI+ (m/z): [M+H]+ calcd for $C_{20}H_{22}FN_4O_3$: 385.16; found: 385.19.

Example 3B.02

Preparation of 2-methoxy-5-(3-methyl-4-((R)-1-((R)-5-oxopyrrolidin-3-yl)ethoxy)-3H-imidazo[4,5-c]pyridin-6-yl)benzonitrile

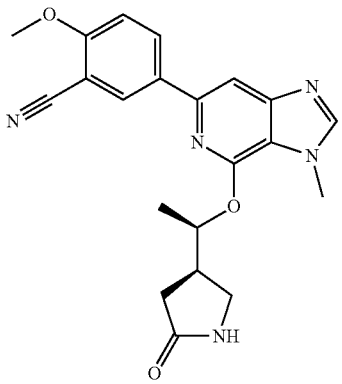

Example 3B.02

Following General Procedure B, beginning with (R)-4-((R)-1-(6-chloro-3-methyl-3H-imidazo[4,5-c]pyridin-4-yloxy)ethyl)pyrrolidin-2-one 2.06 (21 mg, 0.072 mmol) and 3-cyano-4-methoxyphenylboronic acid pinacol ester (24 mg, 0.093 mmol), 2-methoxy-5-(3-methyl-4-((R)-1-((R)-5-oxopyrrolidin-3-yl)ethoxy)-3H-imidazo[4,5-c]pyridin-6-yl)benzonitrile 3B.02 was synthesized.

1H NMR (400 MHz CD3OD) δ 8.33 (d, J=2.4 Hz, 1H), 8.32 (d, J=2.4 Hz, 1H), 8.15 (s, 1H), 7.69 (s, 1H), 7.26 (d, J=9.6 Hz, 1H), 5.76 (p, J=5.6 Hz, 1H), 4.06 (s, 3H), 4.00 (s, 3H), 3.63 (dd, J=10.2, 8.6 Hz, 1H), 3.39 (dd, J=10.2, 5.6 Hz, 1H), 3.03-2.92 (m, 1H), 2.65-2.47 (m, 2H), 1.51 (d, J=6 Hz, 3H).

LCMS-ESI+ (m/z): [M+H]+ calcd for $C_{21}H_{22}N_5O_3$: 392.16; found: 392.17.

Example 3B.03

Preparation of (R)-4-((R)-1-(6-(2,2-difluorobenzo[d][1,3]dioxol-5-yl)-3-methyl-3H-imidazo[4,5-c]pyridin-4-yloxy)ethyl)pyrrolidin-2-one

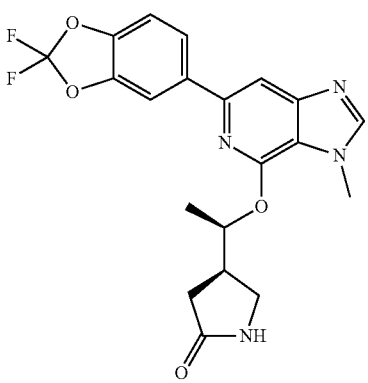

Example 3B.03

Following General Procedure B, beginning with (R)-4-((R)-1-(6-chloro-3-methyl-3H-imidazo[4,5-c]pyridin-4-yloxy)ethyl)pyrrolidin-2-one 2.06 (22.1 mg, 0.075 mmol) and 2,2-difluorobenzo[d][1,3]dioxol-5-ylboronic acid (18.2 mg, 0.090 mmol), (R)-4-((R)-1-(6-(2,2-difluorobenzo[d][1,3]dioxol-5-yl)-3-methyl-3H-imidazo[4,5-c]pyridin-4-yloxy)ethyl)pyrrolidin-2-one 3B.03 was synthesized.

1H NMR (400 MHz CD3OD) δ 8.33 (s, 1H), 7.93 (d, J=1.6 Hz, 1H), 7.89 (dd, J=8.6, 1.6 Hz, 1H), 7.70 (s, 1H), 7.26 (d, J=8.4 Hz, 1H), 5.75 (p, J=5.6 Hz, 1H), 4.06 (s, 3H), 3.63 (dd, J=9.8, 8.8 Hz, 1H), 3.38 (dd, J=10.2, 5.2 Hz, 1H), 3.01-2.92 (m, 1H), 2.64-2.50 (m, 2H), 1.51 (d, J=6 Hz, 3H).

LCMS-ESI+ (m/z): [M+H]+ calcd for $C_{20}H_{19}F_2N_4O_4$: 417.13; found: 417.20.

Example 3B.04

Preparation of (R)-4-((R)-1-(3-methyl-6-(4-methyl-3,4-dihydro-2H-benzo[b][1,4]oxazin-6-yl)-3H-imidazo[4,5-c]pyridin-4-yloxy)ethyl)pyrrolidin-2-one

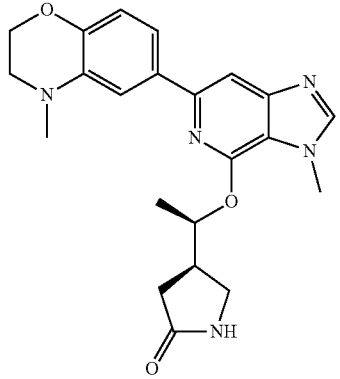

Example 3B.04

Following General Procedure B, beginning with (R)-4-((R)-1-(6-chloro-3-methyl-3H-imidazo[4,5-c]pyridin-4-yloxy)ethyl)pyrrolidin-2-one 2.06 (22.1 mg, 0.075 mmol) and 4-methyl-3,4-dihydro-2H-benzo[b][1,4]oxazin-6-ylboronic acid (17.4 mg, 0.09 mmol), (R)-4-((R)-1-(3-methyl-6-(4-methyl-3,4-dihydro-2H-benzo[b][1,4]oxazin-6-yl)-3H-imidazo[4,5-c]pyridin-4-yloxy)ethyl)pyrrolidin-2-one 3B.04 was synthesized.

1H NMR (400 MHz CD3OD) δ 8.10 (s, 1H), 7.55 (s, 1H), 7.43 (d, J=2.4 Hz, 1H), 7.31 (dd, J=8, 2 Hz, 1H), 6.74 (d, J=8.8 Hz, 1H), 5.71 (p, J=5.2 Hz, 1H), 4.32-4.28 (m, 2H), 4.04 (s, 3H), 3.62 (dd, J=9.8, 8.8 Hz, 1H), 3.39 (dd, J=10.2, 5.2 Hz, 1H), 3.31-3.25 (m, 3H), 3.02-2.93 (m, 1H), 2.96 (s, 3H), 2.64-2.50 (m, 2H), 1.51 (d, J=6 Hz, 3H).

LCMS-ESI+ (m/z): [M+H]+ calcd for $C_{22}H_{26}N_5O_3$: 408.20; found: 408.21.

Example 3B.05

Preparation of (R)-4-((R)-1-(6-(3,4-dihydro-2H-benzo[b][1,4]oxazin-6-yl)-3-methyl-3H-imidazo[4,5-c]pyridin-4-yloxy)ethyl)pyrrolidin-2-one

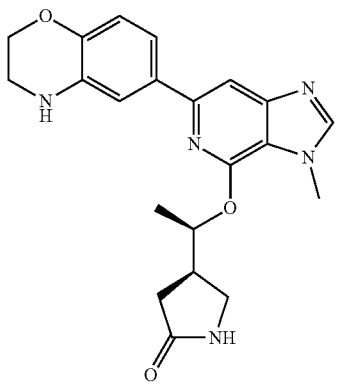
Example 3B.05

Following General Procedure B, beginning with (R)-4-((R)-1-(6-chloro-3-methyl-3H-imidazo[4,5-c]pyridin-4-yloxy)ethyl)pyrrolidin-2-one 2.06 (22.5 mg, 0.076 mmol) and 3,4-dihydro-2H-benzo[b][1,4]oxazin-6-ylboronic acid (16.2 mg, 0.091 mmol), (R)-4-((R)-1-(6-(3,4-dihydro-2H-benzo[b][1,4]oxazin-6-yl)-3-methyl-3H-imidazo[4,5-c]pyridin-4-yloxy)ethyl)pyrrolidin-2-one 3B.05 was synthesized.

$^1$H NMR (400 MHz, CD$_3$OD) δ 8.09 (s, 1H), 7.52 (s, 1H), 7.36 (d, J=2.1 Hz, 1H), 7.28 (dd, J=8.4, 2.2 Hz, 1H), 6.73 (d, J=8.4 Hz, 1H), 5.75 (p, J=6.0 Hz, 1H), 4.28-4.15 (m, 2H), 4.04 (s, 3H), 3.62 (dd, J=10.2, 8.7 Hz, 1H), 3.45-3.34 (m, 3H), 3.02-2.87 (m, 1H), 2.71-2.44 (m, 2H), 1.49 (d, J=6.3 Hz, 3H).

LCMS-ESI$^+$ (m/z): [M+H]$^+$ calcd for C$_{21}$H$_{24}$N$_5$O$_3$: 394.18; found: 394.18.

Example 3B.06

Preparation of (R)-4-((R)-1-(3-methyl-6-(4-methyl-3,4-dihydro-2H-benzo[b][1,4]oxazin-7-yl)-3H-imidazo[4,5-c]pyridin-4-yloxy)ethyl)pyrrolidin-2-one

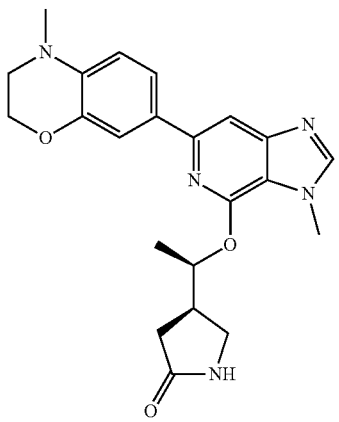
Example 3B.06

Following General Procedure B, beginning with (R)-4-((R)-1-(6-chloro-3-methyl-3H-imidazo[4,5-c]pyridin-4-yloxy)ethyl)pyrrolidin-2-one 2.06 (22.1 mg, 0.075 mmol) and 4-methyl-7-(4,4,5,5-tetramethyl-1,3,2-dioxaborolan-2-yl)-3,4-dihydro-2H-benzo[b][1,4]oxazine (25 mg, 0.091 mmol) (R)-4-((R)-1-(3-methyl-6-(4-methyl-3,4-dihydro-2H-benzo[b][1,4]oxazin-7-yl)-3H-imidazo[4,5-c]pyridin-4-yloxy)ethyl)pyrrolidin-2-one 3B.06 was synthesized.

$^1$H NMR (400 MHz, CD$_3$OD) δ 8.08 (d, J=0.6 Hz, 1H), 7.54-7.45 (m, 2H), 7.42 (d, J=2.1 Hz, 1H), 6.76 (d, J=8.5 Hz, 1H), 5.79-5.69 (m, 1H), 4.33-4.24 (m, 2H), 4.03 (s, 3H), 3.62 (dd, J=10.1, 8.6 Hz, 1H), 3.39 (dd, J=10.2, 5.6 Hz, 1H), 3.32-3.26 (m, 2H), 3.02-2.93 (m, 1H), 2.92 (s, 3H), 2.64-2.47 (m, 2H), 1.50 (d, J=6.2 Hz, 3H).

LCMS-ESI$^+$ (m/z): [M+H]$^+$ calcd for C$_{22}$H$_{26}$N$_5$O$_3$: 408.20; found: 408.17.

Example 3B.07

Preparation of (R)-4-((R)-1-(3-methyl-6-(1-(oxetan-3-yl)-1H-pyrazol-4-yl)-3H-imidazo[4,5-c]pyridin-4-yloxy)ethyl)pyrrolidin-2-one

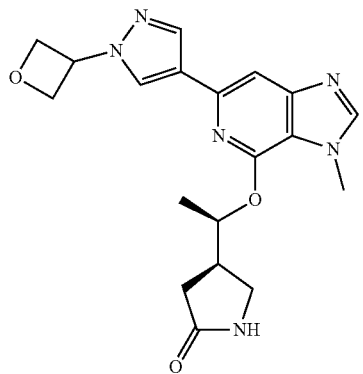
Example 3B.07

Following General Procedure B, beginning with crude (R)-4-((R)-1-(6-chloro-3-methyl-3H-imidazo[4,5-c]pyridin-4-yloxy)ethyl)pyrrolidin-2-one 2.06 (25 mg, 0.085 mmol) and 1-(3-oxetanyl)-1H-pyrazole-4-boronic acid pinacol ester (28 mg, 0.11 mmol), (R)-4-((R)-1-(3-methyl-6-(1-(oxetan-3-yl)-1H-pyrazol-4-yl)-3H-imidazo[4,5-c]pyridin-4-yloxy)ethyl)pyrrolidin-2-one 3B.07 was isolated as the trifluoroacetic acid salt, following prep HPLC (2-95% acetonitrile in water, 0.1% trifluoroacetic acid buffer).

$^1$H NMR (400 MHz, DMSO-d$_6$) δ 8.64 (s, 1H), 8.42 (s, 1H), 8.17 (s, 1H), 7.59 (s, 1H), 7.56 (s, 1H), 5.71-5.47 (m, 2H), 4.94 (d, J=7.1 Hz, 4H), 4.00 (s, 3H), 3.42 (t, J=9.2 Hz, 1H), 3.17 (dd, J=9.8, 6.2 Hz, 1H), 2.84-2.75 (m, 1H), 2.45-2.17 (m, 2H), 1.39 (d, J=6.2 Hz, 3H).

LCMS-ESI$^+$ (m/z): [M+H]$^+$ calcd for C$_{19}$H$_{22}$N$_6$O$_3$: 383.2; found 383.1.

Example 3B.08

Preparation of (R)-4-((R)-1-(6-(1-(2-fluoroethyl)-1H-pyrazol-4-yl)-3-methyl-3H-imidazo[4,5-c]pyridin-4-yloxy)ethyl)pyrrolidin-2-one Example 3B.08

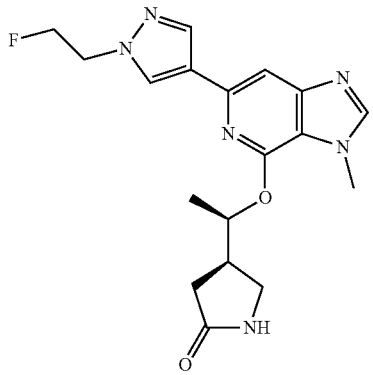

Following General Procedure B, beginning with crude (R)-4-((R)-1-(6-chloro-3-methyl-3H-imidazo[4,5-c]pyridin-4-yloxy)ethyl)pyrrolidin-2-one 2.06 (27 mg, 0.092 mmol) and 1-(2-fluoroethyl)-4-(4,4,5,5-tetramethyl-1,3,2-dioxaborolan-2-yl)-1H-pyrazole (29 mg, 0.12 mmol), (R)-4-((R)-1-(6-(1-(2-fluoroethyl)-1H-pyrazol-4-yl)-3-methyl-3H-imidazo[4,5-c]pyridin-4-yloxy)ethyl)pyrrolidin-2-one 3B.08 was isolated as the trifluoroacetic acid salt, following prep HPLC (2-95% acetonitrile in water, 0.1% trifluoroacetic acid buffer).

$^1$H NMR (400 MHz, DMSO-$d_6$) δ 8.75 (s, 1H), 8.31 (s, 1H), 8.09 (d, J=0.7 Hz, 1H), 7.59 (s, 1H), 7.55 (s, 1H), 5.54 (p, J=6.1 Hz, 1H), 4.86 (t, J=4.7 Hz, 1H), 4.75 (t, J=4.7 Hz, 1H), 4.51 (t, J=4.7 Hz, 1H), 4.44 (t, J=4.7 Hz, 1H), 4.01 (s, 3H), 3.42 (t, J=9.1 Hz, 1H), 3.17 (dd, J=9.8, 6.2 Hz, 1H), 2.94-2.71 (m, 1H), 2.44-2.16 (m, 2H), 1.40 (d, J=6.2 Hz, 3H).

LCMS-ESI$^+$ (m/z): [M+H]$^+$ calcd for $C_{18}H_{21}FN_6O_2$: 373.2; found 373.2.

Example 3B.09

Preparation of (R)-4-((R)-1-(3-methyl-6-(1-(2,2,2-trifluoroethyl)-1H-pyrazol-4-yl)-3H-imidazo[4,5-c]pyridin-4-yloxy)ethyl)pyrrolidin-2-one Example 3B.09

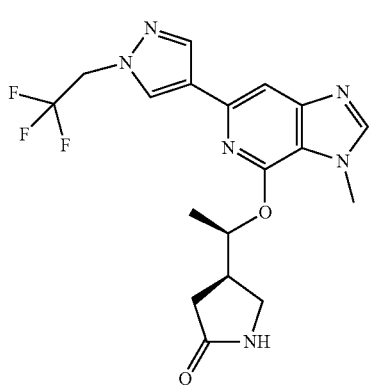

Following General Procedure B, beginning with crude (R)-4-((R)-1-(6-chloro-3-methyl-3H-imidazo[4,5-c]pyridin-4-yloxy)ethyl)pyrrolidin-2-one 2.06 (34 mg, 0.12 mmol) and 4-(4,4,5,5-tetramethyl-1,3,2-dioxaborolan-2-yl)-1-(2,2,2-trifluoroethyl)-1H-pyrazole (41 mg, 0.15 mmol), (R)-4-((R)-1-(3-methyl-6-(1-(2,2,2-trifluoroethyl)-1H-pyrazol-4-yl)-3H-imidazo[4,5-c]pyridin-4-yloxy)ethyl)pyrrolidin-2-one 3B.09 was isolated as the trifluoroacetic acid salt, following prep HPLC (2-95% acetonitrile in water, 0.1% trifluoroacetic acid buffer).

$^1$H NMR (400 MHz, DMSO-$d_6$) δ 8.41 (s, 1H), 8.33 (s, 1H), 8.16 (s, 1H), 7.58 (s, 2H), 5.54-5.48 (m, 1H), 5.18 (q, J=9.1 Hz, 2H), 3.97 (s, 3H), 3.42 (t, J=9.2 Hz, 1H), 3.16 (dd, J=9.7, 6.2 Hz, 1H), 2.90-2.73 (m, 1H), 2.44-2.16 (m, 2H), 1.40 (d, J=6.2 Hz, 3H).

LCMS-ESI$^+$ (m/z): [M+H]$^+$ calcd for $C_{18}H_{19}F_3N_6O_2$: 409.2; found 409.1.

Example 3B.10

Preparation of (R)-4-((R)-1-(6-(1-isopropyl-1H-pyrazol-4-yl)-3-methyl-3H-imidazo[4,5-c]pyridin-4-yloxy)ethyl)pyrrolidin-2-one Example 3B.10

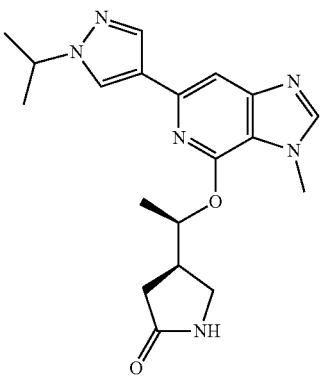

Following General Procedure B, beginning with crude (R)-4-((R)-1-(6-chloro-3-methyl-3H-imidazo[4,5-c]pyridin-4-yloxy)ethyl)pyrrolidin-2-one 2.06 (30.0 mg, 0.102 mmol) and 1-isopropyl-1H-pyrazole-4-boronic ester (31.2 mg, 0.132 mmol) (R)-4-((R)-1-(6-(1-isopropyl-1H-pyrazol-4-yl)-3-methyl-3H-imidazo[4,5-c]pyridin-4-yloxy)ethyl)pyrrolidin-2-one 3B.10 was isolated as the trifluoroacetic acid salt, following prep HPLC (2-95% acetonitrile in water, 0.1% trifluoroacetic acid buffer).

$^1$H NMR (400 MHz, DMSO-$d_6$) δ 8.66 (s, 1H), 8.29 (s, 1H), 7.99 (s, 1H), 7.57 (s, 1H), 7.52 (s, 1H), 5.55 (p, J=6.1 Hz, 1H), 4.54 (p, J=6.7 Hz, 1H), 4.00 (s, 3H), 3.42 (t, J=9.2 Hz, 1H), 3.17 (dd, J=9.8, 6.2 Hz, 1H), 2.90-2.74 (m, 1H), 2.42-2.21 (m, 2H), 1.46 (d, J=6.7 Hz, 6H), 1.40 (d, J=6.2 Hz, 3H).

LCMS-ESI$^+$ (m/z): [M+H]$^+$ calcd for $C_{19}H_{24}N_6O_2$: 369.2; found 369.3.

Example 3B.11

Preparation of (R)-4-((R)-1-(3-methyl-6-(1-(tetrahydro-2H-pyran-4-yl)-1H-pyrazol-4-yl)-3H-imidazo[4,5-c]pyridin-4-yloxy)ethyl)pyrrolidin-2-one Example 3B.11

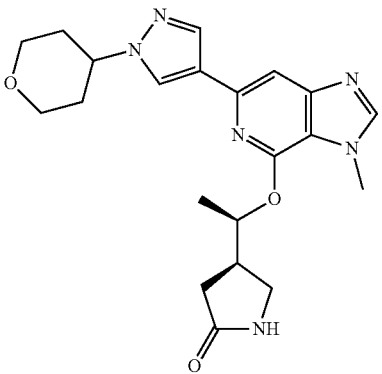

Following General Procedure B, beginning with crude (R)-4-((R)-1-(6-chloro-3-methyl-3H-imidazo[4,5-c]pyridin-4-yloxy)ethyl)pyrrolidin-2-one 2.06 (30.0 mg, 0.102 mmol) and 1-(tetrahydro-pyran-4-yl)-1H-pyrazole-4-boronic acid pinacol ester (36.8 mg, 0.132 mmol), (R)-4-((R)-1-(3-methyl-6-(1-(tetrahydro-2H-pyran-4-yl)-1H-pyrazol-4-yl)-3H-imidazo[4,5-c]pyridin-4-yloxy)ethyl)pyrrolidin-2-one 3B.11 was isolated as the trifluoroacetic acid salt, following prep HPLC (2-95% acetonitrile in water, 0.1% trifluoroacetic acid buffer).

$^1$H NMR (400 MHz, DMSO-$d_6$) δ 8.68 (s, 1H), 8.34 (s, 1H), 8.03 (s, 1H), 7.57 (s, 1H), 7.53 (s, 1H), 5.56 (p, J=6.1 Hz, 1H), 4.48-4.41 (m, 1H), 4.00-3.94 (m, 5H), 3.59-3.34 (m, 3H), 3.17 (dd, J=9.8, 6.2 Hz, 1H), 2.86-2.77 (m, 1H), 2.44-2.20 (m, 2H), 2.02-1.97 (m, 4H), 1.40 (d, J=6.1 Hz, 3H).

LCMS-ESI$^+$ (m/z): [M+H]$^+$ calcd for $C_{21}H_{26}N_6O_3$: 411.2; found 411.2.

Example 3B.12

Preparation of (R)-4-((R)-1-(3-methyl-6-(1-methyl-1H-pyrazol-4-yl)-3H-imidazo[4,5-c]pyridin-4-yloxy)ethyl)pyrrolidin-2-one

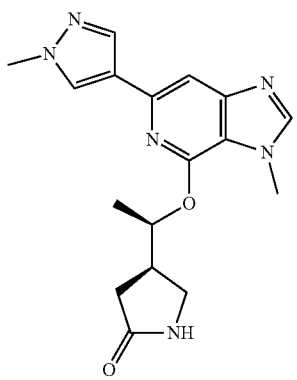

Example 3B.12

Following General Procedure B, beginning with crude (R)-4-((R)-1-(6-chloro-3-methyl-3H-imidazo[4,5-c]pyridin-4-yloxy)ethyl)pyrrolidin-2-one 2.06 (28 mg, 0.095 mmol) and 1-methyl-1H-pyrazole-4-boronic acid (16 mg, 0.12 mmol), (R)-4-((R)-1-(3-methyl-6-(1-methyl-1H-pyrazol-4-yl)-3H-imidazo[4,5-c]pyridin-4-yloxy)ethyl)pyrrolidin-2-one 3B.12 was isolated as the trifluoroacetic acid salt, following prep HPLC (2-95% acetonitrile in water, 0.1% trifluoroacetic acid buffer).

$^1$H NMR (400 MHz, DMSO-$d_6$) δ 8.58 (s, 1H), 8.21 (s, 1H), 7.98 (d, J=0.8 Hz, 1H), 7.57 (s, 1H), 7.49 (s, 1H), 5.53 (p, J=6.1 Hz, 1H), 3.99 (s, 3H), 3.88 (s, 3H), 3.42 (t, J=9.1 Hz, 1H), 3.17 (dd, J=9.7, 6.2 Hz, 1H), 2.86-2.77 (m, 1H), 2.44-2.17 (m, 2H), 1.39 (d, J=6.2 Hz, 3H).

LCMS-ESI$^+$ (m/z): [M+H]$^+$ calcd for $C_{17}H_{20}N_6O_2$: 341.2; found 341.2.

Example 3B.13

Preparation of (R)-4-((R)-1-(6-(4-fluoro-3-methoxyphenyl)-3-methyl-3H-imidazo[4,5-c]pyridin-4-yloxy)ethyl)pyrrolidin-2-one

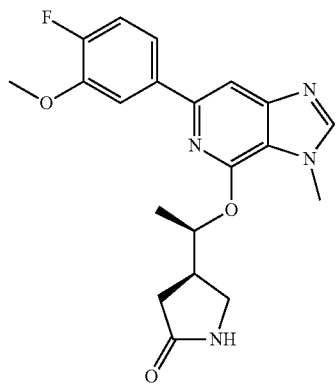

Example 3B.13

Following General Procedure B, beginning with (R)-4-((R)-1-(6-chloro-3-methyl-3H-imidazo[4,5-c]pyridin-4-yloxy)ethyl)pyrrolidin-2-one 2.06 (42 mg, 0.143 mmol) and 2-(4-fluoro-3-methoxyphenyl)-4,4,5,5-tetramethyl-1,3,2-dioxaborolane (44 mg, 0.175 mmol), (R)-4-((R)-1-(6-(4-fluoro-3-methoxyphenyl)-3-methyl-3H-imidazo[4,5-c]pyridin-4-yloxy)ethyl)pyrrolidin-2-one 3B.13 was synthesized.

$^1$H NMR (400 MHz, CD$_3$OD) δ 8.15 (s, 1H), 7.79 (dd, J=8.4, 2.1 Hz, 1H), 7.67 (s, 1H), 7.61 (ddd, J=8.5, 4.3, 2.2 Hz, 1H), 7.14 (dd, J=11.2, 8.5 Hz, 1H), 5.78-5.68 (m, 1H), 4.06 (s, 3H), 3.97 (s, 3H), 3.63 (dd, J=10.2, 8.6 Hz, 1H), 3.39 (dd, J=10.2, 5.5 Hz, 1H), 3.04-2.91 (m, 1H), 2.67-2.47 (m, 2H), 1.52 (d, J=6.2 Hz, 3H).

LCMS-ESI$^+$ (m/z): [M+H]$^+$ calcd for $C_{20}H_{22}FN_4O_3$: 385.16; found: 385.16.

Example 3B.14

Preparation of 2-methoxy-4-(3-methyl-4-((R)-1-((R)-5-oxopyrrolidin-3-yl)ethoxy)-3H-imidazo[4,5-c]pyridin-6-yl)benzonitrile

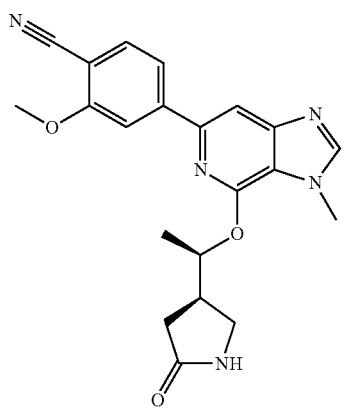

Example 3B.14

Following General Procedure B, beginning with (R)-4-((R)-1-(6-chloro-3-methyl-3H-imidazo[4,5-c]pyridin-4-yloxy)ethyl)pyrrolidin-2-one 2.06 (41 mg, 0.139 mmol) and 4-cyano-3-methoxyphenylboronic acid (31 mg, 0.18 mmol), 2-methoxy-4-(3-methyl-4-((R)-14(R)-5-oxopyrrolidin-3-yl)ethoxy)-3H-imidazo[4,5-c]pyridin-6-yl)benzonitrile 3B.14 was synthesized.

$^1$H NMR (400 MHz, CD$_3$OD) δ 8.20 (s, 1H), 7.87 (d, J=1.5 Hz, 1H), 7.86 (d, J=0.7 Hz, 1H), 7.79 (dd, J=8.1, 1.5 Hz, 1H), 7.67 (d, J=8.1 Hz, 1H), 5.80-5.67 (m, 1H), 4.08 (s, 3H), 4.06 (s, 3H), 3.68-3.58 (m, 1H), 3.39 (dd, J=10.2, 5.5 Hz, 1H), 3.05-2.94 (m, 1H), 2.68-2.43 (m, 2H), 1.53 (d, J=6.2 Hz, 3H).

LCMS-ESI$^+$ (m/z): [M+H]$^+$ calcd for C$_{21}$H$_{22}$N$_5$O$_3$: 392.16; found: 392.18.

Example 3B.15

Preparation of tert-butyl 4-(4-(3-methyl-4-((R)-1-((R)-5-oxopyrrolidin-3-yl)ethoxy)-3H-imidazo[4,5-c]pyridin-6-yl)phenyl)piperazine-1-carboxylate Example 3B.15

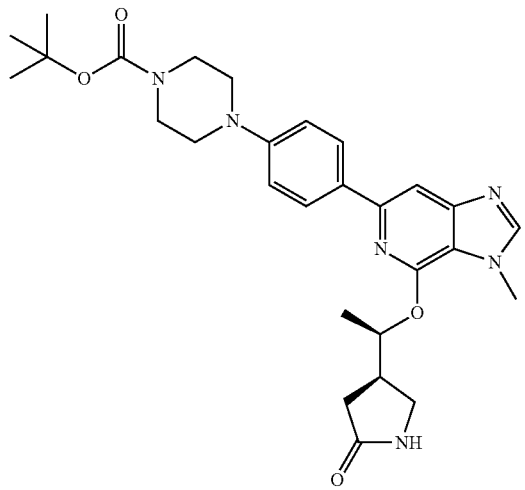

Following General Procedure B, beginning with crude (R)-4-((R)-1-(6-chloro-3-methyl-3H-imidazo[4,5-c]pyridin-4-yloxy)ethyl)pyrrolidin-2-one 2.06 (34 mg, 0.12 mmol) and 4-(4-BOC-piperazino)phenylboronic acid (46 mg, 0.15 mmol), the residue was purified via prep HPLC (2-95% acetonitrile in water, 0.1% trifluoroacteic acid buffer) followed by neutralization to isolate tert-butyl 4-(4-(3-methyl-4-((R)-1-((R)-5-oxopyrrolidin-3-yl)ethoxy)-3H-imidazo[4,5-c]pyridin-6-yl)phenyl)piperazine-1-carboxylate 3B.15.

$^1$H NMR (400 MHz, DMSO-d6) δ 8.19 (s, 1H), 7.96 (d, J=8.8 Hz, 2H), 7.66 (s, 1H), 7.56 (s, 1H), 7.02 (d, J=8.8 Hz, 2H), 5.54 (p, J=6.0 Hz, 1H), 3.96 (s, 3H), 3.49-3.40 (m, 5H), 3.20-3.15 (m, 5H), 2.87-2.80 (m, 1H), 2.40-2.25 (m, 2H), 1.43-1.41 (m, 12H).

LCMS-ESI$^+$ (m/z): [M+H]$^+$ calcd for C$_{28}$H$_{36}$N$_6$O$_4$: 521.3; found 521.2.

Example 3B.16

Preparation of (R)-4-((R)-1-(6-(1-(difluoromethyl)-1H-pyrazol-4-yl)-3-methyl-3H-imidazo[4,5-c]pyridin-4-yloxy)ethyl)pyrrolidin-2-one Example 3B.16

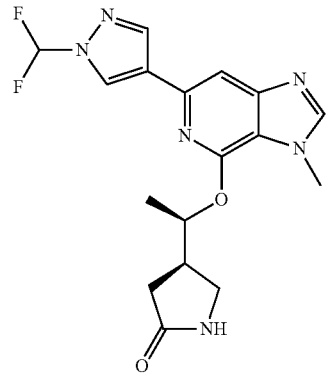

Following General Procedure B, beginning with crude (R)-4-((R)-1-(6-chloro-3-methyl-3H-imidazo[4,5-c]pyridin-4-yloxy)ethyl)pyrrolidin-2-one 2.06 (28 mg, 0.095 mmol) and 1-(difluoromethyl)-4-(4,4,5,5-tetramethyl-1,3,2-dioxaborolan-2-yl)-1H-pyrazole (30 mg, 0.124 mmol), the residue was purified via prep HPLC (2-95% acetonitrile in water, 0.1% trifluoroacteic acid buffer) to isolate (R)-4-((R)-1-(6-(1-(difluoromethyl)-1H-pyrazol-4-yl)-3-methyl-3H-imidazo[4,5-c]pyridin-4-yloxy)ethyl)pyrrolidin-2-one 3B.16 as the trifluoroacetic acid salt.

$^1$H NMR (400 MHz, DMSO-d$_6$) δ 8.72 (s, 1H), 8.43 (s, 1H), 8.38 (s, 1H), 8.05-7.63 (m, 2H), 7.56 (s, 1H), 5.57 (p, J=6.0 Hz, 1H), 3.98 (s, 3H), 3.42 (t, J=9.2 Hz, 1H), 3.18 (dd, J=9.7, 6.2 Hz, 1H), 2.86-2.79 (m, 1H), 2.42-2.17 (m, 2H), 1.40 (d, J=6.2 Hz, 3H). LCMS-ESI$^+$ (m/z): [M+H]+ calcd for C$_{17}$H$_{18}$F$_2$N$_6$O$_2$: 377.2; found: 377.0.

Example 3B.17

Preparation of (R)-4-((R)-1-(3-methyl-6-(5-methyl-1H-pyrazol-3-yl)-3H-imidazo[4,5-c]pyridin-4-yloxy)ethyl)pyrrolidin-2-one Example 3B.17

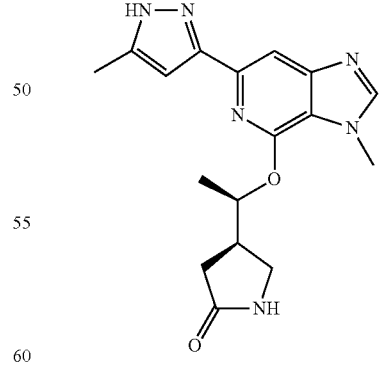

Following General Procedure B, beginning with crude (R)-4-((R)-1-(6-chloro-3-methyl-3H-imidazo[4,5-c]pyridin-4-yloxy)ethyl)pyrrolidin-2-one 2.06 (28 mg, 0.095 mmol) and (5-methyl-1H-pyrazol-3-yl)boronic acid, (16 mg, 0.127 mmol), the residue was purified via prep HPLC (2-95% acetonitrile in water, 0.1% trifluoroacteic acid buffer) to isolate (R)-4-((R)-1-(3-methyl-6-(5-methyl-1H-pyrazol-3-yl)-3H-imidazo[4,5-c]pyridin-4-yloxy)ethyl)pyrrolidin-2-one 3B.17 as the trifluoroacetic acid salt.

¹H NMR (400 MHz, DMSO-d6) δ 8.73 (s, 1H), 7.71 (s, 1H), 7.57 (s, 1H), 6.61 (s, 1H), 5.69-5.61 (m, 1H), 4.02 (s, 3H), 3.42 (t, J=9.3 Hz, 1H), 3.18 (t, J=7.9 Hz, 1H), 2.84-2.79 (m, 1H), 2.45-2.16 (m, 5H), 1.38 (d, J=5.9 Hz, 3H).

LCMS-ESI⁺ (m/z): [M+H]+ calcd for $C_{17}H_{20}N_6O_2$: 341.2; found: 341.1.

Example 3B.18

Preparation of (R)-4-((R)-1-(3-methyl-6-(4-(methylsulfonyl)phenyl)-3H-imidazo[4,5-c]pyridin-4-yloxy)ethyl)pyrrolidin-2-one Example 3B.18

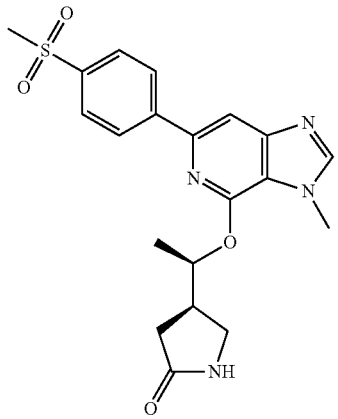

Following General Procedure B, beginning with (R)-4-((R)-1-(6-chloro-3-methyl-3H-imidazo[4,5-c]pyridin-4-yloxy)ethyl)pyrrolidin-2-one 2.06 (50 mg, 0.17 mmol) and 4-(methylsulfonyl)phenylboronic acid (44.1 mg, 0.22 mmol), (R)-4-((R)-1-(3-methyl-6-(4-(methylsulfonyl)phenyl)-3H-imidazo[4,5-c]pyridin-4-yloxy)ethyl)pyrrolidin-2-one 3B.18 was synthesized. ¹H NMR (400 MHz, Methanol-d₄) δ 9.04 (s, 1H), 8.42-8.26 (m, 2H), 8.14-7.99 (m, 2H), 7.93 (s, 1H), 5.91-5.69 (m, 1H), 4.20 (d, J=0.7 Hz, 3H), 3.65 (dd, J=10.2, 8.6 Hz, 1H), 3.40 (dd, J=10.2, 5.5 Hz, 1H), 3.16 (s, 3H), 3.00 (tdd, J=11.3, 7.2, 4.7 Hz, 1H), 2.72-2.32 (m, 2H), 1.55 (d, J=6.2 Hz, 3H). LCMS-ESI⁺ (m/z): [M+H]⁺ calcd $C_{20}H_{22}N_4O_4S$: 415.14; found 415.1.

Example 3B.19

Preparation of (R)-4-((R)-1-(6-(6-methoxypyridin-3-yl)-3-methyl-3H-imidazo[4,5-c]pyridin-4-yloxy)ethyl)pyrrolidin-2-one Example 3B.19

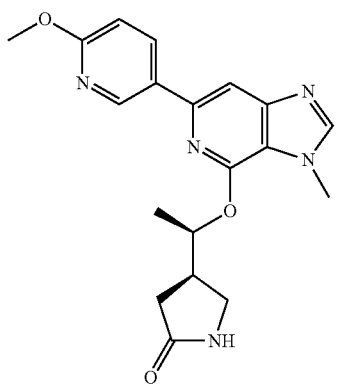

Following General Procedure B, beginning (R)-4-((R)-1-(6-chloro-3-methyl-3H-imidazo[4,5-c]pyridin-4-yloxy)ethyl)pyrrolidin-2-one 2.06 (25 mg, 0.085 mmol) and 6-methoxypyridin-3-ylboronic acid (16.8 mg, 0.11 mmol), (R)-4-((R)-1-(6-(6-methoxypyridin-3-yl)-3-methyl-3H-imidazo[4,5-c]pyridin-4-yloxy)ethyl)pyrrolidin-2-one 3B.19 was synthesized. 1H NMR (400 MHz, Methanol-d4) δ 8.92-8.70 (m, 2H), 8.37 (dd, J=8.8, 2.5 Hz, 1H), 7.72 (s, 1H), 6.92 (dd, J=8.7, 0.8 Hz, 1H), 5.89-5.58 (m, 1H), 4.16 (s, 3H), 3.98 (s, 3H), 3.70-3.55 (m, 1H), 3.38 (dd, J=10.2, 5.5 Hz, 1H), 3.10-2.91 (m, 1H), 2.72-2.39 (m, 2H), 1.53 (d, J=6.2 Hz, 3H). LCMS-ESI⁺ (m/z): [M+H]⁺ calcd for $C_{19}H_{21}N_5O_3$: 368.16; found 368.1.

Example 3B.22

Preparation of (R)-4-((R)-1-(5-(1-tert-butyl-1H-pyrazol-4-yl)-1-methyl-1H-benzo[d]imidazol-7-yloxy)ethyl)pyrrolidin-2-one 3B.22

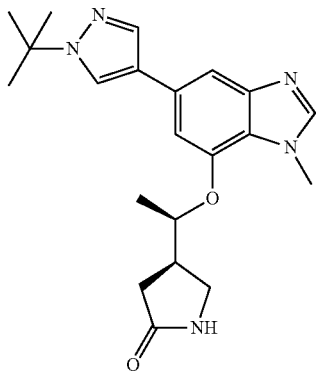

Following General Procedure B, beginning with crude (R)-4-((R)-1-(5-bromo-1-methyl-1H-benzo[d]imidazol-7-yloxy)ethyl)pyrrolidin-2-one 2.58 (50 mg, 0.15 mmol) and 1-tert-butyl-4-(4,4,5,5-tetramethyl-1,3,2-dioxaborolan-2-yl)-1H-pyrazole (74 mg, 0.30 mmol), (R)-4-((R)-1-(5-(1-tert-butyl-1H-pyrazol-4-yl)-1-methyl-1H-benzo[d]imidazol-7-yloxy)ethyl)pyrrolidin-2-one 3B.22 was isolated as the trifluoroacetic acid salt, following reverse phase chromatography. LC/MS found for $C_{21}H_{27}N_5O_2$ as (M+H)⁺ 382.2 ¹H NMR (400 MHz, DMSO-d₆) δ 9.25 (s, 1H), 8.41 (s, 1H); 8.00 (s, 1H); 7.63 (s, 1H); 7.48 (s, 1H); 7.35 (s, 1H); 4.97 (m, 1H), 4.07 (s, 3H), 3.45-3.41 (m, 1H), 3.16-3.12 (m, 1H), 2.82-2.79 (m, 1H), 2.42-2.21 (m, 2H), 1.55 (s, 9H); 1.35 (d, J=6.0 Hz, 3H).

Example 3B.23

Preparation of (R)-4-((R)-1-(1-methyl-5-(6-(trifluoromethyl)pyridin-2-yl)-1H-benzo[d]imidazol-7-yloxy)ethyl)pyrrolidin-2-one 3B.23

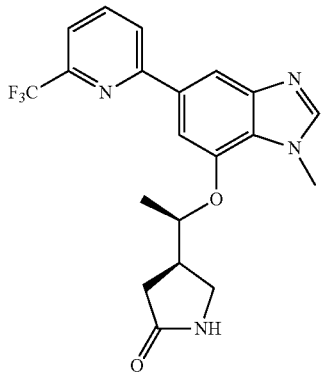

Following General Procedure B, beginning with crude (R)-4-((R)-1-(5-bromo-1-methyl-1H-benzo[d]imidazol-7-yloxy)ethyl)pyrrolidin-2-one 2.58 (50 mg, 0.15 mmol) and 2-(4,4,5,5-tetramethyl-1,3,2-dioxaborolan-2-yl)-6-(trifluoromethyl)pyridine (81 mg, 0.30 mmol), the title compound 3B.23 was isolated as the trifluoroacetic acid salt, following reverse phase chromatography. LC/MS found for $C_{20}H_{19}F_3N_4O_2$ as $(M+H)^+$ 405.1 $^1$H NMR (400 MHz, DMSO-$d_6$) δ 9.07 (s, 1H), 8.45 (d, J=8.4 Hz, 1H), 8.20 (t, J=8.0 Hz, 1H); 8.07 (s, 1H), 7.89 (d, J=8.0 Hz, 1H), 7.75 (s, 1H), 7.62 (s, 1H), 4.99-4.93 (m, 1H); 4.09 (s, 3H), 3.42-3.40 (m, 1H), 3.17-3.14 (m, 1H), 2.87-2.81 (m, 1H), 2.42-2.23 (m, 2H), 1.36 (d, J=6.0 Hz, 3H).

Example 3B.24

Preparation of (R)-4-((R)-1-(5-(6-methoxypyridin-2-yl)-1-methyl-1H-benzo[d]imidazol-7-yloxy)ethyl)pyrrolidin-2-one

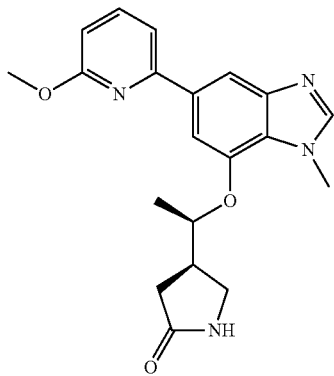

3B.24

Following General Procedure B, beginning with crude (R)-4-((R)-1-(5-bromo-1-methyl-1H-benzo[d]imidazol-7-yloxy)ethyl)pyrrolidin-2-one 2.58 (50 mg, 0.15 mmol) and 6-methoxypyridin-2-ylboronic acid (45 mg, 0.30 mmol), the title compound 3B.24 was isolated as the trifluoroacetic acid salt, following reverse phase chromatography.

LC/MS found for $C_{20}H_{22}N_4O_3$ as $(M+H)^+$ 367.1 $^1$H NMR (400 MHz, DMSO-$d_6$) δ 9.09 (s, 1H), 8.02 (s, 1H), 7.83 (t, J=7.6 Hz, 1H); 7.76 (s, 1H), 7.71 (d, J=7.6 Hz, 1H), 7.61 (s, 1H), 6.82 (d, J=8.0 Hz, 1H), 4.97-4.94 (m, 1H); 4.09 (s, 3H), 3.97 (s, 3H), 3.44-3.39 (m, 1H), 3.17-3.15 (m, 1H), 2.84-2.81 (m, 1H), 2.42-2.21 (m, 2H), 1.36 (d, J=6.0 Hz, 3H).

Example 3B.26

Preparation of (R)-4-((R)-1-(6-(4-(dimethylamino)-3-methylphenyl)-3-methyl-3H-imidazo[4,5-c]pyridin-4-yloxy)ethyl)pyrrolidin-2-one

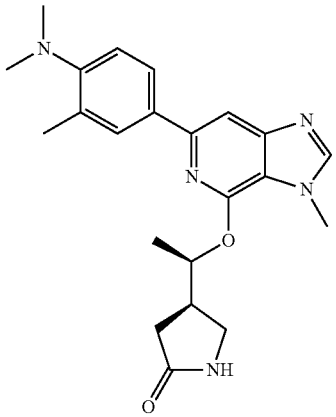

3B.26

Following General Procedure B, beginning with (R)-4-((R)-1-hydroxyethyl)-1-((R)-1-(4-methoxyphenyl)ethyl)pyrrolidin-2-one 2.62 (50 mg, 0.15 mmol) and 4-(dimethylamino)-3-methylphenylboronic acid (53 mg, 0.30 mmol), the title compound 3B.26 was isolated as the trifluoroacetic acid salt, following reverse phase chromatography. LC/MS found for $C_{22}H_{27}N_5O_2$ as $(M+H)^+$ 394.2 $^1$H NMR (400 MHz, dmso-$d_6$): δ 8.47 (s, 1H); 7.93 (m, 2H), 7.78 (s, 1H), 7.56 (s, 1H), 5.55 (m, 1H), 3.98 (s, 3H), 3.43-3.33 (m, 1H), 3.16-3.14 (m, 1H), 2.88 (s, 6H), 2.36 (s, 3H), 2.83-2.80 (m, 1H), 2.40-2.22 (m, 2H), 1.35 (d, J=6.4 Hz, 3H).

Example 3B.27

Preparation of (R)-4-((R)-1-(6-(benzo[d]thiazol-5-yl)-3-methyl-3H-imidazo[4,5-c]pyridin-4-yloxy)ethyl)pyrrolidin-2-one

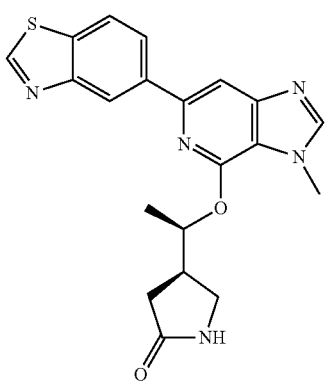

3B.27

Following General Procedure B, beginning with crude (R)-4-((R)-1-(6-chloro-3-methyl-3H-imidazo[4,5-c]pyridin-4-yloxy)ethyl)pyrrolidin-2-one 2.06 (50 mg, 0.17 mmol) and 5-(4,4,5,5-tetramethyl-1,3,2-dioxaborolan-2-yl)benzo[d]thiazole (49 mg, 0.19 mmol), (R)-4-((R)-1-(6-(benzo[d]thiazol-5-yl)-3-methyl-3H-imidazo[4,5-c]pyridin-4-yloxy)ethyl)pyrrolidin-2-one 3B.27 was isolated, following column chromatography.

¹H NMR (400 MHz, Chloroform-d) δ 9.03 (s, 1H), 8.83 (d, 1H), 8.11 (m 1H), 8.01 (m, 1H), 7.85 (s, 2H), 5.85 (m, 1H), 5.75 (s, 1H), 4.038 (s, 3H), 3.61 (m, 1H), 3.41 (m, 1H), 2.94 (m, 1H), 2.56 (m, 2H), 1.52 (d, 3H).

LCMS-ESI⁺ (m/z): [M+H]⁺ calcd for $C_{20}H_{19}N_5O_2S$: 394.13; found 394.14.

Example 3B.28

Preparation of (R)-4-((R)-1-(3-methyl-6-(2-methyl-benzo[d]thiazol-5-yl)-3H-imidazo[4,5-c]pyridin-4-yloxy)ethyl)pyrrolidin-2-one

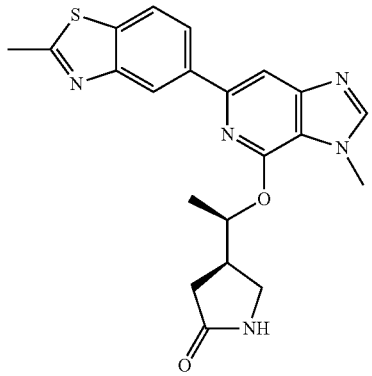

3B.28

Following General Procedure B, beginning with crude (R)-4-((R)-1-(6-chloro-3-methyl-3H-imidazo[4,5-c]pyridin-4-yloxy)ethyl)pyrrolidin-2-one 2.06 (31 mg, 0.104 mmol) and 2-methyl-5-(4,4,5,5-tetramethyl-1,3,2-dioxaborolan-2-yl)benzo[d]thiazole (22 mg, 0.114 mmol), (R)-4-((R)-1-(3-methyl-6-(2-methylbenzo[d]thiazol-5-yl)-3H-imidazo[4,5-c]pyridin-4-yloxy)ethyl)pyrrolidin-2-one 3B.28 was isolated, following column chromatography.

¹H NMR (400 MHz, Chloroform-d) δ 9.08.455 (d, J=1.2 Hz, 1H), 8.09 (m, 1H), 7.98 (m, 1H), 7.83 (s, 1H), 7.79 (s, 1H), 5.88 (s, 1H), 5.794 (m, 1H), 4.022 (s, 3H), 3.608 (t, J=9.6 Hz, 1H), 3.41 (m, 1H), 2.95 (m, 1H), 2.854 (s, 3H), 2.55 (m, 2H), 1.52 (d, J=6.4 Hz, 3H). LCMS-ESI⁺ (m/z): [M+H]⁺ calcd for $C_{21}H_{21}N_5O_2S$: 408.14; found 408.11.

Example 3B.29

Preparation of (R)-4-((R)-1-(3-methyl-6-(1-methyl-1H-indazol-5-yl)-3H-imidazo[4,5-c]pyridin-4-yloxy)ethyl)pyrrolidin-2-one

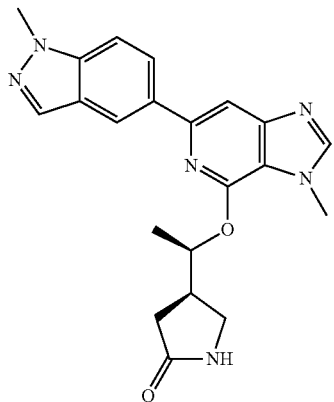

3B.29

Following General Procedure B, beginning with crude (R)-4-((R)-1-(6-chloro-3-methyl-3H-imidazo[4,5-c]pyridin-4-yloxy)ethyl)pyrrolidin-2-one 2.06 (35 mg, 0.119 mmol) and 1-methyl-1H-indazol-5-ylboronic acid (23 mg, 0.131 mmol), (R)-4-((R)-1-(3-methyl-6-(1-methyl-1H-indazol-5-yl)-3H-imidazo[4,5-c]pyridin-4-yloxy)ethyl)pyrrolidin-2-one 3B.29 was isolated, following column chromatography.

¹H NMR (400 MHz, Chloroform-d) δ 8.365 (s, 1H), 8.082 (d, 1H), 8.058 (s, 1H), 7.839 (s, 1H), 7.762 (s, 1H), 7.45 (d, J=8.8 Hz), 5.81 (m, 1H), 5.728 (s, 1H), 4.104 9s, 3H), 4.028 (s, 3H), 3.61 (t, J=9.2 Hz), 1H), 3.42 (m, 1H), 2.56 (m, 2H), 1.53 (d, J=6.4 Hz, 3H).

LCMS-ESI⁺ (m/z): [M+H]⁺ calcd for $C_{21}H_{22}N_6O_2$: 391.18; found 391.16.

Example 3B.30

Preparation of (R)-4-((R)-1-(3-methyl-6-(1-methyl-1H-indazol-6-yl)-3H-imidazo[4,5-c]pyridin-4-yloxy)ethyl)pyrrolidin-2-one

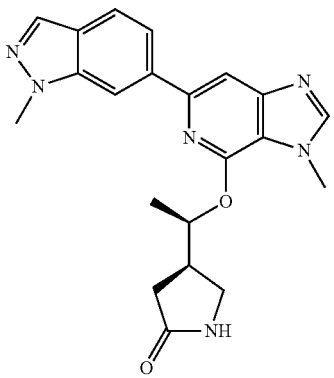

3B.30

Following General Procedure B, beginning with crude (R)-4-((R)-1-(6-chloro-3-methyl-3H-imidazo[4,5-c]pyridin-4-yloxy)ethyl)pyrrolidin-2-one 2.06 (35 mg, 0.119 mmol) and 1-methyl-1H-indazol-6-ylboronic acid (23 mg, 0.131 mmol), (R)-4-((R)-1-(3-methyl-6-(1-methyl-1H-indazol-6-yl)-3H-imidazo[4,5-c]pyridin-4-yloxy)ethyl)pyrrolidin-2-one 3B.30 was isolated, following column chromatography.

¹H NMR (400 MHz, Chloroform-d) δ 7.99 (m, 2H), 7.842 (m, 2H), 7.82 (s, 1H), 7.785 (s, 1H), 5.796 (m, 1H), 5.661 (s, 1H), 4.148 (s, 3H), 4.042 (s, 3H), 3.617 (t, 1H), 3.427 (m, 1H), 2.97 (m, 1H), 2.57 (m, 2H), 1.55 (d, 3H).

LCMS-ESI⁺ (m/z): [M+H]⁺ calcd for $C_{21}H_{22}N_6O_2$: 391.18; found 391.15.

Example 3B.31

Preparation of (R)-4-((R)-1-(6-(1,3-dimethyl-1H-indazol-5-yl)-3-methyl-3H-imidazo[4,5-c]pyridin-4-yloxy)ethyl)pyrrolidin-2-one

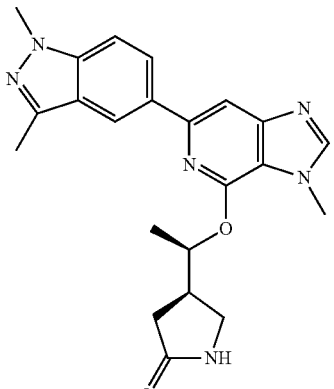

3B.31

Following General Procedure B, beginning with crude (R)-4-((R)-1-(6-chloro-3-methyl-3H-imidazo[4,5-c]pyridin-4-yloxy)ethyl)pyrrolidin-2-one 2.06 (45 mg, 0.153 mmol) and 1,3-dimethyl-1H-indazol-5-ylboronic acid (35 mg, 0.183 mmol), (R)-4-((R)-1-(6-(1,3-dimethyl-1H-indazol-5-yl)-3-methyl-3H-imidazo[4,5-c]pyridin-4-yloxy)ethyl)pyrrolidin-2-one 3B.31 was isolated, following column chromatography.

$^1$H NMR (400 MHz, Methanol-d) δ 8.224 (s, 1H), 8.05 (d, J=8 Hz, 1H), 7.799 (s, 1H), 7.742 (s, 1H), 7.35 (d, 8.4 Hz, 1H), 6.35 (s, 1H), 3.998 (s, 6H), 3.586 (m, 1H), 3.415 (m, 1H), 2.943 (m, 1H), 2.61 (s, 3H), 2.535 (m, 2H), 1.515 (d, J=4.8 Hz, 3H).

LCMS-ESI$^+$ (m/z): [M+H]$^+$ calcd for $C_{22}H_{24}N_6O_2$: 405.2; found 405.17.

General Procedure C for Synthesis of Examples 3C.01-3C.02

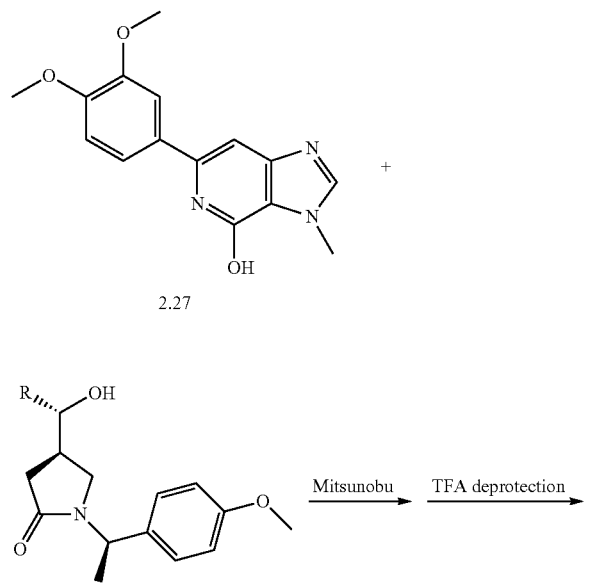

Examples 3C.01-3C.02

To a mixture of alcohol (1.5-2 eq), PPh$_3$ (1.5-2 eq), and DEAD (1.5-2 eq) was added THF and the reaction was stirred for 5 minutes. 6-(3,4-dimethoxyphenyl)-3-methyl-3H-imidazo[4,5-c]pyridin-4-ol 2.27 (1 eq) was added and the reaction was heated to 40° C. for 2 hours. Water and EtOAc were added, the layers separated, and the aqueous layer was extracted with EtOAc, and the combined organics were dried, filtered and concentrated under reduced pressure. The residue was purified by silica gel column chromatography. The isolated material was transferred to sealable vial, TFA was added and the reaction was heated to 60° C. for 12-18 hours. The reaction was concentrated and the residue was purified by RP-HPLC to yield Examples 3C.01-3C.02.

Example 3C.01

Preparation of (R)-4-((6-(3,4-dimethoxyphenyl)-3-methyl-3H-imidazo[4,5-c]pyridin-4-yloxy)methyl)pyrrolidin-2-one

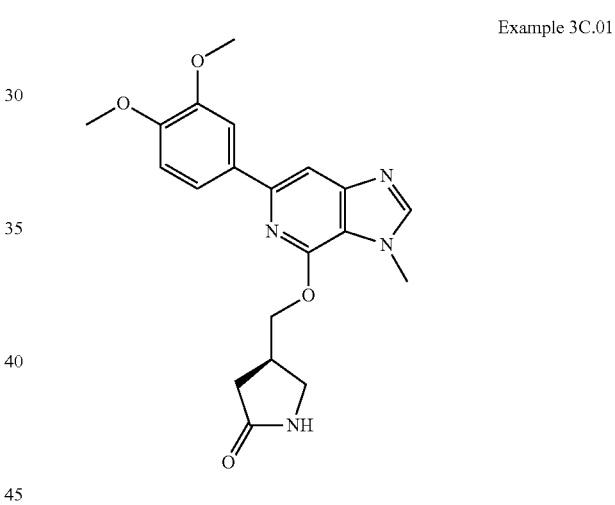

Example 3C.01

Following General Procedure C, beginning with 6-(3,4-dimethoxyphenyl)-3-methyl-3H-imidazo[4,5-c]pyridin-4-ol 2.27 (30 mg, 0.105 mmol) and (R)-4-(hydroxymethyl)-1-((R)-1-(4-methoxyphenyl)ethyl)pyrrolidin-2-one 1.06 (52 mg, 0.210 mmol), the residue was purified via prep HPLC (2-95% acetonitrile in water, 0.1% HCl buffer) to isolate (R)-4-((6-(3,4-dimethoxyphenyl)-3-methyl-3H-imidazo[4,5-c]pyridin-4-yloxy)methyl)pyrrolidin-2-one 3C.01 as the HCl salt.

$^1$H NMR (400 MHz, DMSO-d6) δ 8.82 (s, 1H), 7.83 (s, 1H), 7.67 (t, J=9.2 Hz, 3H), 7.03 (d, J=8.4 Hz, 1H), 4.53-4.62 (m, 2H), 4.04 (s, 3H), 3.85 (s, 3H), 3.79 (s, 3H), 3.48 (t, J=8.8 Hz, 1H), 3.22 (dd, J=5.6, 10 Hz, 1H), 2.96-2.99 (m, 1H), 2.40 (dd, J=8.8, 16.4 Hz, 1H), 2.17 (dd, J=6.8, 16.8 Hz, 1H).

LCMS-ESI+ (m/z): [M+H]+ calcd for C20H22N4O4: 382.4; found 383.1.

Example 3C.02

Preparation of (R)-4-((S)-1-(6-(3,4-dimethoxyphenyl)-3-methyl-3H-imidazo[4,5-c]pyridin-4-yloxy)ethyl)pyrrolidin-2-one Example 3C.02

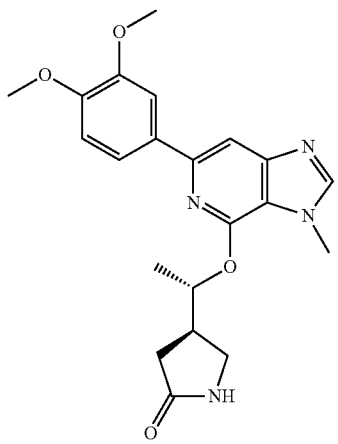

Following General Procedure C, beginning with 6-(3,4-dimethoxyphenyl)-3-methyl-3H-imidazo[4,5-c]pyridin-4-ol 2.27 (31 mg, 0.109 mmol) and (R)-4-((R)-1-hydroxyethyl)-1-4R)-1-(4-methoxyphenyl)ethyl)pyrrolidin-2-one 1.04 (43 mg, 0.163 mmol), the residue was purified via prep HPLC (2-95% acetonitrile in water, 0.1% HCl buffer) to isolate (R)-4-((S)-1-(6-(3,4-dimethoxyphenyl)-3-methyl-3H-imidazo[4,5-c]pyridin-4-yloxy)ethyl)pyrrolidin-2-on 3C.02 as the HCl salt.

$^1$H NMR (400 MHz, DMSO-d6) δ 8.6 (br s, 1H), 7.79 (s, 1H), 7.67 (s, 1H), 7.65 (s, 1H), 7.60 (s, 1H), 7.02 (d, J=8.8 Hz, 1H), 5.46-5.51 (m, 1H), 4.00 (s, 3H), 3.85 (s, 3H), 3.79 (s, 3H), 3.45 (t, J=9.2 Hz, 1H), 3.28 (dd, J=6.0, 7.2 Hz, 1H), 2.80-2.93 (m, 1H), 2.28-2.34 (m, 1H), 2.16 (dd, J=8.2, 16.8 Hz, 1H), 1.43 (d, J=6.0 Hz, 3H).

LCMS-ESI+ (m/z): [M+H]+ calcd for C21H24N4O4: 396.4; found 397.2.

General Procedure D for Synthesis of Examples 3D.01-3D.09

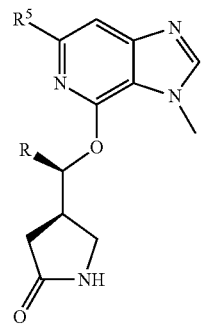

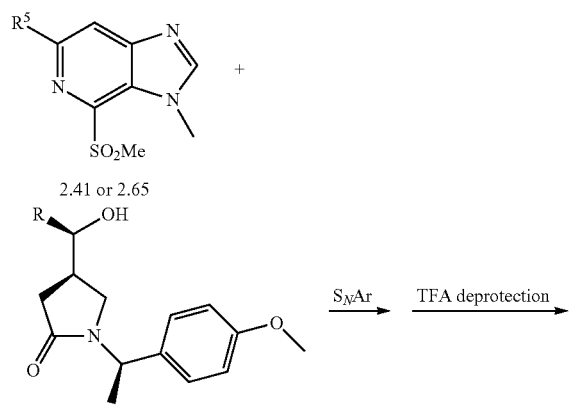

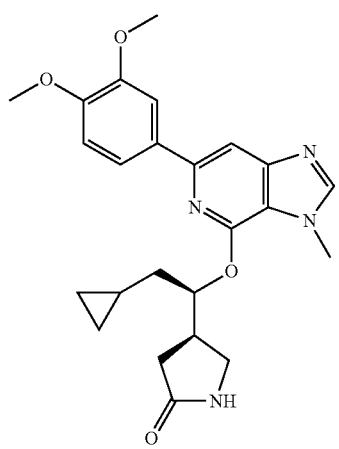

Examples 3D.01-3D.09

To a solution of alcohol (1.0-1.2 eq) in DMF was added NaHMDS (1.0M in THF, 1.3 eq), and the reaction was stirred for 15 min. 2.41 or 2.65 (1.0 eq) was added and the reaction was stirred at RT for 2 hours. Water and EtOAc were added, the layers separated, and the aqueous layer was extracted with EtOAc, and the combined organics were dried, filtered and concentrated under reduced pressure. The residue was purified by silica gel column chromatography. The isolated material was transferred to sealable vial, TFA was added and the reaction was heated to 60° C. for 12-18 hours. The reaction was concentrated and the residue was purified by RP-HPLC to yield Examples 3D.01-3D.09.

Example 3D.01

Preparation of (R)-4-((R)-2-cyclopropyl-1-(6-(3,4-dimethoxyphenyl)-3-methyl-3H-imidazo[4,5-c]pyridin-4-yloxy)ethyl)pyrrolidin-2-one Example 3D.01

Following General Procedure D, beginning with 6-(1-tert-butyl-1H-pyrazol-4-yl)-3-methyl-4-(methylsulfonyl)-3H-imidazo[4,5-c]pyridine 2.41 (43 mg, 0.142 mmol) and (R)-4-((R)-2-cyclopropyl-1-hydroxyethyl)-1-((R)-1-(4-methoxyphenyl)ethyl)pyrrolidin-2-one 1.09 (45 mg, 0.149 mmol), the residue was purified via prep HPLC (2-95% acetonitrile in water, 0.1% HCl buffer) to isolate (R)-4-((R)-2-cyclopropyl-1-(6-(3,4-dimethoxyphenyl)-3-methyl-3H-imidazo[4,5-c]pyridin-4-yloxy)ethyl)pyrrolidin-2-one 3D.01 as the HCl salt.

$^1$H NMR (400 MHz, CD3OD) δ 9.35 (s, 1H), 7.76 (s, 1H), 7.69-7.71 (m, 2H), 7.08 (t, J=8.8 Hz, 1H), 6.03 (dd, J=4.4, 10.8 Hz, 1H), 4.26 (s, 3H), 3.95 (s, 3H), 3.90 (s, 3H), 3.64-3.69 (m, 1H), 3.39 (dd, J=4.8, 10.0 Hz, 1H), 3.16-3.20 (m, 1H), 2.61 (dd, J=9.2, 17.2 Hz, 1H), 2.54 (dd, J=6.8, 17.2 Hz,

1H), 1.89-1.98 (m, 1H), 1.67-1.74 (m, 1H), 0.81-0.86 (m, 1H), 0.43-0.47 (m, 2H), 0.14-0.19 (m, 2H).

LCMS-ESI$^+$ (m/z): [M+H]$^+$ calcd for C$_{24}$H$_{28}$N$_4$O$_4$: 437.2; found 437.3.

Example 3D.02

Preparation of (R)-4-((S)-1-(6-(1-tert-butyl-1H-pyrazol-4-yl)-3-methyl-3H-imidazo[4,5-c]pyridin-4-yloxy)-2-fluoroethyl)pyrrolidin-2-one

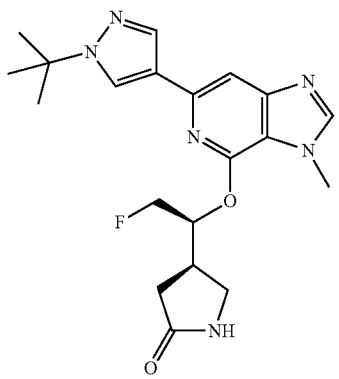

Example 3D.02

Following General Procedure D, beginning with 6-(1-tert-butyl-1H-pyrazol-4-yl)-3-methyl-4-(methylsulfonyl)-3H-imidazo[4,5-c]pyridine 2.41 (21.5 mg, 0.064 mmol) and (R)-4-((S)-1-(6-(1-tert-butyl-1H-pyrazol-4-yl)-3-methyl-3H-imidazo[4,5-c]pyridin-4-yloxy)-2-fluoroethyl)pyrrolidin-2-one 1.12 (18.0 mg, 0.064 mmol), the residue was purified via prep HPLC (2-95% acetonitrile in water, 0.1% HCl buffer) to isolate (R)-4-((S)-1-(6-(1-tert-butyl-1H-pyrazol-4-yl)-3-methyl-3H-imidazo[4,5-c]pyridin-4-yloxy)-2-fluoroethyl)pyrrolidin-2-one 3D.02 as the HCl salt.

$^1$H NMR (400 MHz, CD$_3$OD) δ 9.42 (s, 1H), 8.65 (s, 1H), 8.45 (s, 1H), 7.79 (s, 1H), 6.04-6.12 (m, 1H), 4.84-4.90 (m, 1H), 4.76-4.79 (m, 1H), 4.27 (s, 3H), 3.70 (t, J=10.0 Hz, 1H), 3.51 (dd, J=5.6, 10.0 Hz, 1H), 3.18-3.25 (m, 1H), 2.60-2.66 (m, 2H), 1.71 (s, 9H).

LCMS-ESI$^+$ (m/z): [M+H]$^+$ calcd for C$_{20}$H$_{25}$FN$_6$O$_2$: 401.2; found 401.2.

Example 3D.03

Preparation of (R)-4-((S)-1-(6-(1-tert-butyl-1H-pyrazol-4-yl)-3-methyl-3H-imidazo[4,5-c]pyridin-4-yloxy)-2-methoxyethyl)pyrrolidin-2-one

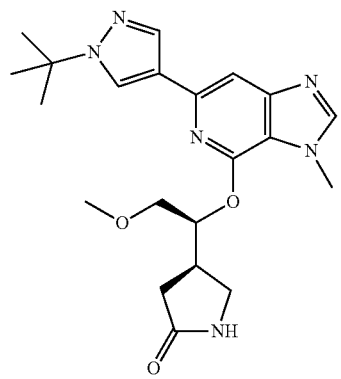

Example 3D.03

Following General Procedure D, beginning with 6-(1-tert-butyl-1H-pyrazol-4-yl)-3-methyl-4-(methylsulfonyl)-3H-imidazo[4,5-c]pyridine 2.41 (31 mg, 0.093 mmol) and 1.15 (27 mg, 0.092 mmol), the residue was purified via prep HPLC (2-95% acetonitrile in water, 0.1% HCl buffer) to isolate (R)-4-((S)-1-(6-(1-tert-butyl-1H-pyrazol-4-yl)-3-methyl-3H-imidazo[4,5-c]pyridin-4-yloxy)-2-methoxyethyl)pyrrolidin-2-one 3D.03 as the HCl salt.

$^1$H NMR (400 MHz, CD$_3$OD) δ 9.37 (s, 1H), 8.55 (s, 1H), 8.33 (s, 1H), 7.71 (s, 1H), 5.96-5.99 (m, 1H), 4.25 (s, 3H), 3.82 (dd, J=5.2, 10.4 Hz, 1H), 3.75 (dd, J=3.6, 10.8 Hz, 1H), 3.66 (t, J=9.2 Hz, 1H), 4.48 (dd, J=4.8, 9.6 Hz, 1H), 3.38 (s, 3H), 3.10-3.14 (m, 1H), 2.60 (d, J=8.0 Hz, 2H), 1.69 (s, 9H).

LCMS-ESI$^+$ (m/z): [M+H]$^+$ calcd for C$_{21}$H$_{28}$N$_6$O$_3$: 413.2; found 413.2.

Example 3D.04

Preparation of ((R)-4-((R)-1-(6-(1-tert-butyl-1H-pyrazol-4-yl)-3-methyl-3H-imidazo[4,5-c]pyridin-4-yloxy)but-3-enyl)pyrrolidin-2-one

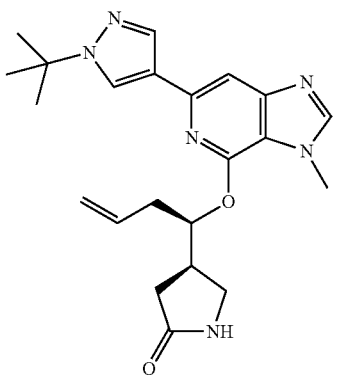

Example 3D.04

Following General Procedure D, beginning with 6-(1-tert-butyl-1H-pyrazol-4-yl)-3-methyl-4-(methylsulfonyl)-3H-imidazo[4,5-c]pyridine 2.41 (100 mg, 0.30 mmol) and 1.08 (87 mg, 0.030 mmol), the residue was purified via prep HPLC (2-95% acetonitrile in water, 0.1% TFA buffer) to isolate (R)-4-((R)-1-(6-(1-tert-butyl-1H-pyrazol-4-yl)-3-methyl-3H-imidazo[4,5-c]pyridin-4-yloxy)but-3-enyl)pyrrolidin-2-one 3D.04 as the TFA salt.

$^1$H NMR (400 MHz, CD$_3$OD) δ 9.21 (s, 1H), 8.33 (s, 1H), 8.27 (s, 1H), 7.55 (s, 1H), 5.90-5.97 (m, 2H), 5.19 (d, J=16.8 Hz, 1H), 5.09 (d, J=10.4 Hz, 1H), 4.20 (s, 3H), 3.60-3.65 (m, 1H), 3.37-3.42 (m, 1H), 3.02-3.10 (m, 1H), 2.68-2.72 (m, 1H), 2.55-2.65 (m, 3H), 1.64 (s, 9H).

LCMS-ESI$^+$ (m/z): [M+H]$^+$ calcd for C$_{22}$H$_{28}$N$_6$O$_2$: 409.2; found 409.2.

Example 3D.05

Preparation of (R)-4-((R)-1-(6-(1-tert-butyl-1H-pyrazol-4-yl)-3-methyl-3H-imidazo[4,5-c]pyridin-4-yloxy)-3-methoxypropyl)pyrrolidin-2-one

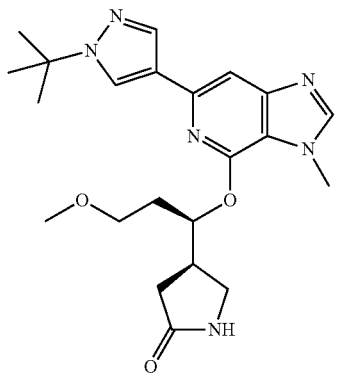

Example 3D.05

Following General Procedure D, beginning with 6-(1-tert-butyl-1H-pyrazol-4-yl)-3-methyl-4-(methylsulfonyl)-3H-imidazo[4,5-c]pyridine 2.41 (32 mg, 0.097 mmol) and 1.21 (33 mg, 0.106 mmol), the residue was purified via prep HPLC (2-95% acetonitrile in water, 0.1% TFA buffer) to isolate (R)-4-((R)-1-(6-(1-tert-butyl-1H-pyrazol-4-yl)-3-methyl-3H-imidazo[4,5-c]pyridin-4-yloxy)-3-methoxypropyl)pyrrolidin-2-one 3D.05 as the TFA salt.

$^1$H NMR (400 MHz, CD$_3$OD) δ 8.94 (s, 1H), 8.32 (s, 1H), 8.07 (s, 1H), 7.52 (s, 1H), 6.00-6.05 (m, 1H), 4.17 (s, 3H), 3.60-3.64 (m, 1H), 3.50-3.55 (m, 2H), 3.37-3.41 (m, 1H), 3.23 (s, 3H), 3.02-3.07 (m, 1H), 2.52-2.58 (m, 2H), 2.14-2.18 (m, 1H), 1.99-2.05 (m, 1H), 1.64 (s, 9H).

LCMS-ESI$^+$ (m/z): [M+H]$^+$ calcd for C$_{22}$H$_{30}$N$_6$O$_3$: 427.2; found 427.2.

Example 3D.06

Preparation of (R)-4-((R)-1-(6-(1-tert-butyl-1H-pyrazol-4-yl)-3-methyl-3H-imidazo[4,5-c]pyridin-4-yloxy)propyl)pyrrolidin-2-one

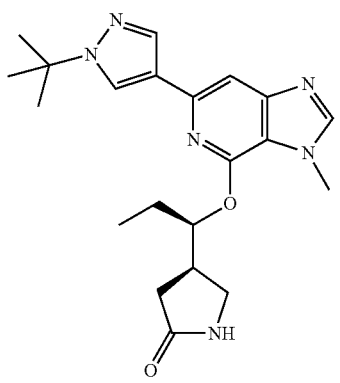

Example 3D.06

Following General Procedure D, beginning with 6-(1-tert-butyl-1H-pyrazol-4-yl)-3-methyl-4-(methylsulfonyl)-3H-imidazo[4,5-c]pyridine 2.41 (30 mg, 0.090 mmol) and 1.23 (27.5 mg, 0.099 mmol), the residue was purified via prep HPLC (2-95% acetonitrile in water, 0.1% TFA buffer) to isolate (R)-4-((R)-1-(6-(1-tert-butyl-1H-pyrazol-4-yl)-3-methyl-3H-imidazo[4,5-c]pyridin-4-yloxy)propyl)pyrrolidin-2-one 3D.06 as the TFA salt.

$^1$H NMR (400 MHz, CD$_3$OD) δ 9.09 (s, 1H), 8.31 (s, 1H), 8.05 (s, 1H), 7.53 (s, 1H), 5.20-5.84 (m, 1H), 4.19 (s, 3H), 3.61 (dd, J=8.0, 10.0 Hz, 1H), 3.39 (dd, J=5.2, 10.0 Hz, 1H), 3.03-3.08 (m, 1H), 2.47-2.60 (m, 2H), 1.82-1.98 (m, 2H), 1.64 (s, 9H), 1.05, (t, J=7.2 Hz, 3H).

LCMS-ESI$^+$ (m/z): [M+H]$^+$ calcd for C$_{21}$H$_{28}$N$_6$O$_2$: 397.2; found 397.2.

Example 3D.07

Preparation of (R)-4-((S)-1-(6-(1-tert-butyl-1H-pyrazol-4-yl)-3-methyl-3H-imidazo[4,5-c]pyridin-4-yloxy)-2,2-difluoroethyl)pyrrolidin-2-one

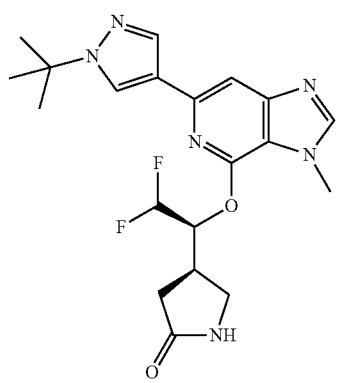

Example 3D.07

Following General Procedure D, beginning with 6-(1-tert-butyl-1H-pyrazol-4-yl)-3-methyl-4-(methylsulfonyl)-3H-imidazo[4,5-c]pyridine 2.41 (30 mg, 0.090 mmol) and 1.24 (29.6 mg, 0.099 mmol, mixture of 4 diastereomers). After the SnAr reaction, two of the undesired diastereomers were separated from the desired via RP-HPLC (Gemini column, water/CH$_3$CN/HCl, latest eluting peak was desired). The remaining two diastereomers were subjected to TFA deprotection and the residue was purified via prep HPLC (2-95% acetonitrile in water, 0.1% TFA buffer). This material was subjected to chiral HPLC chromatography (CHIRALPAK IC, 100% EtOH, later eluting diastereomer) to isolate (R)-4-((R)-1-(6-(1-tert-butyl-1H-pyrazol-4-yl)-3-methyl-3H-imidazo[4,5-c]pyridin-4-yloxy)propyl)pyrrolidin-2-one 3D.07.

$^1$H NMR (400 MHz, CD$_3$OD) δ 8.29 (s, 1H), 8.15 (s, 1H), 8.00 (s, 1H), 7.52 (s, 1H), 6.29 (dt, J=3.2, 54.8 Hz, 1H), 6.04-6.12 (m, 1H), 4.08 (s, 3H), 3.68 (dd, J=8.8, 10.4 Hz, 1H), 3.51 (dd, J=6.4, 10.4 Hz, 1H), 3.22-3.26 (m, 1H), 2.68 (dd, J=6.8, 17.6 Hz, 2H), 2.57 (dd, J=9.6, 17.6 Hz, 1H), 1.64 (s, 9H).

LCMS-ESI$^+$ (m/z): [M+H]$^+$ calcd for C$_{20}$H$_{24}$F$_2$N$_6$O$_2$: 419.2; found 419.2.

Example 3D.08

Preparation of (R)-4-48)-1-(6-(1-tert-butyl-1H-pyrazol-4-yl)-3-methyl-3H-imidazo[4,5-c]pyridin-4-yloxy)-2,2-difluoroethyl)pyrrolidin-2-one Example 3D.08

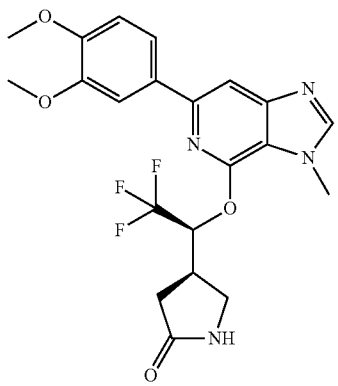

Following General Procedure D, beginning with 6-(3,4-dimethoxyphenyl)-3-methyl-4-(methylsulfonyl)-3H-imidazo[4,5-c]pyridine 2.65 (30 mg, 0.086 mmol) and 1.29 (32.9 mg, 0.104 mmol). The residue was purified via prep HPLC (2-95% acetonitrile in water, 0.1% TFA buffer) to isolate(R)-4-((S)-1-(6-(3,4-dimethoxyphenyl)-3-methyl-3H-imidazo[4,5-c]pyridin-4-yloxy)-2,2,2-trifluoroethyl)pyrrolidin-2-one 3D.08 as the TFA salt.

1H NMR (400 MHz, Methanol-d4) δ 8.86 (s, 1H), 7.84 (d, J=1.1 Hz, 1H), 7.70 (d, J=2.1 Hz, 1H), 7.70-7.64 (m, 1H), 7.09 (d, J=8.3 Hz, 1H), 6.65-6.54 (m, 1H), 4.19 (s, 3H), 3.96 (s, 3H), 3.91 (s, 3H), 3.80-3.69 (m, 1H), 3.59-3.50 (m, 1H), 2.77-2.57 (m, 2H). LCMS-ESI+ (m/z): [M+H]+ calcd for $C_{21}H_{21}F_3N_4O_4$: 451.2; found 451.1.

Example 3D.09

Preparation of ((R)-4-((R)-1-(6-(3,4-dimethoxyphenyl)-3-methyl-3H-imidazo[4,5-c]pyridin-4-yloxy)propyl)pyrrolidin-2-one Example 3D.09

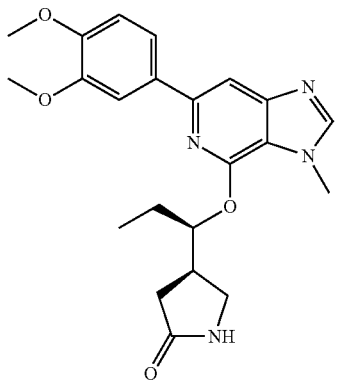

Following General Procedure D, beginning with 6-(3,4-dimethoxyphenyl)-3-methyl-4-(methylsulfonyl)-3H-imidazo[4,5-c]pyridine 2.65 (30 mg, 0.086 mmol) and 1.29 (28.7 mg, 0.104 mmol). The residue was purified via prep HPLC (2-95% acetonitrile in water, 0.1% TFA buffer) to isolate(R)-4-((R)-1-(6-(3,4-dimethoxyphenyl)-3-methyl-3H-imidazo[4,5-c]pyridin-4-yloxy)propyl)pyrrolidin-2-one 3D.09 as the TFA salt.

1H NMR (400 MHz, Methanol-d4) δ 8.86 (s, 1H), 7.77-7.62 (m, 3H), 7.08 (d, J=8.4 Hz, 1H), 5.83 (q, J=5.7 Hz, 1H), 4.20 (s, 3H), 3.96 (s, 3H), 3.92 (s, 3H), 3.65 (t, J=10.1, 8.6 Hz, 1H), 3.42 (q, J=10.2, 5.4 Hz, 2H), 3.18-3.02 (m, 1H), 2.58 (dd, J=7.9, 2.8 Hz, 2H), 2.06-1.78 (m, 2H), 1.10 (t, J=7.4 Hz, 3H).

LCMS-ESI+ (m/z): [M+H]+ calcd for $C_{22}H_{26}N_4O_4$: 411.2; found 411.2.

Example 3D.10

Preparation of (R)-4-((R)-1-((6-(3,4-dimethoxyphenyl)-3-methyl-3H-imidazo[4,5-c]pyridin-4-yl)oxy)-3-methoxypropyl)pyrrolidin-2-one

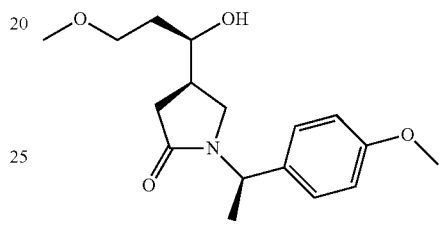

1.21

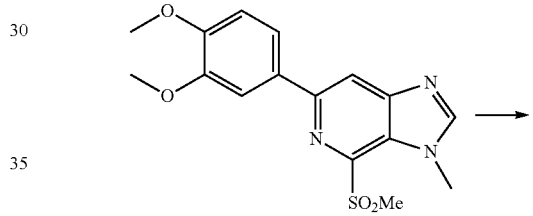

2.65

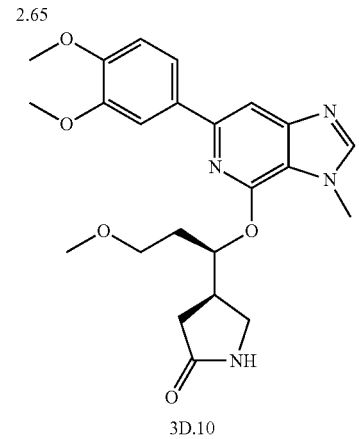

3D.10

Following General Procedure D, beginning with 6-(3,4-dimethoxyphenyl)-3-methyl-4-(methylsulfonyl)-3H-imidazo[4,5-c]pyridine 2.65 (50 mg, 0.14 mmol) and (R)-4-((R)-1-hydroxy-3-methoxypropyl)-1-((R)-1-(4-methoxyphenyl)ethyl)pyrrolidin-2-one 1.21 (53 mg, 0.17 mmol), the residue was purified via prep HPLC (2-95% acetonitrile in water, 0.1% TFA buffer) to isolate (R)-4-((R)-1-((6-(3,4-dimethoxyphenyl)-3-methyl-3H-imidazo[4,5-c]pyridin-4-yl)oxy)-3-methoxypropyl)pyrrolidin-2-one 3D.10 as the TFA salt.

1H NMR (400 MHz, Chloroform-d) δ 8.90 (s, 1H), 7.80 (s, 1H), 7.64 (dd, J=8.4, 2.1 Hz, 1H), 7.56 (d, J=2.0 Hz, 1H), 6.97

(d, J=8.4 Hz, 1H), 6.37 (s, 1H), 6.12-6.03 (m, 1H), 4.19 (s, 3H), 3.98 (d, J=19.4 Hz, 6H), 3.69 (t, J=9.3 Hz, 1H), 3.55-3.37 (m, 3H), 3.22 (s, 3H), 3.10 (s, 1H), 2.72-2.54 (m, 2H), 2.25-2.15 (m, 1H), 2.04-1.96 (m, 1H).

LCMS-ESI+ (m/z): [M+H]+ calcd for $C_{23}H_{28}N_4O_5$: 441.2; found 441.2.

General Procedure E for Synthesis of Examples 3E.01-3E.05

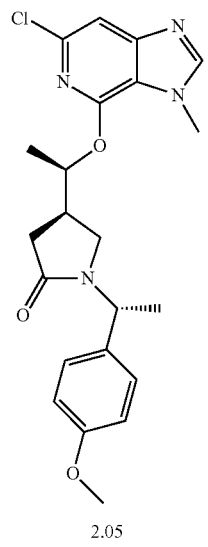

2.05

Suzuki ⟶ TFA deprotection ⟶

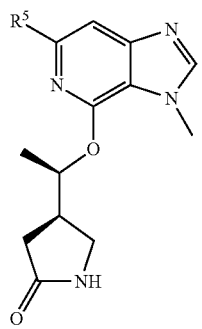

Examples 3E.01-3E.05

To an appropriate sized container charged with a magnetic stir bar, (R)-4-((R)-1-(6-chloro-3-methyl-3H-imidazo[4,5-c]pyridin-4-yloxy)ethyl)-1-((R)-1-(4-methoxyphenyl)ethyl)pyrrolidin-2-one 2.05 (1 equiv), boronic acid or ester (1.2 equiv), dipotassium phosphate (3.0 equiv), X-phos (0.5 equiv) and $Pd_2(dba)_3$ (0.1 equiv) were added and reagents were taken up in isopropanol. After evacuating and backfilling with argon, mixture was heated at 100° C. for one to three hours. After cooling to room temperature, mixture is poured into water and extracted with ethyl acetate. Combined organics were dried over $MgSO_4$, filtered, and concentrated under reduced pressure and resulting residues were used for next step without further purification. Residues were dissolved in trifluoroacetic acid and were heated at 55-60° C. overnight. After cooling to room temperature, mixture was concentrated under reduced pressure, taken up in ethyl acetate, washed with saturated $NaHCO_{3\ (aq)}$, and layers separated. Organic layer was washed with brine, dried over $MgSO_4$, filtered, and concentrated under reduced pressure to yield residues. Residues were purified via reverse phase chromatography to yield examples 3E.01-3E.05.

Example 3E.01

Preparation of (R)-4-((R)-1-(3-methyl-6-(3-morpholinophenyl)-3H-imidazo[4,5-c]pyridin-4-yloxy)ethyl)pyrrolidin-2-one

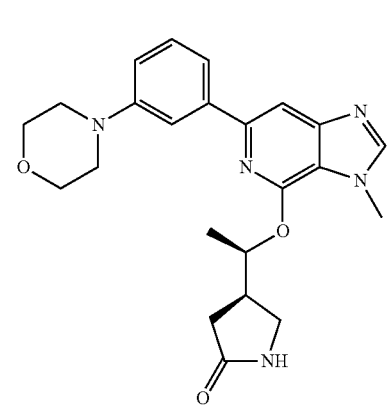

Example 3E.01

Following General Procedure E, beginning with (R)-4-((R)-1-(6-chloro-3-methyl-3H-imidazo[4,5-c]pyridin-4-yloxy)ethyl)-1-((R)-1-(4-methoxyphenyl)ethyl)pyrrolidin-2-one 2.05 (30 mg, 0.07 mmol) and 4-(3-(4,4,5,5-tetramethyl-1,3,2-dioxaborolan-2-yl)phenyl)morpholine (24.3 mg, 0.084 mmol), (R)-4-((R)-1-(3-methyl-6-(3-morpholinophenyl)-3H-imidazo[4,5-c]pyridin-4-yloxy)ethyl)pyrrolidin-2-one 3E.01 was synthesized.

1H NMR (400 MHz, Methanol-d4) δ 9.26-9.11 (m, 1H), 7.81 (d, J=2.0 Hz, 2H), 7.69 (ddd, J=7.6, 1.6, 0.9 Hz, 1H), 7.44 (t, J=8.0 Hz, 1H), 7.18 (ddd, J=8.3, 2.6, 0.9 Hz, 1H), 5.86-5.67 (m, 1H), 4.21 (s, 3H), 3.96-3.84 (m, 4H), 3.65 (dd, J=10.2, 8.6 Hz, 1H), 3.44-3.34 (m, 1H), 3.32-3.20 (m, 4H), 3.12-2.93 (m, 1H), 2.72-2.37 (m, 2H), 1.55 (d, J=6.2 Hz, 3H).

LCMS-ESI⁺ (m/z): [M+H]⁺ calcd for $C_{23}H_{28}N_5O_3$: 422.21; found 422.2.

Example 3E.02

Preparation of 7-(3-methyl-4-((R)-1-((R)-5-oxopyrrolidin-3-yl)ethoxy)-3H-imidazo[4,5-c]pyridin-6-yl)-3,4-dihydrobenzo[f][1,4]oxazepin-5(2H)-one

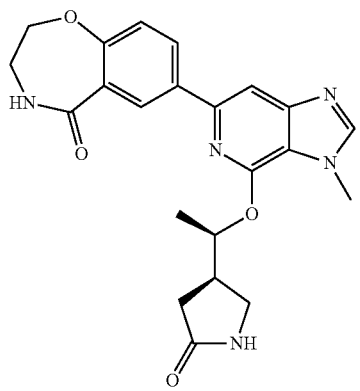

Example 3E.02

Following General Procedure E, beginning with (R)-4-((R)-1-(6-chloro-3-methyl-3H-imidazo[4,5-c]pyridin-4-yloxy)ethyl)-1-((R)-1-(4-methoxyphenyl)ethyl)pyrrolidin-2-one 2.05 (30 mg, 0.07 mmol) and 7-(4,4,5,5-tetramethyl-1,3,2-dioxaborolan-2-yl)-3,4-dihydrobenzo[f][1,4]oxazepin-5(2H)-one (24.3 mg, 0.084 mmol), 7-(3-methyl-4-((R)-1-((R)-5-oxopyrrolidin-3-yl)ethoxy)-3H-imidazo[4,5-c]pyridin-6-yl)-3,4-dihydrobenzo[f][1,4]oxazepin-5(2H)-one 3E.02 was synthesized.

1H NMR (400 MHz, Methanol-d4) δ 8.92 (s, 1H), 8.60 (d, J=2.4 Hz, 1H), 8.20 (dd, J=8.6, 2.4 Hz, 1H), 7.77 (s, 1H), 7.16 (d, J=8.6 Hz, 1H), 5.95-5.74 (m, 1H), 4.54-4.37 (m, 2H), 4.17 (s, 3H), 3.64 (dd, J=10.2, 8.6 Hz, 1H), 3.50 (t, J=4.8 Hz, 2H), 3.40 (dd, J=10.2, 5.5 Hz, 1H), 2.99 (td, J=14.5, 12.5, 6.0 Hz, 1H), 2.67-2.35 (m, 2H), 1.53 (d, J=6.2 Hz, 3H).

LCMS-ESI$^+$ (m/z): [M+H]$^+$ calcd for $C_{22}H_{24}N_5O_4$: 422.18; found 422.2.

Example 3E.03

Preparation of 4-(3-methyl-4-((R)-1-((R)-5-oxopyrrolidin-3-yl)ethoxy)-3H-imidazo[4,5-c]pyridin-6-yl)pyridin-2(1H)-one Example 3E.03

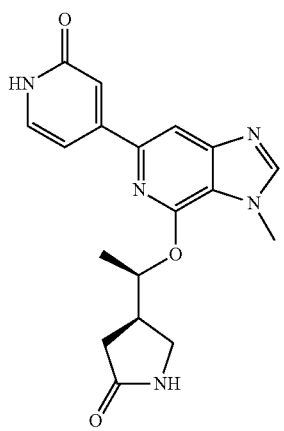

Following General Procedure E, beginning with (R)-4-((R)-1-(6-chloro-3-methyl-3H-imidazo[4,5-c]pyridin-4-yloxy)ethyl)-1-((R)-1-(4-methoxyphenyl)ethyl)pyrrolidin-2-one 2.05 (30 mg, 0.07 mmol) and 2-tert-butoxy-4-(4,4,5,5-tetramethyl-1,3,2-dioxaborolan-2-yl)pyridine (23.3 mg, 0.084 mmol), 4-(3-methyl-4-((R)-1-((R)-5-oxopyrrolidin-3-yl)ethoxy)-3H-imidazo[4,5-c]pyridin-6-yl)pyridin-2(1H)-one 3E.03 was synthesized. 1H NMR (400 MHz, Methanol-d4) δ 8.81 (s, 1H), 7.91 (s, 1H), 7.58 (dd, J=7.0, 0.7 Hz, 1H), 7.34 (dd, J=1.8, 0.7 Hz, 1H), 7.17 (dd, J=6.9, 1.8 Hz, 1H), 5.89-5.58 (m, 1H), 4.16 (s, 3H), 3.64 (dd, J=10.2, 8.6 Hz, 1H), 3.38 (dd, J=10.2, 5.5 Hz, 1H), 3.07-2.88 (m, 1H), 2.73-2.37 (m, 2H), 1.53 (d, J=6.2 Hz, 3H).

LCMS-ESI$^+$ (m/z): [M+H]$^+$ calcd for $C_{18}H_{20}N_5O_3$: 354.15; found 354.1.

Example 3E.04

Preparation of (R)-4-((R)-1-(3-methyl-6-(3-(methylsulfonyl)phenyl)-3H-imidazo[4,5-c]pyridin-4-yloxy)ethyl)pyrrolidin-2-one Example 3E.04

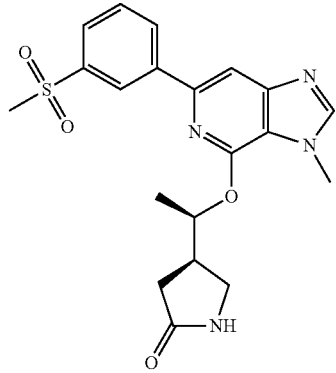

Following General Procedure E, beginning with (R)-4-((R)-1-(6-chloro-3-methyl-3H-imidazo[4,5-c]pyridin-4-yloxy)ethyl)-1-((R)-1-(4-methoxyphenyl)ethyl)pyrrolidin-2-one 2.05 (30 mg, 0.07 mmol) and 4,4,5,5-tetramethyl-2-(3-(methylsulfonyl)phenyl)-1,3,2-dioxaborolane (23.7 mg, 0.084 mmol), (R)-4-((R)-1-(3-methyl-6-(3-(methylsulfonyl)phenyl)-3H-imidazo[4,5-c]pyridin-4-yloxy)ethyl)pyrrolidin-2-one 3E.04 was synthesized.

1H NMR (400 MHz, Methanol-d4) δ 8.65 (t, J=1.8 Hz, 1H), 8.50-8.32 (m, 1H), 8.20 (s, 1H), 7.93 (ddd, J=7.8, 1.9, 1.0 Hz, 1H), 7.85 (s, 1H), 7.72 (t, J=7.8 Hz, 1H), 5.90-5.67 (m, 1H), 4.08 (s, 3H), 3.68-3.57 (m, 1H), 3.40 (dd, J=10.2, 5.5 Hz, 1H), 3.19 (s, 3H), 3.06-2.91 (m, 1H), 2.71-2.43 (m, 2H), 1.53 (d, J=6.2 Hz, 3H). LCMS-ESI$^+$ (m/z): [M+H]$^+$ calcd for $C_{20}H_{23}N_4O_4S$: 415.14; found 415.2.

Example 3E.05

Preparation of N,N-dimethyl-4-(3-methyl-4-((R)-1-((R)-5-oxopyrrolidin-3-yl)ethoxy)-3H-imidazo[4,5-c]pyridin-6-yl)benzenesulfonamide Example 3E.05

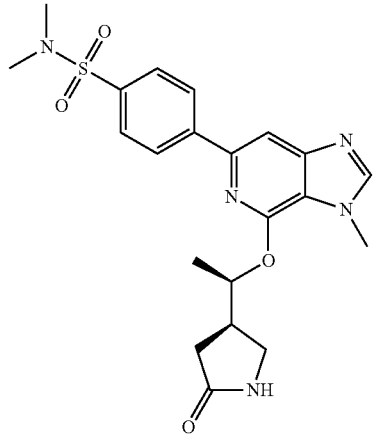

Following General Procedure E, beginning with (R)-4-((R)-1-(6-chloro-3-methyl-3H-imidazo[4,5-c]pyridin-4- yloxy)ethyl)-1-((R)-1-(4-methoxyphenyl)ethyl)pyrrolidin-2-one 2.05 (1 eq) and 4-(N,N-dimethylsulfamoyl)phenylboronic acid (1.2 eq), N,N-dimethyl-4-(3-methyl-4-((R)-1-((R)-5-oxopyrrolidin-3-yl)ethoxy)-3H-imidazo[4,5-c]pyridin-6-yl)benzenesulfonamide 3E.05 was synthesized.

<sup>1</sup>H NMR (400 MHz, Methanol-d$_4$) δ 9.05 (s, 1H), 8.38-8.18 (m, 2H), 7.96-7.76 (m, 3H), 5.90-5.66 (m, 1H), 4.21 (d, J=0.7 Hz, 3H), 3.65 (dd, J=10.2, 8.6 Hz, 1H), 3.40 (dd, J=10.2, 5.5 Hz, 1H), 3.01 (ddt, J=14.8, 8.9, 5.7 Hz, 1H), 2.71 (s, 6H), 2.68-2.39 (m, 2H), 1.55 (d, J=6.2 Hz, 3H). LCMS-ESI$^+$ (m/z): [M+H]$^+$ calcd for $C_{21}H_{26}N_5O_4S$: 444.16; found 444.1.

Example 3F.01

Preparation of (R)-4-((R)-1-(3-methyl-6-(4-(4-(methylsulfonyl)piperazin-1-yl)phenyl)-3H-imidazo[4,5-c]pyridin-4-yloxy)ethyl)pyrrolidin-2-one Example 3F.01

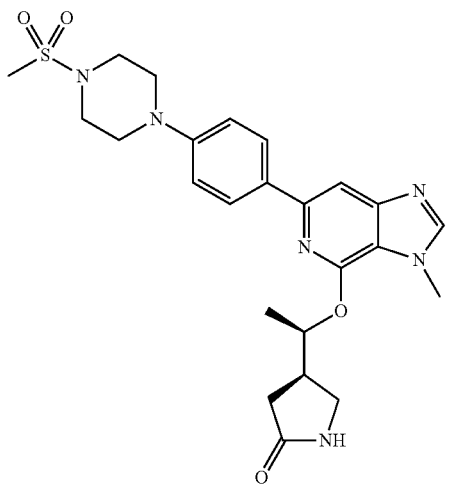

To an appropriate sized microwave vial, the trifluoroacetic acid salt of (R)-4-((R)-1-(3-methyl-6-(4-(piperazin-1-yl)phenyl)-3H-imidazo[4,5-c]pyridin-4-yloxy)ethyl)pyrrolidin-2-one 3A.14 (75 mg, 0.14 mmol), triethylamine (59 µL, 0.42 mmol) and dichloromethane (1.5 mL) were added. The solution was cooled to 0° C. and methanesulfonyl chloride (10 µL, 0.13 mmol) was added. The solution was stirred at 0° C. for 30 minutes and subsequently poured into water. The mixture was concentrated under reduced pressure and the residue was purified via prep HPLC (2-95% acetonitrile in water, 0.1% trifluoroacteic acid buffer) to isolate (R)-4-((R)-1-(3-methyl-6-(4-(4-(methylsulfonyl)piperazin-1-yl)phenyl)-3H-imidazo[4,5-c]pyridin-4-yloxy)ethyl)pyrrolidin-2-one 3F.01 as the trifluoroacetic acid salt.

1H NMR (400 MHz, DMSO-d6) δ 8.65 (s, 1H), 7.99 (d, J=8.8 Hz, 2H), 7.71 (s, 1H), 7.58 (s, 1H), 7.07 (d, J=8.9 Hz, 2H), 5.56 (p, J=6.3 Hz, 1H), 4.01 (s, 3H), 3.50-3.12 (m, 10H), 2.93 (s, 3H), 2.87-2.83 (m, 1H), 2.43-2.19 (m, 2H), 1.43 (d, J=6.1 Hz, 3H).

LCMS-ESI$^+$ (m/z): [M+H]+ calcd for $C_{24}H_{30}N_6O_4S$: 499.2; found: 499.0.

Example 3F.02

Preparation of (R)-4-((R)-1-(3-methyl-6-(4-(4-(oxetan-3-yl)piperazin-1-yl)phenyl)-3H-imidazo[4,5-c]pyridin-4-yloxy)ethyl)pyrrolidin-2-one Example 3F.02

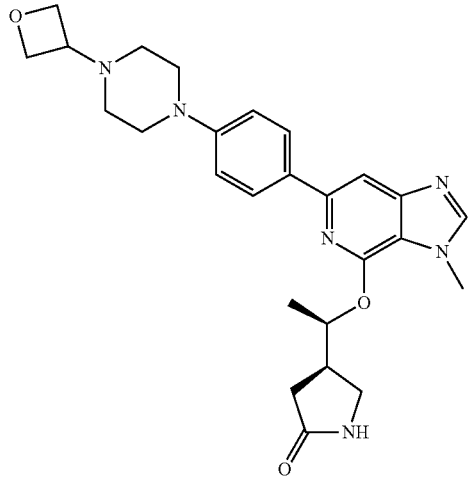

To an appropriate sized microwave vial, (R)-4-((R)-1-(3-methyl-6-(4-(piperazin-1-yl)phenyl)-3H-imidazo[4,5-c]pyridin-4-yloxy)ethyl)pyrrolidin-2-one 3A.14 (44 mg, 0.11 mmol), 3-oxetanone (22 µL, 0.37 mmol) and THF (1 mL) were added. Sodium triacetoxyborohydride (100 mg, 0.47 mmol) was added and the mixture was heated at 50° C. for 45 min. The mixture was poured into a saturated aqueous solution of sodium bicarbonate and concentrated under reduced pressure. The residue was purified via prep HPLC (2-95% acetonitrile in water, 0.1% trifluoroacteic acid buffer) to isolate (R)-4-((R)-1-(3-methyl-6-(4-(4-(oxetan-3-yl)piperazin-1-yl)phenyl)-3H-imidazo[4,5-c]pyridin-4-yloxy)pyrrolidin-2-one 3F.02 as the trifluoroacetic acid salt.

<sup>1</sup>H NMR (400 MHz, DMSO-d6) δ 8.52 (s, 1H), 8.01 (d, J=8.8 Hz, 2H), 7.73 (s, 1H), 7.59 (s, 1H), 7.11 (d, J=8.9 Hz, 2H), 5.54 (p, J=6.0 Hz, 1H), 4.90-4.70 (m, 4H), 4.54-4.37 (m, 1H), 4.00 (s, 3H), 3.75-2.75 (broad m, 11H), 2.44-2.21 (m, 2H), 1.43 (d, J=6.2 Hz, 3H). LCMS-ESI$^+$ (m/z): [M+H]+ calcd for $C_{26}H_{32}N_6O_3$: 477.3; found: 477.2.

Example 3F.03

Preparation of (R)-4-((R)-1-(6-(4-(4-acetylpiperazin-1-yl)phenyl)-3-methyl-3H-imidazo[4,5-c]pyridin-4-yloxy)ethyl)pyrrolidin-2-one Example 3F.03

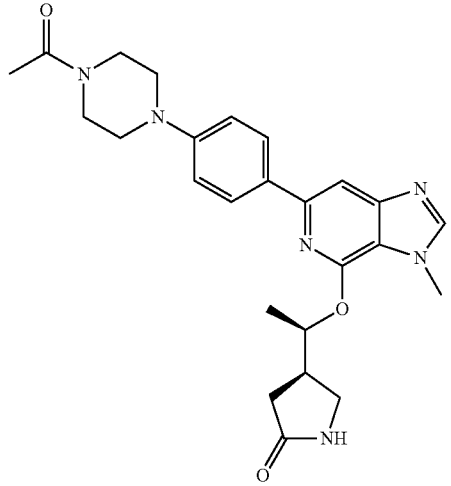

To an appropriate sized microwave vial, (R)-4-((R)-1-(3-methyl-6-(4-(piperazin-1-yl)phenyl)-3H-imidazo[4,5-c]pyridin-4-yloxy)ethyl)pyrrolidin-2-one 3A.14 (50 mg, 0.12 mmol), HATU (90 mg, 0.24 mmol), N-methylmorpholine (52 µL, 0.48 mmol) and DMF (2 mL). Acetic acid (8 µL, 0.14 mmol) was added and the solution was stirred at room temperature for 18 h. The solution was concentrated under reduced pressure and the residue was purified via prep HPLC (2-95% acetonitrile in water, 0.1% trifluoroacetic acid buffer) to isolate (R)-4-((R)-1-(6-(4-(4-acetylpiperazin-1-yl)phenyl)-3-methyl-3H-imidazo[4,5-c]pyridin-4-yloxy)ethyl)pyrrolidin-2-one 3F.03 as the trifluoroacetic acid salt.

$^1$H NMR (400 MHz, DMSO-d6) δ 8.58 (s, 1H), 7.98 (d, J=8.9 Hz, 2H), 7.70 (s, 1H), 7.58 (s, 1H), 7.04 (d, J=8.8 Hz, 2H), 5.56 (p, J=6.1 Hz, 1H), 4.00 (s, 3H), 3.63-3.57 (m, 4H), 3.42 (t, J=9.1 Hz, 1H), 3.32-3.11 (m, 5H), 2.89-2.79 (m, 1H), 2.43-2.19 (m, 2H), 2.05 (s, 3H), 1.43 (d, J=6.2 Hz, 3H).

LCMS-ESI$^+$ (m/z): [M+H]+ calcd for $C_{25}H_{30}N_6O_3$: 463.3; found: 463.3.

Example 3.01

Preparation of (R)-4-((R)-1-(6-(3,4-dimethoxyphenyl)-3-methyl-3H-imidazo[4,5-c]pyridin-4-yloxy)ethyl)pyrrolidin-2-one

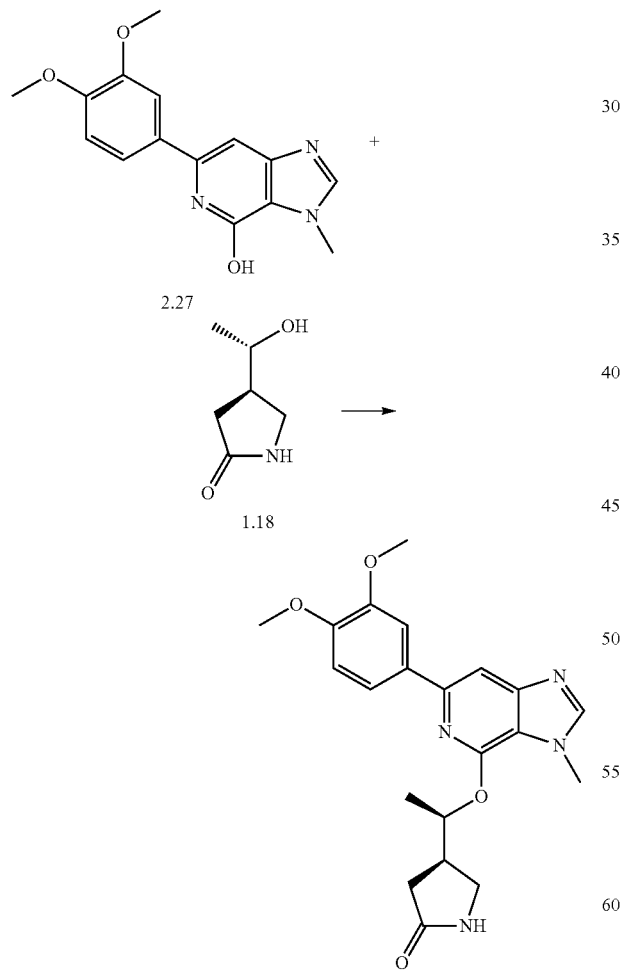

Example 3.01

To a mixture of (R)-4-((R)-1-hydroxyethyl)pyrrolidin-2-one 1.18 (350 mg, 2.73 mmol), PPh$_3$ (720 mg, 2.73 mmol), and 6-(3,4-dimethoxyphenyl)-3-methyl-3H-imidazo[4,5-c]pyridin-4-ol 2.27 (130 mg, 0.60 mmol) in $CH_2Cl_2$ (6 mL) was added DEAD (475 mg, 2.73 mmol) and the reaction was stirred overnight. Water (10 mL) and EtOAc (20 mL) were added and the layers were separated. The organic layer was washed with brine (1×10 mL), dried ($Na_2SO_4$), filtered and concentrated. The residue was purified by flash chromatography ($CH_2Cl_2$→10% MeOH in $CH_2Cl_2$) to afford (R)-4-((R)-1-(6-(3,4-dimethoxyphenyl)-3-methyl-3H-imidazo[4,5-c]pyridin-4-yloxy)ethyl)pyrrolidin-2-one 3.01.

1H NMR (300 MHz, DMSO-d6) δ 8.20 (s, 1H), 7.76 (s, 1H), 7.67-7.61 (m, 3H), 7.56 (bs, 1H), 7.03 (d, 1H), 5.56 (q, 1H), 3.95 (s, 3H), 3.85 (s, 3H), 3.78 (s, 3H), 3), 3.47-3.34 (m, 1H), 3.23-3.12 (m, 1H), 2.83 (m, 1H), 2.43-2.21 (m, 2H), 1.42 (d, J=6.2 Hz, 3H).

LCMS-ESI+ (m/z): [M+H]+ calcd for $C_{21}H_{24}N_4O_4$: 397.2; found: 396.8.

Example 3.02

Preparation of (R)-4-((R)-1-(3-(difluoromethyl)-6-(3,4-dimethoxyphenyl)-3H-imidazo[4,5-c]pyridin-4-yloxy)ethyl)pyrrolidin-2-one

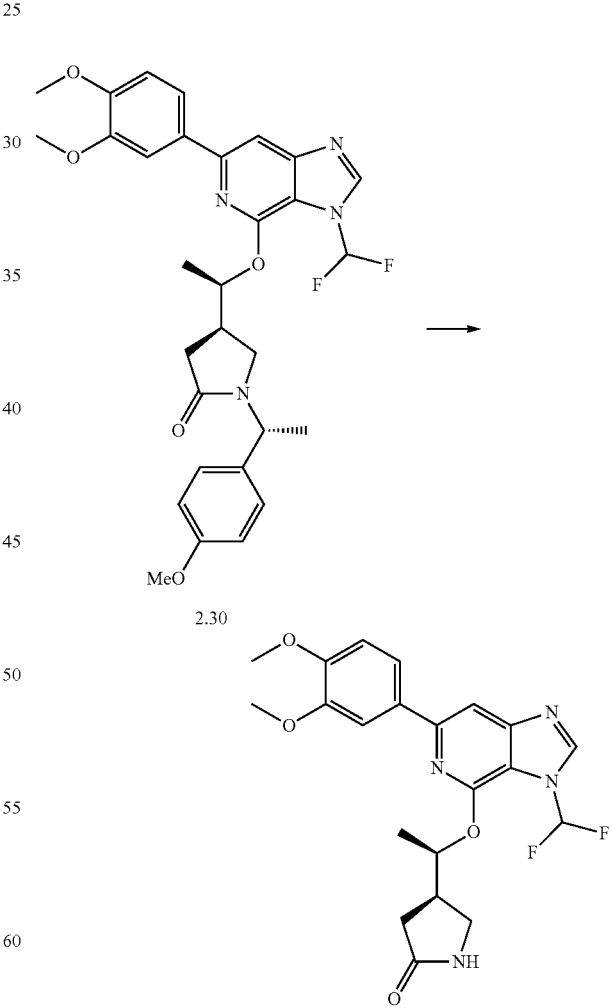

Example 3.02

(R)-4-((R)-1-(3-(difluoromethyl)-6-(3,4-dimethoxyphenyl)-3H-imidazo[4,5-c]pyridin-4-yloxy)ethyl)-1-((R)-1-(4- methoxyphenyl)ethyl)pyrrolidin-2-one 2.30 (max. 0.153 mmol) was dissolved in TFA (2 mL) and heated to 60° C. with stirring. After 22 h, the red solution was concentrated in vacuo and diluted with EtOAc (20 mL) and saturated aqueous NaHCO$_3$ (20 mL). The phases were separated and the aqueous phase was extracted with EtOAc (20 mL). The combined organic phase was dried over Na$_2$SO$_4$, filtered, and concentrated onto 2 g silica gel. Purification by silica gel chromatography (0% to 2.5% to 5% MeOH in DCM) provided (R)-4-((R)-1-(3-(difluoromethyl)-6-(3,4-dimethoxyphenyl)-3H-imidazo[4,5-c]pyridin-4-yloxy)ethyl)pyrrolidin-2-one 3.02.

LCMS-ESI$^+$ (m/z): [M+H]$^+$ calcd for C$_{21}$H$_{23}$F$_2$N$_4$O$_4$: 433.2; found 432.9.

$^1$H NMR (400 MHz, Chloroform-d) δ 8.28 (s, 1H), 7.74 (s, 1H), 7.62 (t, J=61.0 Hz, 1H), 7.61-7.55 (m, 2H), 6.96 (d, J=8.1 Hz, 1H), 6.31 (s, 1H), 5.75-5.61 (m, 1H), 3.98 (s, 3H), 3.93 (s, 3H), 3.58 (t, J=9.1 Hz, 1H), 3.37 (dd, J=9.8, 6.1 Hz, 1H), 3.02-2.88 (m, 1H), 2.56 (dd, J=17.2, 9.4 Hz, 1H), 2.46 (dd, J=17.2, 7.3 Hz, 1H), 1.51 (d, J=6.2 Hz, 3H).

Example 3.03

Preparation of (R)-4-((R)-1-(6-(1-tert-butyl-1H-pyrazol-4-yl)-3-(difluoromethyl)-3H-imidazo[4,5-c]pyridin-4-yloxy)ethyl)pyrrolidin-2-one (R)-4-((R)-1-(6-(1-tert-butyl-1H-pyrazol-4-yl)-3-(difluoromethyl)-3H-imidazo[4,5-c]pyridin-4-yloxy)ethyl)-1-((R)-1-(4-methoxyphenyl)ethyl)pyrrolidin-2-one 2.34 (max. 0.107 mmol) was dissolved in TFA (2 mL) and heated to 60° C. with stirring. After 15 h, the red solution was concentrated in vacuo and diluted with EtOAc (20 mL) and 1:1 saturated aqueous NaHCO$_3$: brine (20 mL). The phases were separated and the aqueous phase was extracted with EtOAc (20 mL). The combined organic phase was dried over Na$_2$SO$_4$, filtered, and concentrated onto silica gel. Purification by silica gel chromatography (40% to 100% acetone in hexanes) provided (R)-4-((R)-1-(6-(1-tert-butyl-1H-pyrazol-4-yl)-3-(difluoromethyl)-3H-imidazo[4,5-c]pyridin-4-yloxy)ethyl)pyrrolidin-2-one 3.03.

LCMS-ESI$^+$ (m/z): [M+H]$^+$ calcd for C$_{20}$H$_{25}$F$_2$N$_6$O$_2$: 419.2; found 419.1.

$^1$H NMR (400 MHz, Chloroform-d) δ 8.24 (s, 1H), 7.97 (s, 1H), 7.93 (s, 1H), 7.59 (t, J=61.3 Hz, 1H), 7.48 (s, 1H), 6.24 (s, 1H), 5.70-5.58 (m, 1H), 3.62-3.52 (m, 1H), 3.36 (dd, J=9.8, 6.1 Hz, 1H), 2.99-2.86 (m, 1H), 2.54 (dd, J=17.2, 9.3 Hz, 1H), 2.44 (dd, J=17.2, 7.3 Hz, 1H), 1.64 (d, J=1.0 Hz, 9H), 1.47 (d, J=6.3 Hz, 3H).

Example 3.04

Preparation of (R)-4-((R)-1-(3-cyclopropyl-6-(3,4-dimethoxyphenyl)-3H-imidazo[4,5-c]pyridin-4-yloxy)ethyl)pyrrolidin-2-one

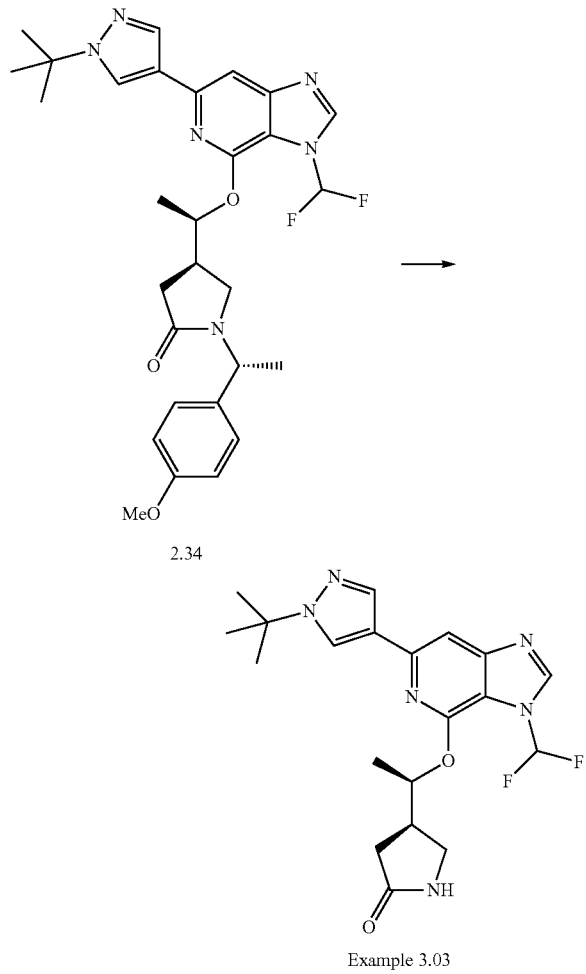

2.34

Example 3.03

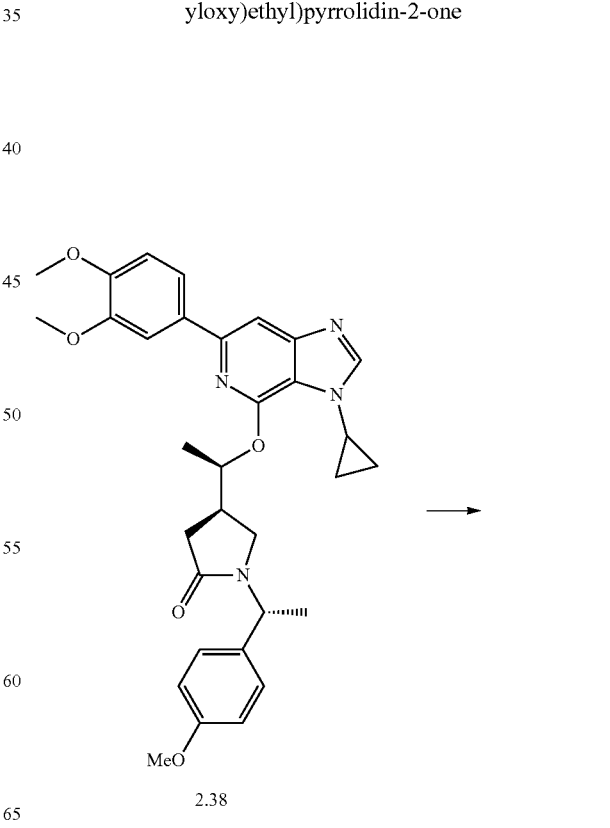

2.38

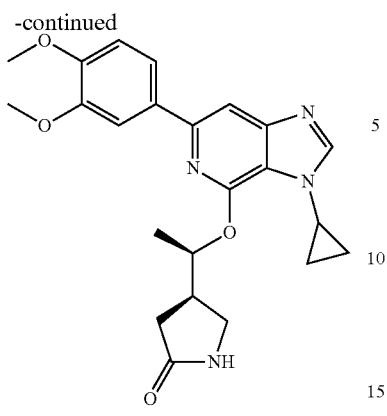

Example 3.04

(R)-4-((R)-1-(3-cyclopropyl-6-(3,4-dimethoxyphenyl)-3H-imidazo[4,5-c]pyridin-4-yloxy)ethyl)-1-((R)-1-(4-methoxyphenyl)ethyl)pyrrolidin-2-one 2.38 (80 mg, 0.14 mmol) was dissolved in TFA (2 mL) and heated to 60° C. with stirring. After 1.75 h, the temperature was increased to 65° C. After an additional 4.25 h, the temperature was decreased to 55° C. After an additional 18 h, the red solution was concentrated in vacuo and diluted with EtOAc (15 mL) and saturated aqueous NaHCO₃ (15 mL). The phases were separated and the aqueous phase was extracted with EtOAc (2×15 mL). The combined organic phase was dried over Na₂SO₄, filtered, and concentrated onto silica gel. Purification by silica gel chromatography (0% to 10% MeOH in DCM) provided (R)-4-((R)-1-(3-cyclopropyl-6-(3,4-dimethoxyphenyl)-3H-imidazo[4,5-c]pyridin-4-yloxy)ethyl)pyrrolidin-2-one 3.04

LCMS-ESI⁺ (m/z): [M+H]⁺ calcd for $C_{23}H_{27}N_4O_4$: 423.2; found 423.7.

¹H NMR (400 MHz, Chloroform-d) δ 7.87 (s, 1H), 7.65 (s, 1H), 7.62-7.54 (m, 2H), 6.95 (d, J=8.7 Hz, 1H), 6.24 (s, 1H), 5.78-5.68 (m, 1H), 3.97 (s, 3H), 3.92 (s, 3H), 3.65-3.52 (m, 2H), 3.41 (dd, J=9.6, 6.5 Hz, 1H), 2.94 (dq, J=11.5, 4.4, 3.2 Hz, 1H), 2.63-2.47 (m, 2H), 1.50 (d, J=6.1 Hz, 3H), 1.22-1.00 (m, 4H).

Example 3.05

Preparation of (R)-4-((R)-1-(6-(3,4-dimethoxyphenyl)-2,3-dimethyl-3H-imidazo[4,5-c]pyridin-4-yloxy)ethyl)pyrrolidin-2-one

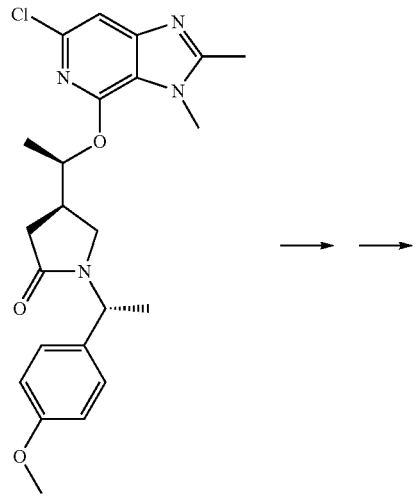

2.48

⟶ ⟶

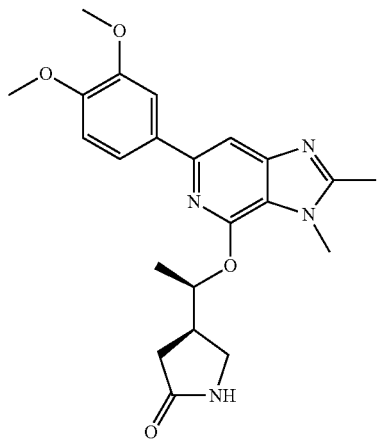

Example 3.05

In a microwave vial, (R)-4-((R)-1-(6-chloro-2,3-dimethyl-3H-imidazo[4,5-c]pyridin-4-yloxy)ethyl)-1-((R)-1-(4-methoxyphenyl)ethyl)pyrrolidin-2-one 2.48 (0.1 g, 0.22 mmol), 3,4-dimethoxyphenylboronic acid (43 mg, 0.23 mmol), K₂HPO₄ (154 mg, 0.67 mmol), X-phos (54 mg, 0.11 mmol) and Pd₂(dba)₃ (21 mg, 0.023 mmol) were added. Vial was sealed and reagents were taken up in isopropanol (5 mL). After evacuating and backfilling with argon, mixture was heated at 100° C. for one to three hours. After cooling to room temperature, mixture is poured into water and extracted with ethyl acetate. Combined organics were dried over MgSO₄, filtered, and concentrated under reduced pressure and resulting residues were used for next step without further purification. Residues were dissolved in trifluoroacetic acid (3 mL), and were heated at 55-60° C. for 6 hr. After cooling to room temperature, mixture was concentrated under reduced pressure, taken up in ethyl acetate, washed with saturated NaHCO₃ (aq), and layers separated. Combined organic layers were washed with brine, dried over MgSO₄, filtered, and concentrated under reduced pressure to yield residues. Residues were purified via reverse phase chromatography to yield (R)-4-((R)-1-(6-(3,4-dimethoxyphenyl)-2,3-dimethyl-3H-imidazo[4,5-c]pyridin-4-yloxy)ethyl)pyrrolidin-2-one 3.05.

¹H NMR (400 MHz, DMSO-d₆) δ 7.74 (s, 1H), 7.66 (dt, J=4.0, 2.0 Hz, 2H), 7.58 (s, 1H), 7.03 (d, J=9.0 Hz, 1H), 5.54 (p, J=6.0 Hz, 1H), 3.93 (s, 3H), 3.85 (s, 3H), 3.79 (s, 4H), 3.41 (t, J=9.2 Hz, 2H), 3.16 (dd, J=9.8, 6.2 Hz, 1H), 2.94-2.77 (m, 1H), 2.64 (s, 2H), 2.42-2.16 (m, 2H), 1.43 (d, J=6.1 Hz, 2H).

LCMS-ESI⁺ (m/z): [M+H]⁺ calcd for $C_{22}H_{26}N_4O_4$: 411.2; found 411.3.

Example 3.06

Preparation of (R)-4-((R)-1-(6-(3,4-dimethoxyphenyl)-3-ethyl-3H-imidazo[4,5-c]pyridin-4-yloxy)ethyl)pyrrolidin-2-one

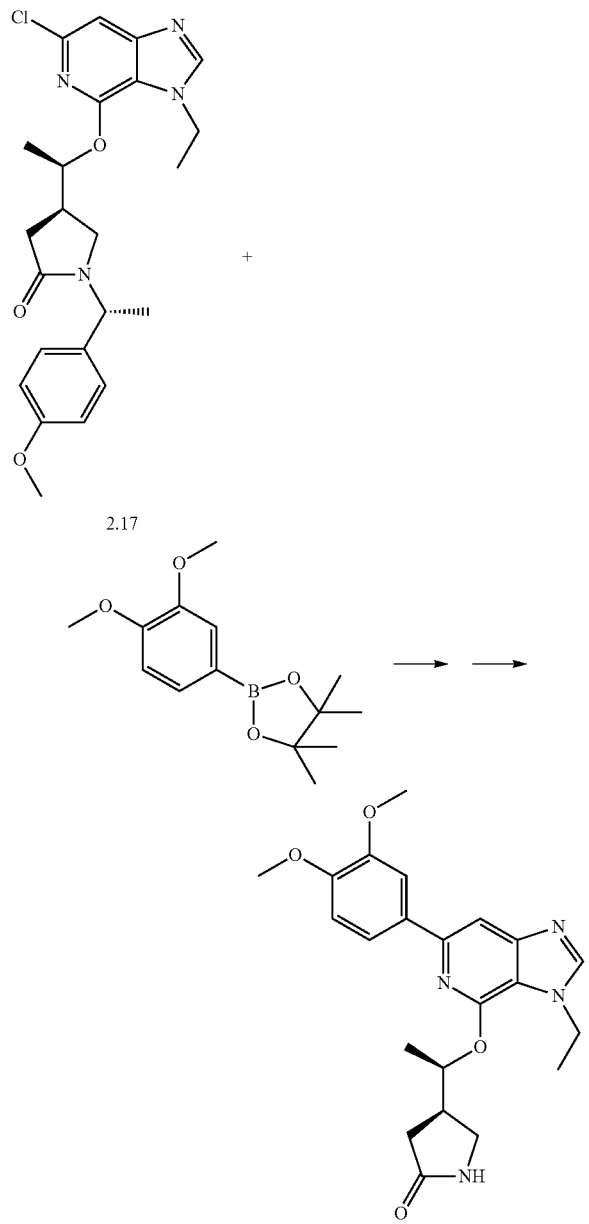

Example 3.06

Following the procedure of Example 3.05, beginning with (R)-4-((R)-1-(6-chloro-3-ethyl-3H-imidazo[4,5-c]pyridin-4-yloxy)ethyl)-1-((R)-1-(4-methoxyphenyl)ethyl)pyrrolidin-2-one 2.17 (107 mg, 0.24 mmol), (R)-4-((R)-1-(6-(3,4-dimethoxyphenyl)-3-ethyl-3H-imidazo[4,5-c]pyridin-4-yloxy)ethyl)pyrrolidin-2-one 3.06 was synthesized.

$^1$H NMR (400 MHz, CDCl$_3$): δ 7.99 (br, 1H), 7.78 (s, 1H), 7.259 (s, 1H), 6.95 (d, 1H), 6.056 (s, 1H), 7.743 (t, 1H), 4.374 (d, 2H), 3.973 (s, 3H), 3.927 (s, 3H), 3.583 (t, 1H), 3.399 (t, 1H), 3.0 (s, 1H), 2.532 (m, 2H), 2.08 (s, 1H), 1.525 (s, 3H, 1.51 (t, 3H).

LCMS [M+H]$^+$: 411.13.

Example 3.07

Preparation of (R)-4-((R)-1-(6-(3,4-dimethoxyphenyl)-3-isopropyl-3H-imidazo[4,5-c]pyridin-4-yloxy)ethyl)pyrrolidin-2-one

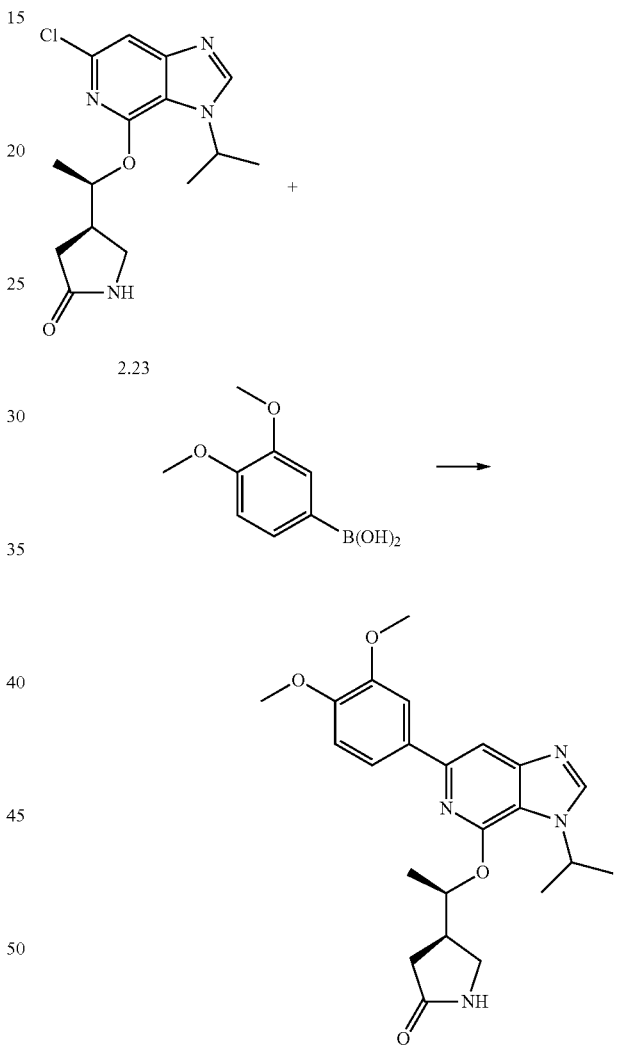

Example 3.07

Following the procedure of Example 3.08, beginning with (R)-4-((R)-1-(6-chloro-3-isopropyl-3H-imidazo[4,5-c]pyridin-4-yloxy)ethyl)pyrrolidin-2-one 2.23 (52 mg crude), R)-4-((R)-1-(6-(3,4-dimethoxyphenyl)-3-isopropyl-3H-imidazo[4,5-c]pyridin-4-yloxy)ethyl)pyrrolidin-2-one 3.07 was synthesized.

LCMS [M+H]$^+$: 425.22.

$^1$H NMR (400 MHz, CDCl$_3$): δ 8.342 (s, 1H), 7.683 (s, 1H), 7.63 (m, 2H), 7.024 (d, 1H), 5.772 (m, 1H), 5.089 (m,

1H), 3.918 (s, 3H), 3.868 (s, 3H), 3.625 (t, 1H), 3.38 (m, 1H), 3.0 (m, 1H), 2.56 (m, 2H), 1.62 (d, 6H), 1.51 (d, 3H).

Examples 3.08 and 3.09

Preparation of (R)-4-((R)-1-(6-(3,4-dimethoxyphenyl)-3-((2-(trimethylsilyl)ethoxy)methyl)-3H-imidazo[4,5-c]pyridin-4-yloxy)ethyl)pyrrolidin-2-one and (R)-4-((R)-1-(6-(3,4-dimethoxyphenyl)-3H-imidazo[4,5-c]pyridin-4-yloxy)ethyl)pyrrolidin-2-one

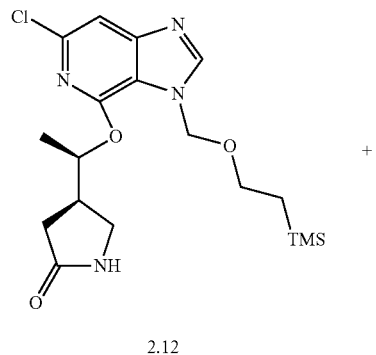

2.12

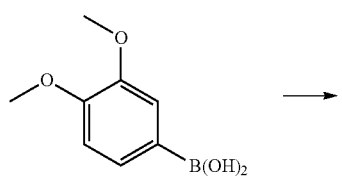

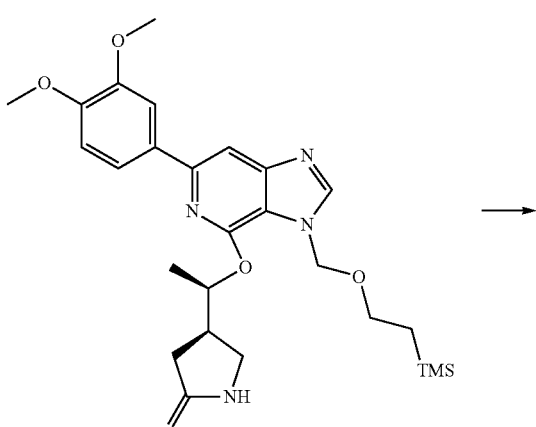

Example 3.08

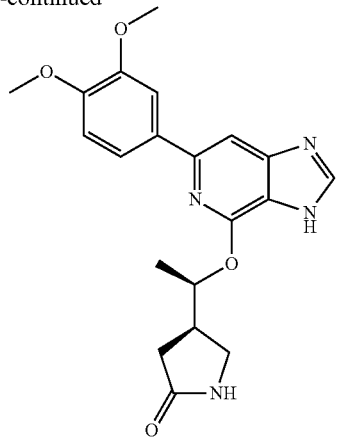

Example 3.09

Into the solution of (R)-4-((R)-1-(6-chloro-3-((2-(trimethylsilyl)ethoxy)methyl)-3H-imidazo[4,5-c]pyridin-4-yloxy)ethyl)pyrrolidin-2-one 2.12 (267 mg, 0.65 mmol) and 3,4-dimethoxyphenylboronic acid (142 mg, 0.78 mmol) in 2:1 DME:water (10 ml) was added cesium carbonate (3 equiv), and PEPPSI-IPr catalyst (0.1 equiv). Mixture was refluxed for 3 h, cooled to room temperature, poured into water and extracted with ethyl acetate (100 mL). Separated organic layer was washed with Brine (2×50 mL), dried (MgSO$_4$), filtered, and concentrated under reduced pressure to yield residues which were purified by silica gel column chromatography to isolate (R)-4-((R)-1-(6-(3,4-dimethoxyphenyl)-3-((2-(trimethylsilyl)ethoxy)methyl)-3H-imidazo[4,5-c]pyridin-4-yloxy)ethyl)pyrrolidin-2-one 3.08.

$^1$H NMR (400 MHz, CDCl$_3$): δ 8.12 (s, 1H), 7.764 (s, 1H), 7.64 (d, 1H), 7.63 (s, 1H), 7.0 (d, 1H), 5.77 (m, 1H), 5.72 (s, 2H), 5.64 (s, 1H), 4.023 (s, 3H), 3.98 (s, 3H), 3.586 (m, 2H), 3.45 (m, 1H), 3.01 (m, 1H), 2.58 (d, 2H), 1.55 (d, 3H), 0.92 (m, 2H), 0.00 (s, 9H).

LCMS [M+H]$^+$: 513.03.

Into the solution of (R)-4-((R)-1-(6-(3,4-dimethoxyphenyl)-3-((2-(trimethylsilyl)ethoxy)methyl)-3H-imidazo[4,5-c]pyridin-4-yloxy)ethyl)pyrrolidin-2-one 3.08 (200 mg, 0.39 mmol) in THF (5 mL), was added 1 M solution of TBAF in THF (3.9 mL, 3.9 mmol). After reflux for 12 h, the reaction mixture was taken up with ethyl acetate (150 mL) and washed with brine, dried (MgSO$_4$), filtered, and concentrated under reduced pressure to yield residues which were purified by silica gel column chromatography to isolate (R)-4-((R)-1-(6-(3,4-dimethoxyphenyl)-3H-imidazo[4,5-c]pyridin-4-yloxy)ethyl)pyrrolidin-2-one 3.09.

$^1$H NMR (400 MHz, CDCl$_3$): δ 8.2 (br., 1H), 7.669 (s, 1H), 7.59 (d, 2H), 6.98 (d, 1H), 5.68 (s, 1H), 4.72 (q, 1H), 3.904 (s, 3H), 3.85 (s, 3H), 3.53 (m, 2H), 3.0 (m, 1H), 2.537 (m, 2H), 1.477 (d, 3H).

LCMS [M+H]$^+$: 382.94.

Example 3.10 and 3.11

Preparation of (R)-4-((R)-1-(6-(3,4-dimethoxyphenyl)-3-(2,2,2-trifluoroethyl)-3H-imidazo[4,5-c]pyridin-4-yloxy)ethyl)pyrrolidin-2-one and (R)-4-((R)-1-(6-(3,4-dimethoxyphenyl)-1-(2,2,2-trifluoroethyl)-1H-imidazo[4,5-c]pyridin-4-yloxy)ethyl)pyrrolidin-2-one

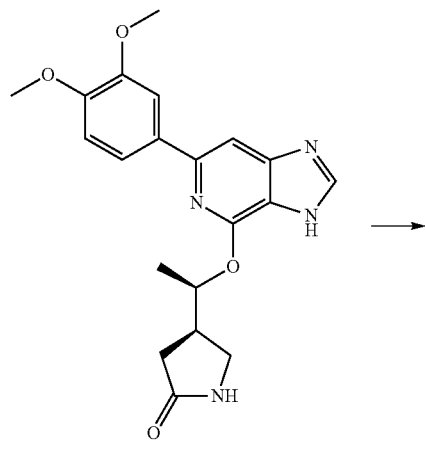

Example 3.09

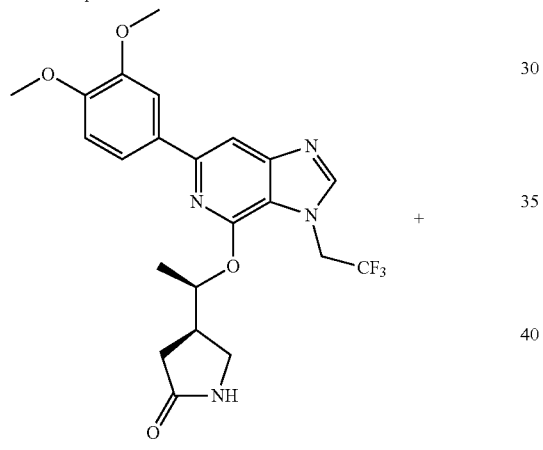

Example 3.10

2,2,2-trifluoroethyl trifluoromethanesulfonate (13 mg, 0.056 mmol) was added to a solution of (R)-4-((R)-1-(6-(3,4-dimethoxyphenyl)-3H-imidazo[4,5-c]pyridin-4-yloxy)ethyl)pyrrolidin-2-one 3.09 (20 mg, 0.052 mmol) and cesium carbonate (43 mg, 0.132 mmol) in 5 mL of DMF at room temperature. After 1 h, reaction mixture was taken up in ethyl acetate (100 mL) and washed with saturated NaHCO$_3$ $_{(aq)}$ (2×100 mL) and brine. The separated organic layers were dried (MgSO$_4$), filtered, and concentrated under reduced pressure. The resulting residue was purified by silica gel column chromatography to yield (R)-4-((R)-1-(6-(3,4-dimethoxyphenyl)-3-(2,2,2-trifluoroethyl)-3H-imidazo[4,5-c]pyridin-4-yloxy)ethyl)pyrrolidin-2-one 3.10 and (R)-4-((R)-1-(6-(3,4-dimethoxyphenyl)-1-(2,2,2-trifluoroethyl)-1H-imidazo[4,5-c]pyridin-4-yloxy)ethyl)pyrrolidin-2-one 3.11.

For (R)-4-((R)-1-(6-(3,4-dimethoxyphenyl)-3-(2,2,2-trifluoroethyl)-3H-imidazo[4,5-c]pyridin-4-yloxy)ethyl)pyrrolidin-2-one 3.10:

$^1$H NMR (400 MHz, CDCl$_3$): δ: 7.974 (s, 1H), 7.719 (s, 1H), 7.57 (d, 1H), 7.567 (s, 1H), 6.96 (d, 1H), 5.928 (s, 1H), 5.78 (m, 1H), 4.98 (m, 2H), 3.984 (s, 3H), 3.934 (s, 3H), 3.58 (m, 1H), 3.39 (m, 1H), 2.97 (m, 1H), 2.56 (m, 1H), 2.44 (m, 1H), 1.48 (d, 3H).

LCMS [M+H]$^+$: 465.16.

Example 3.12

Preparation of (R)-4-((R)-1-(3-(2,2-difluoroethyl)-6-(3,4-dimethoxyphenyl)-3H-imidazo[4,5-c]pyridin-4-yloxy)ethyl)pyrrolidin-2-one

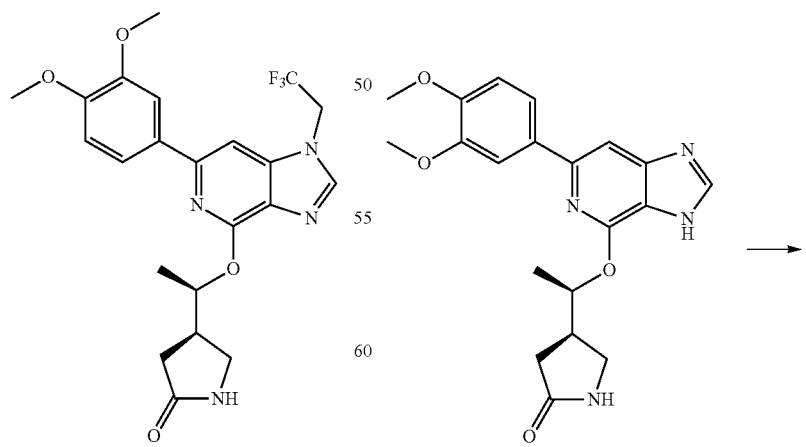

Example 3.11            Example 3.09

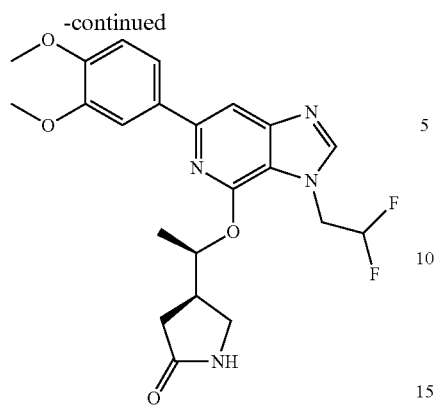

Example 3.12

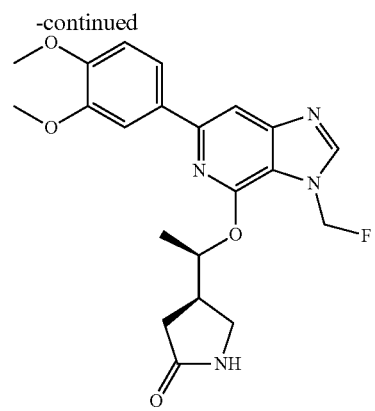

Example 3.13

To a solution of crude (R)-4-((R)-1-(6-(3,4-dimethoxyphenyl)-3H-imidazo[4,5-c]pyridin-4-yloxy)ethyl)pyrrolidin-2-one 3.09 (ca. 0.13 mmol) in DMF (1 mL) was added Cs$_2$CO$_3$ (114 mg, 0.35 mmol) followed by 2,2-difluoroethyl trifluoromethanesulfonate (36 mg, 0.17 mmol). After 40 min, an additional portion of 2,2-difluoroethyl trifluoromethanesulfonate (7 mg, 0.03 mmol) was added. After an additional 30 min, the reaction mixture was diluted with EtOAc (20 mL), water (10 mL), and brine (10 mL). The phases were separated, and the aqueous phase was extracted with EtOAc (20 mL). The combined organic phase was dried over Na$_2$SO$_4$, filtered, and concentrated. The crude product was purified by silica gel chromatography (0% to 10% MeOH in DCM) to afford (R)-4-((R)-1-(3-(2,2-difluoroethyl)-6-(3,4-dimethoxyphenyl)-3H-imidazo[4,5-c]pyridin-4-yloxy)ethyl)pyrrolidin-2-one 3.12.

$^1$H NMR (400 MHz, Chloroform-d) δ 7.98 (s, 1H), 7.71 (s, 1H), 7.61-7.54 (m, 2H), 6.98-6.92 (m, 1H), 6.30 (s, 1H), 6.29-5.96 (m, 1H), 5.80-5.70 (m, 1H), 4.79-4.64 (m, 2H), 3.97 (s, 3H), 3.92 (s, 3H), 3.60 (t, J=9.2 Hz, 1H), 3.38 (dd, J=9.8, 5.5 Hz, 1H), 3.02-2.84 (m, 1H), 2.57 (dd, J=17.3, 9.6 Hz, 1H), 2.45 (dd, J=17.2, 6.6 Hz, 1H), 1.48 (d, J=6.2 Hz, 3H).

LCMS-ESI$^+$ (m/z): [M+H]$^+$ calcd for C$_{22}$H$_{25}$F$_2$N$_4$O$_4$: 447.2; found 447.2.

Example 3.13

Preparation of (R)-4-((R)-1-(6-(3,4-dimethoxyphenyl)-3-(fluoromethyl)-3H-imidazo[4,5-c]pyridin-4-yloxy)ethyl)pyrrolidin-2-one To crude (R)-4-((R)-1-(6-(3,4-dimethoxyphenyl)-3H-imidazo[4,5-c]pyridin-4-yloxy)ethyl)pyrrolidin-2-one 3.09 (ca. 0.12 mmol) as a solution in DMF (1 mL) was added Cs$_2$CO$_3$ (110 mg, 0.34 mmol). Chlorofluoromethane was continuously bubbled through the resulting stirred suspension at a rate of ca. 5 bubbles/sec. After 1.5 h, addition of chlorofluoromethane was ceased, and the reaction was diluted with EtOAc (20 mL), water (10 mL), and brine (10 mL). The phases were separated, and the aqueous phase was extracted with EtOAc (20 mL). The combined organic phase was dried over Na$_2$SO$_4$, filtered, and concentrated onto silica gel. Sequential purification by silica gel chromatography (First run: 0% to 10% MeOH in DCM; second run: 49:49:2 to 47.5:47.5:5 DCM:THF:MeOH) provided (R)-4-((R)-1-(6-(3,4-dimethoxyphenyl)-3-(fluoromethyl)-3H-imidazo[4,5-c]pyridin-4-yloxy)ethyl)pyrrolidin-2-one 3.13.

$^1$H NMR (400 MHz, Chloroform-d) δ 8.08 (s, 1H), 7.72 (s, 1H), 7.63-7.56 (m, 2H), 7.01-6.93 (m, 1H), 6.40-6.13 (m, 2H), 5.98 (s, 1H), 5.75-5.64 (m, 1H), 3.98 (s, 3H), 3.94 (s, 3H), 3.58 (t, J=9.1 Hz, 1H), 3.40 (dd, J=9.7, 6.2 Hz, 1H), 3.06-2.88 (m, 1H), 2.64-2.42 (m, 2H), 1.53 (d, J=6.2 Hz, 3H).

LCMS-ESI$^+$ (m/z): [M+H]$^+$ calcd for C$_{21}$H$_{24}$FN$_4$O$_4$: 415.2; found 414.9.

Example 3.14

Preparation of (R)-4-((R)-1-(6-(3,4-dimethoxyphenyl)-3-(oxetan-3-yl)-3H-imidazo[4,5-c]pyridin-4-yloxy)ethyl)pyrrolidin-2-one

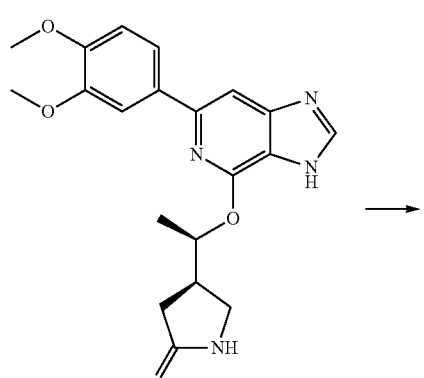

Example 3.09

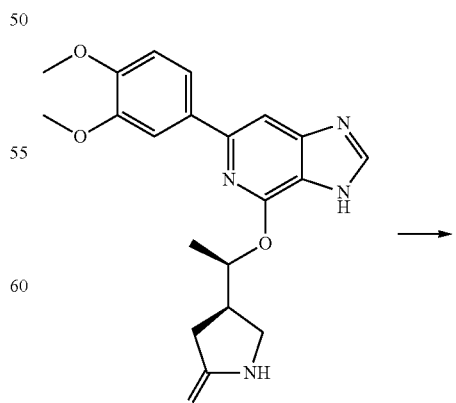

Example 3.09

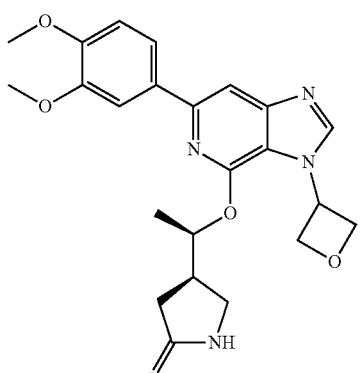

Example 3.14

To crude (R)-4-((R)-1-(6-(3,4-dimethoxyphenyl)-3H-imidazo[4,5-c]pyridin-4-yloxy)ethyl)pyrrolidin-2-one 3.09 (0.064 mmol) as a solution in DMF (1 mL) was added Cs$_2$CO$_3$ (52 mg, 0.16 mmol) followed by 3-iodo-oxetane (7.0 μL, 0.078 mmol). After stirring 30 min, the reaction temperature was increased to 60° C. After an additional 40 min, 3-iodo-oxetane (7.0 μL, 0.078 mmol) was added and the reaction temperature was increased to 100° C. After stirring an additional 35 min at 100° C., 3-iodo-oxetane (3.0 μL, 0.034 mmol) was added. After an additional 40 min, the reaction mixture was cooled to r.t. and was diluted with EtOAc (20 mL), water (10 mL), and brine (10 mL). The phases were separated, and the aqueous phase was extracted with EtOAc (20 mL). The combined organic phase was dried over Na$_2$SO$_4$, filtered, and concentrated, and the crude product was purified by silica gel chromatography (0% to 10% MeOH in DCM) to afford (R)-4-((R)-1-(6-(3,4-dimethoxyphenyl)-3-(oxetan-3-yl)-3H-imidazo[4,5-c]pyridin-4-yloxy)ethyl)pyrrolidin-2-one 3.14.

$^1$H NMR (400 MHz, Chloroform-d) δ 8.43 (s, 1H), 7.72 (s, 1H), 7.63-7.53 (m, 2H), 6.96 (d, J=8.3 Hz, 1H), 6.19 (s, 1H), 5.90-5.82 (m, 1H), 5.82-5.75 (m, 1H), 5.22-5.13 (m, 2H), 5.10-5.04 (m, 1H), 5.03-4.97 (m, 1H), 3.98 (s, 3H), 3.93 (s, 3H), 3.60 (t, J=9.2 Hz, 1H), 3.39 (dd, J=9.8, 5.9 Hz, 1H), 3.07-2.90 (m, 1H), 2.58 (dd, J=17.1, 9.4 Hz, 1H), 2.47 (dd, J=17.1, 7.0 Hz, 1H), 1.50 (d, J=6.2 Hz, 3H).

LCMS-ESI$^+$ (m/z): [M+H]$^+$ calcd for C$_{23}$H$_{27}$N$_4$O$_5$: 439.2; found 438.9.

Example 3.15

Preparation of ((R)-4-((R)-1-(5-(3,4-dimethoxyphenyl)-1-methyl-1H-benzo[d]imidazol-7-yloxy)ethyl)pyrrolidin-2-one

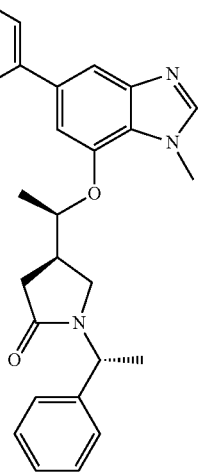

Example 2.55

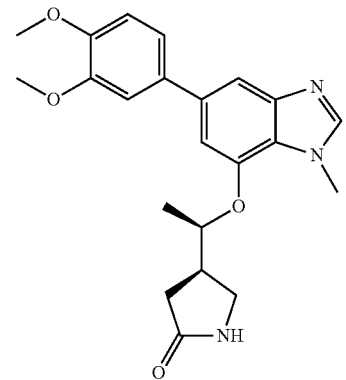

Example 3.15

A solution of (R)-4-((R)-1-(5-(3,4-dimethoxyphenyl)-1-methyl-1H-benzo[d]imidazol-7-yloxy)ethyl)-1-((R)-1-phenylethyl)pyrrolidin-2-one 2.55 (60 mg, 0.12 mmol) in TFA (3 mL) was heated in the microwave for 2 h at 150° C. The reaction mixture was concentrated and purified by reverse phase chromatography to give ((R)-4-((R)-1-(5-(3,4-dimethoxyphenyl)-1-methyl-1H-benzo[d]imidazol-7-yloxy)ethyl)pyrrolidin-2-one 3.15 as HCl salt.

$^1$H NMR (400 MHz, dmso-d$_6$): δ 9.04 (s, 1H); 7.63 (s, 1H), 7.49 (s, 1H), 7.40-7.24 (m, 3H), 7.08 (d, J=8.0 Hz, 1H), 5.03 (m, 1H), 4.14 (s, 3H), 3.85 (s, 3H), 3.67 (s, 3H). 3.43 (t, J=9.6 Hz, 1H), 3.19-3.12 (m, 1H), 2.87-2.80 (m, 1H), 2.40-2.22 (m, 2H), 1.33 (d, J=6.0 Hz, 3H).

LC/MS found for C$_{22}$H$_{25}$N$_3$O$_4$ as (M+H)$^+$ 396.2.

Example 3.16

Preparation of (R)-4-((R)-1-(5-(5,6-dimethoxypyridin-2-yl)-1-methyl-1H-benzo[d]imidazol-7-yloxy)ethyl)pyrrolidin-2-one

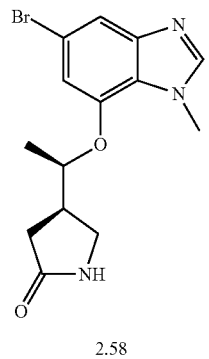

2.58

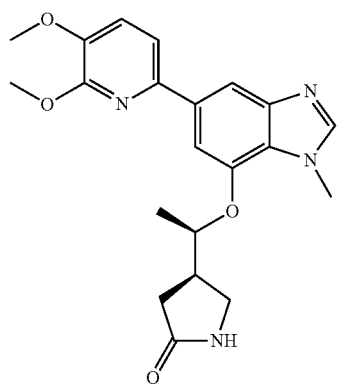

Example 3.16

To a mixture of (R)-4-((R)-1-(5-bromo-1-methyl-1H-benzo[d]imidazol-7-yloxy)ethyl)pyrrolidin-2-one 2.58 (22 mg, 0.066 mmol), 2,3-dimethoxy-6-(4,4,5,5-tetramethyl-1,3,2-dioxaborolan-2-yl)pyridine (35 mg, 0.132 mmol), Cs₂CO₃ (107 mg, 0.33 mmol) and PEPPSI"-IPr catalyst (3 mg, 0.003 mmol) was added DME and water (1:1, 2 mL) and the reaction mixture was heated to 110° C. for 1 hr. The mixture was then concentrated and purified by reverse phase chromatography to give (R)-4-((R)-1-(5-(5,6-dimethoxypyridin-2-yl)-1-methyl-1H-benzo[d]imidazol-7-yloxy)ethyl)pyrrolidin-2-one 3.16 as TFA salt.

$^1$H NMR (400 MHz, DMSO-$d_6$): δ 8.82 (s, 1H); 7.90 (s, 1H), 7.63-7.60 (m, 2H), 7.36 (d, J=8.0 Hz, 1H), 4.92 (m, 1H), 4.04 (s, 3H), 3.99 (s, 3H), 3.71 (s, 3H), 3.43-3.33 (m, 1H), 3.16-3.14 (m, 1H), 2.83-2.80 (m, 1H), 2.40-2.22 (m, 2H), 1.35 (d, J=6.4 Hz, 3H).

LC/MS found for $C_{21}H_{24}N_4O_4$ as (M+H)$^+$ 397.2.

Example 3.17

Preparation of (R)-4-((R)-1-(3-methyl-6-phenyl-3H-imidazo[4,5-c]pyridin-4-yloxy)ethyl)pyrrolidin-2-one

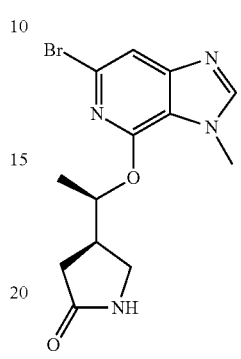

2.62

Example 3.17

To a mixture of (R)-4-((R)-1-(6-bromo-3-methyl-3H-imidazo[4,5-c]pyridin-4-yloxy)ethyl)pyrrolidin-2-one 2.62 (50 mg, 0.15 mmol), Phenyl boronic acid (36 mg, 0.30 mmol), Cs₂CO₃ (240 mg, 0.74 mmol) and PEPPSI"-IPr catalyst (5 mg, 0.007 mmol) was added DME and water (2:1, 3 mL) and the reaction was heated to 110° C. for 30 min. The reaction mixture was concentrated and purified by reverse phase chromatography to give (R)-4-((R)-1-(3-methyl-6-phenyl-3H-imidazo[4,5-c]pyridin-4-yloxy)ethyl) pyrrolidin-2-one 3.17 as TFA salt.

$^1$H NMR (400 MHz, DMSO-$d_6$) δ 8.43 (s, 1H), 8.16-8.06 (m, 2H), 7.82 (s, 1H), 7.58 (s, 1H), 7.46 (t, J=7.6 Hz, 2H), 7.37 (m, 1H), 5.58-5.55 (m, 1H), 3.99 (s, 3H), 3.41 (t, J=9.2 Hz, 1H), 3.18 (dd, J=9.8, 6.3 Hz, 1H), 2.82 (s, 1H), 2.41-2.23 (m, 2H), 1.42 (d, J=6.2 Hz, 3H).

LC/MS found for $C_{19}H_{20}N_4O_2$ as (M+H)$^+$ 337.4.

Example 3.18

Preparation of (R)-4-((R)-1-(6-(5,6-dimethoxypyridin-2-yl)-3-methyl-3H-imidazo[4,5-c]pyridin-4-yloxy)ethyl)pyrrolidin-2-one

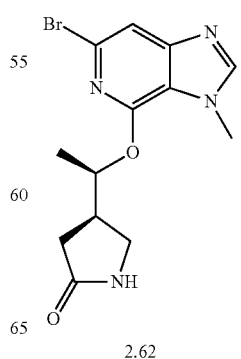

2.62

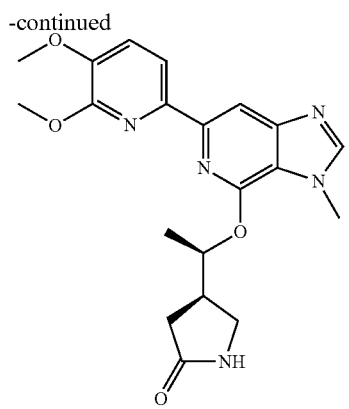

Example 3.18

To a mixture of (R)-4-((R)-1-(6-bromo-3-methyl-3H-imidazo[4,5-c]pyridin-4-yloxy)ethyl)pyrrolidin-2-one 2.62 (50 mg, 0.15 mmol), 2,3-dimethoxy-6-(4,4,5,5-tetramethyl-1,3,2-dioxaborolan-2-yl)pyridine (78 mg, 0.30 mmol), Cs$_2$CO$_3$ (240 mg, 0.74 mmol) and PEPPSI"-IPr catalyst (5 mg, 0.007 mmol) was added DME and water (2:1, 3 mL) and the reaction was heated to 110° C. for 30 min. The reaction mixture was concentrated and purified by reverse phase chromatography to give (R)-4-((R)-1-(3-methyl-6-phenyl-3H-imidazo[4,5-c]pyridin-4-yloxy)ethyl)pyrrolidin-2-one 3.18 as TFA salt.

$^1$H NMR (400 MHz, DMSO-d$_6$) δ 8.56 (s, 1H), 8.08 (s, 1H), 7.86 (d, J=8.1 Hz, 1H), 7.59 (s, 1H), 7.38 (d, J=8.2 Hz, 1H), 5.57-5.54 (m, 1H), 4.00 (s, 6H), 3.82 (s, 3H), 3.42 (t, J=9.2 Hz, 1H), 3.25-3.13 (m, 1H), 2.84 (d, J=7.4 Hz, 1H), 2.42-2.23 (m, 2H), 1.43 (d, J=6.2 Hz, 3H).

LC/MS found for C$_{20}$H$_{23}$N$_5$O$_4$ as (M+H)$^+$ 398.2.

Example 3.19

Preparation of (R)-4-((R)-1-(6-cyclohexenyl-3-methyl-3H-imidazo[4,5-c]pyridin-4-yloxy)ethyl)pyrrolidin-2-one

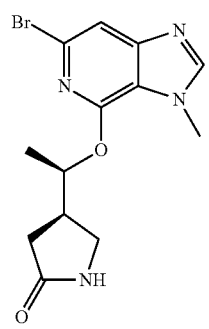
2.62

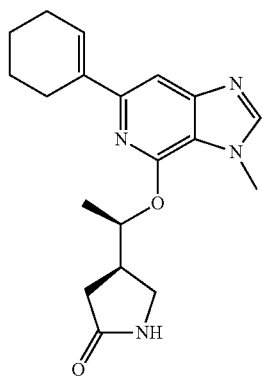
Example 3.19

To a mixture of (R)-4-((R)-1-(6-bromo-3-methyl-3H-imidazo[4,5-c]pyridin-4-yloxy)ethyl)pyrrolidin-2-one 2.62 (50 mg, 0.15 mmol), 2-cyclohexenyl-4,4,5,5-tetramethyl-1,3,2-dioxaborolane (31 mg, 0.30 mmol), Cs$_2$CO$_3$ (240 mg, 0.74 mmol) and PEPPSI"-IPr catalyst (5 mg, 0.007 mmol) was added DME and water (2:1, 3 mL) and the reaction was heated to 110° C. for 30 min. The reaction mixture was concentrated and purified by reverse phase chromatography to give (R)-4-((R)-1-(3-methyl-6-phenyl-3H-imidazo[4,5-c]pyridin-4-yloxy)ethyl)pyrrolidin-2-one 3.19 as TFA salt.

$^1$H NMR (400 MHz, DMSO-d$_6$) δ 8.69 (s, 1H), 7.57 (s, 1H), 7.23 (s, 1H), 6.82 (d, J=4.9 Hz, 1H), 5.52-5.37 (m, 1H), 3.98 (s, 3H), 3.38 (dd, J=10.8, 8.0 Hz, 1H), 3.13 (dd, J=9.7, 6.1 Hz, 1H), 2.78 (d, J=8.7 Hz, 1H), 2.38-2.15 (m, 4H), 1.72 (q, J=6.6, 6.0 Hz, 2H), 1.61 (d, J=6.6 Hz, 2H), 1.36 (d, J=6.2 Hz, 3H), 1.25 (t, J=6.3 Hz, 1H), 1.08 (t, J=7.0 Hz, 1H).

LC/MS found for C$_{19}$H$_{24}$N$_4$O$_2$ as (M+H)$^+$ 341.2.

Example 3.20

Preparation of (R)-4-((R)-1-(3-methyl-6-(pyrazolo[1,5-a]pyridin-3-yl)-3H-imidazo[4,5-c]pyridin-4-yloxy)ethyl)pyrrolidin-2-one

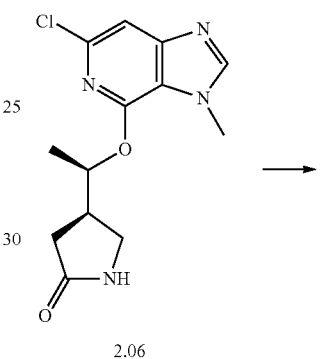
2.06

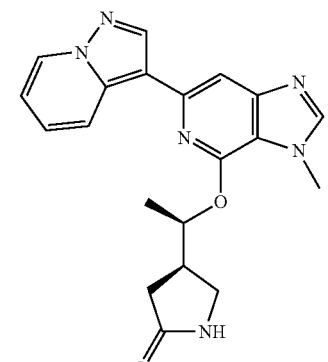
Example 3.20

Under Ar, (R)-4-((R)-1-(6-chloro-3-methyl-3H-imidazo[4,5-c]pyridin-4-yloxy)ethyl)pyrrolidin-2-one 2.06 (21.7 mg, 0.074 mmol), 3-(4,4,5,5-tetramethyl-1,3,2-dioxaborolan-2-yl)pyrazolo[1,5-a]pyridine (40 mg, 0.16 mmol), K$_3$PO$_4$ (57 mg, 0.27 mmol) and bis(di-tert-butyl(4-dimethylaminophenyl)phosphine)dichloropalladium(II) (3.3 mg, 0.0047 mmol) were taken up in dioxane (0.65 mL) and water (0.07 mL). The stirred mixture was heated to 100° C. for 70 min, at which time additional boronic ester (28 mg, 0.12 mmol), K$_3$PO$_4$ (45 mg, 0.21 mmol) and precatalyst (3.3 mg, 0.0047 mmol) were added. The mixture was stirred for an additional 15 h and was then cooled to r.t. and diluted with EtOAc (20 mL), water (10 mL) and brine (10 mL). The phases were separated, and the aqueous phase was extracted with EtOAc (20 mL). The combined organic phase was dried over Na$_2$SO$_4$, filtered, and concentrated directly onto silica gel.

Purification by silica gel chromatography (0% to 15% MeOH in CH$_2$Cl$_2$) provided (R)-4-((R)-1-(3-methyl-6-(pyrazolo[1,5-a]pyridin-3-yl)-3H-imidazo[4,5-c]pyridin-4-yloxy)ethyl)pyrrolidin-2-one 3.20.

$^1$H NMR (400 MHz, Chloroform-d) δ 8.53-8.46 (m, 1H), 8.41 (s, 1H), 8.32-8.26 (m, 1H), 7.85 (s, 1H), 7.63 (s, 1H), 7.22 (ddd, J=9.1, 6.7, 1.2 Hz, 1H), 6.86-6.76 (m, 1H), 5.78 (s, 1H), 5.76-5.68 (m, 1H), 4.02 (s, 3H), 3.65-3.58 (m, 1H), 3.42 (dd, J=9.7, 6.0 Hz, 1H), 3.05-2.92 (m, 1H), 2.65-2.50 (m, 2H), 1.54 (d, J=6.3 Hz, 3H).

LCMS-ESI$^+$ (m/z): [M+H]$^+$ calcd for C$_{20}$H$_{21}$N$_6$O$_2$: 377.2; found 377.2.

Example 3.21

Preparation of (R)-4-((R)-1-(6-(1-tert-butyl-1H-pyrazol-4-yl)-3-methyl-3H-imidazo[4,5-c]pyridin-4-yloxy)-3,3-difluoropropyl)pyrrolidin-2-one

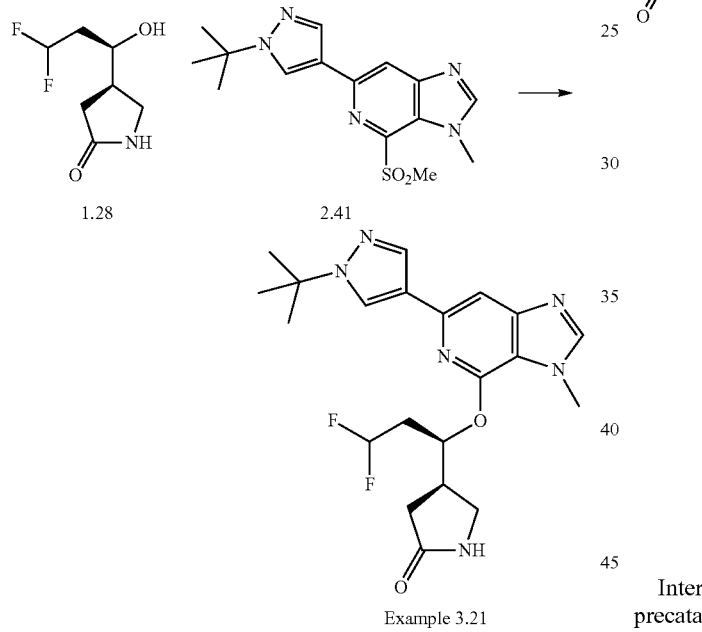

Example 3.21

To a solution of 1.28 (16 mg, 0.090 mmol) in DMF (0.5 mL) was added NaHMDS (0.10 mL, 0.10 mmol) and the mixture was stirred for 15 minutes. A solution of 2.41 (30 mg, 0.90 mmol) in DMF (1.0 mL) was added and the reaction was heated at 50° C. for an additional 4 hours. Water and EtOAc were added, the layers were separated, the organic layer was concentrated and the residue was purified via prep HPLC (2-95% acetonitrile in water, 0.1% TFA buffer) to isolate (R)-4-((R)-1-(6-(1-tert-butyl-1H-pyrazol-4-yl)-3-methyl-3H-imidazo[4,5-c]pyridin-4-yloxy)-3,3-difluoropropyl)pyrrolidin-2-one 3.21 as the TFA salt.

$^1$H NMR (400 MHz, CD$_3$OD) δ 9.07 (s, 1H), 8.34 (s, 1H), 8.08 (s, 1H), 7.57 (s, 1H), 6.10-6.16 (m, 2H), 4.23 (d, J=5.2 Hz, 1H), 4.18 (s, 3H), 3.64 (dd, J=8.4, 10.0 Hz, 1H), 3.39 (dd, J=4.8, 10.0 Hz, 1H), 3.06-3.12 (m, 1H), 2.54-2.65 (m, 1H), 2.33-2.37 (m, 1H), 1.64 (s, 9H).

LCMS-ESI$^+$ (m/z): [M+H]$^+$ calcd for C$_{21}$H$_{26}$F$_2$N$_3$O$_2$: 433.2; found 433.1.

Example 3.22

Preparation of (R)-4-((R)-1-(6-(benzo[d]thiazol-4-yl)-3-methyl-3H-imidazo[4,5-c]pyridin-4-yloxy)ethyl)pyrrolidin-2-one

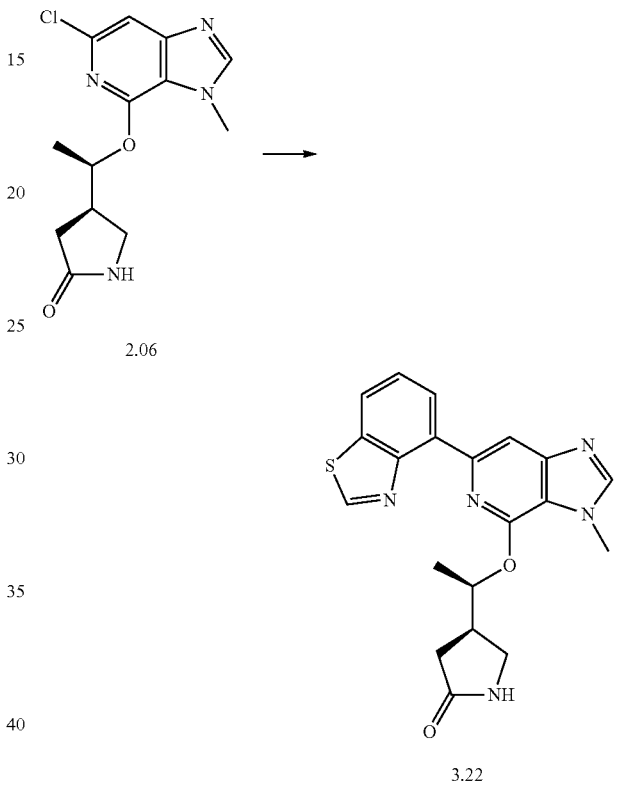

Intermediate 2.06 (30.3 mg, 0.103 mmol), Pd-PEPPSI-IPr precatalyst (7.1 mg, 0.010 mmol), 4-(4,4,5,5-tetramethyl-1,3,2-dioxaborolan-2-yl)benzo[d]thiazole (34 mg, 0.13 mmol), and Cs$_2$CO$_3$ (102 mg, 0.313 mmol) were taken up in DME (1.15 mL) under Ar. Water (0.57 mL) was added and the resulting mixture was heated to 100° C. After 2.5 h, additional Pd-PEPPSI-IPr precatalyst (7.4 mg, 0.011 mmol), 4-(4,4,5,5-tetramethyl-1,3,2-dioxaborolan-2-yl)benzo[d]thiazole (34 mg, 0.13 mmol), and Cs$_2$CO$_3$ (100 mg, 0.31 mmol) were added, and the mixture was stirred for an additional 16 h. The reaction mixture was diluted with EtOAc (20 mL) and water (20 mL) and the phases were separated. The aqueous phase was extracted with EtOAc and the combine organic phase was dried over Na$_2$SO$_4$, filtered, and concentrated to afford a crude residue that was purified by silica gel chromatography to provide (R)-4-((R)-1-(6-(benzo[d]thiazol-4-yl)-3-methyl-3H-imidazo[4,5-c]pyridin-4-yloxy)ethyl)pyrrolidin-2-one 3.22. LCMS-ESI$^+$ (m/z): [M+H]$^+$ calcd for C$_{20}$H$_{20}$N$_5$O$_2$S: 394.1; found 394.2. $^1$H NMR (400 MHz, Chloroform-d) δ 9.07 (s, 1H), 8.68 (s, 1H), 8.20 (dd, J=7.6, 1.2 Hz, 1H), 7.96 (dd, J=8.0, 1.2 Hz, 1H), 7.88 (s, 1H), 7.59-7.49 (m, 1H), 5.84-5.73 (m, 2H), 4.04 (s, 3H), 3.63-3.53 (m, 1H), 3.41 (dd, J=9.7, 6.1 Hz, 1H), 3.02-2.86 (m, 1H), 2.58-2.52 (m, 2H), 1.51 (d, J=6.2 Hz, 3H).

Example 3.23

Preparation of (R)-4-((R)-1-(3-methyl-6-(1-methyl-1H-thieno[3,2-c]pyrazol-5-yl)-3H-imidazo[4,5-c]pyridin-4-yloxy)ethyl)pyrrolidin-2-one

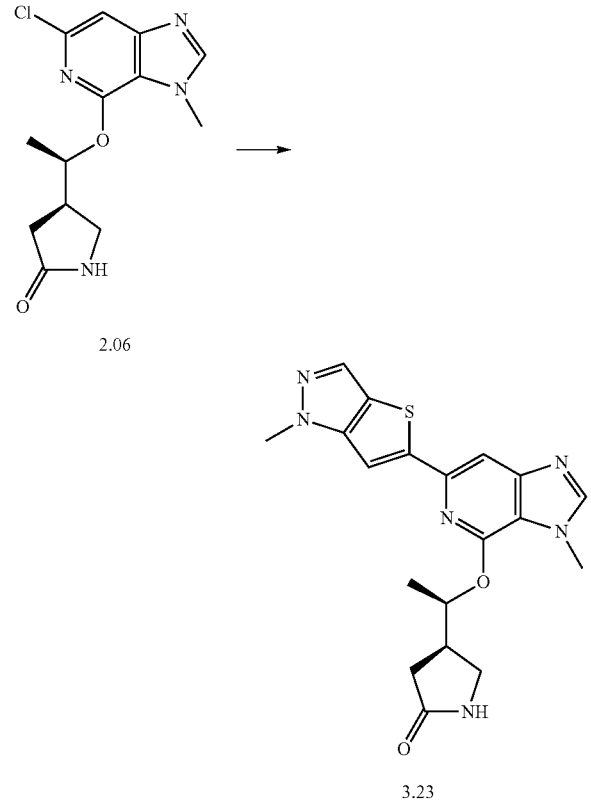

Intermediate 2.06 (29 mg, 0.098 mmol), Pd-PEPPSI-IPent precatalyst (4 mg, 0.005 mmol), cesium fluoride (32 mg, 0.21 mmol) and powdered 4 Å molecular sieves (25 mg) were taken up in dioxane (1 mL) under Ar. 1-methyl-5-(tributylstannyl)-1H-thieno[3,2-c]pyrazole (46 µL, 0.13 mmol) was added and the resulting mixture was heated to 65-70° C. After 2 h, the reaction temperature was increased to 80° C. After 18 additional hours, additional Pd-PEPPSI-IPent precatalyst (3 mg, 0.004 mmol), CsF (35 mg, 0.23 mmol) and stannane (23 µL, 0.065 mmol) were added and the reaction was heated to 80° C. After an additional 3 h, additional Pd-PEPPSI-IPent precatalyst (5 mg, 0.006 mmol) was added and the reaction was stirred at 80° C. overnight. After 16 additional hours, the reaction mixture was partitioned between EtOAc and water. The phases were separated, and the aqueous phase was extracted with EtOAc. The combined organic phase was dried over $Na_2SO_4$, filtered, and concentrated to afford a crude residue that was purified by silica gel chromatography (MeOH in DCM) to provide (R)-4-((R)-1-(3-methyl-6-(1-methyl-1H-thieno[3,2-c]pyrazol-5-yl)-3H-imidazo[4,5-c]pyridin-4-yloxy)ethyl)pyrrolidin-2-one 3.23. LCMS-ESI$^+$ (m/z): [M+H]$^+$ calcd for $C_{19}H_{21}N_6O_2S$: 397.1; found: 397.2. $^1$H NMR (400 MHz, Chloroform-d) δ 7.86 (s, 1H), 7.70 (s, 1H), 7.63 (d, J=0.7 Hz, 1H), 7.35 (d, J=0.7 Hz, 1H), 5.74-5.65 (m, 1H), 5.53 (s, 1H), 4.06 (s, 3H), 4.02 (d, J=0.4 Hz, 3H), 3.66-3.58 (m, 1H), 3.45-3.39 (m, 1H), 3.02-2.88 (m, 1H), 2.63-2.48 (m, 2H), 1.52 (d, J=6.3 Hz, 3H).

Example 3.24

Preparation of (R)-4-((R)-1-(3-(difluoromethyl)-6-(4-morpholinophenyl)-3H-imidazo[4,5-c]pyridin-4-yloxy)ethyl)pyrrolidin-2-one Intermediate 2.64 (24 mg, 0.073 mmol), 4-morpholinophenylboronic acid (33 mg, 0.16 mmol), Bis[di-tert-butyl (4-dimethylaminophenyl)phosphine]dichloropalladium(II) (1.7 mg, 0.0024 mmol) and $K_3PO_4$ (52 mg, 0.25 mmol) were taken up in 1,4-dioxane (0.9 mL) under Ar. Water (0.1 mL) was added and the resulting stirred mixture was heated to 100° C. After 1.75 h, the reaction mixture was cooled to r.t. and was diluted with EtOAc (2 mL), water (1 mL), and brine (1 mL). The phases were separated, and the aqueous phase was extracted with EtOAc (4×1.5 mL). The combined organic phase was dried over $Na_2SO_4$, filtered, and concentrated. The resulting crude residue was purified by silica gel chromatography (0% to 15% MeOH in DCM) to afford (R)-4-((R)-1-(3-(difluoromethyl)-6-(4-morpholinophenyl)-3H-imidazo[4,5-c]pyridin-4-yloxy)ethyl)pyrrolidin-2-one 3.24. LCMS-ESI$^+$ (m/z): [M+H]$^+$ calcd for $C_{23}H_{26}F_2N_5O_3$: 458.2; found 458.0. $^1$H NMR (400 MHz, Chloroform-d) δ 8.26 (s, 1H), 7.99-7.88 (m, 2H), 7.72 (s, 1H), 7.61 (t, J=61.1 Hz, 1H), 7.05-6.95 (m, 2H), 6.05 (s, 1H), 5.79-5.67 (m, 1H), 3.94-3.83 (m, 4H), 3.62-3.53 (m, 1H), 3.37 (dd, J=9.7, 6.2 Hz, 1H), 3.28-3.19 (m, 4H), 3.00-2.88 (m, 1H), 2.56 (dd, J=17.2, 9.3 Hz, 1H), 2.45 (dd, J=17.2, 7.4 Hz, 1H), 1.50 (d, J=6.2 Hz, 3H).

Example 3.25

Preparation of (R)-4-((R)-1-(3-(difluoromethyl)-6-(4-morpholinophenyl)-3H-imidazo[4,5-c]pyridin-4-yloxy)ethyl)pyrrolidin-2-one

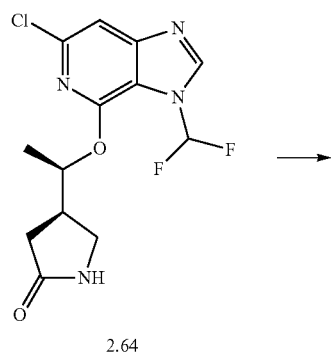

2.64

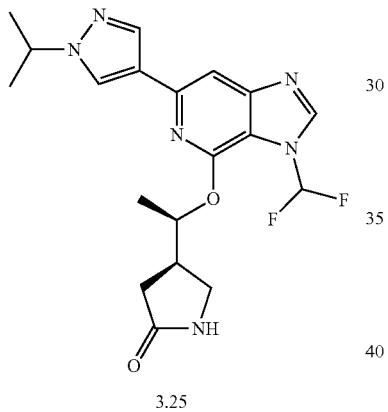

3.25

Example 3.26

(R)-4-((R)-1-(6-(1-(2,2-difluoroethyl)-1H-pyrazol-4-yl)-3-(difluoromethyl)-3H-imidazo[4,5-c]pyridin-4-yloxy)ethyl)pyrrolidin-2-one

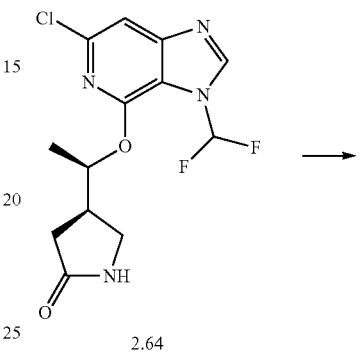

2.64

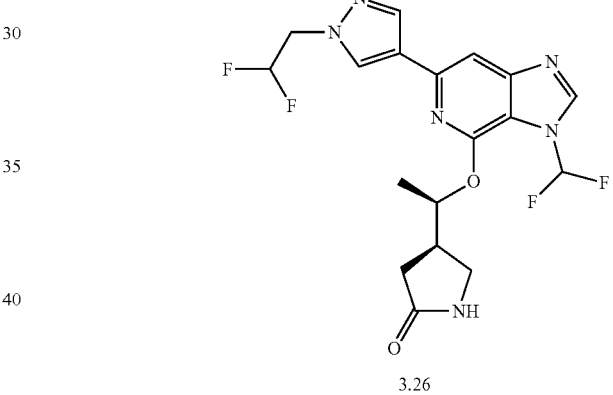

3.26

Intermediate 2.64 (27 mg, 0.082 mmol), 1-isopropyl-4-(4,4,5,5-tetramethyl-1,3,2-dioxaborolan-2-yl)-1H-pyrazole (40 mg, 0.17 mmol), Bis[di-tert-butyl(4-dimethylaminophenyl)phosphine]dichloropalladium(II) (1.8 mg, 0.0025 mmol) and $K_3PO_4$ (52 mg, 0.25 mmol) were taken up in 1,4-dioxane (0.9 mL) under Ar. Water (0.1 mL) was added and the resulting stirred mixture was heated to 100° C. After 1.25 h, the reaction mixture was cooled to r.t. and was diluted with EtOAc (2 mL), water (1 mL), and brine (1 mL). The phases were separated, and the aqueous phase was extracted with EtOAc (4×1.5 mL). The combined organic phase was dried over $Na_2SO_4$, filtered, and concentrated. The resulting crude residue was purified by silica gel chromatography (0% to 15% MeOH in DCM) to afford (R)-4-((R)-1-(3-(difluoromethyl)-6-(4-morpholinophenyl)-3H-imidazo[4,5-c]pyridin-4-yloxy)ethyl)pyrrolidin-2-one 3.25. LCMS-ESI$^+$ (m/z): [M+H]$^+$ calcd for $C_{19}H_{23}F_2N_6O_2$: 405.2; found 405.1. 1H NMR (400 MHz, Chloroform-d) δ 8.24 (s, 1H), 7.95 (d, J=0.7 Hz, 1H), 7.85 (s, 1H), 7.59 (t, J=61.1 Hz, 1H), 7.48 (s, 1H), 6.12 (s, 1H), 5.71-5.61 (m, 1H), 4.63-4.46 (m, 1H), 3.63-3.50 (m, 1H), 3.37 (dd, J=9.7, 6.1 Hz, 1H), 2.99-2.87 (m, 1H), 2.55 (dd, J=17.2, 9.3 Hz, 1H), 2.45 (dd, J=17.2, 7.4 Hz, 1H), 1.56 (d, J=6.7 Hz, 6H), 1.47 (d, J=6.2 Hz, 3H).

Intermediate 2.64 (25 mg, 0.076 mmol), 1-(2,2-difluoroethyl)-4-(4,4,5,5-tetramethyl-1,3,2-dioxaborolan-2-yl)-1H-pyrazole (40 mg, 0.16 mmol), bis[di-tert-butyl(4-dimethylaminophenyl)phosphine]dichloropalladium(II) (1.6 mg, 0.0023 mmol) and $K_3PO_4$ (52 mg, 0.25 mmol) were taken up in 1,4-dioxane (0.9 mL) under Ar. Water (0.1 mL) was added and the resulting stirred mixture was heated to 100° C. After 1.25 h, the reaction mixture was cooled to r.t. and was diluted with EtOAc (2 mL), water (1 mL), and brine (1 mL). The phases were separated, and the aqueous phase was extracted with EtOAc (4×1.5 mL). The combined organic phase was dried over $Na_2SO_4$, filtered, and concentrated. The resulting crude residue was purified by silica gel chromatography (0% to 15% MeOH in DCM) to afford (R)-4-((R)-1-(6-(1-(2,2-difluoroethyl)-1H-pyrazol-4-yl)-3-(difluoromethyl)-3H-imidazo[4,5-c]pyridin-4-yloxy)ethyl)pyrrolidin-2-one 3.26. LCMS-ESI$^+$ (m/z): [M+H]$^+$ calcd for $C_{15}H_{19}F_4N_6O_2$: 427.2; found 426.8. $^1$H NMR (400 MHz, Chloroform-d) δ 8.26 (s, 1H), 8.01 (s, 1H), 7.91 (s, 1H), 7.60 (t, J=61.1 Hz, 1H), 7.51 (s, 1H), 6.32-5.97 (m, 2H), 5.72-5.58 (m, 1H), 4.51 (td, J=13.5, 4.3 Hz, 2H), 3.65-3.52 (m, 1H), 3.36 (dd, J=9.7, 6.1

Hz, 1H), 3.00-2.84 (m, 1H), 2.55 (dd, J=17.2, 9.3 Hz, 1H), 2.44 (dd, J=17.2, 7.3 Hz, 1H), 1.48 (d, J=6.2 Hz, 3H).

Example 3.27

Preparation of (R)-4-((R)-1-(3-cyclobutyl-6-(3,4-dimethoxyphenyl)-3H-imidazo[4,5-c]pyridin-4-yloxy)ethyl)pyrrolidin-2-

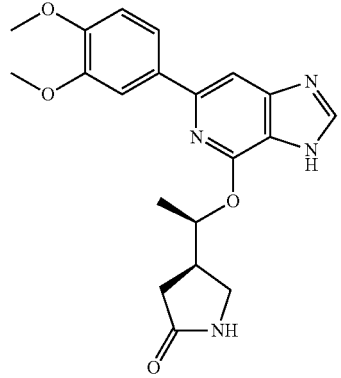

Example 3.09

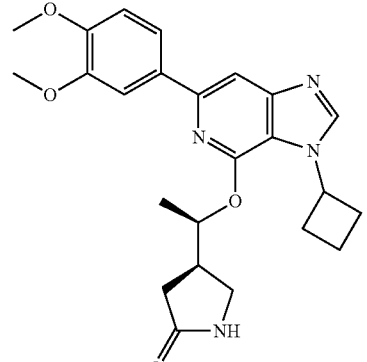

Example 3.27

Bromocyclobutane (18 mg, 0.137 mmol) was added to a mixture of (R)-4-((R)-1-(6-(3,4-dimethoxyphenyl)-3H-imidazo[4,5-c]pyridin-4-yloxy)ethyl)pyrrolidin-2-one 3.09 (50 mg, 0.131 mmol) and cesium carbonate (127 mg, 0.392 mmol) in 5 mL of DMF at room temperature. Reaction mixture was heated at 80° C. in a microwave reactor for one hour. Reaction mixture was taken up in ethyl acetate and washed with saturated NaHCO$_3$ $_{(aq)}$ and brine. The separated organic layers were dried (MgSO$_4$), filtered, and concentrated under reduced pressure. Residues were purified via reverse phase chromatography to yield (R)-4-((R)-1-(3-cyclobutyl-6-(3,4-dimethoxyphenyl)-3H-imidazo[4,5-c]pyridin-4-yloxy)ethyl)pyrrolidin-2-one 3.27.

$^1$H NMR (400 MHz, Chloroform-d) δ 8.05 (s, 1H), 7.69 (d, J=8.4 Hz, 1H), 7.65-7.52 (m, 2H), 7.04-6.90 (m, 1H), 5.76 (p, J=6.2 Hz, 1H), 5.63 (d, J=12.2 Hz, 1H), 5.24-5.02 (m, 1H), 3.95 (d, J=17.4 Hz, 6H), 3.58 (dd, J=9.9, 8.2 Hz, 1H), 3.48 (d, J=5.5 Hz, 2H), 3.40 (dd, J=9.6, 6.3 Hz, 1H), 3.00 (dtd, J=14.7, 8.6, 5.8 Hz, 1H), 2.67-2.49 (m, 4H), 1.98 (tt, J=9.8, 7.3 Hz, 2H), 1.55-1.43 (m, 3H). LCMS-ESI$^+$ (m/z): [M+H]$^+$ calcd for C$_{24}$H$_{28}$N$_4$O$_4$: 437.2; found 437.2.

Example 3.28

Preparation (R)-4-((R)-1-(3-(difluoromethyl)-6-(3,4-dimethoxyphenyl)-2-methyl-3H-imidazo[4,5-c]pyridin-4-yloxy)ethyl)pyrrolidin-2-one

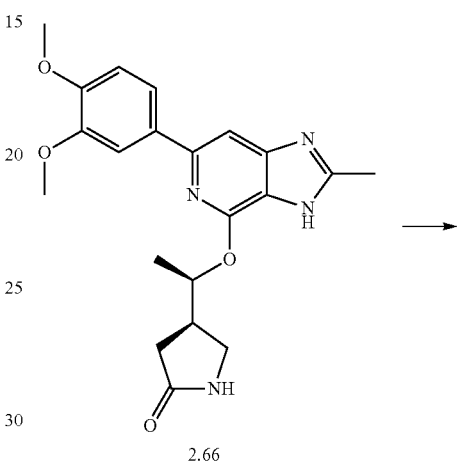

2.66

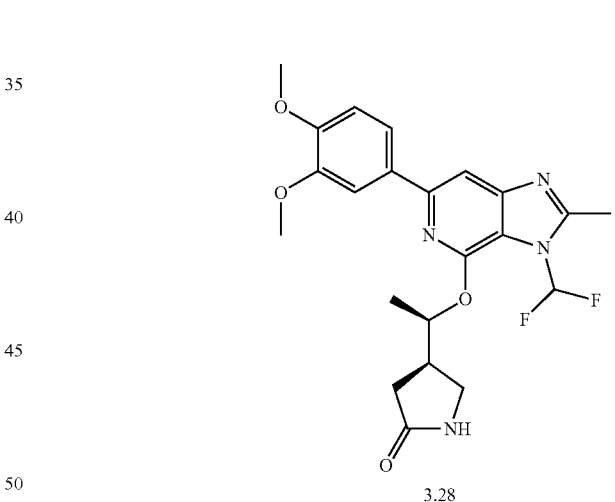

3.28

Following a procedure analogous to that used to prepare example 2.28, beginning with (R)-4-((R)-1-(6-(3,4-dimethoxyphenyl)-2-methyl-3H-imidazo[4,5-c]pyridin-4-yloxy)ethyl)pyrrolidin-2-one 2.66 and chlorodifluoromethane, (R)-4-((R)-1-(3-(difluoromethyl)-6-(3,4-dimethoxyphenyl)-2-methyl-3H-imidazo[4,5-c]pyridin-4-yloxy)ethyl)pyrrolidin-2-one 3.28 was synthesized.

1H NMR (400 MHz, Methanol-d4) δ 7.91 (t, J=57.9 Hz, 1H), 7.73-7.68 (m, 2H), 7.64 (dd, J=8.4, 2.1 Hz, 1H), 7.05 (d, J=8.5 Hz, 1H), 5.70 (p, J=6.3 Hz, 1H), 3.91 (d, J=18.4 Hz, 6H), 3.55 (dd, J=10.0, 8.4 Hz, 1H), 3.40 (dd, J=10.0, 6.9 Hz, 1H), 3.07-2.92 (m, 1H), 2.73 (s, 3H), 2.53 (dd, J=8.7, 2.0 Hz, 1H), 1.49 (d, J=6.2 Hz, 3H). LCMS-ESI⁺ (m/z): [M+H]⁺ calcd for C$_{22}$H$_{24}$F$_2$N$_4$O$_4$: 447.2; found 447.1.

Example 3.29

(R)-4-((R)-1-(6-(3,4-dimethoxyphenyl)-3-isopropyl-2-methyl-3H-imidazo[4,5-c]pyridin-4-yloxy)ethyl)pyrrolidin-2-one

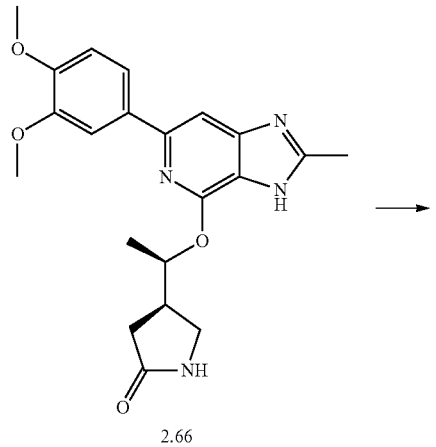

2.66

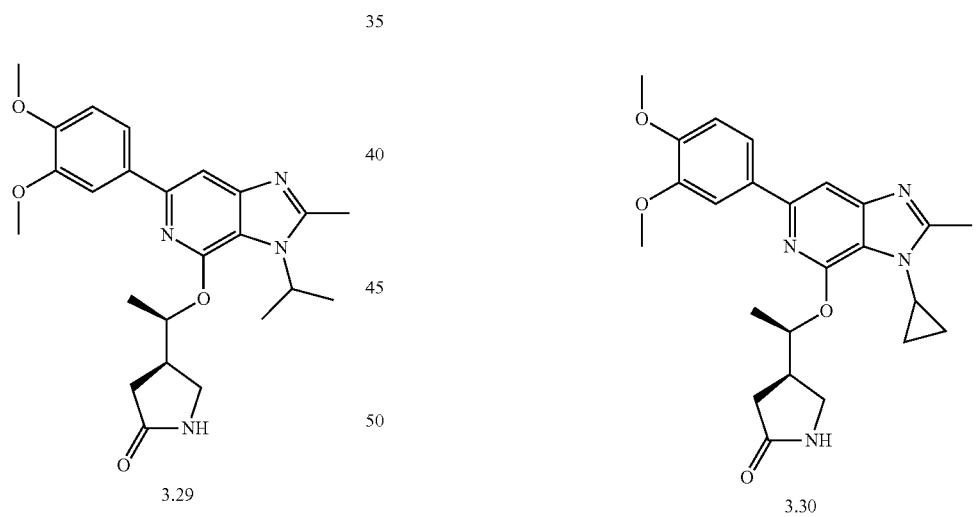

3.29

Following a procedure analogous to that used to prepare example 2.18, beginning with (R)-4-((R)-1-(6-(3,4-dimethoxyphenyl)-2-methyl-3H-imidazo[4,5-c]pyridin-4-yloxy)ethyl)pyrrolidin-2-one 2.66 (1 eq) and 2-iodopropane (2 eq), (R)-4-((R)-1-(6-(3,4-dimethoxyphenyl)-3-isopropyl-2-methyl-3H-imidazo[4,5-c]pyridin-4-yloxy)ethyl)pyrrolidin-2-one 3.29 was synthesized.

1H NMR (400 MHz, Methanol-d4) δ 7.82-7.59 (m, 3H), 7.05 (d, J=8.2 Hz, 1H), 5.88 (s, 1H), 5.47-5.07 (m, 1H), 3.90 (d, J=16.5 Hz, 6H), 3.65 (dd, J=10.2, 8.7 Hz, 1H), 3.40 (dd, J=10.2, 6.0 Hz, 1H), 3.20-3.01 (m, 1H), 2.93 (s, 3H), 2.61 (dd, J=17.3, 9.7 Hz, 1H), 2.49 (dd, J=17.3, 7.1 Hz, 1H), 1.75 (dd, J=8.1, 6.8 Hz, 6H), 1.55 (d, J=6.2 Hz, 3H). LCMS-ESI⁺ (m/z): [M+H]⁺ calcd for C$_{24}$H$_{30}$N$_4$O$_4$: 439.2; found 439.2.

Example 3.30

(R)-4-((R)-1-(3-cyclopropyl-6-(3,4-dimethoxyphenyl)-2-methyl-3H-imidazo[4,5-c]pyridin-4-yloxy)ethyl)pyrrolidin-2-one

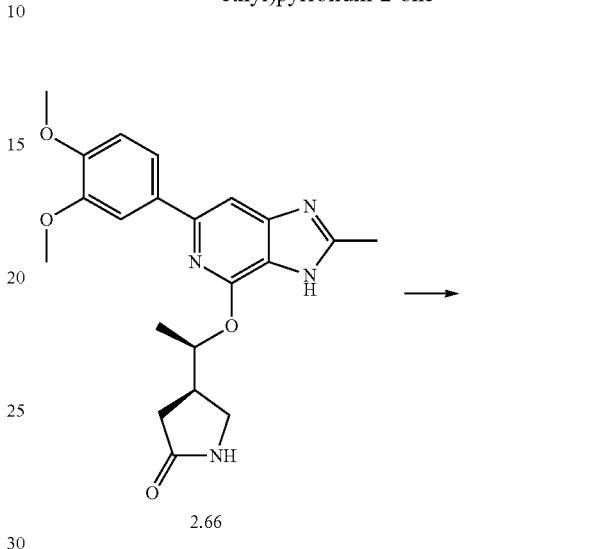

3.30

Following a procedure analogous to that used to prepare example 2.35, beginning with (R)-4-((R)-1-(6-(3,4-dimethoxyphenyl)-2-methyl-3H-imidazo[4,5-c]pyridin-4-yloxy)ethyl)pyrrolidin-2-one 2.66 (1 eq), (R)-4-((R)-1-(3-cyclopropyl-6-(3,4-dimethoxyphenyl)-2-methyl-3H-imidazo[4,5-c]pyridin-4-yloxy)ethyl)pyrrolidin-2-one 3.30 was synthesized.

1H NMR (400 MHz, Methanol-d4) δ 7.76-7.59 (m, 3H), 7.06 (d, J=9.0 Hz, 1H), 5.84 (p, J=6.1 Hz, 1H), 3.91 (d, J=15.6 Hz, 6H), 3.73-3.56 (m, 2H), 3.41 (dd, J=10.2, 5.9 Hz, 1H), 3.12-2.98 (m, 1H), 2.90 (s, 3H), 2.56 (qd, J=17.2, 8.2 Hz, 2H), 1.54 (d, J=6.2 Hz, 3H), 1.49-1.37 (m, 2H), 1.37-1.19 (m, 2H). LCMS-ESI⁺ (m/z): [M+H]⁺ calcd for C24H28N4O4: 437.2; found 437.2.

Example 3.31

Preparation of (R)-4-((R)-1-(5-(5,6-dimethoxypyridin-2-yl)-1,2-dimethyl-1H-benzo[d]imidazol-7-yloxy)ethyl)pyrrolidin-2-one

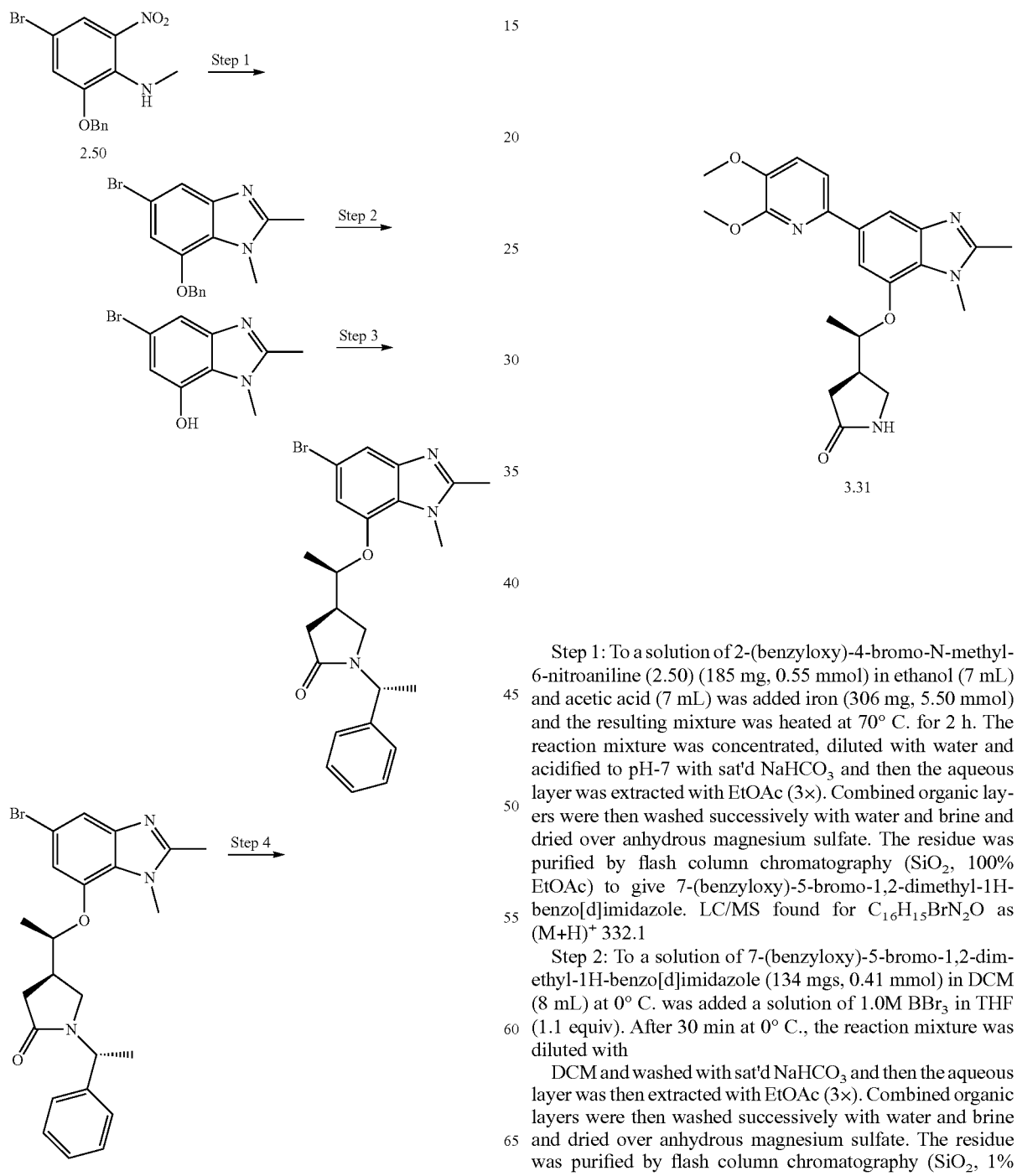

3.31

Step 1: To a solution of 2-(benzyloxy)-4-bromo-N-methyl-6-nitroaniline (2.50) (185 mg, 0.55 mmol) in ethanol (7 mL) and acetic acid (7 mL) was added iron (306 mg, 5.50 mmol) and the resulting mixture was heated at 70° C. for 2 h. The reaction mixture was concentrated, diluted with water and acidified to pH-7 with sat'd NaHCO₃ and then the aqueous layer was extracted with EtOAc (3×). Combined organic layers were then washed successively with water and brine and dried over anhydrous magnesium sulfate. The residue was purified by flash column chromatography (SiO₂, 100% EtOAc) to give 7-(benzyloxy)-5-bromo-1,2-dimethyl-1H-benzo[d]imidazole. LC/MS found for C₁₆H₁₅BrN₂O as (M+H)⁺ 332.1

Step 2: To a solution of 7-(benzyloxy)-5-bromo-1,2-dimethyl-1H-benzo[d]imidazole (134 mgs, 0.41 mmol) in DCM (8 mL) at 0° C. was added a solution of 1.0M BBr₃ in THF (1.1 equiv). After 30 min at 0° C., the reaction mixture was diluted with DCM and washed with sat'd NaHCO₃ and then the aqueous layer was then extracted with EtOAc (3×). Combined organic layers were then washed successively with water and brine and dried over anhydrous magnesium sulfate. The residue was purified by flash column chromatography (SiO₂, 1% MeOH/EtOAc-20% MeOH/EtOAc) to give of 5-bromo-1,2- dimethyl-1H-benzo[d]imidazol-7-ol. LC/MS found for C₉H₉BrN₂O as (M+H)⁺ 242.1.

Example 3.32

Preparation of (R)-4-((R)-1-((6-(3,4-dimethoxyphenyl)-3-(1-methylcyclopropyl)-3H-imidazo[4,5-c]pyridin-4-yl)oxy)ethyl)pyrrolidin-2-one

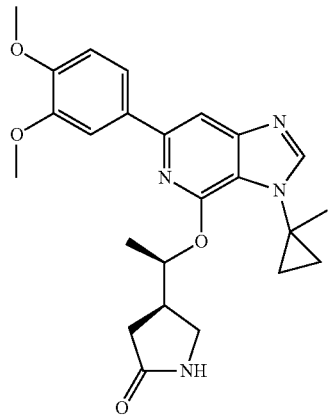

3.32

Following the protocol described in General Procedure 3A starting with mixture 2.72 of (R)-4-((R)-1-((6-bromo-3-(1-methylcyclopropyl)-3H-imidazo[4,5-c]pyridin-4-yl)oxy)ethyl)-1-((R)-1-(4-methoxyphenyl)ethyl)pyrrolidin-2-one and (R)-4-((R)-1-((6-chloro-3-(1-methylcyclopropyl)-3H-imidazo[4,5-c]pyridin-4-yl)oxy)ethyl)-1-((R)-1-(4-methoxyphenyl)ethyl)pyrrolidin-2-one (50 mg, ~0.1 mmol) and (3,4-dimethoxyphenyl)boronic acid (21.27 mg, 0.117 mmol), of (R)-4-((R)-1-((6-(3,4-dimethoxyphenyl)-3-(1-methylcyclopropyl)-3H-imidazo[4,5-c]pyridin-4-yl)oxy)ethyl)pyrrolidin-2-one 3.32 (49 mg) was synthesized.

¹H NMR (400 MHz, Methanol-d4) δ 9.42 (s, 1H), 7.79-7.58 (m, 3H), 7.06 (d, J=9.0 Hz, 1H), 5.89 (p, J=6.1 Hz, 1H), 3.92 (s, 3H), 3.88 (s, 3H), 3.65 (dd, J=10.1, 8.8 Hz, 1H), 3.45 (dd, J=10.2, 6.4 Hz, 1H), 3.16-3.01 (m, 1H), 2.65-2.41 (m, 2H), 1.79 (s, 3H), 1.55 (d, J=6.2 Hz, 3H), 1.54-1.46 (m, 2H), 1.28-1.15 (m, 2H).

LCMS-ESI⁺ (m/z): [M+H]⁺ calcd for C₂₄H₂₉N₄O₄: 437.2; found: 437.2.

Example 3.33

Preparation of (R)-4-((R)-1-((6-(3,4-dimethoxyphenyl)-2-ethyl-3-methyl-3H-imidazo[4,5-c]pyridin-4-yl)oxy)ethyl)pyrrolidin-2-one

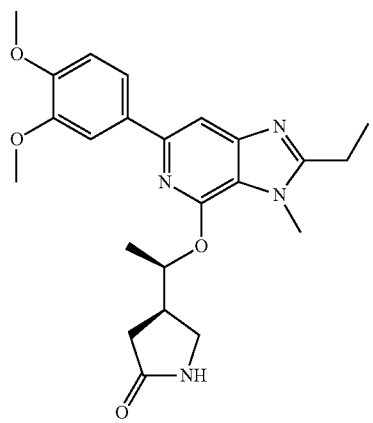

3.33

Following General Procedure 3A, beginning with (R)-4-((R)-1-((6-bromo-2-ethyl-3-methyl-3H-imidazo[4,5-c]pyridin-4-yl)oxy)ethyl)-1-((S)-1-(4-methoxyphenyl)ethyl)pyrrolidin-2-one 2.80 (200 mg, 0.39 mmol) and (3,4-dimethoxyphenyl)boronic acid (87 mg, 0.0.48 mmol) the compound (R)-4-((R)-1-((6-(3,4-dimethoxyphenyl)-2-ethyl-3-methyl-3H-imidazo[4,5-c]pyridin-4-yl)oxy)ethyl)pyrrolidin-2-one 3.33 was synthesized (15 mg).

¹H NMR (400 MHz, DMSO-d6) δ 7.73 (s, 1H), 7.68-7.62 (m, 2H), 7.56 (s, 1H), 7.07-6.96 (m, 1H), 5.55 (p, J=6.0 Hz, 1H), 3.95 (s, 3H), 3.85 (s, 3H), 3.79 (s, 3H), 3.41 (t, J=9.1 Hz, 1H), 3.17 (dd, J=9.7, 7.1 Hz, 1H), 3.05-2.91 (m, 2H), 2.86-2.82 (m, 1H), 2.40-2.18 (m, 2H), 1.43 (d, J=6.2 Hz, 3H), 1.33 (t, J=7.5 Hz, 3H).

LCMS-ESI⁺ (m/z): [M+H]⁺ calcd for C₂₃H₂₉N₄O₄: 425.2; found: 425.2.

Example 3.34

Preparation of (R)-4-((R)-1-((3-methyl-6-(4-(4-(tetrahydro-2H-pyran-4-yl)piperazin-1-yl)phenyl)-3H-imidazo[4,5-c]pyridin-4-yl)oxy)ethyl)pyrrolidin-2-one

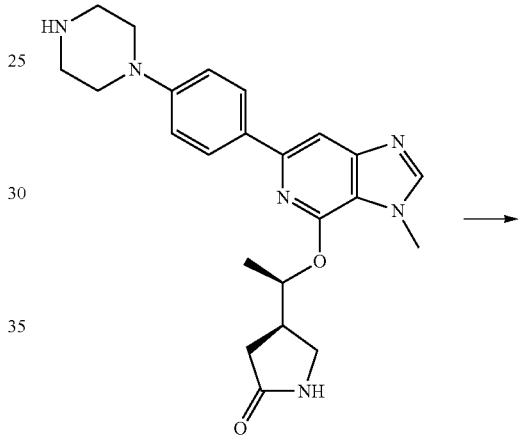

Example 3A.13

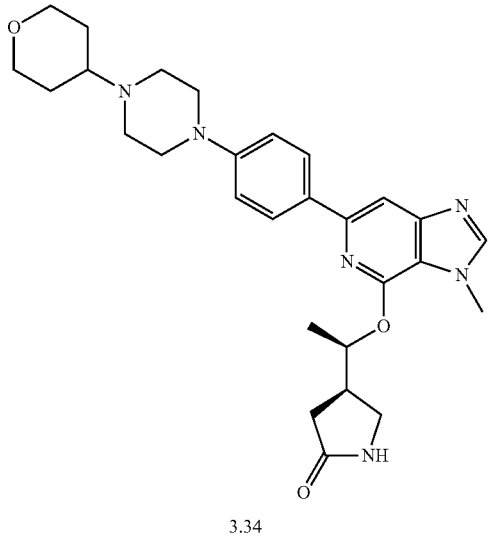

3.34

A mixture of (R)-4-((R)-1-(3-methyl-6-(4-(piperazin-1-yl)phenyl)-3H-imidazo[4,5-c]pyridin-4-yloxy)ethyl)pyrrolidin-2-one 3A.13 (44.0 mg, 0.105 mmol), 4-oxotetrahydropyran (37.7 mg, 0.366 mmol) and sodium triacetoxyborohydride (100 mg, 0.471 mmol) in 1,2-dichloroethane (1.0 mL) was stirred at room temperature over the weekend. The reaction was diluted with saturated NaHCO₃ (aq) and methanol. The mixture was concentrated to dryness and the residue was purified via prep HPLC (2-95% acetonitrile in water, 0.1% trifluoroacetic acid buffer) to isolate (R)-4-((R)-1-((3-methyl-6-(4-(4-(tetrahydro-2H-pyran-4-yl)piperazin-1-yl)phenyl)-3H-imidazo[4,5-c]pyridin-4-yl)oxy)ethyl)pyrrolidin-2-one 3.34 (26 mg) as its trifluoroacetic acid salt.

¹H NMR (400 MHz, DMSO-d6) δ 9.68 (s, 1H), 8.46 (s, 1H), 8.01 (d, J=8.8 Hz, 2H), 7.73 (s, 1H), 7.59 (s, 1H), 7.11 (d, J=9.0 Hz, 2H), 5.54 (p, J=5.9 Hz, 1H), 4.08-3.89 (m, 7H), 3.71-3.59 (m, 2H), 3.56-3.47 (m, 1H), 3.43 (t, J=9.1 Hz, 1H), 3.38-3.27 (m, 2H), 3.27-3.11 (m, 3H), 3.10-3.95 (m, 2H), 2.90-2.76 (m, 1H), 2.44-2.21 (m, 2H), 2.11-1.98 (m, 2H), 1.77-1.58 (m, 2H), 1.43 (d, J=6.2 Hz, 3H).

LCMS-ESI+ (m/z): [M+H]+ calcd for $C_{28}H_{37}N_6O_3$: 505.3; found: 505.4.

Example 3.35

Preparation of (R)-4-((R)-1-((6-(4-(4-isopropylpiperazin-1-yl)phenyl)-3-methyl-3H-imidazo[4,5-c]pyridin-4-yl)oxy)ethyl)pyrrolidin-2-one A mixture of (R)-4-((R)-1-(3-methyl-6-(4-(piperazin-1-yl)phenyl)-3H-imidazo[4,5-c]pyridin-4-yloxy)ethyl)pyrrolidin-2-one 3A.13 (29 mg, 0.069 mmol), acetone (18 µL, 0.24 mmol) and sodium triacetoxyborohydride (66 mg, 0.31 mmol) in THF (1.0 mL) was stirred at room temperature over the weekend. The reaction was diluted with saturated NaHCO₃ (aq) and methanol. The mixture was concentrated to dryness and the residue was purified via prep HPLC (2-95% acetonitrile in water, 0.1% trifluoroacetic acid buffer) to isolate (R)-4-((R)-1-((6-(4-(4-isopropylpiperazin-1-yl)phenyl)-3-methyl-3H-imidazo[4,5-c]pyridin-4-yl)oxy)ethyl)pyrrolidin-2-one 3.35 (19 mg) as its trifluoroacetic acid salt.

¹H NMR (400 MHz, DMSO-d6) δ 9.31 (s, 1H), 8.36 (s, 1H), 8.01 (d, J=8.7 Hz, 2H), 7.72 (s, 1H), 7.58 (s, 1H), 7.10 (d, J=8.8 Hz, 2H), 5.54 (p, J=5.9 Hz, 1H), 4.00-3.90 (m, 5H), 3.63-3.50 (m, 2H), 3.43 (t, J=9.1 Hz, 1H), 3.30-3.10 (m, 4H), 3.10-2.94 (m, 2H), 2.90-77 (m, 1H), 2.44-2.19 (m, 2H), 1.42 (d, J=6.2 Hz, 3H), 1.31 (d, J=6.6 Hz, 6H).

LCMS-ESI+ (m/z): [M+H]+ calcd for $C_{26}H_{35}N_6O_2$: 463.3; found: 463.3.

Example 3.36

Preparation of (R)-4-((R)-1-((6-(4-(4-isobutyrylpiperazin-1-yl)phenyl)-3-methyl-3H-imidazo[4,5-c]pyridin-4-yl)oxy)ethyl)pyrrolidin-2-one

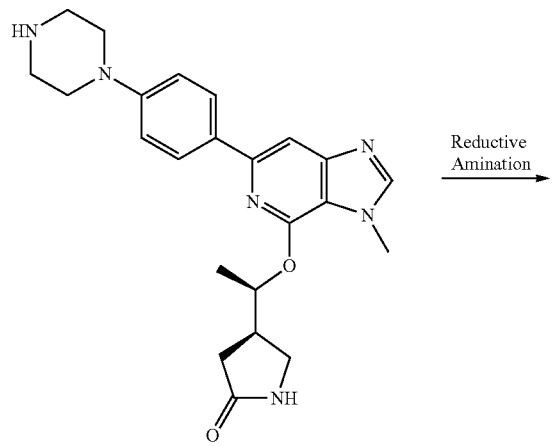

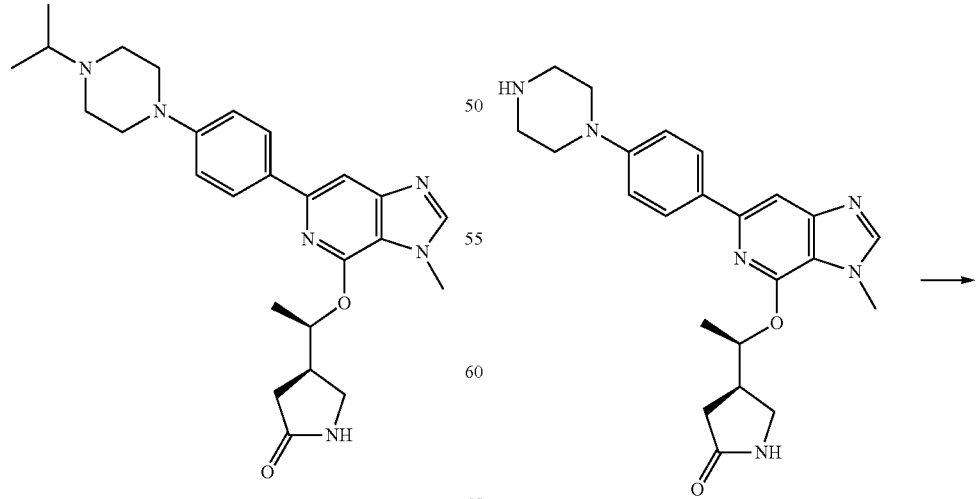

-continued

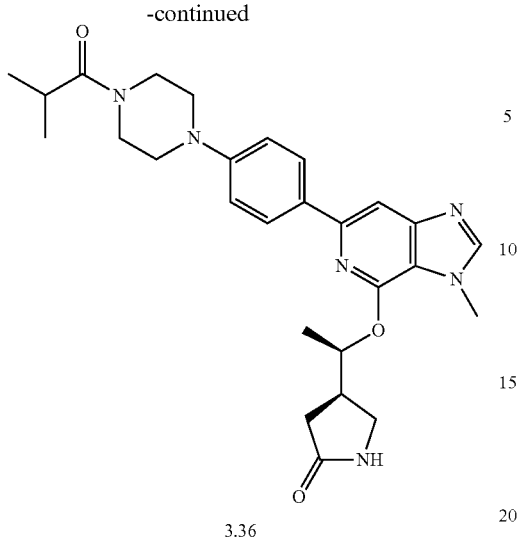

3.36

A vial was charged with (R)-4-((R)-1-(3-methyl-6-(4-(piperazin-1-yl)phenyl)-3H-imidazo[4,5-c]pyridin-4-yloxy)ethyl)pyrrolidin-2-one 3A.13 (32 mg, 0.076 mmol), HATU (58 mg, 0.15 mmol) and N-methylmorpholine (33 μL, 0.30 mmol) in DMF (2.0 mL). Isobutyric acid (8.5 μL, 0.091 mmol) was added and the reaction was stirred at room temperature for 18 h. The reaction was concentrated under reduced pressure and the residue was purified via prep HPLC (2-95% acetonitrile in water, 0.1% trifluoroacetic acid buffer) to isolate (R)-4-((R)-1-((6-(4-(4-isobutyrylpiperazin-1-yl)phenyl)-3-methyl-3H-imidazo[4,5-c]pyridin-4-yl)oxy)ethyl)pyrrolidin-2-one 3.36 (21 mg) as the trifluoroacetic acid salt.

$^1$H NMR (400 MHz, DMSO-d6) δ 8.87-8.60 (m, 1H), 7.99 (d, J=8.7 Hz, 2H), 7.71 (s, 1H), 7.58 (s, 1H), 7.05 (d, J=8.6 Hz, 2H), 5.56 (p, J=6.1 Hz, 1H), 4.02 (s, 3H), 3.70-3.59 (m, 4H), 3.43 (t, J=9.1 Hz, 1H), 3.33-3.08 (m, 5H), 3.01-2.77 (m, 2H), 2.43-2.17 (m, 2H), 1.43 (d, J=6.1 Hz, 3H), 1.03 (d, J=6.7 Hz, 6H).

LCMS-ESI+ (m/z): [M+H]+ calcd for $C_{27}H_{35}N_6O_3$: 491.3; found: 491.2.

Example 3.37

Preparation of (R)-4-((R)-1-((6-(4-(4-(2,2-difluoroethyl)piperazin-1-yl)phenyl)-3-methyl-3H-imidazo[4,5-c]pyridin-4-yl)oxy)ethyl)pyrrolidin-2-one

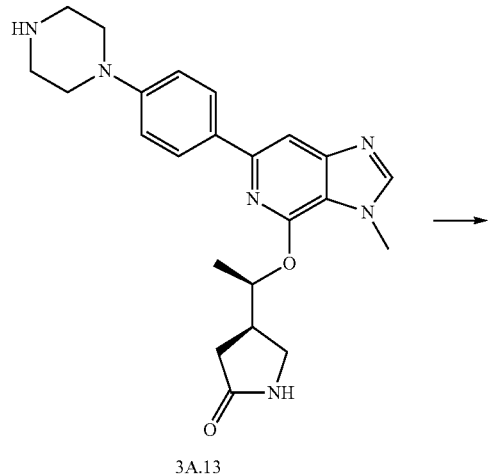

3A.13

-continued

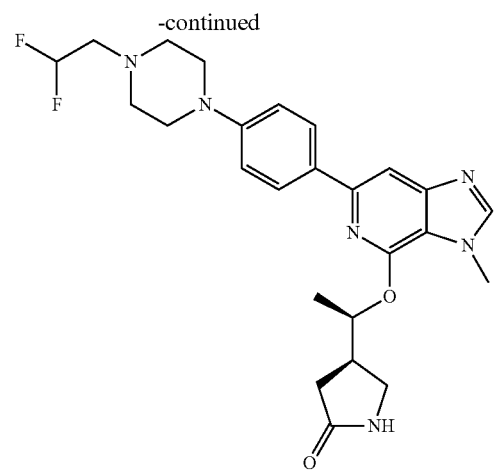

3.37

To an appropriate sized vial, (R)-4-((R)-1-((3-methyl-6-(4-(piperazin-1-yl)phenyl)-3H-imidazo[4,5-c]pyridin-4-yl)oxy)ethyl)pyrrolidin-2-one 3A.13 (40 mg, 0.062 mmol) and triethylamine (247 mg, 0.248 mmol) were dissolved in DCM (5 mL). To this mixture 2,2-difluoroethyl trifluoromethanesulfonate (13 mg, 0.062 mmol) was added and mixture stirred at room temperature for 30 min. The solution was concentrated under reduced pressure and the residue was purified via prep HPLC (2-65% acetonitrile in water, 0.1% trifluoroacteic acid) to provide (R)-4-((R)-1-((6-(4-(4-(2,2-difluoroethyl)piperazin-1-yl)phenyl)-3-methyl-3H-imidazo[4,5-c]pyridin-4-yl)oxy)ethyl)pyrrolidin-2-one 3.37 as its trifluoroacetic acid salt.

$^1$H NMR (400 MHz, Methanol-d4) δ 9.24 (s, 1H), 8.12-7.96 (m, 2H), 7.73 (s, 1H), 7.25-7.05 (m, 2H), 6.46 (t, J=3.6 Hz, 1H), 5.90-5.66 (m, 1H), 4.21 (s, 3H), 3.79 (td, J=15.0, 3.6 Hz, 2H), 3.72-3.50 (m, 9H), 3.39 (dd, J=10.3, 5.5 Hz, 1H), 3.07-2.90 (m, 1H), 2.69-2.38 (m, 2H), 1.54 (d, J=6.2 Hz, 3H).

LCMS-ESI+ (m/z): [M+H]+ calcd for $C_{25}H_{31}F_2N_6O_2$: 485.2; found: 485.2.

Example 3.38

Preparation of (R)-4-((R)-1-((3-methyl-6-(5-(4-(oxetan-3-yl)piperazin-1-yl)pyridin-2-yl)-3H-imidazo[4,5-c]pyridin-4-yl)oxy)ethyl)pyrrolidin-2-one

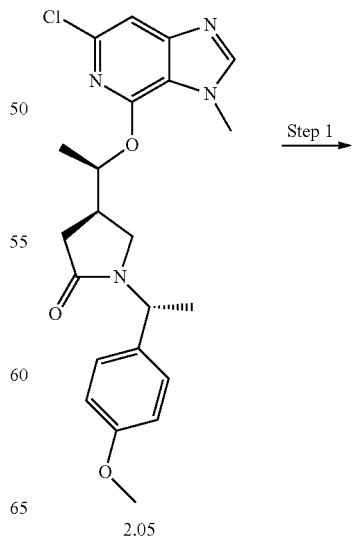

2.05

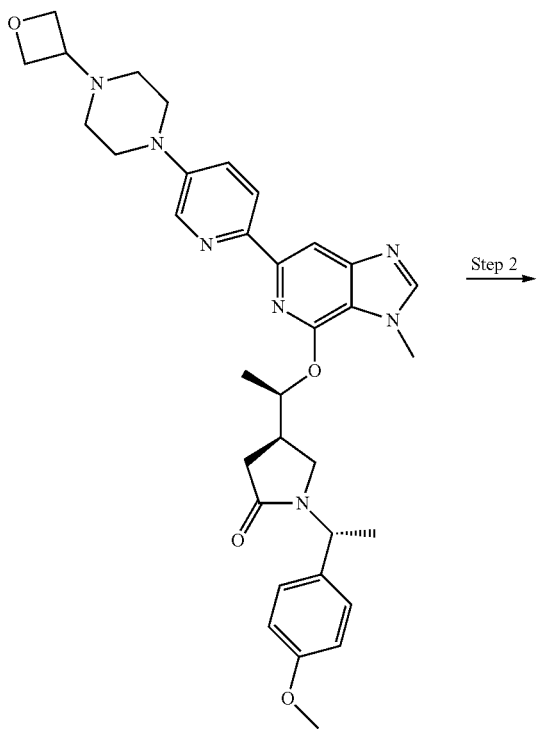

yl)piperazine 7.16 (78 mg, 0.154 mmol) in dioxane (3 mL) was added tetrakis(triphenylphosphine)palladium (16 mg) and KF (24 mg). Then the mixture was flushed with Argon, and heated by microwave at 140° C. for 20 min. The reaction was diluted with 50 mL of ethyl acetate and filtered to remove the solid. After removal of solvent, the residue was purified by silica gel column chromatography to provide 86 mg of (R)-1-((R)-1-(4-methoxyphenyl)ethyl)-4-((R)-1-((3-methyl-6-(5-(4-(oxetan-3-yl)piperazin-1-yl)pyridin-2-yl)-3H-imidazo[4,5-c]pyridin-4-yl)oxy)ethyl)pyrrolidin-2-one. LCMS [M+H]$^+$: 612.27.

Step 2: Following the TFA-mediated deprotection protocol described in procedure 3A, starting from (R)-1-((R)-1-(4-methoxyphenyl)ethyl)-4-((R)-1-((3-methyl-6-(5-(4-(oxetan-3-yl)piperazin-1-yl)pyridin-2-yl)-3H-imidazo[4,5-c]pyridin-4-yl)oxy)ethyl)pyrrolidin-2-one (14 mg, 0.023 mmol), 4.5 mg of (R)-4-((R)-1-((3-methyl-6-(5-(4-(oxetan-3-yl)piperazin-1-yl)pyridin-2-yl)-3H-imidazo[4,5-c]pyridin-4-yl)oxy)ethyl)pyrrolidin-2-one 3.38 was synthesized.

$^1$H NMR (400 MHz, CDCl$_3$) ppm: δ 8.436 (s, 1H), 8.247 (s, 1H), 8.13 (d, J=8.4 Hz, 1H), 7.83 (s, 1H), 7.31 (d, J=6 Hz, 1H), 5.82 (s, 1H), 5.567 (s, 1H), 4.73-4.6 (m, 4H), 4.017 (s, 3H), 3.63-3.5 (m, 4H), 3.43 (m, 1H), 3.347 (t, J=4 Hz, 4H), 2.94 (m, 1H), 2.538 (m, 4H), 1.5 (t, J=6.4 Hz, 3H).

LCMS-ESI$^+$ (m/z): [M+H]$^+$ calcd for C$_{25}$H$_{32}$N$_7$O$_3$: 478.3; found: 478.2.

Example 3.39

Preparation of (R)-4-((R)-1-((3-methyl-6-(5-(piperazin-1-yl)pyridin-2-yl)-3H-imidazo[4,5-c]pyridin-4-yl)oxy)ethyl)pyrrolidin-2-one

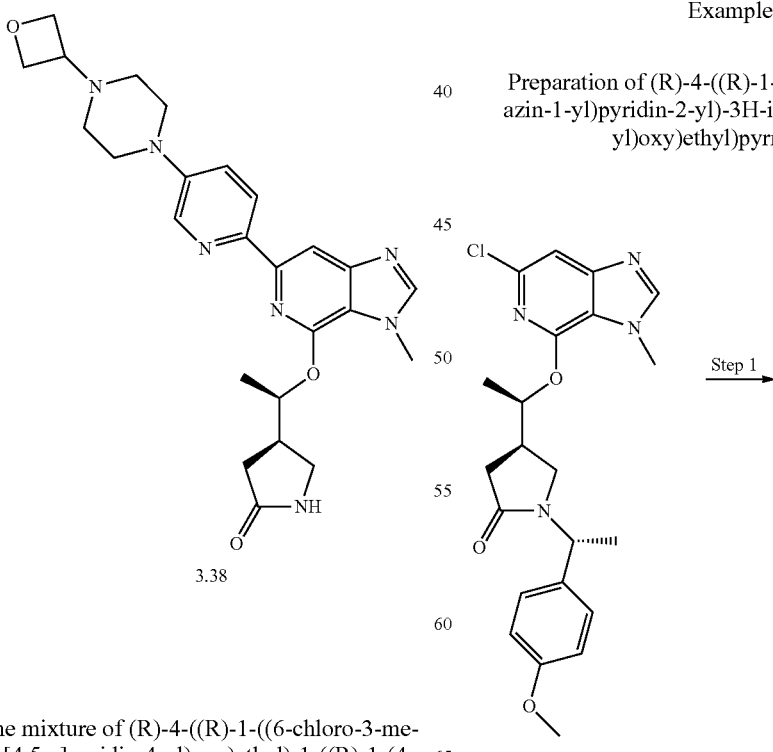

Step 1: Into the mixture of (R)-4-((R)-1-((6-chloro-3-methyl-3H-imidazo[4,5-c]pyridin-4-yl)oxy)ethyl)-1-((R)-1-(4-methoxyphenyl)ethyl)pyrrolidin-2-one 2.05 (60 mg, 0.14 mmol) and 1-(oxetan-3-yl)-4-(6-(tributylstannyl)pyridin-3-

341
-continued

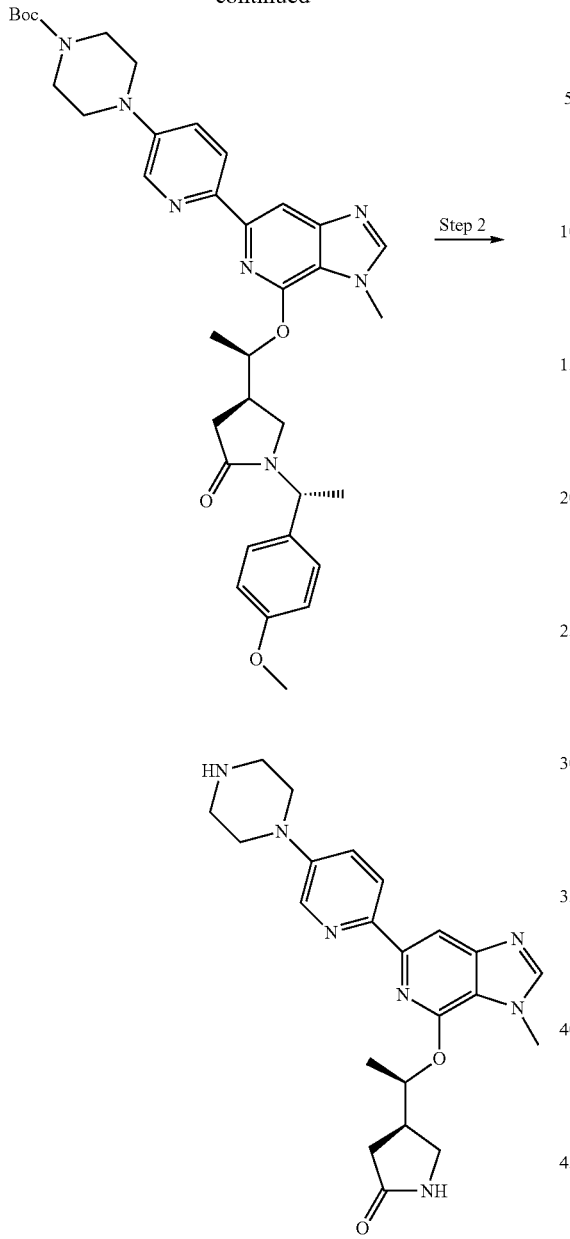

3.39

342 din-2-yl)-3H-imidazo[4,5-c]pyridin-4-yl)oxy)ethyl)pyrrolidin-2-one 3.39 was synthesized. LCMS [M+H]⁺: 422.16.

Example 3.40

Preparation of (R)-4-((R)-1-((6-(5-(4-acetylpiperazin-1-yl)pyridin-2-yl)-3-methyl-3H-imidazo[4,5-c]pyridin-4-yl)oxy)ethyl)pyrrolidin-2-one

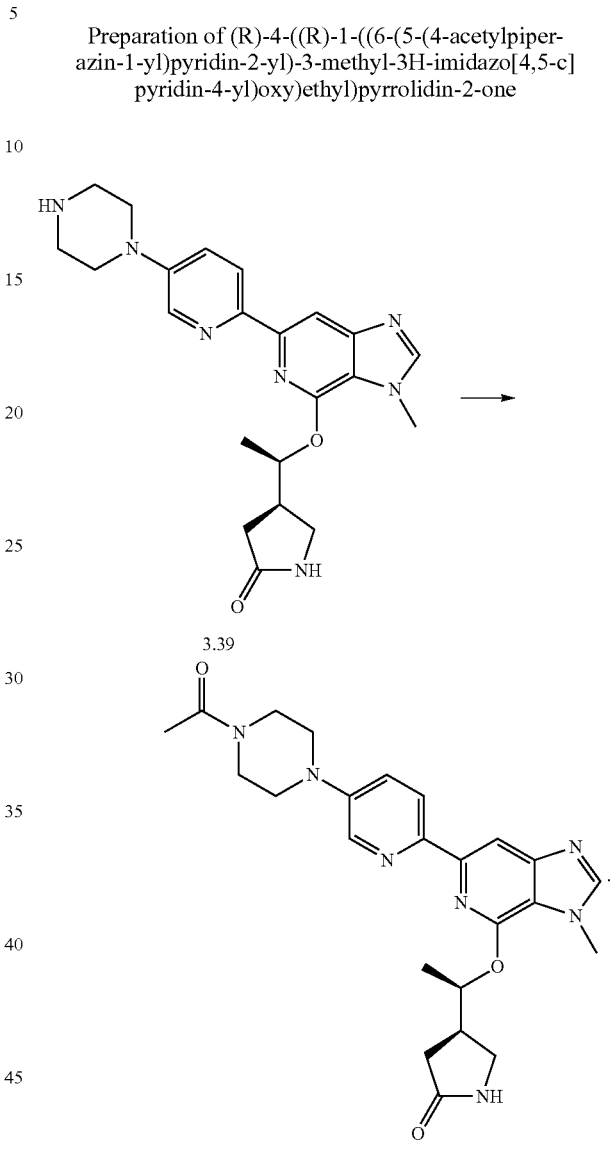

3.39

3.40

Step 1: Following the procedure described for intermediate 3.38, starting from (R)-4-((R)-1-((6-chloro-3-methyl-3H-imidazo[4,5-c]pyridin-4-yl)oxy)ethyl)-1-((R)-1-(4-methoxyphenyl)ethyl)pyrrolidin-2-one 2.05 (200 mg, 0.466 mmol) and tert-butyl 4-(6-(tributylstannyl)pyridin-3-yl)piperazine-1-carboxylate 7.14 (283 mg, 0.51 mmol), 141 mg of tert-butyl 4-(6-(4-((R)-1-((R)-1-((R)-1-(4-methoxyphenyl)ethyl)-5-oxopyrrolidin-3-yl)ethoxy)-3-methyl-3H-imidazo[4,5-c]pyridin-6-yl)pyridin-3-yl)piperazine-1-carboxylate was prepared. LCMS [M+H]⁺: 656.27.

Step 2: Following the TFA-mediated deprotection protocol described in General Procedure 3A, starting from tert-butyl 4-(6-(4-((R)-1-((R)-1-((R)-1-(4-methoxyphenyl)ethyl)-5-oxopyrrolidin-3-yl)ethoxy)-3-methyl-3H-imidazo[4,5-c]pyridin-6-yl)pyridin-3-yl)piperazine-1-carboxylate (141 mg), 91 mg of (R)-4-((R)-1-((3-methyl-6-(5-(piperazin-1-yl)pyri- Into a solution of (R)-4-((R)-1-((3-methyl-6-(5-(piperazin-1-yl)pyridin-2-yl)-3H-imidazo[4,5-c]pyridin-4-yl)oxy)ethyl)pyrrolidin-2-one 3.39 (50 mg, 0.119 mmol) and TEA (0.12 g) in DCM (2 mL) was added acetic anhydride (0.02 g, 0.18 mmol) at 0° C. The reaction mixture was warmed to rt and stirred for 2 h. Then the reaction mixture was extracted with ethyl acetate and washed with brine. After drying, the solvent was removed, the residue was purified by silica chromatographgy to provide 36 mg of (R)-4-((R)-1-((6-(5-(4-acetylpiperazin-1-yl)pyridin-2-yl)-3-methyl-3H-imidazo[4,5-c]pyridin-4-yl)oxy)ethyl)pyrrolidin-2-one 3.40.

¹H NMR (400 MHz, CDCl₃) ppm: δ 8.381 (s, 1H), 8.261 (s, 1H), 8.145 (d, J=8.4 Hz, 1H), 7.286 (d, J=2.4 Hz, 1H), 5.95 (s, 1H), 5.734 (m, 1H), 3.996 (s, 3H), 3.799 (t, J=4.8 Hz, 2H), 3.657 (m, 2H), 3.585 (t, J=9.2 Hz, 1H), 3.392 (t, J=9.2 Hz, 1H), 3.279 (m, 2H), 3.229 (m, 2H), 2.93 (m, 1H), 2.53 (m, 2H), 2.141 (s, 3H), 1.49 (d, J=6.4 Hz, 3H)

LCMS-ESI+ (m/z): [M+H]+ calcd for $C_{24}H_{30}N_7O_3$: 464.2; found: 464.2.

Example 3.41

Preparation of (R)-4-((R)-1-((3-methyl-6-(5-(4-(methylsulfonyl)piperazin-1-yl)pyridin-2-yl)-3H-imidazo[4,5-c]pyridin-4-yl)oxy)ethyl)pyrrolidin-2-one

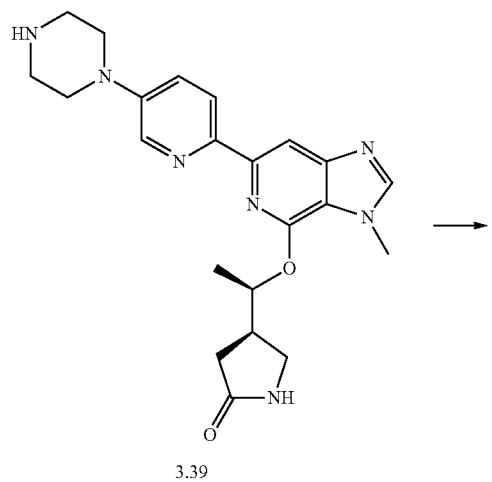

3.39

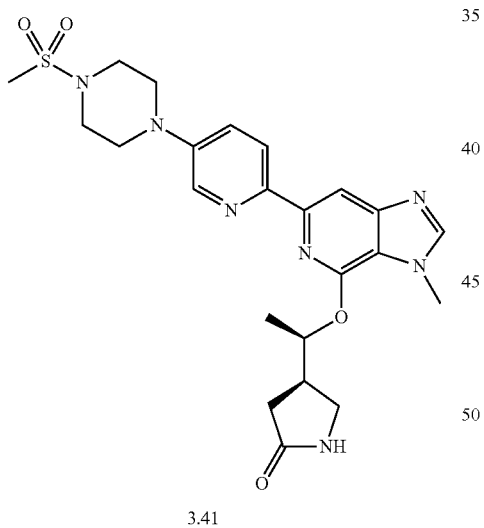

3.41

Following the same procedure described for intermediate 3.40 by using methylsufonic anhydride (25 mg) instead of acetic anhydride, 47.2 mg of (R)-4-((R)-1-((3-methyl-6-(5-(4-(methylsulfonyl)piperazin-1-yl)pyridin-2-yl)-3H-imidazo[4,5-c]pyridin-4-yl)oxy)ethyl)pyrrolidin-2-one 3.41 was synthesized.

$^1$H NMR (400 MHz, CDCl$_3$) ppm: δ 8.474 (s, 1H), 8.235 (s, 1H), 8.143 (d, J=8.8 Hz, 1H), 7.819 (s, 1H), 7.325 (d, J=3.2 Hz, 1H), 5.993 (s, 1H), 5.78 (m, 1H), 4.0 (s, 3H), 3.587 (t, J=9.6 Hz, 1H), 3.4-3.36 (m, 8H), 3.12 (m, 1H), 2.91 (m, 1H), 2.833 (s, 3H), 2.53 (m, 2H), 1.48 (d, J=6.4 Hz, 3H).

LCMS-ESI+ (m/z): [M+H]+ calcd for $C_{23}H_{30}N_7O_4S$: 500.21; found: 500.18.

Example 3.42

Preparation of (R)-4-((R)-1-((3-cyclopropyl-6-(4-(piperazin-1-yl)phenyl)-3H-imidazo[4,5-c]pyridin-4-yl)oxy)ethyl)pyrrolidin-2-one

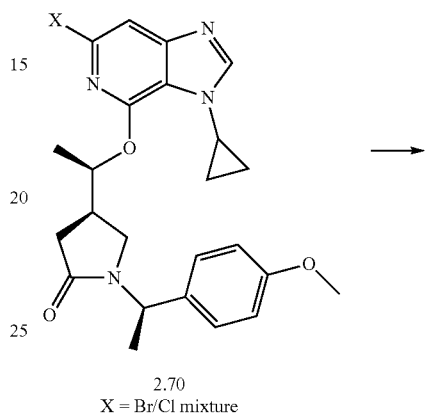

2.70
X = Br/Cl mixture

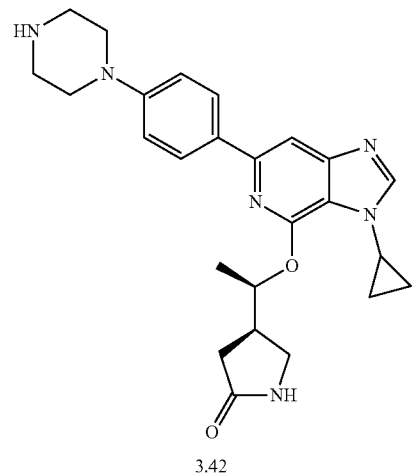

3.42

Using General Procedure 3A, beginning with a mixture of (R)-4-((R)-1-((6-bromo-3-cyclopropyl-3H-imidazo[4,5-c]pyridin-4-yl)oxy)ethyl)-1-((R)-1-(4-methoxyphenyl)ethyl)pyrrolidin-2-one and (R)-4-((R)-1-((6-chloro-3-cyclopropyl-3H-imidazo[4,5-c]pyridin-4-yl)oxy)ethyl)-1-((R)-1-(4-methoxyphenyl)ethyl)pyrrolidin-2-one (2.70) (400 mg, 0.8 mmol) along with (4-(4-(tert-butoxycarbonyl)piperazin-1-yl)phenyl)boronic acid (319 mg, 1.04 mmol), (R)-4-((R)-1-((3-cyclopropyl-6-(4-(piperazin-1-yl)phenyl)-3H-imidazo[4,5-c]pyridin-4-yl)oxy)ethyl)pyrrolidin-2-one 3.42 was prepared as its TFA salt (215 mg, 0.48 mmol).

$^1$H NMR (400 MHz, Methanol-d4) δ 9.34 (s, 1H), 8.17-7.97 (m, 2H), 7.70 (s, 1H), 7.26-7.03 (m, 2H), 5.95-5.68 (m, 1H), 3.98 (dq, J=11.1, 5.8, 5.1 Hz, 1H), 3.70-3.57 (m, 1H), 3.53 (dd, J=6.7, 3.7 Hz, 4H), 3.46-3.34 (m, 5H), 3.10-2.93 (m, 1H), 2.69-2.41 (m, 2H), 1.54 (d, J=6.2 Hz, 3H), 1.42-1.24 (m, 4H).

LCMS-ESI+ (m/z): [M+H]+ calcd for $C_{25}H_{31}N_6O_2$: 447.3; found: 447.2.

Example 3.43

Preparation of (R)-4-((R)-1-((3-cyclopropyl-6-(4-(4-(oxetan-3-yl)piperazin-1-yl)phenyl)-3H-imidazo[4,5-c]pyridin-4-yl)oxy)ethyl)pyrrolidin-2-one

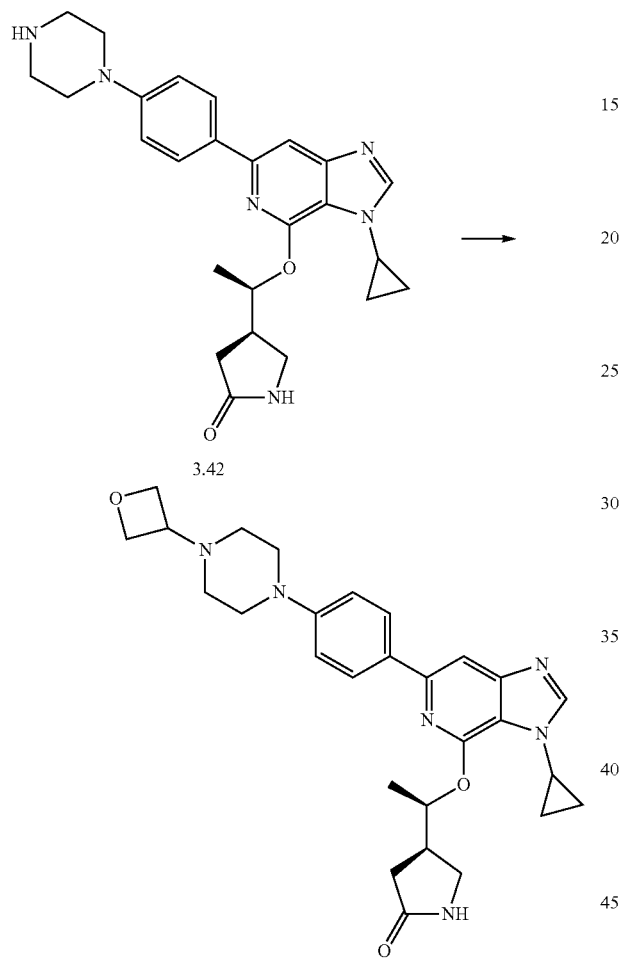

In an appropriate sized vial the trifluoroacetic acid salt (R)-4-((R)-1-((3-cyclopropyl-6-(4-(piperazin-1-yl)phenyl)-3H-imidazo[4,5-c]pyridin-4-yl)oxy)ethyl)pyrrolidin-2-one 3.42 (50 mg, 0.063 mmol) and 3-oxetanone (13 µL, 0.22 mmol) were dissolved in THF (3 mL). To this mixture sodium triacetoxyborohydride (67 mg, 0.28 mmol) was added and the mixture was heated at 50° C. for 45 min. Mixture was poured into a saturated aqueous solution of sodium bicarbonate and concentrated under reduced pressure. Residues were purified via prep HPLC (5-65% acetonitrile in water, 0.1% trifluoroacteic acid) to isolate (R)-4-((R)-1-((3-cyclopropyl-6-(4-(4-(oxetan-3-yl)piperazin-1-yl)phenyl)-3H-imidazo[4,5-c]pyridin-4-yl)oxy)ethyl)pyrrolidin-2-one 3.43 as its trifluoroacetic acid salt.

$^1$H NMR (400 MHz, Methanol-d4) δ 9.22 (s, 1H), 8.16-7.92 (m, 2H), 7.70 (s, 1H), 7.25-7.02 (m, 2H), 5.95-5.66 (m, 1H), 4.95-4.8 (m, 4H), 4.50 (tt, J=7.0, 5.7 Hz, 1H), 3.96-3.89 (m, 1H), 3.70-3.51 (m, 4H), 3.48-3.2 (m, 6H), 3.10-2.91 (m, 1H), 2.68-2.44 (m, 2H), 1.53 (d, J=6.2 Hz, 3H), 1.34-1.27 (m, 4H).

LCMS-ESI+ (m/z): [M+H]+ calcd for $C_{28}H_{35}N_6O_3$: 503.3; found: 503.2.

Example 3.44

Preparation of (R)-4-((R)-1-((6-(4-(4-acetylpiperazin-1-yl)phenyl)-3-cyclopropyl-3H-imidazo[4,5-c]pyridin-4-yl)oxy)ethyl)pyrrolidin-2-one

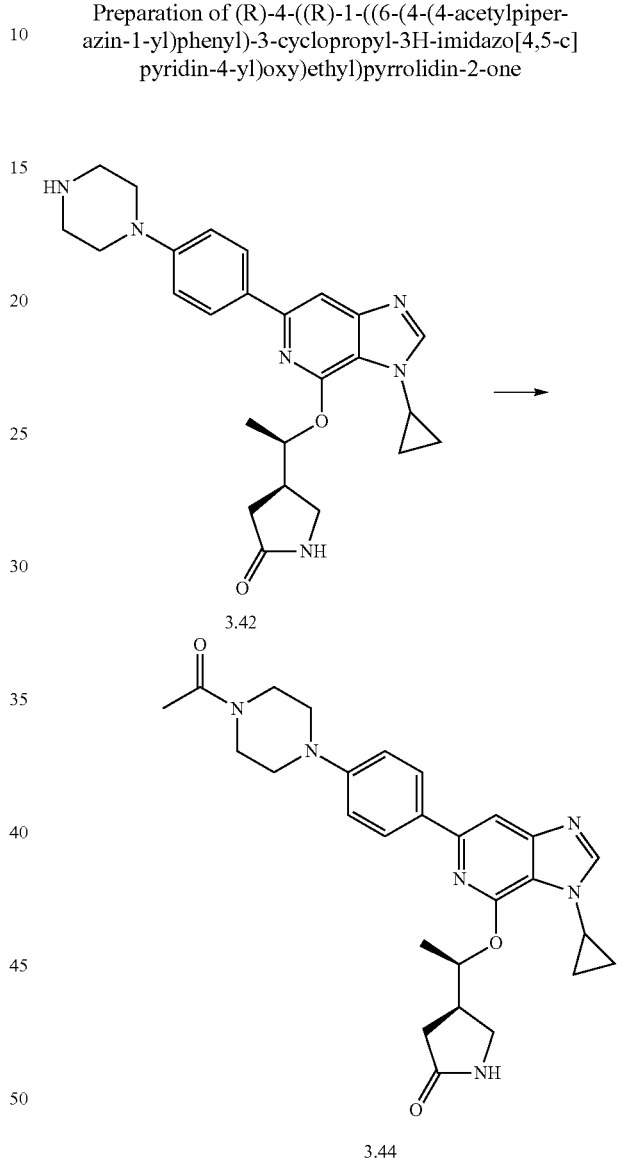

In an appropriate sized vial the trifluoroacetic acid salt (R)-4-((R)-1-((3-cyclopropyl-6-(4-(piperazin-1-yl)phenyl)-3H-imidazo[4,5-c]pyridin-4-yl)oxy)ethyl)pyrrolidin-2-one 3.42 (120 mg, 0.214 mmol) and triethylamine (130 mg, 1.27 mmol) were dissolved in DCM (5 mL). To this mixture acetic anhydride (26 mg, 0.25 mmol) was added. Mixture was stirred at room temperature for 30 min. After reaction was complete the solution was concentrated under reduced pressure and the residue was purified via prep HPLC (2-65% acetonitrile in water, 0.1% trifluoroacteic acid) to provide (R)-4-((R)-1-((6-(4-(4-acetylpiperazin-1-yl)phenyl)-3-cyclopropyl-3H-imidazo[4,5-c]pyridin-4-yl)oxy)ethyl)pyrrolidin-2-one 3.44 as its trifluoroacetic acid salt.

¹H NMR (400 MHz, Methanol-d4) δ 9.28 (d, J=0.9 Hz, 1H), 8.17-7.85 (m, 2H), 7.66 (s, 1H), 7.19-6.93 (m, 2H), 5.97-5.64 (m, 1H), 3.96 (p, J=5.9 Hz, 1H), 3.74 (m, 4H), 3.62-3.59 (m, 1H), 3.41 (dd, J=10.2, 5.9 Hz, 1H), 3.4-3.3 (m, 4H), 3.02 (d, J=7.5 Hz, 1H), 2.65-2.48 (m, 2H), 2.16 (s, 3H), 1.54 (d, J=6.2 Hz, 3H), 1.35-1.28 (m, 4H).
LCMS-ESI⁺ (m/z): [M+H]⁺ calcd for C$_{27}$H$_{33}$N$_6$O$_3$: 489.3; found: 489.2.

Example 3.45

Preparation of (R)-4-((R)-1-((3-cyclopropyl-6-(4-(4-(methylsulfonyl)piperazin-1-yl)phenyl)-3H-imidazo[4,5-c]pyridin-4-yl)oxy)ethyl)pyrrolidin-2-one

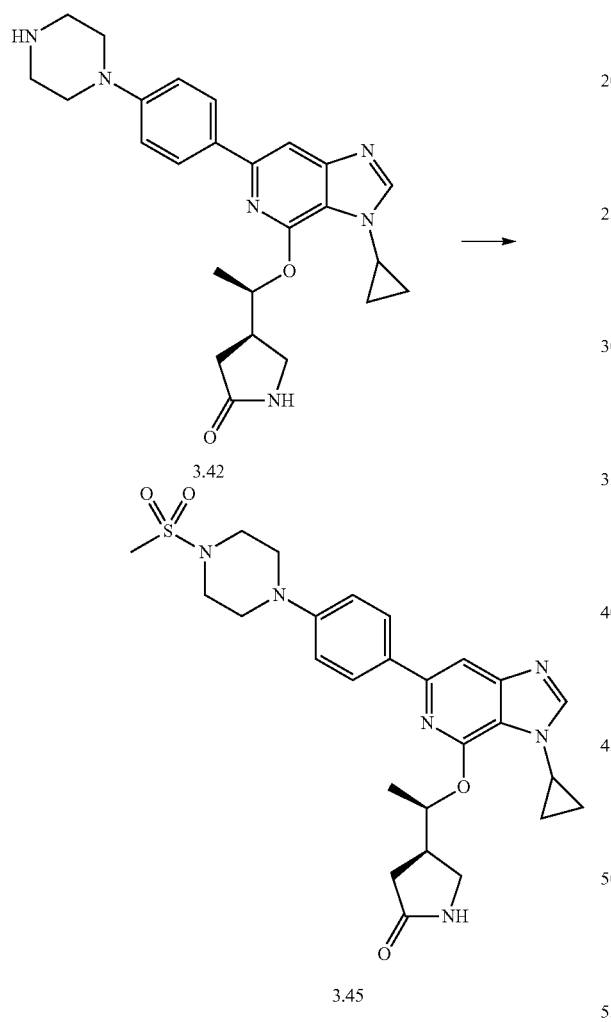

In an appropriate sized vial the trifluoroacetic acid salt of (R)-4-((R)-1-((3-cyclopropyl-6-(4-(piperazin-1-yl)phenyl)-3H-imidazo[4,5-c]pyridin-4-yl)oxy)ethyl)pyrrolidin-2-one 3.42 (50 mg, 0.089 mmol) and triethylamine (45 mg, 0.54 mmol) were dissolved in DCM (5 mL). To this mixture methanesulfonic anhydride (19 mg, 0.11 mmol) was added and the mixture was stirred at room temperature for 30 min. After reaction was complete the solution was concentrated under reduced pressure and the residue was purified via prep HPLC (2-65% acetonitrile in water, 0.1% trifluoroacteic acid) to provide (R)-4-((R)-1-((3-cyclopropyl-6-(4-(4-(methylsulfo-nyl)piperazin-1-yl)phenyl)-3H-imidazo[4,5-c]pyridin-4-yl)oxy)ethyl)pyrrolidin-2-one 3.45 as its trifluoroacetic acid salt.

¹H NMR (400 MHz, Methanol-d4) δ 8.14 (s, 1H), 8.05-7.83 (m, 2H), 7.56 (s, 1H), 7.17-6.87 (m, 2H), 5.88-5.56 (m, 1H), 3.69 (ddd, J=11.1, 6.7, 4.5 Hz, 1H), 3.59 (dd, J=10.1, 8.7 Hz, 1H), 3.47-3.38 (m, 1H), 3.37-3.252 (m, 8H), 2.97 (m, 1H), 2.87 (s, 3H), 2.61-2.41 (m, 2H), 1.49 (d, J=6.2 Hz, 3H), 1.20-0.92 (m, 4H)
LCMS-ESI⁺ (m/z): [M+H]⁺ calcd for C$_{26}$H$_{33}$N$_6$O$_4$S: 525.2; found: 525.2.

Example 3.46

Preparation of (R)-4-((R)-1-((3-cyclopropyl-6-(4-(4-(2,2-difluoroethyl)piperazin-1-yl)phenyl)-3H-imidazo[4,5-c]pyridin-4-yl)oxy)ethyl)pyrrolidin-2-one

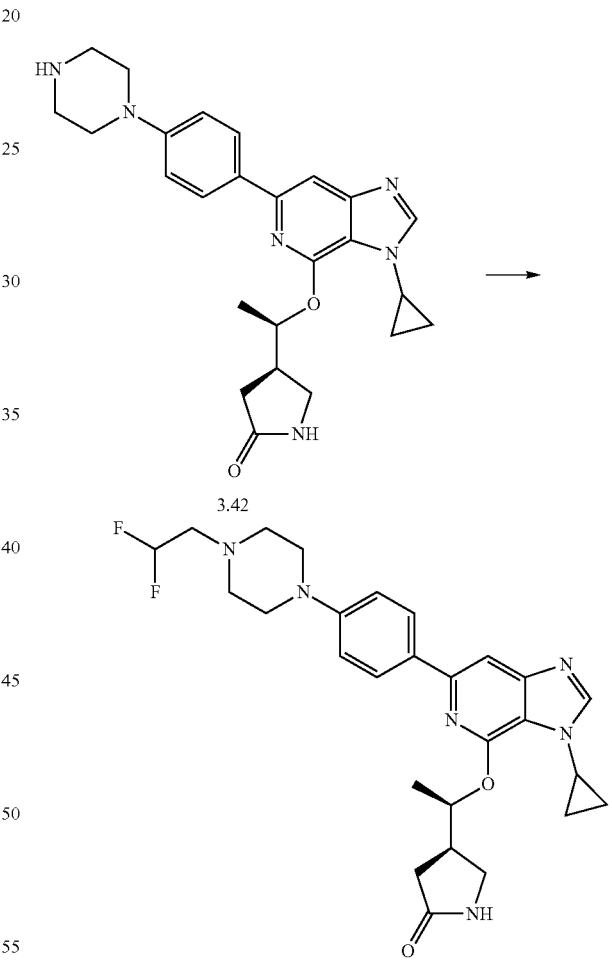

In an appropriate sized vial the trifluoroacetic acid salt of (R)-4-((R)-1-((3-cyclopropyl-6-(4-(piperazin-1-yl)phenyl)-3H-imidazo[4,5-c]pyridin-4-yl)oxy)ethyl)pyrrolidin-2-one 3.42 (25 mg, 0.044 mmol) and triethylamine (27 mg, 0.27 mmol) were dissolved in DCM (1.5 mL). To this mixture 2,2-difluoroethyl trifluoromethanesulfonate (11 mg, 0.051 mmol) was added and mixture was stirred at room temperature for 30 min. The solution was concentrated under reduced pressure and the residue was purified via prep HPLC (2-65% acetonitrile in water, 0.1% trifluoroacteic acid) to isolate (R)-4-((R)-1-((3-cyclopropyl-6-(4-(4-(2,2-difluoroethyl)piperazin-1-yl)phenyl)-3H-imidazo[4,5-c]pyridin-4-yl)oxy)ethyl)pyrrolidin-2-one 3.46 as a trifluoroacetic acid salt.

¹H NMR (400 MHz, Methanol-d4) δ 9.04 (s, 1H), 8.15-7.98 (m, 2H), 7.68 (s, 1H), 7.19-7.05 (m, 2H), 6.42 (t, J=3.6 Hz, 1H), 5.94-5.67 (m, 1H), 3.90 (p, J=5.6 Hz, 1H), 3.80-3.48 (m, 8H), 3.45-3.3 (m, 4H), 3.14-2.82 (m, 1H), 2.73-2.35 (m, 2H), 1.53 (d, J=6.3 Hz, 3H), 1.42-1.13 (m, 4H).

LCMS-ESI⁺ (m/z): [M+H]⁺ calcd for $C_{27}H_{33}F_2N_6O_2$: 511.3; found: 511.2.

Example 3.47

Preparation of (R)-4-((R)-1-((3-cyclopropyl-6-(4-(4-(2,2,2-trifluoroethyl)piperazin-1-yl)phenyl)-3H-imidazo[4,5-c]pyridin-4-yl)oxy)ethyl)pyrrolidin-2-one

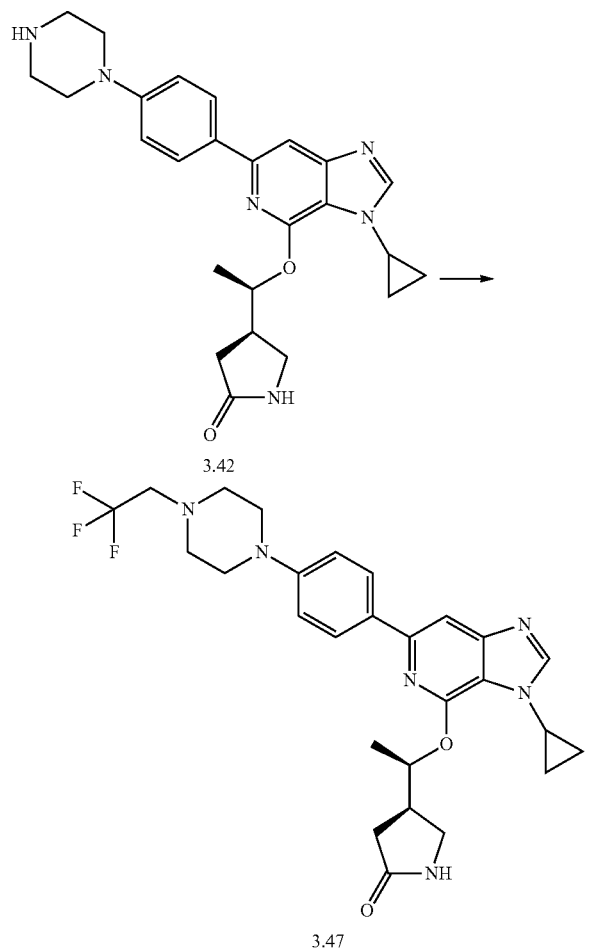

In an appropriate sized vial the trifluoroacetic acid salt (R)-4-((R)-1-((3-cyclopropyl-6-(4-(piperazin-1-yl)phenyl)-3H-imidazo[4,5-c]pyridin-4-yl)oxy)ethyl)pyrrolidin-2-one 3.42 (25 mg, 0.046 mmol) and triethylamine (27 mg, 0.27 mmol) were dissolved in DCM (1.5 mL). To this mixture 2,2,2-trifluoroethyl trifluoromethanesulfonate (12 mg, 0.053 mmol) was added and the mixture was stirred at room temperature for 24 h. The mixture was concentrated under reduced pressure and the residue was purified via prep HPLC (2-65% acetonitrile in water, 0.1% trifluoroacteic acid) to provide (R)-4-((R)-1-((3-cyclopropyl-6-(4-(4-(2,2,2-trifluoroethyl)piperazin-1-yl)phenyl)-3H-imidazo[4,5-c]pyridin-4-yl)oxy)ethyl)pyrrolidin-2-one 3.47 as its trifluoroacetic acid salt.

¹H NMR (400 MHz, Methanol-d4) δ 9.24 (d, J=0.9 Hz, 1H), 8.18-7.95 (m, 2H), 7.69 (s, 1H), 7.28-7.04 (m, 2H), 5.92-5.67 (m, 1H), 4.07-3.85 (m, 1H), 3.63 (dd, J=10.2, 8.7 Hz, 1H), 3.53-3.37 (m, 8H), 3.11-2.89 (m, 4H), 2.71-2.30 (m, 2H), 1.53 (d, J=6.2 Hz, 3H), 1.32 (m, 4H).

LCMS-ESI⁺ (m/z): [M+H]⁺ calcd for $C_{27}H_{32}F_3N_6O_2$: 529.3; found: 529.3.

Example 3.48

Preparation of (R)-4-((R)-1-((3-cyclopropyl-6-(4-morpholinophenyl)-3H-imidazo[4,5-c]pyridin-4-yl)oxy)ethyl)pyrrolidin-2-one

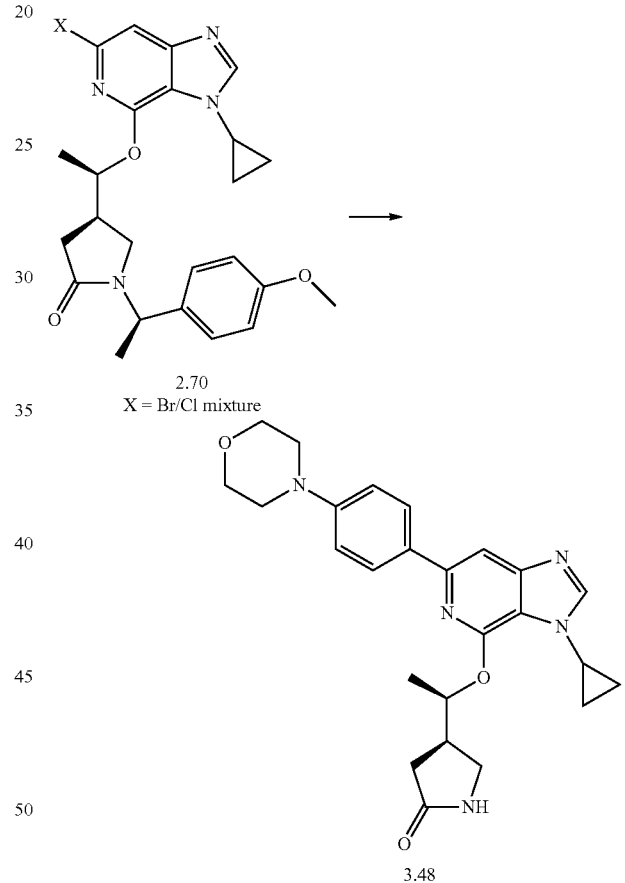

Using General Procedure 3A, beginning with a mixture of (R)-4-((R)-1-((6-bromo-3-cyclopropyl-3H-imidazo[4,5-c]pyridin-4-yl)oxy)ethyl)-1-((R)-1-(4-methoxyphenyl)ethyl)pyrrolidin-2-one: and (R)-4-((R)-1-((6-chloro-3-cyclopropyl-3H-imidazo[4,5-c]pyridin-4-yl)oxy)ethyl)-1-((R)-1-(4-methoxyphenyl)ethyl)pyrrolidin-2-one: (2.70) (30 mg, 0.06 mmol) along with (4-morpholinophenyl)boronic acid (15 mg, 0.072 mmol) (R)-4-((R)-1-((3-cyclopropyl-6-(4-morpholinophenyl)-3H-imidazo[4,5-c]pyridin-4-yl)oxy)ethyl)pyrrolidin-2-one: 3.48 (2.7 mg) was prepared as a trifluoroacetic acid salt.

¹H NMR (400 MHz, Methanol-d4) δ 8.85 (s, 1H), 8.19-7.81 (m, 2H), 7.62 (s, 1H), 7.19-6.82 (m, 2H), 5.95-5.68 (m, 1H), 3.97-3.74 (m, 5H), 3.63 (dd, J=10.1, 8.7 Hz, 1H), 3.41 (dd, J=10.1, 5.9 Hz, 1H), 3.24 (dd, J=5.9, 3.8 Hz, 4H), 3.06-2.86 (m, 1H), 2.58 (dd, J=8.3, 2.7 Hz, 2H), 1.52 (d, J=6.2 Hz, 3H), 1.38-1.02 (m, 4H).

LCMS-ESI+ (m/z): [M+H]+ calcd for $C_{25}H_{29}N_5O_3$: 448.2; found: 448.2.

Example 3.49

Preparation of (R)-4-((R)-1-((3-cyclopropyl-6-(5-(4-(oxetan-3-yl)piperazin-1-yl)pyridin-2-yl)-3H-imidazo[4,5-c]pyridin-4-yl)oxy)ethyl)pyrrolidin-2-one

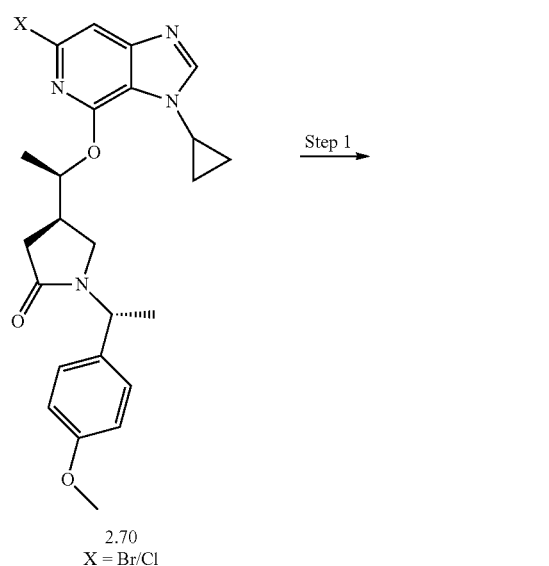

2.70
X = Br/Cl

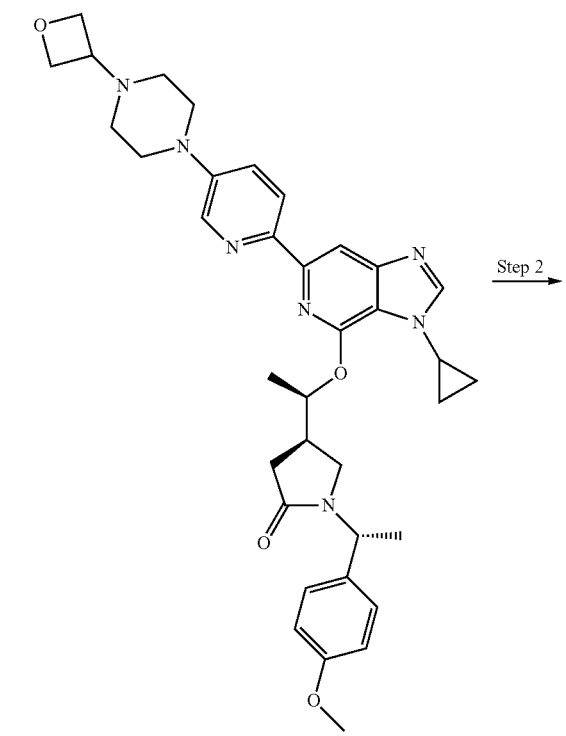

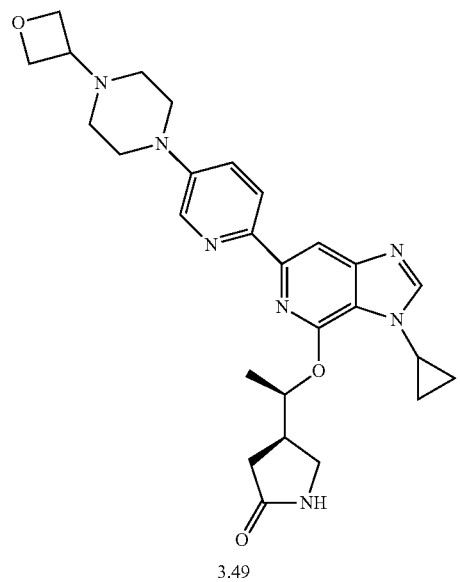

3.49

Step 1: Following the procedure described for the preparation of intermediate 3.38, starting with a mixture of (R)-4-((R)-1-((6-bromo-3-cyclopropyl-3H-imidazo[4,5-c]pyridin-4-yl)oxy)ethyl)-1-((R)-1-(4-methoxyphenyl)ethyl) pyrrolidin-2-one: and (R)-4-((R)-1-((6-chloro-3-cyclopropyl-3H-imidazo[4,5-c]pyridin-4-yl)oxy)ethyl)-1-((R)-1-(4-methoxyphenyl)ethyl)pyrrolidin-2-one: (2.70) (61 mg, 0.12 mmol), and 1-(oxetan-3-yl)-4-(6-(tributylstannyl) pyridin-3-yl)piperazine 7.16, (R)-4-((R)-1-((3-cyclopropyl-6-(5-(4-(oxetan-3-yl)piperazin-1-yl)pyridin-2-yl)-3H-imidazo[4,5-c]pyridin-4-yl)oxy)ethyl)-1-4R)-1-(4-methoxyphenyl)ethyl)pyrrolidin-2-one: (60 mg) was synthesized. LCMS [M+H]+: 638.3.

Step 2: Following the TFA-mediated deprotection protocol described in General Procedure 3A, starting from (R)-4-((R)-1-((3-cyclopropyl-6-(5-(4-(oxetan-3-yl)piperazin-1-yl)pyridin-2-yl)-3H-imidazo[4,5-c]pyridin-4-yl)oxy)ethyl)-1-((R)-1-(4-methoxyphenyl)ethyl)pyrrolidin-2-one: (60 mg, 0.094 mmol), (R)-4-((R)-1-((3-cyclopropyl-6-(5-(4-(oxetan-3-yl) piperazin-1-yl)pyridin-2-yl)-3H-imidazo[4,5-c]pyridin-4-yl)oxy)ethyl)pyrrolidin-2-one: 3.49 (35.3 mg) was synthesized.

1H NMR (400 MHz, CDCl3) ppm: δ 8.364 (s, 1H), 8.245 (s, 1H), 8.14 (d, J=8.8 Hz, 1H), 7.86 (s, 1H), 7.275 (d, J=2.8 Hz, 1H), 5.94 (s, 1H), 5.753 (m, 1H), 4.699 (t, J=6.4 Hz, 2H), 4.649 (t, J=6.4 Hz, 2H), 3.75 (m, 1H), 3.566 (m, 4H), 3.427 (t, J=6.8 Hz, 1H), 3.316 (m, 4H), 2.96 (m, 1H), 2.532 (m, 4H), 1.49 (d, J=6 Hz, 3H), 1.252 (m, 1H), 1.144 (m, 1H), 1.087 (m, 1H), 0.87 (m, 1H).

LCMS-ESI+ (m/z): [M+H]+ calcd for $C_{27}H_{34}N_7O_3$: 504.27; found: 504.23.

Example 3.50

Preparation of (R)-4-((R)-1-((6-(5-(4-acetylpiperazin-1-yl)pyridin-2-yl)-3-cyclopropyl-3H-imidazo[4,5-c]pyridin-4-yl)oxy)ethyl)pyrrolidin-2-one

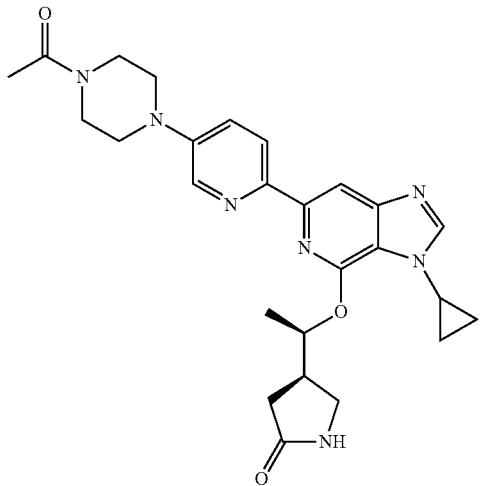

3.50

Following the protocols described for intermediate 3.39 and example 3.40, starting with a mixture of (R)-4-((R)-1-((6-bromo-3-cyclopropyl-3H-imidazo[4,5-c]pyridin-4-yl)oxy)ethyl)-1-((R)-1-(4-methoxyphenyl)ethyl)pyrrolidin-2-one: and (R)-4-((R)-1-((6-chloro-3-cyclopropyl-3H-imidazo[4,5-c]pyridin-4-yl)oxy)ethyl)-1-((R)-1-(4-methoxyphenyl)ethyl)pyrrolidin-2-one: (2.70) (200 mg), (R)-4-((R)-1-((6-(5-(4-acetylpiperazin-1-yl)pyridin-2-yl)-3-cyclopropyl-3H-imidazo[4,5-c]pyridin-4-yl)oxy)ethyl)pyrrolidin-2-one: 3.50 (42 mg) was synthesized.

$^1$H NMR (400 MHz, CDCl$_3$) ppm: δ 8.437 (s, 1H), 8.226 (s, 1H), 8.145 (d, J=8.4 Hz, 1H), 7.874 (s, 1H), 7.31 (d, J=3.2 Hz, 1H), 5.946 (s, 1H), 5.794 (m, 1H), 3.801 (m, 2H), 3.66 (m, 2H), 3.59 (m, 2H), 3.426 (m, 1H), 3.293 (m, 2H), 3.24 (m, 2H), 3.12 (m, 1H), 2.55 (m, 2H), 2.142 (s, 3H), 1.483 (d, J=6 Hz, 3H), 1.309 (m, 1H), 1.157 (m, 1H), 1.089 (m, 1H), 0.867 (m, 1H).

LCMS-ESI$^+$ (m/z): [M+H]$^+$ calcd for C$_{26}$H$_{32}$N$_7$O$_3$: 490.26; found: 490.22.

Example 3.50a

Preparation of (R)-4-((R)-1-((3-cyclopropyl-6-(5-(4-(methylsulfonyl)piperazin-1-yl)pyridin-2-yl)-3H-imidazo[4,5-c]pyridin-4-yl)oxy)ethyl)pyrrolidin-2-one

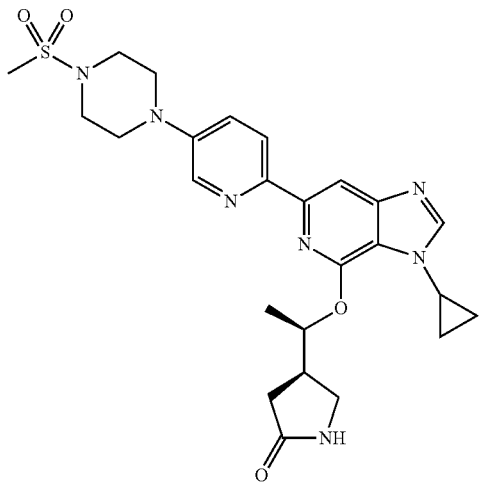

3.50a

Following the procedure described for intermediate 3.39 and example 3.41, starting with a mixture of (R)-4-((R)-1-((6-bromo-3-cyclopropyl-3H-imidazo[4,5-c]pyridin-4-yl)oxy)ethyl)-1-((R)-1-(4-methoxyphenyl)ethyl)pyrrolidin-2-one: and (R)-4-((R)-1-((6-chloro-3-cyclopropyl-3H-imidazo[4,5-c]pyridin-4-yl)oxy)ethyl)-1-((R)-1-(4-methoxyphenyl)ethyl)pyrrolidin-2-one: (2.70) (200 mg), (R)-4-((R)-1-((3-cyclopropyl-6-(5-(4-(methylsulfonyl)piperazin-1-yl)pyridin-2-yl)-3H-imidazo[4,5-c]pyridin-4-yl)oxy)ethyl)pyrrolidin-2-one: 3.50a (36 mg) was synthesized.

$^1$H NMR (400 MHz, CDCl$_3$) ppm: δ 8.367 (d, J=2.4 Hz, 1H), 8.257 (s, 1H), 8.162 (d, J=8.8 Hz, 1H), 7.871 (s, 1H), 7.282 (d, d, J=2.4, 9.2 Hz, 1H), 5.997 (s, 1H), 5.747 (m, 1H), 3.7-3.55 (m, 3H), 3.417 (m, 4H), 3.372 (m, 4H), 2.98 (m, 1H), 2.833 (s, 3H), 2.55 (m, 2H), 1.49 (d, J=6 Hz, 3H), 1.251 (m, 1H), 1.137 (m, 1H), 1.091 (m, 1H), 0.87 (m, 1H).

LCMS-ESI$^+$ (m/z): [M+H]$^+$ calcd for C$_{25}$H$_{32}$N$_7$O$_4$S: 526.2; found: 526.2.

Example 3.51

Preparation of (R)-4-((R)-1-((3-cyclopropyl-6-(3-methoxy-4-(piperazin-1-yl)phenyl)-3H-imidazo[4,5-c]pyridin-4-yl)oxy)ethyl)pyrrolidin-2-one

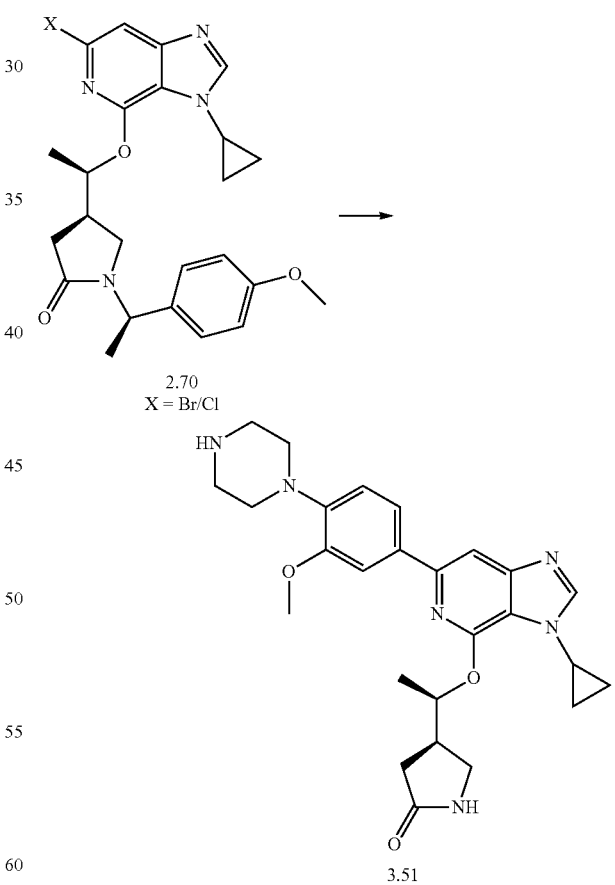

Following General Procedure 3A, beginning with a mixture of (R)-4-((R)-1-((6-bromo-3-cyclopropyl-3H-imidazo[4,5-c]pyridin-4-yl)oxy)ethyl)-1-((R)-1-(4-methoxyphenyl)ethyl)pyrrolidin-2-one: and (R)-4-((R)-1-((6-chloro-3-cyclopropyl-3H-imidazo[4,5-c]pyridin-4-yl)oxy)ethyl)-1-

((R)-1-(4-methoxyphenyl)ethyl)pyrrolidin-2-one: (2.70) (100 mg, ~0.2 mmol) along with tert-butyl 4-(2-methoxy-4-(4,4,5,5-tetramethyl-1,3,2-dioxaborolan-2-yl)phenyl)piperazine-1-carboxylate 7.08 (125 mg, 0.29 mmol), (R)-4-((R)-1-((3-cyclopropyl-6-(3-methoxy-4-(piperazin-1-yl)phenyl)-3H-imidazo[4,5-c]pyridin-4-yl)oxy)ethyl)pyrrolidin-2-one: 3.51 was synthesized (100 mg) as a trifluoroacetic acid salt.

$^1$H NMR (400 MHz, Methanol-d4) δ 8.97 (s, 1H), 7.86-7.55 (m, 3H), 7.08 (d, J=8.3 Hz, 1H), 5.95-5.57 (m, 1H), 3.99 (s, 3H), 3.89 (p, J=5.6 Hz, 1H), 3.74-3.54 (m, 1H), 3.46-3.32 (m, 9H), 3.10-2.94 (m, 1H), 2.64-2.54 (m, 2H), 1.55 (d, J=6.2 Hz, 3H), 1.36-1.19 (m, 4H).

LCMS-ESI$^+$ (m/z): [M+H]$^+$ calcd for $C_{26}H_{33}N_6O_3$: 477.3; found: 477.2.

Example 3.52

Preparation of (R)-4-((R)-1-((6-(4-(4-acetylpiperazin-1-yl)-3-methoxyphenyl)-3-cyclopropyl-3H-imidazo[4,5-c]pyridin-4-yl)oxy)ethyl)pyrrolidin-2-one

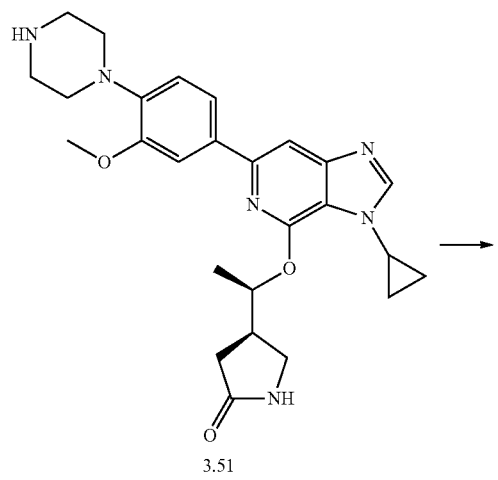

3.51

To an appropriate sized vial the trifluoroacetic acid salt of (R)-4-((R)-1-((3-cyclopropyl-6-(3-methoxy-4-(piperazin-1-yl)phenyl)-3H-imidazo[4,5-c]pyridin-4-yl)oxy)ethyl)pyrrolidin-2-one: 3.51 (80 mg, 0.085 mmol) and triethylamine (52 mg, 0.51 mmol) were dissolved in DCM (4 mL). To this mixture acetic anhydride (10.5 mg, 0.1 mmol) was added and the mixture was stirred at room temperature for 30 min. After reaction was complete the solution was concentrated under reduced pressure and the residue was purified via prep HPLC (2-65% acetonitrile in water, 0.1% trifluoroacteic acid buffer) to provide (R)-4-((R)-1-((6-(4-(4-acetylpiperazin-1-yl)-3-methoxyphenyl)-3-cyclopropyl-3H-imidazo[4,5-c]pyridin-4-yl)oxy)ethyl)pyrrolidin-2-one: 3.52 as its trifluoroacetic acid salt.

$^1$H NMR (400 MHz, Methanol-d4) δ 9.00 (s, 1H), 7.81-7.57 (m, 3H), 7.12 (d, J=8.4 Hz, 1H), 5.91-5.69 (m, 1H), 4.00 (s, 3H), 3.91 (p, J=5.6 Hz, 1H), 3.80-3.73 (m, 4H), 3.63 (dd, J=10.1, 8.7 Hz, 1H), 3.42 (dd, J=10.2, 5.8 Hz, 1H), 3.22-3.13 (m, 4H), 3.09-2.92 (m, 1H), 2.67-2.45 (m, 2H), 2.15 (s, 3H), 1.55 (d, J=6.2 Hz, 3H), 1.44-1.05 (m, 4H).

LCMS-ESI$^+$ (m/z): [M+H]$^+$ calcd for $C_{28}H_{35}N_6O_4$: 519.3; found: 519.2.

Example 3.53

Preparation of (R)-4-((R)-1-((3-cyclopropyl-6-(3-methoxy-4-(4-(oxetan-3-yl)piperazin-1-yl)phenyl)-3H-imidazo[4,5-c]pyridin-4-yl)oxy)ethyl)pyrrolidin-2-one

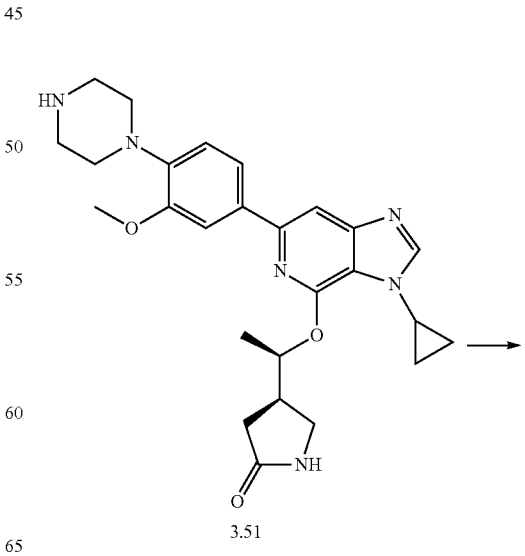

3.51

Example 3.54

Preparation of (R)-4-((R)-1-((3-cyclopropyl-6-(3-methoxy-4-(4-(methylsulfonyl)piperazin-1-yl)phenyl)-3H-imidazo[4,5-c]pyridin-4-yl)oxy)ethyl)pyrrolidin-2-one

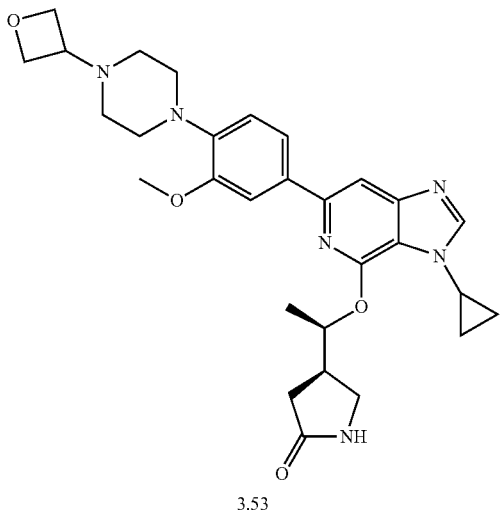

3.53

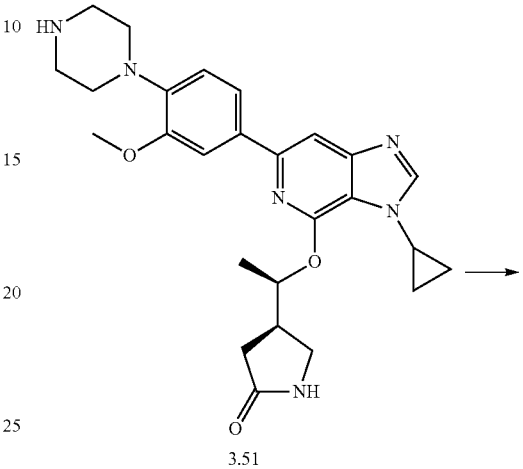

3.51

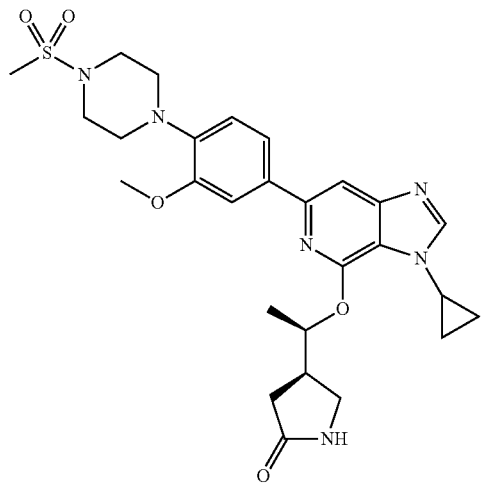

3.54

To an appropriate sized vial, the trifluoroacetic acid salt (R)-4-((R)-1-((3-cyclopropyl-6-(3-methoxy-4-(piperazin-1-yl)phenyl)-3H-imidazo[4,5-c]pyridin-4-yl)oxy)ethyl)pyrrolidin-2-one: 3.51 (18 mg, 0.025 mmol) and 3-oxetanone (5.2 µL, 0.089 mmol) were dissolved in THF (3 mL). To this mixture sodium triacetoxyborohydride (24 mg, 0.11 mmol) was added and the mixture was heated at 50° C. for 45 min. The mixture was poured into a saturated aqueous solution of sodium bicarbonate and concentrated under reduced pressure. The residue was purified via prep HPLC (5-65% acetonitrile in water, 0.1% trifluoroacteic acid) to provide (R)-4-((R)-1-((3-cyclopropyl-6-(3-methoxy-4-(4-(oxetan-3-yl)piperazin-1-yl)phenyl)-3H-imidazo[4,5-c]pyridin-4-yl)oxy)ethyl)pyrrolidin-2-one: 3.53 as its trifluoroacetic acid salt.

$^1$H NMR (400 MHz, Methanol-d4) δ 9.24 (s, 1H), 7.85-7.55 (m, 3H), 7.09 (dd, J=8.3, 6.4 Hz, 1H), 5.96-5.65 (m, 1H), 4.9-4.7 (m, 4H), 4.51 (tt, J=7.3, 5.6 Hz, 1H), 3.99-3.85 (m, 4H), 3.64 (dd, J=10.2, 8.7 Hz, 1H), 3.45-3.25 (m, 9H), 3.14-2.96 (m, 1H), 2.77-2.41 (m, 2H), 1.55 (d, J=6.2 Hz, 3H), 1.36-1.29 (m, 4H).

LCMS-ESI$^+$ (m/z): [M+H]$^+$ calcd for C$_{29}$H$_{37}$N$_6$O$_4$: 533.3; found: 533.2.

To an appropriate sized vial, the trifluoroacetic acid salt of (R)-4-((R)-1-((3-cyclopropyl-6-(3-methoxy-4-(piperazin-1-yl)phenyl)-3H-imidazo[4,5-c]pyridin-4-yl)oxy)ethyl)pyrrolidin-2-one: 3.51 (18 mg, 0.025 mmol) and triethylamine (15.5 mg, 0.15 mmol) were dissolved in DCM (1.5 mL). To this mixture methanesulfonic anhydride (5.3 mg, 0.03 mmol) was added and the mixture was stirred at room temperature for 30 min. After reaction was complete the solution was concentrated under reduced pressure and the residue was purified via prep HPLC (2-65% acetonitrile in water, 0.1% trifluoroacetic acid) to provide (R)-4-((R)-1-((3-cyclopropyl-6-(3-methoxy-4-(4-(methylsulfonyl)piperazin-1-yl)phenyl)-3H-imidazo[4,5-c]pyridin-4-yl)oxy)ethyl)pyrrolidin-2-one: 3.54 as its trifluoroacetic acid salt.

$^1$H NMR (400 MHz, Methanol-d4) δ 9.25 (s, 1H), 7.85-7.56 (m, 3H), 7.12 (d, J=8.3 Hz, 1H), 5.94-5.71 (m, 1H), 3.99 (s, 4H), 3.64 (dd, J=10.2, 8.7 Hz, 1H), 3.48-3.37 (m, 5H), 3.25 (dd, J=6.1, 3.6 Hz, 4H), 3.11-2.97 (m, 1H), 2.90 (s, 3H), 2.67-2.48 (m, 2H), 1.56 (d, J=6.2 Hz, 3H), 1.35-1.29 (m, 4H).

LCMS-ESI+ (m/z): [M+H]+ calcd for C27H35N6O5S: 555.2; found: 555.2.

Example 3.55

Preparation of (R)-4-((R)-1-((3-cyclopropyl-6-(4-(1,1-dioxidothiomorpholino)phenyl)-3H-imidazo[4,5-c]pyridin-4-yl)oxy)ethyl)pyrrolidin-2-one

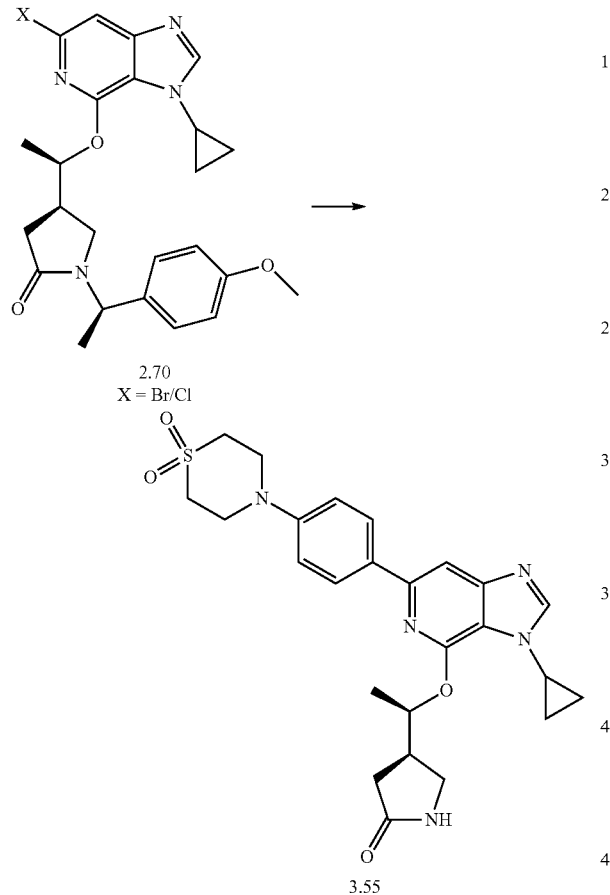

3.55

Following General Procedure 3A, beginning with a mixture of (R)-4-((R)-1-((6-bromo-3-cyclopropyl-3H-imidazo[4,5-c]pyridin-4-yl)oxy)ethyl)-1-((R)-1-(4-methoxyphenyl)ethyl)pyrrolidin-2-one: and (R)-4-((R)-1-((6-chloro-3-cyclopropyl-3H-imidazo[4,5-c]pyridin-4-yl)oxy)ethyl)-1-((R)-1-(4-methoxyphenyl)ethyl)pyrrolidin-2-one: (2.70) (42 mg, ~0.084 mmol) along with 4-(4-(4,4,5,5-tetramethyl-1,3,2-dioxaborolan-2-yl)phenyl)thiomorpholine 1,1-dioxide (49 mg, 0.1 mmol), (R)-4-((R)-1-((3-cyclopropyl-6-(4-(1,1-dioxidothiomorpholino)phenyl)-3H-imidazo[4,5-c]pyridin-4-yl)oxy)ethyl)pyrrolidin-2-one: 3.55 was synthesized (8 mg) as its trifluoroacetic acid salt.

$^1$H NMR (400 MHz, Methanol-d4) δ 8.88 (s, 1H), 8.14-7.90 (m, 2H), 7.64 (s, 1H), 7.30-6.93 (m, 2H), 5.82 (p, J=6.0 Hz, 1H), 3.96 (dd, J=7.3, 3.4 Hz, 4H), 3.92-3.78 (m, 1H), 3.63 (dd, J=10.1, 8.7 Hz, 1H), 3.41 (dd, J=10.1, 5.9 Hz, 1H), 3.15 (t, J=5.2 Hz, 4H), 3.02 (dt, J=8.5, 3.4 Hz, 1H), 2.72-2.37 (m, 2H), 1.53 (d, J=6.3 Hz, 3H), 1.3-1.26 (m, 4H).

LCMS-ESI+ (m/z): [M+H]+ calcd for C25H30N5O4S: 496.2; found: 496.2.

Example 3.56

Preparation of 4-(4-(3-cyclopropyl-4-((R)-1-((R)-5-oxopyrrolidin-3-yl)ethoxy)-3H-imidazo[4,5-c]pyridin-6-yl)phenyl)morpholin-3-one

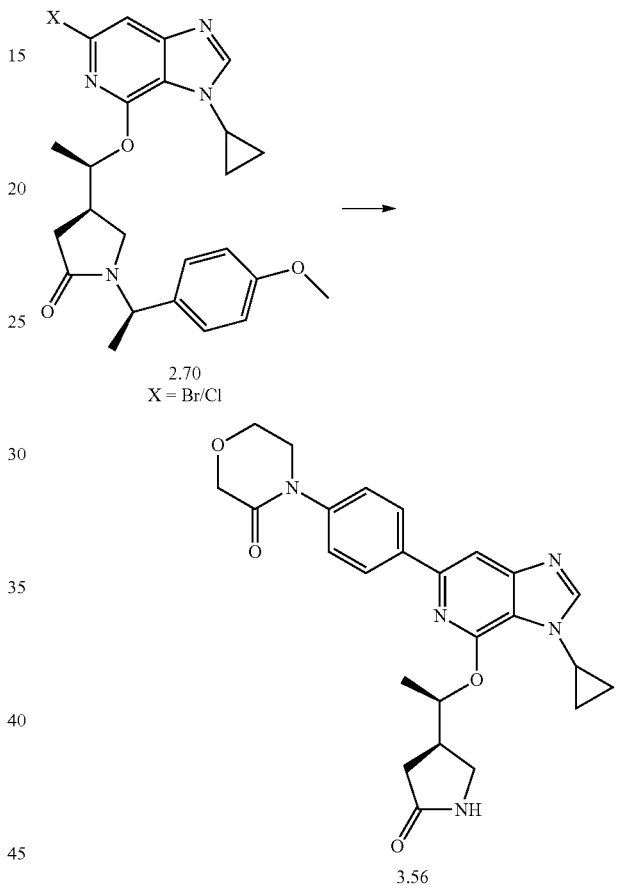

3.56

Following General Procedure 3A, beginning with a mixture of (R)-4-((R)-1-((6-bromo-3-cyclopropyl-3H-imidazo[4,5-c]pyridin-4-yl)oxy)ethyl)-1-((R)-1-(4-methoxyphenyl)ethyl)pyrrolidin-2-one: and (R)-4-((R)-1-((6-chloro-3-cyclopropyl-3H-imidazo[4,5-c]pyridin-4-yl)oxy)ethyl)-1-((R)-1-(4-methoxyphenyl)ethyl)pyrrolidin-2-one: (2.70) (50 mg, ~0.1 mmol) along with 4-(4-(4,4,5,5-tetramethyl-1,3,2-dioxaborolan-2-yl)phenyl)morpholin-3-one (36 mg, 0.12 mmol), 4-(4-(3-cyclopropyl-4-((R)-1-((R)-5-oxopyrrolidin-3-yl)ethoxy)-3H-imidazo[4,5-c]pyridin-6-yl)phenyl)morpholin-3-one 3.56 (9.5 mg) was synthesized as its trifluoroacetic acid salt.

$^1$H NMR (400 MHz, Methanol-d4) δ 9.29-8.91 (m, 1H), 8.27-8.04 (m, 2H), 7.80 (s, 1H), 7.63-7.37 (m, 2H), 5.98-5.63 (m, 1H), 4.31 (s, 1H), 4.18-4.04 (m, 2H), 4.04-3.91 (m, 2H), 3.91-3.74 (m, 2H), 3.63 (dd, J=10.1, 8.7 Hz, 1H), 3.41 (dd, J=10.2, 5.9 Hz, 1H), 3.02 (ddt, J=14.3, 8.7, 4.3 Hz, 1H), 2.73-2.34 (m, 2H), 1.54 (d, J=6.2 Hz, 3H), 1.41-1.14 (m, 4H).

LCMS-ESI⁺ (m/z): [M+H]⁺ calcd for C₂₅H₂₈N₅O₄: 462.2.; found: 462.1.

Example 3.57

Preparation of (R)-4-((R)-1-((3-cyclopropyl-6-(4-(dimethylamino)-3-methylphenyl)-3H-imidazo[4,5-c]pyridin-4-yl)oxy)ethyl)pyrrolidin-2-one

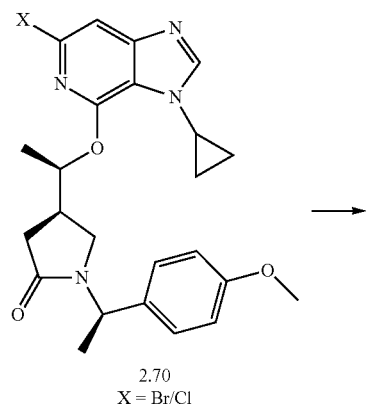

Following General Procedure 3A, beginning with a mixture of (R)-4-((R)-1-((6-bromo-3-cyclopropyl-3H-imidazo[4,5-c]pyridin-4-yl)oxy)ethyl)-1-((R)-1-(4-methoxyphenyl)ethyl)pyrrolidin-2-one: and (R)-4-((R)-1-((6-chloro-3-cyclopropyl-3H-imidazo[4,5-c]pyridin-4-yl)oxy)ethyl)-1-((R)-1-(4-methoxyphenyl)ethyl)pyrrolidin-2-one: (2.70) (50 mg, 0.1 mmol) along with (4-(dimethylamino)-3-methylphenyl)boronic acid (22.4 mg, 0.125 mmol), (R)-4-((R)-1-((3-cyclopropyl-6-(4-(dimethylamino)-3-methylphenyl)-3H-imidazo[4,5-c]pyridin-4-yl)oxy)ethyl)pyrrolidin-2-one: 3.57 (14 mg) was synthesized as its trifluoroacetic acid salt.

¹H NMR (400 MHz, Methanol-d4) δ 9.05 (s, 1H), 8.33-8.07 (m, 2H), 7.87 (s, 1H), 7.81 (d, J=8.7 Hz, 1H), 6.00-5.60 (m, 1H), 3.92 (p, J=5.6 Hz, 1H), 3.75-3.56 (m, 2H), 3.41 (dd, J=10.2, 5.8 Hz, 1H), 3.34 (s, 6H), 3.09-2.92 (m, 1H), 2.63 (s, 3H), 2.62-2.48 (m, 1H), 1.54 (d, J=6.2 Hz, 3H), 1.36-1.17 (m, 4H).

LCMS-ESI⁺ (m/z): [M+H]⁺ calcd for C₂₄H₃₀N₅O₂: 420.2; found: 420.2.

Example 3.59

(R)-4-((R)-1-((5-(5-(4-acetylpiperazin-1-yl)pyridin-2-yl)-1-cyclopropyl-1H-benzo[d]imidazol-7-yl)oxy)ethyl)pyrrolidin-2-one

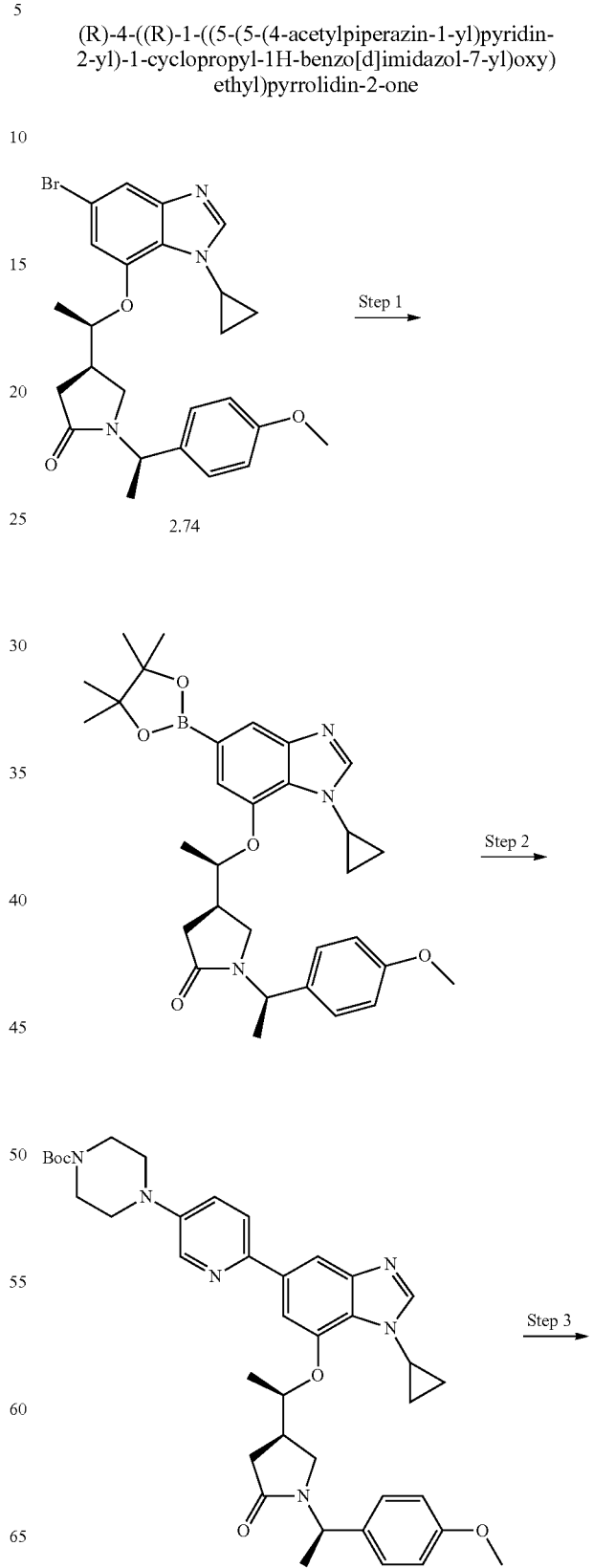

-continued

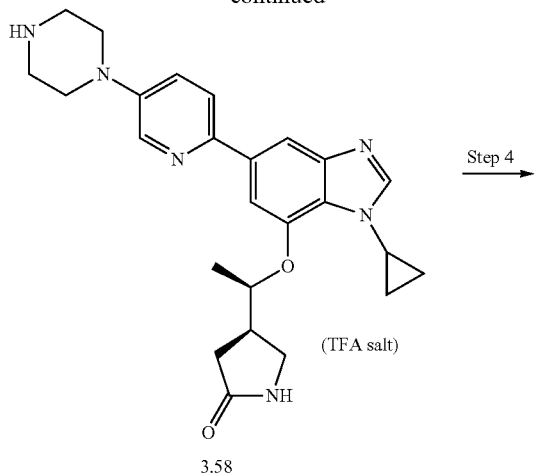

3.58 (TFA salt)

3.59

Step 1: To a solution of (R)-4-((R)-1-((5-bromo-1-cyclopropyl-1H-benzo[d]imidazol-7-yl)oxy)ethyl)-1-((R)-1-(4-methoxyphenyl)ethyl)pyrrolidin-2-one: 2.74 (305 mg, 0.612 mmol) in dioxane (5 mL) was added 4,4,4',4',5,5,5',5'-octamethyl-2,2'-bi(1,3,2-dioxaborolane) (249 mg, 0.980 mmol), potassium acetate (180 mg, 1.84 mmol), Pd(dppf)Cl$_2$.CH$_2$Cl$_2$ (25 mg, 0.031 mmol). The resulting mixture was stirred for 16 h at 80° C. Concentration followed by flash chromatography using 0%-20% MeOH in ethyl acetate gave (R)-4-((R)-1-((1-cyclopropyl-5-(4,4,5,5-tetramethyl-1,3,2-dioxaborolan-2-yl)-1H-benzo[d]imidazol-7-yl)oxy)ethyl)-1-((R)-1-(4-methoxyphenyl)ethyl)pyrrolidin-2-one. LCMS-ESI$^+$ (m/z): [M+H]$^+$ calcd for C$_{31}$H$_{41}$BN$_3$O$_5$: 546.3; found: 546.3.

Step 2: To a mixture of (R)-4-((R)-1-((1-cyclopropyl-5-(4,4,5,5-tetramethyl-1,3,2-dioxaborolan-2-yl)-1H-benzo[d]imidazol-7-yl)oxy)ethyl)pyrrolidin-2-one: (178 mg, 0.326 mmol), tert-butyl 4-(6-bromopyridin-3-yl)piperazine-1-carboxylate 7.13 (156 mg, 0.457 mmol), Cs$_2$CO$_3$ (318 mg, 0.98 mmol) and PEPPSI-IPr (22 mg, 0.03 mmol) was added DME and water (2.5:1.2, 3.7 mL) and the reaction mixture was heated to 100° C. for 2 h.

The mixture was then concentrated and purified by flash chromatography (0%-20% MeOH/ethyl acetate) to give tert-butyl 4-(6-(1-cyclopropyl-7-((R)-1-((R)-1-((R)-1-(4-methoxyphenyl)ethyl)-5-oxopyrrolidin-3-yl)ethoxy)-1H-benzo[d]imidazol-5-yl)pyridin-3-yl)piperazine-1-carboxylate. LCMS-ESI$^+$ (m/z): [M+H]$^+$ calcd for C$_{39}$H$_{49}$N$_6$O$_5$: 681.4; found: 681.3

Step 3: tert-butyl 4-(6-(1-cyclopropyl-7-((R)-1-((R)-1-((R)-1-(4-methoxyphenyl)ethyl)-5-oxopyrrolidin-3-yl)ethoxy)-1H-benzo[d]imidazol-5-yl)pyridin-3-yl)piperazine-1-carboxylate (129 mg, 0.189 mmol) was treated with TFA (3 mL) at 60° C. for 14 h. The reaction mixture was then concentrated to give (R)-4-((R)-1-((1-cyclopropyl-5-(5-(piperazin-1-yl)pyridin-2-yl)-1H-benzo[d]imidazol-7-yl)oxy)ethyl)pyrrolidin-2-one: 3.58 as a TFA salt which was used further without purification. LCMS-ESI$^+$ (m/z): [M+H]$^+$ calcd for C$_{25}$H$_{31}$N$_6$O$_2$: 447.3; found 447.2.

Step 4: To the TFA salt of (R)-4-((R)-1-((1-cyclopropyl-5-(5-(piperazin-1-yl)pyridin-2-yl)-1H-benzo[d]imidazol-7-yl)oxy)ethyl)pyrrolidin-2-one: (45 mg, 0.1 mmol) in DCM (1 mL) and TEA (0.07 mL, 0.5 mmol) was added acetic anhydride (0.014 mL, 0.15 mmol). The reaction was stirred at rt for 2 h. The mixture was then concentrated and purified by prep-HPLC (MeCN:water gradient; TFA modified) to give (R)-4-((R)-1-((5-(5-(4-acetylpiperazin-1-yl)pyridin-2-yl)-1-cyclopropyl-1H-benzo[d]imidazol-7-yl)oxy)ethyl)pyrrolidin-2-one: 3.59 as a TFA salt. The salt was then converted to the free base by treatment with MP carbonate resin.

$^1$H NMR (400 MHz, DMSO-d$_6$) δ 8.37 (m, 1H), 8.07 (s, 1H), 7.88 (d, J=8.8 Hz, 1H), 7.76 (s, 1H), 7.57 (d, J=12.0 Hz, 2H), 7.41-7.39 (m, 1H), 4.80-4.77 (m, 1H), 3.68-3.66 (m, 1H); 3.59 (m, 4H), 3.41-3.34 (m, 1H), 3.19 (m, 4H), 3.08 (m, 1H), 2.81-2.79 (m, 1H), 2.33-2.23 (m, 2H), 2.04 (s, 3H), 1.32 (d, J=6.0 Hz, 3H), 1.09-0.98 (m, 4H).

LCMS-ESI$^+$ (m/z): [M+H]$^+$ calcd for C$_{27}$H$_{33}$N$_6$O$_3$: 489.3; found: 489.3.

Example 3.60

(R)-4-((R)-1-((1-cyclopropyl-5-(5-(4-(methylsulfonyl)piperazin-1-yl)pyridin-2-yl)-1H-benzo[d]imidazol-7-yl)oxy)ethyl)pyrrolidin-2-one

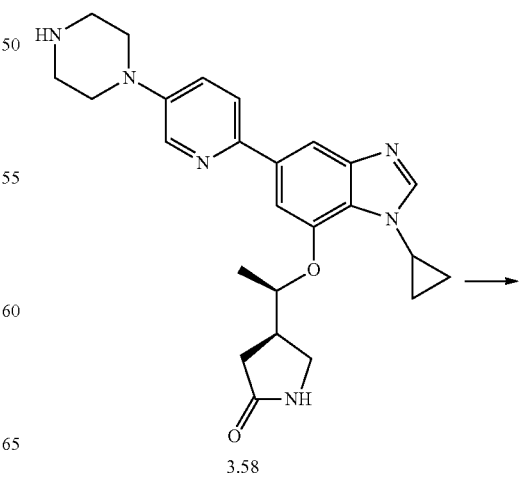

3.58

-continued

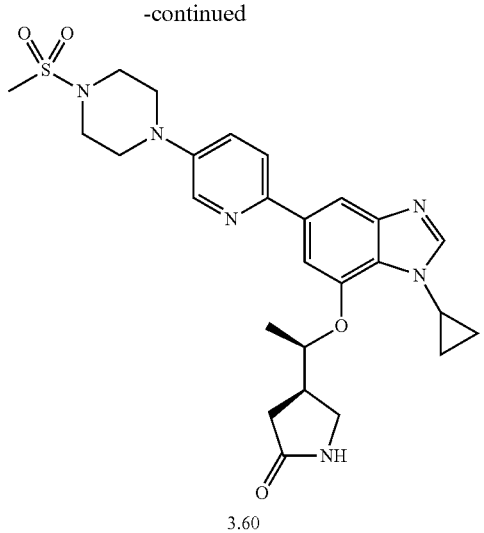

3.60

To the TFA salt of (R)-4-((R)-1-((1-cyclopropyl-5-(5-(piperazin-1-yl)pyridin-2-yl)-1H-benzo[d]imidazol-7-yl)oxy)ethyl)pyrrolidin-2-one: 3.58 (45 mg, 0.1 mmol) in DCM (1 mL) and TEA (0.07 mL, 0.5 mmol) was added methanesulfonic anhydride (26 mg, 0.15 mmol) and the mixture was stirred at rt for 1 h. The mixture was then concentrated and purified by prep HPLC (MeCN:water gradient; TFA modified) to give (R)-4-((R)-1-((1-cyclopropyl-5-(5-(4-(methylsulfonyl)piperazin-1-yl)pyridin-2-yl)-1H-benzo[d]imidazol-7-yl)oxy)ethyl)pyrrolidin-2-one: 3.60 as a TFA salt. The salt was then converted to the free base with MP carbonate resin.

$^1$H NMR (400 MHz, DMSO-$d_6$) δ 8.39 (m, 1H), 8.06 (s, 1H), 7.88 (d, J=8.8 Hz, 1H), 7.77 (s, 1H), 7.53 (d, J=13.6 Hz, 2H), 7.44-7.41 (m, 1H), 4.82-4.77 (m, 1H), 3.72-3.66 (m, 1H), 3.36-3.34 (m, 4H), 3.29-3.15 (m, 6H), 2.92 (s, 3H), 2.81-2.79 (m, 1H), 2.37-2.05 (m, 2H), 1.32 (d, J=6.0 Hz, 3H), 1.10-1.01 (m, 4H).

LCMS-ESI$^+$ (m/z): [M+H]$^+$ calcd for $C_{26}H_{33}N_6O_4S$: 525.2; found: 525.2.

Example 3.62

Preparation of (R)-4-((R)-1-((1-cyclopropyl-5-(4-(4-(oxetan-3-yl)piperazin-1-yl)phenyl)-1H-benzo[d]imidazol-7-yl)oxy)ethyl)pyrrolidin-2-one

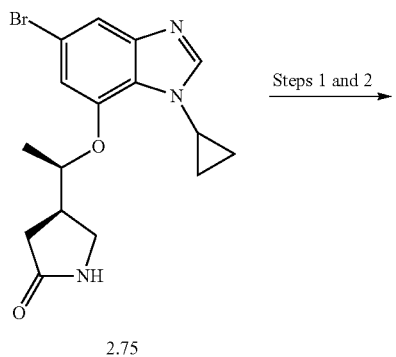

2.75

Steps 1 and 2 →

-continued

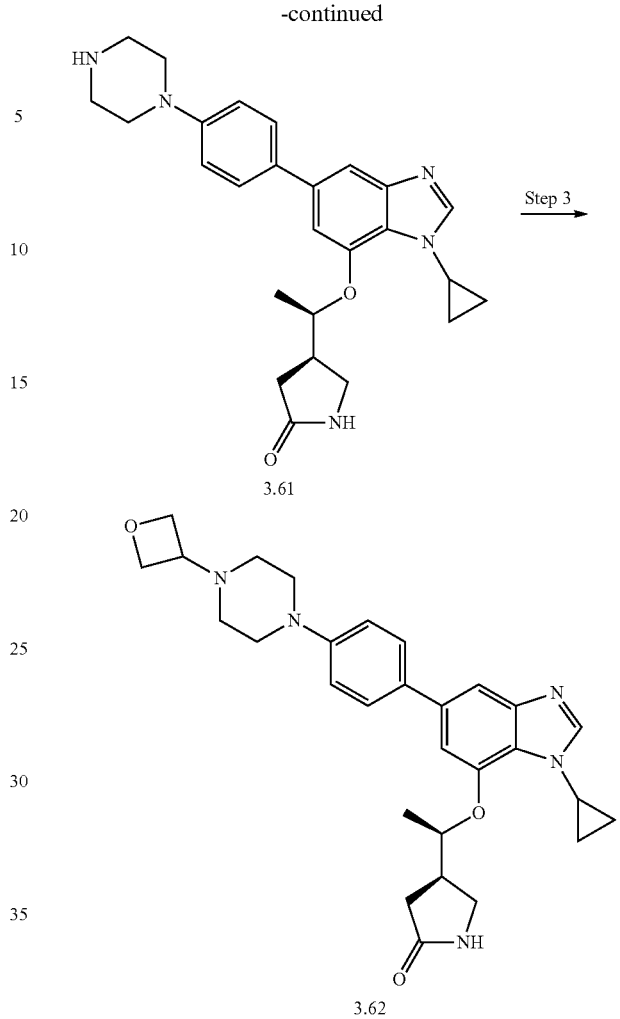

3.61

Step 3 →

3.62

Step 1: Intermediate 2.75 (120 mg, 0.33 mmol), (4-(4-(tert-butoxycarbonyl)piperazin-1-yl)phenyl)boronic acid (180 mg, 0.59 mmol), K$_3$PO$_4$ (240 mg, 1.1 mmol) and Bis[di-tert-butyl(4-dimethylaminophenyl)phosphine]dichloropalladium (II) (12 mg, 0.017 mmol) were taken up in 1,4-dioxane (5.3 mL) and water (0.53 mL). The stirred reaction mixture was heated to 100° C. for 2 h and was then cooled and partitioned between EtOAc, water and brine. The phases were separated and the aqueous phase was extracted with EtOAc. The combined organic phase was dried over Na$_2$SO$_4$, filtered, and concentrated. The crude residue was purified by silica gel chromatography (0-25% MeOH in DCM) to provide tert-butyl 4-(4-(1-cyclopropyl-7-((R)-1-((R)-5-oxopyrrolidin-3-yl)ethoxy)-1H-benzo[d]imidazol-5-yl)phenyl)piperazine-1-carboxylate. LCMS-ESI$^+$ (m/z): [M+H]$^+$ calcd for $C_{31}H_{40}N_5O_4$: 546.3; found: 546.1.

Step 2: tert-butyl 4-(4-(1-cyclopropyl-7-((R)-1-((R)-5-oxopyrrolidin-3-yl)ethoxy)-1H-benzo[d]imidazol-5-yl)phenyl)piperazine-1-carboxylate (167 mg, 0.306 mmol) was dissolved in TFA (3.5 mL). After stirring for 2 h, the reaction mixture was concentrated and the crude TFA salt of (R)-4-((R)-1-((1-cyclopropyl-5-(4-(piperazin-1-yl)phenyl)-1H-benzo[d]imidazol-7-yl)oxy)ethyl)pyrrolidin-2-one: (3.61) was used without further purification. LCMS-ESI$^+$ (m/z): [M+H]$^+$ calcd for $C_{26}H_{32}N_5O_2$: 446.3; found: 446.1.

Step 3: The crude TFA salt of (3.61) (0.15 mmol) was dissolved in THF (3 mL) and iPr₂NEt (27 μL, 0.16 mmol) was added followed by oxetan-3-one (50 μL, 0.8 mmol) and sodium triacetoxyborohydride (145 mg, 0.68 mmol). The reaction mixture was stirred at 50° C. for 6 h and was diluted with brine, 5% (w/v) aqueous Na₂CO₃, and EtOAc. The phases were separated, and the aqueous phase was extracted with EtOAc. The combined organic phase was dried over Na₂SO₄, filtered, and concentrated to afford a crude residue that was purified by silica gel chromatography (0-25% MeOH in DCM) to yield (R)-4-((R)-1-((1-cyclopropyl-5-(4-(4-(oxetan-3-yl)piperazin-1-yl)phenyl)-1H-benzo[d]imidazol-7-yl)oxy)ethyl)pyrrolidin-2-one: (3.62).

¹H NMR (400 MHz, Chloroform-d) δ 7.79 (s, 1H), 7.54-7.47 (m, 3H), 7.02-6.96 (m, 2H), 6.87 (s, 1H), 6.29 (s, 1H), 4.75-4.63 (m, 5H), 3.65-3.51 (m, 3H), 3.38 (dd, J=9.6, 6.7 Hz, 1H), 3.31-3.24 (m, 4H), 2.96-2.84 (m, 1H), 2.58-2.43 (m, 6H), 1.43 (d, J=6.0 Hz, 3H), 1.15-1.01 (m, 4H).

LCMS-ESI⁺ (m/z): [M+H]⁺ calcd for C₂₉H₃₆N₅O₃: 502.3; found: 502.1.

Example 3.64

Preparation of (R)-4-((R)-1-((6-(4-(4-acetylpiperazin-1-yl)phenyl)-3-(difluoromethyl)-3H-imidazo[4,5-c]pyridin-4-yl)oxy)ethyl)pyrrolidin-2-one

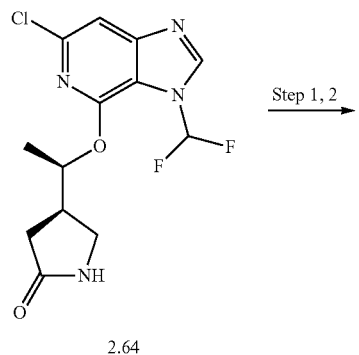

2.64

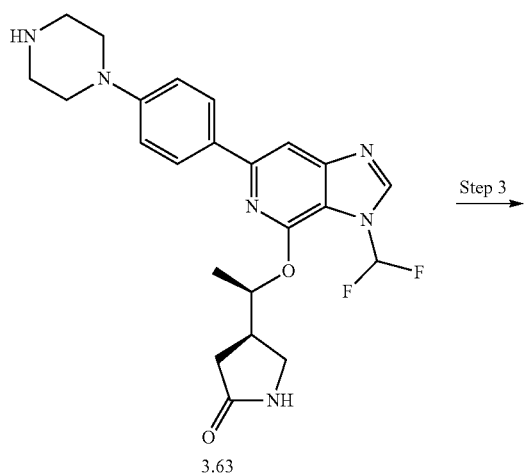

3.63

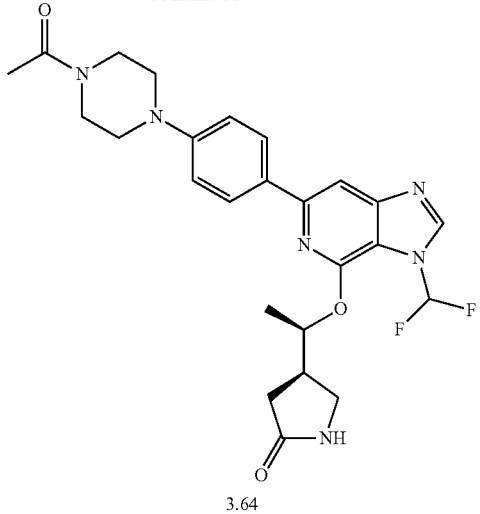

3.64

Step 1: (R)-4-((R)-1-(6-chloro-3-(difluoromethyl)-3H-imidazo[4,5-c]pyridin-4-yloxy)ethyl)pyrrolidin-2-one: 2.64 (192 mg, 0.581 mmol), (4-(4-(tert-butoxycarbonyl)piperazin-1-yl)phenyl)boronic acid (355 mg, 1.16 mmol), K₃PO₄ (400 mg, 1.9 mmol) and Bis[di-tert-butyl(4-dimethylaminophenyl)phosphine]dichloropalladium (II) (21 mg, 0.029 mmol) were taken up in 1,4-dioxane (10 mL) and water (1 mL). The stirred reaction mixture was heated to 100° C. for 1.5 h and was then cooled and partitioned between EtOAc (30 mL), water and brine. The phases were separated and the aqueous phase was extracted with EtOAc. The combined organic phase was dried over Na₂SO₄, filtered, and concentrated. The crude residue was purified by silica gel chromatography (0-12.5% MeOH in DCM) to provide tert-butyl 4-(4-(3-(difluoromethyl)-4-((R)-1-((R)-5-oxopyrrolidin-3-yl)ethoxy)-3H-imidazo[4,5-c]pyridin-6-yl)phenyl)piperazine-1-carboxylate. LCMS-ESI⁺ (m/z): [M+H]⁺ calcd for C₂₈H₃₅F₂N₆O₄: 557.3; found: 557.1.

Step 2: tert-butyl 4-(4-(3-(difluoromethyl)-4-4R)-1-((R)-5-oxopyrrolidin-3-yl)ethoxy)-3H-imidazo[4,5-c]pyridin-6-yl)phenyl)piperazine-1-carboxylate (313 mg, 0.562 mmol) was dissolved in TFA (10 mL). After stirring for 1.5 h, the reaction mixture was concentrated and the crude TFA salt of (R)-4-((R)-1-((3-(difluoromethyl)-6-(4-(piperazin-1-yl)phenyl)-3H-imidazo[4,5-c]pyridin-4-yl)oxy)ethyl)pyrrolidin-2-one: (3.63) was used without further purification. LCMS-ESI⁺ (m/z): [M+H]⁺ calcd for C₂₃H₂₇F₂N₆O₂: 457.2; found: 457.2.

Step 3: The TFA salt of 3.63 (0.06 mmol) was dissolved in DCM (1 mL) and triethylamine (60 μL, 0.43 mmol) was added followed by acetic anhydride (6.8 μL, 0.072 mmol). The reaction mixture was stirred for 3 h and was diluted with EtOAc, water and brine. The phases were separated and the aqueous phase was extracted with EtOAc. The combined organic phase was dried over Na₂SO₄, filtered, and concentrated. The crude residue was purified by silica gel chromatography (0-20% MeOH in DCM) to provide (R)-4-((R)-1-((6-(4-(4-acetylpiperazin-1-yl)phenyl)-3-(difluoromethyl)-3H-imidazo[4,5-c]pyridin-4-yl)oxy)ethyl)pyrrolidin-2-one: (3.64).

¹H NMR (400 MHz, Chloroform-d) δ 8.27 (s, 1H), 7.97-7.91 (m, 2H), 7.72 (s, 1H), 7.61 (t, J=61.1 Hz, 1H), 7.04-6.97 (m, 2H), 6.06 (s, 1H), 5.81-5.65 (m, 1H), 3.83-3.77 (m, 2H), 3.68-3.62 (m, 2H), 3.62-3.53 (m, 1H), 3.37 (dd, J=9.7, 6.2 Hz, 1H), 3.31-3.20 (m, 4H), 3.01-2.88 (m, 1H), 2.56 (dd, J=17.2, 9.3 Hz, 1H), 2.45 (dd, J=17.2, 7.4 Hz, 1H), 2.15 (s, 3H), 1.50 (d, J=6.2 Hz, 3H).

LCMS-ESI+ (m/z): [M+H]+ calcd for C25H29F2N6O3: 499.2; found: 499.3.

Example 3.65

Preparation of (R)-4-((R)-1-((3-(difluoromethyl)-6-(4-(4-(methylsulfonyl)piperazin-1-yl)phenyl)-3H-imidazo[4,5-c]pyridin-4-yl)oxy)ethyl)pyrrolidin-2-one

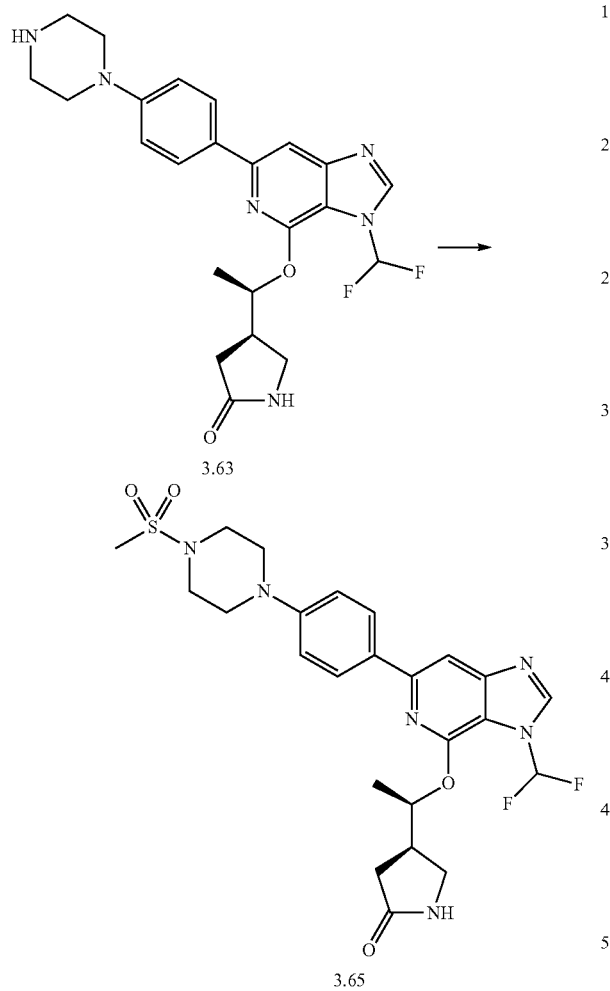

The crude TFA salt of (R)-4-((R)-1-((3-(difluoromethyl)-6-(4-(piperazin-1-yl)phenyl)-3H-imidazo[4,5-c]pyridin-4-yl)oxy)ethyl)pyrrolidin-2-one: 3.63 (0.06 mmol) was suspended in DCM (1 mL) and Et3N (60 µL, 0.43 mmol) was added followed by methanesulfonic anhydride (10.5 mg, 0.06 mmol). The resulting mixture was stirred 3 h and was partitioned between EtOAc, water, and brine. The phases were separated, and the aqueous phase was extracted with EtOAc. The combined organic phase was dried over Na2SO4, filtered, and concentrated. The crude product was purified by silica gel chromatography (0-20% MeOH in DCM) to afford (R)-4-((R)-1-((3-(difluoromethyl)-6-(4-(4-(methylsulfonyl)piperazin-1-yl)phenyl)-3H-imidazo[4,5-c]pyridin-4-yl)oxy)ethyl)pyrrolidin-2-one: (3.65).

1H NMR (400 MHz, Chloroform-d) δ 8.27 (s, 1H), 7.98-7.91 (m, 2H), 7.73 (s, 1H), 7.62 (t, J=61.1 Hz, 1H), 7.05-6.97 (m, 2H), 6.00 (s, 1H), 5.77-5.69 (m, 1H), 3.58 (dd, J=9.7, 8.5 Hz, 1H), 3.45-3.33 (m, 9H), 3.01-2.88 (m, 1H), 2.84 (s, 3H), 2.56 (dd, J=17.2, 9.3 Hz, 1H), 2.45 (dd, J=17.2, 7.4 Hz, 1H), 1.50 (d, J=6.2 Hz, 3H).

LCMS-ESI+ (m/z): [M+H]+ calcd for C24H29F2N6O4S: 535.2; found: 535.1.

Example 3.66

Preparation of (R)-4-((R)-1-((3-(difluoromethyl)-6-(4-(4-(oxetan-3-yl)piperazin-1-yl)phenyl)-3H-imidazo[4,5-c]pyridin-4-yl)oxy)ethyl)pyrrolidin-2-one

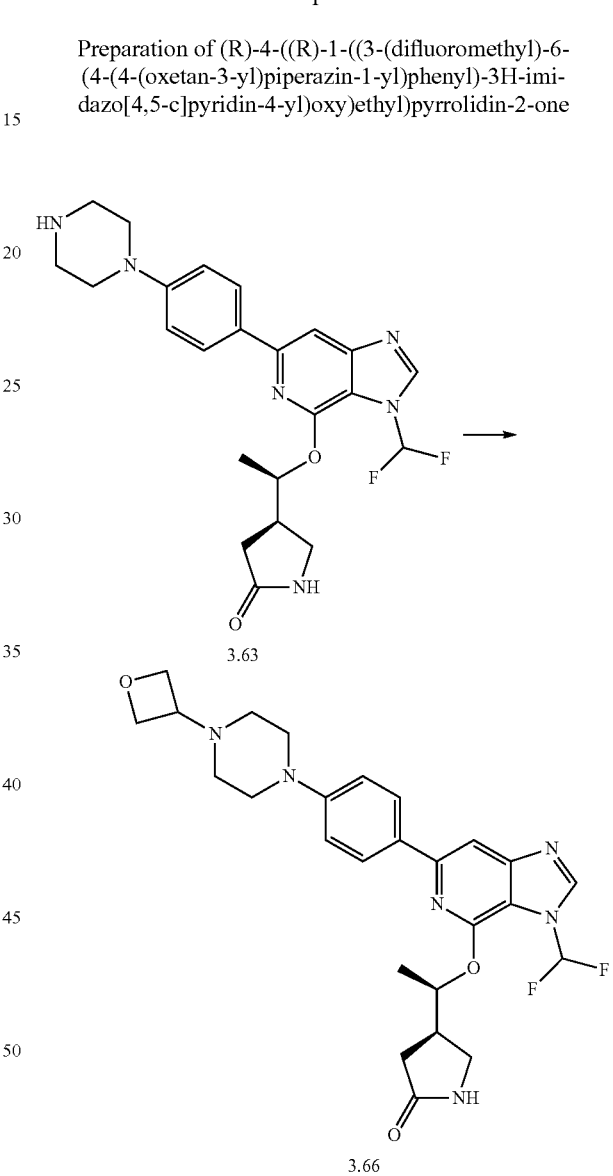

The crude TFA salt of (R)-4-((R)-1-((3-(difluoromethyl)-6-(4-(piperazin-1-yl)phenyl)-3H-imidazo[4,5-c]pyridin-4-yl)oxy)ethyl)pyrrolidin-2-one: (3.63) (0.06 mmol) was dissolved in THF (1.05 mL) and iPr2NEt (11 µL, 0.063 mmol) was added followed by oxetan-3-one (15 µL, 0.26 mmol) and sodium triacetoxyborohydride (57 mg, 0.27 mmol). The reaction mixture was stirred at 50-55° C. for 3 h and was diluted with water, 5% (w/v) aqueous Na2CO3, and EtOAc. The phases were separated, and the aqueous phase was extracted with EtOAc. The combined organic phase was dried over Na2SO4, filtered, and concentrated to afford a crude residue that was purified by silica gel chromatography (0-25% MeOH in DCM) to yield (R)-4-((R)-1-((3-(difluoromethyl)-6-(4-(4-(oxetan-3-yl)piperazin-1-yl)phenyl)-3H-imidazo[4,5-c]pyridin-4-yl)oxy)ethyl)pyrrolidin-2-one: (3.66).

$^1$H NMR (400 MHz, Chloroform-d) δ 8.26 (s, 1H), 7.95-7.89 (m, 2H), 7.72 (s, 1H), 7.61 (t, J=61.1 Hz, 1H), 7.03-6.97 (m, 2H), 5.96 (s, 1H), 5.79-5.66 (m, 1H), 4.77-4.61 (m, 4H), 3.66-3.50 (m, 2H), 3.43-3.27 (m, 5H), 3.05-2.84 (m, 1H), 2.62-2.50 (m, 5H), 2.45 (dd, J=17.2, 7.4 Hz, 1H), 1.49 (d, J=6.3 Hz, 3H).

LCMS-ESI$^+$ (m/z): [M+H]$^+$ calcd for $C_{26}H_{31}F_2N_6O_3$: 513.2; found: 512.9.

Example 3.67

Preparation of (R)-4-((R)-1-((3-(difluoromethyl)-6-(3-methoxy-4-(piperazin-1-yl)phenyl)-3H-imidazo[4,5-c]pyridin-4-yl)oxy)ethyl)pyrrolidin-2-one

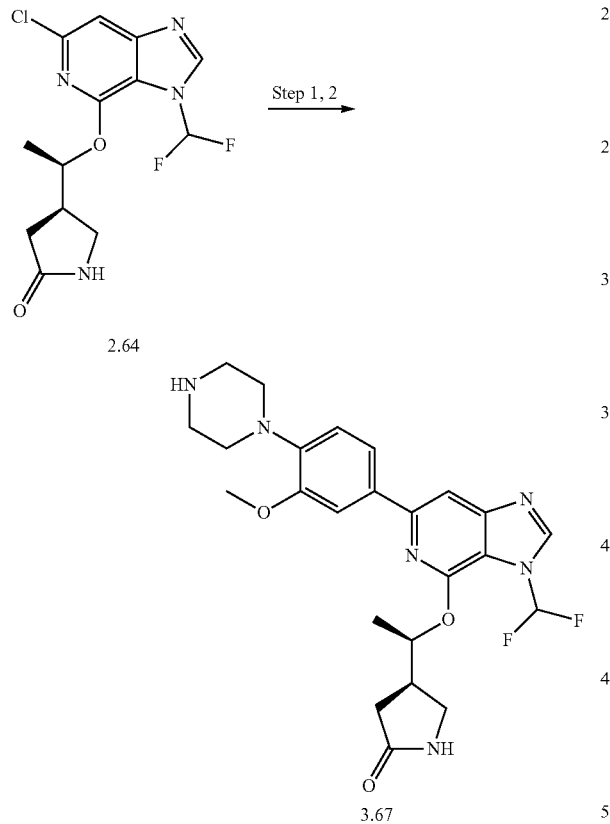

Step 1: (R)-4-((R)-1-(6-chloro-3-(difluoromethyl)-3H-imidazo[4,5-c]pyridin-4-yloxy)ethyl)pyrrolidin-2-one: 2.64 (102 mg, 0.308 mmol), tert-butyl 4-(2-methoxy-4-(4,4,5,5-tetramethyl-1,3,2-dioxaborolan-2-yl)phenyl)piperazine-1-carboxylate 7.08 (160 mg, 0.38 mmol), K$_3$PO$_4$ (191 mg, 0.9 mmol) and Bis[di-tert-butyl(4-dimethylaminophenyl)phosphine]dichloropalladium (II) (7.2 mg, 0.01 mmol) were taken up in 1,4-dioxane (4.4 mL) and water (0.44 mL). The stirred reaction mixture was heated to 100° C. for 1.5 h and was then cooled and partitioned between EtOAc, water and brine. The phases were separated and the aqueous phase was extracted with EtOAc. The combined organic phase was dried over Na$_2$SO$_4$, filtered, and concentrated. The crude residue was purified by silica gel chromatography (0-15% MeOH in DCM) to provide tert-butyl 4-(4-(3-(difluoromethyl)-4-((R)-1-((R)-5-oxopyrrolidin-3-yl)ethoxy)-3H-imidazo[4,5-c]pyridin-6-yl)-2-methoxyphenyl)piperazine-1-carboxylate.

LCMS-ESI$^+$ (m/z): [M+H]$^+$ calcd for $C_{29}H_{37}F_2N_6O_5$: 587.3; found: 587.2.

Step 2: tert-butyl 4-(4-(3-(difluoromethyl)-4-4R)-1-((R)-5-oxopyrrolidin-3-yl)ethoxy)-3H-imidazo[4,5-c]pyridin-6-yl)-2-methoxyphenyl)piperazine-1-carboxylate (158 mg, 0.269 mmol) was dissolved in TFA (5 mL). After stifling 1 h, the solution was concentrated to afford the TFA salt of (R)-4-((R)-1-((3-(difluoromethyl)-6-(3-methoxy-4-(piperazin-1-yl)phenyl)-3H-imidazo[4,5-c]pyridin-4-yl)oxy)ethyl)pyrrolidin-2-one: (3.67) that was used without further purification.

$^1$H NMR (400 MHz, DMSO-d$_6$) δ 8.76 (s, 1H), 8.72 (broad s, 2H), 8.00 (t, J=59.5 Hz, 1H), 7.96 (s, 1H), 7.74-7.64 (m, 2H), 7.54 (s, 1H), 7.01 (d, J=8.1 Hz, 1H), 5.58-5.45 (m, 1H), 3.91 (s, 3H), 3.42-3.31 (m, 1H), 3.31-3.11 (m, 9H), 2.92-2.78 (m, 1H), 2.37-2.22 (m, 2H), 1.41 (d, J=6.1 Hz, 3H).

LCMS-ESI$^+$ (m/z): [M+H]$^+$ calcd for $C_{24}H_{29}F_2N_6O_3$: 487.2; found: 487.2.

Example 3.68

Preparation of (R)-4-((R)-1-((3-(difluoromethyl)-6-(3-methoxy-4-(4-(methylsulfonyl)piperazin-1-yl)phenyl)-3H-imidazo[4,5-c]pyridin-4-yl)oxy)ethyl)pyrrolidin-2-one

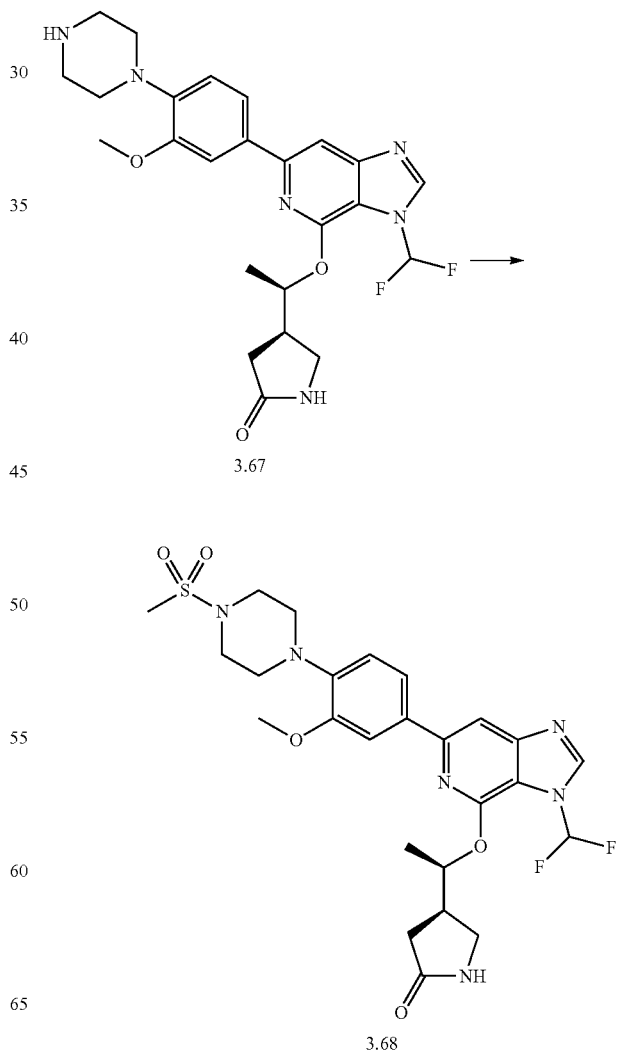

6-(3-methoxy-4-(piperazin-1-yl)phenyl)-3H-imidazo[4,5-c]pyridin-4-yl)oxy)ethyl)pyrrolidin-2-one: 3.67 (0.054 mmol) was suspended in DCM (1 mL) and Et₃N (60 μL, 0.43 mmol) was added followed by methanesulfonic anhydride (10 mg, 0.06 mmol). The resulting mixture was stirred 1.5 h and was partitioned between EtOAc, water, and brine. The phases were separated, and the aqueous phase was extracted with EtOAc (4×1.5 mL). The combined organic phase was dried over Na₂SO₄, filtered, and concentrated. The crude product was purified by silica gel chromatography (0-15% MeOH in DCM) to afford (R)-4-((R)-1-((3-(difluoromethyl)-6-(3-methoxy-4-(4-(methylsulfonyl)piperazin-1-yl)phenyl)-3H-imidazo[4,5-c]pyridin-4-yl)oxy)ethyl)pyrrolidin-2-one: (3.68).

¹H NMR (400 MHz, Chloroform-d) δ 8.29 (s, 1H), 7.76 (s, 1H), 7.62 (t, J=61.1 Hz, 1H), 7.60 (dd, J=8.2, 2.0 Hz, 1H), 7.55 (d, J=1.9 Hz, 1H), 7.08-6.99 (m, 1H), 5.92 (s, 1H), 5.74-5.66 (m, 1H), 3.98 (s, 3H), 3.63-3.55 (m, 1H), 3.51-3.41 (m, 4H), 3.37 (dd, J=9.7, 6.1 Hz, 1H), 3.30-3.17 (m, 4H), 3.03-2.89 (m, 1H), 2.84 (s, 3H), 2.57 (dd, J=17.2, 9.3 Hz, 1H), 2.46 (dd, J=17.2, 7.3 Hz, 1H), 1.52 (d, J=6.2 Hz, 3H).

LCMS-ESI⁺ (m/z): [M+H]⁺ calcd for $C_{25}H_{31}F_2N_6O_5S$: 565.2; found: 565.1.

Example 3.69

Preparation of (R)-4-((R)-1-((6-(4-(4-acetylpiperazin-1-yl)-3-methoxyphenyl)-3-(difluoromethyl)-3H-imidazo[4,5-c]pyridin-4-yl)oxy)ethyl)pyrrolidin-2-one

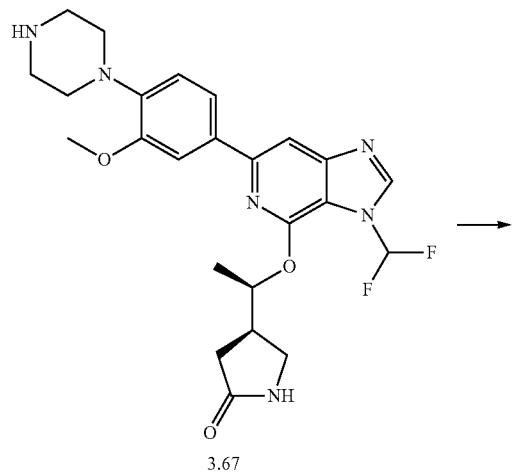

3.67

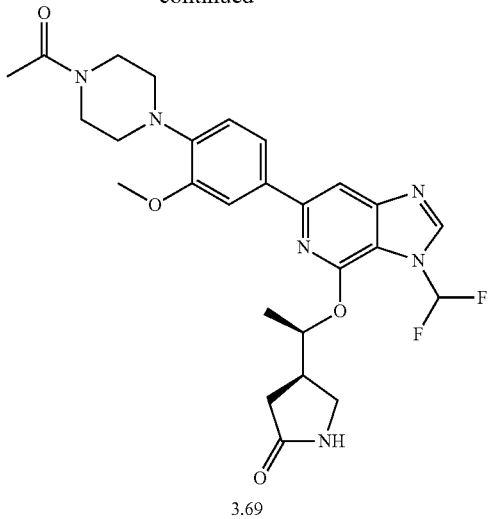

3.69

The crude TFA salt of (R)-4-((R)-1-((3-(difluoromethyl)-6-(3-methoxy-4-(piperazin-1-yl)phenyl)-3H-imidazo[4,5-c]pyridin-4-yl)oxy)ethyl)pyrrolidin-2-one: 3.67 (0.064 mmol) was dissolved in DCM (1 mL) and triethylamine (70 μL, 0.5 mmol) was added followed by acetic anhydride (7.5 μL, 0.079 mmol). The reaction mixture was stirred for 1.5 h and was diluted with EtOAc, water and brine. The phases were separated and the aqueous phase was extracted with EtOAc. The combined organic phase was dried over Na₂SO₄, filtered, and concentrated. The crude residue was purified by silica gel chromatography (0-15% MeOH in DCM) to provide (R)-4-((R)-1-((6-(4-(4-acetylpiperazin-1-yl)-3-methoxyphenyl)-3-(difluoromethyl)-3H-imidazo[4,5-c]pyridin-4-yl)oxy)ethyl)pyrrolidin-2-one (3.69).

¹H NMR (400 MHz, Chloroform-d) δ 8.30 (s, 1H), 7.77 (s, 1H), 7.62 (t, J=61.1 Hz, 1H), 7.62-7.56 (m, 2H), 7.24-6.9 (broad, 1H), 5.75-5.66 (m, 1H), 5.50 (s, 1H), 4.00 (s, 3H), 3.97-3.64 (m, 4H), 3.64-3.55 (m, 1H), 3.38 (dd, J=9.5, 5.9 Hz, 1H), 3.33-3.06 (m, 4H), 3.04-2.90 (m, 1H), 2.58 (dd, J=17.2, 9.4 Hz, 1H), 2.46 (dd, J=17.2, 7.3 Hz, 1H), 2.16 (s, 3H), 1.53 (d, J=6.2 Hz, 3H).

LCMS-ESI⁺ (m/z): [M+H]⁺ calcd for $C_{26}H_{31}F_2N_6O_4$: 529.2; found: 528.8.

Example 3.70

Preparation of (R)-4-((R)-1-((3-(difluoromethyl)-6-(3-methoxy-4-(4-(oxetan-3-yl)piperazin-1-yl)phenyl)-3H-imidazo[4,5-c]pyridin-4-yl)oxy)ethyl)pyrrolidin-2-one

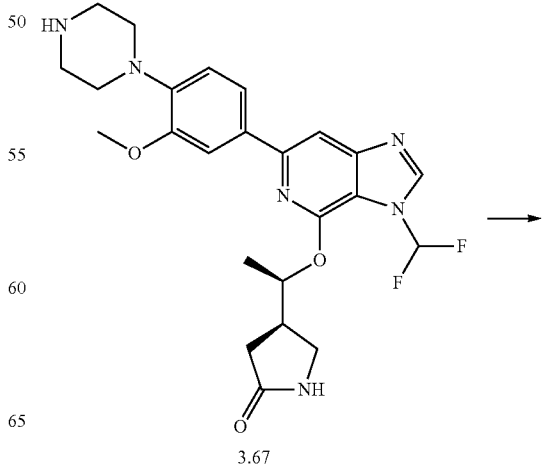

3.67

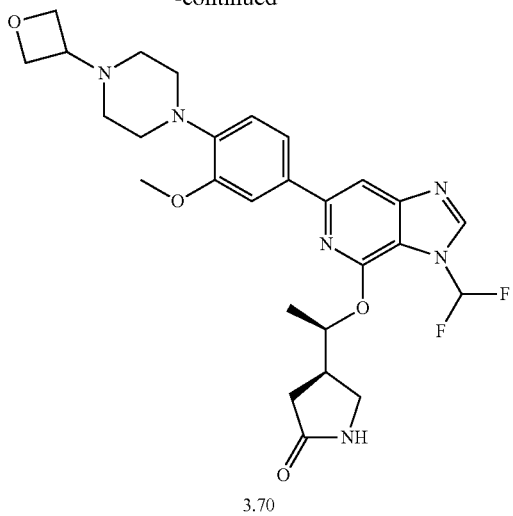

3.70

The crude TFA salt of (R)-4-((R)-1-((3-(difluoromethyl)-6-(3-methoxy-4-(piperazin-1-yl)phenyl)-3H-imidazo[4,5-c]pyridin-4-yl)oxy)ethyl)pyrrolidin-2-one: 3.67 (0.064 mmol) was dissolved in THF (1 mL) and iPr$_2$NEt (12 μL, 0.07 mmol) was added followed by oxetan-3-one (18 μL, 0.30 mmol) and sodium triacetoxyborohydride (61 mg, 0.29 mmol). The reaction mixture was stirred at 50-55° C. for 18 h and was diluted with water, 5% (w/v) aqueous Na$_2$CO$_3$, and EtOAc. The phases were separated, and the aqueous phase was extracted with EtOAc. The combined organic phase was dried over Na$_2$SO$_4$, filtered, and concentrated to afford a crude residue that was purified by silica gel chromatography (0-20% MeOH in DCM) to yield (R)-4-((R)-1-((3-(difluoromethyl)-6-(3-methoxy-4-(4-(oxetan-3-yl)piperazin-1-yl)phenyl)-3H-imidazo[4,5-c]pyridin-4-yl)oxy)ethyl)pyrrolidin-2-one (3.70).

$^1$H NMR (400 MHz, Chloroform-d) δ 8.28 (s, 1H), 7.75 (s, 1H), 7.62 (t, J=61.1 Hz, 1H), 7.59 (dd, J=8.2, 1.9 Hz, 1H), 7.54 (d, J=1.9 Hz, 1H), 7.02 (d, J=8.3 Hz, 1H), 5.88 (s, 1H), 5.76-5.65 (m, 1H), 4.76-4.63 (m, 4H), 3.96 (s, 3H), 3.66-3.53 (m, 2H), 3.37 (dd, J=9.7, 6.1 Hz, 1H), 3.30-3.13 (m, 4H), 3.02-2.89 (m, 1H), 2.67-2.51 (m, 5H), 2.46 (dd, J=17.2, 7.3 Hz, 1H), 1.51 (d, J=6.2 Hz, 3H).

LCMS-ESI$^+$ (m/z): [M+H]$^+$ calcd for C$_{27}$H$_{33}$F$_2$N$_6$O$_4$: 543.2; found: 543.4.

Example 3.71

Preparation of 2-(3-(1-cyclopropyl-7-((R)-1-((R)-5-oxopyrrolidin-3-yl)ethoxy)-1H-benzo[d]imidazol-5-yl)-1H-pyrazol-1-yl)-2-methylpropanoic acid

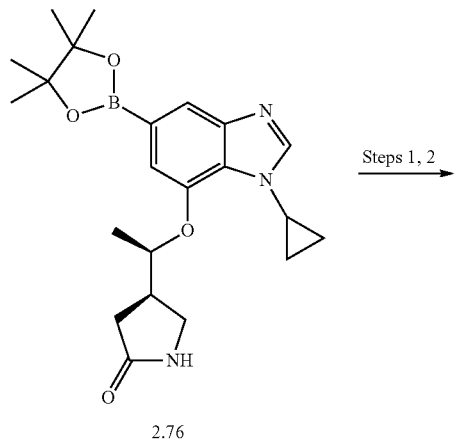

2.76

Steps 1, 2 →

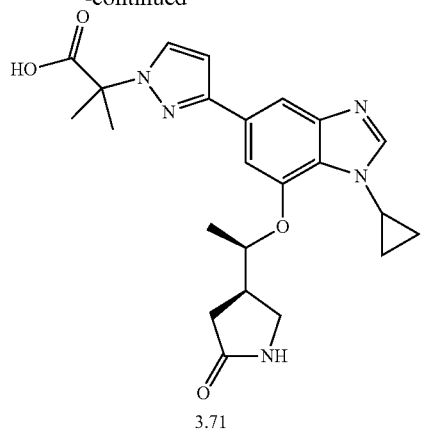

3.71

Step 1: (R)-4-((R)-1-((1-cyclopropyl-5-(4,4,5,5-tetramethyl-1,3,2-dioxaborolan-2-yl)-1H-benzo[d]imidazol-7-yl)oxy)ethyl)pyrrolidin-2-one: 2.76 (40 mg, 0.097 mmol), tert-butyl 2-(3-iodo-1H-pyrazol-1-yl)-2-methylpropanoate 7.03 (65 mg, 0.19 mmol), bis(di-tert-butyl(4-dimethylaminophenyl)phosphine)dichloropalladium (II) (1.4 mg, 0.002 mmol), and K$_3$PO$_4$ (71 mg, 0.34 mmol) were taken up in 1,4-dioxane (1.6 mL) and water (0.16 mL) under Ar. The stirred reaction mixture was heated to 100° C. for 2.5 h and was then cooled and diluted with EtOAc, water, and brine. The phases were separated, and the aqueous phase was extracted with EtOAc. The combined organic phase was dried over Na$_2$SO$_4$, filtered, and concentrated. The crude residue was purified by silica gel chromatography (0-15% MeOH in DCM), and the major product obtained was used directly in the following step.

Step 2: The product from above was dissolved in DCM (2 mL) and TFA (2 mL). The reaction mixture was stirred at r.t. for 4 h and was then concentrated in vacuo. The resulting residue was lyophilized from a water:acetonitrile mixture to afford 2-(3-(1-cyclopropyl-7-((R)-1-((R)-5-oxopyrrolidin-3-yl)ethoxy)-1H-benzo[d]imidazol-5-yl)-1H-pyrazol-1-yl)-2-methylpropanoic acid (3.71) as its TFA salt.

$^1$H NMR (400 MHz, Methanol-d$_4$) δ 9.27 (s, 1H), 7.88 (d, J=2.5 Hz, 1H), 7.71 (d, J=1.1 Hz, 1H), 7.66 (s, 1H), 6.80 (d, J=2.5 Hz, 1H), 5.06-4.96 (m, 1H), 4.07-3.96 (m, 1H), 3.63 (dd, J=10.1, 8.8 Hz, 1H), 3.38 (dd, J=10.1, 6.2 Hz, 1H), 3.08-2.93 (m, 1H), 2.61 (dd, J=17.3, 9.5 Hz, 1H), 2.50 (dd, J=17.3, 7.4 Hz, 1H), 1.90 (s, 6H), 1.47 (d, J=6.0 Hz, 3H), 1.39-1.24 (m, 4H).

LCMS-ESI$^+$ (m/z): [M+H]$^+$ calcd for C$_{23}$H$_{28}$N$_5$O$_4$: 438.21; found: 438.31.

Example 3.72

Preparation of 6'-(3-cyclopropyl-4-((R)-1-4R)-5-oxopyrrolidin-3-yl)ethoxy)-3H-imidazo[4,5-c]pyridin-6-yl)spiro[cyclopropane-1,3'-indolin]-2'-one

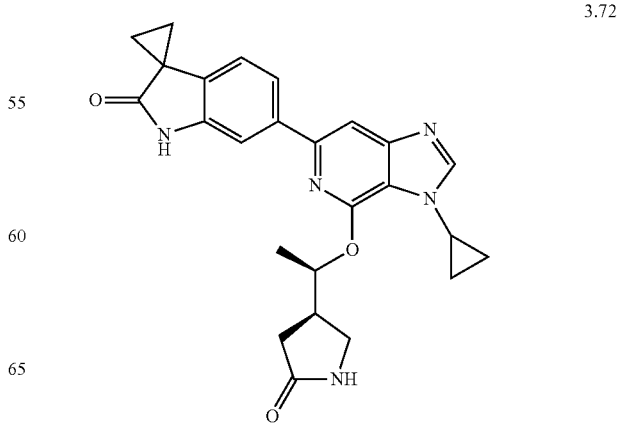

3.72

Following general procedure 3A, starting from a mixture of (R)-4-((R)-1-((6-bromo-3-cyclopropyl-3H-imidazo[4,5-c]pyridin-4-yl)oxy)ethyl)-1-((R)-1-(4-methoxyphenyl)ethyl)pyrrolidin-2-one: and (R)-4-((R)-1-((6-chloro-3-cyclopropyl-3H-imidazo[4,5-c]pyridin-4-yl)oxy)ethyl)-1-((R)-1-(4-methoxyphenyl)ethyl)pyrrolidin-2-one: (mixture=2.70) (54 mg) and 6'-(4,4,5,5-tetramethyl-1,3,2-dioxaborolan-2-yl)spiro[cyclopropane-1,3'-indolin]-2'-one 7.61 (40 mg), 6'-(3-cyclopropyl-4-((R)-1-((R)-5-oxopyrrolidin-3-yl)ethoxy)-3H-imidazo[4,5-c]pyridin-6-yl)spiro[cyclopropane-1,3'-indolin]-2'-one 3.72 (20 mg) was synthesized.

$^1$H NMR (400 MHz, Chloroform-d) δ 9.09 (s, 1H), 7.91 (s, 1H), 7.72-7.61 (m, 2H), 6.88 (d, J=7.6 Hz, 1H), 6.29 (s, 1H), 6.15 (s, 1H), 5.78 (t, J=5.9 Hz, 1H), 3.81 (t, J=6.2 Hz, 1H), 3.64-3.53 (m, 2H), 3.50-3.38 (m, 2H), 3.22 (dd, J=9.6, 6.7 Hz, 1H), 2.95 (m, 1H), 2.55 (dd, J=20.7, 8.1 Hz, 2H), 2.02 (m, 1H), 1.52 (d, J=6 Hz, 3H), 1.32-0.82 (m, 4H).

LCMS-ESI$^+$ (m/z): [M+H]$^+$ calcd for $C_{25}H_{26}N_5O_3$: 444.2; found: 444.2.

Example 3.74

Preparation of 6-(3-cyclopropyl-4-((R)-1-((R)-5-oxopyrrolidin-3-yl)ethoxy)-3H-imidazo[4,5-c]pyridin-6-yl)-1,3,3-trimethylindolin-2-one

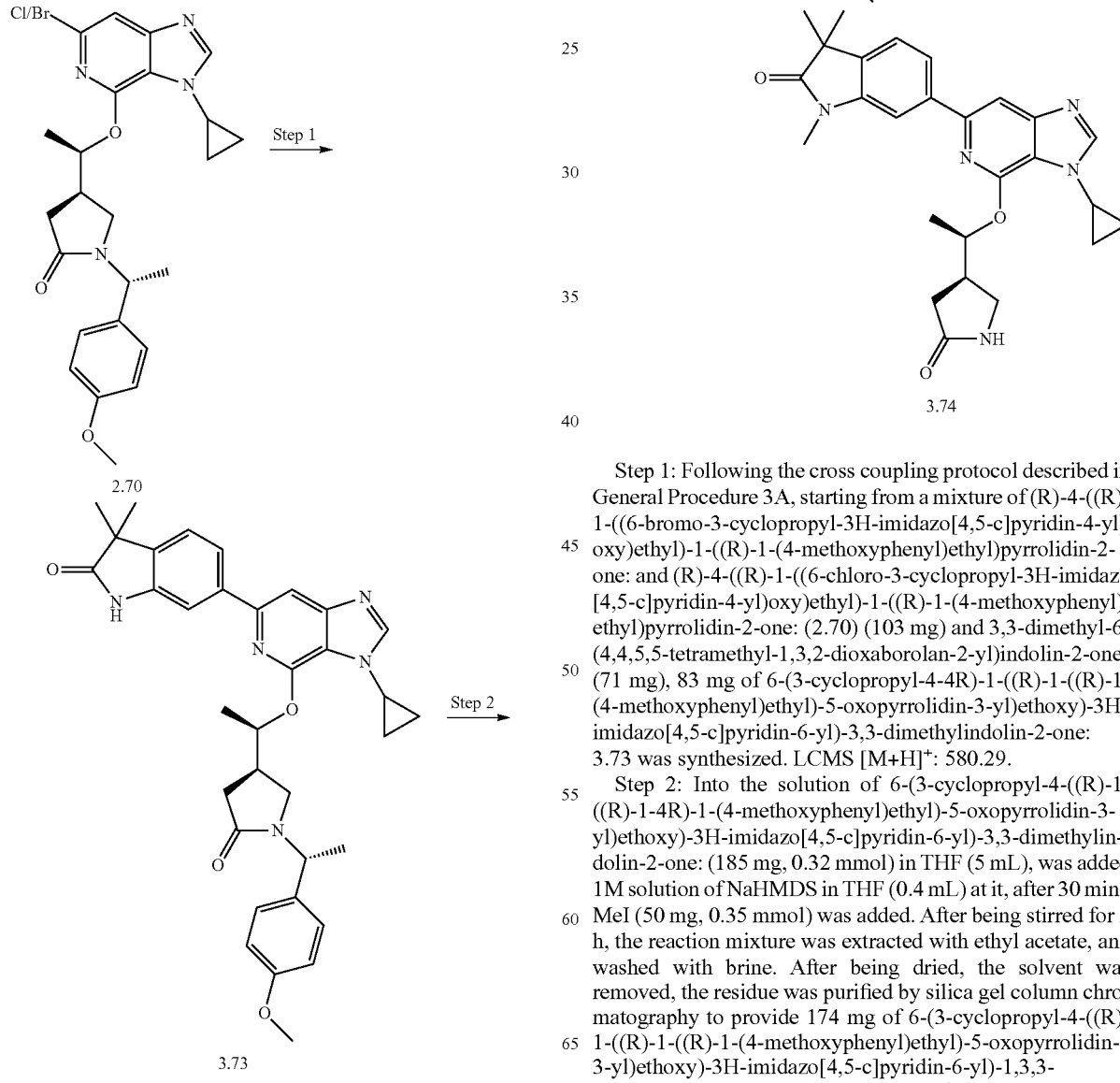

Step 1: Following the cross coupling protocol described in General Procedure 3A, starting from a mixture of (R)-4-((R)-1-((6-bromo-3-cyclopropyl-3H-imidazo[4,5-c]pyridin-4-yl)oxy)ethyl)-1-((R)-1-(4-methoxyphenyl)ethyl)pyrrolidin-2-one: and (R)-4-((R)-1-((6-chloro-3-cyclopropyl-3H-imidazo[4,5-c]pyridin-4-yl)oxy)ethyl)-1-((R)-1-(4-methoxyphenyl)ethyl)pyrrolidin-2-one: (2.70) (103 mg) and 3,3-dimethyl-6-(4,4,5,5-tetramethyl-1,3,2-dioxaborolan-2-yl)indolin-2-one: (71 mg), 83 mg of 6-(3-cyclopropyl-4-4R)-1-((R)-1-((R)-1-(4-methoxyphenyl)ethyl)-5-oxopyrrolidin-3-yl)ethoxy)-3H-imidazo[4,5-c]pyridin-6-yl)-3,3-dimethylindolin-2-one: 3.73 was synthesized. LCMS [M+H]$^+$: 580.29.

Step 2: Into the solution of 6-(3-cyclopropyl-4-((R)-1-((R)-1-4R)-1-(4-methoxyphenyl)ethyl)-5-oxopyrrolidin-3-yl)ethoxy)-3H-imidazo[4,5-c]pyridin-6-yl)-3,3-dimethylindolin-2-one: (185 mg, 0.32 mmol) in THF (5 mL), was added 1M solution of NaHMDS in THF (0.4 mL) at it, after 30 min., MeI (50 mg, 0.35 mmol) was added. After being stirred for 2 h, the reaction mixture was extracted with ethyl acetate, and washed with brine. After being dried, the solvent was removed, the residue was purified by silica gel column chromatography to provide 174 mg of 6-(3-cyclopropyl-4-((R)-1-((R)-1-(4-methoxyphenyl)ethyl)-5-oxopyrrolidin-3-yl)ethoxy)-3H-imidazo[4,5-c]pyridin-6-yl)-1,3,3-trimethylindolin-2-one:. LCMS [M+H]$^+$: 594.24.

Step 3: Following the TFA-mediated deprotection protocol described in general procedure A, starting from 6-(3-cyclopropyl-4-((R)-1-((R)-1-((R)-1-(4-methoxyphenyl)ethyl)-5-oxopyrrolidin-3-yl)ethoxy)-3H-imidazo[4,5-c]pyridin-6-yl)-1,3,3-trimethylindolin-2-one: (174 mg), 90 mg of 6-(3-cyclopropyl-4-((R)-1-((R)-5-oxopyrrolidin-3-yl)ethoxy)-3H-imidazo[4,5-c]pyridin-6-yl)-1,3,3-trimethylindolin-2-one: (3.74) was synthesized.

$^1$H NMR (400 MHz, Chloroform-d) δ 7.905 (s, 1H), 7.72 (s, 1H), 7.7 (d, J=1.4 Hz, 1H), 7.46 (d, J=1.4 Hz, 1H), 7.27 (d. J=8.4 Hz, 1H), 5.97 (s, 1H), 5.76 (m, 1H), 3.65-3.55 (m, 2H), 3.42 (m, 1H), 3.3 (s, 3H), 2.97 (m, 1H), 2.56 (m, 2H), 1.52 (d, J=6 Hz, 3H), 1.4 (s, 6H), 1.18-0.96 (m, 4H).

LCMS-ESI$^+$ (m/z): [M+H]$^+$ calcd for $C_{26}H_{30}N_5O_3$: 460.23; found: 460.16.

Example 3.75

Preparation of 6-(3-cyclopropyl-4-((R)-1-((R)-5-oxopyrrolidin-3-yl)ethoxy)-3H-imidazo[4,5-c]pyridin-6-yl)-1-(2,2-difluoroethyl)-3,3-dimethylindolin-2-one Following Steps 2 and 3 from the procedure described for Example 3.74, starting from 6-(3-cyclopropyl-4-((R)-1-((R)-1-((R)-1-(4-methoxyphenyl)ethyl)-5-oxopyrrolidin-3-yl)ethoxy)-3H-imidazo[4,5-c]pyridin-6-yl)-3,3-dimethylindolin-2-one: 3.73 (25 mg) and 2-bromo-1,1-difluoroethane, 9.3 mg of 6-(3-cyclopropyl-4-((R)-1-((R)-5-oxopyrrolidin-3-yl)ethoxy)-3H-imidazo[4,5-c]pyridin-6-yl)-1-(2,2-difluoroethyl)-3,3-dimethylindolin-2-one: 3.75 was synthesized.

$^1$H NMR (400 MHz, Chloroform-d) δ 7.95 (s, 1H), 7.73 (s, 1H), 7.7 (s, 1H), 7.66 (s, 1H), 7.29 (d. J=8.4 Hz, 1H), 5.97 (m, 1H), 5.76 (m, 1H), 4.17 (m, 2H), 3.65-3.57 (m, 2H), 3.42 (m, 1H), 2.97 (m, 1H), 2.56 (m, 2H), 1.52 (d, J=6 Hz, 3H), 1.44 (s, 6H), 1.18-0.96 (m, 4H).

LCMS-ESI$^+$ (m/z): [M+H]$^+$ calcd for $C_{27}H_{30}F_2N_5O_3$: 510.23; found: 510.19.

Example 3.76

Preparation of 6-(3-cyclopropyl-4-((R)-1-((R)-5-oxopyrrolidin-3-yl)ethoxy)-3H-imidazo[4,5-c]pyridin-6-yl)-1-(2-(dimethylamino)ethyl)-3,3-dimethylindolin-2-one

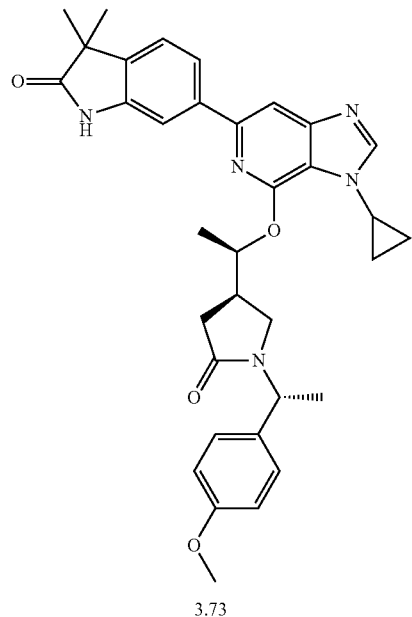

3.73

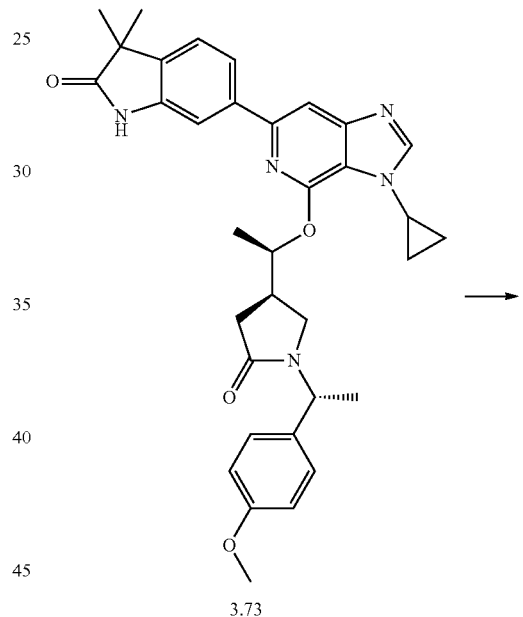

3.73

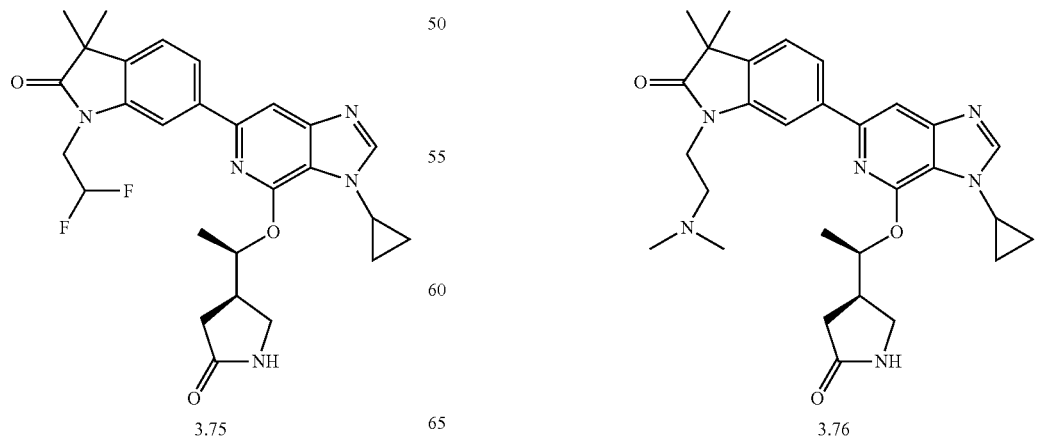

3.75

3.76

Following Steps 2 and 3 from the procedure described for Example 3.74, starting from 6-(3-cyclopropyl-4-((R)-1-((R)-1-((R)-1-(4-methoxyphenyl)ethyl)-5-oxopyrrolidin-3-yl)ethoxy)-3H-imidazo[4,5-c]pyridin-6-yl)-3,3-dimethylindolin-2-one: 3.73 (72 mg) and 2-chloro-N,N-dimethylethanamine hydrochloride, 6-(3-cyclopropyl-4-4R)-1-((R)-5-oxopyrrolidin-3-yl)ethoxy)-3H-imidazo[4,5-c]pyridin-6-yl)-1-(2-(dimethylamino)ethyl)-3,3-dimethylindolin-2-one: 3.76 (17 mg) was synthesized.

¹H NMR (400 MHz, Chloroform-d) δ 7.89 (s, 1H), 7.71 (s, 1H), 7.67 (s, 1H), 7.55 (s, 1H), 7.26 (d. J=8 Hz, 1H), 6.1 (m, 1H), 5.8 (m, 1H), 3.95 (m, 2H), 3.6 (m, 2H), 3.4 (m, 1H), 2.9 (m, 1H), 2.67 (m, 2H), 2.54 (m, 2H), 2.38 (s, 6H), 1.52 (d, J=6 Hz, 3H), 1.39 (s, 6H), 1.25-0.86 (m, 4H).

LCMS-ESI⁺ (m/z): [M+H]⁺ calcd for $C_{29}H_{37}N_6O_3$: 517.3; found: 517.2.

Example 3.77

Preparation of 6-(3-cyclopropyl-4-((R)-1-((R)-5-oxopyrrolidin-3-yl)ethoxy)-3H-imidazo[4,5-c]pyridin-6-yl)-1-(3-hydroxypropyl)-3,3-dimethylindolin-2-one

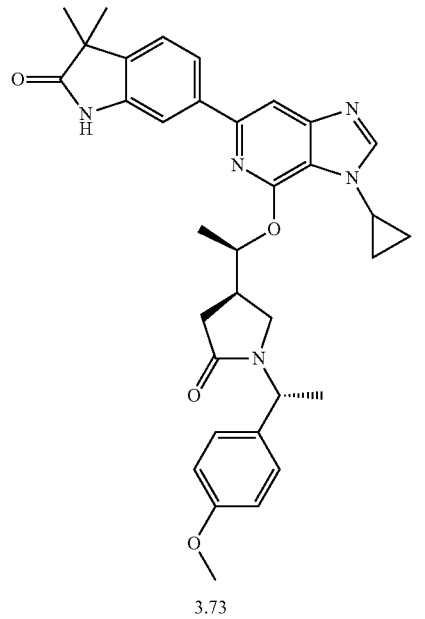

3.73

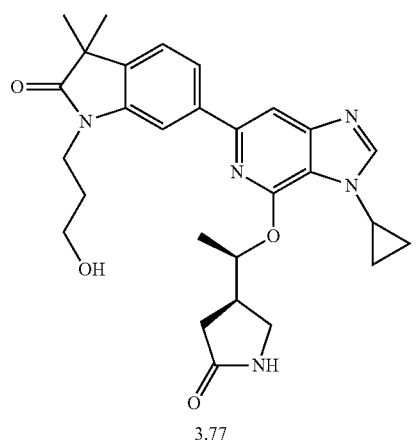

3.77

Following Steps 2 and 3 from the procedure described for Example 3.74, starting from 6-(3-cyclopropyl-4-((R)-1-((R)-1-((R)-1-(4-methoxyphenyl)ethyl)-5-oxopyrrolidin-3-yl)ethoxy)-3H-imidazo[4,5-c]pyridin-6-yl)-3,3-dimethylindolin-2-one: 3.73 (41 mg) and 3-bromopropan-1-ol, 5 mg of 6-(3-cyclopropyl-4-((R)-1-((R)-5-oxopyrrolidin-3-yl)ethoxy)-3H-imidazo[4,5-c]pyridin-6-yl)-1-(3-hydroxypropyl)-3,3-dimethylindolin-2-one: 3.77 was synthesized.

¹H NMR (400 MHz, Chloroform-d) δ 7.97 (s, 1H), 7.73 (s, 1H), 7.71 (s, 1H), 7.54 (s, 1H), 7.29 (d. J=8.4 Hz, 1H), 5.77 (m, 1H), 5.68 (m, 1H), 3.98 (t, J=6.2 Hz, 2H), 3.65-3.57 (m, 2H), 3.42 (m, 1H), 2.97 (m, 1H), 2.57 (m, 2H), 1.93 (t, J=6.2 Hz, 2H), 1.52 (d, J=6 Hz, 3H), 1.43 (s, 6H), 1.36 (m, 2H), 1.18-0.96 (m, 4H).

LCMS-ESI⁺ (m/z): [M+H]⁺ calcd for $C_{28}H_{34}N_5O_4$: 504.26; found: 504.23.

Example 3.78

Preparation of 6-(3-cyclopropyl-4-((R)-1-((R)-5-oxopyrrolidin-3-yl)ethoxy)-3H-imidazo[4,5-c]pyridin-6-yl)spiro[indoline-3,4'-piperidin]-2-one

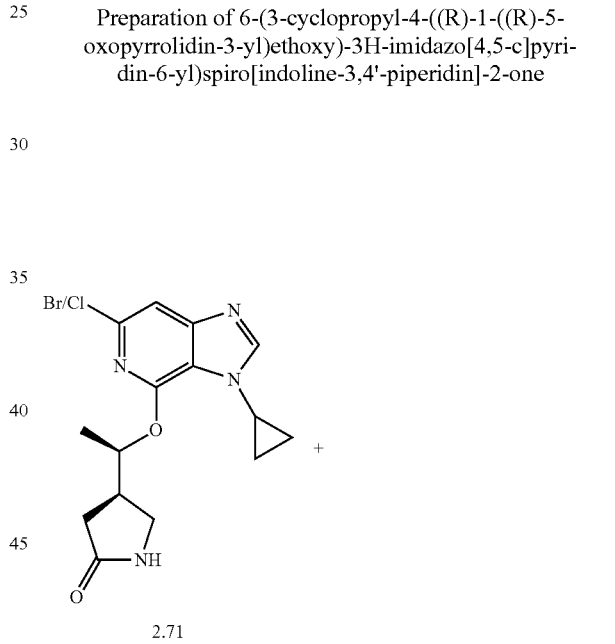

2.71

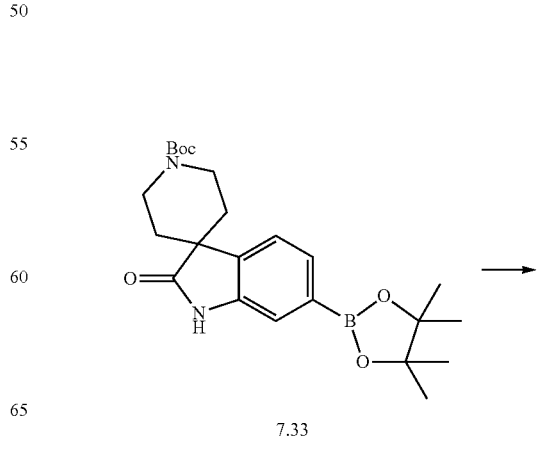

7.33

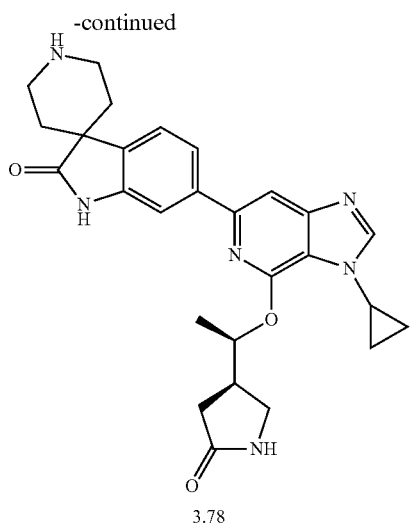

3.78

Following the protocols described in General Procedure 3A, starting with tert-butyl 2-oxo-6-(4,4,5,5-tetramethyl-1,3,2-dioxaborolan-2-yl)spiro[indoline-3,4'-piperidine]-1'-carboxylate 7.33 (111 mg), and a mixture of (R)-4-((R)-1-((6-chloro-3-cyclopropyl-3H-imidazo[4,5-c]pyridin-4-yl)oxy)ethyl)pyrrolidin-2-one: and (R)-4-((R)-1-((6-bromo-3-cyclopropyl-3H-imidazo[4,5-c]pyridin-4-yl)oxy)ethyl)pyrrolidin-2-one: 2.71 (118 mg), 32 mg of 6-(3-cyclopropyl-4-((R)-1-((R)-5-oxopyrrolidin-3-yl)ethoxy)-3H-imidazo[4,5-c]pyridin-6-yl)spiro[indoline-3,4'-piperidin]-2-one: 3.78 was synthesized.

$^1$H NMR (400 MHz, Chloroform-d) δ 7.85 (s, 1H), 7.66 (s, 1H), 7.65 (s, 1H), 7.64 (s, 1H), 7.5 (s, 1H), 7.38 (d, J=8.2 Hz, 1H), 6.16 (s, 1H), 5.73 (m, 1H), 3.65-3.5 (m, 6H), 3.49-3.35 (m, 4H), 3.35 (m, 1H), 2.99 (m, 1H), 2.56 (m, 2H), 1.9 (d, J=6 Hz, 3H), 1.44-1.1 (m, 4H).

LCMS-ESI$^+$ (m/z): [M+H]$^+$ calcd for C$_{27}$H$_{31}$N$_6$O$_3$: 487.2; found: 487.2.

Example 3.79

Preparation of 6-(3-cyclopropyl-4-((R)-1-((R)-5-oxopyrrolidin-3-yl)ethoxy)-3H-imidazo[4,5-c]pyridin-6-yl)-1'-(oxetan-3-yl)spiro[indoline-3,4'-piperidin]-2-one

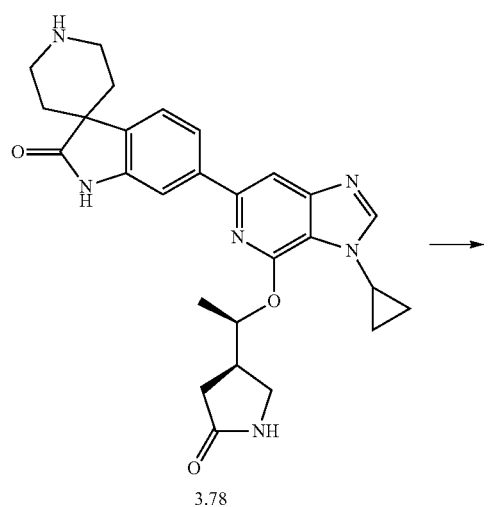

3.78

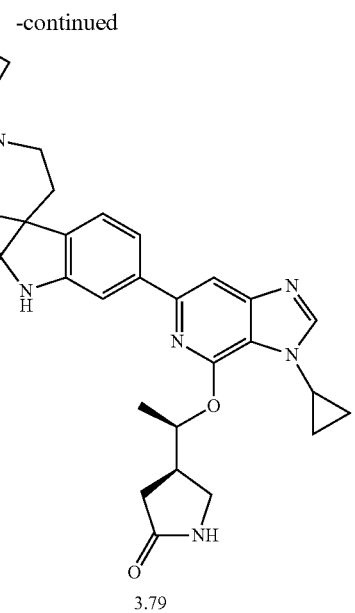

3.79

To a solution of 6-(3-cyclopropyl-4-((R)-1-((R)-5-oxopyrrolidin-3-yl)ethoxy)-3H-imidazo[4,5-c]pyridin-6-yl)spiro[indoline-3,4'-piperidin]-2-one: 3.78 (TFA salt) (28 mg) in DCM (2 mL) and MeOH (1 mL) was added oxetan-3-one (4.98 mg, 0.069 mmol) and TEA (1 mL) (to neutralize TFA). The mixture was stirred for 45 minutes then followed by addition of Na(CN)BH$_3$ (5.1 mg, 0.081 mmol). Reaction mixture was stirred for 30 minutes. Reaction was done based on LCMS. The solvent was removed and the residue was purified by prep HPLC (MeCN:water gradient, TFA modified) to provide 6-(3-cyclopropyl-4-((R)-1-((R)-5-oxopyrrolidin-3-yl)ethoxy)-3H-imidazo[4,5-c]pyridin-6-yl)-1'-(oxetan-3-yl)spiro[indoline-3,4'-piperidin]-2-one: (3.79) as a TFA salt.

$^1$H NMR (400 MHz, Methanol-d4) δ 8.78 (s, 1H), 7.86-7.78 (m, 1H), 7.74 (s, 1H), 7.69 (d, J=7.7 Hz, 1H), 7.51-7.29 (m, 1H), 5.87-5.74 (m, 1H), 5.00-4.85 (m, 4H), 4.18-3.37 (m, 11H), 3.09-2.96 (m, 1H), 2.70-2.04 (m, 5H), 1.53 (d, J=6.2 Hz, 3H), 1.36-1.16 (m, 4H).

LCMS-ESI$^+$ (m/z): [M+H]$^+$ calcd for C$_{30}$H$_{35}$N$_6$O$_4$: 543.26; found 543.22.

Example 3.80

Preparation of 6-(3-cyclopropyl-4-((R)-1-((R)-5-oxopyrrolidin-3-yl)ethoxy)-3H-imidazo[4,5-c]pyridin-6-yl)-1'-(2,2,2-trifluoroethyl)spiro[indoline-3,4'-piperidin]-2-one

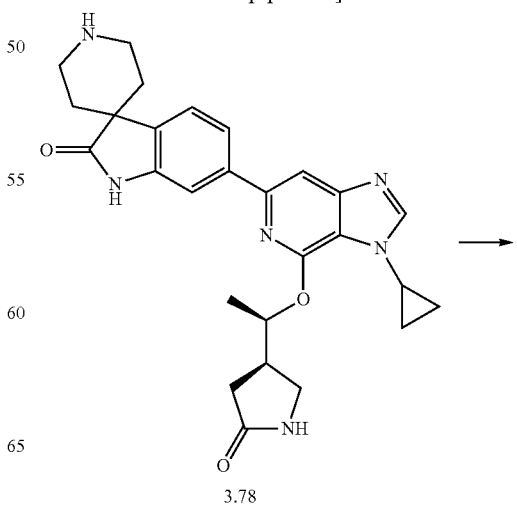

3.78

385

-continued

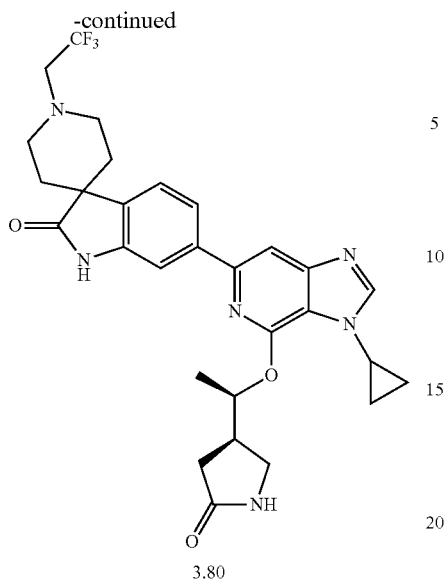

3.80

To a solution of 6-(3-cyclopropyl-4-((R)-1-((R)-5-oxopyrrolidin-3-yl)ethoxy)-3H-imidazo[4,5-c]pyridin-6-yl)spiro[indoline-3,4'-piperidin]-2-one: 3.78 (94 mg, 0.19 mmol) in DMF was added TEA (117 mg, 1.1 mmol), then followed by the addition of 2,2,2-trifluoroethyl trifluoromethanesulfonate (45 mg, 0.19 mmol). Reaction mixture was stirred at r.t. overnight, and LC-MS showed reaction was complete. The reaction mixture was filtered and purified by prep HPLC (MeCN:water gradient, TFA modified) to provide 6-(3-cyclopropyl-4-((R)-1-((R)-5-oxopyrrolidin-3-yl)ethoxy)-3H-imidazo[4,5-c]pyridin-6-yl)-1'-(2,2,2-trifluoroethyl)spiro[indoline-3,4'-piperidin]-2-one: 3.80 as its TFA salt.

$^1$H NMR (400 MHz, Methanol-d4) δ 8.80 (s, 1H), 7.72-7.66 (m, 1H), 7.64 (s, 1H), 7.59 (d, J=1.5 Hz, 1H), 7.42 (d, J=7.9 Hz, 1H), 5.72 (p, J=6.1 Hz, 1H), 3.79 (p, J=5.6 Hz, 1H), 3.63 (q, J=9.5 Hz, 2H), 3.54 (dd, J=10.1, 8.7 Hz, 1H), 3.51-3.38 (m, 2H), 3.36-3.24 (m, 1H), 3.20-3.10 (m, 2H), 2.99-2.86 (m, 1H), 2.61-2.39 (m, 2H), 1.98 (q, J=4.8 Hz, 4H), 1.44 (d, J=6.2 Hz, 3H), 1.28-1.11 (m, 4H).

LCMS-ESI$^+$ (m/z): [M+H]$^+$ calcd for $C_{30}H_{34}N_6O_4$: 569.24; found 569.21.

Example 3.81

Preparation of 1'-acetyl-6-(3-cyclopropyl-4-((R)-1-((R)-5-oxopyrrolidin-3-yl)ethoxy)-3H-imidazo[4,5-c]pyridin-6-yl)spiro[indoline-3,4'-piperidin]-2-one

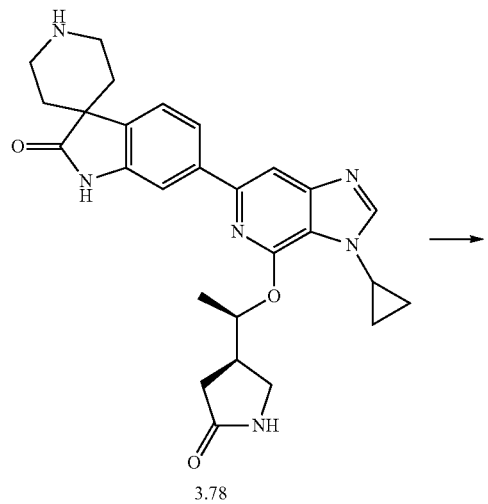

3.78

386

-continued

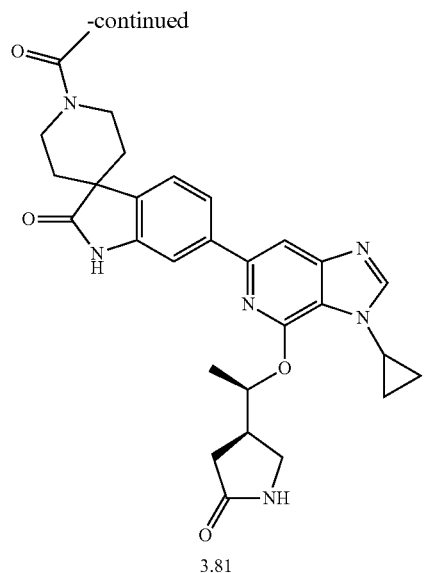

3.81

To solution of 6-(3-cyclopropyl-4-((R)-1-((R)-5-oxopyrrolidin-3-yl)ethoxy)-3H-imidazo[4,5-c]pyridin-6-yl)spiro[indoline-3,4'-piperidin]-2-one: 3.78 (0.1 g, 0.21 mmol) in DMF was added TEA (0.062 g, 0.62 mmol) followed by acetyl chloride (0.019 g, 0.25 mmol). Reaction mixture was stirred at r.t. for 20 min, and LCMS showed reaction was complete. The reaction mixture was purified by prep HPLC (MeCN:water gradient, TFA modified) to provide 6-(3-cyclopropyl-4-((R)-1-((R)-5-oxopyrrolidin-3-yl)ethoxy)-3H-imidazo[4,5-c]pyridin-6-yl)-1'-(2,2,2-trifluoroethyl)spiro[indoline-3,4'-piperidin]-2-one: 3.81 as its TFA salt.

$^1$H NMR (400 MHz, Methanol-d4) δ 8.86 (d, J=3.7 Hz, 1H), 7.68 (dt, J=7.8, 2.2 Hz, 1H), 7.64 (s, 1H), 7.58 (d, J=1.5 Hz, 1H), 7.39 (dd, J=7.9, 6.0 Hz, 1H), 5.72 (p, J=6.1 Hz, 1H), 4.11-3.89 (m, 2H), 3.89-3.68 (m, 4H), 3.54 (dd, J=10.1, 8.7 Hz, 1H), 3.31 (dd, J=10.1, 5.9 Hz, 1H), 2.99-2.87 (m, 2H), 2.58-2.41 (m, 2H), 2.18 (s, 1H), 2.10 (s, 2H), 1.92-1.69 (m, 4H), 1.44 (d, J=6.2 Hz, 3H), 1.18 (m, J=8.8, 6.2, 3.9 Hz, 4H).

LCMS-ESI$^+$ (m/z): [M+H]$^+$ calcd for $C_{30}H_{34}N_6O_4$: 529.25; found 529.21.

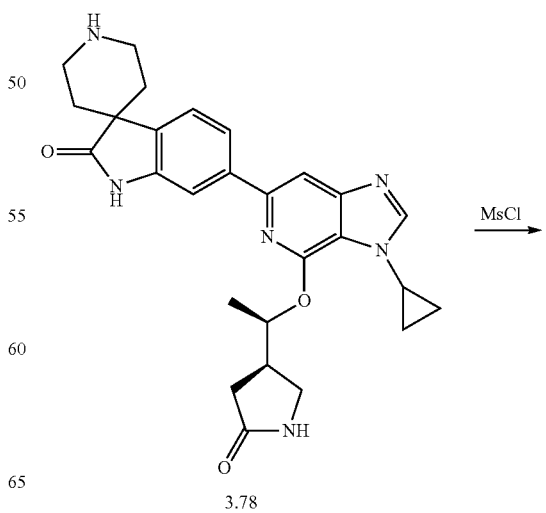

3.78

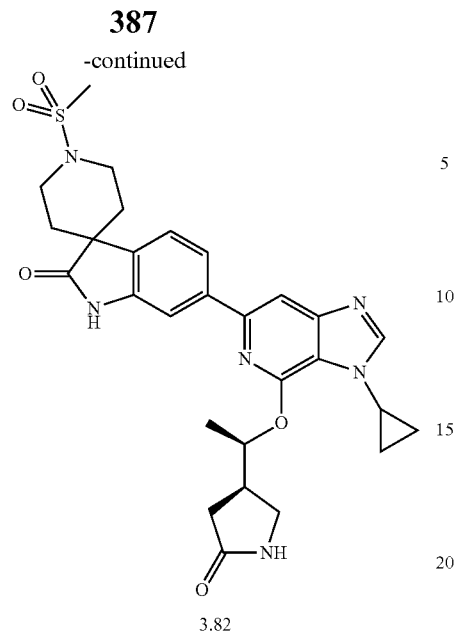

3.82

Preparation 6-(3-cyclopropyl-4-((R)-1-((R)-5-oxopyrrolidin-3-yl)ethoxy)-3H-imidazo[4,5-c]pyridin-6-yl)-1'-(methylsulfonyl)spiro[indoline-3,4'-piperidin]-2-one:

To solution of 6-(3-cyclopropyl-4-((R)-1-((R)-5-oxopyrrolidin-3-yl)ethoxy)-3H-imidazo[4,5-c]pyridin-6-yl)spiro[indoline-3,4'-piperidin]-2-one: (0.094 g, 0.193 mmol) in DMF was added TEA (0.119 g, 1 mmol), then followed by the addition of methanesulfonyl chloride (0.022 g, 0.193 mmol). Reaction was stirred at 0° C. for 10 minutes; LC-MS showed reaction was complete. TFA was added, and the crude material was purified by HPLC.

1H NMR (400 MHz, Methanol-d4) δ 8.95 (s, 1H), 8.55-8.33 (m, 1H), 7.78 (dd, J=7.9, 1.6 Hz, 1H), 7.76-7.66 (m, 2H), 7.48 (d, J=7.9 Hz, 1H), 7.40 (s, 1H), 5.89-5.72 (m, 1H), 4.27-3.99 (m, 1H), 4.00-3.82 (m, 1H), 3.80-3.53 (m, 6H), 2.95 (s, 4H), 2.72-2.44 (m, 3H), 2.16-1.85 (m, 3H), 1.54 (d, J=6.2 Hz, 3H), 1.44 (d, J=6.2 Hz, 2H), 1.37-1.10 (m, 9H). LCMS-ESI$^+$ (m/z): [M+H]$^+$ calcd. for $C_{26}H_{30}N_5O_3$: 565.66; found: 565.22.

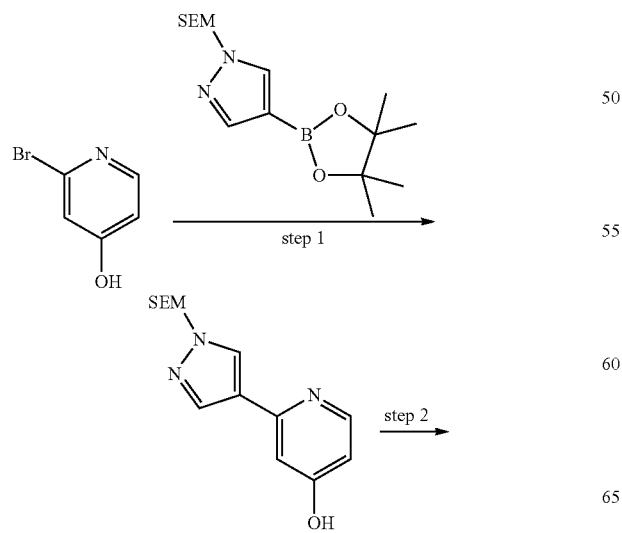

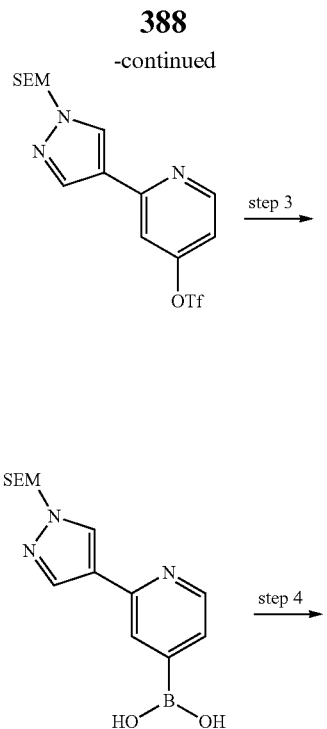

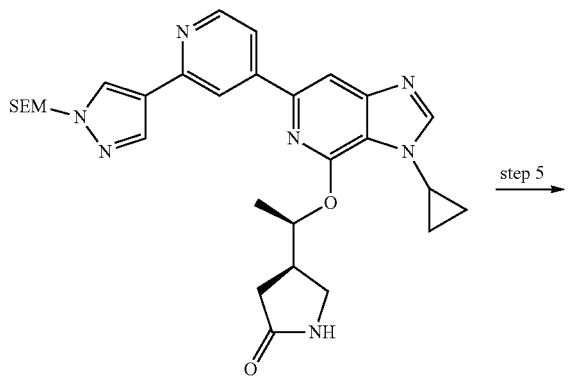

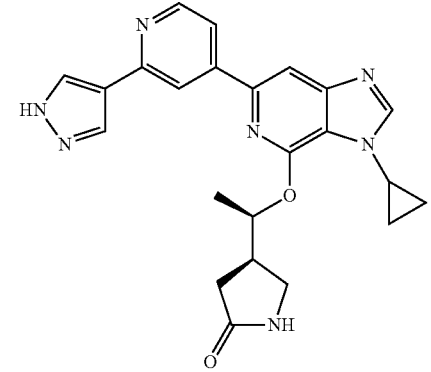

(R)-4-((R)-1-((6-(2-(1H-pyrazol-4-yl)pyridin-4-yl)-3-cyclopropyl-3H-imidazo[4,5-c]pyridin-4-yl)oxy)ethyl)pyrrolidin-2-one Step 1: To solution of 2-bromopyridin-4-ol (0.4 g, 2 mmol) and 4-(4,4,5,5-tetramethyl-1,3,2-dioxaborolan-2-yl)-1-((2-(trimethylsilyl)ethoxy)methyl)-1H-pyrazole (0.99 g, 3 mmol) in Dioxane/H2O (3 ml/1.5 ml) was added PEPSI-IPr catalyst (0.078 g, 0.115 mmol) and followed by the addition of $Cs_2CO_3$ (1.65 g, 5 mmol). The reaction mixture was stirred at 90° C. for 30 minutes. The reaction mixture was diluted with EtOAc and washed with HCl (1N). Two phases were separated and the aqueous phase was extracted with EtOAc (3×). Organic phase were combined and concentrated down under vacuo. The residue was purified by silicone gel column. And 2-(1-((2-(trimethylsilyl)ethoxy)methyl)-1H-pyrazol-4-yl)pyridin-4-ol was obtained (0.61 g, 91.1%). LCMS-ESI⁺ (m/z): [M+H]⁺ calcd. for $C_{26}H_{30}N_5O_3$: 292.42; found: 292.11.

Step 2: To solution of 2-(1-((2-(trimethylsilyl)ethoxy)methyl)-1H-pyrazol-4-yl)pyridin-4-ol (0.67 g, 2 mmol) in DCM was added TEA (0.69 g, 7 mmol) and the mixture was stirred at OC, $(Tf)_2O$ (0.843 g, 3 mmol) was added slowly. The resulting reaction mixture was steered at r.t. for one hour. Solvent was removed under vacuo. And the residue was purified by silicone gel column to afford 2414(2-(trimethylsilyl)ethoxy)methyl)-1H-pyrazol-4-yl)pyridin-4-yl trifluoromethanesulfonate (0.56 g, 58%) LCMS-ESI⁺ (m/z): [M+H]⁺ calcd. for $C_{26}H_{30}N_5O_3$: 424.48; found: 424.05.

Step 3: To a solution of 2-(1-((2-(trimethylsilyl)ethoxy)methyl)-1H-pyrazol-4-yl)pyridin-4-yl trifluoromethanesulfonate (0.14 g, 0.3 mmol) in dioxane was added dppf (0.0184 g, 0.033 mmol), $Pd(dppf)_2Cl_2$ (0.013 g, 0.017 mmol), Bis(pinacolato)Diboron (0.125 g, 0.496 mmol) and KOAc (0.064 g, 0.66 mmol). The resulting mixture was stirred at 90° C. for 90 minutes. LC-MS showed complete conversion. The reaction mixture was filtered through celite and washed with EtOAc, The solvent was removed, the residue taken up in DME, and used directly to next step. LCMS-ESI⁺ (m/z): [M+H]⁺ calcd. for $C_{26}H_{30}N_5O_3$: 320.24; found: 320.22

Step 4: To solution of (R)-4-((R)-1-((6-bromo-3-cyclopropyl-3H-imidazo[4,5-c]pyridin-4-yl)oxy)ethyl)pyrrolidin-2-one: (0.12 g, 0.33 mmol) and (2-(1-((2-(trimethylsilyl)ethoxy)methyl)-1H-pyrazol-4-yl)pyridin-4-yl)boronic acid (0.105 g, 0.33 mmol) in Dioxane/H2O (3 ml/1.5 ml) was added PEPSI-IPr catalyst (0.011 g, 0.016 mmol) and followed by the addition of $Cs_2CO_3$ (0.21 g, 0.66 mmol). The reaction mixture was stirred at 90° C. for 60 minutes. The reaction mixture was concentrated down under vacuo. The residue was used directly to next step. LCMS-ESI⁺ (m/z): [M+H]⁺ calcd. for $C_{26}H_{30}N_5O_3$: 560.73; found: 560.31

Step 5: the crude material (R)-4-((R)-1-((3-cyclopropyl-6-(2-(1-((2-(trimethylsilyl)ethoxy)methyl)-1H-pyrazol-4-yl)pyridin-4-yl)-3H-imidazo[4,5-c]pyridin-4-yl)oxy)ethyl)pyrrolidin-2-one: was treated with TFA at rt for 30 minute. LC-MS showed reaction was complete. Reaction mixture was stripped off and purified by HPLC to afford title compound.

1H NMR (400 MHz, Methanol-d4) δ 8.89-8.84 (m, 1H), 8.63 (d, J=6.4 Hz, 1H), 8.54 (s, 2H), 8.51 (dd, J=6.5, 1.8 Hz, 1H), 8.45 (s, 1H), 8.35 (s, 1H), 5.85 (t, J=5.9 Hz, 1H), 3.93-3.76 (m, 1H), 3.65 (d, J=1.0 Hz, 8H), 3.43 (dd, J=10.1, 5.8 Hz, 1H), 3.04 (q, J=7.1 Hz, 1H), 2.76-2.44 (m, 2H), 1.56 (dd, J=6.3, 1.0 Hz, 3H), 1.24 (tq, J=6.5, 3.0 Hz, 4H). LCMS-ESI⁺ (m/z): [M+H]⁺ calcd. for $C_{26}H_{30}N_5O_3$: 430.47; found: 430.21.

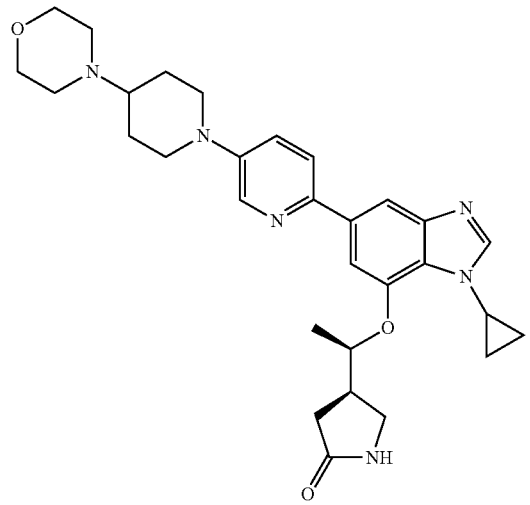 [SMILES: C[C@@H](Oc1cc(-c2ccc(N3CCC(N4CCOCC4)CC3)cn2)cc2ncn(C3CC3)c12)[C@H]1CNC(=O)C1]

Preparation of (R)-4-((R)-1-((1-cyclopropyl-5-(5-(4-morpholinopiperidin-1-yl)pyridin-2-yl)-1H-benzo[d]imidazol-7-yl)oxy)ethyl)pyrrolidin-2-one Following general procedure, starting from (R)-4-((R)-1-((1-cyclopropyl-5-(4,4,5,5-tetramethyl-1,3-dioxolan-2-yl)-1H-benzo[d]imidazol-7-yl)oxy)ethyl)pyrrolidin-2-one (25 mg) and 4-(1-(6-bromopyridin-3-yl)piperidin-4-yl)morpholine (24 mg), 20 mg of (R)-4-((R)-1-((1-cyclopropyl-5-(5-(4-morpholinopiperidin-1-yl)pyridin-2-yl)-1H-benzo[d]imidazol-7-yl)oxy)ethyl)pyrrolidin-2-one: was synthesized.

LCMS [M+H]⁺: 531.41.

1H NMR (400 MHz, DMSO-d) δ 8.77 (s, 1H), 8.75 (s, 1H), 8.18 (d, J=9.6 Hz, 1H), 7.97 (s, 1H), 7.92 (d, J=9.6 Hz, 1H), 7.79 (s, 1H), 5.18 (m. 1H), 4.22 (m, 1H), 4.18 (m, 6H), 4.02 (m, 6H), 3.77 (m, 1H), 3.22 (m, 2H), 3.08 (m, 1H), 2.69 (m, 2H), 2.43 (m, 2H), 2.19 (m, 2H), 1.56 (d, J=6.2 Hz, 3H), 1.2 (m, 4H).

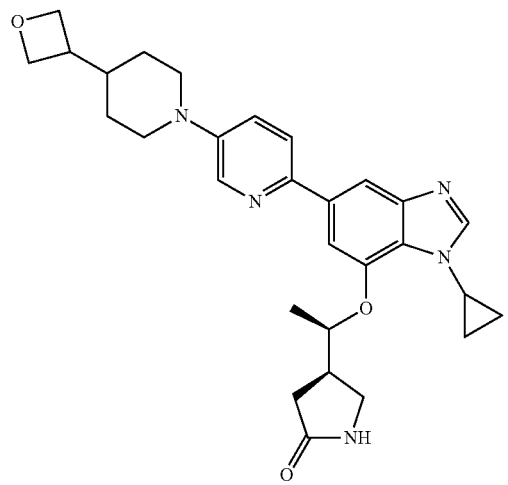 [SMILES: C[C@@H](Oc1cc(-c2ccc(N3CCC(C4COC4)CC3)cn2)cc2ncn(C3CC3)c12)[C@H]1CNC(=O)C1]

Preparation of (R)-4-((R)-1-((1-cyclopropyl-5-(5-(4-(oxetan-3-yl)piperidin-1-yl)pyridin-2-yl)-1H-benzo[d]imidazol-7-yl)oxy)ethyl)pyrrolidin-2-one Following general procedure, starting from (R)-4-((R)-1-((1-cyclopropyl-5-(4,4,5,5-tetramethyl-1,3-dioxolan-2-yl)-1H-benzo[d]imidazol-7-yl)oxy)ethyl)pyrrolidin-2-one (25 mg) and 2-bromo-5-(4-(oxetan-3-yl)piperidin-1-yl)pyridine (22 mg), 25 mg of (R)-4-((R)-1-((1-cyclopropyl-5-(5-(4-(oxetan-3-yl)piperidin-1-yl)pyridin-2-yl)-1H-benzo[d]imidazol-7-yl)oxy)ethyl)pyrrolidin-2-one: was synthesized.

LCMS [M+H]+: 502.45.

1H NMR (400 MHz, CD₃Cl) δ 8.77 (s, 1H), 8.82 (d, J=2.8 Hz, 1H), 8.63 (s, 1H), 8.01 (d, J=9.6 Hz, 1H), 7.95 (s, 1H), 7.86 (s, 1H), 6.64 (d, d, J=2.8 Hz, J=9.6 Hz, 1H), 6.54 (s, 1H), 5.24 (m. 1H), 4.81 (m, 2H), 4.51 (m, 2H), 3.95 (m, 1H), 3.85 (m, 1H), 3.69 (m, 1H), 3.44 (m, 2H), 3.06 (m, 2H), 2.95 (m, 2H), 2.8 (m, 1H), 2.62 (m, 2H), 2.01 (m, 1H), 1.84 (m, 2H), 1.46 (d, J=6.2 Hz, 3H), 1.3-1.05 (m, 4H).

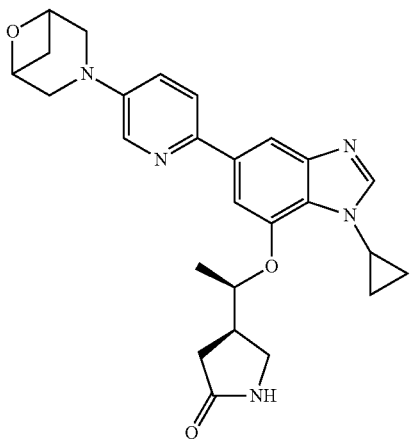 [SMILES: C[C@@H](Oc1cc(-c2ccc(N3CC4CC(C3)O4)cn2)cc2ncn(C3CC3)c12)[C@H]1CNC(=O)C1]

Preparation of (4R)-4-((1R)-1-(5-(5-(6-oxa-3-azabicyclo[3.1.1]heptan-3-yl)pyridin-2-yl)-1-cyclopropyl-1H-benzo[d]imidazol-7-yl)oxy)ethyl)pyrrolidin-2-one Following general procedure, starting from (R)-4-((R)-1-((1-cyclopropyl-5-(4,4,5,5-tetramethyl-1,3-dioxolan-2-yl)-1H-benzo[d]imidazol-7-yl)oxy)ethyl)pyrrolidin-2-one: (50 mg) and 3-(6-bromopyridin-3-yl)-6-oxa-3-azabicyclo[3.1.1]heptane (34 mg), 34 mg of (4R)-4-((1R)-1-(5-(5-(6-oxa-3-azabicyclo[3.1.1]heptan-3-yl)pyridin-2-yl)-1-cyclopropyl-1H-benzo[d]imidazol-7-yl)oxy)ethyl)pyrrolidin-2-one: was synthesized.

LCMS [M+H]+: 460.27.

1H NMR (400 MHz, CD₃Cl) δ 8.83 (d, J=3.0 Hz, 1H), 8.60 (s, 1H), 8.07 (d, J=9.2 Hz, 1H), 7.95 (d, J=1.3 Hz, 1H), 7.88 (s, 1H), 7.63 (dd, J=9.3, 2.9 Hz, 1H), 6.39 (s, 1H), 5.26 (s, 1H), 4.86 (d, J=6.4 Hz, 2H), 3.87-3.76 (m, 3H), 3.72-3.64 (m, 3H), 3.48-3.37 (m, 2H), 2.95 (m, 1H), 2.69-2.57 (m, 2H), 2.01 (d, J=9.1 Hz, 1H), 1.48 (d, J=6.1 Hz, 3H), 1.35-1.24 (m, 4H).

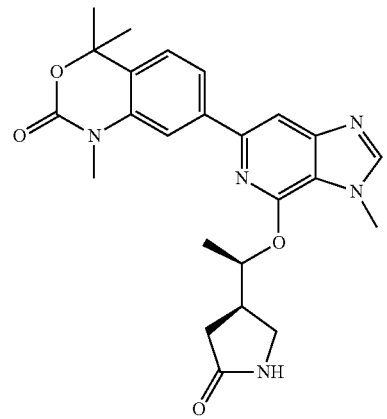 [SMILES: C[C@@H](Oc1nc(-c2ccc3c(c2)N(C)C(=O)OC3(C)C)cc2ncn(C)c12)[C@H]1CNC(=O)C1]

Preparation of 1,4,4-trimethyl-7-(3-methyl-4-((R)-1-((R)-5-oxopyrrolidin-3-yl)ethoxy)-3H-imidazo[4,5-c]pyridin-6-yl)-1H-benzo[d][1,3]oxazin-2(4H)-one Following general procedure A, starting from (R)-4-((R)-1-((6-chloro-3-methyl-3H-imidazo[4,5-c]pyridin-4-yl)oxy)ethyl)pyrrolidin-2-one: (63 mg), and 1,4,4-trimethyl-7-(4,4,5,5-tetramethyl-1,3,2-dioxaborolan-2-yl)-1H-benzo[d][1,3]oxazin-2(4H)-one (67 mg), 55 mg of 1,4,4-trimethyl-7-(3-methyl-4-4R)-1-((R)-5-oxopyrrolidin-3-yl)ethoxy)-3H-imidazo[4,5-c]pyridin-6-yl)-1H-benzo[d][1,3]oxazin-2(4H)-one was synthesized.

LCMS [M+H]+: 450.29.

1H NMR (400 MHz, Chloroform-d) δ 7.98 (s, 1H), 7.77-7.67 (m, 2H), 7.61 (d, J=1.6 Hz, 1H), 7.24 (s, 1H), 5.74 (m, 1H), 5.59 (s, 1H), 4.1 (s, 3H), 3.69-3.55 (m, 2H), 3.51 (s, 3H), 3.42 (m, 1H), 2.61-2.51 (m, 2H), 1.72 (s, 6H), 1.53 (d, J=6.2 Hz, 3H).

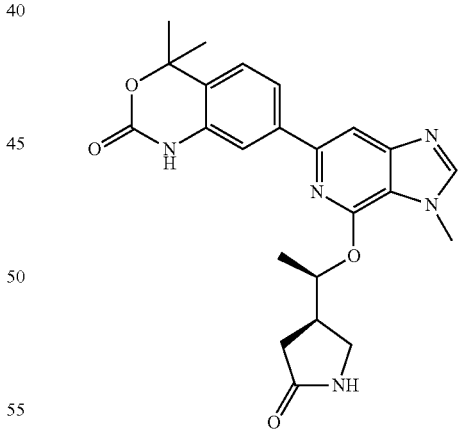

Preparation of 4,4-dimethyl-7-(3-methyl-4-4R)-1-((R)-5-oxopyrrolidin-3-yl)ethoxy)-3H-imidazo[4,5-c]pyridin-6-yl)-1H-benzo[d][1,3]oxazin-2(4H)-one Following general procedure A, starting from (R)-4-((R)-1-((6-chloro-3-methyl-3H-imidazo[4,5-c]pyridin-4-yl)oxy)ethyl)pyrrolidin-2-one: (41 mg), and 4,4-dimethyl-7-(4,4,5,5-tetramethyl-1,3,2-dioxaborolan-2-yl)-1H-benzo[d][1,3]oxazin-2(4H)-one (46 mg), 35 mg of 4,4-dimethyl-7-(3- methyl-4-4R)-1-((R)-5-oxopyrrolidin-3-yl)ethoxy)-3H-imidazo[4,5-c]pyridin-6-yl)-1H-benzo[d][1,3]oxazin-2(4H)-one was synthesized.

LCMS [M+H]+: 436.41.

1H NMR (400 MHz, Methanol-d4) δ 8.61 (s, 1H), 7.78 (m, 2H), 7.59 (s, 1H), 7.13 (d, J=8.4 Hz, 1H), 6.6 (m, 1H), 6.24 (m, 1H), 5.7 (m, 1H), 4.1 (s, 3H), 3.81 (m, 1H), 3.55 (m, 1H), 3.33 (m, 1H), 2.49 (m, 2H), 1.63 (s, 6H), 1.44 (d, J=6 Hz, 3H).

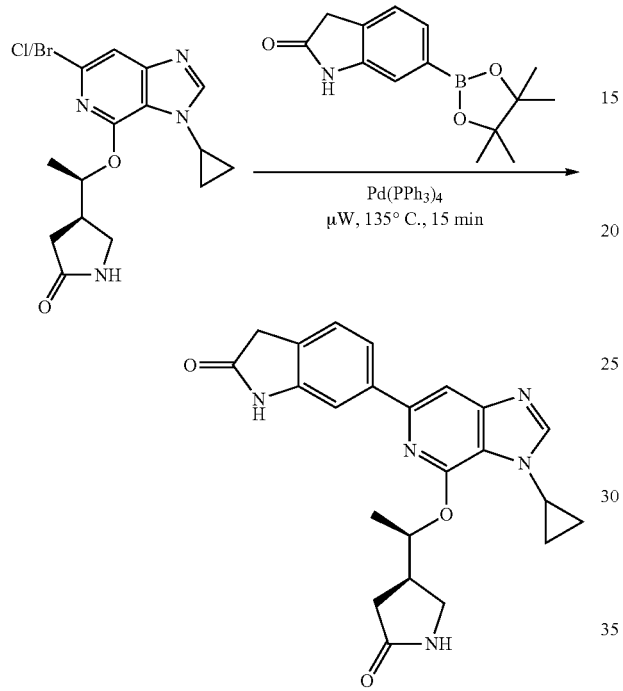

Preparation of 6-(3-cyclopropyl-4-((R)-1-((R)-5-oxopyrrolidin-3-yl)ethoxy)-3H-imidazo[4,5-c]pyridin-6-yl)indolin-2-one: In a microwave reaction vessel were placed a mixture of (R)-4-((R)-1-((6-chloro-3-cyclopropyl-3H-imidazo[4,5-c]pyridin-4-yl)oxy)ethyl)pyrrolidin-2-one: and (R)-4-((R)-1-((6-bromo-3-cyclopropyl-3H-imidazo[4,5-c]pyridin-4-yl)oxy)ethyl)pyrrolidin-2-one: (50.0 mg, 0.14 mmol), 6-(4,4,5,5-tetramethyl-1,3,2-dioxaborolan-2-yl)indolin-2-one: (141.9 mg, 0.55 mmol), and Pd(PPh3)4 (11.1 mg, 0.010 mmol) in dioxane (1 ml) and 2N Na2CO3 (1 ml). The mixture was sonicated for 15 sec. and degassed with nitrogen gas for 30 sec. Then it was placed in the microwave reactor at 135° C. for 15 min. The reaction mixture was directly loaded onto the pre-packed silica cartridge, and purified by flash chromatography (100% dichloromethane to 25% MeOH in dichloromethane). The fractions were collected, concentrated, and further purified by reverse phase chromatography. The fractions were collected, neutralized with sat. NaHCO3, and extracted with EtOAc. The combined organic layers were washed with water and brine, dried (Na2SO4), filtered, and concentrated to give 17 mg (30%) of 6-(3-cyclopropyl-4-((R)-1-((R)-5-oxopyrrolidin-3-yl)ethoxy)-3H-imidazo[4,5-c]pyridin-6-yl)indolin-2-one:. 1H NMR (300 MHz, d6-DMSO) δ 10.42 (s, 1H), 8.29 (s, 1H), 7.70 (s, 1H), 7.64 (m, 3H), 7.26 (d, J=8.0 Hz, 1H), 5.55 (m, 1H), 3.72 (m, 1H), 3.45 (m, 3H), 3.24 (m, 1H), 2.86 (m, 1H), 2.48 (m, 2H), 1.43 (d, J=6.4 Hz, 3H), 1.11 (m, 4H). MS (ESI+) m/z 418.1 (M+H).

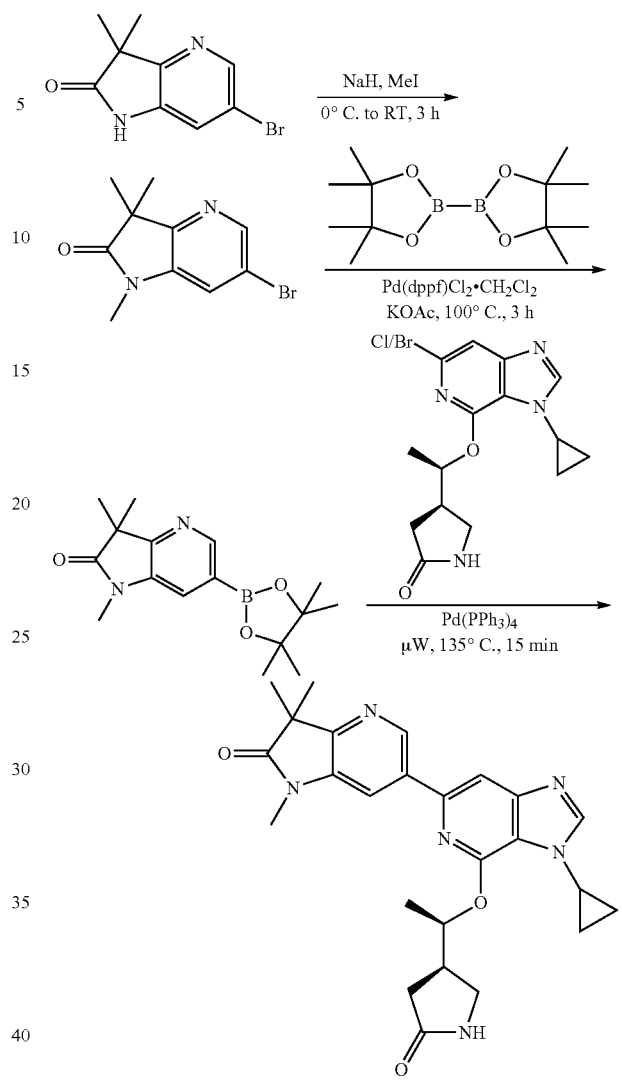

Preparation of 6-bromo-1,3,3-trimethyl-1H-pyrrolo[3,2-b]pyridin-2(3H)-one: In a 25-mL, round-bottomed, single-necked flask was placed 6-bromo-3,3-dimethyl-1H-pyrrolo[3,2-b]pyridin-2(3H)-one (500 mg, 2.07 mmol) in DMF (5 mL). The mixture was cooled to 0° C. followed by an addition of NaH (60%, 99.55 mg, 2.49 mmol). The reaction mixture was stirred at 0° C. for 20 min. To this was added MeI (0.39 ml, 6.22 mmol) at 0° C. Then, it was slowly warmed to room temperature and stirred for 3 h. The reaction mixture was quenched with sat. NH4Cl (5 mL) and the organic layers were extracted with EtOAc (3×5 mL). The combined organic layers were washed with water (2×5 mL) and brine (1×5 mL), dried (Na2SO4), concentrated, and purified by flash chromatography (100% Hexane to 100% EtOAc) to give 455 mg (86%) of 6-bromo-1,3,3-trimethyl-1H-pyrrolo[3,2-b]pyridin-2(3H)-one.

Preparation of 1,3,3-trimethyl-6-(4,4,5,5-tetramethyl-1,3,2-dioxaborolan-2-yl)-1H-pyrrolo[3,2-b]pyridin-2(3H)-one: Prepared by the procedure, previously described for the synthesis of Example 7.17, using instead 6-bromo-1,3,3-trimethyl-1H-pyrrolo[3,2-b]pyridin-2(3H)-one (130 mg, 0.51 mmol) as a starting material to afford 1,3,3-trimethyl-6-(4,4,5,5-tetramethyl-1,3,2-dioxaborolan-2-yl)-1H-pyrrolo[3,2-b]pyridin-2(3H)-one (125 mg, ca. 90% purity), which was used in the next step without further purification.

Preparation of 6-(3-cyclopropyl-4-((R)-1-((R)-5-oxopyrrolidin-3-yl)ethoxy)-3H-imidazo[4,5-c]pyridin-6-yl)-1,3,3-trimethyl-1H-pyrrolo[3,2-b]pyridin-2(3H)-one Prepared by Suzuki coupling reaction procedure, as previously described for the synthesis of 6-(3-cyclopropyl-4-((R)-1-((R)-5-oxopyrrolidin-3-yl)ethoxy)-3H-imidazo[4,5-c]pyridin-6-yl)indolin-2-one:, using instead 1,3,3-trimethyl-6-(4,4,5,5-tetramethyl-1,3,2-dioxaborolan-2-yl)-1H-pyrrolo[3,2-b]pyridin-2(3H)-one as a starting material to afford 27.2 mg (43%) of 6-(3-cyclopropyl-4-((R)-1-((R)-5-oxopyrrolidin-3-yl)ethoxy)-3H-imidazo[4,5-c]pyridin-6-yl)-1,3,3-trimethyl-1H-pyrrolo[3,2-b]pyridin-2(3H)-one. $^1$H NMR (300 MHz, d$_6$-DMSO) δ 8.92 (d, J=1.8 Hz, 1H), 8.33 (s, 1H), 7.99 (m, 2H), 7.58 (s, 1H), 5.60 (m, 1H), 3.72 (m, 1H), 3.42 (m, 1H), 3.26 (m, 4H), 2.86 (m, 1H), 2.48 (m, 2H), 1.31 (s, 6H), 1.43 (d, J=6.4 Hz, 3H), 1.11 (m, 4H). MS (ESI+) m/z 461.1 (M+H)

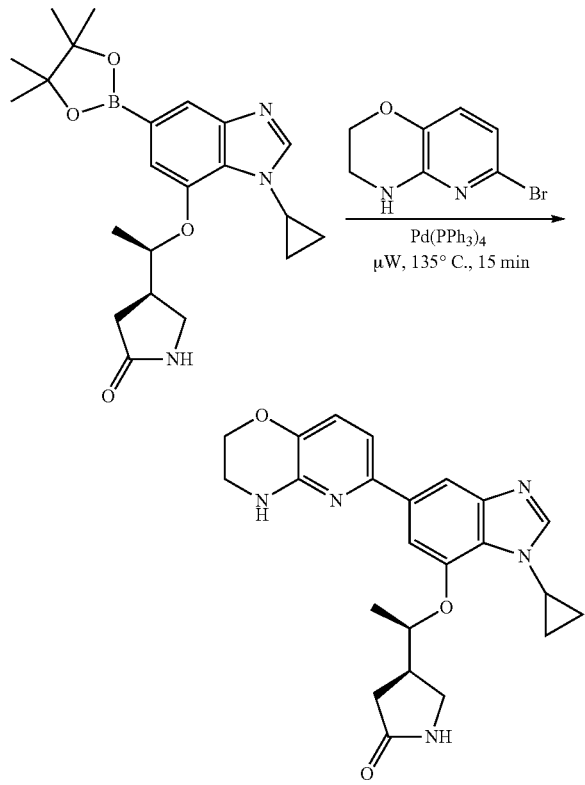

Preparation of (R)-4-((R)-1-((1-cyclopropyl-5-(3,4-dihydro-2H-pyrido[3,2-b][1,4]oxazin-6-yl)-1H-benzo[d]imidazol-7-yl)oxy)ethyl)pyrrolidin-2-one: In a 10 ml microwave reactor vial were placed (R)-4-((R)-1-((1-cyclopropyl-5-(4,4,5,5-tetramethyl-1,3,2-dioxaborolan-2-yl)-1H-benzo[d]imidazol-7-yl)oxy)ethyl)pyrrolidin-2-one: (150.0 mg, 0.36 mmol), 6-bromo-3,4-dihydro-2H-pyrido[3,2-b][1,4]oxazine (172.5 mg, 0.8 mmol), and Pd(PPh$_3$)$_4$ (21.1 mg, 0.02 mmol) in DME (1 ml) and 2N Na$_2$CO$_3$ (1 ml). The mixture was sonicated and degassed for 1 min, placed in the microwave reactor, and heated at 135° C. for 15 min. Then it was directly loaded onto the pre-packed silica cartridge and purified using flash chromatography (100% dichloromethane to 25% MeOH in dichloromethane). The fractions were collected, concentrated, and further purified by reverse phase flash chromatography. The fractions were collected, neutralized with sat. NaHCO$_3$, and extracted with EtOAc. The combined organic layers were washed with water and brine, dried (Na$_2$SO$_4$), filtered, and concentrated to give 52.7 mg (34%) of (R)-4-((R)-1-((1-cyclopropyl-5-(3,4-dihydro-2H-pyrido[3,2-b][1,4]oxazin-6-yl)-1H-benzo[d]imidazol-7-yl)oxy)ethyl)pyrrolidin-2-one:. $^1$H NMR (300 MHz, d$_6$-DMSO) δ 8.06 (s, 1H), 7.70 (d, J=1.5 Hz, 1H), 7.60 (s, 1H), 7.39 (m, 1H), 7.07 (d, J=8.1 Hz, 1H), 6.97 (d, J=8.4 Hz, 1H), 6.74 (s, 1H), 4.76 (m, 1H), 4.13 (m, 2H), 3.67 (m, 1H), 3.42 (m, 3H), 3.19 (m, 1H), 2.82 (m, 1H), 2.36 (m, 2H), 1.31 (d, J=5.8 Hz, 3H), 1.05 (m, 4H). MS (ESI+) m/z 420.2 (M+H).

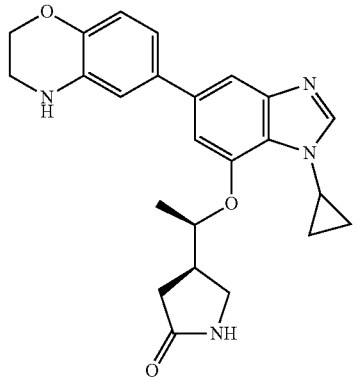 [SMILES: C[C@@H](Oc1cc(-c2ccc3c(c2)NCCO3)cc2ncn(C3CC3)c12)[C@H]1CNC(=O)C1]

Preparation of (R)-4-((R)-1-((1-cyclopropyl-5-(3,4-dihydro-2H-benzo[b][1,4]oxazin-6-yl)-1H-benzo[d]imidazol-7-yl)oxy)ethyl)pyrrolidin-2-one: Prepared by Suzuki coupling reaction procedure, as previously described for the synthesis of (R)-4-((R)-1-((1-cyclopropyl-5-(3,4-dihydro-2H-pyrido[3,2-b][1,4]oxazin-6-yl)-1H-benzo[d]imidazol-7-yl)oxy)ethyl)pyrrolidin-2-one:, using instead 6-bromo-3,4-dihydro-2H-benzo[b][1,4]oxazine as a starting material to afford 27.9 mg (18%) of (R)-4-((R)-1-((1-cyclopropyl-5-(3,4-dihydro-2H-benzo[b][1,4]oxazin-6-yl)-1H-benzo[d]imidazol-7-yl)oxy)ethyl)pyrrolidin-2-one:. $^1$H NMR (300 MHz, d$_6$-DMSO) δ 8.06 (s, 1H), 7.59 (s, 1H), 7.24 (m, 1H), 6.78 (m, 4H), 5.80 (s, 1H), 4.79 (m, 1H), 4.13 (m, 2H), 3.69 (m, 1H), 3.39 (m, 1H), 3.31 (m, 1H), 3.25 (m, 2H), 2.82 (m, 1H), 2.32 (m, 2H), 1.37 (d, J=6.4 Hz, 3H), 1.11 (m, 4H). MS (ESI+) m/z 419.2 (M+H)

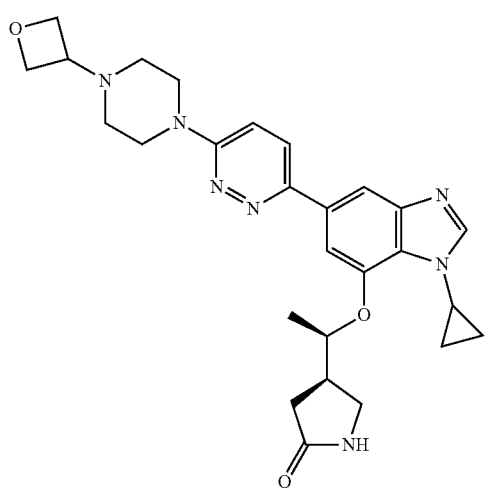 [SMILES: C[C@@H](Oc1cc(-c2ccc(N3CCN(C4COC4)CC3)nn2)cc2ncn(C3CC3)c12)[C@H]1CNC(=O)C1]

Preparation of (R)-4-((R)-1-((1-cyclopropyl-5-(6-(4-(oxetan-3-yl)piperazin-1-yl)pyridazin-3-yl)-1H-benzo[d]imidazol-7-yl)oxy)ethyl)pyrrolidin-2-one: Prepared by Suzuki coupling reaction procedure, as previously described for the synthesis of (R)-4-((R)-1-((1-cyclopropyl-5-(3,4-dihydro-2H-pyrido[3,2-b][1,4]oxazin-6-yl)-1H-benzo[d]imidazol-7-yl)oxy)ethyl)pyrrolidin-2-one:, using instead 3-bromo-6-(4-(oxetan-3-yl)piperazin-1-yl)pyridazine as a starting material to afford 52.7 mg (61%) of (R)-4-((R)-1-((1-cyclopropyl-5-(6-(4-(oxetan-3-yl)piperazin-1-yl)pyridazin-3-yl)-1H-benzo[d]imidazol-7-yl)oxy)ethyl)pyrrolidin-2-one:. $^1$H NMR (300 MHz, d$_6$-DMSO) δ 8.12 (s, 1H), 8.04 (d, J=9.9 Hz, 1H), 7.80 (d, J=1.1 Hz, 1H), 7.62 (m, 2H), 7.35 (d, J=9.9 Hz, 1H), 4.81 (m, 1H), 4.52 (m, 4H), 3.69 (m, 5H), 3.41 (m, 2H), 3.20 (m, 1H), 2.54 (m, 1H), 2.37 (m, 6H), 1.34 (d, J=6.3 Hz, 3H), 1.09 (m, 4H). MS (ESI+) m/z 504.3 (M+H).

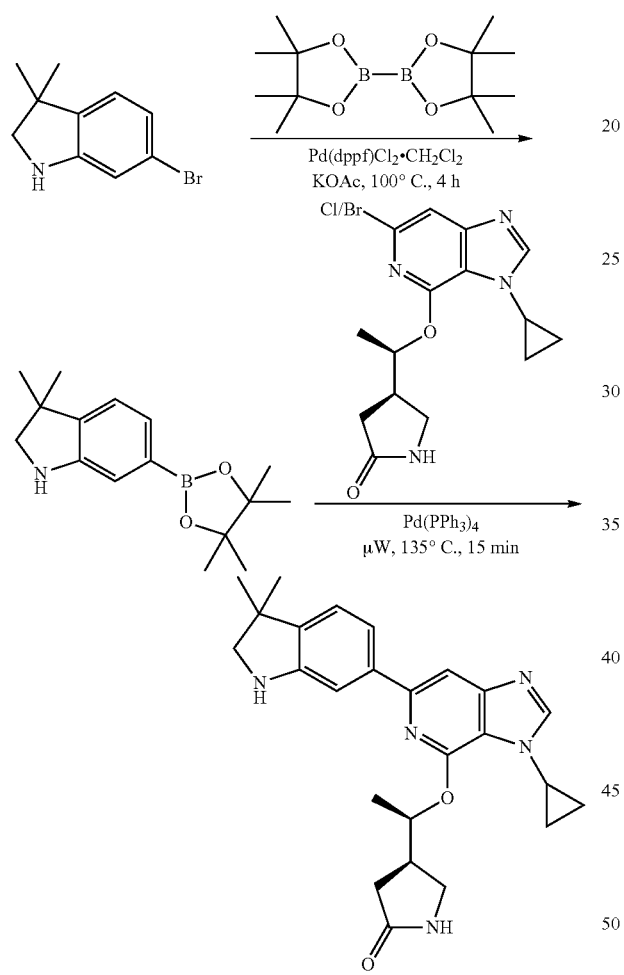

Preparation of 3,3-dimethyl-6-(4,4,5,5-tetramethyl-1,3,2-dioxaborolan-2-yl)indoline: Prepared by the procedure, previously described for the synthesis of Example 7.17, using instead 6-bromo-3,3-dimethylindoline (450.0 mg, 1.99 mmol) as a starting material to afford 330.0 mg (61%) of 3,3-dimethyl-6-(4,4,5,5-tetramethyl-1,3,2-dioxaborolan-2-yl)indoline.

Preparation of (R)-4-((R)-1-((3-cyclopropyl-6-(3,3-dimethylindolin-6-yl)-3H-imidazo[4,5-c]pyridin-4-yl)oxy)ethyl)pyrrolidin-2-one: Prepared by Suzuki coupling reaction procedure, as previously described for the synthesis of 6-(3-cyclopropyl-4-((R)-1-((R)-5-oxopyrrolidin-3-yl)ethoxy)-3H-imidazo[4,5-c]pyridin-6-yl)indolin-2-one:, using instead 3,3-dimethyl-6-(4,4,5,5-tetramethyl-1,3,2-di-oxaborolan-2-yl)indoline as a starting material to afford 22.0 mg (19%) of (R)-4-((R)-1-((3-cyclopropyl-6-(3,3-dimethylindolin-6-yl)-3H-imidazo[4,5-c]pyridin-4-yl)oxy)ethyl)pyrrolidin-2-one:. $^1$H NMR (300 MHz, d$_6$-DMSO) δ 8.24 (s, 1H), 7.56 (s, 2H), 7.25 (dd, J=7.7 Hz, J=1.4 Hz, 1H), 7.15 (d, J=1.5 Hz, 1H), 7.01 (d, J=7.7 Hz, 1H), 5.53 (m, 2H), 3.68 (m, 1H), 3.41 (m, 1H), 3.20 (m, 3H), 2.82 (m, 1H), 2.33 (m, 2H), 1.40 (d, J=6.2 Hz, 3H), 1.23 (s, 6H), 1.18 (m, 5H). MS (ESI+) m/z 432.2 (M+H).

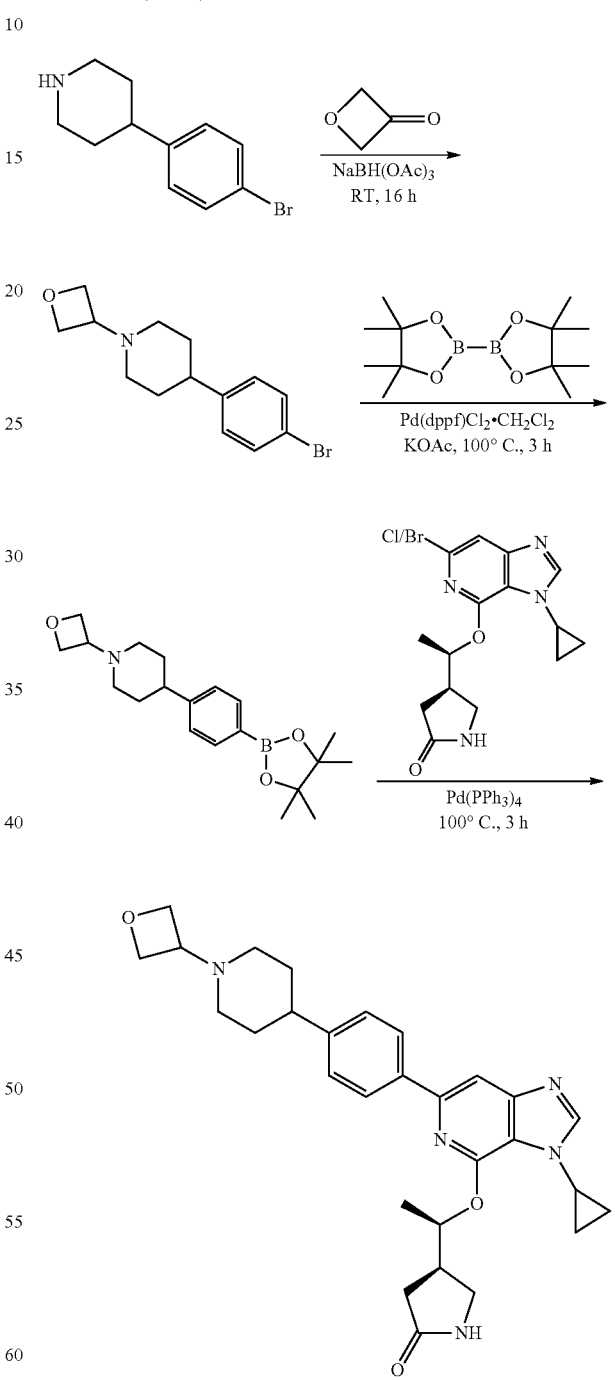

Preparation of 4-(4-bromophenyl)-1-(oxetan-3-yl)piperidine: In a round-bottomed, single-necked, 100-mL flask were placed 4-(4-bromophenyl)piperidine (500.0 mg, 2.08 mmol), N,N-diisopropylethylamine (0.36 mL, 2.08 mmol), 3-oxetanone (0.27 mL, 4.16 mmol), and sodium triacetoxyborohydride (1544.5 mg, 7.3 mmol) in THF (15 mL). The mixture was stirred at room temperature for 16 h. Then, it was quenched with water and the organic layers extracted with EtOAc (3×5 mL). The combined organic layers were washed with water (2×5 mL) and brine (1×5 mL), dried ($Na_2SO_4$), concentrated, and purified by flash chromatography (100% Hexane to 100% EtOAc) to give 350.0 mg (57%) of 4-(4-bromophenyl)-1-(oxetan-3-yl)piperidine.

Preparation of 1-(oxetan-3-yl)-4-(4-(4,4,5,5-tetramethyl-1,3,2-dioxaborolan-2-yl)phenyl)piperidine: Prepared by the procedure, previously described for the synthesis of Example 7.17, using instead 4-(4-bromophenyl)-1-(oxetan-3-yl)piperidine as a starting material to afford 110.0 mg (24%) of 1-(oxetan-3-yl)-4-(4-(4,4,5,5-tetramethyl-1,3,2-dioxaborolan-2-yl)phenyl)piperidine.

Preparation of (R)-4-((R)-1-((3-cyclopropyl-6-(4-(1-(oxetan-3-yl)piperidin-4-yl)phenyl)-3H-imidazo[4,5-c]pyridin-4-yl)oxy)ethyl)pyrrolidin-2-one: In a round-bottomed, 100-mL, single-necked flask equipped with a reflux condenser were placed a mixture of (R)-4-((R)-1-((6-chloro-3-cyclopropyl-3H-imidazo[4,5-c]pyridin-4-yl)oxy)ethyl)pyrrolidin-2-one: and (R)-4-((R)-1-((6-bromo-3-cyclopropyl-3H-imidazo[4,5-c]pyridin-4-yl)oxy)ethyl)pyrrolidin-2-one: (85.0 mg, 0.23 mmol), 1-(oxetan-3-yl)-4-(4-(4,4,5,5-tetramethyl-1,3,2-dioxaborolan-2-yl)phenyl)piperidine (103.9 mg, 0.30 mmol), and tetrakis(triphenylphosphine)palladium (10.3 mg, 0.010 mmol) in DME (3 mL) and 2N $Na_2CO_3$ (2 mL). The reaction mixture was sonicated for 30 sec, degassed with nitrogen gas for 30 sec, and heated at 100° C. for 3 h. Then, it was cooled to room temperature, quenched with water, and the organic layers extracted with EtOAc (3×5 mL). The combined organic layers were washed with water (2×5 mL) and brine (1×5 mL), dried ($Na_2SO_4$), concentrated, and purified by flash chromatography (100% dichloromethane to 25% MeOH in dichloromethane) to afford 55.9 mg (48%) of (R)-4-((R)-1-((3-cyclopropyl-6-(4-(1-(oxetan-3-yl)piperidin-4-yl)phenyl)-3H-imidazo[4,5-c]pyridin-4-yl)oxy)ethyl)pyrrolidin-2-one:. $^1$H NMR (300 MHz, $d_6$-DMSO) δ 8.28 (s, 1H), 8.00 (d, J=8.4 Hz, 2H), 7.74 (s, 1H), 7.57 (s, 1H), 7.34 (s, 1H), 5.57 (m, 1H), 4.50 (m, 4H), 3.71 (m, 1H), 3.42 (m, 2H), 3.21 (m, 1H), 2.82 (m, 3H), 2.51 (m, 1H), 2.32 (m, 2H), 1.79 (m, 6H), 1.41 (d, J=6.3 Hz, 3H), 1.18 (m, 4H). MS (ESI+) m/z 502.2 (M+H).

-continued

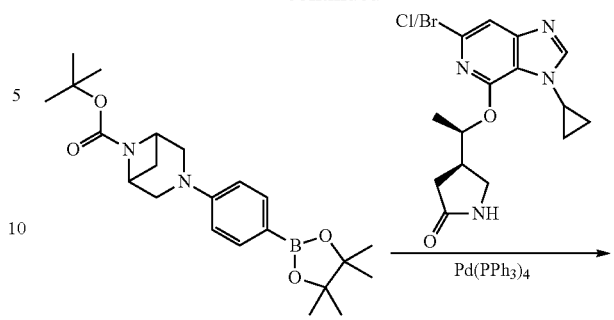

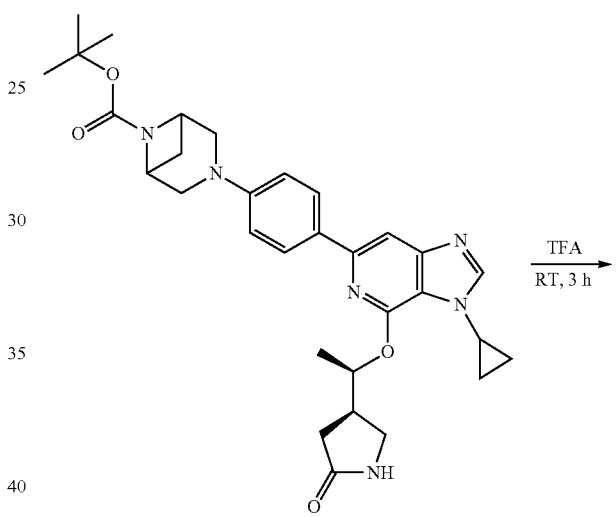

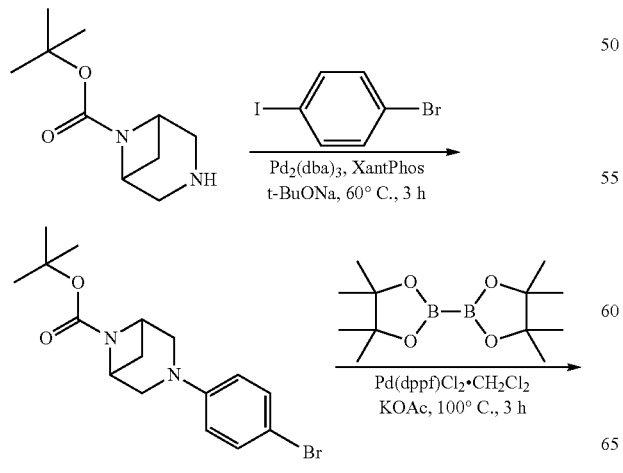

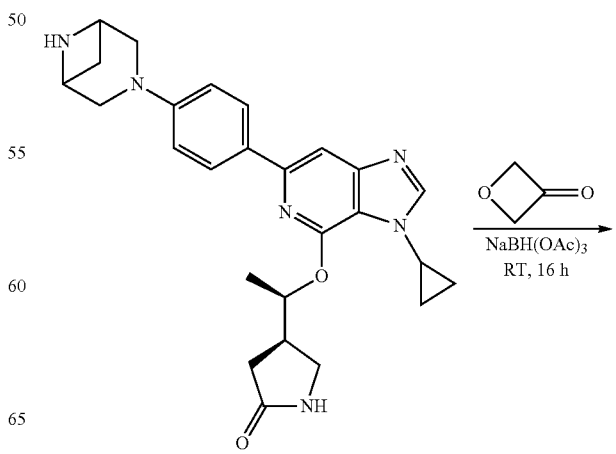

-continued

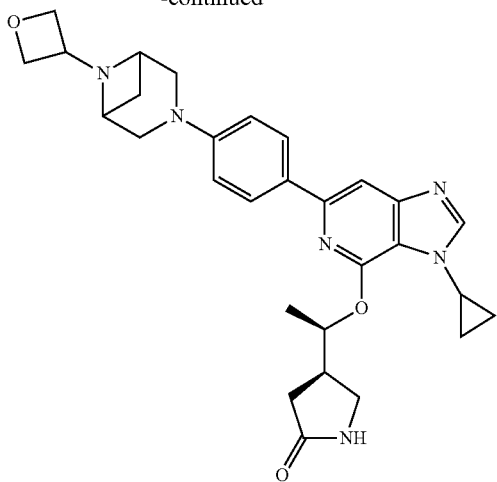

Preparation of tert-butyl 3-(4-bromophenyl)-3,6-diazabicyclo[3.1.1]heptane-6-carboxylate: In a 48 mL sealed tube were placed 1-bromo-4-iodobenzene (1498.3 mg, 5.30 mmol), tert-butyl 3,6-diazabicyclo[3.1.1]heptane-6-carboxylate (1000.0 mg, 5.04 mmol), $Pd_2(dba)_3$ (138.6 mg, 0.15 mmol), XantPhos (262.7 mg, 0.45 mmol), and sodium t-butoxide (1454.2 mg, 15.13 mmol) in toluene (36 ml). The reaction mixture was stirred at 60° C. for 3 h. Then it was cooled to room temperature. Then it was quenched with water and the organic layers were extracted with EtOAc (3×10 mL). The combined organic layers were washed with water (2×10 mL) and brine (1×10 mL), dried ($Na_2SO_4$), concentrated, and purified by flash chromatography (100% Hexane to 100% EtOAc) to give 500.0 mg (28%) of tert-butyl 3-(4-bromophenyl)-3,6-diazabicyclo[3.1.1]heptane-6-carboxylate.

Preparation of tert-butyl 3-(4-(4,4,5,5-tetramethyl-1,3,2-dioxaborolan-2-yl)phenyl)-3,6-diazabicyclo[3.1.1]heptane-6-carboxylate: Prepared by the procedure, previously described for the synthesis of Example 7.17, using instead tert-butyl 3-(4-bromophenyl)-3,6-diazabicyclo[3.1.1]heptane-6-carboxylate as a starting material to afford 566.6 mg (53%) of tert-butyl 3-(4-(4,4,5,5-tetramethyl-1,3,2-dioxaborolan-2-yl)phenyl)-3,6-diazabicyclo[3.1.1]heptane-6-carboxylate.

Preparation of tert-butyl 3-(4-(3-cyclopropyl-4-((R)-1-((R)-5-oxopyrrolidin-3-yl)ethoxy)-3H-imidazo[4,5-c]pyridin-6-yl)phenyl)-3,6-diazabicyclo[3.1.1]heptane-6-carboxylate: Prepared by Suzuki coupling reaction procedure, as previously described for the synthesis of (R)-4-((R)-1-((3-cyclopropyl-6-(4-(1-(oxetan-3-yl)piperidin-4-yl)phenyl)-3H-imidazo[4,5-c]pyridin-4-yl)oxy)ethyl)pyrrolidin-2-one:, using instead tert-butyl 3-(4-(4,4,5,5-tetramethyl-1,3,2-dioxaborolan-2-yl)phenyl)-3,6-diazabicyclo[3.1.1]heptane-6-carboxylate (289.4 mg, 0.72 mmol), and $Pd(PPh_3)_4$ (34.8 mg, 0.030 mmol) in DME (3 mL) and 2N $Na_2CO_3$ (2 mL). The reaction mixture was sonicated for 30 sec and degassed with nitrogen gas for 30 sec, and heated at 100 C for 1 h. Then it was cooled to room temperature, directly loaded on the prepacked silica cartridge, and purified by flash chromatography (100% dichloromethane to 25% MeOH in dichloromethane) to give 200.0 mg (59%) of tert-butyl 3-(4-(3-cyclopropyl-4-((R)-1-((R)-5-oxopyrrolidin-3-yl)ethoxy)-3H-imidazo[4,5-c]pyridin-6-yl)phenyl)-3,6-diazabicyclo[3.1.1]heptane-6-carboxylate.

Preparation of (4R)-4-((1R)-1-((6-(4-(3,6-diazabicyclo[3.1.1]heptan-3-yl)phenyl)-3-cyclopropyl-3H-imidazo[4,5-c]pyridin-4-yl)oxy)ethyl)pyrrolidin-2-one: In a round-bottomed, 100-mL, single-necked flask was placed tert-butyl 3-(4-(3-cyclopropyl-4-((R)-1-((R)-5-oxopyrrolidin-3-yl)ethoxy)-3H-imidazo[4,5-c]pyridin-6-yl)phenyl)-3,6-diazabicyclo[3.1.1]heptane-6-carboxylate (200.0 mg, 0.27 mmol) in dichloromethane (1 mL). To this was added trifluoroacetic acid (3.1 ml, 40.81 mmol). The mixture was stirred at room temperature for 3 h. Then, it was neutralized with sat. $NaHCO_3$ and the organic layers were extracted with dichloromethane (3×5 mL). The combined organic layers were washed with water (2×5 mL) and brine (1×5 mL), dried ($Na_2SO_4$), concentrated, and purified by flash chromatography (100% dichloromethane to 25% MeOH in dichloromethane) to give 124.8 mg (71%) of (4R)-4-((1R)-1-((6-(4-(3,6-diazabicyclo[3.1.1]heptan-3-yl)phenyl)-3-cyclopropyl-3H-imidazo[4,5-c]pyridin-4-yl)oxy)ethyl)pyrrolidin-2-one:. $^1$H NMR (300 MHz, $d_6$-DMSO) δ 8.22 (s, 1H), 7.98 (d, J=8.8 Hz, 2H), 7.61 (s, 1H), 7.57 (s, 1H), 6.78 (d, J=9.1 Hz, 2H), 5.57 (m, 1H), 3.57 (m, 8H), 2.84 (m, 2H), 2.57 (m, 1H), 2.39 (m, 3H), 1.53 (m, 1H), 1.41 (d, J=6.3 Hz, 3H), 1.18 (m, 4H). MS (ESI+) m/z 459.1 (M+H).

Preparation of (4R)-4-0R)-1-((3-cyclopropyl-6-(4-(6-(oxetan-3-yl)-3,6-diazabicyclo[3.1.1]heptan-3-yl)phenyl)-3H-imidazo[4,5-c]pyridin-4-yl)oxy)ethyl)pyrrolidin-2-one: Prepared by the procedure, previously described for the synthesis of 4-(4-bromophenyl)-1-(oxetan-3-yl)piperidine, using instead (4R)-4-((1R)-1-((6-(4-(3,6-diazabicyclo[3.1.1]heptan-3-yl)phenyl)- 3-cyclopropyl-3H-imidazo[4,5-c]pyridin-4-yl)oxy)ethyl)pyrrolidin-2-one: as a starting material to afford 10.1 mg (11%) of (4R)-4-((1R)-1-((3-cyclopropyl-6-(4-(6-(oxetan-3-yl)-3,6-diazabicyclo[3.1.1]heptan-3-yl)phenyl)-3H-imidazo[4,5-c]pyridin-4-yl)oxy)ethyl)pyrrolidin-2-one:. $^1$H NMR (300 MHz, $d_6$-DMSO) δ 8.22 (s, 1H), 7.98 (d, J=8.8 Hz, 2H), 7.61 (s, 1H), 7.57 (s, 1H), 6.78 (d, J=8.8 Hz, 2H), 5.57 (m, 1H), 4.57 (m, 2H), 4.27 (m, 2H), 3.78 (m, 4H), 3.42 (m, 1H), 3.22 (m, 2H), 2.84 (m, 1H), 2.34 (m, 3H), 1.53 (m, 1H), 1.41 (d, J=6.3 Hz, 3H), 1.18 (m, 7H). MS (ESI+) m/z 515.1 (M+H).

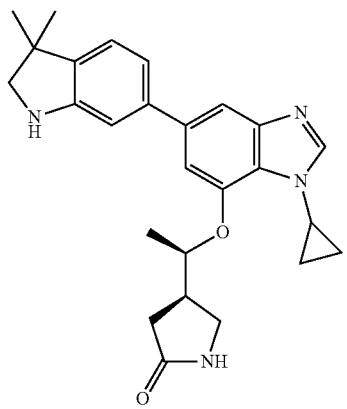 [SMILES: C[C@@H](Oc1cc(-c2ccc3c(c2)NCC3(C)C)cc2ncn(C3CC3)c12)[C@H]1CNC(=O)C1]

Preparation of (R)-4-((R)-1-((1-cyclopropyl-5-(3,3-dimethylindolin-6-yl)-1H-benzo[d]imidazol-7-yl)oxy)ethyl)pyrrolidin-2-one: In a microwave reactor vial were placed (R)-4-((R)-1-((1-cyclopropyl-5-(4,4,5,5-tetramethyl-1,3,2-dioxaborolan-2-yl)-1H-benzo[d]imidazol-7-yl)oxy)ethyl)pyrrolidin-2-one: (150.0 mg, 0.36 mmol), 6-bromo-3,4-dihydro-2H-pyrido[3,2-b][1,4]oxazine (172.5 mg, 0.80 mmol), and $Pd(PPh_3)_4$ (21.1 mg, 0.020 mmol) in DME (1 ml) and 2N $Na_2CO_3$ (1 ml). The reaction mixture was sonicated for 30 sec and degassed with nitrogen gas for 1 min, placed in the microwave reactor, and heated at 135° C. for 15 min. Then it was directly loaded onto the pre-packed silica cartridge and purified using flash chromatography (100% dichloromethane to 25% MeOH in dichloromethane). The fractions were collected and further purified by reverse phase flash chromatography. The fractions were collected, neutralized with sat. NaHCO$_3$, and the organic layers were extracted with EtOAc (3×10 mL). The combined organic layers were washed with water (2×5 mL) and brine (1×5 mL), dried (Na$_2$SO$_4$), filtered, and concentrated to give 52.7 mg (30%) of (R)-4-((R)-1-((1-cyclopropyl-5-(3,3-dimethylindolin-6-yl)-1H-benzo[d]imidazol-7-yl)oxy)ethyl)pyrrolidin-2-one:. $^1$H NMR (300 MHz, d$_6$-DMSO) δ 8.09 (s, 1H), 7.59 (s, 1H), 7.28 (s, 1H), 7.02 (d, J=7.6 Hz, 1H), 6.94 (s, 1H), 6.83 (m, 1H), 6.74 (m, 1H), 5.51 (s, 1H), 4.80 (m, 1H), 3.69 (m, 1H), 3.36 (m, 1H), 3.20 (m, 3H), 2.81 (m, 1H), 2.32 (m, 2H), 1.31 (d, J=6.2 Hz, 3H), 1.23 (s, 6H), 1.11 (m, 4H). MS (ESI+) m/z 431.2 (M+H).

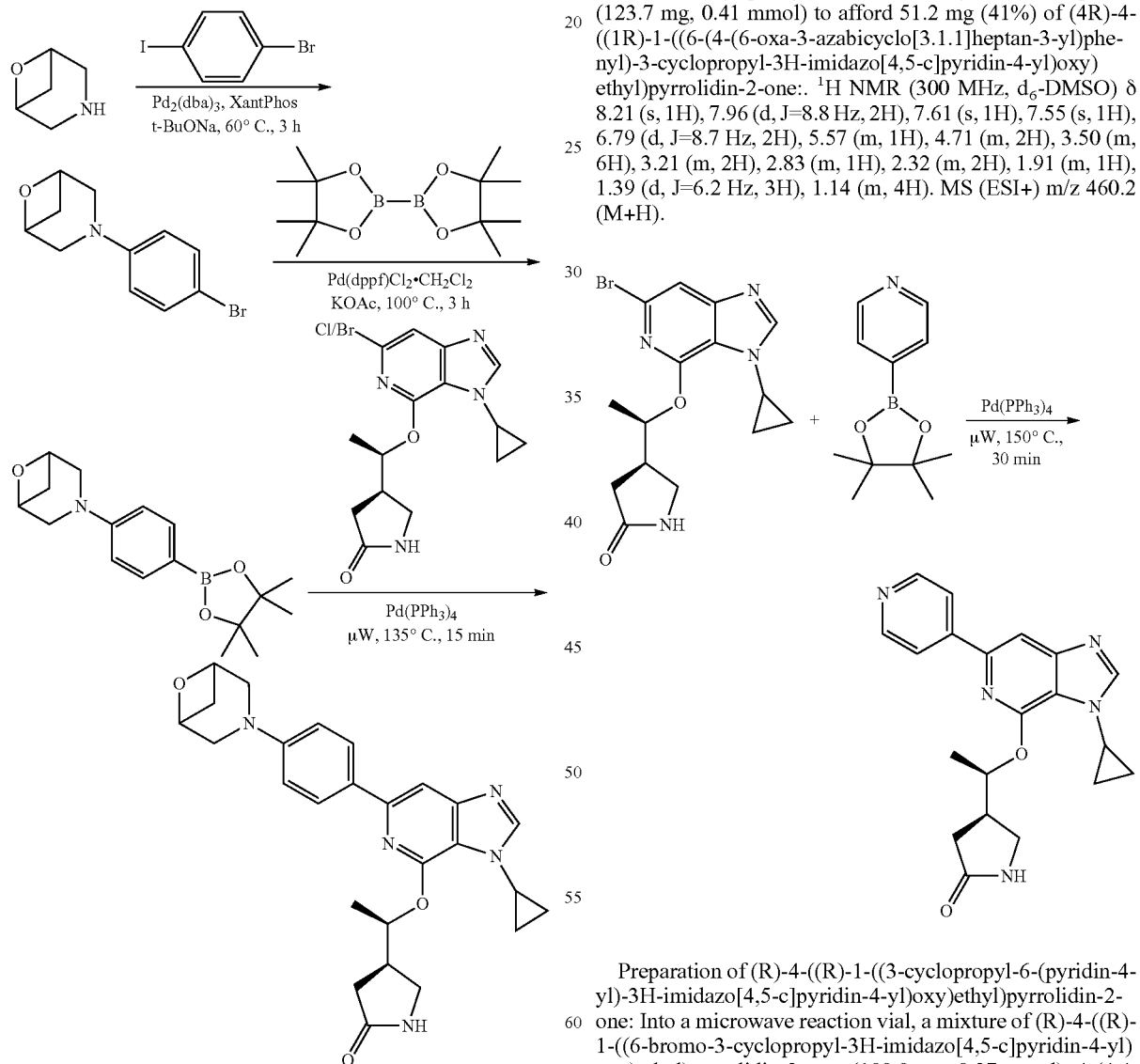

Preparation of 3-(4-bromophenyl)-6-oxa-3-azabicyclo[3.1.1]heptane: Prepared by the procedure, previously described for the synthesis of tert-butyl 3-(4-bromophenyl)-3,6-diazabicyclo[3.1.1]heptane-6-carboxylate, using instead 6-oxa-3-azabicyclo[3.1.1]heptane as a starting material to afford 570.0 mg (61%) of 3-(4-bromophenyl)-6-oxa-3-azabicyclo[3.1.1]heptane.

Preparation of 3-(4-(4,4,5,5-tetramethyl-1,3,2-dioxaborolan-2-yl)phenyl)-6-oxa-3-azabicyclo[3.1.1]heptane: Prepared by the procedure, previously described for the synthesis of Example 7.17, using instead 3-(4-bromophenyl)-6-oxa-3-azabicyclo[3.1.1]heptane as a starting material to afford 245.0 mg (65%) of. 3-(4-(4,4,5,5-tetramethyl-1,3,2-dioxaborolan-2-yl)phenyl)-6-oxa-3-azabicyclo[3.1.1]heptane.

Preparation of (4R)-4-((1R)-1-((6-(4-(6-oxa-3-azabicyclo[3.1.1]heptan-3-yl)phenyl)-3-cyclopropyl-3H-imidazo[4,5-c]pyridin-4-yl)oxy)ethyl)pyrrolidin-2-one: Prepared by Suzuki coupling reaction procedure, as previously described for the synthesis of 6-(3-cyclopropyl-4-((R)-1-((R)-5-oxopyrrolidin-3-yl)ethoxy)-3H-imidazo[4,5-c]pyridin-6-yl)indolin-2-one:, using instead 3-(4-(4,4,5,5-tetramethyl-1,3,2-dioxaborolan-2-yl)phenyl)-6-oxa-3-azabicyclo[3.1.1]heptane (123.7 mg, 0.41 mmol) to afford 51.2 mg (41%) of (4R)-4-((1R)-1-((6-(4-(6-oxa-3-azabicyclo[3.1.1]heptan-3-yl)phenyl)-3-cyclopropyl-3H-imidazo[4,5-c]pyridin-4-yl)oxy)ethyl)pyrrolidin-2-one:. $^1$H NMR (300 MHz, d$_6$-DMSO) δ 8.21 (s, 1H), 7.96 (d, J=8.8 Hz, 2H), 7.61 (s, 1H), 7.55 (s, 1H), 6.79 (d, J=8.7 Hz, 2H), 5.57 (m, 1H), 4.71 (m, 2H), 3.50 (m, 6H), 3.21 (m, 2H), 2.83 (m, 1H), 2.32 (m, 2H), 1.91 (m, 1H), 1.39 (d, J=6.2 Hz, 3H), 1.14 (m, 4H). MS (ESI+) m/z 460.2 (M+H).

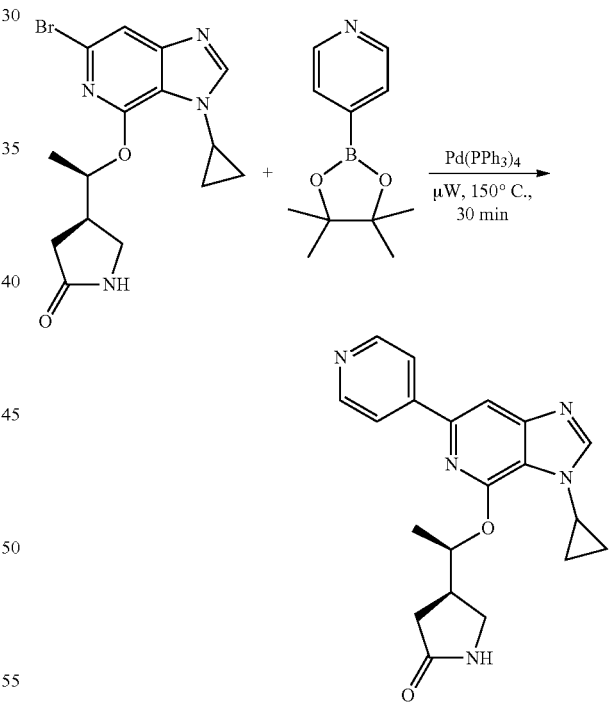

Preparation of (R)-4-((R)-1-((3-cyclopropyl-6-(pyridin-4-yl)-3H-imidazo[4,5-c]pyridin-4-yl)oxy)ethyl)pyrrolidin-2-one: Into a microwave reaction vial, a mixture of (R)-4-((R)-1-((6-bromo-3-cyclopropyl-3H-imidazo[4,5-c]pyridin-4-yl)oxy)ethyl)pyrrolidin-2-one: (100.0 mg, 0.27 mmol), 4-(4,4,5,5-tetramethyl-1,3,2-dioxaborolan-2-yl)pyridine (168.4 mg, 0.82 mmol), sodium carbonate (116.0 mg, 1.10 mmol) and Pd(PPh$_3$)$_4$ (31.6 mg, 0.027 mmol) were placed in dioxane (4 mL) and water (1 mL). The reaction mixture was placed in the microwave reactor and heated at 150° C. for 30 min. Then, it was filtered through a pad of Celite and partitioned between EtOAc (2×30 mL) and brine (2×10 mL). The combined organic layers were washed with water (2×5 mL), concentrated, and purified by flash chromatography (100% EtOAc to 20% MeOH in EtOAc) to give 52.0 mg (52.3%) of (R)-4-((R)-1-((3-cyclopropyl-6-(pyridin-4-yl)-3H-imidazo[4,5-c]pyridin-4-yl)oxy)ethyl)pyrrolidin-2-one:. 1H NMR (300 MHz, DMSO-d6) δ 8.44 (dd, J=1.8, 1.2 Hz, 2H), 8.162 (s, 1H), 7.896-7.863 (m, 3H), 7.383 (s, 1H), 5.438-5.398 (m, 1H), 3.551-3.492 (m, 1H), 3.22 (t, J=9.5 Hz, 1H), 3.03 (dd, J=6.6, 6.6 Hz, 1H), 2.701-2.633 (m, 1H), 2.15 (dd, J=2.3, 1.7 Hz, 2H), 1.24 (d, J=6.5 Hz, 3H), 1.0-0.828 (m, 4H). LCMS-ESI+ (m/z): [M+H]+ calcd $C_{20}H_{21}N_5O_2$: 363.17; found 364.14.

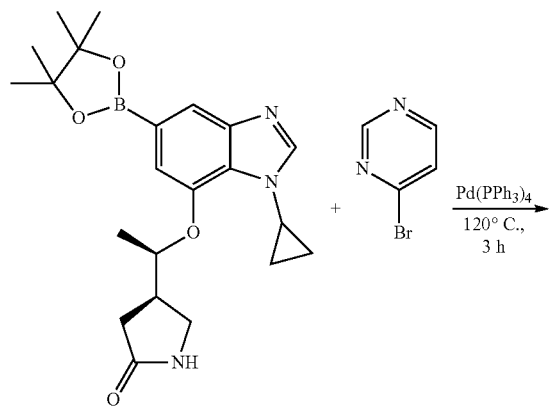

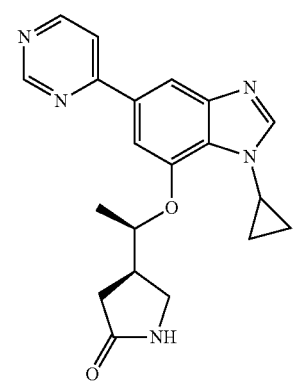

Preparation of (R)-4-((R)-1-((1-cyclopropyl-5-(pyrimidin-4-yl)-1H-benzo[d]imidazol-7-yl)oxy)ethyl)pyrrolidin-2-one: Into an appropriate sized reaction vessel, a mixture of (R)-4-((R)-1-((1-cyclopropyl-5-(4,4,5,5-tetramethyl-1,3,2-dioxaborolan-2-yl)-1H-benzo[d]imidazol-7-yl)oxy)ethyl)pyrrolidin-2-one: (100.0 mg, 0.24 mmol), 4-bromopyrimidine (77.3 mg, 0.49 mmol), sodium carbonate (77.3 mg, 0.73 mmol) and Pd(PPh3)4 (14.04 mg, 0.01 mmol) was added Dioxane (8 ml), water (1 ml). The reaction mixture was stirred and heated at 120° C. for 3 h. Then, it was filtered through a pad of Celite and partitioned between EtOAc (2×30 mL) and brine (2×10 mL). The combined organic layers were washed with water (2×5 mL), concentrated, and purified by flash chromatography (100% EtOAc to 20% MeOH in EtOAc) to give 45.0 mg (50.9%) of (R)-4-((R)-1-((1-cyclopropyl-5-(pyrimidin-4-yl)-1H-benzo[d]imidazol-7-yl)oxy)ethyl)pyrrolidin-2-one:. 1H NMR (300 MHz, DMSO-d6) δ 9.211 (d, J=1.2 Hz, 1H), 8.80 (d, J=5.1 Hz, 1H), 8.19 (dd, J=2.4, 0.9 Hz, 2H), 8.11 (s, 1H), 7.719 (s, 1H). 7.603 (s, 1H), 4.91-4.83 (m, 1H), 3.77-3.70 (m, 1H), 3.41 (t, J=9.2 Hz, 1H), 3.21 (dd, J=6.6, 6.9 Hz, 1H), 2.87-2.82 (m, 1H), 2.41-2.24 (m, 2H), 1.34 (d, J=6 Hz, 3H), 1.20-1.01 (m, 4H). LCMS-ESI+ (m/z): [M+H]+ calcd for C20H21N5O2: 363.17; found 364.04.

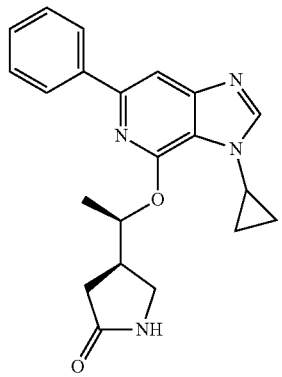

Preparation of (R)-4-((R)-1-((3-cyclopropyl-6-phenyl-3H-imidazo[4,5-c]pyridin-4-yl)oxy)ethyl)pyrrolidin-2-one: Prepared by Suzuki coupling reaction procedure, as previously described for the synthesis of (R)-4-((R)-1-((3-cyclopropyl-6-(pyridin-4-yl)-3H-imidazo[4,5-c]pyridin-4-yl) oxy)ethyl)pyrrolidin-2-one:, using instead phenylboronic acid (100.0 mg, 0.82 mmol) as a starting material to afford 32.6 mg (33.3%) of (R)-4-((R)-1-((3-cyclopropyl-6-phenyl-3H-imidazo[4,5-c]pyridin-4-yl)oxy)ethyl) pyrrolidin-2-one:. 1H NMR (300 MHz, DMSO-d6) δ 8.295 (s, 1H), 8.09 (dd, J=1.8, 5.4 Hz, 2H), 7.801 (s, 1H), 7.57 (s, 1H), 7.45 (t, J=7.2 Hz, 2H), 7.375-7.346 (m, 1H), 5.61-5.74 (m, 1H), 3.73-3.68 (m, 1H), 3.42 (t, J=9.3 Hz, 1H), 3.22 (dd J=6.3, 6.3 Hz, 1H), 2.87-2.82 (m, 1H), 2.34 (d, 9 Hz, 2H), 1.43 (d, J=6.6 Hz, 3H), 1.15-1.03 (m, 4H). LCMS-ESI+ (m/z): [M+H]+ calcd for $C_{21}H_{22}N_4O_2$: 362.17; found 363.09.

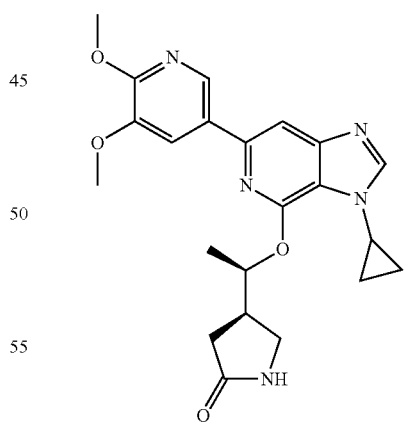

Preparation of (R)-4-((R)-1-((3-cyclopropyl-6-(5,6-dimethoxypyridin-3-yl)-3H-imidazo[4,5-c]pyridin-4-yl) oxy)ethyl)pyrrolidin-2-one: Prepared by Suzuki coupling reaction procedure, as previously described for the synthesis of (R)-4-((R)-1-((3-cyclopropyl-6-(pyridin-4-yl)-3H-imidazo[4,5-c]pyridin-4-yl)oxy)ethyl)pyrrolidin-2-one:, using instead 2,3-dimethoxy-5-(4,4,5,5-tetramethyl-1,3,2-dioxaborolan-2-yl)pyridine (217.8 mg, 0.82 mmol) as a starting material, to afford 70.0 mg (60.3%) of (R)-4-((R)-1-((3-cyclopropyl-6-(5,6-dimethoxypyridin-3-yl)-3H-imidazo[4,5-c]pyridin-4yl)oxy)ethyl)pyrrolidin-2-one:. 1H NMR (300 MHz, DMSO-d6) δ 8.46 (d, J=2.4 Hz 1H), 8.287 (s, 1H), 7.90 (d, J=2.4 Hz 1H), 7.879 (s, 1H), 7.57 (s, 1H). 5.59-5.55 (m, 1H), 3.9 (d, J=2.4 Hz 6H), 3.71-3.66 (m, 1H), 3.38 (t, J=18 Hz, 1H), 3.25 (dd, J=12, 15 Hz, 1H), 2.89-2.82 (m, 1H), 2.36-2.3 (m, 2H), 1.43 (d, J=6.4 Hz, 3H), 1.119-1.09 (m, 4H). LCMS-ESI$^+$ (m/z): [M+H]$^+$ calcd for $C_{22}H_{25}N_5O_4$:423.19; found 424.08.

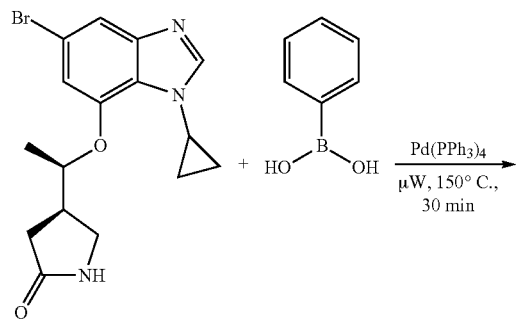

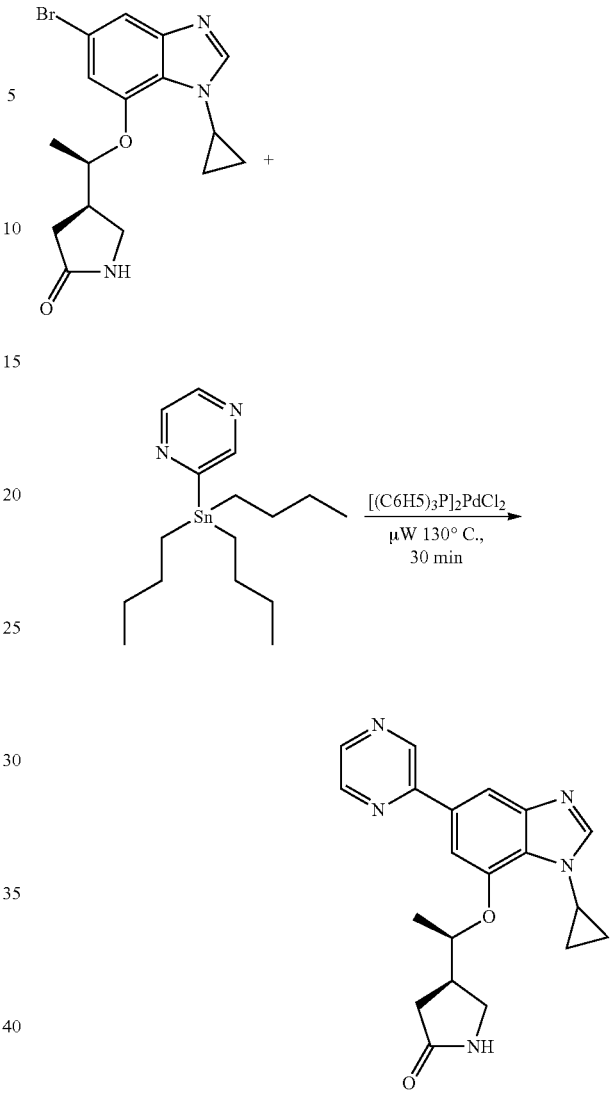

Preparation of (R)-4-((R)-1-((1-cyclopropyl-5-phenyl-1H-benzo[d]imidazol-7-yl)oxy)ethyl)pyrrolidin-2-one: Into a microwave reaction vial, a mixture of (R)-4-((R)-1-((5-bromo-1-cyclopropyl-M-benzo[d]imidazol-7-yl)oxy)ethyl)pyrrolidin-2-one: (100.0 mg, 0.274 mmol), phenylboronic acid (100.0 mg, 0.82 mmol), Sodium carbonate (116.4 mg, 1.1 mmol) and Pd(PPh$_3$)$_4$ (31.6 mg, 0.027 mmol) was added dioxane (4 L) and water (1 mL). The reaction mixture was placed in the microwave reactor and heated at 150° C. for 30 min. Then, it was filtered through a pad of Celite and partitioned between EtOAc (2×30 mL) and brine (2×10 mL). The combined organic layers were washed with water (2×5 mL), concentrated, and purified by flash chromatography (100% EtOAc to 20% MeOH in EtOAc) to give 70.0 mg (60.3%) of (R)-4-((R)-1-((1-cyclopropyl-5-phenyl-1 h-benzo[d]imidazol-7-yl)oxy)ethyl)pyrrolidin-2-one:. 1H NMR (300 MHz, DMSO-d6) δ 8.103 (s, 1H), 7.71-7.62 (m, 2H), 7.59 (s, 1H), 7.471-7.424 (m, 3H), 7.355-7.3 (m, 1H), 7.08 (s, 1H), 4.897-4.86 (m, 1H), 3.73-3.67 (m, 1H), 3.4 (t, J=9.2 Hz, 1H), 3.19 (dd, J=6.6, 7.2 Hz, 1H), 2.83-2.78 (m, 1H), 2.40-2.23 (m, 2H), 1.32 (d, J=5.7 Hz, 3H), 1.119-0.95 (m, 4H). LCMS-ESI$^+$ (m/z): [M+H]$^+$ calcd $C_{22}H_{23}N_3O_2$:361.18; found 362.09.

Preparation of (R)-4-((R)-1-((1-cyclopropyl-5-(pyrazin-2-yl)-1H-benzo[d]imidazol-7-yl)oxy)ethyl)pyrrolidin-2-one:
Into a microwave-tube, a mixture of (R)-4-((R)-1-((5-bromo-1-cyclopropyl-1 h-benzo[d]imidazol-7-yl)oxy)ethyl)pyrrolidin-2-one: (100.0 mg, 0.27 mmol), 2-(tributylstannyl)pyrazine (152.0 mg, 0.91 mmol), Bis(triphenylphosphine)palladium(II) dichloride (28.9 mg, 0.04 mmol) and dioxane (8 mL). The reaction mixture was placed in the microwave reactor and heated at 130° C. for 30 min. Quenched with saturated KF, extracted with EtOAc (3×30 ml). The combined organic layers were washed with water (2×5 mL), concentrated, and purified by flash chromatography (100% EtOAc to 20% MeOH/EtOAc) to give 23.0 mg (23.0%) of (R)-4-((R)-1-((1-cyclopropyl-5-(pyrazin-2-yl)-1H-benzo[d]imidazol-7-yl)oxy)ethyl)pyrrolidin-2-one:. 1H NMR (300 MHz, DMSO-d6) δ 9.34 (d, J=1.8 Hz, 1H), 8.69 (dd, J=1.8, 1.2 Hz, 1H), 8.56 (d, J=2.1 Hz 1H), 8.174 (s, 1H), 8.016 (d, J=0.9 Hz 1H), 7.62 (d, J=6 Hz 2H), 4.91-4.85 (m, 1H), 3.76-3.695 (m, 1H), 3.41 (t, J=9.2 Hz, 1H), 3.20 (dd, J=6.6, 6.9 Hz, 1H), 2.87-2.80 (m, 1H), 2.41-2.24 (m, 2H), 1.34 (d, J=6 Hz, 3H), 1.23-1.0 (m, 4H). LCMS-ESI$^+$ (m/z): [M+H]$^+$ calcd $C_{20}H_{21}N_5O_2$:363.17; found 364.09.

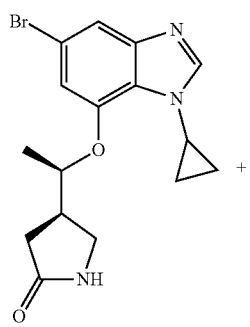

+

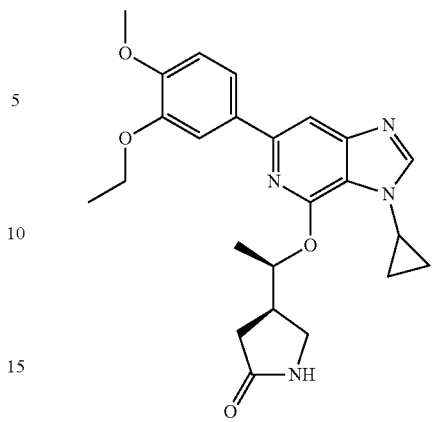

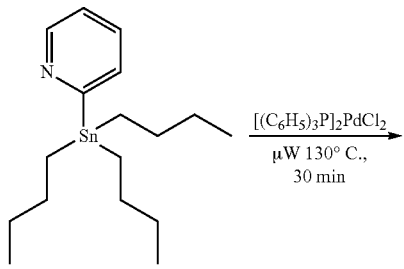

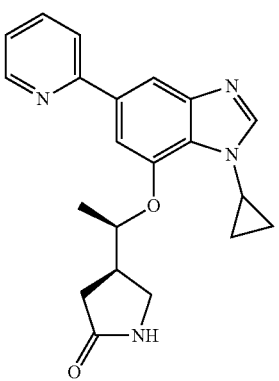 [SMILES: C[C@@H](Oc1nc(-c2ccccc2)cc2ncn(C3CC3)c12)[C@H]1CNC(=O)C1]

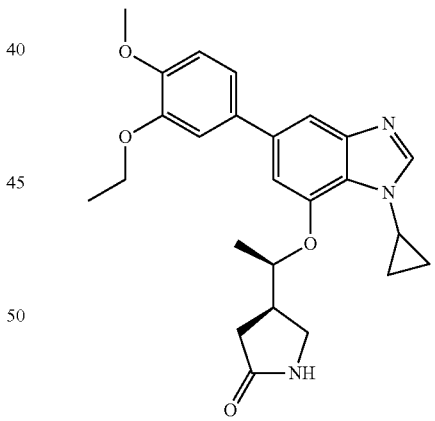

Preparation of (R)-4-((R)-1-((1-cyclopropyl-5-(pyridin-2-yl)-1H-benzo[d]imidazol-7-yl)oxy)ethyl)pyrrolidin-2-one: Into a microwave-tube, a mixture of (R)-4-((R)-1-((5-bromo-1-cyclopropyl-1H-benzo[d]imidazol-7-yl)oxy)ethyl)pyrrolidin-2-one: (100.0 mg, 0.275 mmol), 2-(tributylstannyl)pyridine (152.0 mg, 0.412 mmol) Bis(triphenylphosphine) palladium(II) dichloride (28.9 mg, 0.04 mmol) and dioxane (8 mL). The reaction mixture was placed in the microwave reactor and heated at 130° C. for 30 min. Quenched with saturated KF, extracted with EtOAc (3×30 ml). The combined organic layers were washed with water (2×5 mL), concentrated, and purified by flash chromatography (100% EtOAc to 20% MeOH/EtOAc) to give 18.0 mg (18.1%) of (R)-4-((R)-1-((1-cyclopropyl-5-(pyridin-2-yl)-1H-benzo[d]imidazol-7-yl)oxy)ethyl)pyrrolidin-2-one. 1H NMR (300 MHz, DMSO-d6) δ 8.65 (d, J=7.5 Hz 1H), 8.127 (s, 1H), 8.04 (d, J=9.6 Hz 1H), 7.90-7.81 (m, 2H), 7.62 (d, J=0.9 Hz 1H), 7.60 (s, 1H), 7.324-7.283 (m, 1H), 4.856-4.815 (m, 1H), 3.742-3.695 (m, 1H), 3.41 (t, J=9.5 Hz, 1H), 3.21 (dd, J=6.3, 6.9 Hz, 1H), 2.862-2.811 (m, 1H), 2.426-2.24 (m, 2H), 1.33 (d, J=6.6 Hz, 3H), 1.266-1.016 (m, 4H). LCMS-ESI+ (m/z): [M+H]+ calcd $C_{21}H_{22}N_4O_2$:362.17; found 363.1.

Preparation of (R)-4-((R)-1-((3-cyclopropyl-6-(3-ethoxy-4-methoxyphenyl)-3H-imidazo[4,5-c]pyridin-4-yl)oxy)ethyl)pyrrolidin-2-one: Prepared by Suzuki coupling reaction procedure, as previously described for the synthesis of (R)-4-((R)-1-((3-cyclopropyl-6-(pyridin-4-yl)-3H-imidazo[4,5-c]pyridin-4-yl)oxy)ethyl)pyrrolidin-2-one:, using instead (3-ethoxy-4-methoxyphenyl)boronic acid (80.5 mg, 0.41 mmol) as a starting material to afford 38.8 mg (32.5%) of (R)-4-((R)-1-((3-cyclopropyl-6-(3-ethoxy-4-methoxyphenyl)-3H-imidazo[4,5-c]pyridin-4-yl)oxy)ethyl)pyrrolidin-2-one:. 1H NMR (300 MHz, DMSO-d6) δ 8.232 (s, 1H), 7.723 (s, 1H), 7.61 (d, J=8.7 Hz 2H), 7.545 (s, 1H), 7.00 (d, J=8.4 Hz, 1H). 5.51 (t, J=5.6 Hz, 1H), 4.1 (q, J=6.9 Hz, 2H), 3.77 (s, 3H), 3.65 (d, J=3.3 Hz, 1H), 3.39 (t, J=9 Hz, 1H), 3.29 (s, 2H) 3.20 (t, J=8 Hz, 1H), 2.84 (d, J=6 Hz, 1H), 2.32 (d, J=8.7 Hz, 2H), 1.414-1.342 (m, 6H), 1.088-1.032 (m, 4H). LCMS-ESI+ (m/z): [M+H]+ calcd for $C_{24}H_{28}N_4O_4$:436.21; found 437.18.

Preparation of (R)-4-((R)-1-((1-cyclopropyl-5-(3-ethoxy-4-methoxyphenyl)-1H-benzo[d]imidazol-7-yl)oxy)ethyl)pyrrolidin-2-one: Prepared by Suzuki coupling reaction procedure, as previously described for the synthesis of (R)-4-((R)-1-((1-cyclopropyl-5-phenyl-1H-benzo[d]imidazol-7-yl)oxy)ethyl)pyrrolidin-2-one:, using instead 2-(3-ethoxy-4-methoxyphenyl)-4,4,5,5-tetramethyl-1,3,2-dioxaborolane (106.3 mg, 0.411 mmol) as a starting material to afford 51.0 mg (42.7%) of (R)-4-((R)-1-((1-cyclopropyl-5-(3-ethoxy-4-methoxyphenyl)-1H-benzo[d]imidazol-7-yl)oxy)ethyl)pyrrolidin-2-one:. 1H NMR (300 MHz, DMSO-d6) δ 8.058 (s, 1H), 7.576 (s, 1H), 7.367 (d, J=1.2 Hz 1H), 7.184 (s, 1H), 7.155 (d, J=1.8 Hz, 1H). 6.99 (t, J=4.4 Hz 2H), 4.84 (t J=5.9 Hz, 1H), 4.11 (dd, J=7.2, 6.6 Hz, 2H), 3.768 (s, 3H), 3.709-3.637 (m, 1H), 3.38 (t, J=9 Hz, 1H) 3.18 (dd, J=6.9, 9.3 Hz, 1H), 2.83-2.75 (m, 1H), 2.379-2.207 (m, 2H), 1.358-1.282 (m, 6H), 1.125-1.00 (m, 4H). LCMS-ESI$^+$ (m/z): [M+H]$^+$ calcd for C$_{25}$H$_{29}$N$_3$O$_4$:435.22; found 436.18.

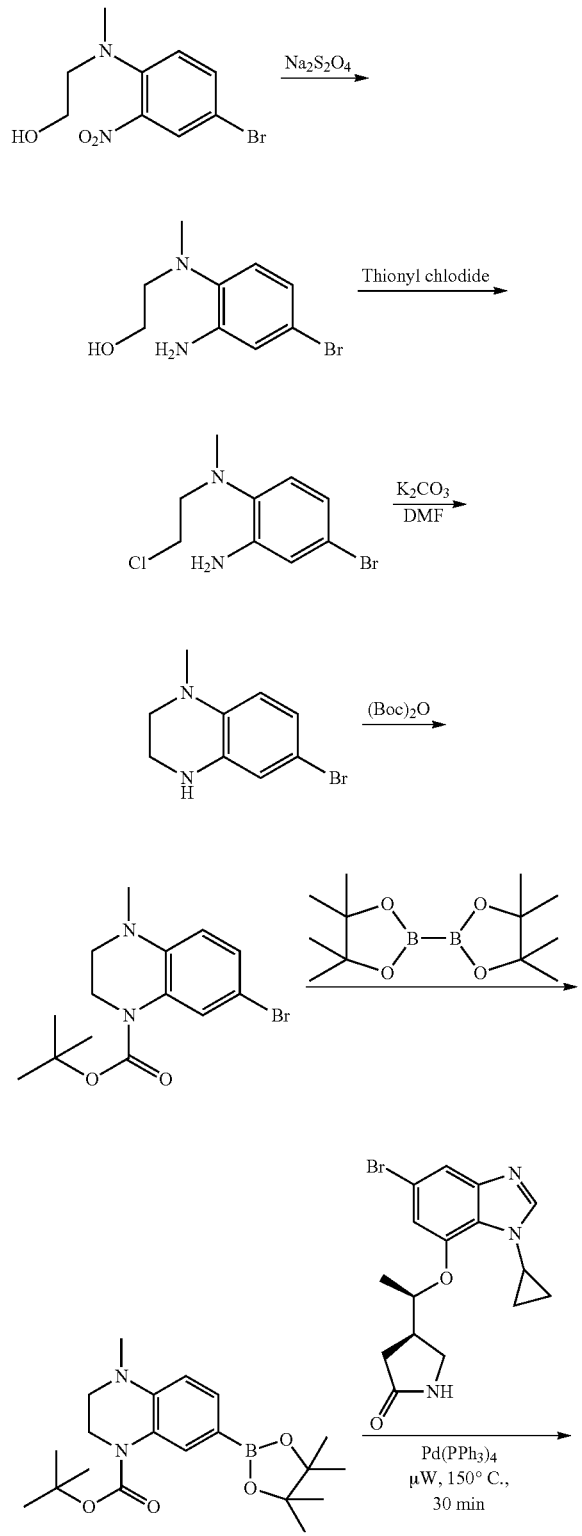

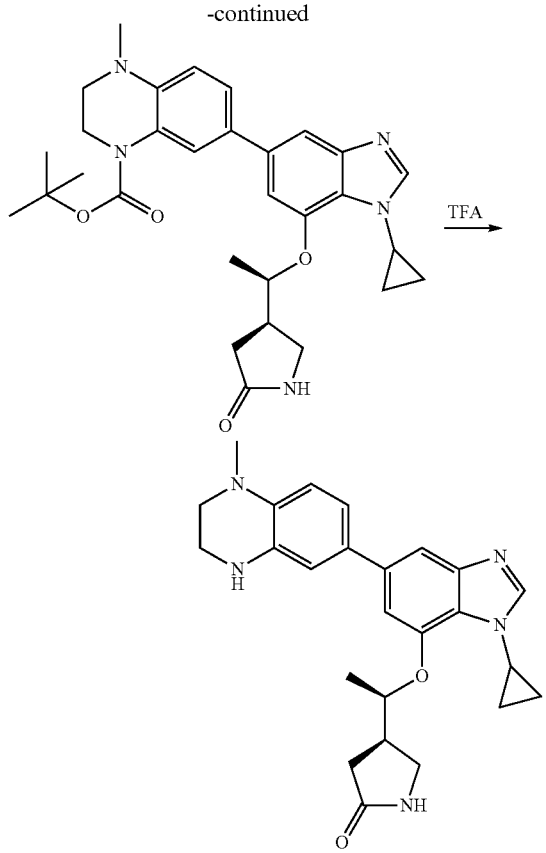

2-((2-amino-4-bromophenyl)(methyl)amino)ethanol: 2-((4-bromo-2-nitrosophenyl)(methyl)amino)ethanol (6.5 g, 0.025 mol) was dissolved in THF (100 ml), Sodium hydrosulfite (26.2 g, 0.15 mol in water 150 mL) was added. The reaction was stirred at rt for 1 h. The mixture was extracted with EtOAc (2×100 ml). The combined organic layers was concentrated and purified by flash chromatography eluted with EtOAc to give 3.1 g, (50.3%) of 2-((2-amino-4-bromophenyl)(methyl)amino)ethanol LCMS-ESI$^+$ (m/z): [M+H]$^+$ calcd for C$_9$H$_{13}$BrN$_2$O$_4$:244.03; found 244.96, 246.91.

4-bromo-N1-(2-chloroethyl)-N1-methylbenzene-1,2-diamine: 2-((2-amino-4-bromophenyl)(methyl)amino)ethanol (3.09 g, 0.013 mol) was dissolved in DCM (100 mL) with DMF (10 drop), Thionyl chloride (1.8 g, 0.015 mol in 10 ml DCM) was added dropwise at 0° C. The reaction was stirred at rt for 10 min then 80° C. for 30 min, rt for 16 h. The mixture was partitioned between 1N NaOH and DCM (2×30 ml). The combined organic layers was concentrated to give 3.2 g, (96.3%) of 4-bromo-N1-(2-chloroethyl)-N1-methylbenzene-1,2-diamine LCMS-ESI$^+$ (m/z): [M+H]$^+$ calcd for C$_9$H$_{12}$BrClN$_2$:261.99; found 262.9.

6-bromo-1-methyl-1,2,3,4-tetrahydroquinoxaline: 4-bromo-N1-(2-chloroethyl)-N1-methylbenzene-1,2-diamine 1 (3.1 g, 0.012 mol) was dissolved in DMF (6 ml), Potassium carbonate (3.3 g, 0.024 mol) was added. The reaction was stirred at 100° C. for 2 h. The mixture was partitioned between water and EtOAc (2×30 mL) The combined organic layers was concentrated and purified by flash chromatography eluted with EtOAc to give 1.9 g, (69.6%) of 6-bromo-1-methyl-1,2,3,4-tetrahydroquinoxaline. 1H NMR (300 MHz, DMSO-d6) δ 6.50-6.45 (m, 2H), 6.31 (d, J=8.2 Hz, 1H), 5.79

(s, 1H), 3.29 (s, 4H). 3.07 (t, J=2.4 Hz, 2H), 2.71 (s, 3H), LCMS-ESI⁺ (m/z): [M+H]⁺ calcd for C₉H₁₁BrN₂:226.01; found 226.96.

tert-butyl 7-bromo-4-methyl-3,4-dihydroquinoxaline-1 (2H)-carboxylate 6-bromo-1-methyl-1,2,3,4-tetrahydroquinoxaline (1.1 g, 4.8 mmol) was dissolved in DCM (4 ml), di-tert-butyl dicarbonate (1.3 g, 5.8 mmol) was added followed by N,N-dimethylpyridin-4-amine (59 mg, 0.48 mmol). The reaction was stirred at 45° C. for 3 h. The mixture was partitioned between EtOAc (2×30 ml) and water (2×20 ml). The combined organic layers was concentrated and purified by flash chromatography eluted with 20% EtOAc to give 1.4 g, (86.6%). LCMS-ESI⁺ (m/z): [M+H]⁺ calcd for C₁₄H₁₉BrN₂O₂:326.06; found 327.04.

tert-butyl 4-methyl-7-(4,4,5,5-tetramethyl-1,3,2-dioxaborolan-2-yl)-3,4-dihydroquinoxaline-1(2H)-carboxylate A mixture of tert-butyl 7-bromo-4-methyl-3,4-dihydroquinoxaline-1(2H)-carboxylate (1.1 g, 3.36 mmol), 4,4,4',4',5,5,5',5'-octamethyl-2,2'-bi(1,3,2-dioxaborolane) (1.28 g, 5 mmol), KOAc (1.3 g, 13.5 mmol), Pd(dppf).CH₂Cl₂ (137 mg, 0.168 mmol) was added dioxane (30 mL). The reaction was stirred at 100° C. for 2 day. Filtered, concentrated, and purified by flash chromatography eluted with 5% to 20% EtOAc/hexane to give 0.7, (55.6%) of tert-butyl 4-methyl-7-(4,4,5,5-tetramethyl-1,3,2-dioxaborolan-2-yl)-3,4-dihydroquinoxaline-1(2H)-carboxylate.

LCMS-ESI⁺ (m/z): [M+H]⁺ calcd for C₂₀H₃₁BN₂O₄; 374.24 found 375.14.

tert-butyl 7-(1-cyclopropyl-7-((R)-1-((R)-5-oxopyrrolidin-3-yl)ethoxy)-1H-benzo[d]imidazol-5-yl)-4-methyl-3,4-dihydroquinoxaline-1(2H)-carboxylate: Prepared by Suzuki coupling reaction procedure, as previously described for the synthesis of (R)-4-((R)-1-((1-cyclopropyl-5-phenyl-1H-benzo[d]imidazol-7-yl)oxy)ethyl)pyrrolidin-2-one:, using instead tert-butyl 4-methyl-7-(4,4,5,5-tetramethyl-1,3,2-dioxaborolan-2-yl)-3,4-dihydroquinoxaline-1(2H)-carboxylate (92.0 mg, 0.24 mmol) as a starting material to afford 40.0 mg (45.6%) of tert-butyl 7-(1-cyclopropyl-7-((R)-1-((R)-5-oxopyrrolidin-3-yl)ethoxy)-1H-benzo[d]imidazol-5-yl)-4-methyl-3,4 dihydroquinoxaline-1(2H)-carboxylate. LCMS-ESI⁺ (m/z): [M+H]⁺ calcd for C₃₀H₃₇N₅O₄:531.28; found 532.23.

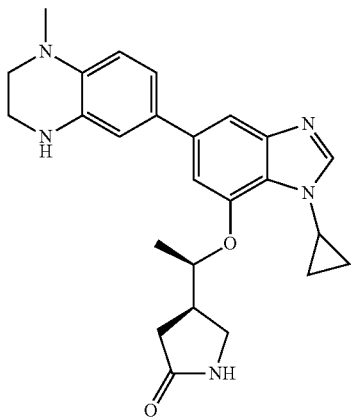

(R)-4-((R)-1-((1-cyclopropyl-5-(1-methyl-1,2,3,4-tetrahydroquinoxalin-6-yl)-1H-benzo[d]imidazol-7-yl)oxy)ethyl)pyrrolidin-2-one: tert-butyl 7-(1-cyclopropyl-7-((R)-1-((R)-5-oxopyrrolidin-3-yl)ethoxy)-1H-benzo[d]imidazol-5-yl)-4-methyl-3,4-dihydroquinoxaline-1(2H)-carboxylate (40 mg, 0.075 mmol) was dissolved in DCM (2 mL), TFA (0.29 mL, 3.76 mmol) was added. The reaction was stirred at rt for 16 h. The mixture was quenched with saturated NaHCO₃, extracted with EtOAc (3×30 ml). The combined organic layers were washed with water (2×5 mL), concentrated and purified by flash chromatography eluted with 5% to 20% MeOH/EtOAc to give 23.8 mg, (73.3%) of (R)-4-((R)-1-((1-cyclopropyl-5-(1-methyl-1,2,3,4-tetrahydroquinoxalin-6-yl)-1H-benzo[d]imidazol-7yl)oxy)ethyl)pyrrolidin-2-one:.. 1H NMR (300 MHz, DMSO-d6) δ 8.01 (s, 1H), 7.57 (s, 1H), 7.19 (s, 1H), 6.88 (s, 1H), 6.74 (dd, J=2.4, 2.4 Hz, 1H), 6.68 (d, J=2.4 Hz, 1H), 6.48 (d, J=8.1 Hz, 1H), 5.54 (s, 1H), 4.76-4.73 (m, 1H), 3.67-3.63 (m, 1H), 3.40-3.30 (m, 3H), 3.20-3.11 (m, 3H), 2.77 (s, 4H), 2.38-2.23 (m, 2H), 1.29 (d, J=6 Hz, 3H), 1.06-0.96 (m, 4H), LCMS-ESI⁺ (m/z): [M+H]⁺ calcd for C₂₅H₂₉N₅O₂:431.23; found 432.22.

Preparation of tert-butyl 7-(3-cyclopropyl-4-((R)-1-((R)-5-oxopyrrolidin-3-yl)ethoxy)-3H-imidazo[4,5-c]pyridin-6-yl)-4-methyl-3,4-dihydroquinoxaline-1 (2H)-carboxylate: Prepared by Suzuki coupling reaction procedure, as previously described for the synthesis of (R)-4-((R)-1-((3-cyclopropyl-6-(pyridin-4-yl)-3H-imidazo[4,5-c]pyridin-4-yl)oxy)ethyl)pyrrolidin-2-one:, using instead tert-butyl 4-methyl-7-(4,4,5,5-tetramethyl-1,3,2-dioxaborolan-2-yl)-3,4-dihydroquinoxaline-1(2H)-carboxylate (92.2 mg, 0.24 mmol) as a starting material to afford 15.0 mg (17.1%) of tert-butyl 7-(3-cyclopropyl-4-((R)-1-((R)-5-oxopyrrolidin-3-yl)ethoxy)-3H-imidazo[4,5-c]pyridin-6-A-4-methyl-3,4-dihydroquinoxaline-1(2H)-carboxylate. LCMS-ESI⁺ (m/z): [M+H]⁺ calcd for C₂₉H₃₆N₆O₄:532.28; found 533.23.

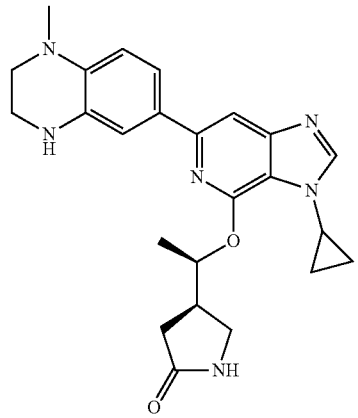 [SMILES: C[C@@H](Oc1nc(-c2ccc3c(c2)NCCN3C)cc2ncn(C3CC3)c12)[C@H]1CNC(=O)C1]

Preparation of (R)-4-((R)-1-((3-cyclopropyl-6-(1-methyl-1,2,3,4-tetrahydroquinoxalin-6-yl)-3H-imidazo[4,5-c]pyridin-4-yl)oxy)ethyl)pyrrolidin-2-one: Prepared by Boc protection procedure, as previously described for the synthesis of (R)-4-((R)-1-((1-cyclopropyl-5-(1-methyl-1,2,3,4-tetrahydroquinoxalin-6-yl)-1H-benzo[d]imidazol-7-yl)oxy)ethyl)pyrrolidin-2-one:, using instead tert-butyl 7-(3-cyclopropyl-4-((R)-1-((R)-5-oxopyrrolidin-3-yl)ethoxy)-3H-imidazo[4,5-c]pyridin-6-yl)-4-methyl-3,4-dihydroquinoxaline-1(2H)-carboxylate (15.0 mg, 0.028 mmol) as a starting material to afford 10.0 mg (82.1%) of (R)-4-((R)-1-((3-cyclopropyl-6-(1-methyl-1,2,3,4-tetrahydroquinoxalin-6-A-3H-imidazo[4,5-c]pyridin-4-yl)oxy)ethyl)pyrrolidin-2-one. 1H NMR (300 MHz, DMSO-d6) δ 8.12 (s, 1H), 7.55 (s, 1H), 7.41 (s, 1H), 7.12 (dd, J=2.4, 2.4 Hz, 1H), 7.106 (d, J=1.8 Hz, 1H). 6.48 (d, J=8.1 Hz, 1H), 5.55-5.49 (m, 2H), 3.66-3.60 (m, 1H), 3.43-3.31 (m, 3H), 3.21-3.14 (m, 3H), 2.86-2.79 (m, 4H), 2.33-

2.30 (m, 2H), 1.38 (d, J=6 Hz, 3H), 1.125-0.98 (m, 4H), LCMS-ESI+ (m/z): [M+H]+ calcd for C24H28N6O2:432.23; found 433.16.

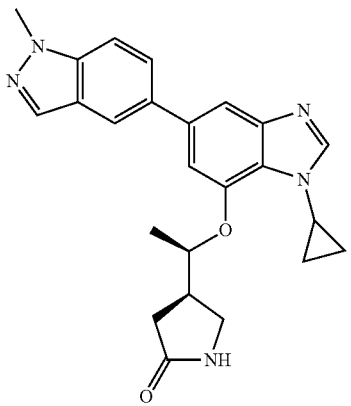 [SMILES: C[C@@H](Oc1cc(-c2ccc3c(cnn3C)c2)cc2ncn(C3CC3)c12)[C@H]1CNC(=O)C1]

Preparation of (R)-4-((R)-1-((1-cyclopropyl-5-(1-methyl-1H-indazol-5-yl)-1H-benzo[d]imidazol-7-yl)oxy)ethyl)pyrrolidin-2-one: Prepared by Suzuki coupling reaction procedure, as previously described for the synthesis of (R)-4-((R)-1-((1-cyclopropyl-5-phenyl-1H-benzo[d]imidazol-7-yl)oxy)ethyl)pyrrolidin-2-one:, using instead 1-methyl-5-(4,4,5,5-tetramethyl-1,3,2-dioxaborolan-2-yl)-1H-indazole (106.3 mg, 0.41 mmol), as a starting material to afford 65.0 mg (57.0%) of (R)-4-((R)-1-((5-bromo-1-cyclopropyl-1H-benzo[d]imidazol-7-yl)oxy)ethyl)pyrrolidin-2-one:. 1H NMR (300 MHz, DMSO-d6) δ 8.08 (s, 1H), 8.06 (d, J=0.9 Hz, 1H), 8.01 (d, J=1.8 Hz, 1H), 7.74 (dd, J=1.8, 1.8 Hz, 1H), 7.67 (d, J=8.7 Hz, 1H). 7.58 (s, 1H), 7.43 (d, J=1.2 Hz, 1H), 7.11 (s, 1H), 4.90-4.86 (m, 1H), 4.05 (s, 3H), 3.71-3.65 (m, 1H), 3.39 (t, J=9 Hz, 1H), 3.19 (dd, J=6.9, 7.2 Hz, 1H), 2.84-2.77 (m, 1H), 2.36-2.22 (m, 2H), 1.31 (d, J=5.7 Hz, 3H), 1.10-0.99 (m, 4H), LCMS-ESI+ (m/z): [M+H]+ calcd for C24H25N5O2:415.2; found 416.2.

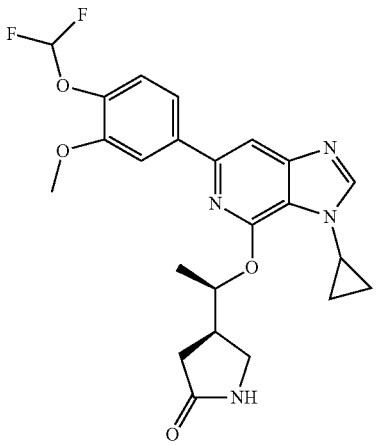 [SMILES: COc1cc(-c2cc3ncn(C4CC4)c3c(O[C@H](C)[C@H]3CNC(=O)C3)n2)ccc1OC(F)F]

Preparation of (R)-4-((R)-1-((3-cyclopropyl-6-(4-(difluoromethoxy)-3-methoxyphenyl)-3H-imidazo[4,5-c]pyridin-4-yl)oxy)ethyl)pyrrolidin-2-one: Prepared by Suzuki coupling reaction procedure, as previously described for the synthesis of (R)-4-((R)-1-((3-cyclopropyl-6-(pyridin-4-yl)-3H-imidazo[4,5-c]pyridin-4-yl)oxy)ethyl)pyrrolidin-2-one:, using instead 2-(4-(difluoromethoxy)-3-methoxyphenyl)-4,4,5,5-tetramethyl-1,3,2-dioxaborolane (123.3 mg, 0.411 mmol) as a starting material to afford 50.0 mg (39.8%) of (R)-4-((R)-1-((3-cyclopropyl-6-(4-(difluoromethoxy)-3-methoxyphenyl)-3H-imidazo[4,5-c]pyridin-4-yl)oxy)ethyl)pyrrolidin-2-one:. 1H NMR (300 MHz, DMSO-d6) δ 8.28 (s, 1H), 7.88 (s, 1H), 7.81 (d, J=1.5 Hz, 1H), 7.68 (dd, J=1.8, 2.4 Hz, 1H), 7.55 (s, 1H), 7.21 (d, J=8.4 Hz, 1H). 7.07 (t, J=75 Hz, 1H), 5.58-5.50 (m, 1H), 3.92 (s, 3H), 3.72-3.65 (m, 1H), 3.39 (t, J=9.5 Hz, 1H), 3.20 (dd, J=4.8, 6.9 Hz, 1H), 2.88-2.81 (m, 1H), 2.34-2.28 (m, 2H), 1.41 (d, J=5.7 Hz, 3H), 1.11-0.99 (m, 4H), LCMS-ESI+ (m/z): [M+H]+ calcd for C23H24F2N4O4: 458.18; found 459.09.

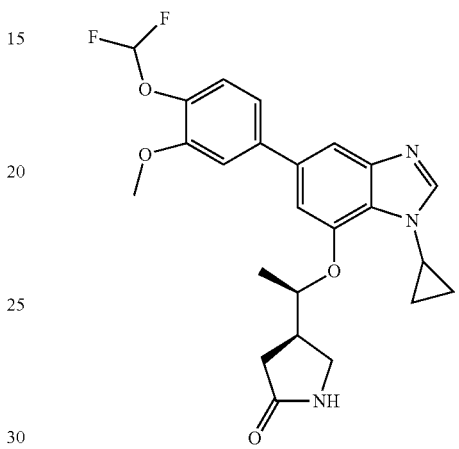

Preparation of (R)-4-((R)-1-((1-cyclopropyl-5-(4-(difluoromethoxy)-3-methoxyphenyl)-1H-benzo[d]imidazol-7-yl)oxy)ethyl)pyrrolidin-2-one(GS0697836): Prepared by Suzuki coupling reaction procedure, as previously described for the synthesis of (R)-4-((R)-1-((1-cyclopropyl-5-phenyl-1H-benzo[d]imidazol-7-yl)oxy)ethyl)pyrrolidin-2-one:, using instead 2-(4-(difluoromethoxy)-3-methoxyphenyl)-4,4,5,5-tetramethyl-1,3,2-dioxaborolane (123.6 mg, 0.412 mmol) as a starting material to afford 60.0 mg (47.8%) of (R)-4-((R)-1-((1-cyclopropyl-5-(4-(difluoromethoxy)-3-methoxyphenyl)-1H-benzo[d]imidazol-7-yl)oxy)ethyl)pyrrolidin-2-one: (GS0697836). 1H NMR (300 MHz, DMSO-d6) δ 8.09 (s, 1H), 7.58 (s, 1H), 7.47 (d, J=1.2 Hz, 1H), 7.37 (d, J=1.8, 1H), 7.26-7.19 (m, 2H), 7.06 (t, J=8.4 Hz, 1H). 7.06 (t, J=75 Hz, 1H), 7.05 (s, 1H), 4.88-4.82 (m, 1H), 3.92 (s, 3H), 3.72-3.65 (m, 1H), 3.38 (t, J=9.3 Hz, 1H), 3.18 (dd, J=6.3, 6.9 Hz, 1H), 2.83-2.76 (m, 1H), 2.39-2.21 (m, 2H), 1.30 (d, J=6 Hz, 3H), 1.15-0.99 (m, 4H), LCMS-ESI+ (m/z): [M+H]+ calcd for C24H25F2N3O4:457.18; found 458.17.

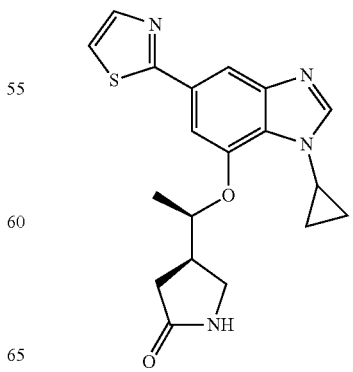

Preparation of (R)-4-((R)-1-((1-cyclopropyl-5-(thiazol-2-yl)-1H-benzo[d]imidazol-7-yl)oxy)ethyl)pyrrolidin-2-one: To a microwave tube equipped with a stifling bar, (R)-4-((R)-1-((1-cyclopropyl-5-(4,4,5,5-tetramethyl-1,3,2-dioxaborolan-2-yl)-1H-benzo[d]imidazol-7-yl)oxy)ethyl)pyrrolidin-2-one: (300 mg, 0.729 mmol), 2-bromo-4-chlorothiazole (144.8 mg, 0.729 mmol), 1,2-dimethoxyethane (3 mL), 1 N Na$_2$CO$_3$ aqueous solution (2.41 mL, 2.41 mmol) were added, the mixture was bubbled N$_2$ for 5 minutes before Pd(PPh$_3$)$_4$ (84.3 mg, 0.073 mmol) was added. The tube was sealed and heated in an oil bath at 100° C. for 2.5 hrs. DCM (200 mL) was added and the resulting mixture was washed with saturated NaHCO$_3$ aqueous solution (20 mL×4), brine (20 mL×1), dried over anhydrous Na$_2$SO$_4$, filtered, removed solvents in vacuo. The resulting residue was passed a ISCO silica gel column (MeOH:DCM=5:95) to give yellow solids, 16.4 mg (yield 6.1%). $^1$H NMR (300 MHz, DMSO-d$_6$) δ 8.18 (s, 1H), 7.88 (d, J=3.3 Hz, 1H), 7.73 (d, J=3.3 Hz, 1H), 7.62-7.57 (m, 2H), 7.45-7.42 (m, 1H), 4.82 (p, J=5.9 Hz, 1H), 3.72 (m, 1H), 3.45-3.36 (m, 1H), 3.27-3.15 (m, 1H), 2.90-2.74 (m, 1H), 2.37-2.20 (m, 2H), 1.34 (d, J=6.0 Hz, 3H), 1.16-1.09 (m, 2H), 1.09-0.98 (m, 2H) ppm; MS (ESI+) m/z 369 (M+H).

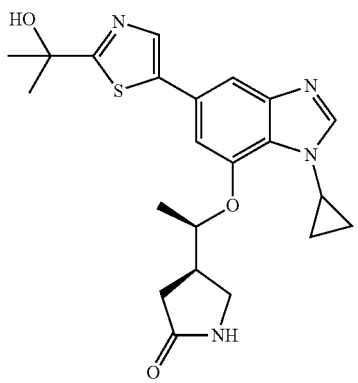 [SMILES: C[C@@H](Oc1cc(-c2cnc(C(C)(C)O)s2)cc2ncn(C3CC3)c12)[C@H]1CNC(=O)C1]

Preparation of (R)-4-((R)-1-((1-cyclopropyl-5-(2-(2-hydroxypropan-2-yl)thiazol-5-yl)-1H-benzo[d]imidazol-7-yl)oxy)ethyl)pyrrolidin-2-one: To a microwave tube equipped with a stirring bar, (R)-4-((R)-1-((1-cyclopropyl-5-(4,4,5,5-tetramethyl-1,3,2-dioxaborolan-2-yl)-1H-benzo[d]imidazol-7-yl)oxy)ethyl)pyrrolidin-2-one (100 mg, 0.243 mmol), 2-(5-bromothiazol-2-yl)propan-2-ol (80 mg, 0.36 mmol), 1,2-dimethoxyethane (3 mL), 1 N Na$_2$CO$_3$ aqueous solution (1.08 mL, 1.08 mmol) were added, the mixture was bubbled N$_2$ for 5 minutes before Pd(PPh$_3$)$_4$ (20.8 mg, 0.018 mmol) was added. The tube was sealed and heated in an oil bath at 100° C. for 2 hrs. DCM (200 mL) was added and the resulting mixture was washed with saturated NaHCO$_3$ aqueous solution (20 mL×4), brine (20 mL×1), dried over anhydrous Na$_2$SO$_4$, filtered, removed solvents in vacuo. The resulting residue was passed a ISCO silica gel column (MeOH:DCM=5:95) to give off-white solids, 51.5 mg (yield 33.5%). $^1$H NMR (300 MHz, DMSO-d$_6$) δ 8.12 (s, 1H), 8.01 (s, 1H), 7.60 (s, 1H), 7.41 (d, J=1.2 Hz, 1H), 7.05 (m, 1H), 5.99 (s, 1H), 4.85 (m, 1H), 3.69 (m, 1H), 3.40-3.35 (m, 1H), 3.22-3.16 (m, 1H), 2.87-2.75 (m, 1H), 2.40-2.20 (m, 2H), 1.53 (s, 6H), 1.31 (d, J=6.0 Hz, 3H), 1.14-1.07 (m, 2H), 1.06-0.97 (m, 2H) ppm; MS (ESI+) m/z 427.18 (M+H).

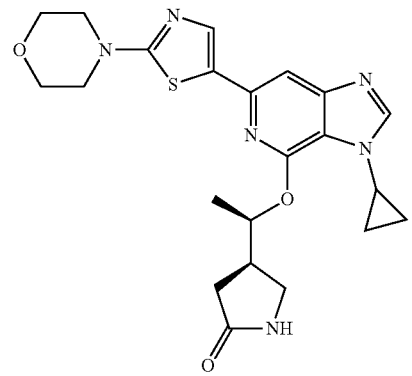

Preparation of (R)-4-((R)-1-((3-cyclopropyl-6-(2-morpholinothiazol-5-yl)-3H-imidazo[4,5-c]pyridin-4-yl)oxy)ethyl)pyrrolidin-2-one: To a microwave tube equipped with a stirring bar, (R)-4-((R)-1-((3-cyclopropyl-6-(4,4,5,5-tetramethyl-1,3,2-dioxaborolan-2-yl)-3H-imidazo[4,5-c]pyridin-4-yl)oxy)ethyl)pyrrolidin-2-one: (165.5 mg, 0.401 mmol), 4-(5-bromothiazol-2-yl)morpholine (120 mg, 0.482 mmol), 1,2-dimethoxyethane (2 mL), 1 N Na$_2$CO$_3$ aqueous solution (1.20 mL, 1.20 mmol) were added, the mixture was bubbled N$_2$ for 5 minutes before Pd(PPh$_3$)$_4$ (23.2 mg, 0.02 mmol) was added. The tube was sealed and heated in an oil bath at 100° C. for 2 hrs. DCM (200 mL) was added and the resulting mixture was washed with saturated NaHCO$_3$ aqueous solution (20 mL×4), brine (20 mL×1), dried over anhydrous Na$_2$SO$_4$, filtered, removed solvents in vacuo. The resulting residue was passed a ISCO silica gel column (MeOH:DCM=5:95) to give brown solids, 28.3 mg (yield 15.5%). $^1$H NMR (300 MHz, DMSO-d$_6$) δ 8.25 (s, 1H), 7.81 (s, 1H), 7.59 (s, 1H), 7.56 (s, 1H), 5.38 (p, J=5.9 Hz, 1H), 3.76-3.69 (m, 4H), 3.69-3.60 (m, 1H), 3.42 (m, 4H), 3.40-3.36 (m, 1H), 3.23-3.13 (m, 1H), 2.93-2.71 (m, 1H), 2.33-2.30 (m, 2H), 1.39 (d, J=6.1 Hz, 3H), 1.12-1.09 (m, 2H), 1.09-1.02 (m, 2H) ppm; MS (ESI+) m/z 455.18 (M+H).

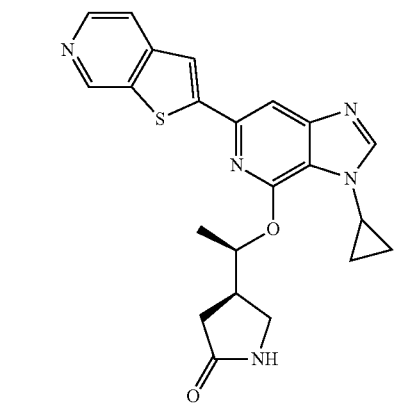 [SMILES: C[C@@H](Oc1nc(-c2cc3ccncc3s2)cc2ncn(C3CC3)c12)[C@H]1CNC(=O)C1]

Preparation of (4R)-4-((1R)-1-((3-cyclopropyl-6-(2,3-dihydrothieno[2,3-c]pyridin-2-yl)-3H-imidazo[4,5-c]pyridin-4-yl)oxy)ethyl)pyrrolidin-2-one: To a microwave tube equipped with a stirring bar, (R)-4-((R)-1-((3-cyclopropyl-6-(4,4,5,5-tetramethyl-1,3,2-dioxaborolan-2-yl)-3H-imidazo[4,5-c]pyridin-4-yl)oxy)ethyl)pyrrolidin-2-one: (165.5 mg, 0.401 mmol), 2-bromothieno[2,3-c]pyridine (128.9 mg, 0.602 mmol), 1,2-dimethoxyethane (2 mL), 1 N Na$_2$CO$_3$ aqueous solution (1.20 mL, 1.20 mmol) were added, the mixture was bubbled N₂ for 5 minutes before Pd(PPh₃)₄ (23.2 mg, 0.02 mmol) was added. The tube was sealed and heated in an oil bath at 100° C. for 2 hrs. DCM (200 mL) was added and the resulting mixture was washed with saturated NaHCO₃ aqueous solution (20 mL×4), brine (20 mL×1), dried over anhydrous Na₂SO₄, filtered, removed solvents in vacuo. The resulting residue was passed a ISCO silica gel column (MeOH: DCM=5:95) to give brown solids, 37.4 mg (yield 22.2%). ¹H NMR (300 MHz, DMSO-d₆) δ 9.21 (s, 1H), 8.44 (d, J=5.5 Hz, 1H), 8.38 (s, 1H), 8.14 (s, 1H), 8.09 (s, 1H), 7.77 (dd, J=5.5, 1.1 Hz, 1H), 7.59 (s, 1H), 5.52 (p, J=6.0 Hz, 1H), 3.72 (m, 1H), 3.50-3.36 (m, 1H), 3.24 (m, 1H), 2.99-2.80 (m, 1H), 2.36 (dd, J=8.6, 1.3 Hz, 2H), 1.48 (d, J=6.1 Hz, 3H), 1.15 (m, 2H), 1.12-1.00 (m, 2H) ppm; MS (ESI+) m/z 420.14 (M+H).

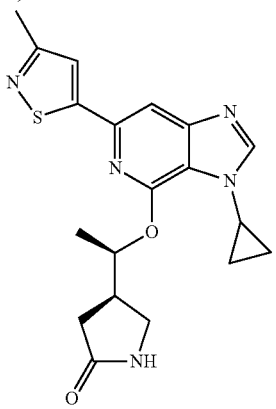

Preparation of (R)-4-((R)-1-((3-cyclopropyl-6-(3-methylisothiazol-5-yl)-3H-imidazo[4,5-c]pyridin-4-yl)oxy)ethyl)pyrrolidin-2-one: To a microwave tube equipped with a stirring bar, (R)-4-((R)-1-((3-cyclopropyl-6-(4,4,5,5-tetramethyl-1,3,2-dioxaborolan-2-yl)-3H-imidazo[4,5-c]pyridin-4-yl)oxy)ethyl)pyrrolidin-2-one: (133.6 mg, 0.324 mmol), 5-bromo-3-methylisothiazole (69.2 mg, 0.389 mmol), 1,2-dimethoxyethane (2 mL), 1 N Na₂CO₃ aqueous solution (0.97 mL, 0.97 mmol) were added, the mixture was bubbled N₂ for 5 minutes before Pd(PPh₃)₄ (18.7 mg, 0.016 mmol) was added. The tube was sealed and heated in an oil bath at 100° C. for 2 hrs. DCM (200 mL) was added and the resulting mixture was washed with saturated NaHCO₃ aqueous solution (20 mL×4), brine (20 mL×1), dried over anhydrous Na₂SO₄, filtered, removed solvents in vacuo. The resulting residue was passed a ISCO silica gel column (MeOH:DCM=5:95) to give white solids, 7.9 mg (yield 6.4%). ¹H NMR (300 MHz, DMSO-d₆) δ 8.35 (s, 1H), 7.88 (s, 1H), 7.74 (s, 1H), 7.57 (s, 1H), 5.45-5.32 (m, 1H), 3.70 (m, 1H), 3.41 (t, J=9.1 Hz, 1H), 3.21 (dd, J=9.7, 6.6 Hz, 1H), 2.90-2.80 (m, 1H), 2.44 (s, 3H), 2.33 (d, J=8.8 Hz, 2H), 1.42 (d, J=6.1 Hz, 3H), 1.14 (m, 2H), 1.10-0.98 (m, 2H) ppm; MS (ESI+) m/z 384.88 (M+H).

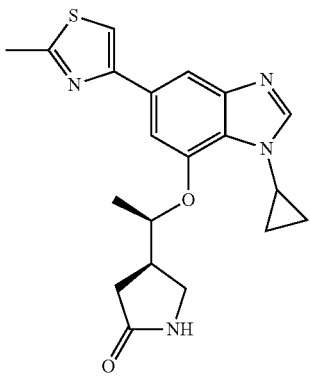 [SMILES: Cc1nc(-c2cc(O[C@H](C)[C@H]3CNC(=O)C3)c3c(c2)ncn3C2CC2)cs1]

Preparation of (R)-4-((R)-1-((1-cyclopropyl-5-(2-methylthiazol-4-yl)-1H-benzo[d]imidazol-7-yl)oxy)ethyl)pyrrolidin-2-one: To a microwave tube equipped with a stifling bar, (R)-4-((R)-1-((1-cyclopropyl-5-(4,4,5,5-tetramethyl-1,3,2-dioxaborolan-2-yl)-1H-benzo[d]imidazol-7-yl)oxy)ethyl)pyrrolidin-2-one: (120 mg, 0.292 mmol), 4-bromo-2-methylthiazole (103.9 mg, 0.584 mmol), 1,2-dimethoxyethane (3 mL), 1 N Na₂CO₃ aqueous solution (0.96 mL, 0.96 mmol) were added, the mixture was bubbled N₂ for 5 minutes before Pd(PPh₃)₄ (33.7 mg, 0.029 mmol) was added. The tube was sealed and heated in an oil bath at 100° C. for 2 hrs. DCM (200 mL) was added and the resulting mixture was washed with saturated NaHCO₃ aqueous solution (20 mL×4), brine (20 mL×1), dried over anhydrous Na₂SO₄, filtered, removed solvents in vacuo. The resulting residue was passed a ISCO silica gel column (MeOH:DCM=5:95) to give white solids, 9.0 mg. ¹H NMR (300 MHz, DMSO-d₆) δ 8.94 (s, 1H), 8.13 (s, 1H), 7.59 (s, 1H), 7.41 (d, J=1.2 Hz, 1H), 7.14 (d, J=1.3 Hz, 1H), 4.74 (p, J=6.0 Hz, 1H), 3.72 (tt, J=7.2, 3.9 Hz, 1H), 3.45-3.35 (m, 1H), 3.23-3.14 (m, 1H), 2.82 (m, 1H), 2.60 (s, 3H), 2.43-2.19 (m, 2H), 1.32 (d, J=6.0 Hz, 3H), 1.11 (m, 2H), 1.08-0.98 (m, 2H) ppm; MS (ESI+) m/z 384.24 (M+H).

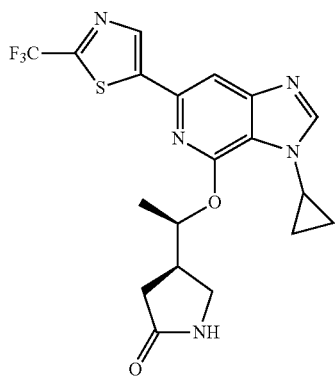 [SMILES: C[C@@H](Oc1nc(-c2cnc(C(F)(F)F)s2)cc2ncn(C3CC3)c12)[C@H]1CNC(=O)C1]

Preparation of (R)-4-((R)-1-((3-cyclopropyl-6-(2-(trifluoromethyl)thiazol-5-yl)-3H-imidazo[4,5-c]pyridin-4-yl)oxy)ethyl)pyrrolidin-2-one: To a microwave tube equipped with a stifling bar, (R)-4-((R)-1-((3-cyclopropyl-6-(4,4,5,5-tetramethyl-1,3,2-dioxaborolan-2-yl)-3H-imidazo[4,5-c]pyridin-4-yl)oxy)ethyl)pyrrolidin-2-one: (133.6 mg, 0.324 mmol), 5-bromo-2-(trifluoromethyl)thiazole (90.2 mg, 0.389 mmol), 1,2-dimethoxyethane (2 mL), 1 N Na₂CO₃ aqueous solution (0.97 mL, 0.97 mmol) were added, the mixture was bubbled N₂ for 5 minutes before Pd(PPh₃)₄ (18.7 mg, 0.016 mmol) was added. The tube was sealed and heated in an oil bath at 100° C. for 2 hrs. DCM (200 mL) was added and the resulting mixture was washed with saturated NaHCO₃ aqueous solution (20 mL×4), brine (20 mL×1), dried over anhydrous Na₂SO₄, filtered, removed solvents in vacuo. The resulting residue was passed a ISCO silica gel column (MeOH: DCM=5:95) to give off-white solids, 22.8 mg (yield 16.1%). ¹H NMR (300 MHz, DMSO-d₆) δ 8.74 (m, 1H), 8.38 (d, J=0.5 Hz, 1H), 8.09 (s, 1H), 7.57 (broad s, 1H), 5.43 (p, J=6.0 Hz, 1H), 3.71 (m, 1H), 3.41 (m, 1H), 3.26-3.18 (m, 1H), 2.82-2.87 (m, 1H), 2.35-2.31 (m, 2H), 1.42 (d, J=6.2 Hz, 3H), 1.14 (m, 2H), 1.11-0.98 (m, 2H) ppm; MS (ESI+) m/z 438 (M+H).

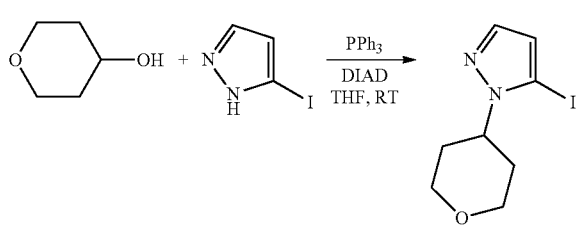 [SMILES: OC1CCOCC1 ; Ic1ccn[nH]1 ; Ic1ccnn1C1CCOCC1 ; "PPh3"]

Preparation of 5-iodo-1-(tetrahydro-2H-pyran-4-yl)-1H-pyrazole: To a round-bottomed flask equipped with a stirring bar and a $N_2$ tee, tetrahydro-2H-pyran-4-ol (1.05 g, 10.31 mmol), 5-iodo-1H-pyrazole (2.00 g, 10.31 mmol), triphenylphosphine (3.33 g, 12.68 mmol), (g, mmol) and THF (22.9 mL) were added. Followed by the addition of DIAD (2.71 g, 13.4 mmol), the resulting mixture was stirred at room temperature for 3 hrs. The mixture was removed most solvents in vauo, and ethyl acetate (200 mL) was added. The resulting solution were washed with $H_2O$ (50 mL×1), brine (50 mL×1), and dried over $Na_2SO_4$. The organic phase was filtered and removed solvent in vacuo, and passed a silica gel column (ethyl acetate: hexanes=0:100 to 100:0), off-white solids were obtained as the desired product. 920 mg (yield 32.1%). $^1$H NMR (300 MHz, DMSO-$d_6$) δ 7.63-7.47 (m, 1H), 6.62-6.38 (m, 1H), 4.48 (tt, J=11.4, 4.3 Hz, 1H), 3.96 (ddt, J=11.8, 4.7, 1.2 Hz, 2H), 3.49 (td, J=12.0, 2.1 Hz, 2H), 2.00 (dddd, J=13.1, 12.0, 11.2, 4.6 Hz, 2H), 1.90-1.71 (m, 2H) ppm; MS (ESI+) m/z 279.30 (M+H).

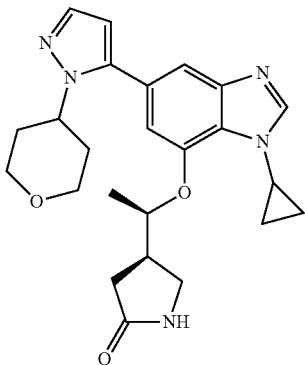 [SMILES: C[C@@H](Oc1cc(-c2ccnn2C2CCOCC2)cc2ncn(C3CC3)c12)[C@H]1CNC(=O)C1]

Preparation of (R)-4-((R)-1-((1-cyclopropyl-5-(1-(tetrahydro-2H-pyran-4-yl)-1H-pyrazol-5-yl)-1H-benzo[d]imidazol-7-yl)oxy)ethyl)pyrrolidin-2-one: To a microwave tube equipped with a stirring bar, (R)-4-((R)-1-((1-cyclopropyl-5-(4,4,5,5-tetramethyl-1,3,2-dioxaborolan-2-yl)-1H-benzo[d]imidazol-7-yl)oxy)ethyl)pyrrolidin-2-one (120 mg, 0.292 mmol), 5-iodo-1-(tetrahydro-2H-pyran-4-yl)-1H-pyrazole (97.4 mg, 0. 0.35 mmol), 1,2-dimethoxyethane (2 mL), 1 N $Na_2CO_3$ aqueous solution (0.88 mL, 0.88 mmol) were added, the mixture was bubbled $N_2$ for 5 minutes before $Pd(PPh_3)_4$ (16.9 mg, 0.015 mmol) was added. The tube was sealed and heated in an oil bath at 100° C. for 2 hrs. DCM (200 mL) was added and the resulting mixture was washed with saturated $NaHCO_3$ aqueous solution (20 mL×4), brine (20 mL×1), dried over anhydrous $Na_2SO_4$, filtered, removed solvents in vacuo. The resulting residue was passed a ISCO silica gel column (MeOH:DCM=5:95) to give white solids, 72.6 mg (yield 57.1%). $^1$H NMR (300 MHz, DMSO-$d_6$) δ 8.18 (s, 1H), 7.59 (broad s, 1H), 7.53 (d, J=1.5 Hz, 1H), 7.21 (d, J=1.1 Hz, 1H), 6.82 (broad s, 1H), 6.31 (d, J=1.8 Hz, 1H), 4.78 (p, J=5.9 Hz, 1H), 4.51-4.34 (m, 1H), 3.98-3.84 (m, 2H), 3.73 (dddd, J=7.9, 3.9, 2.6, 0.6 Hz, 1H), 3.43-3.36 (m, 2H), 3.35 (m, 1H), 3.20-3.12 (m, 1H), 2.93-2.73 (m, 1H), 2.41-2.24 (m, 2H), 2.25-2.03 (m, 2H), 1.94-1.69 (m, 2H), 1.30 (d, J=5.9 Hz, 3H), 1.17-1.09 (m, 2H), 1.09-0.97 (m, 2H) ppm; MS (ESI+) m/z 436.16 (M+H).

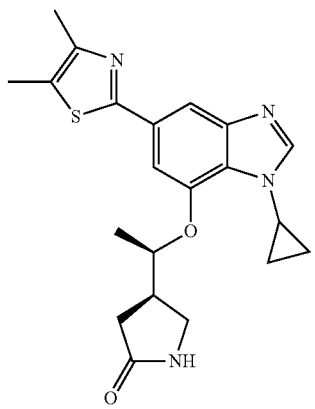 [SMILES: Cc1nc(-c2cc(O[C@H](C)[C@H]3CNC(=O)C3)c3c(c2)ncn3C2CC2)sc1C]

Preparation of (R)-4-((R)-1-((1-cyclopropyl-5-(4,5-dimethylthiazol-2-yl)-1H-benzo[d]imidazol-7-yl)oxy)ethyl)pyrrolidin-2-one: To a microwave tube equipped with a stirring bar, (R)-4-((R)-1-((1-cyclopropyl-5-(4,4,5,5-tetramethyl-1,3,2-dioxaborolan-2-yl)-1H-benzo[d]imidazol-7-yl)oxy)ethyl)pyrrolidin-2-one: (120 mg, 0.292 mmol), 2-bromo-4,5-dimethylthiazole (112.1 mg, 0.584 mmol), 1,2-dimethoxyethane (2 mL), 1 N $Na_2CO_3$ aqueous solution (0.73 mL, 0.73 mmol) were added, the mixture was bubbled $N_2$ for 5 minutes before $Pd(PPh_3)_4$ (14.0 mg, 0.012 mmol) were added. The tube was sealed and heated in an oil bath at 100° C. for 2 hrs. DCM (200 mL) was added and the resulting mixture was washed with saturated $NaHCO_3$ aqueous solution (20 mL×4), brine (20 mL×1), dried over anhydrous $Na_2SO_4$, filtered, removed solvents in vacuo. The resulting residue was passed a ISCO silica gel column (MeOH:DCM=5:95) to give off-white solids, 56.0 mg (yield 48.4%). $^1$H NMR (300 MHz, DMSO-$d_6$) δ 8.15 (s, 1H), 7.59 (s, 1H), 7.58 (d, J=1.2 Hz, 1H), 7.32 (d, J=1.4 Hz, 1H), 4.79 (p, J=6.0 Hz, 1H), 3.70 (m, 1H), 3.44-3.35 (m, 1H), 3.25-3.15 (m, 1H), 2.91-2.72 (m, 1H), 2.37 (s, 3H), 2.32 (s, 3H), 2.41-2.22 (m, 2H), 1.33 (d, J=6.0 Hz, 3H), 1.16-1.07 (m, 2H), 1.07-0.97 (m, 2H) ppm; MS (ESI+) m/z 397.14 (M+H).

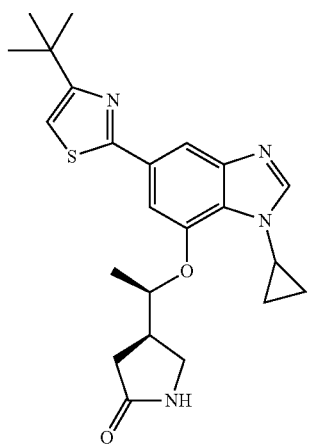 [SMILES: C[C@@H](Oc1cc(-c2nc(C(C)(C)C)cs2)cc2ncn(C3CC3)c12)[C@H]1CNC(=O)C1]

Preparation of (R)-4-((R)-1-((5-(4-(tert-butyl)thiazol-2-yl)-1-cyclopropyl-1H-benzo[d]imidazol-7-yl)oxy)ethyl)pyrrolidin-2-one: To a microwave tube equipped with a stirling bar, (R)-4-((R)-1-((1-cyclopropyl-5-(4,4,5,5-tetramethyl-1,3,2-dioxaborolan-2-yl)-1H-benzo[d]imidazol-7-yl)oxy)ethyl)pyrrolidin-2-one: (120 mg, 0.292 mmol), 2-bromo-4-(tert-butyl)thiazole (128.5 mg, 0.584 mmol), 1,2-dimethoxyethane (2 mL), 1 N Na$_2$CO$_3$ aqueous solution (0.73 mL, 0.73 mmol) were added, the mixture was bubbled N$_2$ for 5 minutes before Pd(PPh$_3$)$_4$ (14.0 mg, 0.012 mmol) was added. The tube was sealed and heated in an oil bath at 100° C. for 2 hrs. DCM (200 mL) was added and the resulting mixture was washed with saturated NaHCO$_3$ aqueous solution (20 mL×4), brine (20 mL×1), dried over anhydrous Na$_2$SO$_4$, filtered, removed solvents in vacuo. The resulting residue was passed a ISCO silica gel column (MeOH:DCM=5:95) to give off-white solids, 44.5 mg (yield 35.9%). $^1$H NMR (300 MHz, DMSO-d$_6$) δ 8.16 (s, 1H), 7.65 (d, J=1.2 Hz, 1H), 7.61-7.58 (m, 1H), 7.59 (s, 1H), 7.35 (d, J=1.2 Hz, 1H), 4.81 (p, J=6.0 Hz, 1H), 3.77-3.65 (m, 1H), 3.45-3.35 (m, 1H), 3.25-3.14 (m, 1H), 2.89-2.74 (m, 1H), 2.41-2.20 (m, 2H), 1.35-1.29 (d, J=6 Hz, 3H), 1.16-1.08 (m, 2H), 1.08-0.98 (m, 2H) ppm; MS (ESI+) m/z 425.16 (M+H).

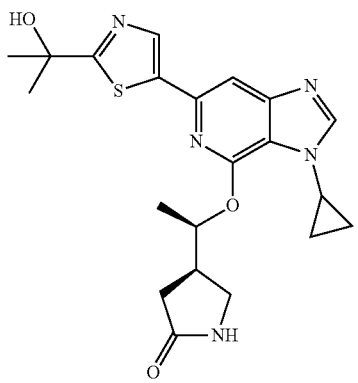 [SMILES: C[C@@H](Oc1nc(-c2cnc(C(C)(C)O)s2)cc2ncn(C3CC3)c12)[C@H]1CNC(=O)C1]

Preparation of (R)-4-((R)-1-((3-cyclopropyl-6-(2-(2-hydroxypropan-2-yl)thiazol-5-yl)-3H-imidazo[4,5-c]pyridin-4-yl)oxy)ethyl)pyrrolidin-2-one: To a microwave tube equipped with a stirring bar, (R)-4-((R)-1-((3-cyclopropyl-6-(4,4,5,5-tetramethyl-1,3,2-dioxaborolan-2-yl)-3H-imidazo[4,5-c]pyridin-4-yl)oxy)ethyl)pyrrolidin-2-one: (167.0 mg, 0.405 mmol), 2-(5-bromothiazol-2-yl)propan-2-ol (90.0 mg, 0.405 mmol), 1,2-dimethoxyethane (2 mL), 1 N Na$_2$CO$_3$ aqueous solution (0.55 mL, 0.55 mmol) were added, the mixture was bubbled N$_2$ for 5 minutes before Pd(PPh$_3$)$_4$ (10.6 mg, 0.009 mmol) was added. The tube was sealed and heated in an oil bath at 100° C. for 2 hrs. DCM (200 mL) was added and the resulting mixture was washed with saturated NaHCO$_3$ aqueous solution (20 mL×4), brine (20 mL×1), dried over anhydrous Na$_2$SO$_4$, filtered, removed solvents in vacuo. The resulting residue was passed a ISCO silica gel column (MeOH:DCM=5:95) to give brown solids, 26.1 mg (yield 15.1%). $^1$H NMR (300 MHz, DMSO-d$_6$) δ 8.31 (s, 1H), 8.22 (s, 1H), 7.77 (s, 1H), 7.60-7.53 (broad s, 1H), 5.97 (s, 1H), 5.52-5.36 (m, 1H), 3.73-3.64 (m, 1H), 3.46-3.35 (m, 1H), 3.24-3.15 (m, 1H), 2.94-2.75 (m, 1H), 2.36-2.28 (m, 2H), 1.52 (d, J=1.2 Hz, 6H), 1.41 (d, J=6.2 Hz, 3H), 1.17-1.10 (m, 2H), 1.10-0.99 (m, 2H) ppm; MS (ESI+) m/z 428.06 (M+H).

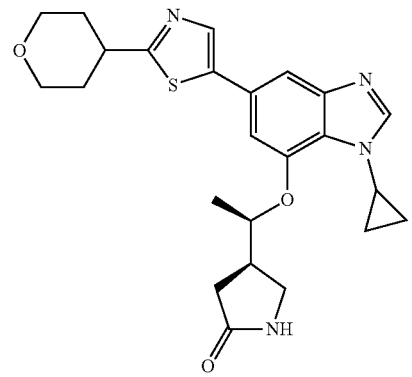 [SMILES: C[C@@H](Oc1cc(-c2cnc(C3CCOCC3)s2)cc2ncn(C3CC3)c12)[C@H]1CNC(=O)C1]

Preparation of (R)-4-((R)-1-((1-cyclopropyl-5-(2-(tetrahydro-2H-pyran-4-yl)thiazol-5-yl)-1H-benzo[d]imidazol-7-yl)oxy)ethyl)pyrrolidin-2-one: To a microwave tube equipped with a stirring bar, (R)-4-((R)-1-((1-cyclopropyl-5-(4,4,5,5-tetramethyl-1,3,2-dioxaborolan-2-yl)-1H-benzo[d]imidazol-7-yl)oxy)ethyl)pyrrolidin-2-one (100 mg, 0.243 mmol), 5-bromo-2-(tetrahydro-2H-pyran-4-yl)thiazole (65.5 mg, 0.264 mmol), 1,2-dimethoxyethane (2 mL), 1 N Na$_2$CO$_3$ aqueous solution (0.60 mL, 0.60 mmol) were added, the mixture was bubbled N$_2$ for 5 minutes before Pd(PPh$_3$)$_4$ (11.6 mg, 0.01 mmol) was added. The tube was sealed and heated in an oil bath at 100° C. for 2 hrs. DCM (200 mL) was added and the resulting mixture was washed with saturated NaHCO$_3$ aqueous solution (20 mL×4), brine (20 mL×1), dried over anhydrous Na$_2$SO$_4$, filtered, removed solvents in vacuo. The resulting residue was passed a ISCO silica gel column (MeOH:DCM=5:95) to give off-white solids, 57.5 mg (yield 52.3%). $^1$H NMR (300 MHz, DMSO-d$_6$) δ 8.12 (s, 1H), 8.08 (s, 1H), 7.60 (s, 1H), 7.40 (d, J=1.2 Hz, 1H), 7.07 (d, J=1.3 Hz, 1H), 4.85 (p, J=5.9 Hz, 1H), 4.00-3.88 (m, 2H), 3.76-3.62 (m, 1H), 3.55-3.42 (m, 2H), 3.42-3.36 (m, 1H), 3.28-3.14 (m, 1H), 2.88-2.71 (m, 1H), 2.41-2.19 (m, 2H), 2.06-1.93 (m, 2H), 1.85-1.65 (m, 2H), 1.31 (d, J=6.0 Hz, 3H), 1.14-1.06 (m, 2H), 1.06-0.96 (m, 2H) ppm; MS (ESI+) m/z 453.09 (M+H).

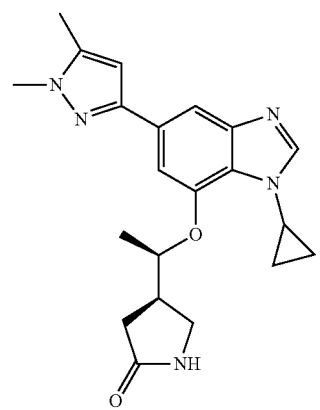 [SMILES: Cc1cc(-c2cc(O[C@H](C)[C@H]3CNC(=O)C3)c3c(c2)ncn3C2CC2)nn1C]

Preparation of (R)-4-((R)-1-((1-cyclopropyl-5-(1,5-dimethyl-1H-pyrazol-3-yl)-1H-benzo[d]imidazol-7-yl)oxy)ethyl)pyrrolidin-2-one: To a microwave tube equipped with a stirring bar, (R)-4-((R)-1-((1-cyclopropyl-5-(4,4,5,5-tetramethyl-1,3,2-dioxaborolan-2-yl)-1H-benzo[d]imidazol-7-yl)oxy)ethyl)pyrrolidin-2-one: (120 mg, 0.292 mmol), 3-iodo-1,5-dimethyl-1H-pyrazole (129.6 mg, 0.584 mmol), 1,2-dimethoxyethane (2 mL), 1 N Na$_2$CO$_3$ aqueous solution (0.96 mL, 0.96 mmol) were added, the mixture was bubbled N$_2$ for 5 minutes before Pd(PPh$_3$)$_4$ (33.7 mg, 0.029 mmol) was added. The tube was sealed and heated in an oil bath at 100° C. for 2 hrs. DCM (200 mL) was added and the resulting mixture was washed with saturated NaHCO$_3$ aqueous solution (20 mL×4), brine (20 mL×1), dried over anhydrous Na$_2$SO$_4$, filtered, removed solvents in vacuo. The resulting residue was passed a ISCO silica gel column (MeOH:DCM=5:95) to give off-white solids, 69.2 mg (yield 62.5%). $^1$H NMR (300 MHz, DMSO-d$_6$) δ 8.04 (s, 1H), 7.59 (broad s, 1H), 7.49 (d, J=1.1 Hz, 1H), 7.23 (d, J=1.2 Hz, 1H), 6.50 (s, 1H), 4.75 (p, J=6.0 Hz, 1H), 3.75 (s, 3H), 3.72-3.63 (m, 1H), 3.44-3.35 (m, 1H), 3.26-3.15 (m, 1H), 2.91-2.71 (m, 1H), 2.41-2.20 (m, 2H), 2.28 (s, 3H), 1.31 (d, J=6.0 Hz, 3H), 1.13-1.05 (m, 2H), 1.05-0.95 (m, 1H) ppm; MS (ESI+) m/z 381.01 (M+H).

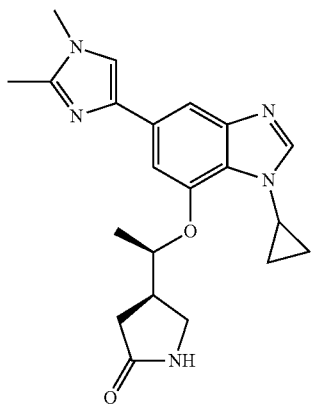 [SMILES: Cc1nc(-c2cc(O[C@H](C)[C@H]3CNC(=O)C3)c3c(c2)ncn3C2CC2)cn1C]

Preparation of (R)-4-((R)-1-((1-cyclopropyl-5-(1,2-dimethyl-1H-imidazol-4-yl)-1H-benzo[d]imidazol-7-yl)oxy)ethyl)pyrrolidin-2-one: To a microwave tube equipped with a stifling bar, (R)-4-((R)-1-((1-cyclopropyl-5-(4,4,5,5-tetramethyl-1,3,2-dioxaborolan-2-yl)-1H-benzo[d]imidazol-7-yl)oxy)ethyl)pyrrolidin-2-one: (120 mg, 0.292 mmol), 4-bromo-1,2-dimethyl-1H-imidazole (102.1 mg, 0.584 mmol), 1,2-dimethoxyethane (2 mL), 1 N Na$_2$CO$_3$ aqueous solution (0.96 mL, 0.96 mmol) were added, the mixture was bubbled N$_2$ for 5 minutes before Pd(PPh$_3$)$_4$ (33.7 mg, 0.029 mmol) was added. The tube was sealed and heated in an oil bath at 100° C. for 2 hrs. DCM (200 mL) was added and the resulting mixture was washed with saturated NaHCO$_3$ aqueous solution (20 mL×4), brine (20 mL×1), dried over anhydrous Na$_2$SO$_4$, filtered, removed solvents in vacuo. The resulting residue was passed a ISCO silica gel column (MeOH: DCM=5:95) to give white solids, 19.7 mg (yield 17.8%). $^1$H NMR (300 MHz, DMSO-d$_6$) δ 7.99 (s, 1H), 7.59 (s, 1H), 7.47 (s, 1H), 7.45 (d, J=1.1 Hz, 1H), 7.20 (m, 1H), 4.73 (p, J=5.9 Hz, 1H), 3.71-3.61 (m, 1H), 3.56 (s, 3H), 3.45-3.36 (m, 1H), 3.23-3.14 (m, 1H), 2.91-2.67 (m, 1H), 2.31 (s, 3H), 2.42-2.19 (m, 2H), 1.30 (d, J=6.0 Hz, 3H), 1.14-1.04 (m, 2H), 1.04-0.93 (m, 2H) ppm; MS (ESI+) m/z 380.12 (M+H).

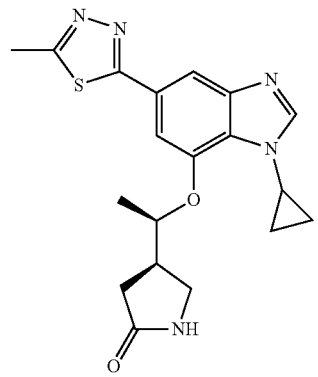 [SMILES: Cc1nnc(-c2cc(O[C@H](C)[C@H]3CNC(=O)C3)c3c(c2)ncn3C2CC2)s1]

Preparation of (R)-4-((R)-1-((1-cyclopropyl-5-(5-methyl-1,3,4-thiadiazol-2-yl)-1H-benzo[d]imidazol-7-yl)oxy)ethyl)pyrrolidin-2-one: To a microwave tube equipped with a stirring bar, (R)-4-((R)-1-((1-cyclopropyl-5-(4,4,5,5-tetramethyl-1,3,2-dioxaborolan-2-yl)-1H-benzo[d]imidazol-7-yl)oxy)ethyl)pyrrolidin-2-one: (120 mg, 0.292 mmol), 2-bromo-5-methyl-1,3,4-thiadiazole (104.5 mg, 0.584 mmol), 1,2-dimethoxyethane (2 mL), 1 N Na$_2$CO$_3$ aqueous solution (0.96 mL, 0.96 mmol) were added, the mixture was bubbled N$_2$ for 5 minutes before Pd(PPh$_3$)$_4$ (33.7 mg, 0.029 mmol) was added. The tube was sealed and heated in an oil bath at 100° C. for 2 hrs. DCM (200 mL) was added and the resulting mixture was washed with saturated NaHCO$_3$ aqueous solution (20 mL×4), brine (20 mL×1), dried over anhydrous Na$_2$SO$_4$, filtered, removed solvents in vacuo. The resulting residue was passed a ISCO silica gel column (MeOH: DCM=5:95) to give light yellow solids, 58.1 mg (yield 51.9%). $^1$H NMR (300 MHz, DMSO-d$_6$) δ 8.22 (s, 1H), 7.69 (d, J=1.2 Hz, 1H), 7.60 (broad s, 1H), 7.44 (d, J=1.3 Hz, 1H), 4.84 (p, J=6.0 Hz, 1H), 3.73 (m, 1H), 3.46-3.36 (m, 1H), 3.26-3.15 (m, 1H), 2.90-2.79 (m, 1H), 2.76 (s, 3H), 2.47-2.20 (m, 2H), 1.34 (d, J=6.0 Hz, 3H), 1.19-1.09 (m, 2H), 1.06 (m, 2H) ppm; MS (ESI+) m/z 384 (M+H).

Preparation of 1-(tert-butyl)-3-iodo-1H-pyrazole: To a round-bottomed flask equipped with a stifling bar and a N$_2$ tee, 3-iodo-1H-pyrazole (2.00 g, 10 mmol), 2-methylpropan-2-ol (7.64 g, 103 mmol), and concentrated sulfuric acid (1.08 g, 11 mmol) were added. The resulting mixture was heated at 100° C. for 3 hrs.

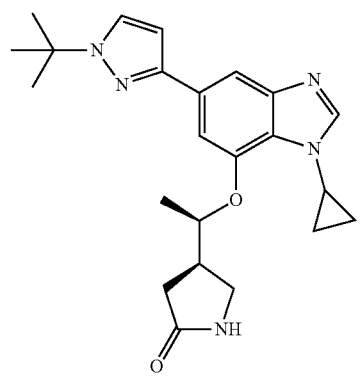 [SMILES: C[C@@H](Oc1cc(-c2ccn(C(C)(C)C)n2)cc2ncn(C3CC3)c12)[C@H]1CNC(=O)C1]

Preparation of (R)-4-((R)-1-((5-(1-(tert-butyl)-1H-pyrazol-3-yl)-1-cyclopropyl-1H-benzo[d]imidazol-7-yl)oxy)ethyl)pyrrolidin-2-one: To a microwave tube equipped with a stirring bar, (R)-4-((R)-1-((1-cyclopropyl-5-(4,4,5,5-tetramethyl-1,3,2-dioxaborolan-2-yl)-1H-benzo[d]imidazol-7-yl)oxy)ethyl)pyrrolidin-2-one: (120 mg, 0.292 mmol), 1-(tert-butyl)-3-iodo-1H-pyrazole (145.9 mg, 0.584 mmol), 1,2-dimethoxyethane (3 mL), 1 N Na$_2$CO$_3$ aqueous solution (0.96 mL, 0.96 mmol) were added, the mixture was bubbled N$_2$ for 5 minutes before Pd(PPh$_3$)$_4$ (33.7 mg, 0.029 mmol) was added. The tube was sealed and heated in an oil bath at 100° C. for 2 hrs. DCM (200 mL) was added and the resulting mixture was washed with saturated NaHCO$_3$ aqueous solution (20 mL×4), brine (20 mL×1), dried over anhydrous Na$_2$SO$_4$, filtered, removed solvents in vacuo. The resulting residue was passed a ISCO silica gel column (MeOH:DCM=5:95) to give yellow solids, 71.6 mg (yield 60.2%). $^1$H NMR (300 MHz, DMSO-d$_6$) δ 8.07 (s, 1H), 7.83 (d, J=2.4 Hz, 1H), 7.59 (broad s, 2H), 7.27 (s, 1H), 6.71 (d, J=2.3 Hz, 1H), 4.78 (p, J=5.9 Hz, 1H), 3.70 (m, 1H), 3.46-3.35 (m, 1H), 3.21 (m, 1H), 2.88-2.72 (m, 1H), 2.41-2.25 (m, 2H), 1.57 (s, 9H), 1.32 (d, J=5.9 Hz, 3H), 1.14-1.06 (m, 2H), 1.06-0.95 (m, 2H) ppm; MS (ESI+) m/z 408 (M+H).

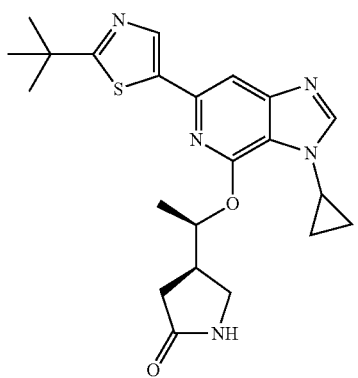 [SMILES: C[C@@H](Oc1nc(-c2cnc(C(C)(C)C)s2)cc2ncn(C3CC3)c12)[C@H]1CNC(=O)C1]

Preparation of (R)-4-((R)-1-((6-(2-(tert-butyl)thiazol-5-yl)-3-cyclopropyl-3H-imidazo[4,5-c]pyridin-4-yl)oxy)ethyl)pyrrolidin-2-one: To a microwave tube equipped with a stirring bar, (R)-4-((R)-1-((3-cyclopropyl-6-(4,4,5,5-tetramethyl-1,3,2-dioxaborolan-2-yl)-3H-imidazo[4,5-c]pyridin-4-yl)oxy)ethyl)pyrrolidin-2-one: (167.0 mg, 0.405 mmol), 5-bromo-2-(tert-butyl)thiazole (133.8 mg, 0.608 mmol), 1,2-dimethoxyethane (2 mL), 1 N Na$_2$CO$_3$ aqueous solution (0.55 mL, 0.55 mmol) were added, the mixture was bubbled N$_2$ for 5 minutes before Pd(PPh$_3$)$_4$ (10.6 mg, 0.009 mmol) was added. The tube was sealed and heated in an oil bath at 100° C. for 2 hrs. DCM (200 mL) was added and the resulting mixture was washed with saturated NaHCO$_3$ aqueous solution (20 mL×4), brine (20 mL×1), dried over anhydrous Na$_2$SO$_4$, filtered, removed solvents in vacuo. The resulting residue was passed a ISCO silica gel column (MeOH:DCM=5:95) to give off-white solids, 9.8 mg (yield 5.7%). $^1$H NMR (300 MHz, DMSO-d$_6$) δ 8.30 (s, 1H), 8.24 (s, 1H), 7.77 (s, 1H), 7.56 (broad s, 1H), 5.43 (m, 1H), 3.73-3.63 (m, 1H), 3.47-3.36 (m, 1H), 3.25-3.14 (m, 1H), 2.93-2.75 (m, 1H), 2.38-2.28 (m, 2H), 1.41 (s, 9H), 1.40-1.39 (m, 3H), 1.17-1.10 (m, 2H), 1.10-0.97 (m, 2H) ppm; MS (ESI+) m/z 426.61 (M+H).

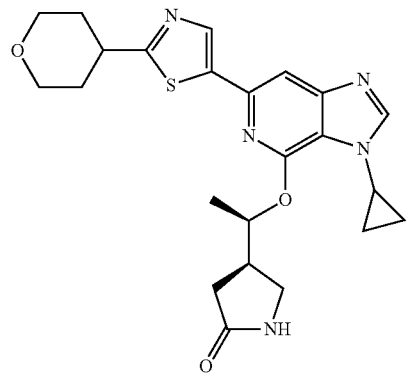

Preparation of (R)-4-((R)-1-((3-cyclopropyl-6-(2-(tetrahydro-2H-pyran-4-yl)thiazol-5-yl)-3H-imidazo[4,5-c]pyridin-4-yl)oxy)ethyl)pyrrolidin-2-one: To a microwave tube equipped with a stirring bar, (R)-4-((R)-1-((3-cyclopropyl-6-(4,4,5,5-tetramethyl-1,3,2-dioxaborolan-2-yl)-3H-imidazo[4,5-c]pyridin-4-yl)oxy)ethyl)pyrrolidin-2-one: (182.8 mg, 0.443 mmol), 5-bromo-2-(tetrahydro-2H-pyran-4-yl)thiazole (50 mg, 0.201 mmol), 1,2-dimethoxyethane (2 mL), 1 N Na$_2$CO$_3$ aqueous solution (0.60 mL, 0.60 mmol) were added, the mixture was bubbled N$_2$ for 5 minutes before Pd(PPh$_3$)$_4$ (11.6 mg, 0.01 mmol) was added. The tube was sealed and heated in an oil bath at 100° C. for 2 hrs. DCM (200 mL) was added and the resulting mixture was washed with saturated NaHCO$_3$ aqueous solution (20 mL×4), brine (20 mL×1), dried over anhydrous Na$_2$SO$_4$, filtered, removed solvents in vacuo. The resulting residue was passed a ISCO silica gel column (MeOH:DCM=5:95) to give light yellow solids, 9.2 mg (yield 10.1%). $^1$H NMR (300 MHz, DMSO-d$_6$) δ 8.31 (s, 1H), 8.28 (s, 1H), 7.79 (s, 1H), 7.57 (broad s, 1H), 5.49-5.35 (m, 1H), 3.94 (dm, J=11.5 Hz, 2H), 3.73-3.63 (m, 1H), 3.52-3.43 (m, 2H), 3.43-3.36 (m, 1H), 3.27-3.15 (m, 2H), 2.92-2.76 (m, 1H), 2.37-2.28 (m, 2H), 2.05-1.92 (m, 2H), 1.85-1.65 (m, 2H), 1.40 (d, J=6.2 Hz, 3H), 1.17-1.09 (m, 2H), 1.10-0.98 (m, 2H) ppm; MS (ESI+) m/z 454.65 (M+H).

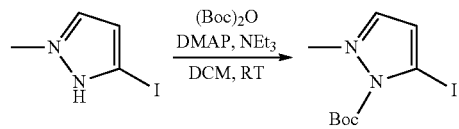

Preparation of tert-butyl 5-iodo-2-methyl-1H-imidazole-1-carboxylate: To a round-bottomed flask equipped with a stirring bar and a N$_2$ tee, 5-iodo-2-methyl-1H-imidazole (1.00 g, 4.81 mmol), di-tert-butyl dicarbonate (1.574 g, 7.212 mmol), DCM (11 mL), NEt$_3$ (2.432 g, 24.04 mmol), and DMAP (58.7 mg, 0.481 mmol) were added. The resulting mixture was heated at room temperature for 1 hr. Water (200 mL) was added and the resulting mixture was extracted with ethyl acetate (50 mL×3), the combined organic phases were washed with H$_2$O (50 mL×1), brine (50 mL×1), and dried over Na$_2$SO$_4$. The organic phase was filtered and removed solvent in vacuo, and passed a silica gel column (ethyl acetate: hexanes=0:100 to 100:0), yellow oil was obtained as the desired product. 1.23 g (yield 83.0%).

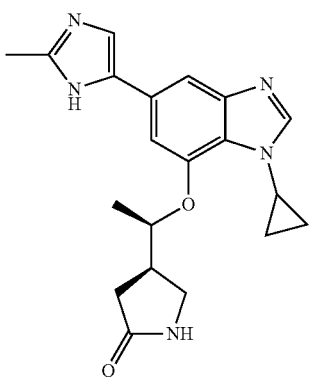 [SMILES: Cc1ncc(-c2cc(O[C@H](C)[C@H]3CNC(=O)C3)c3c(c2)ncn3C2CC2)[nH]1]

Preparation of (R)-4-((R)-1-((1-cyclopropyl-5-(2-methyl-1H-imidazol-5-yl)-1H-benzo[d]imidazol-7-yl)oxy)ethyl)pyrrolidin-2-one: To a microwave tube equipped with a stirring bar, (R)-4-((R)-1-((1-cyclopropyl-5-(4,4,5,5-tetramethyl-1,3,2-dioxaborolan-2-yl)-1H-benzo[d]imidazol-7-yl)oxy)ethyl)pyrrolidin-2-one: (200 mg, 0.486 mmol), tert-butyl 5-iodo-2-methyl-1H-imidazole-1-carboxylate (299.7 mg, 0.973 mmol), 1,4-dioxane (1.1 mL), water (0.82 mL), $K_3PO_4$ (355 mg, 1.673 mmol) were added, the mixture was bubbled $N_2$ for 5 minutes before bis(di-tert-butyl(4-dimethylaminophenyl)phosphine)dichloropalladium(II) (27.5 mg, 0.039 mmol) was added. The tube was sealed and heated in an oil bath at 100° C. overnight. DCM (200 mL) was added and the resulting mixture was washed with saturated $NaHCO_3$ aqueous solution (20 mL×4), brine (20 mL×1), dried over anhydrous $Na_2SO_4$, filtered, removed solvents in vacuo. The resulting residue was passed a ISCO silica gel column (MeOH:DCM=5:95) to give light brown solids, 1.1 mg (yield 0.6%). $^1$H NMR (300 MHz, DMSO-$d_6$) δ 11.71 (broad s, 1H), 8.00 (s, 1H), 7.59 (s, 1H), 7.49 (s, 1H), 7.44 (s, 1H), 7.24 (s, 1H), 4.81-4.70 (m, 1H), 3.66 (m, 1H), 3.47-3.33 (m, 1H), 3.19 (m, 1H), 2.81 (m, 1H), 2.31 (s, 3H), 2.42-2.20 (m, 2H), 1.31 (d, J=6.0 Hz, 3H), 1.13-1.04 (m, 2H), 1.04-0.93 (m, 2H) ppm; MS (ESI+) m/z 366.54 (M+H).

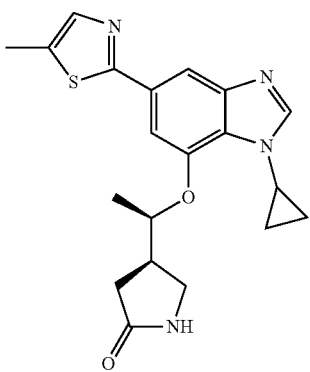 [SMILES: Cc1cnc(-c2cc(O[C@H](C)[C@H]3CNC(=O)C3)c3c(c2)ncn3C2CC2)s1]

Preparation of (R)-4-((R)-1-((1-cyclopropyl-5-(5-methylthiazol-2-yl)-1H-benzo[d]imidazol-7-yl)oxy)ethyl)pyrrolidin-2-one: To a microwave tube equipped with a stifling bar, (R)-4-((R)-1-((1-cyclopropyl-5-(4,4,5,5-tetramethyl-1,3,2-dioxaborolan-2-yl)-1H-benzo[d]imidazol-7-yl)oxy)ethyl)pyrrolidin-2-one: (120 mg, 0.292 mmol), 2-bromo-5-methylthiazole (103.9 mg, 0.584 mmol), 1,2-dimethoxyethane (2 mL), 1 N $Na_2CO_3$ aqueous solution (0.96 mL, 0.96 mmol) were added, the mixture was bubbled $N_2$ for 5 minutes before $Pd(PPh_3)_4$ (33.7 mg, 0.029 mmol) was added. The tube was sealed and heated in microwave at 140° C. for 15 minutes. DCM (200 mL) was added and the resulting mixture was washed with saturated $NaHCO_3$ aqueous solution (20 mL×4), brine (20 mL×1), dried over anhydrous $Na_2SO_4$, filtered, removed solvents in vacuo. The resulting residue was passed a ISCO silica gel column (MeOH:DCM=5:95) to give off-white solids, 42.2 mg (yield 37.8%). $^1$H NMR (300 MHz, DMSO-d6) δ 8.17 (s, 1H), 7.62 (d, J=1.3 Hz, 1H), 7.60 (broad s, 1H), 7.55 (m, 1H), 7.37 (d, J=1.3 Hz, 1H), 4.79 (p, J=6.0 Hz, 1H), 3.78-3.64 (m, 1H), 3.45-3.35 (m, 1H), 3.24-3.15 (m, 1H), 2.92-2.72 (m, 1H), 2.48 (d, J=1.2 Hz, 3H), 2.42-2.21 (m, 2H), 1.33 (d, J=6.0 Hz, 3H), 1.16-1.07 (m, 2H), 1.06-0.99 (m, 2H) ppm; MS (ESI+) m/z 383.90 (M+H).

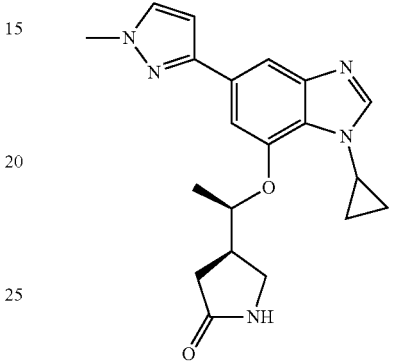

Preparation of (R)-4-((R)-1-((1-cyclopropyl-5-(1-methyl-1H-pyrazol-3-yl)-1H-benzo[d]imidazol-7-yl)oxy)ethyl)pyrrolidin-2-one: To a microwave tube equipped with a stirring bar, (R)-4-((R)-1-((1-cyclopropyl-5-(4,4,5,5-tetramethyl-1,3,2-dioxaborolan-2-yl)-1H-benzo[d]imidazol-7-yl)oxy)ethyl)pyrrolidin-2-one: (120 mg, 0.292 mmol), 3-iodo-1-methyl-1H-pyrazole (121.4 mg, 0.584 mmol), 1,2-dimethoxyethane (3 mL), 1 N $Na_2CO_3$ aqueous solution (0.96 mL, 0.96 mmol) were added, the mixture was bubbled $N_2$ for 5 minutes before $Pd(PPh_3)_4$ (33.7 mg, 0.029 mmol) was added. The tube was sealed and heated in an oil bath at 100° C. for 2 hrs. DCM (200 mL) was added and the resulting mixture was washed with saturated $NaHCO_3$ aqueous solution (20 mL×4), brine (20 mL×1), dried over anhydrous $Na_2SO_4$, filtered, removed solvents in vacuo. The resulting residue was passed a ISCO silica gel column (MeOH:DCM=5:95) to give white solids, 40.5 mg (yield 38.0%). $^1$H NMR (300 MHz, DMSO-$d_6$) δ 8.06 (s, 1H), 7.70 (d, J=2.2 Hz, 1H), 7.59 (broad s, 1H), 7.56 (d, J=1.1 Hz, 1H), 7.28 (broad s, 1H), 6.72 (d, J=2.2 Hz, 1H), 4.77 (m, 1H), 3.88 (s, 3H), 3.74-3.62 (m, 1H), 3.45-3.35 (m, 1H), 3.24-3.14 (m, 1H), 2.88-2.75 (m, 1H), 2.42-2.21 (m, 2H), 1.32 (d, J=6.0 Hz, 3H), 1.12-1.06 (m, 2H), 1.02 (m, 2H) ppm; MS (ESI+) m/z 366.34 (M+H).

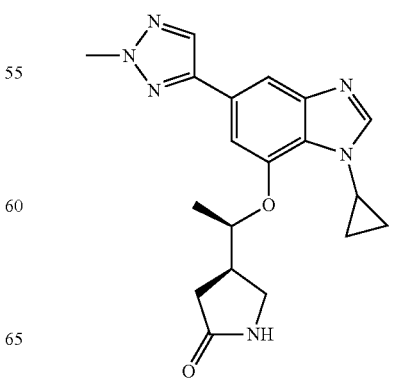

Preparation of (R)-4-((R)-1-((1-cyclopropyl-5-(2-methyl-2H-1,2,3-triazol-4-yl)-1H-benzo[d]imidazol-7-yl)oxy)ethyl)pyrrolidin-2-one: To a microwave tube equipped with a stifling bar, (R)-4-((R)-1-((1-cyclopropyl-5-(4,4,5,5-tetramethyl-1,3,2-dioxaborolan-2-yl)-1H-benzo[d]imidazol-7-yl)oxy)ethyl)pyrrolidin-2-one: (120 mg, 0.292 mmol), 4-bromo-2-methyl-2H-1,2,3-triazole (94.5 mg, 0.584 mmol), 1,2-dimethoxyethane (3 mL), 1 N Na$_2$CO$_3$ aqueous solution (0.96 mL, 0.96 mmol) were added, the mixture was bubbled N$_2$ for 5 minutes before Pd(PPh$_3$)$_4$ (33.7 mg, 0.029 mmol) was added. The tube was sealed and heated in microwave at 140° C. for 15 minutes. DCM (200 mL) was added and the resulting mixture was washed with saturated NaHCO$_3$ aqueous solution (20 mL×4), brine (20 mL×1), dried over anhydrous Na$_2$SO$_4$, filtered, removed solvents in vacuo. The resulting residue was passed a ISCO silica gel column (MeOH:DCM=5:95) to give off-white solids, 81.7 mg (yield 76.4%). $^1$H NMR (300 MHz, DMSO-d$_6$) δ 8.25 (s, 1H), 8.11 (broad s, 1H), 7.66 (s, 1H), 7.60 (broad s, 1H), 7.27 (s, 1H), 4.80 (p, J=6.0 Hz, 1H), 4.18 (s, 3H), 3.79-3.60 (m, 1H), 3.46-3.35 (m, 1H), 3.24-3.14 (m, 1H), 2.92-2.72 (m, 1H), 2.50-2.19 (m, 2H), 1.32 (d, J=6.0 Hz, 3H), 1.14-1.05 (m, 2H), 1.05-0.96 (m, 2H) ppm; MS (ESI+) m/z 367 (M+H).

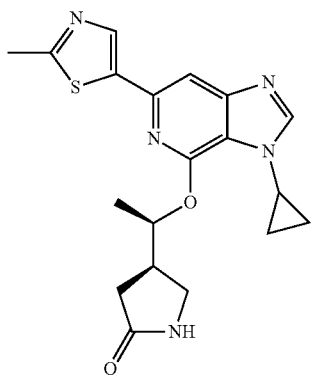 [SMILES: Cc1ncc(-c2cc3ncn(C4CC4)c3c(O[C@H](C)[C@H]3CNC(=O)C3)n2)s1]

Preparation of (R)-4-((R)-1-((3-cyclopropyl-6-(2-methylthiazol-5-yl)-3H-imidazo[4,5-c]pyridin-4-yl)oxy)ethyl)pyrrolidin-2-one: To a microwave tube equipped with a stirring bar, (R)-4-((R)-1-((6-bromo-3-cyclopropyl-3H-imidazo[4,5-c]pyridin-4-yl)oxy)ethyl)pyrrolidin-2-one: (100 mg, 0.274 mmol), 2-methyl-5-(4,4,5,5-tetramethyl-1,3,2-dioxaborolan-2-yl)thiazole (184.9 mg, 0.821 mmol), 1,2-dimethoxyethane (1.1 mL), 1 N Na$_2$CO$_3$ aqueous solution (0.82 mL, 0.82 mmol) were added, the mixture was bubbled N$_2$ for 5 minutes before Pd(PPh$_3$)$_4$ (31.6 mg, 0.027 mmol) was added. The tube was sealed and heated in a microwave at 140° C. for 20 minutes. DCM (200 mL) was added and the resulting mixture was washed with saturated NaHCO$_3$ aqueous solution (20 mL×4), brine (20 mL×1), dried over anhydrous Na$_2$SO$_4$, filtered, removed solvents in vacuo. The resulting residue was passed a ISCO silica gel column (MeOH:DCM=5:95) to give off-white solids, 15.3 mg (yield 14.6%). $^1$H NMR (300 MHz, DMSO-d$_6$) δ 8.31 (s, 1H), 8.21 (s, 1H), 7.77 (s, 1H), 7.57 (broad s, 1H), 5.41 (p, J=6.0 Hz, 1H), 3.70-3.65 (m, 1H), 3.44-3.38 (m, 1H), 3.22-3.16 (m, 1H), 2.94-2.75 (m, 1H), 2.65 (s, 3H), 2.32 (dd, J=8.6, 2.3 Hz, 2H), 1.40 (d, J=6.1 Hz, 3H), 1.20-1.11 (m, 2H), 1.10-1.02 (m, 2H) ppm; MS (ESI+) m/z 384 (M+H).

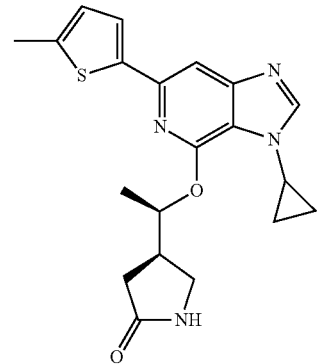 [SMILES: Cc1ccc(-c2cc3ncn(C4CC4)c3c(O[C@H](C)[C@H]3CNC(=O)C3)n2)s1]

Preparation of (R)-4-((R)-1-((3-cyclopropyl-6-(5-methylthiophen-2-yl)-3H-imidazo[4,5-c]pyridin-4-yl)oxy)ethyl)pyrrolidin-2-one: To a microwave tube equipped with a stirring bar, (R)-4-((R)-1-((6-bromo-3-cyclopropyl-3H-imidazo[4,5-c]pyridin-4-yl)oxy)ethyl)pyrrolidin-2-one: (100 mg, 0.274 mmol), (5-methylthiophen-2-yl)boronic acid (70.0 mg, 0.493 mmol), 1,2-dimethoxyethane (1.1 mL), 1 N Na$_2$CO$_3$ aqueous solution (0.55 mL, 0.55 mmol) were added, the mixture was bubbled N$_2$ for 5 minutes before Pd(PPh$_3$)$_4$ (31.6 mg, 0.027 mmol) was added. The tube was sealed and heated in a microwave at 150° C. for 20 minutes. DCM (200 mL) was added and the resulting mixture was washed with saturated NaHCO$_3$ aqueous solution (20 mL×4), brine (20 mL×1), dried over anhydrous Na$_2$SO$_4$, filtered, removed solvents in vacuo. The resulting residue was passed a ISCO silica gel column (MeOH:DCM=5:95) to give off-white solids, 57.2 mg (yield 54.6%). $^1$H NMR (300 MHz, DMSO-d$_6$) δ 8.25 (s, 1H), 7.63 (s, 1H), 7.56 (broad s, 1H), 7.48 (d, J=3.6 Hz, 1H), 6.78 (dm, J=3.6 Hz, 1H), 5.50-5.36 (m, 1H), 3.71-3.61 (m, 1H), 3.46-3.36 (m, 1H), 3.24-3.15 (m, 1H), 2.91-2.76 (m, 1H), 2.45 (s, 3H), 2.36-2.28 (m, 2H), 1.41 (d, J=6.2 Hz, 3H), 1.15-1.09 (m, 2H), 1.08-1.01 (m, 2H) ppm; MS (ESI+) m/z 383 (M+H).

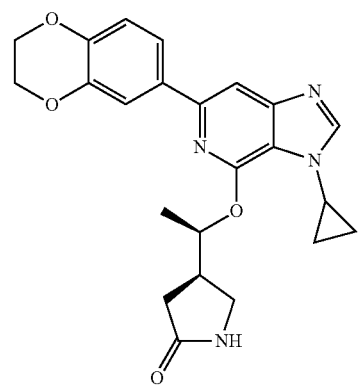 [SMILES: C[C@@H](Oc1nc(-c2ccc3c(c2)OCCO3)cc2ncn(C3CC3)c12)[C@H]1CNC(=O)C1]

(R)-4-((R)-1-((3-cyclopropyl-6-(2,3-dihydrobenzo[b][1,4]dioxin-6-yl)-3H-imidazo[4,5-c]pyridin-4-yl)oxy)ethyl)pyrrolidin-2-one: To a 25 ml 3-neck flask with condenser and magnetic stir bar was added (R)-4-((R)-1-((6-bromo-3-cyclopropyl-3H-imidazo[4,5-c]pyridin-4-yl)oxy)ethyl)pyrroli din-2-on (100 mg, 0.27 mmol), 2-(2,3-dihydrobenzo[b][1,4]dioxin-6-yl)-4,4,5,5-tetramethyl-1,3,2-dioxaborolane (90 mg, 0.34 mmol) and Pd(PPh3)4 (32 mg, 0.027 mmol) then evacuated and filled with N2 3×. Added 2 mL DME and 2N sodium carbonate (0.41 ml, 0.82 mmol) via syringe and heated in a 105° C. oil bath for ~2 hrs at which time LC-MS indicated a complete reaction Let cool, added EtOAc and water, separated, washed with brine, dried over Na2SO4, filtered and concentrated. Purified by chromatography: ISCO 50 g C18 reverse phase 0-30% water/acetonitrile/0.1% TFA. Partially concentrated under reduced pressure added EtOAc and sat.aq.bicarb, separated, washed with brine, dried over Na2SO4, filtered and concentrated to give a white solid.

$^1$H NMR (300 MHz, DMSO-d$_6$) δ 8.23 (s, 1H), 7.65 (s, 1H), 7.60-7.49 (m, 3H), 6.89 (dd, J=8.0, 0.7 Hz, 1H), 5.52 (p, 1H), 4.25 (s, 4H), 3.66 (tt, J=7.2, 4.0 Hz, 1H), 3.45-3.31 (m, 1H), 3.25-3.13 (m, 1H), 2.89-2.75 (m, 1H), 2.31 (d, J=8.6 Hz, 2H), 1.39 (d, J=6.2 Hz, 3H), 1.15-0.95 (m, 4H). [M+H]=420.9

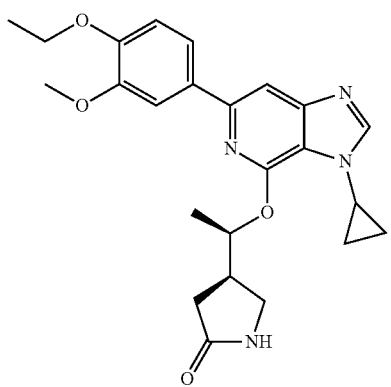 [SMILES: CCOc1ccc(-c2cc3ncn(C4CC4)c3c(O[C@H](C)[C@H]3CNC(=O)C3)n2)cc1OC]

(R)-4-((R)-1-((3-cyclopropyl-6-(4-ethoxy-3-methoxyphenyl)-3H-imidazo[4,5-c]pyridin-4-yl)oxy)ethyl)pyrrolidin-2-one: To a 25 ml 3-neck flask with condenser and magnetic stir bar was added (R)-4-((R)-1-((6-bromo-3-cyclopropyl-3H-imidazo[4,5-c]pyridin-4-yl)oxy)ethyl)pyrrolidin-2-on (100 mg, 0.27 mmol), (4-ethoxy-3-methoxyphenyl)boronic acid (64 mg, 0.33 mmol) and Pd(PPh3)4 (32 mg, 0.027 mmol) then evacuated and filled with N2 3×. Added 2 mL DME and 2N SODIUM CARBONATE (0.41 ml, 0.82 mmol) via syringe and heated in a 105° C. oil bath for 2 hrs at which time LC-MS indicated a complete reaction. Let cool, added EtOAc and water, separated, washed with brine, dried over Na2SO4, filtered and concentrated. Purified by chromatography: ISCO 50 g C18 reverse phase 0-30% water/acetonitrile/0.1% TFA. Partially concentrated under reduced pressure added EtOAc and sat.aq.bicarb, separated, washed with brine, dried over Na2SO4, filtered and concentrated to give a white solid.

$^1$H NMR (300 MHz, DMSO-d$_6$) δ 8.23 (s, 1H), 7.74 (s, 1H), 7.69-7.57 (m, 2H), 7.54 (s, 1H), 6.98 (d, J=8.3 Hz, 1H), 5.53 (p, J=6.1 Hz, 1H), 4.03 (q, J=7.0 Hz, 2H), 3.84 (s, 3H), 3.66 (td, J=7.2, 6.7, 3.5 Hz, 1H), 3.39 (t, J=9.0 Hz, 1H), 3.20 (dd, J=9.5, 6.4 Hz, 1H), 2.84 (d, J=7.6 Hz, 1H), 2.32 (d, J=8.5 Hz, 2H), 1.41 (d, J=6.1 Hz, 3H), 1.32 (t, J=6.9 Hz, 3H), 1.27-0.95 (m, 5H). [M+H]=436.9

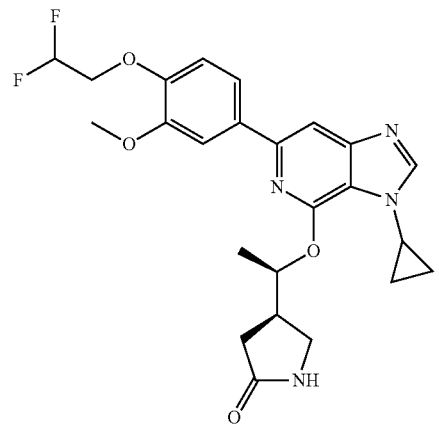 [SMILES: COc1cc(-c2cc3ncn(C4CC4)c3c(O[C@H](C)[C@H]3CNC(=O)C3)n2)ccc1OCC(F)F]

(R)-4-((R)-1-((3-cyclopropyl-6-(4-(2,2-difluoroethoxy)-3-methoxyphenyl)-3H-imidazo[4,5-c]pyridin-4-yl)oxy)ethyl)pyrrolidin-2-one: In a 50 mL 3-neck flask with a magnetic stir bar and condenser was placed (R)-4-((R)-1-((6-bromo-3-cyclopropyl-3H-imidazo[4,5-c]pyridin-4-yl)oxy)ethyl)pyrrolidin-2-on (125 mg, 0.34 mmol), 2-(4-(2,2-difluoroethoxy)-3-methoxyphenyl)-4,4,5,5-tetramethyl-1,3,2-dioxaborolane (135 mg, 0.43 mmol) and Pd(PPh3)4 (40 mg, 0.027 mmol). Evacuated and filled with nitrogen 3×. Added 2.5 mL DME and 2N sodium carbonate (0.51 ml, 1.03 mmol) via syringe and heated in a 105° C. oil bath for 2 hrs at which time LC-MS indicated a complete reaction. Let cool, added EtOAc and water, separated, washed with brine, dried over Na2SO4, filtered and concentrated. Purified by chromatography: ISCO 50 g C18 reverse phase 0-30% water/acetonitrile/0.1% TFA. Partially concentrated under reduced pressure added EtOAc and sat.aq.bicarb, separated, washed with brine, dried over Na2SO4, filtered and concentrated to give a white solid.

$^1$H NMR (300 MHz, DMSO-d$_6$) δ 8.25 (s, 1H), 7.79 (s, 1H), 7.74-7.59 (m, 2H), 7.55 (s, 1H), 7.07 (d, J=8.5 Hz, 1H), 6.38 (tt, J=54.6, 3.6 Hz, 1H), 5.53 (p, J=6.0 Hz, 1H), 4.29 (td, J=14.5, 3.7 Hz, 2H), 3.67 (tt, J=7.4, 4.1 Hz, 1H), 3.48-3.31 (m, 1H), 3.20 (dd, J=9.7, 6.5 Hz, 1H), 2.91-2.75 (m, 1H), 2.32 (d, J=8.6 Hz, 2H), 1.41 (d, J=6.1 Hz, 3H), 1.24-0.95 (m, 5H). [M+H]=473.2

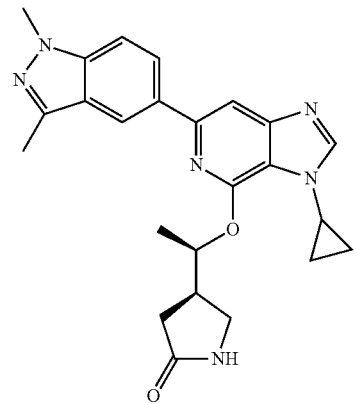 [SMILES: Cc1nn(C)c2ccc(-c3cc4ncn(C5CC5)c4c(O[C@H](C)[C@H]4CNC(=O)C4)n3)cc12]

(R)-4-((R)-1-((3-cyclopropyl-6-(1,3-dimethyl-1H-indazol-5-yl)-3H-imidazo[4,5-c]pyridin-4-yl)oxy)ethyl)pyrrolidin-2-one: To a 25 ml 3-neck flask with condenser and magnetic stir bar was added (R)-4-((R)-1-((6-bromo-3-cyclopropyl-3H-imidazo[4,5-c]pyridin-4-yl)oxy)ethyl)pyrrolidin-2-on (120 mg, 0.33 mmol), 1,3-dimethyl-5-(4,4,5, 5-tetramethyl-1,3,2-dioxaborolan-2-yl)-1H-indazole (112 mg, 0.41 mmol) and Pd(PPh3)4 (32 mg, 0.027 mmol) then evacuated and filled with N2 3×. Added 2 mL DME and 2N SODIUM CARBONATE (0.41 ml, 0.82 mmol) via syringe and heated in a 105° C. oil bath for 2 hrs at which time LC-MS indicated a complete reaction. Let cool. Workup: EtOAc, water, brine, dried over Na2SO4, filtered and concentrated. Purified by chromatography: ISCO, 24 g silica Gold, 0-6% MeOH/DCM to give desired product as a white solid.

$^1$H NMR (300 MHz, DMSO-d$_6$) δ 8.36 (s, 1H), 8.24 (s, 1H), 8.19-8.09 (m, 1H), 7.84 (s, 1H), 7.56 (d, J=9.2 Hz, 2H), 5.59 (p, J=6.0 Hz, 1H), 3.95 (s, 3H), 3.67 (dd, J=10.2, 5.4 Hz, 1H), 3.39 (q, J=10.7, 10.2 Hz, 1H), 3.22 (dd, J=9.7, 6.5 Hz, 1H), 2.86 (q, J=7.3 Hz, 1H), 2.51 (s, 3H), 2.34 (d, J=8.5 Hz, 3H), 1.43 (d, J=6.1 Hz, 3H), 1.27-0.96 (m, 6H). [M+H]= 431.3

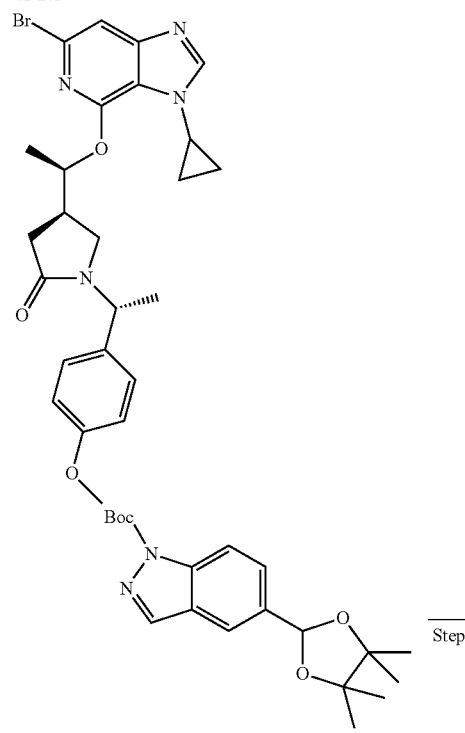

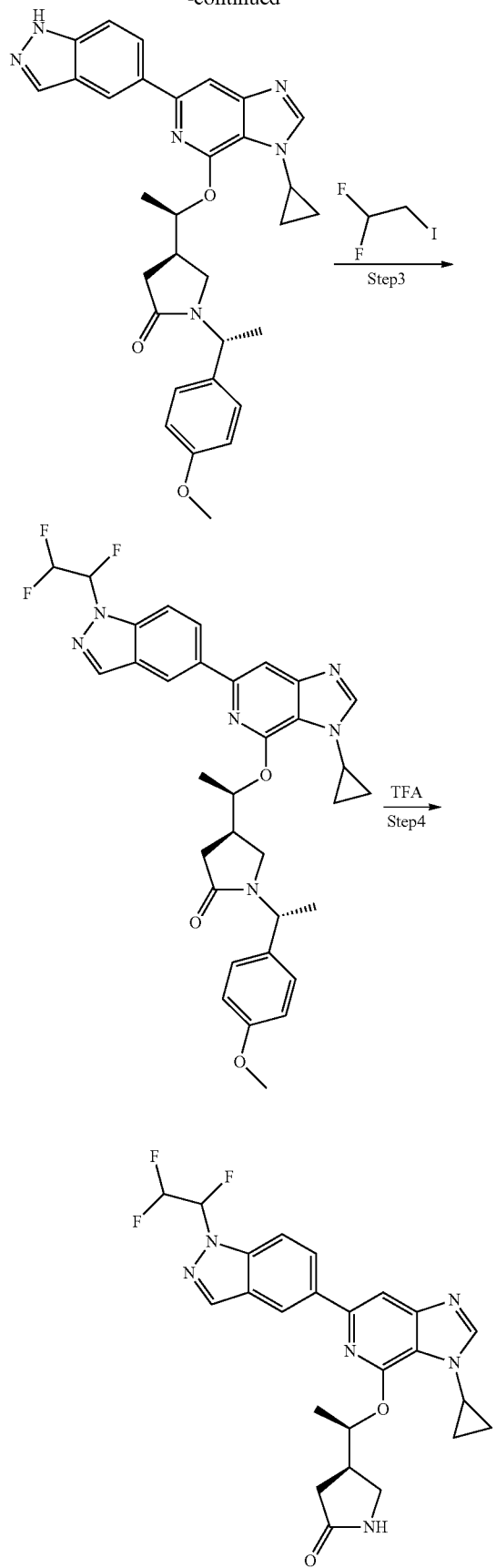

Step 1. tert-butyl 5-(3-cyclopropyl-4-((R)-1-((R)-1-((R)-1-(4-methoxyphenyl)ethyl)-5-oxopyrrolidin-3-yl)ethoxy)-3H-imidazo[4,5-c]pyridin-6-yl)-1H-indazole-1-carboxylate: To a 100 mL 3-neck flask fitted with a condenser and magnetic stir bar was added (R)-4-((R)-1-((6-bromo-3-cyclopropyl-3H-imidazo[4,5-c]pyridin-4-yl)oxy)ethyl)-1-((R)-1-(4-methoxyphenyl)ethyl)pyrrolidin-2-one: (1500 mg, 3 mmol), tert-butyl 5-(4,4,5,5-tetramethyl-1,3,2-dioxaborolan-2-yl)-1H-indazole-1-carboxylate (1292 mg, 3.75 mmol) and Pd(PPh3)4 (347 mg, 0.3 mmol) evacuated and filled with N2 3×. Added 20 mL DME and 2N SODIUM CARBONATE (3.3 ml, 6.6 mmol) heated in a 110° C. oil bath for ~1 hr at which time LC-MS indicated a complete reaction. Let cool. Added EtOAc and water, separated, washed with brine, dried over Na2SO4, filtered and concentrated. Ran column: ISCO 40 g silica with 20 g solid loader to give the desired product. Correct by NMR and LC-MS.

Step 2. (R)-4-((R)-1-((3-cyclopropyl-6-(1H-indazol-5-yl)-3H-imidazo[4,5-c]pyridin-4-yl)oxy)ethyl)-1-((R)-1-(4-methoxyphenyl)ethyl)pyrrolidin-2-one: In a 250 mL RBF placed the product from Step 1 (930 mg, 1.46 mmol) and dissolved in Methanol (11 mL) then added 4M Hydrogen chlodie in 1,4-Dioxane (11 ml, 44 mmol). Let stir at room temp overnight. Concentrated under reduced pressure, added EtOAc and sat.aq.bicarbonate and stirred for 0.5 hr. Separated, washed with brine, dried over Na2SO4, filtered and concentrated to give the named product, 750 mg, 96%.

Step 3. (R)-4-((R)-1-((3-cyclopropyl-6-(1-(2,2-difluoroethyl)-1H-indazol-5-yl)-3H-imidazo[4,5-c]pyridin-4-yl)oxy)ethyl)-1-((R)-1-(4-methoxyphenyl)ethyl)pyrrolidin-2-one: In a dry flask under N2 was placed the product from Step 2 (150 mg, 0.28 mmol) and dissolved in DMF 2 mL Added NaH (60% in oil) (22 mg, 0.56 mmol) and stirred for 10 min. Added 1,1-difluoro-2-iodoethane (0.074 ml, 0.84 mmol) via syringe and let stir 4 hrs. Quenched with water, extracted with EtOAc, washed with brine, dried over Na4SO4, filtered and concentrated. Purified by chromatography: ISCO 24 g GOLD silica, 0-10% MeOH/DCM to give the named product.

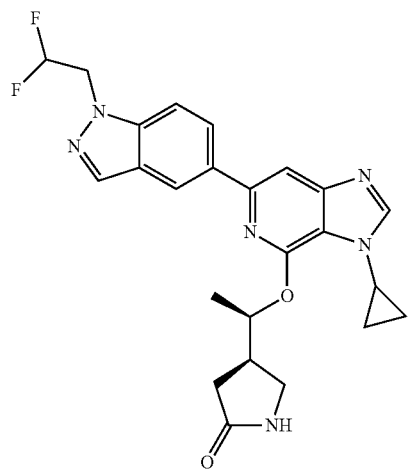 [SMILES: C[C@@H](Oc1nc(-c2ccc3c(cnn3CC(F)F)c2)cc2ncn(C3CC3)c12)[C@H]1CNC(=O)C1]

Step 4. (R)-4-((R)-1-((3-cyclopropyl-6-(1-(2,2-difluoroethyl)-1H-indazol-5-yl)-3H-imidazo[4,5-c]pyridin-4-yl)oxy)ethyl)pyrrolidin-2-one: In a microwave vial was placed the product from Step 3 (100 mg, 0.17 mmol) and dissolved in 1.5 mL TFA. Heated in microwave reactor for 20 min at 100° C. Concentrated under reduced pressure, added EtOAc and sat.aq.bicarb, stirred for 15 min, separated, washed with brine, dried over Na2SO4, filtered and concentrated under reduced pressure then dried under vacuum to give the named product as a white solid.

$^1$H NMR (300 MHz, DMSO-$d_6$) δ 8.46 (d, J=1.7 Hz, 1H), 8.27 (s, 1H), 8.20 (s, 1H), 8.18 (dd, J=9.0, 1.7 Hz, 1H), 7.81 (s, 1H), 7.76 (d, J=8.9 Hz, 1H), 7.55 (s, 1H), 6.69-6.17 (tt, J=55.3 Hz 1H), 5.62 (p, J=6.1 Hz, 1H), 4.94 (td, J=15.3, 3.6 Hz, 2H), 3.69 (tt, J=7.4, 4.2 Hz, 1H), 3.41 (t, J=9.2 Hz, 1H), 3.22 (dd, J=9.7, 6.6 Hz, 1H), 2.95-2.76 (m, 1H), 2.34 (d, J=8.6 Hz, 3H), 1.43 (d, J=6.1 Hz, 3H), 1.27-0.96 (m, 5H). [M+H]= 467.0.

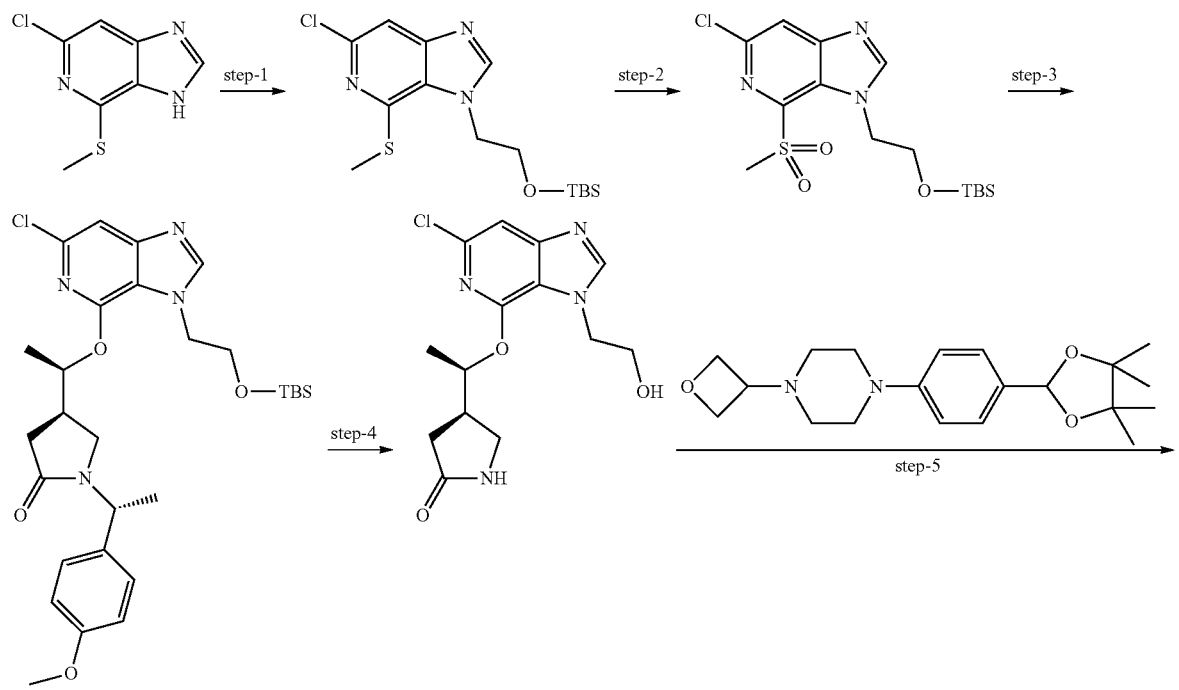

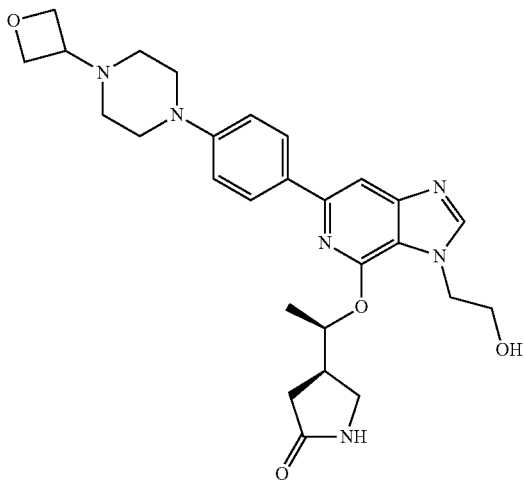

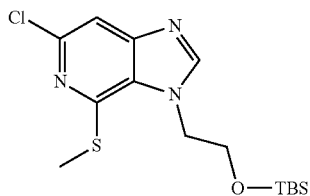

Step 1. 3-(2-((tert-butyldimethylsilyl)oxy)ethyl)-6-chloro-4-(methylthio)-3H-imidazo[4,5-c]pyridine: 6-chloro-4-(methylthio)-3H-imidazo[4,5-c]pyridine (1.1 g, 5.5 mmol) was dissolved in DMF (10 mL) and added (2-bromoethoxy)(tert-butyl)dimethylsilane (1.5 g, 6.6 mmol) and cesium carbonate (5.4 g, 16.5 mmol), were added and the mixture was stirred at 100° C. for 45 minutes. Chromatography on silica eluting with hexanes and ethyl acetate provided a mixture of the desired 3-(2-((tert-butyldimethylsilyl)oxy)ethyl)-6-chloro-4-(methylthio)-3H-imidazo[4,5-c]pyridine (373 mg) eluting first and the regioisomeric product 1-(2-((tert-butyldimethylsilyl)oxy)ethyl)-6-chloro-4-(methylthio)-1H-imidazo[4,5-c]pyridine (0.942 mg).

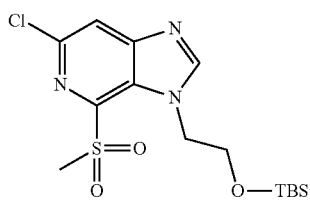

Step 2. 3-(2-((tert-butyldimethylsilyl)oxy)ethyl)-6-chloro-4-(methylsulfonyl)-3H-imidazo[4,5-c]pyridine: 3-(2-((tert-butyldimethylsilyl)oxy)ethyl)-6-chloro-4-(methylthio)-3H-imidazo[4,5-c]pyridine (373 mg, 1.1 mmol) was dissolved in dichloromethane, added MCPBA (886 mg, 2.5 mmol, 75% purity) at 25° C. and let stir for 4 h. Chromatography on silica eluting with hexanes and ethyl acetate provided 3-(2-((tert-butyldimethylsilyl)oxy)ethyl)-6-chloro-4-(methylsulfonyl)-3H-imidazo[4,5-c]pyridine.

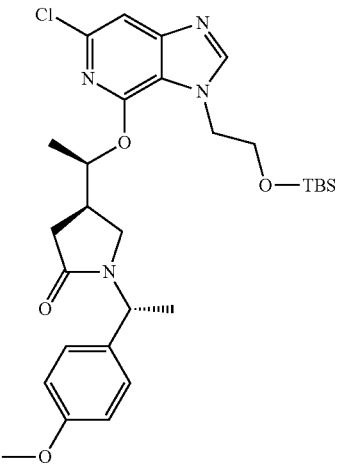

Step 3. (R)-4-((R)-1-((3-(2-((tert-butyldimethylsilyl)oxy)ethyl)-6-chloro-3H-imidazo[4,5-c]pyridin-4-yl)oxy)ethyl)-1-((R)-1-(4-methoxyphenyl)ethyl)pyrrolidin-2-one: (R)-4-((R)-1-hydroxyethyl)-1-((R)-1-(4-methoxyphenyl)ethyl)pyrrolidin-2-one (320 mg, 0.821 mmol) was dissolved in DMF (25 mL) and added sodium hexamethyldisilazide (1 mL, 1M THF) at 25° C. and stirred for 15 minutes. 3-(2-((tert-butyldimethylsilyl)oxy)ethyl)-6-chloro-4-(methylsulfonyl)-3H-imidazo[4,5-c]pyridine (260 mg, 0.985 mmol) was added and the mixture allowed to stir overnight. Chromatography on silica eluting with dichloromethane and methanol provided (R)-4-((R)-1-((3-(2-((tert-butyldimethylsilyl)oxy)ethyl)-6-chloro-3H-imidazo[4,5-c]pyridin-4-yl)oxy)ethyl)-1-((R)-1-(4-methoxyphenyl)ethyl)pyrrolidin-2-one.

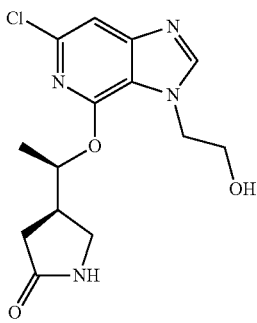 [SMILES: C[C@@H](Oc1nc(Cl)cc2ncn(CCO)c12)[C@H]1CNC(=O)C1]

Step 4. (R)-4-((R)-1-((6-chloro-3-(2-hydroxyethyl)-3H-imidazo[4,5-c]pyridin-4-yl)oxy)ethyl)pyrrolidin-2-one: (R)-4-((R)-1-((3-(2-((tert-butyldimethylsilyl)oxy)ethyl)-6-chloro-3H-imidazo[4,5-c]pyridin-4-yl)oxy)ethyl)-1-((R)-1-(4-methoxyphenyl)ethyl) pyrrolidin-2-one (250 mg, 0.436 mmol) was dissolved in dichloromethane (5 mL), added trifluoroacetic acid (5 mL), and heated to 70° C. for 24 h. Chromatography on silica eluting with dichloromethane and methanol provided (R)-4-((R)-1-((6-chloro-3-(2-hydroxyethyl)-3H-imidazo[4,5-c]pyridin-4-yl)oxy)ethyl)pyrrolidin-2-one.

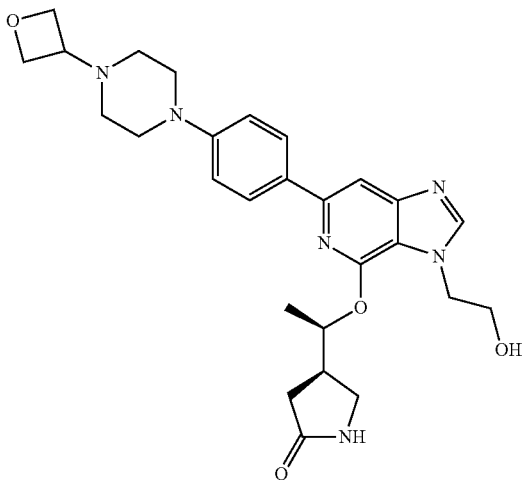 [SMILES: C[C@@H](Oc1nc(-c2ccc(N3CCN(C4COC4)CC3)cc2)cc2ncn(CCO)c12)[C@H]1CNC(=O)C1]

Step 5. Preparation of (R)-4-((R)-1-((3-(2-hydroxyethyl)-6-(4-(4-(oxetan-3-yl)piperazin-1-yl)phenyl)-3H-imidazo[4,5-c]pyridin-4-yl)oxy)ethyl)pyrrolidin-2-one: In a 25 mL sealed tube a mixture of (R)-4-((R)-1-((6-chloro-3-(2-hydroxyethyl)-3H-imidazo[4,5-c]pyridin-4-yl)oxy)ethyl)pyrrolidin-2-one (85 mg, 0.26 mmol), 1-(oxetan-3-yl)-4-(4-(4,4,5,5-tetramethyl-1,3,2-dioxaborolan-2-yl)phenyl)piperazine (108.12 mg, 0.31 mmol), Cesium Carbonate (255 mg, 0.78 mmol), & PEPPSI"-IPr catalyst (20 mg, 0.03 mmol) were taken up in dioxane (4 ml) and water (1 mL). and heated at 100° C. for 90 minutes. Chromatography on silica eluting with dichloromethane and methanol provided 28.1 mg of a white solid. $^1$H NMR (300 MHz, DMSO-$d_6$) δ 8.25 (s, 1H), 8.01-7.91 (m, 2H), 7.71-7.57 (m, 2H), 7.05-6.95 (m, 2H), 5.82-5.64 (m, 2H), 4.63-4.34 (m, 6H), 3.69 (td, J=7.0, 3.5 Hz, 1H), 3.55-3.34 (m, 2H), 3.37-3.12 (m, 9H), 2.98 (p, J=7.9 Hz, 1H), 2.50-2.32 (m, 6H), 2.20 (dd, J=16.7, 7.0 Hz, 1H), 1.27-0.97 (m, 6H). ESI MS m/z 507 [M+H]$^+$; HPLC, 1.24 min, 95.5% (AUC).

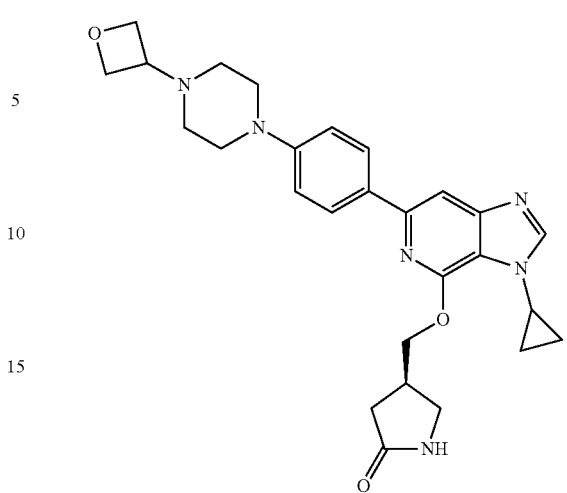

Preparation of (R)-4-(((3-cyclopropyl-6-(4-(4-(oxetan-3-yl)piperazin-1-yl)phenyl)-3H-imidazo[4,5-c]pyridin-4-yl)oxy)methyl)pyrrolidin-2-one: (R)-4-(((6-bromo-3-cyclopropyl-3H-imidazo[4,5-c]pyridin-4-yl)oxy)methyl)pyrrolidin-2-one (50 mg, 0.14 mmol), 1-(oxetan-3-yl)-4-(4-(4,4,5,5-tetramethyl-1,3,2-dioxaborolan-2-yl)phenyl)piperazine (63.28 mg, 0.18 mmol), Cesium Carbonate (137.18 mg, 0.42 mmol), & PEPPSI"-IPr catalyst (20 mg, 0.03 mmol) were taken up in dioxane (4 ml) and water (1 mL) and heated in a sealed tube at 100° C. for 45 minutes. Reaction was then chromatographed in silica gel 0-30% DCM/MeOH providing 94 mg of (R)-4-(((3-cyclopropyl-6-(4-(4-(oxetan-3-yl)piperazin-1-yl)phenyl)-3H-imidazo[4,5-c]pyridin-4-yl)oxy)methyl)pyrrolidin-2-one. (68 mg, 84%) as a yellow solid: $^1$H NMR (300 MHz, DMSO-$d_6$) δ 8.25 (s, 1H), 8.01-7.91 (m, 2H), 7.71-7.57 (m, 2H), 7.05-6.95 (m, 2H), 5.82-5.64 (m, 2H), 4.63-4.34 (m, 6H), 3.69 (td, J=7.0, 3.5 Hz, 1H), 3.55-3.34 (m, 2H), 3.37-3.12 (m, 9H), 2.98 (p, J=7.9 Hz, 1H), 2.50-2.32 (m, 6H), 2.20 (dd, J=16.7, 7.0 Hz, 1H), 1.27-0.97 (m, 6H). ESI MS m/z 489 [M+H]$^+$; HPLC, 1.24 min, 97.5% (AUC).

General Procedures for Preparation of Examples 3G.01-3G.31 and 3H.01-3H.14

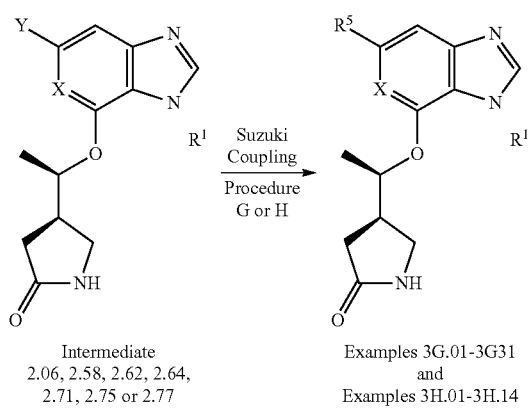

Intermediate 2.06, 2.58, 2.62, 2.64, 2.71, 2.75 or 2.77

Suzuki Coupling Procedure G or H

Examples 3G.01-3G31 and Examples 3H.01-3H.14

General Procedure G for Preparation of Examples 3G.01-3G.31.

To an appropriate sized reaction vessel was added (as specified) aryl halide intermediate 2.06, 2.58, 2.62, 2.64, 2.71, or 2.77 (1 eq.), boronic acid or ester (1-2 eq.), cesium carbonate (ca. 3 eq.), and PEPPSI-IPr precatalyst (ca. 0.1 eq.). The reagents were taken up in 2:1 DME:water. After evacuating and backfilling with argon, the stirred mixture was heated at 100° C. Once the reaction was judged complete, reaction mixture was cooled to r.t. and was diluted with water and extracted with ethyl acetate. Combined organics were dried, filtered, and concentrated under reduced pressure. Residues were purified by silica gel column chromatography or reverse phase HPLC to yield Examples 3G.01-3G.31 as free bases or as TFA salts, depicted in Table 3A below.

General Procedure H for Preparation of Examples 3H.01-3H.14

To an appropriate sized reaction vessel was added (as specified) aryl halide intermediate 2.06, 2.58, 2.62, 2.64, 2.71, or 2.77 (1 eq.), boronic acid or ester (1-3 eq.), $K_3PO_4$ (3-4 eq.), and bis[di-tert-butyl(4-dimethylaminophenyl)phosphine]dichloropalladium (II) (2-15 mol %). The reagents were taken up in 10:1 1,4-dioxane:water (ca. 0.05 M with respect to limiting reagent) under Ar or $N_2$. The stirred mixture was heated to ca. 100-110° C. until the reaction was judged complete (in certain cases, additional boronic acid/ester, base, and/or precatalyst were added to drive the reaction to completion). The reaction mixture was then cooled to r.t. and was diluted with water and brine and extracted with ethyl acetate. Combined organics were dried, filtered, and concentrated under reduced pressure. Residues were purified by silica gel column chromatography or reverse phase HPLC to yield Examples 3H.01-3H.14 as free bases or as TFA salts, depicted in Table 3A below.

TABLE 3A

Examples 3G.01-3G.31 and 3H.01-3H.14.

| Example # | Aryl Halide | Boronic Acid/Ester | Product/Salt Proton NMR | LCMS-ESI+ (m/z): [M + H]+ |
|---|---|---|---|---|
| 3H.01 | 2.71 | 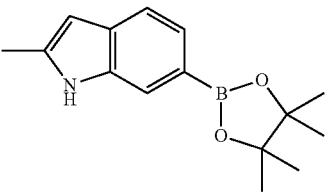 7.50 | 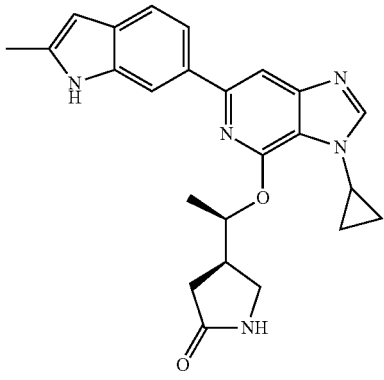 [SMILES: Cc1cc2ccc(-c3cc4ncn(C5CC5)c4c(O[C@H](C)[C@H]4CNC(=O)C4)n3)cc2[nH]1] $^1$H NMR (400 MHz, Chloroform-d) δ 8.36 (s, 1H), 7.94 (s, 1H), 7.84 (s, 1H), 7.78-7.71 (m, 2H), 7.54 (d, J = 8.3 Hz, 1H), 6.24-6.17 (m, 1H), 6.03 (s, 1H), 5.86-5.75 (m, 1H), 3.62-3.46 (m, 2H), 3.39 (dd, J = 9.6, 6.5 Hz, 1H), 2.98-2.86 (m, 1H), 2.62-2.47 (m, 2H), 2.44 (s, 3H), 1.48 (d, J = 6.2 Hz, 3H) 1.18-1.03 (m, 4H). | Calc: 416.2 Found: 416.1 |
| 3H.02 | 2.06 | 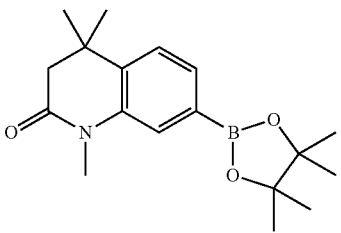 [SMILES: CN1C(=O)CC(C)(C)c2ccc(B3OC(C)(C)C(C)(C)O3)cc21] 7.42 | 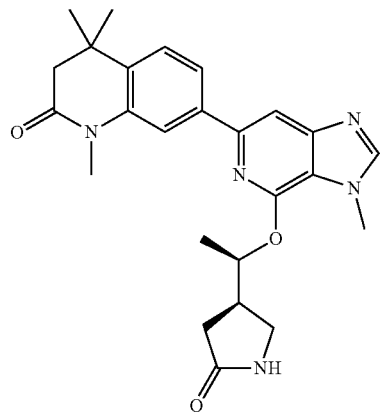 [SMILES: C[C@@H](Oc1nc(-c2ccc3c(c2)N(C)C(=O)CC3(C)C)cc2ncn(C)c12)[C@H]1CNC(=O)C1] $^1$H NMR (400 MHz, Chloroform-d) δ 7.83 (s, 1H), 7.73 (s, 1H), 7.70-7.65 (m, 2H), 7.39-7.34 (m, 1H), 6.18 (s, 1H), 5.72-5.65 (m, 1H), 4.02 (s, 3H), 3.64-3.54 (m, 1H), 3.48 (s, 3H), 3.38 (dd, J = 9.7, 6.1 Hz, 1H), 3.00-2.86 (m, 1H) 2.61-2.44 (m, 4H), 1.51 (d, J = 6.2 Hz, 3H), 1.32 (s, 6H). | Calc: 448.2 Found: 448.2 |

TABLE 3A-continued

Examples 3G.01-3G.31 and 3H.01-3H.14.

| Example # | Aryl Halide | Boronic Acid/Ester | Product/Salt Proton NMR | LCMS-ESI+ (m/z): [M + H]+ |
|---|---|---|---|---|
| 3H.03 | 2.06 | | | Calc: 434.22 Found: 434.29 |

7.52

¹H NMR (400 MHz, Chloroform-d) δ 9.82 (s, 1H), 7.87 (s, 1H), 7.74 (s, 1H), 7.66-7.62 (m, 2H), 7.34 (d, J = 7.9 Hz, 1H), 7.03 (s, 1H), 5.86-5.75 (m, 1H), 4.02 (s, 3H), 3.63-3.52 (m, 1H), 3.46 (dd, J = 9.9, 5.2 Hz, 1H), 3.11-2.95 (m, 1H), 2.74 (dd, J = 17.3, 9.7 Hz, 1H), 2.55-2.45 (m, 3H), 1.48 (d, J = 6.3 Hz, 3H), 1.35 (d, J = 1.8 Hz, 6H).

| 3H.04 | 2.71 | | | Calc: 417.20 Found: 417.18 |

¹H NMR (400 MHz, Chloroform-d) δ 8.11-8.07 (m, 1H) 7.92 (s, 1H), 7.79 (d, J = 6.5 Hz, 2H), 7.73-7.67 (m, 1H), 6.08 (s, 1H), 5.86-5.77 (m, 1H), 3.66-3.54 (m, 2H), 3.42 (dd, J = 9.6, 6.4 Hz, 1H), 3.01-2.88 (m, 1H), 2.61 (s, 3H), 2.61-2.49 (m, 2H), 1.51 (d, J = 6.2 Hz, 3H), 1.21-1.06 (m, 4H).

| 3H.05 | 2.71 | | | Calc: 417.20 Found: 417.26 |

¹H NMR (400 MHz, Chloroform-d) δ 8.01-7.97 (m, 2H), 7.93 (s, 1H), 7.85-7.81 (m, 2H), 7.77 (dd, J = 8.5, 0.8 Hz, 1H), 5.87-5.76 (m, 2H), 4.15 (s, 3H), 3.69-3.57 (m, 2H), 3.45 (dd, J = 9.6, 6.5 Hz, 1H), 3.04-2.93 (m, 1H), 2.67-2.50 (m, 2H), 1.54 (d, J = 6.3 Hz, 3H), 1.25-1.08 (m, 4H).

TABLE 3A-continued
Examples 3G.01-3G.31 and 3H.01-3H.14.
| Example # | Aryl Halide | Boronic Acid/Ester | Product/Salt Proton NMR | LCMS-ESI+ (m/z): [M + H]+ |
|---|---|---|---|---|
| 3H.06 | 2.71 | 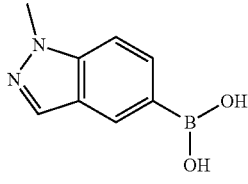 | 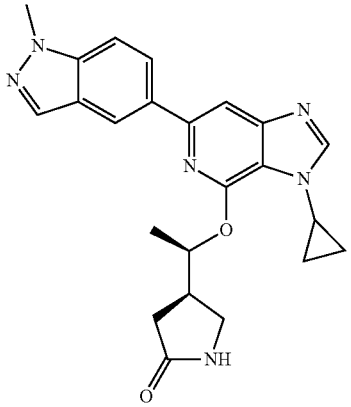 [SMILES: C[C@@H](Oc1nc(-c2ccc3c(cnn3C)c2)cc2ncn(C3CC3)c12)[C@H]1CNC(=O)C1]<br>¹H NMR (400 MHz, Chloroform-d) δ 8.37 (s, 1H), 8.10-8.04 (m, 2H), 7.91 (s, 1H), 7.75 (s, 1H), 7.48-7.42 (m, 1H), 5.88-5.80 (m, 1H), 5.73 (s, 1H), 4.11 (s, 3H), 3.68-3.54 (m, 2H), 3.45 (dd, J = 9.6, 6.5 Hz, 1H), 3.05-2.90 (m, 1H), 2.61 (dd, J = 17.1, 7.8 Hz, 1H), 2.55 (dd, J = 17.0, 9.5 Hz, 1H), 1.53 (d, J = 6.2 Hz, 3H), 1.24-1.06 (m, 4H). | Calc: 417.20<br>Found: 417.22 |
| 3H.07 | 2.71 | 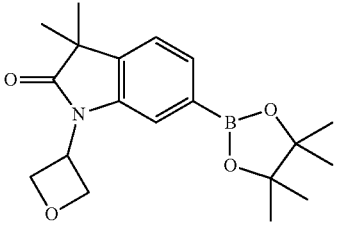 [SMILES: CC1(C)C(=O)N(C2COC2)c2cc(B3OC(C)(C)C(C)(C)O3)ccc21]<br>7.43 | 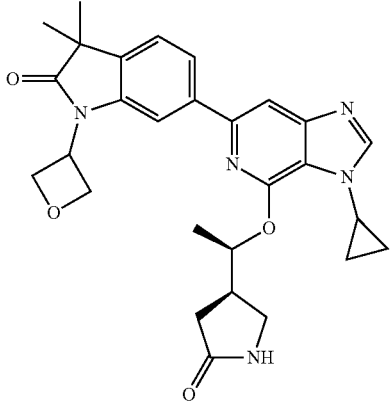 [SMILES: C[C@@H](Oc1nc(-c2ccc3c(c2)N(C2COC2)C(=O)C3(C)C)cc2ncn(C3CC3)c12)[C@H]1CNC(=O)C1]<br>¹H NMR (400 MHz, Chloroform-d) δ 8.48 (s, 1H), 7.91 (s, 1H), 7.78 (s, 1H), 7.73 (dd, J = 7.8, 1.4 Hz, 1H), 7.32 (d, J = 7.8 Hz, 1H), 5.84-5.74 (m, 2H), 5.73-5.63 (m, 1H), 5.33-5.20 (m, 2H), 5.15-5.04 (m, 2H), 3.67-3.59 (m, 1H), 3.59-3.52 (m, 1H), 3.41 (dd, J = 9.6, 6.6 Hz, 1H), 3.02-2.86 (m, 1H) 2.62-2.45 (m, 2H), 1.48 (d, J = 6.2 Hz, 3H), 1.41 (s, 6H), 1.24-1.01 (m, 4H). | Calc: 502.24<br>Found: 502.41 |

TABLE 3A-continued

Examples 3G.01-3G.31 and 3H.01-3H.14.

| Example # | Aryl Halide | Boronic Acid/Ester | Product/Salt Proton NMR | LCMS-ESI+ (m/z): [M + H]+ |
|---|---|---|---|---|
| 3H.08 | 2.71 | 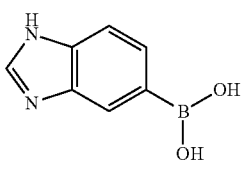 [SMILES: OB(O)c1ccc2[nH]cnc2c1] | 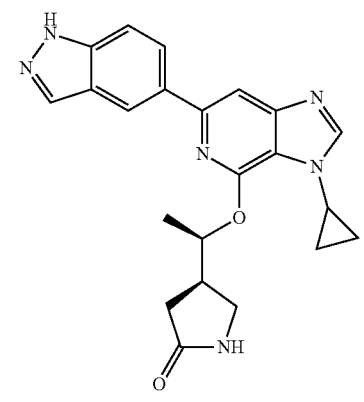 [SMILES: C[C@@H](Oc1nc(-c2ccc3[nH]ncc3c2)cc2ncn(C3CC3)c12)[C@H]1CNC(=O)C1] | Calc: 403.19 Found: 403.22 |

¹H NMR (400 MHz, Methanol-d4) δ 8.50-8.40 (m, 1H), 8.18 (s, 1H), 8.16-8.09 (m, 2H), 7.70 (s, 1H), 7.59 (d, J = 8.8 Hz, 1H), 5.89-5.80 (m, 1H), 3.77-3.68 (m, 1H), 3.62 (dd, J = 10.1, 8.8 Hz, 1H), 3.44 (dd, J = 10.1, 6.0 Hz, 1H), 3.06-2.94 (m, 1H), 2.65-2.51 (m, 2H), 1.53 (d, J = 6.2 Hz, 3H), 1.25-1.10 (m, 4H).

| 3H.09 | 2.71 | 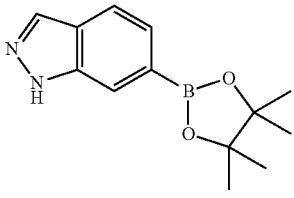 [SMILES: CC1(C)OB(c2ccc3cn[nH]c3c2)OC1(C)C] | 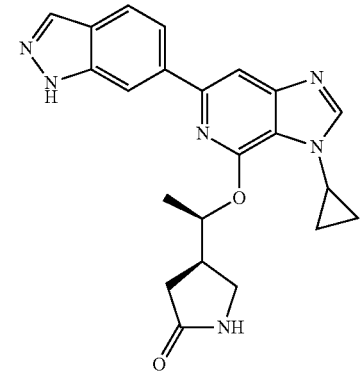 [SMILES: C[C@@H](Oc1nc(-c2ccc3cn[nH]c3c2)cc2ncn(C3CC3)c12)[C@H]1CNC(=O)C1] | Calc: 403.19 Found: 403.18 |

¹H NMR (400 MHz, Methanol-d4) δ 8.23 (s, 2H), 8.04 (s, 1H), 7.86 (dd, J = 8.7, 1.4 Hz, 1H), 7.81 (d, J = 8.6 Hz, 1H), 7.76 (s, 1H), 5.89-5.77 (m, 1H), 3.78-3.67 (m, 1H), 3.67-3.57 (m, 1H), 3.43 (dd, J = 10.1, 5.9 Hz, 1H), 3.07-2.94 (m, 1H), 2.63-2.55 (m, 2H), 1.54 (d, J = 6.2 Hz, 3H), 1.26-1.09 (m, 4H).

| 3H.10 | 2.71 | 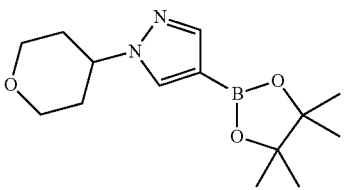 [SMILES: CC1(C)OB(c2cnn(C3CCOCC3)c2)OC1(C)C] | 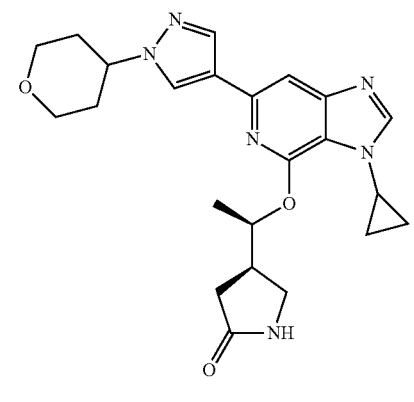 [SMILES: C[C@@H](Oc1nc(-c2cnn(C3CCOCC3)c2)cc2ncn(C3CC3)c12)[C@H]1CNC(=O)C1] | Calc: 437.2 Found: 437.2 |

¹H NMR (400 MHz, Chloroform-d) δ 7.97-7.93 (m, 1H), 7.88-7.83 (m, 2H), 7.41 (s, 1H), 5.84 (s, 1H), 5.75-5.65 (m, 1H), 4.45-4.31 (m, 1H), 4.17-4.08 (m, 2H), 3.65-3.49 (m, 4H), 3.41 (dd, J = 9.6, 6.5 Hz, 1H), 3.01-2.85 (m, 1H), 2.62-2.46 (m, 2H), 2.20-2.08 (m, 4H), 1.47 (d, J = 6.2 Hz, 3H) 1.20-1.03 (m, 4H).

TABLE 3A-continued

Examples 3G.01-3G.31 and 3H.01-3H.14.

| Example # | Aryl Halide | Boronic Acid/Ester | Product/Salt Proton NMR | LCMS-ESI+ (m/z): [M + H]+ |
|---|---|---|---|---|
| 3H.11 | 2.64 | | | Calc: 447.20 Found: 447.13 |

$^1$H NMR (400 MHz, Chloroform-d) δ 8.27 (s, 1H), 7.97 (d, J = 0.7 Hz, 1H), 7.89 (s, 1H), 7.60 (t, J = 61.1 Hz, 1H), 7.50 (s, 1H), 5.80 (s, 1H), 5.70-5.62 (m, 1H), 4.47-4.36 (m, 1H), 4.18-4.10 (m, 2H), 3.64-3.51 (m, 3H), 3.37 (dd, J = 9.6, 6.0 Hz, 1H), 3.01-2.85 (m, 1H), 2.56 (dd, J = 17.2, 9.3 Hz, 1H), 2.45 (dd, J = 17.2, 7.3 Hz, 1H), 2.21-2.07 (m, 4H), 1.48 (d, J = 6.3 Hz, 3H).

| 3H.12 | 2.71 | | | Calc: 409.23 Found: 409.27 |

$^1$H NMR (400 MHz, Chloroform-d) δ 7.96 (d, J = 0.7 Hz, 1H), 7.91 (d, J = 0.7 Hz, 1H), 7.82 (s, 1H), 7.40 (s, 1H), 5.84 (s, 1H), 5.74-5.66 (m, 1H), 3.63-3.51 (m, 2H), 3.42 (dd, J = 9.6, 6.5 Hz, 1H), 2.99-2.87 (m, 1H), 2.61-2.47 (m, 2H), 1.64 (s, 9H), 1.46 (d, J = 6.3 Hz, 3H), 1.17-1.03 (m, 4H).

| 3H.13 | 2.71 | 7.44 | | Calc: 433.20 Found: 433.28 |

$^1$H NMR (400 MHz, Chloroform-d) δ 9.99 (s, 1H), 8.01-7.90 (m, 1H), 7.81-7.59 (m, 3H), 7.07-6.94 (m, 1H), 6.52-6.35 (m, 1H), 5.88-5.75 (m, 1H), 3.69-3.53 (m, 2H), 3.52-3.38 (m, 4H), 3.07-2.87 (m, 1H), 2.65-2.50 (m, 2H), 1.55-1.45 (m, 3H), 1.23-1.05 (m, 4H).

TABLE 3A-continued

Examples 3G.01-3G.31 and 3H.01-3H.14.

| Example # | Aryl Halide | Boronic Acid/Ester | Product/Salt Proton NMR | LCMS-ESI+ (m/z): [M + H]+ |
|---|---|---|---|---|
| 3H.14 | 2.75 | | | Calc: 425.2 Found: 425.1 |

$^1$H NMR (400 MHz, Chloroform-d) δ 7.83 (d, J = 1.2 Hz, 1H), 7.80 (s, 1H), 7.39 (s, 1H), 7.29 (s, 1H), 6.27 (s, 1H), 4.80-4.72 (m, 1H), 3.66-3.59 (m, 1H), 3.59-3.53 (m, 1H), 3.41 (dd, J = 9.6, 6.8 Hz, 1H), 2.99-2.86 (m, 1H), 2.57-2.50 (m, 2H), 1.49 (s, 9H), 1.44 (d, J = 6.1 Hz, 3H), 1.13-1.04 (m, 4H).

| 3G.01 | 2.71 | 7.52 | (TFA Salt) | Calc: 460.2 Found: 460.1 |

$^1$H NMR (400 MHz, DMSO-d6) δ 10.25 (s, 1H), 8.50 (s, 1H), 7.71-7.62 (m, 3H), 7.59 (s, 1H), 7.36 (d, J = 8.0 Hz, 1H), 5.60 (p, J = 5.9 Hz, 1H), 3.76-3.71 (m, 1H), 3.44 (t, J = 9.1 Hz, 1H), 3.21 (dd, J = 9.7, 6.6 Hz, 1H), 2.93-2.80 (m, 1H), 2.43-2.26 (m, 4H), 1.43 (d, J = 6.2 Hz, 3H), 1.26 (s, 6H), 1.21-1.01 (m, 4H).

| 3G.02 | 2.71 | | | Calc: 417.20 Found: 417.26 |

$^1$H NMR (400 MHz, CD$_3$OD) δ 8.26-8.20 (m, 2H), 8.15 (s, 1H), 8.06 (dd, J = 8.6, 1.6 Hz, 1H), 7.78 (s, 1H), 7.71 (dd, J = 8.6, 0.7 Hz, 1H), 5.91-5.81 (m, 1H), 3.98 (s, 3H), 3.75 (tt, J = 6.3, 4.7 Hz, 1H), 3.64 (dd, J = 10.1, 8.7 Hz, 1H), 3.45 (dd, J = 10.1, 5.9 Hz, 1H), 3.10-2.97 (m, 1H), 2.64-2.57 (m, 2H) 1.55 (d, J = 6.2 Hz, 3H), 1.25-1.12 (m, 4H).

TABLE 3A-continued
Examples 3G.01-3G.31 and 3H.01-3H.14.
| Example # | Aryl Halide | Boronic Acid/Ester | Product/Salt Proton NMR | LCMS-ESI+ (m/z): [M + H]+ |
|---|---|---|---|---|
| 3G.03 | 2.71 | 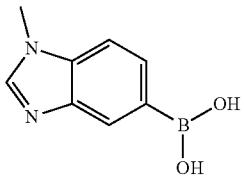 | 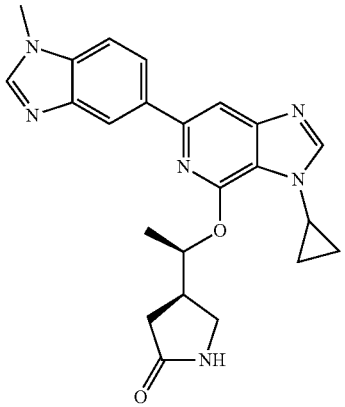 [SMILES: C[C@@H](Oc1nc(-c2ccc3c(c2)ncn3C)cc2ncn(C3CC3)c12)[C@H]1CNC(=O)C1] | Calc: 417.20 Found: 417.21 |
¹H NMR (400 MHz, CD₃OD) δ 8.41 (dd, J = 1.6, 0.7 Hz, 1H), 8.21 (d, J = 0.5 Hz, 1H), 8.15 (s, 1H), 8.07 (dd, J = 8.6, 1.6 Hz, 1H), 7.72 (s, 1H), 7.62 (dd, J = 8.6, 0.7 Hz, 1H), 7.42 (d, J = 7.8 Hz, 0H), 5.93-5.79 (m, 1H), 3.94 (s, 3H), 3.79-3.72 (m, 1H), 3.64 (dd, J = 10.1, 8.7 Hz, 1H), 3.51-3.40 (m, 1H), 3.11-2.96 (m, 1H), 2.65-2.58 (m, 2H), 1.55 (d, J = 6.2 Hz, 3H), 1.25-1.16 (m, 4H).
| 3G.04 | 2.71 | 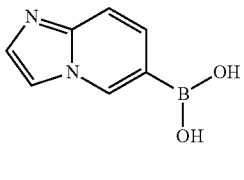 [SMILES: OB(O)c1ccc2nccn2c1] | 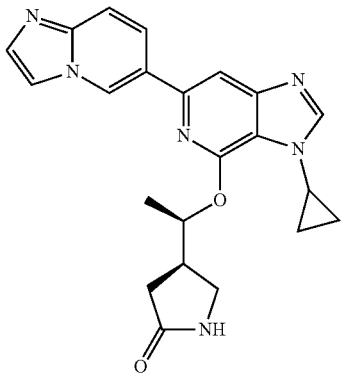 [SMILES: C[C@@H](Oc1nc(-c2ccc3nccn3c2)cc2ncn(C3CC3)c12)[C@H]1CNC(=O)C1] | Calc: 403.20 Found: 403.30 |
¹H NMR (400 MHz, CD₃OD) δ 9.18 (dd, J = 1.8, 1.0 Hz, 1H), 8.24 (s, 1H), 8.03 (dd, J = 9.5, 1.8 Hz, 1H), 7.96 (dd, J = 1.4, 0.7 Hz, 1H), 7.73 (s, 1H), 7.61 (dt, J = 9.5, 0.9 Hz, 1H), 7.59 (d, J = 1.3 Hz, 1H), 5.94-5.76 (m, 1H), 3.81-3.70 (m, 1H), 3.64 (dd, J = 10.1, 8.7 Hz, 1H), 3.44 (dd, J = 10.1, 5.9 Hz, 1H), 3.08-2.92 (m, 1H), 2.60 (d, J = 8.3 Hz, 2H), 1.53 (d, J = 6.2 Hz, 3H), 1.25-1.11 (m, 4H).

TABLE 3A-continued
Examples 3G.01-3G.31 and 3H.01-3H.14.
| Example # | Aryl Halide | Boronic Acid/Ester | Product/Salt Proton NMR | LCMS-ESI+ (m/z): [M + H]+ |
|---|---|---|---|---|
| 3G.05 | 2.71 | 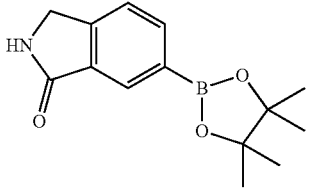 [SMILES: CC1(C)OB(c2ccc3c(c2)C(=O)NC3)OC1(C)C] | 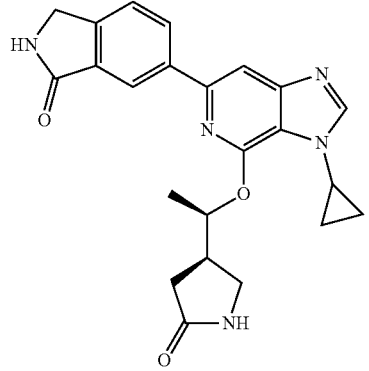 [SMILES: C[C@@H](Oc1nc(-c2ccc3c(c2)C(=O)NC3)cc2ncn(C3CC3)c12)[C@H]1CNC(=O)C1] | Calc: 418.18 Found: 418.26 |
$^1$H NMR (400 MHz, CD$_3$OD) δ 8.54 (dd, J = 1.7, 0.7 Hz, 1H), 8.33 (dd, J = 8.0, 1.7 Hz, 1H), 8.23 (d, J = 0.6 Hz, 1H), 7.77 (s, 1H), 7.66 (dq, J = 7.9, 0.7 Hz, 1H), 5.95-5.83 (m, 1H), 4.52 (d, J = 0.9 Hz, 2H), 3.83-3.71 (m, 1H), 3.63 (dd, J = 10.1, 8.8 Hz, 1H), 3.52-3.38 (m, 1H), 3.09-2.95 (m, 1H), 2.63-2.54 (m, 2H), 1.53 (d, J = 6.2 Hz, 3H), 1.23-1.11 (m, 4H).
| 3G.06 | 2.71 | 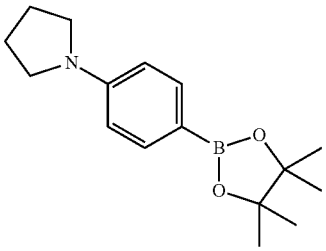 [SMILES: CC1(C)OB(c2ccc(N3CCCC3)cc2)OC1(C)C] | (TFA Salt) 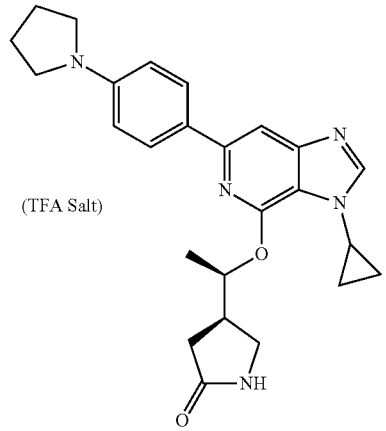 [SMILES: C[C@@H](Oc1nc(-c2ccc(N3CCCC3)cc2)cc2ncn(C3CC3)c12)[C@H]1CNC(=O)C1] | Calc: 432.23 Found: 432.33 |
$^1$H NMR (400 MHz, CD$_3$OD) δ 9.10 (s, 1H), 8.21-8.05 (m, 1H), 7.95 (d, J = 8.7 Hz, 1H), 7.80-7.71 (m, 1H), 7.56 (s, 1H), 6.68 (d, J = 8.6 Hz, 1H), 5.94-5.77 (m, 1H), 3.90 (d, J = 12.3 Hz, 1H), 3.63 (dd, J = 10.1, 8.7 Hz, 1H), 3.46-3.33 (m, 3H), 3.01 (t, J = 8.7 Hz, 1H), 2.69-2.46 (m, 2H), 2.11-2.01 (m, 2H), 1.60-1.47 (m, 3H), 1.40-1.16 (m, 6H).

TABLE 3A-continued

Examples 3G.01-3G.31 and 3H.01-3H.14.

| Example # | Aryl Halide | Boronic Acid/Ester | Product/Salt Proton NMR | LCMS-ESI+ (m/z): [M + H]+ |
|---|---|---|---|---|
| 3G.07 | 2.71 | (benzothiazol-6-yl boronic acid) | (TFA Salt) | Calc: 420.14 Found: 420.25 |

¹H NMR (400 MHz, CD₃OD) δ 9.27 (s, 1H), 8.81 (dd, J = 1.8, 0.7 Hz, 1H), 8.50 (s, 1H), 8.30 (dd, J = 8.7, 1.8 Hz, 1H), 8.14 (dd, J = 8.7, 0.7 Hz, 1H), 7.85 (s, 1H), 5.97-5.82 (m, 1H), 3.82 (p, J = 5.7 Hz, 1H), 3.64 (dd, J = 10.1, 8.7 Hz, 1H), 3.54-3.39 (m, 1H), 3.03 (dt, J = 8.5, 5.5 Hz, 1H), 2.60 (d, J = 8.3 Hz, 2H), 1.55 (d, J = 6.2 Hz, 3H), 1.27-1.17 (m, 4H).

| 3G.08 | 2.71 | 7.17 | | Calc: 434.18 Found: 434.24 |

¹H NMR (400 MHz, CD₃OD) δ 8.20 (s, 1H), 7.67 (dq, J = 4.1, 2.1 Hz, 2H), 7.59 (s, 1H), 7.01 (d, J = 8.9 Hz, 1H), 5.85-5.74 (m, 1H), 4.61 (s, 2H), 3.78-3.68 (m, 1H), 3.62 (dd, J = 10.1, 8.7 Hz, 1H), 3.41 (dd, J = 10.1, 6.0 Hz, 1H), 3.06-2.93 (m, 1H), 2.58 (d, J = 8.3 Hz, 2H), 1.51 (d, J = 6.2 Hz, 3H), 1.23-1.08 (m, 4H).

| 3G.09 | 2.71 | 7.19 | | Calc: 434.18 Found: 434.26 |

¹H NMR (400 MHz, CD₃OD) δ 8.19 (d, J = 0.6 Hz, 1H), 7.72-7.64 (m, 2H), 7.62 (s, 1H), 7.00-6.93 (m, 1H), 5.83-5.73 (m, 1H), 4.62 (s, 2H), 3.79-3.68 (m, 1H), 3.62 (dd, J = 10.1, 8.8 Hz, 1H), 3.41 (dd, J = 10.1, 6.0 Hz, 1H), 3.07-2.92 (m, 1H), 2.63-2.51 (m, 2H), 1.51 (d, J = 6.2 Hz, 3H),

TABLE 3A-continued
Examples 3G.01-3G.31 and 3H.01-3H.14.
| Example # | Aryl Halide | Boronic Acid/Ester | Product/Salt | LCMS-ESI+ (m/z): [M + H]+ |
|---|---|---|---|---|
| | | Proton NMR | | |
1.23-1.10 (m, 4H).
| 3G.10 | 2.71 | 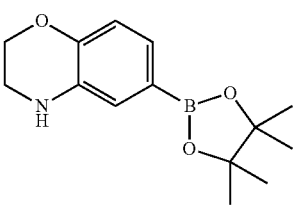 [SMILES: CC1(C)OB(c2ccc3c(c2)NCCO3)OC1(C)C] 7.18 | 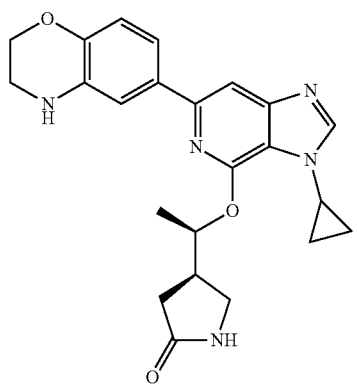 [SMILES: C[C@@H](Oc1nc(-c2ccc3c(c2)NCCO3)cc2ncn(C3CC3)c12)[C@H]1CNC(=O)C1] | Calc: 420.20 Found: 420.28 |
¹H NMR (400 MHz, CD₃OD) δ 8.15 (s, 1H), 7.50 (s, 1H), 7.36 (d, J = 2.1 Hz, 1H), 7.29 (dd, J = 8.4, 2.2 Hz, 1H), 6.74 (d, J = 8.4 Hz, 1H), 5.84-5.74 (m, 1H), 4.26-4.18 (m, 2H), 3.71 (tt, J = 6.6, 4.5 Hz, 1H), 3.61 (dd, J = 10.1, 8.7 Hz, 1H), 3.45-3.40 (m, 1H), 3.40-3.35 (m, 2H), 2.98 (dtd, J = 13.7, 8.7, 5.3 Hz, 1H), 2.61-2.54 (m, 2H), 1.49 (d, J = 6.3 Hz, 3H), 1.24-1.09 (m, 4H).
| 3G.11 | 2.71 | 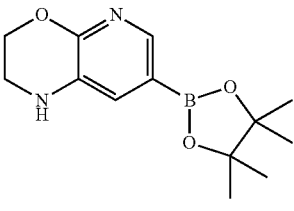 [SMILES: CC1(C)OB(c2cnc3c(c2)NCCO3)OC1(C)C] | 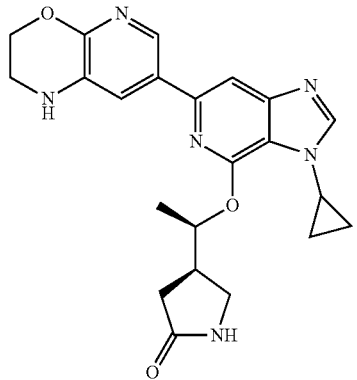 [SMILES: C[C@@H](Oc1nc(-c2cnc3c(c2)NCCO3)cc2ncn(C3CC3)c12)[C@H]1CNC(=O)C1] | Calc: 421.19 Found: 421.16 |
¹H NMR (400 MHz, CD₃OD) δ 8.20 (d, J = 0.6 Hz, 1H), 8.09 (d, J = 2.1 Hz, 1H), 7.63 (d, J = 2.1 Hz, 1H), 7.56 (s, 1H), 5.84-5.69 (m, 1H), 4.45-4.33 (m, 2H) 3.73 (tt, J = 6.5, 4.4 Hz, 1H), 3.61 (dd, J = 10.1, 8.7 Hz, 1H), 3.44-3.36 (m, 3H), 3.05-2.92 (m, 1H), 2.57 (d, J = 8.3 Hz, 2H), 1.49 (d, J = 6.2 Hz, 3H), 1.22-1.11 (m, 4H).

TABLE 3A-continued

Examples 3G.01-3G.31 and 3H.01-3H.14.

| Example # | Aryl Halide | Boronic Acid/Ester | Product/Salt Proton NMR | LCMS-ESI+ (m/z): [M + H]+ |
|---|---|---|---|---|
| 3G.12 | 2.71 | | 7.22 | Calc: 460.19 Found: 460.30 |

1H NMR (400 MHz, CD3OD) δ 8.20 (s, 1H), 7.71-7.62 (m, 2H), 7.60 (s, 1H), 6.91 (d, J = 8.2 Hz, 1H), 5.86-5.76 (m, 1H), 3.73 (tt, J = 6.6, 4.5 Hz, 1H), 3.62 (dd, J = 10.1, 8.7 Hz, 1H), 3.42 (dd, J = 10.1, 6.0 Hz, 1H), 3.07-2.93 (m, 1H), 2.58 (d, J = 8.3 Hz, 2H), 1.51 (d, J = 6.2 Hz, 3H), 1.39-1.33 (m, 2H), 1.26-1.21 (m, 2H), 1.21-1.09 (m, 4H).

| 3G.13 | 2.75 | | | Calc: 420.20 Found: 420.30 |

1H NMR (400 MHz, CD3OD) δ 8.06 (s, 1H), 7.64 (d, J = 2.2 Hz, 1H), 7.33 (d, J = 1.3 Hz, 1H), 7.24 (d, J = 2.2 Hz, 1H), 7.04-6.98 (m, 1H), 4.87 (q, J = 6.0 Hz, 1H), 4.44-4.36 (m, 2H), 3.83-3.70 (m, 3H), 3.60 (dd, J = 10.0, 8.8 Hz, 1H), 3.45-3.35 (m, 3H), 2.97 (dtd, J = 14.4, 8.6, 5.9 Hz, 1H), 2.56 (dd, J = 8.6, 4.1 Hz, 2H), 1.43 (d, J = 6.0 Hz, 3H), 1.20-1.08 (m, 4H).

| 3G.14 | 2.64 | | 7.30 | Calc: 472.17 Found: 472.13 |

1H NMR (400 MHz, CD3OD) δ 8.63 (s, 1H), 7.93 (t, J = 60.0 Hz, 1H), 7.72-7.65 (m, 4H), 7.00 (d, J = 8.4 Hz, 1H), 5.74 (p, J = 6.1 Hz, 1H), 3.59 (dd, J = 10.1, 8.6 Hz, 1H), 3.41-3.33 (m, 1H), 3.00 (qdd, J = 8.6, 6.4, 5.4 Hz, 1H), 2.63-2.47 (m, 2H), 1.54-1.48 (m, 9H).

TABLE 3A-continued

Examples 3G.01-3G.31 and 3H.01-3H.14.

| Example # | Aryl Halide | Boronic Acid/Ester | Product/Salt Proton NMR | LCMS-ESI+ (m/z): [M + H]+ |
|---|---|---|---|---|
| 3G.15 | 2.71 | 7.30 | (TFA Salt) | Calc: 462.2 Found: 462.2 |

$^1$H NMR (400 MHz, DMSO-d6) δ 10.72 (s, 1H), 8.49 (s, 1H), 7.63-7.67 (m, 3H), 7.57 (s, 1H), 6.98 (d, J = 8.4 Hz, 1H), 5.81 (pent, J = 6.0 Hz, 1H), 3.70-3.74 (m, 1H), 3.42 (t, J = 9.6 Hz, 1H), 3.19 (dd, J = 6.8, 9.6 Hz, 1H), 2.81-2.88 (m, 1H), 2.26-2.38 (m, 2H), 1.40-1.46 (m, 9H), 1.04-1.18 (m, 4H).

| 3G.16 | 2.71 | 7.32 | | Calc: 476.2 Found: 476.2 |

$^1$H NMR (400 MHz, DMSO-d6) δ 8.27 (s, 1H), 7.66 (s, 1H), 7.75-7.80 (m, 2H), 7.55 (s, 1H), 7.03 (d, J = 8.4 Hz, 1H), 5.56 (pent, J = 6.4 Hz, 1H), 3.67-3.70 (m, 1H), 3.40 (s, 3H), 3.21 (dd, J = 6.4, 9.2 Hz, 1H), 2.84-2.87 (m, 1H), 2.33 (dd, J = 3.2, 9.6 Hz, 2H), 1.40-1.42 (m, 9H), 1.03-1.12 (m, 4H).

| 3G.17 | 2.71 | 7.47 | (TFA Salt) | Calc: 430.2 Found: 430.2 |

$^1$H NMR (400 MHz, DMSO-d6) δ 8.47 (s, 1H), 8.13 (d, J = 8.4 Hz, 2H), 7.83 (s, 1H), 7.58 (d, J = 8.4 Hz, 2H), 7.56 (s, 1H), 5.58 (pent, J = 5.6 Hz, 1H), 3.70-3.74 (m, 1H), 3.40 (t, J = 9.2 Hz, 1H), 3.20 (dd, J = 6.4, 9.2 Hz, 1H), 2.83-2.87 (m, 1H), 2.28-2.34 (m, 2H), 1.66 (s, 6H), 1.41 (d, J = 6.4 Hz, 3H) 1.04-1.15 (m, 4H).

TABLE 3A-continued

Examples 3G.01-3G.31 and 3H.01-3H.14.

| Example # | Aryl Halide | Boronic Acid/Ester | Product/Salt Proton NMR | LCMS-ESI+ (m/z): [M + H]+ |
|---|---|---|---|---|
| 3G.18 | 2.71 | | (TFA Salt) 7.60 | Calc: 421.2 Found: 421.1 |

¹H NMR (400 MHz, DMSO-d6) δ 8.50 (s, 1H), 7.99 (d, J = 8.4 Hz, 2H), 7.75 (s, 1H), 7.56 (s, 1H), 7.52 (d, J = 8.4 Hz, 2H), 5.58 (pent, J = 5.6 Hz, 1H), 3.69-3.74 (m, 1H), 3.40 (t, J = 9.2 Hz, 1H), 3.20 (dd, J = 6.4, 9.2 Hz, 1H), 2.82-2.87 (m, 1H), 2.28-2.34 (m, 2H), 1.44 (s, 6H), 1.41 (d, J = 6.0 Hz, 3H) 1.04-1.15 (m, 4H).

| 3G.19 | 2.75 | | (TFA Salt) | Calc: 423.2 Found: 423.2 |

¹H NMR (400 MHz, DMSO-d₆) δ 8.92 (s, 1H), 7.86 (s, 1H), 7.67-7.60 (m, 3H), 7.36 (d, J = 8.0 Hz, 1H), 4.93 (m, 1H), 3.98 (s, 3H), 3.82 (s, 3H). 3.59-3.52 (m, 2H), 3.42-3.38 (m, 1H), 2.81-2.79 (m, 1H), 2.39-2.23 (m, 2H), 1.32 (d, J = 5.6 Hz, 3H), 1.20-1.07 (m, 4H).

| 3G.20 | 2.58 | | (TFA Salt) | Calc: 395.2 Found: 395.1 |

¹H NMR (400 MHz, DMSO-d₆): δ 9.16 (s, 1H); 7.84 (s, 1H), 7.67-7.63 (m, 3H), 7.40 (d, J = 8.0 Hz, 1H), 4.93-4.91 (m, 1H), 4.46-4.39 (m, 2H), 4.30-4.28 (m, 2H), 4.08 (s, 3H), 3.41-3.38 (m, 1H), 3.18-3.14 (m, 1H), 2.83-2.79 (m, 1H), 2.40-2.33 (m, 1H); 2.23-2.19 (m, 1H), 1.35 (d, J = 5.6 Hz, 3H).

TABLE 3A-continued
Examples 3G.01-3G.31 and 3H.01-3H.14.
| Example # | Aryl Halide | Boronic Acid/Ester | Product/Salt Proton NMR | LCMS-ESI+ (m/z): [M + H]+ |
|---|---|---|---|---|
| 3G.21 | 2.58 | 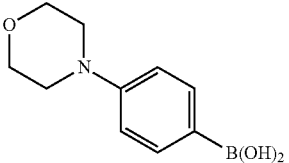 [SMILES: OB(O)c1ccc(N2CCOCC2)cc1] | 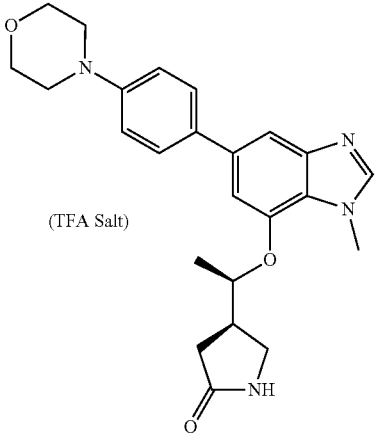 [SMILES: C[C@@H](Oc1cc(-c2ccc(N3CCOCC3)cc2)cc2ncn(C)c12)[C@H]1CNC(=O)C1] (TFA Salt) | Calc: 421.2 Found: 421.1 |
¹H NMR (400 MHz, DMSO-d₆): δ 9.31 (s, 1H), 7.64-7.61 (m, 3H), 7.45 (s, 1H), 7.31 (s, 1H), 7.05 (d, J = 8.8 Hz, 2H), 5.02 (m, 1H), 4.01 (s, 3H), 3.76-3.74 (m, 4H), 3.43-3.39 (m, 1H), 3.17-3.13 (m, 5H), 2.84-2.79 (m, 1H), 2.40-2.33 (m, 1H), 2.23-2.19 (m, 1H), 1.35 (d, J = 6.8 Hz, 3H).
| 3G.22 | 2.58 | 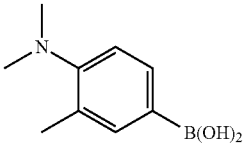 | 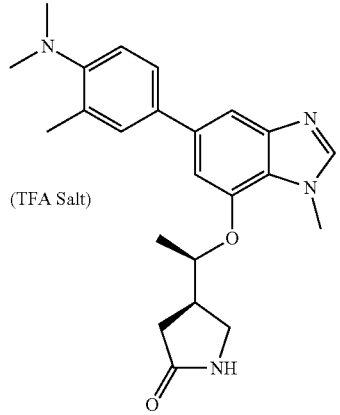 [SMILES: Cc1cc(-c2cc(O[C@H](C)[C@H]3CNC(=O)C3)c3c(c2)ncn3C)ccc1N(C)C] (TFA Salt) | Calc: 393.2 Found: 393.1 |
¹H NMR (400 MHz, DMSO-d₆): δ 9.14 (s, 1H); 7.60-7.54 (m, 3H), 7.46 (s, 1H), 7.27 (m, 2H), 4.98 (m, 1H), 4.09 (s, 3H), 3.43-3.39 (m, 1H), 3.17-3.13 (m, 1H), 2.83-2.80 (m, 1H), 2.78 (s, 6H), 2.36 (s, 3H), 2.40-2.22 (m, 2H), 1.35 (d, J = 6.0 Hz, 3H).

TABLE 3A-continued

Examples 3G.01-3G.31 and 3H.01-3H.14.

| Example # | Aryl Halide | Boronic Acid/Ester | Product/Salt | LCMS-ESI+ (m/z): [M + H]+ |
|---|---|---|---|---|
| | | | Proton NMR | |
| 3G.23 | 2.06 | (4-sulfamoylphenyl boronic acid) | (TFA Salt) | Calc: 416.1 Found: 416.1 |

$^1$H NMR (400 MHz, Methanol-d4) δ 9.10 (s, 1H), 8.26 (d, J = 8.2 Hz, 2H), 8.05-7.95 (m, 2H), 7.90 (s, 1H), 5.81 (p, J = 6.1 Hz, 1H), 4.21 (s, 3H), 3.75-3.58 (m, 1H), 3.40 (dd, J = 10.3, 5.5 Hz, 1H), 3.00 (d, J = 10.4 Hz, 1H), 2.71-2.30 (m, 2H), 1.55 (d, J = 6.2 Hz, 3H).

| 3G.24 | 2.71 | (3,3-dimethyloxindole pinacol boronate) | | Calc: 446.2 Found: 446.2 |

$^1$H NMR (400 MHz, Chloroform-d) δ 8.801 (s, 1H), 7.942 (s, 1H), 7.706 (s, 1H), 7.69 (d, J = 8.2 Hz, 1H), 7.579 (s, 1H), 7.238 (s, 1H), 6.175 (s, 1H), 5.788 (m, 1H), 3.656-3.56 (m, 2H), 3.45 (m, 1H), 2.99 (m, 1H), 2.58 (d, J = 8.5 Hz, 2H), 1.5 (d, J = 6 Hz, 3H), 1.43 (s, 6H), 1.26-0.89 (m, 4H).

TABLE 3A-continued

Examples 3G.01-3G.31 and 3H.01-3H.14.

| Example # | Aryl Halide | Boronic Acid/Ester | Product/Salt | LCMS-ESI+ (m/z): [M + H]+ |
|---|---|---|---|---|
| | | | Proton NMR | |

3G.25  2.64

Calc: 456.18
Found: 456.05

¹H NMR (400 MHz, Chloroform-d) δ 8.769 (s, 1H), 8.313 (s, 1H), 7.784 (s, 1H), 7.653 (s, 1H), 7.578 (s, 1H), 6.395 (s, 1H), 5.762 (m, 1H), 3.606 (m, 1H), 3.409 (m, 1H), 2.999 (m, 1H), 2.615 (m, 1H), 2.514 (m, 1H), 1.76 (m, 2H), 1.513 (d, J = 6 Hz, 3H), 1.432 (s, 6H).

3G.26  2.71

7.34

Calc: 476.19
Found: 476.14

1H NMR (400 MHz, Chloroform-d) δ 9.21 (s, 1H), 7.96 (s, 1H), 7.73 (s, 1H), 7.69 (s, 1H), 7.5 (s, 1H), 7.38 (d, J = 8 Hz, 1H), 6.31 (s, 1H), 5.73 (m, 1H), 4.57 (s, 2H), 4.33 (s, 2H), 3.55 (m, 2H), 3.4 (m, 1H), 2.95 (m, 1H), 2.56 (d, J = 8.8 Hz, 2H), 1.46 (d, J = 5.6 Hz, 3H), 1.26-1.1 (m, 4H).

TABLE 3A-continued

Examples 3G.01-3G.31 and 3H.01-3H.14.

| Example # | Aryl Halide | Boronic Acid/Ester | Product/Salt Proton NMR | LCMS-ESI+ (m/z): [M + H]+ |
|---|---|---|---|---|
| 3G.27 | 2.71 | 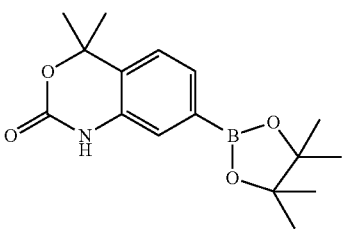 [SMILES: CC1(C)OC(=O)Nc2cc(B3OC(C)(C)C(C)(C)O3)ccc21] 7.39 | 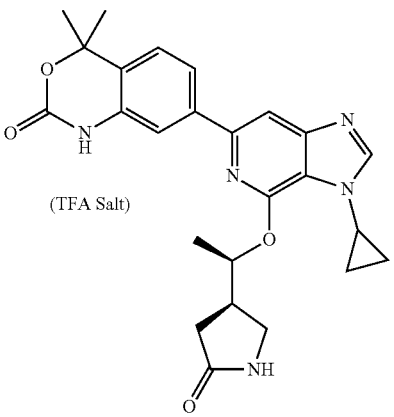 [SMILES: C[C@@H](Oc1nc(-c2ccc3c(c2)NC(=O)OC3(C)C)cc2ncn(C3CC3)c12)[C@H]1CNC(=O)C1] (TFA Salt) | Calc: 462.21 Found: 462.21 |

1H NMR (400 MHz, Methanol-d4) δ 8.89 (s, 1H), 7.67 (m, 2H), 7.59 (s, 1H), 7.27 (d, J = 8.4 Hz, 1H), 5.7 (m, 1H), 3.81 (m, 1H), 3.55 (m, 1H), 3.33 (m, 1H), 2.93 (m, 1H), 2.49 (m, 2H), 1.63 (s, 6H), 1.44 (d, J = 6 Hz, 3H), 1.19 (m, 4H).

| 3G.28 | 2.71 | 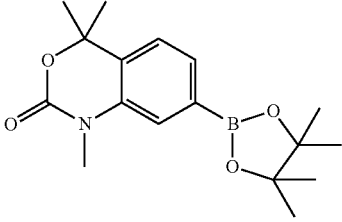 [SMILES: CN1C(=O)OC(C)(C)c2ccc(B3OC(C)(C)C(C)(C)O3)cc21] 7.40 | 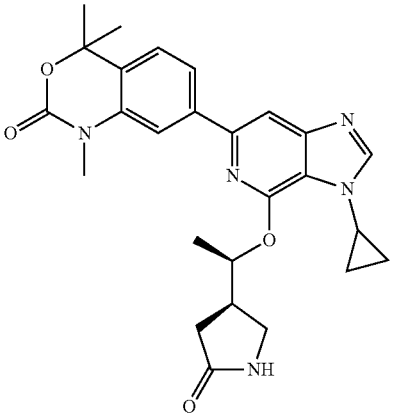 [SMILES: C[C@@H](Oc1nc(-c2ccc3c(c2)N(C)C(=O)OC3(C)C)cc2ncn(C3CC3)c12)[C@H]1CNC(=O)C1] | Calc: 476.23 Found: 476.15 |

1H NMR (400 MHz, Chloroform-d) δ 7.98 (s, 1H), 7.77-7.67 (m, 2H), 7.61 (d, J = 1.6 Hz, 1H), 7.24 (s, 1H), 5.74 (m, 1H), 5.59 (s, 1H), 3.69-3.55 (m, 2H), 3.51 (s, 3H), 3.42 (m, 1H), 2.97 (m, 1H), 2.61-2.51 (m, 2H), 1.72 (s, 6H), 1.53 (d, J = 6.2 Hz, 3H), 1.25-1.08 (m, 4H).

| 3G.29 | 2.77 | 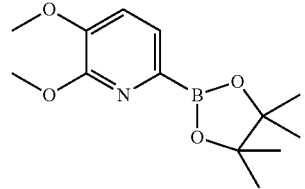 | 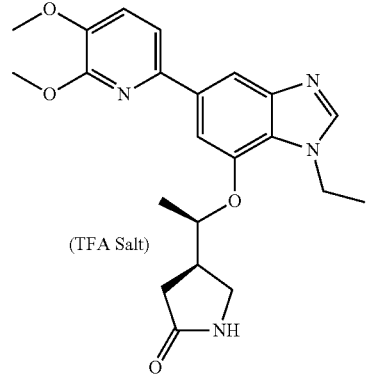 [SMILES: CCn1cnc2cc(-c3ccc(OC)c(OC)n3)cc(O[C@H](C)[C@H]3CNC(=O)C3)c21] (TFA Salt) | Calc: 411.2 Found: 411.2 |

1H NMR (400 MHz, DMSO-d6): δ 9.14 (s, 1H); 7.93 (s, 1H), 7.72-7.63 (m, 3H), 7.38 (d, J = 8.4 Hz, 1H), 5.03 (m, 1H), 4.53 (q, J = 7.2 Hz, 2H). 3.99 (s, 3H), 3.83 (s, 3H), 3.45-3.33 (m, 1H), 3.18-3.15 (m, 1H), 2.86-2.75 (m, 1H), 2.40-2.22 (m, 2H), 1.49 (t, J = 7.2 Hz, 3H), 1.35 (d, J = 6.0 Hz, 3H).

TABLE 3A-continued

Examples 3G.01-3G.31 and 3H.01-3H.14.

| Example # | Aryl Halide | Boronic Acid/Ester | Product/Salt Proton NMR | LCMS-ESI+ (m/z): [M + H]+ |
|---|---|---|---|---|
| 3G.30 | 2.71 | (structure) 7.24 | (structure) | Calc: 446.21 Found: 446.25 |

1H NMR (400 MHz, CD$_3$OD) δ 8.16 (s, 1H), 7.52 (s, 1H), 7.44 (d, J = 2.1 Hz, 1H), 7.30 (dd, J = 8.4, 2.1 Hz, 1H), 6.69 (d, J = 8.4 Hz, 1H), 5.88-5.72 (m, 1H), 3.76-3.67 (m, 1H), 3.61 (dd, J = 10.1, 8.7 Hz, 1H), 3.42 (dd, J = 10.1, 6.0 Hz, 1H), 3.35-3.28 (m, 2H), 2.98 (dtd, J = 13.8, 8.6, 5.4 Hz, 1H), 2.61-2.54 (m, 2H), 1.50 (d, J = 6.3 Hz, 3H), 1.21-1.09 (m, 4H), 1.02-0.94 (m, 2H), 0.79-0.69 (m, 2H).

| 3G.31 NO GS# | 2.71 | (structure) 7.36 | (structure) | Calc: 584.25 Found: 584.23 |
| 3G.32 | 2.71 | (structure) 7.63 | (structure) | Calc: 419.20 Found: 419.31 |

$^1$H NMR (400 MHz, CD$_3$OD) δ 8.82 (s, 1H), 8.25-8.19 (m, 2H), 8.12-8.07 (m, 2H), 7.85 (s, 1H), 5.91-5.78 (m, 1H), 3.91-3.84 (m, 1H), 3.64 (dd, J = 10.1, 8.7 Hz, 1H), 3.42 (dd, J = 10.1, 5.9 Hz, 1H), 3.10 (q, J = 7.2 Hz, 2H) 3.07-2.96 (m, 1H), 2.59 (dd, J = 8.3, 3.0 Hz, 2H), 1.54 (d, J = 6.2 Hz, 3H), 1.32-1.18 (m, 4H), 1.21 (t, J = 7.2 Hz, 2H).

TABLE 3A-continued

Examples 3G.01-3G.31 and 3H.01-3H.14.

| Example # | Aryl Halide | Boronic Acid/Ester | Product/Salt | LCMS-ESI+ (m/z): [M + H]+ |
|---|---|---|---|---|
| | | Proton NMR | | |
| 3H.01 | 2.71 | | | Calc: 434.2 Found: 433.7 |

1H NMR (400 MHz, Chloroform-d) δ 7.91 (s, 1H), 7.79 (dd, J = 8.4, 1.7 Hz, 1H), 7.69 (s, 1H), 7.56 (d, J = 1.7 Hz, 1H), 7.28-7.23 (m, 2H), 5.81-5.67 (m, 2H), 3.68-3.55 (m, 2H), 3.48 (s, 3H), 3.42 (dd, J = 9.6, 6.4 Hz, 1H), 3.04-2.91 (m, 1H), 2.66-2.52 (m, 2H), 1.52 (d, J = 6.2 Hz, 2H), 1.22-1.03 (m, 4H).

| 3H.02 | 2.71 | 7.62 | | Calc: 447.2 Found: 447.1 |

1H NMR (400 MHz, Chloroform-d) δ 7.87 (s, 1H), 7.77 (dd, J = 8.2, 1.6 Hz, 1H), 7.68 (s, 1H), 7.60 (d, J = 1.6 Hz, 1H), 7.02 (d, J = 8.2 Hz, 1H), 6.10 (s, 1H), 5.76 (qd, J = 6.2, 4.7 Hz, 1H), 3.68-3.53 (m, 2H), 3.49 (s, 3H), 3.46-3.40 (m, 4H), 3.02-2.90 (m, 1H), 2.65-2.47 (m, 2H), 1.51 (d, J = 6.2 Hz, 3H), 1.22-1.04 (m, 4H).

TABLE 3A-continued

Examples 3G.01-3G.31 and 3H.01-3H.14.

| Example # | Aryl Halide | Boronic Acid/Ester | Product/Salt Proton NMR | LCMS-ESI+ (m/z): [M + H]+ |
|---|---|---|---|---|
| 3H.03 | 2.71 | (structure shown) | (structure shown)<br>1H NMR (400 MHz, DMSO-d6) δ 12.57 (s, 1H), 8.29 (s, 1H), 8.10 (s, 1H), 7.83 (s, 1H), 7.82-7.75 (m, 2H), 7.56 (s, 1H), 5.65-5.56 (m, 1H), 3.75-3.64 (m, 1H), 3.47-3.38 (m, 1H), 3.22 (dd, J = 9.7, 6.6 Hz, 1H), 2.93-2.81 (m, 1H), 2.38-2.32 (m, 2H), 2.32-2.21 (m, 1H), 1.45 (d, J = 6.1 Hz, 3H), 1.18-0.89 (m, 8H). | Calc: 443.2<br>Found: 443.1 |

Example 3.82

Preparation of 6-(3-cyclopropyl-4-((R)-1-((R)-5-oxopyrrolidin-3-yl)ethoxy)-3H-imidazo[4,5-c]pyridin-6-yl)-3,3-difluoroindolin-2-one

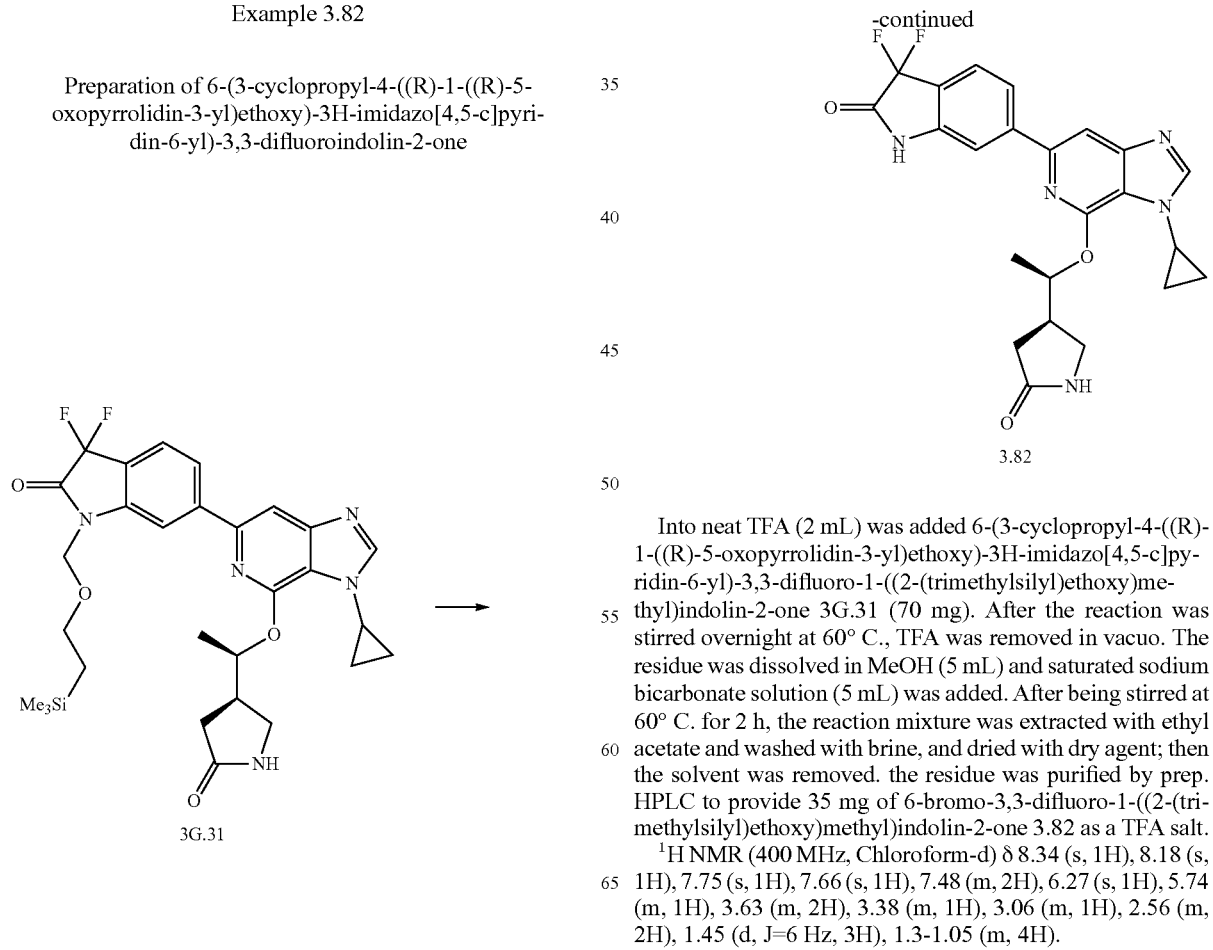

Into neat TFA (2 mL) was added 6-(3-cyclopropyl-4-((R)-1-((R)-5-oxopyrrolidin-3-yl)ethoxy)-3H-imidazo[4,5-c]pyridin-6-yl)-3,3-difluoro-1-((2-(trimethylsilyl)ethoxy)methyl)indolin-2-one 3G.31 (70 mg). After the reaction was stirred overnight at 60° C., TFA was removed in vacuo. The residue was dissolved in MeOH (5 mL) and saturated sodium bicarbonate solution (5 mL) was added. After being stirred at 60° C. for 2 h, the reaction mixture was extracted with ethyl acetate and washed with brine, and dried with dry agent; then the solvent was removed. the residue was purified by prep. HPLC to provide 35 mg of 6-bromo-3,3-difluoro-1-((2-(trimethylsilyl)ethoxy)methyl)indolin-2-one 3.82 as a TFA salt.

$^1$H NMR (400 MHz, Chloroform-d) δ 8.34 (s, 1H), 8.18 (s, 1H), 7.75 (s, 1H), 7.66 (s, 1H), 7.48 (m, 2H), 6.27 (s, 1H), 5.74 (m, 1H), 3.63 (m, 2H), 3.38 (m, 1H), 3.06 (m, 1H), 2.56 (m, 2H), 1.45 (d, J=6 Hz, 3H), 1.3-1.05 (m, 4H).

LCMS-ESI+ (m/z): [M+H]+ calcd for C23H22F2N5O3: 454.17; found: 454.14.

Example 3.83

Preparation of 6-(3-cyclopropyl-4-((R)-1-((R)-5-oxopyrrolidin-3-yl)ethoxy)-3H-imidazo[4,5-c]pyridin-6-yl)indoline-2,3-dione

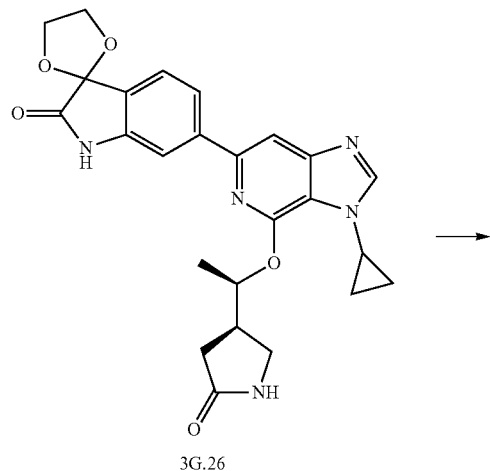

3G.26

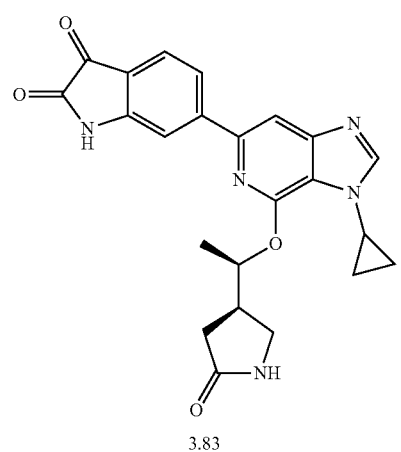

3.83

Into the solution of 6'-(3-cyclopropyl-4-((R)-1-((R)-5-oxopyrrolidin-3-yl)ethoxy)-3H-imidazo[4,5-c]pyridin-6-yl)spiro[[1,3]dioxolane-2,3'-indolin]-2'-one 3G.26 (20 mg) in MeOH (3 mL) was added aqueous HCl (37%, 1 mL). After reflux for 4 h, the solvent was removed, and extracted with ethyl acetate, washed with saturated sodium bicarbonate and brine. After being dried, the solvent was removed and the residue was dissolved in DCM and the desired product was precipitated out by adding hexane. After filtration and vacuum dry, 6-(3-cyclopropyl-4-((R)-1-((R)-5-oxopyrrolidin-3-yl)ethoxy)-3H-imidazo[4,5-c]pyridin-6-yl)indoline-2,3-dione 3.83 (5 mg) was obtained.

$^1$H NMR (400 MHz, Chloroform-d) δ 8.15 (s, 1H), 8.01 (s, 1H), 7.72 (s, 1H), 7.69 (s, 1H), 7.54 (s, 1H), 7.46 (d, J=8 Hz, 1H), 5.77 (m, 2H), 3.65 (m, 2H), 3.42 (m, 1H), 2.97 (m, 1H), 2.58 (d, J=8.8 Hz, 2H), 1.5 (d, J=6 Hz, 3H), 1.3-0.89 (m, 4H).

LCMS-ESI+ (m/z): [M+H]+ calcd for C23H22N5O4: 432.17; found: 432.19.

Example 3.84

Preparation of tert-butyl 6'-(3-cyclopropyl-4-((R)-1-((R)-5-oxopyrrolidin-3-yl)ethoxy)-3H-imidazo[4,5-c]pyridin-6-yl)-1'-methyl-2'-oxospiro[azetidine-3,3'-indoline]-1-carboxylate (NO GS#)

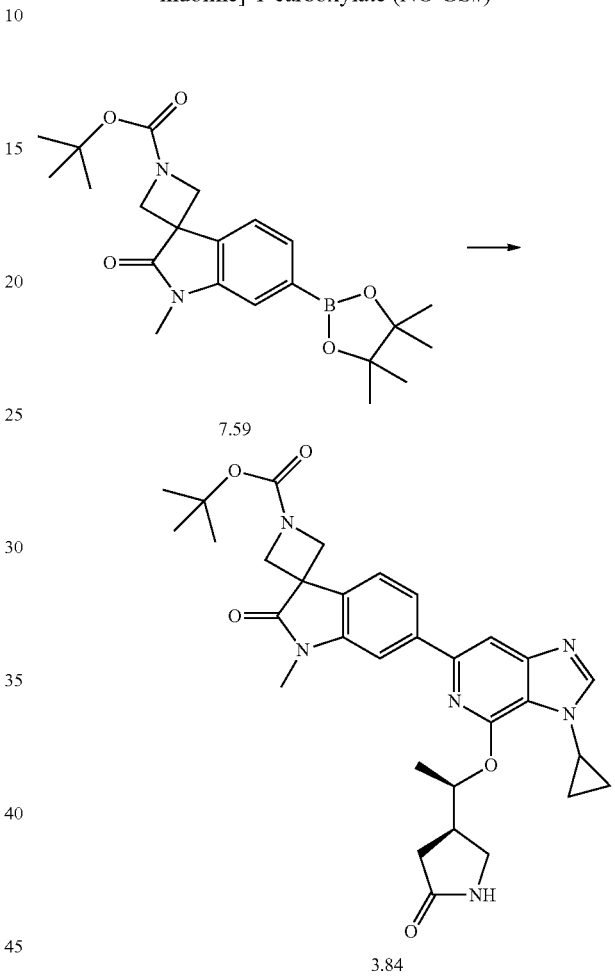

7.59

3.84

In a 5 mL microwave vial, a mixture of (R)-4-((R)-1-((6-chloro-3-cyclopropyl-3H-imidazo[4,5-c]pyridin-4-yl)oxy)ethyl)pyrrolidin-2-one and (R)-4-((R)-1-((6-bromo-3-cyclopropyl-3H-imidazo[4,5-c]pyridin-4-yl)oxy)ethyl)pyrrolidin-2-one 2.71 (50 mg, 0.14 mmol), tert-butyl 1'-methyl-2'-oxo-6'-(4,4,5,5-tetramethyl-1,3,2-dioxaborolan-2-yl)spiro[azetidine-3,3'-indoline]-1-carboxylate 7.59 (68 mg, 0.16 mmol), cesium carbonate (140 mg, 0.43 mmol), and PEPPSI-IPr catalyst (8.2 mg, 0.01 mmol) were taken up in dimethoxyethane (1.8 mL) and water (0.9 mL). After evacuating and backfilling with argon, mixture was heated at 100° C. for 90 minutes in a microwave reactor. After cooling to rt, reaction mixture was poured into water and extracted with ethyl acetate. Combined organics were dried (Na2SO4), filtered, and concentrated under reduced pressure. The resulting residue was purified via silica gel column chromatography (0-10% methanol/dichloromethane) to yield tert-butyl 6'-(3-cyclopropyl-4-((R)-1-((R)-5-oxopyrrolidin-3-yl)ethoxy)-3H-imidazo[4,5-c]pyridin-6-yl)-1'-methyl-2'-oxospiro[azetidine-3,3'-indoline]-1-carboxylate 3.84 (53 mg). LCMS-ESI⁺ (m/z): [M+H]⁺ calcd for $C_{31}H_{37}N_6O_5$: 573.27; found: 573.27.

Example 3.85

Preparation of 6'-(3-cyclopropyl-4-((R)-1-((R)-5-oxopyrrolidin-3-yl)ethoxy)-3H-imidazo[4,5-c]pyridin-6-yl)-1'-methylspiro[azetidine-3,3'-indolin]-2'-one

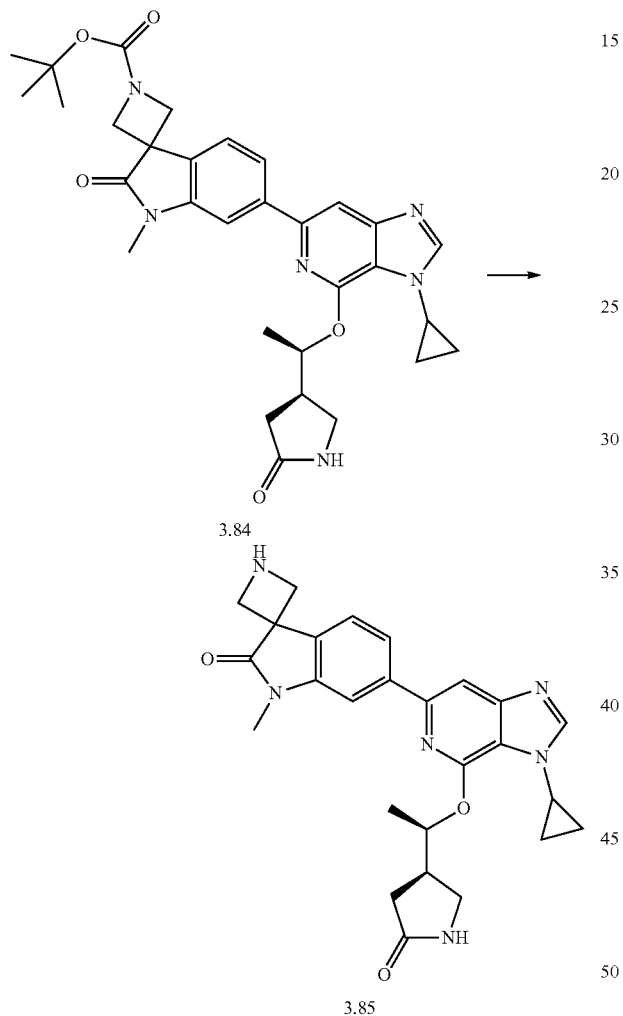

TFA (1.3 mL) was added to a solution of tert-butyl 6'-(3-cyclopropyl-4-((R)-1-((R)-5-oxopyrrolidin-3-yl)ethoxy)-3H-imidazo[4,5-c]pyridin-6-yl)-1'-methyl-2'-oxospiro[azetidine-3,3'-indoline]-1-carboxylate 3.84 (53 mg, 0.09 mmol) in dichloromethane (5 mL). After two hours, reaction mixture was concentrated under reduced pressure and resulting residue was taken up in 1.5 mL methanol and loaded onto an Agilent StratoSpheres™ PL-HCO₃ MP Resin neutralization column (pre-conditioned with methanol). Column was washed with methanol and collected liquids were concentrated under reduced pressure to yield 6'-(3-cyclopropyl-4-((R)-1-((R)-5-oxopyrrolidin-3-yl)ethoxy)-3H-imidazo[4,5-c]pyridin-6-yl)-1'-methylspiro[azetidine-3,3'-indolin]-2'-one 3.85 (9 mg).

¹H NMR (400 MHz, CDCl₃) δ 8.33 (d, J=7.9 Hz, 1H), 8.01 (d, J=7.9 Hz, 1H), 7.92 (s, 1H), 7.75 (s, 1H), 7.41 (s, 1H), 5.84-5.70 (m, 1H), 4.66-4.57 (m, 2H), 4.35 (m, 1H), 3.71-3.57 (m, 2H), 3.47-3.38 (m, 1H), 3.35-3.29 (m, 1H), 3.31 (s, 3H), 2.95 (d, J=9.8 Hz, 1H), 2.58 (t, J=7.0 Hz, 2H), 1.51 (d, 3H), 1.24-1.07 (m, 4H).

LCMS-ESI⁺ (m/z): [M+H]⁺ calcd for $C_{26}H_{29}N_6O_3$: 473.22; found: 473.12.

Example 3.86

Preparation of 6'-(3-cyclopropyl-4-((R)-1-((R)-5-oxopyrrolidin-3-yl)ethoxy)-3H-imidazo[4,5-c]pyridin-6-yl)-1,1'-dimethylspiro[azetidine-3,3'-indolin]-2'-one

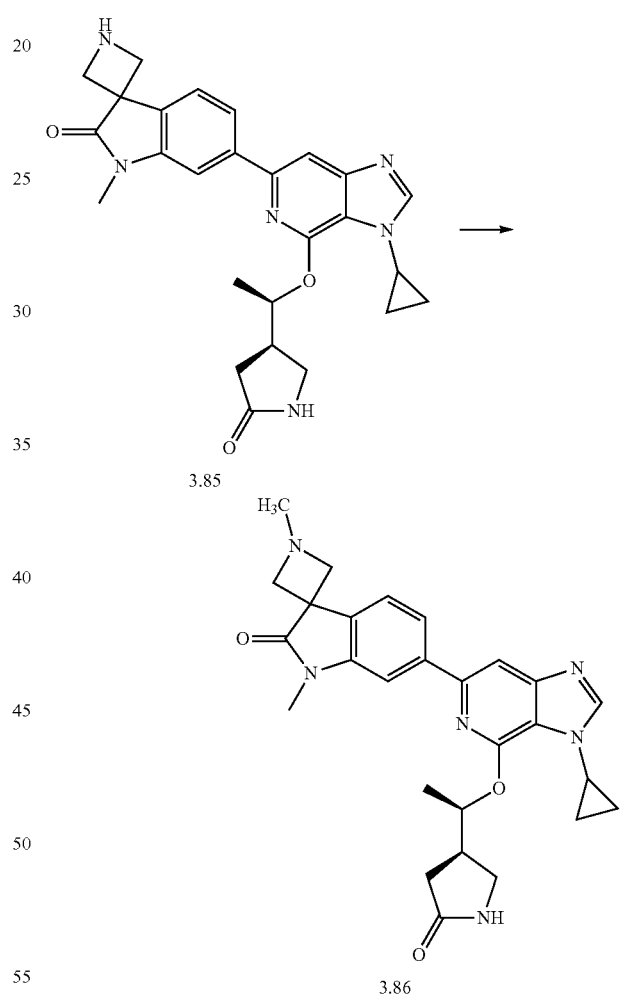

Formaldehyde in water (37%, 0.07 mL, 0.89 mmol) was added to a mixture of 6'-(3-cyclopropyl-4-((R)-1-((R)-5-oxopyrrolidin-3-yl)ethoxy)-3H-imidazo[4,5-c]pyridin-6-yl)-1'-methylspiro[azetidine-3,3'-indolin]-2'-one 3.85 (42 mg, 0.089 mmol) in 1,2-dichloroethane (1.5 mL). After 15 min, sodium triacetoxyborohydride (78 mg, 0.37 mmol) was added and mixture stirred at room temperature overnight. The reaction mixture was then diluted with water and ethyl acetate. The phases were separated, and the aqueous phase was extracted with ethyl acetate. The combined organic phase was dried over sodium sulfate, filtered, and concentrated under reduced pressure. The resulting residue was purified via silica gel column chromatography (0-20% methanol in dichloromethane) to afford 6'-(3-cyclopropyl-4-((R)-1-((R)-5-oxopyrrolidin-3-yl)ethoxy)-3H-imidazo[4,5-c]pyridin-6-yl)-1,1'-dimethylspiro[azetidine-3,3'-indolin]-2'-one 3.86.

$^1$H NMR (400 MHz, CD$_3$OD) δ 8.22 (d, J=0.5 Hz, 1H), 7.92 (dd, J=7.8, 1.5 Hz, 1H), 7.83 (d, J=7.8 Hz, 1H), 7.75 (s, 1H), 7.64 (d, J=1.4 Hz, 1H), 5.81 (dd, J=6.4, 5.0 Hz, 1H), 3.81-3.70 (m, 1H), 3.64 (dd, J=9.2, 1.7 Hz, 5H), 3.43 (dd, J=10.1, 5.9 Hz, 1H), 3.29 (s, 3H), 3.01 (q, J=6.4, 5.9 Hz, 1H), 2.60 (s, 1H), 2.58 (d, J=1.9 Hz, 1H), 2.52 (s, 3H), 1.53 (d, J=6.2 Hz, 3H), 1.27-1.07 (m, 4H).

LCMS-ESI$^+$ (m/z): [M+H]$^+$ calcd. for C$_{27}$H$_{31}$N$_6$O$_3$: 487.24; found: 487.14.

Examples 3.88 and 3.89

Preparation of (E)-6-(3-cyclopropyl-4-((R)-1-((R)-5-oxopyrrolidin-3-yl)ethoxy)-3H-imidazo[4,5-c]pyridin-6-yl)-3-(methoxyimino)indolin-2-one and (Z)-6-(3-cyclopropyl-4-((R)-1-((R)-5-oxopyrrolidin-3-yl)ethoxy)-3H-imidazo[4,5-c]pyridin-6-yl)-3-(methoxyimino)indolin-2-one

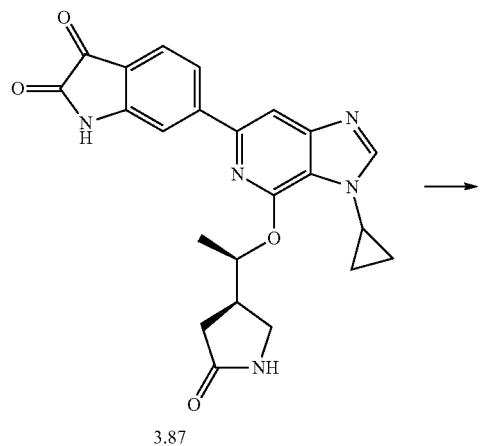

3.87

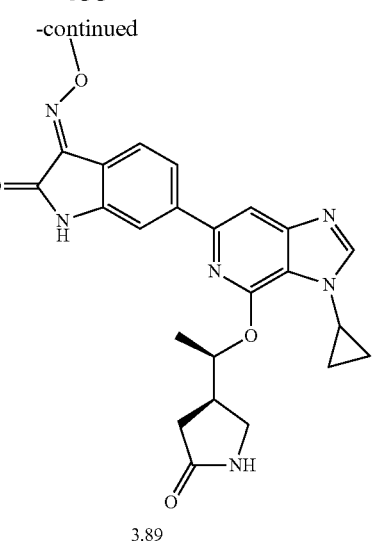

3.89

Into the solution of crude 6-(3-cyclopropyl-4-((R)-1-((R)-5-oxopyrrolidin-3-yl)ethoxy)-3H-imidazo[4,5-c]pyridin-6-yl)indoline-2,3-dione 3.87 (150 mg) in MeOH (20 mL) was added O-methylhydroxylamine hydrochloride (29 mg) and saturated sodium bicarbonate (2 mL). After it was heated at 60° C. for 2 h, the solvent was removed and the residue was purified and separated by prep HPLC to provide 15 mg of the early eluting isomer 3.88 and 6 mg of second eluting isomer 3.89. Geometry of the products was not rigorously assigned.

Characterization data for the first eluting isomer 3.88:
1H NMR (400 MHz, Methanol-d4) δ 8.45 (br., 2H), 7.89 (d, J=8.4 Hz, 1H), 7.7 (m, 1H), 7.66 (m, 1H), 7.56 (s, 1H), 7.53 (s, 1H), 5.7 (m, 2H), 4.2 (s, 3H), 3.69 (m, 1H), 3.55 (m, 1H), 2.93 (m, 1H), 2.49 (m, 2H), 1.45 (d, J=6 Hz, 3H), 1.2-1.1 (m, 4H LCMS-ESI$^+$ (m/z): [M+H]$^+$ calcd for C$_{24}$H$_{25}$N$_6$O$_4$: 461.19; found: 461.16.

Characterization data for the second eluting isomer 3.89:
1H NMR (400 MHz, Methanol-d4) δ 8.75 (br., 1H), 7.89 (d, J=8.4 Hz, 1H), 7.75 (m, 1H), 7.67 (m, 2H), 7.49 (s, 1H), 7.3 (d, J=8 Hz, 1H), 5.7 (m, 2H), 4.22 (s, 3H), 3.76 (m, 1H), 3.54 (m, 1H), 2.9 (m, 1H), 2.49 (m, 2H), 1.44 (d, J=6 Hz, 3H), 1.2-1.1 (m, 4H).

LCMS-ESI$^+$ (m/z): [M+H]$^+$ calcd for C$_{24}$H$_{25}$N$_6$O$_4$: 461.19; found: 461.16.

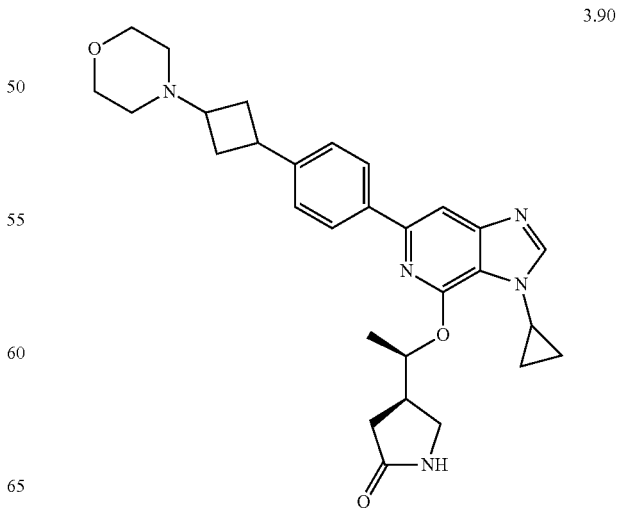

3.90

Preparation of (R)-4-((R)-1-((3-cyclopropyl-6-(4-(3-morpholinoazetidin-1-yl)phenyl)-3H-imidazo[4,5-c]pyridin-4-yl)oxy)ethyl)pyrrolidin-2-one Step-2 Preparation of 4-(1-(4-(4,4,5,5-tetramethyl-1,3,2-dioxaborolan-2-yl)phenyl)azetidin-3-yl)morpholine

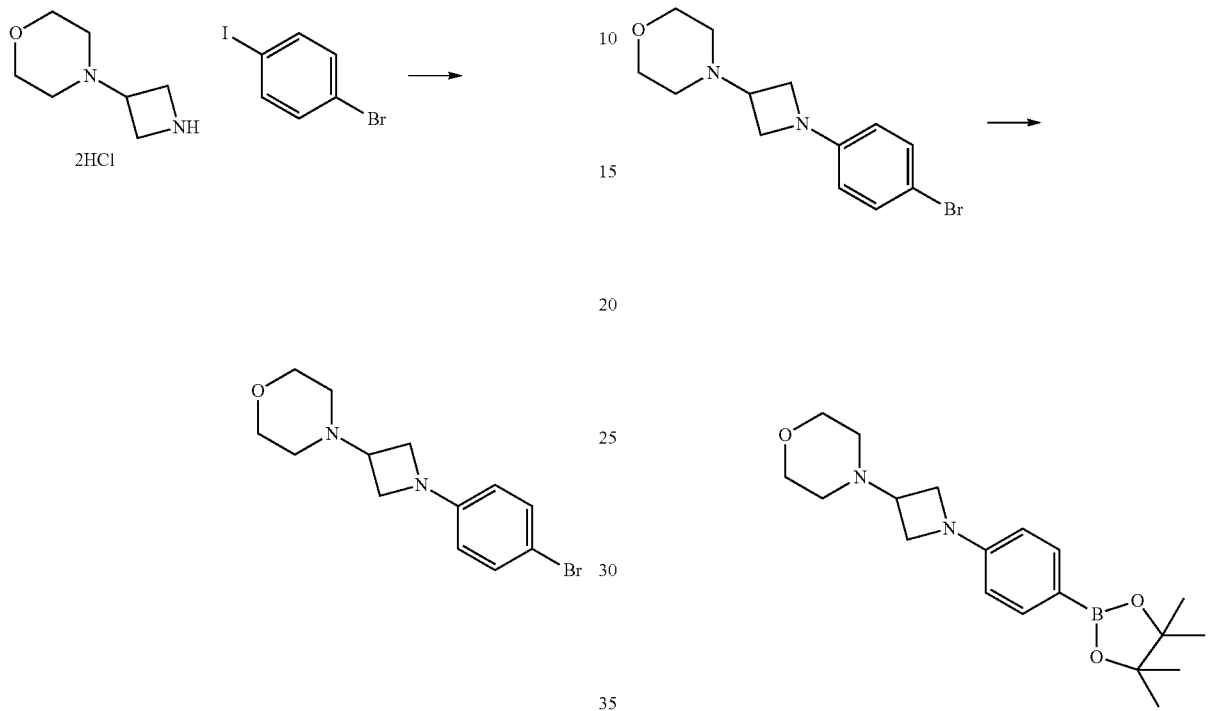

Step-1 Preparation of 4-(1-(4-bromophenyl)azetidin-3-yl)morpholine

Following the procedure described for intermediate 7.13, starting from 1-bromo-4-iodobenzene (172.61 mg, 0.61 mmol) and 4-(azetidin-3-yl)morpholine dihydrochloride (250 mg, 0.58 mmol), 530 mg of 4-(1-(4-bromophenyl)azetidin-3-yl)morpholine was synthesized.

Following the procedure described for intermediate 7.17, starting from 4-(1-(4-bromophenyl)azetidin-3-yl)morpholine, 200 mg of 4-(1-(4-(4,4,5,5-tetramethyl-1,3,2-dioxaborolan-2-yl)phenyl)azetidin-3-yl)morpholine was synthesized.

Step-3 Preparation of (R)-4-((R)-1-((3-cyclopropyl-6-(4-(3-morpholinoazetidin-1-yl)phenyl)-3H-imidazo[4,5-c]pyridin-4-yl)oxy)ethyl)pyrrolidin-2-one

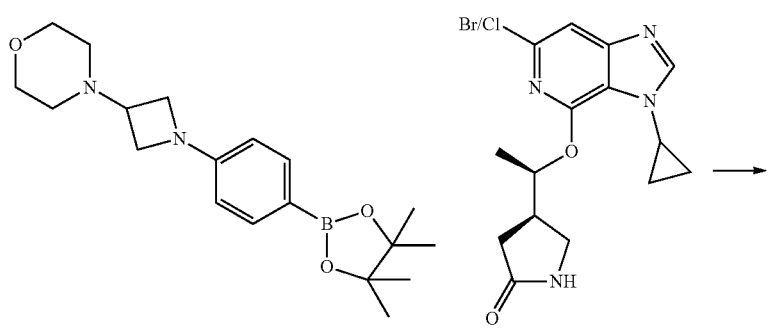

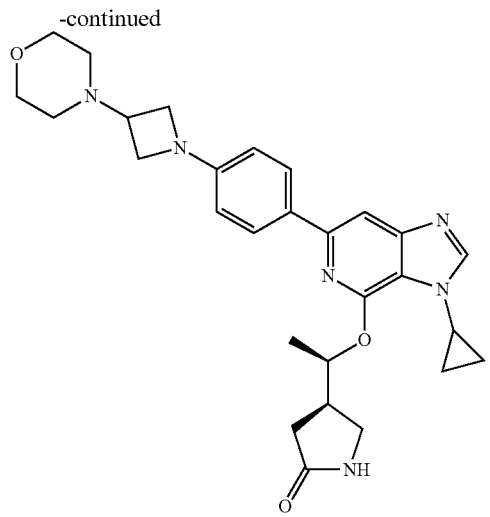

To a 2-5 ml microwave vial, combined (R)-4-((R)-1-((6-bromo-3-cyclopropyl-3H-imidazo[4,5-c]pyridin-4-yl)oxy)ethyl)pyrrolidin-2-one (85 mg, 0.23 mmol), 4-(1-(4-(4,4,5,5-tetramethyl-1,3,2-dioxaborolan-2-yl)phenyl)azetidin-3-yl)morpholine (100.15 mg, 0.29 mmol), tetrakis(triphenylphosphine)palladium (26.89 mg, 0.02 mmol), 1M Sodium carbonate soln in water (0.7 ml) in dioxane (2.3 mL) and blown down with nitrogen. The reaction was irradiated for 20 mins at 150 C. The reaction was diluted with water, extracted with DCM, combined organics, dried (Na2SO4), filtered, concentrated. Residues were purified by silica gel column chromatography to yield the title compound (4.2 mg, 3.6%) as a free base.

$^1$H NMR (400 MHz, DMSO-d6) δ 8.20 (s, 1H), 7.89 (d, J=8.7 Hz, 2H), 7.56 (d, J=11.1 Hz, 2H), 6.47 (d, J=8.7 Hz, 2H) 5.75-5.55 (m, 1H), 3.65-3.61 (m, 4H), 3.58 (t, J=4.1 Hz, 2H), 3.40 (t, 14.65 Hz, 1H), 3.15-3.40 (m, 2H), 2.85-2.75 (m, 1H) 2.41-2.30 (m, 6H), 1.39 (d, J=6.4 Hz, 2H), 1.15-0.95 (m, 3H).

LCMS-ESI$^+$ (m/z): [M+H]$^+$ calcd. for C$_{28}$H$_{34}$N$_6$O$_4$: 503.61; found: 503.21.

3.91

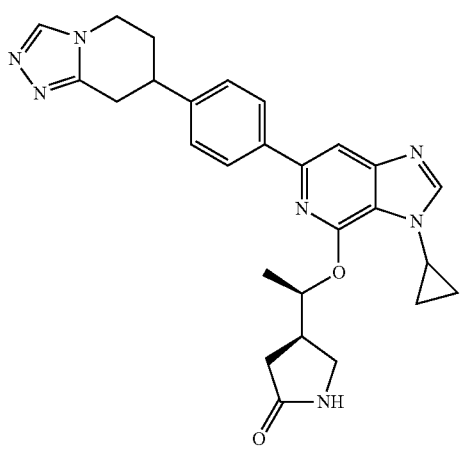

Preparation of (R)-4-((R)-1-((3-cyclopropyl-6-(4-(5,6-dihydro-[1,2,4]triazolo[4,3-a]pyrazin-7(8H)-yl)phenyl)-3H-imidazo[4,5-c]pyridin-4-yl)oxy)ethyl)pyrrolidin-2-one Step-1 Preparation of 7-(4-bromophenyl)-5,6,7,8-tetrahydro-[1,2,4]triazolo[4,3-a]pyrazine

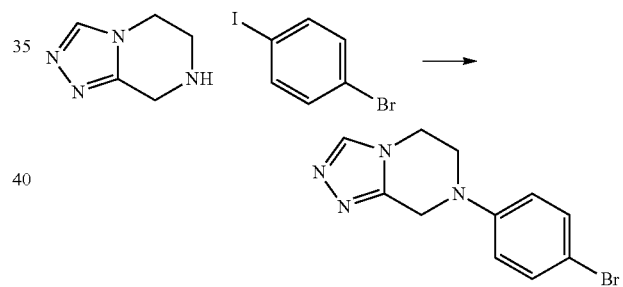

Following the procedure described for intermediate 7.13, starting from 1-bromo-4-iodobenzene (1196.39 mg, 4.23 mmol) and 5,6,7,8-tetrahydro-[1,2,4]triazolo[4,3-a]pyrazine (500 mg, 4.03 mmol), 1124 mg of 7-(4-bromophenyl)-5,6,7,8-tetrahydro-[1,2,4]triazolo[4,3-a]pyrazine was synthesized.

Step-2 Preparation of 7-(4-(4,4,5,5-tetramethyl-1,3,2-dioxaborolan-2-yl)phenyl)-5,6,7,8-tetrahydro-[1,2,4]triazolo[4,3-a]pyrazine

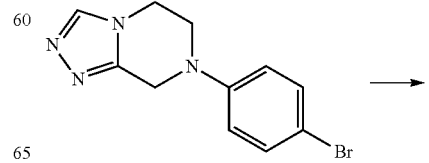

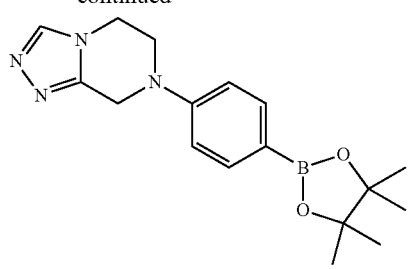

Following the procedure described for intermediate 7.17, starting from 7-(4-bromophenyl)-5,6,7,8-tetrahydro-[1,2,4]triazolo[4,3-a]pyrazine (220 mg, 0.79 mmol), 220 mg of 7-(4-(4,4,5,5-tetramethyl-1,3,2-dioxaborolan-2-yl)phenyl)-5,6,7,8-tetrahydro-[1,2,4]triazolo[4,3-a]pyrazine was synthesized.

Step-3 (R)-4-((R)-1-((3-cyclopropyl-6-(4-(5,6-dihydro-[1,2,4]triazolo[4,3-a]pyrazin-7(8H)-yl)phenyl)-3H-imidazo[4,5-c]pyridin-4-yl)oxy)ethyl)pyrrolidin-2-one

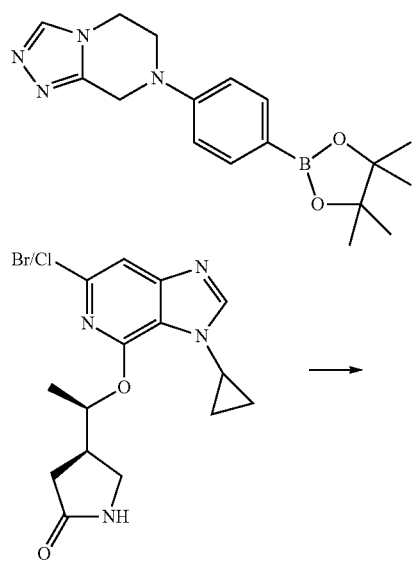

Following the procedure described for Example Example 3.90, starting from (R)-4-((R)-1-((6-bromo-3-cyclopropyl-3H-imidazo[4,5-c]pyridin-4-yl)oxy)ethyl)pyrrolidin-2-one (100 mg, 0.27 mmol), 49.5 mg of (R)-4-((R)-1-((3-cyclopropyl-6-(4-(5,6-dihydro-[1,2,4]triazolo[4,3-a]pyrazin-7(8H)-yl)phenyl)-3H-imidazo[4,5-c]pyridin-4-yl)oxy)ethyl)pyrrolidin-2-one was synthesized.

$^1$H NMR (400 MHz, DMSO-d6) δ 8.46 (s, 1H), 8.22 (s, 1H), 7.94 (d, J=8.8 Hz, 2H), 7.66 (s, 1H), 7.55 (s, 1H), 7.13 (d, J=9.4 Hz, 2H), 5.56-5.53 (m, 1H), 4.61 (s, 2H), 4.15 (t, J=5.3 Hz, 2H), 3.77 (t, 4.7 Hz, 2H), 3.68-3.65 (m, 1H), 3.93 (t, J=9.1 Hz, 1H) 3.20 (t, J=7.8 Hz 1H), 2.84-2.82 (m, 1H), 2.32 (d, J=8.7 Hz, 2H), 1.40 (d, J=6.9 Hz, 2H), 1.01-0.98 (m, 3H).

LCMS-ESI$^+$ (m/z): [M+H]$^+$ calcd. for $C_{26}H_{28}N_8O_2$: 485.55; found: 485.18.

3.92

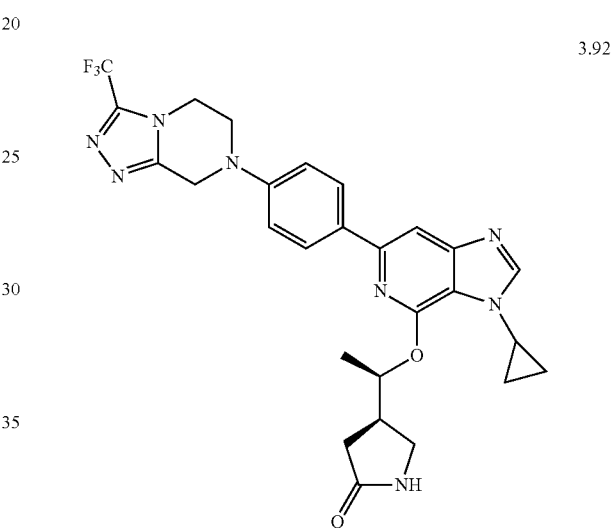

Preparation of (R)-4-((R)-1-((3-cyclopropyl-6-(4-(3-(trifluoromethyl)-5,6-dihydro-[1,2,4]triazolo[4,3-a]pyrazin-7(8H)-yl)phenyl)-3H-imidazo[4,5-c]pyridin-4-yl)oxy)ethyl)pyrrolidin-2-one Step-1 Preparation of 7-(4-bromophenyl)-3-(trifluoromethyl)-5,6,7,8-tetrahydro-[1,2,4]triazolo[4,3-a]pyrazine

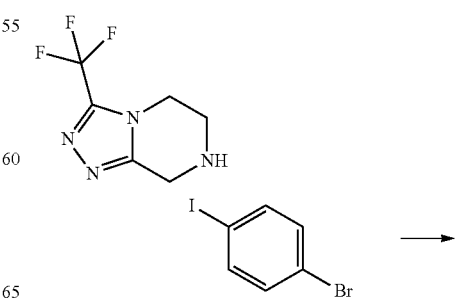

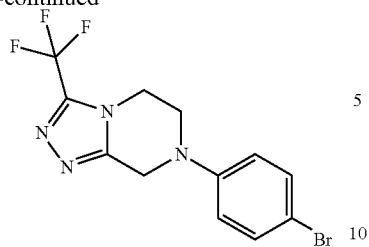

Following the procedure described for intermediate 7.13, starting from 1-bromo-4-iodobenzene (773 mg, 2.73 mmol) and 3-(trifluoromethyl)-5,6,7,8-tetrahydro-[1,2,4]triazolo[4,3-a]pyrazine (500 mg, 2.6 mmol), 220 mg of 7-(4-bromophenyl)-3-(trifluoromethyl)-5,6,7,8-tetrahydro-[1,2,4]triazolo[4,3-a]pyrazine was synthesized.

Step-2 Preparation of 7-(4-(4,4,5,5-tetramethyl-1,3,2-dioxaborolan-2-yl)phenyl)-3-(trifluoromethyl)-5,6,7,8-tetrahydro-[1,2,4]triazolo[4,3-a]pyrazine

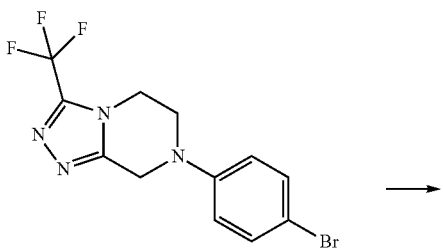

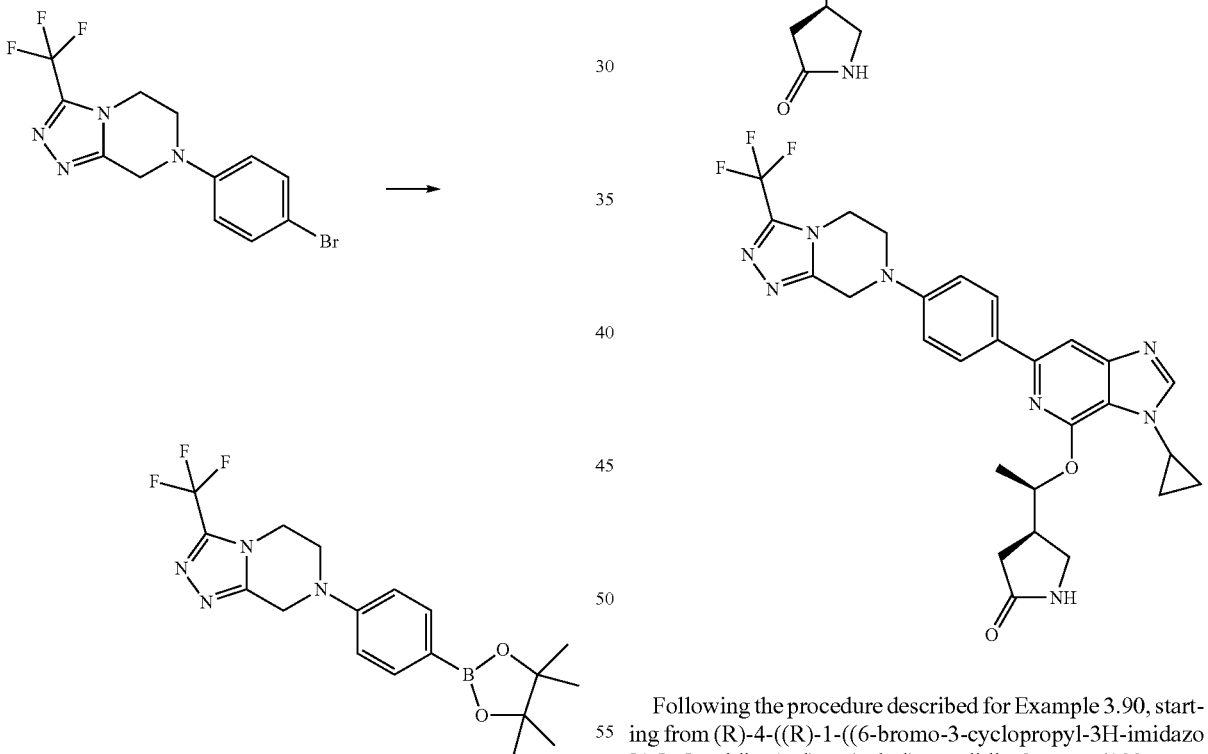

Following the procedure described for intermediate 7.17, starting 7-(4-bromophenyl)-3-(trifluoromethyl)-5,6,7,8-tetrahydro-[1,2,4]triazolo[4,3-a]pyrazine (220 mg, 0.63 mmol), 170 mg of 7-(4-(4,4,5,5-tetramethyl-1,3,2-dioxaborolan-2-yl)phenyl)-3-(trifluoromethyl)-5,6,7,8-tetrahydro-[1,2,4]triazolo[4,3-a]pyrazine was synthesized.

Step-3 (R)-4-((R)-1-((3-cyclopropyl-6-(4-(3-(trifluoromethyl)-5,6-dihydro-[1,2,4]triazolo[4,3-a]pyrazin-7(8H)-yl)phenyl)-3H-imidazo[4,5-c]pyridin-4-yl)oxy)ethyl)pyrrolidin-2-one Following the procedure described for Example 3.90, starting from (R)-4-((R)-1-((6-bromo-3-cyclopropyl-3H-imidazo[4,5-c]pyridin-4-yl)oxy)ethyl)pyrrolidin-2-one (100 mg, 0.27 mmol), 58.6 mg of (R)-4-((R)-1-((3-cyclopropyl-6-(4-(3-(trifluoromethyl)-5,6-dihydro-[1,2,4]triazolo[4,3-a]pyrazin-7(8H)-yl)phenyl)-3H-imidazo[4,5-c]pyridin-4-yl)oxy)ethyl)pyrrolidin-2-one was synthesized.

$^1$H NMR (400 MHz, DMSO-d6) δ 8.23 (s, 1H), 7.99 (d, J=8.8 Hz, 2H), 7.68 (s, 1H), 7.55 (s, 1H), 7.17 (d, J=9.4 Hz, 2H), 5.57-5.51 (m, 1H), 4.73 (s, 2H), 4.27 (t, J=5.3 Hz, 2H), 3.85 (t, 5.3 Hz, 2H), 3.70-3.63 (m, 1H), 3.95 (t, J=9.4 Hz, 1H) 3.29-3.17 (m, 1H), 2.87-2.70 (m, 1H), 2.32 (d, J=9.3 Hz, 2H), 1.39 (d, J=6.4 Hz, 2H), 1.10-0.98 (m, 3H).

LCMS-ESI⁺ (m/z): [M+H]⁺ calcd. for $C_{27}H_{27}N_8O_2$: 553.55; found: 552.93.

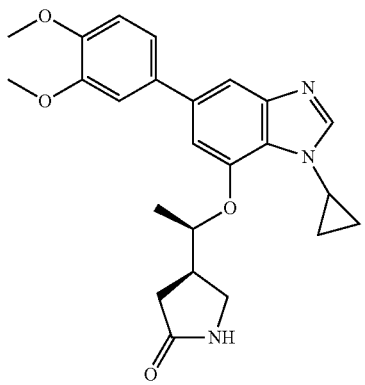

Preparation of (R)-4-((R)-1-((3-cyclopropyl-6-(3,4-dimethoxyphenyl)-3H-imidazo[4,5-c]pyridin-4-yl)oxy)ethyl)pyrrolidin-2-one Step-1 Preparation of (R)-4-((R)-1-((3-cyclopropyl-6-(3,4-dimethoxyphenyl)-3H-imidazo[4,5-c]pyridin-4-yl)oxy)ethyl)pyrrolidin-2-one

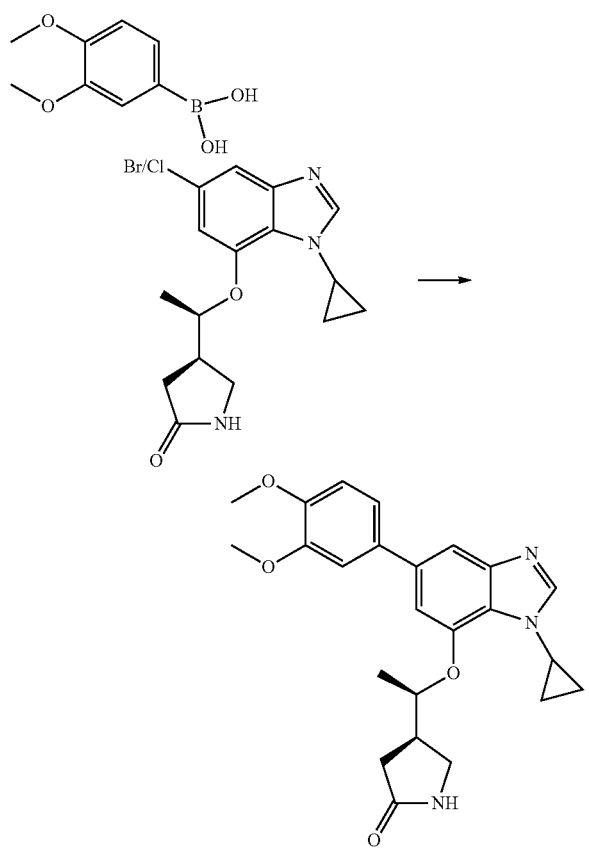

Following the procedure described for Example 3.90, starting from (R)-4-((R)-1-((5-bromo-1-cyclopropyl-1H-benzo[d]imidazol-7-yl)oxy)ethyl)pyrrolidin-2-one (100 mg, 0.27 mmol), 34.8 mg of (R)-4-((R)-1-((3-cyclopropyl-6-(3,4-dimethoxyphenyl)-3H-imidazo[4,5-c]pyridin-4-yl)oxy)ethyl)pyrrolidin-2-one was synthesized.

¹H NMR (400 MHz, DMSO-d6) δ 8.06 (s, 1H), 7.57 (s, 1H), 7.39 (s, 1H), 7.08 (d, J=49.3 Hz, 2H), 7.07 (d, J=55.1 Hz, 2H), 4.86-4.82 (m, 1H), 3.83 (s, 3H), 3.76 (s, 3H), 3.70-3.65 (m, 1H), 3.38 (t, J=9.1 Hz, 1H), 3.17 (t, J=7.0 Hz, 1H) 2.38-2.20 (m, 1H), 1.29 (d, J=6.5 Hz, 2H), 1.09-0.98 (m, 3H).

LCMS-ESI⁺ (m/z): [M+H]⁺ calcd. for $C_{24}H_{27}N_3O_4$: 422.49; found: 422.95.

3.94

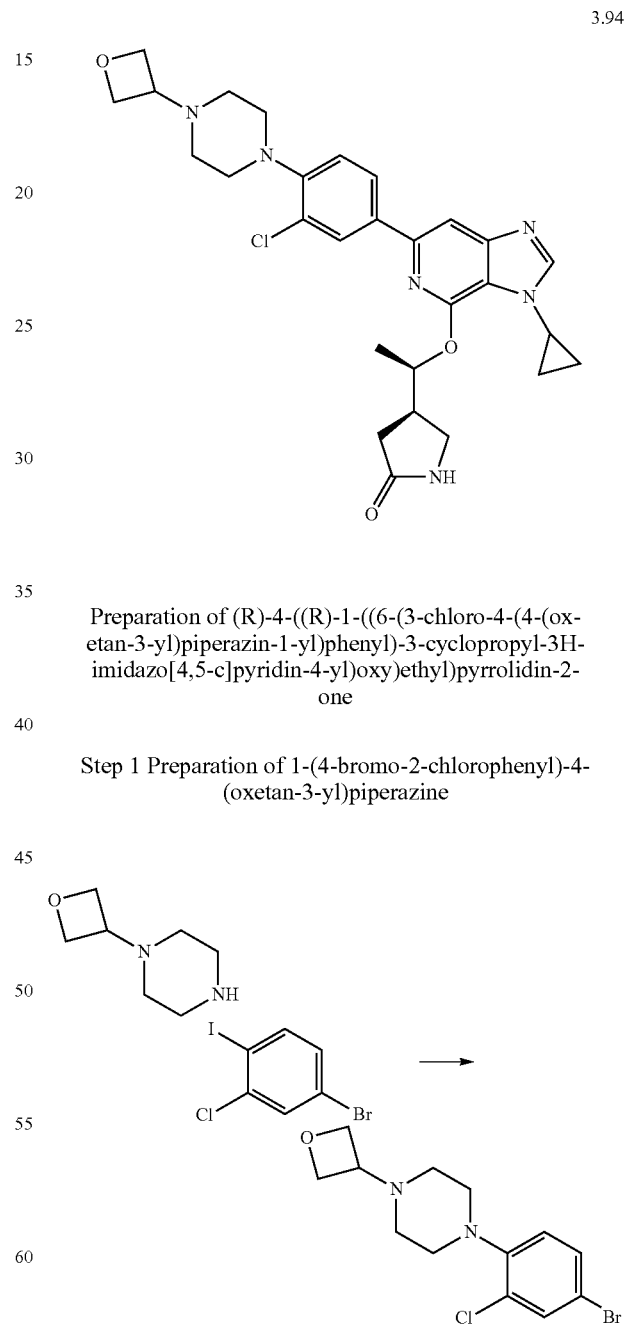

Preparation of (R)-4-((R)-1-((6-(3-chloro-4-(4-(oxetan-3-yl)piperazin-1-yl)phenyl)-3-cyclopropyl-3H-imidazo[4,5-c]pyridin-4-yl)oxy)ethyl)pyrrolidin-2-one Step 1 Preparation of 1-(4-bromo-2-chlorophenyl)-4-(oxetan-3-yl)piperazine Following the procedure described for intermediate 7.13, starting from 4-bromo-2-chloro-1-iodobenzene (2108.99 mg, 6.65 mmol) and 1-(oxetan-3-yl)piperazine (900 mg, 6.33 mmol), 1180 mg of 1-(4-bromo-2-chlorophenyl)-4-(oxetan-3-yl)piperazine was synthesized.

Step-2 Preparation of 1-(2-chloro-4-(4,4,5,5-tetramethyl-1,3,2-dioxaborolan-2-yl)phenyl)-4-(oxetan-3-yl)piperazine

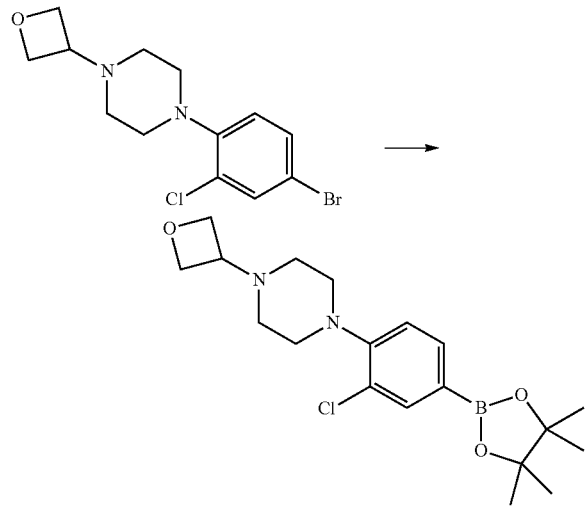

Following the procedure described for intermediate 7.17, starting 1-(4-bromo-2-chlorophenyl)-4-(oxetan-3-yl)piperazine (500 mg, 1.51 mmol), 520 mg 1-(2-chloro-4-(4,4,5,5-tetramethyl-1,3,2-dioxaborolan-2-yl)phenyl)-4-(oxetan-3-yl)piperazine was synthesized.

Step-3 (R)-4-((R)-1-((6-(3-chloro-4-(4-(oxetan-3-yl)piperazin-1-yl)phenyl)-3-cyclopropyl-3H-imidazo[4,5-c]pyridin-4-yl)oxy)ethyl)pyrrolidin-2-one

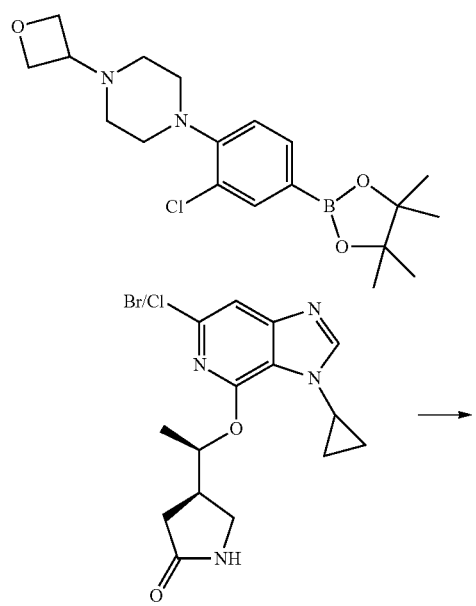

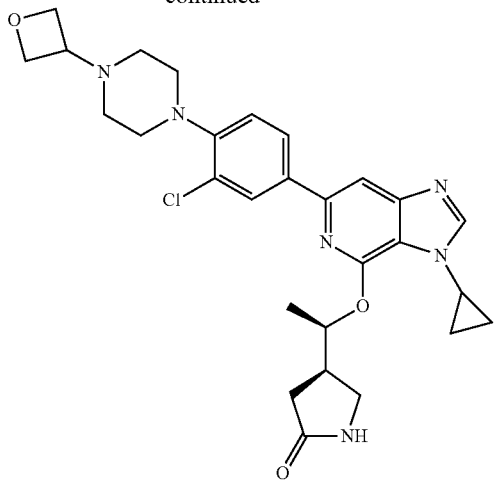

Following the procedure described for Example 3.90, starting from (R)-4-((R)-1-((6-bromo-3-cyclopropyl-3H-imidazo[4,5-c]pyridin-4-yl)oxy)ethyl)pyrrolidin-2-one (100 mg, 0.27 mmol), 5.0 mg of (R)-4-((R)-1-((6-(3-chloro-4-(4-(oxetan-3-yl)piperazin-1-yl)phenyl)-3-cyclopropyl-3H-imidazo[4,5-c]pyridin-4-yl)oxy)ethyl)pyrrolidin-2-one was synthesized.

$^1$H NMR (400 MHz, DMSO-d6) δ 8.26 (s, 1H), 8.07 (d, J=2.9 Hz, 1H), 8.0 (dd, J=1.9 Hz, 1H), 7.77 (s, 1H) 7.54 (s, 1H), 7.21 (d, J=8.5 Hz 1H), 5.55-5.51 (m, 1H), 4.5 (dt, J =6.4 Hz, 15 Hz, 4H), 3.67-3.66 (m, 1H), 3.50-3.36 (m, 1H) 3.19 (t, J=8 Hz, 1H), 3.04 (s, 4H), 2.85-2.70 (m, 1H). 2.32 (d, J=8.8 Hz, 2H), 1.39 (d, J=5.8 Hz, 3H), 1.11-1.04 (m, 4H).

LCMS-ESI$^+$ (m/z): [M+H]$^+$ calcd. for $C_{28}H_{33}ClN_6O_3$: 538.05; found: 537.15.

3.95

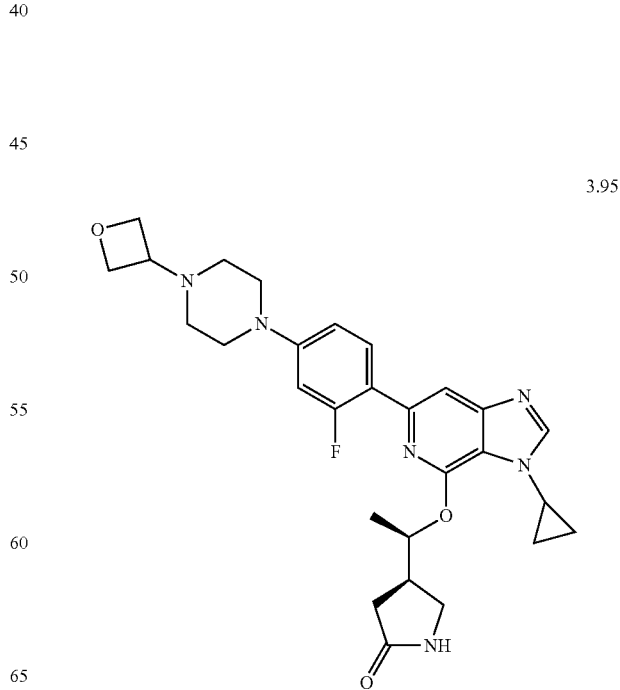

501

Preparation of (R)-4-((R)-1-((3-cyclopropyl-6-(2-fluoro-4-(4-(oxetan-3-yl)piperazin-1-yl)phenyl)-3H-imidazo[4,5-c]pyridin-4-yl)oxy)ethyl)pyrrolidin-2-one

Step-1 Preparation of 1-(4-bromo-3-fluorophenyl)-4-(oxetan-3-yl)piperazine

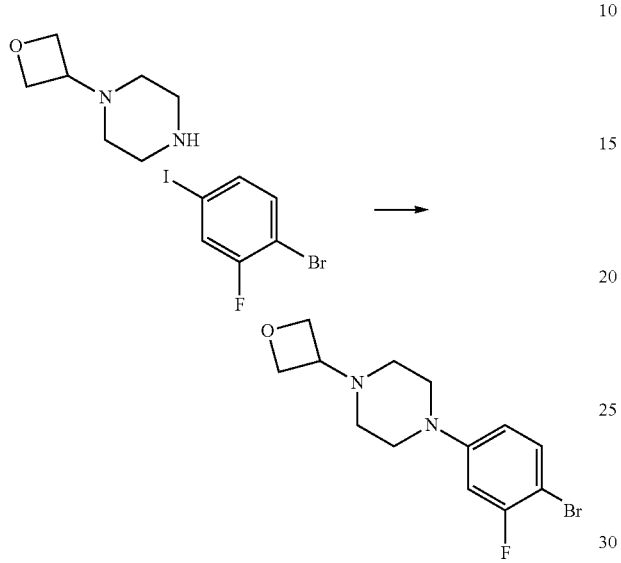

Following the procedure described for intermediate 7.13, starting from 1-bromo-2-fluoro-4-iodobenzene (1999.63 mg, 6.65 mmol) and 1-(oxetan-3-yl)piperazine (900 mg, 6.33 mmol), 1650 mg of 1-(4-bromo-3-fluorophenyl)-4-(oxetan-3-yl)piperazine was synthesized.

Step-2 Preparation of 1-(3-fluoro-4-(4,4,5,5-tetramethyl-1,3,2-dioxaborolan-2-yl)phenyl)-4-(oxetan-3-yl)piperazine

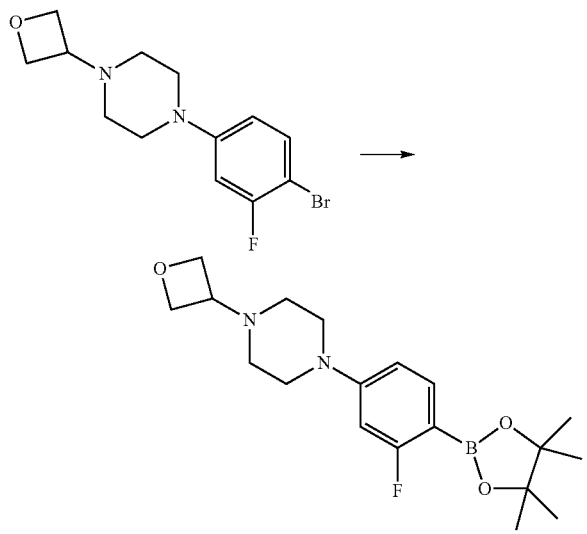

Following the procedure described for intermediate 7.17, starting with 1-(4-bromo-3-fluorophenyl)-4-(oxetan-3-yl)piperazine (800 mg, 2.54 mmol), 340 mg of 1-(3-fluoro-4-(4,4,5,5-tetramethyl-1,3,2-dioxaborolan-2-yl)phenyl)-4-(oxetan-3-yl)piperazine was synthesized.

Step-3 (R)-4-((R)-1-((3-cyclopropyl-6-(2-fluoro-4-(4-(oxetan-3-yl)piperazin-1-yl)phenyl)-3H-imidazo[4,5-c]pyridin-4-yl)oxy)ethyl)pyrrolidin-2-one

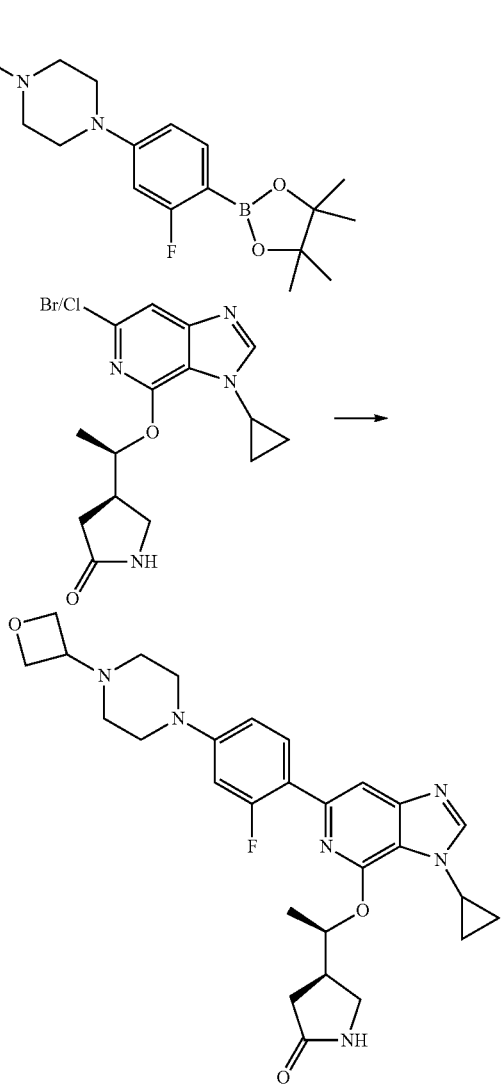

Following the procedure described for Example 3.90, starting from (R)-4-((R)-1-((6-bromo-3-cyclopropyl-3H-imidazo[4,5-c]pyridin-4-yl)oxy)ethyl)pyrrolidin-2-one (100 mg, 0.27 mmol), 54.0 mg of (R)-4-((R)-1-((3-cyclopropyl-6-(2-fluoro-4-(4-(oxetan-3-yl)piperazin-1-yl)phenyl)-3H-imidazo[4,5-c]pyridin-4-yl)oxy)ethyl)pyrrolidin-2-one was synthesized.

$^1$H NMR (400 MHz, DMSO-d6) δ 8.25 (s, 1H), 8.87 (t, J=9.0 Hz, 1H), 7.52 (dd, J =1.5 Hz, 13.3 Hz, 2H), 6.88-6.77 (m, 2H) 5.51-5.47 (m, 1H), 5.0 (dt, J=6.4 Hz, 15.8 Hz, 4H), 3.69-3.64 (m, 1H), 3.45-3.35 (m, 1H) 3.28 (t, J=1.9 Hz, 4H), 3.20-3.15 (m, 1H), 2.83-2.70 (m, 1H). 3.38 (t, J=4.9 Hz, 4H), 2.32 (dd, J=1.5 Hz, 0.6 Hz, 2H), 1.37 (d, J=6.4 Hz, 3H), 1.11-1.00 (m, 4H).

LCMS-ESI$^+$ (m/z): [M+H]$^+$ calcd. for $C_{28}H_{33}FN_6O_3$: 521.60; found: 521.18.

503

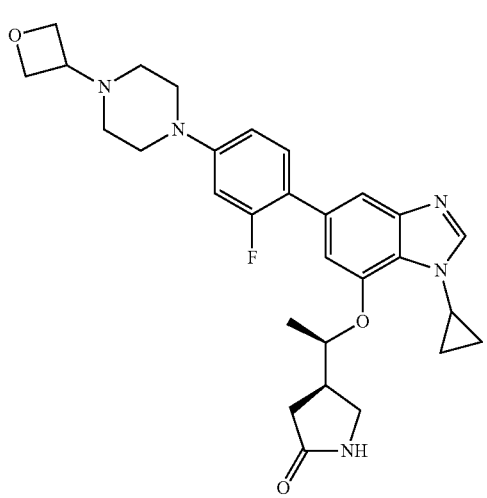

Preparation of (R)-4-((R)-1-((1-cyclopropyl-5-(2-fluoro-4-(4-(oxetan-3-yl)piperazin-1-yl)phenyl)-1H-benzo[d]imidazol-7-yl)oxy)ethyl)pyrrolidin-2-one Step-1 Preparation of 1-(4-bromo-2-chlorophenyl)-4-(oxetan-3-yl)piperazine

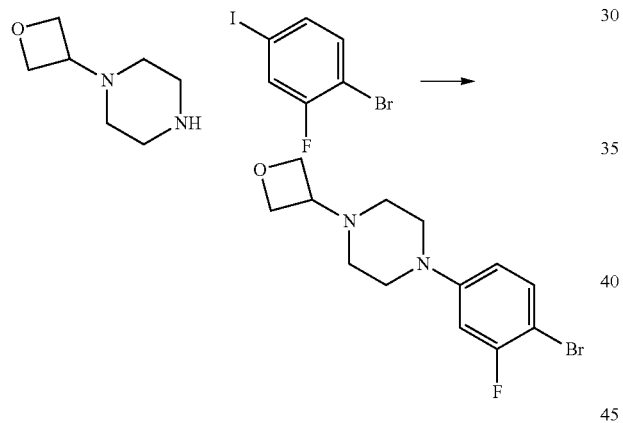

Following the procedure described for intermediate 7.13, starting from 1-bromo-2-fluoro-4-iodobenzene (1999.63 mg, 6.65 mmol) and 1-(oxetan-3-yl)piperazine (900 mg, 6.33 mmol), 1650 mg of 1-(4-bromo-3-fluorophenyl)-4-(oxetan-3-yl)piperazine was synthesized.

Step-2 Preparation of 1-(3-fluoro-4-(4,4,5,5-tetramethyl-1,3,2-dioxaborolan-2-yl)phenyl)-4-(oxetan-3-yl)piperazine

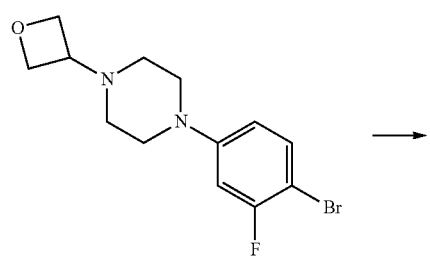

504
-continued

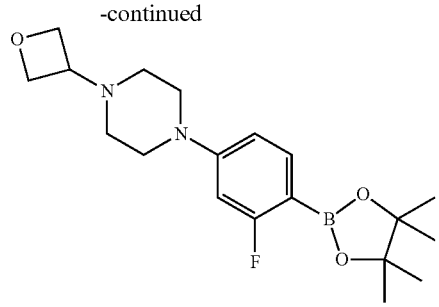

Following the procedure described for intermediate 7.17, starting with 1-(4-bromo-3-fluorophenyl)-4-(oxetan-3-yl)piperazine (800 mg, 2.54 mmol), 340 mg of 1-(3-fluoro-4-(4,4,5,5-tetramethyl-1,3,2-dioxaborolan-2-yl)phenyl)-4-(oxetan-3-yl)piperazine was synthesized.

Step-3 (R)-4-((R)-1-((1-cyclopropyl-5-(2-fluoro-4-(4-(oxetan-3-yl)piperazin-1-yl)phenyl)-1H-benzo[d]imidazol-7-yl)oxy)ethyl)pyrrolidin-2-one

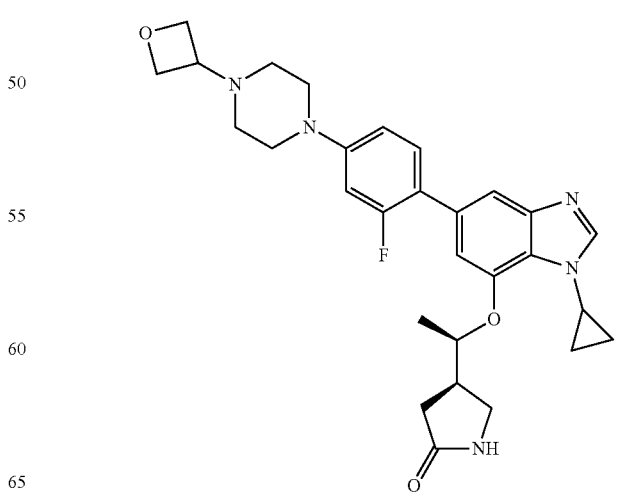

Following the procedure described for Example 3.90, starting from (R)-4-((R)-1-((5-bromo-1-cyclopropyl-1H-benzo[d]imidazol-7-yl)oxy)ethyl)pyrrolidin-2-one (100 mg, 0.27 mmol), 58.6 mg of (R)-4-((R)-1(R)-4-((R)-1-((1-cyclopropyl-5-(2-fluoro-4-(4-(oxetan-3-yl)piperazin-1-yl)phenyl)-1H-benzo[d]imidazol-7-yl)oxy)ethyl)pyrrolidin-2-one was synthesized.

¹H NMR (400 MHz, DMSO-d6) δ 8.07 (s, 1H), 7.56 (s, 1H), 7.37 (t, J=9.3 Hz, 1H), 7.22 (t, J=1.3 Hz, 1H), 6.87-6.79 (m, 3H) 4.74-4.70 (m, 1H), 4.51 (dt, J=6.4 Hz, 6.4 Hz, 4H), 3.70-3.65 (m, 1H), 3.54-3.33 (m, 2H) 3.23-3.13 (m, 5H), 3.79-3.70 (m, 1H), 3.85 (t, J=5.1 Hz, 4H), 2.31-2.21 (m, 1H), 1.28 (d, J=6.1 Hz, 3H), 1.09-0.98 (m, 4H).

LCMS-ESI⁺ (m/z): [M+H]⁺ calcd. for $C_{29}H_{33}FN_5O_3$: 520.61; found: 520.11.

3.97

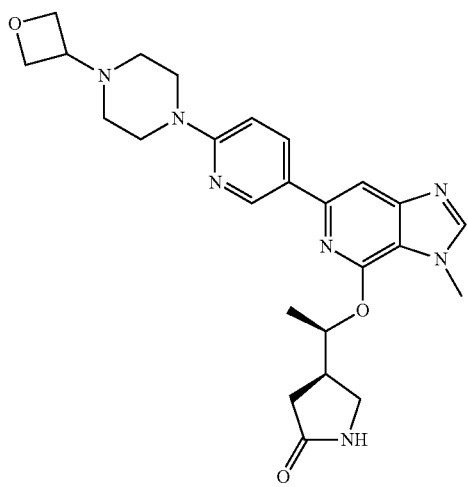

Preparation of (R)-4-((R)-1-((3-methyl-6-(6-(4-(oxetan-3-yl)piperazin-1-yl)pyridin-3-yl)-3H-imidazo[4,5-c]pyridin-4-yl)oxy)ethyl)pyrrolidin-2-one Step-1 Preparation of tert-butyl 4-(5-bromopyridin-2-yl)piperazine-1-carboxylate

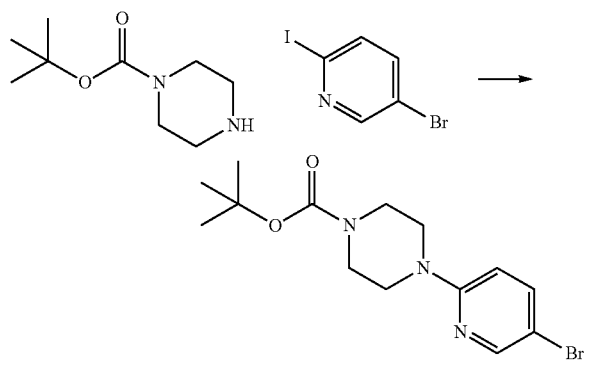

Following the procedure described for intermediate 7.13, starting from 5-bromo-2-iodopyridine (4001.14 mg, 14.09 mmol), Boc-Piperazine (2500 mg, 13.42 mmol), 3640 mg of tert-butyl 4-(5-bromopyridin-2-yl)piperazine-1-carboxylate was synthesized.

Step-2 Preparation of tert-butyl 4-(5-(4,4,5,5-tetramethyl-1,3,2-dioxaborolan-2-yl)pyridin-2-yl)piperazine-1-carboxylate

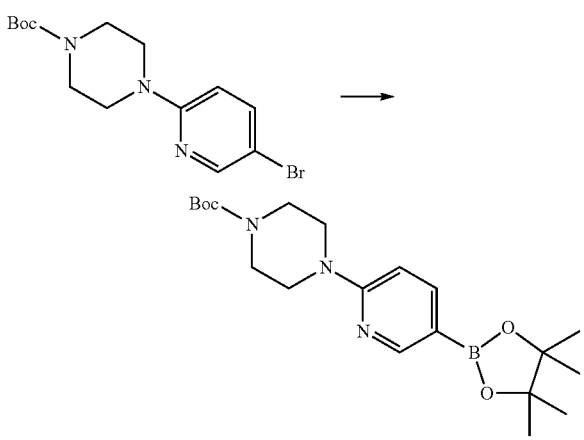

Following the procedure described for intermediate 7.17, starting with tert-butyl 4-(5-bromopyridin-2-yl)piperazine-1-carboxylate (3000 mg, 8.77 mmol), 1600 mg of tert-butyl 4-(5-(4,4,5,5-tetramethyl-1,3,2-dioxaborolan-2-yl)pyridin-2-yl)piperazine-1-carboxylate was synthesized.

Step-3 tert-butyl 4-(5-(3-methyl-4-((R)-1-((R)-5-oxopyrrolidin-3-yl)ethoxy)-3H-imidazo[4,5-c]pyridin-6-yl)pyridin-2-yl)piperazine-1-carboxylate

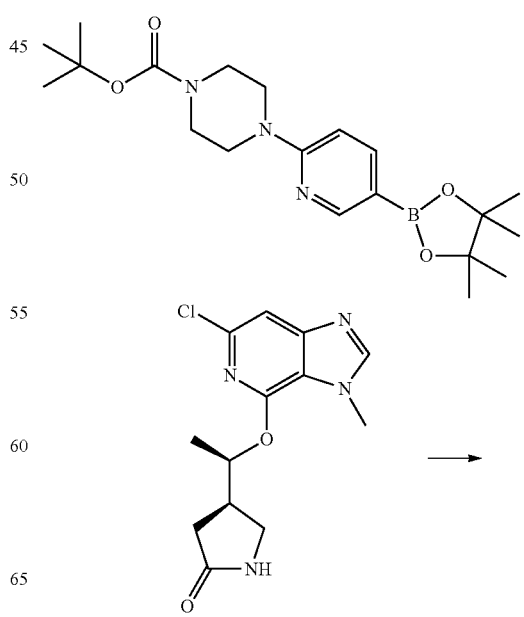

507
-continued

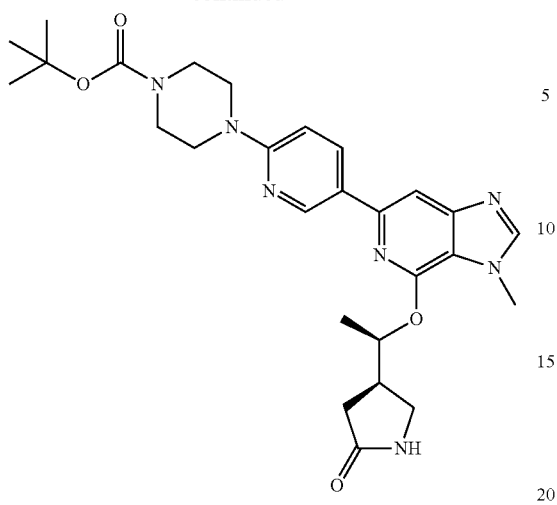

(R)-4-((R)-1-((6-chloro-3-methyl-3H-imidazo[4,5-c]pyridin-4-yl)oxy)ethyl)pyrrolidin-2-one (150 mg, 0.51 mmol), tert-butyl 4-(5-(4,4,5,5-tetramethyl-1,3,2-dioxaborolan-2-yl)pyridin-2-yl)piperazine-1-carboxylate (277.37 mg, 0.71 mmol), potassium phosphate tribasic (324 mg, 0.1.53 mmol), Bis[di-tert-butyl(4 dimethylaminophenyl)phosphine]dichloropalladium(II) (11.92 mg, 0.017 mmol) were combined in water (0.72 ml) and 1,4-Dioxane (9 ml). The reaction was stirred at 100 C for 90 mins. The reaction was diluted with dichloromethane, washed with water, dried, filtered and concentrated. Residues were purified by silica gel column chromatography to yield the title compound as a free base.

508
-continued

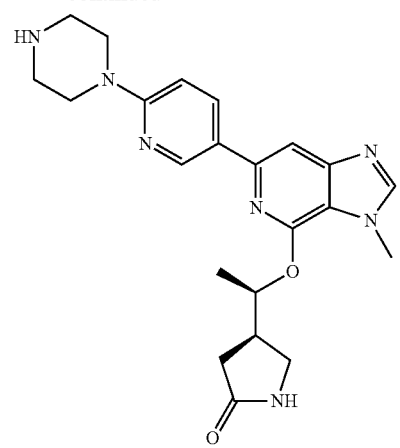

Tert-butyl 4-(5-(3-methyl-4-((R)-1-((R)-5-oxopyrrolidin-3-yl)ethoxy)-3H-imidazo[4,5-c]pyridin-6-yl)pyridin-2-yl)piperazine-1-carboxylate (76%, 265 mg, 0.39 mmol)) was dissolved in TFA (4.4 mL) and stirred at room temperature for 15 mins. The reaction was cooled to OC, neutralized to a pH of 7 using satd. sodium bicarbonate, extracted with 30 mL of dichloromethane to remove impurities and then 25% methanol/dichloromethane (300 mL), dried, filtered, concentrated to provide the (R)-4-((R)-1-((3-methyl-6-(6-(piperazin-1-yl)pyridin-3-yl)-3H-imidazo[4,5-c]pyridin-4-yl)oxy)ethyl)pyrrolidin-2-one (130 mg, 80% for two steps).

Step-4 (R)-4-((R)-1-((3-methyl-6-(6-(piperazin-1-yl)pyridin-3-yl)-3H-imidazo[4,5-c]pyridin-4-yl)oxy)ethyl)pyrrolidin-2-one Step-5 (R)-4-((R)-1-((3-methyl-6-(6-(4-(oxetan-3-yl)piperazin-1-yl)pyridin-3-yl)-3H-imidazo[4,5-c]pyridin-4-yl)oxy)ethyl)pyrrolidin-2-one

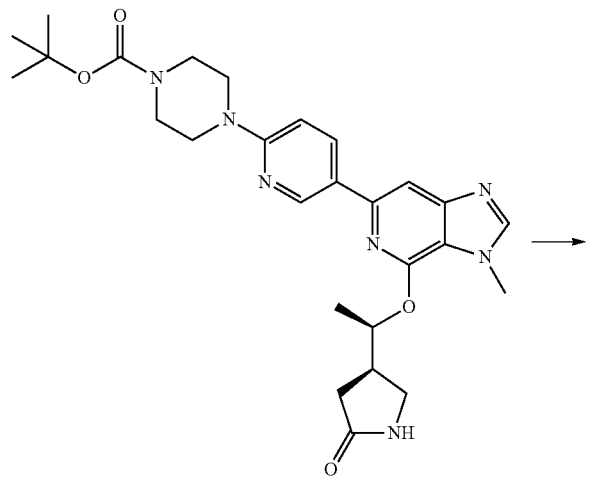

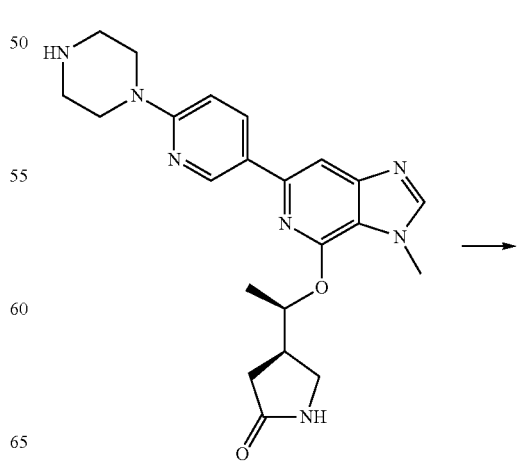

-continued

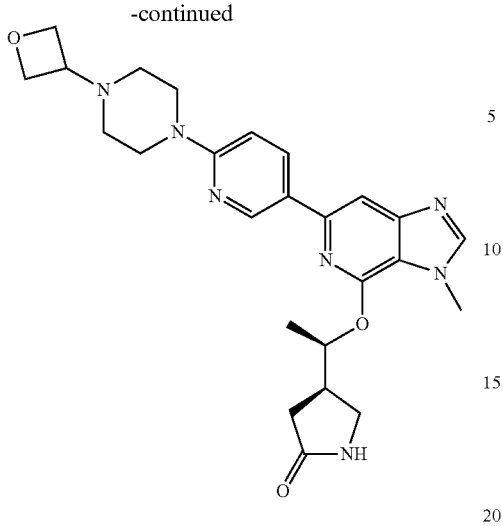

(R)-4-((R)-1-((3-methyl-6-(6-(piperazin-1-yl)pyridin-3-yl)-3H-imidazo[4,5-c]pyridin-4-yl)oxy)ethyl)pyrrolidin-2-one (130 mg, 0.31 mmol) was dissolved in THF (7.71 ml), followed by the addition of Hunig's base (0.05 ml, 0.31 mmol), 3-oxetanone (0.2 ml, 3.08 mmol), sodium triacetoxyborohydride (228.79 mg, 1.08 mmol) and stirred at 50 C for 90 minutes. The reaction was diluted with 25% methanol/dichloromethane, washed with water, dried, filtered and concentrated. Residues were purified by silica gel column chromatography to yield the (R)-4-((R)-1-((3-methyl-6-(6-(4-(oxetan-3-yl)piperazin-1-yl)pyridin-3-yl)-3H-imidazo[4,5-c]pyridin-4-yl)oxy)ethyl)pyrrolidin-2-one (32.9 mg, 22%)

$^1$H NMR (400 MHz, DMSO-d$_6$) δ 8.87-8.79 (m, 1H), 8.23-8.12 (m, 2H), 7.67 (s, 1H), 7.54 (s, 1H), 6.87 (d, J=8.8 Hz, 1H), 5.56-5.45 (m, 1H), 4.50 (dt, J=24.7, 6.2 Hz, 4H), 3.93 (s, 3H), 3.55 (t, 5.3 Hz, 4H), 3.43-3.29 (m, 2H), 3.16 (dd, J=9.7, 6.2 Hz, 1H), 2.81-2.70 (m, 1H), 2.45-2.17 (m, 6H), 1.39 (d, J=6.2 Hz, 3H).

LCMS-ESI$^+$ (m/z): [M+H]$^+$ calcd. for C$_{25}$H$_{31}$N$_7$O$_3$: 478.56; found: 478.19.

3.98

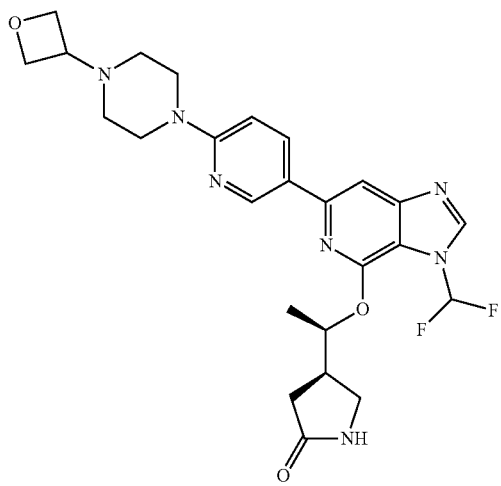

Preparation of (R)-4-((R)-1-((3-(difluoromethyl)-6-(6-(4-(oxetan-3-yl)piperazin-1-yl)pyridin-3-yl)-3H-imidazo[4,5-c]pyridin-4-yl)oxy)ethyl)pyrrolidin-2-one Step-1 tert-butyl 4-(5-(3-(difluoromethyl)-4-((R)-1-((R)-5-oxopyrrolidin-3-yl)ethoxy)-3H-imidazo[4,5-c]pyridin-6-yl)pyridin-2-yl)piperazine-1-carboxylate

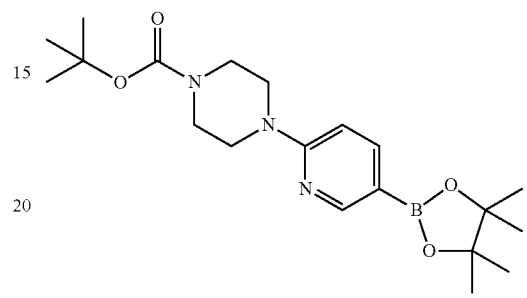

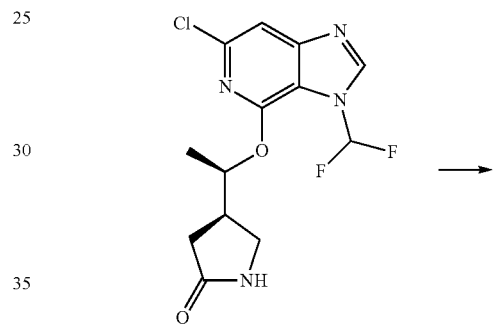

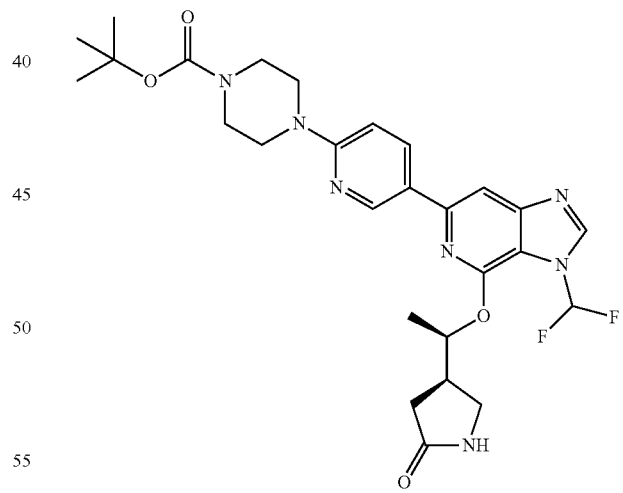

Following the procedure described for intermediate from Step-3, Example 3.97, starting from (R)-4-((R)-1-((6-chloro-3-(difluoromethyl)-3H-imidazo[4,5-c]pyridin-4-yl)oxy)ethyl)pyrrolidin-2-one (200 mg, 0.6 mmol), tert-butyl 4-(5-(4,4,5,5-tetramethyl-1,3,2-dioxaborolan-2-yl)pyridin-2-yl)piperazine-1-carboxylate (329.6 mg, 0.85 mmol), tert-butyl 4-(5-(3-(difluoromethyl)-4-((R)-1-((R)-5-oxopyrrolidin-3-yl)ethoxy)-3H-imidazo[4,5-c]pyridin-6-yl)pyridin-2-yl)piperazine-1-carboxylate was synthesized.

Step-2 (R)-4-((R)-1-((3-(difluoromethyl)-6-(6-(piperazin-1-yl)pyridin-3-yl)-3H-imidazo[4,5-c]pyridin-4-yl)oxy)ethyl)pyrrolidin-2-one

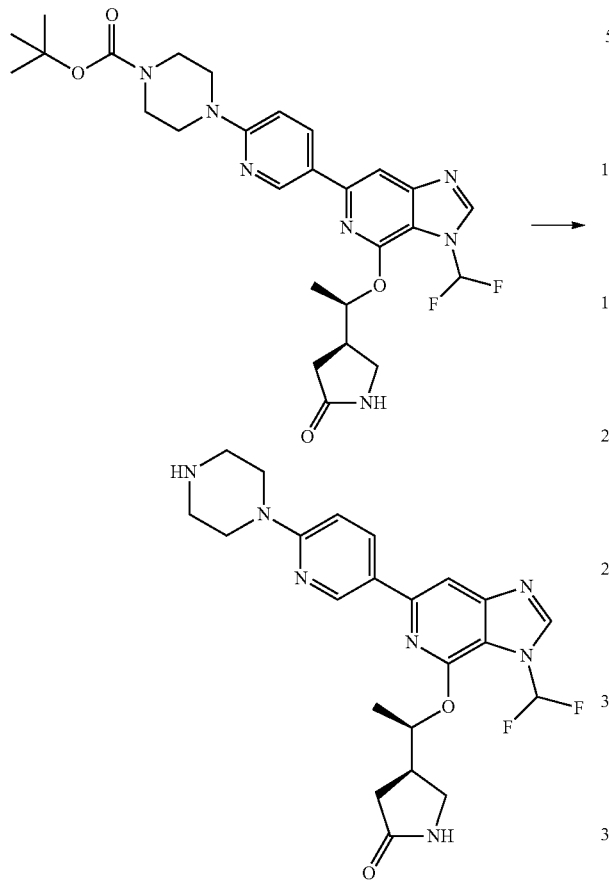

Following the procedure described for intermediate from Step-4, Example 3.97, starting from tert-butyl 4-(5-(3-(difluoromethyl)-4-((R)-1-((R)-5-oxopyrrolidin-3-yl)ethoxy)-3H-imidazo[4,5-c]pyridin-6-yl)pyridin-2-yl)piperazine-1-carboxylate (190 mg, 0.26 mmol), 100 mg of (R)-4-((R)-1-((3-(difluoromethyl)-6-(6-(piperazin-1-yl)pyridin-3-yl)-3H-imidazo[4,5-c]pyridin-4-yl)oxy)ethyl)pyrrolidin-2-one was synthesized (130 mg, 80% for two steps).

Step-3 (R)-4-((R)-1-((3-(difluoromethyl)-6-(6-(4-(oxetan-3-yl)piperazin-1-yl)pyridin-3-yl)-3H-imidazo[4,5-c]pyridin-4-yl)oxy)ethyl)pyrrolidin-2-one

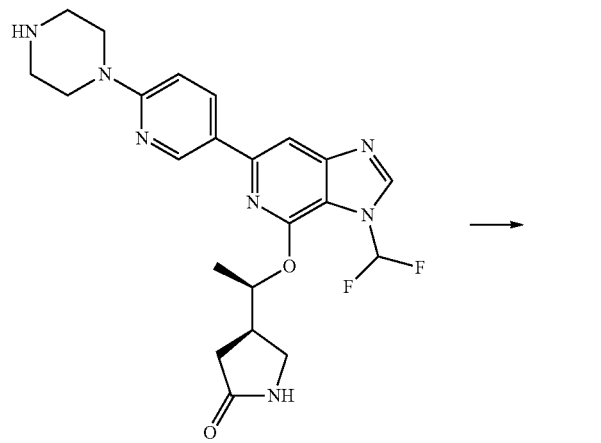

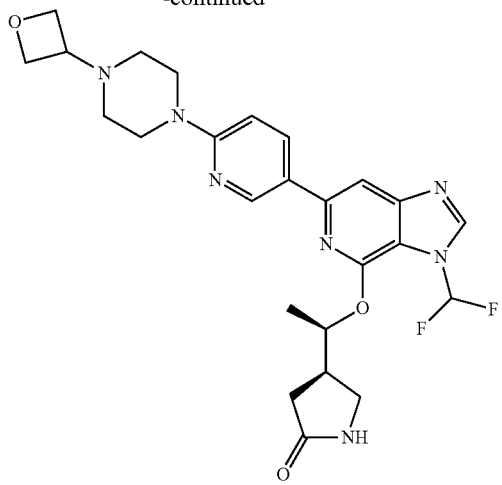

Following the procedure described for intermediate from Step-5, Example 3.97, starting from (R)-4-((R)-1-((3-(difluoromethyl)-6-(6-(piperazin-1-yl)pyridin-3-yl)-3H-imidazo[4,5-c]pyridin-4-yl)oxy)ethyl)pyrrolidin-2-one (100 mg, 0.22 mmol), 29.8 mg of (R)-4-((R)-1-((3-(difluoromethyl)-6-(6-(4-(oxetan-3-yl)piperazin-1-yl)pyridin-3-yl)-3H-imidazo[4,5-c]pyridin-4-yl)oxy)ethyl)pyrrolidin-2-one was synthesized.

$^1$H NMR (400 MHz, DMSO-d$_6$) δ 8.87 (dd, J=2.5, 0.6 Hz, 1H), 8.73 (s, 1H), 8.27-8.14 (m, 1H), 7.84 (s, 1H), 7.53 (s, 1H), 6.95-6.86 (m, 1H), 5.52 (p, J=6.1 Hz, 1H), 4.50 (dt, J=24.5, 6.3 Hz, 4H), 3.57 (t, J=4.73 Hz, 4H), 3.44-3.32 (m, 2H), 3.25-3.09 (m, 1H), 2.81 (q, J=7.2 Hz, 1H), 2.48-2.22 (m, 6H), 1.38 (d, J=6.2 Hz, 3H).

LCMS-ESI$^+$ (m/z): [M+H]$^+$ calcd. for C$_{25}$H$_{29}$F2N$_7$O$_3$: 514.54; found: 515.10.

3.99

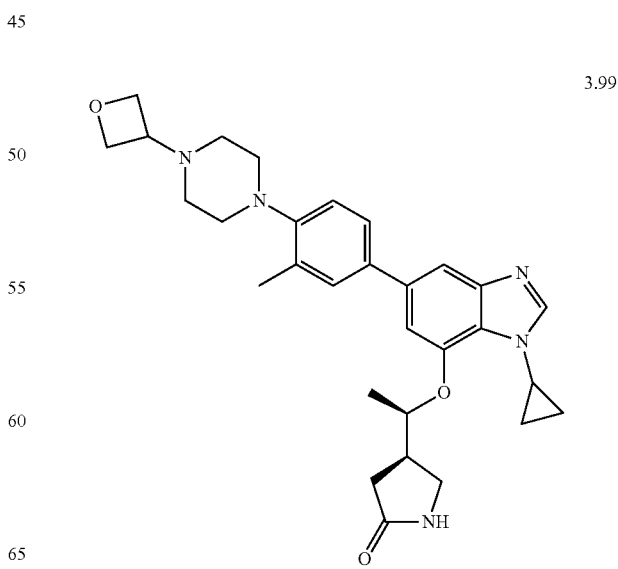

Preparation of (R)-4-((R)-1-((1-cyclopropyl-5-(3-methyl-4-(4-(oxetan-3-yl)piperazin-1-yl)phenyl)-1H-benzo[d]imidazol-7-yl)oxy)ethyl)pyrrolidin-2-one Step-1 Preparation of tert-butyl 4-(4-bromo-2-methylphenyl)piperazine-1-carboxylate Following the procedure described for intermediate 7.13, starting from 4-bromo-1-iodo-2-methylbenzene (4184.9 mg, 14.09 mmol), Boc-Piperazine (2500 mg, 13.42 mmol), 4760 mg of tert-butyl 4-(4-bromo-2-methylphenyl)piperazine-1-carboxylate was synthesized.

Step-2 Preparation of tert-butyl 4-(5-(4,4,5,5-tetramethyl-1,3,2-dioxaborolan-2-yl)pyridin-2-yl)piperazine-1-carboxylate Following the procedure described for intermediate 7.17, starting with tert-butyl 4-(5-bromopyridin-2-yl)piperazine-1-carboxylate (3000 mg, 8.77 mmol), 1600 mg of tert-butyl 4-(5-(4,4,5,5-tetramethyl-1,3,2-dioxaborolan-2-yl)pyridin-2-yl)piperazine-1-carboxylate was synthesized.

Step-3 tert-butyl 4-(4-(1-cyclopropyl-7-((R)-1-((R)-5-oxopyrrolidin-3-yl)ethoxy)-1H-benzo[d]imidazol-5-yl)-2-methylphenyl)piperazine-1-carboxylate

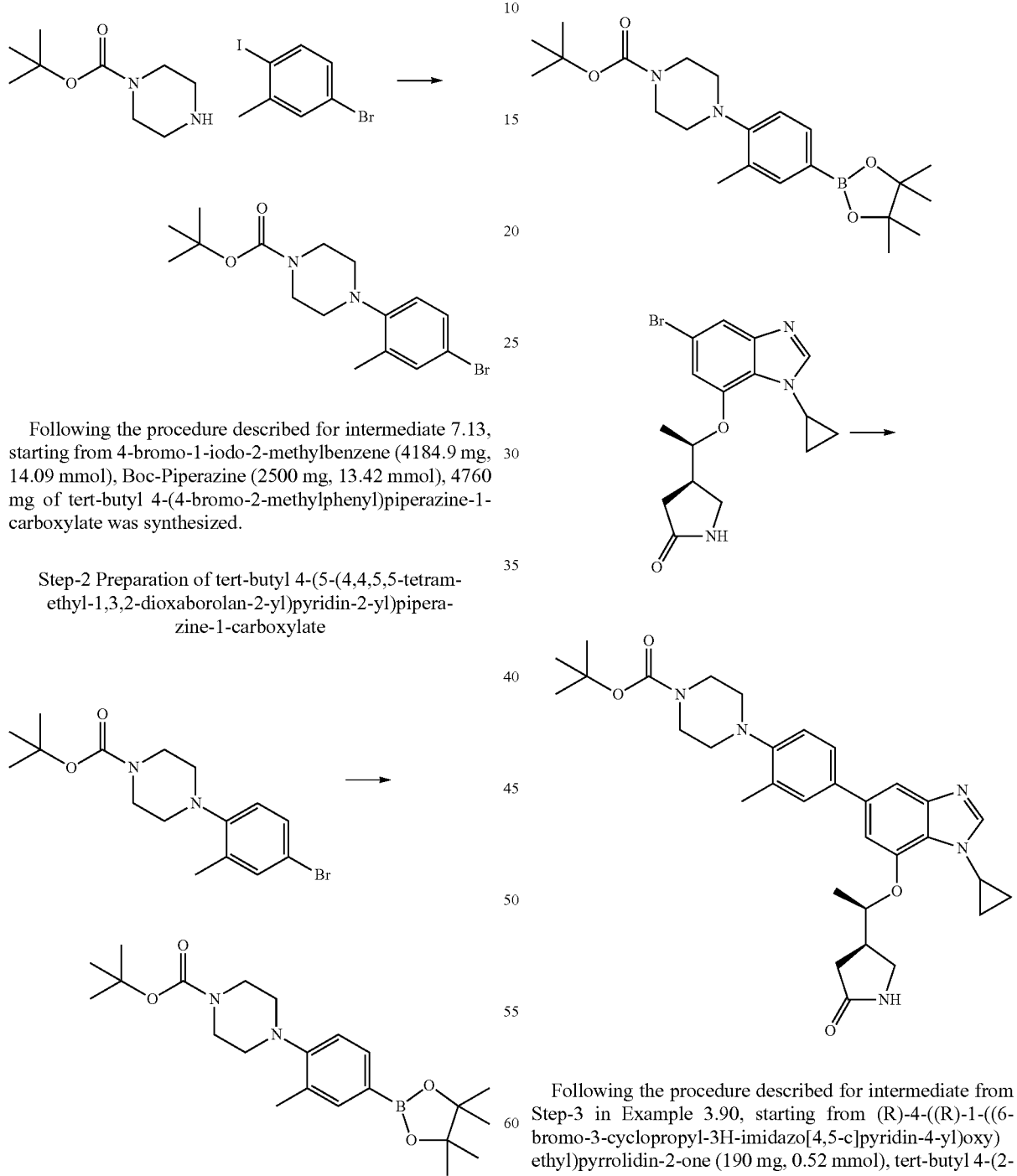

Following the procedure described for intermediate from Step-3 in Example 3.90, starting from (R)-4-((R)-1-((6-bromo-3-cyclopropyl-3H-imidazo[4,5-c]pyridin-4-yl)oxy)ethyl)pyrrolidin-2-one (190 mg, 0.52 mmol), tert-butyl 4-(2-methyl-4-(4,4,5,5-tetramethyl-1,3,2-dioxaborolan-2-yl)phenyl)piperazine-1-carboxylate (219.77 mg, 0.55 mmol), 260 mg tert-butyl 4-(4-(1-cyclopropyl-7-((R)-1-((R)-5-oxopyrrolidin-3-yl)ethoxy)-1H-benzo[d]imidazol-5-yl)-2-methylphenyl)piperazine-1-carboxylate was synthesized.

Step-4 (R)-4-((R)-1-((1-cyclopropyl-5-(3-methyl-4-(piperazin-1-yl)phenyl)-1H-benzo[d]imidazol-7-yl)oxy)ethyl)pyrrolidin-2-one

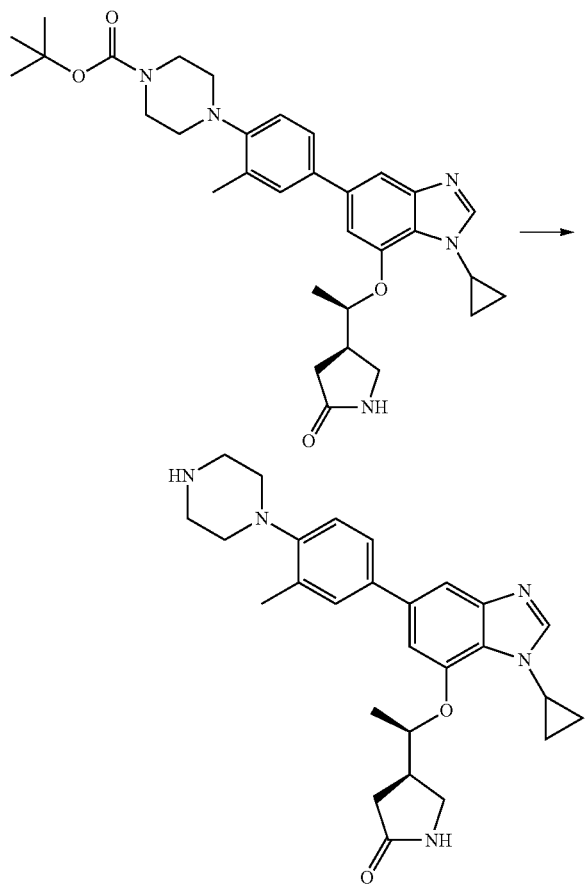

Following the procedure described for intermediate from Step-4 in Example 3.97, starting tert-butyl 4-(4-(1-cyclopropyl-7-((R)-1-((R)-5-oxopyrrolidin-3-yl)ethoxy)-1H-benzo[d]imidazol-5-yl)-2-methylphenyl)piperazine-1-carboxylate (190 mg, 0.26 mmol), 100 mg of (R)-4-((R)-1-((1-cyclopropyl-5-(3-methyl-4-(piperazin-1-yl)phenyl)-1H-benzo[d]imidazol-7-yl)oxy)ethyl)pyrrolidin-2-one was synthesized.

Step-5 (R)-4-((R)-1-((1-cyclopropyl-5-(3-methyl-4-(4-(oxetan-3-yl)piperazin-1-yl)phenyl)-1H-benzo[d]imidazol-7-yl)oxy)ethyl)pyrrolidin-2-one

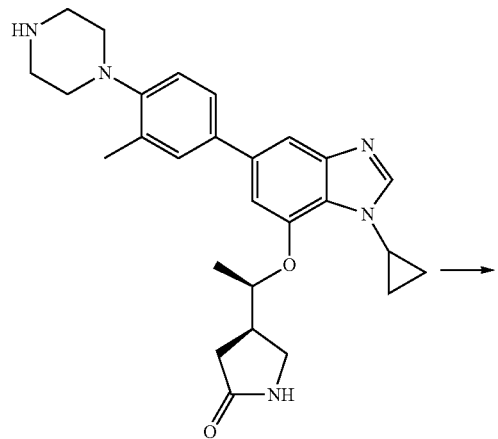

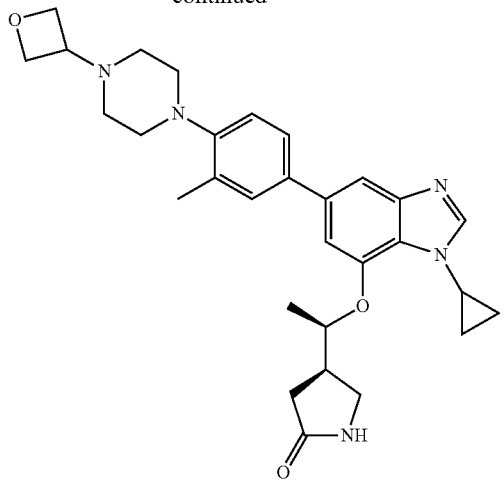

Following the procedure described for intermediate from Step-5 in Example 3.97, starting from (R)-4-((R)-1-((1-cyclopropyl-5-(3-methyl-4-(piperazin-1-yl)phenyl)-1H-benzo[d]imidazol-7-yl)oxy)ethyl)pyrrolidin-2-one (90 mg, 0.2 mmol), 35.4 mg of (R)-4-((R)-1-((1-cyclopropyl-5-(3-methyl-4-(4-(oxetan-3-yl)piperazin-1-yl)phenyl)-1H-benzo[d]imidazol-7-yl)oxy)ethyl)pyrrolidin-2-one was synthesized.

$^1$H NMR (400 MHz, DMSO-d$_6$) δ 8.05 (s, 1H), 7.57 (s, 1H), 7.51-7.39 (m, 2H), 7.34 (d, J=1.1 Hz, 1H), 7.12-6.96 (m, 2H), 4.83 (t, J=6.0 Hz, 1H), 4.50 (dt, J=26.3, 6.3 Hz, 4H), 3.67 (td, J=7.3, 6.8, 3.5 Hz, 1H), 3.50-3.29 (m, 2H), 3.27-3.15 (m, 1H), 2.93-2.83 (m, 5H), 2.50-2.25 (m, 9H), 1.29 (d, J=6.0 Hz, 3H), 1.12-0.96 (m, 4H).

LCMS-ESI$^+$ (m/z): [M+H]$^+$ calcd. for C$_{30}$H$_{37}$N$_5$O$_3$: 516.65; found: 516.19.

3.100

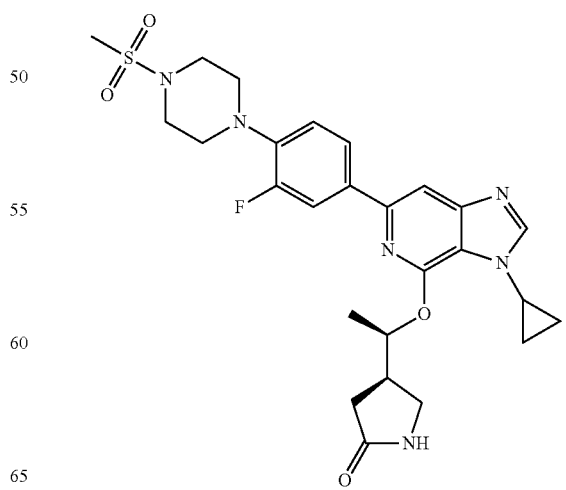

517

Preparation of (R)-4-((R)-1-((3-cyclopropyl-6-(3-fluoro-4-(4-(methylsulfonyl)piperazin-1-yl)phenyl)-3H-imidazo[4,5-c]pyridin-4-yl)oxy)ethyl)pyrrolidin-2-one

Step-1 Preparation of tert-butyl 4-(4-bromo-2fluorophenyl)piperazine-1-carboxylate

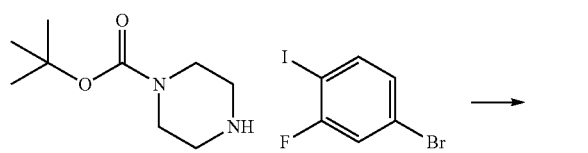

Following the procedure described for intermediate 7.13, starting from 4-bromo-2-fluoro-1-iodobenzene (4240.77 mg, 14.09 mmol), Boc-Piperazine (2500 mg, 13.42 mmol), 4800 mg tert-butyl 4-(4-bromo-2-fluorophenyl)piperazine-1-carboxylate was synthesized.

Step-2 Preparation of tert-butyl 4-(2-fluoro-4-(4,4,5,5-tetramethyl-1,3,2-dioxaborolan-2-yl)phenyl)piperazine-1-carboxylate

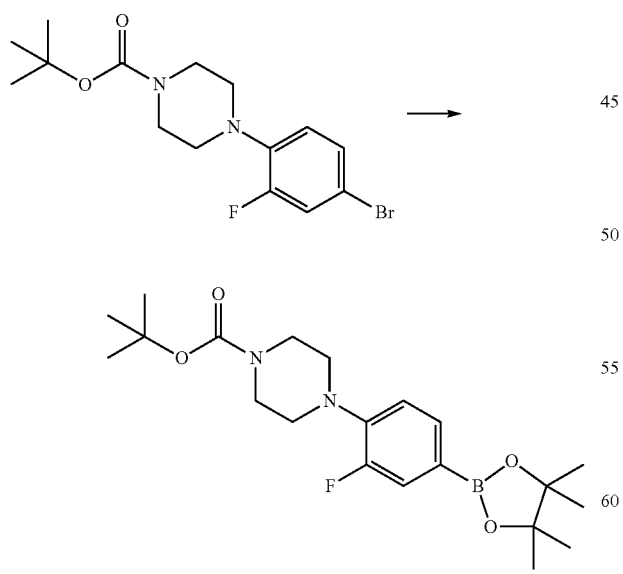

Following the procedure described for intermediate 7.17, starting with tert-butyl 4-(4-bromo-2-fluorophenyl)piperazine-1-carboxylate (2400 mg, 6.68 mmol), 2360 mg of tert-butyl 4-(2-fluoro-4-(4,4,5,5-tetramethyl-1,3,2-dioxaborolan-2-yl)phenyl)piperazine-1-carboxylate was synthesized.

Step-3 tert-butyl 4-(4-(3-cyclopropyl-4-((R)-1-((R)-5-oxopyrrolidin-3-yl)ethoxy)-3H-imidazo[4,5-c]pyridin-6-yl)-2-fluorophenyl)piperazine-1-carboxylate

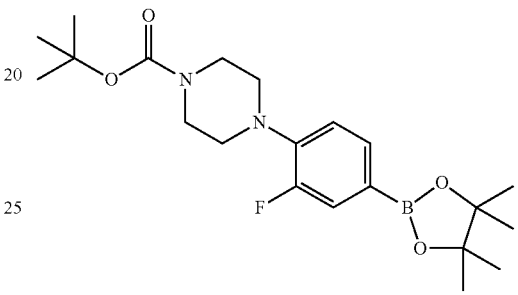

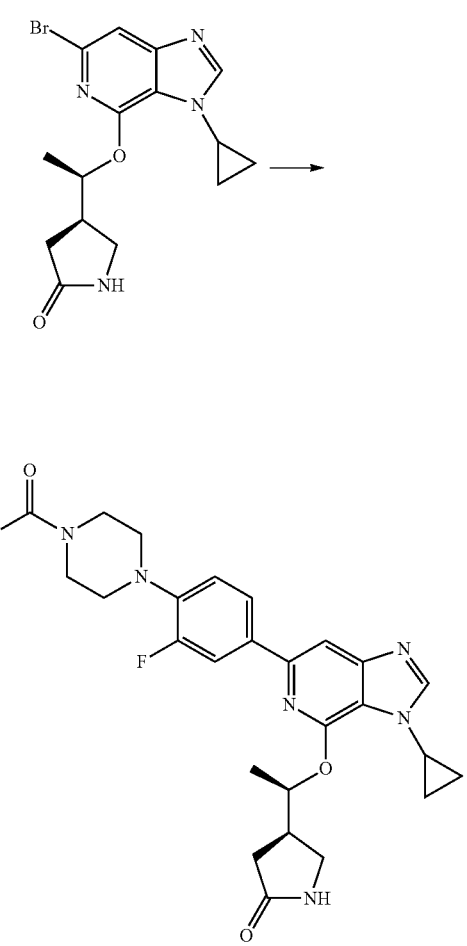

519

Following the procedure described for intermediate from Step-3 in Example 3.90, starting from combined (R)-4-((R)-1-((6-bromo-3-cyclopropyl-3H-imidazo[4,5-c]pyridin-4-yl)oxy)ethyl)pyrrolidin-2-one (85 mg, 0.23 mmol (215 mg, 0.59 mmol), tert-butyl 4-(2-fluoro-4-(4,4,5,5-tetramethyl-1,3,2-dioxaborolan-2-yl)phenyl)piperazine-1-carboxylate (299 mg, 0.74 mmol), 320 mg tert-butyl 4-(4-(3-cyclopropyl-4-((R)-1-((R)-5-oxopyrrolidin-3-yl)ethoxy)-3H-imidazo[4,5-c]pyridin-6-yl)-2-fluorophenyl)piperazine-1-carboxylate was synthesized.

Step-4 (R)-4-((R)-1-((3-cyclopropyl-6-(3-fluoro-4-(piperazin-1-yl)phenyl)-3H-imidazo[4,5-c]pyridin-4-yl)oxy)ethyl)pyrrolidin-2-one

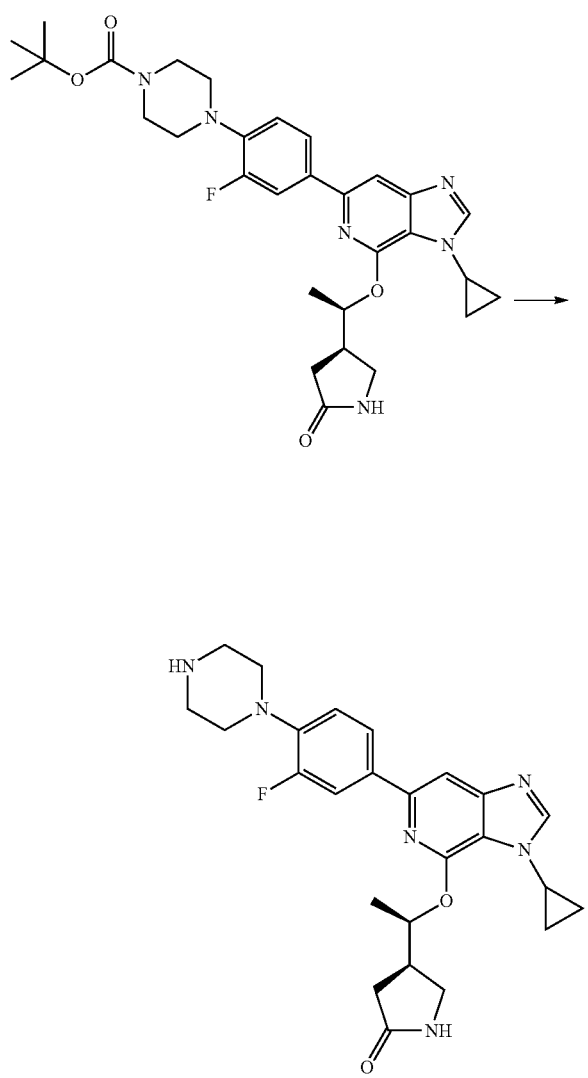

Following the procedure described for intermediate from Step-4 in Example 3.97, starting tert-butyl 4-(4-(3-cyclopropyl-4-((R)-1-((R)-5-oxopyrrolidin-3-yl)ethoxy)-3H-imidazo[4,5-c]pyridin-6-yl)-2-fluorophenyl)piperazine-1-carboxylate (320 mg, 0.43 mmol), 200 mg of (R)-4-((R)-1-((3-cyclopropyl-6-(3-fluoro-4-(piperazin-1-yl)phenyl)-3H-imidazo[4,5-c]pyridin-4-yl)oxy)ethyl)pyrrolidin-2-one was synthesized.

520

Step-5 (R)-4-((R)-1-((3-cyclopropyl-6-(3-fluoro-4-(4-(methylsulfonyl)piperazin-1-yl)phenyl)-3H-imidazo[4,5-c]pyridin-4-yl)oxy)ethyl)pyrrolidin-2-one

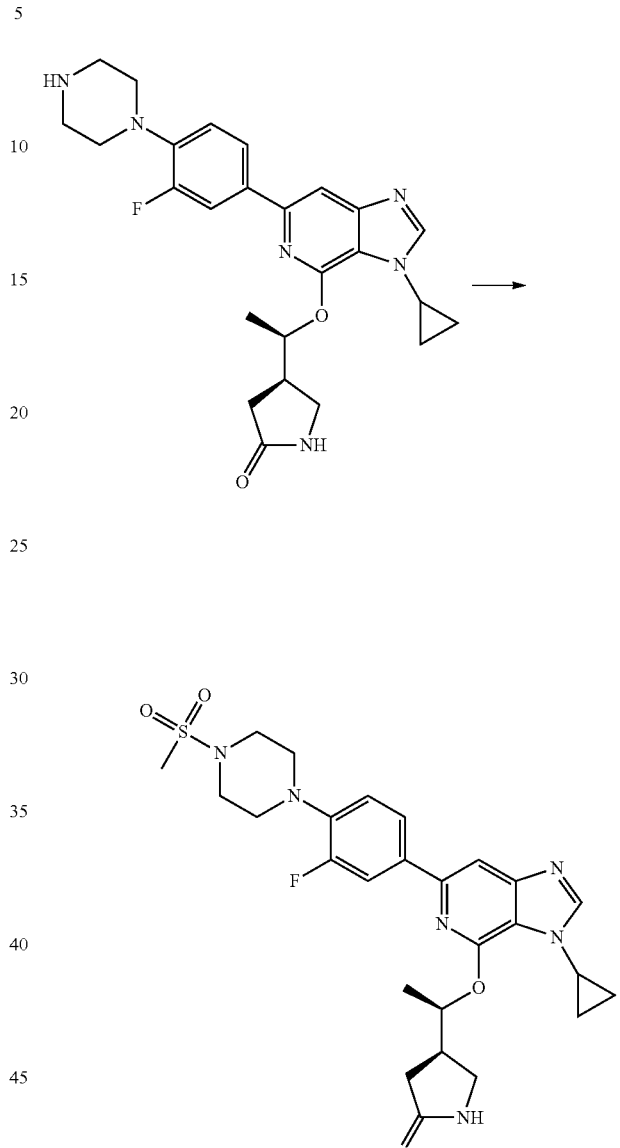

Following the procedure described for 3.45, starting from (R)-4-((R)-1-((3-cyclopropyl-6-(3-fluoro-4-(piperazin-1-yl)phenyl)-3H-imidazo[4,5-c]pyridin-4-yl)oxy)ethyl)pyrrolidin-2-one (130 mg, 0.0003 mmol), 52 mg of (R)-4-((R)-1-((3-cyclopropyl-6-(3-fluoro-4-(4-(methylsulfonyl)piperazin-1-yl)phenyl)-3H-imidazo[4,5-c]pyridin-4-yl)oxy)ethyl)pyrrolidin-2-one was synthesized.

$^1$H NMR (400 MHz, DMSO-$d_6$) δ 8.27 (s, 1H), 7.91-7.74 (m, 3H), 7.55 (s, 1H), 7.12 (t, J=8.8 Hz, 1H), 5.61-5.50 (m, 1H), 3.68 (ddt, J=11.3, 7.1, 3.9 Hz, 1H), 3.99 (t, J =9.0 Hz, 1H), 3.29-3.14 (m, 5H), 2.93 (s, 3H), 2.87-2.71 (m, 1H), 2.32 (d, J=8.7 Hz, 2H), 1.40 (d, J=6.2 Hz, 3H), 1.07 (ddd, J=15.9, 8.8, 4.9 Hz, 4H).

LCMS-ESI$^+$ (m/z): [M+H]$^+$ calcd. for $C_{26}H_{31}FN_6O_4$: 543.63; found: 544.49.

521

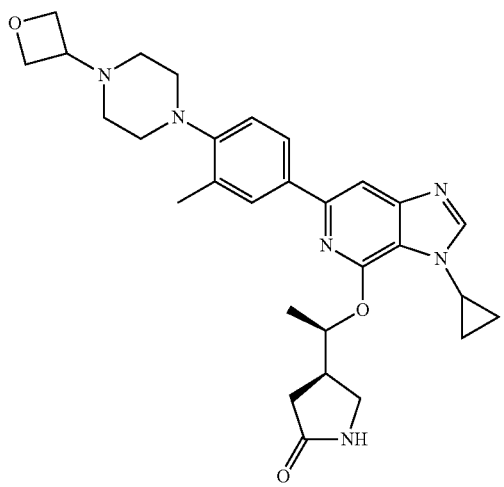

Preparation of (R)-4-((R)-1-((3-cyclopropyl-6-(3-methyl-4-(4-(oxetan-3-yl)piperazin-1-yl)phenyl)-3H-imidazo[4,5-c]pyridin-4-yl)oxy)ethyl)pyrrolidin-2-one Step-1 tert-butyl 4-(4-(3-cyclopropyl-4-((R)-1-((R)-5-oxopyrrolidin-3-yl)ethoxy)-3H-imidazo[4,5-c]pyridin-6-yl)-2-methylphenyl)piperazine-1-carboxylate

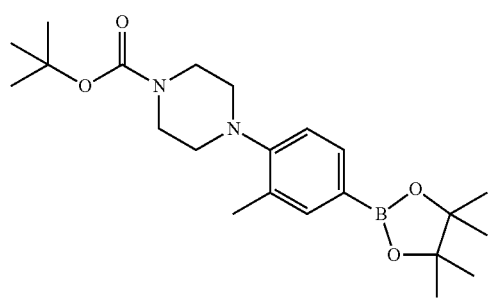

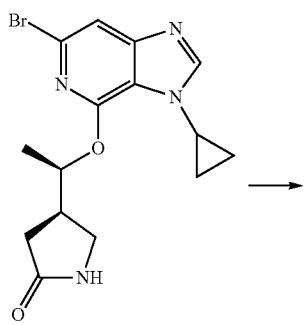

522

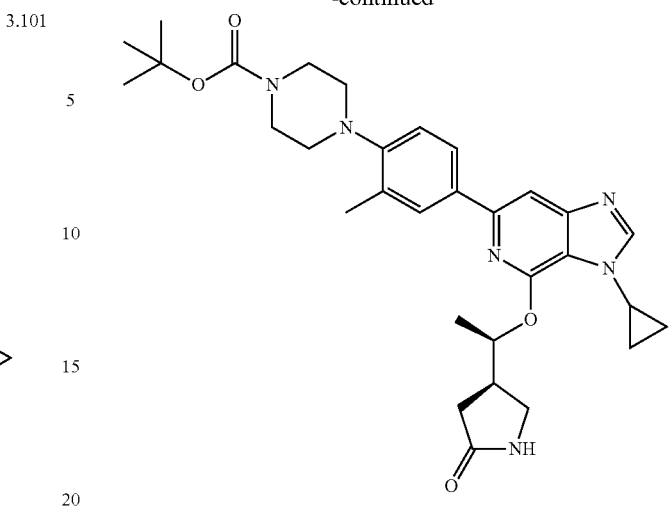

Following the procedure described for example 3.90, starting from (R)-4-((R)-1-((5-bromo-1-cyclopropyl-1H-benzo[d]imidazol-7-yl)oxy)ethyl)pyrrolidin-2-one (245 mg, 0.67 mmol) and tert-butyl 4-(2-methyl-4-(4,4,5,5-tetramethyl-1,3,2-dioxaborolan-2-yl)phenyl)piperazine-1-carboxylate (284.16 mg, 0.71 mmol) (B10), 260 mg of tert-butyl 4-(4-(3-cyclopropyl-4-((R)-1-((R)-5-oxopyrrolidin-3-yl)ethoxy)-3H-imidazo[4,5-c]pyridin-6-yl)-2-methylphenyl)piperazine-1-carboxylate.]

Step-2 (R)-4-((R)-1-((3-cyclopropyl-6-(3-methyl-4-(piperazin-1-yl)phenyl)-3H-imidazo[4,5-c]pyridin-4-yl)oxy)ethyl)pyrrolidin-2-one

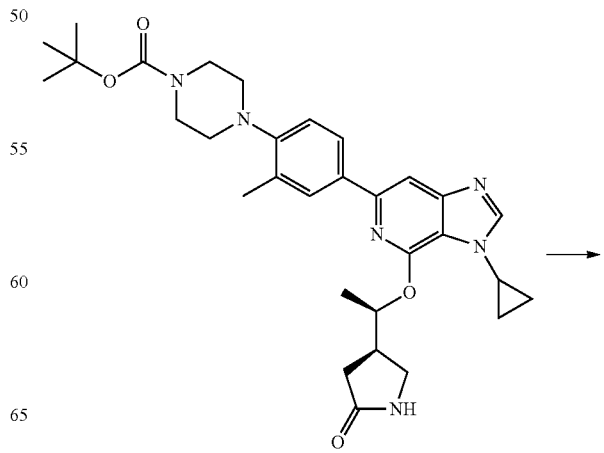

523
-continued

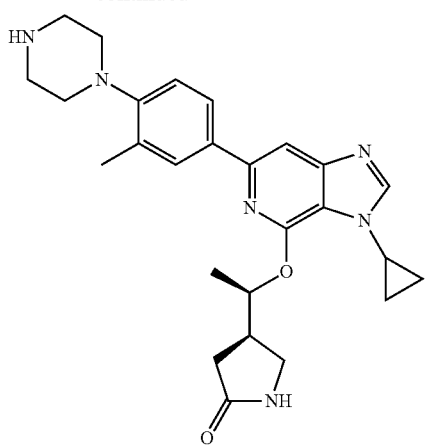

Following the procedure described for intermediate from Step-4 in Example 3.97, starting tert-butyl 4-(4-(3-cyclopropyl-4-((R)-1-((R)-5-oxopyrrolidin-3-yl)ethoxy)-3H-imidazo[4,5-c]pyridin-6-yl)-2-methylphenyl)piperazine-1-carboxylate (260 mg, 0.35 mmol), 160 mg of (R)-4-((R)-1-((3-cyclopropyl-6-(3-methyl-4-(piperazin-1-yl)phenyl)-3H-imidazo[4,5-c]pyridin-4-yl)oxy)ethyl)pyrrolidin-2-one was synthesized.

Step-3 (R)-4-((R)-1-((3-cyclopropyl-6-(3-methyl-4-(4-(oxetan-3-yl)piperazin-1-yl)phenyl)-3H-imidazo[4,5-c]pyridin-4-yl)oxy)ethyl)pyrrolidin-2-one 524
-continued

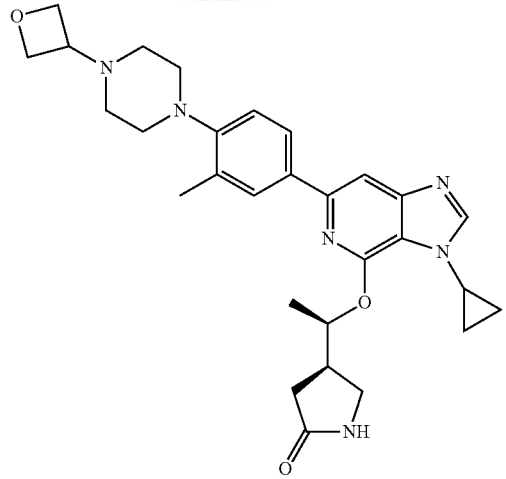

Following the procedure described for intermediate from Step-5 in Example 3.97, starting from 5-(3-cyclopropyl-4-((R)-1-((R)-5-oxopyrrolidin-3-yl)ethoxy)-3H-imidazo[4,5-c]pyridin-6-yl)-2-(piperazin-1-yl)benzonitrile (110 mg, 0.23 mmol), 22 mg of (R)-4-((R)-1-((3-cyclopropyl-6-(3-methyl-4-(4-(oxetan-3-yl)piperazin-1-yl)phenyl)-3H-imidazo[4,5-c]pyridin-4-yl)oxy)ethyl)pyrrolidin-2-one was synthesized.

$^1$H NMR (400 MHz, DMSO-$d_6$) δ 8.24 (s, 1H), 7.90-7.80 (m, 2H), 7.67 (s, 1H), 7.55 (s, 1H), 7.07 (d, J=9.0 Hz, 1H), 5.60-5.50 (m, 1H), 4.51 (dt, J=25.9, 6.3 Hz, 4H), 3.66 (td, J=7.0, 3.8 Hz, 1H), 3.55-3.37 (m, 2H), 3.29-3.17 (m, 1H) 2.95-2.79 (m, 5H), 2.46-2.30 (m, 9H), 1.40 (d, J=6.2 Hz, 3H), 1.16-0.96 (m, 3H).

LCMS-ESI$^+$ (m/z): [M+H]$^+$ calcd. for $C_{29}H_{36}N_5O_3$: 517.63; found: 517.21.

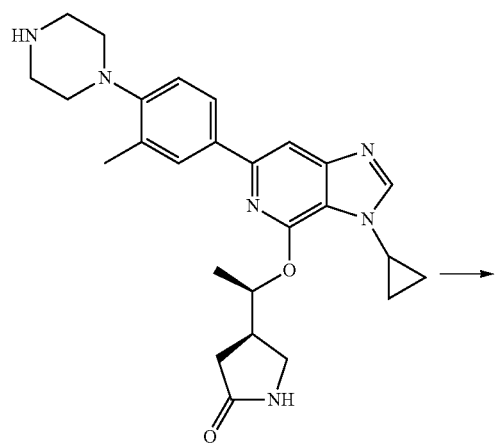

3.102

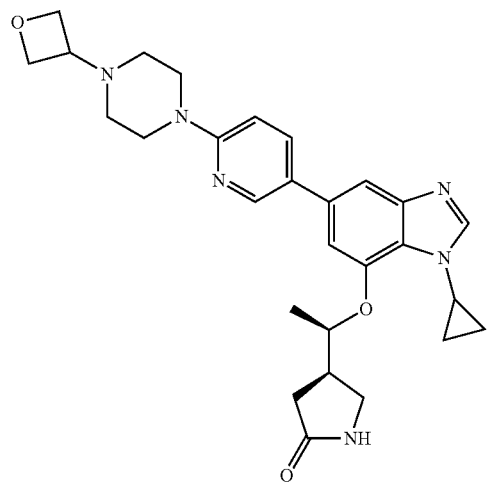

525

Preparation of (R)-4-((R)-1-((1-cyclopropyl-5-(6-(4-(oxetan-3-yl)piperazin-1-yl)pyridin-3-yl)-1H-benzo[d]imidazol-7-yl)oxy)ethyl)pyrrolidin-2-one Step-1 tert-butyl 4-(5-(1-cyclopropyl-7-((R)-1-((R)-5-oxopyrrolidin-3-yl)ethoxy)-1H-benzo[d]imidazol-5-yl)pyridin-2-yl)piperazine-1-carboxylate

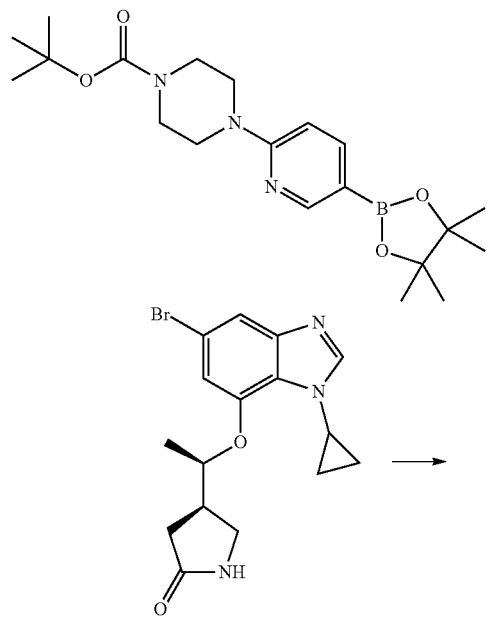

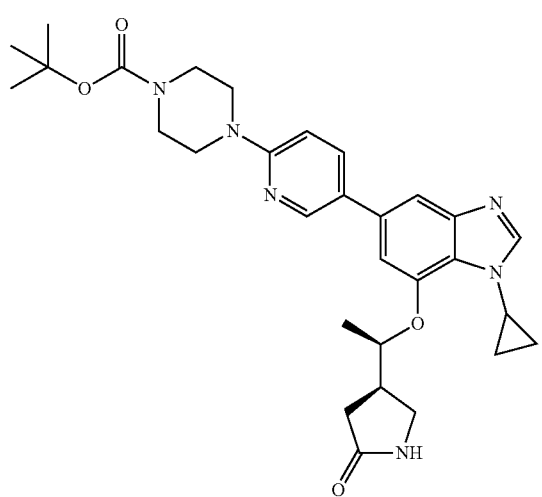

Following the procedure described for intermediate from Step-3 in Example 3.90, starting from (R)-4-((R)-1-((5-bromo-1-cyclopropyl-1H-benzo[d]imidazol-7-yl)oxy)ethyl)pyrrolidin-2-one (245 mg, 0.67 mmol), tert-butyl 4-(2-methyl-4-(4,4,5,5-tetramethyl-1,3,2-dioxaborolan-2-yl)phenyl)piperazine-1-carboxylate (284.16 mg, 0.71 mmol) (BB8), 250 mg tert-butyl 4-(5-(1-cyclopropyl-7-((R)-1-((R)-5-oxopyrrolidin-3-yl)ethoxy)-1H-benzo[d]imidazol-5-yl)pyridin-2-yl)piperazine-1-carboxylate was synthesized.

526

Step-2 (R)-4-((R)-1-((1-cyclopropyl-5-(6-(piperazin-1-yl)pyridin-3-yl)-1H-benzo[d]imidazol-7-yl)oxy)ethyl)pyrrolidin-2-one

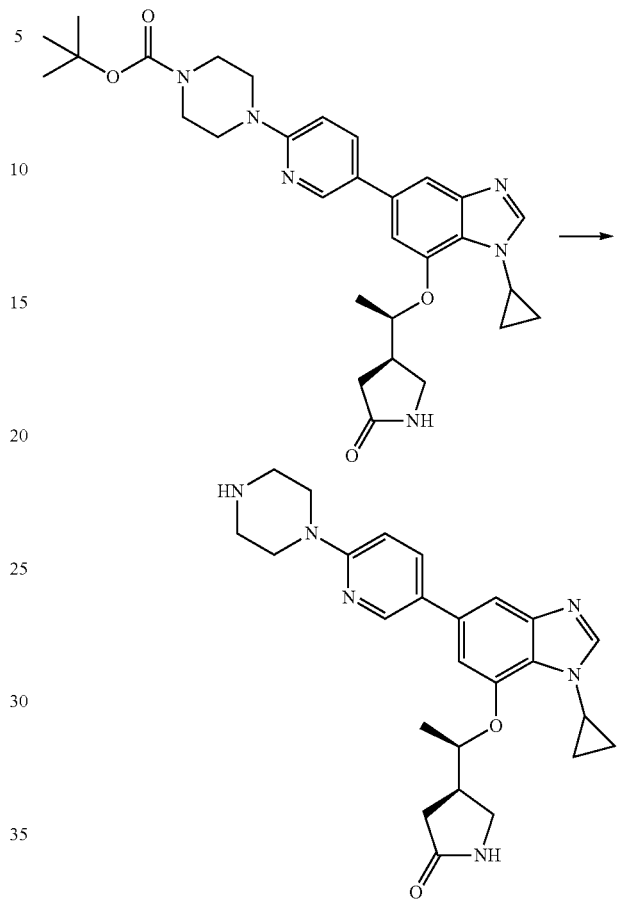

Following the procedure described for intermediate from Step-4 in Example 3.97, starting tert-butyl 4-(5-(1-cyclopropyl-7-((R)-1-((R)-5-oxopyrrolidin-3-yl)ethoxy)-1H-benzo[d]imidazol-5-yl)pyridin-2-yl)piperazine-1-carboxylate (250 mg, 0.35 mmol), 150 mg of (R)-4-((R)-1-((1-cyclopropyl-5-(6-(piperazin-1-yl)pyridin-3-yl)-1H-benzo[d]imidazol-7-yl)oxy)ethyl)pyrrolidin-2-one was synthesized.

Step-3 (R)-4-((R)-1-((1-cyclopropyl-5-(6-(4-(oxetan-3-yl)piperazin-1-yl)pyridin-3-yl)-1H-benzo[d]imidazol-7-yl)oxy)ethyl)pyrrolidin-2-one

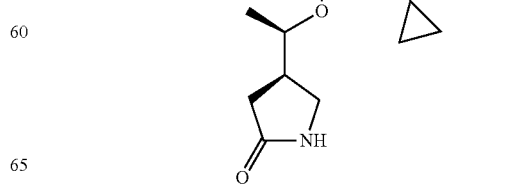

527
-continued

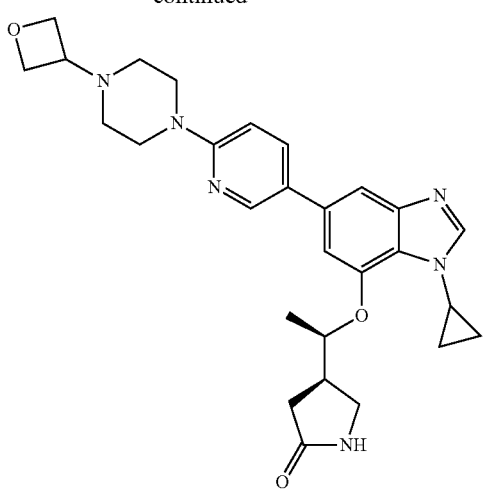

Following the procedure described for intermediate from Step-5 in Example 3.97, starting from (R)-4-((R)-1-((1-cyclopropyl-5-(6-(piperazin-1-yl)pyridin-3-yl)-1H-benzo[d]imidazol-7-yl)oxy)ethyl)pyrrolidin-2-one (150 mg, 0.34 mmol), 14.1 mg (R)-4-((R)-1-((1-cyclopropyl-5-(6-(4-(oxetan-3-yl)piperazin-1-yl)pyridin-3-yl)-1H-benzo[d]imidazol-7-yl)oxy)ethyl)pyrrolidin-2-one was synthesized.

$^1$H NMR (400 MHz, DMSO-d$_6$) δ 8.46 (dd, J=2.6, 0.7 Hz, 1H), 8.06 (s, 1H), 7.87 (dd, J=8.9, 2.6 Hz, 1H), 7.58 (s, 1H), 7.36 (d, J=1.3 Hz, 1H), 7.02 (d, J=1.3 Hz, 1H), 6.94-6.84 (m, 1H), 4.85 (m, 1H), 4.51 (dt, J=25.0, 6.3 Hz, 4H), 3.73-3.61 (m, 1H), 3.50-3.11 (m, 6H), 3.20-3.15 (m, 1H), 2.84-2.72 (m, 1H), 2.49-2.17 (m, 6H), 1.29 (d, J=6.0 Hz, 3H), 1.13-0.94 (m, 4H).

LCMS-ESI$^+$ (m/z): [M+H]$^+$ calcd. for C$_{29}$H$_{35}$N$_6$O$_3$: 502.62; found: 503.21.

3.103

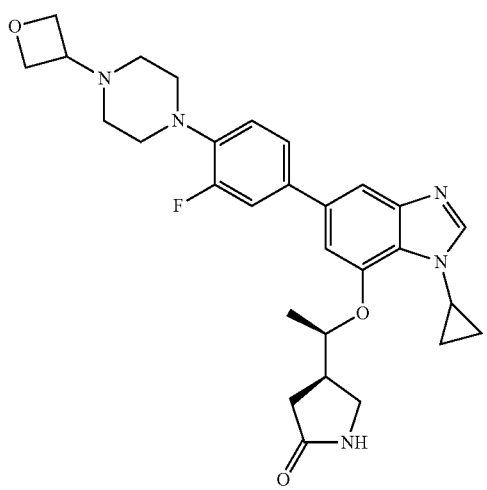

528

Preparation of (R)-4-((R)-1-((1-cyclopropyl-5-(3-fluoro-4-(4-(oxetan-3-yl)piperazin-1-yl)phenyl)-1H-benzo[d]imidazol-7-yl)oxy)ethyl)pyrrolidin-2-one 3.98

Step-1 tert-butyl 4-(4-(1-cyclopropyl-7-((R)-1-((R)-5-oxopyrrolidin-3-yl)ethoxy)-1H-benzo[d]imidazol-5-yl)-2-fluorophenyl)piperazine-1-carboxylate

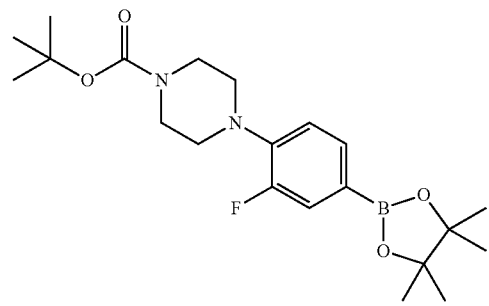

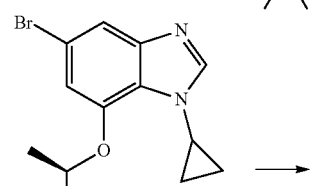

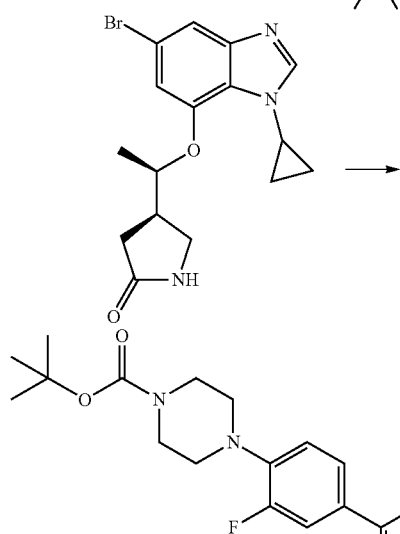

Following the procedure described for intermediate from Step-3 in Example 3.100, starting from combined (R)-4-((R)-1-((5-bromo-1-cyclopropyl-1H-benzo[d]imidazol-7-yl)oxy)ethyl)pyrrolidin-2-one (250 mg, 0.69 mmol) and tert-butyl 4-(2-fluoro-4-(4,4,5,5-tetramethyl-1,3,2-dioxaborolan-2-yl)phenyl)piperazine-1-carboxylate (348.59 mg, 0.86 mmol) (B11), 250 mg tert-butyl 4-(4-(3-cyclopropyl-4-((R)-1-((R)-5-oxopyrrolidin-3-yl)ethoxy)-3H-imidazo[4,5-c]pyridin-6-yl)-2-fluorophenyl)piperazine-1-carboxylate was synthesized.

Step-2 (R)-4-((R)-1-((1-cyclopropyl-5-(3-fluoro-4-(piperazin-1-yl)phenyl)-1H-benzo[d]imidazol-7-yl)oxy)ethyl)pyrrolidin-2-one

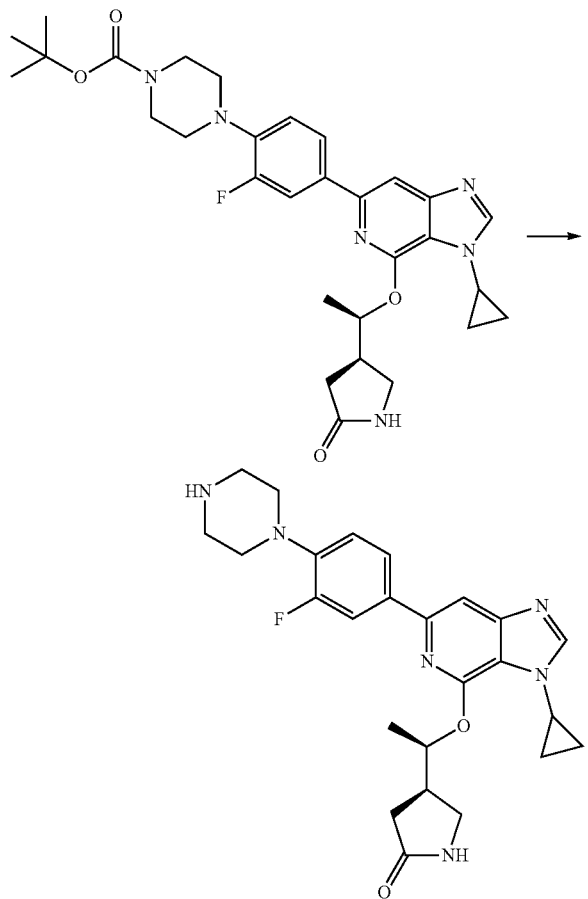

Following the procedure described for intermediate from Step-4 in Example 3.97, starting tert-butyl 4-(4-(1-cyclopropyl-7-((R)-1-((R)-5-oxopyrrolidin-3-yl)ethoxy)-1H-benzo[d]imidazol-5-yl)-2-fluorophenyl)piperazine-1-carboxylate (250 mg, 0.34 mmol), 150 mg of (R)-4-((R)-1-((1-cyclopropyl-5-(3-fluoro-4-(piperazin-1-yl)phenyl)-1H-benzo[d]imidazol-7-yl)oxy)ethyl)pyrrolidin-2-one was synthesized.

Step-3 (R)-4-((R)-1-((1-cyclopropyl-5-(3-fluoro-4-(4-(oxetan-3-yl)piperazin-1-yl)phenyl)-1H-benzo[d]imidazol-7-yl)oxy)ethyl)pyrrolidin-2-one

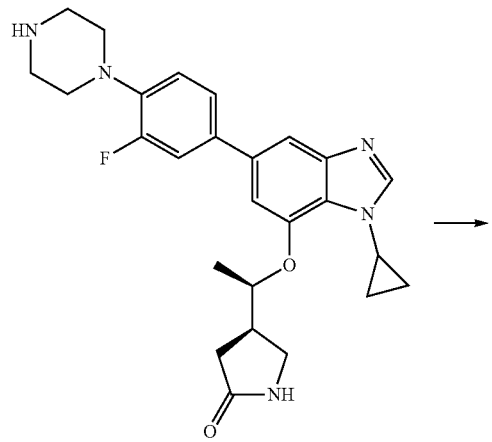

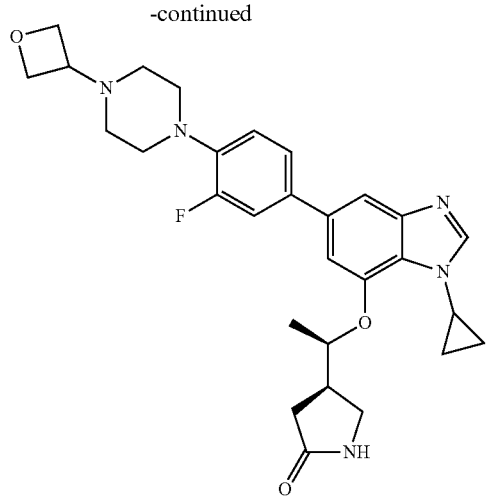

Following the procedure described for intermediate from Step-5 in Example 3.97, starting from (R)-4-((R)-1-((1-cyclopropyl-5-(3-fluoro-4-(piperazin-1-yl)phenyl)-1H-benzo[d]imidazol-7-yl)oxy)ethyl)pyrrolidin-2-one (150 mg, 0.32 mmol), 108.1 mg of (R)-4-((R)-1-((1-cyclopropyl-5-(3-fluoro-4-(4-(oxetan-3-yl)piperazin-1-yl)phenyl)-1H-benzo[d]imidazol-7-yl)oxy)ethyl)pyrrolidin-2-one was synthesized.

$^{1}$H NMR (400 MHz, DMSO-d$_{6}$) δ 8.08 (s, 1H), 7.61-7.37 (m, 4H), 7.14-7.01 (m, 2H), 4.88 (m, 1H), 4.51 (dt, J=28.8, 6.3 Hz, 4H), 3.75-3.61 (m, 1H), 3.54-3.33 (m, 2H), 3.13 (t, 1.4 Hz, 1H), 3.08 (t, J=0.4 Hz, 4H), 2.83-2.75 (m, 1H), 2.43 (t, J=3.6 Hz, 4H), 2.38-2.20 (m, 2H), 1.29 (d, J=6.0 Hz, 3H), 1.14-0.92 (m, 4H).

LCMS-ESI$^{+}$ (m/z): [M+H]$^{+}$ calcd. for C$_{29}$H$_{34}$FN$_{5}$O$_{3}$: 520.61; found: 520.19.

3.102

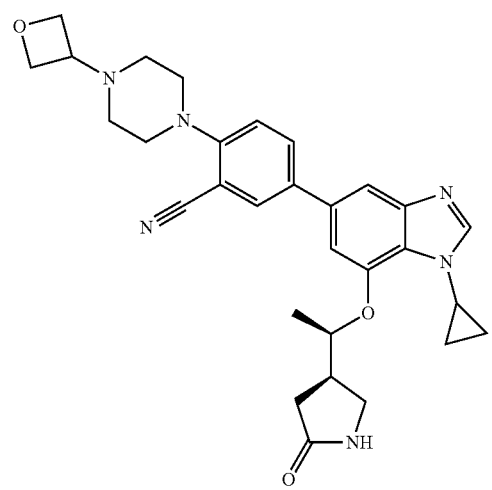

531

Preparation of 5-(1-cyclopropyl-7-((R)-1-((R)-5-oxopyrrolidin-3-yl)ethoxy)-1H-benzo[d]imidazol-5-yl)-2-(4-(oxetan-3-yl)piperazin-1-yl)benzonitrile Step-1 Preparation tert-butyl 4-(4-bromo-2-cyanophenyl)piperazine-1-carboxylate

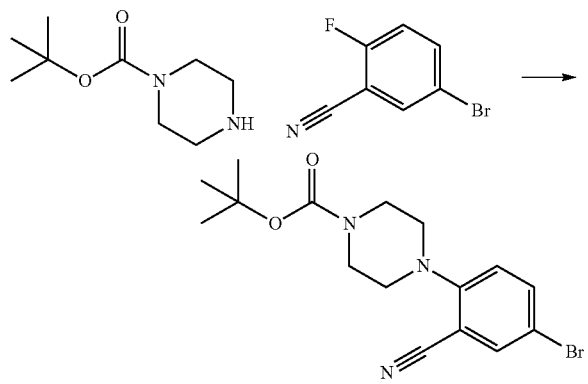

In a pressure tube, 5-bromo-2-fluorobenzonitrile (2500 mg, 12.5 mmol), tert-butyl piperazine-1-carboxylate (2444.45 mg, 13.12 mmol), triethylamine (5.23 ml, 37.5 mmol) in dimethylsulfoxide (10 ml) were combined and refluxed at 100 C for ovn. The mixture was cooled, and partitioned between ethyl acetate and saturated aqueous sodium bicarbonate. The organic phase was dried using sodium sulfate and concentrated. The residue was purified by flash column chromatography on silica gel 5-60% ethyl acetate/hexane to provide a light brown oil, tert-butyl 4-(4-bromo-2-cyanophenyl)piperazine-1-carboxylate (3660 mg, 80%).

Step-2 tert-butyl 4-(2-cyano-4-(4,4,5,5-tetramethyl-1,3,2-dioxaborolan-2-yl)phenyl)piperazine-1-carboxylate

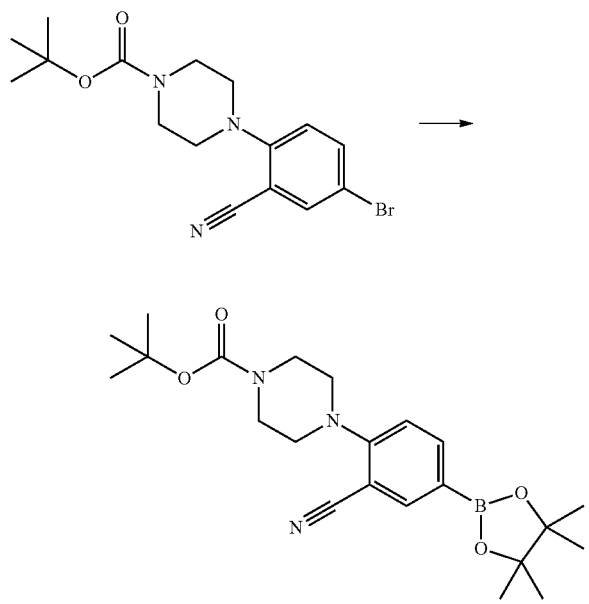

532

Following the procedure described for intermediate 7.17, starting with tert-butyl 4-(4-bromo-2-cyanophenyl)piperazine-1-carboxylate (450 mg, 1.23 mmol), 500 mg tert-butyl 4-(2-cyano-4-(4,4,5,5-tetramethyl-1,3,2-dioxaborolan-2-yl)phenyl)piperazine-1-carboxylate was synthesized.

Step-3 tert-butyl 4-(2-cyano-4-(3-cyclopropyl-4-((R)-1-((R)-5-oxopyrrolidin-3-yl)ethoxy)-3H-imidazo[4,5-c]pyridin-6-yl)phenyl)piperazine-1-carboxylate

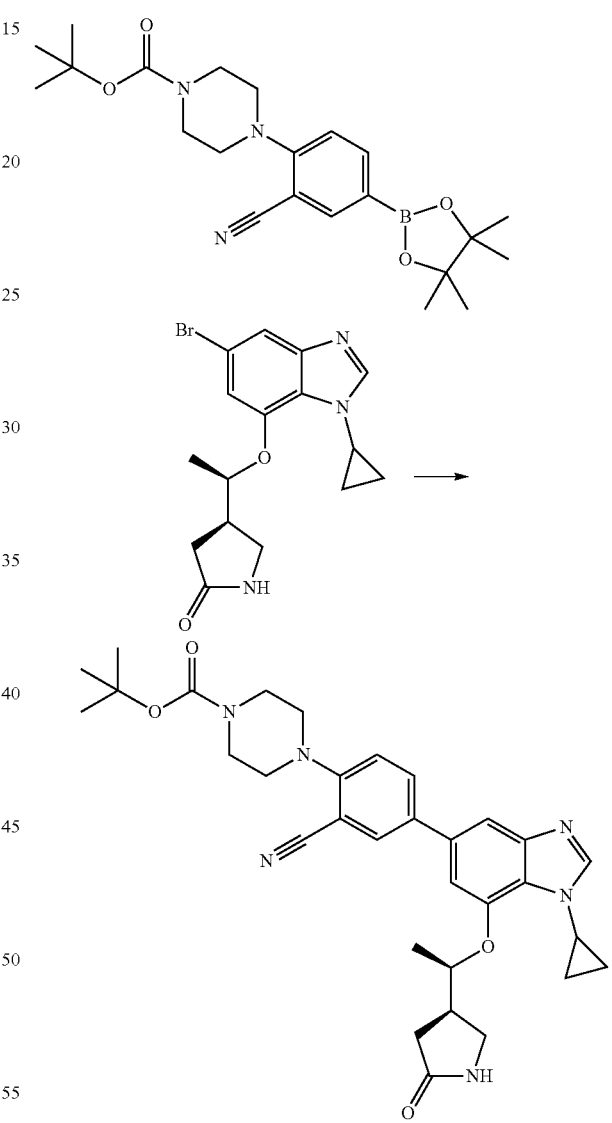

Following the procedure described for intermediate from Step-3 in Example 3.90, starting from (R)-4-((R)-1-((6-bromo-3-cyclopropyl-3H-imidazo[4,5-c]pyridin-4-yl)oxy)ethyl)pyrrolidin-2-one (215 mg, 0.59 mmol) and tert-butyl 4-(2-cyano-4-(4,4,5,5-tetramethyl-1,3,2-dioxaborolan-2-yl)phenyl)piperazine-1-carboxylate (255.48 mg, 0.62 mmol), 160 mg of tert-butyl 4-(2-cyano-4-(3-cyclopropyl-4-((R)-1-((R)-5-oxopyrrolidin-3-yl)ethoxy)-3H-imidazo[4,5-c]pyridin-6-yl)phenyl)piperazine-1-carboxylate was synthesized.

Step-4 5-(1-cyclopropyl-7-((R)-1-((R)-5-oxopyrrolidin-3-yl)ethoxy)-1H-benzo[d]imidazol-5-yl)-2-(piperazin-1-yl)benzonitrile

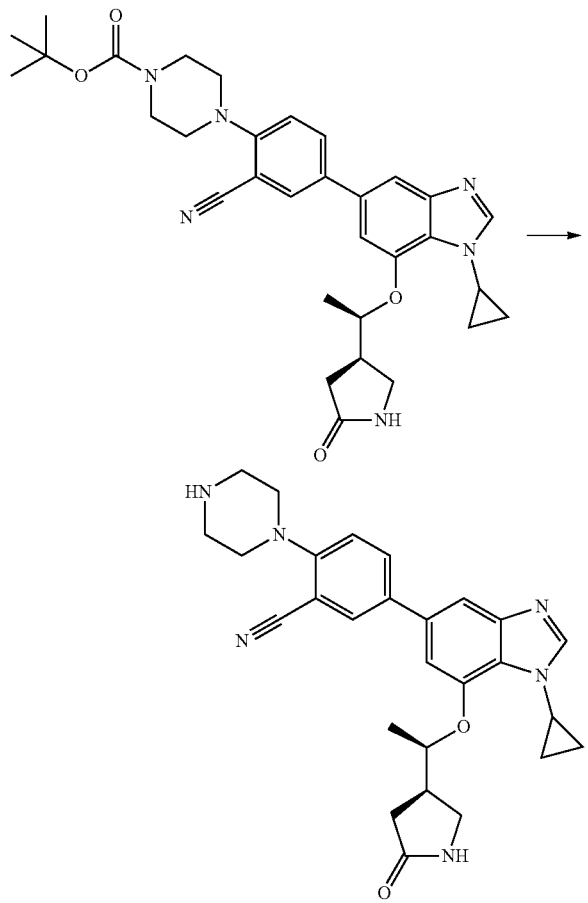

Following the procedure described for intermediate from Step-4 in Example 3.97, starting tert-butyl 4-(2-cyano-4-(1-cyclopropyl-7-((R)-1-((R)-5-oxopyrrolidin-3-yl)ethoxy)-1H-benzo[d]imidazol-5-yl)phenyl)piperazine-1-carboxylate (130 mg, 0.17 mmol), 80 mg of 5-(1-cyclopropyl-7-((R)-1-((R)-5-oxopyrrolidin-3-yl)ethoxy)-1H-benzo[d]imidazol-5-yl)-2-(piperazin-1-yl)benzonitrile was synthesized.

Step-5 5-(1-cyclopropyl-7-((R)-1-((R)-5-oxopyrrolidin-3-yl)ethoxy)-1H-benzo[d]imidazol-5-yl)-2-(4-(oxetan-3-yl)piperazin-1-yl)benzonitrile

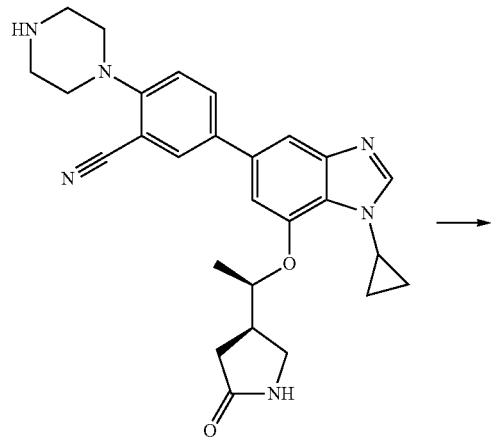

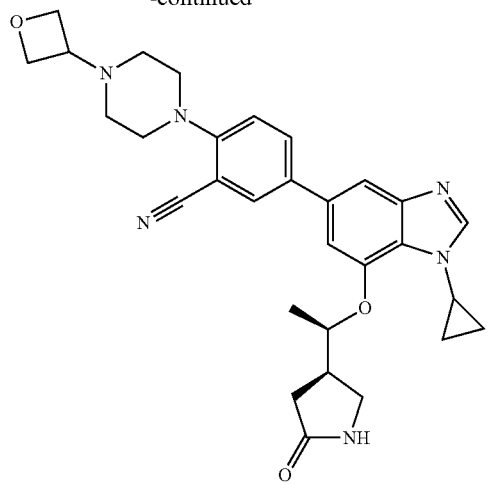

Following the procedure described for intermediate from Step-5 in Example 3.97, starting from 5-(3-cyclopropyl-4-((R)-1-((R)-5-oxopyrrolidin-3-yl)ethoxy)-3H-imidazo[4,5-c]pyridin-6-yl)-2-(piperazin-1-yl)benzonitrile (110 mg, 0.23 mmol), 33.3 mg of 5-(1-cyclopropyl-7-((R)-1-((R)-5-oxopyrrolidin-3-yl)ethoxy)-1H-benzo[d]imidazol-5-yl)-2-(4-(oxetan-3-yl)piperazin-1-yl)benzonitrile was synthesized.

$^1$H NMR (400 MHz, DMSO-d$_6$) δ 8.12 (s, 1H), 8.07 (d, J=2.7 Hz, 1H), 7.96 (dd, J=8.7, 2.4 Hz, 1H), 7.60 (s, 1H), 7.47 (d, J=1.2 Hz, 1H), 7.23 (d, J=8.7 Hz, 1H), 7.11 (s, 1H), 4.94 (q, J=6.0 Hz, 1H), 4.53 (dt, J=28.7, 6.3 Hz, 4H), 3.77-3.63 (m, 1H), 3.59-3.37 (m, 2H), 3.24-3.16 (m, 5H), 2.81 (q, J=7.2 Hz, 1H), 2.47-2.19 (m, 2H), 1.31 (d, J=5.9 Hz, 3H), 1.15-0.95 (m, 4H).

LCMS-ESI$^+$ (m/z): [M+H]$^+$ calcd. for C$_{30}$H$_{34}$N$_6$O$_3$: 527.63; found: 527.21.

3.105

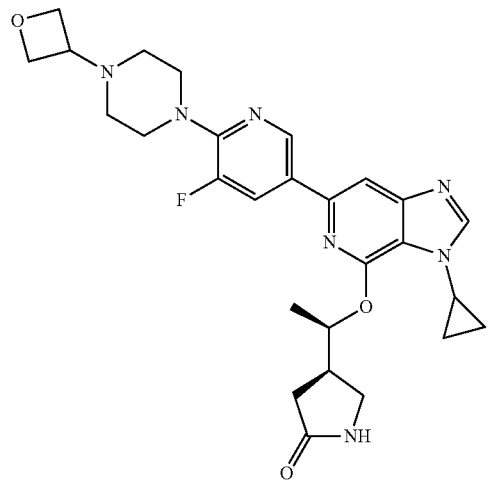

Preparation of (R)-4-((R)-1-((3-cyclopropyl-6-(5-fluoro-6-(4-(oxetan-3-yl)piperazin-1-yl)pyridin-3-yl)-3H-imidazo[4,5-c]pyridin-4-yl)oxy)ethyl)pyrrolidin-2-one Step-1 Preparation of tert-butyl 4-(5-bromo-3-fluoropyridin-2-yl)piperazine-1-carboxylate

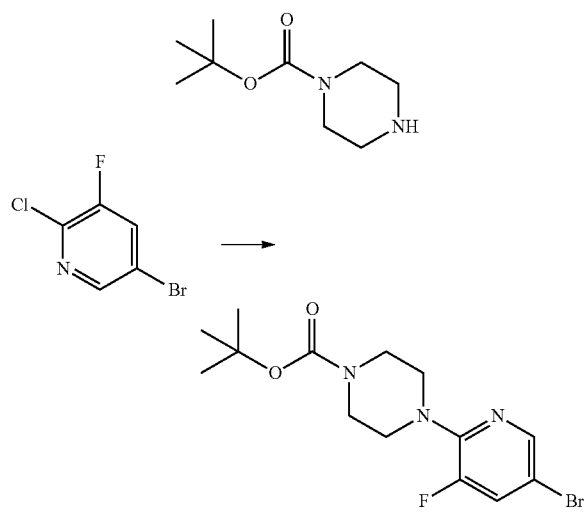

In a pressure tube, 5-bromo-2-chloro-3-fluoropyridine (7.89 ml, 49.9 mmol), tert-butyl piperazine-1-carboxylate (9293.48 mg, 49.9 mmol), potassium carbonate (8275.33 mg, 59.88 mmol) in dimethylsulfoxide (40 ml) were combined and refluxed at 120 C for ovn. The reaction was cooled down, diluted with ethyl ether (100 mL). The solution was washed with water (40 mL×2), brine (50 mL), filtered, dried, and concentrated. The reaction was purified on silica by flash chromatography to provide of tert-butyl 4-(5-bromo-3-fluoropyridin-2-yl)piperazine-1-carboxylate (5000 mg, 28%).

Step-2 Preparation tert-butyl 4-(3-fluoro-5-(4,4,5,5-tetramethyl-1,3,2-dioxaborolan-2-yl)pyridin-2-yl)piperazine-1-carboxylate

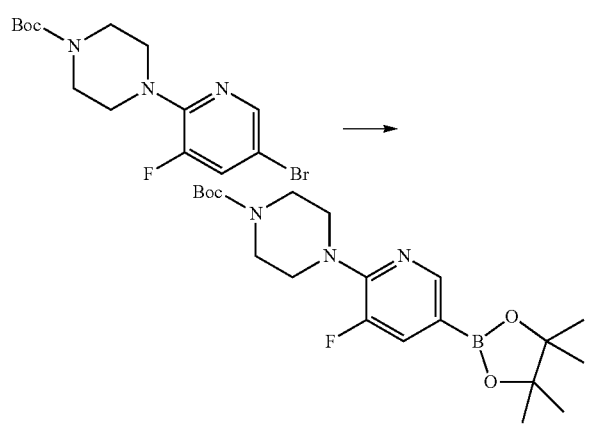

Following the procedure described for intermediate 7.17, starting with tert-butyl 4-(5-bromopyridin-2-yl)piperazine-1-carboxylate (3000 mg, 8.77 mmol), 1600 mg tert-butyl 4-(3-fluoro-5-(4,4,5,5-tetramethyl-1,3,2-dioxaborolan-2-yl)pyridin-2-yl)piperazine-1-carboxylate was synthesized.

Step-3 tert-butyl 4-(5-(3-cyclopropyl-4-((R)-1-((R)-5-oxopyrrolidin-3-yl)ethoxy)-3H-imidazo[4,5-c]pyridin-6-yl)-3-fluoropyridin-2-yl)piperazine-1-carboxylate

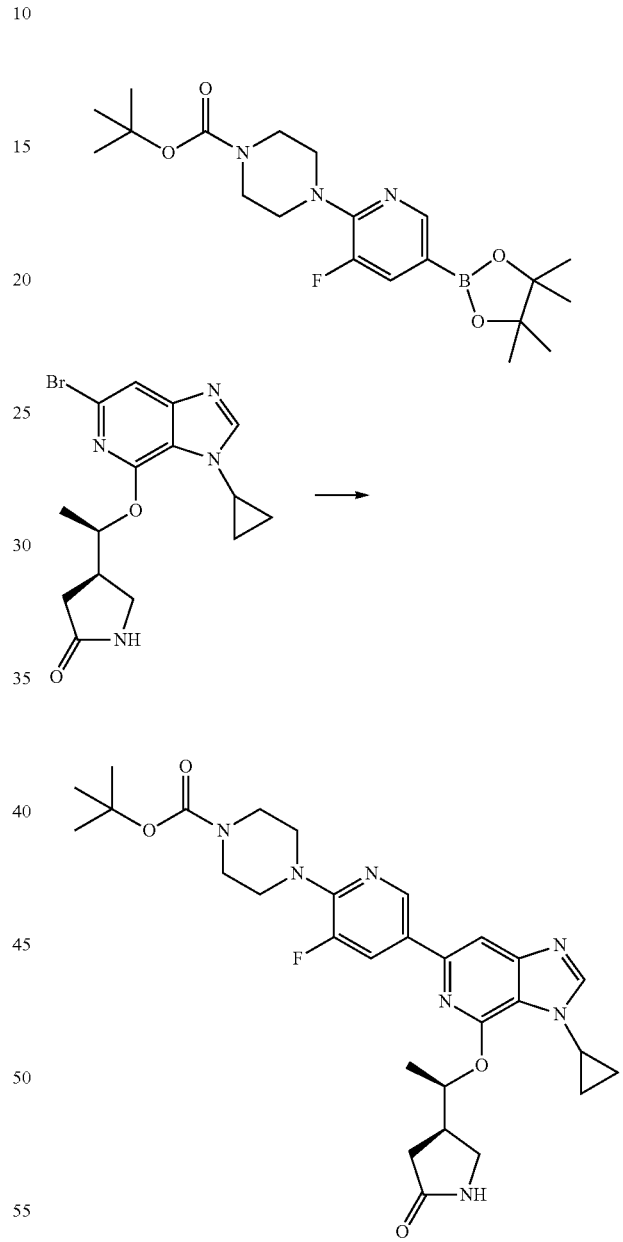

Following the procedure described for example 2.52, starting (R)-4-((R)-1-((6-bromo-3-cyclopropyl-3H-imidazo[4,5-c]pyridin-4-yl)oxy)ethyl)pyrrolidin-2-one (215 mg, 0.59 mmol), tert-butyl 4-(3-fluoro-5-(4,4,5,5-tetramethyl-1,3,2-dioxaborolan-2-yl)pyridin-2-yl)piperazine-1-carboxylate (287.71 mg, 0.71 mmol), 230 mg of tert-butyl 4-(5-(3-cyclopropyl-4-((R)-1-((R)-5-oxopyrrolidin-3-yl)ethoxy)-3H-imidazo[4,5-c]pyridin-6-yl)-3-fluoropyridin-2-yl)piperazine-1-carboxylate.

Step-4 (R)-4-((R)-1-((3-cyclopropyl-6-(5-fluoro-6-(piperazin-1-yl)pyridin-3-yl)-3H-imidazo[4,5-c]pyridin-4-yl)oxy)ethyl)pyrrolidin-2-one

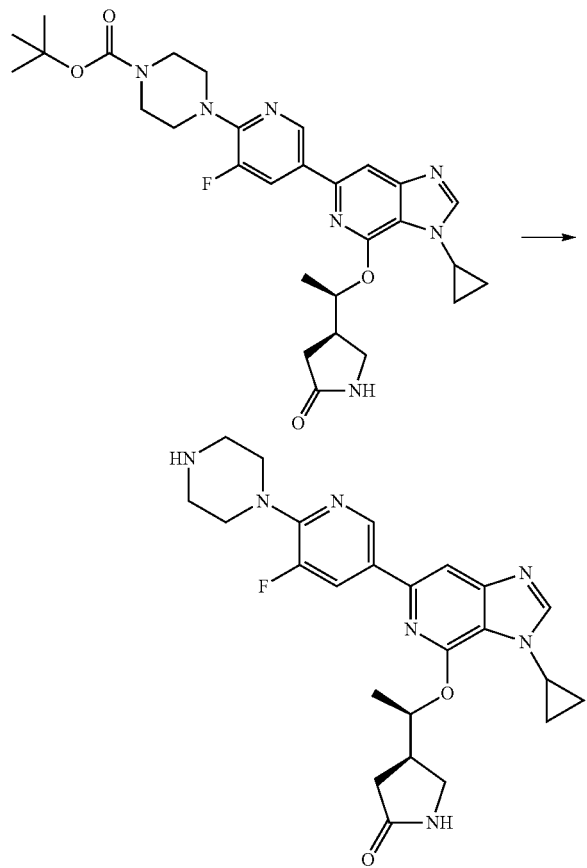

Following the procedure described for intermediate from Step-4 in Example 3.97, starting tert-butyl 4-(5-(3-cyclopropyl-4-((R)-1-((R)-5-oxopyrrolidin-3-yl)ethoxy)-3H-imidazo[4,5-c]pyridin-6-yl)-3-fluoropyridin-2-yl)piperazine-1-carboxylate (230 mg, 0.31 mmol), 140 mg (R)-4-((R)-1-((3-cyclopropyl-6-(5-fluoro-6-(piperazin-1-yl)pyridin-3-yl)-3H-imidazo[4,5-c]pyridin-4-yl)oxy)ethyl)pyrrolidin-2-one was synthesized.

Step-5 (R)-4-((R)-1-((3-cyclopropyl-6-(5-fluoro-6-(4-(oxetan-3-yl)piperazin-1-yl)pyridin-3-yl)-3H-imidazo[4,5-c]pyridin-4-yl)oxy)ethyl)pyrrolidin-2-one

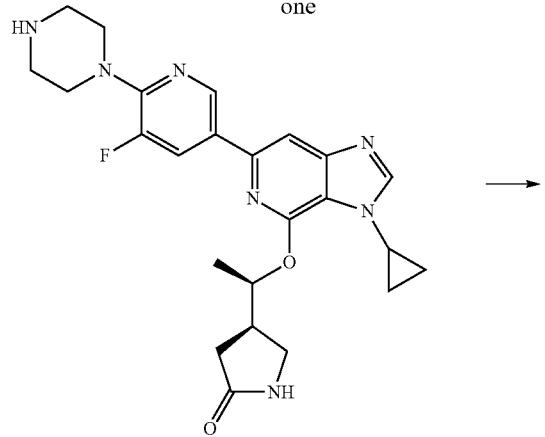

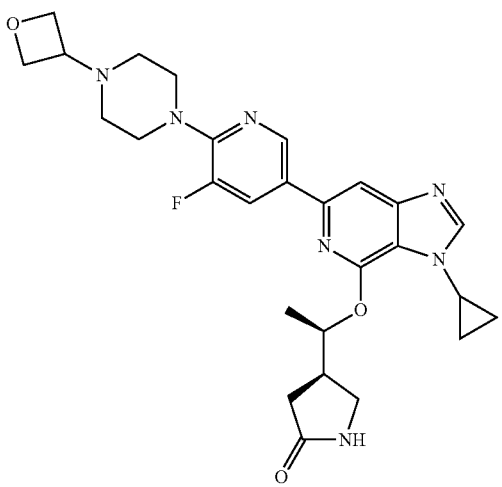

Following the procedure described for intermediate from Step-5 in Example 3.97, starting from (R)-4-((R)-1-((3-cyclopropyl-6-(5-fluoro-6-(piperazin-1-yl)pyridin-3-yl)-3H-imidazo[4,5-c]pyridin-4-yl)oxy)ethyl)pyrrolidin-2-one (140 mg, 0.3 mmol), 81 mg of (R)-4-((R)-1-((3-cyclopropyl-6-(5-fluoro-6-(4-(oxetan-3-yl)piperazin-1-yl)pyridin-3-yl)-3H-imidazo[4,5-c]pyridin-4-yl)oxy)ethyl)pyrrolidin-2-one was synthesized.

$^1$H NMR (400 MHz, DMSO-d$_6$) δ 8.78 (t, J=1.7 Hz, 1H), 8.29 (s, 1H), 8.14 (dd, J=15.0, 1.9 Hz, 1H), 7.83 (s, 1H), 7.56 (s, 1H), 5.63-5.53 (m, 1H), 4.52 (dt, J=24.8, 6.3 Hz, 4H), 3.69 (tt, J=7.2, 3.9 Hz, 1H), 3.47-3.25 (m, 6H), 3.22 (dd, J=9.7, 6.6 Hz, 1H), 2.88-2.78 (m, 1H), 2.47-2.28 (m, 7H), 1.40 (d, J=6.2 Hz, 3H), 1.16-0.97 (m, 4H).

LCMS-ESI$^+$ (m/z): [M+H]$^+$ calcd. for C$_{27}$H$_{32}$FN$_7$O$_3$: 522.59; found: 522.14.

3.106

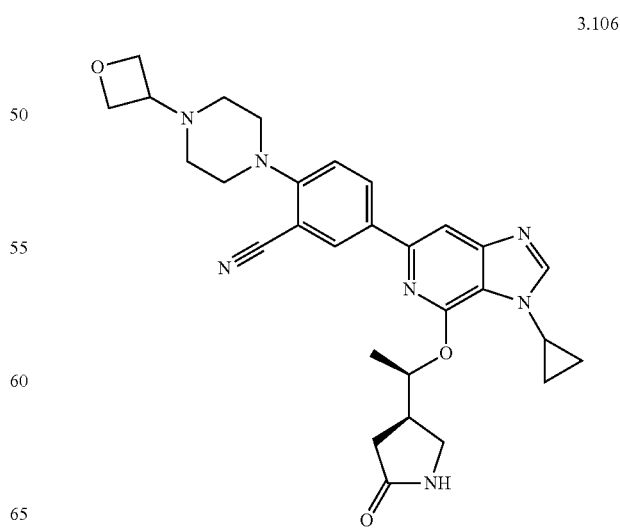

539

Preparation of 5-(3-cyclopropyl-4-((R)-1-((R)-5-oxopyrrolidin-3-yl)ethoxy)-3H-imidazo[4,5-c]pyridin-6-yl)-2-(4-(oxetan-3-yl)piperazin-1-yl)benzonitrile Step-1 tert-butyl 4-(2-cyano-4-(3-cyclopropyl-4-((R)-1-((R)-5-oxopyrrolidin-3-yl)ethoxy)-3H-imidazo[4,5-c]pyridin-6-yl)phenyl)piperazine-1-carboxylate

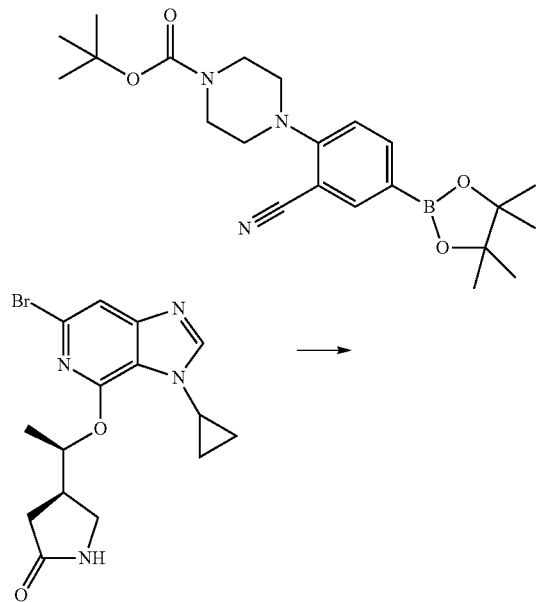

Following the procedure described for intermediate 2.52, starting from (R)-4-((R)-1-((6-bromo-3-cyclopropyl-3H-imidazo[4,5-c]pyridin-4-yl)oxy)ethyl)pyrrolidin-2-one (215 mg, 0.59 mmol), tert-butyl 4-(2-cyano-4-(4,4,5,5-tetramethyl-1,3,2-dioxaborolan-2-yl)phenyl)piperazine-1-carboxylate (255.48 mg, 0.62 mmol), 160 mg tert-butyl 4-(2-cyano-4-(3-cyclopropyl-4-((R)-1-((R)-5-oxopyrrolidin-3-yl)ethoxy)-3H-imidazo[4,5-c]pyridin-6-yl)phenyl)piperazine-1-carboxylate was synthesized.

Step-2 5-(3-cyclopropyl-4-((R)-1-((R)-5-oxopyrrolidin-3-yl)ethoxy)-3H-imidazo[4,5-c]pyridin-6-yl)-2-(piperazin-1-yl)benzonitrile

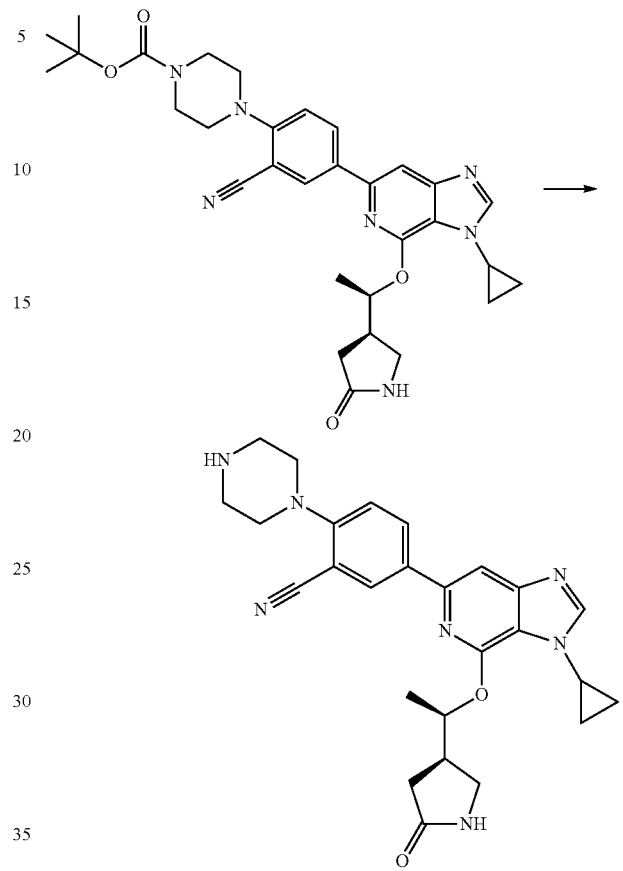

Following the procedure described for intermediate from Step-4 in Example 3.97, starting tert-butyl 4-(2-cyano-4-(3-cyclopropyl-4-((R)-1-((R)-5-oxopyrrolidin-3-yl)ethoxy)-3H-imidazo[4,5-c]pyridin-6-yl)phenyl)piperazine-1-carboxylate (160 mg, 0.28 mmol), 110 mg of 5-(3-cyclopropyl-4-((R)-1-((R)-5-oxopyrrolidin-3-yl)ethoxy)-3H-imidazo[4,5-c]pyridin-6-yl)-2-(piperazin-1-yl)benzonitrile was synthesized.

Step-3 5-(3-cyclopropyl-4-((R)-1-((R)-5-oxopyrrolidin-3-yl)ethoxy)-3H-imidazo[4,5-c]pyridin-6-yl)-2-(4-(oxetan-3-yl)piperazin-1-yl)benzonitrile

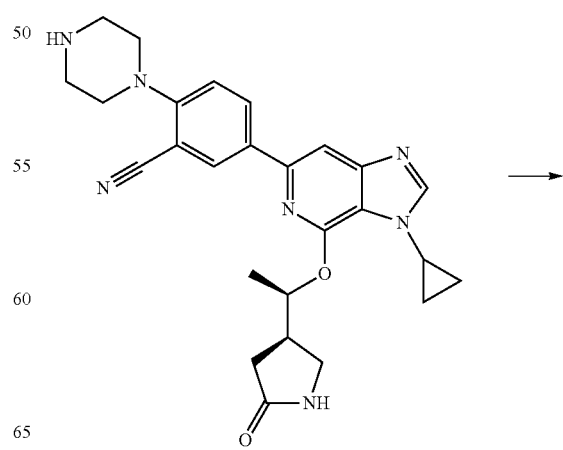

541

-continued

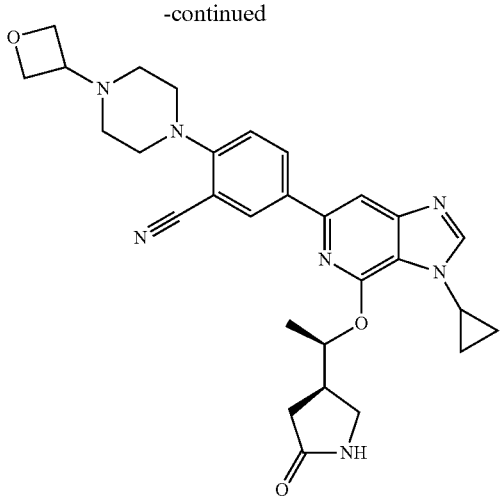

Following the procedure described for intermediate from Step-5 in Example 3.97, starting from 5-(3-cyclopropyl-4-((R)-1-((R)-5-oxopyrrolidin-3-yl)ethoxy)-3H-imidazo[4,5-c]pyridin-6-yl)-2-(piperazin-1-yl)benzonitrile (110 mg, 0.23 mmol), 70.1 mg of 5-(3-cyclopropyl-4-((R)-1-((R)-5-oxopyrrolidin-3-yl)ethoxy)-3H-imidazo[4,5-c]pyridin-6-yl)-2-(4-(oxetan-3-yl)piperazin-1-yl)benzonitrile was synthesized.

$^1$H NMR (400 MHz, DMSO-d$_6$) δ 8.40-8.26 (m, 3H), 7.86 (s, 1H), 7.56 (s, 1H), 7.24 (d, J=8.7 Hz, 1H), 5.63-5.52 (m, 1H), 4.53 (dt, J=28.3, 6.3 Hz, 4H), 3.69 (td, J=6.9, 3.6 Hz, 1H), 3.56-3.37 (m, 2H), 3.24-3.18 (m, 4H), 2.92-2.81 (m, 1H), 2.34 (d, J=8.7 Hz, 2H), 1.41 (d, J=6.1 Hz, 3H), 1.18-0.97 (m, 4H).

LCMS-ESI$^+$ (m/z): [M+H]$^+$ calcd. for C$_{29}$H$_{33}$N$_7$O$_3$: 528.62; found: 528.14.

3.107

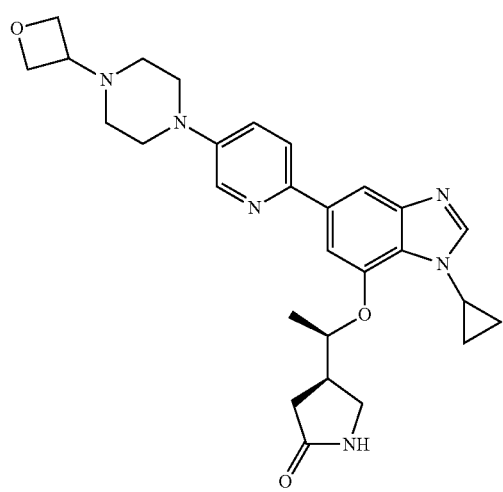

542

Preparation of (R)-4-((R)-1-((1-cyclopropyl-5-(5-(4-(oxetan-3-yl)piperazin-1-yl)pyridin-2-yl)-1H-benzo[d]imidazol-7-yl)oxy)ethyl)pyrrolidin-2-one Step-1 Preparation (R)-4-((R)-1-((1-cyclopropyl-5-(5-(4-(oxetan-3-yl)piperazin-1-yl)pyridin-2-yl)-1H-benzo[d]imidazol-7-yl)oxy)ethyl)pyrrolidin-2-one

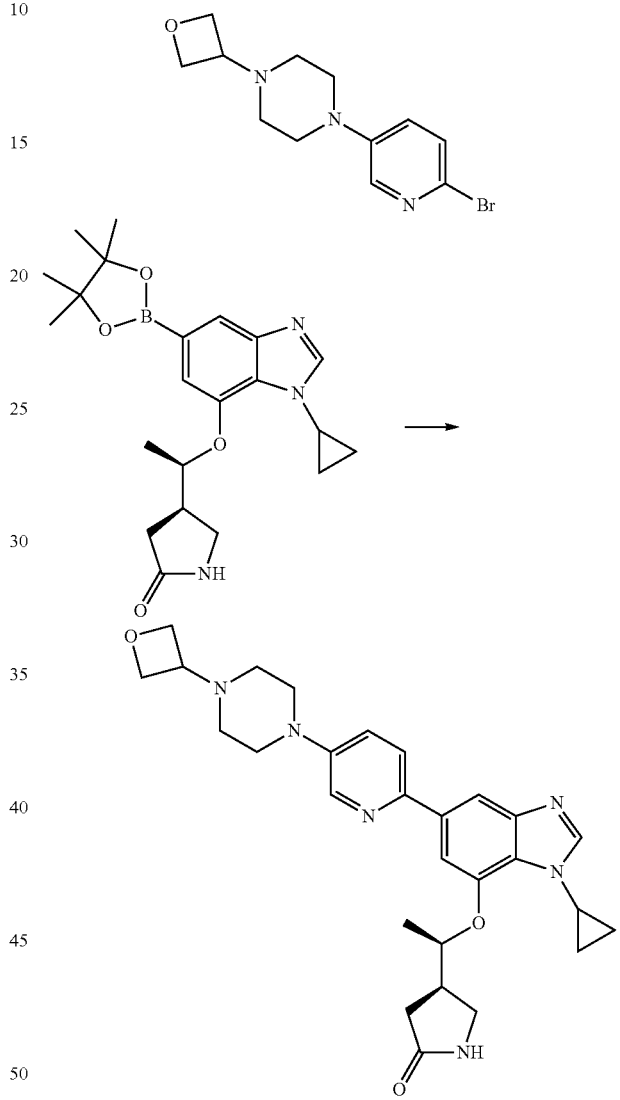

Following the procedure described for intermediate 2.52, starting from (R)-4-((R)-1-((6-bromo-3-cyclopropyl-3H-imidazo[4,5-c]pyridin-4-yl)oxy)ethyl)pyrrolidin-2-one (172.42 mg, 0.42 mmol) and 1-(6-bromopyridin-3-yl)-4-(oxetan-3-yl)piperazine (100.00 mg, 0.34 mmol), 41.5 mg of (R)-4-((R)-1-((1-cyclopropyl-5-(5-(4-(oxetan-3-yl)piperazin-1-yl)pyridin-2-yl)-1H-benzo[d]imidazol-7-yl)oxy)ethyl)pyrrolidin-2-one was synthesized.

$^1$H NMR (400 MHz, DMSO-d$_6$) δ 8.37 (d, J=2.8 Hz, 1H), 8.08 (s, 1H), 7.86 (d, J=8.9 Hz, 1H), 7.76 (d, J=1.2 Hz, 1H), 7.63-7.51 (m, 2H), 7.39 (dd, J=8.9, 3.0 Hz, 1H), 4.79 (m, 1H), 4.53 (dt, J=28.6, 6.3 Hz, 4H), 3.69 (m, 1H), 3.53-3.37 (m, 2H), 3.29-3.19 (m, 6H), 2.89-2.77 (m, 1H), 2.50-2.41 (m, 4H), 2.37-2.23 (m, 2H), 1.33 (d, J=6.0 Hz, 3H), 1.14-0.95 (m, 3H).

543

LCMS-ESI+ (m/z): [M+H]+ calcd. for $C_{28}H_{34}N_6O_3$: 503.61; found: 503.22.

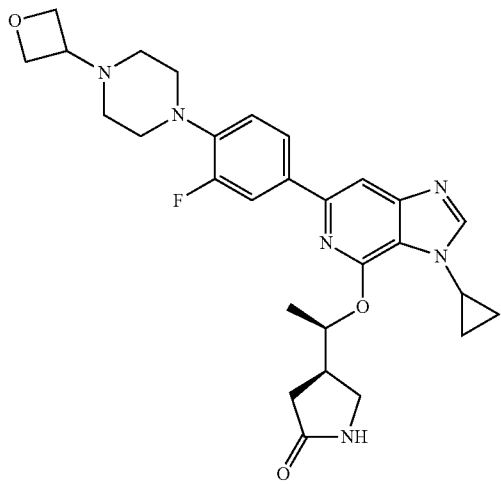

Preparation of (R)-4-((R)-1-((3-cyclopropyl-6-(3-fluoro-4-(4-(oxetan-3-yl)piperazin-1-yl)phenyl)-3H-imidazo[4,5-c]pyridin-4-yl)oxy)ethyl)pyrrolidin-2-one Step-1 tert-butyl 4-(4-(3-cyclopropyl-4-((R)-1-((R)-5-oxopyrrolidin-3-yl)ethoxy)-3H-imidazo[4,5-c]pyridin-6-yl)-2-fluorophenyl)piperazine-1-carboxylate

544

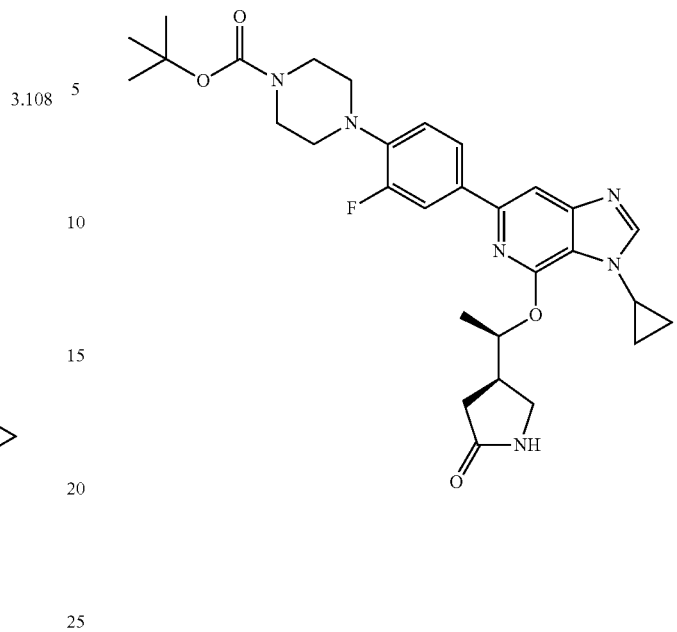

Following the procedure described for intermediate 2.52, starting from combined (R)-4-((R)-1-((6-bromo-3-cyclopropyl-3H-imidazo[4,5-c]pyridin-4-yl)oxy)ethyl)pyrrolidin-2-one (215 mg, 0.59 mmol) and tert-butyl 4-(2-fluoro-4-(4,4,5,5-tetramethyl-1,3,2-dioxaborolan-2-yl)phenyl)piperazine-1-carboxylate (298.97 mg, 0.74 mmol), 320 tert-butyl 4-(4-(3-cyclopropyl-4-((R)-1-((R)-5-oxopyrrolidin-3-yl)ethoxy)-3H-imidazo[4,5-c]pyridin-6-yl)-2-fluorophenyl)piperazine-1-carboxylate was synthesized.

Step-2 (R)-4-((R)-1-((3-cyclopropyl-6-(3-fluoro-4-(piperazin-1-yl)phenyl)-3H-imidazo[4,5-c]pyridin-4-yl)oxy)ethyl)pyrrolidin-2-one

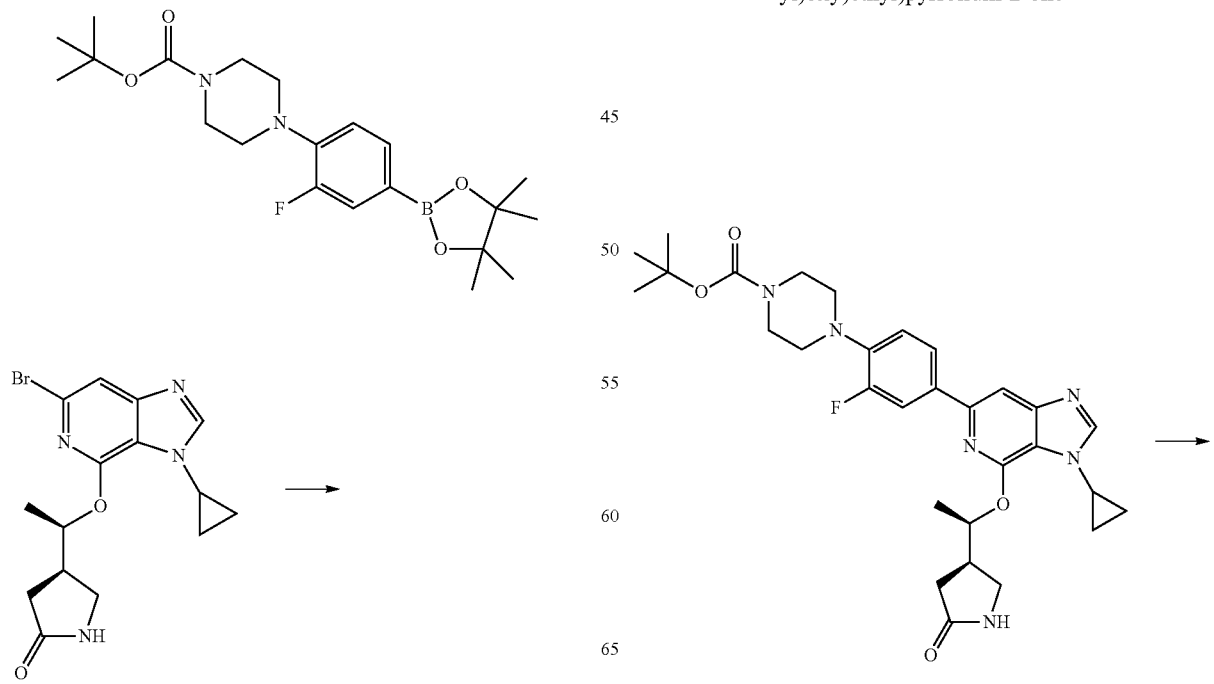

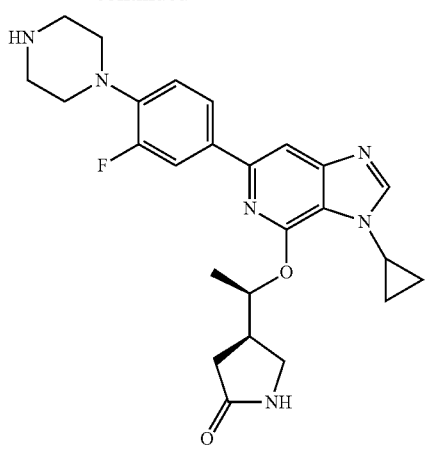

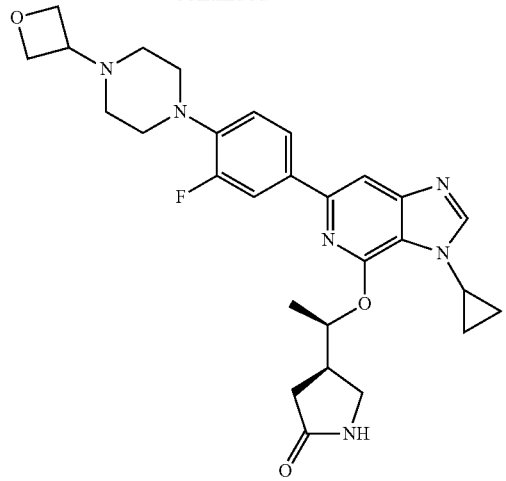

Following the procedure described for intermediate from Step-4 in Example 3.97, starting (3-cyclopropyl-4-((R)-1-((R)-5-oxopyrrolidin-3-yl)ethoxy)-3H-imidazo[4,5-c]pyridin-6-yl)-2-fluorophenyl)piperazine-1-carboxylate (320 mg, 0.43 mmol), 200 mg of (R)-4-((R)-1-((3-cyclopropyl-6-(3-fluoro-4-(piperazin-1-yl)phenyl)-3H-imidazo[4,5-c]pyridin-4-yl)oxy)ethyl)pyrrolidin-2-one was synthesized.

Step-3 (R)-4-((R)-1-((3-cyclopropyl-6-(3-fluoro-4-(4-(oxetan-3-yl)piperazin-1-yl)phenyl)-3H-imidazo[4,5-c]pyridin-4-yl)oxy)ethyl)pyrrolidin-2-one Following the procedure described for intermediate from Step-5 in Example 3.97, starting from (R)-4-((R)-1-((3-cyclopropyl-6-(3-fluoro-4-(piperazin-1-yl)phenyl)-3H-imidazo[4,5-c]pyridin-4-yl)oxy)ethyl)pyrrolidin-2-one (200 mg, 0.43 mmol), 108.1 mg of (R)-4-((R)-1-((3-cyclopropyl-6-(3-fluoro-4-(4-(oxetan-3-yl)piperazin-1-yl)phenyl)-3H-imidazo[4,5-c]pyridin-4-yl)oxy)ethyl)pyrrolidin-2-one was synthesized.

$^1$H NMR (400 MHz, DMSO-d$_6$) δ 8.27 (d, J=0.4 Hz, 1H), 7.91-7.81 (m, 3H), 7.77 (s, 1H). 7.56 (s, 1H), 7.09 (t, J=9.0 Hz, 1H), 5.62-5.51 (m, 1H), 4.52 (dt, J=28.3, 6.3 Hz, 4H), 3.68 (td, J=7.0, 3.6 Hz, 1H), 3.53-3.30 (m, 2H), 3.31-3.15 (m, 1H), 3.10 (dd, J=6.2, 3.6 Hz, 4H), 2.92-2.80 (m, 1H), 2.46-2.26 (m, 6H), 1.41 (d, J=6.2 Hz, 3H), 1.17-0.99 (m, 3H).

LCMS-ESI$^+$ (m/z): [M+H]$^+$ calcd. for C$_{27}$H$_{33}$FN$_7$O$_3$: 504.60; found: 504.15.

3.109

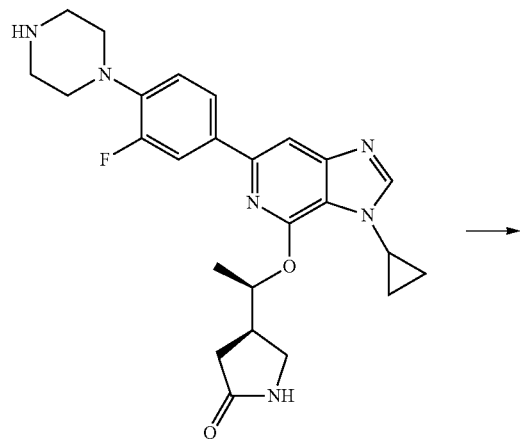

→

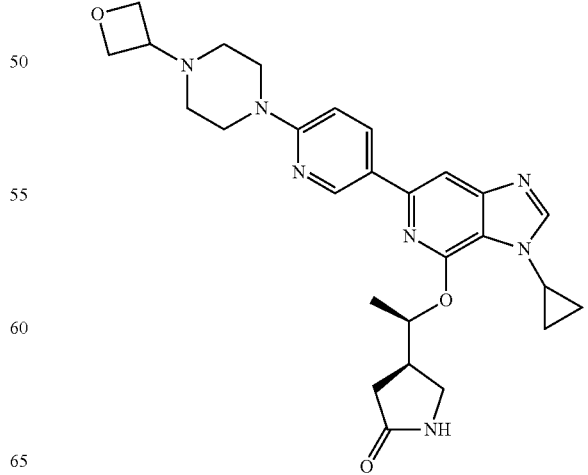

547

Preparation of (R)-4-((R)-1-((3-cyclopropyl-6-(6-(4-(oxetan-3-yl)piperazin-1-yl)pyridin-3-yl)-3H-imidazo[4,5-c]pyridin-4-yl)oxy)ethyl)pyrrolidin-2-one Step-1 tert-butyl 4-(5-(3-cyclopropyl-4-((R)-1-((R)-5-oxopyrrolidin-3-yl)ethoxy)-3H-imidazo[4,5-c]pyridin-6-yl)pyridin-2-yl)piperazine-1-carboxylate

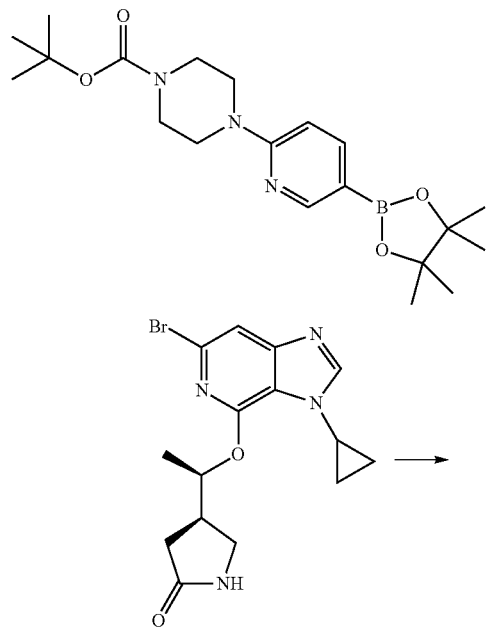

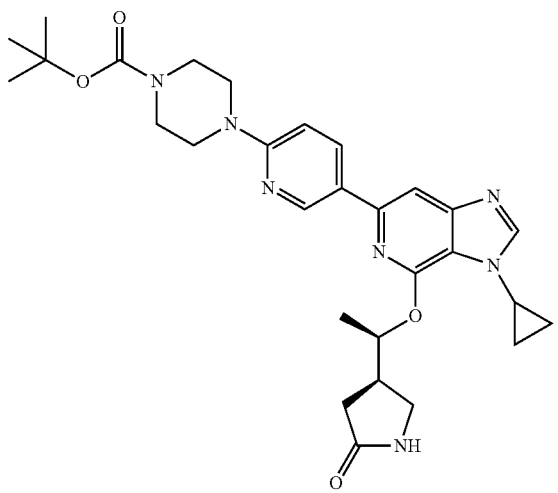

Following the procedure described for intermediate 2.52, starting from (R)-4-((R)-1-((5-bromo-1-cyclopropyl-1H-benzo[d]imidazol-7-yl)oxy)ethyl)pyrrolidin-2-one (250 mg, 0.69 mmol), tert-butyl 4-(2-methyl-4-(4,4,5,5-tetramethyl-1,3,2-dioxaborolan-2-yl)phenyl)piperazine-1-carboxylate (333.1 mg, 0.86 mmol), 330 mg tert-butyl 4-(5-(3-cyclopropyl-4-((R)-1-((R)-5-oxopyrrolidin-3-yl)ethoxy)-3H-imidazo[4,5-c]pyridin-6-yl)pyridin-2-yl)piperazine-1-carboxylate was synthesized.

548

Step-2 (R)-4-((R)-1-((3-cyclopropyl-6-(6-(piperazin-1-yl)pyridin-3-yl)-3H-imidazo[4,5-c]pyridin-4-yl)oxy)ethyl)pyrrolidin-2-one

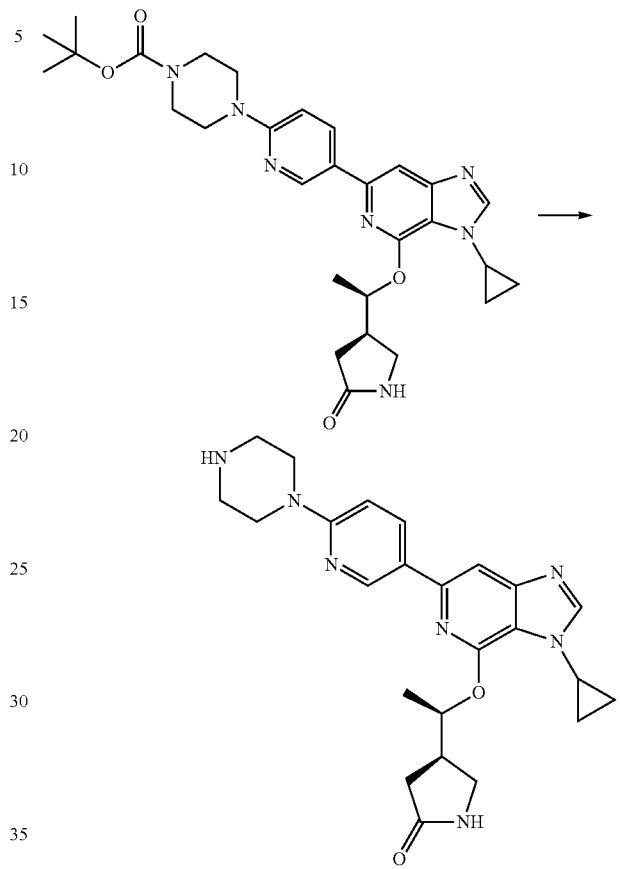

Following the procedure described for intermediate from Step-4 in Example 3.97, starting tert-butyl 4-(5-(3-cyclopropyl-4-((R)-1-((R)-5-oxopyrrolidin-3-yl)ethoxy)-3H-imidazo[4,5-c]pyridin-6-yl)pyridin-2-yl)piperazine-1-carboxylate (330 mg, 0.46 mmol), 180 mg of (R)-4-((R)-1-((3-cyclopropyl-6-(6-(piperazin-1-yl)pyridin-3-yl)-3H-imidazo[4,5-c]pyridin-4-yl)oxy)ethyl)pyrrolidin-2-one.

Step-3 (R)-4-((R)-1-((3-cyclopropyl-6-(6-(4-(oxetan-3-yl)piperazin-1-yl)pyridin-3-yl)-3H-imidazo[4,5-c]pyridin-4-yl)oxy)ethyl)pyrrolidin-2-one

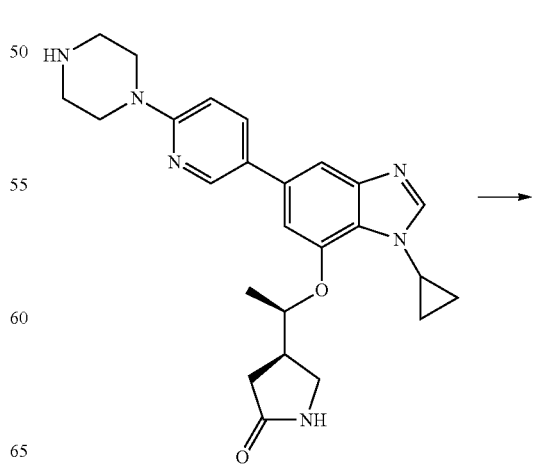

549

-continued

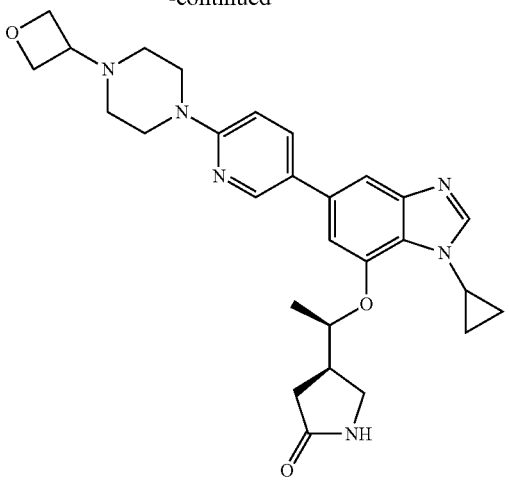

Following the procedure described for intermediate from Step-5 in Example 3.97, starting from (R)-4-((R)-1-((3-cyclopropyl-6-(6-(piperazin-1-yl)pyridin-3-yl)-3H-imidazo[4,5-c]pyridin-4-yl)oxy)ethyl)pyrrolidin-2-one (100 mg, 0.22 mmol), 98.4 mg (R)-4-((R)-1-((3-cyclopropyl-6-(6-(4-(oxetan-3-yl)piperazin-1-yl)pyridin-3-yl)-3H-imidazo[4,5-c]pyridin-4-yl)oxy)ethyl)pyrrolidin-2-one was synthesized.

$^1$H NMR (400 MHz, DMSO-d$_6$) δ 8.86 (d, J=2.4 Hz, 1H), 8.25 (s, 1H), 8.20 (dd, J =2.0, 7.0 Hz, 1H), 7.69 (s, 1H), 7.56 (s, 1H), 6.90 (d, J=9.0 Hz, 1H), 5.55 (q, J=5.9 Hz, 1H), 4.52 (dt, J=24.6, 6.3 Hz, 4H), 3.69-3.66 (m, 1H), 3.57 (t, J=4.9 Hz, 1H), 3.46-3.37 (m, 2H), 3.24-3.19 (m, 1H), 2.85-2.72 (m, 1H), 2.43-2.31 (m, 6H), 1.41 (d, J=6.1 Hz, 3H), 1.17-0.98 (m, 4H).

LCMS-ESI$^+$ (m/z): [M+H]$^+$ calcd. for C$_{28}$H$_{33}$FN$_6$O$_3$: 503.61; found: 503.22.

3.110

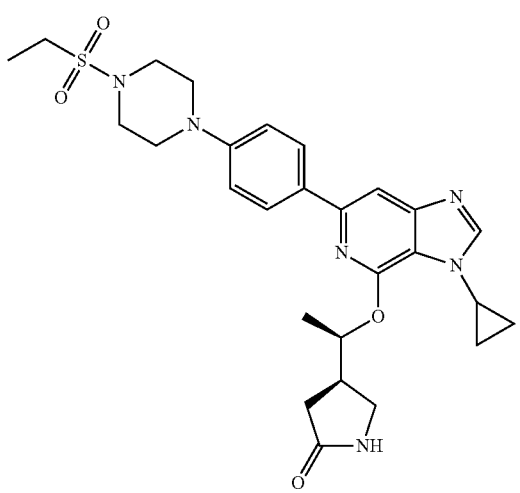

550

Preparation of (R)-4-((R)-1-((3-cyclopropyl-6-(4-(4-(ethylsulfonyl)piperazin-1-yl)phenyl)-3H-imidazo[4,5-c]pyridin-4-yl)oxy)ethyl)pyrrolidin-2-one Step-1 Preparation of (R)-4-((R)-1-((3-cyclopropyl-6-(4-(4-(ethylsulfonyl)piperazin-1-yl)phenyl)-3H-imidazo[4,5-c]pyridin-4-yl)oxy)ethyl)pyrrolidin-2-one

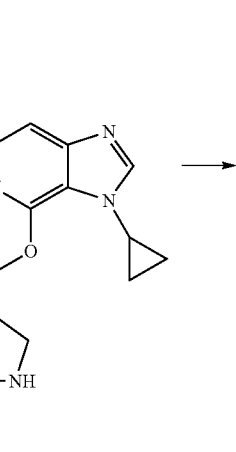

3.42

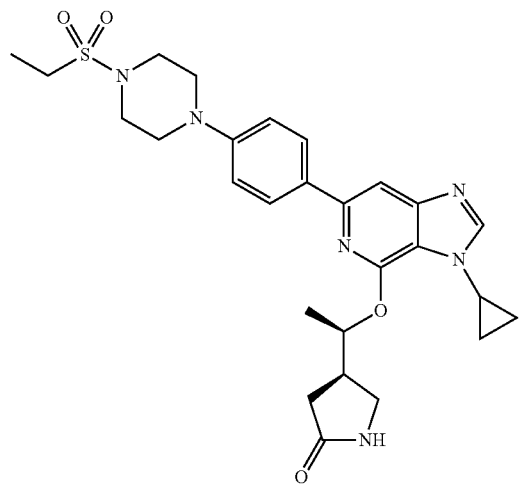

Following the procedure described for intermediate 3.45, starting from (R)-4-((R)-1-((3-cyclopropyl-6-(4-(piperazin-1-yl)phenyl)-3H-imidazo[4,5-c]pyridin-4-yl)oxy)ethyl)pyrrolidin-2-one (100 mg, 0.22 mmol) and ethanesulfonyl chloride (0.02 ml, 0.25 mmol), to provide 49.3 mg of (R)-4-((R)-1-((3-cyclopropyl-6-(4-(4-(ethylsulfonyl)piperazin-1-yl)phenyl)-3H-imidazo[4,5-c]pyridin-4-yl)oxy)ethyl)pyrrolidin-2-one.

$^1$H NMR (400 MHz, DMSO-d$_6$) δ 8.24 (s, 1H), 7.97 (d, J=8.8 Hz, 2H), 7.67 (s, 1H), 7.56 (s, 1H), 7.04 (d, J=8.9 Hz, 2H), 5.61-5.51 (m, 1H), 3.68 (m, 1H), 3.48-3.04 (m, 5H), 2.85 (m, 1H), 2.33 (d, J=8.6 Hz, 3H), 1.41 (d, J=6.2 Hz, 3H), 1.24 (t, J=7.4 Hz, 3H), 1.16-1.00 (m, 4H).

LCMS-ESI$^+$ (m/z): [M+H]$^+$ calcd. for C$_{27}$H$_{34}$N$_6$SO$_4$: 539.66; found: 538.93.

3.111

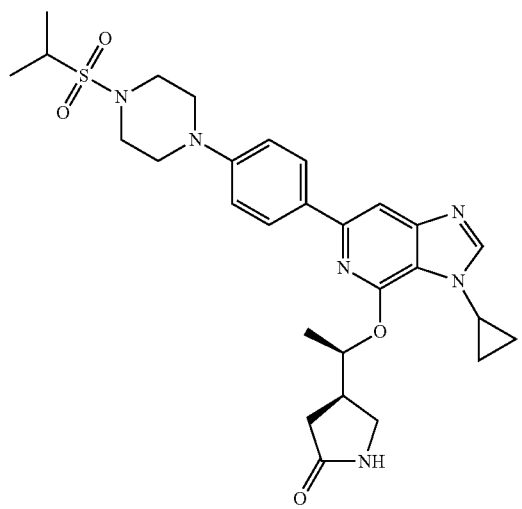

Preparation of (R)-4-((R)-1-((3-cyclopropyl-6-(4-(4-(isopropylsulfonyl)piperazin-1-yl)phenyl)-3H-imidazo[4,5-c]pyridin-4-yl)oxy)ethyl)pyrrolidin-2-one Step-1 Preparation of (R)-4-((R)-1-((3-cyclopropyl-6-(4-(4-(isopropylsulfonyl)piperazin-1-yl)phenyl)-3H-imidazo[4,5-c]pyridin-4-yl)oxy)ethyl)pyrrolidin-2-one

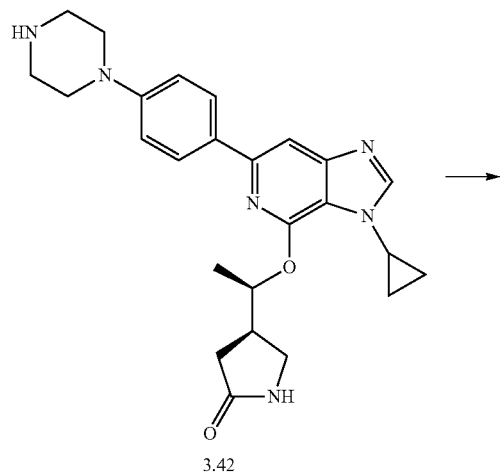
3.42

-continued

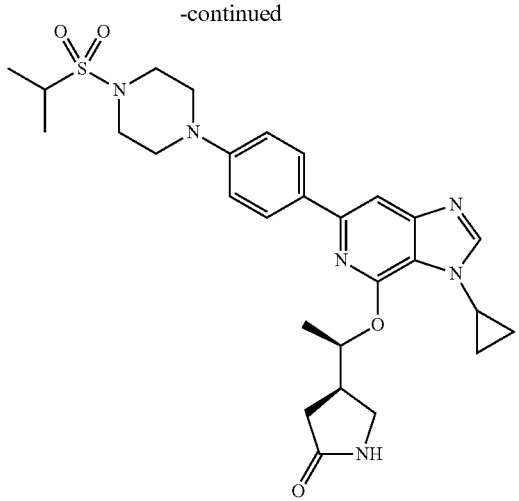

Following the procedure described for intermediate 3.45, starting from (R)-4-((R)-1-((3-cyclopropyl-6-(4-(piperazin-1-yl)phenyl)-3H-imidazo[4,5-c]pyridin-4-yl)oxy)ethyl)pyrrolidin-2-one (90 mg, 0.2 mmol) and propane-2-sulfonyl chloride (0.02 ml, 0.22 mmol) to provide 16.6 mg of (R)-4-((R)-1-((3-cyclopropyl-6-(4-(4-(isopropylsulfonyl)piperazin-1-yl)phenyl)-3H-imidazo[4,5-c]pyridin-4-yl)oxy)ethyl)pyrrolidin-2-one.

$^1$H NMR (400 MHz, DMSO-d$_6$) δ 8.24 (s, 1H), 8.02-7.91 (m, 2H), 7.65 (s, 1H), 7.56 (s, 1H), 7.08-6.98 (m, 2H), 5.55 (q, J=5.9 Hz, 1H), 3.68 (m, 1H), 3.48-3.04 (m, 8H), 2.86 (ddt, J=12.0, 8.9, 6.0 Hz, 1H), 2.38-2.28 (m, 2H), 1.41 (d, J=6.2 Hz, 3H), 1.34-1.18 (m, 6H), 1.23-0.97 (m, 4H).

LCMS-ESI$^+$ (m/z): [M+H]$^+$ calcd. for C$_{28}$H$_{36}$N$_6$SO$_4$: 553.69; found: 554.50.

3.112

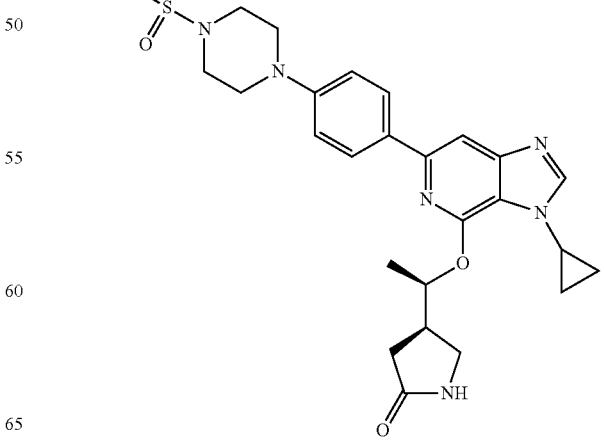

Preparation of (R)-4-((R)-1-((3-cyclopropyl-6-(4-(4-(cyclopropylsulfonyl)piperazin-1-yl)phenyl)-3H-imidazo[4,5-c]pyridin-4-yl)oxy)ethyl)pyrrolidin-2-one Step-1 Preparation of (R)-4-((R)-1-((3-cyclopropyl-6-(4-(4-(cyclopropylsulfonyl)piperazin-1-yl)phenyl)-3H-imidazo[4,5-c]pyridin-4-yl)oxy)ethyl)pyrrolidin-2-one

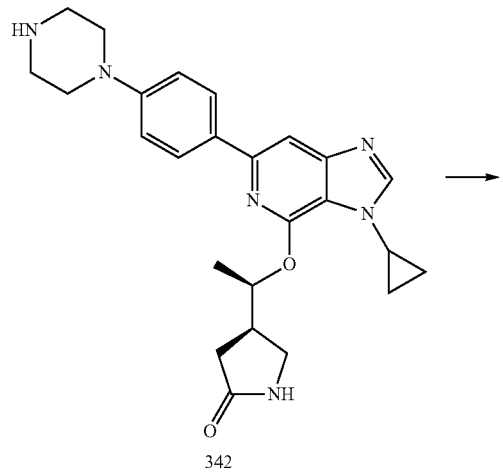
342

Following the procedure described for intermediate 3.45, starting from (R)-4-((R)-1-((3-cyclopropyl-6-(4-(piperazin-1-yl)phenyl)-3H-imidazo[4,5-c]pyridin-4-yl)oxy)ethyl)pyrrolidin-2-one (180 mg, 0.4 mmol) and cyclopropanesulfonyl chloride (0.05 ml, 0.44 mmol), to provide 25.3 mg of (R)-4-((R)-1-((3-cyclopropyl-6-(4-(4-(cyclopropylsulfonyl)piperazin-1-yl)phenyl)-3H-imidazo[4,5-c]pyridin-4-yl)oxy)ethyl)pyrrolidin-2-one.

$^1$H NMR (400 MHz, DMSO-$d_6$) δ 8.28 (s, 1H), 7.97 (d, J=8.8 Hz, 2H), 7.67 (s, 1H), 7.57 (s, 1H), 7.10-7.00 (m, 2H), 5.62-5.51 (m, 1H), 3.75-3.62 (m, 1H), 3.44-3.19 (m, 8H), 2.86 (dd, J=8.3, 5.9 Hz, 1H), 2.66 (tt, J=7.8, 4.9 Hz, 1H), 2.48-2.39 (m, 2H), 2.33 (d, J=8.5 Hz, 2H), 1.42 (d, J=6.2 Hz, 3H), 1.17-0.91 (m, 8H).

LCMS-ESI$^+$ (m/z): [M+H]$^+$ calcd. for $C_{28}H_{34}N_6SO_4$: 551.62; found: 550.81.

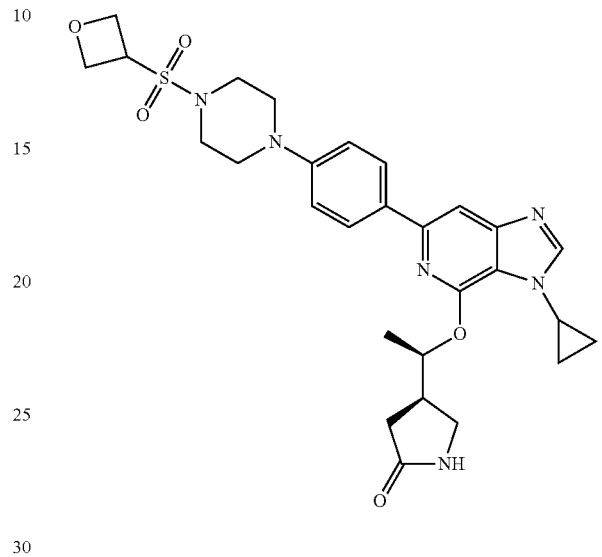
3.113

Preparation of (R)-4-((R)-1-((3-cyclopropyl-6-(4-(4-(oxetan-3-ylsulfonyl)piperazin-1-yl)phenyl)-3H-imidazo[4,5-c]pyridin-4-yl)oxy)ethyl)pyrrolidin-2-one Step-1 Preparation of Example A24. Preparation (R)-4-((R)-1-((3-cyclopropyl-6-(4-(4-(oxetan-3-ylsulfonyl)piperazin-1-yl)phenyl)-3H-imidazo[4,5-c]pyridin-4-yl)oxy)ethyl)pyrrolidin-2-one.

3.42

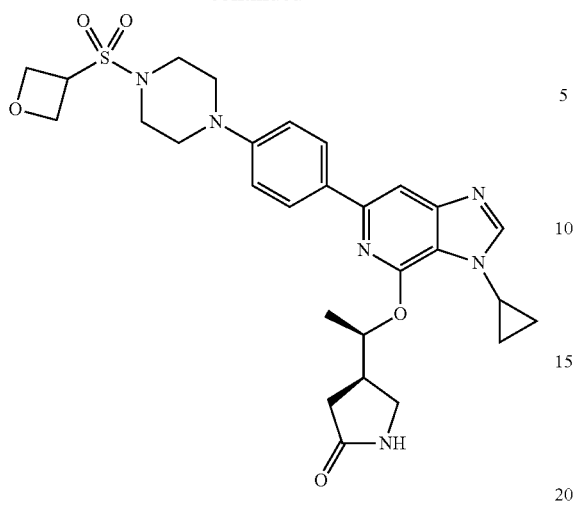

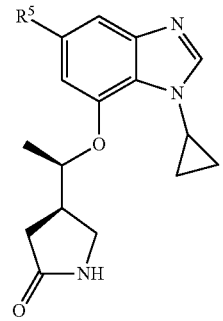

Examples 3I.01-3I.07 and
Examples 3J.01-3J.06

Following the procedure described for intermediate 3.45, starting from (R)-4-((R)-1-((3-cyclopropyl-6-(4-(piperazin-1-yl)phenyl)-3H-imidazo[4,5-c]pyridin-4-yl)oxy)ethyl)pyrrolidin-2-one (90 mg, 0.2 mmol) and oxetane-3-sulfonyl chloride (0.12 ml, 0.89 mmol) to provide 42.4 mg of (R)-4-((R)-1-((3-cyclopropyl-6-(4-(4-(oxetan-3-ylsulfonyl)piperazin-1-yl)phenyl)-3H-imidazo[4,5-c]pyridin-4-yl)oxy)ethyl)pyrrolidin-2-one.

$^1$H NMR (400 MHz, DMSO-$d_6$) δ 8.28 (s, 1H), 7.96 (d, J=8.8 Hz, 2H), 7.67 (s, 1H), 7.57 (s, 1H), 7.10-7.25 (d, J=8.7 Hz, 2H), 5.62-5.51 (m, 1H), 3.75-3.62 (m, 1H), 3.48-3.15 (m, 7H), 2.86 (m, 1H), 2.33 (d, J=8.5 Hz, 2H), 1.42 (d, J=6.2 Hz, 3H), 1.17-0.91 (m, 8H).

LCMS-ESI$^+$ (m/z): [M+H]$^+$ calcd. for $C_{28}H_{34}N_6SO_5$: 567.67; found: 566.81.

General Procedures for Preparation of Examples 3I.01-3I.07 and 3J.01-3J.06

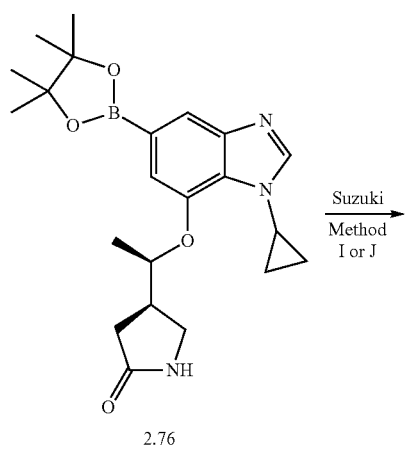

2.76

General Procedure I for Synthesis of Examples 3I.01-3I.07

To an appropriate-sized vial was added (R)-4-((R)-1-((1-cyclopropyl-5-(4,4,5,5-tetramethyl-1,3,2-dioxaborolan-2-yl)-1H-benzo[d]imidazol-7-yl)oxy)ethyl)pyrrolidin-2-one 2.76 (1 eq.), aryl or heteroaryl halide (~1.1-3 eq.), bis(di-tert-butyl(4-dimethylaminophenyl)phosphine)dichloropalladium(II) (1-10 mol %), and K$_3$PO$_4$ (~3 eq.). The vessel was purged with Ar, and the reagents were taken up in ~10:1 (v/v) dioxane:water (ca. 0.05 M with respect to limiting reagent). The resulting mixture was stirred at 100-105° C. until the reaction was judged complete by HPLC, LC/MS or TLC. The mixture was diluted with EtOAc, water and brine, and the phases were separated. The aqueous phase was extracted with EtOAc. The combined organic phase was dried over Na$_2$SO$_4$, filtered, and concentrated. The residue was purified by silica gel chromatography to provide Examples 3I.01-3I.07 in Table 3B below.

General Procedure J for Synthesis of Examples 3J.01-3J.06

To an appropriate-sized vial was added (R)-4-((R)-1-((1-cyclopropyl-5-(4,4,5,5-tetramethyl-1,3,2-dioxaborolan-2-yl)-1H-benzo[d]imidazol-7-yl)oxy)ethyl)pyrrolidin-2-one 2.76 (1 eq.), aryl or heteroaryl halide (~1.1-3 eq.), PEPPSI-IPr (1-10 mol %), and Cs$_2$CO$_3$ (~2-3 eq.). The vessel was purged with neutral atmosphere, and the reagents were taken up in 2:1 (v/v) DME:water (ca. 0.03-0.05 M with respect to limiting reagent). The resulting mixture was stirred at 85-100° C. until the reaction was judged complete by HPLC, LCMS or TLC. The mixture was diluted with EtOAc and water, and the aqueous phase was extracted with EtOAc. The combined organic phase was dried, filtered, and concentrated. The residue was purified by silica gel chromatography or reverse phase prep HPLC to provide Examples 3J.01-3J.06 in Table 3B below.

TABLE 3B

Examples 3I.01-3I.07 and Examples 3J.01-3J.06.

| Example # | Boronic Acid/ Ester | Aryl Halide | Product/Salt Proton NMR | LCMS-ESI+ (m/z): [M + H]+ |
|---|---|---|---|---|
| 3I.01 | 2.76 | | | Calc: 380.21 Found: 380.33 |

¹H NMR (400 MHz, Chloroform-d) δ 7.81 (s, 1H), 7.67 (d, J = 1.1 Hz, 1H), 7.42 (d, J = 2.3 Hz, 1H), 7.33 (s, 1H), 6.56 (d, J = 2.3 Hz, 1H), 5.76 (s, 1H), 4.86-4.78 (m, 1H), 4.22 (q, J = 7.3 Hz, 2H), 3.67-3.59 (m, 1H), 3.59-3.52 (m, 1H), 3.40 (dd, J = 9.5, 6.9 Hz, 1H), 2.98-2.85 (m, 1H), 2.58-2.46 (m, 2H), 1.54 (t, J = 7.3 Hz, 3H), 1.43 (d, J = 6.1 Hz, 3H), 1.15-1.03 (m, 4H).

| 3I.02 | 2.76 | 7.02 | | Calc: 416.19 Found: 416.21 |

¹H NMR (400 MHz, Chloroform-d) δ 7.77-7.73 (m, 1H), 7.64-7.59 (m, 1H), 7.44-7.40 (m, 1H), 7.24-7.18 (m, 1H), 6.58-6.55 (m, 1H), 6.30-5.90 (m, 2H), 4.79-4.66 (m, 1H), 4.49-4.36 (m, 2H), 3.62-3.44 (m, 2H), 3.39-3.27 (m, 1H), 2.93-2.78 (m, 1H), 2.52-2.43 (m, 2H), 1.42-1.34 (m, 3H), 1.13-0.94 (m, 4H).

| 3I.03 | 2.76 | 7.53 | | Calc: 408.20 Found: 408.32 |

¹H NMR (400 MHz, Chloroform-d) δ 7.83 (s, 1H), 7.69 (d, J = 1.2 Hz, 1H), 7.61 (d, J = 2.4 Hz, 1H), 7.39 (s, 1H), 6.65 (d, J = 2.4 Hz, 1H), 5.91 (s, 1H), 5.56-5.42 (m, 1H), 5.21-5.12 (m, 2H), 5.11-5.02 (m, 2H), 4.87-4.76 (m, 1H), 3.68-3.61 (m, 1H), 3.61-3.55 (m, 1H), 3.42 (dd, J = 9.5, 6.8 Hz, 1H), 3.00-2.87 (m, 1H), 2.58-2.52 (m, 2H), 1.45 (d, J = 6.1 Hz, 3H), 1.15-1.03 (m, 4H).

TABLE 3B-continued

Examples 3I.01-3I.07 and Examples 3J.01-3J.06.

| Example # | Boronic Acid/ Ester | Aryl Halide | Product/Salt Proton NMR | LCMS-ESI+ (m/z): [M + H]+ |
|---|---|---|---|---|
| 3I.04 | 2.76 | 7.05 | | Calc: 437.2 Found: 437.1 |

$^1$H NMR (400 MHz, Chloroform-d) δ 7.82 (s, 1H), 7.73 (d, J = 1.1 Hz, 1H), 7.65 (d, J = 2.5 Hz, 1H), 7.30 (s, 1H), 6.65 (d, J = 2.5 Hz, 1H), 6.28 (s, 1H), 6.14 (s, 1H), 5.66 (s, 1H), 4.80-4.70 (m, 1H), 3.67-3.54 (m, 2H), 3.41 (dd, J = 9.6, 6.7 Hz, 1H), 2.98-2.85 (m, 1H), 2.54 (d, J = 8.7 Hz, 2H), 1.92 (s, 3H), 1.92 (s, 3H), 1.44 (d, J = 6.1 Hz, 3H), 1.16-1.00 (m, 4H).

| 3I.05 | 2.76 | 7.01 | | Calc: 394.22 Found: 394.32 |

$^1$H NMR (400 MHz, Chloroform-d) δ 7.81 (s, 1H), 7.68 (d, J = 1.1 Hz, 1H), 7.45 (d, J = 2.3 Hz, 1H), 7.33 (s, 1H), 6.56 (d, J = 2.3 Hz, 1H), 5.82 (s, 1H), 4.87-4.74 (m, 1H), 4.65-4.48 (m, 1H), 3.67-3.59 (m, 1H), 3.59-3.52 (m, 1H), 3.41 (dd, J = 9.5, 6.9 Hz, 1H), 2.99-2.83 (m, 1H), 2.54 (d, J = 8.8 Hz, 2H), 1.55 (d, J = 6.7 Hz, 6H), 1.43 (d, J = 6.1 Hz, 3H), 1.15-1.02 (m, 4H).

| 3I.06 | 2.76 | 7.07 | | Calc: 419.2 Found: 418.5 |

$^1$H NMR (400 MHz, Chloroform-d) δ 7.81 (s, 1H), 7.69 (d, J = 1.1 Hz, 1H), 7.67 (d, J = 2.5 Hz, 1H), 7.32 (s, 1H), 6.65 (d, J = 2.5 Hz, 1H), 6.01 (s, 1H), 4.85-4.72 (m, 1H), 3.69-3.51 (m, 2H), 3.42 (dd, J = 9.5, 6.9 Hz, 1H), 3.00-2.82 (m, 1H), 2.55 (d, J = 8.8 Hz, 2H), 2.06 (s, 6H), 1.44 (d, J = 6.1 Hz, 3H), 1.15-1.02 (m, 4H).

TABLE 3B-continued

Examples 3I.01-3I.07 and Examples 3J.01-3J.06.

| Example # | Boronic Acid/ Ester | Aryl Halide | Product/Salt Proton NMR | LCMS-ESI+ (m/z): [M + H]+ |
|---|---|---|---|---|
| 3I.07 | 2.76 | (structure) 7.06 | (structure) | Calc: 507.3 Found: 507.2 |

¹H NMR (400 MHz, Chloroform-d) δ 7.81 (s, 1H), 7.69 (d, J = 1.1 Hz, 1H), 7.49 (d, J = 2.4 Hz, 1H), 7.33 (s, 1H), 6.66 (d, J = 2.4 Hz, 1H), 5.86 (s, 1H), 4.84-4.72 (m, 1H), 3.67-3.55 (m, 2H), 3.88-2.82 (m, broad, 8H), 3.42 (dd, J = 9.5, 6.8 Hz, 1H), 3.01-2.85 (m, 1H), 2.60-2.49 (m, 2H), 1.86 (s, 3H), 1.84 (s, 3H), 1.44 (d, J = 6.1 Hz, 3H), 1.17-1.01 (m, 4H).

| 3J.01 | 2.76 | (structure) | (structure) | Calc: 434.18 Found: 434.31 |

1H NMR (400 MHz, CD₃OD) δ 8.07 (s, 1H), 7.80 (d, J = 1.2 Hz, 1H), 7.58 (d, J = 1.3 Hz, 1H), 7.53 (d, J = 8.3 Hz, 1H), 7.36 (d, J = 8.3 Hz, 1H), 4.89 (q, J = 6.0 Hz, 1H), 4.68 (s, 2H), 3.82-3.71 (m, 1H), 3.62 (dd, J = 10.0, 8.8 Hz, 1H), 3.39 (dd, J = 10.1, 6.3 Hz, 1H), 3.05-2.90 (m, 1H), 2.66-2.49 (m, 2H), 1.45 (d, J = 6.1 Hz, 3H), 1.19-1.07 (m, 4H).

TABLE 3B-continued

Examples 3I.01-3I.07 and Examples 3J.01-3J.06.

| Example # | Boronic Acid/ Ester | Aryl Halide | Product/Salt Proton NMR | LCMS-ESI+ (m/z): [M + H]+ |
|---|---|---|---|---|
| 3J.02 | 2.76 | | | Calc: 434.18 Found: 434.33 |

1H NMR (400 MHz, CD3OD) δ 8.08 (s, 1H), 7.73 (d, J = 1.3 Hz, 1H), 7.56 (d, J = 8.1 Hz, 1H), 7.53 (d, J = 1.3 Hz, 1H), 7.35 (d, J = 8.0 Hz, 1H), 4.96-4.88 (m, 1H), 4.86 (s, 2H), 3.76 (ddd, J = 11.0, 6.4, 4.6 Hz, 1H), 3.61 (dd, J = 10.0, 8.8 Hz, 1H), 3.40 (dd, J = 10.1, 6.3 Hz, 1H), 3.05-2.92 (m, 1H), 2.56 (dd, J = 8.6, 3.7 Hz, 2H), 1.45 (d, J = 6.1 Hz, 3H), 1.21-1.06 (m, 4H).

| 3J.03 | 2.76 | | (TFA salt) | Calc: 462.2 Found: 462.2 |

7.27

1H NMR (400 MHz, DMSO-d6) δ 11.29 (s, 1H), 8.88 (bs, 1H), 7.86 (s, 1H), 7.71 (d, J = 8.3 Hz, 1H), 7.64 (d, J = 3.8 Hz, 2H), 7.45 (d, J = 8.3 Hz, 1H), 4.91 (p, J = 5.8 Hz, 1H), 3.94-3.77 (m, 1H), 3.43 (t, J = 9.2 Hz, 1H), 3.19 (dd, J = 9.6, 6.7 Hz, 1H), 2.90-2.81 (m, 1H), 2.42-2.23 (m, 2H), 1.47 (s, 6H), 1.35 (d, J = 6.0 Hz, 3H), 1.26-1.05 (m, 4H).

| 3J.04 | 2.76 | | (TFA salt) | Calc: 418.2 Found: 418.2 |

1H NMR (400 MHz, DMSO-d6) δ 11.09 (s, 1H), 9.16 (bs, 1H), 7.90 (s, 1H), 7.70-7.61 (m, 4H), 4.99-4.92 (m, 1H), 3.95-3.86 (m, 1H), 3.61 (s, 2H), 3.43 (t, J = 9.1 Hz, 1H), 3.19 (dd, J = 9.7, 6.5 Hz, 1H), 2.91-2.81 (m, 1H), 2.44 2.21 (m, 2H), 1.35 (d, J = 6.0 Hz, 3H), 1.27-1.10 (m, 4H). -

TABLE 3B-continued
Examples 3I.01-3I.07 and Examples 3J.01-3J.06.
| Example # | Boronic Acid/ Ester | Aryl Halide | Product/Salt Proton NMR | LCMS-ESI+ (m/z): [M + H]+ |
|---|---|---|---|---|
| 3J.05 | 2.76 | 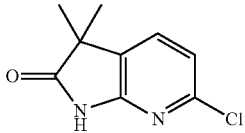 7.29 | 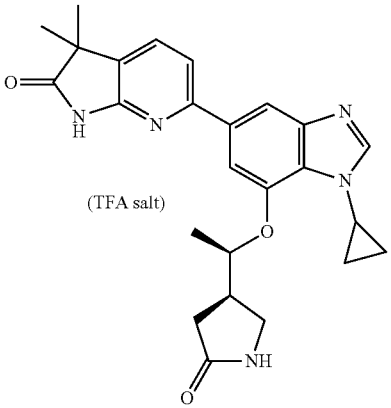 [SMILES: C[C@@H](Oc1cc(-c2ccc3c(n2)NC(=O)C3(C)C)cc2ncn(C3CC3)c12)[C@H]1CNC(=O)C1] (TFA salt) | Calc: 446.2 Found: 446.2 |
¹H NMR (400 MHz, DMSO-d6) δ 11.08 (s, 1H), 9.16 (bs, 1H), 7.89 (s, 1H), 7.79 (d, J = 7.6 Hz, 1H), 7.75-7.55 (m, 3H), 4.96 (p, J = 6.6 Hz, 1H), 3.95-3.87 (m, 1H), 3.43 (t, J = 9.2 Hz, 1H), 3.19 (dd, J = 9.7, 6.6 Hz, 1H), 2.91-2.81 (m, 1H), 2.46-2.20 (m, 2H), 1.42-1.03 (m, 13H).
| 3J.06 | 2.76 | 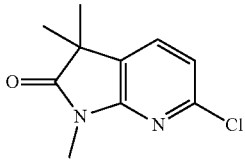 7.28 | 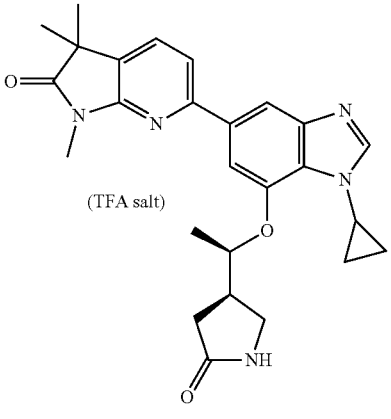 [SMILES: C[C@@H](Oc1cc(-c2ccc3c(n2)N(C)C(=O)C3(C)C)cc2ncn(C3CC3)c12)[C@H]1CNC(=O)C1] (TFA salt) | Calc: 460.2 Found: 460.2 |
¹H NMR (400 MHz, DMSO-d6) δ 9.05 (bs, 1H), 7.99 (s 1H), 7.84 (d, J = 7.6 Hz, 1H), 7.80-7.70 (m, 2H), 7.63 (s, 1H), 4.98 (p, J = 6.6, 6.1 Hz, 1H), 3.93-3.86 (m, 1H), 3.43 (t, J = 9.1 Hz, 1H), 3.27 (s, 3H), 3.21 (dd, J = 9.7, 6.7 Hz, 1H), 2.91-2.82 (m, 1H), 2.44-2.22 (m, 2H), 1.40-1.30 (m, 9H), 1.30 -1.05 (m, 4H).

TABLE 3B-continued

Examples 3I.01-3I.07 and Examples 3J.01-3J.06.

| Example # | Boronic Acid/ Ester | Aryl Halide | Product/Salt Proton NMR | LCMS-ESI+ (m/z): [M + H]+ |
|---|---|---|---|---|
| 3J.07 | 2.76 | H₂N—pyridine—Br | H₂N-pyridine-benzimidazole-O-ethyl-pyrrolidinone structure | Calc: 378.19 Found: 378.30 |

¹H NMR (400 MHz, CD₃OD) δ 8.08 (s, 1H), 7.67 (d, J = 1.2 Hz, 1H), 7.52 (dd, J = 8.2, 7.5 Hz, 1H), 7.45-7.39 (m, 1H), 7.05 (dd, J = 7.5, 0.8 Hz, 1H), 6.52 (dd, J = 8.2, 0.7 Hz, 1H), 4.89 (q, J = 6.3 Hz, 1H), 3.81-3.70 (m, 1H), 3.61 (dd, J = 10.0, 8.8 Hz, 1H), 3.39 (dd, J = 10.1, 6.3 Hz, 1H), 2.98 (dtd, J = 14.4, 8.6, 5.9 Hz, 1H), 2.57 (dd, J = 8.5, 3.7 Hz, 2H), 1.45 (d, J = 6.1 Hz, 3H), 1.23-1.07 (m, 4H).

Step 3: To a solution of 5-bromo-1-methyl-1H-benzo[d]imidazol-7-ol (30 mgs, 0.124 mmol) in DMF (3 mL) was added (S)-1-((R)-5-oxo-1-((R)-1-phenylethyl)pyrrolidin-3-yl)ethyl methanesulfonate 1.17 (60 mgs, 0.193 mmol) and Cs₂CO₃ (69 mgs, 0.212 mmol) and the reaction mixture was heated at 90° C. for 1 h. The reaction mixture was then diluted with ethylacetate and washed with water (3×), brine and dried over anhydrous magnesium sulfate. Filtration, followed by concentration gave (R)-4-((R)-1-(5-bromo-1,2-dimethyl-1H-benzo[d]imidazol-7-yloxy)ethyl)-1-((R)-1-phenylethyl)pyrrolidin-2-one, which was used for next step without further purification.

LC/MS found for C₂₃H₂₆BrN₃O₂ as (M+H)⁺ 457.1.

Step 4: (R)-4-((R)-1-(5-bromo-1,2-dimethyl-1H-benzo[d]imidazol-7-yloxy)ethyl)-1-((R)-1-phenylethyl)pyrrolidin-2-one in TFA (3 mL) was heated in a microwave reactor for 3 h at 140° C. The reaction mixture was then concentrated to give (R)-4-((R)-1-(5-bromo-1,2-dimethyl-1H-benzo[d]imidazol-7-yloxy)ethyl)pyrrolidin-2-one which was used for next step without further purification. LC/MS found for C₁₅H₁₈BrN₃O₂ as (M+H)⁺ 353.1.

Step 5: To a mixture of (R)-4-((R)-1-(5-bromo-1,2-dimethyl-1H-benzo[d]imidazol-7-yloxy)ethyl)pyrrolidin-2-one (12 mg, 0.034 mmol), 2,3-dimethoxy-6-(4,4,5,5-tetramethyl-1,3,2-dioxaborolan-2-yl)pyridine (18 mg, 0.068 mmol), Cs₂CO₃ (33 mg, 0.10 mmol) and PEPPSI"-IPr catalyst (3 mg, 0.003 mmol) was added DME and water (1.5:0.75, 2.25 mL) and the reaction mixture was heated to 110° C. for 1 hr. The mixture was then concentrated and purified by reverse phase HPLC to give the title compound 3.31 as TFA salt. LC/MS found for C₂₂H₂₆N₄O₄ as (M+H)⁺ 411.2 ¹H NMR (400 MHz, DMSO-d₆) δ 7.84 (s, 1H), 7.69-7.62 (m, 2H), 7.37 (d, J=8.0 Hz, 1H), 4.93 (m, 1H), 4.01 (s, 6H), 3.82 (s, 3H), 3.42 (m, 1H), 3.17-3.13 (m, 1H), 2.69-2.63 (m, 1H), 2.48 (s, 3H); 2.42-2.23 (m, 2H), 1.35 (d, J =6.0 Hz, 3H).

General Procedures for Preparation of Examples 3K.01-3K.12

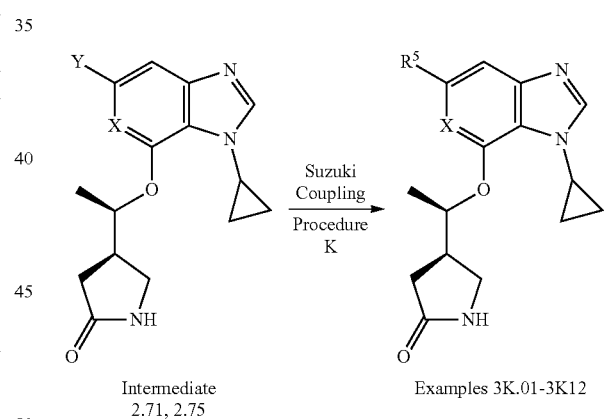

Intermediate 2.71, 2.75 → Suzuki Coupling Procedure K → Examples 3K.01-3K12

To an appropriate sized reaction vessel was added (as specified) aryl halide intermediate 2.71, 2.75, or 2.76 (1 eq.), boronic acid or ester (1-2 eq.), sodium carbonate (ca. 3 eq.), and tetrakis-triphenylphosphine-Pd(0) (ca. 0.1 eq.). The reagents were taken up in 2:1 DME:water. After evacuating and backfilling with nitrogen, the stirred mixture was heated at 100° C. Once the reaction was judged complete, reaction mixture was cooled to r.t. and was diluted with water and extracted with either ethyl acetate or 10% methanolic dichloromethane. Combined organics were dried, filtered, and concentrated under reduced pressure. Residues were purified by silica gel column chromatography or reverse phase HPLC to yield Examples 3K.01-3K.12 as free bases, depicted in Table 3A below.

TABLE 3A

| Example # | Pyrazole | Halide | Product | LCMS-ESI+ (m/z): [M + H]+ |
|---|---|---|---|---|
| | | Proton NMR | | |
| 3K.01 | | 2.71 | | Calc: 336.4 Found: 367.3 |

¹H NMR (300 MHz, DMSO-d₆) δ 8.23-8.10 (m, 2H), 7.93 (d, J = 0.7 Hz, 1H), 7.54 (s, 1H), 7.44 (s, 1H), 5.80-5.68 (m, 1H), 5.60-5.45 (m, 1H), 3.71-3.57 (m, 1H), 3.46-3.13 (m, 5H), 2.81 (dt, J = 8.9, 6.2 Hz, 1H), 2.31 (dd, J = 8.6, 2.2 Hz, 2H), 1.37 (d, J = 6.2 Hz, 3H), 1.23 (d, J = 3.6 Hz, 1H), 1.14-0.76 (m, 4H).

| 3K.02 | | 2.75 | | Calc: 365.4 Found: 366.2 |

¹H NMR (300 MHz, DMSO-d₆) δ 8.12 (d, J = 0.8 Hz, 1H), 8.01 (s, 1H), 7.86 (d, J = 0.8 Hz, 1H), 7.58 (s, 1H), 7.35 (d, J = 1.1 Hz, 1H), 7.04-6.97 (m, 1H), 4.80 (t, J = 5.9 Hz, 1H), 3.72-3.58 (m, 1H), 3.46-3.23 (m, 4H), 3.23-3.10 (m, 1H), 2.79 (q, J = 7.1 Hz, 1H), 2.46-2.17 (m, 3H), 1.29 (d, J = 6.0 Hz, 4H), 1.11-0.91 (m, 4H).

| 3K.03 | | 2.71 | | Calc: 408.5 Found: 409.3 |

¹H NMR (300 MHz, DMSO-d₆) δ 8.35 (d, J = 0.7 Hz, 1H), 8.22 (s, 1H), 8.12 (s, 1H), 7.54 (d, J = 11.8 Hz, 2H), 5.81-5.70 (m, 1H), 5.70-5.51 (m, 2H), 4.94 (d, J = 7.0 Hz, 4H), 3.66 (td, J = 6.8, 3.6 Hz, 1H), 3.47-3.14 (m, 5H), 2.89-2.76 (m, 1H), 2.50-2.27 (m, 3H), 1.38 (d, J = 6.1 Hz, 3H), 1.25 (s, 1H), 1.16-0.90 (m, 4H).

TABLE 3A-continued

| Example # | Pyrazole | Halide | Product | LCMS-ESI+ (m/z): [M + H]+ |
|---|---|---|---|---|
| | | Proton NMR | | |
| 3K.04 | [structure] | 2.75 | [structure] | Calc: 407.5 Found: 408.4 |

¹H NMR (300 MHz, DMSO-d₆) δ 8.38 (d, J = 0.8 Hz, 1H), 8.07-7.98 (m, 2H), 7.59 (s, 1H), 7.40 (d, J = 1.1 Hz, 1H), 7.05 (s, 1H), 5.55 (p, J = 7.0 Hz, 1H), 4.99-4.76 (m, 5H), 3.72-3.58 (m, 1H), 3.46-3.11 (m, 4H), 2.84-2.72 (m, 1H), 2.52-2.17 (m, 4H), 1.33-1.18 (m, 4H), 1.11-0.93 (m, 4H).

| 3K.05 | [structure] | 2.75 | [structure] | Calc: 407.5 Found: 409.5 |

¹H NMR (300 MHz, DMSO-d₆) δ 8.24 (d, J = 0.8 Hz, 1H), 7.99 (s, 1H), 7.87 (d, J = 0.8 Hz, 1H), 7.58 (s, 1H), 7.39 (d, J = 1.1 Hz, 1H), 7.03 (d, J = 1.1 Hz, 1H), 4.82 (t, J = 5.9 Hz, 1H), 3.64 (td, J = 6.6, 3.4 Hz, 1H), 3.39 (t, J = 9.1 Hz, 1H), 3.17 (dd, J = 9.8, 6.6 Hz, 1H), 2.79 (d, J = 8.1 Hz, 1H), 2.38-2.23 (m, 2H), 1.54 (s, 9H), 1.28 (d, J = 5.9 Hz, 4H), 1.09-0.92 (m, 4H).

| 3K.06 | [structure] | 2.71 | [structure] | Calc: 429.5 Found: 430.1 |

¹H NMR (300 MHz, DMSO-d₆) δ 9.15 (d, J = 0.6 Hz, 1H), 8.73-8.63 (m, 2H), 8.42 (d, J = 0.5 Hz, 1H), 8.27 (s, 1H), 7.98-7.89 (m, 2H), 7.75-7.65 (m, 1H), 7.58 (s, 1H), 5.72-5.61 (m, 1H), 3.69 (ddd, J = 7.4, 6.6, 3.6 Hz, 1H), 3.51-3.15 (m, 13H), 2.92-2.78 (m, 1H), 2.66-2.27 (m, 7H), 1.41 (d, J = 6.2 Hz, 3H), 1.18-0.98 (m, 4H).

TABLE 3A-continued

| Example # | Pyrazole | Halide Proton NMR | Product | LCMS-ESI+ (m/z): [M + H]+ |
|---|---|---|---|---|
| 3K.07 | | 2.75 | | Calc: 428.5 Found: 429.4 |

¹H NMR (300 MHz, DMSO-d₆) δ 9.19 (d, J = 0.7 Hz, 1H), 8.73-8.63 (m, 2H), 8.42 (d, J = 0.6 Hz, 1H), 8.08 (s, 1H), 7.96-7.84 (m, 2H), 7.66-7.57 (m, 2H), 7.24-7.17 (m, 1H), 4.87 (p, J = 5.9 Hz, 1H), 3.70 (tt, J = 7.4, 4.1 Hz, 1H), 3.51-3.15 (m, 3H), 2.94-2.75 (m, 1H), 2.56-2.21 (m, 2H), 1.40-1.19 (m, 4H), 1.16-0.77 (m, 4H).

| 3K.08 | | 2.71 | | Calc: 424.5 Found: 425.2 |

¹H NMR (300 MHz, DMSO-d₆) δ 8.24-8.15 (m, 2H), 7.94 (d, J = 0.7 Hz, 1H), 7.57-7.43 (m, 3H), 5.52 (dd, J = 6.3, 5.1 Hz, 1H), 5.01-4.91 (m, 1H), 3.62 (dd, J = 17.4, 4.7 Hz, 3H), 3.46-3.13 (m, 6H), 2.82 (dt, J = 9.0, 6.1 Hz, 1H), 2.31 (d, J = 8.6 Hz, 2H), 1.49 (s, 6H), 1.37 (d, J = 6.2 Hz, 3H), 1.14-0.94 (m, 4H).

| 3K.09 | | 2.75 | | Calc: 423.5 Found: 424.2 |

¹H NMR (300 MHz, DMSO-d₆) δ 8.21 (d, J = 0.8 Hz, 1H), 8.07-7.95 (m, 1H), 7.89 (d, J = 0.7 Hz, 1H), 7.60 (d, J = 4.2 Hz, 1H), 7.41 (d, J = 1.1 Hz, 1H), 7.06 (s, 1H), 4.85 (t, J = 6.0 Hz, 1H), 3.73-3.52 (m, 4H), 3.41 (t, J = 9.1 Hz, 1H), 3.19 (dd, J = 9.5, 6.7 Hz, 1H), 2.80 (s, 1H), 2.46-2.25 (m, 2H), 1.48 (d, J = 13.1 Hz, 8H), 1.28 (dd, J = 9.3, 6.0 Hz, 4H), 1.11-0.97 (m, 4H).

TABLE 3A-continued

| Example # | Pyrazole | Halide Proton NMR | Product | LCMS-ESI+ (m/z): [M + H]+ |
|---|---|---|---|---|
| 3K.10 | | 2.71 | | Calc: 424.5 Found: 425.2 |

¹H NMR (300 MHz, DMSO-d₆) δ 8.18 (s, 1H), 8.09 (s, 1H), 7.94 (s, 1H), 7.53 (s, 1H), 7.45 (s, 1H), 5.50 (p, J = 6.0 Hz, 1H), 4.70 (s, 1H), 4.01 (s, 2H), 3.64 (tt, J = 7.0, 4.1 Hz, 1H), 3.38 (t, J = 9.0 Hz, 1H), 3.18 (dd, J = 9.7, 6.5 Hz, 1H), 2.80 (dd, J = 11.4, 5.7 Hz, 1H), 2.30 (d, J = 8.6 Hz, 2H), 1.37 (d, J = 6.1 Hz, 3H), 1.21 (s, 7H), 1.12-0.96 (m, 10H).

| 3K.11 | | 2.75 | | Calc: 423.5 Found: 424.7 |

¹H NMR (300 MHz, DMSO-d₆) δ 8.10 (d, J = 0.8 Hz, 1H), 8.02 (s, 1H), 7.90 (d, J = 0.8 Hz, 1H), 7.60 (s, 1H), 7.38 (d, J = 1.2 Hz, 1H), 7.03 (d, J = 1.3 Hz, 1H), 4.84 (p, J = 6.0 Hz, 1H), 4.73 (s, 1H), 4.02 (s, 2H), 3.67 (tt, J = 7.0, 4.0 Hz, 1H), 3.41 (t, J = 9.1 Hz, 1H), 3.19 (dd, J = 9.7, 6.7 Hz, 1H), 2.81 (q, J = 7.5 Hz, 1H), 2.48-2.19 (m, 2H), 1.30 (d, J = 5.9 Hz, 3H), 1.14-0.92 (m, 10H).

TABLE 3A-continued

| Example # | Pyrazole | Halide Proton NMR | Product | LCMS-ESI+ (m/z): [M + H]+ |
|---|---|---|---|---|
| 3K.12 | [structure: oxetanyl-piperidine-pyrazole-Bpin] | 2.75 | [structure: benzimidazole product with cyclopropyl, pyrrolidinone] | Calc: 490.6 Found: 491.2 |

<sup>1</sup>H NMR (300 MHz, DMSO-d<sub>6</sub>) δ 8.26 (d, J = 0.8 Hz, 1H), 8.00 (s, 1H), 7.89 (dd, J = 8.8, 0.8 Hz, 2H), 7.61-7.53 (m, 2H), 7.37 (d, J = 1.0 Hz, 1H), 7.02 (d, J = 1.2 Hz, 1H), 4.85-4.74 (m, 1H), 4.47 (dtd, J = 31.0, 6.3, 3.3 Hz, 7H), 4.11 (s, 2H), 3.70-3.59 (m, 1H), 3.48-3.33 (m, 3H), 3.16 (dd, J = 9.6, 6.6 Hz, 1H), 2.79 (q, J = 8.4, 7.5 Hz, 5H), 2.41-2.16 (m, 3H), 1.96 (dt, J = 16.2, 9.0 Hz, 11H), 1.33-1.18 (m, 4H), 1.09-0.90 (m, 4H).

Example 4.01

Preparation of tert-butyl 4-(6-bromopyridin-3-yl)piperazine-1-carboxylate

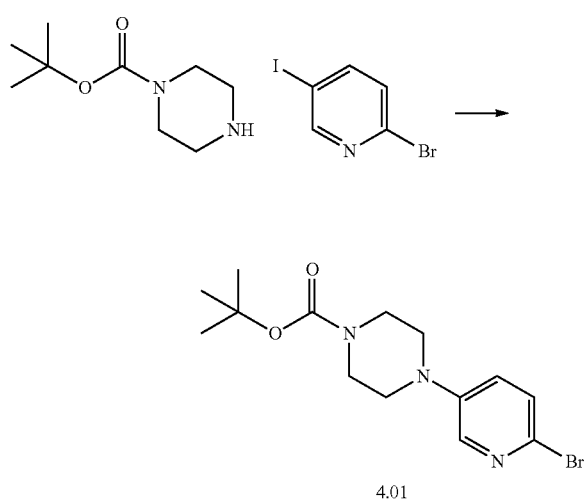

2-bromo-5-iodopyridine (3.00 g, 10.6 mmol), tert-butyl piperazine-1-carboxylate (1.71 g, 9.2 mmol), Pd<sub>2</sub>(dba)<sub>3</sub> (337 mg, 0.368 mmol), and XantPhos (640 mg, 1.1 mmol) were taken up in PhCH<sub>3</sub> (90 mL). The resulting mixture was stirred 24 h at r.t. and was diluted with EtOAc (100 mL) and water (150 mL). The phases were separated, and the organic phase was dried over Na<sub>2</sub>SO<sub>4</sub>, filtered, and concentrated to afford a crude residue that was purified by silica gel chromatography to provide tert-butyl 4-(6-bromopyridin-3-yl)piperazine-1-carboxylate (4.01). LCMS-ESI<sup>+</sup> (m/z): [M+H]<sup>+</sup> calcd for C<sub>14</sub>H<sub>21</sub>BrN<sub>3</sub>O<sub>2</sub>: 342.08; found: 342.15.

Example 4.02

Preparation of 3-iodo-1-isopropyl-1H-pyrazole

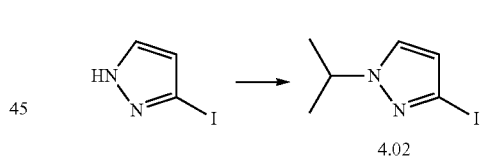

3-iodo-1H-pyrazole (250 mg, 1.29 mmol) was added as a solution in DMF (0.8 mL) to a 1.0 M THF solution of NaHMDS (1.5 mL, 1.5 mmol) that had been pre-cooled in an ice water bath. Additional portions of DMF (2×0.35 mL) were used to ensure complete transfer. 2-iodopropane was added in one portion and the reaction mixture was allowed to warm to r.t. After 3.5 h, the reaction mixture was diluted with saturated aqueous NH<sub>4</sub>Cl (5 mL), water (20 mL), and EtOAc (20 mL). The phases were separated, and the aqueous phase was extracted with EtOAc (20 mL). The combined organic phase was dried over Na<sub>2</sub>SO<sub>4</sub>, filtered, and concentrated to afford a crude residue that was purified by silica gel chromatography to provide 3-iodo-1-isopropyl-1H-pyrazole (4.02). LCMS-ESI<sup>+</sup> (m/z): [M+H]<sup>+</sup> calcd for C<sub>6</sub>H<sub>10</sub>IN<sub>2</sub>: 236.99; found: 236.94.

Example 4.04

Preparation of (R)-4-((R)-1-(5-hydroxybenzo[d]thiazol-7-yloxy)ethyl)pyrrolidin-2-one

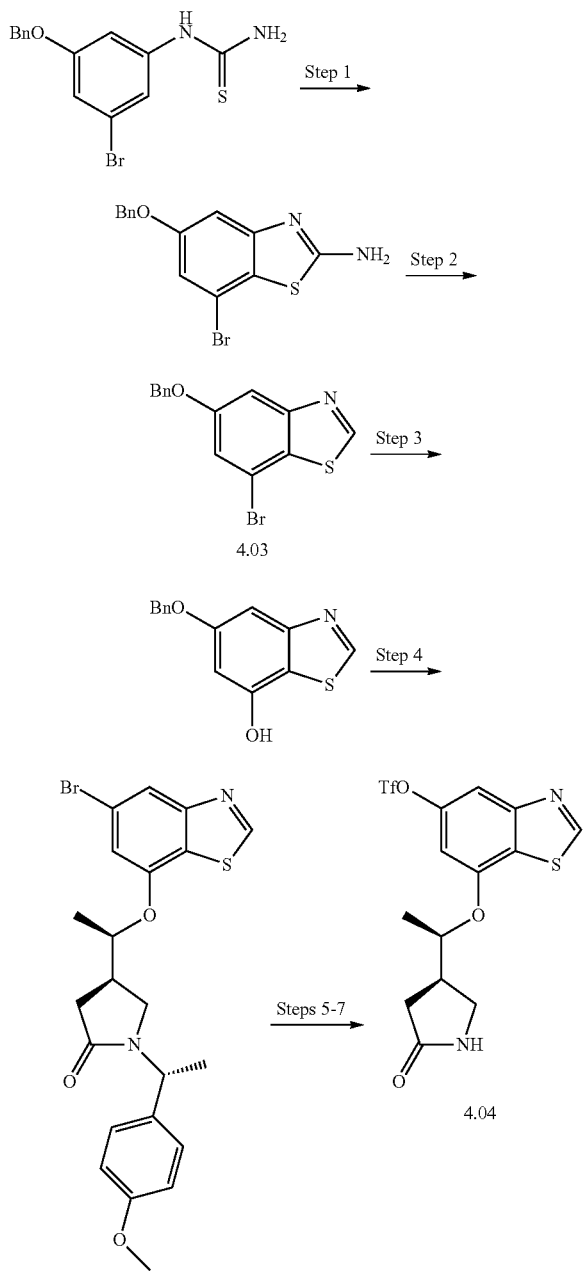

Step 1: 1-(3-(benzyloxy)-5-bromophenyl)thiourea (Prepared as described in WO 2012/045124 A1) (2.07 g, 6.14 mmol) was suspended in CHCl$_3$ (85 mL). The mixture was cooled to −78° C. under Ar. Bromine (0.33 mL, 6.4 mmol) was added as a solution in CHCl$_3$ (20 mL) dropwise over 15 min via syringe pump, rinsing with 5 mL CHCl$_3$. The mixture was warmed to r.t. After 5 min at r.t., the solution was heated to reflux and stirred for 1.25 h. The mixture was then cooled to r.t. and was diluted with water (75 mL), 28% aqueous NH$_4$OH (15 mL), and DCM (50 mL). The phases were separated, and the aqueous phase was extracted with DCM (2×50 mL). The combined organic phase was dried over Na$_2$SO$_4$, filtered, and concentrated to afford 4.02A, which was used without further purification.

LCMS-ESI$^+$ (m/z): [M+H]$^+$ calcd for C$_{14}$H$_{12}$BrN$_2$OS: 334.99; found: 335.11.

Step 2: The crude 4.02A from the previous step (2.02 g, 6.0 mmol) was suspended in 1,4-dioxane (40 mL) under Ar. t-BuONO (1.7 mL, 13 mmol) was added and the resulting mixture was heated to 90° C. After 5 min, the resulting mixture was cooled to r.t. and was diluted with EtOAc (150 mL) and water (100 mL). The phases were separated, and the organic phase was dried over Na$_2$SO$_4$, filtered, and concentrated to a crude residue that was purified by silica gel chromatography to provide 5-(benzyloxy)-7-bromobenzo[d]thiazole (4.03). LCMS-ESI$^+$ (m/z): [M+H]$^+$ calcd for C$_{14}$H$_{11}$BrNOS: 320.0, found 320.1.

Step 3: 5-(benzyloxy)-7-bromobenzo[d]thiazole (0.65 g, 2.0 mmol), Pd$_2$(dba)$_3$ (95 mg, 0.10 mmol), and 2-Di-tert-butylphosphino-2',4',6'-triisopropylbiphenyl (180 mg, 0.42 mmol) were taken up in 1,4-dioxane (7.2 mL) under Ar. Aqueous 2 M KOH (3 mL, 6 mmol) was added and the mixture was heated to 90° C. After 35 min, the mixture was cooled to r.t. and was diluted with EtOAc (20 mL), water (15 mL), and brine (15 mL). The aqueous phase was and acidified with 3 M aqueous HCl (3 mL, 9 mmol). The phases were separated, and the organic phase was dried over Na$_2$SO$_4$, filtered, and concentrated to afford a crude residue that was purified by silica gel chromatography (10-60% EtOAc in hexanes) to provide 5-(benzyloxy)benzo[d]thiazol-7-ol 4.03B. LCMS-ESI$^+$ (m/z): [M+H]$^+$ calcd for C$_{14}$H$_{12}$NO$_2$S: 258.1; found 257.8.

Step 4: 5-(benzyloxy)benzo[d]thiazol-7-ol (420 mg, 1.63 mmol), (R)-4-((S)-1-hydroxyethyl)-1-((R)-1-(4-methoxyphenyl)ethyl)pyrrolidin-2-one (607 mg, 2.31 mmol), and PPh$_3$ (615 mg, 2.35 mmol) were dissolved in THF (15 ml). DEAD (0.36 mL, 2.30 mmol) was added and the resulting mixture was heated to 40° C. After 17 h, additional (R)-4-((S)-1-hydroxyethyl)-1-((R)-1-(4-methoxyphenyl)ethyl)pyrrolidin-2-one (105 mg, 0.40 mmol), PPh$_3$ (110 mg, 0.42 mmol) and DEAD (0.060 mL, 0.38 mmol) were added. The reaction mixture was stirred an additional 1.5 h and was then concentrated directly onto silica gel. Purification by silica gel chromatography (70 to 100% EtOAc in hexanes) provided (R)-4-((R)-1-(5-(benzyloxy)benzo[d]thiazol-7-yloxy)ethyl)-1-((R)-1-(4-methoxyphenyl)ethyl)pyrrolidin-2-one 4.03C. LCMS-ESI$^+$ (m/z): [M+H]$^+$ calcd for C$_{29}$H$_{31}$N$_2$O$_4$S: 503.2; found 503.2.

Step 5: (R)-4-((R)-1-(5-(benzyloxy)benzo[d]thiazol-7-yloxy)ethyl)-1-((R)-1-(4-methoxyphenyl)ethyl)pyrrolidin-2-one (500 mg, 1.0 mmol) was dissolved in DCM (10 mL) under Ar and the resulting solution was cooled to −78° C. A 1.0 M solution of BBr$_3$ (10 mL, 10 mmol) was added dropwise over 5 min, and the resulting mixture was warmed to r.t. After 45 additional min, the reaction mixture was cooled in an ice water bath and MeOH (4 mL. 99 mmol) was added over 2 min. Et$_3$N (5.6 mL, 40 mmol) was added followed by Et$_2$NH (0.25 mL, 2.4 mmol) and the resulting mixture was warmed to r.t. After stirring an additional 30 min, the reaction mixture was concentrated, dissolved in MeOH (20 mL), and concentrated again. The resulting concentrate was partitioned between EtOAc (100 mL) and water (75 mL), and the phases were separated. The aqueous phase was extracted with EtOAc (30 mL), and the combined organic phase was washed with a mixture of 0.2 M aqueous HCl (30 mL) and brine (30 mL) followed by a mixture of saturated aqueous NaHCO$_3$ (20 mL) and brine (20 mL). The organic phase was dried over Na$_2$SO$_4$, filtered, and concentrated to afford (R)-4-((R)-1-(5-hydroxybenzo[d]thiazol-7-yloxy)ethyl)-1-((R)-1-(4-hydroxyphenyl) ethyl)pyrrolidin-2-one that was used without further purification. LCMS-ESI⁺ (m/z): [M+H]⁺ calcd for C$_{21}$H$_{23}$N$_2$O$_4$S: 399.1; found 399.2.

Step 6: The crude (R)-4-((R)-1-(5-hydroxybenz o[d]thiazol-7-yloxy)ethyl)-1-((R)-1-(4-hydroxyphenyl)ethyl)pyrrolidin-2-one (~1 mmol) from the previous step was dissolved in TFA (10 mL, 130 mmol) and the resulting solution was heated to 65° C. After 15 h, additional TFA (5 mL, 65 mmol) was added and the reaction temperature was increased to 70° C. After an additional 2 h, the reaction mixture was concentrated in vacuo and was diluted with EtOAc (50 mL), saturated aqueous NaHCO$_3$ (30 mL) and brine (20 mL). The phases were separated, and the aqueous phase was extracted with EtOAc (50 mL). The combined organic phase was dried over Na$_2$SO$_4$, filtered, and concentrated to afford (R)-4-((R)-1-(5-hydroxybenzo[d]thiazol-7-yloxy)ethyl)pyrrolidin-2-one that was used without further purification. LCMS-ESI⁺ (m/z): [M+H]⁺ calcd for C$_{13}$H$_{15}$N$_2$O$_3$S: 279.1, found 279.1.

Step 7: The crude (R)-4-((R)-1-(5-hydroxybenzo[d]thiazol-7-yloxy)ethyl)pyrrolidin-2-one (~1 mmol) from the previous step was taken up in MeCN (10 mL). Et$_3$N (0.56 mL, 4 mmol) was added followed by PhN(Tf)$_2$ (0.57 g, 1.6 mmol). After stirring 3 h, the reaction mixture was diluted with EtOAc (50 mL), 0.2 M aqueous HCl (30 mL), and brine (20 mL). The phases were separated, and the organic phase was washed with a 1:1 mixture of saturated aqueous NaHCO$_3$ and brine (40 mL). The organic phase was dried over Na$_2$SO$_4$, filtered, and concentrated to afford a crude residue that was purified by silica gel chromatography (20 to 100% acetone in hexanes) to provide 7-((R)-1-((R)-5-oxopyrrolidin-3-yl)ethoxy)benzo[d]thiazol-5-yl trifluoromethanesulfonate (4.04). LCMS-ESI⁺ (m/z): [M+H]⁺ calcd for C$_{14}$H$_{14}$F$_3$N$_2$O$_5$S$_2$: 411.0; found 411.3.

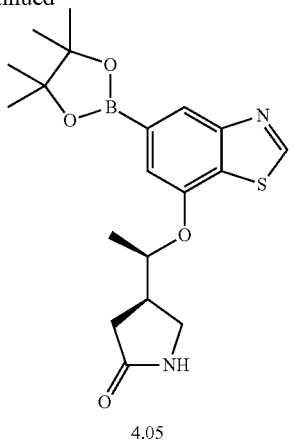

4.05

7-((R)-1-((R)-5-oxopyrrolidin-3-yl)ethoxy)benzo[d]thiazol-5-yl trifluoromethanesulfonate (4.04) (270 mg, 0.66 mmol), bis(pinacolato)diboron (290 mg, 1.14 mmol), KOAc (245 mg, 2.5 mmol) and PdCl$_2$(dppf).CH$_2$Cl$_2$ (27 mg, 0.033 mmol) were taken up in 1,4-dioxane (6.5 mL) under Ar, and the resulting mixture was heated to 110° C. After 2 h, the reaction mixture was cooled to r.t. and diluted with EtOAc (50 mL), water (20 mL) and brine (20 mL). The phases were separated, and the aqueous phase was extracted with EtOAc (30 mL). The combined organic phase was dried over Na$_2$SO$_4$, filtered, and concentrated to afford a crude residue that was purified by silica gel chromatography (50 to 100% acetone in hexanes) to provide (R)-4-((R)-1-(5-(4,4,5,5-tetramethyl-1,3,2-dioxaborolan-2-yl)benzo[d]thiazol-7-yloxy) ethyl)pyrrolidin-2-one (4.05).

LCMS-ESI⁺ (m/z): [M+H]⁺ calcd for C$_{19}$H$_{26}$BN$_2$O$_4$S: 389.2; found: 389.2.

Example 4.06

Preparation of 2-methyl-7-((R)-1-((R)-5-oxopyrrolidin-3-yl)ethoxy)benzo[d]thiazol-5-yl trifluoromethanesulfonate Example 4.05

Preparation of (R)-4-((R)-1-(5-(4,4,5,5-tetramethyl-1,3,2-dioxaborolan-2-yl)benzo[d]thiazol-7-yloxy) ethyl)pyrrolidin-2-one

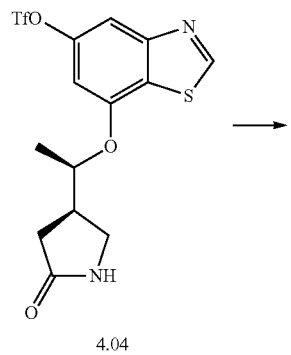

4.04

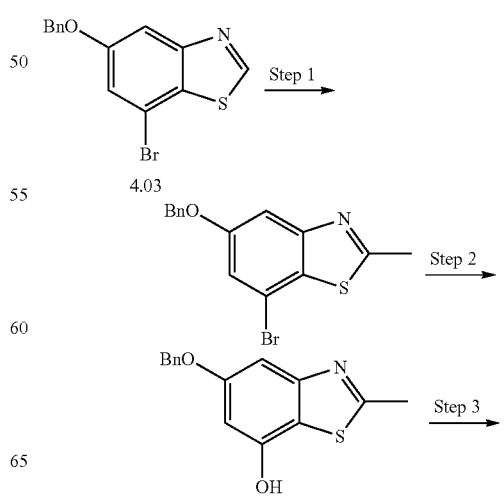

-continued

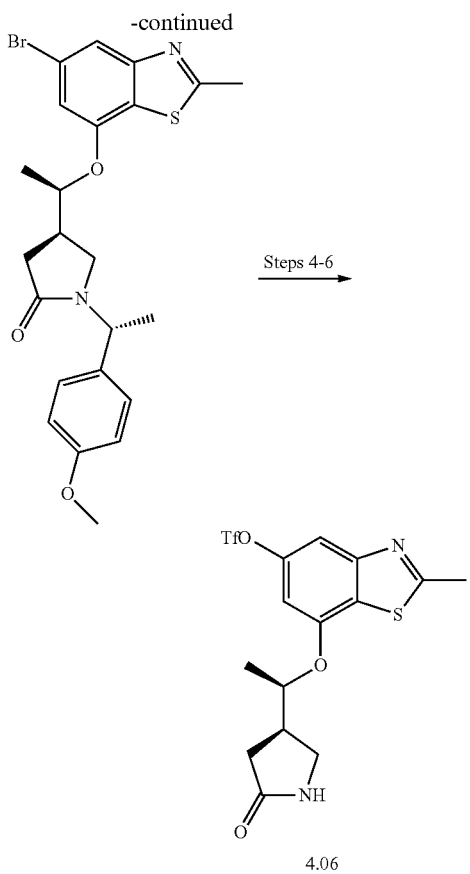

Step 1: A 1.0 M THF solution of LiHMDS (3.0 mL, 3.0 mmol) was diluted into THF (20 mL) under Ar, and the resulting solution was cooled to −78° C. 5-(benzyloxy)-7-bromobenzo[d]thiazole (4.03) (807 mg, 2.52 mmol) was added as a solution in THF (4 mL) over 2 min, washing with additional THF (3×2 mL). The resulting mixture was stirred 30 min, and MeI (0.47 mL, 7.6 mmol) was added in one portion. After stifling an additional 10 min, the mixture was removed from the cold bath and was allowed to warm to r.t. After 1.25 h at r.t., the reaction was diluted with saturated aqueous NH$_4$Cl (50 mL), water (15 mL), and EtOAc (50 mL). The phases were separated, and the organic phase was dried over Na$_2$SO$_4$, filtered, and concentrated to afford a crude residue that was purified by silica gel chromatography (0-20% EtOAc in hexanes) to afford 5-(benzyloxy)-7-bromo-2-methylbenzo[d]thiazole 4.03D. LCMS-ESI$^+$ (m/z): [M+H]$^+$ calcd for C$_{15}$H$_{13}$BrNOS: 334.0. found: 334.0.

Step 2: 5-(benzyloxy)-7-bromo-2-methylbenzo[d]thiazole 4.03D (560 mg, 1.7 mmol) Pd$_2$(dba)$_3$ (77 mg, 0.084 mmol), and 2-Di-tert-butylphosphino-2',4',6'-triisopropylbiphenyl (142 mg, 0.335 mmol) were taken up in 1,4-dioxane (6 mL) under Ar. Aqueous 2 M KOH (2.5 mL, 5 mmol) was added and the mixture was heated to 90° C. After 1 h, the mixture was cooled to r.t. and was diluted with EtOAc (50 mL), and water (30 mL). The aqueous phase was and acidified with 3 M aqueous HCl (1.8 mL, 5.4 mmol). The phases were separated, and the organic phase was washed with saturated aqueous NaHCO$_3$ (30 mL). The organic phase was dried over Na$_2$SO$_4$, filtered, and concentrated to afford a crude residue that was purified by silica gel chromatography (10-55% EtOAc in hexanes) to provide 5-(benzyloxy)-2-methylbenzo[d]thiazol-7-ol 4.03E. LCMS-ESI$^+$ (m/z): [M+H]$^+$ calcd for C$_{15}$H$_{14}$NO$_2$S: 272.1; found 272.1.

Step 3: 5-(benzyloxy)-2-methylbenzo[d]thiazol-7-014.03E (420 mg, 1.55 mmol), (R)-4-((S)-1-hydroxyethyl)-1-((R)-1-(4-methoxyphenyl)ethyl)pyrrolidin-2-one 1.05 (530 mg, 2.0 mmol), and PPh$_3$ (520 mg, 2.0 mmol) were dissolved in THF (10 ml). DEAD (0.31 mL, 2.0 mmol) was added and the resulting mixture was heated to 40° C. After 1.25 h, additional (R)-4-((S)-1-hydroxyethyl)-1-((R)-1-(4-methoxyphenyl)ethyl)pyrrolidin-2-one 1.05 (80 mg, 0.3 mmol), PPh$_3$ (80 mg, 0.3 mmol) and DEAD (0.050 mL, 0.3 mmol) were added. The reaction mixture was stirred an additional 45 min and was then concentrated directly onto silica gel. Purification by silica gel chromatography (10 to 25 to 30% acetone in hexanes) provided (R)-4-((R)-1-(5-(benzyloxy)-2-methylbenzo[d]thiazol-7-yloxy)ethyl)-1-((R)-1-(4-methoxyphenyl)ethyl)pyrrolidin-2-one 4.03F. LCMS-ESI$^+$ (m/z): [M+H]$^+$ calcd for C$_{30}$H$_{33}$N$_2$O$_4$S: 517.2; found 517.1.

Step 4: (R)-4-((R)-1-(5-(benzyloxy)-2-methylbenzo[d]thiazol-7-yloxy)ethyl)-1-((R)-1-(4-methoxyphenyl)ethyl) pyrrolidin-2-one 4.03F (490 mg, 0.95 mmol) was dissolved in DCM (10 mL) under Ar. The solution was cooled to −78° C., and a 1.0 M solution of BBr$_3$ in DCM (7.1 mL, 7.1 mmol) was added over 1 min. The resulting mixture was allowed to warm to r.t. and was stirred for an additional 45 min. The mixture was then cooled in an ice water bath, and MeOH (4.6 mL, 110 mmol) was added over 1 min. Et$_3$N (4.1 mL, 29 mmol) and Et$_2$NH (0.31 mL, 3.0 mmol) were then added, and the mixture was removed from the cold bath. After an additional 15 min, the mixture was concentrated, and the crude residue was dissolved in MeOH (30 mL) and concentrated. The resulting residue was partitioned between EtOAc (50 mL) and water (30 mL). The phases were separated, and the organic phase was washed with a mixture of water (25 mL), 3 M aqueous HCl (7.5 mL), and brine (25 mL). The organic phase was washed with a mixture of saturated aqueous NaHCO$_3$ (20 mL) and brine (20 mL) and was dried over Na$_2$SO$_4$, filtered, and concentrated to afford crude (R)-4-((R)-1-(5-hydroxy-2-methylbenzo[d]thiazol-7-yloxy)ethyl)-1-((R)-1-(4-hydroxyphenyl)ethyl)pyrrolidin-2-one that was used without further purification.

Step 5: The crude product from Step 4 was dissolved in TFA (10 mL, 130 mmol). The resulting solution was heated to 70° C. After stifling 17 h, the reaction mixture was concentrated, and the resulting residue was dissolved in EtOAc (100 mL) and washed with a 1:1 mixture of brine and saturated NaHCO$_3$ (100 mL). The phases were separated, and the aqueous phase was extracted with EtOAc (50 mL). The combined organic phase was dried over Na$_2$SO$_4$, filtered, and concentrated to afford (R)-4-((R)-1-(5-hydroxy-2-methylbenzo[d]thiazol-7-yloxy)ethyl)pyrrolidin-2-one that was used without further purification.

Step 6: The crude (R)-4-((R)-1-(5-hydroxy-2-methylbenzo[d]thiazol-7-yloxy)ethyl)pyrrolidin-2-one described above was taken up in MeCN (10 mL), and Et$_3$N (0.55 mL, 3.9 mmol) was added followed by PhN(Tf)$_2$ (557 mg, 1.6 mmol). The resulting mixture was stirred 1.75 h and was diluted with EtOAc (100 mL), water (30 mL), and brine (30 mL). The aqueous phase was acidified with 3 M aqueous HCl (1.5 mL). The phases were separated and the organic phase was dried over Na$_2$SO$_4$, filtered and concentrated to afford a crude residue that was purified by silica gel chromatography (15-65% acetone in hexanes) to afford 2-methyl-7-((R)-1-((R)-5-oxopyrrolidin-3-yl)ethoxy)benzo[d]thiazol-5-yl trifluoromethanesulfonate (4.06). LCMS-ESI$^+$ (m/z): [M+H]$^+$ calcd for C$_{15}$H$_{16}$F$_3$N$_2$O$_5$S$_2$: 425.1; found: 424.8.

General Procedure 4A for Synthesis of Examples 4.07-4.17

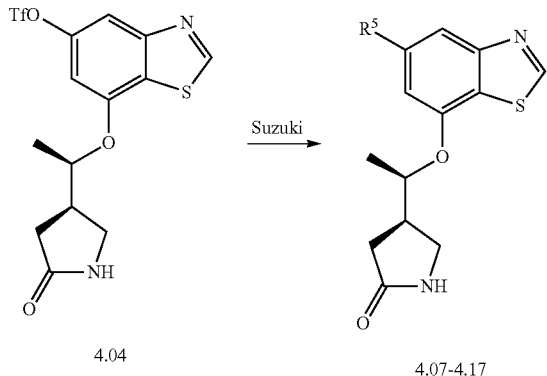

To an appropriate-sized vial was added 7-((R)-1-((R)-5-oxopyrrolidin-3-yl)ethoxy)benzo[d]thiazol-5-yl trifluoromethanesulfonate (4.04) (1 eq.), boronic acid or pinacol ester (~2 eq.), $Pd(OAc)_2$ (3-15 mol %), 2-Dicyclohexylphosphino-2',4',6'-triisopropylbiphenyl (XPhos) (2-3 eq. vs. $Pd(OAc)_2$), and $K_3PO_4$ (~3 eq.). The vessel was purged with Ar, and the reagents were taken up in THF (ca. 25 volumes versus triflate) and water (75-100 eq.). The resulting mixture was stirred at 65° C. until the reaction was judged complete by HPLC, LC/MS or TLC. In certain cases where incomplete conversion was observed, additional boronic acid/ester, $Pd(OAc)_2$, and XPhos were added. The mixture was diluted with EtOAc, water and brine, and the phases were separated. The aqueous phase was extracted with EtOAc. The combined organic phase was dried over $Na_2SO_4$, filtered, and concentrated. The residue was purified by silica gel chromatography to provide Examples 4.07-4.17, summarized in Table B below.

TABLE B

| Example # | Boronic Acid/Ester | Product | LCMS-ESI+ (m/z): [M + H]+ | 1H NMR (400 MHz, Chloroform-d) δ |
|---|---|---|---|---|
| 4.07 | ![structure] | ![structure] | Calc: 399.1 Found: 399.0 | 9.00 (s, 1H), 7.94 (s, 1H), 7.23-7.13 (m, 2H), 7.05 (s, 1H), 6.98 (d, 7 = 8.2 Hz, 1H), 5.85 (s, 1H), 4.68 (p, J = 5.9 Hz, 1H), 3.97 (s, 3H), 3.94 (s, 3H), 3.59-3.50 (m, 1H), 3.36 (dd, J = 9.5, 6.7 Hz, 1H), 2.98-2.86 (m, 1H), 2.62-2.44 (m, 2H), 1.44 (d, J = 6.1 Hz, 3H). |
| 4.08 | ![structure] | ![structure] | Calc: 424.2 Found: 424.1 | 8.98 (s, 1H), 7.93 (d, J = 1.3 Hz, 1H), 7.64-7.52 (m, 2H), 7.09-6.96 (m, 3H), 6.07 (s, 1H), 4.75-4.61 (m, 1H), 3.94-3.85 (m, 4H), 3.60-3.50 (m, 1H), 3.36 (dd, J = 9.6, 6.7 Hz, 1H), 3.29-3.17 (m, 4H), 2.99-2.83 (m, 1H), 2.65-2.41 (m, 2H), 1.43 (d, J = 6.1 Hz, 3H). |

TABLE B-continued

| Example # | Boronic Acid/Ester | Product | LCMS-ESI+ (m/z): [M + H]+ | 1H NMR (400 MHz, Chloroform-d) δ |
|---|---|---|---|---|
| 4.09 | | | Calc: 523.2 Found: 522.9 | 8.97 (s, 1H), 7.93 (d, J = 1.2 Hz, 1H). 7.60-7.54 (m, 2H), 7.07-6.99 (m, 3H), 5.85 (s, 1H), 4.72-4.62 (m, 1H), 3.66-3.58 (m, 4H), 3.58-3.50 (m, 1H), 3.36 (dd, J = 9.6, 6.6 Hz, 1H), 3.25-3.16 (m, 4H), 2.98-2.84 (m, 1H), 2.62-2.42 (m, 2H), 1.49 (s, 9H), 1.43 (d, J = 6.1 Hz, 3H). |
| 4.10 | | | Calc: 383.2 Found: 383.2 | 8.96 (s, 1H), 7.86 (d, J = 1.2 Hz, 1H), 7.83 (s, 1H), 7.75 (s, 1H), 6.97 (s, 1H), 5.95 (s, 1H), 4.91-4.74 (m, 1H), 4.71-4.59 (m, 1H), 3.62-3.50 (m, 1H), 3.36 (dd, J = 9.6, 6.6 Hz, 1H), 2.97-2.82 (m, 1H), 2.70-2.39 (m, 6H), 2.03-1.80 (m, 2H), 1.42 (d, J = 6.1 Hz, 3H). |
| 4.11 | | | Calc: 393.1 Found: 393.2 | 8.99 (s, 1H), 7.91-7.85 (m, 2H), 7.78 (s, 1H), 6.97 (s, 1H), 6.32-5.98 (m, 1H), 5.51 (s, 1H), 4.71-4.62 (m, 1H), 4.53 (td, J = 13.6, 4.3 Hz, 2H), 3.61-3.51 (m, 1H), 3.36 (dd, J = 9.6, 6.6 Hz, 1H), 2.99-2.84 (m, 1H), 2.63-2.42 (m, 2H), 1.44 (d, J = 6.1 Hz, 3H). |

TABLE B-continued

| Example # | Boronic Acid/Ester | Product | LCMS-ESI+ (m/z): [M + H]+ | 1H NMR (400 MHz, Chloroform-d) δ |
|---|---|---|---|---|
| 4.12 | | | Calc: 371.2 Found: 370.9 | 8.96 (s, 1H), 7.87 (d, J = 1.2 Hz, 1H), 7.82 (d, J = 0.8 Hz, 1H), 7.73 (d, J = 0.8 Hz, 1H), 7.00-6.96 (m, 1H), 6.02 (s, 1H), 4.71-4.61 (m, 1H), 4.56 (hept, J = 6.7 Hz, 1H), 3.61-3.50 (m, 1H), 3.36 (dd, J = 9.6, 6.6 Hz, 1H), 3.00-2.82 (m, 1H), 2.62-2.42 (m, 2H), 1.57 (d, J = 6.7 Hz, 6H), 1.42 (d, J = 6.1 Hz, 3H). |
| 4.13 | | | Calc: 385.2 Found: 385.1 | 8.96 (s, 1H), 7.90-7.78 (m, 3H), 6.98 (s, 1H), 6.02 (s, 1H), 4.73-4.61 (m, 1H), 3.62-3.49 (m, 1H), 3.36 (dd, J = 9.6, 6.6 Hz, 1H), 3.00-2.81 (m, 1H), 2.61-2.43 (m, 2H), 1.66 (s, 9H), 1.42 (d, J = 6.1 Hz, 3H). |
| 4.14 | | | Calc: 413.16 Found: 413.29 | 9.03 (s, 1H), 7.89 (d, J = 1.1 Hz, 1H), 7.86 (s, 1H), 7.78 (s, 1H), 7.01-6.96 (m, 1H), 5.63 (s, 1H), 4.67 (q, J = 6.0 Hz, 1H), 4.53-4.37 (m, 1H), 4.22-4.08 (m, 2H), 3.66-3.50 (m, 3H), 3.37 (dd, J = 9.6, 6.5 Hz, 1H), 3.01-2.84 (m, 1H), 2.66-2.43 (m, 2H), 2.29-2.01 (m, 4H), 1.44 (d, J = 6.1 Hz, 3H) |

TABLE B-continued

| Example # | Boronic Acid/Ester | Product | LCMS-ESI+ (m/z): [M + H]+ | 1H NMR (400 MHz, Chloroform-d) δ |
|---|---|---|---|---|
| 4.15 | | | Calc: 400.1 Found: 400.4 | 8.99 (s, 1H), 8.32 (d, J = 1.3 Hz, 1H), 7.63 (s, 1H), 7.41 (d, J = 8.0 Hz, 1H), 7.14 (d, J = 8.1 Hz, 1H), 6.03 (s, 1H), 4.77-4.66 (m, 1H), 4.14 (s, 3H), 3.93 (s, 3H), 3.61-3.50 (m, 1H), 3.38 (dd, J = 9.6, 6.7 Hz, 1H), 3.01-2.84 (m, 1H), 2.62-2.45 (m, 2H), 1.46 (d, J = 6.1 Hz, 3H). |
| 4.16 | | | Calc: 396.1 Found: 396.1 | 9.03 (s, 1H), 9.01 (s, 1H), 8.15 (d, J = 1.2 Hz, 1H), 8.01 (dd, J = 8.0, 1.2 Hz, 1H), 7.68 (dd, J = 7.4, 1.2 Hz, 1H), 7.60-7.52 (m, 1H), 7.47-7.43 (m, 1H), 5.94 (s, 1H), 4.74-4.62 (m, 1H), 3.57-3.49 (m, 1H), 3.37 (dd, J = 9.6, 6.7 Hz, 1H), 3.01-2.85 (m, 1H), 2.62-2.42 (m, 2H), 1.45 (d, J = 6.1 Hz, 3H). |
| 4.17 | | | Calc: 402.1 Found: 401.9 | 8.99 (s, 1H), 7.93 (d, J = 1.3 Hz, 1H), 7.86 (s, 1H), 7.03-6.97 (m, 1H), 6.09 (s, 1H), 4.73-4.60 (m, 1H), 3.62-3.50 (m, 1H), 3.36 (dd, J = 9.6, 6.7 Hz, 1H), 3.01-2.82 (m, 1H), 2.64-2.39 (m, 2H), 1.49 (s, 9H), 1.44 (d, J = 6.1 Hz, 3H). |

General Procedure 4B for Synthesis of Examples 4.18-4.21

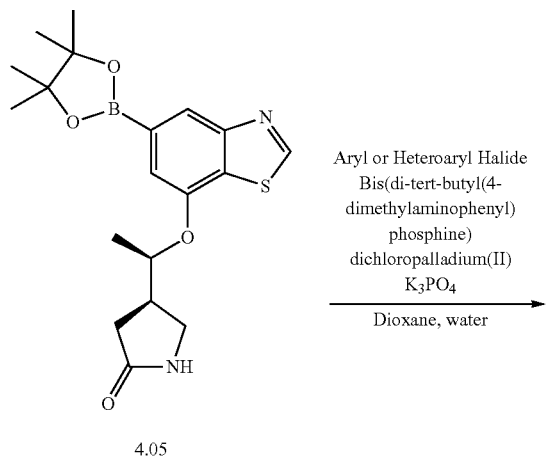

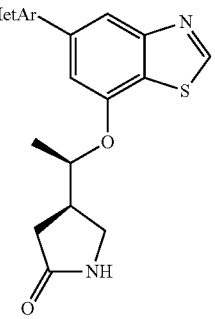

To an appropriate-sized vial was added (R)-4-((R)-1-(5-(4,4,5,5-tetramethyl-1,3,2-dioxaborolan-2-yl)benzo[d]thiazol-7-yloxy)ethyl)pyrrolidin-2-one (4.05) (1 eq.), aryl or heteroaryl halide (~1.3-2 eq.), bis(di-tert-butyl(4-dimethylaminophenyl)phosphine)dichloropalladium(II) (3-10 mol %), and $K_3PO_4$ (~3 eq.). The vessel was purged with Ar, and the reagents were taken up in dioxane (ca. 30-40 volumes versus boronic ester) and water (75-100 eq.). The resulting mixture was stirred at 100° C. until the reaction was judged complete by HPLC, LC/MS or TLC. The mixture was diluted with EtOAc, water and brine, and the phases were separated. The aqueous phase was extracted with EtOAc. The combined organic phase was dried over $Na_2SO_4$, filtered, and concentrated. The residue was purified by silica gel chromatography to provide Examples 4.18-4.21 in Table C below.

TABLE C

| Example # | Aryl/Heteroaryl Halide | Product | LCMS-ESI+ (m/z): [M + H]+ | 1H NMR (400MHz, Chloroform-d) δ |
|---|---|---|---|---|
| 4.18 | | | Calc: 357.14 Found: 357.15 | 8.96 (s, 1H), 8.09 (d, J = 1.2 Hz, 1H), 7.50 (s, 1H), 7.46 (d, J = 2.3 Hz, 1H), 6.63 (d, J = 2.3 Hz, 1H), 5.86 (s, 1H), 4.83-4.70 (m, 1H), 4.25 (q, J = 7.3 Hz, 2H), 3.59-3.46 (m, 1H), 3.36 (dd, J = 9.6, 6.8 Hz, 1H), 2.99-2.81 (m, 1H), 2.63-2.40 (m, 2H), 1.55 (t, J = 7.3 Hz, 3H), 1.43 (d, J = 6.1 Hz, 3H). |
| 4.19 | 4.02 | | Calc: 371.15 Found: 371.12 | 8.96 (s, 1H), 8.10 (d, J = 1.2 Hz, 1H), 7.51-7.46 (m, 2H), 6.63 (d, J = 2.3 Hz, 1H), 5.88 (s, 1H), 4.81-4.71 (m, 1H), 4.58 (hept, J = 6.8 Hz, 1H), 3.57-3.49 (m, 1H), 3.37 (dd, J = 9.6, 6.8 Hz, 1H), 2.99-2.84 (m, 1H), 2.61-2.42 (m, 2H), 1.57 (d, J = 6.7 Hz, 6H), 1.43 (d, J = 6.2 Hz, 3H). |

TABLE C-continued

| Example # | Aryl/Heteroaryl Halide | Product | LCMS-ESI+ (m/z): [M + H]+ | 1H NMR (400MHz, Chloroform-d) δ |
|---|---|---|---|---|
| 4.20 | (Prepared as described in WO2007/11692) | | Calc: 425.2 Found: 425.1 | 8.99 (s, 1H), 8.38 (d, J = 2.9 Hz, 1H), 8.19 (d, J = 1.2 Hz, 1H), 7.78 (d, J = 8.8 Hz, 1H), 7.74 (s, 1H), 7.31 (dd, J = 8.8, 3.0 Hz, 1H), 5.69 (s, 1H), 4.89-4.76 (m, 1H), 3.95-3.86 (m, 4H), 3.59-3.48 (m, 1H), 3.37 (dd, J = 9.6, 6.8 Hz, 1H), 3.31-3.21 (m, 4H), 2.99-2.84 (m, 1H), 2.62-2.43 (m, 2H), 1.45 (d, J = 6.1 Hz, 3H). |
| 4.21 | 4.01 | | Calc: 524.2 Found: 524.2 | 8.98 (s, 1H), 8.39 (d, J = 2.9 Hz, 1H), 8.19 (d, J = 1.2 Hz, 1H), 7.77 (d, 7 = 8.8 Hz, 1H), 7.72 (s, 1H), 7.31 (dd, J = 8.8, 2.9 Hz, 1H), 5.74 (s, 1H), 4.88-4.75 (m, 1H), 3.69-3.58 (m, 4H), 3.57-3.50 (m, 1H), 3.36 (dd, J = 9.5, 6.8 Hz, 1H), 3.28-3.21 (m, 4H), 2.96-2.86 (m, 1H), 2.52 (dd, J = 8.6, 6.8 Hz, 2H), 1.49 (s, 9H), 1.44 (d, J = 6.1 Hz, 3H). |

Example 4.22

Preparation of (R)-4-((R)-1-(5-(1-methyl-1H-thieno[3,2-c]pyrazol-5-yl)benzo[d]thiazol-7-yloxy)ethyl)pyrrolidin-2-one

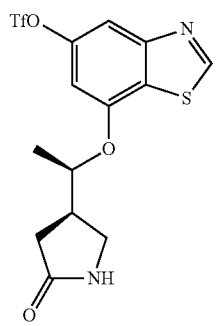

4.04

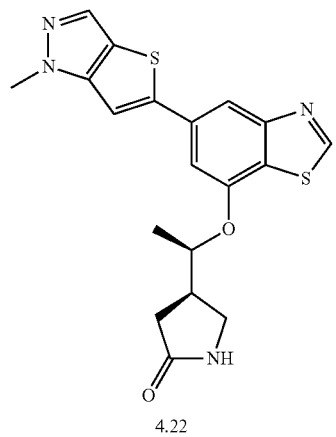

4.22

7-((R)-1-((R)-5-oxopyrrolidin-3-yl)ethoxy)benzo[d]thiazol-5-yl trifluoromethanesulfonate (4.04) (25.5 mg, 0.062 177714 and US2012/043276) (35 mg, 0.082 mmol) were mmol), 1-methyl-5-(tributylstannyl)-1H-thieno[3,2-c]pyrazole (prepared according to protocols described in WO2012/ taken up in DMF (0.6 mL) and CsF (24 mg, 0.16 mmol), CuI (2.7 mg, 0.014 mmol) and Pd(PPh$_3$)$_4$ (8.4 mg, 0.007 mmol) were added. The reaction vessel was flushed with Ar, and the mixture was heated to 45° C. After 16 h, the reaction was diluted with EtOAc (20 mL) and water (20 mL), and the phases were separated. The aqueous phase was extracted with EtOAc (20 mL) and the combined organic phase was washed with water (20 mL), dried over Na$_2$SO$_4$, filtered and concentrated. The resulting residue was purified by silica gel chromatography (0 to 15% MeOH in DCM) to afford of the title compound (4.22). LCMS-ESI$^+$ (m/z): [M+H]$^+$ calcd for C$_{19}$H$_{19}$N$_4$O$_2$S$_2$: 399.1; found: 398.9. $^1$H NMR (400 MHz, Chloroform-d) δ 9.01 (s, 1H), 8.05 (d, J=1.3 Hz, 1H), 7.66 (s, 1H), 7.20 (d, J=0.7 Hz, 1H), 7.11-7.08 (m, 1H), 5.92 (s, 1H), 4.76-4.62 (m, 1H), 4.07 (s, 3H), 3.62-3.53 (m, 1H), 3.37 (dd, J=9.6, 6.6 Hz, 1H), 2.98-2.87 (m, 1H), 2.57 (dd, J=17.2, 9.1 Hz, 1H), 2.49 (dd, J=17.2, 7.9 Hz, 1H), 1.46 (d, J=6.1 Hz, 3H).

Example 4.24

Preparation of (R)-4-((R)-1-(5-(5-(4-acetylpiperazin-1-yl)pyridin-2-yl)benzo[d]thiazol-7-yloxy)ethyl) pyrrolidin-2-one

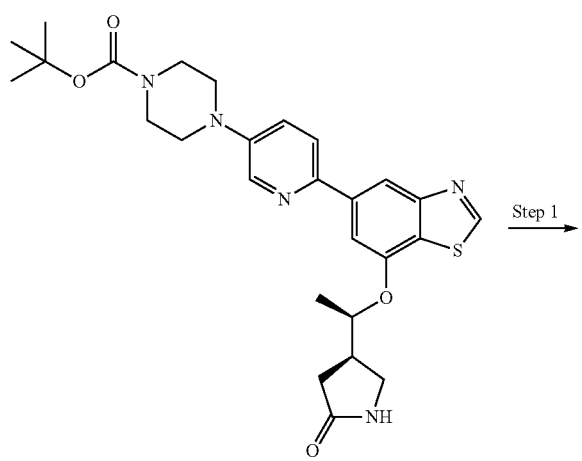

4.21

Step 1

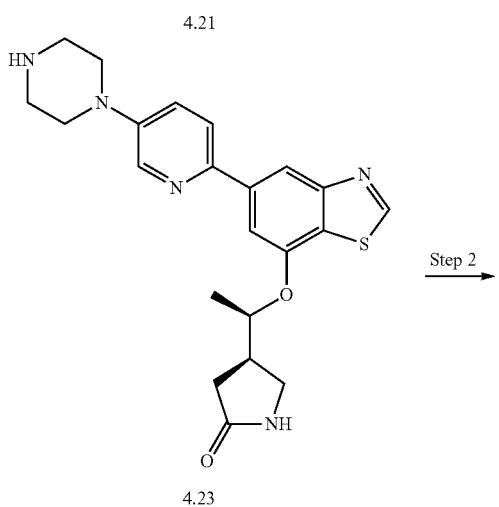

4.23

Step 2

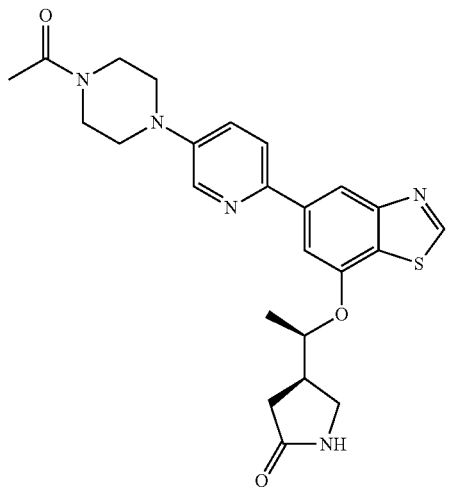

4.24

Step 1: tert-butyl 4-(6-(7-((R)-1-((R)-5-oxopyrrolidin-3-yl)ethoxy)benzo[d]thiazol-5-yl)pyridin-3-yl)piperazine-1-carboxylate (4.21) (157 mg, 0.30 mmol) was dissolved in TFA (5 mL, 65 mmol) and the reaction mixture was stirred 1 h at r.t. The mixture was then concentrated and the resulting crude residue was dissolved in and concentrated from DCM (5 mL) followed by THF (5 mL). The resulting crude TFA salt of (R)-4-((R)-1-(5-(5-(piperazin-1-yl)pyridin-2-yl)benzo[d]thiazol-7-yloxy)ethyl)pyrrolidin-2-one (4.23) was used without further purification.

Step 2: A portion of the crude salt from above (0.06 mmol) was taken up in DCM and Et$_3$N (0.060 mL, 0.43 mmol) was added followed by Ac$_2$O (6.5 µL, 0.070 mmol). The reaction mixture was stirred 2 h and was partitioned between EtOAc (2 mL) and water (1 mL). The aqueous phase was acidified with 0.2 M aqueous HCl. The phases were separated and the aqueous phase was extracted with EtOAc (4×1.5 mL). The combined organic phase was dried over Na$_2$SO$_4$, filtered, and concentrated to a crude residue that was purified by silica gel chromatography to provide of the title compound (4.24). LCMS-ESI$^+$ (m/z): [M+H]$^+$ calcd for C$_{24}$H$_{28}$N$_5$O$_3$S: 466.2; found: 466.2. $^1$H NMR (400 MHz, Chloroform-d) δ 8.99 (s, 1H), 8.40 (d, J=2.9 Hz, 1H), 8.19 (d, J=1.2 Hz, 1H), 7.78 (d, J=8.8 Hz, 1H), 7.72 (s, 1H), 7.33 (dd, J=8.8, 3.0 Hz, 1H), 5.79 (s, 1H), 4.88-4.76 (m, 1H), 3.87-3.78 (m, 2H), 3.72-3.62 (m, 2H), 3.59-3.49 (m, 1H), 3.41-3.22 (m, 5H), 2.99-2.84 (m, 1H), 2.65-2.43 (m, 2H), 2.16 (s, 3H), 1.44 (d, J=6.1 Hz, 3H).

Example 4.25

Preparation of (R)-4-((R)-1-(5-(5-(4-(oxetan-3-yl)piperazin-1-yl)pyridin-2-yl)benzo[d]thiazol-7-yloxy)ethyl)pyrrolidin-2-one

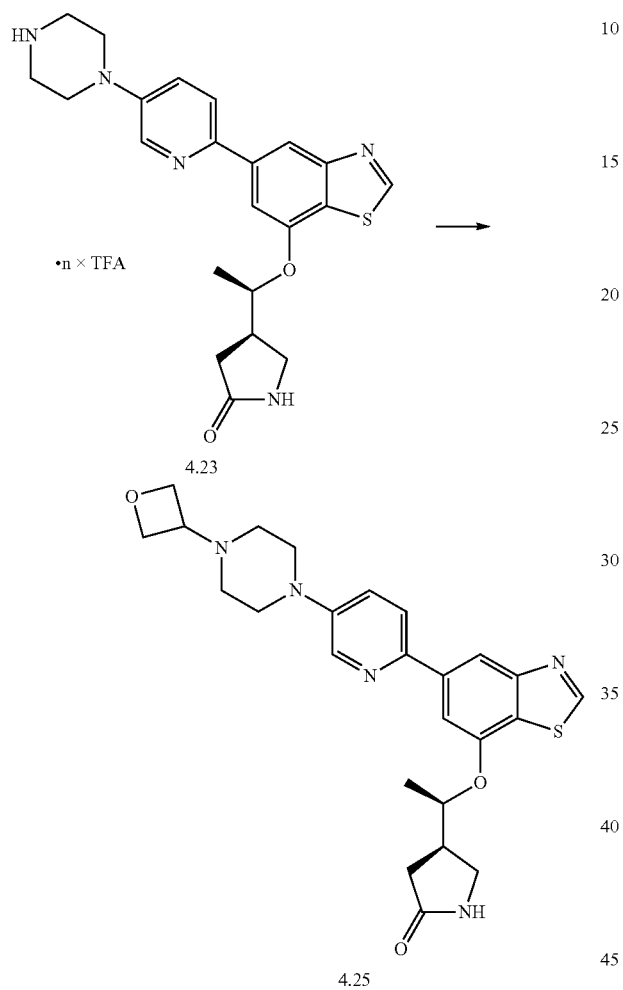

The crude TFA salt of (R)-4-((R)-1-(5-(5-(piperazin-1-yl)pyridin-2-yl)benzo[d]thiazol-7-yloxy)ethyl)pyrrolidin-2-one (4.23) described above (0.06 mmol) was dissolved in THF (1 mL) and iPr$_2$NEt (21 μL, 0.12 mmol) was added followed by oxetan-3-one (12 μL, 0.21 mmol) and sodium triacetoxyborohydride (55 mg, 0.26 mmol). The reaction mixture was stirred at 40° C. for 1.5 h and was diluted with water (1 mL), saturated aqueous NaHCO$_3$ (1 mL), and EtOAc (2 mL). The phases were separated, and the aqueous phase was extracted with EtOAc (3×1.5 mL). The combined organic phase was dried over Na$_2$SO$_4$, filtered, and concentrated to afford a crude residue that was purified by silica gel chromatography (0-25% MeOH in DCM) to yield (R)-4-((R)-1-(5-(5-(4-(oxetan-3-yl)piperazin-1-yl)pyridin-2-yl)benzo[d]thiazol-7-yloxy)ethyl)pyrrolidin-2-one (4.25). LCMS-ESI$^+$ (m/z): [M+H]$^+$ calcd for C$_{25}$H$_{30}$N$_5$O$_3$S: 480.2; found: 479.8. $^1$H NMR (400 MHz, Chloroform-d) δ 9.00-8.95 (m, 1H), 8.43-8.37 (m, 1H), 8.21-8.15 (m, 1H), 7.79-7.69 (m, 2H), 7.31 (dd, J=8.4, 3.8 Hz, 1H), 5.81 (s, 1H), 4.89-4.75 (m, 1H), 4.75-4.63 (m, 4H), 3.65-3.43 (m, 2H), 3.41-3.30 (m, 5H), 3.01-2.81 (m, 1H), 2.62-2.41 (m, 6H), 1.48-1.38 (m, 3H).

Example 4.26

Preparation of (R)-4-((R)-1-(5-(5-(4-(tetrahydro-2H-pyran-4-yl)piperazin-1-yl)pyridin-2-yl)benzo[d]thiazol-7-yloxy)ethyl)pyrrolidin-2-one

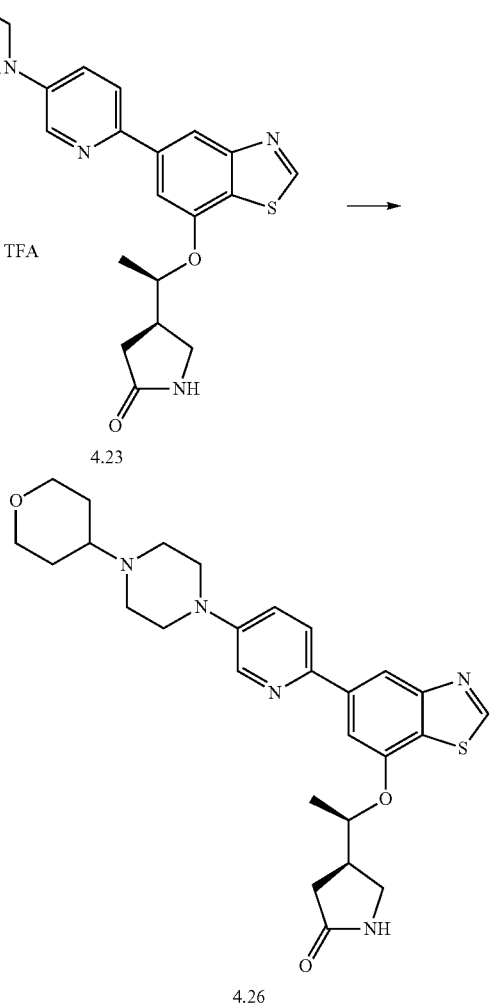

The crude TFA salt of (R)-4-((R)-1-(5-(5-(piperazin-1-yl)pyridin-2-yl)benzo[d]thiazol-7-yloxy)ethyl)pyrrolidin-2-one (4.23) described above (0.06 mmol) was dissolved in THF (1 mL) and iPr$_2$NEt (21 μL, 0.12 mmol) was added followed by dihydro-2H-pyran-4(3H)-one (28 μL, 0.30 mmol) and sodium triacetoxyborohydride (57 mg, 0.27 mmol). The reaction mixture was stirred at 50° C. for 18 h and was diluted with water (1 mL), 5% aqueous Na$_2$CO$_3$ (2 mL), and EtOAc (2 mL). The phases were separated, and the aqueous phase was extracted with EtOAc (4×1.5 mL). The combined organic phase was dried over Na$_2$SO$_4$, filtered, and concentrated to afford a crude residue that was purified by silica gel chromatography (0-25% MeOH in DCM) to yield (R)-4-((R)-1-(5-(5-(4-(tetrahydro-2H-pyran-4-yl)piperazin- 1-yl)pyridin-2-yl)benzo[d]thiazol-7-yloxy)ethyl)pyrrolidin-2-one (4.26). LCMS-ESI+ (m/z): [M+H]+ calcd for $C_{27}H_{34}N_5O_3S$: 508.24; found: 508.41. $^1$H NMR (400 MHz, Chloroform-d) δ 8.98 (s, 1H), 8.40-8.36 (m, 1H), 8.18 (d, J=1.2 Hz, 1H), 7.77-7.72 (m, 1H), 7.71 (s, 1H), 7.29 (dd, J=8.8, 3.0 Hz, 1H), 5.84 (s, 1H), 4.88-4.74 (m, 1H), 4.10-3.99 (m, 2H), 3.57-3.49 (m, 1H), 3.46-3.35 (m, 3H), 3.34-3.29 (m, 4H), 2.97-2.85 (m, 1H), 2.80-2.74 (m, 4H), 2.62-2.43 (m, 3H), 1.86-1.78 (m, 2H), 1.69-1.56 (m, 2H), 1.44 (d, J=6.1 Hz, 3H).

Example 4.28

Preparation of (R)-4-((R)-1-(5-(4-(4-(oxetan-3-yl)piperazin-1-yl)phenyl)benzo[d]thiazol-7-yloxy)ethyl)pyrrolidin-2-one

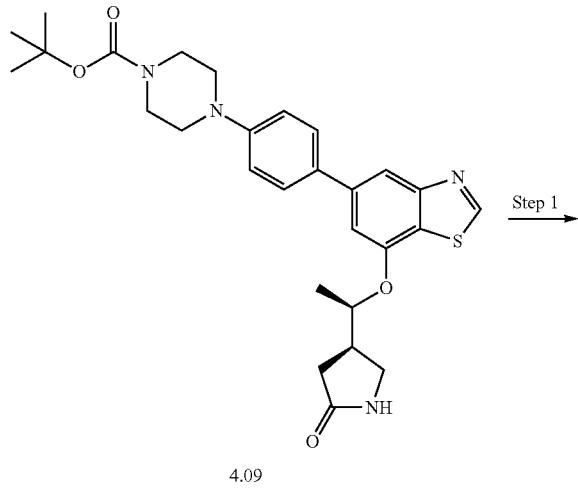

4.09

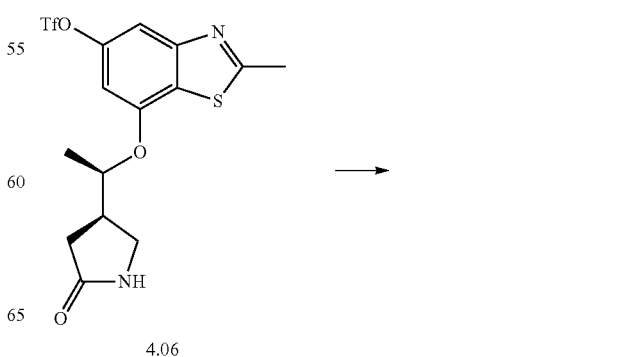

4.27

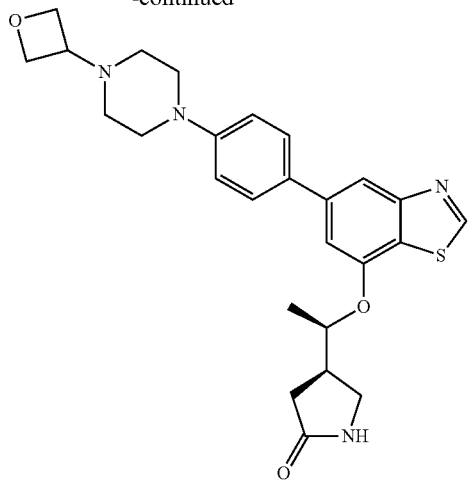

4.28

Step 1: tert-butyl 4-(4-(7-((R)-1-((R)-5-oxopyrrolidin-3-yl)ethoxy)benzo[d]thiazol-5-yl)phenyl)piperazine-1-carboxylate (92 mg, 0.18 mmol) was dissolved in TFA (3 mL, 39 mmol) and the reaction mixture was stirred 45 h at r.t. The mixture was then concentrated and the resulting crude residue was dissolved in and concentrated from a mixture of DCM and PhCH₃. The resulting crude TFA salt of (R)-4-((R)-1-(5-(4-(4-(oxetan-3-yl)piperazin-1-yl)phenyl)benzo[d]thiazol-7-yloxy)ethyl)pyrrolidin-2-one (4.27) was used without further purification. LCMS-ESI+ (m/z): [M+H]+ calcd for $C_{22}H_{26}N_5O_2S$: 424.2; found: 423.4.

Step 2: The crude TFA salt 4.27 (0.058 mmol) was dissolved in THF (1 mL) and iPr₂NEt (10 μL, 0.057 mmol) was added followed by oxetan-3-one (12 μL, 0.21 mmol) and sodium triacetoxyborohydride (55 mg, 0.26 mmol). The reaction mixture was stirred at 50° C. for 2 h and was diluted with water (2 mL) and EtOAc (2 mL). The phases were separated, and the aqueous phase was extracted with EtOAc (3×1.5 mL). The combined organic phase was dried over Na₂SO₄, filtered, and concentrated to afford a crude residue that was purified by silica gel chromatography (0-15% MeOH in DCM) to afford (R)-4-((R)-1-(5-(4-(4-(oxetan-3-yl)piperazin-1-yl)phenyl)benzo[d]thiazol-7-yloxy)ethyl)pyrrolidin-2-one (4.28). LCMS-ESI+ (m/z): [M+H]+ calcd for $C_{26}H_{31}N_4O_3S$: 479.2; found: 479.4. $^1$H NMR (400 MHz, Chloroform-d) δ 8.97 (s, 1H), 7.93 (d, J=1.2 Hz, 1H), 7.60-7.52 (m, 2H), 7.07-6.98 (m, 3H), 5.90 (s, 1H), 4.76-4.61 (m, 5H), 3.65-3.50 (m, 2H), 3.40-3.27 (m, 5H), 2.99-2.83 (m, 1H), 2.62-2.42 (m, 6H), 1.43 (d, J=6.1 Hz, 3H).

Example 4.29

Preparation of (R)-4-((R)-1-(5-(3,4-dimethoxyphenyl)-2-methylbenzo[d]thiazol-7-yloxy)ethyl)pyrrolidin-2-one 4.06

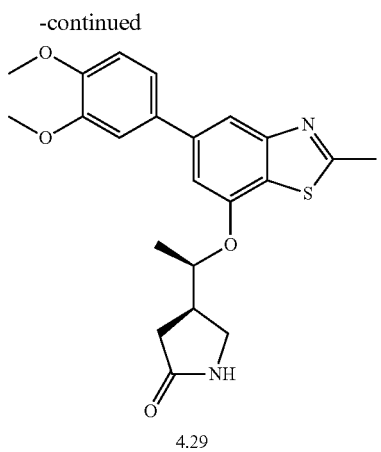

4.29

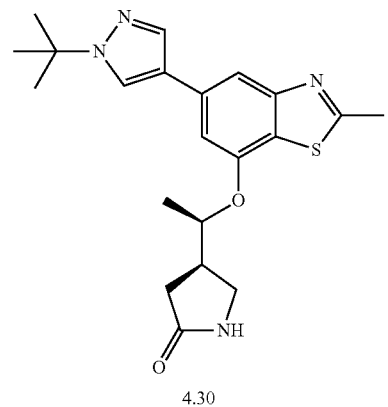

4.30

2-methyl-7-((R)-1-((R)-5-oxopyrrolidin-3-yl)ethoxy)benzo[d]thiazol-5-yl trifluoromethanesulfonate (4.06) (32 mg, 0.075 mmol), 3,4-dimethoxyphenylboronic acid (27 mg, 0.15 mmol), bis(di-tert-butyl(4-dimethylaminophenyl)phosphine)dichloropalladium(II) (1.5 mg, 0.002 mmol), and potassium phosphate (53 mg, 0.25 mmol) were taken up in 1,4-dioxane (1 mL) and water (0.11 mL). The stirred mixture was heated to 100 deg. C. After 4 h, the reaction mixture was diluted with EtOAc (2 mL), water (1 mL), and brine (1 mL). The phases were separated, and the aqueous phase was extracted with EtOAc (4×1.5 mL). The combined organic phase was dried over $Na_2SO_4$, filtered, and concentrated to afford a crude residue that was purified by silica gel chromatography (0-15% MeOH in DCM) to provide (R)-4-((R)-1-(5-(3,4-dimethoxyphenyl)-2-methylbenzo[d]thiazol-7-yloxy)ethyl)pyrrolidin-2-one (4.29). LCMS-ESI$^+$ (m/z): [M+H]$^+$ calcd for $C_{22}H_{25}N_2O_4S$: 413.2; found: 413.1. $^1$H NMR (400 MHz, Chloroform-d) δ 7.76 (d, J=1.3 Hz, 1H), 7.18-7.12 (m, 2H), 6.98-6.94 (m, 2H), 6.02 (s, 1H), 4.68-4.59 (m, 1H), 3.95 (s, 3H), 3.93 (s, 3H), 3.58-3.50 (m, 1H), 3.35 (dd, J=9.6, 6.6 Hz, 1H), 2.94-2.84 (m, 1H), 2.83 (s, 3H), 2.59-2.43 (m, 2H), 1.41 (d, J=6.1 Hz, 3H).

Example 4.30

Preparation of (R)-4-((R)-1-(5-(1-tert-butyl-1H-pyrazol-4-yl)-2-methylbenzo[d]thiazol-7-yloxy)ethyl)pyrrolidin-2-one

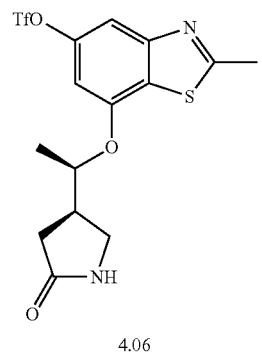

4.06

The title compound 4.30 was prepared from 2-methyl-7-((R)-1-((R)-5-oxopyrrolidin-3-yl)ethoxy)benzo[d]thiazol-5-yl trifluoromethanesulfonate 4.06 in a similar fashion as described in Example 4.29, using 1-tert-butyl-4-(4,4,5,5-tetramethyl-1,3,2-dioxaborolan-2-yl)-1H-pyrazole as the boronic ester coupling partner. LCMS-ESI$^+$ (m/z): [M+H]$^+$ calcd for $C_{21}H_{27}N_4O_2S$: 399.2; found: 399.1. $^1$H NMR (400 MHz, Chloroform-d) 6-7.81 (d, J=0.8 Hz, 1H), 7.78 (d, J=0.8 Hz, 1H), 7.70 (d, J=1.2 Hz, 1H), 6.90 (d, J=1.2 Hz, 1H), 5.72 (s, 1H), 4.67-4.59 (m, 1H), 3.58-3.50 (m, 1H), 3.35 (dd, J=9.6, 6.6 Hz, 1H), 2.94-2.84 (m, 1H), 2.82 (s, 3H), 2.59-2.43 (m, 2H), 1.65 (s, 9H), 1.41 (d, J=6.1 Hz, 3H).

Example 4.31

Preparation of (R)-4-((R)-1-((5-(4-(4-acetylpiperazin-1-yl)phenyl)benzo[d]thiazol-7-yl)oxy)ethyl)pyrrolidin-2-one

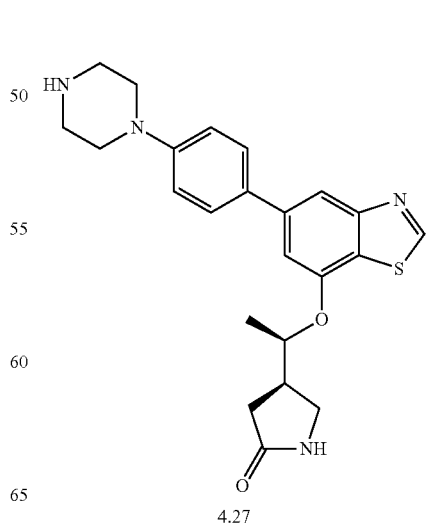

4.27

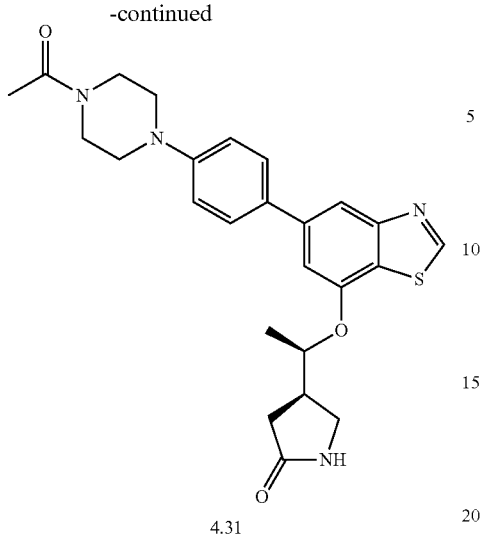

4.31

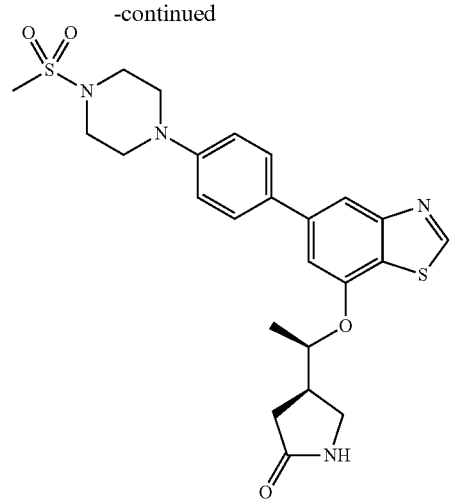

4.32

The crude TFA salt of 4.27 (0.058 mmol) was suspended in DCM (1 mL) and Et₃N (60 μL, 0.43 mmol) was added followed by acetic anhydride (6.5 μL, 0.069 mmol). The resulting mixture was stirred 4 h and was partitioned between EtOAc and water. The aqueous layer was acidified with aqueous HCl. The phases were separated, and the aqueous phase was extracted with EtOAc. The combined organic phase was dried over Na₂SO₄, filtered, and concentrated. The crude product was purified by silica gel chromatography (0-20% MeOH in DCM) to afford (R)-4-((R)-1-((5-(4-(4-acetylpiperazin-1-yl)phenyl)benzo[d]thiazol-7-yl)oxy)ethyl)pyrrolidin-2-one (4.31).

$^1$H NMR (400 MHz, Chloroform-d) δ 8.98 (s, 1H), 7.93 (d, J=1.3 Hz, 1H), 7.61-7.53 (m, 2H), 7.07-6.99 (m, 3H), 5.97 (s, 1H), 4.72-4.61 (m, 1H), 3.86-3.75 (m, 2H), 3.70-3.62 (m, 2H), 3.60-3.50 (m, 1H), 3.36 (dd, J=9.6, 6.6 Hz, 1H), 3.30-3.18 (m, 4H), 2.98-2.84 (m, 1H), 2.56 (dd, J=17.2, 9.1 Hz, 1H), 2.48 (dd, J=17.2, 8.0 Hz, 1H), 2.15 (s, 3H), 1.43 (d, J=6.1 Hz, 3H).

LCMS-ESI$^+$ (m/z): [M+H]$^+$ calcd for C₂₅H₂₉N₄O₃S: 465.2; found: 465.3.

Example 4.32

Preparation of (R)-4-((R)-1-((5-(4-(4-(methylsulfonyl)piperazin-1-yl)phenyl)benzo[d]thiazol-7-yl)oxy)ethyl)pyrrolidin-2-one The crude TFA salt of 4.27 (0.088 mmol) was suspended in DCM (2 mL) and Et₃N (120 μL, 0.88 mmol) was added followed by methanesulfonic anhydride (20 mg, 0.11 mmol). The resulting mixture was stirred 2 h and was partitioned between EtOAc and water. The phases were separated, and the aqueous phase was extracted with EtOAc (2×20 mL). The combined organic phase was dried over Na₂SO₄, filtered, and concentrated. The crude product was purified by silica gel chromatography (0-15% MeOH in DCM) to afford (R)-4-((R)-1-((5-(4-(4-(methylsulfonyl)piperazin-1-yl)phenyl)benzo[d]thiazol-7-yl)oxy)ethyl)pyrrolidin-2-one (4.32).

$^1$H NMR (400 MHz, Chloroform-d) δ 8.98 (s, 1H), 7.93 (d, J=1.3 Hz, 1H), 7.62-7.53 (m, 2H), 7.08-7.00 (m, 3H), 6.10 (s, 1H), 4.75-4.59 (m, 1H), 3.59-3.50 (m, 1H), 3.45-3.39 (m, 4H), 3.39-3.31 (m, 5H), 2.96-2.86 (m, 1H), 2.84 (s, 3H), 2.62-2.42 (m, 2H), 1.43 (d, J=6.1 Hz, 3H).

LCMS-ESI$^+$ (m/z): [M+H]$^+$ calcd for C₂₄H₂₉N₄O₄S₂: 501.2; found: 501.4.

Example 4.33

Preparation of (R)-4-((R)-1-((5-(5-(4-(cyclopropanecarbonyl)piperazin-1-yl)pyridin-2-yl)benzo[d]thiazol-7-yl)oxy)ethyl)pyrrolidin-2-one

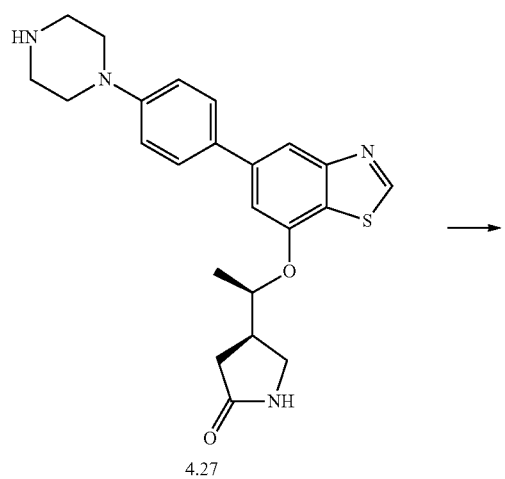

4.27

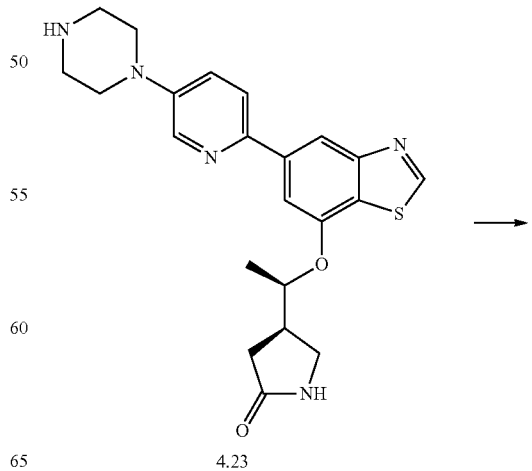

4.23

-continued

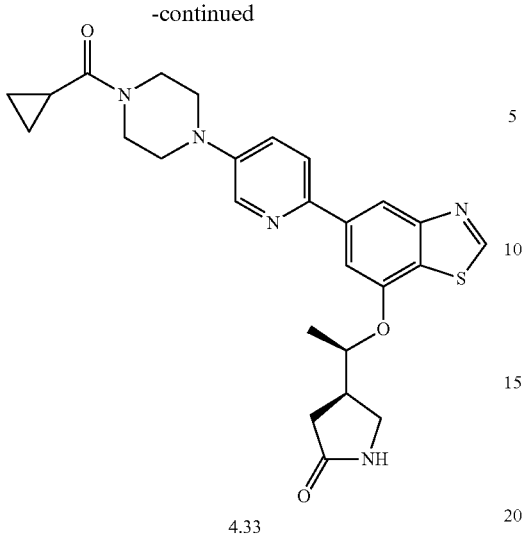

4.33

Cyclopropanecarboxylic acid (9.6 μL, 0.12 mmol) was dissolved in DMF (0.5 mL) along with iPr$_2$NEt (30 μL, 0.17 mmol). To this mixture was added HATU (46 mg, 0.12 mmol). After 10 min, a mixture of the crude TFA salt of 4.23 (0.06 mmol) and iPr$_2$NEt (50 μL, 0.29 mmol) in DMF (0.5 mL) was added. Additional DMF (2×0.25 mL) was used to ensure complete transfer. After 1.5 h, the reaction mixture was partitioned between EtOAc, water, and sat. aq. NaHCO$_3$. The phases were separated, and the aqueous phase was extracted with EtOAc. The combined organic phase was dried over Na$_2$SO$_4$, filtered, and concentrated. The crude product was purified by silica gel chromatography (0-25% MeOH in DCM) to afford (R)-4-((R)-1-((5-(5-(4-(cyclopropanecarbonyl)piperazin-1-yl)pyridin-2-yl)benzo[d]thiazol-7-yl)oxy)ethyl)pyrrolidin-2-one (4.33).

$^1$H NMR (400 MHz, Chloroform-d) δ 8.98 (s, 1H), 8.39 (d, J=2.9 Hz, 1H), 8.19 (d, J=1.2 Hz, 1H), 7.77 (d, J=8.8 Hz, 1H), 7.72 (s, 1H), 7.31 (dd, J=8.8, 3.0 Hz, 1H), 5.85 (s, 1H), 4.86-4.76 (m, 1H), 3.96-3.75 (m, 4H), 3.59-3.50 (m, 1H), 3.41-3.21 (m, 5H), 2.99-2.83 (m, 1H), 2.62-2.39 (m, 2H), 1.83-1.73 (m, 1H), 1.44 (d, J=6.1 Hz, 3H), 1.07-0.98 (m, 2H), 0.87-0.76 (m, 2H).

LCMS-ESI$^+$ (m/z): [M+H]$^+$ calcd for C$_{26}$H$_{30}$N$_5$O$_3$S: 492.2; found: 492.4.

Example 4.35

Preparation of (R)-4-((R)-1-((5-(4-(4-acetylpiperazin-1-yl)-3-methoxyphenyl)benzo[d]thiazol-7-yl)oxy)ethyl)pyrrolidin-2-one

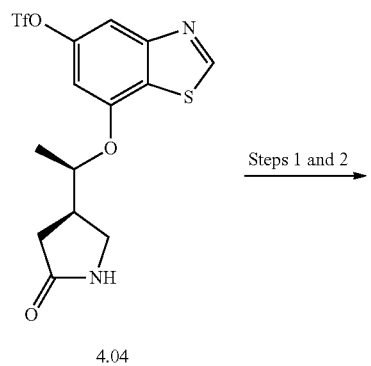

4.04

Steps 1 and 2 →

-continued

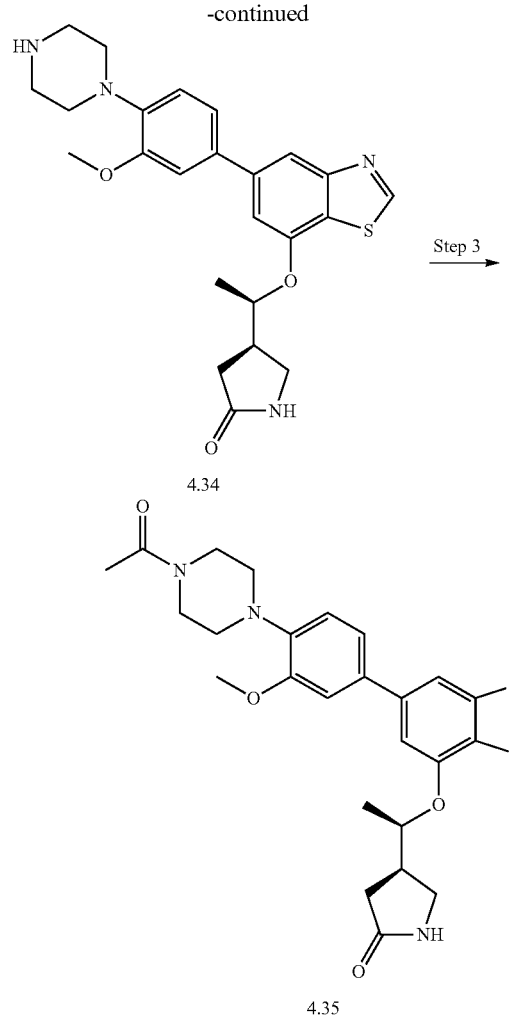

4.34

Step 3 →

4.35

Step 1: 7-((R)-1-((R)-5-oxopyrrolidin-3-yl)ethoxy)benzo[d]thiazol-5-yl trifluoromethanesulfonate (4.04) (100.7 mg, 0.245 mmol), tert-butyl 4-(2-methoxy-4-(4,4,5,5-tetramethyl-1,3,2-dioxaborolan-2-yl)phenyl)piperazine-1-carboxylate 7.08 (144 mg, 0.344 mmol), Pd(OAc)$_2$ (2.8 mg, 0.012 mmol), 2-Dicyclohexylphosphino-2',4',6'-triisopropylbiphenyl (12 mg 0.025 mmol), and K$_3$PO$_4$ (155 mg, 0.73 mmol) were taken up in THF (3.6 mL) under Ar. Water (0.36 mL) was added and the resulting stirred mixture was heated to 65° C. After 1.25 h, the reaction mixture was cooled and was partitioned between EtOAc, water, and brine. The phases were separated, and the aqueous phase was extracted with EtOAc. The combined organic phase was dried over Na$_2$SO$_4$, filtered, and concentrated. The crude residue was purified by silica gel chromatography to afford tert-butyl 4-(2-methoxy-4-(7-((R)-1-((R)-5-oxopyrrolidin-3-yl)ethoxy)benzo[d]thiazol-5-yl)phenyl)piperazine-1-carboxylate. LCMS-ESI$^+$ (m/z): [M+H]$^+$ calcd for C$_{29}$H$_{37}$N$_4$O$_5$S: 553.3; found: 552.8.

Step 2: tert-butyl 4-(2-methoxy-4-(7-((R)-1-((R)-5-oxopyrrolidin-3-yl)ethoxy)benzo[d]thiazol-5-yl)phenyl)piperazine-1-carboxylate (120 mg, 0.22 mmol) was dissolved in TFA (4 mL). The reaction was stirred 1.75 h and was concentrated in vacuo to afford the TFA salt of (R)-4-((R)-1-((5-(3-methoxy-4-(piperazin-1-yl)phenyl)benzo[d]thiazol-7-yl)oxy)ethyl)pyrrolidin-2-one (4.34) as a crude oil used without further purification. LCMS-ESI$^+$ (m/z): [M+H]$^+$ calcd for C$_{24}$H$_{29}$N$_4$O$_3$S: 453.2. found: 452.9.

Step 3: The crude TFA salt of 4.34 (0.072 mmol) was suspended in DCM (1 mL) and Et₃N (72 μL, 0.51 mmol) was added followed by acetic anhydride (8.2 μL, 0.086 mmol). The resulting mixture was stirred 1.5 h and was partitioned between EtOAc, water, and brine. The phases were separated, and the aqueous phase was extracted with EtOAc. The combined organic phase was dried over Na₂SO₄, filtered, and concentrated. The crude product was purified by silica gel chromatography (0-15% MeOH in DCM) to afford (R)-4-((R)-1-((5-(4-(4-acetylpiperazin-1-yl)-3-methoxyphenyl)benzo[d]thiazol-7-yl)oxy)ethyl)pyrrolidin-2-one (4.35).

¹H NMR (400 MHz, Chloroform-d) δ 9.00 (s, 1H), 7.95 (d, J=1.3 Hz, 1H), 7.23-7.15 (m, 2H), 7.2-6.95 (br, 1H), 7.07-7.03 (m, 1H), 5.49 (s, 1H), 4.75-4.62 (m, 1H), 3.99 (s, 3H), 3.95-3.64 (m, 4H), 3.62-3.52 (m, 1H), 3.36 (dd, J=9.6, 6.5 Hz, 1H), 3.30-3.03 (m, 4H), 3.01-2.84 (m, 1H), 2.57 (dd, J=17.1, 9.1 Hz, 1H), 2.49 (dd, J=17.2, 7.9 Hz, 1H), 2.16 (s, 3H), 1.44 (d, J=6.1 Hz, 3H).

LCMS-ESI⁺ (m/z): [M+H]⁺ calcd for $C_{26}H_{31}N_4O_4S$: 495.2; found: 495.1.

Example 4.36

Preparation of (R)-4-((R)-1-((5-(3-methoxy-4-(oxetan-3-yl)piperazin-1-yl)phenyl)benzo[d]thiazol-7-yl)oxy)ethyl)pyrrolidin-2-one Using the procedure described for Example 4.25 starting with the TFA salt of (R)-4-((R)-1-((5-(3-methoxy-4-(piperazin-1-yl)phenyl)benzo[d]thiazol-7-yl)oxy)ethyl)pyrrolidin-2-one 4.34, (R)-4-((R)-1-((5-(3-methoxy-4-(oxetan-3-yl)piperazin-1-yl)phenyl)benzo[d]thiazol-7-yl)oxy)ethyl)pyrrolidin-2-one 4.36 was prepared.

¹H NMR (400 MHz, Chloroform-d) δ 8.99 (s, 1H), 7.95 (d, J=1.3 Hz, 1H), 7.19 (dd, J=8.1, 2.0 Hz, 1H), 7.14 (d, J=2.0 Hz, 1H), 7.08-7.01 (m, 2H), 5.79 (s, 1H), 4.78-4.61 (m, 5H), 3.95 (s, 3H), 3.69-3.60 (m, 1H), 3.60-3.51 (m, 1H), 3.36 (dd, J=9.6, 6.6 Hz, 1H), 3.29-3.14 (m, 4H), 2.99-2.83 (m, 1H), 2.68-2.52 (m, 5H), 2.49 (dd, J=17.2, 7.9 Hz, 1H), 1.43 (d, J=6.1 Hz, 3H).

LCMS-ESI⁺ (m/z): [M+H]⁺ calcd for $C_{27}H_{33}N_4O_4S$: 509.2; found: 509.3.

Example 4.37

Preparation of (R)-4-((R)-1-((5-(3-methoxy-4-(4-(methylsulfonyl)piperazin-1-yl)phenyl)benzo[d]thiazol-7-yl)oxy)ethyl)pyrrolidin-2-one

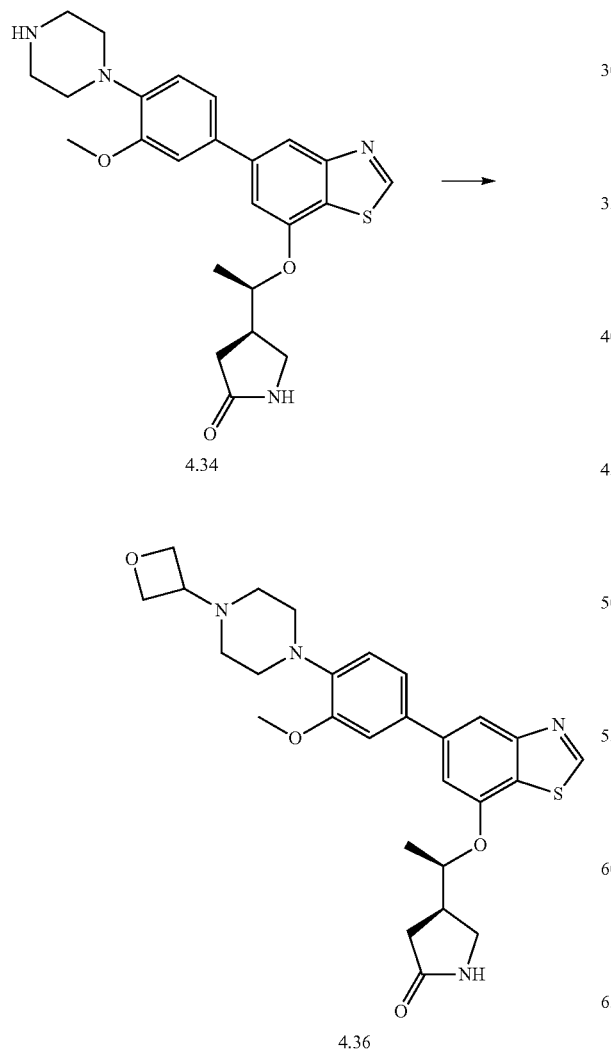

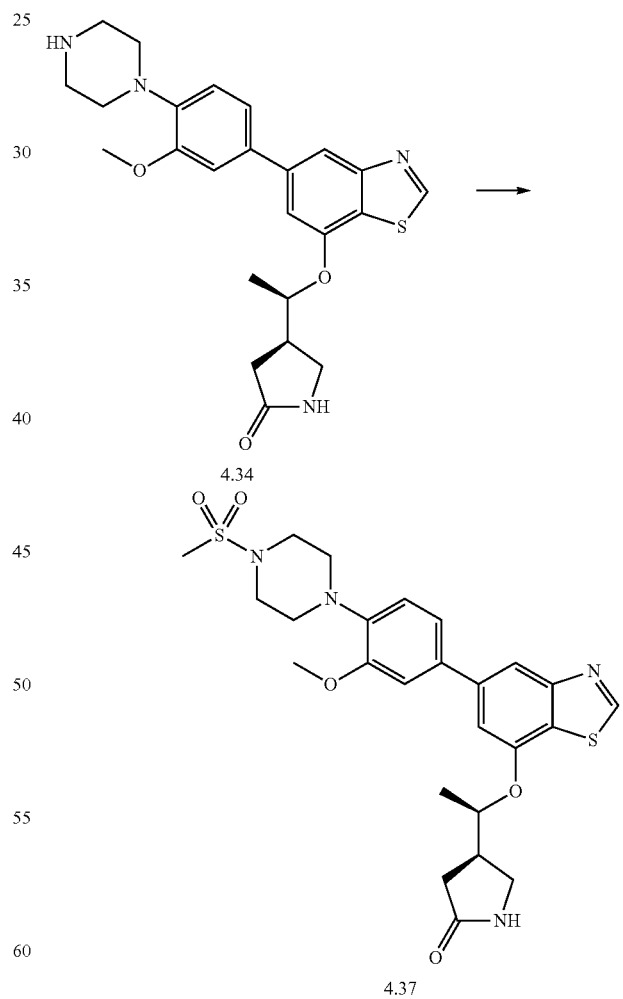

(R)-4-((R)-1-((5-(3-methoxy-4-(4-(methylsulfonyl)piperazin-1-yl)phenyl)benzo[d]thiazol-7-yl)oxy)ethyl)pyrrolidin-2-one 4.37 was prepared using a procedure analogous to that described for Example 4.32 starting with the crude TFA salt of (R)-4-((R)-1-((5-(3-methoxy-4-(piperazin-1-yl)phenyl)benzo[d]thiazol-7-yl)oxy)ethyl)pyrrolidin-2-one 4.34.

¹H NMR (400 MHz, Chloroform-d) δ 8.99 (s, 1H), 7.94 (d, J=1.2 Hz, 1H), 7.22-7.17 (m, 1H), 7.15 (d, J=1.9 Hz, 1H), 7.07-6.99 (m, 2H), 6.14 (s, 1H), 4.73-4.60 (m, 1H), 3.96 (s, 3H), 3.62-3.51 (m, 1H), 3.51-3.40 (m, 4H), 3.35 (dd, J=9.7, 6.6 Hz, 1H), 3.28-3.19 (m, 4H), 2.97-2.86 (m, 1H), 2.83 (s, 3H), 2.63-2.41 (m, 2H), 1.43 (d, J=6.1 Hz, 3H).

LCMS-ESI⁺ (m/z): [M+H]⁺ calcd for $C_{25}H_{31}N_4O_5S_2$: 531.2; found: 531.1.

Example 4.39

Preparation of (R)-4-((R)-1-((5-(5-(4-acetylpiperazin-1-yl)-6-methoxypyridin-2-yl)benzo[d]thiazol-7-yl)oxy)ethyl)pyrrolidin-2-one

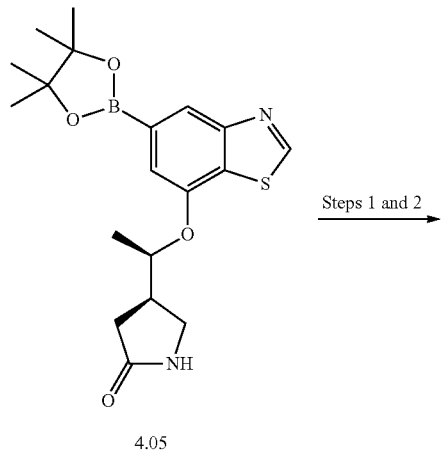

4.05

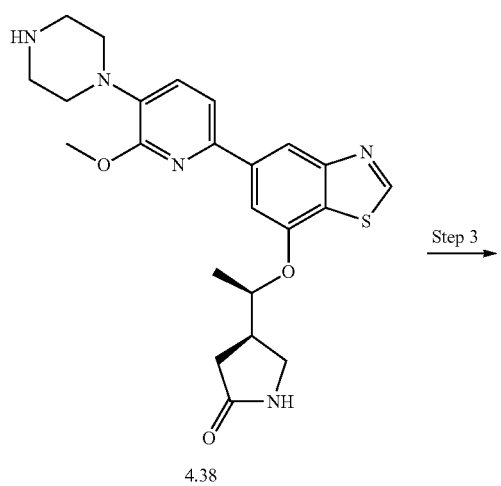

4.38

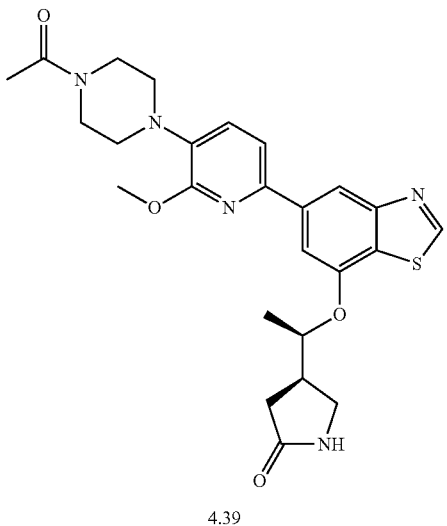

4.39

Step 1: (R)-4-((R)-1-(5-(4,4,5,5-tetramethyl-1,3,2-dioxaborolan-2-yl)benzo[d]thiazol-7-yloxy)ethyl)pyrrolidin-2-one (4.05) (43 mg, 0.11 mmol), tert-butyl 4-(6-chloro-2-methoxypyridin-3-yl)piperazine-1-carboxylate 7.10 (50 mg, 0.15 mmol), K₃PO₄ (70.5 mg, 0.33 mmol), and bis(di-tert-butyl(4-dimethylaminophenyl)phosphine)dichloropalladium(II) (1.8 mg, 0.003 mmol) were taken up in 1,4-dioxane (1.6 mL) and water (0.16 mL) under Ar. The reaction mixture was stirred at 100° C. for 1.5 h and was then partitioned between EtOAc, water, and brine. The phases were separated, and the aqueous phase was dried over Na₂SO₄, filtered, and concentrated. The crude residue was purified to afford tert-butyl 4-(2-methoxy-6-(7-((R)-1-((R)-5-oxopyrrolidin-3-yl)ethoxy)benzo[d]thiazol-5-yl)pyridin-3-yl)piperazine-1-carboxylate. LCMS-ESI⁺ (m/z): [M+H]⁺ calcd for $C_{28}H_{36}N_5O_5S$: 554.2; found: 554.5.

Step 2: tert-butyl 4-(2-methoxy-6-(7-((R)-1-((R)-5-oxopyrrolidin-3-yl)ethoxy)benzo[d]thiazol-5-yl)pyridin-3-yl)piperazine-1-carboxylate (55.7 mg, 0.101 mmol) was dissolved in TFA (3 mL). The reaction was stirred 1.75 h and was concentrated in vacuo to afford the TFA salt of (R)-4-((R)-1-(5-(6-methoxy-5-(piperazin-1-yl)pyridin-2-yl)benzo[d]thiazol-7-yl)oxy)ethyl)pyrrolidin-2-one (4.38) as a crude oil used without further purification. LCMS-ESI⁺ (m/z): [M+H]⁺ calcd for $C_{23}H_{28}N_5O_3S$: 454.2; found: 453.9.

Step 3: (R)-4-((R)-1-((5-(5-(4-acetylpiperazin-1-yl)-6-methoxypyridin-2-yl)benzo[d]thiazol-7-yl)oxy)ethyl)pyrrolidin-2-one 4.39 was prepared using a procedure analogous to that described for Example 4.31 starting with the TFA salt of (R)-4-((R)-1-((5-(6-methoxy-5-(piperazin-1-yl)pyridin-2-yl)benzo[d]thiazol-7-yl)oxy)ethyl)pyrrolidin-2-one 4.38.

¹H NMR (400 MHz, Chloroform-d) δ 8.98 (s, 1H), 8.35 (d, J=1.2 Hz, 1H), 7.64 (s, 1H), 7.42 (d, J=7.9 Hz, 1H), 7.18 (d, J=7.9 Hz, 1H), 5.95 (s, 1H), 4.76-4.66 (m, 1H), 4.14 (s, 3H), 3.88-3.77 (m, 2H), 3.73-3.63 (m, 2H), 3.60-3.51 (m, 1H), 3.38 (dd, J=9.6, 6.6 Hz, 1H), 3.20-3.05 (m, 4H), 3.00-2.86 (m, 1H), 2.62-2.46 (m, 2H), 2.15 (s, 3H), 1.46 (d, J=6.1 Hz, 3H).

LCMS-ESI⁺ (m/z): [M+H]⁺ calcd for $C_{25}H_{30}N_5O_4S$: 496.2; found: 496.1.

Example 4.40

Preparation of (R)-4-((R)-1-((5-(6-methoxy-5-(4-(methylsulfonyl)piperazin-1-yl)pyridin-2-yl)benzo[d]thiazol-7-yl)oxy)ethyl)pyrrolidin-2-one

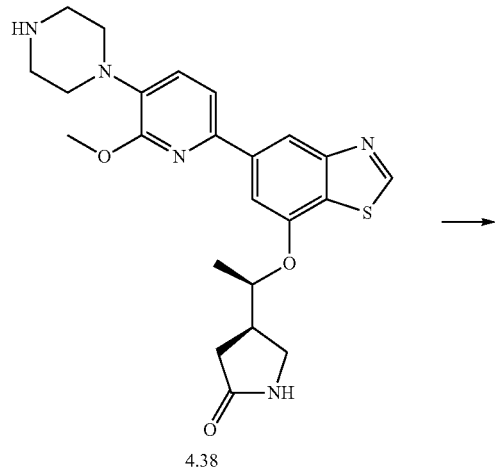

(R)-4-((R)-1-((5-(6-methoxy-5-(4-(methylsulfonyl)piperazin-1-yl)pyridin-2-yl)benzo[d]thiazol-7-yl)oxy)ethyl)pyrrolidin-2-one 4.40 was prepared by a procedure analogous to that described for Example 4.32 starting with the crude TFA salt of 4.38. ¹H NMR (400 MHz, Chloroform-d) δ 8.99 (s, 1H), 8.36 (d, J=1.2 Hz, 1H), 7.63 (s, 1H), 7.43 (d, J=7.9 Hz, 1H), 7.23 (d, J=7.9 Hz, 1H), 5.84 (s, 1H), 4.78-4.63 (m, 1H), 4.14 (s, 3H), 3.59-3.52 (m, 1H), 3.50-3.42 (m, 4H), 3.38 (dd, J=9.6, 6.6 Hz, 1H), 3.29-3.21 (m, 4H), 2.99-2.87 (m, 1H), 2.84 (s, 3H), 2.61-2.45 (m, 2H), 1.46 (d, J=6.1 Hz, 3H).

LCMS-ESI⁺ (m/z): [M+H]⁺ calcd for $C_{24}H_{30}N_5O_5S_2$: 532.2; found: 531.9.

Example 4.41

Preparation of (R)-4-((R)-1-((5-(5-(4-(methylsulfonyl)piperazin-1-yl)pyrazin-2-yl)benzo[d]thiazol-7-yl)oxy)ethyl)pyrrolidin-2-one

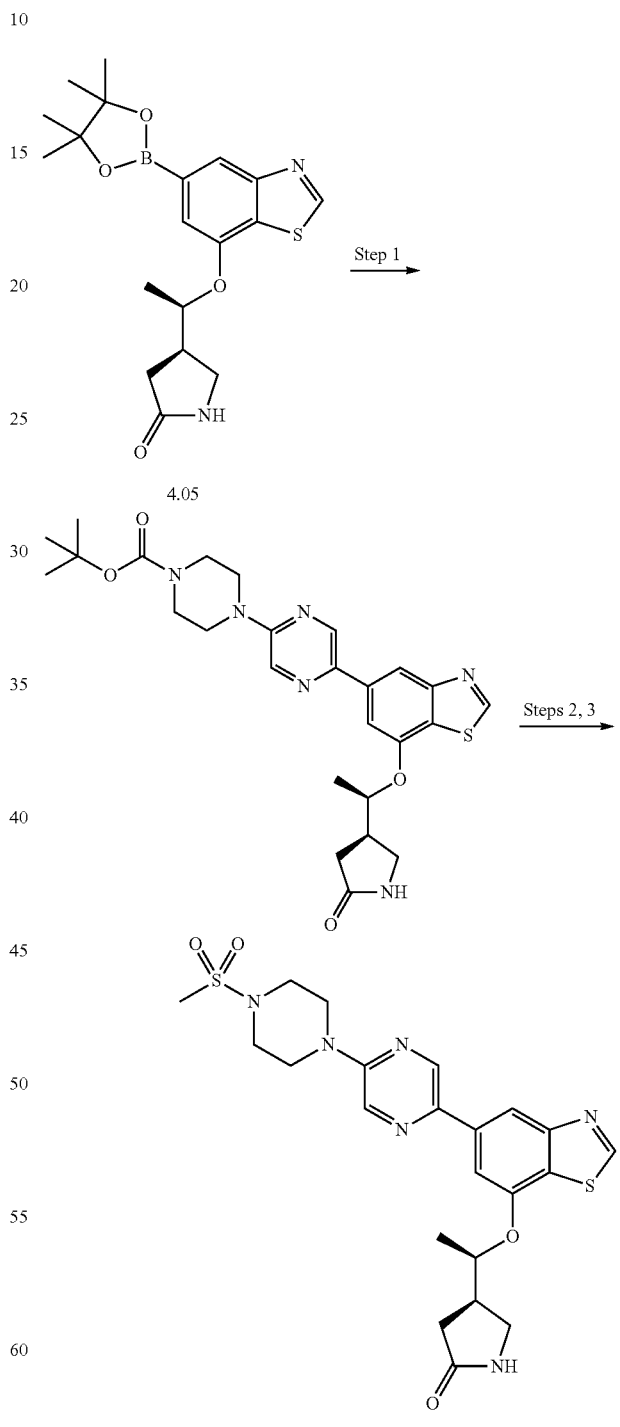

Step 1: (R)-4-((R)-1-(5-(4,4,5,5-tetramethyl-1,3,2-dioxaborolan-2-yl)benzo[d]thiazol-7-yloxy)ethyl)pyrrolidin-2- one 4.05 (40 mg, 0.10 mmol), tert-butyl 4-(5-iodopyrazin-2-yl)piperazine-1-carboxylate 7.11 (48 mg, 0.12 mmol), K₃PO₄ (65.6 mg, 0.31 mmol), and bis(di-tert-butyl(4-dimethylaminophenyl)phosphine)dichloropalladium(II) (1.3 mg, 0.002 mmol) were taken up in 1,4-dioxane (1.5 mL) and water (0.15 mL) under Ar. The reaction mixture was stirred at 100° C. for 40 min and was then partitioned between EtOAc, water, and brine. The phases were separated, and the aqueous phase was extracted with EtOAc. The combined organic phase was dried over Na₂SO₄, filtered, and concentrated. The crude residue was purified by silica gel chromatography (0-15% MeOH in DCM) to afford tert-butyl 4-(5-(7-((R)-1-((R)-5-oxopyrrolidin-3-yl)ethoxy)benzo[d]thiazol-5-yl)pyrazin-2-yl)piperazine-1-carboxylate. LCMS-ESI⁺ (m/z): [M+H]⁺ calcd for C₂₆H₃₃N₆O₄S: 525.2; found: 524.9.

Step 2: tert-butyl 4-(5-(7-((R)-1-((R)-5-oxopyrrolidin-3-yl)ethoxy)benzo[d]thiazol-5-yl)pyrazin-2-yl)piperazine-1-carboxylate (34 mg, 0.065 mmol) was dissolved in TFA (2.5 mL). After stifling 2.5 h, the reaction mixture was concentrated to afford the TFA salt of (R)-4-((R)-1-((5-(5-(piperazin-1-yl)pyrazin-2-yl)benzo[d]thiazol-7-yl)oxy)ethyl)pyrrolidin-2-one that was used directly in the following step.

Step 3: The crude TFA salt of (R)-4-((R)-1-((5-(5-(piperazin-1-yl)pyrazin-2-yl)benzo[d]thiazol-7-yl)oxy)ethyl)pyrrolidin-2-one from step 2 was taken up in DCM (2 mL). Et₃N (0.1 mL, 0.72 mmol) was added followed by methanesulfonic anhydride (15.7 mg, 0.090 mmol). After stirring 1 h, the reaction mixture was concentrated in vacuo and directly purified by silica gel chromatography (0-15% MeOH in DCM) to afford (R)-4-((R)-1-((5-(5-(4-(methylsulfonyl)piperazin-1-yl)pyrazin-2-yl)benzo[d]thiazol-7-yl)oxy)ethyl)pyrrolidin-2-one 4.41.

¹H NMR (400 MHz, Chloroform-d) δ 9.01 (s, 1H), 8.70 (d, J=1.4 Hz, 1H), 8.24 (d, J=1.5 Hz, 1H), 8.21 (d, J=1.2 Hz, 1H), 7.62 (s, 1H), 5.57 (s, 1H), 4.86-4.75 (m, 1H), 3.87-3.78 (m, 4H), 3.61-3.50 (m, 1H), 3.45-3.32 (m, 5H), 2.99-2.88 (m, 1H), 2.84 (s, 3H), 2.63-2.43 (m, 2H), 1.46 (d, J=6.1 Hz, 3H). LCMS-ESI⁺ (m/z): [M+H]⁺ calcd for C₂₂H₂₇N₆O₄S₂: 503.2; found: 502.6.

Example 4.42

Preparation of (R)-4-((R)-1-((5-(6-(4-(methylsulfonyl)piperazin-1-yl)pyridazin-3-yl)benzo[d]thiazol-7-yl)oxy)ethyl)pyrrolidin-2-one

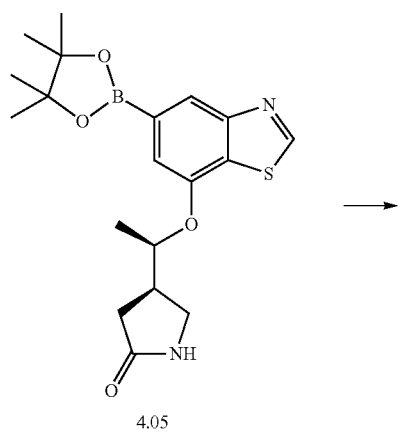

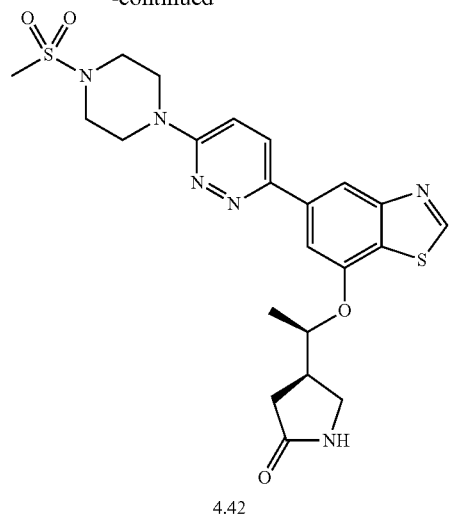

(R)-4-((R)-1-((5-(6-(4-(methylsulfonyl)piperazin-1-yl)pyridazin-3-yl)benzo[d]thiazol-7-yl)oxy)ethyl)pyrrolidin-2-one 4.42 was prepared by a 3-step procedure analogous to that used for Example 4.41 starting with (R)-4-((R)-1-(5-(4,4,5,5-tetramethyl-1,3,2-dioxaborolan-2-yl)benzo[d]thiazol-7-yloxy)ethyl)pyrrolidin-2-one 4.05 and tert-butyl 4-(6-iodopyridazin-3-yl)piperazine-1-carboxylate 7.12.

¹H NMR (400 MHz, Chloroform-d) δ 9.02 (s, 1H), 8.11 (d, J=1.2 Hz, 1H), 8.04 (s, 1H), 7.92 (d, J=9.6 Hz, 1H), 7.16 (d, J=9.5 Hz, 1H), 5.50 (s, 1H), 4.95-4.80 (m, 1H), 3.96-3.86 (m, 4H), 3.62-3.50 (m, 1H), 3.48-3.38 (m, 4H), 3.38-3.29 (m, 1H), 2.98-2.85 (m, 1H), 2.84 (s, 3H), 2.62-2.41 (m, 2H), 1.45 (d, J=6.1 Hz, 3H).

LCMS-ESI⁺ (m/z): [M+H]⁺ calcd for C₂₂H₂₇N₆O₄S₂: 503.2; found: 502.9.

Example 4.43

Preparation of (R)-4-((R)-1-((5-(1-(difluoromethyl)-1H-pyrazol-4-yl)benzo[d]thiazol-7-yl)oxy)ethyl)pyrrolidin-2-one

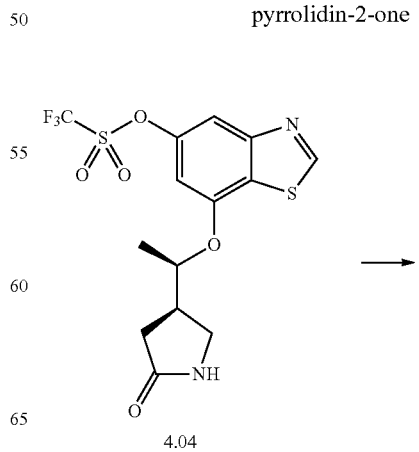

-continued

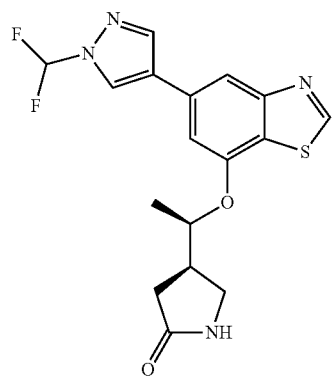

4.43

Following Procedure 4A starting from 7-((R)-1-((R)-5-oxopyrrolidin-3-yl)ethoxy)benzo[d]thiazol-5-yl trifluoromethanesulfonate 4.04 and 1-(difluoromethyl)-4-(4,4,5,5-tetramethyl-1,3,2-dioxaborolan-2-yl)-1H-pyrazole, (R)-4-((R)-1-((5-(1-(difluoromethyl)-1H-pyrazol-4-yl)benzo[d]thiazol-7-yl)oxy)ethyl)pyrrolidin-2-one 4.43 was synthesized.

$^1$HNMR (400 MHz, Chloroform-d) δ 9.02 (s, 1H), 8.11 (s, 1H), 7.99 (s, 1H), 7.92 (d, J=1.2 Hz, 1H), 7.25 (t, J=60.5 Hz, 1H), 6.98 (s, 1H), 5.69 (s, 1H), 4.74-4.63 (m, 1H), 3.62-3.53 (m, 1H), 3.36 (dd, J=9.6, 6.6 Hz, 1H), 3.01-2.86 (m, 1H), 2.64-2.43 (m, 2H), 1.45 (d, J=6.2 Hz, 3H).

LCMS-ESI$^+$ (m/z): [M+H]$^+$ calcd for $C_{17}H_{17}F_2N_4O_2S$: 379.1; found: 379.1.

TABLE C

Analogs 4.44-4.48 prepared using General Method 4B Starting with (R)-4-((R)-1-(5-(4,4,5,5-tetramethyl-1,3,2-dioxaborolan-2-yl)benzo[d]thiazol-7-yloxy)ethyl)pyrrolidin-2-one 4.05

| Example # | Aryl Halide | Product/Salt  Proton NMR | LCMS-ESI$^+$ (m/z): [M + H]$^+$ |
|---|---|---|---|
| 4.44 | 7.53 | | Calc: 385.1  Found: 385.0 |

(400 MHz, Chloroform-d) δ 8.98 (s, 1H), 8.11 (d, J = 1.2 Hz, 1H), 7.64 (d, J = 2.4 Hz, 1H), 7.55-7.52 (m, 1H), 6.72 (d, J = 2.4 Hz, 1H), 5.91 (s, 1H), 5.58-5.48 (m, 1H), 5.20-5.14 (m, 2H), 5.12-5.06 (m, 2H), 4.82-4.73 (m, 1H), 3.60-3.51 (m, 1H), 3.38 (dd, J = 9.6, 6.7 Hz, 1H), 2.98-2.85 (m, 1H), 2.63-2.44 (m, 2H), 1.45 (d, J = 6.1 Hz, 3H)

TABLE C-continued

Analogs 4.44-4.48 prepared using General Method 4B Starting with (R)-4-((R)-1-(5-(4,4,5,5-tetramethyl-1,3,2-dioxaborolan-2-yl)benzo[d]thiazol-7-yloxy)ethyl)pyrrolidin-2-one 4.05

| Example # | Aryl Halide | Product/Salt<br>Proton NMR | LCMS-ESI⁺<br>(m/z): [M + H]⁺ |
|---|---|---|---|
| 4.45 | 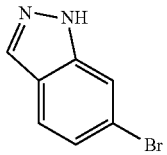 | 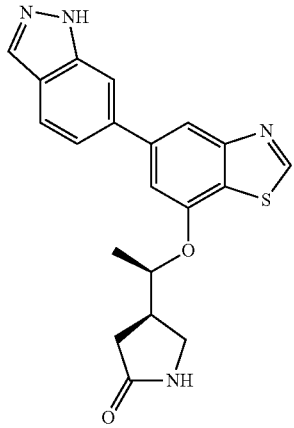 [SMILES: C[C@@H](Oc1cc(-c2ccc3cn[nH]c3c2)cc2ncsc12)[C@H]1CNC(=O)C1]<br>(400 MHz, Chloroform-d) δ 9.01 (s, 1H), 8.13 (s, 1H), 8.03 (d, J = 1.3 Hz, 1H), 7.85 (dd, J = 8.4, 0.8 Hz, 1H), 7.76 (s, 1H), 7.48 (dd, J = 8.4, 1.4 Hz, 1H), 7.14 (s, 1H), 6.16 (s, 1H), 4.76-4.65 (m, 1H), 3.63-3.53 (m, 1H), 3.49 (s, 1H), 3.37 (dd, J = 9.7, 6.4 Hz, 1H), 2.99-2.83 (m, 1H), 2.67-2.45 (m, 2H), 1.45 (d, J = 6.1 Hz, 3H) | Calc: 379.1<br>Found: 379.1 |
| 4.46 | 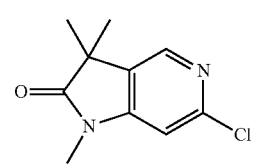 | 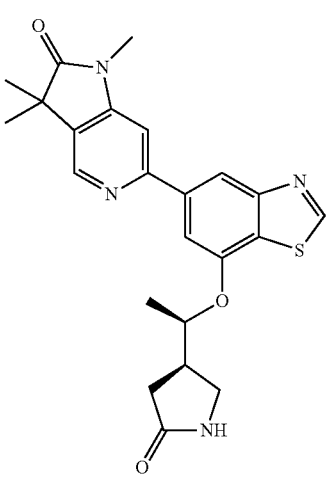 [SMILES: C[C@@H](Oc1cc(-c2cc3c(cn2)C(C)(C)C(=O)N3C)cc2ncsc12)[C@H]1CNC(=O)C1]<br>(400 MHz, Chloroform-d) δ 9.02 (s, 1H), 8.40 (d, J = 0.8 Hz, 1H), 8.25 (d, J = 1.2 Hz, 1H), 7.75 (s, 1H), 7.33 (s, 1H), 5.96 (s, 1H), 4.89-4.78 (m, 1H), 3.60-3.49 (m, 1H), 3.36 (dd, J = 9.6, 6.7 Hz, 1H), 3.31 (s, 3H), 2.99-2.84 (m, 1H), 2.61-2.44 (m, 2H), 1.47 (s, 6H), 1.45 (d, J = 6.2 Hz, 3H). | Calc: 437.2<br>Found: 436.8 |

TABLE C-continued

Analogs 4.44-4.48 prepared using General Method 4B Starting with
(R)-4-((R)-1-(5-(4,4,5,5-tetramethyl-1,3,2-dioxaborolan-2-yl)benzo[d]thiazol-7-
yloxy)ethyl)pyrrolidin-2-one 4.05

| Example # | Aryl Halide | Product/Salt<br>Proton NMR | LCMS-ESI$^+$<br>(m/z): [M + H]$^+$ |
|---|---|---|---|
| 4.47 | 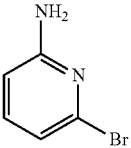 | 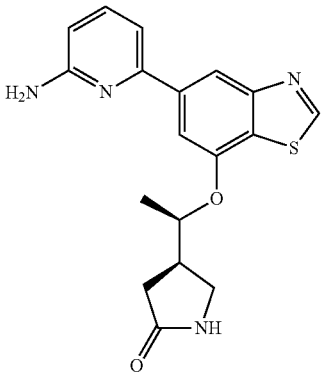 [SMILES: C[C@@H](Oc1cc(-c2cccc(N)n2)cc2ncsc12)[C@H]1CNC(=O)C1] | Calc: 355.1<br>Found: 354.8 |
| | | (400 MHz, Chloroform-d) δ 8.98 (s, 1H), 8.24 (d, J = 1.2 Hz, 1H), 7.70-7.62 (m, 1H), 7.55 (dd, J = 8.1, 7.5 Hz, 1H), 7.20 (dd, J = 7.6, 0.7 Hz, 1H), 6.51 (dd, J = 8.2, 0.7 Hz, 1H), 5.90 (s, 1H), 4.83-4.64 (m, 3H), 3.56-3.46 (m, 1H), 3.34 (dd, J = 9.5, 6.6 Hz, 1H), 2.97-2.82 (m, 1H), 2.61-2.44 (m, 2H), 1.42 (d, J = 6.1 Hz, 3H). | |
| 4.48 | 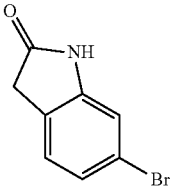 | 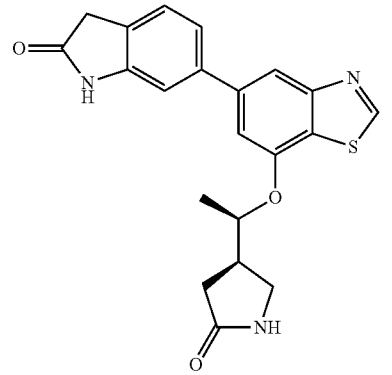 [SMILES: C[C@@H](Oc1cc(-c2ccc3c(c2)NC(=O)C3)cc2ncsc12)[C@H]1CNC(=O)C1] | Calc: 394.2<br>Found: 394.2 |
| | | (400 MHz, Methanol-d4) δ 9.23 (s, 1H), 7.87 (d, J = 1.3 Hz, 1H), 7.36-7.34 (m, 2H), 7.28-7.26 (m, 1H), 7.22-7.20 (m, 1H), 4.90-4.84 (m, 1H), 3.62-3.54 (m, 3H), 3.37-3.31 (m, 1H), 2.99-2.87 (m, 1H), 2.56 (dd, J = 17.2, 9.2 Hz, 1H), 2.47 (dd, J = 17.2, 7.5 Hz, 1H), 1.42 (d, J = 6.1 Hz, 3H). | |

Example 4.49

Preparation of (R)-4-((R)-1-((5-(1H-pyrazolo[3,4-b]pyridin-6-yl)benzo[d]thiazol-7-yl)oxy)ethyl)pyrrolidin-2-one

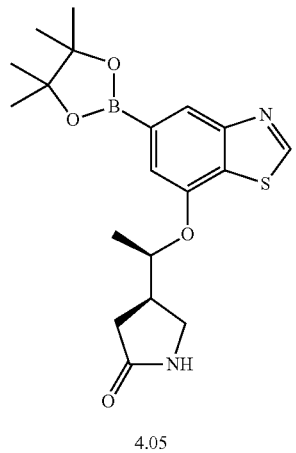

4.05

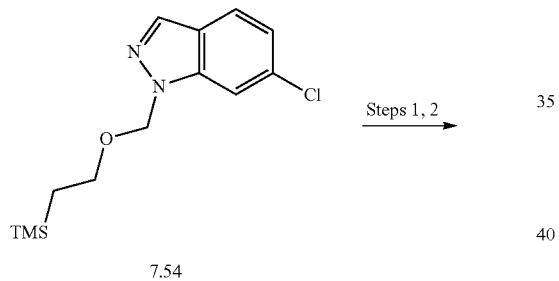

Step 1: (R)-4-((R)-1-(5-(4,4,5,5-tetramethyl-1,3,2-dioxaborolan-2-yl)benzo[d]thiazol-7-yloxy)ethyl)pyrrolidin-2-one (4.05) (20 mg, 0.052 mmol), Intermediate 7.54 (22 mg, 0.077 mmol), K₃PO₄ (40 mg, 0.19 mmol), and bis(di-tert-butyl(4-dimethylaminophenyl)phosphine)dichloropalladium(II) (1 mg, 0.001 mmol) were taken up in 1,4-dioxane (0.9 mL) and water (0.09 mL) under Ar. The stirred reaction mixture was heated to 100° C. After 1 h, the reaction mixture was partitioned between EtOAc, water, and brine. The phases were separated, and the aqueous phase was extracted with EtOAc. The combined organic phase was dried over Na₂SO₄, filtered, and concentrated. The crude residue was purified by silica gel chromatography (40-100% acetone in hexanes) to afford a major product that was used directly in the following step.

Step 2: The major product from above was dissolved in TFA (2 mL). The reaction mixture was stirred 1.25 h and was concentrated in vacuo. The crude residue was dissolved in MeOH and filtered through an Agilent Stratospheres PL-HCO₃ resin cartridge to afford a crude residue. Purification by silica gel chromatography (0-20% MeOH in DCM) provided (R)-4-((R)-1-(5-(1H-pyrazolo[3,4-b]pyridin-6-yl)benzo[d]thiazol-7-yl)oxy)ethyl)pyrrolidin-2-one (4.49).

$^1$H NMR (400 MHz, Chloroform-d) δ 9.05 (s, 1H), 8.38 (d, J=1.3 Hz, 1H), 8.26 (d, J=8.4 Hz, 1H), 8.15 (s, 1H), 7.84 (s, 1H), 7.78 (d, J=8.4 Hz, 1H), 6.06 (s, 1H), 4.96-4.83 (m, 1H), 3.63-3.51 (m, 1H), 3.38 (dd, J=9.7, 6.5 Hz, 1H), 3.01-2.84 (m, 1H), 2.65-2.48 (m, 2H), 1.47 (d, J=6.1 Hz, 3H).

LCMS-ESI⁺ (m/z): [M+H]⁺ calcd for C₁₉H₁₈N₅O₂S: 380.1; found: 379.9.

Example 4.50

Preparation of 3,3-dimethyl-6-(74(R)-1-((R)-5-oxopyrrolidin-3-yl)ethoxy)benzo[d]thiazol-5-yl)-1H-pyrrolo[3,2-c]pyridin-2(3H)-one

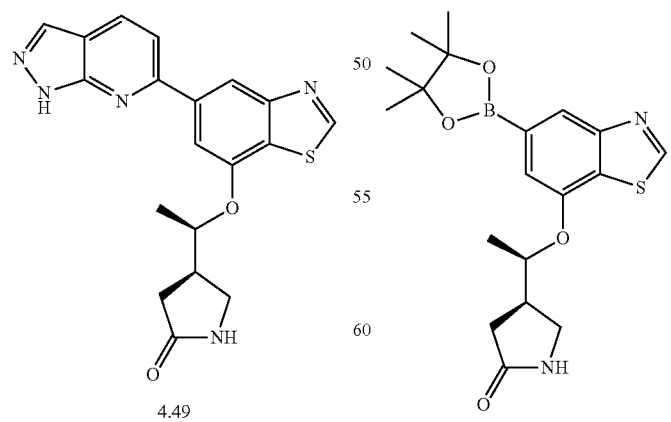

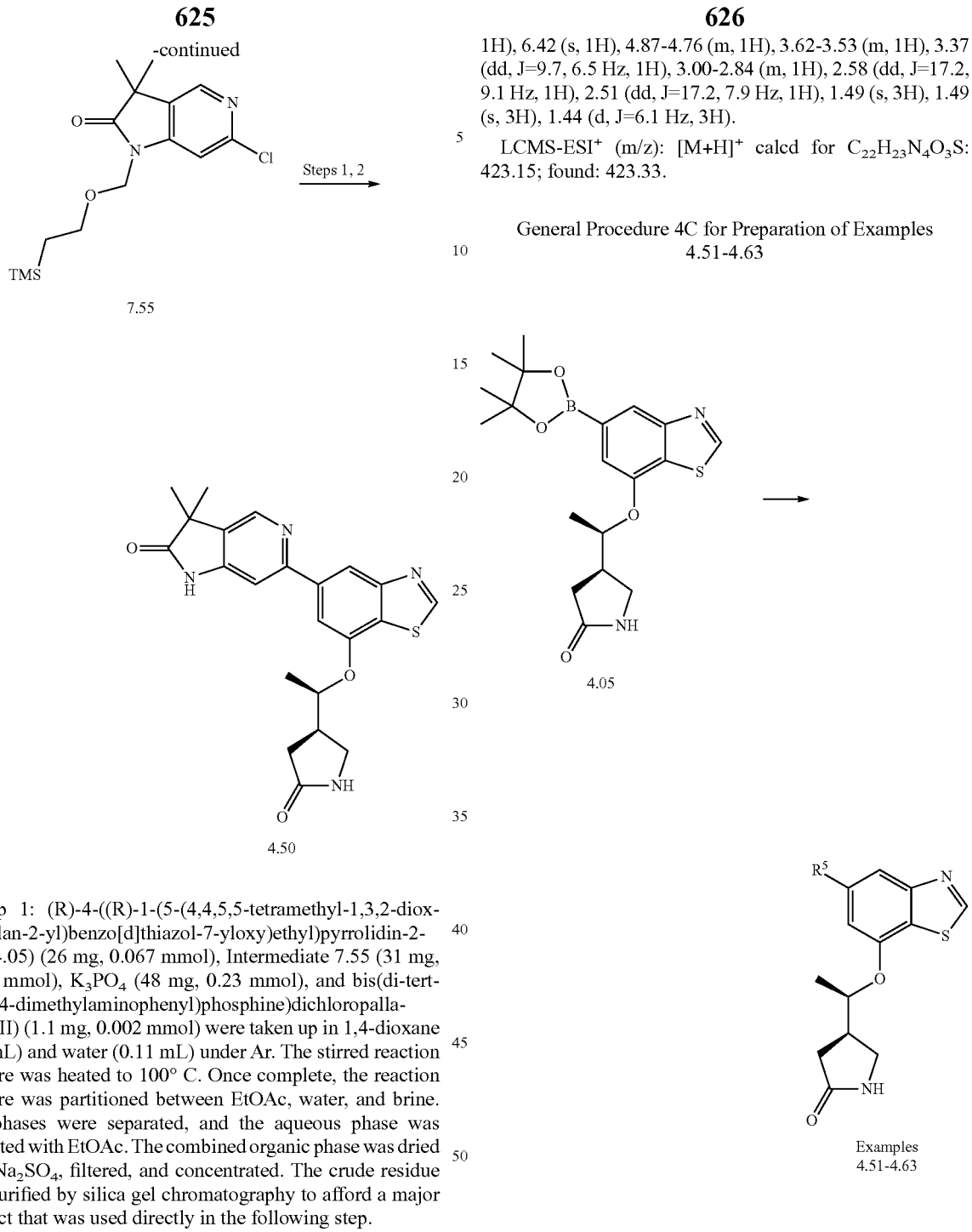

Step 1: (R)-4-((R)-1-(5-(4,4,5,5-tetramethyl-1,3,2-dioxaborolan-2-yl)benzo[d]thiazol-7-yloxy)ethyl)pyrrolidin-2-one (4.05) (26 mg, 0.067 mmol), Intermediate 7.55 (31 mg, 0.094 mmol), K$_3$PO$_4$ (48 mg, 0.23 mmol), and bis(di-tert-butyl(4-dimethylaminophenyl)phosphine)dichloropalladium(II) (1.1 mg, 0.002 mmol) were taken up in 1,4-dioxane (1.1 mL) and water (0.11 mL) under Ar. The stirred reaction mixture was heated to 100° C. Once complete, the reaction mixture was partitioned between EtOAc, water, and brine. The phases were separated, and the aqueous phase was extracted with EtOAc. The combined organic phase was dried over Na$_2$SO$_4$, filtered, and concentrated. The crude residue was purified by silica gel chromatography to afford a major product that was used directly in the following step.

Step 2: The major product from above was dissolved in TFA (1 mL). The reaction mixture was stirred 2.5 h and was concentrated in vacuo. To the resulting crude solid was added 5% aqueous Na$_2$CO$_3$. The mixture was stirred vigorously at r.t. until no formaldehyde hemiaminal was observed via LC/MS. The mixture was diluted with DCM and the phases were separated. The aqueous phase was extracted with EtOAc and the combined organics were dried over Na$_2$SO$_4$, filtered, and concentrated. The crude residue was purified by silica gel chromatography (0-20% MeOH in DCM) to afford 3,3-dimethyl-6-(7-((R)-1-((R)-5-oxopyrrolidin-3-yl)ethoxy)benzo[d]thiazol-5-yl)-1H-pyrrolo[3,2-c]pyridin-2(3H)-one (4.50).

$^1$H NMR (400 MHz, Chloroform-d) δ 9.92 (s, 1H), 9.06 (s, 1H), 8.42 (s, 1H), 8.22 (d, J=1.2 Hz, 1H), 7.73 (s, 1H), 7.44 (s, 1H), 6.42 (s, 1H), 4.87-4.76 (m, 1H), 3.62-3.53 (m, 1H), 3.37 (dd, J=9.7, 6.5 Hz, 1H), 3.00-2.84 (m, 1H), 2.58 (dd, J=17.2, 9.1 Hz, 1H), 2.51 (dd, J=17.2, 7.9 Hz, 1H), 1.49 (s, 3H), 1.49 (s, 3H), 1.44 (d, J=6.1 Hz, 3H).

LCMS-ESI$^+$ (m/z): [M+H]$^+$ calcd for C$_{22}$H$_{23}$N$_4$O$_3$S: 423.15; found: 423.33.

General Procedure 4C for Preparation of Examples 4.51-4.63

Under inert atmosphere, (R)-4-((R)-1-((5-(4,4,5,5-tetramethyl-1,3,2-dioxaborolan-2-yl)benzo[d]thiazol-7-yl)oxy)ethyl)pyrrolidin-2-one 4.05 (1 equiv), aryl halide (1.2-3 equiv), cesium carbonate (3 equiv), and PEPPSI-IPr catalyst (0.01-0.1 equiv) were taken up in 2:1 DME:water. The stirred mixture was heated to 85-100° C. until the reaction was judged complete. The reaction mixture was then diluted with water and extracted with ethyl acetate. The combined organics were dried, filtered, and concentrated under reduced pressure and resulting residues were purified by silica gel column chromatography or reverse phase HPLC (MeCN:water gradient+TFA modifier) to yield Examples 4.51-4.63 as free bases or TFA salts, depicted in Table D below.

TABLE D

| Example # | Aryl Halide | Product/Salt Proton NMR | LCMS-ESI+ (m/z): [M + H]+ |
|---|---|---|---|
| 4.51 | (quinazolinone-Br) | (product, TFA salt) | Calc: 407.11 Found: 407.23 |

¹H NMR (400 MHz, CD₃OD) δ 9.28 (s, 1H), 8.35 (dd, J = 8.3, 0.6 Hz, 1H), 8.18 (s, 1H), 8.07-7.92 (m, 3H), 7.43 (s, 1H), 4.95 (q, J = 6.0 Hz, 1H), 3.59 (dd, J = 10.1, 8.6 Hz, 1H), 3.38-3.34 (m, 1H), 2.95 (d, J = 7.8 Hz, 1H), 2.64-2.40 (m, 2H), 1.45 (d, J = 6.1 Hz, 3H).

| 4.52 | (2-methyl-quinazolinone-Br) 7.26 | (product) | Calc: 421.13 Found: 421.30 |

¹H NMR (400 MHz, CD₃OD) δ 9.27 (d, J = 4.4 Hz, 1H), 8.29 (d, J = 8.3 Hz, 1H), 8.05-7.86 (m, 3H), 7.40 (s, 1H), 5.02-4.90 (m, 1H), 3.59 (dd, J = 10.3, 8.4 Hz, 1H), 2.95 (s, 1H), 2.62-2.32 (m, 3H), 1.48-1.38 (m, 3H), 1.28 (s, 3H).

| 4.53 | (2,2-dimethyl-benzoxazinone-Br) | (product) | Calc: 438.1 Found: 438.0 |

¹H NMR (400 MHz, DMSO-d6) δ 10.66 (s, 1H), 9.38 (s 1H), 7.80 (d, J = 0.8 Hz, 1H), 7.57 (s, 1H), 7.35 (dd, J = 2.4, 8.4 Hz, 1H), 7.27 (s, 1H), 7.23 (d, J = 2.4 Hz, 1H), 7.03 (d, J = 8.4 Hz, 1H), 4.86 (pent, J = 6.0 Hz, 1H), 3.35 (t, J = 8.4 Hz, 1H), 3.09 (dd, J = 2.8, 9.6 Hz, 1H), 2.72-2.79 (m, 1H), 2.26-2.32 (m, 1H), 2.18 (dd, J = 8.0, 16.8 Hz, 1H), 1.42 (s, 6H), 1.30 (d, J = 6.0 Hz, 3H).

TABLE D-continued

| Example # | Aryl Halide | Product/Salt Proton NMR | LCMS-ESI+ (m/z): [M + H]+ |
|---|---|---|---|
| 4.54 | 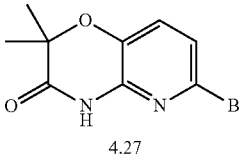 4.27 | 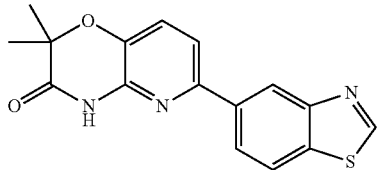 (TFA salt) | Calc: 439.1 Found: 439.1 |

1H NMR (400 MHz, DMSO-d6) δ 11.29 (s, 1H), 9.38 (s, 1H), 8.31 (d, J = 1.2 Hz, 1H), 7.75 (d, J = 8.0 Hz, 1H), 7.73 (s, 1H), 7.58 (s, 1H), 7.45 (d, J = 8.4 Hz, 1H), 4.82 (pent, J = 6.0 Hz, 1H), 3.37 (t, J = 9.2 Hz, 1H), 3.11 (dd, J = 6.8, 9.6 Hz, 1H), 2.75-2.81 (m, 1H), 2.28-2.34 (m, 1H), 2.18 (dd, J = 8.0, 16.8 Hz, 1H), 1.46 (s, 6H), 1.32 (d, J = 6.0 Hz, 3H).

| 4.55 | 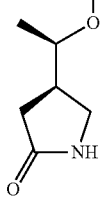 | 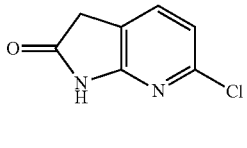 [SMILES: O=C1Cc2ccc(Cl)nc2N1] (TFA salt) | Calc: 395.1 Found: 395.0 |

1H NMR (400 MHz, DMSO-d6) δ 11.08 (s, 1H), 9.39 (s, 1H), 8.32 (s, 1H), 7.64-7.70 (m, 3H), 7.57 (s, 1H), 4.83 (pent, J = 6.0 Hz, 1H), 3.59 (s, 2H), 3.37 (t, J = 8.8 Hz, 1H), 3.10 (dd, J = 6.4, 9.6 Hz, 1H), 2.75-2.80 (m, 1H), 2.16-2.34 (m, 2H), 1.31 (d, J = 6.4 Hz, 3H).

| 4.56 |  7.28 | 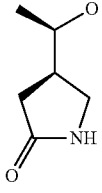 (TFA Salt) | Calc: 437.2 Found: 437.2 |

1H NMR (400 MHz, DMSO-d6) δ 9.40 (s, 1H), 8.41 (s, 1H), 7.79-7.82 (m, 3H), 7.57 (s, 1H), 4.87 (pent, J = 6.0 Hz, 1H), 3.37 (t, J = 9.2 Hz, 1H), 3.27 (s, 3H), 3.10-3.15 (m, 1H), 2.75-2.80 (m, 1H), 2.31 (dd, J = 9.2, 16.8 Hz, 1H), 2.20 (dd, J = 7.6, 16.8 Hz, 1H), 1.32-1.34 (m, 9H).

TABLE D-continued

| Example # | Aryl Halide | Product/Salt Proton NMR | LCMS-ESI+ (m/z): [M + H]+ |
|---|---|---|---|
| 4.57 | 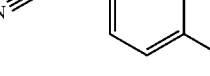 | 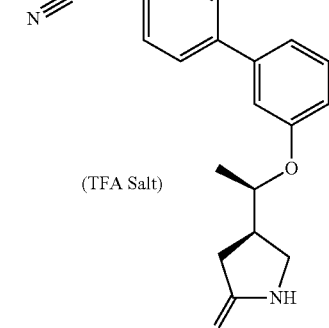 (TFA Salt) | Calc: 406.2 Found: 406.1 |

$^1$H NMR (400 MHz, DMSO-d6) δ 9.39 (s, 1H), 7.96 (s, 1H), 7.84 (d, J = 8.4 Hz, 2H), 7.62 (d, J = 8.4 Hz, 2H), 7.56 (s, 1H), 7.37 (s, 1H), 4.90 (t, J = 6.0 Hz, 1H), 3.36 (t, J = 8.8 Hz, 1H), 3.10 (dd, J = 6.8, 10.0 Hz, 1H), 2.74-2.79 (m, 1H), 2.30 (dd, J = 9.2, 16.8 Hz, 1H), 2.18 (dd, J = 8.0, 16.8 Hz, 1H), 1.73 (s, 6H), 1.30 (d, J = 6.0 Hz, 3H).

| 4.58 | 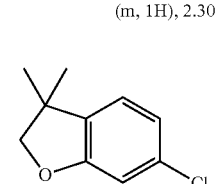 7.48 | 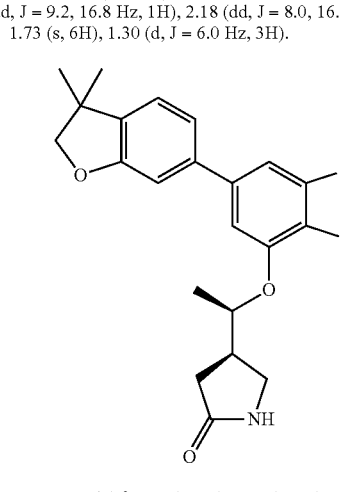 | Calc: 409.2 Found: 409.1 |

$^1$H NMR (400 MHz, DMSO-d6) δ 9.37 (s, 1H), 7.87 (s, 1H), 7.55 (s, 1H), 7.24-7.30 (m, 3H), 7.17 (s, 1H), 4.90 (pent, J = 6.0 Hz, 1H), 4.26 (s, 2H), 3.35 (t, J = 9.2 Hz, 1H), 3.10 (dd, J = 7.2, 10.0 Hz, 1H), 2.72-2.78 (m, 1H), 2.29 (dd, J = 9.2, 16.8 Hz, 1H), 2.17 (dd, J = 8.0, 16.8 Hz, 1H), 1.32 (s, 6H), 1.28 (d, J = 6.4 Hz, 3H).

| 4.59 | 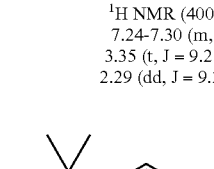 7.29 | 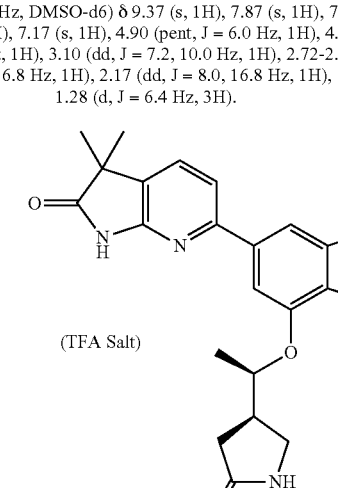 (TFA Salt) | Calc: 423.1 Found: 423.1 |

$^1$H NMR (400 MHz, DMSO-d6) δ 11.06 (s, 1H), 9.39 (s, 1H), 8.31 (s, 1H), 7.77 (d, J = 8.0 Hz, 1H), 7.72 (d, J = 7.2 Hz, 1H), 7.69 (s, 1H), 7.57 (s, 1H), 4.82 (pent, J = 6.0 Hz, 1H), 3.37 (t, J = 8.8 Hz, 1H), 3.11 (dd, J = 6.4, 9.6 Hz, 1H), 2.74-2.80 (m, 1H), 2.31 (dd, J = 9.6, 16.8 Hz, 1H), 2.19 (dd, J = 7.6, 16.8 Hz, 1H), 1.29-1.32 (m, 9H).

TABLE D-continued

| Example # | Aryl Halide | Product/Salt Proton NMR | LCMS-ESI+ (m/z): [M + H]+ |
|---|---|---|---|
| 4.60 | 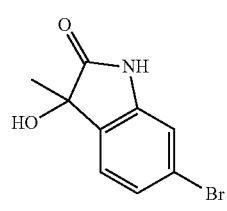 7.45 | 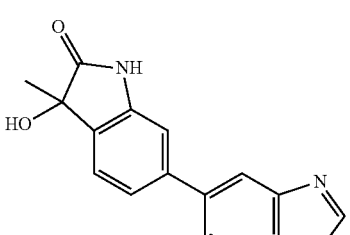 (TFA Salt) (diastereomer mixture) | Calc: 424.1 Found: 424.0 |

1H NMR (400 MHz, DMSO-d6) δ 10.32 (s, 1H), 9.40 (s, 1H), 7.87 (d, J = 1.3 Hz, 1H), 7.58 (s, 1H), 7.44-7.34 (m, 2H), 7.32 (s, 1H), 7.13 (d, J = 1.4 Hz, 1H), 4.96-4.83 (m, 1H), 3.37 (t, J = 9.3 Hz, 1H), 3.12 (dd, J = 9.6, 6.6 Hz, 1H), 2.84-2.71 (m, 1H), 2.37-2.12 (m, 2H), 1.41 (s, 3H), 1.32 (d, J = 6.0 Hz, 3H).

| Example # | Aryl Halide | Product/Salt Proton NMR | LCMS-ESI+ (m/z): [M + H]+ |
|---|---|---|---|
| 4.61 | 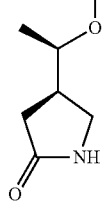 7.46 | 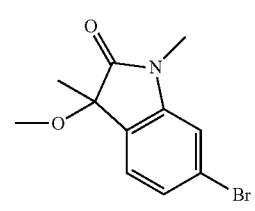 (TFA Salt) (diastereomer mixture) | Calc: 452.2 Found: 452.2 |

1H NMR (400 MHz, DMSO-d6) δ 9.42 (s, 1H), 8.06 (s, 1H), 7.64-7.51 (m, 2H), 7.51-7.36 (m, 3H), 4.93 (p, J = 6.0 Hz, 1H), 3.38 (t, J = 9.1 Hz, 1H), 3.26 (s, 3H), 3.13 (dd, J = 9.7, 6.6 Hz, 1H), 2.91 (s, 3H), 2.84-2.74 (m, 1H), 2.36-2.18 (m, 2H), 1.46 (s, 3H), 1.32 (d, J = 5.8 Hz, 3H).

TABLE D-continued

| Example # | Aryl Halide | Product/Salt Proton NMR | LCMS-ESI⁺ (m/z): [M + H]⁺ |
|---|---|---|---|
| 4.62 | [structure: 4,4-dimethyl-7-bromo-3,4-dihydroquinolin-2(1H)-one] | [structure: product (TFA Salt)] <br> ¹H NMR (400 MHz, DMSO-d6) δ 10.17 (s, 1H), 9.40 (s, 1H), 7.83 (d, J = 1.2 Hz, 1H), 7.58 (s, 1H), 7.39 (d, J = 2.7 Hz, 2H), 7.26 (d, J = 14.9 Hz, 2H), 4.85 (p, J = 6.2, 5.8 Hz, 1H), 3.37 (t, J = 9.1 Hz, 1H), 3.12 (dd, J = 9.7, 6.6 Hz, 1H), 2.85-2.72 (m, 1H), 2.40 (s, 2H), 2.35-2.16 (m, 2H), 1.33 (d, J = 6.0 Hz, 3H), 1.28 (s, 6H). | Calc: 436.2 <br> Found: 436.2 |
| 4.63 | [structure: spirocyclopentane-benzofuranone bromide] <br> 7.51 | [structure: product (TFA Salt)] <br> ¹H NMR (400 MHz, DMSO-d6) δ 11.72 (bs, 1H), 9.60 (s, 1H), 9.39 (s, 1H), 7.82 (d, J = 1.2 Hz, 1H), 7.57 (s, 1H), 7.30-7.25 (m, 2H), 7.14 (dd, J = 8.0, 1.9 Hz, 1H), 7.10 (d, J = 1.9 Hz, 1H), 4.92-4.80 (m, 1H), 3.37 (t, J = 9.2 Hz, 1H), 3.11 (dd, J = 9.7, 6.6 Hz, 1H), 2.82-2.73 (m, 1H), 2.38-2.25 (m, 3H), 2.19 (dd, J = 16.8, 7.9 Hz, 1H), 2.05-1.95 (m, 2H), 1.80-1.55 (m, 4H), 1.32 (d, J = 6.1 Hz, 3H). | Calc: 467.2 <br> Found: 467.0 |

Example 4.64

Preparation of 3,3-dimethyl-6-(74(R)-1-((R)-5-oxopyrrolidin-3-yl)ethoxy)benzo[d]thiazol-5-yl)indolin-2-one

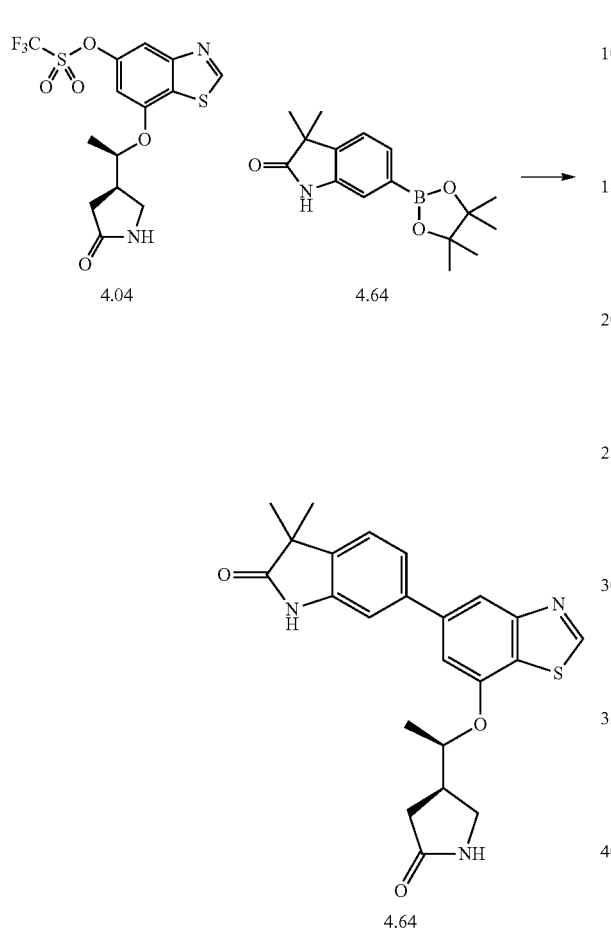

Following General Procedure 4C using 3,3-dimethyl-6-(4,4,5,5-tetramethyl-1,3,2-dioxaborolan-2-yl)indolin-2-one as the boronic ester component (1 eq.) and 7-((R)-1-((R)-5-oxopyrrolidin-3-yl)ethoxy)benzo[d]thiazol-5-yl trifluoromethanesulfonate 4.04 (1 eq.) as an aryl pseudohalide component, 3,3-dimethyl-6-(7-4R)-1-((R)-5-oxopyrrolidin-3-yl)ethoxy)benzo[d]thiazol-5-yl)indolin-2-one 4.64 was synthesized.

$^1$H NMR (400 MHz, Chloroform-d) δ 9.614 (s, 1H), 8.982 (s, 1H), 7.942 (s, 1H), 7.274 (m, 3H), 7.061 (s, 1H), 6.825 (s, 1H), 4.706 (m, 1H), 3.585 (m, 1H), 3.399 (m, 1H), 2.91 (m, 1H), 2.55 (m, 2H), 1.434 (s, 6H), 1.34 (d, J=6 Hz, 3H).

LCMS-ESI$^+$ (m/z): [M+H]$^+$ calcd for $C_{23}H_{24}N_3O_3S$: 422.2; found: 422.2.

Example 4.65

Preparation of (R)-4-((R)-1-((5-(6-aminopyrazin-2-yl)benzo[d]thiazol-7-yl)oxy)ethyl)pyrrolidin-2-one

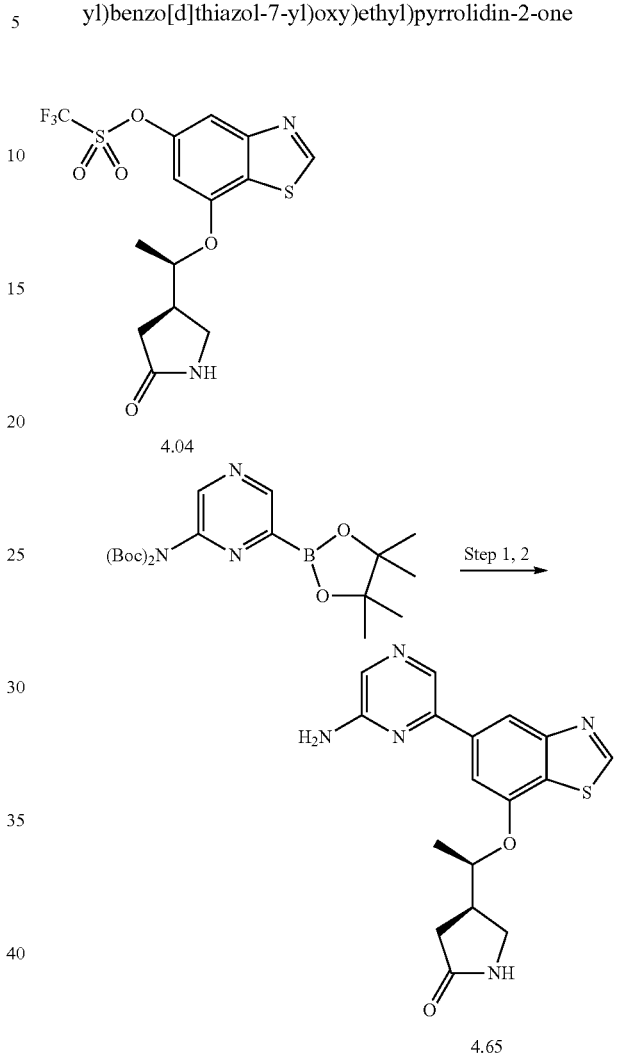

Step 1: Following the General Procedure 4C using 2-Bis(tert-butoxycarbonyl)amino-(6-(4,4,5,5-tetramethyl-1,3,2-dioxaborolan-2-yl))pyrazine as the boronate ester component (1.5 eq.) and 7-((R)-1-((R)-5-oxopyrrolidin-3-yl)ethoxy) benzo[d]thiazol-5-yl trifluoromethanesulfonate (1 eq.) as an aryl pseudohalide component, (R)-4-((R)-1-((5-(6-aminopyrazin-2-yl)benzo[d]thiazol-7-yl)oxy)ethyl)pyrrolidin-2-one was prepared and was used without purification.

Step 2: The crude (R)-4-((R)-1-(5-(6-aminopyrazin-2-yl)benzo[d]thiazol-7-yl)oxy)ethyl)pyrrolidin-2-one from Step 1 was taken up in 10:1 DCM:TFA. After stirring 3 h, the reaction mixture was concentrated and the residue was purified by prep HPLC (MeCN:water gradient, TFA-modified) to afford (R)-4-((R)-1-((5-(6-aminopyrazin-2-yl)benzo[d]thiazol-7-yl)oxy)ethyl)pyrrolidin-2-one as its TFA salt.

$^1$H NMR (400 MHz, DMSO-d6) δ 9.39 (s, 1H), 8.45 (s, 1H), 8.32 (s, 1H), 7.87 (s, 1H), 7.70 (s, 1H), 7.57 (s, 1H), 6.80 (br s, 2H), 4.84 (pent, J=6.0 Hz, 1H), 3.36 (t, J=8.8 Hz, 1H), 3.11 (dd, J=6.8, 10.0 Hz, 1H), 2.72-2.82 (m, 1H), 2.30 (dd, J=9.6, 16.8 Hz, 1H), 2.19 (dd, J=8.0, 16.8 Hz, 1H), 1.31 (d, J=6.0 Hz, 3H).

LCMS-ESI+ (m/z): [M+H]+ calcd for C₁₇H₁₈N₅O₂S: 356.1; found: 356.1.

Example 5.01

Preparation of ethyl 1-(2-(3,4-dimethoxyphenyl)-2-oxoethyl)-1H-pyrazole-5-carboxylate

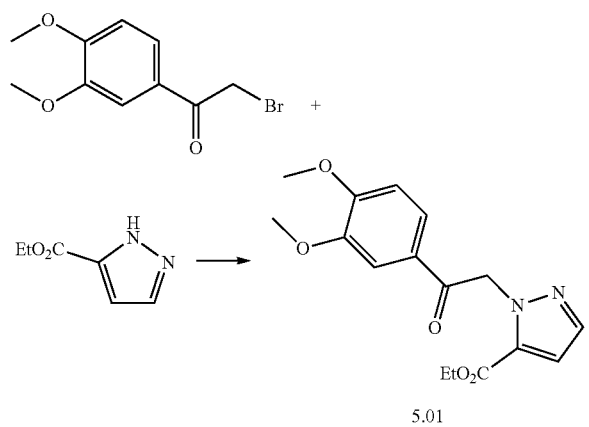

5.01

To a mixture of 2-bromo-1-(3,4-dimethoxyphenyl)ethanone (1.95 g, 7.53 mmol) and ethyl 1H-pyrazole-3-carboxylate (1.22 g, 8.72 mmol) in acetone (36 mL) at room temperature was added potassium carbonate (1.28 g, 9.23 mmol). Mixture stirred vigorously overnight and then was concentrated under reduced pressure. Resulting residue was taken up in ethyl acetate and washed with 4:1 water/brine. Layers were separated and aqueous was extracted with ethyl acetate. Combined organic layers were dried (Na₂SO₄), filtered, and concentrated under reduced pressure. Resulting residue was purified by silica gel column chromatography (10-60% ethyl acetate in hexanes) to yield ethyl 1-(2-(3,4-dimethoxyphenyl)-2-oxoethyl)-1H-pyrazole-5-carboxylate 5.01.

¹H NMR (400 MHz CDCl₃) δ 7.64-7.60 (m, 2H), 7.51 (d, J=4 Hz, 1H), 6.96-6.92 (m, 2H), 6.01 (s, 2H), 4.27 (q, J=8 Hz, 2H), 3.97 (s, 3H), 3.92 (s, 3H), 1.30 (t, J=8 Hz, 3H).

LCMS-ESI+ (m/z): [M+H]+ calcd for C₁₆H₁₉N₂O₅: 319.12; found: 319.05.

Example 5.02

Preparation of 6-(3,4-dimethoxyphenyl)pyrazolo[1,5-a]pyrazin-4(5H)-one

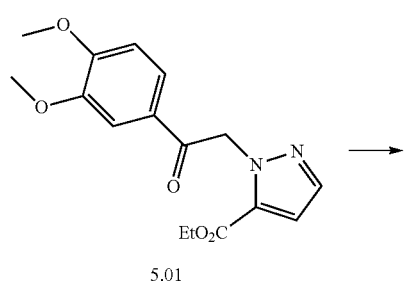

5.01

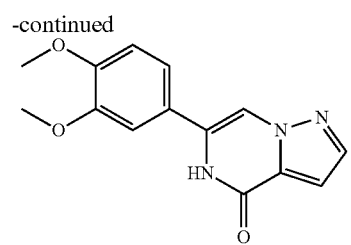

5.02

Ammonium acetate (4.16 g, 54.0 mmol) was added to a solution of ethyl 1-(2-(3,4-dimethoxyphenyl)-2-oxoethyl)-1H-pyrazole-5-carboxylate 5.01 (195 mg, 0.61 mmol) in Acetic Acid (5.4 mL) at room temperature. Mixture was heated at 110° C. overnight. An additional 900 mg of ammonium acetate was added and mixture was heated at 110° C. for 3.5 hours, and then cooled to room temperature. Acetic acid was concentrated and residue was taken up in ethyl acetate and washed with 1:1 water/saturated NaHCO₃ (aq). Layers were separated and aqueous was extracted with ethyl acetate. Combined organic layers were washed with 1:1 brine/saturated NaHCO₃ (aq), dried (Na₂SO₄), filtered, and concentrated under reduced pressure to yield 6-(3,4-dimethoxyphenyl)pyrazolo[1,5-a]pyrazin-4(5H)-one 5.02, which was used without further purification.

LCMS-ESI+ (m/z): [M+H]+ calcd for C₁₄H₁₄N₃O₃: 272.10; found: 272.14.

Example 5.03

Preparation of 4-chloro-6-(3,4-dimethoxyphenyl)pyrazolo[1,5-a]pyrazine

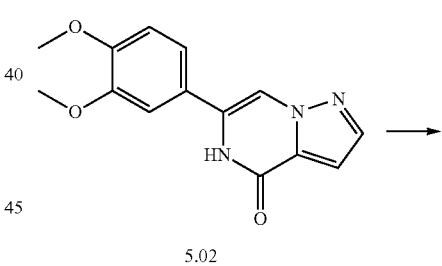

5.02

5.03

6-(3,4-dimethoxyphenyl)pyrazolo[1,5-a]pyrazin-4(5H)-one 5.02 (74 mg, 0.27 mmol) was taken up in phosphorous oxychloride (1.4 mL, 15 mmol) and mixture was heated to 95° C. for two hours. After cooling to room temperature, mixture was carefully added via pipet to vigorously stirring water (15 mL) with internal temperature monitoring, at a rate to keep the internal temperature below 45° C. Reaction flask was washed with 15 mL of ethyl acetate and added to aqueous mixture to ensure complete transfer. Layers were separated and aqueous was extracted with ethyl acetate. Combined organic layers were washed with 1:1 brine/saturated NaHCO$_3$ (aq), dried (Na$_2$SO$_4$), filtered, and concentrated under reduced pressure to yield 4-chloro-6-(3,4-dimethoxyphenyl)pyrazolo[1,5-a]pyrazine 5.03. LCMS-ESI$^+$ (m/z): [M+H]$^+$ calcd for C$_{14}$H$_{13}$ClN$_3$O$_2$: 290.06; found: 290.10.

Example 5.04

Preparation of (R)-4-((R)-1-(6-(3,4-dimethoxyphenyl)pyrazolo[1,5-a]pyrazin-4-yloxy)ethyl)pyrrolidin-2-one

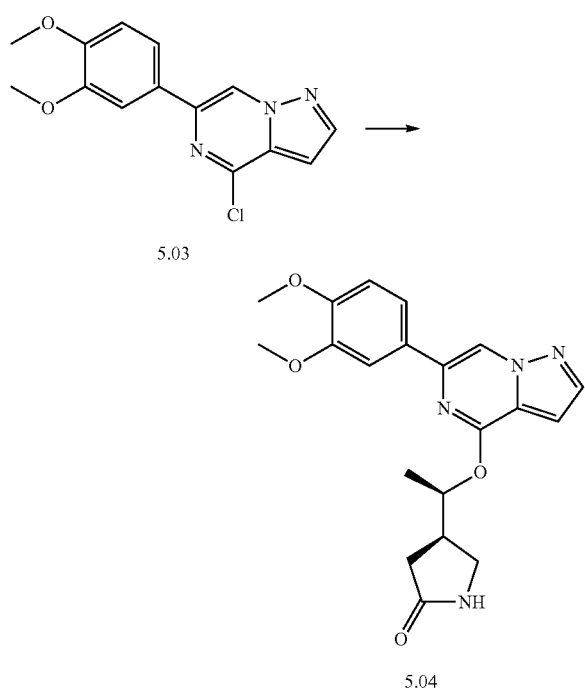

A solution of 1M sodium bis(trimethylsilyl) amide in THF (0.18 mL, 0.18 mmol) was added to a solution of (R)-4-((R)-1-hydroxyethyl)pyrrolidin-2-one 1.18 (22.9 mg, 0.18 mmol) in DMF (1 mL) at room temperature, forming a white precipitate. After 8 minutes, a solution of 4-chloro-6-(3,4-dimethoxyphenyl)pyrazolo[1,5-a]pyrazine 5.03 (34 mg, 0.12 mmol) in DMF (1.1 mL) was added under argon. Dark brown solution stirred at room temperature overnight. Mixture was quenched by addition of water, brine and ethyl acetate and layers were separated. Aqueous was extracted with ethyl acetate and combined organic layers were washed with 50% brine, dried (Na$_2$SO$_4$), filtered, and concentrated under reduced pressure. Resulting residue was purified by silica gel column chromatography (0-10% methanol in dichloromethane) to yield (R)-4-((R)-1-(6-(3,4-dimethoxyphenyl)pyrazolo[1,5-a]pyrazin-4-yloxy)ethyl)pyrrolidin-2-one 5.04.

$^1$H NMR (400 MHz CD$_3$OD) δ 8.62 (d, J=1.0 Hz, 1H), 7.96 (d, J=2.4 Hz, 1H), 7.61 (d, J=6.9 Hz, 2H), 7.05 (d, J=9.0 Hz, 1H), 6.81 (d, J=2.4 Hz, 1H), 5.80-5.57 (m, 1H), 3.93 (s, 3H), 3.88 (s, 3H), 3.60 (dd, J=10.2, 8.4 Hz, 1H), 3.36 (d, J=5.6 Hz, 1H), 2.97 (d, J=7.2 Hz, 1H), 2.63-2.42 (m, 2H), 1.52 (d, J=6.3 Hz, 3H).

LCMS-ESI$^+$ (m/z): [M+H]$^+$ calcd for C$_{20}$H$_{23}$N$_4$O$_4$: 383.16; found: 383.03.

Example 5.05 ethyl 1-(2-(3,4-dimethoxyphenyl)-2-oxoethyl)-4-methyl-1H-pyrazole-5-carboxylate

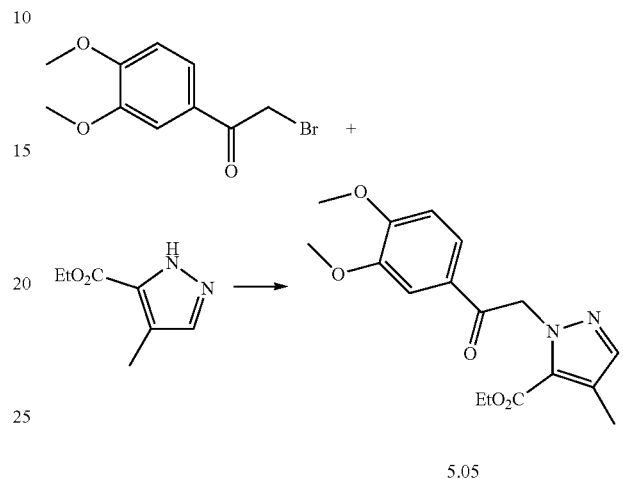

Following the procedure of Example 5.01, beginning with 2-bromo-1-(3,4-dimethoxyphenyl)ethanone (1.02 g, 3.92 mmol) and ethyl 4-methylpyrazole-3-carboxylate (637 mg, 4.13 mmol), ethyl 1-(2-(3,4-dimethoxyphenyl)-2-oxoethyl)-4-methyl-1H-pyrazole-5-carboxylate 5.05 was synthesized.

LCMS-ESI$^+$ (m/z): [M+H]$^+$ calcd for C$_{17}$H$_{21}$N$_2$O$_5$: 333.14; found: 333.09.

Example 5.06

Preparation of 6-(3,4-dimethoxyphenyl)-3-methylpyrazolo[1,5-a]pyrazin-4(5H)-one

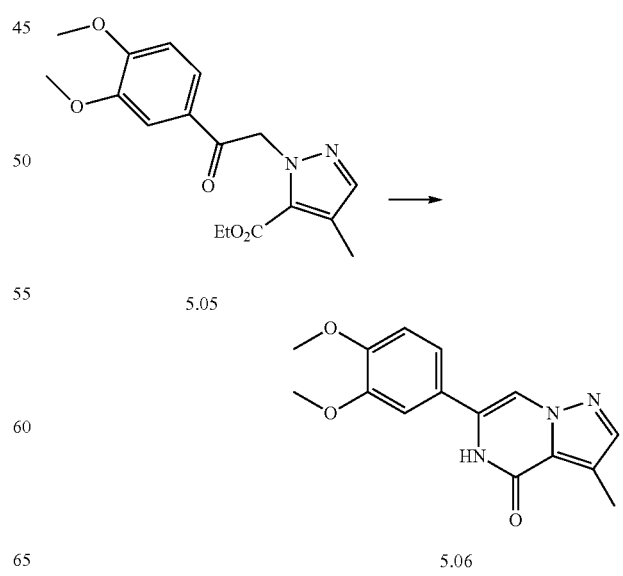

Following the procedure of Example 5.02, beginning with ethyl 1-(2-(3,4-dimethoxyphenyl)-2-oxoethyl)-4-methyl-1H-pyrazole-5-carboxylate 5.05 (93 mg, 0.28 mmol), 6-(3,4-dimethoxyphenyl)-3-methylpyrazolo[1,5-a]pyrazin-4(5H)-one 5.06 (78 mg) was synthesized.

LCMS-ESI$^+$ (m/z): [M+H]$^+$ calcd for $C_{15}H_{16}N_3O_3$: 286.11; found: 286.15.

Example 5.07

Preparation of 4-chloro-6-(3,4-dimethoxyphenyl)-3-methylpyrazolo[1,5-a]pyrazine

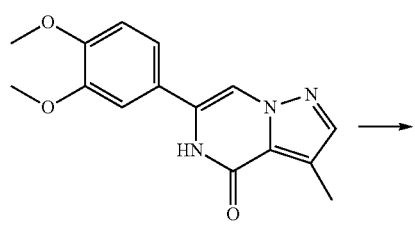
5.06

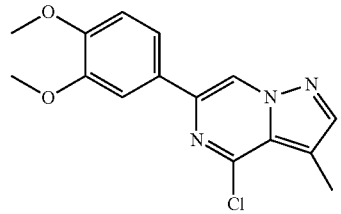
5.07

Following the procedure of Example 5.03, beginning with 6-(3,4-dimethoxyphenyl)-3-methylpyrazolo[1,5-a]pyrazin-4(5H)-one 5.06 (78 mg, 0.273 mmol), 4-chloro-6-(3,4-dimethoxyphenyl)-3-methylpyrazolo[1,5-a]pyrazine 5.07 was synthesized.

LCMS-ESI$^+$ (m/z): [M+H]$^+$ calcd for $C_{15}H_{15}ClN_3O_2$: 304.08; found: 304.13.

Example 5.08

Preparation of (R)-4-((R)-1-(6-(3,4-dimethoxyphenyl)-3-methylpyrazolo[1,5-a]pyrazin-4-yloxy)ethyl)pyrrolidin-2-one

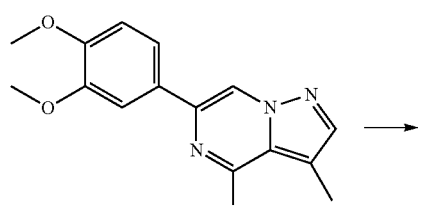
5.07

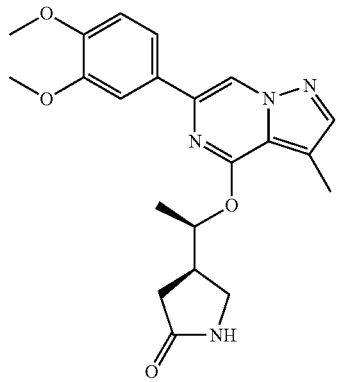
5.08

Following the procedure of Example 5.04, beginning with 4-chloro-6-(3,4-dimethoxyphenyl)-3-methylpyrazolo[1,5-a]pyrazine 5.07 (58 mg, 0.191 mmol), (R)-4-((R)-1-(6-(3,4-dimethoxyphenyl)-3-methylpyrazolo[1,5-a]pyrazin-4-yloxy)ethyl)pyrrolidin-2-one 5.08 was synthesized.

$^1$H NMR (400 MHz, CD$_3$OD) δ 8.48 (s, 1H), 7.75 (d, J=0.8 Hz, 1H), 7.58 (dq, J=4.4, 2.1 Hz, 2H), 7.04 (d, J=9.0 Hz, 1H), 5.68 (dt, J=11.9, 6.1 Hz, 1H), 3.93 (s, 3H), 3.88 (s, 3H), 3.61 (dd, J=10.1, 8.7 Hz, 1H), 3.41-3.34 (m, 1H), 2.99 (dd, J=9.3, 4.6 Hz, 1H), 2.62-2.48 (m, 2H), 2.45 (d, J=0.7 Hz, 3H), 1.53 (d, J=6.3 Hz, 3H).

LCMS-ESI$^+$ (m/z): [M+H]$^+$ calcd for $C_{21}H_{25}N_4O_4$: 397.18; found: 397.03.

Example 5.09

Preparation of ethyl 4-methyl-1-(2-(4-morpholinophenyl)-2-oxoethyl)-1H-pyrazole-5-carboxylat

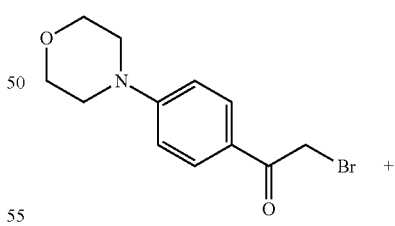

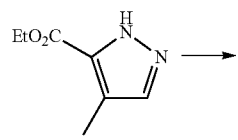

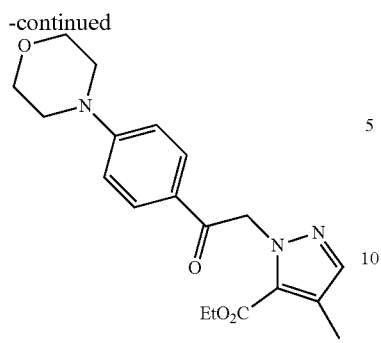

5.09

Following the procedure of Example 5.01, beginning with 2-bromo-1-(4-morpholinophenyl)ethanone (1.45 g, 5.12 mmol) and ethyl 4-methylpyrazole-3-carboxylate (837 mg, 5.43 mmol), ethyl 4-methyl-1-(2-(4-morpholinophenyl)-2-oxoethyl)-1H-pyrazole-5-carboxylate 5.09 was synthesized.

LCMS-ESI$^+$ (m/z): [M+H]$^+$ calcd for $C_{20}H_{24}N_3O_4$: 358.17; found: 358.15.

Example 5.10

Preparation of 3-methyl-6-(4-morpholinophenyl)pyrazolo[1,5-a]pyrazin-4(5H)-one

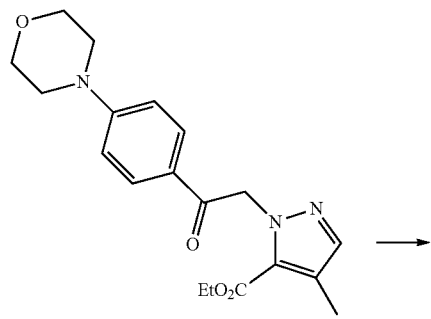

5.10

Following the procedure of Example 5.02, beginning with ethyl 4-methyl-1-(2-(4-morpholinophenyl)-2-oxoethyl)-1H-pyrazole-5-carboxylate 5.09 (96 mg, 0.269 mmol), 3-methyl-6-(4-morpholinophenyl)pyrazolo[1,5-a]pyrazin-4(5H)-one 5.10 was synthesized.

LCMS-ESI$^+$ (m/z): [M+H]$^+$ calcd for $C_{17}H_{19}N_4O_2$: 311.14; found: 311.19.

Example 5.11

Preparation of 4-(4-(4-chloro-3-methylpyrazolo[1,5-a]pyrazin-6-yl)phenyl)morpholine

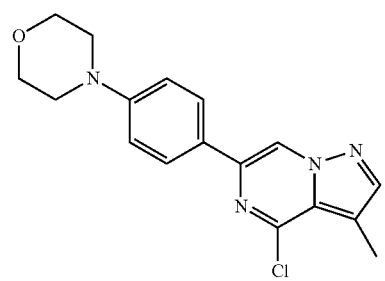

5.10

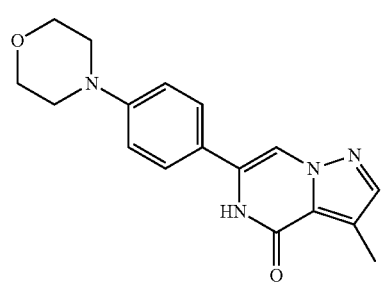

5.11

Following the procedure of Example 5.03, beginning with 3-methyl-6-(4-morpholinophenyl)pyrazolo[1,5-a]pyrazin-4(5H)-one 5.10 (45 mg, 0.145 mmol), 4-(4-(4-chloro-3-methylpyrazolo[1,5-a]pyrazin-6-yl)phenyl)morpholine 5.11 was synthesized.

LCMS-ESI$^+$ (m/z): [M+H]$^+$ calcd for $C_{17}H_{18}ClN_4O$: 329.11; found: 329.17.

Example 5.12

Preparation of (R)-1-((R)-1-(4-methoxyphenyl)ethyl)-4-((R)-1-(3-methyl-6-(4-morpholinophenyl)pyrazolo[1,5-a]pyrazin-4-yloxy)ethyl)pyrrolidin-2-one

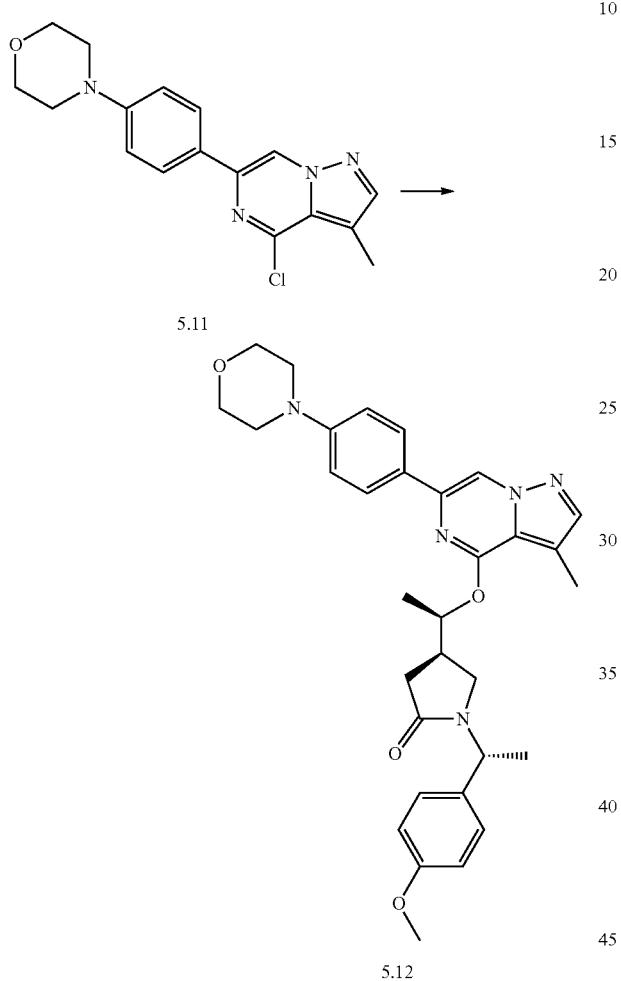

A solution of 1M potassium tertbutoxide in THF (0.10 mL, 0.10 mmol) was added to a solution of (R)-4-((R)-1-hydroxyethyl)-1-4R)-1-(4-methoxyphenyl)ethyl)pyrrolidin-2-one 1.04 (27 mg, 0.1 mmol) in THF (0.5 mL) at room temperature. After 15 minutes, a solution of 4-(4-(4-chloro-3-methylpyrazolo[1,5-a]pyrazin-6-yl)phenyl)morpholine 5.11 (20 mg, 0.06 mmol) in THF (1.2 mL) was added under argon. After 90 minutes, an additional 14 mg of (R)-4-((R)-1-hydroxyethyl)-1-((R)-1-(4-methoxyphenyl)ethyl)pyrrolidin-2-one 1.04 and 0.05 mL of 1M potassium tertbutoxide in THF were added. After 5 hours, mixture was quenched by addition of sat. NH$_4$Cl (aq) and extracted with ethyl acetate. Combined organics were washed with 1:1 water/brine, dried (Na2SO4), filtered, and concentrated under reduced pressure to yield (R)-1-((R)-1-(4-methoxyphenyl)ethyl)-4-((R)-1-(3-methyl-6-(4-morpholinophenyl)pyrazolo[1,5-a]pyrazin-4-yloxy)ethyl)pyrrolidin-2-one 5.12, which was used without further purification.

LCMS-ESI$^+$ (m/z): [M+H]$^+$ calcd for C$_{32}$H$_{38}$1 N$_5$O$_4$: 556.28; found: 556.28.

Example 5.13

Preparation of (R)-4-((R)-1-(3-methyl-6-(4-morpholinophenyl)pyrazolo[1,5-a]pyrazin-4-yloxy)ethyl)pyrrolidin-2-one

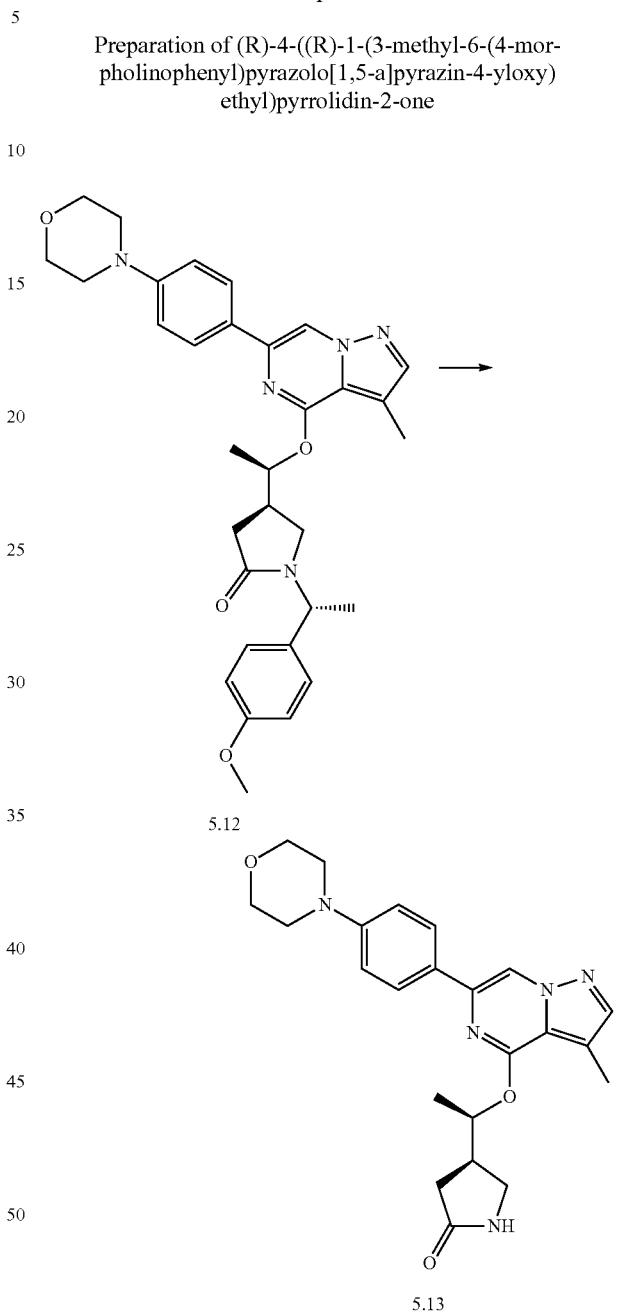

(R)-1-((R)-1-(4-methoxyphenyl)ethyl)-4-4R)-1-(3-methyl-6-(4-morpholinophenyl)pyrazolo[1,5-a]pyrazin-4-yloxy)ethyl)pyrrolidin-2-one 5.12 (34 mg, 0.061 mmol) was taken up in TFA (1.5 mL) and mixture was heated at 60° C. overnight. After cooling to room temperature, mixture was concentrated under reduced pressure and resulting film was taken up in ethyl acetate and washed with saturated aqueous sodium bicarbonate. Layers were separated and aqueous was extracted with ethyl acetate. Combined organics were washed with 1:1 brine/saturated aqueous sodium bicarbonate, dried (Na$_2$SO$_4$), filtered, and concentrated under reduced pressure. Resulting residue was purified by prep HPLC and then silica gel column chromatography (0-15% methanol in dichloromethane) to yield (R)-4-((R)-1-(3-methyl-6-(4-morpholinophenyl)pyrazolo[1,5-a]pyrazin-4-yloxy)ethyl)pyrrolidin-2-one 5.13.

1H NMR (400 MHz, CDCl₃) δ 8.41 (s, 1H), 8.09-8.02 (m, 2H), 8.02-7.94 (m, 3H), 7.77 (s, 1H), 5.63-5.55 (m, 1H), 4.51-4.33 (m, 4H), 3.65-3.53 (m, 5H), 3.42-3.33 (m, 1H), 3.03-2.91 (m, 1H), 2.63-2.45 (m, 2H), 2.45 (s, 3H), 1.53 (d, J=6.2 Hz, 3H).

LCMS-ESI⁺ (m/z): [M+H]⁺ calcd for $C_{23}H_{28}N_5O_3$: 422.21; found: 422.07.

Example 5.14

Preparation of 1-(1-tert-butyl-1H-pyrazol-4-yl)ethanone

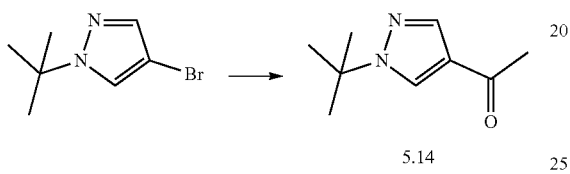

5.14

A solution of 4-bromo-1-tert-butyl-1H-pyrazole (973 mg, 4.79 mmol) in anhydrous THF (9.5 ml) was cooled to −78° C. under argon. A solution of n-BuLi in Hexanes (1.6 M, 3.2 mL, 5.12 mmol) was then added dropwise over 5 min and reaction mixture was stirred at −78° C. for 80 min. A solution of N-methoxy-N-methylacetamide (0.55 ml, 5.17 mmol) in THF (3 mL) was added dropwise and mixture was warmed to 0° C. After 4 hours, reaction mixture was quenched via addition of NH₄Cl (aq) (10 mL) and mixture was extracted with ethyl acetate. Combined organic layers were washed with 50% brine, dried (Na₂SO₄), filtered, and concentrated under reduced pressure. Resulting residue was purified by silica gel column chromatography (0-50% ethyl acetate in hexanes) to yield 1-(1-tert-butyl-1H-pyrazol-4-yl)ethanone 5.14.

1H NMR (400 MHz, CDCl₃) δ 8.01 (d, J=0.7 Hz, 1H), 7.91 (d, J=0.8 Hz, 1H), 2.43 (s, 3H), 1.61 (s, 9H).

Example 5.15

Preparation of 2-bromo-1-(1-tert-butyl-1H-pyrazol-4-yl)ethanone

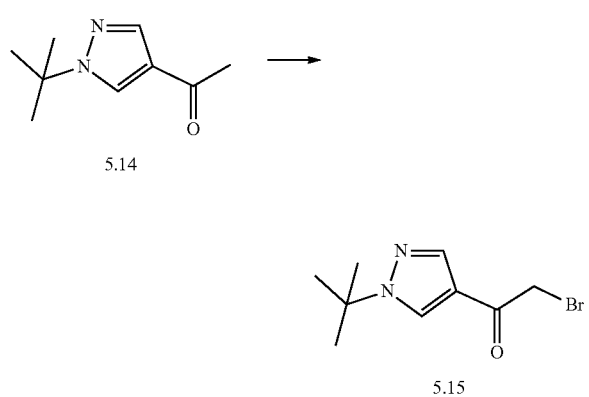

Pyridinium tribromide (930 mg, 2.89 mmol) was added slowly to a solution of 1-(1-tert-butyl-1H-pyrazol-4-yl)ethanone 5.14 (478 mg, 2.88 mmol) in dichloromethane (9.8 mL) and absolute ethanol (2.5 mL). Mixture stirred at room temperature for 24 hours.

An additional 45 mg of pyridinium tribromide was added. After an additional seven hours, mixture was quenched via addition of 35 mL of water and extracted with dichloromethane Combined organics were washed with 50% brine, dried (Na₂SO₄), filtered, and concentrated under reduced pressure to yield 2-bromo-1-(1-tert-butyl-1H-pyrazol-4-yl)ethanone 5.15, which was used in the next step without further purification.

1H NMR (400 MHz, CDCl₃) δ 8.11 (d, J=0.7 Hz, 1H), 7.99 (d, J=0.7 Hz, 1H), 4.19 (s, 2H), 1.62 (s, 9H).

Example 5.16

Preparation of ethyl 1-(2-(1-tert-butyl-1H-pyrazol-4-yl)-2-oxoethyl)-4-methyl-1H-pyrazole-5-carboxylate

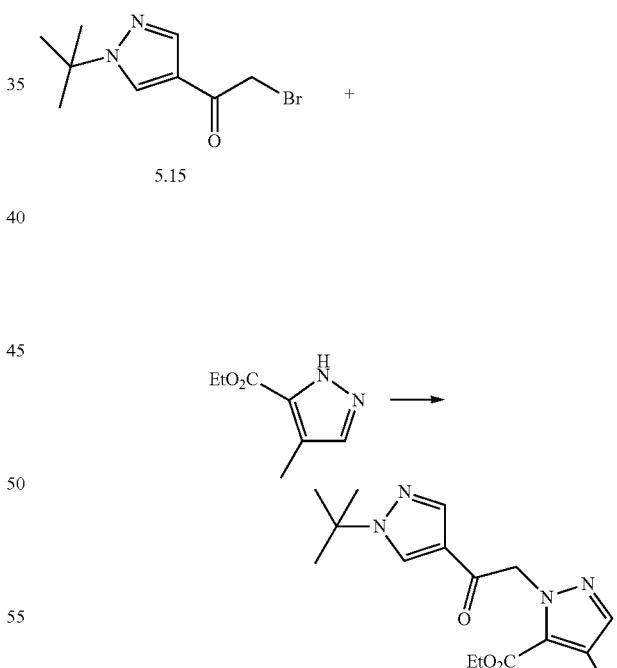

Following the procedure of Example 5.01, beginning with 2-bromo-1-(1-tert-butyl-1H-pyrazol-4-yl)ethanone 5.15 (715 mg, 94% purity, 2.74 mmol) and ethyl 4-methyl-1H-pyrazole-3-carboxylate (488 mg, 3.17 mmol), ethyl 1-(2-(1-tert-butyl-1H-pyrazol-4-yl)-2-oxoethyl)-4-methyl-1H-pyrazole-5-carboxylate 5.16 was synthesized.

LCMS-ESI⁺ (m/z): [M+H]⁺ calcd for $C_{16}H_{23}N_4O_3$: 319.17; found: 319.10.

Example 5.17

Preparation of 6-(1-tert-butyl-1H-pyrazol-4-yl)-3-methylpyrazolo[1,5-a]pyrazin-4(5H)-one

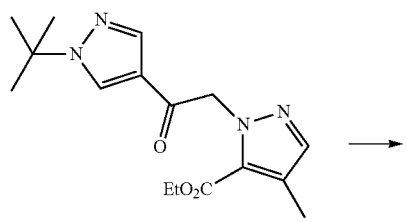

5.16

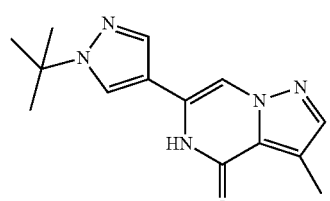

5.17

Following the procedure of Example 5.02, beginning with ethyl 1-(2-(1-tert-butyl-1H-pyrazol-4-yl)-2-oxoethyl)-4-methyl-1H-pyrazole-5-carboxylate 5.16 (77 mg, 0.227 mmol), 6-(1-tert-butyl-1H-pyrazol-4-yl)-3-methylpyrazolo[1,5-a]pyrazin-4(5H)-one 5.17 was synthesized.

LCMS-ESI⁺ (m/z): [M+H]⁺ calcd for $C_{14}H_{18}N_5O$: 272.14; found: 272.00.

Example 5.18

Preparation of 6-(1-tert-butyl-1H-pyrazol-4-yl)-4-chloro-3-methylpyrazolo[1,5-a]pyrazine

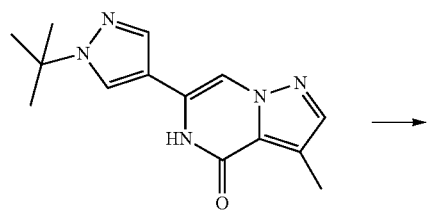

5.17

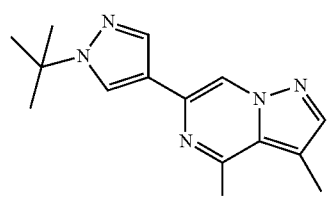

5.18

Following the procedure of Example 5.03, beginning with 6-(1-tert-butyl-1H-pyrazol-4-yl)-3-methylpyrazolo[1,5-a]pyrazin-4(5H)-one 5.17 (47 mg, 0.172 mmol), 6-(1-tert-butyl-1H-pyrazol-4-yl)-4-chloro-3-methylpyrazolo[1,5-a]pyrazine 5.18 was synthesized.

LCMS-ESI⁺ (m/z): [M+H]⁺ calcd for $C_{14}H_{17}ClN_5$: 290.11; found: 289.94.

Example 5.19

Preparation of (R)-4-((R)-1-(6-(1-tert-butyl-1H-pyrazol-4-yl)-3-methylpyrazolo[1,5-a]pyrazin-4-yloxy)ethyl)-1-((R)-1-(4-methoxyphenyl)ethyl)pyrrolidin-2-one

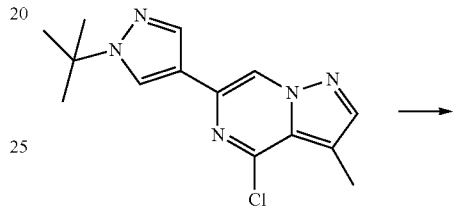

5.18

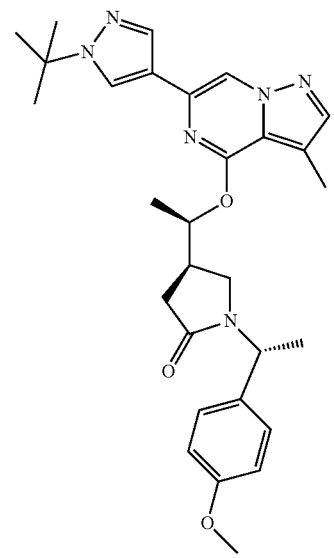

5.19

Following the procedure of Example 5.12, beginning with 6-(1-tert-butyl-1H-pyrazol-4-yl)-4-chloro-3-methylpyrazolo[1,5-a]pyrazine 5.18 (50 mg, 0.172 mmol) and (R)-4-((R)-1-hydroxyethyl)-1-((R)-1-(4-methoxyphenyl)ethyl)pyrrolidin-2-one 1.04 (79 mg, 0.300 mmol), (R)-4-((R)-1-(6-(1-tert-butyl-1H-pyrazol-4-yl)-3-methylpyrazolo[1,5-a]pyrazin-4-yloxy)ethyl)-1-((R)-1-(4-methoxyphenyl)ethyl)pyrrolidin-2-one 5.19 was synthesized.

LCMS-ESI+ (m/z): [M+H]+ calcd for $C_{29}H_{37}N_6O_3$: 517.28; found: 517.08.

Example 5.20

Preparation of (R)-4-((R)-1-(6-(1-tert-butyl-1H-pyrazol-4-yl)-3-methylpyrazolo[1,5-a]pyrazin-4-yloxy)ethyl)pyrrolidin-2-one

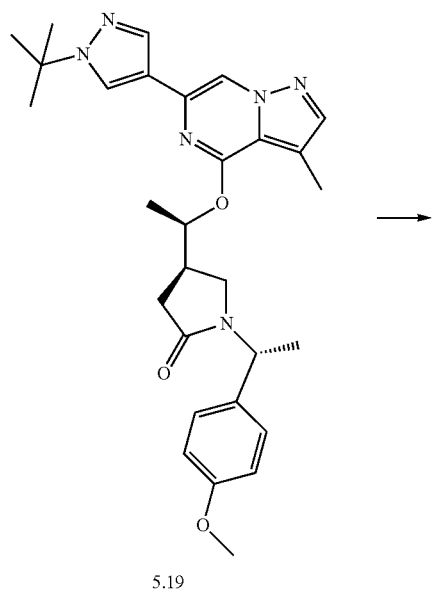

5.19

→

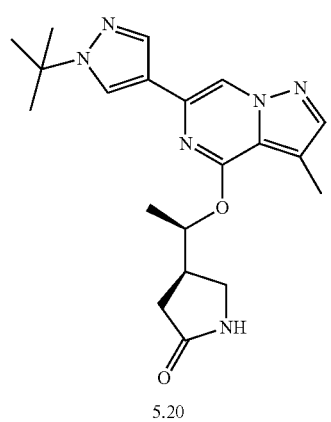

5.20

Following the procedure of Example 5.13, beginning with (R)-4-((R)-1-(6-(1-tert-butyl-1H-pyrazol-4-yl)-3-methylpyrazolo[1,5-a]pyrazin-4-yloxy)ethyl)-1-((R)-1-(4-methoxyphenyl)ethyl)pyrrolidin-2-one 5.19 (65 mg, 0.126 mmol), (R)-4-((R)-1-(6-(1-tert-butyl-1H-pyrazol-4-yl)-3-methylpyrazolo[1,5-a]pyrazin-4-yloxy)ethyl)pyrrolidin-2-one 5.20 was synthesized.

$^1$H NMR (400 MHz, CD$_3$OD) δ 8.33 (s, 1H), 8.20 (d, J=0.7 Hz, 1H), 7.96 (d, J=0.7 Hz, 1H), 7.70 (d, J=0.9 Hz, 1H), 5.75-5.59 (m, 1H), 3.60 (dd, J=10.1, 8.7 Hz, 1H), 3.36 (dd, J=10.1, 6.1 Hz, 1H), 3.06-2.87 (m, 1H), 2.62-2.46 (m, 2H), 2.43 (d, J=0.7 Hz, 3H), 1.63 (s, 9H), 1.49 (d, J=6.2 Hz, 3H).

LCMS-ESI+ (m/z): [M+H]+ calcd for $C_{20}H_{27}N_6O_2$: 383.21; found: 383.11.

Example 5.21

Preparation of ethyl 4-chloro-1-(2-(3,4-dimethoxyphenyl)-2-oxoethyl)-1H-pyrazole-5-carboxylate

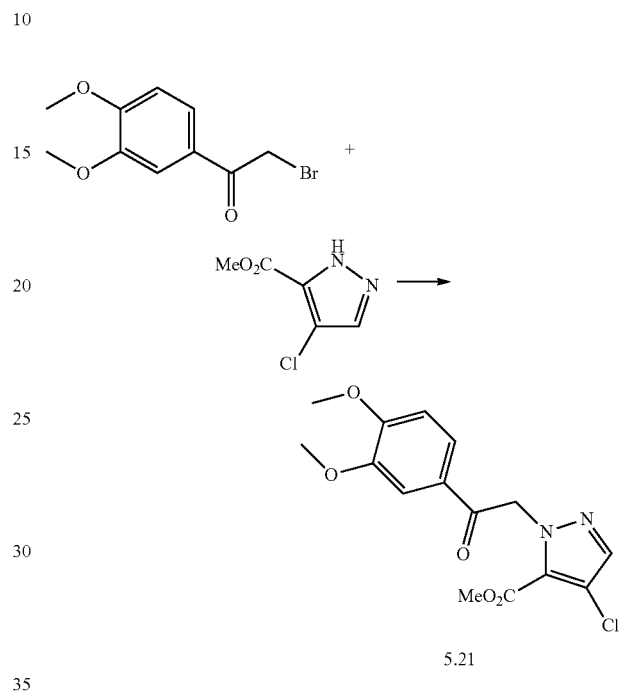

5.21

Following the procedure of Example 5.01, beginning with 2-bromo-1-(3,4-dimethoxyphenyl)ethanone (1.20 g, 4.63 mmol) and methyl 4-chloro-1H-pyrazole-5-carboxylate (855 mg, 5.33 mmol), methyl 4-chloro-1-(2-(3,4-dimethoxyphenyl)-2-oxoethyl)-1H-pyrazole-5-carboxylate 5.21 was synthesized.

LCMS-ESI+ (m/z): [M+H]+ calcd for $C_{15}H_{16}ClN_2O_5$: 339.07; found: 339.03.

Example 5.22

Preparation of 3-chloro-6-(3,4-dimethoxyphenyl)pyrazolo[1,5-a]pyrazin-4(5H)-one

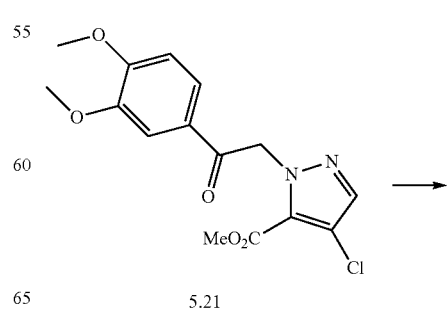

5.21

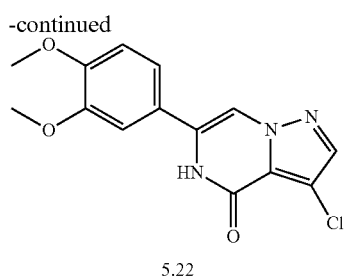

5.22

Following the procedure of Example 5.02, beginning with methyl 4-chloro-1-(2-(3,4-dimethoxyphenyl)-2-oxoethyl)-1H-pyrazole-5-carboxylate 5.21 (110 mg, 0.331 mmol), 3-chloro-6-(3,4-dimethoxyphenyl)pyrazolo[1,5-a]pyrazin-4(5H)-one 5.22 was synthesized.

LCMS-ESI$^+$ (m/z): [M+H]$^+$ calcd for $C_{14}H_{13}ClN_3O_3$: 306.06; found: 306.12.

Example 5.23

Preparation of (R)-4-((R)-1-(3-chloro-6-(3,4-dimethoxyphenyl)pyrazolo[1,5-a]pyrazin-4-yloxy)ethyl)-1-((R)-1-(4-methoxyphenyl)ethyl)pyrrolidin-2-one

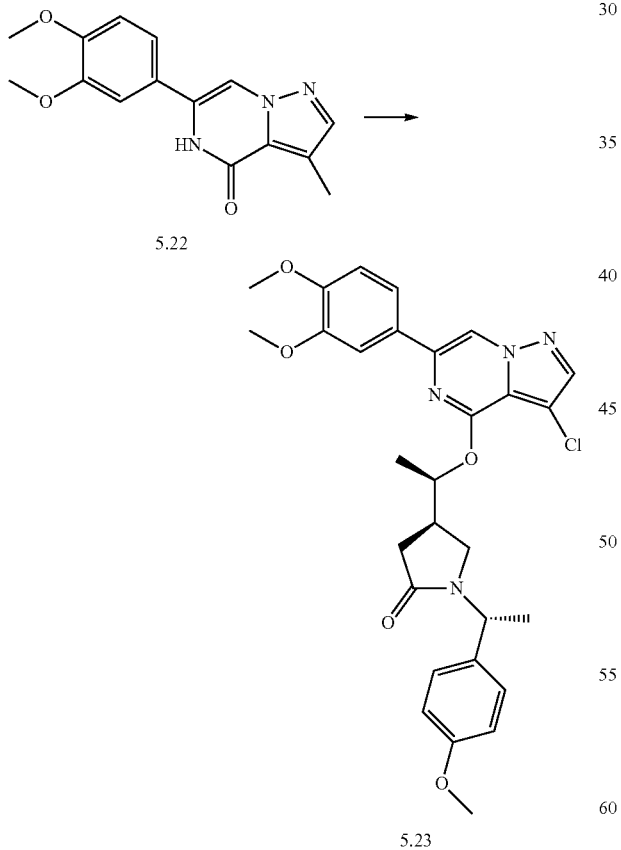

5.23

A mixture of 3-chloro-6-(3,4-dimethoxyphenyl)pyrazolo[1,5-a]pyrazin-4(5H)-one 5.22 (88 mg, 0.288 mmol), (S)-1-((R)-1-((R)-1-(4-methoxyphenyl)ethyl)-5-oxopyrrolidin-3-yl)ethyl methanesulfonate 1.30 (129 mg, 0.38 mmol), and cesium carbonate (144 mg, 0.44 mmol) in DMF (2.5 mL) was heated at 90° C. for 6 hours. After cooling to room temperature, mixture was poured into water and extracted with ethyl acetate. Combined organic layers were washed with 50% brine, dried (Na$_2$SO$_4$), filtered, and concentrated under reduced pressure. Resulting residue was purified by silica gel column chromatography (0-100% ethyl acetate in hexanes) to yield (R)-4-((R)-1-(3-chloro-6-(3,4-dimethoxyphenyl)pyrazolo[1,5-a]pyrazin-4-yloxy)ethyl)-1-4R)-1-(4-methoxyphenyl)ethyl)pyrrolidin-2-one 5.23.

LCMS-ESI$^+$ (m/z): [M+H]$^+$ calcd for $C_{29}H_{32}ClN_4O_5$: 551.20; found: 550.88.

Example 5.24

Preparation of (R)-4-((R)-1-(3-chloro-6-(3,4-dimethoxyphenyl)pyrazolo[1,5-a]pyrazin-4-yloxy)ethyl)pyrrolidin-2-one

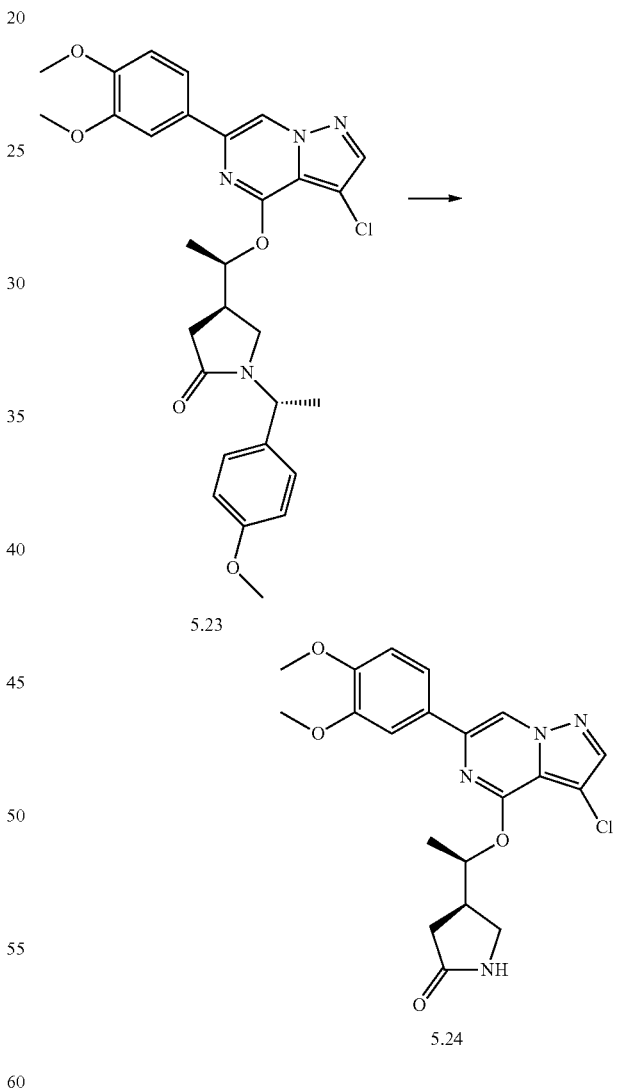

Following the procedure of Example 5.13, beginning with (R)-4-((R)-1-(3-chloro-6-(3,4-dimethoxyphenyl)pyrazolo[1,5-a]pyrazin-4-yloxy)ethyl)-1-((R)-1-(4-methoxyphenyl)ethyl)pyrrolidin-2-one 5.23 (30 mg, 0.054 mmol), (R)-4-((R)-1-(3-chloro-6-(3,4-dimethoxyphenyl)pyrazolo[1,5-a]pyrazin-4-yloxy)ethyl)pyrrolidin-2-one 5.24 was synthesized.

$^1$H NMR (400 MHz, CD$_3$OD) δ 8.58 (s, 1H), 7.93 (s, 1H), 7.67-7.54 (m, 2H), 7.04 (d, J=8.1 Hz, 1H), 5.69-5.56 (m, 1H), 3.92 (s, 3H), 3.88 (s, 3H), 3.60 (dd, J=10.0, 8.8 Hz, 1H), 3.37 (dd, J=10.1, 6.6 Hz, 1H), 3.08-2.93 (m, 1H), 2.66-2.50 (m, 2H), 1.55 (d, J=6.2 Hz, 3H).

LCMS-ESI$^+$ (m/z): [M+H]$^+$ calcd for C$_{20}$H$_{22}$ClN$_4$O$_4$: 417.13; found: 416.97.

Example 5.25

Preparation of ethyl 1-(2-(3,4-dimethoxyphenyl)-2-oxoethyl)-3-methyl-1H-pyrazole-5-carboxylate

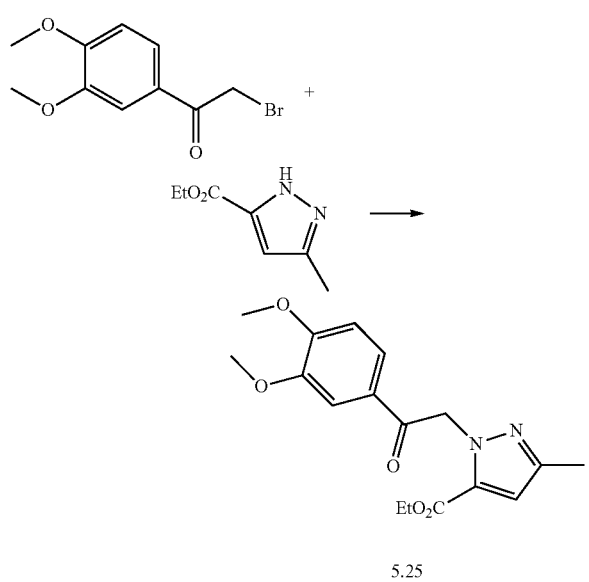

Following the procedure of Example 5.01, beginning with 2-bromo-1-(3,4-dimethoxyphenyl)ethanone (1.19 g, 4.59 mmol) and ethyl 3-methylpyrazole-5-carboxylate (820 mg, 5.32 mmol), ethyl 1-(2-(3,4-dimethoxyphenyl)-2-oxoethyl)-3-methyl-1H-pyrazole-5-carboxylate 5.25 was synthesized.

LCMS-ESI$^+$ (m/z): [M+H]$^+$ calcd for C$_{17}$H$_{21}$N$_2$O$_5$: 333.14; found: 333.14.

Example 5.26

Preparation of 6-(3,4-dimethoxyphenyl)-2-methylpyrazolo[1,5-a]pyrazin-4(5H)-one

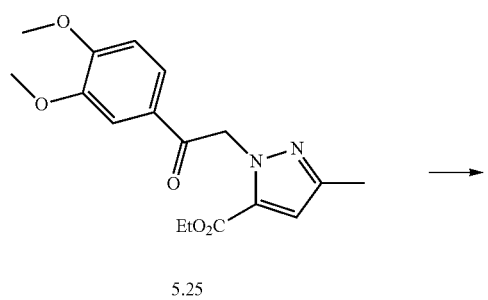

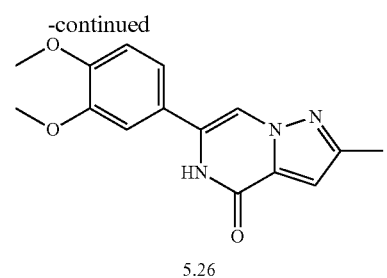

Following the procedure of Example 5.02, beginning with ethyl 1-(2-(3,4-dimethoxyphenyl)-2-oxoethyl)-3-methyl-1H-pyrazole-5-carboxylate 5.25 (316 mg, 0.951 mmol), 6-(3,4-dimethoxyphenyl)-2-methylpyrazolo[1,5-a]pyrazin-4(5H)-one 5.26 was synthesized.

LCMS-ESI$^+$ (m/z): [M+H]$^+$ calcd for C$_{15}$H$_{16}$N$_3$O$_3$: 286.11; found: 286.14.

Example 5.27

Preparation of (R)-4-((R)-1-(6-(3,4-dimethoxyphenyl)-2-methylpyrazolo[1,5-a]pyrazin-4-yloxy)ethyl)-1-4R)-1-(4-methoxyphenyl)ethyl)pyrrolidin-2-one

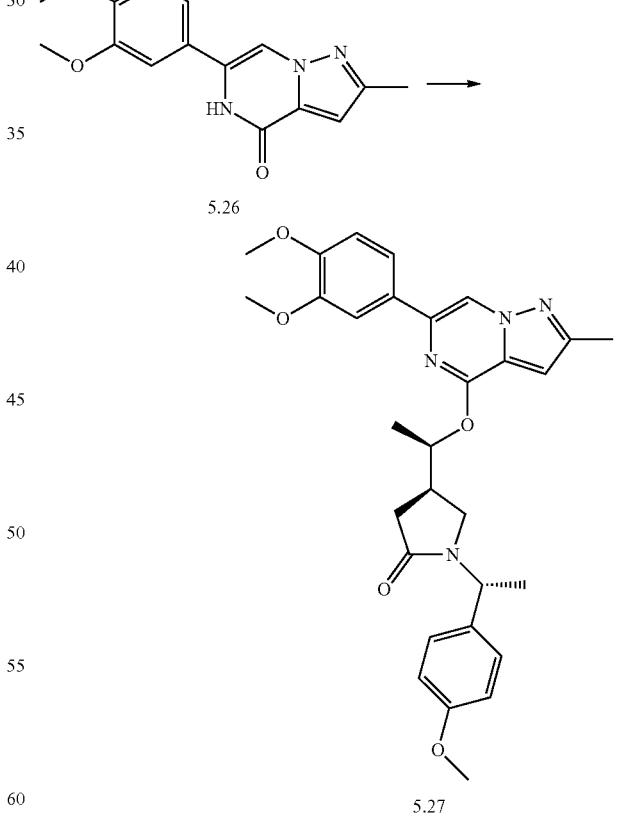

Following the procedure of Example 5.23, beginning with 6-(3,4-dimethoxyphenyl)-2-methylpyrazolo[1,5-a]pyrazin-4(5H)-one 5.26 (80 mg, 0.28 mmol) and (S)-1-((R)-1-((R)-1-(4-methoxyphenyl)ethyl)-5-oxopyrrolidin-3-yl)ethyl methanesulfonate 1.30 (124 mg, 0.363 mmol), (R)-4-((R)-1-

(6-(3,4-dimethoxyphenyl)-2-methylpyrazolo[1,5-a]pyrazin-4-yloxy)ethyl)-1-((R)-1-(4-methoxyphenyl)ethyl)pyrrolidin-2-one 5.27 was synthesized.

LCMS-ESI+ (m/z): [M+H]+ calcd for C30H35N4O5: 531.25; found: 531.00.

Example 5.28

Preparation of (R)-4-((R)-1-(6-(3,4-dimethoxyphenyl)-2-methylpyrazolo[1,5-a]pyrazin-4-yloxy)ethyl)pyrrolidin-2-one

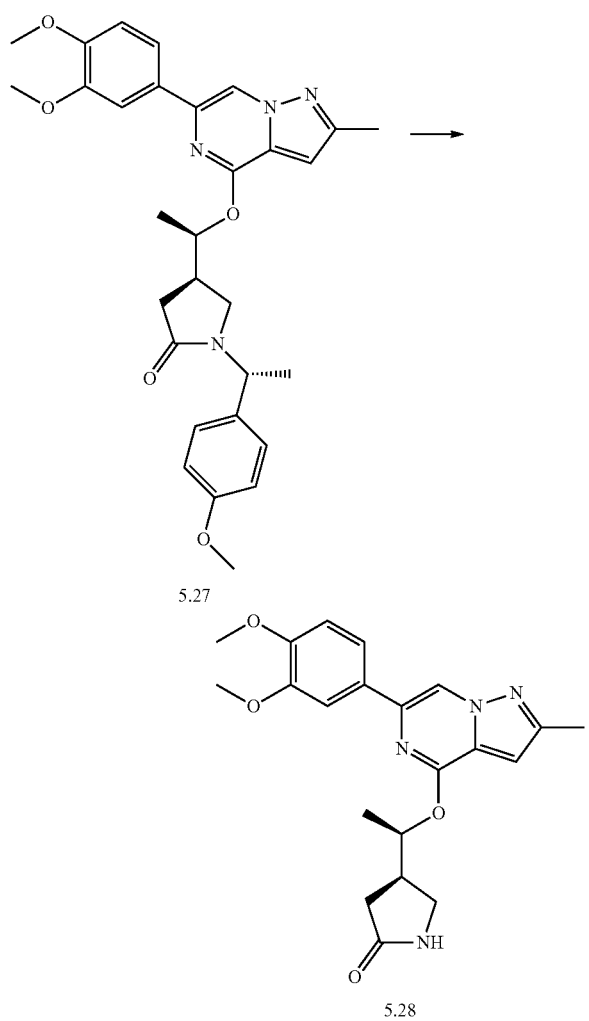

Following the procedure of Example 5.13, beginning with (R)-4-((R)-1-(6-(3,4-dimethoxyphenyl)-2-methylpyrazolo[1,5-a]pyrazin-4-yloxy)ethyl)-1-((R)-1-(4-methoxyphenyl)ethyl)pyrrolidin-2-one 5.27 (45 mg, 0.085 mmol), (R)-4-((R)-1-(6-(3,4-dimethoxyphenyl)-2-methylpyrazolo[1,5-a]pyrazin-4-yloxy)ethyl)pyrrolidin-2-one 5.28 was synthesized.

$^1$H NMR (400 MHz, CD$_3$OD) δ 8.47 (d, J=0.9 Hz, 1H), 7.62-7.53 (m, 2H), 7.03 (d, J=8.9 Hz, 1H), 6.62-6.53 (m, 1H), 5.71-5.59 (m, 1H), 3.93 (s, 3H), 3.88 (s, 3H), 3.59 (dd, J=10.2, 8.4 Hz, 1H), 3.38-3.32 (m, 1H), 3.02-2.90 (m, 1H), 2.60-2.48 (m, 2H), 2.47 (s, 3H), 1.50 (d, J=6.2 Hz, 3H).

LCMS-ESI+ (m/z): [M+H]+ calcd for C21H25N4O4: 397.18; found: 397.06.

Example 5.29

Preparation of ethyl 4-bromo-1-(2-(3,4-dimethoxyphenyl)-2-oxoethyl)-1H-pyrazole-5-carboxylate

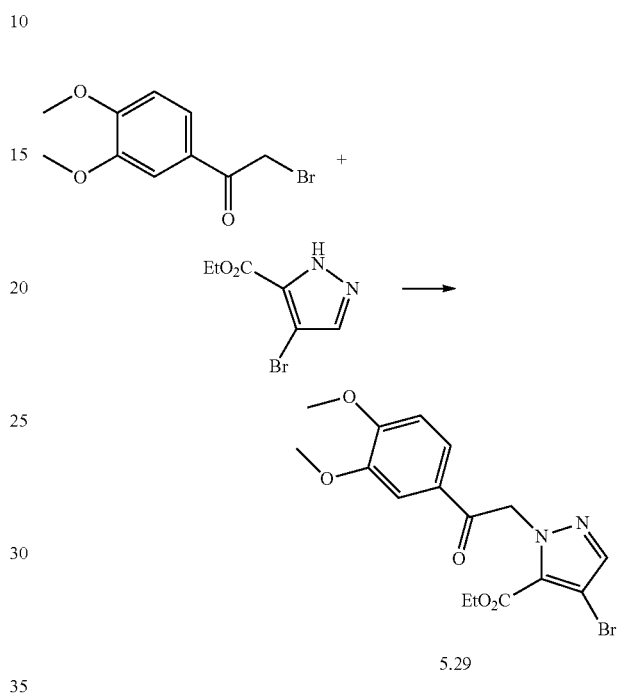

Following the procedure of Example 5.01, beginning with 2-bromo-1-(3,4-dimethoxyphenyl)ethanone (999 mg, 3.86 mmol) and ethyl 4-bromo-1H-pyrazole-5-carboxylate (995 mg, 4.54 mmol), ethyl 4-bromo-1-(2-(3,4-dimethoxyphenyl)-2-oxoethyl)-1H-pyrazole-5-carboxylate 5.29 (143 mg) was synthesized.

LCMS-ESI+ (m/z): [M+H]+ calcd for C16H18BrN2O5: 397.03; found: 396.99.

Example 5.30

Preparation of 3-bromo-6-(3,4-dimethoxyphenyl)pyrazolo[1,5-a]pyrazin-4(5H)-one

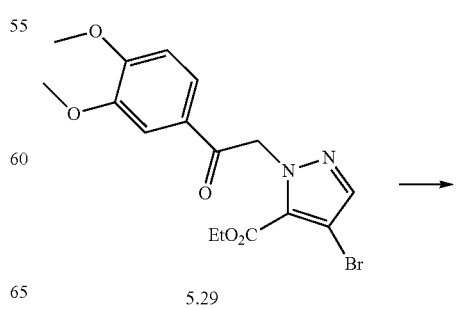

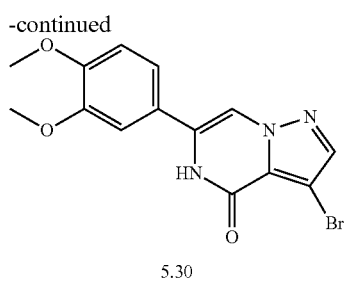

5.30

Following the procedure of Example 5.02, beginning with ethyl 4-bromo-1-(2-(3,4-dimethoxyphenyl)-2-oxoethyl)-1H-pyrazole-5-carboxylate 5.29 (92 mg, 0.231 mmol), 3-bromo-6-(3,4-dimethoxyphenyl)pyrazolo[1,5-a]pyrazin-4 (5H)-one 5.30 (61 mg) was synthesized.

LCMS-ESI+ (m/z): [M+H]+ calcd for $C_{14}H_{13}BrN_3O_3$: 350.01; found: 350.15.

Example 5.31

Preparation of (R)-4-((R)-1-(3-bromo-6-(3,4-dimethoxyphenyl)pyrazolo[1,5-a]pyrazin-4-yloxy)ethyl)-1-((R)-1-(4-methoxyphenyl)ethyl)pyrrolidin-2-one

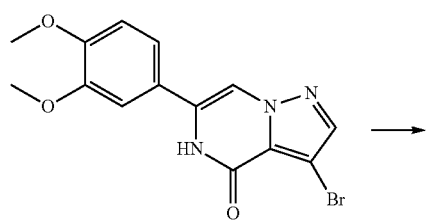

5.30

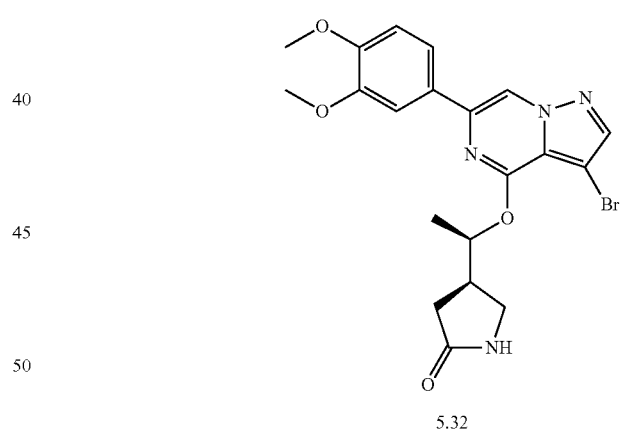

5.31

Following the procedures of Examples 5.12 and 5.12, beginning with 3-bromo-6-(3,4-dimethoxyphenyl)pyrazolo[1,5-a]pyrazin-4(5H)-one 5.30 (61 mg, 0.175 mmol), (R)-4-((R)-1-(3-bromo-6-(3,4-dimethoxyphenyl)pyrazolo[1,5-a]pyrazin-4-yloxy)ethyl)-1-((R)-1-(4-methoxyphenyl)ethyl)pyrrolidin-2-one 5.31 was synthesized (60 mg).

LCMS-ESI+ (m/z): [M+H]+ calcd for $C_{29}H_{32}BrN_4O_5$: 595.15; found: 594.65.

Example 5.32

Preparation of (R)-4-((R)-1-(3-bromo-6-(3,4-dimethoxyphenyl)pyrazolo[1,5-a]pyrazin-4-yloxy)ethyl)pyrrolidin-2-one

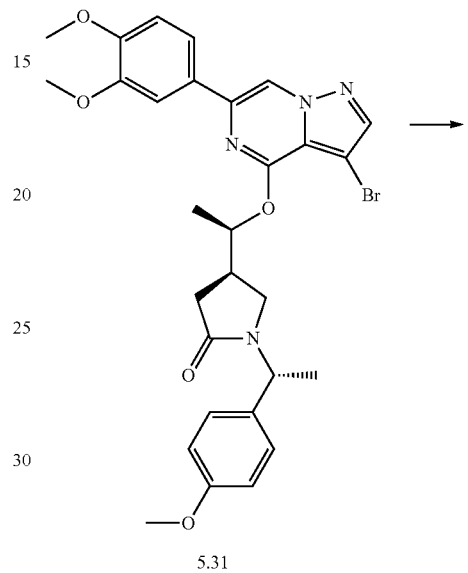

5.31

5.32

Following the procedure of Example 5.13, beginning with (R)-4-((R)-1-(3-bromo-6-(3,4-dimethoxyphenyl)pyrazolo[1,5-a]pyrazin-4-yloxy)ethyl)-1-((R)-1-(4-methoxyphenyl)ethyl)pyrrolidin-2-one 5.31 (41 mg, 0.069 mmol), (R)-4-((R)-1-(3-bromo-6-(3,4-dimethoxyphenyl)pyrazolo[1,5-a]pyrazin-4-yloxy)ethyl)pyrrolidin-2-one 5.32 was synthesized (6.5 mg).

1H NMR (400 MHz, CD3OD) δ 8.63 (d, J=1.0 Hz, 1H), 7.95 (d, J=1.0 Hz, 1H), 7.62 (d, J=8.5 Hz, 2H), 7.05 (d, J=8.2 Hz, 1H), 5.62 (s, 1H), 3.93 (d, J=1.0 Hz, 3H), 3.88 (d, J=1.0 Hz, 3H), 3.60 (t, J=9.3 Hz, 1H), 3.42-3.36 (m, 1H), 3.04-2.96 (m, 1H), 2.74-2.52 (m, 2H), 1.55 (d, J=6.3 Hz, 3H).

LCMS-ESI+ (m/z): [M+H]+ calcd for C20H22BrN4O4: 461.07; found: 460.76.

Example 5.33

Preparation of 2-(benzyloxy)-6-chloropyrazine

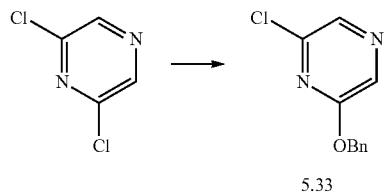 [SMILES: Clc1cncc(Cl)n1 ; Clc1cncc(OCc2ccccc2)n1]

5.33

To a cooled mixture of sodium hydride (60%, 300 mg, 7.5 mmol) in THF (20 mL) at 0° C. was added dropwise benzyl alcohol (0.75 mL, 7.24 mmol). After 30 minutes, 2,6-dichloropyrazine (999 mg, 6.71 mmol) was added and mixture was warmed to room temperature and stirred overnight. After quenching with sat. NH4Cl$_{(aq)}$, mixture was extracted with ethyl acetate and combined organics were washed with water then brine. Organics were dried, filtered, and concentrated under reduce pressure to yield 2-(benzyloxy)-6-chloropyrazine 5.33 (1.45 g), which was used in the next step without further purification.

1H NMR (400 MHz, CDCl3) δ 8.17 (dd, J=3.7, 0.6 Hz, 2H), 7.50-7.44 (m, 2H), 7.44-7.33 (m, 3H), 5.39 (s, 2H).

Example 5.34

Preparation of 1-amino-3-(benzyloxy)-5-chloropyrazin-1-ium 2,4,6-trimethylbenzenesulfonate

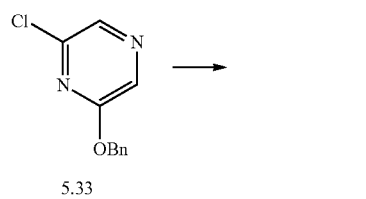

A solution of 2-(benzyloxy)-6-chloropyrazine 5.33 (559 mg, 2.53 mmol) in dichloromethane (12 mL) was cooled to 0° C. under argon. O-(mesitylsulfonyl)hydroxylamine (644 mg, 2.99 mmol, prepared using a procedure similar to that reported in *Org. Proc. Res. Dev.* 2009, 13, 263-267) was added, washing with additional DCM (2 mL), and mixture was warmed to rt. After 72 hours, reaction mixture was concentrated under reduced pressure to yield 1-amino-3-(benzyloxy)-5-chloropyrazin-1-ium 2,4,6-trimethylbenzenesulfonate 5.34, which was used in the next step without further purification.

LCMS-ESI+ (m/z): [M]+ calcd for C11H11ClN3O: 236.06; found: 236.08.

Example 5.35

Preparation of methyl 4-(benzyloxy)-6-chloropyrazolo[1,5-a]pyrazine-3-carboxylate

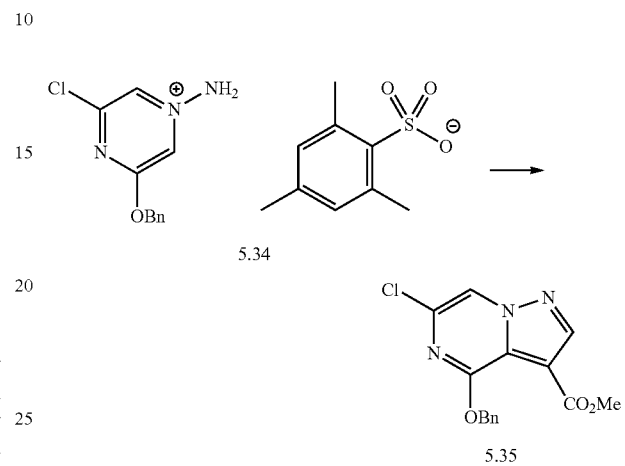

Potassium carbonate (457 mg, 3.31 mmol) was added to a mixture of 1-amino-3-(benzyloxy)-5-chloropyrazin-1-ium 2,4,6-trimethylbenzenesulfonate 5.34 (992 mg, 2.28 mmol) and methyl propiolate (0.24 mL, 2.66 mmol) in DMF (11 mL) at room temperature. After stifling overnight, reaction mixture was poured into water and extracted with ethyl acetate. Combined organics were washed with 50% brine, dried, filtered, and concentrated under reduced pressure. The resulting residue was purified by silica gel column chromatography (0-30% ethyl acetate/hexanes) to yield methyl 4-(benzyloxy)-6-chloropyrazolo[1,5-a]pyrazine-3-carboxylate 5.35 (320 mg).

LCMS-ESI+ (m/z): [M+H]+ calcd for C15H13ClN3O3: 318.06; found: 318.00.

Example 5.36

Preparation of 6-chloro-4-methoxypyrazolo[1,5-a]pyrazine

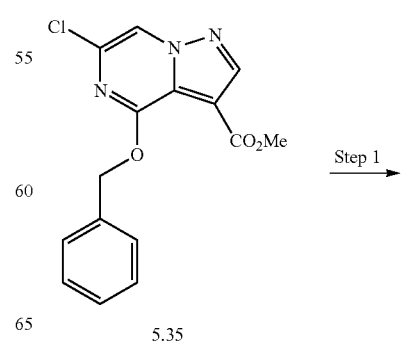

5.35 Step 1

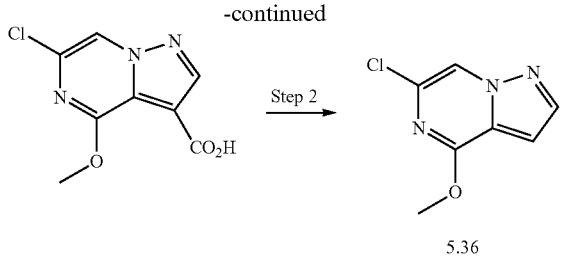

Step 1: methyl 4-(benzyloxy)-6-chloropyrazolo[1,5-a]pyrazine-3-carboxylate (5.35) (894 mg, 2.81 mmol) was suspended in THF (7.5 mL), water (2.5 mL), and MeOH (2.5 mL). After stifling at 30° C. for 5 h, HPLC demonstrated one primary product. The reaction mixture was acidified with aqueous HCl and was partitioned between water, EtOAc and 2-Me-THF. The phases were separated and the aqueous phase was extracted 3 times with a mixture of EtOAc and 2-Me-THF. The combined organic phase was concentrated to afford crude 6-chloro-4-methoxypyrazolo[1,5-a]pyrazine-3-carboxylic acid that was used without further purification. LCMS-ESI$^+$ (m/z): [M+H]$^+$ calcd for $C_8H_7ClN_3O_3$: 228.0; found: 228.1.

Step 2: Crude 6-chloro-4-methoxypyrazolo[1,5-a]pyrazine-3-carboxylic acid from above (611 mg, 2.68 mmol) was dissolved along with palladium(II) trifluoroacetate (401 mg, 1.2 mmol) in DMF (24 mL). DMSO (1.6 mL) and TFA (2 mL, 26 mmol) were added and the resulting mixture was heated to 110° C. After stirring 2.5 h, the reaction mixture was cooled and filtered. The filtrate was concentrated in vacuo and was partitioned between EtOAc, saturated aqueous NaHCO$_3$ and water. The phases were separated, and the aqueous phase was extracted with EtOAc. The combined organic phase was washed with water and was dried over Na$_2$SO$_4$, filtered, and concentrated. The concentrate was purified by silica gel (5-30% EtOAc in hexanes) to provide 6-chloro-4-methoxypyrazolo[1,5-a]pyrazine 5.36. LCMS-ESI$^+$ (m/z): [M+H]$^+$ calcd for $C_7H_7ClN_3O$: 184.0; found: 184.2.

Example 5.37 and 5.38

Preparation of 6-chloropyrazolo[1,5-a]pyrazin-4-ol and 6-bromopyrazolo[1,5-a]pyrazin-4-ol

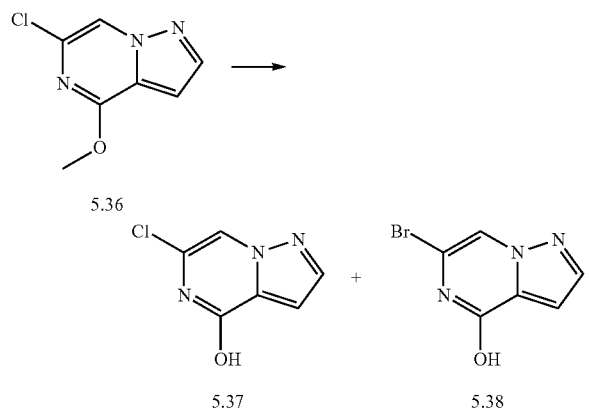

In a pressure vial, HBr (0.25 mL, 4.6 mmol) in water was added to a solution of 6-chloro-4-methoxypyrazolo[1,5-a]pyrazine 5.36 (117 mg, 0.64 mmol) in acetic acid (7 mL). Solution was heated in the sealed vial at 60° C. After 3.5 hours, reaction mixture was cooled to rt and carefully partitioned between ethyl acetate and sat aqueous NaHCO$_3$. Solid NaHCO$_3$ was added until bubbling slowed and pH became >7. Layers were separated and aqueous was extracted with ethyl acetate. Combined organics were washed with 1:1 brine/sat. NaHCO$_3$ $_{(aq)}$. Organic layers were dried, filtered, and concentrated under reduced pressure to yield a mixture of 6-chloropyrazolo[1,5-a]pyrazin-4-ol 5.37 and 6-bromopyrazolo[1,5-a]pyrazin-4-ol 5.38 (122 mg), which was used in the next step without further purification.

6-chloropyrazolo[1,5-a]pyrazin-4-ol 5.37:
LCMS-ESI+ (m/z): [M+H]+ calcd for $C_6H_5ClN_3O$: 170.00; found: 169.97.

6-bromopyrazolo[1,5-a]pyrazin-4-ol 5.38:
LCMS-ESI+ (m/z): [M+H]+ calcd for $C_6H_5BrN_3O$: 213.95; found: 213.97.

Example 5.39 and 5.40

Preparation of (R)-4-((R)-1-((6-chloropyrazolo[1,5-a]pyrazin-4-yl)oxy)ethyl)-1-((R)-1-(4-methoxyphenyl)ethyl)pyrrolidin-2-one and (R)-4-((R)-1-((6-bromopyrazolo[1,5-a]pyrazin-4-yl)oxy)ethyl)-1-((R)-1-(4-methoxyphenyl)ethyl)pyrrolidin-2-one

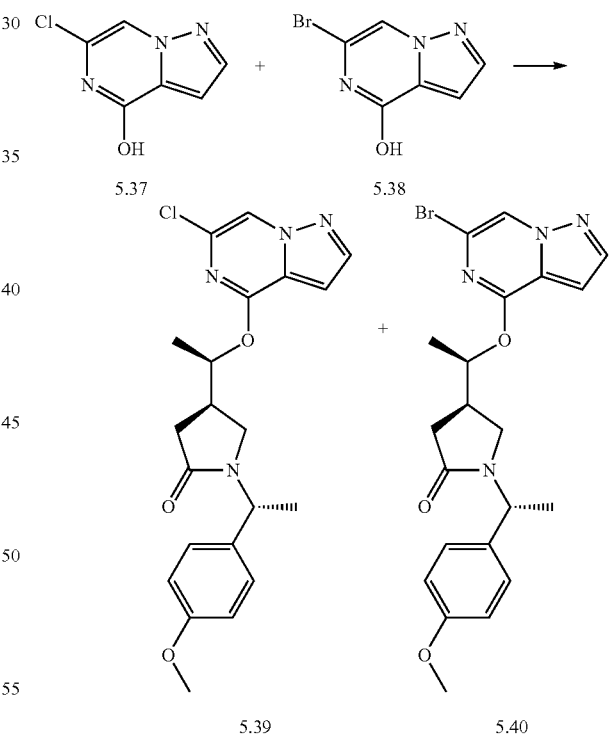

A mixture of 6-chloropyrazolo[1,5-a]pyrazin-4-ol 5.37 and 6-bromopyrazolo[1,5-a]pyrazin-4-ol 5.38 (122 mg), cesium carbonate (304 mg, 0.93 mmol), and (S)-1-((R)-1-((R)-1-(4-methoxyphenyl)ethyl)-5-oxopyrrolidin-3-yl)ethyl methanesulfonate 1.30 (328 mg, 0.96 mmol) in DMF (5 mL) was heated at 90° C. After 5 hours, An additional 102 mg of mesylate 1.30 was added. After an additional 3 h, 26 mg of mesylate 1.30 and 30 mg Cs$_2$CO$_3$ were added and mixture was stirred overnight. Mixture was then cooled to rt, poured into water, and extracted with ethyl acetate. Combined organics were washed with 50% brine, dried, filtered, and concentrated under reduced pressure. The resulting residue was purified by silica gel column chromatography (0-50% ethyl acetate/hexanes) to yield a mixture of (R)-4-((R)-1-((6-chloropyrazolo[1,5-a]pyrazin-4-yl)oxy)ethyl)-1-((R)-1-(4-methoxyphenyl)ethyl)pyrrolidin-2-one 5.39 and (R)-4-((R)-1-((6-bromopyrazolo[1,5-a]pyrazin-4-yl)oxy)ethyl)-1-((R)-1-(4-methoxyphenyl)ethyl)pyrrolidin-2-one 5.40 (129 mg).

LC/MS of (R)-4-((R)-1-((6-chloropyrazolo[1,5-a]pyrazin-4-yl)oxy)ethyl)-1-((R)-1-(4-methoxyphenyl)ethyl)pyrrolidin-2-one 5.39:
LCMS-ESI+ (m/z): [M+H]+ calcd for $C_{21}H_{24}ClN_4O_3$: 415.15; found: 414.92.

LC/MS of (R)-4-((R)-1-((6-bromopyrazolo[1,5-a]pyrazin-4-yl)oxy)ethyl)-1-((R)-1-(4-methoxyphenyl)ethyl)pyrrolidin-2-one 5.40:
LCMS-ESI+ (m/z): [M+H]+ calcd for $C_{21}H_{24}BrN_4O_3$: 459.10; found: 458.86.

Example 5.41 and 5.42

Preparation of (R)-4-((R)-1-((6-chloropyrazolo[1,5-a]pyrazin-4-yl)oxy)ethyl)pyrrolidin-2-one and (R)-4-((R)-1-((6-bromopyrazolo[1,5-a]pyrazin-4-yl)oxy)ethyl)pyrrolidin-2-one 5-a]pyrazin-4-yloxy)ethyl)-1-((R)-1-(4-methoxyphenyl)ethyl)pyrrolidin-2-one 5.40 (111 mg) in TFA (5 mL) was heated at 60° C. for 24 hours. After cooling to rt, residue was taken up in 25 mL of ethyl acetate and washed with 15 mL sat aqueous NaHCO₃. Layers were separated and aqueous was extracted with ethyl acetate. Combined organics were washed with 1:1 brine/sat NaHCO₃ $_{(aq)}$, dried, filtered, and concentrated under reduced pressure to yield a mixture of (R)-4-((R)-1-((6-chloropyrazolo[1,5-a]pyrazin-4-yl)oxy)ethyl)pyrrolidin-2-one 5.41 and (R)-4-((R)-1-((6-bromopyrazolo[1,5-a]pyrazin-4-yl)oxy)ethyl)pyrrolidin-2-one 5.42 (75 mg), which was used without further purification.

(R)-4-((R)-1-((6-chloropyrazolo[1,5-a]pyrazin-4-yl)oxy)ethyl)pyrrolidin-2-one 5.41:
LCMS-ESI+ (m/z): [M+H]+ calcd for $C_{12}H_{14}ClN_4O_2$: 281.07; found: 281.01.

(R)-4-((R)-1-((6-bromopyrazolo[1,5-a]pyrazin-4-yl)oxy)ethyl)pyrrolidin-2-one 5.42:
LCMS-ESI+ (m/z): [M+H]+ calcd for $C_{12}H_{14}BrN_4O_2$: 325.02; found: 325.03.

Example 5.41

Preparation of tert-butyl 4-(4-(4-((R)-1-((R)-5-oxopyrrolidin-3-yl)ethoxy)pyrazolo[1,5-a]pyrazin-6-yl)phenyl)piperazine-1-carboxylate

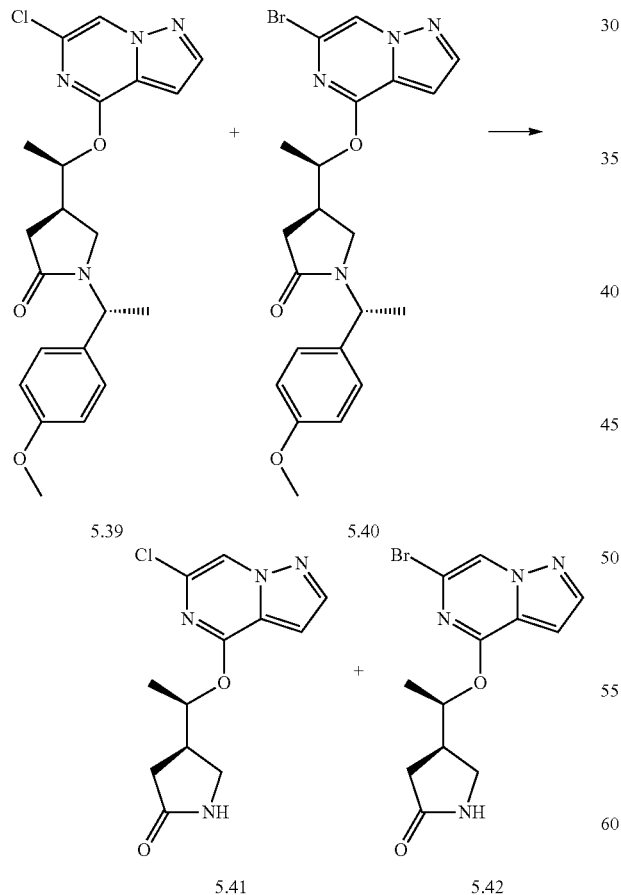
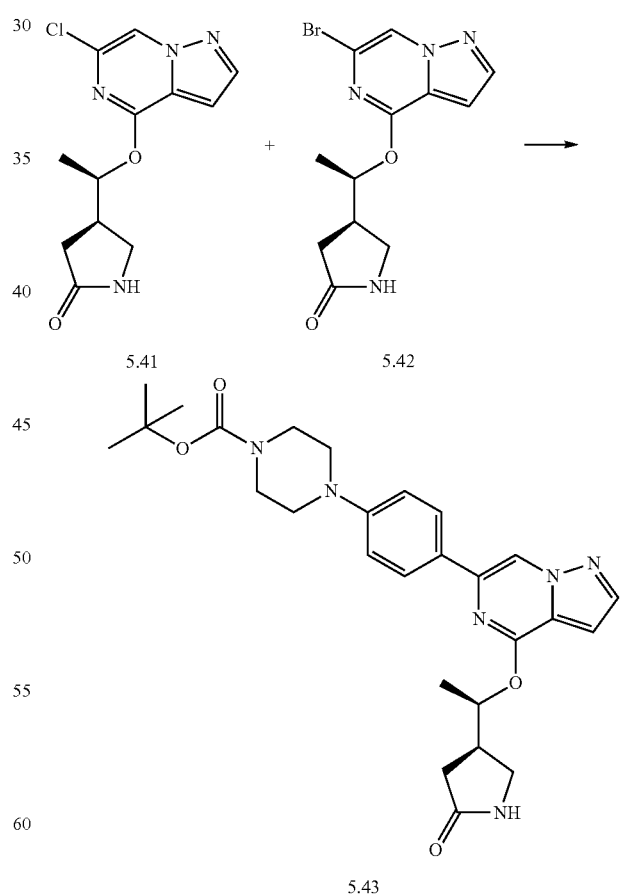

A mixture of (R)-4-((R)-1-(6-chloropyrazolo[1,5-a]pyrazin-4-yloxy)ethyl)-1-((R)-1-(4-methoxyphenyl)ethyl)pyrrolidin-2-one 5.39 and (R)-4-((R)-1-(6-chloropyrazolo[1, In a 5 mL microwave vial, a mixture of (R)-4-((R)-1-(6-chloropyrazolo[1,5-a]pyrazin-4-yloxy)ethyl)pyrrolidin-2-one 5.41 and (R)-4-((R)-1-(6-bromopyrazolo[1,5-a]pyrazin- 4-yloxy)ethyl)pyrrolidin-2-one 5.42 (37.6 mg), 4-(4-N-Boc-Piperazino)phenyboronic acid (64 mg, 0.21 mmol), cesium carbonate (138 mg, 0.42 mmol), and Peppsi-IPr catalyst (12 mg, 0.02 mmol) were taken up in dimethoxyethane (1.8 mL) and water (0.9 mL). After evacuating and backfilling with argon, mixture was heated in a microwave reactor at 100° C. for 70 minutes. Reaction mixture was cooled to rt, poured into water and extracted with ethyl acetate. Combine organics were dried, filtered, and concentrated under reduced pressure. The resulting residue was purified by silica gel column chromatography (0-7% MeOH/CH$_2$Cl$_2$) to yield tert-butyl 4-(4-(4-((R)-14(R)-5-oxopyrrolidin-3-yl)ethoxy)pyrazolo[1,5-a]pyrazin-6-yl)phenyl)piperazine-1-carboxylate 5.43 (52.2 mg).

LCMS-ESI+ (m/z): [M-41]+ calcd for C$_{27}$H$_{35}$N$_6$O$_4$: 507.26; found: 507.04.

Example 5.44

Preparation of (R)-4-((R)-1-((6-(4-(piperazin-1-yl)phenyl)pyrazolo[1,5-a]pyrazin-4-yl)oxy)ethyl)pyrrolidin-2-one

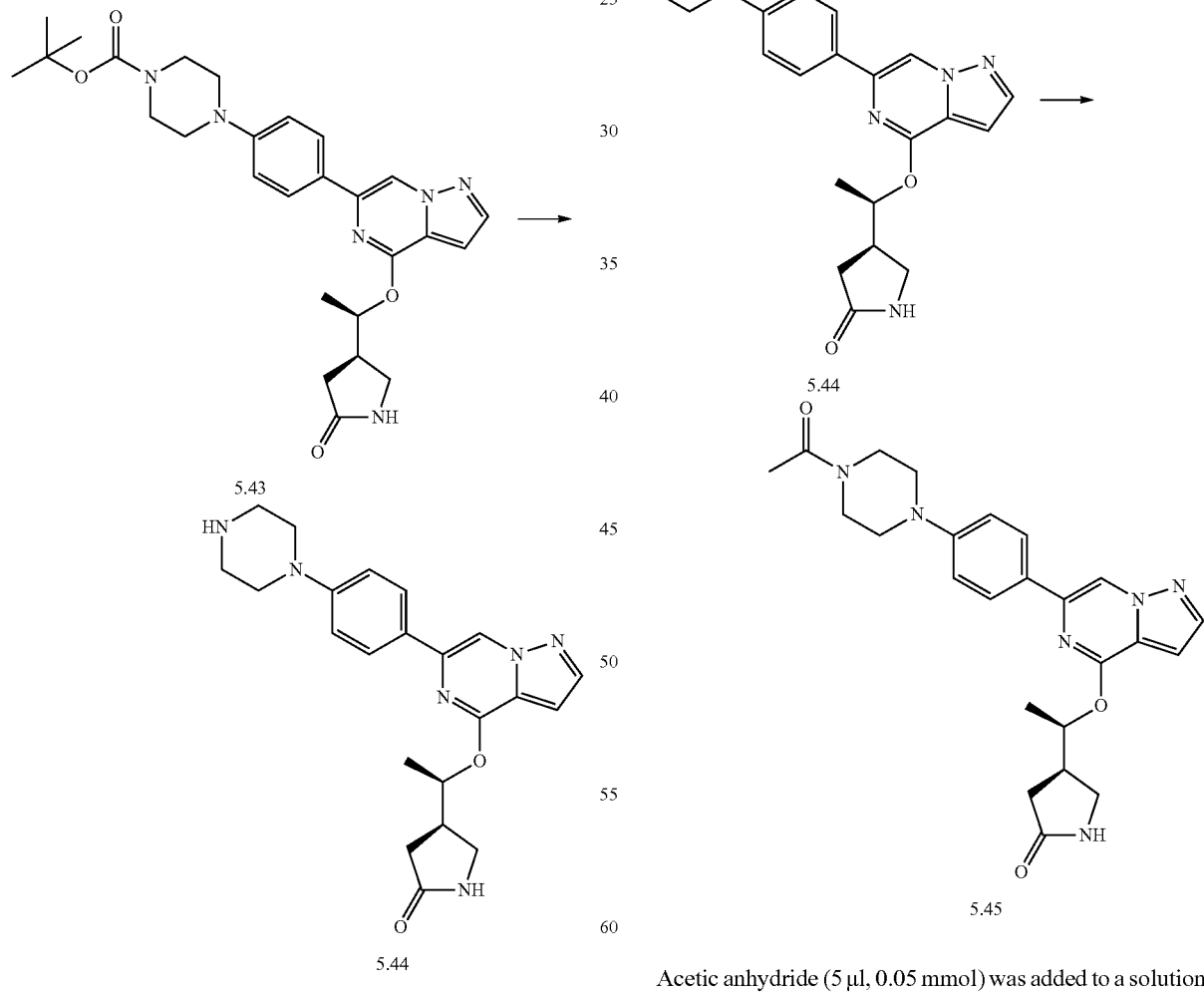

tert-butyl 4-(4-(4-((R)-1-((R)-5-oxopyrrolidin-3-yl)ethoxy)pyrazolo[1,5-a]pyrazin-6-yl)phenyl)piperazine-1-carboxylate 5.43 (51 mg, 0.1 mmol) was dissolved in TFA (4 mL, 52.23 mmol) and mixture was stirred at room temperature. After 4 hours, reaction mixture was concentrated and azeotroped with toluene to yield (R)-4-((R)-1-((6-(4-(piperazin-1-yl)phenyl)pyrazolo[1,5-a]pyrazin-4-yl)oxy)ethyl)pyrrolidin-2-one 5.44 as a trifluroacetic acid salt (41 mg).

1H NMR (400 MHz, CD$_3$OD) δ 8.57 (d, J=0.9 Hz, 1H), 7.96 (dd, J=5.7, 3.2 Hz, 3H), 7.12 (d, J=8.9 Hz, 2H), 6.81 (dd, J=2.4, 0.9 Hz, 1H), 5.68 (t, J=6.1 Hz, 1H), 3.60 (dd, J=10.2, 8.4 Hz, 1H), 3.53-3.45 (m, 4H), 3.42-3.37 (m, 4H), 3.37-3.32 (m, 1H), 3.02-2.92 (m, 1H), 2.62-2.42 (m, 2H), 1.50 (d, J=6.3 Hz, 3H).

LCMS-ESI+ (m/z): [M+H]+ calcd for C$_{22}$H$_{27}$N$_6$O$_2$: 407.21; found: 407.17.

Example 5.45

Preparation of (R)-4-((R)-1-((6-(4-(4-acetylpiperazin-1-yl)phenyl)pyrazolo[1,5-a]pyrazin-4-yl)oxy)ethyl)pyrrolidin-2-one

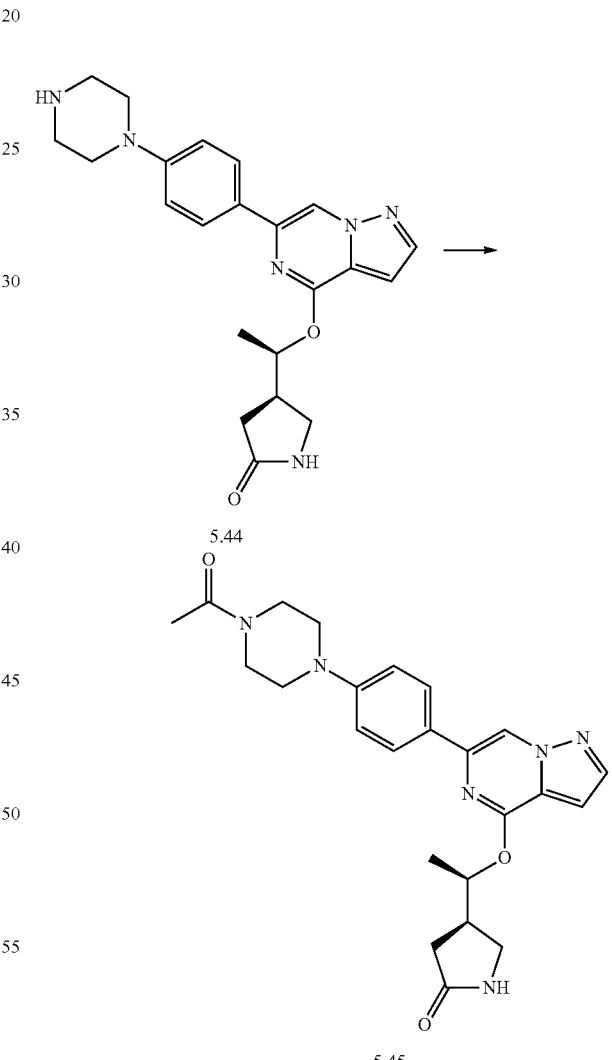

Acetic anhydride (5 µl, 0.05 mmol) was added to a solution of (R)-4-((R)-1-(6-(4-(piperazin-1-yl)phenyl)pyrazolo[1,5-a]pyrazin-4-yloxy)ethyl)pyrrolidin-2-one 2,2,2-trifluoroacetate 5.44 (22.38 mg, 0.04 mmol) and triethylamine (0.05 mL, 0.33 mmol) in dichloromethane (1.8 mL) at room temperature. After 90 min, reaction mixture was loaded directly onto silica gel and purified (0-8% methanol/dichloromethane) to yield (R)-4-((R)-1-((6-(4-(4-acetylpiperazin-1-yl)phenyl)pyrazolo[1,5-a]pyrazin-4-yl)oxy)ethyl)pyrrolidin-2-one 5.45 (17.1 mg).

1H NMR (400 MHz, CD$_3$OD) δ 8.55 (d, J=0.9 Hz, 1H), 8.01-7.86 (m, 3H), 7.14-7.03 (m, 2H), 6.80 (dd, J=2.4, 0.9 Hz, 1H), 5.69 (p, J=6.1 Hz, 1H), 3.73 (ddd, J=15.9, 6.4, 4.1 Hz, 4H), 3.59 (dd, J=10.2, 8.4 Hz, 1H), 3.38-3.33 (m, 1H), 3.32-3.27 (m, 2H), 3.25 (dd, J=6.3, 4.2 Hz, 2H), 3.03-2.90 (m, 1H), 2.61-2.42 (m, 2H), 2.16 (s, 3H), 1.50 (d, J=6.3 Hz, 3H).

LCMS-ESI$^+$ (m/z): [M+H]$^+$ calcd for C$_{24}$H$_{29}$N$_6$O$_3$: 449.22; found: 449.18.

Example 5.46

Preparation of (R)-4-((R)-1-((6-(4-(4-(methylsulfonyl)piperazin-1-yl)phenyl)pyrazolo[1,5-a]pyrazin-4-yl)oxy)ethyl)pyrrolidin-2-one

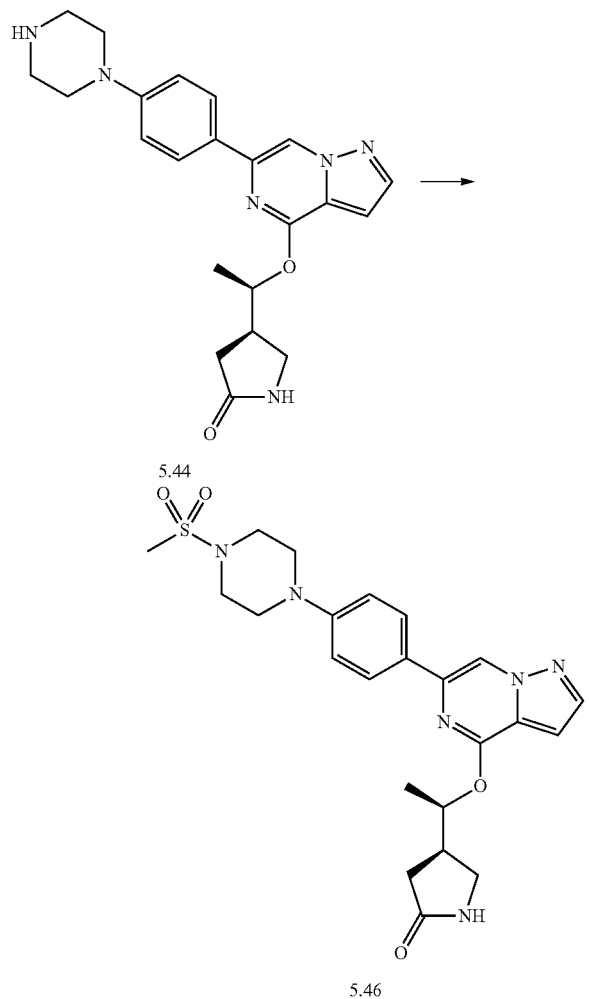

5.44

5.46

Methanesulfonic anhydride (9.3 mg, 0.05 mmol) was added to a solution of (R)-4-((R)-1-(6-(4-(piperazin-1-yl)phenyl)pyrazolo[1,5-a]pyrazin-4-yloxy)ethyl)pyrrolidin-2-one 2,2,2-trifluoroacetate 5.44 (22.38 mg, 0.04 mmol) and triethylamine (0.05 mL, 0.36 mmol) in dichloromethane (1.8 mL). After two hours, reaction mixture was loaded directly onto silica gel and purified (0-8% methanol/dichloromethane) to yield (R)-4-((R)-1-((6-(4-(4-(methylsulfonyl)piperazin-1-yl)phenyl)pyrazolo[1,5-a]pyrazin-4-yl)oxy)ethyl)pyrrolidin-2-one 5.46 (19.2 mg).

1H NMR (400 MHz, CD$_3$OD) δ 8.55 (d, J=0.9 Hz, 1H), 7.99-7.88 (m, 3H), 7.12-7.03 (m, 2H), 6.80 (dd, J=2.4, 0.9 Hz, 1H), 5.75-5.64 (m, 1H), 3.59 (dd, J=10.2, 8.4 Hz, 1H), 3.41-3.33 (m, 9H), 3.03-2.91 (m, 1H), 2.89 (s, 3H), 2.61-2.42 (m, 2H), 1.50 (d, J=6.3 Hz, 3H).

LCMS-ESI$^+$ (m/z): [M+H]$^+$ calcd for C$_{23}$H$_{29}$N$_6$O$_4$S: 485.19; found: 485.16.

Example 5.47

Preparation of tert-butyl 4-(2-methoxy-4-(4-((R)-1-((R)-5-oxopyrrolidin-3-yl)ethoxy)pyrazolo[1,5-a]pyrazin-6-yl)phenyl)piperazine-1-carboxylate

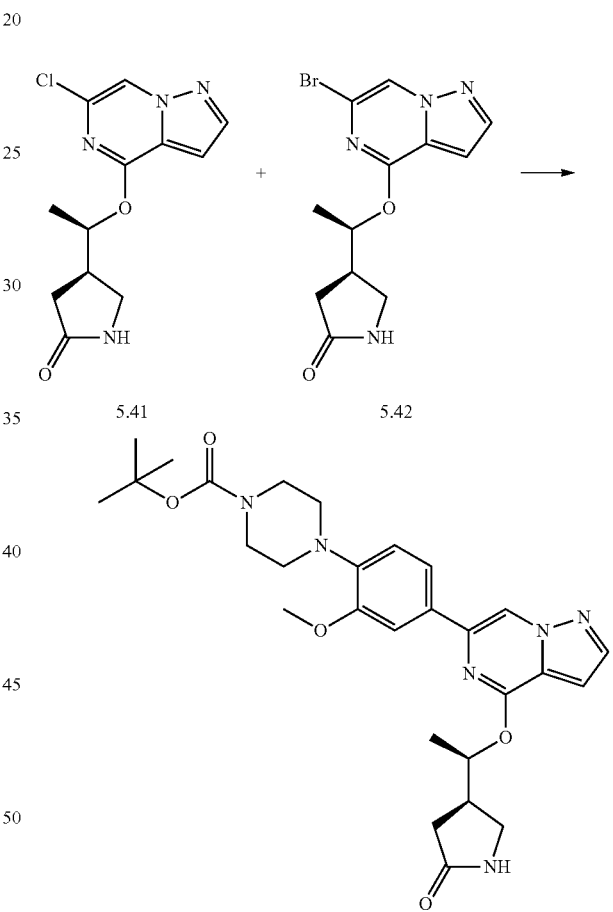

5.41   5.42

5.47

Following the procedure of Example 5.43, beginning with a mixture of (R)-4-((R)-1-(6-chloropyrazolo[1,5-a]pyrazin-4-yloxy)ethyl)pyrrolidin-2-one 5.41 and (R)-4-((R)-1-(6-bromopyrazolo[1,5-a]pyrazin-4-yloxy)ethyl)pyrrolidin-2-one 5.42 (37.62 mg) and tert-butyl 4-(2-methoxy-4-(4,4,5,5-tetramethyl-1,3,2-dioxaborolan-2-yl)phenyl)piperazine-1-carboxylate 7.08 (71 mg, 0.17 mmol), tert-butyl 4-(2-methoxy-4-(4-((R)-1-((R)-5-oxopyrrolidin-3-yl)ethoxy)pyrazolo[1,5-a]pyrazin-6-yl)phenyl)piperazine-1-carboxylate 5.47 (51 mg) was synthesized.

LCMS-ESI+ (m/z): [M+H]+ calcd for C28H37N6O5: 537.27; found: 537.15.

Example 5.48

Preparation of (R)-4-((R)-1-((6-(3-methoxy-4-(piperazin-1-yl)phenyl)pyrazolo[1,5-a]pyrazin-4-yl)oxy)ethyl)pyrrolidin-2-one

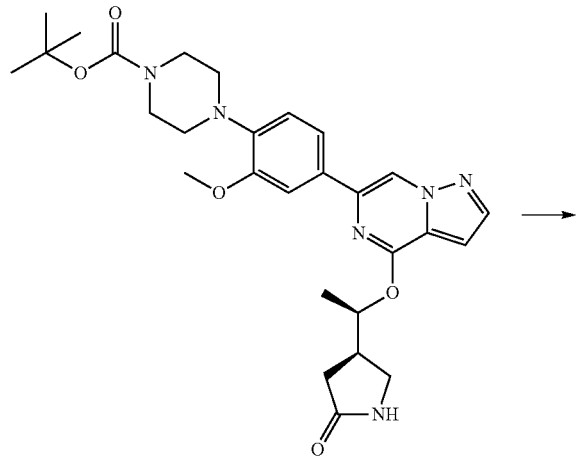

5.48 tert-butyl 4-(2-methoxy-4-(4-((R)-1-((R)-5-oxopyrrolidin-3-yl)ethoxy)pyrazolo[1,5-a]pyrazin-6-yl)phenyl)piperazine-1-carboxylate 5.47 (51 mg, 0.1 mmol) was dissolved in TFA (4 mL, 52.23 mmol) and mixture was stirred at room temperature. After 4 hours, reaction mixture was concentrated and azeotroped with toluene to yield (R)-4-((R)-1-((6-(3-methoxy-4-(piperazin-1-yl)phenyl)pyrazolo[1,5-a]pyrazin-4-yl)oxy)ethyl)pyrrolidin-2-one 5.48 as a trifluoroacetic acid salt (40 mg).

LCMS-ESI+ (m/z): [M+H]+ calcd for C23H29N6O3: 437.22; found: 437.18.

Example 5.49

Preparation of (R)-4-((R)-1-((6-(4-(4-acetylpiperazin-1-yl)-3-methoxyphenyl)pyrazolo[1,5-a]pyrazin-4-yl)oxy)ethyl)pyrrolidin-2-one

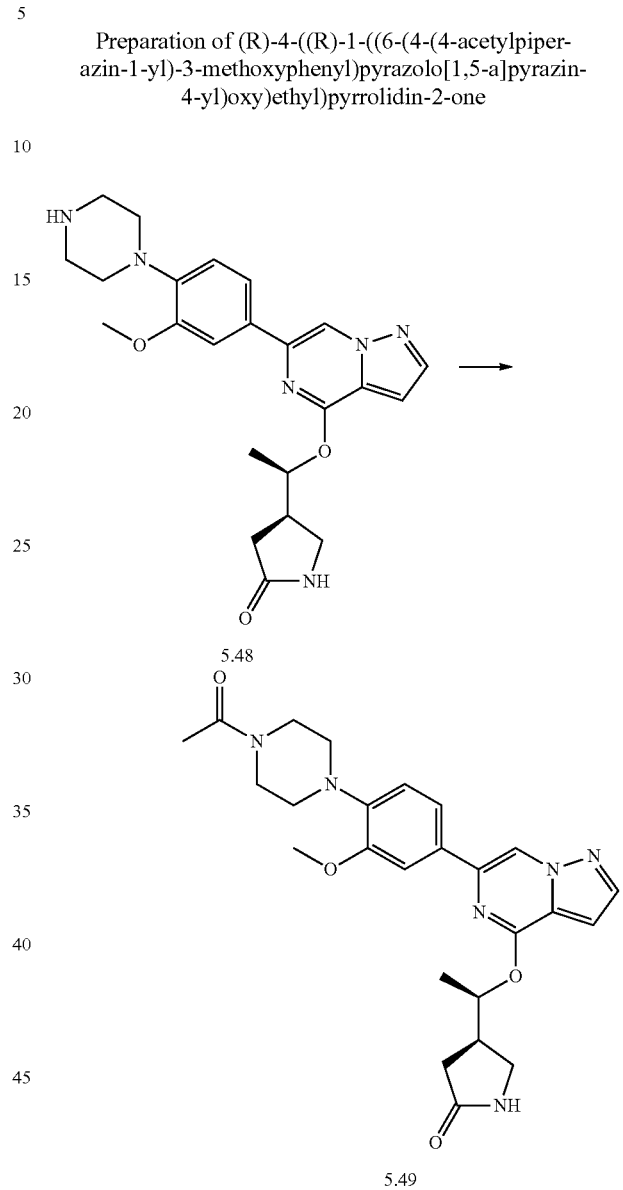

Acetic anhydride (5 µL, 0.05 mmol) was added to a solution of (R)-4-((R)-1-(6-(3-methoxy-4-(piperazin-1-yl)phenyl)pyrazolo[1,5-a]pyrazin-4-yloxy)ethyl)pyrrolidin-2-one 2,2,2-trifluoroacetate 5.48 (22.4 mg, 0.04 mmol) and triethylamine (0.05 ml, 0.33 mmol) in dichloromethane (1.8 mL) at room temperature. After two hours, reaction mixture was loaded directly onto silica and purified (0-8% methanol/dichloromethane) to yield (R)-4-((R)-1-((6-(4-(4-acetylpiperazin-1-yl)-3-methoxyphenyl)pyrazolo[1,5-a]pyrazin-4-yl)oxy)ethyl)pyrrolidin-2-one 5.49 (15.9 mg).

1H NMR (400 MHz, CD3OD) δ 8.64 (d, J=0.9 Hz, 1H), 7.97 (d, J=2.4 Hz, 1H), 7.64-7.57 (m, 2H), 7.04 (d, J=8.2 Hz, 1H), 6.81 (dd, J=2.3, 0.9 Hz, 1H), 5.68 (p, J=6.1 Hz, 1H), 3.98 (s, 3H), 3.73 (dt, J=17.8, 5.1 Hz, 4H), 3.60 (dd, J=10.2, 8.4 Hz, 1H), 3.38-3.32 (m, 1H), 3.14-3.04 (m, 4H), 3.03-2.92 (m, 1H), 2.62-2.43 (m, 2H), 2.15 (s, 3H), 1.52 (d, J=6.2 Hz, 3H).

LCMS-ESI⁺ (m/z): [M+H]⁺ calcd for $C_{25}H_{31}N_6O_4$: 479.23; found: 479.24.

Example 5.50

Preparation of (R)-4-((R)-1-((6-(3-methoxy-4-(4-(methylsulfonyl)piperazin-1-yl)phenyl)pyrazolo[1,5-a]pyrazin-4-yl)oxy)ethyl)pyrrolidin-2-one

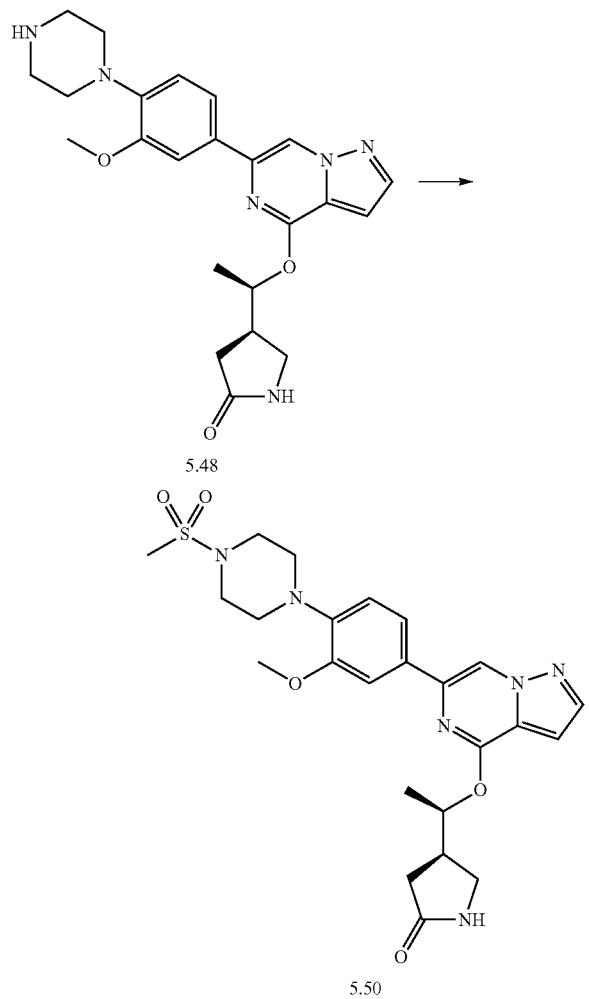

Methanesulfonic anhydride (9.5 mg, 0.05 mmol) was added to a solution of (R)-4-((R)-1-(6-(3-methoxy-4-(piperazin-1-yl)phenyl)pyrazolo[1,5-a]pyrazin-4-yloxy)ethyl)pyrrolidin-2-one 2,2,2-trifluoroacetate 5.48 (22.4 mg, 0.04 mmol) and triethylamine (0.05 mL, 0.36 mmol) in dichloromethane (1.8 mL). After two hours, reaction mixture was loaded directly onto silica and purified (0-8% methanol/dichloromethane) to yield (R)-4-((R)-1-((6-(3-methoxy-4-(4-(methylsulfonyl)piperazin-1-yl)phenyl)pyrazolo[1,5-a]pyrazin-4-yl)oxy)ethyl)pyrrolidin-2-one 5.50 (19 mg).

1H NMR (400 MHz, CD₃OD) δ 8.65 (d, J=0.9 Hz, 1H), 7.97 (d, J=2.3 Hz, 1H), 7.61 (d, J=7.9 Hz, 2H), 7.06 (d, J=8.0 Hz, 1H), 6.82 (dd, J=2.3, 0.9 Hz, 1H), 5.68 (q, J=6.1 Hz, 1H), 3.97 (s, 3H), 3.60 (dd, J=10.2, 8.4 Hz, 1H), 3.39 (dd, J=6.3, 3.5 Hz, 4H), 3.35 (dd, J=10.2, 6.0 Hz, 1H), 3.19 (dd, J=6.2, 3.6 Hz, 4H), 3.06-2.92 (m, 1H), 2.90 (s, 3H), 2.61-2.41 (m, 2H), 1.52 (d, J=6.2 Hz, 3H).

Example 5.51

Preparation of (4-(benzyloxy)-6-chloropyrazolo[1,5-a]pyrazin-3-yl)methanol

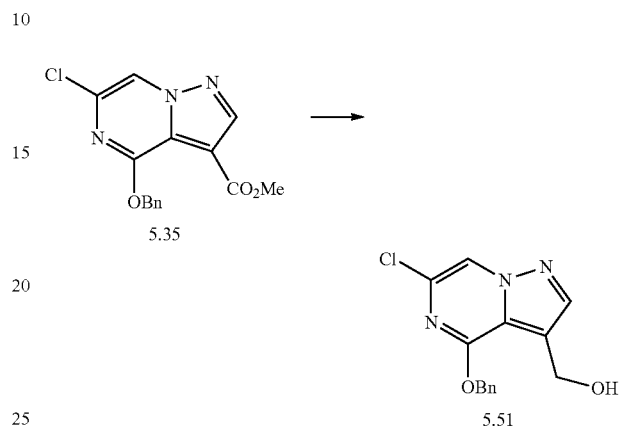

A solution of methyl 4-(benzyloxy)-6-chloropyrazolo[1,5-a]pyrazine-3-carboxylate 5.35 (427 mg, 1.34 mmol) in THF (6 mL) was cooled to 0° C. under argon. A solution of lithium aluminum hydride in THF (1 M, 1.52 mL, 1.52 mmol) was then added slowly and mixture was warmed to rt and stirred for 18 hours. Mixture was diluted with ether and cooled to 0° C. It was then quenched by addition of 0.060 mL water, 0.060 mL 15% NaOH (aq), and 0.18 mL of water and warmed to room temperature. After 15 minutes, MgSO₄ was added and mixture stirred for 20 minutes. Mixture was filtered and filtrate was concentrated under reduced pressure. The resulting residue was purified by silica gel column chromatography (0-50% ethyl acetate/hexanes) to yield (4-(benzyloxy)-6-chloropyrazolo[1,5-a]pyrazin-3-yl)methanol 5.51 (143 mg).

LCMS-ESI⁺ (m/z): [M+H]⁺ calcd for $C_{14}H_{13}ClN_3O_2$: 290.06; found: 290.05.

Example 5.52

Preparation of 6-chloro-3-methylpyrazolo[1,5-a]pyrazin-4-ol

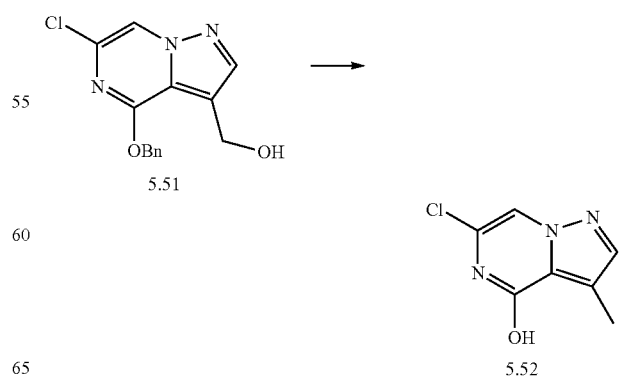

Triethylsilane (0.2 ml, 1.25 mmol) was added slowly to a solution of (4-(benzyloxy)-6-chloropyrazolo[1,5-a]pyrazin-3-yl)methanol 5.51 (142 mg, 0.49 mmol) in TFA (3 mL). After 19 hours, an additional 0.4 mL of triethylsilane was added and mixture was heated to 60 degrees for 4.5 hours. Mixture was cooled to rt and concentrated under reduced pressure. Resulting residue was taken up in DCM and washed with sat. NaHCO$_3$ $_{(aq)}$. Aqueous layer was extracted with DCM. Combined organics were dried, filtered, and concentrated under reduced pressure to yield 6-chloro-3-methylpyrazolo[1,5-a]pyrazin-4-ol 5.52 (90 mg), which was used in the next step without further purification.

LCMS-ESI$^+$ (m/z): [M+H]$^+$ calcd for C$_7$H$_7$ClN$_3$O: 184.02; found: 184.00.

Example 5.53

Preparation of (R)-4-((R)-1-((6-chloro-3-methylpyrazolo[1,5-a]pyrazin-4-yl)oxy)ethyl)-1-((R)-1-(4-methoxyphenyl)ethyl)pyrrolidin-2-one

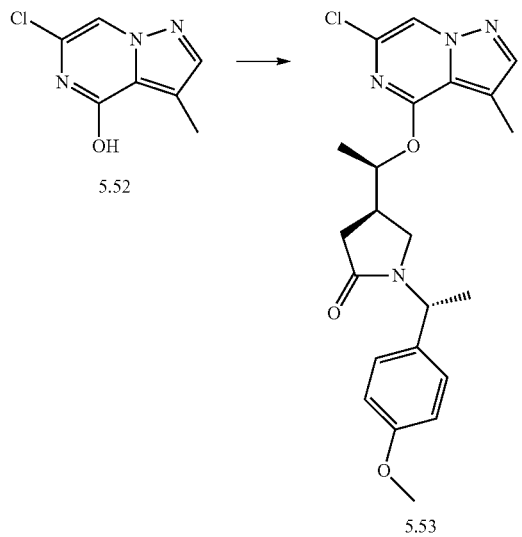 [SMILES: Cc1cnn2cc(Cl)nc(O)c12 ; COc1ccc([C@@H](C)N2C[C@H]([C@@H](C)Oc3nc(Cl)cn4ncc(C)c34)CC2=O)cc1]

A mixture of 6-chloro-3-methylpyrazolo[1,5-a]pyrazin-4-ol 5.52 (48 mg, 0.262 mmol), (S)-1-((R)-1-((R)-1-(4-methoxyphenyl)ethyl)-5-oxopyrrolidin-3-yl)ethyl methanesulfonate 1.30 (135 mg, 0.394 mmol), and cesium carbonate (136 mg, 0.417 mmol) in DMF (2 mL) was heated at 90° C. After 5 hours, reaction mixture was cooled to rt, poured into water, and extracted with ethyl acetate. Combined organics were washed with 50% brine, dried, filtered, and concentrated under reduced pressure. The resulting residue was purified by silica gel column chromatography (0-100% ethyl acetate/hexanes) to yield (R)-4-((R)-1-((6-chloro-3-methylpyrazolo[1,5-a]pyrazin-4-yl)oxy)ethyl)-1-((R)-1-(4-methoxyphenyl)ethyl)pyrrolidin-2-one 5.53 (37 mg).

LCMS-ESI$^+$ (m/z): [M+H]$^+$ calcd for C$_{22}$H$_{26}$ClN$_4$O$_3$: 429.16; found: 428.87.

Example 5.54

Preparation of (R)-4-((R)-1-((6-chloro-3-methylpyrazolo[1,5-a]pyrazin-4-yl)oxy)ethyl)pyrrolidin-2-one

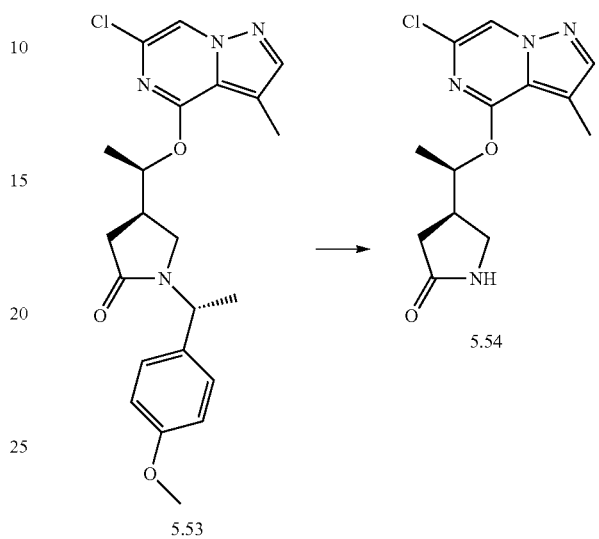

(R)-4-((R)-1-(6-chloro-3-methylpyrazolo[1,5-a]pyrazin-4-yloxy)ethyl)-1-((R)-1-(4-methoxyphenyl)ethyl)pyrrolidin-2-one 5.53 (31 mg, 0.07 mmol) was dissolved in 1.5 mL of TFA and mixture was heated at 60° C. After 17 hours, reaction mixture was cooled to rt and concentrated under reduced pressure. Resulting residue was taken up in ethyl acetate and washed with sat NaHCO$_3$ $_{(aq)}$. Layers were separated and aqueous was extracted with ethyl acetate. Combined organics were washed with 1:1 sat. NaHCO$_3$ $_{(aq)}$/brine, dried, filtered, and concentrated under reduced pressure to yield (R)-4-((R)-1-((6-chloro-3-methylpyrazolo[1,5-a]pyrazin-4-yl)oxy)ethyl)pyrrolidin-2-one 5.54 (21 mg), which was used without further purification.

LCMS-ESI$^+$ (m/z): [M+H]$^+$ calcd for C$_{13}$H$_{16}$ClN$_4$O$_2$: 295.09; found: 295.00.

Example 5.55

Preparation of tert-butyl 4-(4-(3-methyl-4-((R)-1-((R)-5-oxopyrrolidin-3-yl)ethoxy)pyrazolo[1,5-a]pyrazin-6-yl)phenyl)piperazine-1-carboxylate

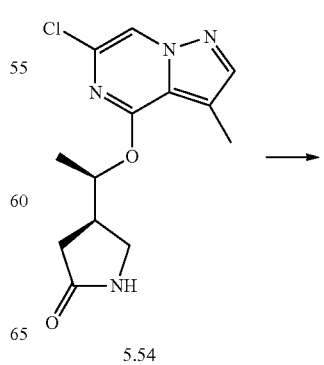

-continued

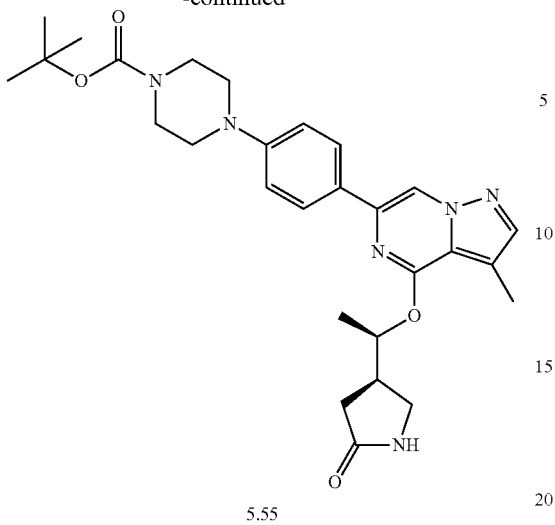

5.55

In a 5 mL microwave vial, (R)-4-((R)-1-(6-chloro-3-methylpyrazolo[1,5-a]pyrazin-4-yloxy)ethyl)pyrrolidin-2-one 5.54 (21 mg, 0.07 mmol), 4-(4-N-Boc-Piperazino)phenyboronic acid (34 mg, 0.11 mmol), cesium carbonate (74 mg, 0.23 mmol), and Peppsi"-IPr catalyst (8 mg, 0.01 mmol) were taken up in dimethoxyethane (1.6 mL) and water (0.8 mL). After evacuating and backfilling with argon, mixture was heated in a microwave reactor at 100° C. for 70 minutes. Reaction mixture was cooled to rt, poured into water and extracted with ethyl acetate. Combined organics were dried, filtered, and concentrated under reduced pressure. The resulting residue was purified by silica gel column chromatography (0-7% MeOH/CH$_2$Cl$_2$) to yield tert-butyl 4-(4-(3-methyl-4-((R)-14(R)-5-oxopyrrolidin-3-yl)ethoxy)pyrazolo[1,5-a]pyrazin-6-yl)phenyl)piperazine-1-carboxylate 5.55 (25.2 mg).

LCMS-ESI$^+$ (m/z): [M+H]$^+$ calcd for C$_{28}$H$_{37}$N$_6$O$_4$: 521.28; found: 520.96.

Example 5.56

Preparation of (R)-4-((R)-1-((3-methyl-6-(4-(piperazin-1-yl)phenyl)pyrazolo[1,5-a]pyrazin-4-yl)oxy)ethyl)pyrrolidin-2-one -continued

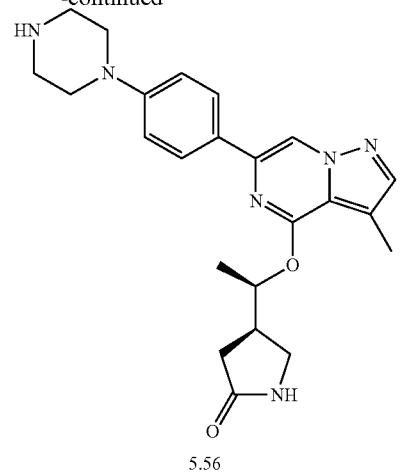

5.56 tert-butyl 4-(4-(3-methyl-4-((R)-1-((R)-5-oxopyrrolidin-3-yl)ethoxy)pyrazolo[1,5-a]pyrazin-6-yl)phenyl)piperazine-1-carboxylate (20.2 mg, 0.04 mmol) 5.55 was dissolved in TFA (1.5 mL, 20 mmol) and mixture stirred at room temperature. After 2 hours, reaction mixture was concentrated and azeotroped with toluene to yield (R)-4-((R)-1-((3-methyl-6-(4-(piperazin-1-yl)phenyl)pyrazolo[1,5-a]pyrazin-4-yl)oxy)ethyl)pyrrolidin-2-one 5.56 as a trifluoroacetic acid salt (21 mg).

LCMS-ESI$^+$ (m/z): [M+H]$^+$ calcd for C$_{23}$H$_{29}$N$_6$O$_2$: 421.23; found: 421.20.

Example 5.57

Preparation of (R)-4-((R)-1-((6-(4-(4-acetylpiperazin-1-yl)phenyl)-3-methylpyrazolo[1,5-a]pyrazin-4-yl)oxy)ethyl)pyrrolidin-2-one

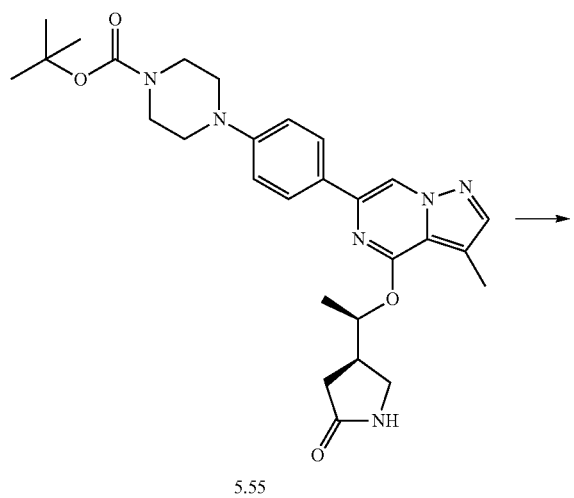

5.55

→

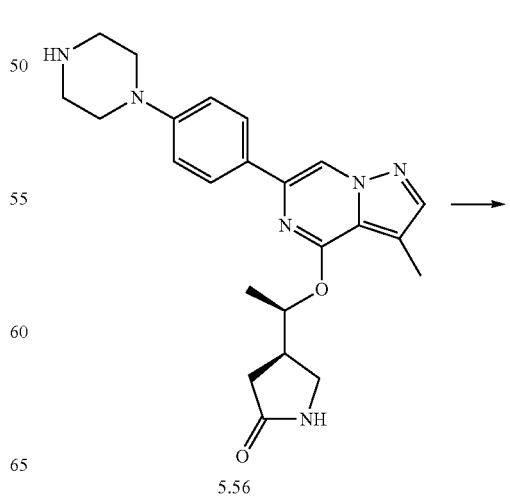

5.56

→

-continued

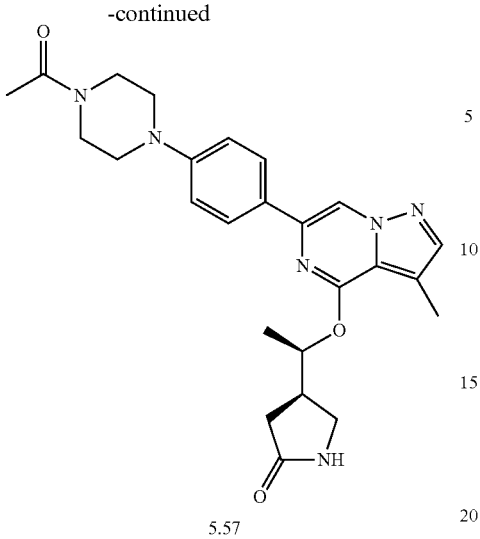

5.57

-continued

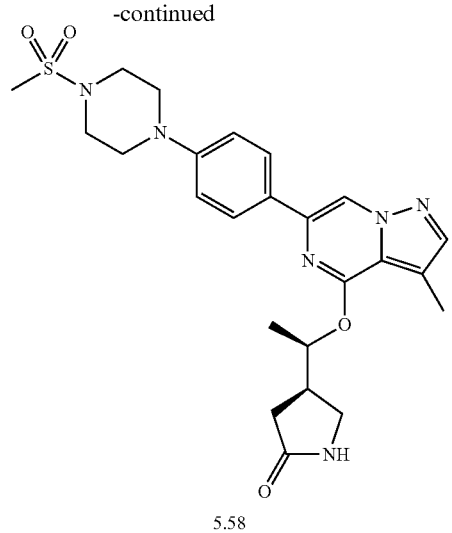

5.58

Acetic anhydride (3.1 µL, 0.03 mmol) was added to a solution of (R)-4-((R)-1-(3-methyl-6-(4-(piperazin-1-yl)phenyl)pyrazolo[1,5-a]pyrazin-4-yloxy)ethyl)pyrrolidin-2-one 2,2,2-trifluoroacetate 5.56 (14.6 mg, 0.03 mmol) and triethylamine (0.03 mL, 0.21 mmol) in dichloromethane (1.5 mL) at room temperature. After two hours, reaction mixture was directly loaded onto silica gel and purified (0-10% methanol/dichloromethane) to yield (R)-4-((R)-1-((6-(4-(4-acetylpiperazin-1-yl)phenyl)-3-methylpyrazolo[1,5-a]pyrazin-4-yl)oxy)ethyl)pyrrolidin-2-one 5.57 (11 mg).

1H NMR (400 MHz, CD$_3$OD) δ 8.41 (d, J=1.0 Hz, 1H), 7.89 (d, J=8.6 Hz, 2H), 7.73 (s, 1H), 7.06 (d, J=8.6 Hz, 2H), 5.68 (q, J=6.0 Hz, 1H), 3.73 (dt, J=15.9, 5.2 Hz, 4H), 3.60 (dd, J=10.1, 8.7 Hz, 1H), 3.36 (dd, J=10.2, 6.1 Hz, 1H), 3.32-3.24 (dt, J=16.0, 5.3 Hz, 4H), 3.07-2.92 (m, 1H), 2.63-2.47 (m, 2H), 2.45 (s, 3H), 2.15 (d, J=1.0 Hz, 3H), 1.51 (dd, J=6.3, 1.0 Hz, 3H).

LCMS-ESI$^+$ (m/z): [M+H]$^+$ calcd for C$_{25}$H$_{31}$N$_6$O$_3$: 463.64; found: 463.20.

Example 5.58

Preparation of (R)-4-((R)-1-((3-methyl-6-(4-(4-(methylsulfonyl)piperazin-1-yl)phenyl)pyrazolo[1,5-a]pyrazin-4-yl)oxy)ethyl)pyrrolidin-2-one

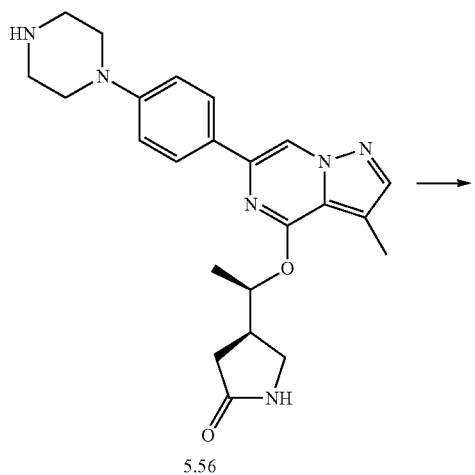

5.56

Triethylamine (0.02 mL, 0.14 mmol) was added to a solution of (R)-4-((R)-1-(3-methyl-6-(4-(piperazin-1-yl)phenyl)pyrazolo[1,5-a]pyrazin-4-yloxy)ethyl)pyrrolidin-2-one 2,2,2-trifluoroacetate 5.56 (5.8 mg, 0.011 mmol) in DCM (1 mL). Methanesulfonic anhydride (2.3 mg, 0.013 mmol) was added and mixture was stirred at room temperature. After 2 hours, an additional 1.4 mg of methanesulfonic anhydride was added. After 30 min, reaction mixture was loaded onto silica and purified (0-7% methanol/dichloromethane) to yield (R)-4-((R)-1-((3-methyl-6-(4-(4-(methylsulfonyl)piperazin-1-yl)phenyl)pyrazolo[1,5-a]pyrazin-4-yl)oxy)ethyl)pyrrolidin-2-one 5.58 (3.8 mg).

1H NMR (400 MHz, CD$_3$OD) δ 8.42 (d, J=1.0 Hz, 1H), 7.98-7.84 (m, 2H), 7.73 (d, J=1.1 Hz, 1H), 7.08 (d, J=8.7 Hz, 2H), 5.69 (p, J=6.0 Hz, 1H), 3.61 (dd, J=10.1, 8.7 Hz, 1H), 3.43-3.33 (m, 9H), 3.00 (p, J=7.3 Hz, 1H), 2.89 (d, J=1.0 Hz, 3H), 2.64-2.47 (m, 2H), 2.45 (s, 3H), 1.51 (dd, J=6.3, 1.0 Hz, 3H).

LCMS-ESI$^+$ (m/z): [M+H]$^+$ calcd for C$_{24}$H$_{31}$N$_6$O$_4$S: 499.20; found: 499.17.

Example 5.59

Preparation of tert-butyl 4-(2-methoxy-4-(3-methyl-4-((R)-1-((R)-5-oxopyrrolidin-3-yl)ethoxy)pyrazolo[1,5-a]pyrazin-6-yl)phenyl)piperazine-1-carboxylate

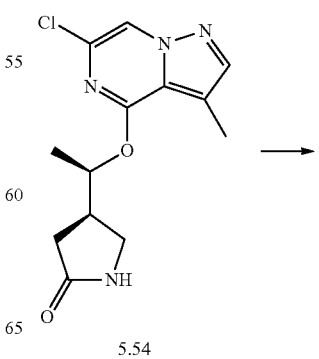

5.54

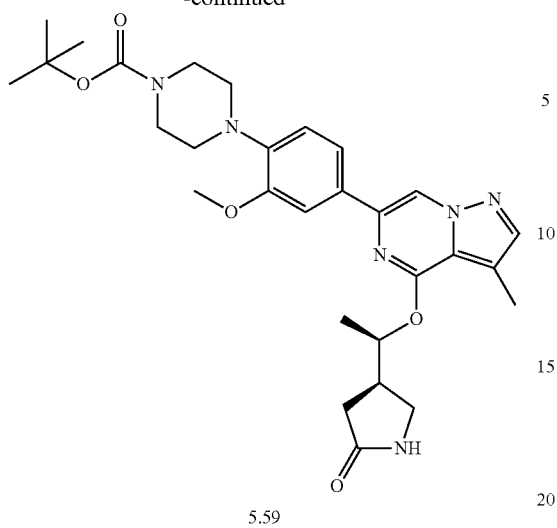

5.59

Following the procedure of Example 5.55, beginning with (R)-4-((R)-1-(6-chloro-3-methylpyrazolo[1,5-a]pyrazin-4-yloxy)ethyl)pyrrolidin-2-one 5.54 (25.3 mg, 0.086 mmol) and tert-butyl 4-(2-methoxy-4-(4,4,5,5-tetramethyl-1,3,2-dioxaborolan-2-yl)phenyl)piperazine-1-carboxylate 7.08 (44 mg, 0.105 mmol), tert-butyl 4-(2-methoxy-4-(3-methyl-4-4R)-1-((R)-5-oxopyrrolidin-3-yl)ethoxy)pyrazolo[1,5-a]pyrazin-6-yl)phenyl)piperazine-1-carboxylate 5.59 (35 mg) was synthesized.

LCMS-ESI$^+$ (m/z): [M+H]$^+$ calcd for $C_{29}H_{39}N_6O_5$: 551.29; found: 551.16.

Example 5.60

Preparation of (R)-4-((R)-1-((6-(3-methoxy-4-(piperazin-1-yl)phenyl)-3-methylpyrazolo[1,5-a]pyrazin-4-yl)oxy)ethyl)pyrrolidin-2-one

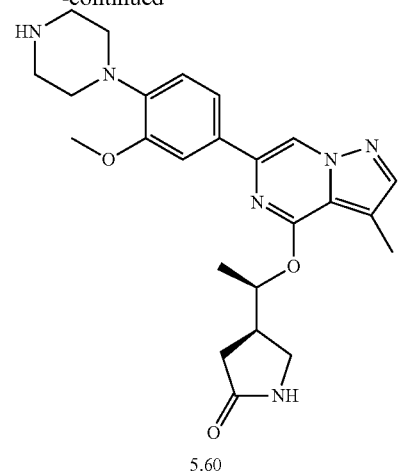

5.60 tert-butyl 4-(2-methoxy-4-(3-methyl-4-((R)-1-((R)-5-oxopyrrolidin-3-yl)ethoxy)pyrazolo[1,5-a]pyrazin-6-yl)phenyl)piperazine-1-carboxylate 5.59 (35 mg, 0.06 mmol) was dissolved in TFA (2.5 mL, 32.7 mmol) and mixture was stirred at room temperature. After 2 hours, reaction mixture was concentrated and azeotroped with toluene to yield (R)-4-((R)-1-((6-(3-methoxy-4-(piperazin-1-yl)phenyl)-3-methylpyrazolo[1,5-a]pyrazin-4-yl)oxy)ethyl)pyrrolidin-2-one 5.60 as a trifluoroacetic acid salt (36 mg).

1H NMR (400 MHz, CD$_3$OD) δ 8.53 (s, 1H), 7.77 (d, J=0.9 Hz, 1H), 7.68-7.56 (m, 2H), 7.06 (d, J=8.2 Hz, 1H), 5.77-5.62 (m, 1H), 3.98 (s, 3H), 3.61 (dd, J=10.1, 8.7 Hz, 1H), 3.38 (q, J=4.8 Hz, 5H), 3.35-3.31 (m, 4H), 3.07-2.95 (m, 1H), 2.64-2.48 (m, 2H), 2.45 (s, 3H), 1.53 (d, J=6.2 Hz, 3H).

LCMS-ESI$^+$ (m/z): [M+H]$^+$ calcd for $C_{24}H_{31}N_6O_3$: 451.24; found: 451.29.

Example 5.61

Preparation of (R)-4-((R)-1-((6-(4-(4-acetylpiperazin-1-yl)-3-methoxyphenyl)-3-methylpyrazolo[1,5-a]pyrazin-4-yl)oxy)ethyl)pyrrolidin-2-one

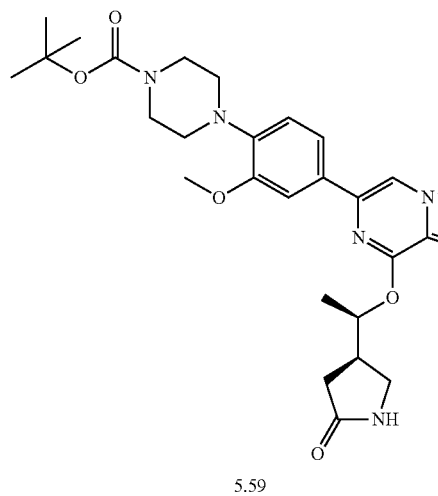

5.59

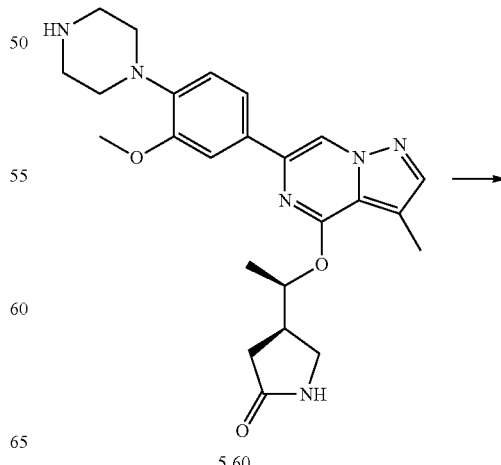

5.60

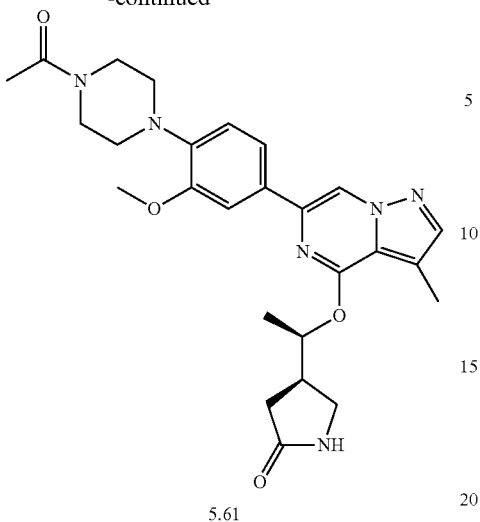

5.61

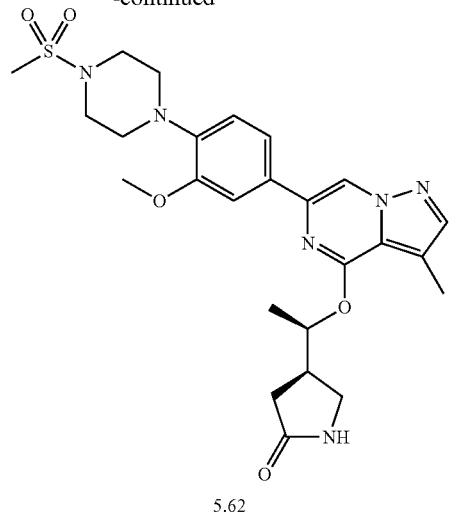

5.62

Acetic Anhydride (4 μl, 0.04 mmol) was added to a solution of (R)-4-((R)-1-(6-(3-methoxy-4-(piperazin-1-yl)phenyl)-3-methylpyrazolo[1,5-a]pyrazin-4-yloxy)ethyl)pyrrolidin-2-one 2,2,2-trifluoroacetate 5.60 (18.1 mg, 0.03 mmol) and triethylamine (0.04 ml, 0.28 mmol) in dichloromethane (2 mL) at room temperature. After 90 min, reaction mixture was directly loaded onto silica gel and purified (0-8% methanol/dichloromethane) to yield (R)-4-((R)-1-((6-(4-(4-acetylpiperazin-1-yl)-3-methoxyphenyl)-3-methylpyrazolo[1,5-a]pyrazin-4-yl)oxy)ethyl)pyrrolidin-2-one 5.61 (13.6 mg).

1H NMR (400 MHz, CD$_3$OD) δ 8.50 (d, J=1.0 Hz, 1H), 7.75 (s, 1H), 7.62-7.54 (m, 2H), 7.03 (d, J=8.2 Hz, 1H), 5.67 (p, J=6.0 Hz, 1H), 3.97 (d, J=1.0 Hz, 3H), 3.73 (dt, J=17.8, 5.2 Hz, 4H), 3.61 (t, J=9.4 Hz, 1H), 3.37 (dd, J=10.2, 6.1 Hz, 1H), 3.14-3.09 (m, 2H), 3.05 (t, J=5.1 Hz, 2H), 3.03-2.95 (m, 1H), 2.64-2.48 (m, 2H), 2.45 (s, 3H), 2.15 (d, J=1.0 Hz, 3H), 1.53 (d, J=6.2 Hz, 3H).

LCMS-ESI$^+$ (m/z): [M+H]$^+$ calcd for C$_{23}$H$_{29}$N$_6$O$_2$: 493.25; found: 493.27.

Example 5.62

Preparation of (R)-4-((R)-1-((6-(3-methoxy-4-(methylsulfonyl)piperazin-1-yl)phenyl)-3-methylpyrazolo[1,5-a]pyrazin-4-yl)oxy)ethyl)pyrrolidin-2-one

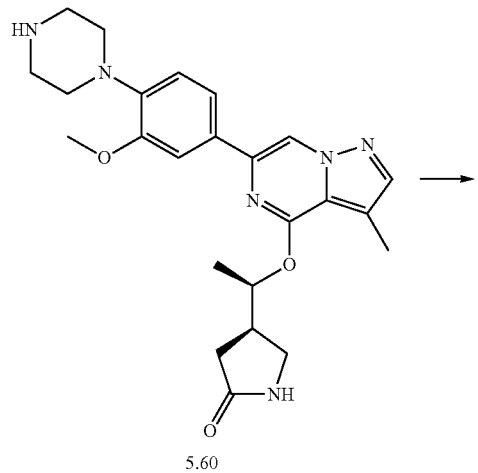

5.60

Triethylamine (0.04 mL, 0.28 mmol) was added to a solution of (R)-4-((R)-1-(6-(3-methoxy-4-(piperazin-1-yl)phenyl)-3-methylpyrazolo[1,5-a]pyrazin-4-yloxy)ethyl)pyrrolidin-2-one 2,2,2-trifluoroacetate 5.60 (15.2 mg, 0.03 mmol) in dichloromethane (1.5 mL). Methanesulfonic anhydride (6.8 mg, 0.04 mmol) was then added to the solution and the mixture was stirred at room temperature. After 3 hours, mixture was loaded directly onto silica gel and purified (0-8% methanol/dichloromethane) to yield (R)-4-((R)-1-((6-(3-methoxy-4-(4-(methylsulfonyl)piperazin-1-yl)phenyl)-3-methylpyrazolo[1,5-a]pyrazin-4-yl)oxy)ethyl)pyrrolidin-2-one 5.62 (12.1 mg). 1H NMR (400 MHz, CD$_3$OD) δ 8.50 (d, J=1.0 Hz, 1H), 7.75 (s, 1H), 7.58 (dt, J=10.7, 1.5 Hz, 2H), 7.05 (d, J=8.2 Hz, 1H), 5.67 (p, J=6.0 Hz, 1H), 3.96 (d, J=1.0 Hz, 3H), 3.61 (dd, J=10.1, 8.7 Hz, 1H), 3.42-3.36 (m, 4H), 3.41-3.35 (m, 1H), 3.22-3.15 (m, 4H), 3.08-2.94 (m, 1H), 2.89 (d, J=1.0 Hz, 3H), 2.63-2.48 (m, 2H), 2.45 (s, 3H), 1.53 (dd, J=6.3, 1.0 Hz, 3H).

LCMS-ESI$^+$ (m/z): [M+H]$^+$ calcd for C$_{25}$H$_{33}$N$_6$O$_5$S: 529.22; found: 529.28.

Example 5.63

Preparation of (R)-4-((R)-1-((6-(3-methoxy-4-(4-oxetan-3-yl)piperazin-1-yl)phenyl)-3-methylpyrazolo[1,5-a]pyrazin-4-yl)oxy)ethyl)pyrrolidin-2-one

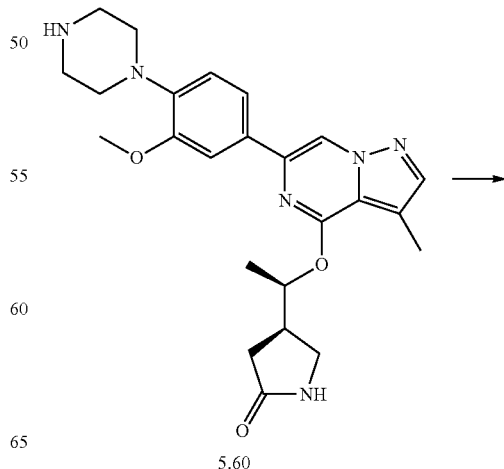

5.60

-continued

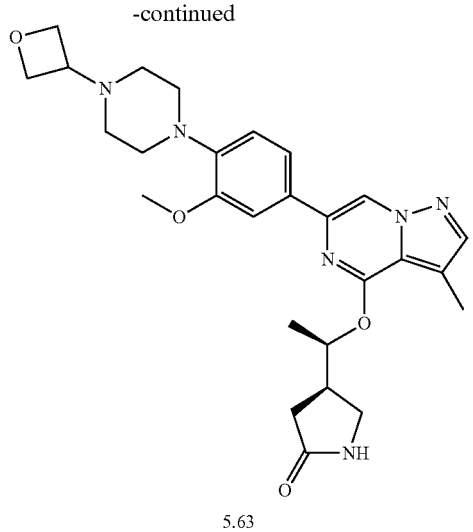

5.63

N,N-diisopropylethylamine (0.02 mL, 0.09 mmol) was added to a mixture of (R)-4-((R)-1-(6-(3-methoxy-4-(piperazin-1-yl)phenyl)-3-methylpyrazolo[1,5-a]pyrazin-4-yloxy)ethyl)pyrrolidin-2-one 2,2,2-trifluoroacetate 5.60 (21.45 mg, 0.04 mmol) in THF (1.5 mL) at room temperature. 3-Oxetanone (0.03 mL, 0.39 mmol) was added, followed by sodium triacetoxyborohydride (58 mg, 0.27 mmol) and mixture was heated at 50° C. After 3 hours, mixture was cooled to room temperature, diluted with 20 mL ethyl acetate, and washed with 8 mL water/10 mL sat $Na_2CO_3$(aq). Layers were separated and aqueous layer was extracted with ethyl acetate. Combined organics were dried, filtered, and concentrated under reduced pressure. The resulting residue was purified by silica gel column chromatography (0-12% MeOH/$CH_2Cl_2$) to yield (R)-4-((R)-1-((6-(3-methoxy-4-(4-(oxetan-3-yl)piperazin-1-yl)phenyl)-3-methylpyrazolo[1,5-a]pyrazin-4-yl)oxy)ethyl)pyrrolidin-2-one 5.63 (9 mg).

1H NMR (400 MHz, $CD_3OD$) δ 8.49 (s, 1H), 7.75 (s, 1H), 7.58 (s, 2H), 7.05 (d, J=8.1 Hz, 1H), 5.68 (p, J=6.1 Hz, 1H), 4.73 (t, J=6.7 Hz, 2H), 4.65 (t, J=6.2 Hz, 2H), 3.95 (s, 3H), 3.68-3.54 (m, 2H), 3.37 (dd, J=10.1, 6.1 Hz, 1H), 3.23-3.09 (m, 4H), 3.07-2.94 (m, 1H), 2.65-2.47 (m, 6H), 2.45 (s, 3H), 1.53 (d, J=6.3 Hz, 3H).

LCMS-ESI$^+$ (m/z): [M+H]$^+$ calcd for $C_{27}H_{35}N_6O_4$: 507.26; found: 507.32.

Example 5.64

Preparation of 6-chloro-4-((R)-1-((R)-1-((R)-1-(4-methoxyphenyl)ethyl)-5-oxopyrrolidin-3-yl)ethoxy)pyrazolo[1,5-a]pyrazine-3-carbonitrile

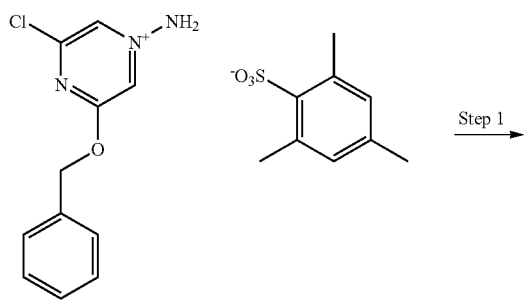

5.34

-continued

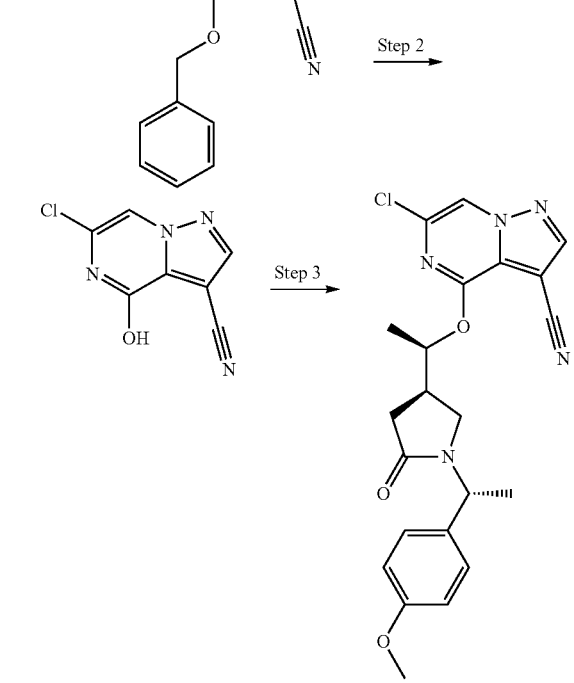

5.64

Step 1: 1-amino-3-(benzyloxy)-5-chloropyrazin-1-ium 2,4,6-trimethylbenzenesulfonate (5.34) (657 mg, 1.51 mmol) was suspended in 1,4-dioxane (5.75 mL) and acrylonitrile (0.23 mL, 3.5 mmol) was added followed by iPr$_2$NEt (0.32 mL, 1.9 mmol). The resulting mixture was stirred for 1.75 h at r.t. and DDQ (720 mg, 3.2 mmol) was added in one portion. The resulting mixture was stirred an additional 1 h and was then partitioned between EtOAc, water and brine. The phases were separated and the aqueous phase was extracted with EtOAc. The combined organic phase was dried over Na$_2$SO$_4$, filtered, and concentrated. The concentrate was purified by silica gel chromatography (0-20% EtOAc in hexanes) to provide 4-(benzyloxy)-6-chloropyrazolo[1,5-a]pyrazine-3-carbonitrile. $^1$H NMR (400 MHz, Chloroform-d) δ 8.22 (s, 1H), 8.18 (s, 1H), 7.61-7.55 (m, 2H), 7.45-7.39 (m, 2H), 7.39-7.33 (m, 1H), 5.67 (s, 2H).

Step 2: 4-(benzyloxy)-6-chloropyrazolo[1,5-a]pyrazine-3-carbonitrile (295 mg, 1.04 mmol) was dissolved in DCM (10 mL) under Ar and the resulting mixture was cooled to −78° C. under Ar. A 1.0 M BBr$_3$ in DCM solution (5.2 mL, 5.2 mmol) was then added, and the resulting mixture was stirred 15 min and was then removed from the cold bath. After stirring an additional 1.25 h, the reaction was quenched with a mixture of Et$_3$N (4.3 mL, 31 mmol), Et$_2$NH (0.21 mL, 2.1 mmol) and MeOH (5 mL). After stirring an additional 10 min, the reaction mixture was concentrated and taken up in MeOH. The mixture was concentrated, and the concentrate was purified by silica gel chromatography (50-100% acetone in hexanes) to provide 6-chloro-4-hydroxypyrazolo[1,5-a]pyrazine-3-carbonitrile. LCMS-ESI$^+$ (m/z): [M+H]$^+$ calcd for C$_7$H$_4$ClN$_4$O: 195.0; found: 194.7.

Step 3: 6-chloro-4-hydroxypyrazolo[1,5-a]pyrazine-3-carbonitrile (122 mg, 0.627 mmol) was dissolved in THF (1 mL). (R)-4-((S)-1-hydroxyethyl)-1-4R)-1-(4-methoxyphenyl)ethyl)pyrrolidin-2-one 1.05 (255 mg, 0.97 mmol) and PPh$_3$ (255 mg, 0.97 mmol) were added followed by diethyl azodicarboxylate (0.16 mL, 1.0 mmol). The resulting mixture was heated to 45° C. and was stirred for 45 min. The mixture was then cooled to r.t., let stand overnight, and concentrated onto 2 g silica gel. Purification by silica gel chromatography (25-100% EtOAc in hexanes) provided 6-chloro-4-((R)-1-((R)-1-((R)-1-(4-methoxyphenyl)ethyl)-5-oxopyrrolidin-3-yl)ethoxy)pyrazolo[1,5-a]pyrazine-3-carbonitrile (5.64). LCMS-ESI⁺ (m/z): [M+H]⁺ calcd for $C_{22}H_{23}ClN_5O_3$: 440.1; found: 439.8.

Example 5.66

Preparation of 6-(3,4-dimethoxyphenyl)-4-((R)-1-4R)-5-oxopyrrolidin-3-yl)ethoxy)pyrazolo[1,5-a]pyrazine-3-carbonitrile

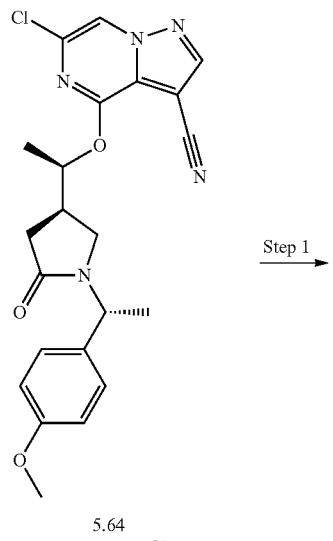

Step 1: Intermediate 5.64 (41 mg, 0.093 mmol) was dissolved in TFA (1.5 mL) and the resulting solution was heated to 70° C. After stirring 6.5 h, the reaction mixture was cooled and concentrated in vacuo. The resulting residue was partitioned between EtOAc, water, and brine. The phases were separated, and the aqueous phase was extracted with EtOAc. The combined organic phase was dried over $Na_2SO_4$, filtered, and concentrated to afford crude 6-chloro-4-((R)-1-((R)-5-oxopyrrolidin-3-yl)ethoxy)pyrazolo[1,5-a]pyrazine-3-carbonitrile (5.65) that was used without further purification. LCMS-ESI⁺ (m/z): [M+H]⁺ calcd for $C_{13}H_{13}ClN_5O_2$: 306.1; found: 305.8.

Step 2: Crude intermediate 5.65 from the previous step, (3,4-dimethoxyphenyl)boronic acid (34 mg, 0.19 mmol), $K_3PO_4$ (79 mg, 0.37 mmol) and bis(di-tert-butyl(4-dimethylaminophenyl)phosphine)dichloropalladium(II) (3.3 mg, 0.005 mmol) were taken up in 1,4-dioxane (1.35 mL) and water (0.14 mL) under Ar. The stirred reaction mixture was heated to 100° C. After stirring 16 h, the reaction mixture was partitioned between EtOAc, water, and brine and the resulting emulsion was filtered through a pad of Celite. The Celite was washed with DCM to elute all product and the resulting filtrate was concentrated in vacuo. The concentrate was purified by silica gel chromatography (0-20% MeOH in DCM) to provide 6-(3,4-dimethoxyphenyl)-4-((R)-1-((R)-5-oxopyrrolidin-3-yl)ethoxy)pyrazolo[1,5-a]pyrazine-3-carbonitrile 5.66. LCMS-ESI⁺ (m/z): [M+H]⁺ calcd for $C_{21}H_{22}N_5O_4$: 408.2; found: 407.9. ¹H NMR (400 MHz, DMSO-d6) δ 9.22 (s, 1H), 8.68 (s, 1H), 7.70 (dd, J=8.4, 2.1 Hz, 1H), 7.66 (d, J=2.1 Hz, 1H), 7.55 (s, 1H), 7.06 (d, J=8.5 Hz, 1H), 5.56-5.45 (m, 1H), 3.86 (s, 3H), 3.80 (s, 3H), 3.41-3.33 (m, 1H), 3.25-3.15 (m, 1H), 2.93-2.81 (m, 1H), 2.35-2.27 (m, 2H), 1.46 (d, J=6.2 Hz, 3H).

Example 5.68

Preparation of 6-(4-(4-acetylpiperazin-1-yl)phenyl)-4-4R)-1-((R)-5-oxopyrrolidin-3-yl)ethoxy)pyrazolo[1,5-a]pyrazine-3-carbonitrile

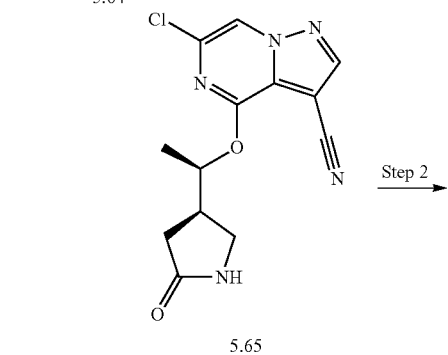

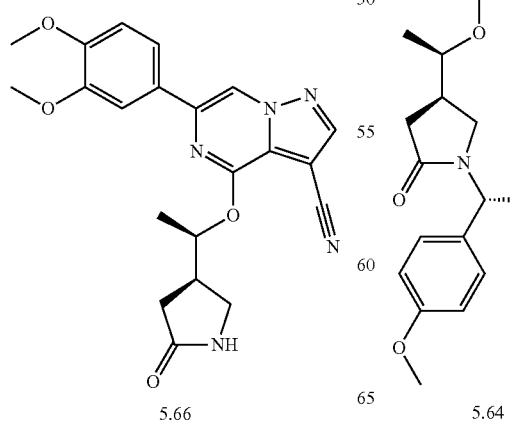

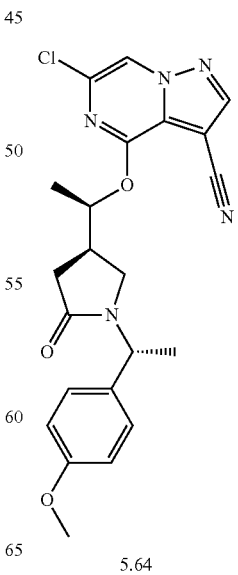

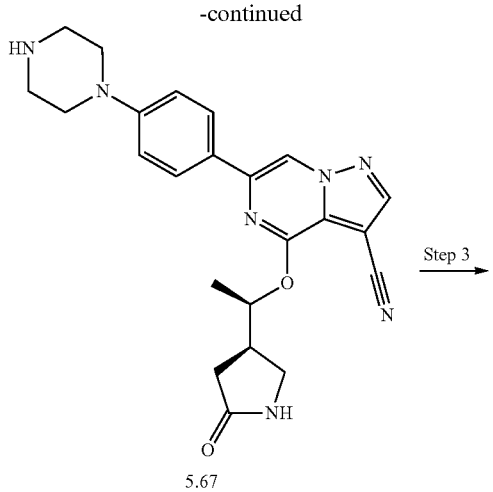

5.67

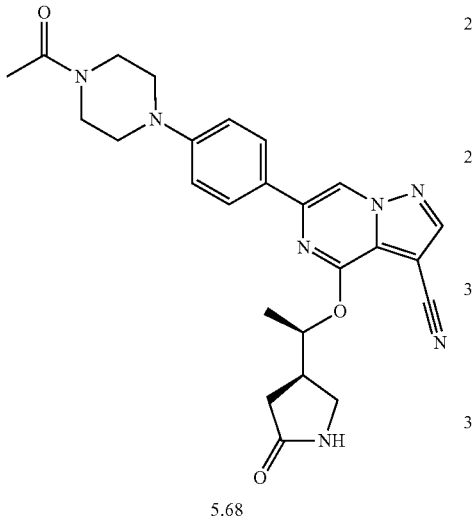

5.68

Step 1: Intermediate 5.64 (218 mg, 0.496 mmol), (4-(4-(tert-butoxycarbonyl)piperazin-1-yl)phenyl)boronic acid (303 mg, 0.99 mmol), $K_3PO_4$ (420 mg, 2.0 mmol) and Bis[di-tert-butyl(4-dimethylaminophenyl)phosphine]dichloropalladium (II) (18 mg, 0.025 mmol) were taken up in 1,4-dioxane (7 mL) and water (0.72 mL). The stirred reaction mixture was heated to 100° C. Once complete, the reaction mixture was partitioned between EtOAc, water, and brine. The phases were separated and the aqueous phase was extracted with EtOAc. The combined organic phase was dried over $Na_2SO_4$, filtered, and concentrated. The crude residue was purified by silica gel chromatography to provide tert-butyl 4-(4-(3-cyano-4-((R)-1-((R)-1-((R)-1-(4-methoxyphenyl)ethyl)-5-oxopyrrolidin-3-yl)ethoxy)pyrazolo[1,5-a]pyrazin-6-yl)phenyl)piperazine-1-carboxylate. LCMS-ESI⁺ (m/z): [M+H]⁺ calcd for $C_{37}H_{44}N_7O_5$: 666.3; found: 666.3.

Step 2: tert-butyl 4-(4-(3-cyano-4-((R)-1-((R)-1-(4-methoxyphenyl)ethyl)-5-oxopyrrolidin-3-yl)ethoxy)pyrazolo[1,5-a]pyrazin-6-yl)phenyl)piperazine-1-carboxylate (215 mg, 0.323 mmol) was dissolved in TFA (7.4 ml) and the resulting solution was heated to 60° C. After stirring 14 h, the reaction mixture was cooled and concentrated. The resulting crude TFA salt of 4-((R)-1-((R)-5-oxopyrrolidin-3-yl)ethoxy)-6-(4-(piperazin-1-yl)phenyl)pyrazolo[1,5-a]pyrazine-3-carbonitrile (5.67) was used without further purification. LCMS-ESI⁺ (m/z): [M+H]⁺ calcd for $C_{23}H_{26}N_7O_2$: 432.2; found: 432.0.

Step 3: The crude TFA salt of 5.67 (0.107 mmol) was dissolved in DCM (2 mL) and was treated with $Et_3N$ (0.15 mL, 1.1 mmol) followed by acetic anhydride (13 μL, 0.13 mmol). After stirring for 1.5 h, the reaction mixture was partitioned between DCM and water, and the aqueous phase was extracted with DCM. The combined organic phase was dried over $Na_2SO_4$, filtered, and concentrated, and the concentrate was purified by silica gel (0-15% MeOH in DCM) to afford 6-(4-(4-acetylpiperazin-1-yl)phenyl)-4-((R)-1-((R)-5-oxopyrrolidin-3-yl)ethoxy)pyrazolo[1,5-a]pyrazine-3-carbonitrile (5.68). LCMS-ESI⁺ (m/z): [M+H]⁺ calcd for $C_{25}H_{28}N_7O_3$: 474.2; found: 474.3. ¹H NMR (400 MHz, Chloroform-d) δ 8.41 (s, 1H), 8.18 (s, 1H), 7.86-7.78 (m, 2H), 7.04-6.96 (m, 2H), 6.10 (s, 1H), 5.65-5.52 (m, 1H), 3.85-3.73 (m, 2H), 3.66 (dd, J=6.4, 4.0 Hz, 2H), 3.63-3.55 (m, 1H), 3.44 (dd, J=9.9, 6.7 Hz, 1H), 3.34-3.23 (m, 4H), 3.12-2.96 (m, 1H), 2.60 (dd, J=17.1, 9.2 Hz, 1H), 2.43 (dd, J=17.1, 8.0 Hz, 1H), 2.15 (s, 3H), 1.54 (d, J=6.2 Hz, 3H).

Example 5.69

Preparation of 6-(4-(4-(methylsulfonyl)piperazin-1-yl)phenyl)-4-4R)-1-4R)-5-oxopyrrolidin-3-yl)ethoxy)pyrazolo[1,5-a]pyrazine-3-carbonitrile

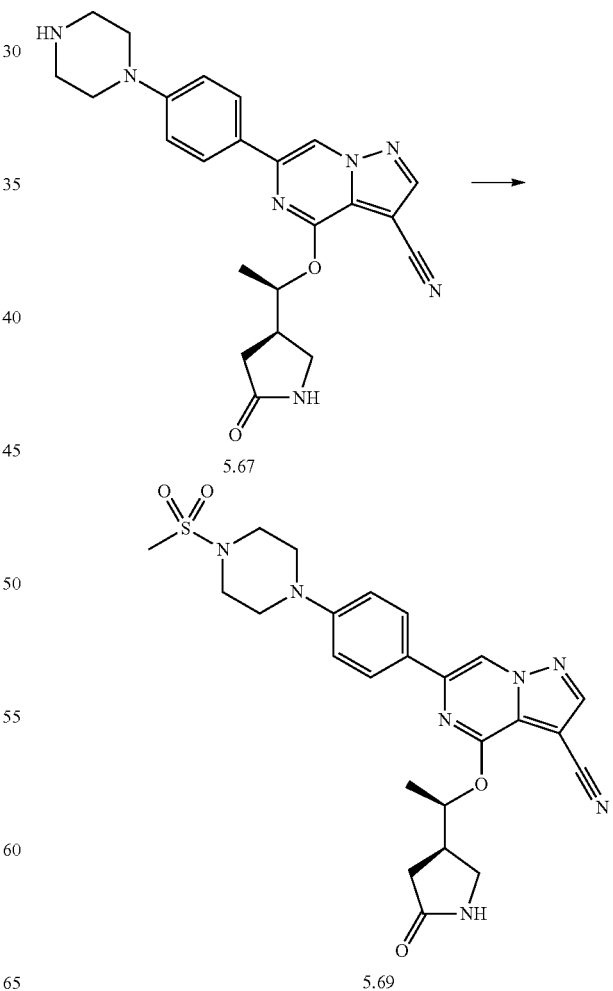

5.67

5.69

The crude TFA salt of 5.67 (0.107 mmol) was taken up in DCM (2 mL) and treated with Et₃N (0.15 mL, 1.1 mmol). Methanesulfonic anhydride (24 mg, 0.14 mmol) was added.

After stifling 30 min, additional methanesulfonic anhydride (12 mg, 0.069 mmol) was added. After stirring an additional 30 min, additional methanesulfonic anhydride (9 mg, 0.05 mmol) was added. After an additional 1 h, the reaction mixture was partitioned between DCM and water and the phases were separated. The aqueous phase was extracted with DCM and the combined organic phase was dried over Na₂SO₄, filtered, and concentrated. The resulting concentrate was purified by silica gel chromatography (0-15% MeOH in DCM) to provide 6-(4-(4-(methylsulfonyl)piperazin-1-yl) phenyl)-4-4R)-1-((R)-5-oxopyrrolidin-3-yl)ethoxy)pyrazolo[1,5-a]pyrazine-3-carbonitrile (5.69). LCMS-ESI⁺ (m/z): [M+H]⁺ calcd for $C_{24}H_{28}N_7O_4S$: 510.2; found: 509.9. ¹H NMR (400 MHz, Chloroform-d) δ 8.42 (s, 1H), 8.19 (s, 1H), 7.87-7.80 (m, 2H), 7.07-7.00 (m, 2H), 5.93 (s, 1H), 5.64-5.53 (m, 1H), 3.65-3.53 (m, 1H), 3.49-3.35 (m, 9H), 3.14-2.98 (m, 1H), 2.84 (s, 3H), 2.60 (dd, J=17.1, 9.2 Hz, 1H), 2.43 (dd, J=17.1, 7.9 Hz, 1H), 1.55 (d, J=6.2 Hz, 3H).

Example 5.70

Preparation of 6-(4-(4-(oxetan-3-yl)piperazin-1-yl) phenyl)-4-4R)-1-4R)-5-oxopyrrolidin-3-yl)ethoxy) pyrazolo[1,5-a]pyrazine-3-carbonitrile

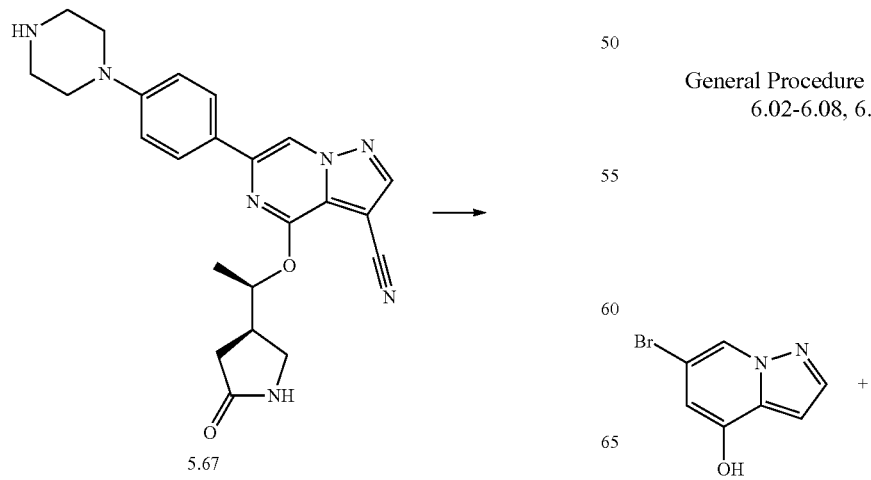

5.67

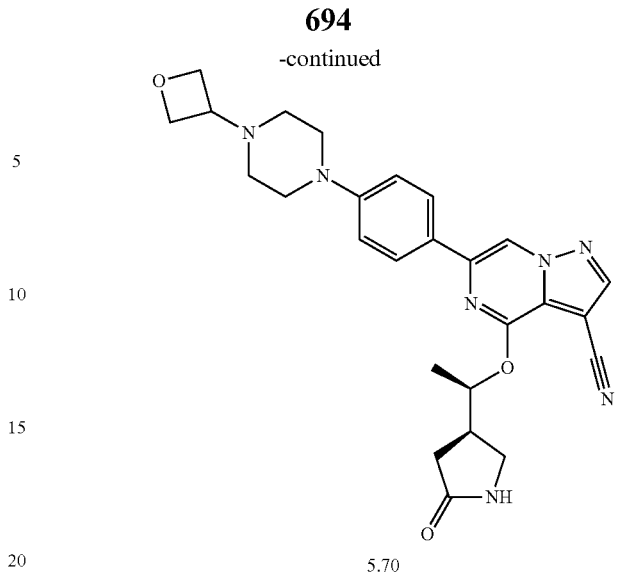

5.70

The crude TFA salt of 5.67 (0.089 mmol) was taken up in THF (2 mL) and was treated with iPr₂NEt (16 µL, 0.089 mmol), 3-oxetanone (29 µL, 0.45 mmol) and sodium triacetoxyborohydride (132 mg, 0.62 mmol). The resulting mixture was heated to 50° C. and was stirred for 3 h. The reaction mixture was then partitioned between DCM, water, and 5% (w/v) saturated aqueous Na₂CO₃ and the phases were separated. The aqueous phase was extracted with DCM (3×20 mL) and the combined organics were dried over Na₂SO₄, filtered, and concentrated. The concentrate was purified by silica gel chromatography (0-20% MeOH in DCM) to provide 6-(4-(4-(oxetan-3-yl)piperazin-1-yl)phenyl)-4-4R)-1-((R)-5-oxopyrrolidin-3-yl)ethoxy)pyrazolo[1,5-a]pyrazine-3-carbonitrile 5.70. LCMS-ESI⁺ (m/z): [M+H]⁺ calcd for $C_{26}H_{30}N_7O_3$: 488.2; found: 488.0. ¹H NMR (400 MHz, Chloroform-d) δ 8.40 (s, 1H), 8.18 (s, 1H), 7.84-7.77 (m, 2H), 7.03-6.96 (m, 2H), 5.99 (s, 1H), 5.64-5.53 (m, 1H), 4.76-4.63 (m, 4H), 3.64-3.51 (m, 2H), 3.50-3.41 (m, 1H), 3.38-3.30 (m, 4H), 3.12-2.97 (m, 1H), 2.60 (dd, J=17.1, 9.2 Hz, 1H), 2.56-2.49 (m, 4H), 2.43 (dd, J=17.1, 8.0 Hz, 1H), 1.54 (d, J=6.2 Hz, 3H).

General Procedure 6A for Synthesis of Examples 6.02-6.08, 6.14, 6.16, 6.32 and 6.34

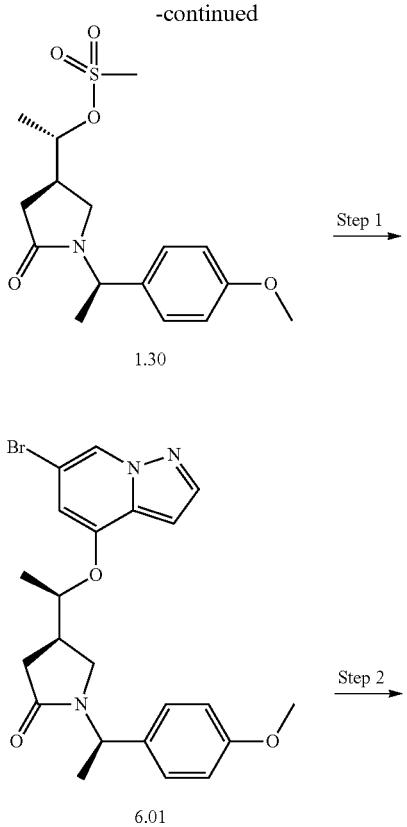

Step 1: To a solution of 6-bromopyrazolo[1,5-a]pyridin-4-ol (125 mg, 0.587 mmol) in DMF (4 mL) was added (S)-1-((R)-1-(4-methoxyphenyl)ethyl)-5-oxopyrrolidin-3-yl)ethyl methanesulfonate 1.30 (220 mg, 0.645 mmol) and Cs₂CO₃ (239 mg, 0.733 mmol) and the reaction mixture was heated at 90° C. for 2 h. The reaction mixture was diluted with EtOAc and water, the layers were separated and the aqueous layer was extracted with EtOAc. The combined organics were dried, filtered, and concentrated. The residue was purified by flash chromatography to afford (R)-4-((R)-1-(6-bromopyrazolo[1,5-a]pyridin-4-yloxy)ethyl)-1-((R)-1-phenylethyl)pyrrolidin-2-one 6.01.

LCMS-ESI⁺ (m/z): [M+H]⁺ calcd for $C_{22}H_{24}^{79}BrN_3O_3$: 458.1; found: 458.1.

Step 2: To a mixture of (R)-4-((R)-1-(6-bromopyrazolo[1,5-a]pyridin-4-yloxy)ethyl)-1-((R)-1-phenylethyl)pyrrolidin-2-one 6.01 (1 equiv), the appropriate boronic acid/ester (1.1-2.0 equiv), and Cs₂CO₃ (3.0 equiv) in a sealable tube was added Dioxane/Water (2:1) and the mixture was degassed for 10 minutes. PEPPSI-IPr (0.1 equiv) was added and the reaction was heated at 100° C. for 30-120 minutes. After aqueous workup, the desired product can be isolated by flash chromatography or RP-HPLC.

Step 3: The product from step 2 was dissolved in TFA and heated to 60° C. overnight. The reaction was concentrated and the residue was purified by RP-HPLC.

The following analogs were prepared according to procedure 6A:

Example 6.02

Preparation of (R)-4-((R)-1-(6-(3,4-dimethoxyphenyl)pyrazolo[1,5-a]pyridin-4-yloxy)ethyl)pyrrolidin-2-one

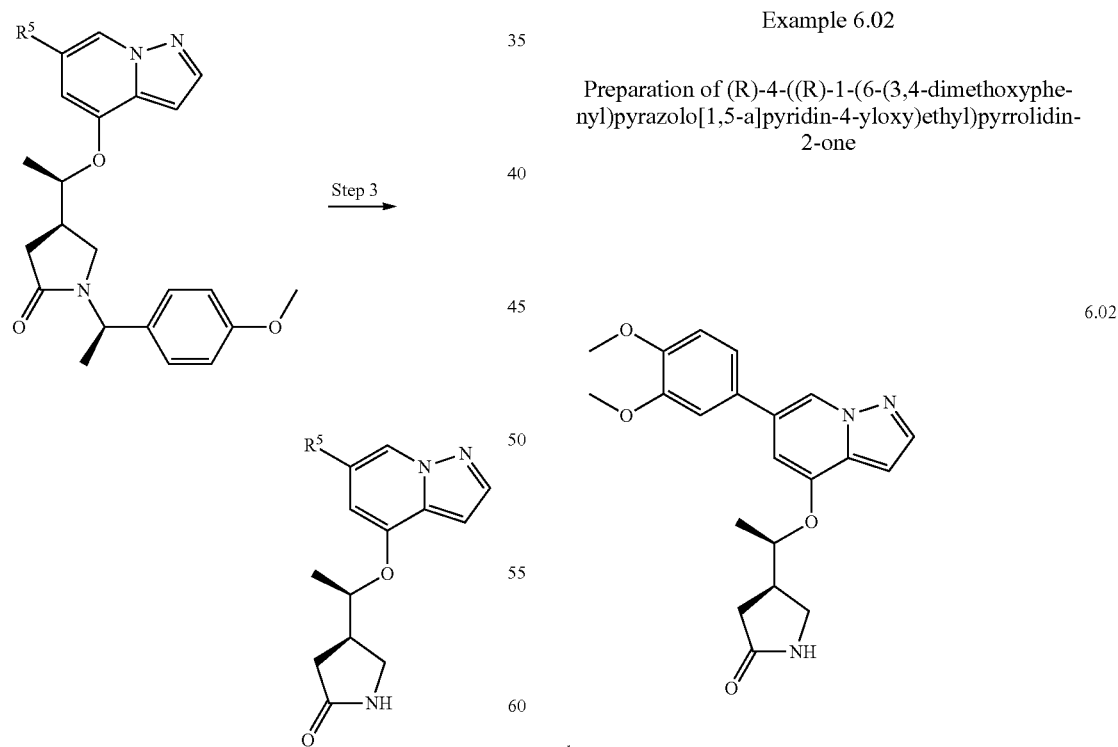

¹H NMR (400 MHz, CD₃OD), TFA salt, δ 8.34 (s, 1H), 7.88 (s, 1H), 7.20-7.24 (m, 2H), 7.04-7.08 (m, 1H), 6.89 (s, 1H), 6.63 (s, 1H), 4.80-4.95 (partially obscured by water peak, 1H), 3.93 (s, 3H), 3.88 (s, 3H), 3.55-3.59 (m, 1H), 3.22-3.40 (partially obscured by MeOH peak, 1H), 2.88-2.93 (m, 1H), 2.46-2.56 (m, 2H), 1.42 (d, J=5.6 Hz, 3H).

LCMS-ESI⁺ (m/z): [M+H]⁺ calcd for C₂₁H₂₃N₃O₄: 382.2; found 382.1.

Example 6.03

Preparation of (R)-4-((R)-1-(6-(5,6-dimethoxypyridin-2-yl)pyrazolo[1,5-a]pyridin-4-yloxy)ethyl)pyrrolidin-2-one

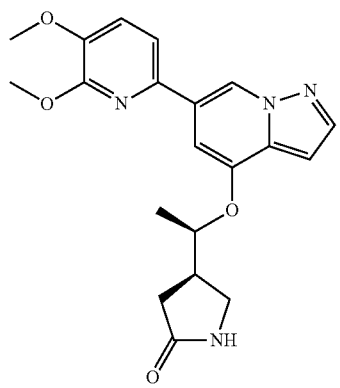

6.03

¹H NMR (400 MHz, DMSO-d6), TFA salt, δ 8.90 (s, 1H), 7.94 (d, J=2.4 Hz, 1H), 7.64 (d, J=8.0 Hz, 1H), 7.56 (s, 1H), 7.35 (d, J=8.0 Hz, 1H), 7.28 (s, 1H), 6.58 (d, J=1.2 Hz, 1H), 4.83 (pent, J=6.0 Hz, 1H), 3.99 (s, 3H), 3.82 (s, 3H), 3.35-3.41 (m, 1H), 3.12 (dd, J=6.4, 9.6 Hz, 1H), 2.75-2.81 (m, 1H), 2.32 (dd, J=8.8, 16.8 Hz, 1H), 2.21 (dd, J=8.0, 16.8 Hz, 1H), 1.42 (d, J=6.0 Hz, 3H).
LCMS-ESI⁺ (m/z): [M+H]⁺ calcd for C₂₀H₂₂N₄O₄: 383.2; found 383.1.

Example 6.04

Preparation of (R)-4-((R)-1-(6-(4-morpholinophenyl)pyrazolo[1,5-a]pyridin-4-yloxy)ethyl)pyrrolidin-2-one

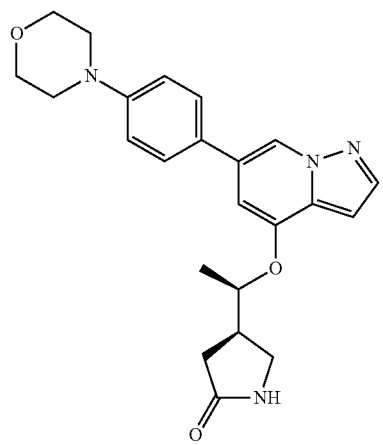

6.04

¹H NMR (400 MHz, Methanol-d₄), TFA salt, δ 8.37 (s, 1H), 7.89 (d, J=2.3 Hz, 1H), 7.68 (d, J=8.8 Hz, 2H), 7.28 (d, J=8.8 Hz, 2H), 6.90 (s, 1H), 6.65 (dd, J=2.3, 0.9 Hz, 1H), 4.83 (q, J=5.9 Hz, 1H), 3.97-3.89 (m, 4H), 3.59 (t, J=10.1, 8.5 Hz, 1H), 3.41-3.35 (m, 4H), 3.34 (d, J=6.0 Hz, 1H), 3.00-2.85 (m, 1H), 2.63-2.42 (m, 2H), 1.43 (d, J=6.1 Hz, 3H).
LCMS-ESI⁺ (m/z): [M+H]⁺ calcd for C₂₃H₂₆N₄O₃: 407.2; found 407.1.

Example 6.05

Preparation of (R)-4-((R)-1-(6-(1-(2,2-difluoroethyl)-1H-pyrazol-4-yl)pyrazolo[1,5-a]pyridin-4-yloxy)ethyl)pyrrolidin-2-one

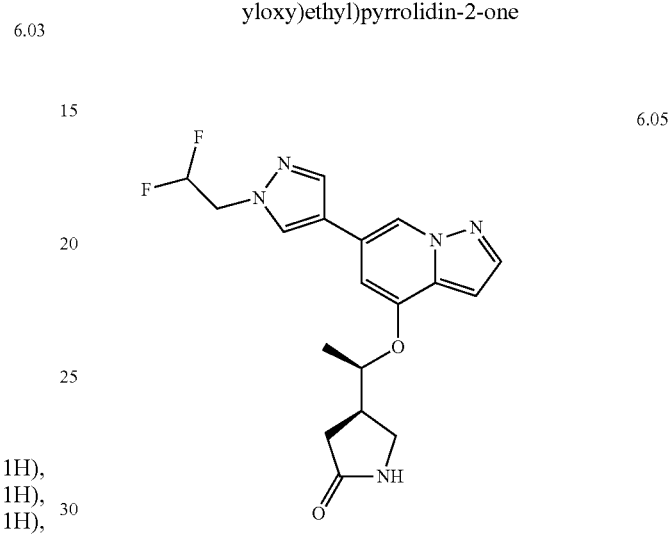

6.05

¹H NMR (400 MHz, Methanol-d₄), TFA salt, δ 8.43 (s, 1H), 8.19 (s, 1H), 8.02 (s, 1H), 7.85 (d, J=2.4 Hz, 1H) 6.89 (s, 1H), 6.64 (dd, J=2.4, 1.0 Hz, 1H), 6.28-6.17 (m, 1H), 4.70-4.51 (m, 3H), 3.61 (t, J=10.1, 8.5 Hz, 1H), 3.35-3.42 (m, 1H) 2.94 (m, 1H), 2.65-2.44 (m, 2H), 1.45 (d, J=6.1 Hz, 3H).
LCMS-ESI⁺ (m/z): [M+H]⁺ calcd for C₁₈H₁₉F₂N₅O₂: 376.2; found 376.1.

Example 6.06

Preparation of (R)-4-((R)-1-(3,4,5-trimethoxyphenyl)pyrazolo[1,5-a]pyridin-4-yloxy)ethyl)pyrrolidin-2-one

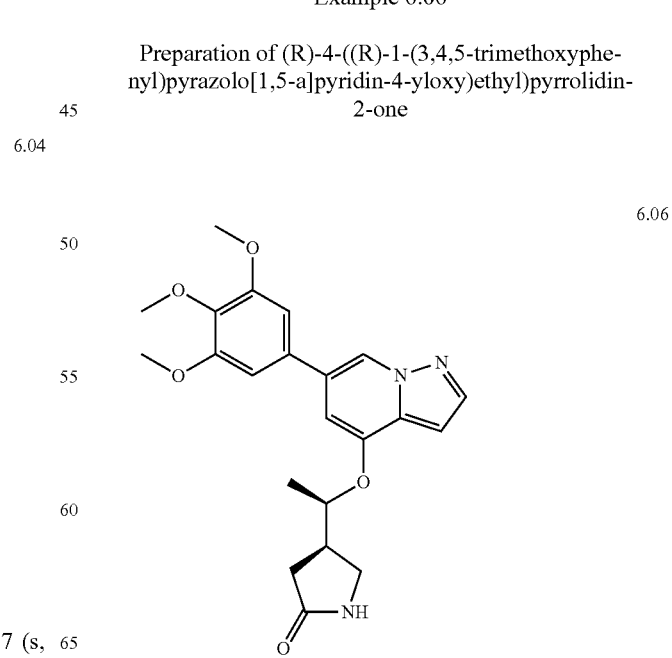

6.06

¹H NMR (400 MHz, Methanol-d₄), TFA salt, δ 8.40 (s, 1H), 7.92 (d, J=2.3 Hz, 1H), 6.95 (s, 2H), 6.92 (s, 1H), 6.67 (dd, J=2.4, 0.9 Hz, 1H), 4.82-4.90 (m, 1H), 3.96 (s, 6H), 3.83 (s, 3H), 3.62 (t, J=10.1, 8.5 Hz, 1H), 3.37 (d, J=6.0 Hz, 3H), 2.95 (d, J=7.6 Hz, 1H), 2.66-2.45 (m, 2H), 1.45 (d, J=6.1 Hz, 3H).

LCMS-ESI⁺ (m/z): [M+H]⁺ calcd for $C_{22}H_{25}N_3O_5$: 412.2; found 412.1.

Example 6.07

Preparation of (R)-4-((R)-1-(6-(1-isopropyl-1H-pyrazol-4-yl)pyrazolo[1,5-a]pyridin-4-yloxy)ethyl)pyrrolidin-2-one

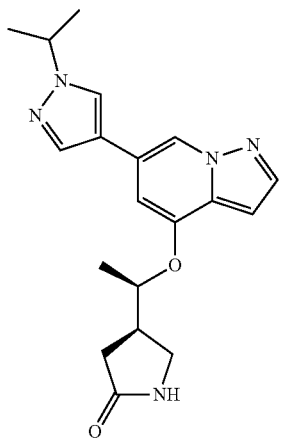

6.07

¹H NMR (400 MHz, Methanol-d₄), TFA salt, δ 8.40 (s, 1H), 8.19 (s, 1H), 7.94 (s, 2H), 7.87 (d, J=2.3 Hz, 1H), 6.91 (s, 1H), 6.63 (dd, J=2.4, 0.9 Hz, 1H), 4.60 (p, J=6.7 Hz, 1H), 3.63-3.57 (m, 1H), 3.30-3.38 (m, 1H), 3.00-2.91 (m, 1H), 2.65-2.42 (m, 2H), 1.57 (d, J=6.7 Hz, 6H), 1.44 (d, J=6.1 Hz, 3H).

LCMS-ESI⁺ (m/z): [M+H]⁺ calcd for $C_{19}H_{23}N_5O_2$: 354.2; found 354.1.

Example 6.08

Preparation of (R)-4-((R)-1-(6-(1-tert-butyl-1H-pyrazol-4-yl)pyrazolo[1,5-a]pyridin-4-yloxy)ethyl)pyrrolidin-2-one

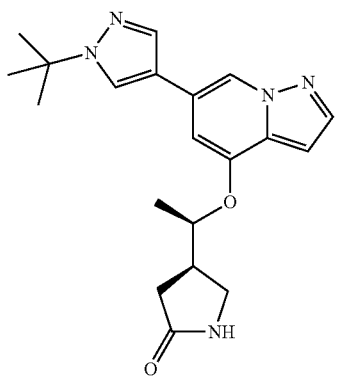

6.08

¹H NMR (400 MHz, CD₃OD), TFA salt, δ 8.40 (s, 1H), 8.25 (s, 1H), 7.93 (s, 1H), 7.84 (s, 1H), 6.91 (s, 1H), 6.61 (s, 1H), 4.80-4.95 (partially obscured by water peak, 1H), 3.59 (t, J=9.2 Hz, 1H), 3.30-3.40 (partially obscured by MeOH peak, 1H), 2.89-2.93 (m, 1H), 2.53-2.60 (m, 1H), 2.44-2.48 (m, 1H), 1.64 (s, 9H), 1.42 (d, J=5.6 Hz, 3H).

LCMS-ESI⁺ (m/z): [M+H]⁺ calcd for $C_{20}H_{25}N_5O_2$: 368.2; found 368.1.

Example 6.14

Preparation of (R)-4-((R)-1-((6-(1-(tetrahydro-2H-pyran-4-yl)-1H-pyrazol-4-yl)pyrazolo[1,5-a]pyridin-4-yl)oxy)ethyl)pyrrolidin-2-one

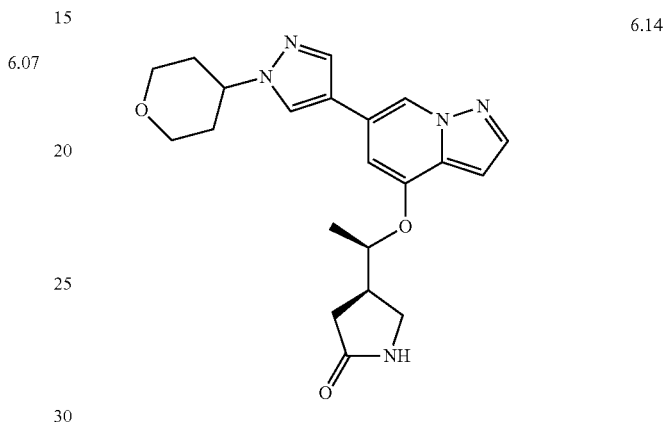

6.14

¹H NMR (400 MHz, Methanol-d₄), TFA salt, δ 8.41 (s, 1H), 8.22 (s, 1H), 7.95 (s, 1H), 7.86 (d, J=2.4 Hz, 1H), 6.90 (s, 1H), 6.63 (dd, J=2.4, 0.9 Hz, 1H), 4.80-4.85 (m, 1H), 4.53-4.40 (m, 1H), 4.15-4.06 (m, 2H), 3.67-3.56 (m, 3H), 3.32-3.40 (partially obscured by MeOH peak, 1H) 2.93 (d, J=7.1 Hz, 1H), 2.64-2.43 (m, 2H), 2.13 (td, J=10.3, 9.4, 4.1 Hz, 4H), 1.43 (d, J=6.1 Hz, 3H).

LCMS-ESI⁺ (m/z): [M+H]⁺ calcd for $C_{21}H_{25}N_5O_3$: 396.2; found 396.1.

Example 6.17

Preparation of (R)-4-((R)-1-((6-(4-(4-(oxetan-3-yl)piperazin-1-yl)phenyl)pyrazolo[1,5-a]pyridin-4-yl)oxy)ethyl)pyrrolidin-2-one

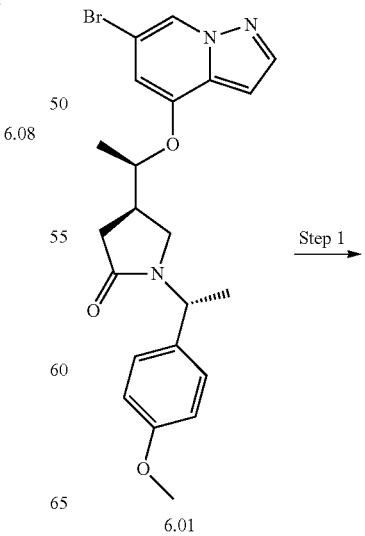

Step 1

6.01

701
-continued

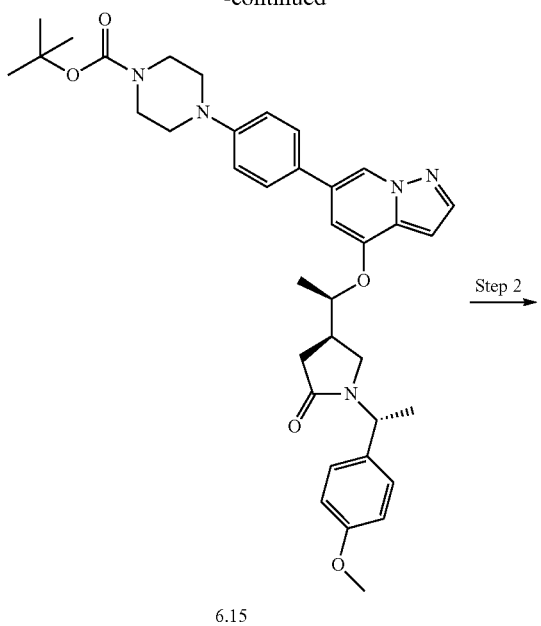

6.15

6.16

6.17

Step 1: Intermediate 6.15 was synthesized in an analogous fashion to Step 2 of General Procedure 6A. LCMS-ESI+ (m/z): [M+H]+ calcd for $C_{37}H_{45}N_5O_5$: 640.3; found: 640.3.

702

Step 2: Tert-butyl 4-(4-(4-(((R)-1-((R)-1-((R)-1-(4-methoxyphenyl)ethyl)-5-oxopyrrolidin-3-yl)ethoxy)pyrazolo[1,5-a]pyridin-6-yl)phenyl)piperazine-1-carboxylate 6.15 (50 mg, 0.078 mmol) was dissolved in TFA (2.0 mL) and heated at 60° C. for 18 h. The reaction was concentrated to dryness (solvent exchange was performed with acetonitrile and toluene) and the residue was passed through a polymer-supported bicarbonate column to provide (R)-4-((R)-1-((6-(4-(piperazin-1-yl)phenyl)pyrazolo[1,5-a]pyridin-4-yl)oxy)ethyl)pyrrolidin-2-one 6.16, as the free base, and was used directly in the next reaction.

LCMS-ESI+ (m/z): [M+H]+ calcd for $C_{23}H_{27}N_5O_2$: 406.2; found: 406.2.

Step 3: To a solution of (R)-4-((R)-1-((6-(4-(piperazin-1-yl)phenyl)pyrazolo[1,5-a]pyridin-4-yl)oxy)ethyl)pyrrolidin-2-one 6.16 (31 mg, 0.078 mmol) in 1,2-dichloroethane (1 mL) was added 3-oxetanone (20 mg, 0.28 mmol). Sodium triacetoxyborohydride (75 mg, 0.36 mmol) was added and the mixture was stirred at room temperature for 48 h. The reaction was quenched with $NaHCO_3$ $_{(aq)}$ and MeOH. Water and EtOAc were added, the layers were separated and the organic layer was dried ($MgSO_4$), filtered, concentrated and the residue was purified via prep HPLC (2-95% acetonitrile in water, 0.1% trifluoroacteic acid buffer) to afford (R)-4-((R)-1-((6-(4-(4-(oxetan-3-yl)piperazin-1-yl)phenyl)pyrazolo[1,5-a]pyridin-4-yl)oxy)ethyl)pyrrolidin-2-one 6.17 as the trifluoroacetic acid salt.

$^1$H NMR (400 MHz, Methanol-d4), TFA salt, δ 8.36 (s, 1H), 7.91 (d, 1H), 7.66 (d, J=8.8 Hz, 2H), 7.18 (d, J=8.8 Hz, 2H), 6.90 (s, 1H), 6.66 (dd, J=2.4, 1.0 Hz, 1H), 5.01-4.92 (m, 2H), 4.90-4.80 (m, 3H), 4.55-4.47 (m, 1H), 3.60-3.30 (m, 10H), 2.97 (t, J=14.8, 7.1 Hz, 1H), 2.63-2.48 (m, 2H), 1.45 (d, J=6.1 Hz, 3H). LCMS-ESI+ (m/z): [M+H]+ calcd for $C_{26}H_{31}N_5O_3$: 462.2; found 462.2.

Example 6.18

Preparation of (R)-4-((R)-1-((6-(4-(4-acetylpiperazin-1-yl)phenyl)pyrazolo[1,5-a]pyridin-4-yl)oxy)ethyl)pyrrolidin-2-one

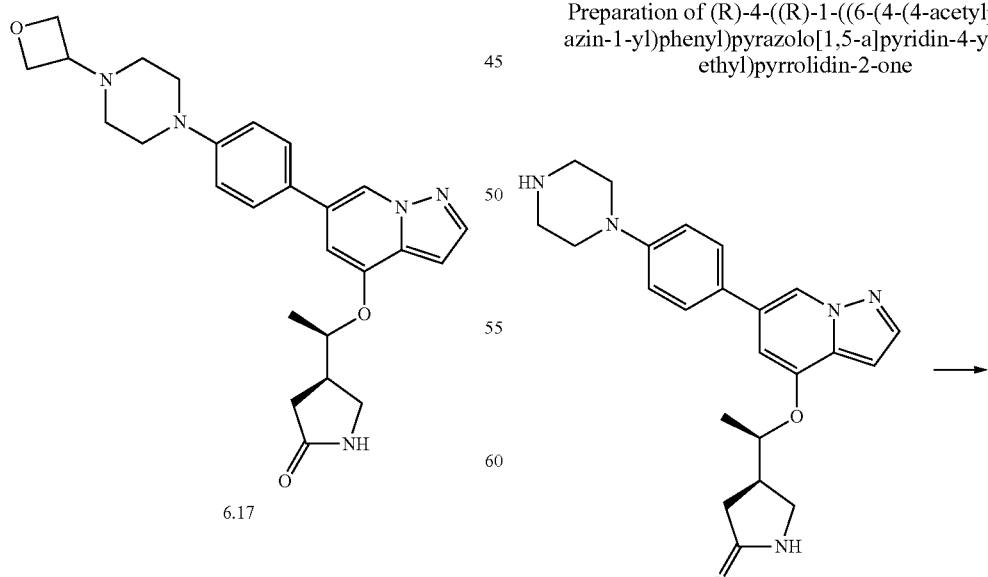

6.16

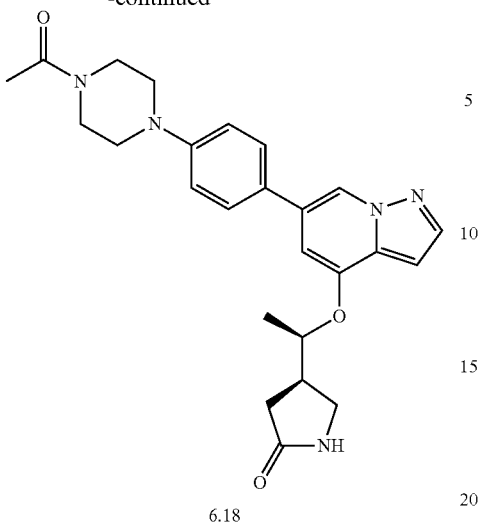

6.18

To a solution of (R)-4-((R)-1-((6-(4-(piperazin-1-yl)phenyl)pyrazolo[1,5-a]pyridin-4-yl)oxy)ethyl)pyrrolidin-2-one 6.16 (36 mg, 0.089 mmol), HATU (68 mg, 0.18 mmol) and N-methylmorpholine (39 μL, 0.36 mmol) in DMF (1 mL) was added AcOH (7.1 μL, 0.12 mmol). The reaction was stirred for 4 h, concentrated and the residue was purified via prep HPLC (2-95% acetonitrile in water, 0.1% trifluoroacteic acid buffer) to afford (R)-4-((R)-1-((6-(4-(4-acetylpiperazin-1-yl)phenyl)pyrazolo[1,5-a]pyridin-4-yl)oxy)ethyl)pyrrolidin-2-one 6.18 as the trifluoroacetic acid salt.

$^1$H NMR (400 MHz, Methanol-d4), TFA salt, δ 8.37 (s, 1H), 7.91 (d, J=2.3 Hz, 1H), 7.65 (d, 2H), 7.19 (d, J=8.7 Hz, 2H), 6.92 (s, 1H), 6.67 (dd, J=2.3, 0.9 Hz, 1H), 4.84-4.89 (m, 1H), 3.85-3.74 (m, 4H), 3.62 (dd, J=10.1, 8.5 Hz, 1H), 3.41-3.27 (m, 5H), 3.01-2.92 (m, 1H), 2.66-2.46 (m, 2H), 2.20 (s, 3H), 1.46 (d, J=6.1 Hz, 3H).

LCMS-ESI+ (m/z): [M+H]+ calcd for $C_{25}H_{29}N_5O_3$: 448.2; found 448.2.

Example 6.22

Preparation of (R)-4-((R)-1-((6-(5-(4-(methylsulfonyl)piperazin-1-yl)pyridin-2-yl)pyrazolo[1,5-a]pyridin-4-yl)oxy)ethyl)pyrrolidin-2-one

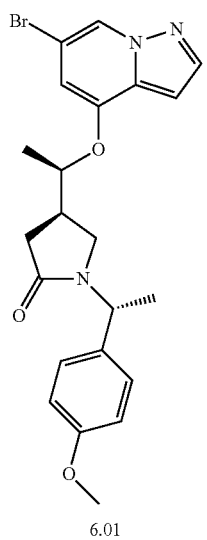

6.01

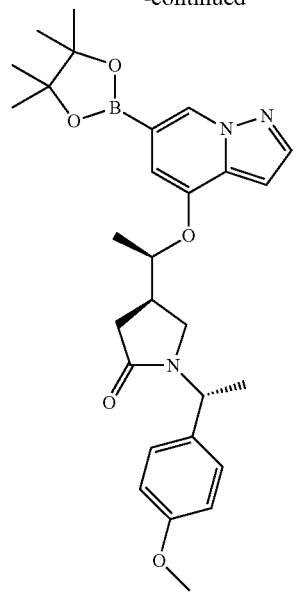

6.19

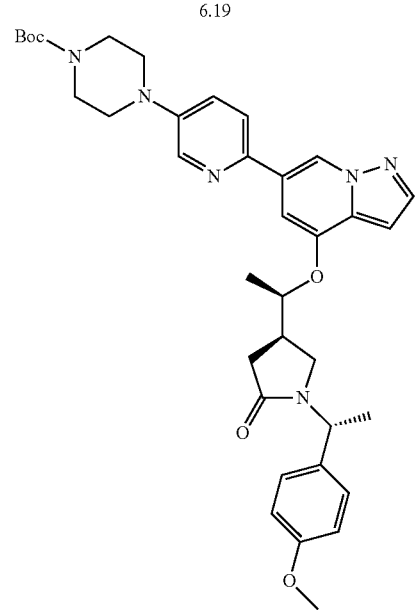

6.20

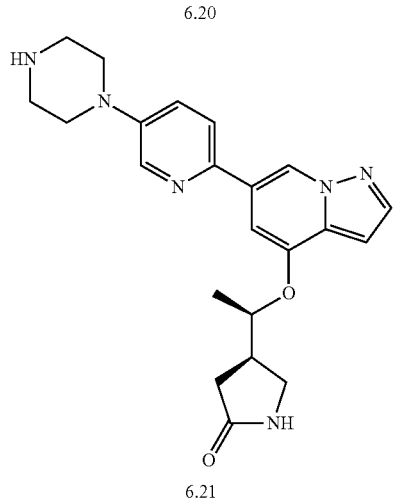

6.21

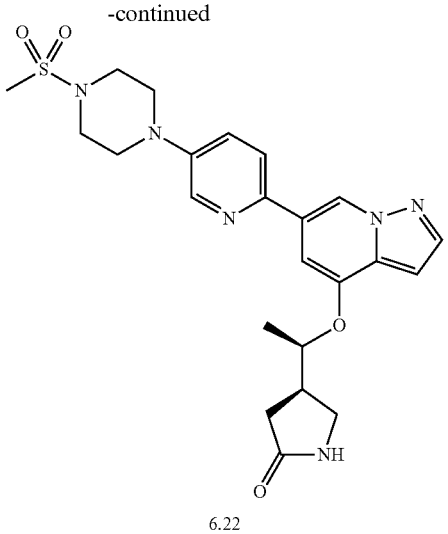

6.22

Step 1: A suspension of (R)-4-((R)-1-((6-bromopyrazolo[1,5-a]pyridin-4-yl)oxy)ethyl)-1-((R)-1-(4-methoxyphenyl)ethyl)pyrrolidin-2-one 6.01 (60.0 mg, 0.131 mmol), bis(pinacolato)diboron (58.2 mg, 0.229 mmol), and potassium acetate (19.3 mg 0.196 mmol) in 1,4-dioxane (2.0 mL) was degassed for 5 minutes. Pd(PPh$_3$)$_2$Cl$_2$ (4.59 mg, 0.00655 mmol) was added and the mixture was heated for 1 h at 100° C. The reaction was cooled and diluted with EtOAc and water. The layers were separated and the organic layer was dried (MgSO$_4$), filtered and concentrated to provide boronate ester 6.19 which was used without any further purification. LCMS-ESI$^+$ (m/z): [M-41]+ calcd for C$_{28}$H$_{36}$BN$_3$O$_5$: 506.3; found: 506.2.

Step 2: (R)-1-((R)-1-(4-methoxyphenyl)ethyl)-4-((R)-1-((6-(4,4,5,5-tetramethyl-1,3,2-dioxaborolan-2-yl)pyrazolo[1,5-a]pyridin-4-yl)oxy)ethyl)pyrrolidin-2-one 6.19 (55.0 mg, 0.109 mmol), tert-butyl 4-(6-bromopyridin-3-yl)piperazine-1-carboxylate 7.13 (65.2 mg, 0.190 mmol) and Cs$_2$CO$_3$ (106 mg, 0.326 mmol) were dissolved in 1,2-dimethoxyethane (3.0 mL) and water (1.5 mL). The mixture was degassed for 5 minutes. PEPPSI-IPr catalyst (7.42 mg, 0.0109 mmol) was added and the mixture was heated for 1 h at 90° C. The reaction was cooled and diluted with EtOAc and water. The layers were separated and the organic layer was dried (MgSO$_4$), filtered and concentrated under reduced pressure. The residue was purified by flash chromatography (50 to 100% EtOAc in hexanes) to provide tert-butyl 4-(6-(4-((R)-1-((R)-1-((R)-1-(4-methoxyphenyl)ethyl)-5-oxopyrrolidin-3-yl)ethoxy)pyrazolo[1,5-a]pyridin-6-yl)pyridin-3-yl)piperazine-1-carboxylate 6.20.

LCMS-ESI$^+$ (m/z): [M+H]+ calcd for C$_{36}$H$_{44}$N$_6$O$_5$: 641.3; found: 641.3.

Step 3: 4-(6-(4-((R)-1-((R)-1-((R)-1-(4-methoxyphenyl)ethyl)-5-oxopyrrolidin-3-yl)ethoxy)pyrazolo[1,5-a]pyridin-6-yl)pyridin-3-yl)piperazine-1-carboxylate 6.20 (30 mg, 0.036 mmol) was dissolved in TFA (2.0 mL) and heated to 60° C. overnight. The reaction was concentrated to dryness (solvent exchange was performed with acetonitrile and toluene). The residue was passed through a polymer-supported bicarbonate column to provide (R)-4-((R)-1-((6-(5-(piperazin-1-yl)pyridin-2-yl)pyrazolo[1,5-a]pyridin-4-yl)oxy)ethyl)pyrrolidin-2-one 6.21, as the free base, and was used without further purification.

LCMS-ESI$^+$ (m/z): [M+H]+ calcd for C$_{22}$H$_{26}$N$_6$O$_2$: 407.2; found: 407.1.

Step 4: To a solution of 6.21 (14.5 mg, 0.0360 mmol) in dichloromethane (1.0 mL) was added triethylamine (10 μL, 0.072 mmol). The mixture was cooled to 0° C. Methanesulfonyl chloride (3.1 μl, 0.040 mmol) was added and the reaction was stirred for 30 minutes and warmed to room temperature. Dichloromethane and NaHCO$_3$ $_{(aq)}$ were added, the layers were separated and the aqueous layer was extracted with dichloromethane (2×). The combined organics were dried (MgSO$_4$), filtered, concentrated and the residue was purified via prep HPLC (2-95% acetonitrile in water, 0.1% trifluoroacetic acid buffer) to isolate (R)-4-((R)-1-((6-(5-(4-(methylsulfonyl)piperazin-1-yl)pyridin-2-yl)pyrazolo[1,5-a]pyridin-4-yl)oxy)ethyl)pyrrolidin-2-one 6.22 as the trifluoroacetic acid salt.

$^1$H NMR (400 MHz, DMSO-d6), TFA salt, δ 8.91 (s, 1H), 8.41 (d, J=2.4 Hz, 1H), 7.98 (d, J=8.8 Hz, 1H), 7.94 (d, J=2.0 Hz, 1H), 7.54 (s, 1H), 7.47-7.50 (m, 1H), 7.33 (s, 1H), 6.58 (d, J=2.4 Hz, 1H), 4.77-4.81 (m, 1H), 3.35-3.46 (m, 4H), 3.25-3.31 (m, 5H), 3.12 (dd, J=6.4, 9.2 Hz, 1H), 2.92 (s, 3H), 2.73 (m, 1H), 2.19-2.35 (m, 2H), 1.32 (d, J=6.4 Hz, 3H).

LCMS-ESI$^+$ (m/z): [M+H]+ calcd for C$_{23}$H$_{28}$N$_6$O$_4$S: 485.2; found: 485.0.

Example 6.23

Preparation of (R)-4-((R)-1-((6-(5-(4-acetylpiperazin-1-yl)pyridin-2-yl)pyrazolo[1,5-a]pyridin-4-yl)oxy)ethyl)pyrrolidin-2-one 6.21

-continued

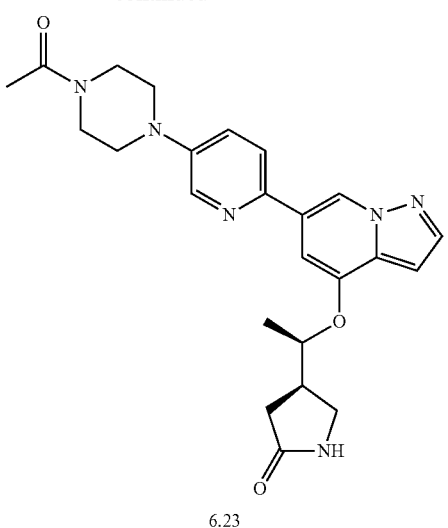

6.23

To a mixture of (R)-4-((R)-1-((6-(5-(piperazin-1-yl)pyridin-2-yl)pyrazolo[1,5-a]pyridin-4-yl)oxy)ethyl)pyrrolidin-2-one 6.21 (15 mg, 0.089 mmol), HATU (28 mg, 0.074 mmol) and N-methylmorpholine (16 μL, 0.15 mmol) in DMF (1 mL) was added AcOH (3.0 μL, 0.052 mmol). The reaction was stirred for 4 h, concentrated and the residue was purified via prep HPLC (2-95% acetonitrile in water, 0.1% trifluoroacteic acid buffer) to afford (R)-4-((R)-1-((6-(5-(4-acetylpiperazin-1-yl)pyridin-2-yl)pyrazolo[1,5-a]pyridin-4-yl)oxy)ethyl)pyrrolidin-2-one 6.23 as the trifluoroacetic acid salt. LCMS-ESI+ (m/z): [M+H]+ calcd for $C_{24}H_{28}N_6O_3$: 449.2; found 449.2.

General Procedure 6B for Synthesis of Examples 6.24-6.27

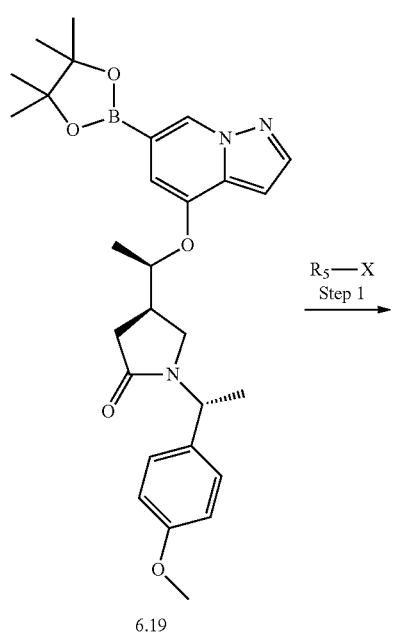

6.19

-continued

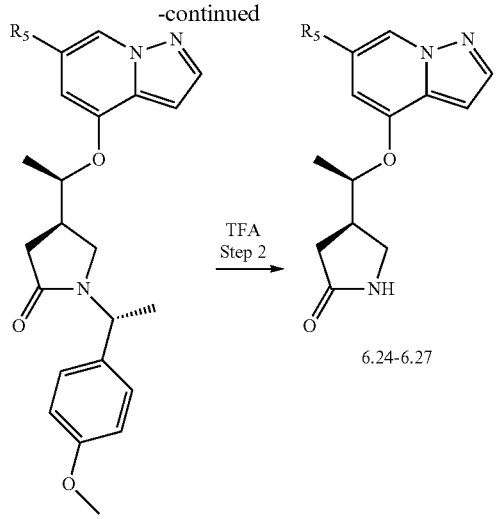

6.24-6.27

Step 1: To an appropriate sized container charged with a magnetic stir bar, crude boronate ester 6.19 (1 equiv), aryl/heteroaryl halide (1.2 equiv), cesium carbonate (3 equiv) and PEPPSI-IPr catalyst (0.1 equiv) were added and the reagents were taken up in 2:1 DME:water (0.05-0.5 M). After evacuating and backfilling with argon, mixture was heated at 90-110° C. for 30-120 minutes. After cooling to room temperature, the mixture was poured into water and extracted with ethyl acetate. Combined organics were dried (MgSO$_4$), filtered and concentrated under reduced pressure to afford a mixture from which desired product can be isolated by flash chromatography or RP-HPLC. Alternatively, the crude residue may be used in subsequent reactions.

Step 2: The product from step 1 was dissolved in TFA and heated at 60° C. for 18 h. The reaction was concentrated and the residue was purified via prep HPLC (2-95% acetonitrile in water, 0.1% trifluoroacteic acid buffer).

Example 6.24

Preparation of (R)-4-((R)-1-((6-(5-morpholinopyridin-2-yl)pyrazolo[1,5-a]pyridin-4-yl)oxy)ethyl)pyrrolidin-2-one

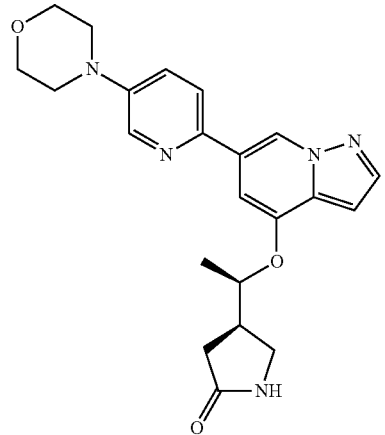

6.24

Following General Procedure 6B, beginning with boronate ester 6.19 and 4-(6-bromopyridin-3-yl)morpholine (Prepared as described in WO2007/116922), (R)-4-((R)-1-((6-(5-morpholinopyridin-2-yl)pyrazolo[1,5-a]pyridin-4-yl)oxy)ethyl)pyrrolidin-2-one 6.24 was isolated as the trifluoroacetic acid salt.

$^1$H NMR (400 MHz, Methanol-d4), TFA salt, δ 8.77 (s, 1H), 8.35-8.29 (m, 1H), 8.11-7.99 (m, 2H), 7.92 (d, J=9.2 Hz, 1H), 7.13 (d, J=1.2 Hz, 1H), 6.75 (d, J=2.2 Hz, 1H), 4.81-4.77 (m, 1H), 3.95-3.87 (m, 4H), 3.63 (dd, J=10.1, 8.5 Hz, 1H), 3.42 (t, J=5.2 Hz, 4H), 3.33-3.30 (m, 1H), 2.97 (m, 1H), 2.61 (dd, J=17.2, 9.3 Hz, 1H), 2.49 (dd, J=17.2, 6.9 Hz, 1H), 1.49 (d, J=6.1 Hz, 3H).

LCMS-ESI+ (m/z): [M+H]+ calcd for $C_{22}H_{25}N_5O_3$: 408.2; found 408.1.

Example 6.25

Preparation of (R)-4-((R)-1-((6-(5,6-dimethylpyridin-2-yl)pyrazolo[1,5-a]pyridin-4-yl)oxy)ethyl)pyrrolidin-2-one

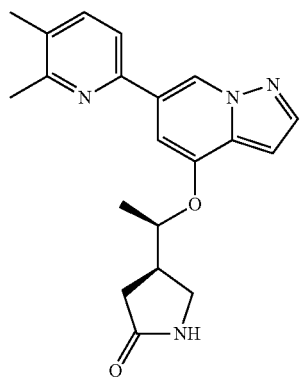

6.25

Following General Procedure 6B, beginning with boronate ester 6.19 and 6-bromo-2,3-dimethylpyridine, (R)-4-((R)-1-((6-(5,6-dimethylpyridin-2-yl)pyrazolo[1,5-a]pyridin-4-yl)oxy)ethyl)pyrrolidin-2-one 6.25 was isolated as the trifluoroacetic acid salt.

$^1$H NMR (400 MHz, Methanol-d4), TFA salt, δ 8.87 (s, 1H), 8.33 (dd, J=8.1, 2.1 Hz, 1H), 8.17-8.03 (m, 2H), 7.12 (s, 1H), 6.81 (dd, J=2.3, 0.9 Hz, 1H), 4.92-4.87 (m 1H), 3.64 (t, J=10.2, 8.5 Hz, 1H), 3.37-3.33 (m, 1H), 3.05-2.91 (m, 1H), 2.81 (s, 3H), 2.68-2.43 (m, 5H), 1.49 (d, J=6.1 Hz, 3H). LCMS-ESI+ (m/z): [M+H]+ calcd for $C_{20}H_{22}N_4O_2$: 351.2; found 351.1.

Example 6.26

Preparation of (R)-4-((R)-1-((6-(5-methoxypyrimidin-2-yl)pyrazolo[1,5-a]pyridin-4-yl)oxy)ethyl)pyrrolidin-2-one

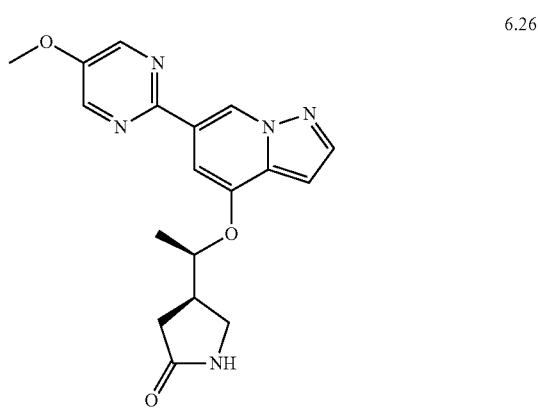 [SMILES: COc1cnc(-c2cc(O[C@H](C)[C@H]3CNC(=O)C3)c3ccnn3c2)nc1]

6.26

Following General Procedure 6B, beginning with boronate ester 6.19 and 2-chloro-5-methoxypyrimidine, (R)-4-((R)-1-((6-(5-methoxypyrimidin-2-yl)pyrazolo[1,5-a]pyridin-4-yl)oxy)ethyl)pyrrolidin-2-one 6.26 was isolated as the trifluoroacetic acid salt.

$^1$H NMR (400 MHz, Methanol-d4), TFA salt, δ 9.16 (s, 1H), 8.60 (s, 2H), 7.99 (d, J=2.3 Hz, 1H), 7.61 (s, 1H), 6.71 (dd, J=2.3, 1.0 Hz, 1H), 4.89-4.86 (m, 1H), 4.04 (s, 3H), 3.64 (dd, J=10.1, 8.5 Hz, 1H), 3.40-3.36 (m, 1H), 2.97 (dd, J=14.8, 7.1 Hz, 1H), 2.68-2.47 (m, 2H), 1.50 (d, J=6.1 Hz, 3H). LCMS-ESI+ (m/z): [M+H]+ calcd for $C_{18}H_{19}N_5O_3$: 354.2; found 354.1.

Example 6.27

Preparation of (R)-4-((R)-1-((6-(5-morpholinopyrimidin-2-yl)pyrazolo[1,5-a]pyridin-4-yl)oxy)ethyl)pyrrolidin-2-one

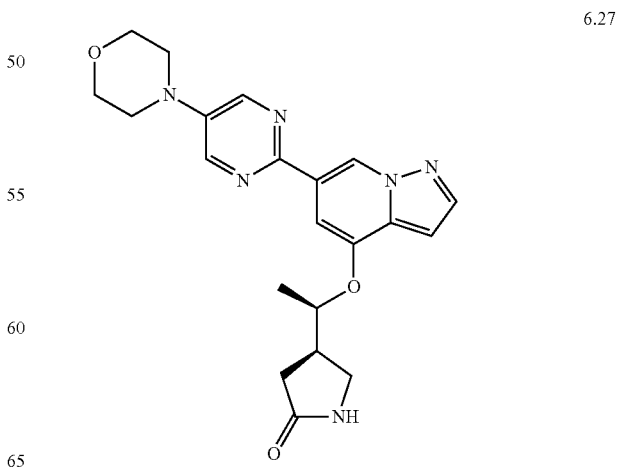

6.27

711

Following General Procedure 6B, beginning with boronate ester 6.19 and 4-(2-bromopyrimidin-5-yl)morpholine, (R)-4-((R)-1-((6-(5-morpholinopyrimidin-2-yl)pyrazolo[1,5-a]pyridin-4-yl)oxy)ethyl)pyrrolidin-2-one 6.27 was isolated as the trifluoroacetic acid salt.

$^1$H NMR (400 MHz, Methanol-d4), TFA salt, δ 9.11 (s, 1H), 8.56 (s, 2H), 7.97 (d, J=2.3 Hz, 1H), 7.58 (s, 1H), 6.70 (dd, J=2.3, 1.0 Hz, 1H), 4.87-4.83 (m, 1H), 3.91 (m, 4H), 3.63 (dd, J=10.1, 8.5 Hz, 1H), 3.42-3.36 (m, 5H), 3.03-2.94 (m, 1H), 2.67-2.47 (m, 2H), 1.49 (d, J=6.1 Hz, 3H). LCMS-ESI+ (m/z): [M+H]+ calcd for $C_{21}H_{24}N_6O_3$: 409.2; found 409.1.

Example 6.29

Preparation of (R)-4-((R)-1-((6-(1-methyl-1H-thieno[3,2-c]pyrazol-5-yl)pyrazolo[1,5-a]pyridin-4-yl)oxy)ethyl)pyrrolidin-2-one

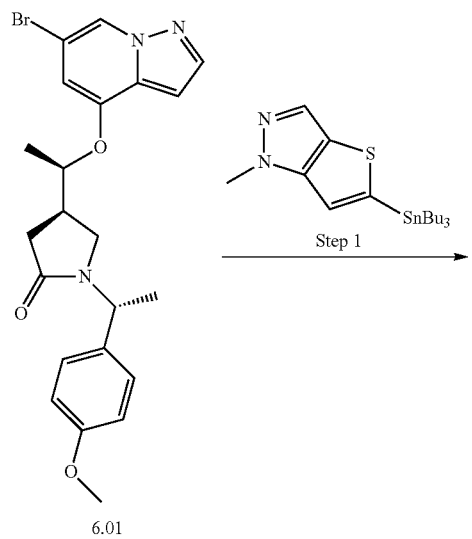

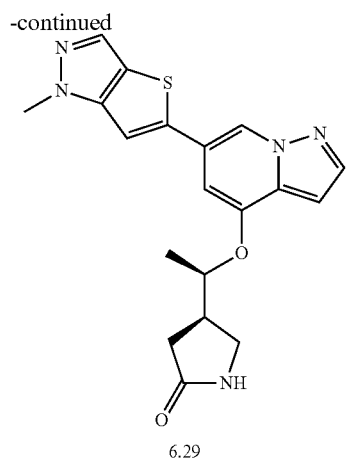

6.29

Step 1: A solution of (R)-4-((R)-1-((6-bromopyrazolo[1,5-a]pyridin-4-yl)oxy)ethyl)-1-((R)-1-(4-methoxyphenyl)ethyl)pyrrolidin-2-one 6.01 (30 mg, 0.065 mmol) and 1-methyl-5-(tributylstannyl)-1H-thieno[3,2-c]pyrazole (36 mg, 0.085 mmol, prepared according to protocols described in WO2012/177714 and US2012/043276) were dissolved in DMF (0.6 mL). Cesium fluoride (20 mg, 0.13 mmol), cuprous iodide (2.5 mg, 0.013 mmol) and Pd(PPh$_3$)$_4$ (7.6 mg, 0.0066 mmol) were added. Argon gas was bubbled through the reaction mixture for 2 minutes and the reaction was heated to 50° C. for 16 h. The reaction was cooled to room temperature, EtOAc and water were added, the layers were separated and the aqueous layer was extracted with EtOAc (1x). The combined organics were washed with water, dried (MgSO$_4$), filtered and concentrated to a residue which was purified by silica gel chromatography (0-5% MeOH in EtOAc) to afford (R)-1-((R)-1-(4-methoxyphenyl)ethyl)-4-((R)-1-((6-(1-methyl-1H-thieno[3,2-c]pyrazol-5-yl)pyrazolo[1,5-a]pyridin-4-yl)oxy)ethyl)pyrrolidin-2-one 6.28.

LCMS-ESI$^+$ (m/z): [M+H]+ calcd for $C_{28}H_{29}N_5O_3S$: 516.2; found: 516.4.

Step 2: A solution of (R)-1-((R)-1-(4-methoxyphenyl)ethyl)-4-((R)-1-((6-(1-methyl-1H-thieno[3,2-c]pyrazol-5-yl)pyrazolo[1,5-a]pyridin-4-yl)oxy)ethyl)pyrrolidin-2-one 6.28 (30 mg, 0.058 mmol) in TFA (1.5 mL) was heated at 60° C. for 18 h. The reaction was concentrated and the residue was purified via prep HPLC (2-95% acetonitrile in water, 0.1% trifluoroacteic acid buffer) to isolate (R)-4-((R)-1-((6-(1-methyl-1H-thieno[3,2-c]pyrazol-5-yl)pyrazolo[1,5-a]pyridin-4-yl)oxy)ethyl)pyrrolidin-2-one 6.29 as the trifluoroacetic acid salt.

$^1$H NMR (400 MHz, DMSO-d6), TFA salt, δ 8.59 (s, 1H), 7.97 (d, J=1.2 Hz, 1H), 7.79 (s, 1H), 7.72 (s, 1H), 7.56 (s, 1H), 6.99 (s, 1H), 6.63 (d, J=1.6 Hz, 1H), 4.85 (pent, J=6.4 Hz, 1H), 4.00 (s, 3H), 3.39 (t, J=9.6 Hz, 1H), 3.11 (dd, J=6.4, 9.2 Hz, 1H), 2.74-2.79 (m, 1H), 2.33 (dd, J=9.2, 16.8 Hz, 1H), 2.21 (dd, J=8.8, 16.8 Hz, 1H), 1.33 (d, J=6.0 Hz, 3H).

LCMS-ESI⁺ (m/z): [M+H]⁺ calcd for $C_{19}H_{19}N_5O_2S$: 382.1; found: 382.0.

Example 6.09

Preparation of (R)-4-((R)-1-(6-(1-tert-butyl-1H-pyrazol-4-yl)-3-methylpyrazolo[1,5-a]pyridin-4-yloxy)ethyl)pyrrolidin-2-one

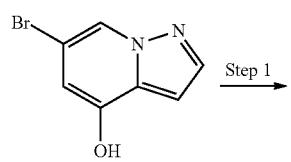

Step 1

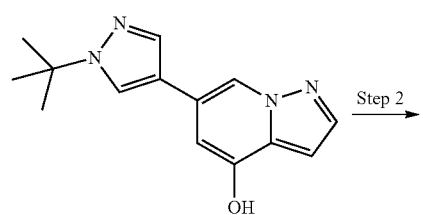

Step 2

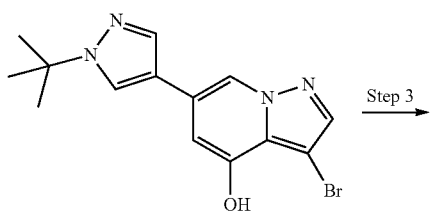

Step 3

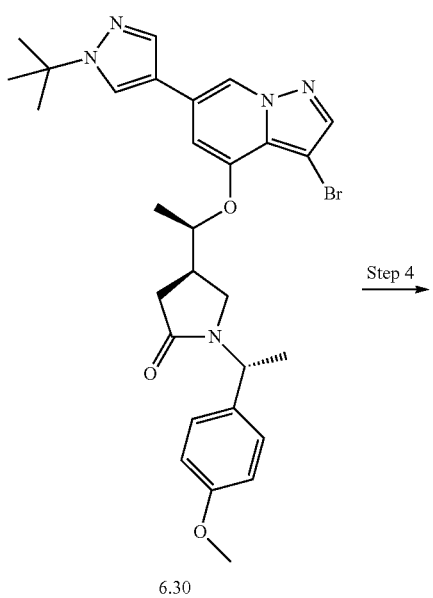

Step 4

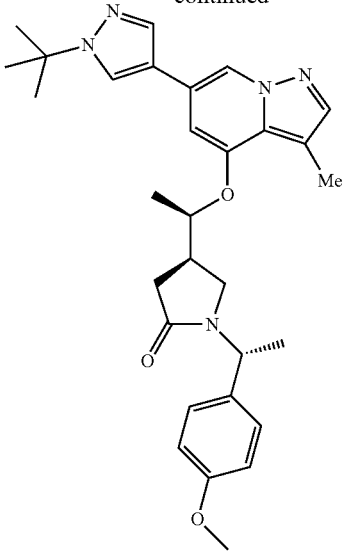

Step 5

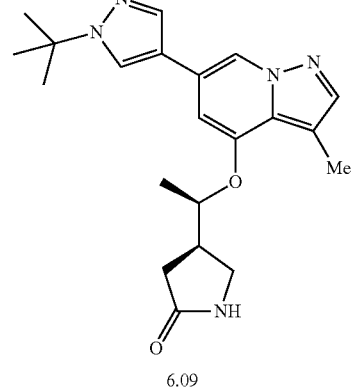

6.09

Step 1: To an appropriate sized microwave vial, 6-bromopyrazolo[1,5a]pyridin-4-ol (100 mg, 0.469 mmol), 1-(tert-butyl)-4-(4,4,5,5-tetramethyl-1,3,2-dioxaborolan-2-yl)-1H-pyrazole (153 mg, 0.612 mmol), cesium carbonate (459 mg, 1.41 mmol), dioxane (3.0 mL) and water (1.5 mL) were added. The mixture was degassed with nitrogen for 10 minutes. PEPPSI-iPr catalyst (32.0 mg, 0.0469 mmol) was added and the solution was heated at 100° C. for 18 h. After cooling to room temperature, the mixture was poured into water, neutralized to pH 7 and extracted with ethyl acetate. The combined organic layers were washed with brine, dried, filtered and concentrated under reduced pressure. The residue was purified by flash column chromatography on silica gel to afford 6-(1-tert-butyl-1H-pyrazol-4-yl)pyrazolo[1,5-a]pyridin-4-ol.

LCMS-ESI⁺ (m/z): [M+H]+ calcd for $C_{14}H_{16}N_4O$: 257.1; found: 257.1.

Step 2: To a solution of 6-(1-tert-butyl-1H-pyrazol-4-yl)pyrazolo[1,5-a]pyridin-4-ol (138 mg, 0.538 mmol) in acetonitrile (6 mL) was added N-bromosuccinimide (105 mg, 0.590 mmol). The solution was stirred at room temperature for 1 h. The reaction was diluted with dichloromethane, washed with water and 2N NaOH. The combined aqueous layers were neutralized and extracted with ethyl acetate. The combined organic layers were washed with brine, dried, filtered and concentrated under reduced pressure. The residue was purified by flash column chromatography on silica gel to afford 3-bromo-6-(1-tert-butyl-1H-pyrazol-4-yl)pyrazolo[1,5-a]pyridin-4-ol.

LCMS-ESI+ (m/z): [M+H]+ calcd for $C_{14}H_{15}{}^{79}BrN_4O$: 335.1; found: 334.9.

Step 3: To an appropriate sized microwave vial, 3-bromo-6-(1-tert-butyl-1H-pyrazol-4-yl)pyrazolo[1,5-a]pyridin-4-ol (60 mg, 0.18 mmol), (S)-1-((R)-1-((R)-1-(4-methoxyphenyl)ethyl)-5-oxopyrrolidin-3-yl)ethyl methanesulfonate 1.30 (73 mg, 0.21 mmol), cesium carbonate (82 mg, 0.25 mmol) and DMF were added. The mixture was heated at 90° C. for 2 h. After cooling to room temperature, the mixture was poured into a saturated aqueous solution of NaHCO$_3$ and extracted with ethyl acetate. The combined organic layers were washed with brine, dried, filtered and concentrated under reduced pressure. The residue was purified by flash column chromatography on silica gel to afford (R)-4-((R)-1-(3-bromo-6-(1-tert-butyl-1H-pyrazol-4-yl)pyrazolo[1,5-a]pyridin-4-yloxy)ethyl)-1-((R)-1-(4-methoxyphenyl)ethyl)pyrrolidin-2-one 6.30.

LCMS-ESI+ (m/z): [M+H]+ calcd for $C_{29}H_{34}{}^{79}BrN_5O_3$: 580.2; found: 580.2.

Step 4: To an appropriate sized microwave vial, (R)-4-((R)-1-(3-bromo-6-(1-tert-butyl-1H-pyrazol-4-yl)pyrazolo[1,5-a]pyridin-4-yloxy)ethyl)-1-((R)-1-(4-methoxyphenyl)ethyl)pyrrolidin-2-one (60 mg, 0.10 mmol) and [1,1'-bis(diphenylphosphino)ferrocene]dichloropalladium(II) (7.7 mg, 0.010 mmol) were added. After evacuating and backfilling with nitrogen, dioxane (1 mL) was added followed by dimethylzinc (0.13 mL, 0.26 mmol, 2M solution in toluene). The mixture was heated at 75° C. for 18 h. After cooling to room temperature, the reaction was diluted with 1N HCl and extracted with ethyl acetate. The combined organic layers were washed with brine, dried, filtered and concentrated under reduced pressure. The residue was purified by flash column chromatography on silica gel to afford a mixture of dehalogenated starting material and title compound (R)-4-((R)-1-(6-(1-tert-butyl-1H-pyrazol-4-yl)-3-methylpyrazolo[1,5-a]pyridin-4-yloxy)ethyl)-1-((R)-1-(4-methoxyphenyl)ethyl)pyrrolidin-2-one. The mixture was used without further purification. LCMS-ESI+ (m/z): [M+H]+ calcd for $C_{30}H_{37}N_5O_3$: 516.3; found: 516.2.

Step 5: To an appropriate sized microwave vial, a mixture of (R)-4-((R)-1-(6-(1-tert-butyl-1H-pyrazol-4-yl)-3-methylpyrazolo[1,5-a]pyridin-4-yloxy)ethyl)-1-((R)-1-(4-methoxyphenyl)ethyl)pyrrolidin-2-one and dehalogenated by-product (19 mg) in TFA (1.5 mL) was heated at 60° C. for 18 h. The reaction was concentrated under reduced pressure. The residue was purified via prep HPLC (2-95% acetonitrile in water, 0.1% trifluoroacteic acid buffer) to isolate (R)-4-((R)-1-(6-(1-tert-butyl-1H-pyrazol-4-yl)-3-methylpyrazolo[1,5-a]pyridin-4-yloxy)ethyl)pyrrolidin-2-one 6.09 as the trifluoroacetic acid salt.

$^1$H NMR (400 MHz, DMSO-d6) δ 8.49 (d, J=0.9 Hz, 1H), 8.38 (d, J=0.5 Hz, 1H), 7.98 (d, J=0.5 Hz, 1H), 7.64 (d, J=0.5 Hz, 1H), 7.60 (s, 1H), 6.81 (s, 1H), 4.88-4.74 (m, 1H), 3.41 (t, J=9.2 Hz, 1H), 3.14 (dd, J=9.6, 6.7 Hz, 1H), 2.87-2.77 (m, 1H), 2.40-2.16 (m, 5H), 1.56 (s, 9H), 1.32 (d, J=6.0 Hz, 3H).

LCMS-ESI+ (m/z): [M+H]+ calcd for $C_{21}H_{27}N_5O_2$: 382.2; found: 382.1.

Examples 6.32 and 6.33

Preparation of (R)-4-((R)-1-((3-methyl-6-(4-(piperazin-1-yl)phenyl)pyrazolo[1,5-a]pyridin-4-yl)oxy)ethyl)pyrrolidin-2-one and (R)-4-((R)-1-((3-methyl-6-(4-(4-(methylsulfonyl)piperazin-1-yl)phenyl)pyrazolo[1,5-a]pyridin-4-yl)oxy)ethyl)pyrrolidin-2-one

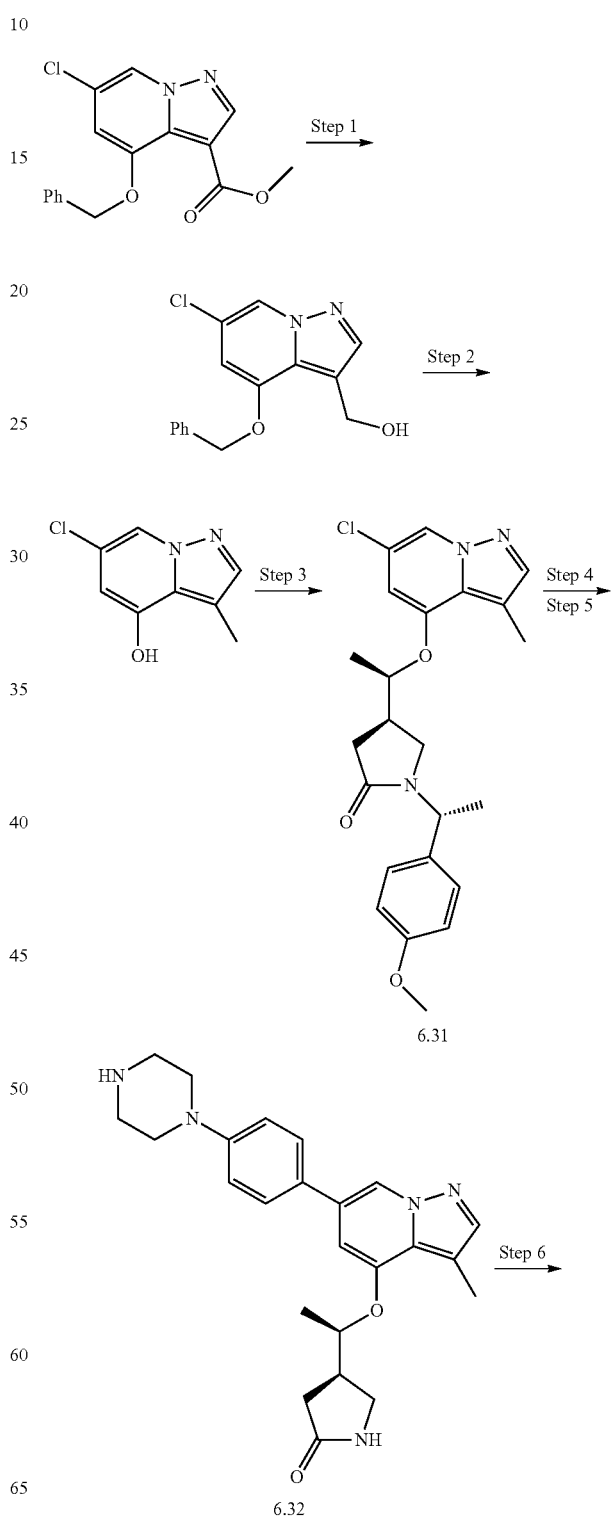

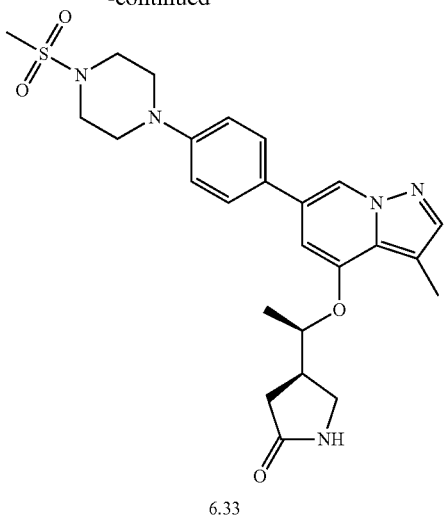

6.33

Step 1: To a solution of methyl 4-(benzyloxy)-6-chloropyrazolo[1,5-a]pyridine-3-carboxylate (220 mg, 0.692 mmol) in THF (3.0 mL) at 0° C. was added lithium aluminum hydride (0.783 mL, 0.783 mmol, 1M solution in THF). The reaction was warmed to room temperature and was stirred for 30 minutes. The reaction was quenched by the addition of a saturated aqueous solution of $KHSO_4$ and was then diluted with EtOAc. The layers were separated and the aqueous layer was washed with EtOAc several times until no longer cloudy. Combined organics were washed with brine, dried ($MgSO_4$), filtered and concentrated to afford (4-(benzyloxy)-6-chloropyrazolo[1,5-a]pyridin-3-yl)methanol which was used directly in the next reaction. LCMS-ESI+ (m/z): [M+H]+ calcd for $C_{15}H_{13}ClN_2O_2$: 289.1; found 289.0.

Step 2: To a solution of (4-(benzyloxy)-6-chloropyrazolo[1,5-a]pyridin-3-yl)methanol (274 mg, 0.946 mmol) in TFA (3.0 mL) was added triethylsilane (0.604 mL, 3.78 mmol). The reaction was stirred at 60° C. overnight. Incomplete removal of the benzyl group was observed. The reaction was concentrated, dissolved in HBr (48%, 3.5 ml) and the reaction was heated at 100° C. overnight. The reaction was cooled and neutralized by the addition of 2N NaOH. The aqueous layer was extracted with EtOAc (3×) and the combined organics were washed with saturated $NaHCO_3$ $_{(aq)}$, brine, dried ($MgSO_4$), filtered and concentrated to provide 6-chloro-3-methylpyrazolo[1,5-a]pyridin-4-ol. LCMS-ES I+(m/z): [M+H]+ calcd for $C_8H_7ClN_2O$: 183.0; found 183.0.

Step 3: This reaction was conducted in an analogous fashion to step 1 in General Procedure 6A, beginning with 6-chloro-3-methylpyrazolo[1,5-a]pyridin-4-ol and mesylate 1.30 to afford (R)-4-((R)-1-((6-chloro-3-methylpyrazolo[1,5-a]pyridin-4-yl)oxy)ethyl)-1-((R)-1-(4-methoxyphenyl)ethyl)pyrrolidin-2-one 6.31. LCMS-ESI+ (m/z): [M+H]+ calcd for $C_{23}H_{26}ClN_3O_3$: 428.2; found 428.2.

Steps 4-5: These reactions were conducted in an analogous fashion to steps 2 and 3 in General Procedure 6A, beginning with (R)-4-((R)-1-((6-chloro-3-methylpyrazolo[1,5-a]pyridin-4-yl)oxy)ethyl)-1-((R)-1-(4-methoxyphenyl)ethyl)pyrrolidin-2-one 6.31 and (4-(4-(tert-butoxycarbonyl)piperazin-1-yl)phenyl)boronic acid to afford (R)-4-((R)-1-((3-methyl-6-(4-(piperazin-1-yl)phenyl)pyrazolo[1,5-a]pyridin-4-yl)oxy)ethyl)pyrrolidin-2-one 6.32 as the trifluoroacetic acid salt.

$^1$H NMR (400 MHz, Methanol-d4), TFA salt, δ 8.24 (s, 1H), 7.70 (s, 1H), 7.64 (d, J=8.7 Hz, 2H), 7.17 (d, J=8.8 Hz, 2H), 6.79 (s, 1H), 4.87-4.83 (m, 1H), 3.64 (dd, J=10.0, 8.8 Hz, 1H), 3.52 (m, 4H), 3.48-3.36 (m, 5H), 3.08-2.94 (m, 1H), 2.67-2.43 (m, 5H), 1.48 (d, J=6.1 Hz, 3H). LCMS-ESI+ (m/z): [M+H]+ calcd for $C_{24}H_{29}N_5O_2$: 420.2; found 420.1.

Step 6: This example was prepared in an analogous fashion to Example 6.54, beginning with (R)-4-((R)-1-((3-methyl-6-(4-(piperazin-1-yl)phenyl)pyrazolo[1,5-a]pyridin-4-yl)oxy)ethyl)pyrrolidin-2-one 6.32 to afford (R)-4-((R)-1-((3-methyl-6-(4-(4-(methylsulfonyl)piperazin-1-yl)phenyl)pyrazolo[1,5-a]pyridin-4-yl)oxy)ethyl)pyrrolidin-2-one 6.33 as the trifluoroacetic acid salt.

$^1$H NMR (400 MHz, Methanol-d4), TFA salt, δ 8.24 (s, 1H), 7.69 (s, 1H), 7.64-7.57 (m, 2H), 7.15 (d, J=8.7 Hz, 2H), 6.80 (s, 1H), 4.87-4.84 (m, 1H), 3.70-3.59 (m, 1H), 3.46-3.38 (m, 9H), 3.01 (m, 1H), 2.94 (s, 3H), 2.67-2.46 (m, 2H), 2.58 (s, 3H), 1.48 (d, J=6.1 Hz, 3H). LCMS-ESI+ (m/z): [M+H]+ calcd for $C_{25}H_{31}N_5O_4S$: 498.2; found 498.1.

Example 6.34

Preparation of (R)-4-((R)-1-((6-(3-methoxy-4-(piperazin-1-yl)phenyl)-3-methylpyrazolo[1,5-a]pyridin-4-yl)oxy)ethyl)pyrrolidin-2-one

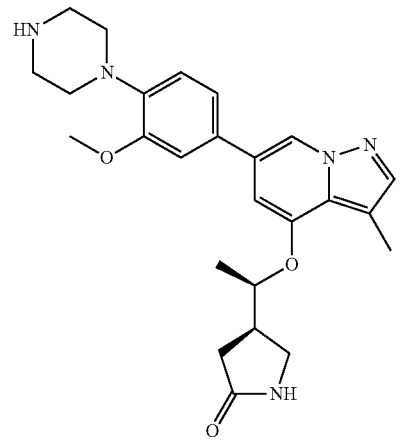

6.34

This example was prepared in an analogous fashion to steps 2 and 3 in General Procedure 6A, beginning with (R)-4-((R)-1-((6-chloro-3-methylpyrazolo[1,5-a]pyridin-4-yl)oxy)ethyl)-1-((R)-1-(4-methoxyphenyl)ethyl)pyrrolidin-2-one 6.31 and tert-butyl 4-(2-methoxy-4-(4,4,5,5-tetramethyl-1,3,2-dioxaborolan-2-yl)phenyl)piperazine-1-carboxylate 7.08 to afford (R)-4-((R)-1-((6-(3-methoxy-4-(piperazin-1-yl)phenyl)-3-methylpyrazolo[1,5-a]pyridin-4-yl)oxy)ethyl)pyrrolidin-2-one 6.34 as the trifluoroacetic acid salt.

$^1$H NMR (400 MHz, Methanol-d4), TFA salt, δ 8.26 (s, 1H), 7.69 (s, 1H), 7.29-7.21 (m, 2H), 7.11 (d, J=8.0 Hz, 1H), 6.79 (s, 1H), 4.87-4.83 (m, 1H), 4.00 (s, 3H), 3.67-3.57 (m, 1H), 3.46-3.38 (m, 5H), 3.38-3.34 (m, 4H), 3.07-2.94 (m, 1H), 2.66-2.45 (m, 5H), 1.46 (d, J=6.1 Hz, 3H). LCMS-ESI+ (m/z): [M+H]+ calcd for $C_{25}H_{31}N_5O_3$: 450.2; found 450.2.

Example 6.35

Preparation of (R)-4-((R)-1-((6-(3-methoxy-4-(4-(methylsulfonyl)piperazin-1-yl)phenyl)-3-methylpyrazolo[1,5-a]pyridin-4-yl)oxy)ethyl)pyrrolidin-2-one

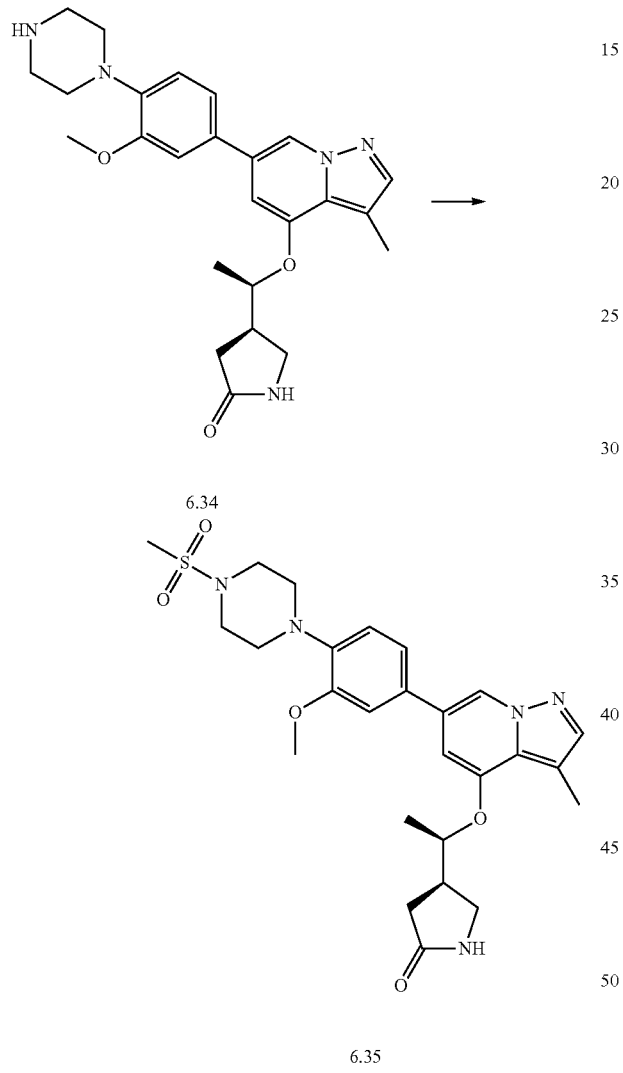

This example was prepared in an analogous fashion to Example 6.54, beginning with (R)-4-((R)-1-((6-(3-methoxy-4-(piperazin-1-yl)phenyl)-3-methylpyrazolo[1,5-a]pyridin-4-yl)oxy)ethyl)pyrrolidin-2-one 6.34 to afford (R)-4-((R)-1-((6-(3-methoxy-4-(4-(methylsulfonyl)piperazin-1-yl)phenyl)-3-methylpyrazolo[1,5-a]pyridin-4-yl)oxy)ethyl) pyrrolidin-2-one 6.35 as the trifluoroacetic acid salt.

$^1$H NMR (400 MHz, Methanol-d4), TFA salt, δ 8.29 (s, 1H), 7.71 (s, 1H), 7.27 (d, J=7.3 Hz, 2H), 7.16 (d, J=8.0 Hz, 1H), 6.81 (s, 1H), 4.91-4.87 (m, 1H), 4.03 (s, 3H), 3.69-3.59 (m, 1H), 3.50-3.35 (m, 5H), 3.27 (t, J=4.8 Hz, 4H), 3.02 (d, J=8.4 Hz, 1H), 2.95 (s, 3H), 2.67-2.47 (m, 5H), 1.48 (d, J=6.1 Hz, 3H). LCMS-ESI+ (m/z): [M+H]+ calcd for $C_{26}H_{33}N_5O_5S$: 528.2; found 528.2.

Intermediate 6.10

Preparation of (R)-4-((R)-1-(6-bromo-3-chloropyrazolo[1,5-a]pyridin-4-yloxy)ethyl)pyrrolidin-2-one

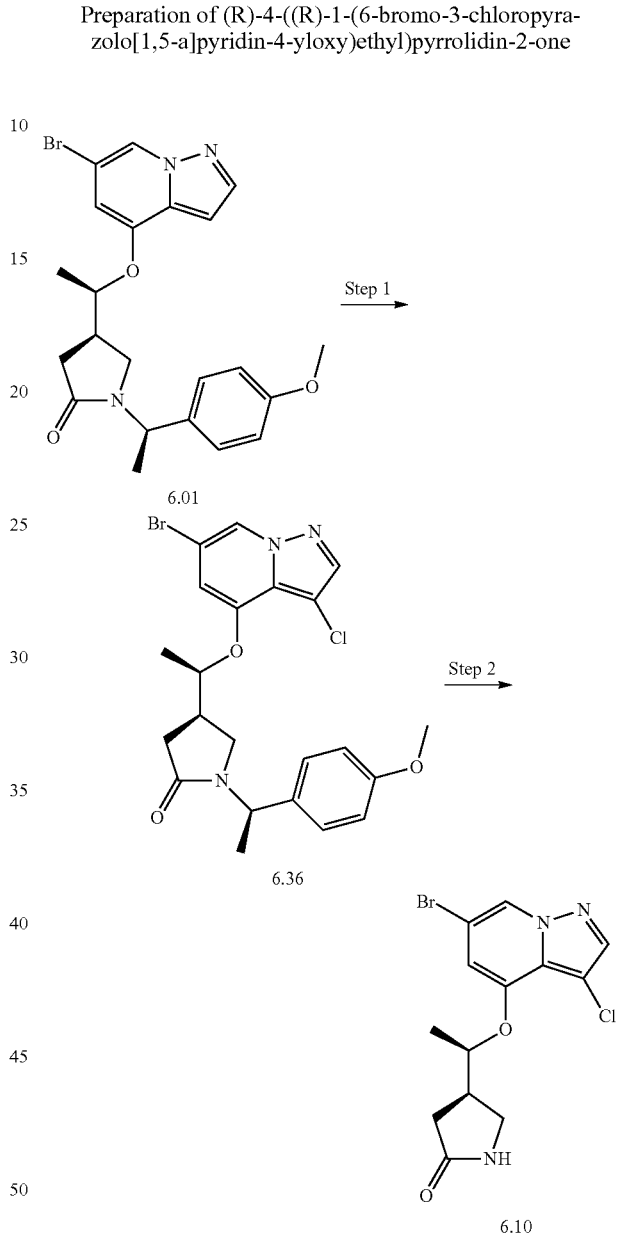

Step 1: To a solution of (R)-4-((R)-1-(6-bromopyrazolo[1,5-a]pyridin-4-yloxy)ethyl)-1-((R)-1-(4-methoxyphenyl) ethyl)pyrrolidin-2-one 6.01 (111 mg, 0.242 mmol) in acetonitrile (2.4 mL) was added N-chlorosuccinimide (38.8 mg, 0.290 mmol). The solution was stirred at room temperature for 3 h. The reaction was poured into 1N NaOH and extracted with dichloromethane. The combined organic layers were washed with brine, dried, filtered and concentrated under reduced pressure to afford (R)-4-((R)-1-(6-bromo-3-chloropyrazolo[1,5-a]pyridin-4-yloxy)ethyl)-1-((R)-1-(4-methoxyphenyl)ethyl)pyrrolidin-2-one 6.36, which was used without further purification.

LCMS-ESI+ (m/z): [M+H]+ calcd for $C_{22}H_{23}{}^{79}Br^{35}ClN_3O_3$: 492.1; found: 492.0.

Step 2: To an appropriate sized microwave vial, crude (R)-4-((R)-1-(6-bromo-3-chloropyrazolo[1,5-a]pyridin-4-yloxy)ethyl)-1-((R)-1-(4-methoxyphenyl)ethyl)pyrrolidin-2-one was heated in TFA (1.5 mL) at 60° C. for 18 h. The reaction was concentrated under reduced pressure to afford (R)-4-((R)-1-(6-bromo-3-chloropyrazolo[1,5-a]pyridin-4-yloxy)ethyl)pyrrolidin-2-one 6.10 as the trifluoroacetic acid salt. The residue was used without further purification.

LCMS-ESI$^+$ (m/z): [M+H]+ calcd for $C_{13}H_{13}{}^{79}Br^{35}ClN_3O_2$: 358.0; found: 358.0.

General Procedure 6C for Synthesis of Examples 6.11-6.13 and 6.37

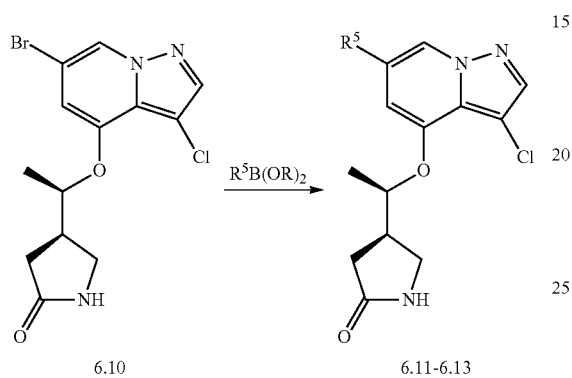

6.10 → 6.11-6.13

To an appropriate sized microwave vial, the crude trifluoroacetic acid salt of (R)-4-((R)-1-(6-bromo-3-chloropyrazolo[1,5-a]pyridin-4-yloxy)ethyl)pyrrolidin-2-one 6.10 (1 equiv), the appropriate boronic acid or ester (1.2-2.0 equiv), cesium carbonate (3 equiv), dioxane and water (2:1, 0.1-0.5M) were added. The mixture was degassed with nitrogen for 10 minutes. Tetrakis(triphenylphosphine)palladium(0) catalyst (0.01-0.10 equiv) was added and the solution was heated at 100° C. for 1 h. After cooling to room temperature, the reaction was concentrated under reduced pressure. The residue was purified via prep HPLC or flash chromatography to provide examples 6.11-6.13.

The following analogs were prepared according to procedure 6C and were isolated as trifluoroacetic acid salts:

Example 6.11

Preparation of (R)-4-((R)-1-(6-(1-tert-butyl-1H-pyrazol-4-yl)-3-chloropyrazolo[1,5-a]pyridin-4-yloxy)ethyl)pyrrolidin-2-one

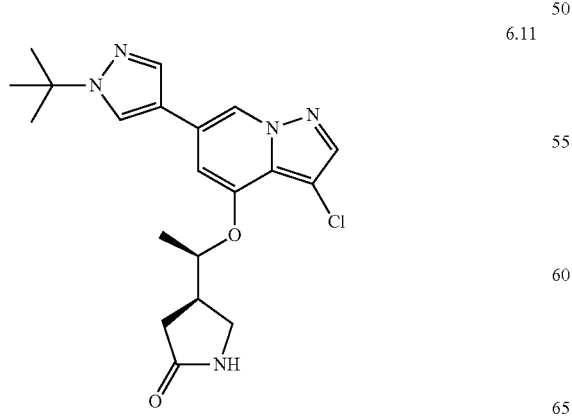

6.11

$^1$H NMR (400 MHz, DMSO-d6), TFA salt, δ 8.63 (d, J=1.0 Hz, 1H), 8.44 (d, J=0.8 Hz, 1H), 8.04 (d, J=0.8 Hz, 1H), 7.96 (s, 1H), 7.58 (s, 1H), 7.01 (d, J=1.1 Hz, 1H), 4.84 (p, J=5.8 Hz, 1H), 3.40 (t, J=9.1 Hz, 1H), 3.15 (dd, J=9.6, 7.0 Hz, 1H), 2.91-2.75 (m, 1H), 2.36-2.27 (m, 2H), 1.56 (s, 9H), 1.33 (d, J=6.0 Hz, 3H).

LCMS-ESI$^+$ (m/z): [M+H]+ calcd for $C_{20}H_{24}ClN_5O_2$: 402.2; found: 402.0.

Example 6.12

Preparation of (R)-4-((R)-1-(3-chloro-6-(3,4-dimethoxyphenyl)pyrazolo[1,5-a]pyridin-4-yloxy)ethyl)pyrrolidin-2-one

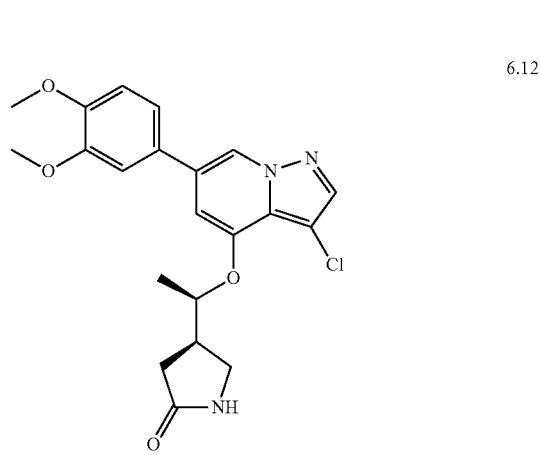 [SMILES: COc1ccc(-c2cc(O[C@H](C)[C@H]3CNC(=O)C3)c3c(Cl)cnn3c2)cc1OC]

6.12

$^1$H NMR (400 MHz, DMSO-d6), TFA salt, δ 8.62 (d, J=1.1 Hz, 1H), 8.03 (s, 1H), 7.57 (s, 1H), 7.32-7.29 (m, 2H), 7.04 (d, J=8.1 Hz, 1H), 6.99 (d, J=1.2 Hz, 1H), 4.89 (p, J=5.9 Hz, 1H), 3.87 (s, 3H), 3.80 (s, 3H), 3.38 (t, J=9.0 Hz, 1H), 3.16 (dd, J=9.6, 7.0 Hz, 1H), 2.87-2.77 (m, 1H), 2.37-2.26 (m, 2H), 1.33 (d, J=6.0 Hz, 3H).

LCMS-ESI$^+$ (m/z): [M+H]$^+$ calcd for $C_{21}H_{22}ClN_3O_2$: 416.1; found: 416.0.

Example 6.13

Preparation of (R)-4-((R)-1-(3-chloro-6-(4-morpholinophenyl)pyrazolo[1,5-a]pyridin-4-yloxy)ethyl)pyrrolidin-2-one

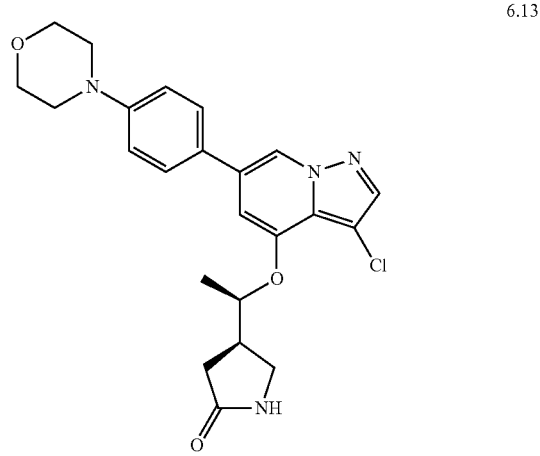 [SMILES: C[C@@H](Oc1cc(-c2ccc(N3CCOCC3)cc2)cn2ncc(Cl)c12)[C@H]1CNC(=O)C1]

6.13

723

$^1$H NMR (400 MHz, DMSO-d6), TFA salt, δ 8.52 (d, J=1.1 Hz, 1H), 8.00 (s, 1H), 7.66 (d, J=8.8 Hz, 2H), 7.57 (s, 1H), 7.04 (d, J=8.9 Hz, 2H), 6.98 (s, 1H), 4.88 (p, J=5.9 Hz, 1H), 3.83-3.67 (m, 4H), 3.38 (t, J=9.1 Hz, 1H), 3.24-3.10 (m, 5H), 2.86-2.76 (m, 1H), 2.31 (d, J=8.8 Hz, 2H), 1.33 (d, J=6.0 Hz, 3H).

LCMS-ESI$^+$ (m/z): [M+H]$^+$ calcd for $C_{23}H_{25}ClN_4O_3$: 441.2; found: 441.1.

Example 6.37

Preparation of (R)-4-((R)-1-((3-chloro-6-(1-(tetrahydro-2H-pyran-4-yl)-1H-pyrazol-4-yl)pyrazolo[1,5-a]pyridin-4-yl)oxy)ethyl)pyrrolidin-2-one

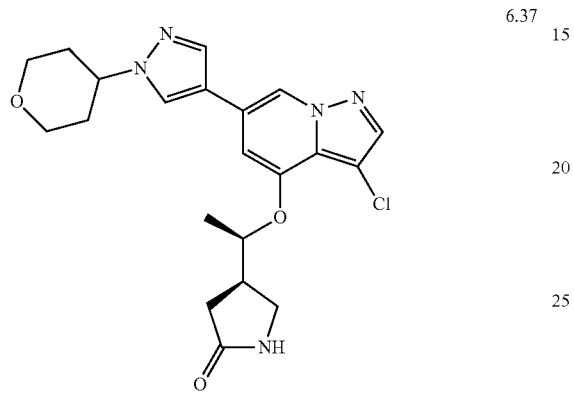

6.37

$^1$H NMR (400 MHz, DMSO-d6), TFA salt, δ 8.61 (d, J=1.0 Hz, 1H), 8.43 (s, 1H), 8.05 (s, 1H), 7.97 (s, 1H), 7.57 (s, 1H), 6.98 (s, 1H), 4.81 (p, J=6.1 Hz, 1H), 4.48-4.32 (m, 1H), 4.05-3.90 (m, 2H), 3.49 (td, J=11.6, 2.4 Hz, 2H), 3.39 (t, J=9.1 Hz, 1H), 3.15 (dd, J=9.6, 7.0 Hz, 1H), 2.91-2.74 (m, 1H), 2.31 (d, J=8.8 Hz, 2H), 2.11-1.84 (m, 4H), 1.33 (d, J=6.0 Hz, 3H).

LCMS-ESI$^+$ (m/z): [M+H]+ calcd for $C_{21}H_{24}ClN_5O_3$: 430.2; found: 430.1.

Examples 6.39 and 6.40

Preparation of (R)-4-((R)-1-((3-chloro-6-(4-(piperazin-1-yl)phenyl)pyrazolo[1,5-a]pyridin-4-yl)oxy)ethyl)pyrrolidin-2-one and (R)-4-((R)-1-((6-(4-(4-acetylpiperazin-1-yl)phenyl)-3-chloropyrazolo[1,5-a]pyridin-4-yl)oxy)ethyl)pyrrolidin-2-one

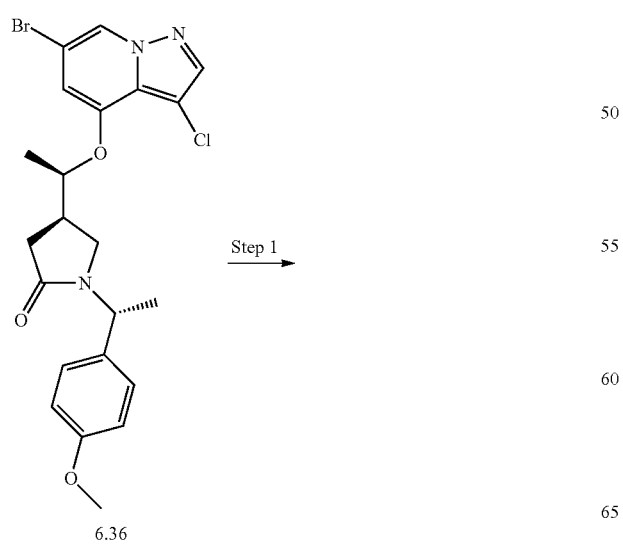

6.36

724

-continued

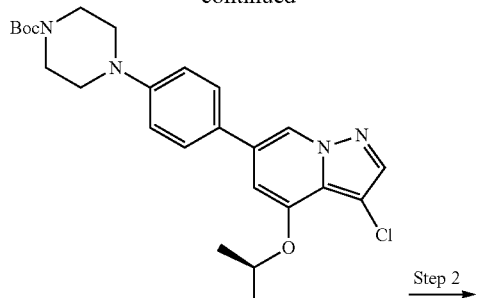

6.38

Step 2

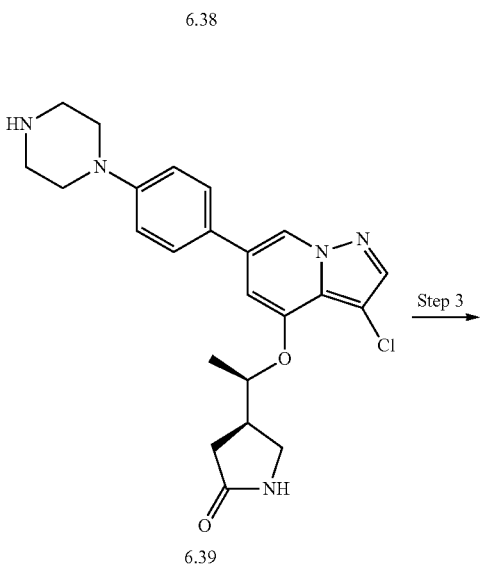

6.39

Step 3

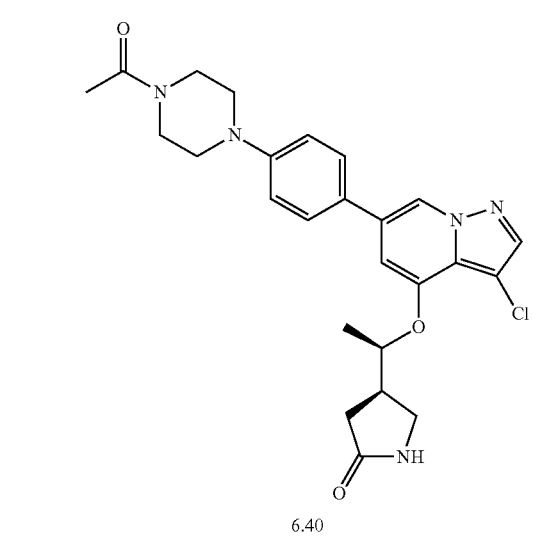 [SMILES: CC(=O)N1CCN(c2ccc(-c3cc(O[C@H](C)[C@H]4CNC(=O)C4)c4c(Cl)cnn4c3)cc2)CC1]

6.40

Step 1: To an appropriate sized microwave vial, (R)-4-((R)-1-((6-bromo-3-chloropyrazolo[1,5-a]pyridin-4-yl)oxy)ethyl)-1-((R)-1-(4-methoxyphenyl)ethyl)pyrrolidin-2-one 6.36 (118 mg, 0.239 mmol), (4-(4-(tert-butoxycarbonyl)piperazin-1-yl)phenyl)boronic acid (73.3 mg, 0.239 mmol), cesium carbonate (234 mg, 0.718 mmol), dioxane (2.0 mL) and water (0.5 mL) were added. The mixture was degassed with nitrogen for 10 minutes. Tetrakis(triphenylphosphine)palladium(0) catalyst (27.7 mg, 0.0239 mmol) was added and the solution was heated at 100° C. for 18 h. After cooling to room temperature, the reaction was concentrated under reduced pressure. The residue was purified by flash column chromatography on silica gel to afford tert-butyl 4-(4-(3-chloro-4-((R)-1-((R)-1-((R)-1-(4-methoxyphenyl)ethyl)-5-oxopyrrolidin-3-yl)ethoxy)pyrazolo[1,5-a]pyridin-6-yl)phenyl)piperazine-1-carboxylate 6.38.

LCMS-ESI$^+$ (m/z): [M+H]+ calcd for $C_{37}H_{44}N_5O_5$: 674.3; found: 674.2.

Step 2: To an appropriate sized microwave vial, tert-butyl 4-(4-(3-chloro-4-((R)-1-((R)-1-((R)-1-(4-methoxyphenyl)ethyl)-5-oxopyrrolidin-3-yl)ethoxy)pyrazolo[1,5-a]pyridin-6-yl)phenyl)piperazine-1-carboxylate 6.38 (15 mg, 0.022 mmol) in TFA (1.0 mL) was heated at 60° C. for 18 h. The reaction was concentrated under reduced pressure. The residue was purified via prep HPLC (2-95% acetonitrile in water, 0.1% trifluoroacteic acid buffer) to isolate (R)-4-((R)-1-((3-chloro-6-(4-(piperazin-1-yl)phenyl)pyrazolo[1,5-a]pyridin-4-yl)oxy)ethyl)pyrrolidin-2-one 6.39 as the trifluoroacetic acid salt.

$^1$H NMR (400 MHz, DMSO-d6), TFA salt, δ 8.68 (bs, 2H), 8.55 (d, J=1.1 Hz, 1H), 8.02 (s, 1H), 7.71 (d, J=8.7 Hz, 2H), 7.57 (s, 1H), 7.09 (d, J=8.8 Hz, 2H), 6.99 (s, 1H), 4.91-4.85 (m, 1H), 3.48-3.32 (m, 5H), 3.30-3.23 (m, 4H), 3.16 (dd, J=9.6, 7.0 Hz, 1H), 2.90-2.72 (m, 1H), 2.31 (d, J=8.8 Hz, 2H), 1.33 (d, J=6.0 Hz, 3H).

LCMS-ESI$^+$ (m/z): [M+H]+ calcd for $C_{23}H_{26}ClN_5O_2$: 440.2; found: 440.0.

Step 3: A 10 mL vial was charged with (R)-4-((R)-1-((3-chloro-6-(4-(piperazin-1-yl)phenyl)pyrazolo[1,5-a]pyridin-4-yl)oxy)ethyl)pyrrolidin-2-one 6.39 (41 mg, 0.093 mmol), HATU (71 mg, 0.19 mmol) and N-methylmorpholine (41 μL, 0.37 mmol) in DMF (2.0 mL). Acetic acid (10 μL, 0.18 mmol) was added and the reaction was stirred at room temperature for 5 h. The reaction was concentrated under reduced pressure and the residue was purified via prep HPLC (2-95% acetonitrile in water, 0.1% trifluoroacetic acid buffer) to isolate ((R)-4-((R)-1-((6-(4-(4-acetylpiperazin-1-yl)phenyl)-3-chloropyrazolo[1,5-a]pyridin-4-yl)oxy)ethyl)pyrrolidin-2-one 6.40 as the trifluoroacetic acid salt.

$^1$H NMR (400 MHz, DMSO-d6), TFA salt, δ 8.57-8.47 (m, 1H), 8.00 (s, 1H), 7.67 (d, J=8.8 Hz, 2H), 7.56 (s, 1H), 7.05 (d, J=8.7 Hz, 2H), 6.99 (d, J=1.2 Hz, 1H), 4.88 (p, J=6.0 Hz, 1H), 3.61-3.58 (m, 4H), 3.38 (t, J=9.1 Hz, 1H), 3.25-3.14 (m, 5H), 2.86-2.76 (m, 1H), 2.31 (d, J=8.7 Hz, 2H), 2.05 (s, 3H), 1.33 (d, J=6.0 Hz, 3H).

LCMS-ESI$^+$ (m/z): [M+H]+ calcd for $C_{25}H_{28}ClN_5O_3$: 482.2; found: 482.2.

Example 6.44

Preparation of (R)-4-((R)-1-((3-chloro-6-(5-(4-(methylsulfonyl)piperazin-1-yl)pyridin-2-yl)pyrazolo[1,5-a]pyridin-4-yl)oxy)ethyl)pyrrolidin-2-one

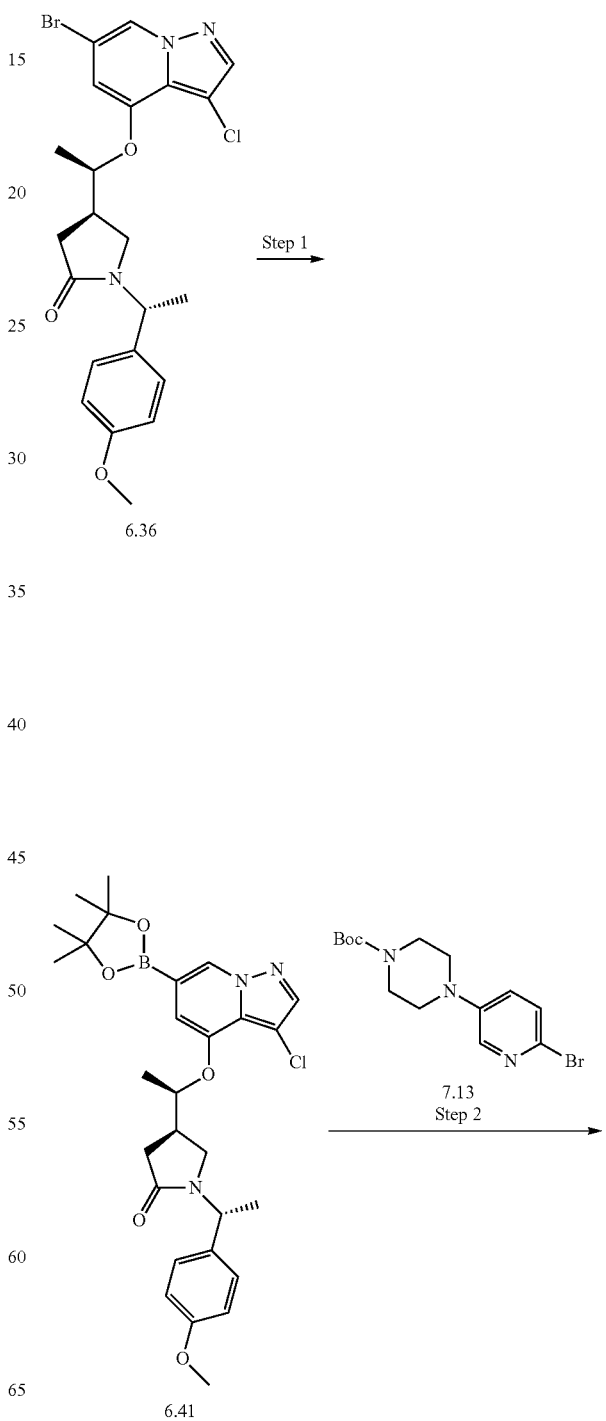

-continued

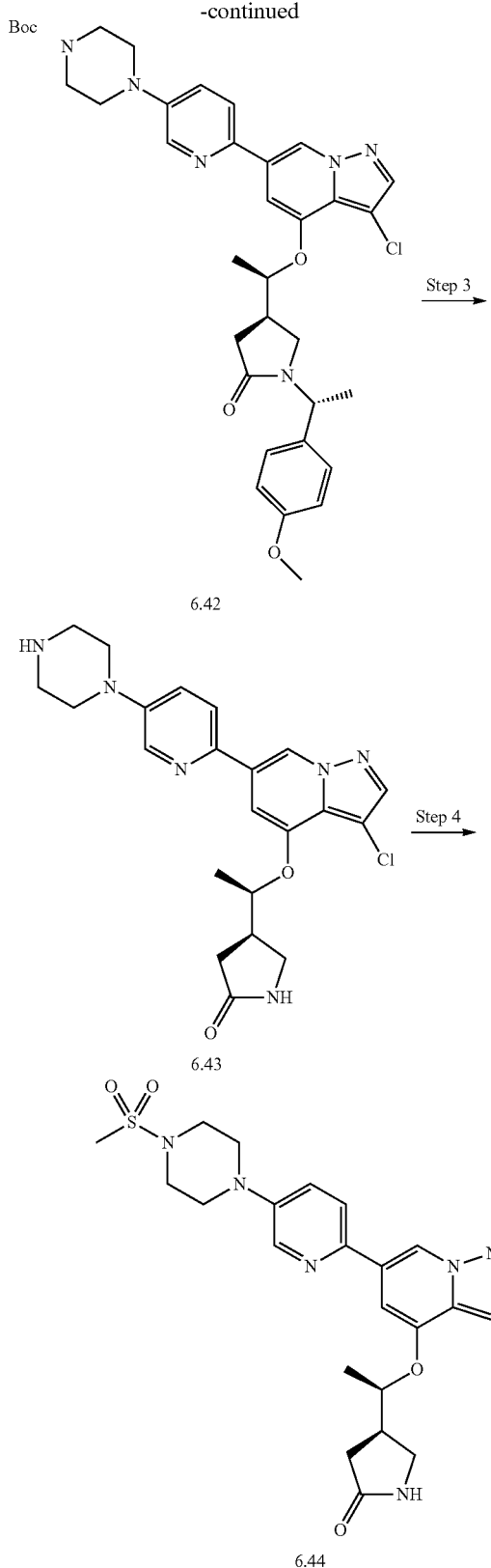

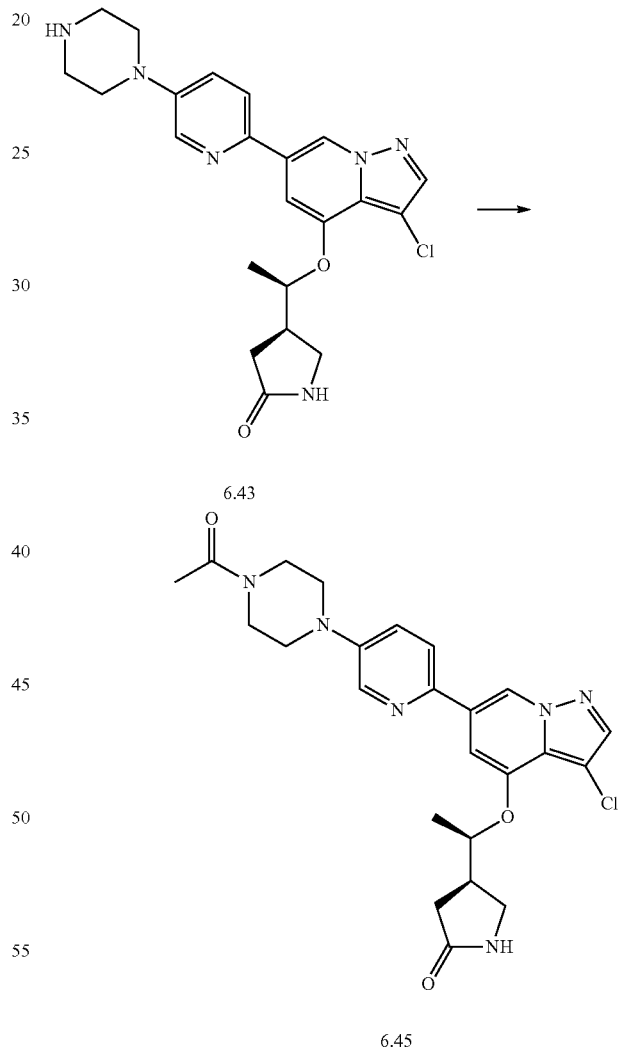

chloro-6-(5-(4-(methylsulfonyl)piperazin-1-yl)pyridin-2-yl)pyrazolo[1,5-a]pyridin-4-yl)oxy)ethyl)pyrrolidin-2-one 6.44 was isolated as the trifluoroacetic acid salt after 4 synthetic steps.

¹H NMR (400 MHz, Methanol-d4), TFA salt, δ 8.71 (s, 1H), 8.37 (d, J=2.9 Hz, 1H), 8.04 (d, J=8.7 Hz, 1H), 7.97 (s, 1H), 7.88 (s, 1H), 7.16 (s, 1H), 4.87-4.83 (m, 1H), 3.55-3.35 (m, 10H), 3.04-2.99 (m, 1H), 2.94 (s, 3H), 2.66 (dd, J=8.0, 16.0 Hz, 1H), 2.58 (dd, J=8, 16 Hz, 1H), 1.51 (d, J=6.1 Hz, 3H). LCMS-ESI+ (m/z): [M+H]+ calcd for $C_{23}H_{27}ClN_6O_4S$: 519.2; found 519.1.

Example 6.45

Preparation of (R)-4-((R)-1-((6-(5-(4-acetylpiperazin-1-yl)pyridin-2-yl)-3-chloropyrazolo[1,5-a]pyridin-4-yl)oxy)ethyl)pyrrolidin-2-one Following procedure for the synthesis of 6.23, beginning with (R)-4-((R)-1-((3-chloro-6-(5-(piperazin-1-yl)pyridin-2-yl)pyrazolo[1,5-a]pyridin-4-yl)oxy)ethyl)pyrrolidin-2-one 6.43, (R)-4-((R)-1-((6-(5-(4-acetylpiperazin-1-yl)pyridin-2-yl)-3-chloropyrazolo[1,5-a]pyridin-4-yl)oxy)ethyl)pyrrolidin-2-one 6.45 was isolated as the trifluoroacetic acid salt.

Example 6.44 was prepared according to Example 6.22, beginning with (R)-4-((R)-1-(6-bromo-3-chloropyrazolo[1,5-a]pyridin-4-yloxy)ethyl)pyrrolidin-2-one 6.36 as starting material and 7.13 as coupling partner, (R)-4-((R)-1-((3-

729

¹H NMR (400 MHz, Methanol-d4), TFA salt, δ 8.72 (s, 1H), 8.40 (d, J=2.9 Hz, 1H), 8.03 (d, J=9.0 Hz, 1H), 7.96 (s, 1H), 7.90-7.85 (m, 1H), 7.18 (s, 1H), 4.87-4.83 (m, 1H), 3.84-3.79 (m, 4H), 3.65-3.60 (m, 1H), 3.52-3.35 (m, 5H), 3.05-2.99 (m, 1H), 2.69-2.52 (m, 2H), 2.20 (s, 3H), 1.51 (d, J=6.1 Hz, 3H). LCMS-ESI+ (m/z): [M+H]+ calcd for $C_{24}H_{27}ClN_6O_3$: 483.2; found 483.1.

Example 6.47

Preparation of (R)-4-((R)-1-((6-(1-(tert-butyl)-1H-pyrazol-4-yl)-3-cyclopropylpyrazolo[1,5-a]pyridin-4-yl)oxy)ethyl)pyrrolidin-2-one

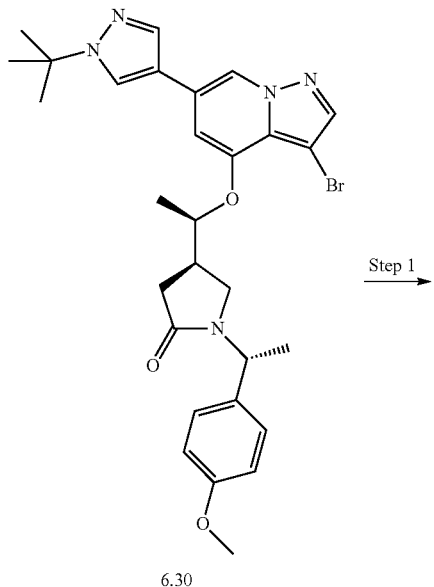

6.30

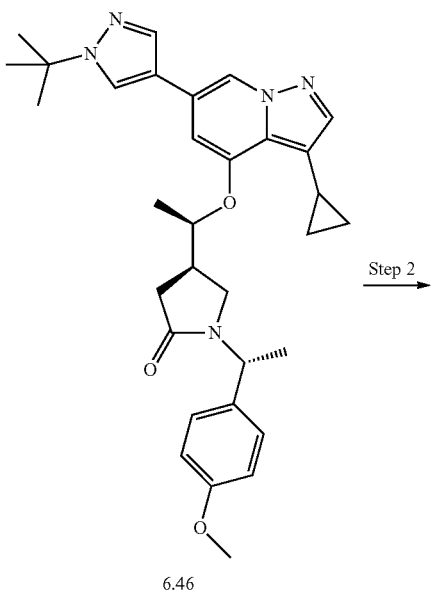

6.46

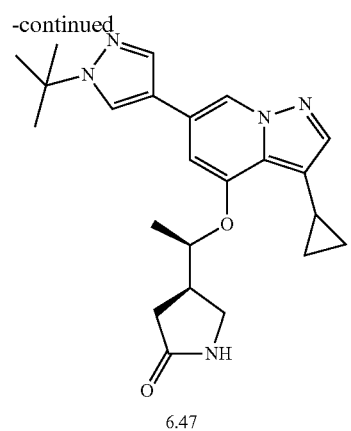

6.47

Step 1: To an appropriate sized microwave vial, (R)-4-((R)-1-((3-bromo-6-(1-(tert-butyl)-1H-pyrazol-4-yl)pyrazolo[1,5-a]pyridin-4-yl)oxy)ethyl)-1-((R)-1-(4-methoxyphenyl)ethyl)pyrrolidin-2-one 6.30 (48 mg, 0.083 mmol) and [(2-dicyclohexylphosphino-2',6'-bis(N,N-dimethylamino)-1,1'-biphenyl)-2-(2'-amino-1,1'-biphenyl)]palladium(II) methanesulfonate (8.7 mg, 0.011 mmol) were added. After evacuating and backfilling with nitrogen, THF (3.0 mL) was added followed by cyclopropylzinc bromide (0.83 mL, 0.41 mmol, 0.5M solution in THF). The mixture was stirred at room temperature for 15 min. The reaction was diluted with 1N HCl and extracted with ethyl acetate. The combined organic layers were washed with brine, dried (MgSO₄), filtered and concentrated under reduced pressure. The residue was purified by flash column chromatography on silica gel to afford (R)-4-((R)-1-((6-(1-(tert-butyl)-1H-pyrazol-4-yl)-3-cyclopropylpyrazolo[1,5-a]pyridin-4-yl)oxy)ethyl)-1-((R)-1-(4 methoxyphenyl)ethyl)pyrrolidin-2-one 6.46.

LCMS-ESI⁺ (m/z): [M+H]+ calcd for $C_{32}H_{39}N_5O_3$: 542.3; found: 542.3.

Step 2: To an appropriate sized microwave vial, (R)-4-((R)-1-((6-(1-(tert-butyl)-1H-pyrazol-4-yl)-3-cyclopropylpyrazolo[1,5-a]pyridin-4-yl)oxy)ethyl)-1-4R)-1-(4-methoxyphenyl)ethyl)pyrrolidin-2-one 6.46 (15 mg, 0.028 mmol) in TFA (1.5 mL) was heated at 60° C. for 24 h. The reaction was concentrated under reduced pressure. The residue was purified via prep HPLC (2-95% acetonitrile in water, 0.1% trifluoroacetic acid buffer) to isolate (R)-4-((R)-1-((6-(1-(tert-butyl)-1H-pyrazol-4-yl)-3-cyclopropylpyrazolo[1,5-a]pyridin-4-yl)oxy)ethyl)pyrrolidin-2-one 6.47 as the trifluoroacetic acid salt.

¹H NMR (400 MHz, DMSO-d6), TFA salt, δ 8.57-8.43 (s, 1H), 8.38 (s, 1H), 7.99 (s, 1H), 7.58 (s, 1H), 7.52 (s, 1H), 6.83 (s, 1H), 4.84 (p, J=6.0 Hz, 1H), 3.41 (t, J=9.2 Hz, 1H), 3.16 (dd, J=9.7, 6.7 Hz, 1H), 2.91-2.73 (m, 1H), 2.39-2.22 (m, 2H), 2.23-2.14 (m, 1H), 1.56 (s, 9H), 1.34 (d, J=6.0 Hz, 3H), 0.84 (dd, J=8.5, 2.0 Hz, 2H), 0.67-0.51 (m, 2H).

LCMS-ESI⁺ (m/z): [M+H]+ calcd for $C_{23}H_{29}N_5O_2$: 408.2; found: 408.2.

Examples 6.50, 6.51 and 6.52

Preparation of (R)-4-((R)-1-((3-cyclopropyl-6-(5-(piperazin-1-yl)pyridin-2-yl)pyrazolo[1,5-a]pyridin-4-yl)oxy)ethyl)pyrrolidin-2-one, (R)-4-((R)-1-((3-cyclopropyl-6-(5-(4-(methylsulfonyl)piperazin-1-yl)pyridin-2-yl)pyrazolo[1,5-a]pyridin-4-yl)oxy)ethyl)pyrrolidin-2-one, and (R)-4-((R)-1-((6-(5-(4-acetylpiperazin-1-yl)pyridin-2-yl)-3-cyclopropylpyrazolo[1,5-a]pyridin-4-yl)oxy)ethyl)pyrrolidin-2-one

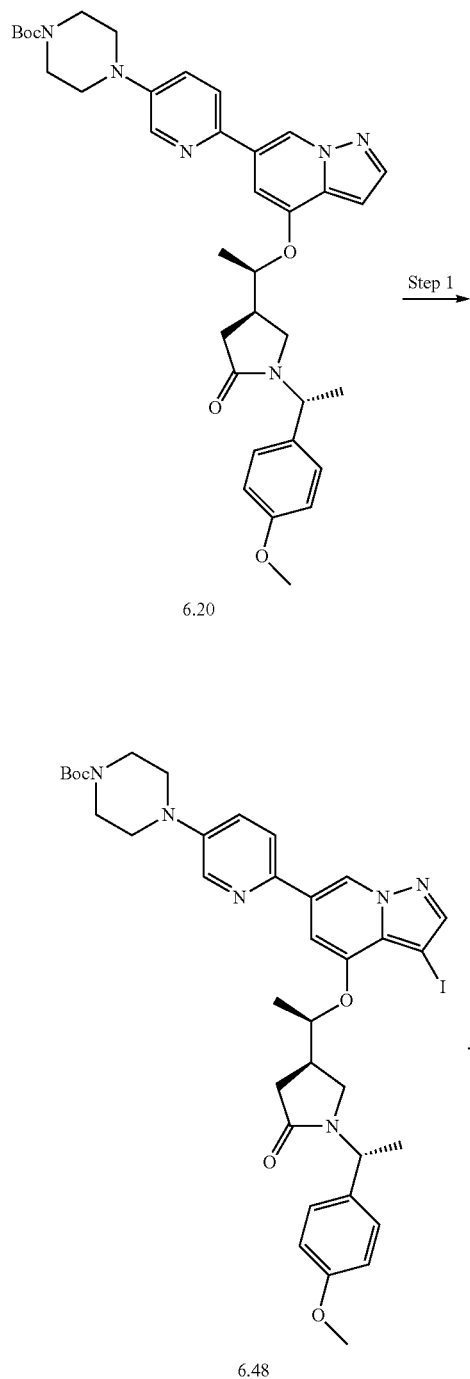

6.20

6.48

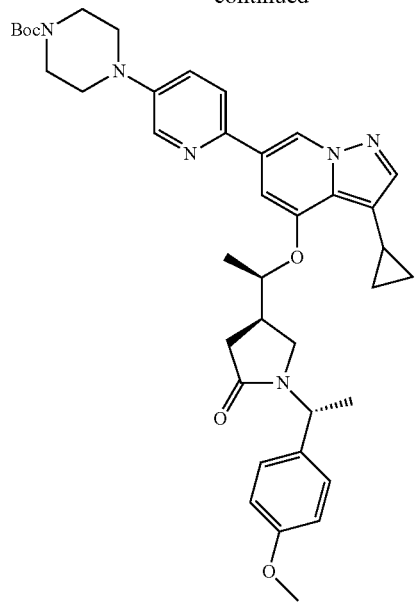

6.49

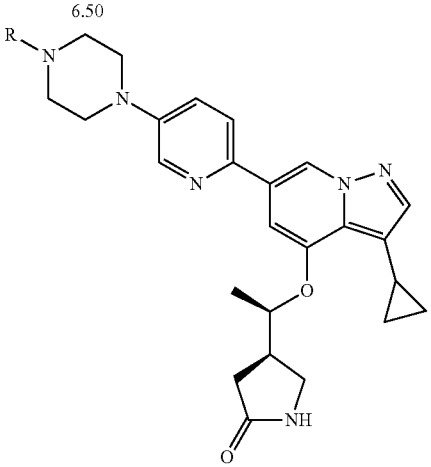

6.50

6.51 (R = Ms)
6.52 (R = Ac)

Step 1: To an appropriate sized microwave vial, tert-butyl 4-(6-(4-((R)-1-((R)-1-((R)-1-(4-methoxyphenyl)ethyl)-5-oxopyrrolidin-3-yl)ethoxy)pyrazolo[1,5-a]pyridin-6-yl)pyridin-3-yl)piperazine-1-carboxylate 6.20 (47 mg, 0.073 mmol) and acetonitrile (3.0 mL) were added. N-iodosuccinimide (17 mg, 0.076 mmol) was added and the solution was stirred at room temperature for 5 minutes. The reaction was diluted with DCM. The organic layer was washed with 1M NaOH followed by an aqueous solution of sodium thiosulfate. The organic layer was dried (MgSO$_4$), filtered and concentrated under reduced pressure to afford tert-butyl 4-(6-(3-iodo-4-((R)-1-((R)-1-((R)-1-(4-methoxyphenyl)ethyl)-5-oxopyrrolidin-3-yl)ethoxy)pyrazolo[1,5-a]pyridin-6-yl)pyridin-3-yl)piperazine-1-carboxylate 6.48 without further purification.

LCMS-ESI$^+$ (m/z): [M+H]+ calcd for $C_{36}H_{43}IN_6O_5$: 767.2; found: 767.2.

Step 2: To an appropriate sized microwave vial, 4-(6-(3-iodo-4-((R)-1-((R)-1-((R)-1-(4-methoxyphenyl)ethyl)-5-oxopyrrolidin-3-yl)ethoxy)pyrazolo[1,5-a]pyridin-6-yl)pyridin-3-yl)piperazine-1-carboxylate 6.48 (35 mg, 0.046 mmol) and [(2-dicyclohexylphosphino-2',6'-bis(N,N-dimethylamino)-1,1'-biphenyl)-2-(2'-amino-1,1'-biphenyl)]palladium(II) methanesulfonate (3.7 mg, 0.0046 mmol) were added. After evacuating and backfilling with nitrogen, THF (1.0 mL) was added followed by cyclopropylzinc bromide (0.55 mL, 0.27 mmol, 0.5M solution in THF). The mixture was stirred at room temperature for 15 min. The reaction was diluted with a saturated aqueous solution of ammonium chloride and extracted with ethyl acetate. The combined organic layers were washed with brine, dried (MgSO$_4$), filtered and concentrated under reduced pressure. The residue was purified by flash column chromatography on silica gel to afford tert-butyl 4-(6-(3-cyclopropyl-4-((R)-1-((R)-1-((R)-1-(4-methoxyphenyl)ethyl)-5-oxopyrrolidin-3-yl)ethoxy)pyrazolo[1,5-a]pyridin-6-yl)pyridin-3-yl)piperazine-1-carboxylate 6.49.

LCMS-ESI$^+$ (m/z): [M+H]+ calcd for $C_{39}H_{48}N_6O_5$: 681.4; found: 681.4.

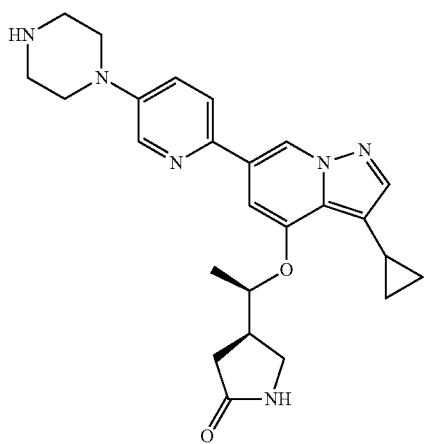

6.50

Step 3: To an appropriate sized microwave vial, tert-butyl 4-(6-(3 cyclopropyl-4-((R)-1-((R)-1-((R)-1-(4-methoxyphenyl)ethyl)-5-oxopyrrolidin-3-yl)ethoxy)pyrazolo[1,5-a]pyridin-6-yl)pyridin-3-yl)piperazine-1-carboxylate 6.49 (16 mg, 0.024 mmol) in TFA (1.5 mL) was heated at 60° C. for 18 h. The reaction was concentrated under reduced pressure and the residue was purified via prep HPLC (2-95% acetonitrile in water, 0.1% trifluoroacetic acid buffer) to isolate (R)-4-((R)-1-((3-cyclopropyl-6-(5-(piperazin-1-yl)pyridin-2-yl)pyrazolo[1,5-a]pyridin-4-yl)oxy)ethyl)pyrrolidin-2-one 6.50 as the trifluoroacetic acid salt.

$^1$H NMR (400 MHz, DMSO-d6), TFA salt, δ 8.81 (d, J=1.1 Hz, 1H), 8.73 (bs, 2H), 8.44 (d, J=2.9 Hz, 1H), 7.99 (d, J=8.8 Hz, 1H), 7.62 (s, 1H), 7.59 (s, 1H), 7.50 (dd, J=8.9, 3.0 Hz, 1H), 7.22 (s, 1H), 4.81 (p, J=5.9 Hz, 1H), 3.54-3.45 (m, 4H), 3.40 (t, J=9.2 Hz, 1H), 3.35-3.23 (m, 4H), 3.18 (dd, J=9.6, 6.8 Hz, 1H), 2.90-2.74 (m, 1H), 2.40-2.13 (m, 3H), 1.36 (d, J=6.0 Hz, 3H), 0.87 (dd, J=8.4, 2.5 Hz, 2H), 0.73-0.51 (m, 2H).

LCMS-ESI$^+$ (m/z): [M+H]+ calcd for $C_{25}H_{30}N_6O_2$: 447.3; found: 447.2.

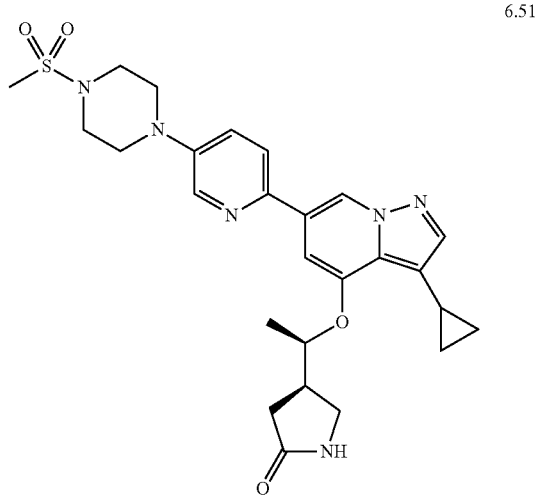 [SMILES: C[C@@H](Oc1cc(-c2ccc(N3CCN(S(C)(=O)=O)CC3)cn2)cn2ncc(C3CC3)c12)[C@H]1CNC(=O)C1]

6.51

Step 4a: To an appropriate sized microwave vial, trifluoroacetic acid salt of (R)-4-((R)-1-((3-cyclopropyl-6-(5-(piperazin-1-yl)pyridin-2-yl)pyrazolo[1,5-a]pyridin-4-yl)oxy)ethyl)pyrrolidin-2-one 6.50 (28 mg, 0.050 mmol), triethylamine (56 µL, 0.40 mmol) and dichloromethane (1.0 mL) were added. Methanesulfonyl chloride (3.9 µL, 0.050 mmol) was added and the reaction was stirred at room temperature for 1.5 h. The reaction was concentrated under reduced pressure and the residue was purified via prep HPLC (2-95% acetonitrile in water, 0.1% trifluoroacetic acid buffer) to afford (R)-4-((R)-1-((3-cyclopropyl-6-(5-(4-(methylsulfonyl)piperazin-1-yl)pyridin-2-yl)pyrazolo[1,5-a]pyridin-4-yl)oxy)ethyl)pyrrolidin-2-one 6.51 as the trifluoroacetic acid salt.

$^1$H NMR (400 MHz, DMSO-d6), TFA salt, δ 8.79 (d, J=1.1 Hz, 1H), 8.42 (d, J=2.9 Hz, 1H), 7.97 (d, J=8.8 Hz, 1H), 7.61 (s, 1H), 7.58 (s, 1H), 7.49 (d, J=8.8 Hz, 1H), 7.21 (s, 1H), 4.82 (p, J=6.2 Hz, 1H), 3.46-3.34 (m, 5H), 3.29-3.27 (m, J=6.2, 3.7 Hz, 4H), 3.18 (dd, J=9.7, 6.8 Hz, 1H), 2.94 (s, 3H), 2.90-2.75 (m, 1H), 2.40-2.13 (m, 3H), 1.36 (d, J=6.0 Hz, 3H), 0.87 (dd, J=8.4, 2.4 Hz, 2H), 0.71-0.54 (m, 2H).

LCMS-ESI$^+$ (m/z): [M+H]+ calcd for $C_{26}H_{32}N_6O_4S$: 525.2; found: 525.1.

6.52

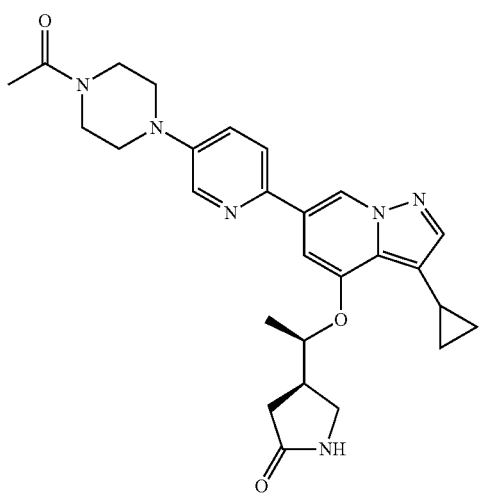

Step 4b: To an appropriate sized microwave vial, trifluoroacetic acid salt of (R)-4-((R)-1-((3-cyclopropyl-6-(5-(piperazin-1-yl)pyridin-2-yl)pyrazolo[1,5-a]pyridin-4-yl)oxy)ethyl)pyrrolidin-2-one 6.50 (6.5 mg, 0.012 mmol), triethylamine (30 μL, 0.22 mmol) and dichloromethane (1.0 mL) were added. Acetic anhydride (7.0 μL, 0.074 mmol) was added and the reaction was stirred at room temperature for 1.5 h. The reaction was concentrated under reduced pressure and the residue was purified via prep HPLC (2-95% acetonitrile in water, 0.1% trifluoroacetic acid buffer) to afford (R)-4-((R)-1-((6-(5-(4-acetylpiperazin-1-yl)pyridin-2-yl)-3-cyclopropylpyrazolo[1,5-a]pyridin-4-yl)oxy)ethyl)pyrrolidin-2-one 6.52 as the trifluoroacetic acid salt.

$^1$H NMR (400 MHz, DMSO-d6), TFA salt, δ 8.78 (d, J=1.1 Hz, 1H), 8.39 (d, J=2.9 Hz, 1H), 7.97 (d, J=8.9 Hz, 1H), 7.61 (s, 1H), 7.58 (s, 1H), 7.50 (d, J=9.0 Hz, 1H), 7.20 (s, 1H), 4.82 (p, J=6.3 Hz, 1H), 3.63-3.60 (m, 4H), 3.40 (t, J=9.2 Hz, 1H), 3.36-3.22 (m, 4H), 3.18 (dd, J=9.7, 6.7 Hz, 1H), 2.92-2.74 (m, 1H), 2.40-2.14 (m, 3H), 2.06 (s, 3H), 1.36 (d, J=6.0 Hz, 3H), 0.87 (dd, J=8.4, 2.4 Hz, 2H), 0.72-0.50 (m, 2H).

LCMS-ESI$^+$ (m/z): [M+H]+ calcd for C$_{27}$H$_{32}$N$_6$O$_3$: 489.3; found: 489.2.

Example 6.53

Preparation of (R)-4-((R)-1-((3-cyclopropyl-6-(3-methoxy-4-(piperazin-1-yl)phenyl)pyrazolo[1,5-a]pyridin-4-yl)oxy)ethyl)pyrrolidin-2-one

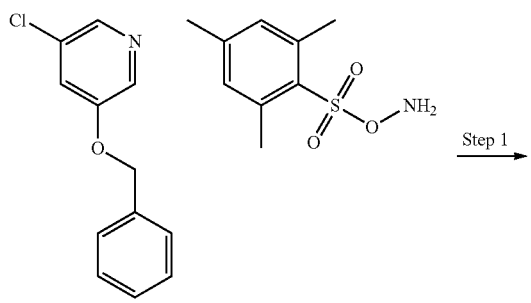

Step 1

-continued

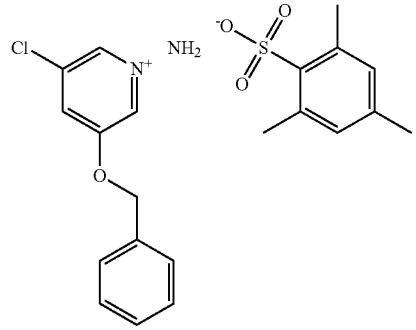

Step 2

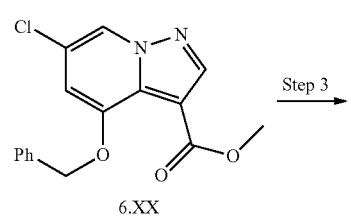

6.XX

Step 3

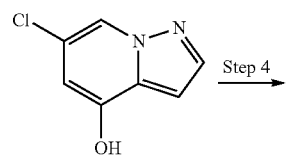

Step 4

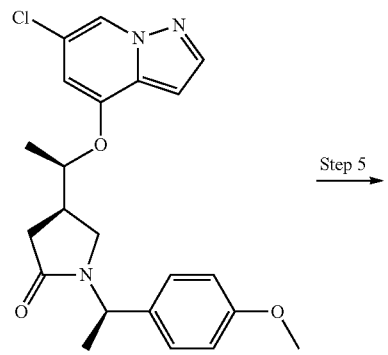

Step 5

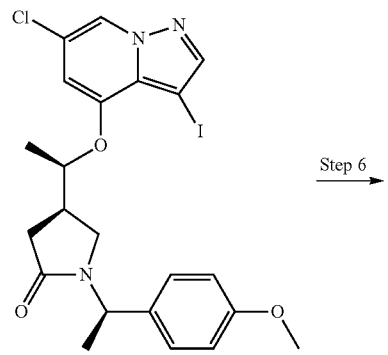

Step 6

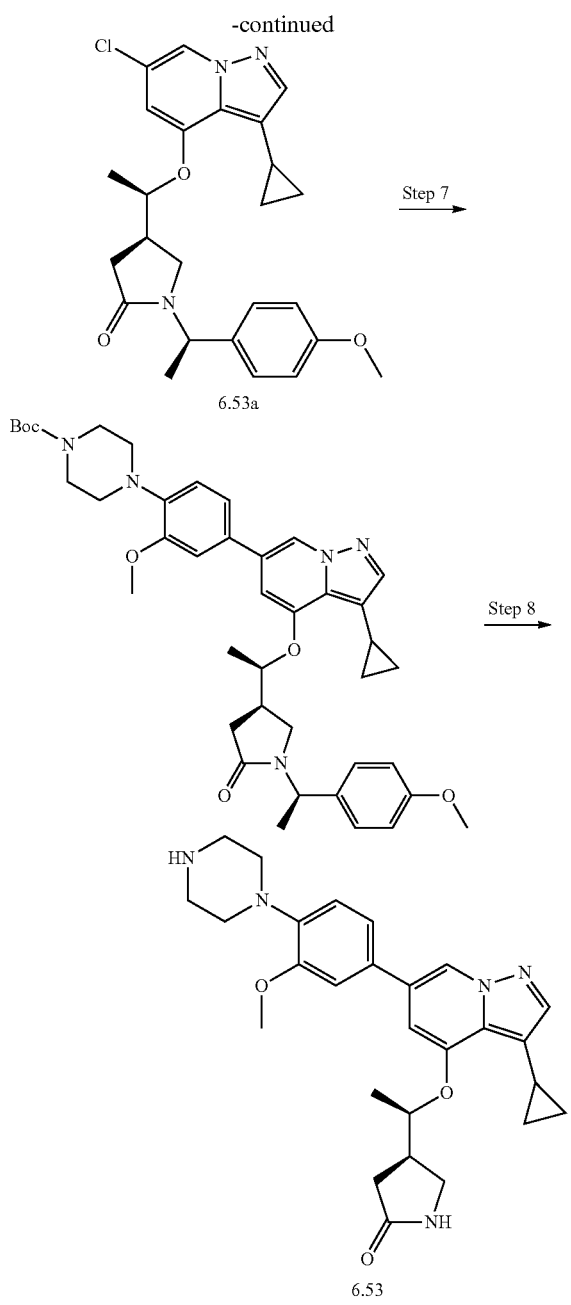

propiolate (2.11 g, 25.1 mmol) was added and the reaction was stirred overnight open to air to afford a mixture of diastereomers. EtOAc and a saturated aqueous solution of NaHCO₃ were added, the layers were separated and the organic layer was washed with brine, dried (MgSO₄), filtered and concentrated. The residue was purified by flash chromatography (5-20% EtOAc in hexanes) to afford methyl 4-(benzyloxy)-6-chloropyrazolo[1,5-a]pyridine-3-carboxylate, which was the first eluting diastereomer.

LCMS-ESI⁺ (m/z): [M]+ calcd for $C_{16}H_{13}ClN_2O_3$: 317.1; found: 317.0.

Step 3: Methyl 4-(benzyloxy)-6-chloropyrazolo[1,5-a]pyridine-3-carboxylate (152 mg, 0.480 mmol) was dissolved in HBr (48%, 2.0 mL) and the reaction was heated to 100° C. for 1.5 h. AcOH/HBr (1.0 mL) was added and the reaction was stirred overnight. The mixture was cooled to 0° C. and neutralized with 1M NaOH. The aqueous layer was extracted with dichloromethane (3×) and the combined organics were washed with brine, dried (MgSO₄), filtered and concentrated to afford 6-chloropyrazolo[1,5-a]pyridin-4-ol.

LCMS-ESI⁺ (m/z): [M]+ calcd for $C_7H_5ClN_2O$: 169.0; found: 169.1.

Step 4: 6-chloropyrazolo[1,5-a]pyridin-4-ol (120 mg, 0.712 mmol), (S)-1-((R)-1-((R)-1-(4-methoxyphenyl)ethyl)-5-oxopyrrolidin-3-yl)ethyl methanesulfonate 1.30 (365 mg, 1.07 mmol) and cesium carbonate (278 mg, 0.854 mmol) were suspended in DMF (2.0 mL). The mixture was heated at 90° C. for 3 h. After cooling to room temperature, the mixture was poured into a saturated aqueous solution of NaHCO₃ and extracted with ethyl acetate. The combined organic layers were washed with brine, dried (MgSO₄), filtered and concentrated under reduced pressure. The residue was purified by flash column chromatography (30-100% EtOAc in hexanes) on silica gel to afford (R)-4-((R)-1-((6-chloropyrazolo[1,5-a]pyridin-4-yl)oxy)ethyl)-1-((R)-1-(4-methoxyphenyl)ethyl)pyrrolidin-2-one.

LCMS-ESI⁺ (m/z): [M+H]+ calcd for $C_{22}H_{24}ClN_3O_3$: 414.2; found: 414.1.

Step 5: (R)-4-((R)-1-((6-chloropyrazolo[1,5-a]pyridin-4-yl)oxy)ethyl)-1-((R)-1-(4-methoxyphenyl)ethyl)pyrrolidin-2-one (216 mg, 0.522 mmol) was dissolved in acetonitrile (10.0 mL) and N-iodosuccinimide (124 mg, 0.548 mmol) was added. The solution was stirred at room temperature for 5 minutes. The reaction was diluted with DCM. The organic layer was washed with 1M NaOH followed by an aqueous solution of sodium thiosulfate. The organic layer was dried (MgSO₄), filtered and concentrated under reduced pressure to afford (R)-4-((R)-1-((6-chloro-3-iodopyrazolo[1,5-a]pyridin-4-yl)oxy)ethyl)-1-((R)-1-(4-methoxyphenyl)ethyl)pyrrolidin-2-one.

LCMS-ESI+ (m/z): [M+H]+ calcd for $C_{22}H_{23}IN_3O_3$: 540.1; found: 540.2.

Step 6: (R)-4-((R)-1-((6-chloro-3-iodopyrazolo[1,5-a]pyridin-4-yl)oxy)ethyl)-1-((R)-1-(4-methoxyphenyl)ethyl)pyrrolidin-2-one (58 mg, 0.11 mmol) and [(2-dicyclohexylphosphino-2',6'-bis(N,N-dimethylamino)-1,1'-biphenyl)-2-(2'-amino-1,1'-biphenyl)]palladium(II) methanesulfonate (8.7 mg, 0.011 mmol) were added. After evacuating and backfilling with nitrogen, THF (1.1 mL) was added followed by cyclopropylzinc bromide (1.3 mL, 0.65 mmol, 0.5M solution in THF). The mixture was stirred at room temperature for 15 min. The reaction was diluted with 1N HCl and extracted with ethyl acetate. The combined organic layers were washed with brine, dried (MgSO₄), filtered and concentrated under reduced pressure. The residue was purified by flash column chromatography on silica gel (30-100% EtOAc in hexanes) to Step 1: A solution of 3-(benzyloxy)-5-chloropyridine (4.00 g, 18.2 mmol) in dichloromethane (30.0 mL) was cooled to 0° C. under argon. O-(mesitylsulfonyl)hydroxylamine (5.23 g, 10% water, 21.9 mmol, prepared using a procedure similar to that reported in Org. Proc. Res. Dev. 2009, 13, 263-267) was added slowly and the mixture stirred at 0° C. for 1 h. 100 mL of ether was added, stirred for 5 minutes and filtered. The solids were washed with cold ether and dried on the frit to afford 1-amino-3-(benzyloxy)-5-chloropyridin-1-ium 2,4,6-trimethylbenzenesulfonate.

LCMS-ESI⁺ (m/z): [M]+ calcd for $C_{12}H_{12}ClN_2O^+$: 235.1; found: 235.0.

Step 2: To a solution of 1-amino-3-(benzyloxy)-5-chloropyridin-1-ium 2,4,6-trimethylbenzenesulfonate (2.18 g, 5.01 mmol) in DMF (50.0 mL) was added K₂CO₃ (1.73 g, 12.5 mmol) and the reaction was stirred for 5 minutes. Methyl afford (R)-4-((R)-1-((6-chloro-3-cyclopropylpyrazolo[1,5-a]pyridin-4-yl)oxy)ethyl)-1-((R)-1-(4-methoxyphenyl)ethyl)pyrrolidin-2-one.

LCMS-ESI⁺ (m/z): [M+H]+ calcd for $C_{25}H_{28}ClN_3O_3$: 454.2; found: 454.2.

Step 7: (R)-4-((R)-1-((6-chloro-3-cyclopropylpyrazolo[1,5-a]pyridin-4-yl)oxy)ethyl)-1-((R)-1-(4-methoxyphenyl)ethyl)pyrrolidin-2-one (32 mg, 0.070 mmol), tert-butyl 4-(2-methoxy-4-(4,4,5,5-tetramethyl-1,3,2-dioxaborolan-2-yl)phenyl)piperazine-1-carboxylate Intermediate 7.08 (44 mg, 0.11 mmol) and $Cs_2CO_3$ (69 mg, 0.21 mmol) were dissolved in 1,2-dimethoxyethane (6.0 mL) and water (3.0 mL). The mixture was degassed with nitrogen for 5 minutes and PEPPSI-IPr catalyst (4.8 mg, 0.0071 mmol) was added. The mixture was heated for 10 minutes at 95° C., cooled and diluted with EtOAc and water. The layers were separated and organics were dried ($MgSO_4$), filtered and concentrated to provide tert-butyl 4-(4-(3-cyclopropyl-4-((R)-1-((R)-1-((R)-1-(4-methoxyphenyl)ethyl)-5-oxopyrrolidin-3-yl)ethoxy)pyrazolo[1,5-a]pyridin-6-yl)-2-methoxyphenyl)piperazine-1-carboxylate which was used directly in the next reaction. LCMS-ESI+ (m/z): [M+H]+ calcd for $C_{41}H_{51}N_5O_6$: 710.4; found: 710.3.

Step 8: Tert-butyl 4-(4-(3-cyclopropyl-4-((R)-1-((R)-1-((R)-1-(4-methoxyphenyl)ethyl)-5-oxopyrrolidin-3-yl)ethoxy)pyrazolo[1,5-a]pyridin-6-yl)-2-methoxyphenyl)piperazine-1-carboxylate (50 mg, 0.070 mmol) was dissolved in TFA (1.5 mL) and heated at 60° C. for 18 h. The reaction was concentrated and the residue was purified via prep HPLC (2-95% acetonitrile in water, 0.1% trifluoroacteic acid buffer) to isolate (R)-4-((R)-1-((3-cyclopropyl-6-(3-methoxy-4-(piperazin-1-yl)phenyl)pyrazolo[1,5-a]pyridin-4-yl)oxy)ethyl)pyrrolidin-2-one 6.53 as the trifluoroacetic acid salt.

¹H NMR (400 MHz, DMSO-d6), TFA salt, δ 8.38 (s, 1H), 7.56 (s, 1H), 7.24-7.27 (m, 3H), 7.05 (d, J=8.0 Hz, 1H), 6.75 (s, 1H), 6.60 (br s, 1H), 4.82 (pent, J=6.0 Hz, 1H), 3.96 (s, 3H), 3.58 (t, J=9.2 Hz, 1H), 3.32-3.37 (m, 9H), 2.95-3.01 (m, 1H), 2.49-2.56 (m, 2H), 2.22-2.29 (m, 1H), 1.42 (d, J=6.0 Hz, 3H) 0.92 (d, J=8.4 Hz, 2H), 0.61-0.68 (m, 2H).

LCMS-ESI⁺ (m/z): [M+H]+ calcd for $C_{27}H_{33}N_5O_3$: 476.3; found: 476.3.

Example 6.54

Preparation of (R)-4-((R)-1-((3-cyclopropyl-6-(3-methoxy-4-(4-(methylsulfonyl)piperazin-1-yl)phenyl)pyrazolo[1,5-a]pyridin-4-yl)oxy)ethyl)pyrrolidin-2-one

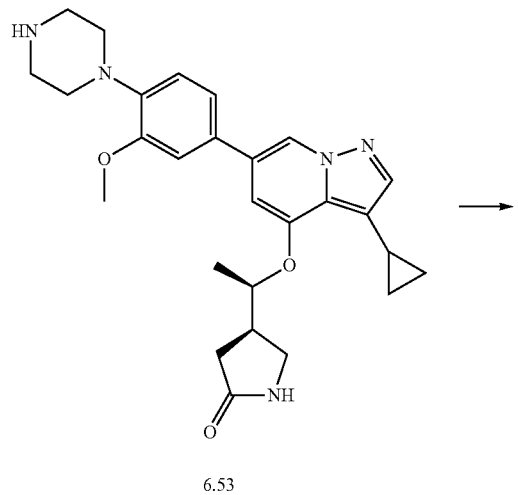

6.53

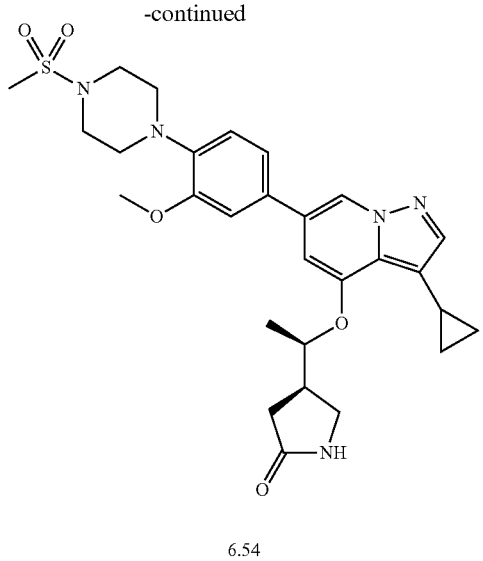

6.54

To a solution of 6.53 (25 mg, 0.053 mmol) in dichloromethane (2.0 mL) was added $Et_3N$ (44 µL, 0.32 mmol) and the mixture was cooled to 0° C. Methanesulfonyl chloride (4.0 µl, 0.053 mmol) was added and the reaction was stirred for 45 minutes at room temperature. EtOAc and a saturated aqueous solution of $NaHCO_3$ were added, the layers were separated and the aqueous layer was extracted with EtOAc (3×). The combined organics were dried ($MgSO_4$), filtered, concentrated and the residue was purified via prep HPLC (2-95% acetonitrile in water, 0.1% trifluoroacteic acid buffer) to isolate (R)-4-((R)-1-((3-cyclopropyl-6-(3-methoxy-4-(4-(methylsulfonyl)piperazin-1-yl)phenyl)pyrazolo[1,5-a]pyridin-4-yl)oxy)ethyl)pyrrolidin-2-one 6.54 as the trifluoroacetic acid salt.

¹H NMR (400 MHz, DMSO-d6), TFA salt, δ 8.33 (s, 1H), 7.51 (s, 1H), 7.25-7.28 (m, 2H), 7.09 (d, J=8.4 Hz, 1H), 6.73 (s, 1H), 6.08 (s, 1H), 4.82 (pent, J=6.0 Hz, 1H), 3.97 (s, 3H), 3.80 (t, J=9.2 Hz, 1H), 3.36-3.39 (m, 2H), 3.29 (dd, J=6.4, 9.6 Hz, 1H), 3.23-3.28 (m, 2H), 2.88-3.02 (m, 5H), 2.86 (s, 3H), 2.38-2.45 (m, 2H), 2.25-2.29 (m, 1H), 1.42 (d, J=6.0 Hz, 3H), 0.91-0.93 (m 2H), 0.63-0.66 (m, 2H). LCMS-ESI⁺ (m/z): [M+H]+ calcd for $C_{28}H_{35}N_5O_5S$: 554.2; found: 554.1.

Examples 6.55, 6.56, and 6.57

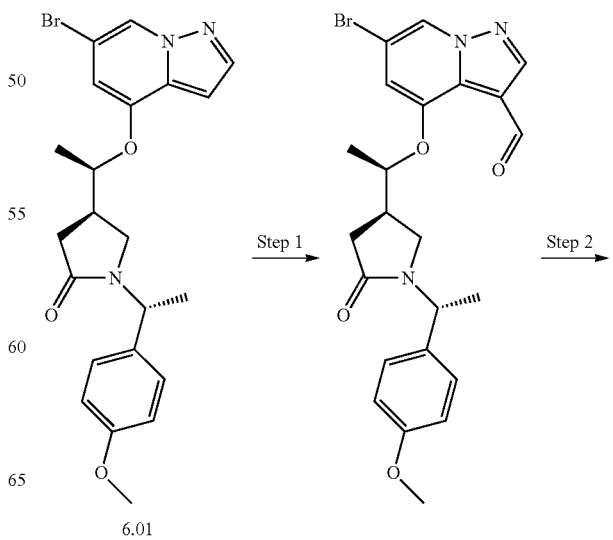

6.01

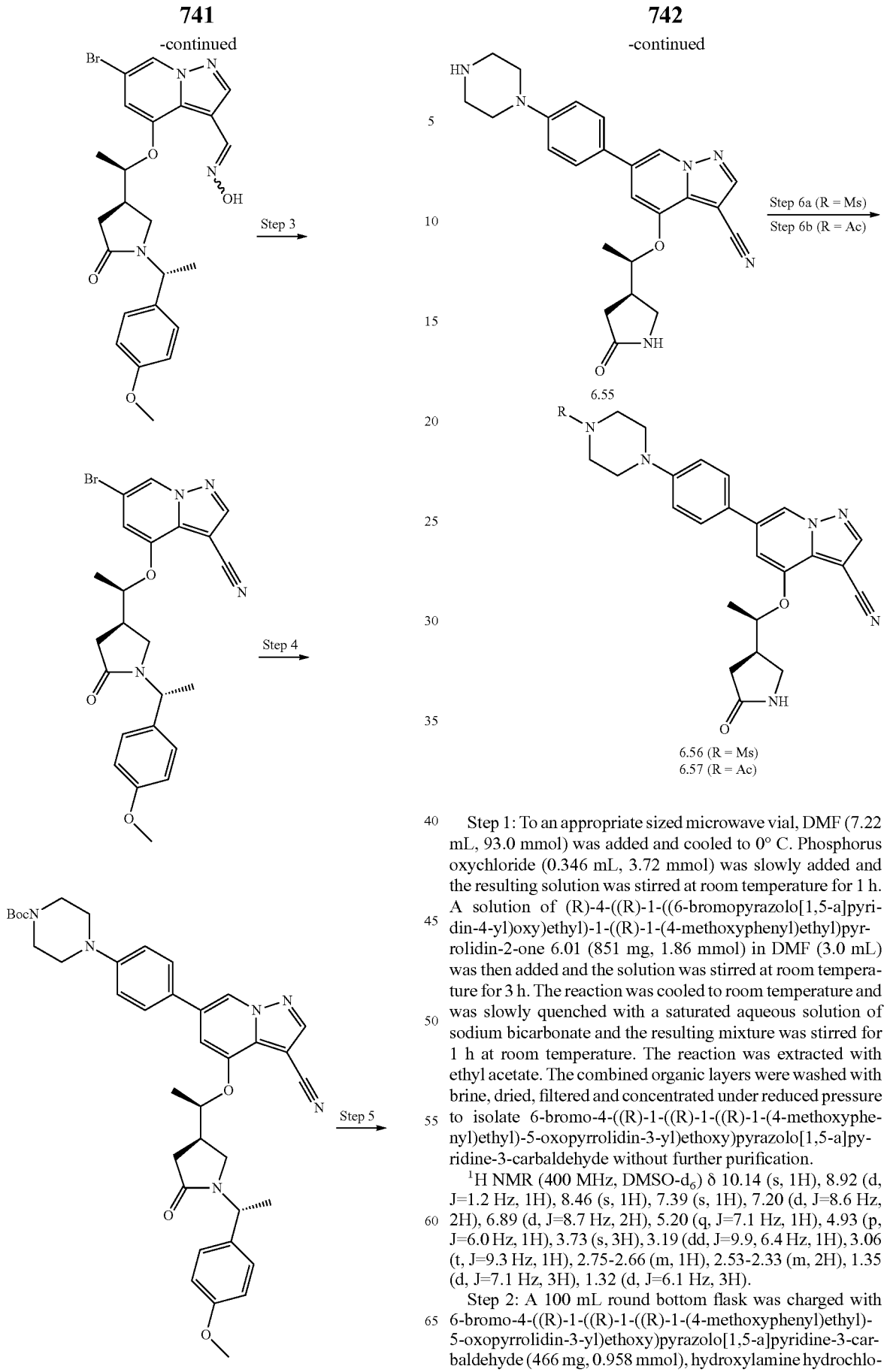

Step 1: To an appropriate sized microwave vial, DMF (7.22 mL, 93.0 mmol) was added and cooled to 0° C. Phosphorus oxychloride (0.346 mL, 3.72 mmol) was slowly added and the resulting solution was stirred at room temperature for 1 h. A solution of (R)-4-((R)-1-((6-bromopyrazolo[1,5-a]pyridin-4-yl)oxy)ethyl)-1-((R)-1-(4-methoxyphenyl)ethyl)pyrrolidin-2-one 6.01 (851 mg, 1.86 mmol) in DMF (3.0 mL) was then added and the solution was stirred at room temperature for 3 h. The reaction was cooled to room temperature and was slowly quenched with a saturated aqueous solution of sodium bicarbonate and the resulting mixture was stirred for 1 h at room temperature. The reaction was extracted with ethyl acetate. The combined organic layers were washed with brine, dried, filtered and concentrated under reduced pressure to isolate 6-bromo-4-((R)-1-((R)-1-((R)-1-(4-methoxyphenyl)ethyl)-5-oxopyrrolidin-3-yl)ethoxy)pyrazolo[1,5-a]pyridine-3-carbaldehyde without further purification.

$^1$H NMR (400 MHz, DMSO-$d_6$) δ 10.14 (s, 1H), 8.92 (d, J=1.2 Hz, 1H), 8.46 (s, 1H), 7.39 (s, 1H), 7.20 (d, J=8.6 Hz, 2H), 6.89 (d, J=8.7 Hz, 2H), 5.20 (q, J=7.1 Hz, 1H), 4.93 (p, J=6.0 Hz, 1H), 3.73 (s, 3H), 3.19 (dd, J=9.9, 6.4 Hz, 1H), 3.06 (t, J=9.3 Hz, 1H), 2.75-2.66 (m, 1H), 2.53-2.33 (m, 2H), 1.35 (d, J=7.1 Hz, 3H), 1.32 (d, J=6.1 Hz, 3H).

Step 2: A 100 mL round bottom flask was charged with 6-bromo-4-((R)-1-((R)-1-((R)-1-(4-methoxyphenyl)ethyl)-5-oxopyrrolidin-3-yl)ethoxy)pyrazolo[1,5-a]pyridine-3-carbaldehyde (466 mg, 0.958 mmol), hydroxylamine hydrochloride (79.9 mg, 1.15 mmol), sodium bicarbonate (96.6 mg, 1.15 mmol) and ethanol (8.0 mL). The mixture was stirred at room temperature for 3 h. The reaction was concentrated under reduced pressure to afford (E)-6-bromo-4-((R)-1-((R)-1-((R)-1-(4-methoxyphenyl)ethyl)-5-oxopyrrolidin-3-yl)ethoxy)pyrazolo[1,5-a]pyridine-3-carbaldehyde oxime without further purification.

LCMS-ESI+ (m/z): [M+1-1]+ calcd for $C_{23}H_{25}{}^{79}BrN_4O_4$: 501.1; found: 501.1.

Step 3: To an appropriate sized microwave vial, crude (E)-6-bromo-4-((R)-1-((R)-1-((R)-1-(4-methoxyphenyl)ethyl)-5-oxopyrrolidin-3-yl)ethoxy)pyrazolo[1,5-a]pyridine-3-carbaldehyde oxime (511 mg, 1.02 mmol) was heated in acetic anhydride (5.0 mL) at 100° C. for 24 h. The reaction was concentrated under reduced pressure, neutralized with a saturated aqueous solution of sodium bicarbonate and extracted with ethyl acetate. The combined organic layers were washed with brine, dried, filtered and concentrated under reduced pressure. The residue was purified by flash column chromatography on silica gel to afford 6-bromo-4-((R)-1-((R)-1-((R)-1-(4-methoxyphenyl)ethyl)-5-oxopyrrolidin-3-yl)ethoxy)pyrazolo[1,5-a]pyridine-3-carbonitrile.

LCMS-ESI+ (m/z): [M+1-1]+ calcd for $C_{23}H_{23}{}^{79}BrN_4O_3$: 483.1; found: 483.0.

Step 4: To an appropriate sized microwave vial, 6-bromo-4-((R)-1-((R)-1-((R)-1-(4-methoxyphenyl)ethyl)-5-oxopyrrolidin-3-yl)ethoxy)pyrazolo[1,5-a]pyridine-3-carbonitrile (91.0 mg, 0.188 mmol), (4-(4-(tert-butoxycarbonyl)piperazin-1-yl)phenyl)boronic acid (86.5 mg, 0.282 mmol), cesium carbonate (184 mg, 0.565 mmol), dioxane (2.0 mL) and water (0.5 mL) were added. The mixture was degassed with nitrogen for 10 minutes. Tetrakis(triphenylphosphine)palladium(0) catalyst (21.8 mg, 0.0188 mmol) was added and the solution was heated at 100° C. for 45 minutes. After cooling to room temperature, the reaction was concentrated under reduced pressure. The residue was purified by flash column chromatography on silica gel (100% EtOAc) to afford tert-butyl 4-(4-(3-cyano-4-((R)-1-((R)-1-((R)-1-(4-methoxyphenyl)ethyl)-5-oxopyrrolidin-3-yl)ethoxy)pyrazolo[1,5-a]pyridin-6-yl)phenyl)piperazine-1-carboxylate.

LCMS-ESI+ (m/z): [M+H]+ calcd for $C_{38}H_{44}N_6O_5$: 665.4; found: 665.3.

Example 6.55

Preparation of 4-((R)-1-((R)-5-oxopyrrolidin-3-yl)ethoxy)-6-(4-(piperazin-1-yl)phenyl)pyrazolo[1,5-a]pyridine-3-carbonitrile

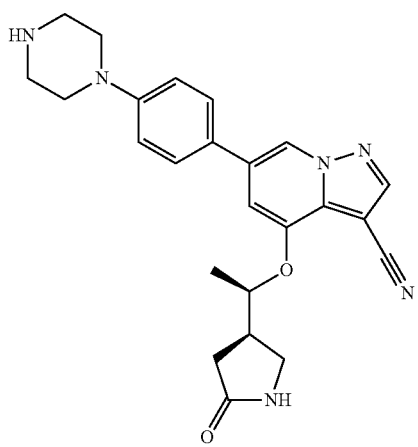

6.55

Step 5: Tert-butyl 4-(4-(3-cyano-4-((R)-1-((R)-1-((R)-1-(4-methoxyphenyl)ethyl)-5-oxopyrrolidin-3-yl)ethoxy)pyrazolo[1,5-a]pyridin-6-yl)phenyl)piperazine-1-carboxylate (120 mg, 0.181 mmol) in TFA (1.5 mL) was heated at 60° C. for 4 h. The reaction was cooled to room temperature and was concentrated under reduced pressure. An aliquot of the residue was purified via prep HPLC (2-95% acetonitrile in water, 0.1% trifluoroacetic acid buffer) to afford 4-((R)-1-((R)-5-oxopyrrolidin-3-yl)ethoxy)-6-(4-(piperazin-1-yl)phenyl)pyrazolo[1,5-a]pyridine-3-carbonitrile 6.55 as the trifluoroacetic acid salt. The remaining residue was used crude as the trifluoroacetic acid salt in the following reactions.

¹H NMR (400 MHz, DMSO-d6), TFA salt, δ 8.81 (d, J=0.9 Hz, 1H), 8.73 (bs, 2H), 8.57 (s, 1H), 7.76 (d, J=8.8 Hz, 2H), 7.60 (s, 1H), 7.36 (d, J=1.2 Hz, 1H), 7.11 (d, J=8.8 Hz, 2H), 4.99 (p, J=6.0 Hz, 1H), 3.50-3.32 (m, 5H), 3.30-3.23 (m, 4H), 3.19 (dd, J=9.7, 7.3 Hz, 1H), 2.90-2.73 (m, 1H), 2.30 (dd, J=9.0, 2.0 Hz, 2H), 1.34 (d, J=6.0 Hz, 3H).

LCMS-ESI+ (m/z): [M+H]+ calcd for $C_{24}H_{26}N_6O_2$: 431.2; found: 431.0.

Example 6.56

Preparation of 6-(4-(4-(methylsulfonyl)piperazin-1-yl)phenyl)-4-((R)-1-((R)-5-oxopyrrolidin-3-yl)ethoxy)pyrazolo[1,5-a]pyridine-3-carbonitrile

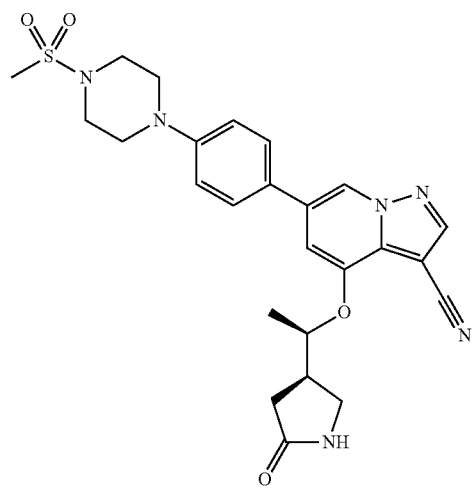

6.56

Step 6a: To an appropriate sized microwave vial, trifluoroacetic acid salt of 4-((R)-1-((R)-5-oxopyrrolidin-3-yl)ethoxy)-6-(4-(piperazin-1-yl)phenyl)pyrazolo[1,5-a]pyridine-3-carbonitrile 6.55 (46 mg, 0.085 mmol), triethylamine (94 μL, 0.68 mmol) and dichloromethane (1.0 mL) were added. Methanesulfonyl chloride (6.5 μL, 0.085 mmol) was added and the reaction was stirred at room temperature for 45 min. The reaction was concentrated under reduced pressure and the residue was purified via prep HPLC (2-95% acetonitrile in water, 0.1% trifluoroacetic acid buffer) to afford 6-(4-(4-(methylsulfonyl)piperazin-1-yl)phenyl)-4-4R)-1-((R)-5-oxopyrrolidin-3-yl)ethoxy)pyrazolo[1,5-a]pyridine-3-carbonitrile 6.56 as the trifluoroacetic acid salt.

¹H NMR (400 MHz, DMSO-d6), TFA salt, δ 8.79 (d, J=0.9 Hz, 1H), 8.56 (s, 1H), 7.73 (d, J=8.8 Hz, 2H), 7.59 (s, 1H), 7.36 (s, 1H), 7.10 (d, J=8.8 Hz, 2H), 4.99 (p, J=5.7 Hz, 1H), 3.40-3.27 (m, 9H), 3.19 (dd, J=9.4, 7.6 Hz, 1H), 2.94 (s, 3H), 2.88-2.78 (m, 1H), 2.30 (d, J=8.9 Hz, 2H), 1.34 (d, J=6.0 Hz, 3H).

LCMS-ESI⁺ (m/z): [M+H]+ calcd for $C_{25}H_{28}N_6O_4S$: 509.2; found: 509.3.

Example 6.57

Preparation of 6-(4-(4-acetylpiperazin-1-yl)phenyl)-4-((R)-1-((R)-5-oxopyrrolidin-3-yl)ethoxy)pyrazolo[1,5-a]pyridine-3-carbonitrile)

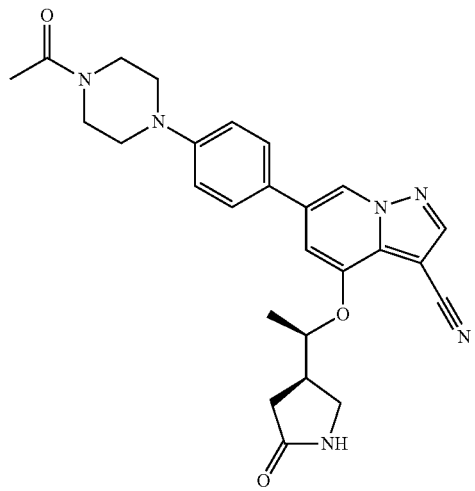

6.57

Step 6b: To an appropriate sized microwave vial, trifluoroacetic acid salt of 4-((R)-14(R)-5-oxopyrrolidin-3-yl)ethoxy)-6-(4-(piperazin-1-yl)phenyl)pyrazolo[1,5-a]pyridine-3-carbonitrile 6.55 (40 mg, 0.074 mmol), triethylamine (82 µL, 0.59 mmol) and dichloromethane (1.0 mL) were added. Acetic anhydride (6.2 µL, 0.066 mmol) was added and the reaction was stirred at room temperature for 1.5 h. The reaction was concentrated under reduced pressure and the residue was purified via prep HPLC (2-95% acetonitrile in water, 0.1% trifluoroacetic acid buffer) to afford 6-(4-(4-acetylpiperazin-1-yl)phenyl)-4-((R)-1-((R)-5-oxopyrrolidin-3-yl)ethoxy)pyrazolo[1,5-a]pyridine-3-carbonitrile 6.57 as the trifluoroacetic acid salt.

¹H NMR (400 MHz, DMSO-d6), TFA salt, δ 8.78 (d, J=1.1 Hz, 1H), 8.55 (s, 1H), 7.72 (d, J=8.7 Hz, 2H), 7.58 (s, 1H), 7.35 (s, 1H), 7.07 (d, J=8.7 Hz, 2H), 4.99 (p, J=6.0 Hz, 1H), 3.66-3.53 (m, 4H), 3.38 (t, J=9.1 Hz, 1H), 3.27-3.17 (m, 5H), 2.89-2.74 (m, 1H), 2.30 (d, J=8.9 Hz, 2H), 2.05 (s, 3H), 1.34 (d, J=6.0 Hz, 3H).

LCMS-ESI⁺ (m/z): [M+H]+ calcd for $C_{26}H_{28}N_6O_3$: 473.2; found: 473.3.

Example 6.58

Preparation of 5-chloro-2-(prop-1-yn-1-yl)-3-((2-(trimethylsilyl)ethoxy)methoxy)pyridine

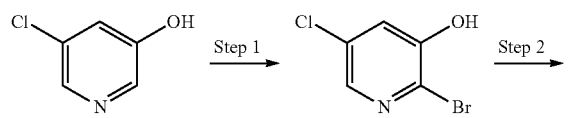

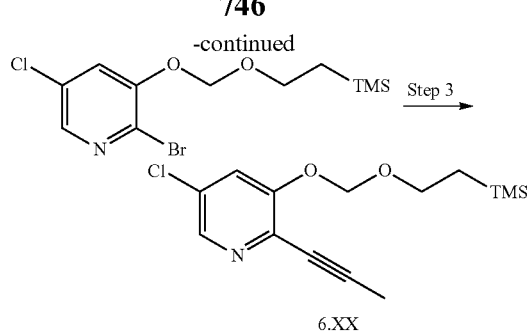

6.XX

Step 1: A solution of Bromine (8.82 g) in 10% of aqueous sodium hydroxide (53 mL) was added drop-wise to a solution of 5-chloropyridin-3-ol (7.2 g) with stirring in 10% aqueous sodium hydroxide (50 mL). After addition was completed, the mixture was cooled with ice-bath and neutralized with concentrated HCl. The product was precipitated, collected by filtration and washed with water to provide 3.5 g of 2-bromo-5-chloropyridin-3-ol was obtained. LCMS [M+H]⁺: 209.13.

Step 2: Into a solution of 2-bromo-5-chloropyridin-3-ol (2.6 g) in DMF (50 mL) was added a 1 M solution of NaHMDS in THF (15 mL), after 30 min., (2-(chloromethoxy)ethyl)trimethylsilane (2.496 g) was added. After stifling for 2 hours at rt., The reaction mixture was extracted with ethyl acetate and washed with brine. After drying and removing the solvent, the residue was purified by silica gel chromatography to provide 3.9 g of 2-bromo-5-chloro-3-((2-(trimethylsilyl)ethoxy)methoxy)pyridine. LCMS [M+H]⁺: 339.8. ¹HNMR (400 MHz, CDCl₃) ppm: δ 8.01 (d, J=2.2 Hz, 1H), 7.45 (d, J=2.2 Hz, 1H), 5.31 (s, 2H), 3.79 (t, J=8.4 Hz, 2H), 0.92 (t, J=8.4 Hz, 2H), 0.08 (s, 9H).

Step 3: Into a solution of (2-(chloromethoxy)ethyl)trimethylsilane (3.73 g) in THF (100 mL) was added TEA (2.79 g), CuI (0.21 g) and trans-dichlorobis(triphenylphosphine)palladium(ii) (0.775 g). Then prop-1-yne was added to replace air. After overnight uner prop-1-yne atmosphere, the reaction mixture was extracted with ethyl acetate and washed with brine, the organic layer was dried with MgSO₄ and solvent was removed in vacuo. The residue was purified by silica gel chromatography to provide 2.85 g of 5-chloro-2-(prop-1-yn-1-yl)-3-((2-(trimethylsilyl)ethoxy)methoxy)pyridine 6.58. ¹HNMR (400 MHz, CDCl₃) ppm: δ 8.15 (d, J=2.2 Hz, 1H), 7.48 (d, J=2.2 Hz, 1H), 5.28 (s, 2H), 3.787 (t, J=8.4 Hz, 2H), 2.108 (s, 3H), 0.947 (t, J=8.4 Hz, 2H), 0.08 (s, 9H).

Example 6.59

Preparation of 6-chloro-2-methylpyrazolo[1,5-a]pyridin-4-ol

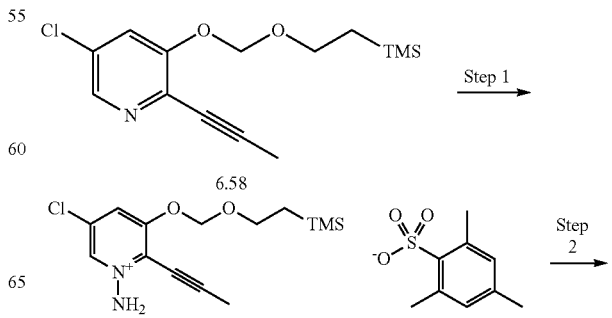

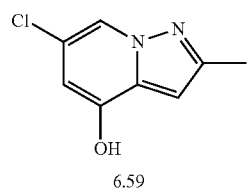
6.59

Step 1: A solution of 5-chloro-2-(prop-1-yn-1-yl)-3-((2-(trimethylsilyl)ethoxy)methoxy)pyridine 6.58 (969 mg, 3 mmol) in MeCN (10 mL) was cooled to 0° C. under argon. O-(mesitylsulfonyl)hydroxylamine (700 mg, 3 mmol, prepared using a procedure similar to that reported in *Org. Proc. Res. Dev.* 2009, 13, 263-267) was added, and mixture was warmed to rt. After 2 hours, reaction mixture was concentrated under reduced pressure to yield 1-amino-5-chloro-2-(prop-1-yn-1-yl)-3-((2-(trimethylsilyl)ethoxy)methoxy)pyridin-1-ium 2,4,6-trimethylbenzenesulfonate which was used in the next step without further purification. LCMS [M+H]$^+$: 314.91.

Step 2: AcOH (5 mL) was added to 1-amino-5-chloro-2-(prop-1-yn-1-yl)-3-((2-(trimethylsilyl)ethoxy)methoxy)pyridin-1-ium 2,4,6-trimethylbenzenesulfonate. After stirring overnight, the AcOH was removed under vaco., the residue was treated with 2 M solution of LiOH (5 mL) at rt., and extracted with ethyl acetate. Combined organics were washed with brine, dried, filtered, and concentrated under reduced pressure. The resulting residue was purified by silica gel column chromatography to provide of 6-chloro-2-methylpyrazolo[1,5-a]pyridin-4-ol 6.59. LCMS [M+H]$^+$: 183.09. $^1$H NMR (400 MHz, CDCl$_3$) ppm: δ 8.028 (s, 1H), 6.419 (d, J=6.8 Hz, 1H), 6.398 (d, J=6.8 Hz, 1H), 2.395 (s, 3H).

Example 6.60

Preparation of (R)-4-((R)-1-((6-(1-(tert-butyl)-1H-pyrazol-4-yl)-2-methylpyrazolo[1,5-a]pyridin-4-yl)oxy)ethyl)pyrrolidin-2-one

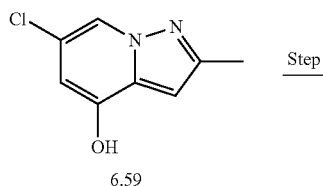
6.59

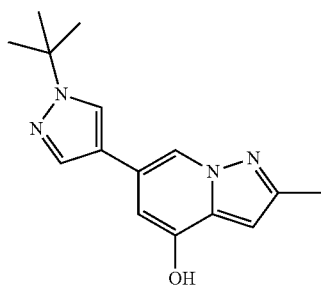

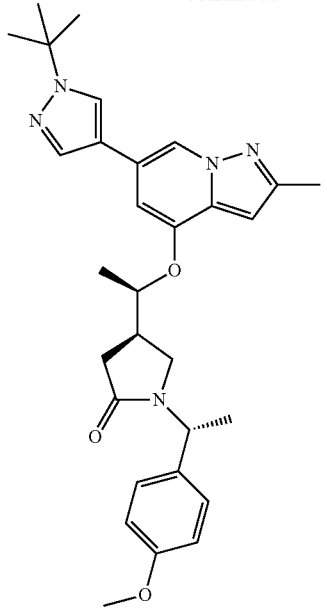

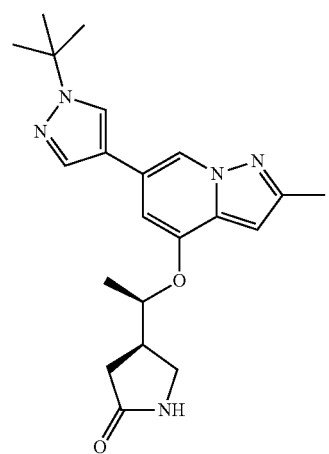
6.60

Step 1: To a mixture 6-chloro-2-methylpyrazolo[1,5-a]pyridin-4-ol 6.59 (17 mg), 1-(tert-butyl)-4-(4,4,5,5-tetramethyl-1,3,2-dioxaborolan-2-yl)-1H-pyrazole (19 mg), Cs$_2$CO$_3$ (76 mg) and PEPPSI-IPr (6 mg) was added DME and water (2:1, 3 mL) and the reaction mixture was heated to 80° C. for 2 h. The mixture was then extracted with ethyl acetate. Combined organics were washed with brine, dried, filtered, and concentrated under reduced pressure. The resulting residue was purified by silica gel column chromatography to provide 10 mg of 6-(1-(tert-butyl)-1H-pyrazol-4-yl)-2-methylpyrazolo[1,5-a]pyridin-4-ol. LCMS [M+H]$^+$: 271.12.

Step 2: To a solution of 6-(1-(tert-butyl)-1H-pyrazol-4-yl)-2-methylpyrazolo[1,5-a]pyridin-4-ol (5 mg) in DMF (3 mL) was added (S)-1-((R)-5-oxo-1-((R)-1-phenylethyl)pyrrolidin-3-yl)ethyl methanesulfonate 1.30 (9 mg) and 1 M solution of NaHMDS in THF (0.15 mL) at rt. After 2 h. the reaction mixture was extracted with ethyl acetate. Combined organics were washed with brine, dried, filtered, and concentrated under reduced pressure. The resulting residue was purified by silica gel column chromatography to provide to provide 3 mg of (R)-4-((R)-1-((6-(1-(tert-butyl)-1H-pyrazol-4-yl)-2-methylpyrazolo[1,5-a]pyridin-4-yl)oxy)ethyl)-1-((R)-1-(4-methoxyphenyl)ethyl)pyrrolidin-2-one. LCMS [M+H]$^+$: 517.18.

Step 3: A solution of (R)-4-((R)-1-((6-(1-(tert-butyl)-1H-pyrazol-4-yl)-2-methylpyrazolo[1,5-a]pyridin-4-yl)oxy)ethyl)-1-((R)-1-(4-methoxyphenyl)ethyl)pyrrolidin-2-one (5 mg) in TFA (2 mL) was heated at 60° C. for overnight, cooled to rt. and then removed TFA under vaco., the residue was diluted with ethyl acetate, and washed with brine, dried, filtered, and concentrated under reduced pressure. The resulting residue was purified by silica gel column chromatography to provide 3 mg of (R)-4-((R)-1-((6-(1-(tert-butyl)-1H-pyrazol-4-yl)-2-methylpyrazolo[1,5-a]pyridin-4-yl)oxy)ethyl)pyrrolidin-2-one 6.60.

$^1$H NMR (400 MHz, CDCl$_3$) ppm: δ 8.21 (s, 1H), 7.721 (s, 1H), 7.691 (s, 1H), 6.474 (s, 1H), 6.349 (s, 1H), 5.587 (s, 1H), 4.596 (m, 1H), 3.558 (m, 1H), 3.344 (m, 1H), 2.9 (m, 1H), 2.525 (m, 2H), 2.472 (s, 3H), 1.643 (s, 9H), 1.42 (d, J=6 Hz, 3H).

LCMS-ESI$^+$ (m/z): [M+H]+ calcd for C$_{21}$H$_{28}$N$_5$O$_2$: 382.22; found: 382.17.

Example 6.61

Preparation of 6-(3-cyclopropyl-4-((R)-1-((R)-5-oxopyrrolidin-3-yl)ethoxy)pyrazolo[1,5-a]pyridin-6-yl)-3,3-dimethylindolin-2-one

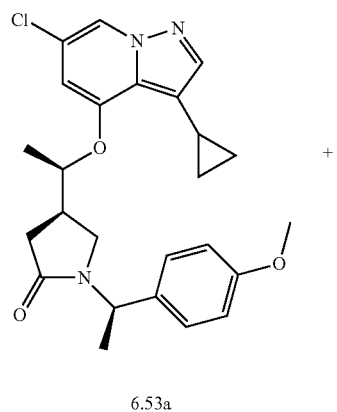

6.53a

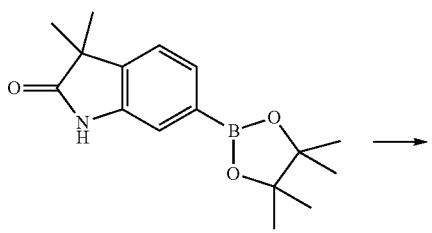

+

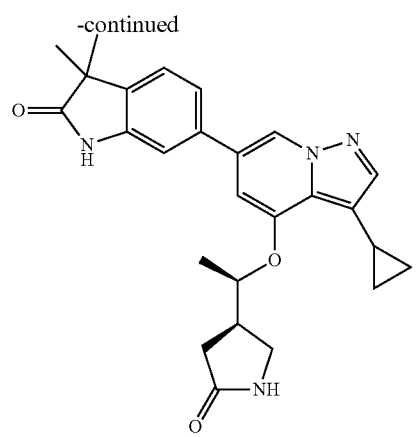

6.61

Following Steps 7 and 8 from the procedure used to prepare Example 6.53, starting from (R)-4-((R)-1-((6-chloro-3-cyclopropylpyrazolo[1,5-a]pyridin-4-yl)oxy)ethyl)pyrrolidin-2-one 6.53a (55 mg) and 3,3-dimethyl-6-(4,4,5,5-tetramethyl-1,3,2-dioxaborolan-2-yl)indolin-2-one, 13 mg of 6-(3-cyclopropyl-4-4R)-1-((R)-5-oxopyrrolidin-3-yl)ethoxy)pyrazolo[1,5-a]pyridin-6-yl)-3,3-dimethylindolin-2-one was synthesized.

$^1$H NMR (400 MHz, Chloroform-d) δ 9.179 (s, 1H), 8.220 (s, 1H), 7.514 (s, 1H), 7.25 (m, 2H), 7.109 (s, 1H), 6.55 (br., 1H), 6.485 (s, 1H), 4.672 (m, 1H), 3.591 (m, 1H), 3.433 (m, 1H), 2.949 (m, 1H), 2.57 (m, 2H), 2.181 (m, 1H), 1.47 (d, J=6 Hz, 3H), 1.433 (s, 6H), 0.98-0.82 (m, 3H), 0.64 (m, 1H).

LCMS-ESI$^+$ (m/z): [M+H]+ calcd for C$_{26}$H$_{29}$N$_4$O$_3$: 445.22; found: 445.17.

Example 7.01

Preparation of 3-iodo-1-isopropyl-1H-pyrazole

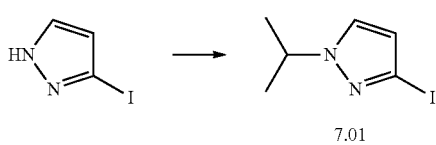

7.01

3-iodo-1H-pyrazole (250 mg, 1.29 mmol) was added as a solution in DMF (0.8 mL) to a 1.0 M THF solution of NaHMDS (1.5 mL, 1.5 mmol) that had been pre-cooled in an ice water bath. Additional portions of DMF (2×0.35 mL) were used to ensure complete transfer. 2-iodopropane was added in one portion and the reaction mixture was allowed to warm to r.t. After 3.5 h, the reaction mixture was diluted with saturated aqueous NH$_4$Cl (5 mL), water (20 mL), and EtOAc (20 mL). The phases were separated, and the aqueous phase was extracted with EtOAc (20 mL). The combined organic phase was dried over Na$_2$SO$_4$, filtered, and concentrated to afford a crude residue that was purified by silica gel chromatography to provide 3-iodo-1-isopropyl-1H-pyrazole (7.01). LCMS-ESI$^+$ (m/z): [M+H]$^+$ calcd for C$_6$H$_{10}$IN$_2$: 236.99; found: 236.94.

Example 7.02

Preparation of
1-(2,2-difluoroethyl)-3-iodo-1H-pyrazole

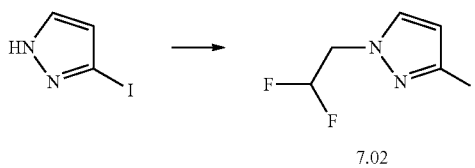

7.02

A stirred solution of NaHMDS in THF (1.0 M, 3.1 mL, 3.1 mmol) was cooled in an ice water bath under Ar. 3-iodo-1H-pyrazole (500 mg, 2.6 mmol) was added as a solution in DMF (1 mL), washing with additional DMF (2×1 mL). 1,1-difluoro-2-iodoethane (0.47 mL, 5.2 mmol) was added in one portion and the mixture was removed from the cold bath. After 1.25 h, the reaction mixture was diluted with water and EtOAc. The phases were separated, and the organic phase was washed with water and brine, dried over $Na_2SO_4$, filtered and concentrated. The residue was purified by silica gel (0-15% EtOAc in hexanes) to provide 1-(2,2-difluoroethyl)-3-iodo-1H-pyrazole 7.02 (339 mg). Regiochemistry was assigned by NOE studies. LCMS-ESI$^+$ (m/z): [M+H]$^+$ calcd for $C_5H_6F_2IN_2$: 259.0; found: 258.2. $^1$H NMR (400 MHz, Chloroform-d) δ 7.29 (d, J=2.4 Hz, 1H), 6.46 (d, J=2.4 Hz, 1H), 6.06 (tt, J=55.4, 4.3 Hz, 1H), 4.45 (td, J=13.4, 4.3 Hz, 2H).

Example 7.03

Preparation of tert-butyl 2-(3-iodo-1H-pyrazol-1-yl)-2-methylpropanoate

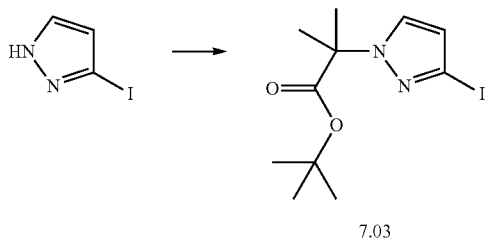 [SMILES: Ic1cc[nH]n1 ; CC(C)(C)OC(=O)C(C)(C)n1ccc(I)n1]

7.03

A stirred solution of NaHMDS in THF (1.0 M, 3.1 mL, 3.1 mmol) was cooled in an ice water bath under Ar. 3-iodo-1H-pyrazole (500 mg, 2.6 mmol) was added as a solution in DMF (1 mL), washing with additional DMF (2×1 mL). tert-butyl 2-bromo-2-methylpropanoate (0.58 mL, 3.1 mmol) was added and the reaction mixture was removed from the cold bath and heated to 40° C. After 16 h, the reaction mixture was cooled and diluted with water and EtOAc. The phases were separated, and the organic phase was washed with water and brine, dried over $Na_2SO_4$, filtered and concentrated. The crude residue was purified by silica gel chromatography (0-20% EtOAc in hexanes) to afford tert-butyl 2-(3-iodo-1H-pyrazol-1-yl)-2-methylpropanoate 7.03 (649 mg). $^1$H NMR (400 MHz, Chloroform-d) δ 7.36 (d, J=2.4 Hz, 1H), 6.42 (d, J=2.4 Hz, 1H), 1.79 (s, 6H), 1.38 (s, 9H).

Example 7.04

Preparation of
2-(3-iodo-1H-pyrazol-1-yl)-2-methylpropanoic acid

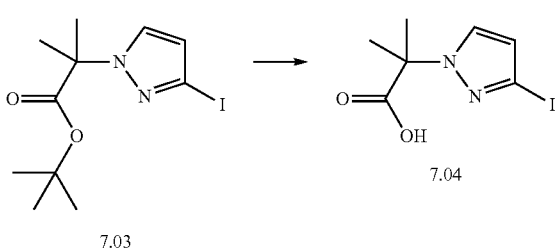 [SMILES: CC(C)(C)OC(=O)C(C)(C)n1ccc(I)n1 ; CC(C)(C(=O)O)n1ccc(I)n1]

tert-butyl 2-(3-iodo-1H-pyrazol-1-yl)-2-methylpropanoate 7.03 (530 mg, 1.58 mmol) was dissolved in DCM (7 mL) and TFA (7 mL). The reaction was stirred at r.t. for 18 h and was concentrated in vacuo to afford crude 2-(3-iodo-1H-pyrazol-1-yl)-2-methylpropanoic acid 7.04 that was used without further purification. LCMS-ESI$^+$ (m/z): [M+H]$^+$ calcd for $C_7H_{10}IN_2O_2$: 280.98; found: 280.91.

Example 7.05

Preparation of
2-(3-iodo-1H-pyrazol-1-yl)-2-methylpropanamide

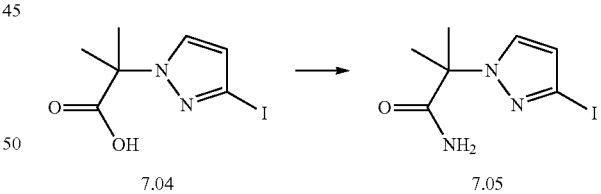

2-(3-iodo-1H-pyrazol-1-yl)-2-methylpropanoic acid 7.04 (200 mg, 0.71 mmol) was suspended in DCM (7 mL) under Ar. Oxalyl chloride (0.12 mL, 1.4 mmol) was added followed by DMF (1 drop). The reaction mixture was stirred for 2 h and was concentrated in vacuo. The residue was dissolved in THF (2 mL) and was added to saturated aqueous $NH_4OH$ (2 mL). Additional THF (2×1.5 mL) was used to ensure complete transfer. After 20 min, the reaction mixture was diluted with EtOAc and water. The phases were separated, and the aqueous phase was extracted with EtOAc. The combined organic phase was washed with saturated aqueous $NH_4Cl$, dried over $Na_2SO_4$, filtered, and concentrated to afford 2-(3-iodo-1H-pyrazol-1-yl)-2-methylpropanamide 7.05 (180 mg) that was used without further purification. LCMS-ESI⁺ (m/z): [M+H]⁺ calcd for $C_7H_{11}IN_3O$: 280.0; found: 279.9.

Example 7.06

Preparation of 2-(3-iodo-1H-pyrazol-1-yl)-2-methyl-1-morpholinopropan-1-one

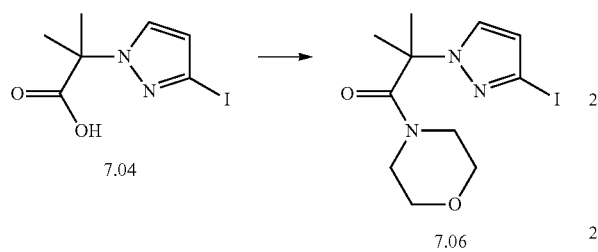

7.06

Intermediate 7.06 was synthesized in a manner analogous to intermediate 7.05 substituting morpholine (10 eq. vs. 7.04) for NH₄OH. The resulting crude 2-(3-iodo-1H-pyrazol-1-yl)-2-methyl-1-morpholinopropan-1-one was used without further purification. LCMS-ESI⁺ (m/z): [M+H]⁺ calcd for $C_{11}H_{16}IN_3O_2$: 349.0; found: 350.1.

Example 7.07

Preparation of 2-(3-iodo-1H-pyrazol-1-yl)-2-methylpropanenitrile

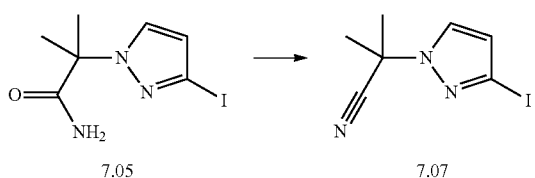

7.05                    7.07

2-(3-iodo-1H-pyrazol-1-yl)-2-methylpropanamide 7.05 (100 mg, 0.36 mmol) was dissolved in DCM (3 mL) and pyridine (1 mL). Trifluoroacetic anhydride (70 µL, 0.50 mmol) was added and the resulting mixture was stirred at r.t. for 24 h. The reaction mixture was diluted with EtOAc and water, and the phases were separated. The organic phase was washed twice with aqueous HCl (second wash remained acidic) followed by water and was dried over Na₂SO₄, filtered and concentrated to afford 2-(3-iodo-1H-pyrazol-1-yl)-2-methylpropanenitrile 7.07 that was used without further purification. LCMS-ESI⁺ (m/z): [M+H]⁺ calcd for $C_7H_9IN_3$: 262.0; found: 261.9.

Example 7.08

Preparation of tert-butyl 4-(2-methoxy-4-(4,4,5,5-tetramethyl-1,3,2-dioxaborolan-2-yl)phenyl)piperazine-1-carboxylate

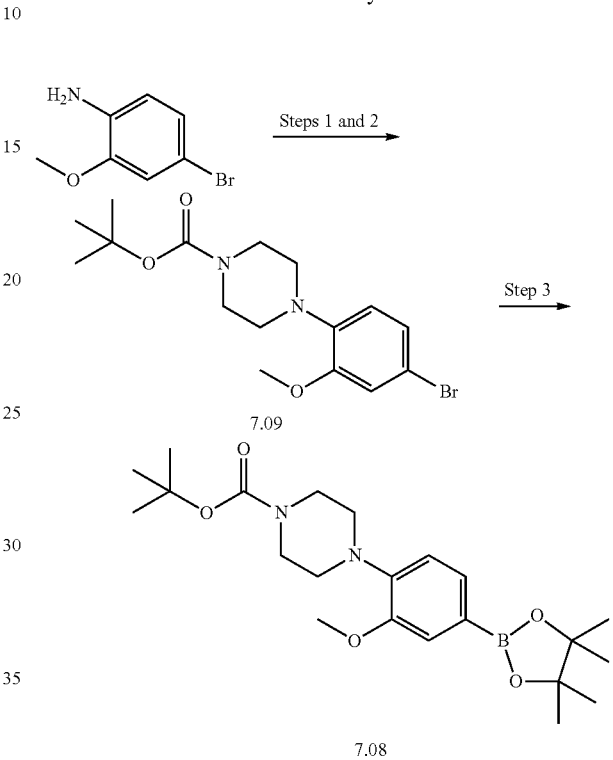

Step 1: To a solution of 4-bromo-2-methoxyaniline (2.0 g, 9.9 mmol) in MeCN (50 mL) was added para-toluenesulfonic acid (5.1 g, 27 mmol). The resulting mixture was cooled in an ice water bath. A solution of NaNO₂ (1.36 g, 19.7 mmol) and KI (4.11 g, 24.8 mmol) in water (50 mL) was then added, and the resulting mixture was stirred for 5 min. The mixture was then removed from the ice water bath. Once consumption of starting material was observed, the reaction mixture was partitioned between water and EtOAc. The organic phase was concentrated and the resulting crude residue was purified by silica gel chromatography to afford 4-bromo-1-iodo-2-methoxybenzene.

Step 2: 4-bromo-1-iodo-2-methoxybenzene (647 mg, 2.07 mmol), tert-butyl piperazine-1-carboxylate (350 mg, 1.88 mmol), sodium tert-butoxide (541 mg, 5.6 mmol), Pd₂(dba)₃ (52 mg, 0.056 mmol) and XantPhos (98 mg, 0.17 mmol) were taken up in toluene (18 mL) under Ar. The reaction mixture was stirred for 18 h and was then heated to 45° C. After an additional 2.5 h, the temperature was increased to 65° C. After an additional 3 h, the reaction mixture was cooled and partitioned between water and EtOAc. The phases were separated, and the organic phase was dried over Na₂SO₄, filtered, and concentrated. The crude residue was purified by silica gel chromatography (0-25% EtOAc in hexanes) to afford tert-butyl 4-(4-bromo-2-methoxyphenyl)piperazine-1-carboxylate 7.09. LCMS-ESI⁺ (m/z): [M-41]⁺ calcd for $C_{16}H_{24}BrN_2O_3$: 371.1; found: 370.8.

Step 3: 4-(4-bromo-2-methoxyphenyl)piperazine-1-carboxylate (630 mg, 1.70 mmol), KOAc (600 mg, 6.1 mmol), 4,4,4',4',5,5,5',5'-octamethyl-2,2'-bi(1,3,2-dioxaborolane) (750 mg, 3.0 mmol) and PdCl$_2$(dppf)CH$_2$Cl$_2$ (70 mg, 0.086 mmol) were taken up in 1,4-dioxane (17 mL) under Ar. The stirred reaction mixture was heated to 110° C. After 1.5 h, the reaction mixture was cooled and partitioned between EtOAc and water. The phases were separated, and the organic phase was dried over Na$_2$SO$_4$, filtered, and concentrated. The crude residue was purified by silica gel chromatography (5-40% EtOAc in hexanes) to provide tert-butyl 4-(2-methoxy-4-(4,4,5,5-tetramethyl-1,3,2-dioxaborolan-2-yl)phenyl)piperazine-1-carboxylate 7.08. LCMS-ESI$^+$ (m/z): [M+H]$^+$ calcd for C$_{22}$H$_{36}$BN$_2$O$_5$: 419.3; found: 419.3.

Example 7.10

Preparation of tert-butyl 4-(6-chloro-2-methoxypyridin-3-yl)piperazine-1-carboxylate

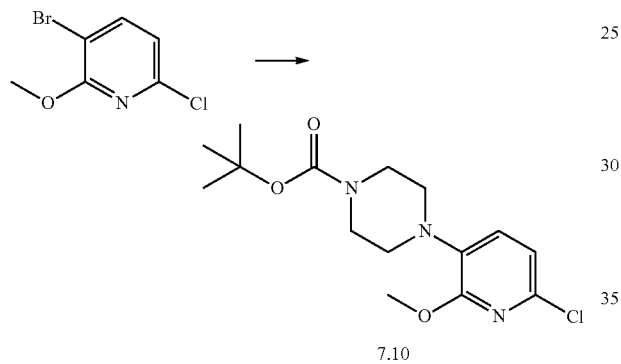

7.10

3-bromo-6-chloro-2-methoxypyridine (1.15 g, 5.17 mmol), tert-butyl piperazine-1-carboxylate (900 mg, 4.8 mmol), sodium tert-butoxide (1.39 g, 14.5 mmol), Pd$_2$(dba)$_3$ (130 mg, 0.15 mmol) and XantPhos (250 mg, 0.44 mmol) were taken up in toluene (36 mL) under Ar. The reaction mixture was heated to 70° C. and was stirred for 18 h. The mixture was cooled and partitioned between water and EtOAc. The phases were separated, and the organic phase was dried over Na$_2$SO$_4$, filtered, and concentrated. The crude residue was purified by silica gel chromatography (0-3% Et$_2$O in DCM) to afford tert-butyl 4-(6-chloro-2-methoxypyridin-3-yl)piperazine-1-carboxylate 7.10. LCMS-ESI$^+$ (m/z): [M+H]$^+$ calcd for C$_{15}$H$_{23}$ClN$_3$O$_3$: 328.1; found: 328.3.

Example 7.11

Preparation of tert-butyl 4-(5-iodopyrazin-2-yl)piperazine-1-carboxylate

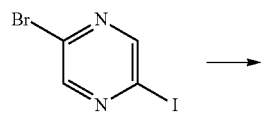

-continued

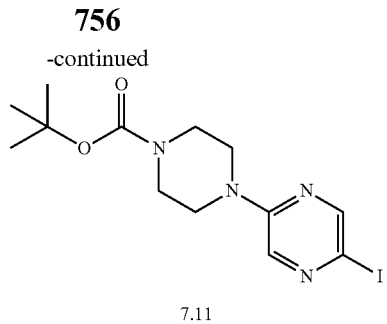

7.11

2-bromo-5-iodopyrazine (503 mg, 1.77 mmol) and tert-butyl piperazine-1-carboxylate (355 mg, 1.91 mmol) were taken up in tBuOH (8 mL). iPr$_2$NEt (400 µL, 2.3 mmol) was added and the stirred reaction mixture was heated to 100° C. After 66 h, the reaction mixture was cooled and was partitioned between EtOAc, water and brine. The phases were separated, and the organic phase was dried over Na$_2$SO$_4$, filtered, and concentrated. The crude residue was purified by silica gel chromatography (10-30% EtOAc in hexanes) to afford tert-butyl 4-(5-iodopyrazin-2-yl)piperazine-1-carboxylate 7.11.

LCMS-ESI$^+$ (m/z): [M+H]$^+$ calcd for C$_{13}$H$_{20}$IN$_4$O$_2$: 391.1; found: 390.8.

Example 7.12

Preparation of tert-butyl 4-(6-iodopyridazin-3-yl)piperazine-1-carboxylate

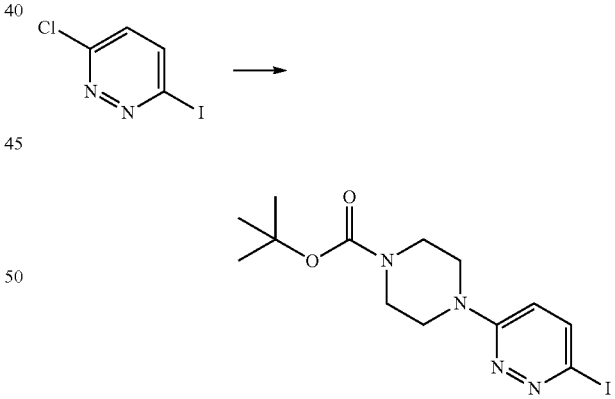

7.12

3-chloro-6-iodopyridazine (510 mg, 2.1 mmol) and tert-butyl piperazine-1-carboxylate (415 mg, 2.23 mmol) were taken up in tBuOH (8 mL). iPr$_2$NEt (480 µL, 2.8 mmol) was added and the stirred reaction mixture was heated to 100° C. After 48 h, the reaction mixture was cooled and was partitioned between EtOAc and water. The phases were separated, and the organic phase was dried over Na$_2$SO$_4$, filtered, and concentrated. The crude residue was purified by silica gel chromatography (0-25% Et$_2$O in DCM) to afford tert-butyl 4-(6-iodopyridazin-3-yl)piperazine-1-carboxylate 7.12. LCMS-ESI⁺ (m/z): [M+H—CO₂tBu]⁺ calcd for $C_8H_{12}IN_4$: 291.0; found: 291.0.

7.13

Preparation of tert-butyl 4-(6-bromopyridin-3-yl)piperazine-1-carboxylate

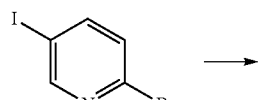

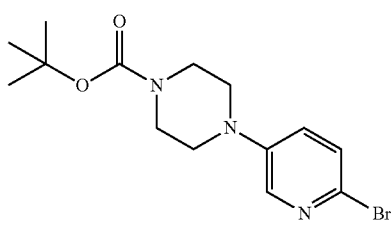

7.13

Into the mixture solution of 2-bromo-5-iodopyridine (9.15 g, 32.2 mmol), tert-butyl piperazine-1-carboxylate (5 g, 27 mmol) in Toluene (90 mL) was added Tris(dibenzylideneacetone)dipalladium (0) (0.983 g, 1.1 mmol), 4,5-Bis(diphenylphosphino)-9,9-dimethylxanthene (0.17 g, 3.2 mmol) and NaOtBu (7.8 g, 80.5 mmol). Then the reaction mixture was flushed with Argon and stirred for 2 h. The reaction mixture was extracted with ethyl acetate and washed with brine. After drying with MgSO₄, the organic solvent was removed under vaco., the residue was purified by crystallization from mixture of DCM and Hexane to get 8.4 g of tert-butyl 4-(6-bromopyridin-3-yl)piperazine-1-carboxylate 7.13. ¹H NMR (400 MHz, CDCl₃) ppm: δ 8.01 (d, J=3.2 H2, 1H), 7.32 (d, J=8.4 Hz, 1H), 7.07 (d, d, J=3.2, 8.4 Hz, 1H), 3.59 (t, J=5.4 Hz, 4H), 3.237 (t, J=5.4 Hz, 4H), 1.478 (s, 9H).

Example 7.14

Preparation of tert-butyl 4-(6-(tributylstannyl)pyridin-3-yl)piperazine-1-carboxylate

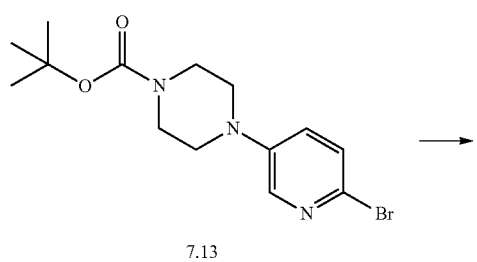

7.13

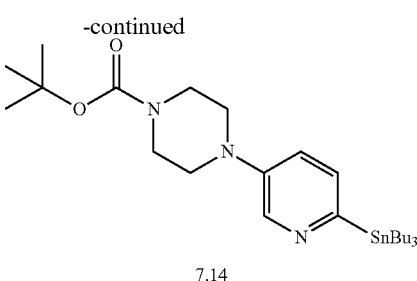

7.14

Into the solution of tert-butyl 4-(6-bromopyridin-3-yl)piperazine-1-carboxylate 7.13 (1.65 g, 4.8 mmol) in THF (30 mL) was added 1M solution of n-BuLi in hexane (5 mL) and n-Bu₃SnCl (1.66 g, 5.1 mmol) at −70° C. After 30 min., the reaction was warmed up to rt. After stirring for 1 h., the reaction mixture was extracted with ethyl acetate and washed with brine. After drying with MgSO₄, the organic solvent was removed under vaco., the residue was purified by silica gel chromatography to obtain 0.58 g of tert-butyl 4-(6-(tributylstannyl)pyridin-3-yl)piperazine-1-carboxylate 7.14. LCMS [M+H]⁺: 554.07.

Example 7.15

Preparation of 1-(6-bromopyridin-3-yl)-4-(oxetan-3-yl)piperazine

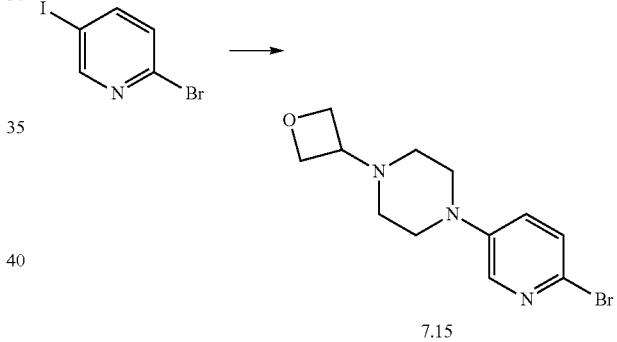

7.15

Following the procedure described for intermediate 7.13, starting from of 2-bromo-5-iodopyridine (3.83 g, 13.5 mmol) and 1-(oxetan-3-yl)piperazine (1.6 g, 11.3 mmol), 2.45 g of 1-(6-bromopyridin-3-yl)-4-(oxetan-3-yl)piperazine 7.15 was synthesized. ¹H NMR (400 MHz, CDCl₃) ppm: δ 8.01 (d, J=3.2 Hz, 1H), 7.3 (d, J=8.8 Hz, 1H), 7.07 (d, d, J=3.2, 8.8 Hz, 1H), 4.697 (t, J=5.2 Hz, 2H), 4.64 (t, J=5.2 Hz, 2H), 3.56 (m, 1H), 3.233 (t, J=5.2 Hz, 4H), 2.497 (t, J=5.2 Hz, 4H).

Example 7.16

Preparation of 1-(oxetan-3-yl)-4-(6-(tributylstannyl)pyridin-3-yl)piperazine

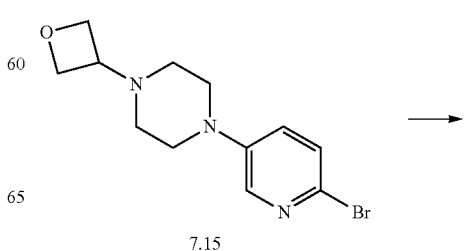

7.15

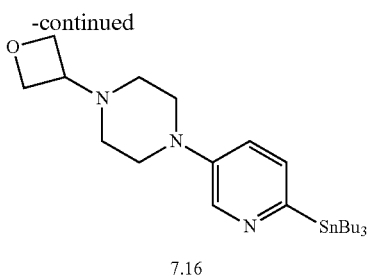

7.16

Following the procedure described for intermediate 7.14, starting from 1-(6-bromopyridin-3-yl)-4-(oxetan-3-yl)piperazine (1.78 g, 5.97 mmol), 1.78 g of 1-(oxetan-3-yl)-4-(6-(tributylstannyl)pyridin-3-yl)piperazine 7.16 was obtained. LCMS [M+H]⁺: 510.07.

Example 7.17

Preparation of 6-(4,4,5,5-tetramethyl-1,3,2-dioxaborolan-2-yl)-2H-benzo[b][1,4]oxazin-3(4H)-one

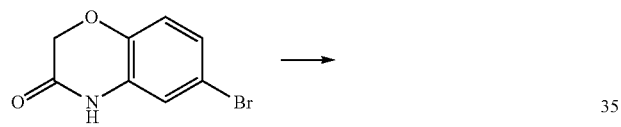

7.17

6-bromo-2H-benzo[b][1,4]oxazin-3(4H)-one (275 mg, 1.21 mmol), 4,4,4',4',5,5,5',5'-octamethyl-2,2'-bi(1,3,2-dioxaborolane) (466 mg, 1.84 mmol), potassium acetate (184 mg, 1.87 mmol), and Dichloro 1,1-bis(diphenylphosphino)ferrocene palladium(II) dichloromethane (47 mg, 0.06 mmol) were added to a flask and container was evacuated and backfilled with argon. Reagents were taken up in dioxane (9 mL) and system was again purged with argon. Mixture was then heated at 100° C. for 4 hours. After cooling to rt, reaction mixture was filtered over celite, washing with ethyl acetate. Filtrate was concentrated under reduced pressure and resulting reside was purified by silica gel column chromatography (0-40% ethyl acetate/hexanes) to yield 6-(4,4,5,5-tetramethyl-1,3,2-dioxaborolan-2-yl)-2H-benzo[b][1,4]oxazin-3 (4H)-one 7.17 (320 mg).

LCMS-ESI⁺ (m/z): [M+H]⁺ calcd for $C_{14}H_{19}BNO_4$: 276.13; found: 276.21.

Example 7.18

Preparation of 6-(4,4,5,5-tetramethyl-1,3,2-dioxaborolan-2-yl)-3,4-dihydro-2H-benzo[b][1,4]oxazine

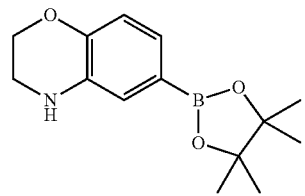

7.18

Following the procedure of Example 7.17, beginning with 6-bromo-3,4-dihydro-2H-benzo[b][1,4]oxazine (258 mg, 1.21 mmol), 6-(4,4,5,5-tetramethyl-1,3,2-dioxaborolan-2-yl)-3,4-dihydro-2H-benzo[b][1,4]oxazine 7.18 was synthesized (308 mg).

LCMS-ESI⁺ (m/z): [M+H]⁺ calcd for $C_{14}H_{21}BNO_3$: 262.15; found: 262.26.

Example 7.19

Preparation of 7-(4,4,5,5-tetramethyl-1,3,2-dioxaborolan-2-yl)-2H-benzo[b][1,4]oxazin-3(4H)-one

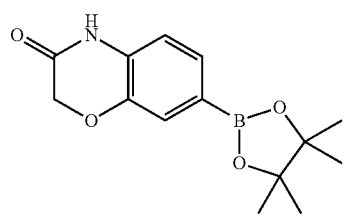

7.19

Following the procedure of Example 7.17, beginning with 7-bromo-2H-benzo[b][1,4]oxazin-3(4H)-one (275 mg, 1.21 mmol), 7-(4,4,5,5-tetramethyl-1,3,2-dioxaborolan-2-yl)-2H-benzo[b][1,4]oxazin-3(4H)-one 7.19 was synthesized (320 mg).

LCMS-ESI⁺ (m/z): [M+H]⁺ calcd for $C_{14}H_{19}BNO_4$: 276.13; found: 276.21.

Example 7.20

Preparation of ethyl 1-(4-bromo-2-nitrophenoxy)cyclopropanecarboxylate

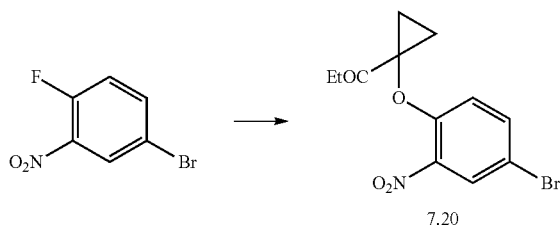

7.20

Sodium hydride (60%, 166 mg, 4.15 mmol) was added to a solution of ethyl 1-hydroxycyclopropanecarboxylate (0.41 mL, 3.59 mmol) in THF (10 mL) at room temperature. After 15 min, 3 drops of 15-crown-5 were added followed by 4-bromo-1-fluoro-2-nitrobenzene (0.42 mL, 3.41 mmol). Mixture was stirred at room temperature for 24 hours. After diluting with 50 mL of ethyl acetate, mixture was quenched by addition of brine (25 mL) and layers were separated. Aqueous phase was extracted with ethyl acetate and combined organics were dried (MgSO4), filtered, and concentrated under reduced pressure. Resulting residue was purified via silica gel column chromatography (0-30% ethyl acetate/hexanes) to yield ethyl 1-(4-bromo-2-nitrophenoxy)cyclopropanecarboxylate 7.20 (750 mg)

LCMS-ESI⁺ (m/z): [M+H]⁺ calcd for $C_{12}H_{13}BrNO_5$: 329.99; found: 330.05.

Example 7.21

Preparation of 6-bromospiro[benzo[b][1,4]oxazine-2,1'-cyclopropan]-3(4H)-one

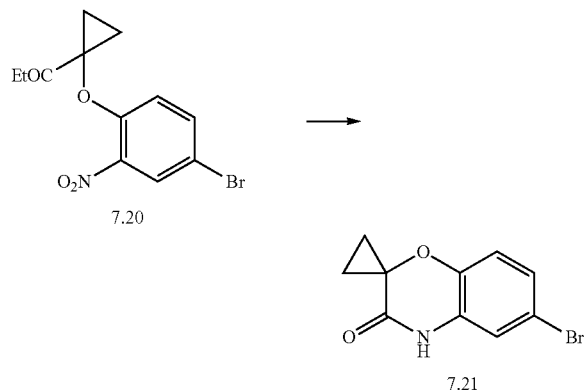

Iron (1173 mg, 21 mmol) was added to a solution of ethyl 1-(4-bromo-2-nitrophenoxy)cyclopropanecarboxylate 7.20 (693 mg, 2.1 mmol) in acetic acid (10 mL) at room temperature. Mixture was heated at 60° C. for 5 hours. Mixture was cooled to rt, diluted with 100 mL ethyl acetate, and filtered over celite. Filtrate was concentrated under reduced pressure to yield 6-bromospiro[benzo[b][1,4]oxazine-2,1'-cyclopropan]-3(4H)-one 7.21 (523 mg), which was used in the next step without further purification.

LCMS-ESI⁺ (m/z): [M+H]⁺ calcd for $C_{10}H_9BrNO_2$: 253.97; found: 253.94.

Example 7.22

Preparation of 6-(4,4,5,5-tetramethyl-1,3,2-dioxaborolan-2-yl)spiro[benzo[b][1,4]oxazine-2,1'-cyclopropan]-3(4H)-one

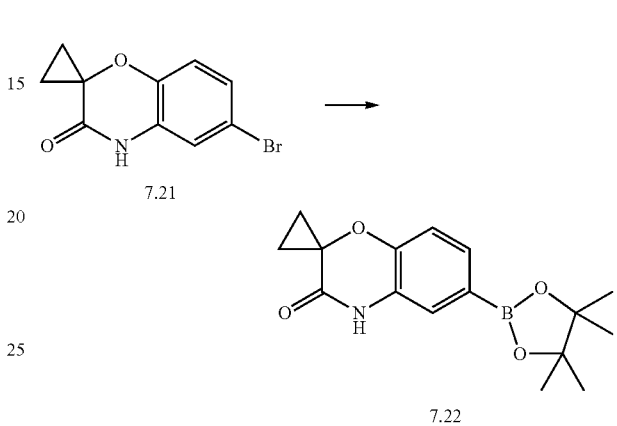

Following the procedure of Example 7.17, beginning with 6-bromospiro[benzo[b][1,4]oxazine-2,1'-cyclopropan]-3 (4H)-one 7.21 (251 mg, 0.988 mmol), 6-(4,4,5,5-tetramethyl-1,3,2-dioxaborolan-2-yl)spiro[benzo[b][1,4]oxazine-2,1'-cyclopropan]-3(4H)-one 7.22 was synthesized (277 mg).

LCMS-ESI⁺ (m/z): [M+H]⁺ calcd for $C_{16}H_{21}BNO_4$: 302.15; found: 302.16.

Example 7.23

Preparation of 6-bromo-3,4-dihydrospiro[benzo[b][1,4]oxazine-2,1'-cyclopropane]

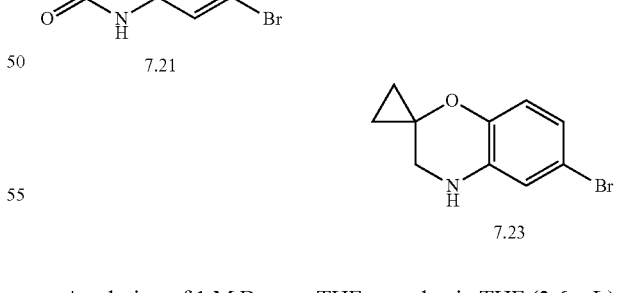

A solution of 1 M Borane-THF complex in THF (2.6 mL) was added to a solution of 6-bromospiro[benzo[b][1,4]oxazine-2,1'-cyclopropan]-3(4H)-one 7.21 (135 mg, 0.53 mmol) in THF (1.5 mL) at room temperature. Mixture was heated at 75° C. for 16 hours. After cooling to room temperature, reaction mixture was quenched with methanol, diluted with ethyl acetate, and washed with sat. NaHCO₃ (aq). Layers were separated and aqueous was extracted with ethyl acetate. Combined organics were washed with brine, dried (Na₂SO₄), filtered, and concentrated under reduced pressure to yield 6-bromo-3,4-dihydrospiro[benzo[b][1,4]oxazine-2,1'-cyclopropane] 7.23 (127 mg), which was used without further purification. LCMS-ESI⁺ (m/z): [M+H]⁺ calcd for $C_{10}H_{11}BrNO$: 239.99; found: 239.96.

Example 7.24

Preparation of 6-(4,4,5,5-tetramethyl-1,3,2-dioxaborolan-2-yl)-3,4-dihydrospiro[benzo[b][1,4]oxazine-2,1'-cyclopropane]

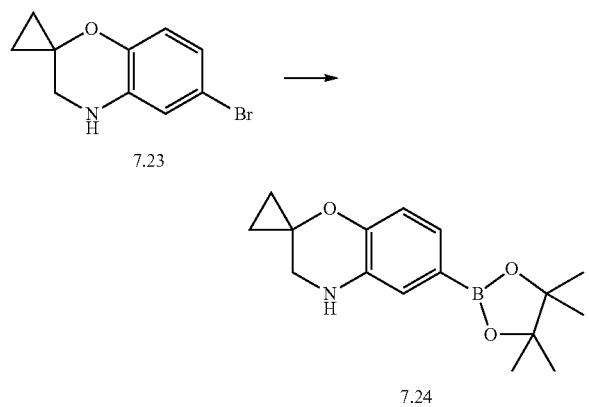

Following the procedure of Example 7.17, beginning with 6-bromo-3,4-dihydrospiro[benzo[b][1,4]oxazine-2,1'-cyclopropane] 7.23 (127 mg, 0.531 mmol), 6-(4,4,5,5-tetramethyl-1,3,2-dioxaborolan-2-yl)-3,4-dihydrospiro[benzo[b][1,4]oxazine-2,1'-cyclopropane] 7.24 was synthesized (76 mg). LCMS-ESI⁺ (m/z): [M+H]⁺ calcd for $C_{16}H_{23}BNO_3$: 288.17; found: 288.16.

Example 7.25

Preparation of 7-bromo-2-methyl-4H-benzo[d][1,3]oxazin-4-one

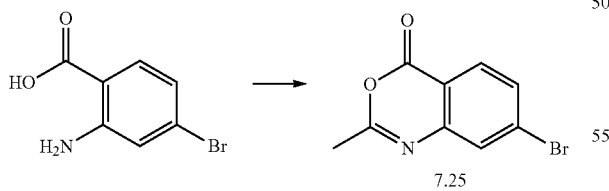

2-amino-4-bromobenzoic acid (825 mg, 3.82 mmol) was taken up in acetic anhydride (5.2 mL, 55.01 mmol) and mixture was heated at 130° C. After 4 hours, reaction mixture was cooled to rt and left there for two hours. The solid that precipitated was filtered and washed with cold ether, and dried in-vacuo to yield 7-bromo-2-methyl-4H-benzo[d][1,3]oxazin-4-one 7.25 (451 mg), which was used in the next step without further purification.

LCMS-ESI⁺ (m/z): [M+H]⁺ calcd for $C_9H_7BrNO_2$: 239.96; found: 240.02.

Example 7.26

Preparation of 7-bromo-2-methylquinazolin-4(3H)-one

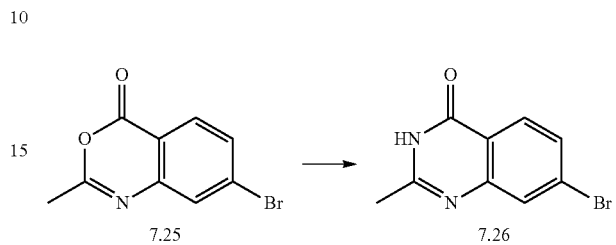

7-bromo-2-methyl-4H-benzo[d][1,3]oxazin-4-one 7.25 (400 mg, 1.58 mmol) was taken up in 26% aqueous ammonium hydroxide (5 mL, 33.38 mmol) and heated in a sealed tube at 80° C. for 4 hours. Mixture was cooled to room temperature and solid was filtered, washing with water. Solid was dried in-vacuo to yield 7-bromo-2-methylquinazolin-4(3H)-one 7.26 (213 mg), which was used in the next step without further purification.

LCMS-ESI⁺ (m/z): [M+H]⁺ calcd for $C_9H_8BrN_2O$: 238.97; found: 239.05.

Example 7.27

Preparation of 6-bromo-2,2-dimethyl-2H-pyrido[3,2-b][1,4]oxazin-3(4H)-one

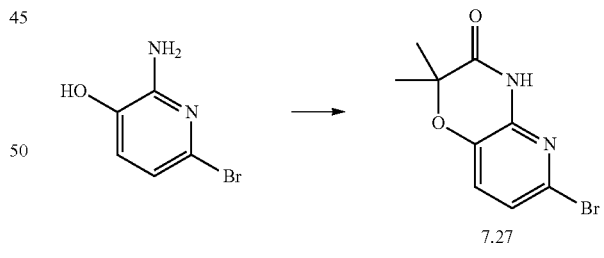

To a suspension of 2-amino-6-bromopyridin-3-ol (250 mg, 1.32 mmol) and $K_2CO_3$ in acetone (5 mL) was added ethyl 2-bromoisobutyrate (0.29 ml, 1.98 mmol) and the reaction was stirred for 1 hour at room temperature and overnight at reflux. The acetone was removed, and to the residue was added dichloromethane and water. The layers were separated and the aqueous was extracted with dichloromethane (1x). The organic layer was dried (MgSO4), filtered, and concentrated to afford 6-bromo-2,2-dimethyl-2H-pyrido[3,2-b][1,4]

oxazin-3(4H)-one 7.27 (300 mg). LCMS-ESI+ (m/z): [M+H]+ calcd for $C_9H_{10}BrN_2O_2$: 257.0; found: 257.1.

Example 7.28

Preparation of 6-chloro-1,3,3-trimethyl-1H-pyrrolo[2,3-b]pyridin-2(3H)-one

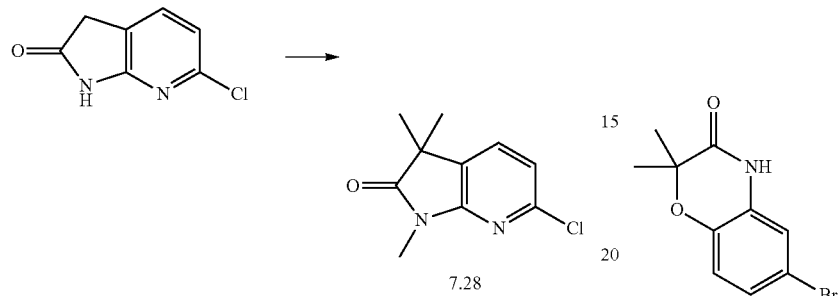

7.28

To a solution of 6-chloro-1H-pyrrolo[2,3-b]pyridin-2(3H)-one (50 mg, 0.30 mmol) in DMF (1 mL) at 0° C. was added NaH (48 mg, 1.2 mmol, 60%), and the reaction was stirred for 5 minutes. Iodomethane (210 mg, 1.5 mmol) was added and the reaction became a thick slurry. DMF (0.5 mL) was added and the reaction was stirred at room temperature for 90 minutes. Water, EtOAc, and brine were added, the layers were separated and the organic layer was washed with brine. The organics were dried over MgSO$_4$, filtered and concentrated to afford 6-chloro-1,3,3-trimethyl-1H-pyrrolo[2,3-b]pyridin-2(3H)-one 7.28 which was used without further purification. LCMS-ESI+ (m/z): [M+H]+ calcd for $C_{10}H_{12}ClN_2O$: 211.1; found: 211.0.

Example 7.29

Preparation of 6-chloro-3,3-dimethyl-1H-pyrrolo[2,3-b]pyridin-2(3H)-one

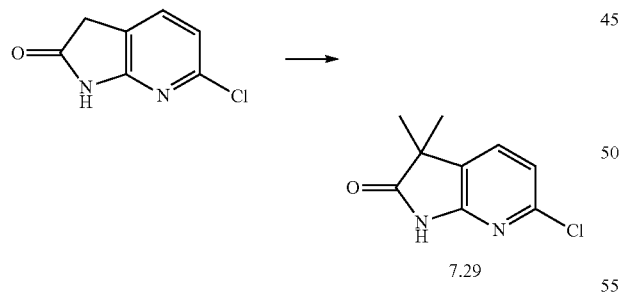

7.29

To a solution of 6-chloro-1H-pyrrolo[2,3-b]pyridin-2(3H)-one (120 mg, 0.712 mmol) in THF at 0° C. was added LDA (2.4 mL, 2.4 mmol, 1M solution in THF/hexanes) dropwise and the reaction was cooled to −78° C. TMEDA (0.30 mL, 2.0 mmol) was added, the reaction was stirred for 5 minutes, and iodomethane (0.15 mL, 2.35 mmol) was added. The reaction was stirred for 30 minutes and warmed to room temperature. Water and EtOAc were added, the layers were separated, and the aqueous layer was extracted with EtOAc. The combined organics were dried (MgSO$_4$), filtered and concentrated. The residue was purified by flash chromatography (20-100% EtOAc in hexanes) to afford 6-chloro-3,3-dimethyl-1H-pyrrolo[2,3-b]pyridin-2(3H)-one 7.29 (68 mg). LCMS-ESI+ (m/z): [M+H]+ calcd for $C_9H_{10}ClN_2O$: 197.0; found: 197.1.

Example 7.30

Preparation of 2,2-dimethyl-6-(4,4,5,5-tetramethyl-1,3,2-dioxaborolan-2-yl)-2H-benzo[b][1,4]oxazin-3(4H)-one

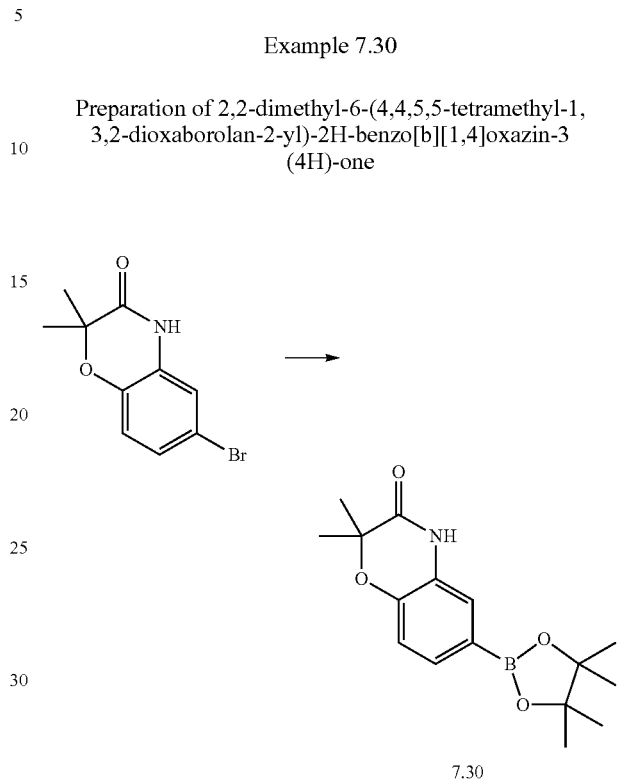

7.30

A suspension of 6-bromo-2,2-dimethyl-2H-benzo[b][1,4]oxazin-3(4H)-one (113 mg, 0.441 mmol), 4,4,4',4',5,5,5',5'-octamethyl-2,2'-bi(1,3,2-dioxaborolane) (168 mg, 0.662 mmol), potassium acetate (65.0 mg, 0.662 mmol) and Pd(dppf)Cl$_2$ (16.1 mg, 0.0220 mmol) in dioxane (2 mL) was degassed and the reaction was heated to 95° C. for 90 minutes. The reaction mixture was concentrated to provide 2,2-dimethyl-6-(4,4,5,5-tetramethyl-1,3,2-dioxaborolan-2-yl)-2H-benzo[b][1,4]oxazin-3(4H)-one 7.30 which was used directly in subsequent reactions.

LCMS-ESI+ (m/z): [M+H]+ calcd for $C_{16}H_{23}BNO_4$: 304.2; found: 305.1.

Examples 7.31 and 7.32

Preparation of 6-bromo-2,2,4-trimethyl-2H-benzo[b][1,4]oxazin-3(4H)-one and 2,2,4-trimethyl-6-(4,4,5,5-tetramethyl-1,3,2-dioxaborolan-2-yl)-2H-benzo[b][1,4]oxazin-3(4H)-one

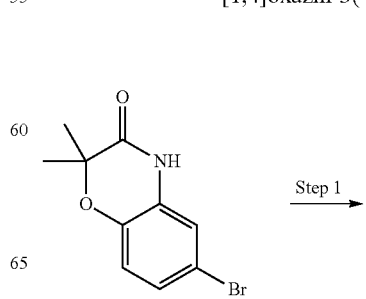 Step 1

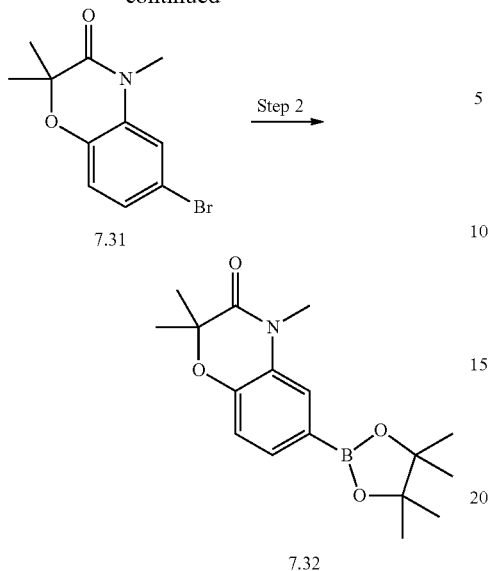

7.31

7.32

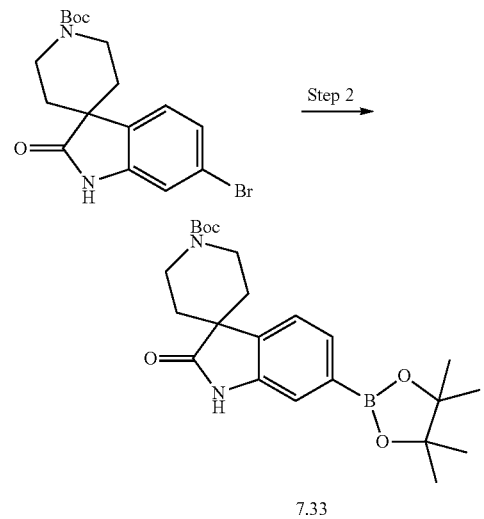

7.33

Step 1: To a solution of 6-bromo-2,2-dimethyl-2H-benzo[b][1,4]oxazin-3(4H)-one (185 mg, 0.722 mmol) in DMF (3 mL) at 0° C. was added NaH (43.3 mg, 1.08 mmol, 60%), and the reaction was stirred for 5 minutes. Iodomethane (205 mg, 1.45 mmol) was added the reaction was stirred at room temperature for 60 minutes. Water, EtOAc, and brine were added, the layers were separated and the organic layer was washed with brine. The organics were dried over MgSO$_4$, filtered and concentrated. The residue was purified by flash chromatography (10-35% EtOAc in hexanes) to afford 6-bromo-2,2,4-trimethyl-2H-benzo[b][1,4]oxazin-3(4H)-one 7.31 (132 mg). LCMS-ESI+ (m/z): [M+H]+ calcd for $C_{11}H_{13}BrNO_2$: 270.0; found: 270.0.

Step 2: A suspension of 6-bromo-2,2,4-trimethyl-2H-benzo[b][1,4]oxazin-3(4H)-one (60 mg, 0.22 mmol), 4,4,4',4',5,5,5',5'-octamethyl-2,2'-bi(1,3,2-dioxaborolane) (85 mg, 0.33 mmol), potassium acetate (33 mg, 0.33 mmol) and Pd(dppf)Cl$_2$ (8.1 mg, 0.011 mmol) in dioxane (2 mL) was degassed and the reaction was heated to 95° C. for 60 minutes. The reaction mixture was concentrated to provide 2,2,4-trimethyl-6-(4,4,5,5-tetramethyl-1,3,2-dioxaborolan-2-yl)-2H-benzo[b][1,4]oxazin-3(4H)-one 7.32 which was used directly in subsequent reactions.

LCMS-ESI+ (m/z): [M+H]+ calcd for $C_{17}H_{25}BNO_4$: 318.2; found: 318.1.

Example 7.33

Preparation of tert-butyl 2-oxo-6-(4,4,5,5-tetramethyl-1,3,2-dioxaborolan-2-yl)spiro[indoline-3,4'-piperidine]-1'-carboxylate

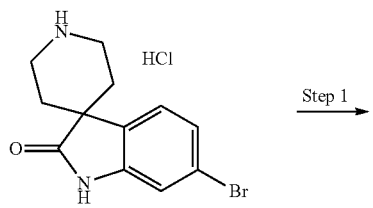

Step 1. A mixture of 6-bromospiro[indoline-3,4'-piperidin]-2-one hydrochloride (0.5 g, 1.6 mmol), di-tert-butyl dicarbonate (0.41 g, 1.89 mmol), and TEA (0.48 g, 4.8 mmol) in DCM (20 mL) was stirred at room temperature. After 6 h, solvent was removed under reduced pressure. Solids re-dissolved and extracted with ethyl acetate and water. Organic layer was washed with brine, dried over MgSO$_4$, filtered, and concentrated under reduced pressure. Residues obtained were purified by column chromatography on silica gel to provide 0.8 g of tert-butyl 6-bromo-2-oxospiro[indoline-3,4'-piperidine]-1'-carboxylate.

Step 2. A suspension of tert-butyl 6-bromo-2-oxospiro[indoline-3,4'-piperidine]-1'-carboxylate (800 mg, 2.1 mmol), 4,4,4',4',5,5,5',5'-octamethyl-2,2'-bi(1,3,2-dioxaborolane) (693 mg, 2.73 mmol), potassium acetate (618 mg, 6.3 mmol) and Pd(dppf)Cl$_2$ (153 mg, 0.21 mmol) in dioxane (10 mL) was degassed and the reaction was heated to 90° C. for 2 h. The reaction mixture was diluted with ethyl acetate, and washed with brine. The organic phase was dried, filtered, and concentrated under reduced pressure. The resulting reside was purified by silica gel column chromatography to provide 679 mg of tert-butyl 2-oxo-6-(4,4,5,5-tetramethyl-1,3,2-dioxaborolan-2-yl)spiro[indoline-3,4'-piperidine]-1'-carboxylate 7.33. LCMS [M+H]+: 428.88.

Example 7.34

Preparation of 6'-(4,4,5,5-tetramethyl-1,3,2-dioxaborolan-2-yl)spiro[[1,3]dioxolane-2,3'-indolin]-2'-one

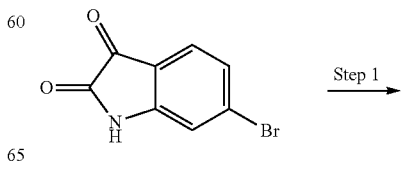

-continued

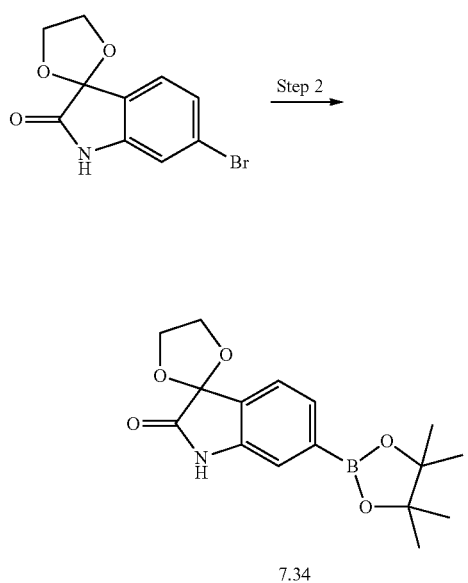

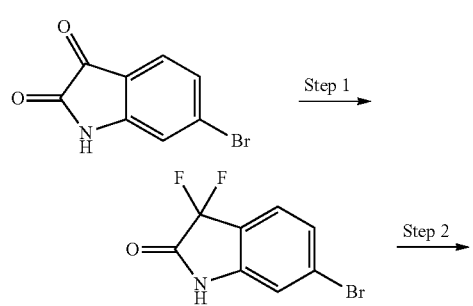

7.34

Step 1: Into the solution of 6-bromoindoline-2,3-dione (3.3 g) in Toluene (90 mL), was added Ethylene Glycol (9 g) and p-TsOH (555 mg). The reaction was heated to reflux and water was removed. After completion of the reaction, Toluene was removed, the residue was purified by silica gel column chromatography to provide 3.38 g of 6'-bromospiro[[1,3]dioxolane-2,3'-indolin]-2'-one. 1H NMR (400 MHz, Chloroform-d) δ 7.59 (br., 1H), 7.21 (d, J=1.1 Hz, 2H), 7.00 (s, 1H), 4.60-4.51 (m, 2H), 4.35-4.27 (m, 2H).

Step 2: Following the procedure described for Example 7.33 (Step 2), starting from 6'-bromospiro[[1,3]dioxolane-2,3'-indolin]-2'-one (1.35 g), 1.38 g of 6'-(4,4,5,5-tetramethyl-1,3,2-dioxaborolan-2-yl)spiro[[1,3]dioxolane-2,3'-indolin]-2'-one 7.34 was synthesized. LCMS [M+H]+: 318.00. 1H NMR (400 MHz, Chloroform-d) δ 7.76 (s, 1H), 7.53 (d, J=7.3, 0.9 Hz, 1H), 7.36 (d, J=7.4 Hz, 1H), 7.25 (d, J=8.5 Hz, 1H), 4.61-4.53 (m, 2H), 4.36-4.28 (m, 2H), 1.34 (s, 12H).

Example 7.35

Preparation of 6-bromo-3,3-difluoro-1-((2-(trimethylsilyl)ethoxy)methyl)indolin-2-one -continued

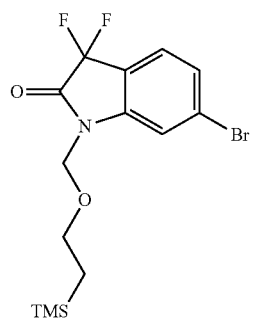

7.35

Step 1: Into the ice cooled solution of 6-bromoindoline-2,3-dione (0.5 g) in DCM (20 mL), was added neat deoxo-fluor (1.5 g), after 30 min., the reaction was warm to room temperature and stirred for overnight. After being quenched with sodium bicarbonate solution, the reaction mixture was extracted with ethyl acetate and washed with brine. The solvent was removed. the residue was purified by silica gel chromatography to provide 0.48 g of 6-bromo-3,3-difluoroindolin-2-one. 1H NMR (400 MHz, Chloroform-d) δ 7.81 (s, 1H), 7.42 (d, t, J=8.2, 1.8 Hz, 1H), 7.33 (d, d, J=8.1, 1.6 Hz, 1H), 7.13 (q, J=1.5 Hz, 1H).

Step 2: Into the solution of 6-bromo-3,3-difluoroindolin-2-one in DMF (5 mL), was added 1M of NaHMDS solution in THF (1.6 mL), after 30 min., (2-(chloromethoxy)ethyl)trimethylsilane (269 mg) was added. After being stirred at rt for 4 h, the reaction mixture was extracted with ethyl acetate and washed with brine, dried and the solvent was removed, the residue was purified by silica gel chromatography to provide 0.46 g of 6-bromo-3,3-difluoro-1-((2-(trimethylsilyl)ethoxy)methyl)indolin-2-one 7.35. 1H NMR (400 MHz, Chloroform-d) δ 7.43 (s, 1H), 7.37 (d, J=8.2 Hz, 1H), 7.33 (d, J=8.1 Hz, 1H), 5.12 (s, 2H), 3.58 (m, 2H), 1.21 (m, 2H), 0.00 (s, 9H).

Example 7.36

Preparation of 3,3-difluoro-6-(4,4,5,5-tetramethyl-1,3,2-dioxaborolan-2-yl)-1-((2-(trimethylsilyl)ethoxy)methyl)indolin-2-one

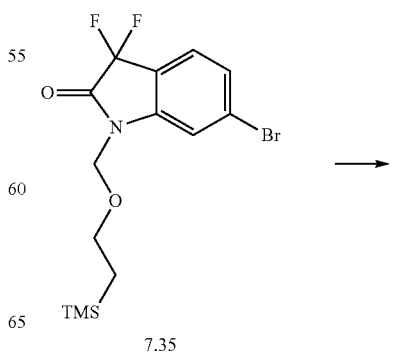

7.35

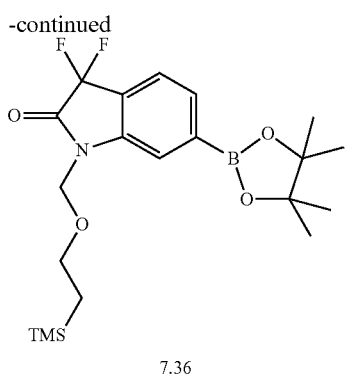

7.36

Following the procedure described for intermediate 7.33 (Step 2), starting from 6-bromo-3,3-difluoro-1-((2-(trimethylsilyl)ethoxy)methyl)indolin-2-one 7.35 (84 mg), 94 mg of crude 3,3-difluoro-6-(4,4,5,5-tetramethyl-1,3,2-dioxaborolan-2-yl)-1-((2-(trimethylsilyl)ethoxy)methyl)indolin-2-one 7.36 was obtained. This material was used without further purification.

Example 7.37

Preparation of 7-bromo-4,4-dimethyl-1H-benzo[d][1,3]oxazin-2(4H)-one

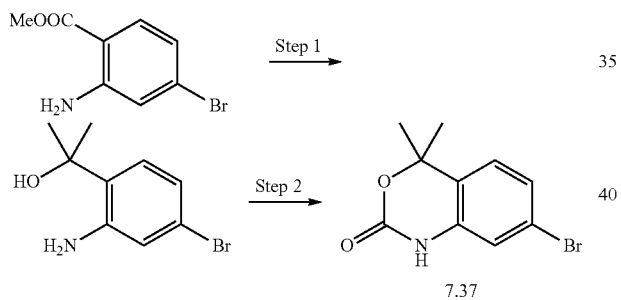

Step 1: Into the solution of 2-amino-4-bromophenyl acetate (2.3 g) in THF (50 mL) was added 1M solution of MeMgBr in THF (50 mL) at 0° C. Then the reaction mixture was warmed to rt., and stirred for another 2 h. The reaction was quenched by saturated NH$_4$Cl water solution, and extracted with ethyl acetate and washed with brine, after being dried, the solvent was removed to provide 2.3 g crude of 2-(2-amino-4-bromophenyl)propan-2-ol. This product was used in the next step reaction without any purification. LCMS [M+H]$^+$: 231.86. $^1$H NMR (400 MHz, Chloroform-d) δ 7.26 (s, 1H), 6.95 (d, J=8.1 Hz, 2H), 6.81-6.73 (m, 3H), 1.64 (s, 6H).

Step 2: Into the solution of 2-(2-amino-4-bromophenyl)propan-2-ol (2.3 g) in THF (50 mL) was added CDI (1.95 g) at rt., then the mixture was warmed to 60° C. and stirred for overnight. After solvent removal, the residue was dissolved in ethyl acetate and washed with 1M of HCl$_{(aq)}$ and brine, and dried with dry agent. After removal of the solvent, the residue was crystallized from DCM and hexane to provide 2.3 g of 7-bromo-4,4-dimethyl-1H-benzo[d][1,3]oxazin-2(4H)-one 7.37 was synthesized. LCMS [M+H]$^+$: 252.71. $^1$H NMR (400 MHz, Chloroform-d) δ 9.30 (s, 1H), 7.18 (d, d, J=8.2, 1.8 Hz, 1H), 7.06 (d, J=1.8 Hz, 1H), 6.99 (d, J=8.2 Hz, 1H), 1.71 (s, 6H).

Example 7.38

Preparation of 7-bromo-1,4,4-trimethyl-1H-benzo[d][1,3]oxazin-2(4H)-one

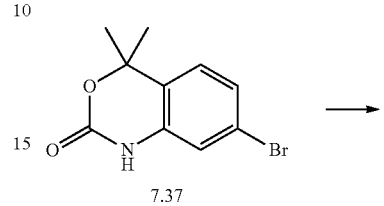

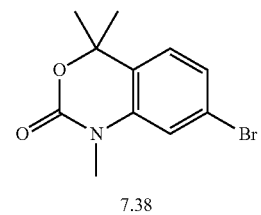

Into the solution of 7-bromo-4,4-dimethyl-1H-benzo[d][1,3]oxazin-2(4H)-one 7.37 (1.35 g) in DMF (20 mL) was added 1M solution of NaHMDS in THF (7 mL) at rt. After 30 min., MeI (0.85 g) was added. After overnight stirring, the reaction mixture was extracted with ethyl acetate and washed with brine, and dried with dry agent. After removal of the solvent, the residue was crystallized from mixture of DCM and Hexane to provide 1.2 g of 7-bromo-1,4,4-trimethyl-1H-benzo[d][1,3]oxazin-2(4H)-one 7.38 was synthesized.

LCMS [M+H]$^+$: 271.97. $^1$H NMR (400 MHz, Chloroform-d) δ 7.22 (d, d, J=8.1, 1.8 Hz, 1H), 7.10-6.99 (m, 2H), 3.38 (s, 3H), 1.66 (s, 6H).

Example 7.39

Preparation of 4,4-dimethyl-7-(4,4,5,5-tetramethyl-1,3,2-dioxaborolan-2-yl)-1H-benzo[d][1,3]oxazin-2(4H)-one

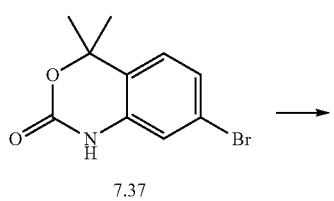

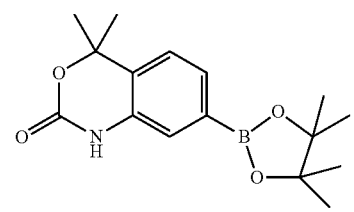

Following the procedure described for intermediate 7.33 (Step 2), starting from 7-bromo-4,4-dimethyl-1H-benzo[d][1,3]oxazin-2(4H)-one 7.37 (60 mg), 77 mg of 4,4-dimethyl-7-(4,4,5,5-tetramethyl-1,3,2-dioxaborolan-2-yl)-1H-benzo[d][1,3]oxazin-2 (4H)-one 7.39 was obtained. LCMS [M+H]⁺: 304.19.

Example 7.40

Preparation of 1,4,4-trimethyl-7-(4,4,5,5-tetramethyl-1,3,2-dioxaborolan-2-yl)-1H-benzo[d][1,3]oxazin-2(4H)-one

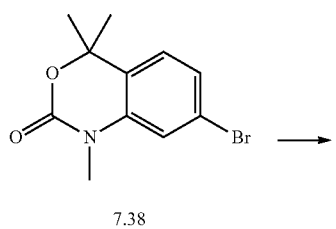

7.38

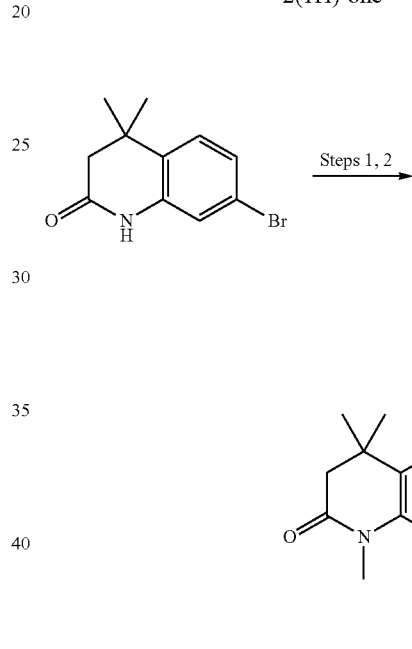

7.40

Following the procedure described for intermediate 7.33 (Step 2), starting from 7-bromo-1,4,4-trimethyl-1H-benzo[d][1,3]oxazin-2(4H)-one 7.38 (540 mg), 560 mg of 1,4,4-trimethyl-7-(4,4,5,5-tetramethyl-1,3,2-dioxaborolan-2-yl)-1H-benzo[d][1,3]oxazin-2(4H)-one 7.40 was obtained. LCMS [M+H]⁺: 318.12.

Example 7.41

Preparation of 6-chloro-1,3,3-trimethyl-1H-pyrrolo[3,2-c]pyridin-2(3H)-one

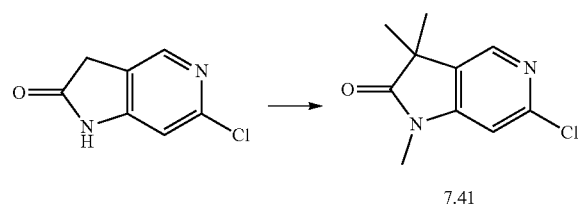

7.41

A suspension of 6-chloro-1H-pyrrolo[3,2-c]pyridin-2(3H)-one (50 mg, 0.30 mmol) in THF under Ar was cooled to −78° C. Iodomethane (0.1 mL, 1.6 mmol) was added followed by a THF solution of LiHMDS (1.0 M, 1.15 mL, 1.15 mmol). After 1 h, remove mixture from cold bath and stir for an additional 15.5 h. The reaction mixture was diluted with EtOAc, water and brine. The phases were separated, and the aqueous phase was extracted with EtOAc. The combined organic phase was dried over Na₂SO₄, filtered, and concentrated. Purification by silica gel chromatography (10-70% EtOAc in hexanes) provided 6-chloro-1,3,3-trimethyl-1H-pyrrolo[3,2-c]pyridin-2(3H)-one (7.41). LCMS-ESI⁺ (m/z): [M+H]⁺ calcd for $C_{10}H_{12}ClN_2O$: 211.1; found: 210.5.

Example 7.42

Preparation of 1,4,4-trimethyl-7-(4,4,5,5-tetramethyl-1,3,2-dioxaborolan-2-yl)-3,4-dihydroquinolin-2(1H)-one Step 1: 7-bromo-4,4-dimethyl-3,4-dihydroquinolin-2(1H)-one (210 mg, 0.83 mmol) and K₂CO₃ (335 mg, 2.42 mmol) were taken up in DMF (5 mL). Iodomethane (0.15 mL, 2.4 mmol) was added and the resulting mixture was stirred for 18 h. Water was added, and the resulting solids were filtered and washed with additional water to provide crude 7-bromo-1,4,4-trimethyl-3,4-dihydroquinolin-2(1H)-one that was used without further purification.

Step 2: 7-bromo-1,4,4-trimethyl-3,4-dihydroquinolin-2(1H)-one (180 mg, 0.67 mmol), KOAc (240 mg, 2.4 mmol), 4,4,4',4',5,5,5',5'-octamethyl-2,2'-bi(1,3,2-dioxaborolane) (290 mg, 1.1 mmol) and PdCl₂(dppf)CH₂Cl₂ (29 mg, 0.035 mmol) were taken up in 1,4-dioxane (7 mL) under Ar. The stirred reaction mixture was heated to 100° C. and stirred for 16 h. The reaction mixture was diluted with water, EtOAc and brine and the phases were separated. The organic phase was dried over Na₂SO₄, filtered, and concentrated. The crude residue was purified by silica gel chromatography (20-100% EtOAc in hexanes) to afford 1,4,4-trimethyl-7-(4,4,5,5-tetramethyl-1,3,2-dioxaborolan-2-yl)-3,4-dihydroquinolin-2

(1H)-one (7.42). LCMS-ESI⁺ (m/z): [M+H]⁺ calcd for $C_{18}H_{27}BNO_3$: 316.2; found: 316.2.

Example 7.43

Preparation of 3,3-dimethyl-1-(oxetan-3-yl)-6-(4,4,5,5-tetramethyl-1,3,2-dioxaborolan-2-yl)indolin-2-one

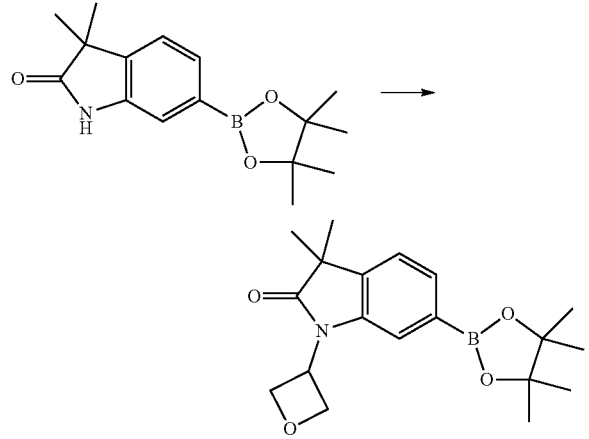

To a solution of 3,3-dimethyl-6-(4,4,5,5-tetramethyl-1,3,2-dioxaborolan-2-yl)indolin-2-one (56 mg, 0.20 mmol) and 3-iodooxetane (85 μL, 0.98 mmol) in DMF (1 mL) was added a THF solution of NaHMDS (1.0 M, 0.21 mL, 0.21 mmol). After 1.5 h, the reaction mixture was heated to 70° C. After an additional 1.5 h, the reaction mixture was cooled to r.t. and additional 3-iodooxetane (30 μL, 0.34 mmol) and NaHMDS solution (0.1 mL, 0.1 mmol) were added. The reaction mixture was heated to 70° C. and was stirred an additional 16 h. The reaction mixture was cooled and diluted with EtOAc, water, and brine, and the layers were separated. The organic phase was washed with brine, dried over $Na_2SO_4$, filtered, and concentrated. The crude residue was purified by silica gel chromatography (0-50% EtOAc in hexanes) to provide 3,3-dimethyl-1-(oxetan-3-yl)-6-(4,4,5,5-tetramethyl-1,3,2-dioxaborolan-2-yl)indolin-2-one (7.43). LCMS-ESI⁺ (m/z): [M+H]⁺ calcd for $C_{19}H_{27}BNO_4$: 344.20; found: 316.25.

Example 7.44

Preparation of 1-methyl-5-(4,4,5,5-tetramethyl-1,3,2-dioxaborolan-2-yl)-1H-benzo[d]imidazol-2(3H)-one

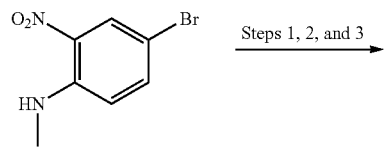

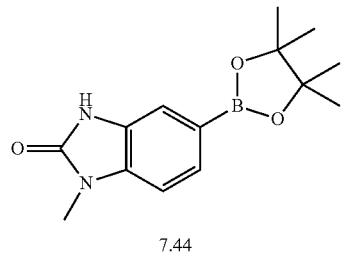

Step 1: A mixture of iron (5.88 g, 105 mmol), ethanol (16 mL) and 2 M hydrochloric acid (3.1 mL) was sparged with nitrogen for 10 min, then heated to reflux. A solution of 4-bromo-N-methyl-2-nitroaniline (1.43 g, 6.19 mmol) in ethanol (14 mL), methanol (3 mL) and ethyl acetate (2 mL) was added to the hot mixture and the reaction stirred at reflux for 1 h. After this time, the reaction was cooled to room temperature and adjusted to pH 8-9 with potassium carbonate (~850 mg). The mixture was filtered through diatomaceous earth and the filter cake washed with methanol (300 mL). The filtrate was concentrated under reduced pressure and the resulting residue purified by chromatography (silica, gradient, methylene chloride to 19:1 methylene chloride/methanol) to afford 4-bromo-N¹-methylbenzene-1,2-diamine. ¹H NMR (400 MHz, DMSO-d₆) δ 6.65 (d, J=2.4 Hz, 1H), 6.60 (dd, J=8.4, 2.4 Hz, 1H), 6.26 (d, J=8.4 Hz, 1H), 4.74 (s, 2H), 4.72-4.69 (m, 1H), 2.67 (d, J=5.2 Hz, 3H).

Step 2: A solution of 4-bromo-N¹-methylbenzene-1,2-diamine (581 mg, 2.89 mmol) in methylene chloride (50 mL) was cooled to 0° C. in an ice/water bath and treated dropwise with a solution of 20% phosgene in toluene (1.52 mL). When the addition was complete, triethylamine (585 mg, 5.78 mmol) was added and the reaction stirred at 0° C. for 30 min. After this time, the reaction was poured into 1 M hydrochloric acid (80 mL) and extracted with methylene chloride. The combined organic layers were washed with water and dried over sodium sulfate. The drying agent was removed by filtration and the filtrate concentrated under reduced pressure. The resulting residue was purified by trituration with ethyl acetate to afford 5-bromo-1-methyl-1H-benzo[d]imidazol-2(3H)-one. ¹H NMR (400 MHz, DMSO-d₆) δ 10.98 (bs, 1H), 7.17 (dd, J=8.4, 1.6 Hz, 1H), 7.10 (d, J=1.6 Hz, 1H), 7.05 (d, J=8.4 Hz, 1H), 3.26 (s, 3H).

Step 3: A mixture of 5-bromo-1-methyl-1H-benzo[d]imidazol-2(3H)-one (300 mg, 1.32 mmol), bis(pinacolato)diboron (403 mg, 1.58 mmol) and potassium acetate (389 mg, 3.96 mmol) in 1,4-dioxane (4.5 mL) was sparged with nitrogen while stirring for 10 min. Dichloro[1,1'-bis(diphenylphosphino)ferrocene]palladium(II) methylene chloride adduct (193 mg, 0.264 mmol) was then added and the reaction stirred at 100° C. for 1.5 h. After this time, the mixture was cooled to room temperature, partitioned between ethyl acetate and water and filtered through diatomaceous earth. The filter cake was washed with ethyl acetate and the filtrate layers separated. The organic phase was washed with water and dried over sodium sulfate. The drying agent was removed by filtration and the filtrate concentrated under reduced pressure. The resulting residue was purified by chromatography (silica, gradient, methylene chloride to 1:1 methylene chloride/ethyl acetate) to afford 1-methyl-5-(4,4,5,5-tetramethyl-1,3,2-dioxaborolan-2-yl)-1H-benzo[d]imidazol-2(3H)-one (7.44).

¹H NMR (400 MHz, DMSO-d₆) δ 10.86 (bs, 1H), 7.36 (d, J=8.0 Hz, 1H), 7.22 (s, 1H), 7.08 (d, J=8.0 Hz, 1H), 3.26 (s, 3H), 1.28 (s, 12H).

Examples 7.45 and 7.46

Preparation of 6-bromo-3-methoxy-1,3-dimethylindolin-2-one

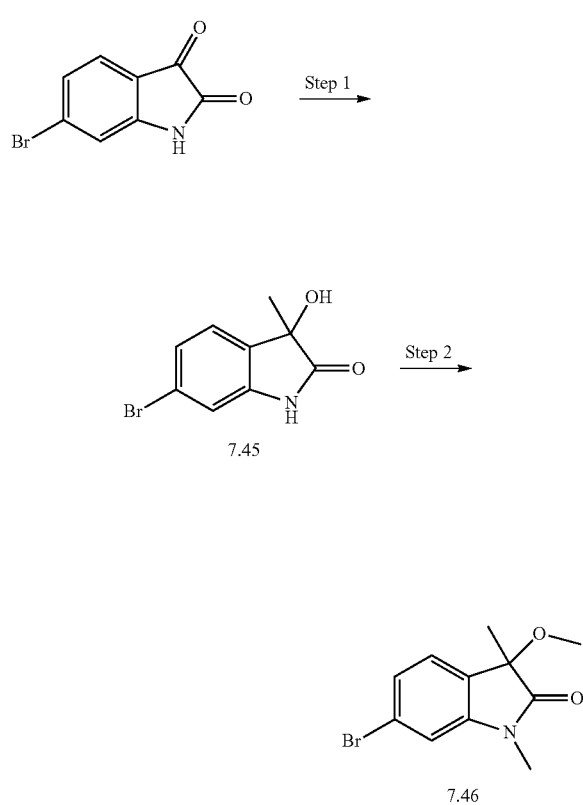

Step 1: To a mixture of 6-bromoisatin (255 mg, 1.13 mmol) in THF (3.0 mL) was added methylmagnesium bromide (1.12 mL, 3.39 mmol, 3M in ether). The solution was stirred at room temperature for 2 hours. The solution was cooled to 0° C. and was quenched with a saturated solution of ammonium chloride. The aqueous layer was extracted with EtOAc (3×), washed with brine, dried over MgSO₄, filtered and concentrated to afford 6-bromo-3-hydroxy-3-methylindolin-2-one 7.45. The solid was used without further purification. ¹H NMR (400 MHz, DMSO-d₆) δ 10.35 (s, 1H), 7.24 (d, J=7.9 Hz, 1H), 7.15 (dd, J=7.9, 1.8 Hz, 1H), 6.94 (d, J=1.8 Hz, 1H), 5.94 (s, 1H), 1.34 (s, 3H).

Step 2: A solution of 6-bromo-3-hydroxy-3-methylindolin-2-one 7.45 (200 mg, 0.826 mmol) in ACN/DMF (2:1, 6 mL) was cooled to 0° C. Cesium carbonate (942 mg, 2.89 mmol) and dimethyl sulfate (274 µL, 2.89 mmol) were added. The reaction was stirred at 0° C. for 90 min then at room temperature for 4 hours. The mixture was filtered over celite, concentrated and the residue was purified by flash column chromatography on silica gel to afford 6-bromo-3-methoxy-1,3-dimethylindolin-2-one 7.46. ¹H NMR (400 MHz, DMSO-d₆) δ 7.39-7.25 (m, 3H), 3.14 (s, 3H), 2.85 (s, 3H), 1.40 (s, 3H).

Example 7.47

Preparation of 2-methyl-2-(4-(4,4,5,5-tetramethyl-1,3,2-dioxaborolan-2-yl)phenyl)propanenitrile

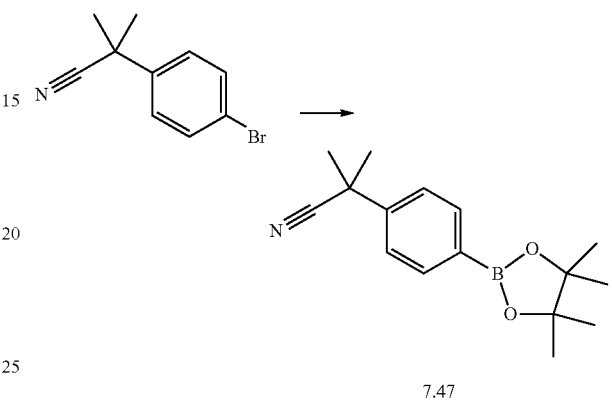

A suspension of 2-(4-bromophenyl)-2-methylpropanenitrile (110 mg, 0.491 mmol), 4,4,4',4',5,5,5',5'-octamethyl-2,2'-bi(1,3,2-dioxaborolane) (187 mg, 0.736 mmol), potassium acetate (72.3 mg, 0.736 mmol) and Pd(dppf)Cl₂ (18.0 mg, 0.0250 mmol) in dioxane (3 mL) was degassed and the reaction was heated to 95° C. for 90 minutes. The reaction mixture was concentrated to provide 2-methyl-2-(4-(4,4,5,5-tetramethyl-1,3,2-dioxaborolan-2-yl)phenyl)propanenitrile which was used directly in subsequent reactions. LCMS-ESI+ (m/z): [M+H]+ calcd for C₁₆H₂₃BNO: 272.2; found: 272.2.

Example 7.48

Preparation of 6-chloro-3,3-dimethyl-2,3-dihydrobenzofuran

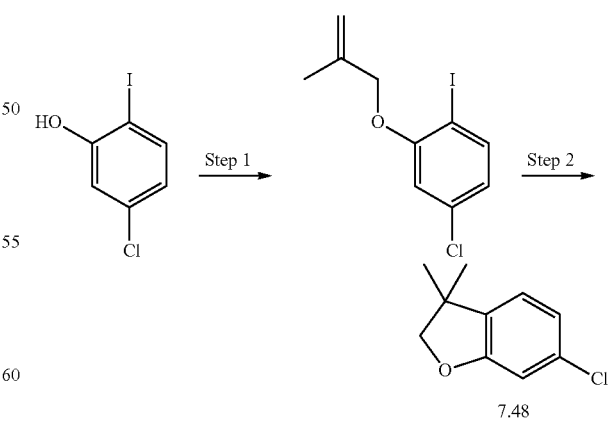

Step 1: To a mixture of 5-chloro-2-iodophenol (1.21 g, 4.76 mmol) and K₂CO₃ (723 mg, 5.23 mmol) in acetone (20 mL) was added 3-bromo-2-methyl-propene (0.53 ml, 5.23 mmol), and the reaction was heated to reflux for 16 hours. The reaction was cooled, diluted with EtOAc and water, and the layers were separated. The aqueous layer was extracted with EtOAc (2×) and the combined organics were dried over MgSO$_4$, filtered and concentrated to afford 4-chloro-1-iodo-2-((2-methylallyl)oxy)benzene which was used directly in the next step without further purification.

Step 2: To a mixture of 4-chloro-1-iodo-2-((2-methylallyl)oxy)benzene (160 mg, 0.519 mmol), sodium formate (35.3 mg, 0.519 mmol), tetrabutylammonium chloride (144 mg, 0.519 mmol), and Pd(OAc)$_2$ (23.3 mg, 0.104 mmol) in degassed DMF (1.5 mL) was added Et$_3$N (0.181 ml, 1.30 mmol) and the reaction was heated to 80° C. After 1 hour, the reaction was cooled, diluted with water and EtOAc, the layers were separated, and the aqueous layer was extracted with EtOAc (1x). The organic layer was dried (MgSO$_4$), filtered, and concentrated. The residue was purified by flash chromatography (5-20% EtOAc in hexanes) to afford 6-chloro-3,3-dimethyl-2,3-dihydrobenzofuran 7.48 (55 mg).

$^1$H NMR (400 MHz, CDCl$_3$) δ 6.99 (d, J=7.6 Hz, 1H), 6.85 (dd, J=2.4, 7.6 Hz, 1H), 6.77 (d, J=2.0 Hz, 1H), 4.25 (s, 2H), 1.32 (s, 6H).

Example 7.49

Preparation of 2-Bis(tert-butoxycarbonyl)amino-(6-(4,4,5,5-tetramethyl-1,3,2-dioxaborolan-2-yl))pyrazine

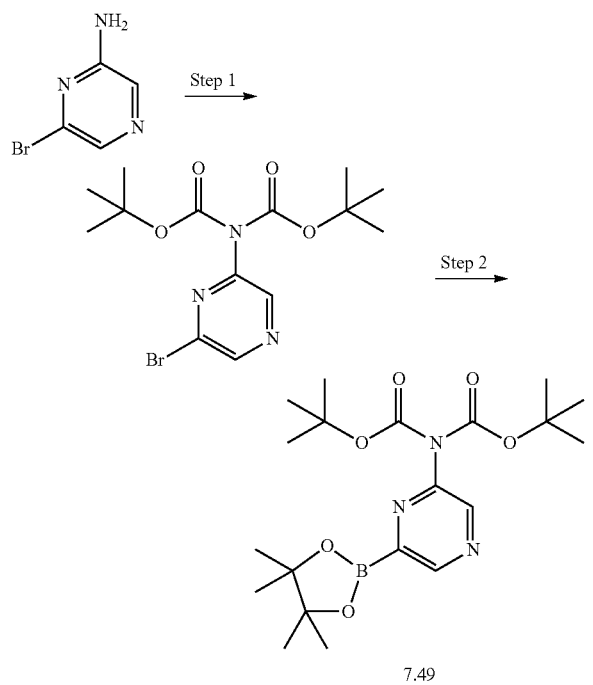

7.49

Step 1: To a mixture of 6-bromopyrazin-2-amine (5 g, 28.7 mmol) and di-tert-butyl dicarbonate (25.1 g, 115 mmol) was added DCM (10 mL) followed by DMAP (0.351 g, 29 mmol). The reaction was heated to 55° C. for 1 h and cooled to RT The reaction was partitioned between water and DCM, purified on silica gel and concentrated to afford 10.75 g of 2-Bis(tert-butoxycarbonyl)amino-6-bromopyrazine.

$^1$H NMR (DMSO-d$_6$) δ 8.84 (m, 2H), 1.39 (s, 18H).

Step 2: To a dry flask was added 2-bis(tert-butoxycarbonyl)amino-6-bromopyrazine (1.0 g, 2.7 mmol), KOAc (790 mg, 8.0 mmol), 4,4,4',4',5,5,5',5'-octamethyl-2,2'-bi(1,3,2-dioxaborolane) (750 mg, 2.9 mmol), Pd$_2$(dba)$_3$ (170 mg, 0.19 mmol) and X-phos (130 mg, 0.27 mmol) followed by 1,4-dioxane (25 mL) and the solution was purged with N$_2$. The reaction was heated at 110° C. for 90 minutes, cooled to room temperature, and filtered through Celite. The filter cake was washed with EtOAc and the filtrate was concentrated to provide 2-Bis(tert-butoxycarbonyl)amino-(6-(4,4,5,5-tetramethyl-1,3,2-dioxaborolan-2-yl))pyrazine 7.49 that was used directly in subsequent reactions.

Example 7.50

Preparation of 2-methyl-6-(4,4,5,5-tetramethyl-1,3,2-dioxaborolan-2-yl)-1H-indole

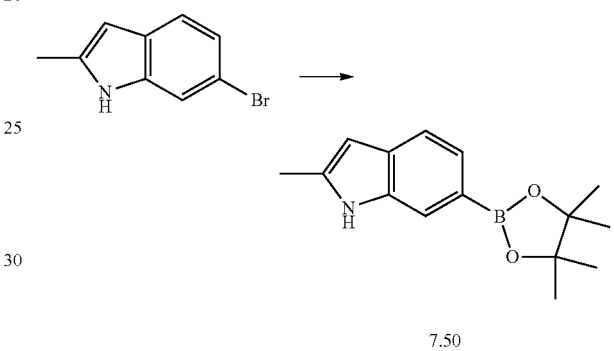

7.50

6-bromo-2-methyl-1H-indole (250 mg, 1.19 mmol), KOAc (410 mg, 4.2 mmol), 4,4,4',4',5,5,5',5'-octamethyl-2,2'-bi(1,3,2-dioxaborolane) (520 mg, 2.0 mmol) and PdCl$_2$(dppf)CH$_2$Cl$_2$ (50 mg, 0.061 mmol) were taken up in 1,4-dioxane (7 mL) under Ar. The stirred reaction mixture was heated to 105° C. and stirred for 14 h. The reaction mixture was diluted with water, EtOAc and brine and the phases were separated. The organic phase was dried over Na$_2$SO$_4$, filtered, and concentrated. The crude residue was purified by silica gel chromatography (10-60% EtOAc in hexanes) to afford 2-methyl-6-(4,4,5,5-tetramethyl-1,3,2-dioxaborolan-2-yl)-1H-indole (7.50). LCMS-ESI$^+$ (m/z): [M+H]$^+$ calcd for C$_{15}$H$_{21}$BNO$_2$: 258.2; found: 257.8.

Example 7.51

Preparation of 6-bromo-2H-spiro[benzofuran-3,1'-cyclopentan]-2-one

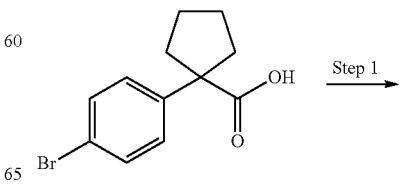

-continued

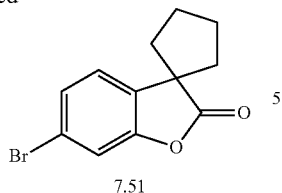

A vial was charged with 1-(4-bromophenyl)cyclopentanecarboxylic acid (200 mg, 0.743 mmol), iodobenzene diacetate (359 mg, 1.11 mmol), Boc-L-valine (48.4 mg, 0.223 mmol), potassium acetate (146 mg, 1.49 mmol) and palladium (II) acetate trimer (8.34 mg, 5 mol %). Tert-butanol (7.4 mL) was added and the mixture was heated at 90° C. for 11 hours, then at room temperature for 8 hours. The reaction mixture was concentrated, diluted with DCM and filtered. The residue was purified by flash column chromatography on silica gel to afford 6-bromo-2H-spiro[benzofuran-3,1'-cyclopentan]-2-one 7.51 (75 mg). LCMS-ESI+ (m/z): [M+H]+ calcd for $C_{12}H_{12}{}^{79}BrO_2$: 267.0; found: 267.0.

Example 7.52

Preparation of 4,4-dimethyl-7-(4,4,5,5-tetramethyl-1,3,2-dioxaborolan-2-yl)-3,4-dihydroquinolin-2(1H)-one

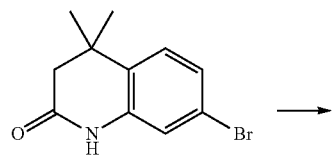

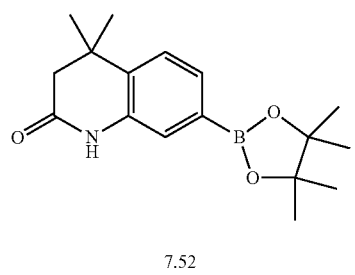

7.52

7-bromo-4,4-dimethyl-3,4-dihydroquinolin-2(1H)-one (210 mg, 0.83 mmol), 4,4,4',4',5,5,5',5'-octamethyl-2,2'-bi(1,3,2-dioxaborolane) (360 mg, 1.4 mmol), potassium acetate (290 mg, 3.0 mmol), and dichloro 1,1-bis(diphenylphosphino)ferrocene palladium(II) dichloromethane (35 mg, 0.043 mmol) were taken up in 1,4-dioxane (7 mL) under Ar. The stirred mixture was then heated to 105° C. for 14 hours. After cooling to rt, reaction mixture was diluted with EtOAc, water and brine. The organic phase was dried over $Na_2SO_4$, filtered and concentrated to afford a crude residue that was purified by silica gel chromatography (10-60% EtOAc in hexanes) to provide 4,4-dimethyl-7-(4,4,5,5-tetramethyl-1,3,2-dioxaborolan-2-yl)-3,4-dihydroquinolin-2(1H)-one 7.52 (245 mg).

LCMS-ESI+ (m/z): [M+H]+ calcd for $C_{17}H_{25}BNO_3$: 302.19; found: 302.34.

Example 7.53

Preparation of 3-iodo-1-(oxetan-3-yl)-1H-pyrazole

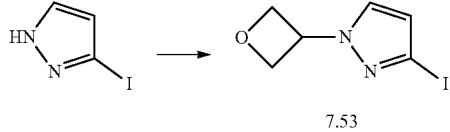 [SMILES: Ic1cc[nH]n1 ; Ic1ccn(C2COC2)n1]

7.53

3-iodo-1H-pyrazole (503 mg, 2.6 mmol) was added as a solution in DMF (1 mL) to a 1.0 M THF solution of NaHMDS (2.9 mL, 2.9 mmol) that had been pre-cooled in an ice water bath. Additional portions of DMF (2×1 mL) were used to ensure complete transfer. 3-iodooxetane (0.41 mL, 4.7 mmol) was added in one portion and the reaction mixture was allowed to warm to r.t. After 1 h, the reaction mixture was heated to 45° C. and allowed to stir for an additional 75 h. The mixture was cooled and diluted with EtOAc, and water. The aqueous phase was extracted with EtOAc. The combined organic phase was washed with water and were dried over $Na_2SO_4$, filtered and concentrated to afford a crude residue that was purified by silica gel chromatography (0-30% EtOAc in hexanes) to provide 3-iodo-1-(oxetan-3-yl)-1H-pyrazole 7.53 (414 mg). Regiochemistry was confirmed as drawn via NOE studies. LCMS-ESI+ (m/z): [M+H]+ calcd for $C_6H_8IN_2O$: 251.0; found: 251.0.

Example 7.54

Preparation of 6-chloro-1-((2-(trimethylsilyl)ethoxy)methyl)-1H-pyrazolo[3,4-b]pyridine/6-chloro-2-((2-(trimethylsilyl)ethoxy)methyl)-2H-pyrazolo[3,4-b]pyridine

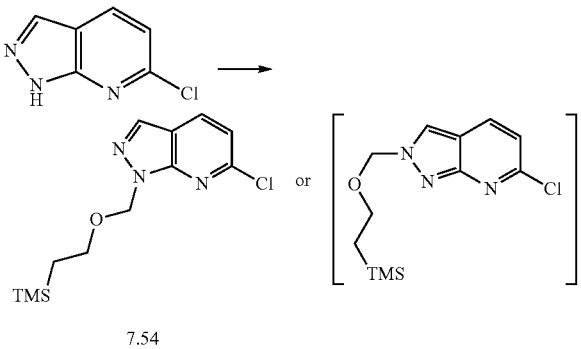

7.54

6-chloro-1H-pyrazolo[3,4-b]pyridine (500 mg, 3.3 mmol) was suspended in DCM (10 mL) and N,N-diisopropylethylamine (1.7 mL, 9.8 mmol) was added followed by 2-(trimethylsilyl)ethoxymethyl chloride (1.2 mL, 6.78 mmol). After stifling 3.5 h, the reaction mixture was diluted with EtOAc and water. The organic phase was dried over $Na_2SO_4$, filtered, and concentrated to afford a crude residue that was purified by silica gel chromatography (5-50% EtOAc in hexanes) to provide 610 mg of the first-eluting isomer 6-chloro-1-((2-(trimethylsilyl)ethoxy)methyl)-1H-pyrazolo[3,4-b]pyridine (or 6-chloro-2-((2-(trimethylsilyl)ethoxy)methyl)-2H-pyrazolo[3,4-b]pyridine, regiochemistry not determined) 7.54. Uncertainty in this assignment is implicit in other depictions of Intermediate 7.54. LCMS-ESI⁺ (m/z): [M+H]⁺ calcd for $C_{12}H_{19}ClN_3OSi$: 284.10; found: 283.79.

Example 7.55

Preparation of 6-chloro-14(2-(trimethylsilyl)ethoxy)methyl)-1H-pyrazolo[3,4-b]pyridine/6-chloro-2-((2-(trimethylsilyl)ethoxy)methyl)-2H-pyrazolo[3,4-b]pyridine

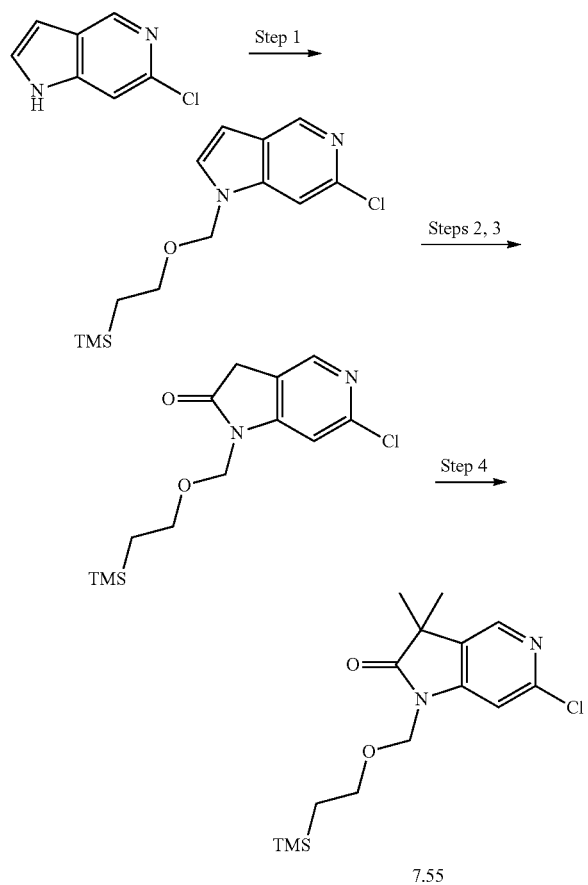

7.55

Step 1: 6-chloro-1H-pyrrolo[3,2-c]pyridine (1 g, 6.6 mmol) was dissolved in DMF (5 mL) under Ar and the solution was cooled in an ice water bath. A 1 M solution of NaHMDS in THF (7.5 mL, 7.5 mmol) was added over 1.5 min and the reaction mixture was stirred 20 min. (2-(chloromethoxy)ethyl)trimethylsilane (1.3 mL, 7.5 mmol) was then added and the reaction mixture was stirred for 2 h. The mixture was then diluted with water and DCM, and the aqueous phase was extracted with DCM (2×). The combined organic phase was washed with brine, dried over $Na_2SO_4$, filtered, and concentrated to afford a crude residue that was purified by silica gel chromatography (0-50% EtOAc in hexanes) to afford 6-chloro-1-((2-(trimethylsilyl)ethoxy)methyl)-1H-pyrrolo[3,2-c]pyridine. LCMS-ESI⁺ (m/z): [M+H]⁺ calcd for $C_{13}H_{20}ClN_2OSi$: 283.10; found: 283.03.

Step 2: 6-chloro-1-((2-(trimethylsilyl)ethoxy)methyl)-1H-pyrrolo[3,2-c]pyridine (1.53 g, 5.4 mmol) was added as a solution in 1,4-dioxane (10 mL) to a mixture of pyridinium tribromide (8.7 g, 27 mmol) in 1,4-dioxane (10 mL) over 30 min. Following complete addition, the reaction mixture was stirred 2 h and was then quenched with water (25 mL). The resulting mixture was stirred 20 min and was then diluted with EtOAc. The aqueous phase was extracted with EtOAc (2×) and the combined organics were washed with water (2×) and brine (2×), dried over $Na_2SO_4$, filtered, and concentrated to afford crude 3,3-dibromo-6-chloro-1-((2-(trimethylsilyl)ethoxy)methyl)-1H-pyrrolo[3,2-c]pyridin-2(3H)-one that was used without further purification. LCMS-ESI⁺ (m/z): [M+H]⁺ calcd for $C_{13}H_{18}Br_2ClN_2O_2Si$: 454.92; found: 454.48.

Step 3: Crude 3,3-dibromo-6-chloro-1-((2-(trimethylsilyl)ethoxy)methyl)-1H-pyrrolo[3,2-c]pyridin-2(3H)-one (~5.4 mmol) was taken up in a mixture of THF (30 mL) and saturated aqueous $NH_4Cl$ (8 mL). Zinc powder (3.6 g, 0.055 mmol) was added, and a modest exotherm was maintained via ice bath. The reaction was stirred at r.t. for 1.5 h, and the reaction was then filtered through Celite, washing with EtOAc. The organic phase was washed with water, and the combined aqueous phase was extracted with EtOAc. The combined organics were dried over $Na_2SO_4$, filtered, and concentrated to afford a crude residue that was purified by silica gel chromatography (10-100% EtOAc in hexanes) to afford 6-chloro-1-((2-(trimethylsilyl)ethoxy)methyl)-1H-pyrrolo[3,2-c]pyridin-2(3H)-one (1.04 g). LCMS-ESI⁺ (m/z): [M+H]⁺ calcd for $C_{13}H_{20}ClN_2O_2Si$: 299.10; found: 298.98.

Step 4: 6-chloro-1-((2-(trimethylsilyl)ethoxy)methyl)-1H-pyrrolo[3,2-c]pyridin-2(3H)-one (188 mg, 0.629 mmol) was dissolved with iodomethane (0.2 mL, 3.2 mmol) in THF (4 mL) under Ar in a 78° C. bath. A 1.0 M solution of LiHMDS in THF (1.6 mL, 1.6 mmol) was added over 30 s. The mixture was let warm to r.t. and was stirred for 25 h. Additional portions of iodomethane (0.2 mL, 3.2 mmol) and LiHMDS solution (0.63 mL, 0.63 mmol) were then added, and the mixture was allowed to stir 1 h. The mixture was then partitioned between water and EtOAc, and the organic phase was dried over $Na_2SO_4$, filtered, and concentrated to afford a crude residue that was purified by silica gel chromatography (0-50% EtOAc in hexanes) to afford 6-chloro-3,3-dimethyl-1-((2-(trimethylsilyl)ethoxy)methyl)-1H-pyrrolo[3,2-c]pyridin-2(3H)-one 7.55 (136 mg). LCMS-ESI⁺ (m/z): [M+H]⁺ calcd for $C_{15}H_{24}ClN_2O_2Si$: 327.13; found: 326.96.

Example 7.56

Preparation of tert-butyl 3-((2-bromo-5-chlorophenyl)carbamoyl)azetidine-1-carboxylate

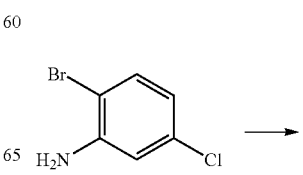

-continued

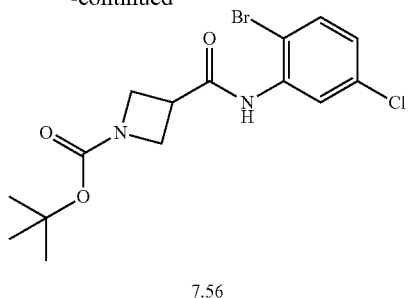

7.56

HATU (980 mg, 2.58 mmol) was added to a mixture of 2-bromo-5-chloroaniline (352 mg, 1.7 mmol) and 1-(tert-butoxycarbonyl)azetidine-3-carboxylic acid (402 mg, 2 mmol) in Acetonitrile (8 mL) at room temperature followed by DIPEA (0.74 mL, 4.26 mmol). After stifling overnight, reaction mixture was concentrated under reduced pressure and resulting residue was purified via silica gel column chromatography (0-50% ethyl acetate/hexanes) to yield tert-butyl 3-((2-bromo-5-chlorophenyl)carbamoyl)azetidine-1-carboxylate 7.56 (490 mg). LCMS-ESI+ (m/z): [M+H]+ calcd for $C_{15}H_{19}BrClN_2O_3$: 389.02; found: 389.57.

Example 7.57

Preparation of tert-butyl 3-((2-bromo-5-chlorophenyl)(methyl)carbamoyl)azetidine-1-carboxylate

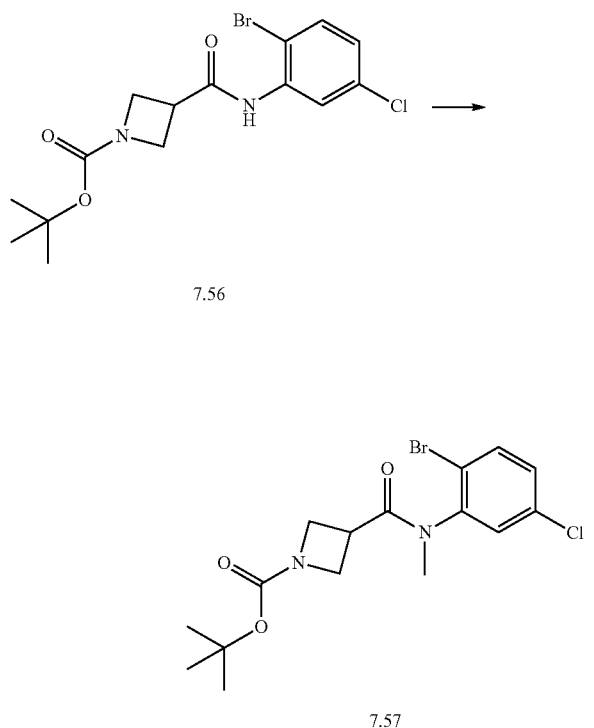

A solution of tert-butyl 3-((2-bromo-5-chlorophenyl)carbamoyl)azetidine-1-carboxylate 7.56 (400 mg, 1.03 mmol) in THF (3 mL) was cooled 0° C. Sodium hydride (60%, 63 mg, 1.58 mmol) was added and mixture stirred at 0° C. for 15 minutes. Iodomethane (0.45 mL, 7.23 mmol) was then added dropwise and the mixture was warmed to rt and stirred overnight. Reaction mixture was quenched with water and taken up in EtOAc. Layers were separated, and aqueous was extracted with ethyl acetate. Combined organics were washed with brine, dried (Na2SO4), filtered, concentrated under reduced pressure. The resulting residue was purified via silica gel column chromatography (0-35% ethyl acetate/hexanes) to yield tert-butyl 3-((2-bromo-5-chlorophenyl)(methyl)carbamoyl)azetidine-1-carboxylate 7.57 (393 mg). LCMS-ESI+ (m/z): [M+H]+ calcd for $C_{16}H_{21}BrClN_2O_3$: 402.03; found: 402.75.

Example 7.58

Preparation of tert-butyl 6'-chloro-1'-methyl-2'-oxospiro[azetidine-3,3'-indoline]-1-carboxylate

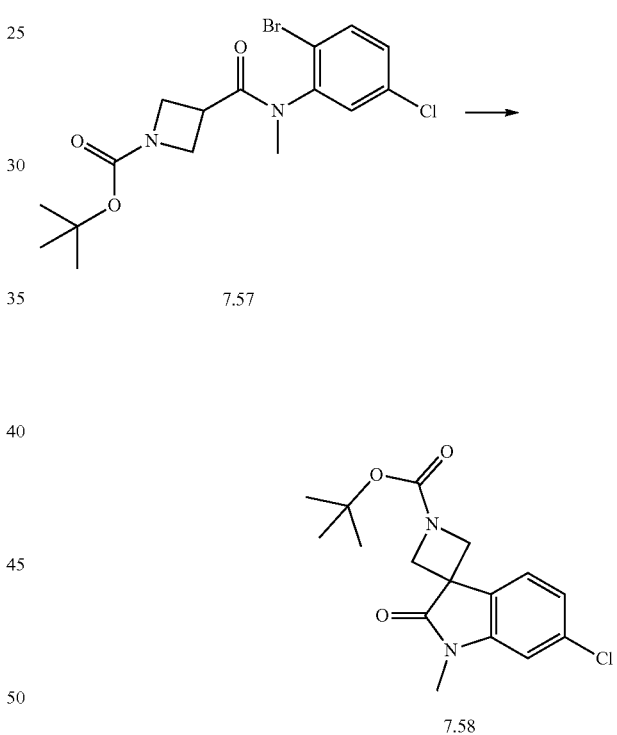

tert-butyl 3-((2-bromo-5-chlorophenyl)(methyl)carbamoyl)azetidine-1-carboxylate 7.57 (112 mg, 0.28 mmol), palladium acetate (6.6 mg, 0.03 mmol), tricyclohexylphosphine (8.4 mg, 0.03 mmol), and sodium t-butoxide (42 mg, 0.44 mmol) were added to a flask and system was evacuated and placed under argon. Dioxane (2 mL) was added and mixture was heated at 80° C. for 20 hours. After cooling to rt, mixture was poured into 50% saturated NH4Cl(aq) and extracted with ethyl acetate. Layers were separated and organics were dried (Na2SO4), filtered, and concentrated under reduced pressure. The resulting residue was purified via silica gel column chromatography (0-30% ethyl acetate/hexanes) to yield tert-butyl 6'-chloro-1'-methyl-2'-oxospiro[azetidine-3,3'-indoline]-1-carboxylate 7.58 (63 mg).

LCMS-ESI⁺ (m/z): [M+H]⁺ calcd for $C_{16}H_{20}ClN_2O_3$: 323.11; found: 323.40.

Example 7.59

Preparation of tert-butyl 1'-methyl-2'-oxo-6'-(4,4,5,5-tetramethyl-1,3,2-dioxaborolan-2-yl)spiro[azetidine-3,3'-indoline]-1-carboxylate

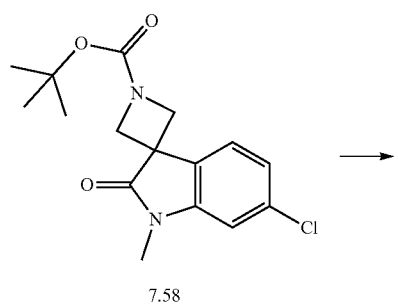

7.58

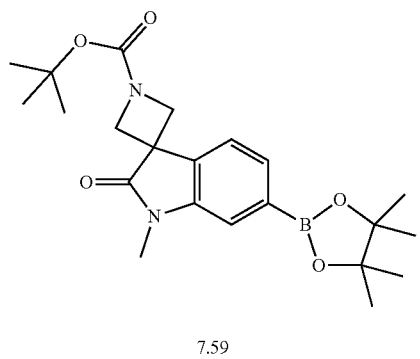

7.59 tert-butyl 6'-chloro-1'-methyl-2'-oxospiro[azetidine-3,3'-indoline]-1-carboxylate 7.58 (53 mg, 0.16 mmol), potassium acetate (50 mg, 0.51 mmol), bis(pinacolato)diboron (128 mg, 0.5 mmol), Tris(dibenzylideneacetone)dipalladium (9.7 mg, 0.01 mmol), and XPhos (18 mg, 0.04 mmol) were added to a flask and system was placed under argon. Reagents were taken up in dioxane (1.5 mL) and system again evacuated and placed under argon. Mixture was then heated at 105° C. for 20 hours. After cooling to rt, mixture was diluted with ethyl acetate and filtered over celite, washing with additional ethyl acetate. The filtrate was concentrated under reduced pressure and the resulting residue was purified via silica gel column chromatography (0-40% ethyl acetate/hexanes) to yield tert-butyl 1'-methyl-2'-oxo-6'-(4,4,5,5-tetramethyl-1,3,2-dioxaborolan-2-yl)spiro[azetidine-3,3'-indoline]-1-carboxylate 7.59 (68 mg). LCMS-ESI⁺ (m/z): [M+H]⁺ calcd for $C_{22}H_{32}BN_2O_5$: 415.23; found: 415.21.

Example 7.60

Preparation of 2-(4-(4,4,5,5-tetramethyl-1,3,2-dioxaborolan-2-yl)phenyl)propan-2-ol

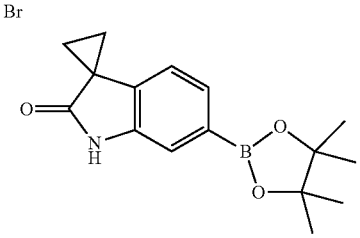

7.60

2-(4-(4,4,5,5-tetramethyl-1,3,2-dioxaborolan-2-yl)phenyl)propan-2-ol 7.60 was prepared using a procedure analogous to that used for Example 7.32 (Step 2). The material was used without further purification in subsequent steps.

Example 7.61

6'-(4,4,5,5-tetramethyl-1,3,2-dioxaborolan-2-yl)spiro[cyclopropane-1,3'-indolin]-2'-one 7.61

A mixture 6'-bromospiro[cyclopropane-1,3'-indolin]-2'-one 3 (4 g, 16.76 mmol), bis(pinacolato)diboron (6.7 g, 26.2 mmol), Dichloro[1,1'-bis(diphenylphosphino)ferrocene]palladium(II) methylene chloride adduct (3.6 g, 4.4 mmol) and potassium acetate (6.4 g, 65.5 mmol) in DMF (50 mL) under nitrogen atmosphere was stirred at 90° C. for 5 h. After this time, the mixture was cooled to room temperature, partitioned between water (500 mL) and ethyl acetate (500 mL) and filtered. The filtrate layers were separated and the aqueous phase extracted with ethyl acetate (2×500 mL). The combined organic layers were dried over sodium sulfate, filtered and the filtrate concentrated under reduced pressure. The residue was purified by silica gel chromatography (PE:

EA=6:1) to provide 6'-(4,4,5,5-tetramethyl-1,3,2-dioxaborolan-2-yl)spiro[cyclopropane-1,3'-indolin]-2'-one 7.61 (4.2 g). LCMS-ESI$^+$ (m/z): [M+H]$^+$ calcd for C$_{16}$H$_{21}$BNO$_3$: 286.2; found: 286.1.

Example 7.62

1,3-dimethyl-5-(4,4,5,5-tetramethyl-1,3,2-dioxaborolan-2-yl)-1H-benzo[d]imidazol-2(3H)-one

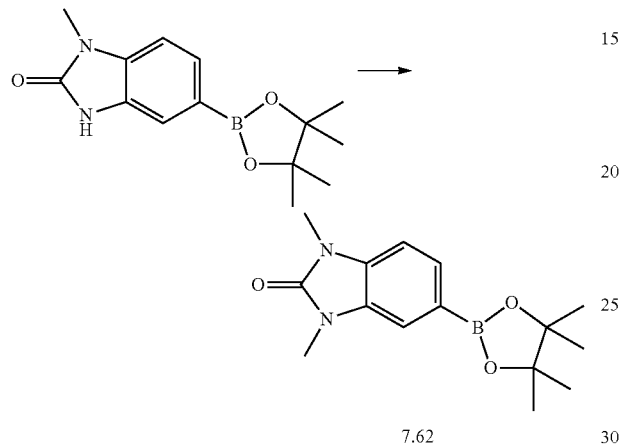

7.62

To a solution of 1-methyl-5-(4,4,5,5-tetramethyl-1,3,2-dioxaborolan-2-yl)-1H-benzo[d]imidazol-2(3H)-one (235 mg, 0.857 mmol) and iodomethane (0.267 mL, 4.29 mmol) in DMF (10 mL) was added K$_2$CO$_3$ (592 mg, 4.29 mmol). The reaction mixture was stirred for 23 h and the product was then precipitated with water. The title compound was collected by filtration. LCMS-ESI$^+$ (m/z): [M+H]$^+$ calcd for C$_{15}$H$_{22}$BN$_2$O$_3$: 289.2; found: 289.1.

Example 7.63

1-(4-(4,4,5,5-tetramethyl-1,3,2-dioxaborolan-2-yl)phenyl)cyclopropanol

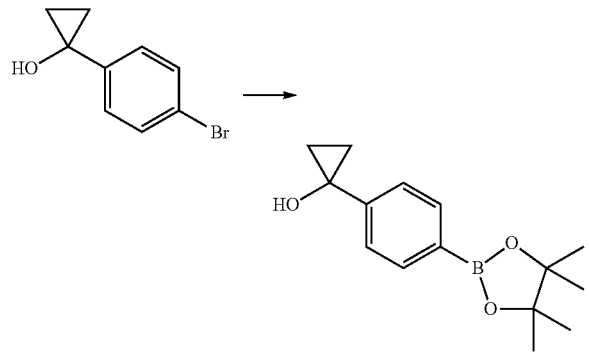

7.63

1-(4-bromophenyl)cyclopropanol (250 mg, 1.17 mmol), potassium acetate (177 mg, 1.8 mmol), Bis(Pinacolato)Diboron (449 mg, 1.77 mmol), and Dichloro 1,1-bis(diphenylphosphino)ferrocene palladium(II) dichloromethane (44 mg, 0.06 mmol) were added to a flask and system was placed under argon. Reagents were taken up in dioxane (10 mL) and system was again evacuated and placed under argon. Mixture was heated at 100° C. for 17 hours. After cooling to room temperature, mixture was filtered over celite, washing with ethyl acetate. Filtrate was concentrated under reduced pressure and resulting residue was purified via silica gel column chromatography (0-50% ethyl acetate in hexanes) to yield 1-(4-(4,4,5,5-tetramethyl-1,3,2-dioxaborolan-2-yl)phenyl)cyclopropanol 7.63.

$^1$H NMR (400 MHz, CDCl$_3$) δ 7.81-7.74 (m, 2H), 7.32-7.27 (m, 2H), 1.36 (s, 1H), 1.34 (s, 12H), 1.32-1.28 (m, 2H), 1.12-1.04 (m, 2H).

Biological Examples

Example 7

High Throughput Syk Biochemical Assay

Syk activity was measured using KinEASE (Cisbio), a time-resolved fluorescence resonance energy transfer (TR-FRET) immunoassay. In this assay, Syk-catalyzes the phosporylation of a XL665-labeled peptide substrate. Europium conjugated phospho-tyrosine specific antibody binds the resulting phosphorylated peptide. Formation of phosphorylated peptide is quantified by TR-FRET with Europium as the donor and XL665 the acceptor in a 2-step endpoint assay. In brief, test compounds serially diluted in DMSO were delivered into Corning white, low volume, non-binding 384 well plates using the Echo 550 acoustic liquid dispenser (Labcyte®). Syk enzyme and substrates were dispensed into assay plates using a Multi-Flo (Bio-Tek Instruments). The standard 5 µL reaction mixture contained 20 µM ATP, 1 µM biotinylated peptide, 0.015 nM of Syk in reaction buffer (50 mM Hepes, pH 7.0, 0.02% NaN$_3$, 0.1% BSA, 0.1 mM Orthovanadate, 5 mM MgCl$_2$, 1 mM DTT, 0.025% NP-40). After 30 min of incubation at room temperature, 5 µL of Stop and Detect Solution (1:200 Europium Cryptate labeled anti-phosphorylated peptide antibody solution and 125 nM strepavidin-XL665 Tracer in a 50 mM Hepes pH 7.0 detection buffer containing sufficient EDTA) was added. The plate was then further incubated for 120 minutes at room temperature and read using an Envision 2103 Multilabeled reader (PerkinElmer) with excitation/emission/FRET emission at 340 nm/615 nm/665 nm, respectively. Fluorescence intensities at 615 nm and 665 nm emission wavelengths were expressed as a ratio (665 nm/615 nm). Percent inhibition was calculated as follows:

% Inhibition=100×(Ratio$_{Sample}$−Ratio$_{0\% \ Inhibition}$)/(Ratio$_{100\% \ Inhibition}$−Ratio$_{0\% \ Inhibition}$)

where 0.1% DMSO (0% inhibition) was the negative control and 1 uM K252a (100% inhibition) was used as the positive control.

TABLE D

| Compound | IC$_{50}$ (nM) |
|---|---|
| (R)-4-((R)-1-(6-(3,4-dimethoxyphenyl)-3-methyl-3H-imidazo[4,5-c]pyridin-4-yloxy)ethyl)pyrrolidin-2-one | 5.1876 |
| (R)-4-((R)-1-(6-(3,4-dimethoxyphenyl)-3-ethyl-3H-imidazo[4,5-c]pyridin-4-yloxy)ethyl)pyrrolidin-2-one | 3.0492 |
| (R)-4-((S)-1-(6-(3,4-dimethoxyphenyl)-3-methyl-3H-imidazo[4,5-c]pyridin-4-yloxy)ethyl)pyrrolidin-2-one | |
| (R)-4-((R)-1-(3-cyclopropyl-6-(3,4-dimethoxyphenyl)-3H-imidazo[4,5-c]pyridin-4-yloxy)ethyl)pyrrolidin-2-one | 1.5984 |
| (R)-4-((R)-1-(3-(difluoromethyl)-6-(3,4-dimethoxyphenyl)-3H-imidazo[4,5-c]pyridin-4-yloxy)ethyl)pyrrolidin-2-one | 1.1047 |
| (R)-4-((R)-1-(3-methyl-6-(3,4,5-trimethoxyphenyl)-3H-imidazo[4,5-c]pyridin-4-yloxy)ethyl)pyrrolidin-2-one | 5.2552 |
| (R)-4-((R)-1-(6-(1-tert-butyl-1H-pyrazol-4-yl)-3-methyl-3H-imidazo[4,5-c]pyridin-4-yloxy)ethyl)pyrrolidin-2-one | 4.9005 |
| (R)-4-((6-(3,4-dimethoxyphenyl)-3-methyl-3H-imidazo[4,5-c]pyridin-4-yloxy)methyl)pyrrolidin-2-one | |
| (R)-4-((R)-2-cyclopropyl-1-(6-(3,4-dimethoxyphenyl)-3-methyl-3H-imidazo[4,5-c]pyridin-4-yloxy)ethyl)pyrrolidin-2-one | |
| (R)-4-((R)-1-(3-methyl-6-(6-morpholinopyridin-3-yl)-3H-imidazo[4,5-c]pyridin-4-yloxy)ethyl)pyrrolidin-2-one | 11.5081 |
| (R)-4-((R)-1-(3-methyl-6-(4-morpholinophenyl)-3H-imidazo[4,5-c]pyridin-4-yloxy)ethyl)pyrrolidin-2-one | 4.5968 |
| (R)-4-((R)-1-(6-(3,4-dimethoxyphenyl)-3H-imidazo[4,5-c]pyridin-4-yloxy)ethyl)pyrrolidin-2-one | 512.552 |
| (R)-4-((R)-1-(6-(3,4-dimethoxyphenyl)-3-isopropyl-3H-imidazo[4,5-c]pyridin-4-yloxy)ethyl)pyrrolidin-2-one | 3.3869 |
| 4-(3-methyl-4-((R)-1-((R)-5-oxopyrrolidin-3-yl)ethoxy)-3H-imidazo[4,5-c]pyridin-6-yl)benzonitrile | 28.3718 |
| (R)-4-((R)-1-((5-(3,4-dimethoxyphenyl)-1-methyl-1H-benzo[d]imidazol-7-yl)oxy)ethyl)pyrrolidin-2-one | 38.2421 |
| (4R)-4-((1R)-1-(6-(3,4-dimethoxyphenyl)-2,3-dimethyl-3a,7a-dihydro-3H-imidazo[4,5-c]pyridin-4-yloxy)ethyl)pyrrolidin-2-one | 25.3578 |
| (R)-4-((R)-1-(6-(2-tert-butylthiazol-4-yl)-3-methyl-3H-imidazo[4,5-c]pyridin-4-yloxy)ethyl)pyrrolidin-2-one | 19.2911 |
| (R)-4-((R)-1-(6-(3,4-dimethoxyphenyl)-3-(2,2,2-trifluoroethyl)-3H-imidazo[4,5-c]pyridin-4-yloxy)ethyl)pyrrolidin-2-one | 51.3458 |
| (R)-4-((R)-1-((5-(3,4-dimethoxyphenyl)benzo[d]thiazol-7-yl)oxy)ethyl)pyrrolidin-2-one | 5.0042 |
| (R)-4-((R)-1-((5-(1-(tert-butyl)-1H-pyrazol-4-yl)benzo[d]thiazol-7-yl)oxy)ethyl)pyrrolidin-2-one | 0.8936 |
| (R)-4-((R)-1-(6-(1-tert-butyl-1H-pyrazol-4-yl)-3-(difluoromethyl)-3H-imidazo[4,5-c]pyridin-4-yloxy)ethyl)pyrrolidin-2-one | 1.2181 |
| (R)-4-((S)-1-(6-(1-tert-butyl-1H-pyrazol-4-yl)-3-methyl-3H-imidazo[4,5-c]pyridin-4-yloxy)-2-fluoroethyl)pyrrolidin-2-one | 20.0617 |
| (R)-4-((S)-1-(6-(1-tert-butyl-1H-pyrazol-4-yl)-3-methyl-3H-imidazo[4,5-c]pyridin-4-yloxy)-2-methoxyethyl)pyrrolidin-2-one | 186.2 |
| (R)-4-((R)-1-(6-(3,4-dimethoxyphenyl)-3-(oxetan-3-yl)-3H-imidazo[4,5-c]pyridin-4-yloxy)ethyl)pyrrolidin-2-one | 54.1457 |
| (R)-4-((R)-1-(3-(2,2-difluoroethyl)-6-(3,4-dimethoxyphenyl)-3H-imidazo[4,5-c]pyridin-4-yloxy)ethyl)pyrrolidin-2-one | 19.5448 |
| (R)-4-((R)-1-(6-(3,4-dimethoxyphenyl)-3-(fluoromethyl)-3H-imidazo[4,5-c]pyridin-4-yloxy)ethyl)pyrrolidin-2-one | 2.4893 |
| (R)-4-((R)-1-(6-(1-(2,2-difluoroethyl)-1H-pyrazol-4-yl)-3-methyl-3H-imidazo[4,5-c]pyridin-4-yloxy)ethyl)pyrrolidin-2-one | 17.7349 |
| (R)-4-((R)-1-(6-(3-fluoro-4-methoxyphenyl)-3-methyl-3H-imidazo[4,5-c]pyridin-4-yloxy)ethyl)pyrrolidin-2-one | 17.1876 |
| 2-methoxy-5-(3-methyl-4-((R)-1-((R)-5-oxopyrrolidin-3-yl)ethoxy)-3H-imidazo[4,5-c]pyridin-6-yl)benzonitrile2-methoxy-5-(3-methyl-4-((R)-1-((R)-5-oxopyrrolidin-3-yl)ethoxy)-3H-imidazo[4,5-c]pyridin-6-yl)benzonitrile | 16.6503 |
| (R)-4-((R)-1-(6-(1-cyclopropyl-1H-pyrazol-4-yl)-3-methyl-3H-imidazo[4,5-c]pyridin-4-yloxy)ethyl)pyrrolidin-2-one | 14.0031 |
| (R)-4-((R)-1-(6-(1-cyclobutyl-1H-pyrazol-4-yl)-3-methyl-3H-imidazo[4,5-c]pyridin-4-yloxy)ethyl)pyrrolidin-2-one | 7.6204 |
| (R)-4-((R)-1-(6-(1-isobutyl-1H-pyrazol-4-yl)-3-methyl-3H-imidazo[4,5-c]pyridin-4-yloxy)ethyl)pyrrolidin-2-one | 15.9082 |
| (R)-4-((R)-1-(6-(1,5-dimethyl-1H-pyrazol-4-yl)-3-methyl-3H-imidazo[4,5-c]pyridin-4-yloxy)ethyl)pyrrolidin-2-one | 41.7356 |
| (R)-4-((R)-1-(3-methyl-6-(1-(oxetan-3-yl)-1H-pyrazol-4-yl)-3H-imidazo[4,5-c]pyridin-4-yloxy)ethyl)pyrrolidin-2-one | 23.5288 |
| (R)-4-((R)-1-(6-(1-(2-fluoroethyl)-1H-pyrazol-4-yl)-3-methyl-3H-imidazo[4,5-c]pyridin-4-yloxy)ethyl)pyrrolidin-2-one | 13.2055 |
| (R)-4-((R)-1-(3-methyl-6-(pyrazolo[1,5-a]pyridin-3-yl)-3H-imidazo[4,5-c]pyridin-4-yloxy)ethyl)pyrrolidin-2-one | 12.7331 |
| (R)-4-((R)-1-(6-(2,2-difluorobenzo[d][1,3]dioxol-5-yl)-3-methyl-3H-imidazo[4,5-c]pyridin-4-yloxy)ethyl)pyrrolidin-2-one | 147.936 |

TABLE D-continued

| Compound | IC$_{50}$ (nM) |
|---|---|
| (R)-4-((R)-1-(3-methyl-6-(4-methyl-3,4-dihydro-2H-benzo[b][1,4]oxazin-6-yl)-3H-imidazo[4,5-c]pyridin-4-yloxy)ethyl)pyrrolidin-2-one | 13.4538 |
| (R)-4-((R)-1-(6-(3,4-dihydro-2H-benzo[b][1,4]oxazin-6-yl)-3-methyl-3H-imidazo[4,5-c]pyridin-4-yloxy)ethyl)pyrrolidin-2-one | 4.0295 |
| (R)-4-((R)-1-(6-(2-tert-butylthiazol-5-yl)-3-methyl-3H-imidazo[4,5-c]pyridin-4-yloxy)ethyl)pyrrolidin-2-one | 9.7312 |
| (R)-4-((R)-1-(3-methyl-6-(1-(2,2,2-trifluoroethyl)-1H-pyrazol-4-yl)-3H-imidazo[4,5-c]pyridin-4-yloxy)ethyl)pyrrolidin-2-one | 20.8051 |
| (R)-4-((R)-1-(6-(5,6-dimethoxypyridin-2-yl)-3-methyl-3H-imidazo[4,5-c]pyridin-4-yloxy)ethyl)pyrrolidin-2-one | 34.0249 |
| (R)-4-((R)-1-(3-methyl-6-phenyl-3H-imidazo[4,5-c]pyridin-4-yloxy)ethyl)pyrrolidin-2-one | 33.8326 |
| (R)-4-((R)-1-(6-cyclohexenyl-3-methyl-3H-imidazo[4,5-c]pyridin-4-yloxy)ethyl)pyrrolidin-2-one | 123.592 |
| (R)-4-((R)-1-(3-methyl-6-(3-morpholinophenyl)-3H-imidazo[4,5-c]pyridin-4-yloxy)ethyl)pyrrolidin-2-one | 102.278 |
| 4-(3-methyl-4-((R)-1-((R)-5-oxopyrrolidin-3-yl)ethoxy)-3H-imidazo[4,5-c]pyridin-6-yl)pyridin-2(1H)-one | 97.4958 |
| 7-(3-methyl-4-((R)-1-((R)-5-oxopyrrolidin-3-yl)ethoxy)-3H-imidazo[4,5-c]pyridin-6-yl)-3,4-dihydrobenzo[f][1,4]oxazepin-5(2H)-one | 30.5839 |
| (R)-4-((R)-1-(3-methyl-6-(4-methyl-3,4-dihydro-2H-benzo[b][1,4]oxazin-7-yl)-3H-imidazo[4,5-c]pyridin-4-yloxy)ethyl)pyrrolidin-2-one | 8.9305 |
| (R)-4-((R)-1-(6-(1-isopropyl-1H-pyrazol-4-yl)-3-methyl-3H-imidazo[4,5-c]pyridin-4-yloxy)ethyl)pyrrolidin-2-one | 8.6515 |
| (R)-4-((R)-1-(3-methyl-6-(1-(tetrahydro-2H-pyran-4-yl)-1H-pyrazol-4-yl)-3H-imidazo[4,5-c]pyridin-4-yloxy)ethyl)pyrrolidin-2-one | 10.239 |
| (R)-4-((R)-1-(3-methyl-6-(1-methyl-1H-pyrazol-4-yl)-3H-imidazo[4,5-c]pyridin-4-yloxy)ethyl)pyrrolidin-2-one | 24.268 |
| (R)-4-((R)-1-((5-(5,6-dimethoxypyridin-2-yl)benzo[d]thiazol-7-yl)oxy)ethyl)pyrrolidin-2-one | 0.6887 |
| (R)-4-((R)-1-((5-(4-morpholinophenyl)benzo[d]thiazol-7-yl)oxy)ethyl)pyrrolidin-2-one | 1.8214 |
| (S)-4-((S)-1-((5-(2-(tert-butyl)thiazol-5-yl)benzo[d]thiazol-7-yl)oxy)ethyl)pyrrolidin-2-one | 1.4953 |
| ((R)-4-((R)-1-(6-(1-tert-butyl-1H-pyrazol-4-yl)-3-methyl-3H-imidazo[4,5-c]pyridin-4-yloxy)but-3-enyl)pyrrolidin-2-one | 18.8864 |
| (R)-4-((R)-1-(6-(1-tert-butyl-1H-pyrazol-4-yl)-3-methyl-3H-imidazo[4,5-c]pyridin-4-yloxy)-3-methoxypropyl)pyrrolidin-2-one | 170.983 |
| (R)-4-((R)-1-(6-(1-tert-butyl-1H-pyrazol-4-yl)-3-methyl-3H-imidazo[4,5-c]pyridin-4-yloxy)propyl)pyrrolidin-2-one | 24.0461 |
| (R)-4-((R)-1-(6-(benzo[d]thiazol-4-yl)-3-methyl-3H-imidazo[4,5-c]pyridin-4-yloxy)ethyl)pyrrolidin-2-one | 184.431 |
| (R)-4-((R)-1-((5-(1-cyclobutyl-1H-pyrazol-4-yl)benzo[d]thiazol-7-yl)oxy)ethyl)pyrrolidin-2-one | 0.6928 |
| (R)-4-((R)-1-([4,5'-bibenzo[d]thiazol]-7'-yloxy)ethyl)pyrrolidin-2-one | 105.497 |
| (R)-4-((R)-1-(3-methyl-6-(5-methyl-1H-pyrazol-3-yl)-3H-imidazo[4,5-c]pyridin-4-yloxy)ethyl)pyrrolidin-2-one | 22.835 |
| (R)-4-((R)-1-(6-(1-(difluoromethyl)-1H-pyrazol-4-yl)-3-methyl-3H-imidazo[4,5-c]pyridin-4-yloxy)ethyl)pyrrolidin-2-one | 32.7938 |
| (R)-4-((R)-1-((6-(1-(tert-butyl)-1H-pyrazol-4-yl)pyrazolo[1,5-a]pyridin-4-yl)oxy)ethyl)pyrrolidin-2-one | 35.5257 |
| (R)-4-((R)-1-((6-(3,4-dimethoxyphenyl)pyrazolo[1,5-a]pyridin-4-yl)oxy)ethyl)pyrrolidin-2-one | 39.1064 |
| (R)-4-((R)-1-((5-(1-(2,2-difluoroethyl)-1H-pyrazol-4-yl)benzo[d]thiazol-7-yl)oxy)ethyl)pyrrolidin-2-one | 1.2392 |
| (R)-4-((R)-1-((5-(1-isopropyl-1H-pyrazol-4-yl)benzo[d]thiazol-7-yl)oxy)ethyl)pyrrolidin-2-one | 0.6974 |
| (R)-4-((R)-1-(3-methyl-6-(3-(methylsulfonyl)phenyl)-3H-imidazo[4,5-c]pyridin-4-yloxy)ethyl)pyrrolidin-2-one | 42.5448 |
| (R)-4-((R)-1-(3-(difluoromethyl)-6-(4-morpholinophenyl)-3H-imidazo[4,5-c]pyridin-4-yloxy)ethyl)pyrrolidin-2-one | 1.5498 |
| (R)-4-((R)-1-(6-(1-(2,2-difluoroethyl)-1H-pyrazol-4-yl)-3-(difluoromethyl)-3H-imidazo[4,5-c]pyridin-4-yloxy)ethyl)pyrrolidin-2-one | 3.3058 |
| (R)-4-((R)-1-(3-(difluoromethyl)-6-(4-morpholinophenyl)-3H-imidazo[4,5-c]pyridin-4-yloxy)ethyl)pyrrolidin-2-one | 1.2548 |
| (R)-4-((R)-1-(3-methyl-6-(4-(piperazin-1-yl)phenyl)-3H-imidazo[4,5-c]pyridin-4-yloxy)ethyl)pyrrolidin-2-one | 8.2817 |
| (R)-4-((R)-1-(6-(1-tert-butyl-1H-pyrazol-4-yl)-3-methyl-3H-imidazo[4,5-c]pyridin-4-yloxy)-3,3-difluoropropyl)pyrrolidin-2-one | 94.8059 |
| tert-butyl 4-(4-(7-((R)-1-((R)-5-oxopyrrolidin-3-yl)ethoxy)benzo[d]thiazol-5-yl)phenyl)piperazine-1-carboxylate | 9.0427 |
| (R)-4-((R)-1-((5-(1-methyl-1H-thieno[3,2-c]pyrazol-5-yl)benzo[d]thiazol-7-yl)oxy)ethyl)pyrrolidin-2-one | 2.9714 |
| (R)-4-((R)-1-(6-(4-(dimethylamino)-3-methylphenyl)-3-methyl-3H-imidazo[4,5-c]pyridin-4-yloxy)ethyl)pyrrolidin-2-one | 5.3132 |

TABLE D-continued

| Compound | IC$_{50}$ (nM) |
|---|---|
| (R)-4-((R)-1-((6-(5,6-dimethoxypyridin-2-yl)pyrazolo[1,5-a]pyridin-4-yl)oxy)ethyl)pyrrolidin-2-one | 4.8408 |
| (R)-4-((R)-1-((6-(1-(tert-butyl)-1H-pyrazol-4-yl)pyrazolo[1,5-a]pyridin-4-yl)oxy)ethyl)pyrrolidin-2-one | 1.1449 |
| tert-butyl 4-(6-(7-((R)-1-((R)-5-oxopyrrolidin-3-yl)ethoxy)benzo[d]thiazol-5-yl)pyridin-3-yl)piperazine-1-carboxylate | 5.1582 |
| (R)-4-((R)-1-((5-(4-(4-(oxetan-3-yl)piperazin-1-yl)phenyl)benzo[d]thiazol-7-yl)oxy)ethyl)pyrrolidin-2-one | 0.6806 |
| (R)-4-((R)-1-((5-(5-morpholinopyridin-2-yl)benzo[d]thiazol-7-yl)oxy)ethyl)pyrrolidin-2-one | 1.8844 |
| (R)-4-((R)-1-((5-(1-ethyl-1H-pyrazol-3-yl)benzo[d]thiazol-7-yl)oxy)ethyl)pyrrolidin-2-one | 3.3572 |
| (R)-4-((R)-1-((3-methyl-6-(4-morpholinophenyl)pyrazolo[1,5-a]pyrazin-4-yl)oxy)ethyl)pyrrolidin-2-one | 0.3771 |
| (R)-4-((R)-1-((5-(4-(oxetan-3-yl)piperazin-1-yl)pyridin-2-yl)benzo[d]thiazol-7-yl)oxy)ethyl)pyrrolidin-2-one | 1.7272 |
| tert-butyl 4-(4-(3-methyl-4-((R)-1-((R)-5-oxopyrrolidin-3-yl)ethoxy)-3H-imidazo[4,5-c]pyridin-6-yl)phenyl)piperazine-1-carboxylate | 18.2577 |
| 2-methoxy-4-(3-methyl-4-((R)-1-((R)-5-oxopyrrolidin-3-yl)ethoxy)-3H-imidazo[4,5-c]pyridin-6-yl)benzonitrile | 74.1767 |
| (R)-4-((R)-1-(6-(4-fluoro-3-methoxyphenyl)-3-methyl-3H-imidazo[4,5-c]pyridin-4-yloxy)ethyl)pyrrolidin-2-one | 39.4976 |
| (R)-4-((R)-1-((5-(1-methyl-1H-thieno[3,2-c]pyrazol-5-yl)benzo[d]thiazol-7-yloxy)ethyl)pyrrolidin-2-one | 7.6818 |
| (R)-4-((R)-1-((5-(1-(tert-butyl)-1H-pyrazol-4-yl)-1-methyl-1H-benzo[d]imidazol-7-yl)oxy)ethyl)pyrrolidin-2-one | 5.3515 |
| (R)-4-((R)-1-((1-methyl-5-(6-(trifluoromethyl)pyridin-2-yl)-1H-benzo[d]imidazol-7-yl)oxy)ethyl)pyrrolidin-2-one | 190.973 |
| (R)-4-((R)-1-((5-(6-methoxypyridin-2-yl)-1-methyl-1H-benzo[d]imidazol-7-yl)oxy)ethyl)pyrrolidin-2-one | 45.6907 |
| (R)-4-((R)-1-(3-methyl-6-(4-(methylsulfonyl)phenyl)-3H-imidazo[4,5-c]pyridin-4-yloxy)ethyl)pyrrolidin-2-one | 27.7148 |
| (R)-4-((R)-1-(6-(6-methoxypyridin-3-yl)-3-methyl-3H-imidazo[4,5-c]pyridin-4-yloxy)ethyl)pyrrolidin-2-one | 71.7269 |
| (R)-4-((R)-1-(3-cyclobutyl-6-(3,4-dimethoxyphenyl)-3H-imidazo[4,5-c]pyridin-4-yloxy)ethyl)pyrrolidin-2-one | 23.4807 |
| (R)-4-((R)-1-((5-(3,4-dimethoxyphenyl)-2-methylbenzo[d]thiazol-7-yl)oxy)ethyl)pyrrolidin-2-one | 69.9737 |
| (R)-4-((R)-1-((5-(1-(tert-butyl)-1H-pyrazol-4-yl)-2-methylbenzo[d]thiazol-7-yl)oxy)ethyl)pyrrolidin-2-one | 22.1769 |
| (R)-4-((R)-1-((6-(4-morpholinophenyl)pyrazolo[1,5-a]pyridin-4-yl)oxy)ethyl)pyrrolidin-2-one | 7.8464 |
| (R)-4-((R)-1-((5-(5-(4-acetylpiperazin-1-yl)pyridin-2-yl)benzo[d]thiazol-7-yl)oxy)ethyl)pyrrolidin-2-one | 1.594 |
| (R)-4-((R)-1-((6-(benzo[d]thiazol-5-yl)-3-methyl-3H-imidazo[4,5-c]pyridin-4-yl)oxy)ethyl)pyrrolidin-2-one | 30.5965 |
| (R)-4-((R)-1-((3-methyl-6-(2-methylbenzo[d]thiazol-5-yl)-3H-imidazo[4,5-c]pyridin-4-yl)oxy)ethyl)pyrrolidin-2-one | 12.414 |
| (R)-4-((R)-1-((3-methyl-6-(1-methyl-1H-indazol-5-yl)-3H-imidazo[4,5-c]pyridin-4-yl)oxy)ethyl)pyrrolidin-2-one | 9.6151 |
| (R)-4-((R)-1-((3-methyl-6-(1-methyl-1H-indazol-6-yl)-3H-imidazo[4,5-c]pyridin-4-yl)oxy)ethyl)pyrrolidin-2-one | 16.8263 |
| (R)-4-((R)-1-((3-chloro-6-(3,4-dimethoxyphenyl)pyrazolo[1,5-a]pyridin-4-yl)oxy)ethyl)pyrrolidin-2-one | 1.0711 |
| (R)-4-((R)-1-((6-(1-(tert-butyl)-1H-pyrazol-4-yl)-3-chloropyrazolo[1,5-a]pyridin-4-yl)oxy)ethyl)pyrrolidin-2-one | 0.2709 |
| (R)-4-((R)-1-((3-chloro-6-(4-morpholinophenyl)pyrazolo[1,5-a]pyridin-4-yl)oxy)ethyl)pyrrolidin-2-one | 0.3102 |
| (R)-4-((R)-1-(3-methyl-6-(4-(4-(methylsulfonyl)piperazin-1-yl)phenyl)-3H-imidazo[4,5-c]pyridin-4-yloxy)ethyl)pyrrolidin-2-one | 4.4585 |
| (R)-4-((R)-1-((3-chloro-6-(3,4-dimethoxyphenyl)pyrazolo[1,5-a]pyrazin-4-yl)oxy)ethyl)pyrrolidin-2-one | 0.3205 |
| (R)-4-((R)-1-((6-(3,4-dimethoxyphenyl)-2-methylpyrazolo[1,5-a]pyrazin-4-yl)oxy)ethyl)pyrrolidin-2-one | 31.4222 |
| ((R)-4-((R)-1-(6-(3,4-dimethoxyphenyl)-3-methyl-3H-imidazo[4,5-c]pyridin-4-yloxy)propyl)pyrrolidin-2-one | 7.6297 |
| (R)-4-((R)-1-((5-(1-isopropyl-1H-pyrazol-3-yl)benzo[d]thiazol-7-yl)oxy)ethyl)pyrrolidin-2-one | 2.5159 |
| (R)-4-((R)-1-((6-(3,4-dimethoxyphenyl)-3,7-dimethylpyrazolo[1,5-a]pyridin-4-yl)oxy)ethyl)pyrrolidin-2-one | 53.678 |
| (R)-4-((R)-1-(3-methyl-6-(4-(4-(oxetan-3-yl)piperazin-1-yl)phenyl)-3H-imidazo[4,5-c]pyridin-4-yloxy)ethyl)pyrrolidin-2-one | 8.2144 |
| (R)-4-((R)-1-(6-(4-(4-acetylpiperazin-1-yl)phenyl)-3-methyl-3H-imidazo[4,5-c]pyridin-4-yloxy)ethyl)pyrrolidin-2-one | 3.142 |
| (R)-7-((R)-1-((3-(difluoromethyl)-6-(3,4-dimethoxyphenyl)-3H-imidazo[4,5-c]pyridin-4-yl)oxy)ethyl)-5-azaspiro[2.4]heptan-4-one | 37.9886 |
| (R)-7-((R)-1-((6-(1-(tert-butyl)-1H-pyrazol-4-yl)-3-(difluoromethyl)-3H-imidazo[4,5-c]pyridin-4-yl)oxy)ethyl)-5-azaspiro[2.4]heptan-4-one | 35.0577 |

TABLE D-continued

| Compound | IC$_{50}$ (nM) |
| --- | --- |
| (R)-4-((R)-1-((6-(1-(2,2-difluoroethyl)-1H-pyrazol-4-yl)pyrazolo[1,5-a]pyridin-4-yl)oxy)ethyl)pyrrolidin-2-one | 10.1744 |
| N,N-dimethyl-4-(3-methyl-4-((R)-1-((R)-5-oxopyrrolidin-3-yl)ethoxy)-3H-imidazo[4,5-c]pyridin-6-yl)benzenesulfonamide | 13.4118 |
| (R)-4-((R)-1-(3-(difluoromethyl)-6-(3,4-dimethoxyphenyl)-2-methyl-3H-imidazo[4,5-c]pyridin-4-yloxy)ethyl)pyrrolidin-2-one | 50.7922 |
| (R)-4-((R)-1-(3-cyclopropyl-6-(3,4-dimethoxyphenyl)-2-methyl-3H-imidazo[4,5-c]pyridin-4-yloxy)ethyl)pyrrolidin-2-one | 95.8387 |
| (R)-4-((R)-1-((5-(1-(tetrahydro-2H-pyran-4-yl)-1H-pyrazol-4-yl)benzo[d]thiazol-7-yl)oxy)ethyl)pyrrolidin-2-one | 0.6987 |
| (R)-4-((R)-1-((6-(1,3-dimethyl-1H-indazol-5-yl)-3-methyl-3H-imidazo[4,5-c]pyridin-4-yl)oxy)ethyl)pyrrolidin-2-one | 10.4832 |
| (R)-4-((R)-1-(6-(3,4-dimethoxyphenyl)-3-isopropyl-2-methyl-3H-imidazo[4,5-c]pyridin-4-yloxy)ethyl)pyrrolidin-2-one | 317.067 |
| (R)-4-((R)-1-((6-(3,4,5-trimethoxyphenyl)pyrazolo[1,5-a]pyridin-4-yl)oxy)ethyl)pyrrolidin-2-one | 85.0681 |
| (R)-4-((R)-1-((5-(5-(4-(tetrahydro-2H-pyran-4-yl)piperazin-1-yl)pyridin-2-yl)benzo[d]thiazol-7-yl)oxy)ethyl)pyrrolidin-2-one | 2.6215 |
| (R)-4-((R)-1-(6-(1-isopropyl-1H-pyrazol-4-yl)pyrazolo[1,5-a]pyridin-4-yloxy)ethyl)pyrrolidin-2-one | 4.1547 |

ALL NEW COMPOUNDS IN 2014

| Compound | Syk IC$_{50}$ (nM) |
| --- | --- |
| 5-(3-cyclopropyl-4-((R)-1-((R)-5-oxopyrrolidin-3-yl)ethoxy)-3H-imidazo[4,5-c]pyridin-6-yl)-3-methylbenzo[d]oxazol-2(3H)-one | 14.412 |
| 5-(3-cyclopropyl-4-((R)-1-((R)-5-oxopyrrolidin-3-yl)ethoxy)-3H-imidazo[4,5-c]pyridin-6-yl)-1,3-dimethyl-1H-benzo[d]imidazol-2(3H)-one | 4.837 |
| (R)-4-((R)-1-((3-cyclopropyl-6-(3-cyclopropyl-1H-indazol-6-yl)-3H-imidazo[4,5-c]pyridin-4-yl)oxy)ethyl)pyrrolidin-2-one | 6.123 |
| (R)-4-((R)-1-((3-cyclopropyl-6-(4-(1-hydroxycyclopropyl)phenyl)-3H-imidazo[4,5-c]pyridin-4-yl)oxy)ethyl)pyrrolidin-2-one | 8.518 |
| 6'-(3-cyclopropyl-4-((R)-1-((R)-5-oxopyrrolidin-3-yl)ethoxy)-3H-imidazo[4,5-c]pyridin-6-yl)-1,1'-dimethylspiro[azetidine-3,3'-indolin]-2'-one | 7.555 |
| (R)-4-((R)-1-((5-(6-aminopyridin-2-yl)-1-cyclopropyl-1H-benzo[d]imidazol-7-yl)oxy)ethyl)pyrrolidin-2-one | 8.429 |
| (R)-4-((R)-1-((1-cyclopropyl-5-(5-(4-morpholinopiperidin-1-yl)pyridin-2-yl)-1H-benzo[d]imidazol-7-yl)oxy)ethyl)pyrrolidin-2-one | 6.850 |
| (R)-4-((R)-1-((1-cyclopropyl-5-(5-(4-(oxetan-3-yl)piperidin-1-yl)pyridin-2-yl)-1H-benzo[d]imidazol-7-yl)oxy)ethyl)pyrrolidin-2-one | 4.651 |
| (4R)-4-((1R)-1-((5-(5-(6-oxa-3-azabicyclo[3.1.1]heptan-3-yl)pyridin-2-yl)-1-cyclopropyl-1H-benzo[d]imidazol-7-yl)oxy)ethyl)pyrrolidin-2-one | 5.574 |
| 1,4,4-trimethyl-7-(3-methyl-4-((R)-1-((R)-5-oxopyrrolidin-3-yl)ethoxy)-3H-imidazo[4,5-c]pyridin-6-yl)-1H-benzo[d][1,3]oxazin-2(4H)-one | 2.505 |
| 4,4-dimethyl-7-(3-methyl-4-((R)-1-((R)-5-oxopyrrolidin-3-yl)ethoxy)-3H-imidazo[4,5-c]pyridin-6-yl)-1H-benzo[d][1,3]oxazin-2(4H)-one | 0.935 |
| (R)-4-((R)-1-((6-(2-(1H-pyrazol-4-yl)pyridin-4-yl)-3-cyclopropyl-3H-imidazo[4,5-c]pyridin-4-yl)oxy)ethyl)pyrrolidin-2-one | 8.435 |
| 6-(3-cyclopropyl-4-((R)-1-((R)-5-oxopyrrolidin-3-yl)ethoxy)-3H-imidazo[4,5-c]pyridin-6-yl)-1'-(methylsulfonyl)spiro[indoline-3,4'-piperidin]-2-one | 1.085 |
| (R)-4-((R)-1-((1-cyclopropyl-5-(1-methyl-1H-pyrazol-4-yl)-1H-benzo[d]imidazol-7-yl)oxy)ethyl)pyrrolidin-2-one | 4.441 |
| (R)-4-((R)-1-((3-cyclopropyl-6-(1-(oxetan-3-yl)-1H-pyrazol-4-yl)-3H-imidazo[4,5-c]pyridin-4-yl)oxy)ethyl)pyrrolidin-2-one | 4.649 |
| (R)-4-((R)-1-((1-cyclopropyl-5-(1-(oxetan-3-yl)-1H-pyrazol-4-yl)-1H-benzo[d]imidazol-7-yl)oxy)ethyl)pyrrolidin-2-one | 3.212 |
| (R)-4-((R)-1-((5-(1-(tert-butyl)-1H-pyrazol-4-yl)-1-cyclopropyl-1H-benzo[d]imidazol-7-yl)oxy)ethyl)pyrrolidin-2-one | 0.454 |
| (R)-4-((R)-1-((3-cyclopropyl-6-(1-(pyridin-4-yl)-1H-pyrazol-4-yl)-3H-imidazo[4,5-c]pyridin-4-yl)oxy)ethyl)pyrrolidin-2-one | 8.286 |
| (R)-4-((R)-1-((1-cyclopropyl-5-(1-(pyridin-4-yl)-1H-pyrazol-4-yl)-1H-benzo[d]imidazol-7-yl)oxy)ethyl)pyrrolidin-2-one | 7.580 |
| (R)-4-((R)-1-((3-cyclopropyl-6-(1-(1-hydroxy-2-methylpropan-2-yl)-1H-pyrazol-4-yl)-3H-imidazo[4,5-c]pyridin-4-yl)oxy)ethyl)pyrrolidin-2-one | 3.430 |
| (R)-4-((R)-1-((1-cyclopropyl-5-(1-(1-hydroxy-2-methylpropan-2-yl)-1H-pyrazol-4-yl)-1H-benzo[d]imidazol-7-yl)oxy)ethyl)pyrrolidin-2-one | 1.992 |
| (R)-4-((R)-1-((3-cyclopropyl-6-(1-(2-hydroxy-2-methylpropyl)-1H-pyrazol-4-yl)-3H-imidazo[4,5-c]pyridin-4-yl)oxy)ethyl)pyrrolidin-2-one | 9.646 |

-continued

| Compound | Syk IC$_{50}$ (nM) |
|---|---|
| (R)-4-((R)-1-((1-cyclopropyl-5-(1-(2-hydroxy-2-methylpropyl)-1H-pyrazol-4-yl)-1H-benzo[d]imidazol-7-yl)oxy)ethyl)pyrrolidin-2-one | 1.726 |
| (R)-4-((R)-1-((1-cyclopropyl-5-(1-(1-(oxetan-3-yl)piperidin-4-yl)-1H-pyrazol-4-yl)-1H-benzo[d]imidazol-7-yl)oxy)ethyl)pyrrolidin-2-one | p |
| (R)-4-((R)-1-((3-cyclopropyl-6-(4-(3-morpholinoazetidin-1-yl)phenyl)-3H-imidazo[4,5-c]pyridin-4-yl)oxy)ethyl)pyrrolidin-2-one | 5.6859 |
| (R)-4-((R)-1-((3-cyclopropyl-6-(4-(5,6-dihydro-[1,2,4]triazolo[4,3-a]pyrazin-7(8H)-yl)phenyl)-3H-imidazo[4,5-c]pyridin-4-yl)oxy)ethyl)pyrrolidin-2-one | 1.3049 |
| (R)-4-((R)-1-((3-cyclopropyl-6-(4-(3-(trifluoromethyl)-5,6-dihydro-[1,2,4]triazolo[4,3-a]pyrazin-7(8H)-yl)phenyl)-3H-imidazo[4,5-c]pyridin-4-yl)oxy)ethyl)pyrrolidin-2-one | 2.1681 |
| (R)-4-((R)-1-((3-cyclopropyl-6-(3,4-dimethoxyphenyl)-3H-imidazo[4,5-c]pyridin-4-yl)oxy)ethyl)pyrrolidin-2-one | 6.5726 |
| (R)-4-((R)-1-((6-(3-chloro-4-(4-(oxetan-3-yl)piperazin-1-yl)phenyl)-3-cyclopropyl-3H-imidazo[4,5-c]pyridin-4-yl)oxy)ethyl)pyrrolidin-2-one | 2.7594 |
| (R)-4-((R)-1-((3-cyclopropyl-6-(2-fluoro-4-(4-(oxetan-3-yl)piperazin-1-yl)phenyl)-3H-imidazo[4,5-c]pyridin-4-yl)oxy)ethyl)pyrrolidin-2-one | 10.0651 |
| (R)-4-((R)-1-((1-cyclopropyl-5-(2-fluoro-4-(4-(oxetan-3-yl)piperazin-1-yl)phenyl)-1H-benzo[d]imidazol-7-yl)oxy)ethyl)pyrrolidin-2-one | 2.7594 |
| (R)-4-((R)-1-((3-methyl-6-(6-(4-(oxetan-3-yl)piperazin-1-yl)pyridin-3-yl)-3H-imidazo[4,5-c]pyridin-4-yl)oxy)ethyl)pyrrolidin-2-one | 12.4222 |
| (R)-4-((R)-1-((3-(difluoromethyl)-6-(6-(4-(oxetan-3-yl)piperazin-1-yl)pyridin-3-yl)-3H-imidazo[4,5-c]pyridin-4-yl)oxy)ethyl)pyrrolidin-2-one | 2.9 |
| (R)-4-((R)-1-((1-cyclopropyl-5-(3-methyl-4-(4-(oxetan-3-yl)piperazin-1-yl)phenyl)-1H-benzo[d]imidazol-7-yl)oxy)ethyl)pyrrolidin-2-one | 2.1488 |
| (R)-4-((R)-1-((3-cyclopropyl-6-(3-fluoro-4-(4-(methylsulfonyl)piperazin-1-yl)phenyl)-3H-imidazo[4,5-c]pyridin-4-yl)oxy)ethyl)pyrrolidin-2-one | 2.0175 |
| (R)-4-((R)-1-((3-cyclopropyl-6-(3-methyl-4-(4-(oxetan-3-yl)piperazin-1-yl)phenyl)-3H-imidazo[4,5-c]pyridin-4-yl)oxy)ethyl)pyrrolidin-2-one | 1.4351 |
| (R)-4-((R)-1-((1-cyclopropyl-5-(6-(4-(oxetan-3-yl)piperazin-1-yl)pyridin-3-yl)-1H-benzo[d]imidazol-7-yl)oxy)ethyl)pyrrolidin-2-one | 7.3801 |
| (R)-4-((R)-1-((1-cyclopropyl-5-(3-fluoro-4-(4-(oxetan-3-yl)piperazin-1-yl)phenyl)-1H-benzo[d]imidazol-7-yl)oxy)ethyl)pyrrolidin-2-one | 3.0831 |
| 5-(1-cyclopropyl-7-((R)-1-((R)-5-oxopyrrolidin-3-yl)ethoxy)-1H-benzo[d]imidazol-5-yl)-2-(4-(oxetan-3-yl)piperazin-1-yl)benzonitrile | 3.1972 |
| (R)-4-((R)-1-((3-cyclopropyl-6-(5-fluoro-6-(4-(oxetan-3-yl)piperazin-1-yl)pyridin-3-yl)-3H-imidazo[4,5-c]pyridin-4-yl)oxy)ethyl)pyrrolidin-2-one | 17.2199 |
| 5-(3-cyclopropyl-4-((R)-1-((R)-5-oxopyrrolidin-3-yl)ethoxy)-3H-imidazo[4,5-c]pyridin-6-yl)-2-(4-(oxetan-3-yl)piperazin-1-yl)benzonitrile | 5.2124 |
| (R)-4-((R)-1-((1-cyclopropyl-5-(5-(4-(oxetan-3-yl)piperazin-1-yl)pyridin-2-yl)-1H-benzo[d]imidazol-7-yl)oxy)ethyl)pyrrolidin-2-one | 4.7182 |
| (R)-4-((R)-1-((3-cyclopropyl-6-(3-fluoro-4-(4-(oxetan-3-yl)piperazin-1-yl)phenyl)-3H-imidazo[4,5-c]pyridin-4-yl)oxy)ethyl)pyrrolidin-2-one | 2.3688 |
| (R)-4-((R)-1-((3-cyclopropyl-6-(6-(4-(oxetan-3-yl)piperazin-1-yl)pyridin-3-yl)-3H-imidazo[4,5-c]pyridin-4-yl)oxy)ethyl)pyrrolidin-2-one | 3.6316 |
| (R)-4-((R)-1-((3-cyclopropyl-6-(4-(4-(ethylsulfonyl)piperazin-1-yl)phenyl)-3H-imidazo[4,5-c]pyridin-4-yl)oxy)ethyl)pyrrolidin-2-one | 1.0476 |
| (R)-4-((R)-1-((3-cyclopropyl-6-(4-(4-(isopropylsulfonyl)piperazin-1-yl)phenyl)-3H-imidazo[4,5-c]pyridin-4-yl)oxy)ethyl)pyrrolidin-2-one | 1.1186 |
| (R)-4-((R)-1-((3-cyclopropyl-6-(4-(4-(cyclopropylsulfonyl)piperazin-1-yl)phenyl)-3H-imidazo[4,5-c]pyridin-4-yl)oxy)ethyl)pyrrolidin-2-one | 1.2985 |
| (R)-4-((R)-1-((3-cyclopropyl-6-(4-(4-(oxetan-3-ylsulfonyl)piperazin-1-yl)phenyl)-3H-imidazo[4,5-c]pyridin-4-yl)oxy)ethyl)pyrrolidin-2-one | 1.3141 |
| (R)-4-((R)-1-((3-(2-hydroxyethyl)-6-(4-(4-(oxetan-3-yl)piperazin-1-yl)phenyl)-3H-imidazo[4,5-c]pyridin-4-yl)oxy)ethyl)pyrrolidin-2-one | 135.25 |
| (R)-4-(((3-cyclopropyl-6-(4-(4-(oxetan-3-yl)piperazin-1-yl)phenyl)-3H-imidazo[4,5-c]pyridin-4-yl)oxy)methyl)pyrrolidin-2-one | 65.334 |
| 6-(3-cyclopropyl-4-((R)-1-((R)-5-oxopyrrolidin-3-yl)ethoxy)-3H-imidazo[4,5-c]pyridin-6-yl)indolin-2-one | 1.746 |
| 6-(3-cyclopropyl-4-((R)-1-((R)-5-oxopyrrolidin-3-yl)ethoxy)-3H-imidazo[4,5-c]pyridin-6-yl)-1,3,3-trimethyl-1H-pyrrolo[3,2-b]pyridin-2(3H)-one | 8.846 |
| (R)-4-((R)-1-((1-cyclopropyl-5-(3,4-dihydro-2H-pyrido[3,2-b][1,4]oxazin-6-yl)-1H-benzo[d]imidazol-7-yl)oxy)ethyl)pyrrolidin-2-one | 4.756 |
| (R)-4-((R)-1-((1-cyclopropyl-5-(3,4-dihydro-2H-benzo[b][1,4]oxazin-6-yl)-1H-benzo[d]imidazol-7-yl)oxy)ethyl)pyrrolidin-2-one | 2.565 |
| (R)-4-((R)-1-((1-cyclopropyl-5-(6-(4-(oxetan-3-yl)piperazin-1-yl)pyridazin-3-yl)-1H-benzo[d]imidazol-7-yl)oxy)ethyl)pyrrolidin-2-one | 11.623 |
| (R)-4-((R)-1-((3-cyclopropyl-6-(3,3-dimethylindolin-6-yl)-3H-imidazo[4,5-c]pyridin-4-yl)oxy)ethyl)pyrrolidin-2-one | 2.327 |
| (R)-4-((R)-1-((3-cyclopropyl-6-(4-(1-(oxetan-3-yl)piperidin-4-yl)phenyl)-3H-imidazo[4,5-c]pyridin-4-yl)oxy)ethyl)pyrrolidin-2-one | 2.305 |

-continued

| Compound | Syk IC$_{50}$ (nM) |
|---|---|
| (4R)-4-((1R)-1-((6-(4-(3,6-diazabicyclo[3.1.1]heptan-3-yl)phenyl)-3-cyclopropyl-3H-imidazo[4,5-c]pyridin-4-yl)oxy)ethyl)pyrrolidin-2-one | 2.286 |
| (4R)-4-((1R)-1-((3-cyclopropyl-6-(4-(6-(oxetan-3-yl)-3,6-diazabicyclo[3.1.1]heptan-3-yl)phenyl)-3H-imidazo[4,5-c]pyridin-4-yl)oxy)ethyl)pyrrolidin-2-one | 2.69 |
| (R)-4-((R)-1-((1-cyclopropyl-5-(3,3-dimethylindolin-6-yl)-1H-benzo[d]imidazol-7-yl)oxy)ethyl)pyrrolidin-2-one | 9.107 |
| (4R)-4-((1R)-1-((6-(4-(6-oxa-3-azabicyclo[3.1.1]heptan-3-yl)phenyl)-3-cyclopropyl-3H-imidazo[4,5-c]pyridin-4-yl)oxy)ethyl)pyrrolidin-2-one | 3.208 |
| (R)-4-((R)-1-((3-cyclopropyl-6-(pyridin-4-yl)-3H-imidazo[4,5-c]pyridin-4-yl)oxy)ethyl)pyrrolidin-2-one | 11.86 |
| (R)-4-((R)-1-((1-cyclopropyl-5-(pyrimidin-4-yl)-1H-benzo[d]imidazol-7-yl)oxy)ethyl)pyrrolidin-2-one | 24.613 |
| (R)-4-((R)-1-((3-cyclopropyl-6-phenyl-3H-imidazo[4,5-c]pyridin-4-yl)oxy)ethyl)pyrrolidin-2-one | 12.489 |
| (R)-4-((R)-1-((3-cyclopropyl-6-(5,6-dimethoxypyridin-3-yl)-3H-imidazo[4,5-c]pyridin-4-yl)oxy)ethyl)pyrrolidin-2-one | 8.378 |
| (R)-4-((R)-1-((1-cyclopropyl-5-phenyl-1H-benzo[d]imidazol-7-yl)oxy)ethyl)pyrrolidin-2-one | 18.039 |
| (R)-4-((R)-1-((1-cyclopropyl-5-(pyrazin-2-yl)-1H-benzo[d]imidazol-7-yl)oxy)ethyl)pyrrolidin-2-one | 66.686 |
| (R)-4-((R)-1-((1-cyclopropyl-5-(pyridin-2-yl)-1H-benzo[d]imidazol-7-yl)oxy)ethyl)pyrrolidin-2-one | 10.55 |
| (R)-4-((R)-1-((3-cyclopropyl-6-(3-ethoxy-4-methoxyphenyl)-3H-imidazo[4,5-c]pyridin-4-yl)oxy)ethyl)pyrrolidin-2-one | 2.925 |
| (R)-4-((R)-1-((1-cyclopropyl-5-(3-ethoxy-4-methoxyphenyl)-1H-benzo[d]imidazol-7-yl)oxy)ethyl)pyrrolidin-2-one | 12.892 |
| (R)-4-((R)-1-((1-cyclopropyl-5-(1-methyl-1,2,3,4-tetrahydroquinoxalin-6-yl)-1H-benzo[d]imidazol-7-yl)oxy)ethyl)pyrrolidin-2-one | 3.833 |
| (R)-4-((R)-1-((3-cyclopropyl-6-(1-methyl-1,2,3,4-tetrahydroquinoxalin-6-yl)-3H-imidazo[4,5-c]pyridin-4-yl)oxy)ethyl)pyrrolidin-2-one | 2.249 |
| (R)-4-((R)-1-((1-cyclopropyl-5-(1-methyl-1H-indazol-5-yl)-1H-benzo[d]imidazol-7-yl)oxy)ethyl)pyrrolidin-2-one | 5.018 |
| (R)-4-((R)-1-((3-cyclopropyl-6-(4-(difluoromethoxy)-3-methoxyphenyl)-3H-imidazo[4,5-c]pyridin-4-yl)oxy)ethyl)pyrrolidin-2-one | 5.218 |
| (R)-4-((R)-1-((1-cyclopropyl-5-(4-(difluoromethoxy)-3-methoxyphenyl)-1H-benzo[d]imidazol-7-yl)oxy)ethyl)pyrrolidin-2-one | 23.075 |
| (R)-4-((R)-1-((3-cyclopropyl-6-(2,3-dihydrobenzo[b][1,4]dioxin-6-yl)-3H-imidazo[4,5-c]pyridin-4-yl)oxy)ethyl)pyrrolidin-2-one | 5.523 |
| (R)-4-((R)-1-((3-cyclopropyl-6-(4-ethoxy-3-methoxyphenyl)-3H-imidazo[4,5-c]pyridin-4-yl)oxy)ethyl)pyrrolidin-2-one | 2.459 |
| (R)-4-((R)-1-((3-cyclopropyl-6-(4-(2,2-difluoroethoxy)-3-methoxyphenyl)-3H-imidazo[4,5-c]pyridin-4-yl)oxy)ethyl)pyrrolidin-2-one | 2.784 |
| (R)-4-((R)-1-((3-cyclopropyl-6-(1,3-dimethyl-1H-indazol-5-yl)-3H-imidazo[4,5-c]pyridin-4-yl)oxy)ethyl)pyrrolidin-2-one | 3.461 |
| (R)-4-((R)-1-((3-cyclopropyl-6-(1-(2,2-difluoroethyl)-1H-indazol-5-yl)-3H-imidazo[4,5-c]pyridin-4-yl)oxy)ethyl)pyrrolidin-2-one | 1.809 |
| (R)-4-((R)-1-((1-cyclopropyl-5-(thiazol-2-yl)-1H-benzo[d]imidazol-7-yl)oxy)ethyl)pyrrolidin-2-one | 9.396 |
| (R)-4-((R)-1-((1-cyclopropyl-5-(2-(2-hydroxypropan-2-yl)thiazol-5-yl)-1H-benzo[d]imidazol-7-yl)oxy)ethyl)pyrrolidin-2-one | 1.4095 |
| (R)-4-((R)-1-((3-cyclopropyl-6-(2-morpholinothiazol-5-yl)-3H-imidazo[4,5-c]pyridin-4-yl)oxy)ethyl)pyrrolidin-2-one | 2.132 |
| (4R)-4-((1R)-1-((3-cyclopropyl-6-(2,3-dihydrothieno[2,3-c]pyridin-2-yl)-3H-imidazo[4,5-c]pyridin-4-yl)oxy)ethyl)pyrrolidin-2-one | 3.088 |
| (R)-4-((R)-1-((3-cyclopropyl-6-(3-methylisothiazol-5-yl)-3H-imidazo[4,5-c]pyridin-4-yl)oxy)ethyl)pyrrolidin-2-one | 2.265 |
| (R)-4-((R)-1-((1-cyclopropyl-5-(2-methylthiazol-4-yl)-1H-benzo[d]imidazol-7-yl)oxy)ethyl)pyrrolidin-2-one | 16.696 |
| (R)-4-((R)-1-((3-cyclopropyl-6-(2-(trifluoromethyl)thiazol-5-yl)-3H-imidazo[4,5-c]pyridin-4-yl)oxy)ethyl)pyrrolidin-2-one | 67.683 |
| (R)-4-((R)-1-((1-cyclopropyl-5-(1-(tetrahydro-2H-pyran-4-yl)-1H-pyrazol-5-yl)-1H-benzo[d]imidazol-7-yl)oxy)ethyl)pyrrolidin-2-one | 411.46 |
| (R)-4-((R)-1-((1-cyclopropyl-5-(4,5-dimethylthiazol-2-yl)-1H-benzo[d]imidazol-7-yl)oxy)ethyl)pyrrolidin-2-one | 1.406 |
| (R)-4-((R)-1-((5-(4-(tert-butyl)thiazol-2-yl)-1-cyclopropyl-1H-benzo[d]imidazol-7-yl)oxy)ethyl)pyrrolidin-2-one | 0.4420 |
| (R)-4-((R)-1-((3-cyclopropyl-6-(2-(2-hydroxypropan-2-yl)thiazol-5-yl)-3H-imidazo[4,5-c]pyridin-4-yl)oxy)ethyl)pyrrolidin-2-one | 7.538 |
| (R)-4-((R)-1-((1-cyclopropyl-5-(2-(tetrahydro-2H-pyran-4-yl)thiazol-5-yl)-1H-benzo[d]imidazol-7-yl)oxy)ethyl)pyrrolidin-2-one | 0.5400 |
| (R)-4-((R)-1-((1-cyclopropyl-5-(1,5-dimethyl-1H-pyrazol-3-yl)-1H-benzo[d]imidazol-7-yl)oxy)ethyl)pyrrolidin-2-one | 2.148 |
| (R)-4-((R)-1-((1-cyclopropyl-5-(1,2-dimethyl-1H-imidazol-4-yl)-1H-benzo[d]imidazol-7-yl)oxy)ethyl)pyrrolidin-2-one | 6.072 |

-continued

| Compound | Syk IC$_{50}$ (nM) |
|---|---|
| (R)-4-((R)-1-((1-cyclopropyl-5-(5-methyl-1,3,4-thiadiazol-2-yl)-1H-benzo[d]imidazol-7-yl)oxy)ethyl)pyrrolidin-2-one | 5.446 |
| (R)-4-((R)-1-((5-(1-(tert-butyl)-1H-pyrazol-3-yl)-1-cyclopropyl-1H-benzo[d]imidazol-7-yl)oxy)ethyl)pyrrolidin-2-one | 5.008 |
| (R)-4-((R)-1-((6-(2-(tert-butyl)thiazol-5-yl)-3-cyclopropyl-3H-imidazo[4,5-c]pyridin-4-yl)oxy)ethyl)pyrrolidin-2-one | 2.096 |
| (R)-4-((R)-1-((3-cyclopropyl-6-(2-(tetrahydro-2H-pyran-4-yl)thiazol-5-yl)-3H-imidazo[4,5-c]pyridin-4-yl)oxy)ethyl)pyrrolidin-2-one | 3.539 |
| (R)-4-((R)-1-((1-cyclopropyl-5-(2-methyl-1H-imidazol-5-yl)-1H-benzo[d]imidazol-7-yl)oxy)ethyl)pyrrolidin-2-one | 20.887 |
| (R)-4-((R)-1-((1-cyclopropyl-5-(5-methylthiazol-2-yl)-1H-benzo[d]imidazol-7-yl)oxy)ethyl)pyrrolidin-2-one | 1.727 |
| (R)-4-((R)-1-((1-cyclopropyl-5-(1-methyl-1H-pyrazol-3-yl)-1H-benzo[d]imidazol-7-yl)oxy)ethyl)pyrrolidin-2-one | 10.558 |
| (R)-4-((R)-1-((1-cyclopropyl-5-(2-methyl-2H-1,2,3-triazol-4-yl)-1H-benzo[d]imidazol-7-yl)oxy)ethyl)pyrrolidin-2-one | 22.412 |
| (R)-4-((R)-1-((3-cyclopropyl-6-(2-methylthiazol-5-yl)-3H-imidazo[4,5-c]pyridin-4-yl)oxy)ethyl)pyrrolidin-2-one | 10.195 |
| (R)-4-((R)-1-((3-cyclopropyl-6-(5-methylthiophen-2-yl)-3H-imidazo[4,5-c]pyridin-4-yl)oxy)ethyl)pyrrolidin-2-one | 7.428 |

What is claimed:

1. A compound of Formula I:

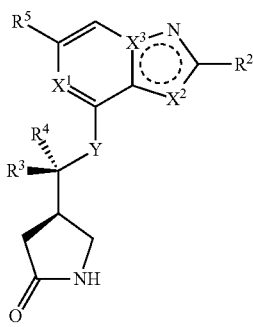

Formula I wherein:

$X^1$ is CH or N;

$X^2$ is $CR^{1a}$, $NR^{1b}$ or S;

$X^3$ is C or N;

wherein, $X^1$, $X^2$ and $X^3$ are arranged in such a way to for a heteroaromatic ring system, and $R^{1a}$ is hydrogen, halo, haloalkyl, cyano, $C_{1-6}$ alkyl, $C_{1-6}$ alkoxy, $C_{3-6}$ cycloalkoxy, $C_{3-12}$ cycloalkyl, $C_{2-12}$ heterocyclyl, $C_{6-12}$ aryl, $C_{2-12}$ heteroaryl, or $-N(R^{20})(R^{22})$, wherein the $C_{1-6}$ alkyl, $C_{3-12}$ cycloalkyl, $C_{2-12}$ heterocyclyl, $C_{6-12}$ aryl, or $C_{2-12}$ heteroaryl moieties may be optionally substituted with one, two, or three substituents independently selected from fluoro, $CH_2F$, $CHF_2$, $CF_3$, $C_{1-6}$ alkyl, $C_{1-6}$ alkoxy, $C_{3-6}$ cycloalkoxy, $C_{3-12}$ cycloalkyl, and $-N(R^{20})(R^{22})$, $R^{1b}$ is hydrogen, haloalkyl, $C_{1-6}$ alkyl, $C_{3-12}$ cycloalkyl, $C_{2-12}$ heterocyclyl, $C_{6-12}$ aryl, or $C_{2-12}$ heteroaryl, wherein the $C_{1-6}$ alkyl, $C_{3-12}$ cycloalkyl, $C_{2-12}$ heterocyclyl, $C_{6-12}$ aryl, or $C_{2-12}$ heteroaryl moieties may be optionally substituted with one, two, or three substituents independently selected from fluoro, $CH_2F$, $CHF_2CF_3$, and $C_{1-6}$ alkyl, $C_{1-6}$ alkoxy, $C_{3-6}$ cycloalkoxy, $C_{3-12}$ cycloalkyl, and $-N(R^{20})(R^{22})$, provided that either (a) or (b) applies:

a) when $X^3$ is N then $X^2$ is $CR^{1a}$, or b) when $X^2$ is S then $X^1$ is CH and $X^3$ is C;

Y is O or NH;

$R^2$ is hydrogen, $C_{1-6}$ alkyl, $C_{3-12}$ cycloalkyl, $C_{2-12}$ heterocyclyl, $C_{1-6}$ alkoxy, or $-N(R^{20})(R^{22})$;

wherein the $C_{1-6}$ alkyl, $C_{3-12}$ cycloalkyl, $C_{2-12}$ heterocyclyl, or $C_{1-6}$ alkoxy moieties may be optionally substituted with one, two, or three substituents independently selected from fluoro, $CH_2F$, $CHF_2$, $CF_3$, $C_{1-6}$ alkyl, and $C_{1-6}$ alkoxy;

each $R^3$ and $R^4$ is independently hydrogen, $C_{1-6}$ alkyl, $C_{3-8}$ cycloalkyl, $C_{2-8}$ heterocyclyl, and $C_{2-6}$ alkenyl, wherein the $C_{1-6}$ alkyl, $C_{3-8}$ cycloalkyl, $C_{2-8}$ heterocyclyl, and $C_{2-6}$ alkenyl moieties may be optionally substituted with one, two, or three substituents independently selected from halogen, $C_{1-6}$ alkyl, $C_{3-6}$ cycloalkyl, $C_{6-12}$ aryl, $C_{2-8}$ heterocyclyl, $C_{2-12}$ heteroaryl, $-OR^{20}$, or $-N(R^{20})(R^{22})$;

$R^5$ is $C_{6-12}$ aryl, $C_{3-12}$ cycloalkyl, $C_{2-8}$ heterocyclyl having one, two, three, or four heteroatoms independently selected from O, N, and S, or $C_{2-12}$ heteroaryl having one, two, three, or four heteroatoms independently selected from O, N, and S;

wherein the $C_{6-12}$ aryl, $C_{3-12}$ cycloalkyl, $C_{2-8}$ heterocyclyl, and $C_{2-12}$ heteroaryl moiety may be optionally substituted with one, two, or three substituents independently selected from the group consisting of $C_{1-6}$ alkyl, $C_{2-6}$ alkynyl, $C_{1-6}$ alkoxy, halo, $-NO_2$, $CH_2F$, $CF_3$, $CHF_2$, $-OCF_3$, $C_{3-6}$ cycloalkyl, $C_{2-8}$ heterocyclyl, $C_{6-12}$ aryl, $C_{2-12}$ heteroaryl, $-S(O)_2R^{20}$, $-S(O)_2-N(R^{20})(R^{22})$, $-N(R^{20})(R^{22})$, $-N(R^{20})-S(O)_2-R^{20}$, $-N(R^{20})-C(O)-R^{22}$, $-C(O)-R^{20}$, $-C(O)-OR^{20}$, $-C(O)-N(R^{20})(R^{22})$, $-CN$, oxo, and $-O-R^{20}$;

wherein the $C_{1-6}$ alkyl, $C_{2-6}$ alkynyl, $C_{1-6}$ alkoxy, $C_{3-8}$ cycloalkyl, $C_{2-8}$ heterocyclyl, $C_{6-12}$ aryl, or $C_{2-12}$ heteroaryl moiety may be optionally further substituted with one, two, or three substituents independently selected from the group consisting of halo, $-NO_2$, $CH_2F$, $-CF_3$, $CHF_2$, $-OCF_3$, $C_{1-6}$ alkyl, $C_{3-6}$ cycloalkyl, $C_{6-12}$ aryl, $C_{2-8}$ heterocyclyl, $C_{2-6}$ heteroaryl, $-N(R^{20})(R^{22})$, $-C(O)-R^{20}$, $-C(O)-OR^{20}$, $-C(O)-N(R^{20})(R^{22})$, $-CN$, $-S(O)_2R^{20}$, $-S(O)_2-N(R^{20})(R^{22})$, $-S(O)_2-R^{20}-N(R^{20})(R^{22})$, oxo, and $-O-R^{20}$;

wherein the $C_{1-6}$ alkyl, $C_{3-6}$ cycloalkyl, $C_{2-8}$ heterocyclyl, $C_{6-12}$ aryl, and $C_{2-6}$ heteroaryl may be further optionally substituted with one, two, or three substituents independently selected from the group consisting of $C_{1-6}$ alkyl, $C_{3-6}$ cycloalkyl, $C_{6-12}$ aryl, $C_{2-6}$ heteroaryl, $C_{2-8}$ heterocyclyl, halo, —$NO_2$, $CH_2F$, $CHF_2$, —$CF_3$, —$OCF_3$, —$N(R^{20})(R^{22})$, —$C(O)$—$R^{20}$, —$C(O)$—$OR^{20}$, —$C(O)$—$N(R^{20})(R^{22})$, —CN, —$S(O)_2$—$R^{20}$, $S(O)_2$—$N(R^{20})(R^{22})$, —$S(O)_2$—$R^{20}$—$N(R^{20})(R^{22})$, oxo, and —O—$R^{20}$; and each $R^{20}$ and $R^{22}$ is independently hydrogen, $C_{1-6}$ alkyl, $C_{2-6}$ alkenyl, $C_{2-6}$ alkynyl, $C_{3-6}$ cycloalkyl, $C_{2-8}$ heterocyclyl, $C_{6-12}$ aryl, or $C_{2-12}$ heteroaryl;

wherein the $C_{1-6}$ alkyl, $C_{2-6}$ alkenyl, $C_{2-6}$ alkynyl, $C_{3-6}$ cycloalkyl, $C_{2-8}$ heterocyclyl, $C_{6-12}$ aryl, and $C_{2-12}$ heteroaryl moieties may be optionally substituted with one, two, or three substituents independently selected from the group consisting of hydroxy, halo, $C_{1-6}$ alkyl, acylamino, oxo, —$NO_2$, —$S(O)_2R^{26}$, —CN, $C_{1-6}$ alkoxy, $C_{3-6}$ cycloalkoxy, $CH_2F$, —$CF_3$, $CHF_2$, —$OCF_3$, —$OCH_2CF_3$, —$C(O)$—$NH_2$, $C_{6-12}$ aryl, $C_{3-6}$ cycloalkyl, $C_{2-8}$ heterocyclyl, and $C_{2-6}$ heteroaryl; and wherein $R^{26}$ is $C_{1-6}$alkyl, $C_{2-6}$ alkenyl, $C_{2-6}$ alkynyl, $C_{3-6}$ cycloalkyl, $C_{2-8}$ heterocyclyl, $C_{6-12}$ aryl, $C_{2-6}$ heteroaryl, acylamino, $NH_2$, $CH_2F$, —$CF_3$, or $CHF_2$;

or a pharmaceutically acceptable salt, ester, stereoisomer, mixture of stereoisomers or tautomer thereof.

2. The compound of claim 1 represented by Formula II

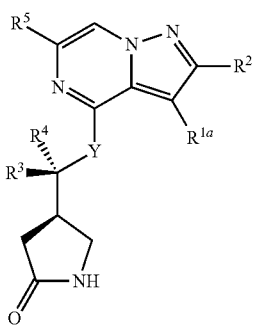

(II)

wherein:
Y is O;
$R^{1a}$ is hydrogen, cyano, chloro, methyl, ethyl, propyl, or butyl;
$R^2$ is hydrogen or methyl;
$R^3$ is methyl, ethyl, propyl, or butyl;
$R^4$ is hydrogen; and
$R^5$ is phenyl or pyrazoiyl,
wherein the phenyl and pyrazolyl moieties may be optionally substituted with one or two substituents independently selected from the group consisting of fluoro, . . . piperazinyl, and morpholino;

wherein the piperazinyl moiety may be optionally substituted with one substituent selected from the group consisting of $C_{2-5}$ heterocyclyl, —$S(O)_2$-alkyl, —$S(O)_2$—$C_{3-6}$ cycloalkyl, —$S(O)_2$—$C_{2-8}$ heterocyclyl, and —$C(O)$—$C_{1-6}$ alkyl; or a pharmaceutically acceptable salt, ester, stereoisomer, mixture of stereoisomers or tautomer thereof.

3. The compound of claim 2,
wherein:
Y is O;
$R^{1a}$ is hydrogen, methyl, cyano, bromo or chloro;
$R^2$ is hydrogen or methyl;
$R^3$ is methyl;
$R^4$ is hydrogen;
$R^5$ is:

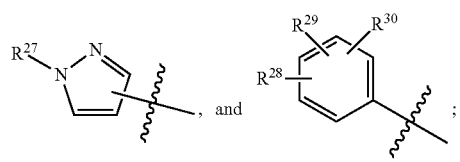

$R^{27}$ is H, $C_{1-4}$ alkyl, —$CH_2F$, $CHF_2$, or $CF_3$;
and (i) $R^{28}$, $R^{29}$ and $R^{30}$ are each independently hydrogen, fluoro, cyano, or —$OC_{1-3}$ alkyl;
or (ii) $R^{28}$ and $R^{29}$ are each independently hydrogen or —$OC_{1-3}$ alkyl, and $R^{30}$ is morpholino or piperazinyl, wherein the piperazinyl moiety may be optionally substituted with one substituent selected from the group consisting of —$S(O)_2H$, —$S(O)_2$—$C_{1-3}$ alkyl, —$S(O)_2$—$C_{3-6}$ cycloalkyl, —$S(O)_2$—$C_{2-8}$ heterocyclyl, $C_{1-4}$ alkyl, —$C(O)$—$C_{1-4}$ alkyl, $C_{3-6}$ cycloalkyl, and $C_{2-5}$ heterocyclyl;

or a pharmaceutically acceptable salt, ester, stereoisomer, mixture of stereoisomers or tautomer thereof.

4. The compound of claim 2,
wherein:
Y is O;
$R^{1a}$ is hydrogen, methyl or chloro;
$R^2$ is hydrogen or methyl;
$R^3$ is methyl;
$R^4$ is hydrogen;
$R^5$ is:

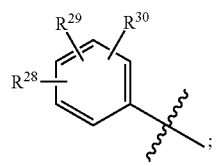

and (i) $R^{28}$, $R^{29}$ and $R^{30}$ are each independently hydrogen or methoxy;
or (ii) $R^{28}$ and $R^{29}$ are hydrogen, and $R^{30}$ is morpholino;
or a pharmaceutically acceptable salt, ester, stereoisomer, mixture of stereoisomers or tautomer thereof.

5. The compound of claim 1 represented by Formula IIa,

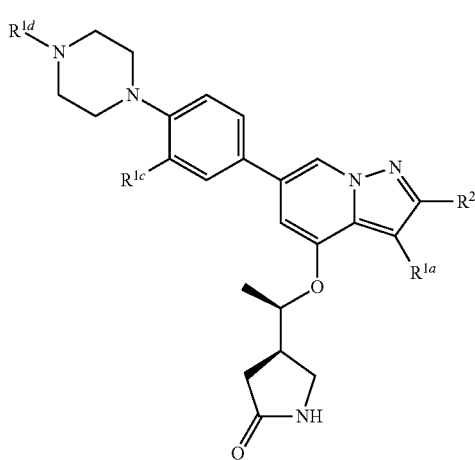

wherein:
$R^{1a}$ is hydrogen, methyl or cyano;
$R^2$ is hydrogen or methyl;
$R^3$ is hydrogen or methoxy; and
$R^{1d}$ is hydrogen, $C_{1-4}$ alkyl, —C(O)—$C_{1-4}$ alkyl, —S(O)$_2$H, —S(O)$_2$—$C_{1-3}$ alkyl, —S(O)$_2$—$C_{3-6}$ cycloalkyl, —S(O)$_2$—$C_{2-8}$ heterocyclyl, $C_{3-6}$ cycloalkyl, or $C_{2-6}$ heterocyclyl;
or a pharmaceutically acceptable salt, ester, stereoisomer, mixture of stereoisomers or tautomer thereof.

6. The compound of claim 1 represented by Formula III:

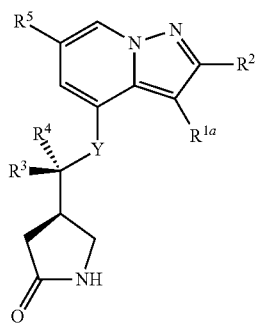

Formula III wherein:
Y is O;
$R^{1a}$ is hydrogen, halo, haloalkyl, cyano, $C_{1-6}$ alkyl, or $C_{3-6}$ cycloalkyl;
$R^2$ is hydrogen;
$R^3$ is $C_{1-6}$ alkyl;
$R^4$ is hydrogen; and
$R^5$ is phenyl, pyridinyl, pyrazolyl, indazolyl, thieno[3,2-c]pyrazolyl, pyimidinyl, imidazolyl, or indolin-2-onyl;
wherein the phenyl, . . . and indolin-2-onyl moieties may be optionally substituted with one, two, or three substituents independently selected from the group consisting of halo, $C_{1-6}$ alkyl, $C_{1-6}$ alkoxy, $C_{2-6}$ alkynyl, $C_{3-6}$ cycloalkyl, $C_{2-8}$ heterocyclyl, —S(O)$_2$R$^{20}$, —S(O)$_2$—NR$^{20}$R$^{22}$, —NO$_2$, —N(R$^{20}$)(R$^{22}$), —C(O)—OR$^{20}$, —CN, oxo, and —O—R$^{20}$;
wherein the alkyl, alkoxy, alkynyl, cycloalkyl, or heterocyclyl moieties are further optionally substituted with zero, one, two or three substituents independently selected from the group consisting, of halo, $C_{1-6}$ alkyl, $C_{3-6}$ cycloalkyl, $C_{6-12}$ aryl, $C_{2-8}$ heterocyclyl, $C_{2-6}$ heteroaryl, —NO$_2$, —S(O)$_2$R$^{20}$, —N(R$^{20}$)(R$^{22}$), —C(O)—R$^{20}$, —C(O)—OR$^{20}$, —C(O)—N(R$^{20}$)(R$^{22}$), —CN, and —O—R$^{20}$; and
$R^{20}$ and $R^{22}$ are each independently hydrogen, . . . or $C_{2-6}$ heteroaryl;
or a pharmaceutically acceptable salt, ester, stereoisomer, mixture of stereoisomers or tautomer thereof.

7. The compound of claim 6,
wherein:
Y is O;
$R^{1a}$ is hydrogen, cyano, chloro, methyl, ethyl, propyl, butyl, or $C_{3-6}$ cycloalkyl;
$R^2$ is hydrogen;
$R^3$ is methyl;
$R^4$ is hydrogen; and
$R^5$ is phenyl, pyridinyl or pyrazolyl;
wherein the phenyl, pyridinyl and pyrazolyl moieties may be optionally substituted with one, two or three substituents independently selected from the group consisting of methyl, ethyl, propyl, butyl, cyano, methoxy, ethoxy, propoxy, morpholinyl, piperazinyl, oxetanyl, $C_{1-4}$ fluoroalkyl, cyclopropyl and cyclobutyl;
or a pharmaceutically acceptable salt, ester, stereoisomer, mixture of stereoisomers or tautomer thereof.

8. The compound of claim 6,
wherein:
Y is O;
$R^{1a}$ is hydrogen, methyl, chloro or cyclopropyl;
$R^2$ is hydrogen or methyl;
$R^3$ is methyl;
$R^4$ is hydrogen;
$R^5$ is:

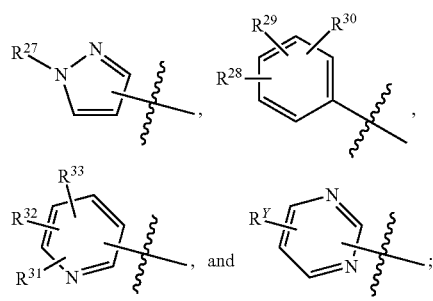

$R^{27}$ is
(i) $R^{28}$, $R^{29}$ and $R^{30}$ are each independently hydrogen or —OC$_{1-3}$ alkyl;
or (ii) $R^{28}$ and $R^{29}$ are each independently hydrogen or —OC$_{1-3}$ alkyl, and $R^{30}$ is morpholino or piperazinyl;
wherein the piperazinyl moiety may be optionally substituted with one substituent selected from the group consisting of —S(O)$_2$H, —S(O)$_2$—$C_{1-3}$ alkyl, —S(O)$_2$—$C_{3-6}$ cycloalkyl, —S(O)$_2$—$C_{2-8}$ heterocyclyl, $C_{1-4}$ alkyl, —C(O)—$C_{1-4}$ alkyl, $C_{3-6}$ cycloalkyl, and $C_{2-6}$ heterocyclyl;
(iii) $R^{31}$, $R^{32}$ and $R^{33}$ are each independently hydrogen, $C_{1-3}$ alkyl, or —OC$_{1-3}$ alkyl;
or (iv) $R^{31}$ and $R^{32}$ are each independently hydrogen or —OC$_{1-3}$ alkyl, and $R^{33}$ is morpholino or piperazinyl;
wherein the piperazinyl moiety may be optionally substituted with one substituent selected from the group consisting of —S(O)$_2$H, —S(O)$_2$—C$_{1-3}$ alkyl, —S(O)$_2$—C$_{3-6}$ cycloalkyl, —S(O)$_2$—C$_{2-8}$ heterocyclyl, C$_{1-4}$ alkyl, —C(O)—C$_{1-4}$ alkyl, C$_{3-6}$ cycloalkyl, and C$_{2-6}$ heterocyclyl; and R$^Y$ is hydrogen, C$_{1-4}$ alkyl, or —OC$_{1-3}$ alkyl;

or a pharmaceutically acceptable salt, ester, stereoisomer, mixture of stereoisomers or tautomer thereof.

9. The compound of claim 1 represented by Formula IIIa,

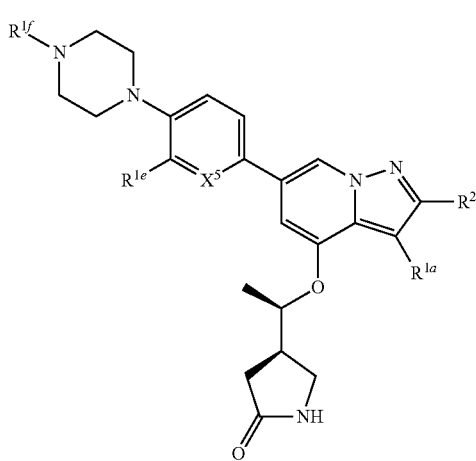

IIIa wherein:

R$^{1a}$ is hydrogen, cyano, methyl, chloro, or cyclopropyl;

R$^2$ is hydrogen or methyl;

X$^5$ is —CH— or nitrogen;

R$^{1e}$ is hydrogen or methoxy; and

R$^{1f}$ is hydrogen, —S(O)$_2$H, —S(O)$_2$—C$_{1-3}$ alkyl, C$_{1-4}$ alkyl, C$_{3-6}$ cycloalkyl, or C$_{2-6}$ heterocyclyl;

or a pharmaceutically acceptable salt, ester, stereoisomer, mixture of stereoisomers or tautomer thereof.

10. The compound of claim 1 represented by Formula IV,

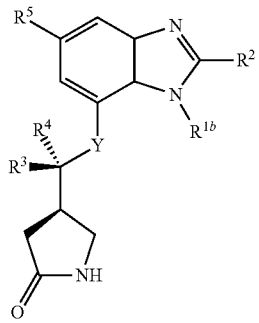

IV wherein:

Y is O;

R$^{1b}$ is hydrogen, C$_{1-4}$ alkyl, or C$_{3-6}$ cycloalkyl;

wherein the C$_{1-4}$ alkyl and C$_{3-6}$ cycloalkyl moieties may be optionally substituted with one, two, or three substituents independently selected from the group consisting of fluoro and C$_{1-6}$ alkyl;

R$^2$ is hydrogen or methyl;

R$^3$ is methyl, ethyl, propyl, or butyl;

R$^4$ is hydrogen; and

R$^5$ is selected from the group consisting of phenyl, pyridinyl, pyrazolyl, 2,3-dihydro-[1,4]dioxino[2,3-b]pyridinyl, benzomorpholinyl, thiazolyl, indolinyl, 1,3,4-thiadiazolyl, pyrimidinyl, imidazolyl, pyrazinyl, pyridazinyl, pyrrolo[2,3-b]pyridin-2(3H)-onyl, pyrido[2,3-b][1,4]oxazin-2(3H)-onyl, pyrido[3,2-b][1,4]oxazin-3(4H)-onyl, 3,4-dihydropyrido[3,2-b][1,4]oxazinyl, benzimidazolyl, and 2,3-dihydro-1H-pyrido[2,3-b][1,4]oxazinyl;

wherein the R$^5$ moiety may be optionally substituted with one, two, or three substituents independently selected from the group consisting of C$_{1-6}$ alkyl, . . . difluoropropyl, . . . and cyclobutyl;

wherein the C$_{1-6}$ alkyl moiety may be optionally substituted with one hydroxy;

wherein the R$^5$ phenyl moiety may be optionally substituted with one substituent selected from the group consisting of morpholino and a group of the formula:

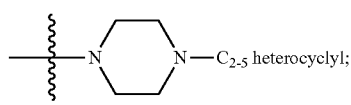

wherein the R$^5$ pyridazinyl moiety may be optionally substituted with one substituent selected from the group consisting of morpholino and a group of the formula:

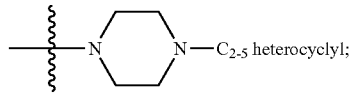

wherein the R$^5$ pyridinyl moiety may be optionally substituted with one substituent selected from the group consisting of a) piperazinyl, optionally substituted with one substituent selected from the group consisting of —C(O)—C$_{1-3}$ alkyl, . . . and —S(O)$_2$—C$_{2-8}$ heterocyclyl, and b) piperidinyl, optionally substituted with one substituent selected from the group consisting of C$_{2-5}$ heterocyclyl and 6-oxa-3-azabicyclo[3.1.1]heptanyl;

wherein the R$^5$ pyrazolyl moiety may be optionally substituted with one, two or three substituents independently selected from the group consisting of a) C$_{2-5}$ heterocyclyl, b) C$_{1-6}$ alkyl, optionally substituted with one or two substituents independently selected from the group consisting of OH, . . . and —C(O)N(C$_{1-3}$ alkyl)$_2$, and c) pyridinyl; and wherein the R$^5$ thiazolyl moiety may be optionally substituted with one substituent selected from the group consisting of a) morpholino, b) C$_{2-5}$ heterocyclyl, and c) C$_{1-6}$ alkyl, optionally substituted with one or two substituents independently selected from the group consisting of OH, . . . and —C(O)N(C$_{1-3}$ alkyl)$_2$;

or a pharmaceutically acceptable salt, ester, stereoisomer, mixture of stereoisomers or tautomer thereof.

11. The compound of claim 1 represented by Formula V,

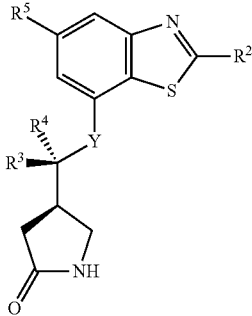

Formula V wherein:
Y is O;
$R^2$ is hydrogen or methyl;
$R^3$ is hydrogen, $C_{1-6}$ alkyl, or $C_{2-3}$ alkenyl;
$R^4$ is hydrogen;
$R^5$ is selected from the group consisting of phenyl, pyridinyl, pyrazolyl, pyrazinyl, pyridazinyl, thiazolyl, benzothiazolyl, benzomorpholinyl, thieno[3,2-c]pyrazolyl, indazolyl, indolin-2-onyl, quinazolin-4(3H)-onyl, pyrrolo[2,3-b]pyridin-2(3H)-onyl, pyrrolo[3,2-c]pyridin-2(3H)-onyl, 3,4-dihydroquinolin-2(1H)onyl, pyrazolo[3,4-b]pyridinyl, 2,3-dihydrobenzofuranyl, 3,4-dihydroquinolin-2(1H)-onyl and 3,4-dihydropyrido[3,2-b][1,4]oxazinyl;
wherein the $R^5$ moiety may be optionally substituted with one, two, or three substituents independently selected from the group consisting of $C_{1-6}$ alkyl, $C_{1-6}$ alkoxy, $C_{3-6}$ cycloalkyl, and $C_{2-8}$ heterocyclyl;
wherein the $C_{1-6}$ alkyl, $C_{1-6}$ alkoxy, $C_{3-6}$ cycloalkyl, and $C_{2-8}$ heterocyclyl moieties may be independently and optionally substituted with one substituent selected from the group consisting of halo, $C_{3-8}$ cycloalkyl, $C_{2-8}$ heterocyclyl, —C(O)O—$R^{20}$, —C(O)$R^{20}$, —NO$_2$, —N($R^{20}$)($R^{22}$), —S(O)$_2R^{20}$, —S(O)$_2$—N($R^{20}$)($R^{22}$), —C(O)—N($R^{20}$)($R^{22}$), oxo, —CN, and —O—$R^{20}$; and
wherein each $R^{20}$ and $R^{22}$ is independently selected from the group consisting of hydrogen, $C_{1-6}$ alkyl, $C_{2-6}$ alkenyl, $C_{2-6}$ alkynyl, $C_{3-6}$ cycloalkyl, $C_{2-8}$ heterocyclyl, $C_{6-12}$ aryl, and $C_{2-6}$ heteroaryl;
or a pharmaceutically acceptable salt, ester, stereoisomer, mixture of stereoisomers or tautomer thereof.

12. The compound of claim 1 represented by Formula VI,

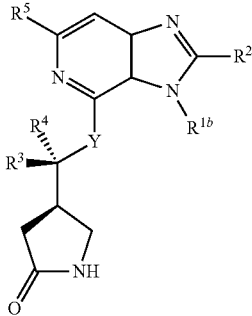

Formula VI wherein;
Y is O;
$R^{1b}$ is hydrogen, halo, $C_{1-6}$ alkyl, $C_{3-6}$ cycloalkyl, or $C_{2-8}$ heterocyclyl;
wherein the $C_{1-6}$ alkyl, $C_{3-6}$ cycloalkyl and $C_{2-8}$ heterocyclyl moieties may be optionally substituted with one, two, or three substituents independently selected from the group consisting of fluoro and $C_{1-6}$ alkyl;
$R^3$ is hydrogen, $C_{1-6}$ alkyl, $C_{2-3}$ alkenyl, or $C_{3-6}$ cycloalkyl;
wherein the $C_{1-6}$ alkyl and $C_{3-6}$ cycloalkyl moieties may be optionally substituted with one, two, or three substituents independently selected from the group consisting of halo and $C_{1-6}$ alkyl;
$R^4$ is hydrogen; and
$R^5$ is phenyl, pyridinyl, pyrazolyl, thiazolyl, indazolyl, cyclohexenyl, thienopyrazolyl, or pyrazolopyridinyl;
wherein the $R^5$ moiety may be optionally substituted with one, two, or three substituents independently selected from the group consisting of halo, $C_{1-6}$ alkyl, $C_{1-6}$ alkoxy, $C_{3-6}$ cycloalkyl, $C_{2-8}$ heterocyclyl, —C(O)O—$R^{20}$, —C(O)$R^{20}$, —NO$_2$, —N($R^{20}$)($R^{22}$), —S(O)$_2R^{20}$, —S(O)$_2$—N($R^{20}$)($R^{22}$), —C(O)—N($R^{20}$)($R^{22}$), —CN, oxo, and —O—$R^{20}$;
wherein the $C_{3-6}$ cycloalkyl and $C_{2-8}$ heterocyclyl moieties may be independently and optionally substituted with one substituent selected from the group consisting of $C_{3-8}$ cycloalkyl, $C_{2-8}$ heterocyclyl, —C(O)O—$R^{20}$, —C(O)$R^{20}$, —NO$_2$, —N($R^{20}$)($R^{22}$), —S(O)$_2R^{20}$, —S(O)$_2$—N($R^{20}$)($R^{22}$), —C(O)—N($R^{20}$)($R^{22}$), —CN, oxo, and —O—$R^{20}$;
wherein each $R^{20}$ and $R^{22}$ is independently selected from the group consisting of hydrogen, $C_{1-6}$ alkyl, $C_{2-6}$ alkenyl, $C_{2-6}$ alkynyl, $C_{3-6}$ cycloalkyl, $C_{2-8}$ heterocyclyl, $C_{6-12}$ aryl, and $C_{2-6}$ heteroaryl;
or a pharmaceutically acceptable salt, ester, stereoisomer, mixture of stereoisomers or tautomer thereof.

13. The compound of claim 1 wherein $R^5$ is phenyl, pyridinyl, pyrazolyl, indazolyl, benzothiazolyl, dihydrobenzoxazinyl, benzodioxolyl, thiazolyl, pyrazolopyridinyl, cyclohexenyl, tetrahydrobenzoxazepanyl, and thienopyrazolyl;
wherein the phenyl, pyridinyl, pyrazolyl, indazolyl, benzothiozolyl, dihydrobenzoxazinyl, benzodioxolyl, thiazolyl, pyrazolopyridinyl, cyclohexenyl, tetrahydrobenzoxazepanyl, and thienopyrazolyl moieties may be optionally substituted with one, two, or three substituents independently selected from the group consisting of halo, $C_{1-6}$ alkyl, $C_{1-6}$ alkoxy, $C_{2-6}$ alkynyl, $C_{3-8}$ cycloalkyl, $C_{2-8}$ heterocyclyl, $C_{6-12}$ aryl, $C_{2-6}$ heteroaryl, —S(O)$_2R^{20}$, —S(O)$_2$—N($R^{20}$)($R^{22}$), —N($R^{20}$)($R^{22}$), —NO$_2$, —N($R^{20}$)—S(O)$_2R^{20}$, —N($R^{20}$)—C(O)—$R^{22}$, —C(O)—$R^{20}$, —C(O)—O$R^{20}$, —C(O)—N($R^{20}$)($R^{22}$), —CN, oxo, and —O—$R^{20}$;
wherein the $C_{1-6}$ alkyl, $C_{3-8}$ cycloalkyl, $C_{2-8}$ heterocyclyl, $C_{6-12}$ aryl, and $C_{2-6}$ heteroaryl moieties may be optionally substituted with one, two, or three substituents independently selected from the group consisting of halo, $C_{1-6}$ alkyl, $C_{3-6}$ cycloalkyl, $C_{6-12}$ aryl, $C_{2-8}$ heterocyclyl, $C_{2-6}$ heteroaryl, —S(O)$_2$—$R^{20}$, —S(O)$_2$—N($R^{20}$)($R^{22}$), —NO$_2$, —N($R^{20}$)($R^{22}$), —C(O)—$R^{20}$, —C(O)—O$R^{20}$, —C(O)—N($R^{20}$)($R^{22}$), —CN, oxo, and —O—$R^{20}$;
wherein each $R^{20}$ and $R^{22}$ is independently selected from the group consisting of hydrogen, $C_{1-6}$ alkyl, $C_{2-6}$ alkenyl, $C_{2-6}$ alkynyl, $C_{3-6}$ cycloalkyl, $C_{2-8}$ heterocyclyl, $C_{6-12}$ aryl, and $C_{2-6}$ heteroaryl;
or a pharmaceutically acceptable salt, ester, stereoisomer, mixture of stereoisomers or tautomer thereof.

14. The compound of claim 1, wherein $R^5$ is phenyl, pyridinyl, pyrazolyl, indazolyl, benzothiazolyl, dihydrobenzoxazinyl, benzodioxolyl, thiazolyl, pyrazolopyridinyl, cyclohexenyl, tetrahydrobenzoxazepanyl, and thienopyrazolyl;

wherein the phenyl, pyridinyl, pyrazolyl, indazolyl, benzothiazolyl, dihydrobenzoxazinyl, benzodioxolyl, thiazolyl, pyrazolopyridinyl, cyclohexenyl, tetrahydrobenzoxazepanyl, and thienopyrazolyl moieties may be optionally substituted with one, two, or three substituents independently selected from the group consisting of halo, $CH_2F$, —$CF_3$, $CHF_2$, $C_{1-6}$ alkyl, $C_{3-6}$ cycloalkyl, $C_{2-8}$ heterocyclyl, —$S(O)_2R^{20}$, —$S(O)_2$—$NR^{20}R^{22}$, —$N(R^{20})(R^{22})$, —$C(O)$—$OR^{20}$, —CN, oxo, and —O—$R^{20}$;

wherein the $C_{1-6}$ alkyl, $C_{3-8}$ cycloalkyl, and $C_{2-8}$ heterocyclyl moieties may be optionally substituted with one, two, or three substituents independently selected from the group consisting of halo, $CH_2F$, —$CF_3$, $CHF_2$, $C_{1-6}$ alkyl, $C_{3-8}$ cycloalkyl, $C_{2-8}$ heterocyclyl, —$N(R^{20})(R^{22})$, —$C(O)$—$R^{20}$, —$C(O)$—$OR^{20}$, —$C(O)$—$N(R^{20})(R^{22})$, —CN, —O—$R^{20}$, —$S(O)_2R^{20}$, —$S(O)_2$—$NR^{20}R^{22}$, and oxo;

wherein each $R^{20}$ and $R^{22}$ is independently selected from the group consisting of hydrogen, $C_{1-6}$ alkyl, $C_{1-6}$ alkoxy, $C_{2-6}$ alkenyl, $C_{2-6}$ alkynyl, $C_{3-8}$ cycloalkyl, $C_{2-8}$ heterocyclyl, $C_{6-12}$ aryl, and $C_{2-6}$ heteroaryl;

or a pharmaceutically acceptable salt, ester, stereoisomer, mixture of stereoisomers or tautomer thereof.

15. The compound of claim 1, wherein:

Y is O;

$R^{1a}$ is hydrogen, halo, haloalkyl, cyano, $C_{1-6}$ alkyl, $C_{3-6}$ cycloalkyl, —$CH_2$—$C_{3-6}$ cycloalkyl, or $C_{2-5}$ heterocyclyl;

$R^2$ is hydrogen or $C_{1-6}$ alkyl, wherein the $C_{1-6}$ alkyl group is substituted by 0, 1, 2, or 3 fluorine atoms or 0 or 1 $C_{1-6}$ alkoxy substituents;

$R^3$ is H, $C_{1-6}$ alkyl or $C_{2-3}$ alkenyl, wherein the $C_{1-6}$ alkyl group is substituted by 0, 1, 2, or 3 fluorine atoms or 0 or 1 substituents selected from hydroxy or $C_{1-6}$ alkoxy;

$R^4$ is hydrogen; and $R^5$ is selected from the group consisting of phenyl, pyrazolyl, pyridinyl, pyrazolo[1,5-a]pyridinyl, benzo[d][1,3]dioxolyl, benzomorpholinyl, thiazolyl, cyclohex-1-enyl, pyridin-2(1H)-onyl, dihydrobenzo[f][1,4]oxazepin-5(2H)-onyl, benzothiazolyl, thieno[3,2-c]pyrazolyl, indazolyl, pyrimidinyl, imidazolyl, indolinyl, pyrazinyl, pyridazinyl, pyrido[3,2-b][1,4]oxazinyl, 2,3-dihydro-[1,4]dioxino[2,3-b]pyridinyl, quinazolin-4(3H)-onyl, pyrrolo[2,3-b]pyridin-2(3H)-onyl, pyrrolo[3,2-c]pyridin-2(3H)-onyl, 3,4-dihydroquinolin-2(1H)-onyl, indolin-2-onyl, pyrazolo[3,4-b]pyridinyl, 2,3-dihydrobenzofuranyl, 2H-benzo[b][1,4]oxazin-3(4H)-onyl, 3,4-dihydroquinolin-2(1H)-onyl, pyrido[3,2-b][1,4]oxazin-3(4H)-onyl, benzimidazolyl, imidazo[1,2-a]pyridinyl, isoindolin-1-onyl, benzomorpholin-3-onyl, benzomorpholin-2-onyl, benzimidazolin-2-onyl, 2,3-dihydro-1H-pyrido[2,3-b][1,4]oxazinyl, pyrido[2,3-b][1,4]oxazin-2(3H)-onyl, spiro[azetidin-3,3'-indolin]-2'-onyl, benzo[d][1,3]oxazin-2(4H)-onyl, spiro[indolin-3,4'piperidin]-2-onyl, 3,4-dihydrospiro[benzo[b][1,4]oxazin-2,1'-cyclopropan]yl, indolyl, benzoxazolin-2-onyl, pyrrolo[3,2-b]pyridin-2(3H)-onyl, thiophenyl, 3,4-dihydropyrido[3,2-b][1,4]oxazinyl, 1,3,4-thiadiazolyl, indolinyl, isothiazolyl, 1,2,3-triazolyl and thieno[2,3-c]pyridinyl;

wherein each of the $R^5$ moieties may be independently, optionally substituted with one, two or three substituents independently selected from the group consisting of halo, $C_{1-6}$ alkyl, $C_{1-6}$ alkoxy, $C_{2-6}$ alkynyl, $C_{3-8}$ cycloalkyl, $C_{2-8}$ heterocyclyl, —$S(O)_2R^{20}$, —$S(O)_2$—$NR^{20}R^{22}$, —$NO_2$, —$N(R^{20})(R^{22})$, —$C(O)$—$OR^{20}$, —CN, oxo, and —O—$R^{20}$;

wherein the $C_{1-6}$ alkyl, $C_{1-6}$ alkoxy, $C_{2-6}$ alkenyl, $C_{3-8}$ cycloalkyl, and $C_{2-8}$ heterocyclyl moieties may be optionally substituted with one, two, or three substituents independently selected from the group consisting of halo, CN, $C_{1-6}$ alkyl, $C_{3-6}$ cycloalkyl, $C_{6-12}$ aryl, $C_{2-8}$ heterocyclyl, $C_{2-6}$ heteroaryl, —$S(O)_2R^{20}$, —$NO_2$, —$N(R^{20})(R^{22})$, —$C(O)$—$R^{20}$, —$C(O)$—$OR^{20}$, —$C(O)$—$N(R^{20})(R^{22})$, —CN, oxo, and —O—$R^{20}$; and wherein each $R^{20}$ and $R^{22}$ is independently selected from the group consisting of hydrogen, $C_{1-6}$ alkyl, $C_{2-6}$ alkenyl, $C_{2-6}$ alkynyl, $C_{3-6}$ cycloalkyl, $C_{2-8}$ heterocyclyl, $C_{6-12}$ aryl, and $C_{2-6}$ heteroaryl;

or a pharmaceutically acceptable salt, ester, stereoisomer, mixture of stereoisomers or tautomer thereof.

16. The compound of claim 1, selected from the group consisting of:

(R)-4-((R)-1((6-(3,4-dimethoxyphenyl)pyrazolo[1,5-a]pyrazin-4-yl)oxy)ethyl)pyrrolidin-2-one;

(R)-4-((R)-1-((6-(3,4-dimethoxyphenyl)-3-methylpyrazolo[1,5-a]pyrazin-4-yl)oxy)ethyl)pyrrolidin-2-one;

(R)-4-((R)-1-((3-methyl-6-(4-morpholinophenyl)pyrazolo[1,5-a]pyrazin-4-yl)oxy)ethyl)pyrrolidin-2-one;

(R)-4-((R)-1-((3-chloro-6-(3,4dimethoxyphenyl)pyrazolo[1,5-a]pyrazin-4-yl)oxy)ethyl)pyrrolidin-2-one;

(R)-4-((R)-1-((6-(3,4-dimethoxyphenyl)-2-methylpyrazolo[1,5-a]pyrazin-4-yl)oxy)ethyl)pyrrolidin-2-one;

(R)-4-((R)-1-((6-(1-(tert-butyl)-1H-pyrazol-4yl)-3-methylpyrazolo[1,5-a]pyrazin-4-yl)oxy)ethyl)pyrrolidin-2-one;

(R)-4-((R)-1-((6-(3,4-dimethoxyphenyl)pyrazolo[1,5-a]pyrazin-4-yl)oxy)ethyl)pyrrolidin-2-one;

(R)-4-((R)-1((6-(3,4-dimethoxyphenyl)-3-methylpyrazolo[1,5-a]pyrazin-4-yl)oxy)ethyl)pyrrolidin-2-one;

(R)-4-((R)-1-((6-(1-(tert-butyl)-1H-pyrazol-4-yl)-3-methylpyrazolo[1,5-a]pyrazin-4-yl)oxy)ethyl)pyrrolidin-2-one;

(R)4-((R)-1-((3-methyl-6-(4-morpholinophenyl)pyrazolo[1,5-a]pyrazin-4-yl)oxy)ethyl)pyrrolidin-2-one;

(R)-4-((R)-1-((3-chloro-6-(3,4-dimethoxyphenyl)pyrazolo[1,5-a]pyrazin-4-yl)oxy)ethyl)pyrrolidin-2-one;

(R)-4-((R)-1-((6-(3,4-dimethoxyphenyl)-2-methylpyrazolo[1,5-a]pyrazin-4-yl)oxy)ethyl)pyrrolidin-2-one;

(R)-4-((R)-1-(3-methyl-6-(4-morpholinophenyl)pyrazolo[1,5-a]pyrazin-4-yl)oxy)ethyl)pyrrolidin-2-one;

(R)-4-((R)-1-(6-(1-tert-butyl-1H-pyrazol-4-yl)-3-methylpyrazolo[1,5-a]pyrazin-4-yloxy)ethyl)-1-((R)-1-(4-methoxyphenyl)ethyl)pyrrolidin-2-one;

(R)-4-((R)-1-(3-chloro-6-(3,4dimethoxyphenyl)pyrazolo[1,5-a]pyrazin-4-yloxy)ethyl)-1-((R)-1-(4-methoxyphenyl)ethyl)pyrrolidin-2-one;

(R)-4-((R)-1-(3-chloro-6-(3,4-dimethoxyphenyl)pyrazolo[1,5-a]pyrazin-4-yloxy)ethyl)pyrrolidin-2-one;

(R)-4-((R)-1-(6-(3,4-dimethoxyphenyl)-2-methylpyrazolo[1,5-a]pyrazin-4-yloxy)ethyl)-1-((R)-1-(4-methoxyphenyl)ethyl)pyrrolidin-2-one;

(R)-4-((R)-1-(6-(3,4-dimethoxyphenyl)-2-methylprazolo[1,5-a]pyrazin-4-yloxy)ethyl)pyrrolidin-2-one;

(R)-4-((R)-1-(3-bromo-6-(3,4-dimethoxyphenyl)pyrazolo[1,5-a]pyrazin-4-yloxy)ethyl)-1-((R)-1-(4-methoxyphenyl)ethyl)pyrrolidin-2-one;

(R)-4-((R)-1-(3-bromo-6-(3,4-dimethoxyphenyl)pyrazolo[1,5-a]pyrazin-4-yloxy)ethyl)pyrrolidin-2-one;

4-(4-(4-((R)-1-((R)-5-oxopyrrolidin-3-yl)ethoxy)pyrazolo[1,5-a]pyrazin-6-yl)phenyl)piperazine-1-carboxylate;
(R)-4-((R)-1-((6-(4-(piperazin-1-yl)phenyl)pyrazolo[1,5-a]pyrazin-4-yl)oxy)ethyl)pyrrolidin-2-one;
(R)-4-((R)-1-((6-(4-(4-acetylpiperazin-1-yl)phenyl)pyrazolo[1,5-a]pyrazin-4-yl)oxy)ethyl)pyrrolidin-2-one;
(R)-4-((R)-1-((6-(4-(4-(methylsulfonyl)piperazin1-yl)phenyl)pyrazolo[1,5-a]pyrazin-4-yl)oxy)ethyl)pyrrolidin-2-one;
tert-butyl 4-(2-methoxy-4-(4-((R)-1-((R)-5-oxopyrrolidin-3-yl)ethoxy)pyrazolo[1,5-a]pyrazin-6-yl)phenyl)piperazine-1-carboxylate;
(R)-4-((R)-1-((6-(3-methoxy-4-(piperazin-1-yl)phenyl)prazolo[1,5-a]pyrazin-4-yl)oxy)ethyl)pyrrolidin-2-one;
(R)-4-((R)-1-((6-(4-(4-acetylpiperazin-1-yl)-3-methoxyphenyl)pyrazolo[1,5-a]pyrazin-4-yl)oxy)ethyl)pyrrolidin-2-one;
(R)-4-((R)-1-((6-(3-methoxy-4-(4-(methylsulfonyl)piperazin-1-yl)phenyl)pyrazolo[1,5-a]pyrazin-4-yl)oxy)ethyl)pyrrolidin-2-one;
tert-butyl 4-(4-(3-methyl-4-((R)-1-((R)-5-oxopyrrolidin-3-yl)ethoxy)pyrazolo[1,5-a]pyrazin-6-yl)phenyl)piperazine-1-carboxylate;
(R)-4-((R)-1-((3-methyl-6-(4-(piperazin-1-yl)phenyl)pyrazolo[1,5-a]pyrazin-4-yl)oxy)ethyl)pyrrolidin-2-one;
(R)-4-((R)-1-((6-(4-(4-acetylpiperazin-1-yl)phenyl)-3methylpyrazolo[1,5-a]pyrazin-4-yl)oxy)ethyl)pyrrolidin-2-one;
(R)-4-((R)-1-((3-methyl-6-(4-(4-(methylsulfonyl)piperazin-1-yl)phenyl)pyrazolo[1,5-a]pyrazin-4-yl)oxy)ethyl)pyrrolidin-2-one;
tert-butyl 4-(2-methoxy-4-(3-methyl-4-((R)-1-((R)-5-oxopyrrolidin-3-yl)ethoxy)pyrazolo[1,5-a]pyrazin-6-yl)phenyl)piperazine-1-carboxylate;
(R)-4-((R)-1-((6-(3-methoxy-4-(piperazin-1-yl)phenyl)-3-methylprazolo[1,5-a]pyrazin-4-yl)oxy)ethyl)pyrrolidin-2-one;
(R)-4-((R)-1-((6(4(4-acetylpiperazin-1-yl)-3-methoxyphenyl)-3-methylprazolo[1,5-a]pyrazin-4-yl)oxy)ethyl)pyrrolidin-2-one;
(R)-4-((R)-1-((6-(3-methoxy-4-(4-(methylsulfonyl)piperazin-1-yl)phenyl)-3-methylpyrazolo[1,5-a]pyrazin-4-yl)oxy)ethyl)pyrrolidin-2-one;
(R)-4-((R)-1-((6-(3-methoxy-4-(oxetan-3-yl)piperazin-1-yl)phenyl)-3-methylpyrazolo[1,5-a]pyrazin-4-yl)oxy)ethyl)pyrrolidin-2-one;
6-chloro-4-((R)-1-((R)-1-((R)-1-(4-methoxyphenyl)ethyl)-5-oxopyrrolidin-3-yl)ethoxy)pyrazolo[1,5-a]pyrazine-3-carbonitrile;
6-(3,4-dimethoxyphenyl)-4-((R)-1-((R)-5-oxopyrrolidin-3-yl)ethoxy)pyrazolo[1,5-a]pyrazine-3-carbonitrile;
6-(4-(4-acetylpiperazin-1-yl)phenyl)-4-((R)-1-((R)-5-oxopyrrolidin-3-yl)ethoxy)pyrazolo[1,5-a]pyrazine-3-carbonitrile;
6-(4-(4-(methylsulfonyl)piperazin-1-yl)phenyl)-4-((R)-1-((R)-5-oxopyrrolidin-3-yl)ethoxy)pyrazolo[1,5-a]pyrazine-3-carbonitrile;
6-(4-(4-(oxetan-3-yl)piperazin-1-yl)phenyl)-4-((R)-1-((R)-5-oxopyrrolidin-3-yl)ethoxy)pyrazolo[1,5-]pyrazine-3-carbonitrile;
(R)-4-((R)-1-(6-(3,4-dimethoxyphenyl)-3-methyl-3H-imidazo[4,5-c]pyridin-4-yloxy)ethyl)pyrrolidin-2-one;
(R)-4-((R)-1-(6-(3,4-dimethoxyphenyl)-3-ethyl-3H-imidazo[4,5-c]pyridin-4-yloxy)ethyl)pyrrolidin-2-one;
(R)-4-((S)-1-(6-(3,4-dimethoxyphenyl)-3-methyl-3H-imidazo[4,5-c]pyridin-4-yloxy)ethyl)pyrrolidin-2-one;
(R)-4-((R)-1-(3-cyclopropyl-6-(3,4-dimethoxyphenyl)-3H-imidazo[4,5-c]pyridin-4-yloxy)ethyl)pyrrolidin-2-one;
(R)-4-((R)-1-(3-(difluoromethyl)-6-(3,4-dimethoxyphenyl)-3H-imidazo[4,5-c]pyridin-4-yloxy)ethyl)pyrrolidin-2-one;
(R)-4((R)-1-(3-methyl-6-(3,4,5-trimethoxyphenyl)-3H-imidazo[4,5-c]pyridin-4-yloxy)ethyl)pyrrolidin-2-one;
(R)-4-((6-(3,4-dimethoxyphenyl)-3methyl-3H-imidazo[4,5-c]pyridin-4-yloxy)methyl)pyrrolidin-2-one;
(R)-4-((R)-2-cyclopropyl-1-(6-(3,4-dimethoxyphenyl)-3-methyl-3H-imidazo[4,5-c]pyridin-4-yloxy)ethyl)pyrrolidin-2-one;
(R)-4-((R)-1-(3-methyl-6-(4-morpholinophenyl)-3H-imidazo[4,5-c]pyridin-4-yloxy)ethyl)pyrrolidin-2-one;
(R)-4-((R)-1-(6-(3dimethoxyphenyl)-3H-imidazo[4,5-c]pyridin-4-yloxy)ethyl)pyrrolidin-2-one;
(R)-4-((R)-1-(6-(3,4-dimethoxyphenyl)-3-isopropyl-3H-imidazo[4,5-c]pyridin-4-yloxy)ethyl)pyrrolidin-2-one;
4-(3-methyl-4-((R)-1-((R)-5-oxopyrrolidin-3-yl)ethoxy)-3H-imidazo[4,5-c]pyridin-6-yl)benzonitrile;
(4R)-4-((1R)-1-(6-(3,4-dimethoxyphenyl)-2,3-dimethyl-3a,7a-dihydro-3H-imidazo[4,5-c]pyridin-4-yloxy)ethyl)pyrrolidin-2-one;
(R)-4-((R)-1-(6-(3,4-dimethoxyphenyl)-3-(2,2,2-trifluoroethyl)-3H-imidazo[4,5-c]pyridin-4-yloxy)ethyl)pyrrolidin-2-one;
(R)-4-((R)-1-(6-(3,4dimethoxyphenyl)-3-(oxetan-3-yl)-3H-imidazo[4,5-c]pyridin-4-yloxy)ethyl)pyrrolidin-2-one;
(R)-4-((R)-1-(3-(2,2-difluoroethyl)-6-(3,4-dimethoxyphenyl)-3H-imidazo[4,5-c]pyridin-4-yloxy)ethyl)pyrrolidin-2-one;
(R)-4-((R)-1-(6-(3,4-dimethoxyphenyl)-3-(fluoromethyl)-3H-imidazo[4,5-c]pyridin-4-yloxy)ethyl)pyrrolidin-2-one;
(R)-4-((R)-1-(6-(3-fluoro-4-methoxyphenyl)-3-methyl-3H-imidazo[4,5-c]pyridin-4-yloxy)ethyl)pyrrolidin-2-one;
2-methoxy-5-(3-methyl-4-((R)-5-oxopyrrolidin-3-yl)ethoxy)-3H-imidzo[4,5-c]pyridin-6-yl)benzonitrile2-methoxy-5-(3-methyl-4-((R)-1-((R)-5-oxopyrrolidin-3-yl)ethoxy)-3H-imidazo[4,5-c]pyridin-6-yl)benzonitrile;
(R)-4-((R)-1-(3methyl-6-phenyl-3H-imidazo[4,5-c]pyridin-4-yloxy)ethyl)pyrrolidin-2-one;
(R)-4-((R)-1-(3-methyl-6-(3morpholinophenyl)-3H-imidazo[4,5-c]pyridin-4-yloxy)ethyl)pyrrolidin-2-one;
(R)-4-((R)-1-(6-(2-tert-butylthiazol-4-yl)-3methyl-3H-imidazo[4,5-c]pyridin-4-yloxy)ethyl)pyrrolidin-2-one;
(R)-4-((R)-1-(3-methyl-6-(pyrazolo[1,5-a]pyridin-3-yl)-3H-imidazo[4,5-c]pyridin-4-yloxy)ethyl)pyrrolidin-2-one;
(R)-4-((R)-1-(6-(2,2-difluorobenzo[d][1,3]dioxol-5-yl)-3-methyl-3H-imidazo[4,5-c]pyridin-4-yloxy)ethyl)pyrrolidin-2-one;
(R)-4((R)-1-(3-methyl-6-(4-methyl-3,4-dihydro-2H-benzo[b][1,4]oxazin-6-yl)-3H-imidazo[4,5-c]pyridin-4-yloxy)ethyl)pyrrolidin-2-one;
(R)-4-((R)-1-(6-(3,4-dihydro-2H-benzo[b][1,4]oxazin-6-yl)-3-methyl-3H-imidazo[4,5-c]pyridin-4-yloxy)ethyl)pyrrolidin-2-one;
(R)-4-((R)-1-(6-(2-tert-butylthiazol-5-yl)-3methyl-3H-imidazo[4,5-c]pyridin-4-yloxy)ethyl)pyrrolidin-2-one;

(R)-4-((R)-1-(6-cyclohexenyl-3-methyl-3H-imidazo[4,5-c]pyridin-4-yloxy)ethyl)pyrrolidin-2-one;
-4-(3-methyl-4-((R)-1-((R)-5-oxopyrrolidin-3-yl)ethoxy)-3H-imidazo[4,5-c]pyridin-6-yl)pyridin-2(1H)-one;
7-(3-methyl-4-((R)-1-((R)-5-oxopyrrolidin-3-yl)ethoxy)-3H-imidazo[4,5-c]pyridin-6-yl)-3,4-dihydrobenzo[f][1,4]oxazepin-5(2H)-one;
(R)-4-((R)-1-(3methyl-6-(4-methyl-3,4-dihydro-2H-benzo[b][1,4]oxazin-7-yl)-3H-imidazo[4,5-c]pyridin-4-yloxy)ethyl)pyrrolidin-2-one;
(R)-4-((R)-1((6-(benzo[d]thiazol-5-yl)-3-methyl-3H-imidazo[4,5-c]pyridin-4-yl)oxy)ethyl)pyrrolidin-2-one;
(R)-4-((R)-1-((3-methyl-6-(2-methylbenzo[d]thiazol-5-yl)-3H-imidazo[4,5-c]pyridin-4-yl)oxy)ethyl)pyrrolidin-2-one;
(R)-4-((R)-1-((3-methyl -6-methyl-1H-indazol-5-yl)-3H-imidazo[4,5-c]pyridin-4-yl)oxy)ethyl)pyrrolidin-2-one;
(R)-4-((R)-1-((3-methyl-6-(1-methyl-1H-indazol-6-yl)-3H-imidazo[4,5-c]pyridin-4-yl)oxy)ethyl)pyrrolidin-2-one;
(R)-4-((R)-1-((6-(1,3-dimethyl-1H-indazol-5-yl)-3-H-imidazo[4,5-c]pyridin-4-yl)oxy)ethyl)pyrrolidin-2-one;
(R)-4-((R)-1-((3-methyl-6-(4-(4-(methylsulfonyl)piperazin-1-yl)phenyl)-3H-imidazo[4,5-c]pyridin-4-yl)oxy)ethyl)pyrrolidin-2-one;
(R)-4-((R)-1-((6-(3,4-dimethoxyphenyl)3-methyl-3H-imidazo[4,5-c]pyridin-4-yl)oxy)propyl)pyrrolidin-2-one;
(R)-4-((S)-1-((6-(3,4-dimethoxyphenyl)-3-methyl-3H-imidazo[4,5-c]pyridin-4-yl)oxy)-2,2,2-trifluoroethyl)pyrrolidin-2-one;
(R)-4-((R)-1-((3-methyl-6-(4-(4-(oxetan-3-yl)piperazin-1-yl)phenyl)-3H-imidazo[4,5-c]pyridin-4-yl)oxy)ethyl)pyrrolidin-2-one;
(R)-4-((R)-1-((6-(4-(4-acetylpiperazin-1-yl)phenyl)-3methyl-3H-imidazo[4,5-c]pyridin-4-yl)oxy)ethyl)pyrrolidin-2-one;
(R)-7-((R)-1-((3-(difluoromethyl)-6-(3,4-dimethoxyphenyl)-3H-imidazo[4,5-c]pyridin-4-yl)oxy)ethyl)-5-azaspiro[2,4]heptan-4-one;
N,N-dimethyl-4-(3-methyl-4-((R)-1-((R)-5-oxopyrrolidin-3-yl)ethoxy)-3H-imidazo[4,5-c]pyridin-6-yl)benzenesulfonamide;
(R)-4-((R)-1-((3-(difluoromethyl)-6-(3,4-dimethoxyphenyl)-2-methyl-3H-imidazo[4,5-c]pyridin-4-yl)oxy)ethyl)pyrrolidin-2-one;
(R)-4-((R)-1-((3-cyclopropyl-6-(3,4-dimethoxyphenyl)-2-methyl-3H-imidazo[4,5-c]pyridin-4-yl)oxy)ethyl)pyrrolidin-2-one; and
(R)-4-((R)-1-((6-(3,4-dimethoxyphenyl)-3-isopropyl-2-methyl-3-H-imidazo[4,5-c]pyridin-4-yl)oxy)ethyl)pyrrolidin-2-one;
(R)-4-((R)-1-((5-(tert-butyl)-1H-pyrazol-4-yl)-1-methyl-1H-benzo[d]imidazol-7-yl)oxy)ethyl)pyrrolidin-2-one;
(R)-4((R)-1-((1-methyl-5-(6-(trifluoromethyl)pyridin-2-yl)-1H-benzo[d]imidazol-7-yl)oxy)ethyl)pyrrolidin-2-one;
(R)-4-((R)-1-((5-(6-methoxypyridin-2-yl)-1-methyl-1H-benzo[d]imidazol-7-yl)oxy)ethyl)pyrrolidin-2-one;
(R)-4-((R)-1-((5-(5,6-dimethoxypyridin-2-yl)-1,2-dimethyl-1H-benzo[d]-imidazol-7-yl)oxy)ethyl)pyrrolidin-2-one;
(R)-4-((R)-1-((5-(5,6-dimethoxypyridin-2-yl)-1-methyl-1H-benzo[d]imidazol-7-yl)oxy)ethyl)pyrrolidin-2-one;
(R)-4-((R)-1-((5-(3,4-dimethoxyphenyl)-1-methyl-1H-benzo[d]imidazol-7-yl)oxy)ethyl)pyrrolidin-2-one;
(R)-4-((R)-1-((5-(6-aminopyridin-2-yl)-1-cyclopropyl-1H-benzo[d]imidazol-7-yl)oxy)ethyl)pyrrolidin-2-one;
(R)-4-((R)-1-((1-cyclopropyl-5-(5-(4-morpholinopiperidin-1yl)pyridin-2-yl)-1H-benzo[d]imidazol-7-yl)oxy)ethyl)pyrrolidin-2-one;
(R)-4-((R)-1-(1-cyclopropyl-5-(5-(4-(oxetan-3-yl)piperidin-1-yl)pyridin-2-yl)-1H-benzo[d]imidazol-7-yl)oxy)ethyl)pyrrolidin-2-one;
(4R)-4-((1R)-1-((5-(5-(6-oxa-3-azabicyclo[3.1.1]heptan-3-yl)pyridin-2yl)-1-cyclopropyl-1H-benzo[d]imidazol-7-yl)oxy)ethyl)pyrrolidin-2-one;
(R)-4-((R)-1-((1-cyclopropyl-5-(1-methyl-1H-pyrazol-4-yl)-1H-benzo[d]imidazol-7-yl)oxy)ethyl)pyrrolidin-2-one;
(R)-4-((R)-1-((1-cyclopropyl-5-(1-(oxetan-3-yl)-1H-pyrazol-4-yl)-1H-benzo[d]imidazol-7-yl)oxy)ethyl)pyrrolidin-2-one;
(R)-4-((R)-1-((5-(1-(tert-butyl)-1H-pyrazol-4-yl)-1-cyclopropyl-1H-benzo[d]imidazol-7-yl)oxy)ethyl)pyrrolidin-2-one;
(R)-4-((R)-1-((1-cyclopropyl-5-(1-(pyridin-4-yl)-1H-pyrazol-4-yl)-1H-benzo[d]imidazol-7-yl)oxy)ethyl)pyrrolidin-2-one;
(R)-4-((R)-1-((1cyclopropyl-5-(1-(1-hydroxy-2-methylpropan-2-yl)-1H-pyrazol-4-yl)-1H-benzo[d]imidazol-7-yl)oxy)ethyl)pyrrolidin-2-one;
(R)-4-((R)-1-((1-cyclopropyl-5-(1-(2-hydroxy-2-methylpropyl)-1H-pyrazol-4-yl)-1H-benzo[d]imidazol-7-yl)oxy)ethyl)pyrrolidin-2-one;
(R)-4-((R)-1-((1-cyclopropyl-5-(1-(1-(oxetan-3-yl)piperidin-4-yl)-1H-pyrazol-4-yl)-1H-benzo[d]imidazol-7-yl)oxy)ethyl)pyrrolidin-2-one;
(R)-4-((R)-1-((1-cyclopropyl-5-(3-fluoro-4-(oxetan-3-yl)piperazin-1-yl)phenyl)-1H-benzo[d]imidazol-7-yl)oxy)ethyl)pyrrolidin-2-one;
5-(1-cyclopropyl-7-((R)-1-((R)-5-oxopyrrolidin-3-yl)ethoxy)-1H-benzo[d]imidazol-5-yl)-2-(4-(oxetan-3-yl)piperazin-1-yl)benzonitrile;
(R)-4-((R)-1-((1-cyclopropyl-5-(5-(4-(oxetan-3-yl)piperazin-1yl)pyridin-2-yl)-1H-benzo[d]imidazol-7-yl)oxy)ethyl)pyrrolidin-2-one;
(R)4-((R)-1-((1cyclopropyl-5-(3,4-dihydro-2H-pyrido[3,2-b][1,4]oxazin-6-yl)-1H-benzo[d]imidazol-7-yl)oxy)ethyl)pyrrolidin-2-one;
(R)-4-((R)-1-((1-cyclopropyl-5-(3,4-dihydro-2H-benzo[b][1,4]oxazin-6-yl)-1H-benzo[d]imidazol-7-yl)oxy)ethyl)pyrrolidin-2-one;
(R)-4-((R)-1-((1-cyclopropyl-5-(6-(4-(oxetan-3-yl)piperazin-1-yl)pyridazin-3-yl)-1-H-benzo[d]imidazol-7-yl)oxy)ethyl)pyrrolidin-2-one;
(R)-4-((R)-1-((1-cyclopropyl-5-(3,3-dimethylindolin-6-yl)1H-benzo[d]imidazol-7-yl)oxy)ethyl)pyrrolidin-2-one;
(R)-4-((R)-1-((1-cyclopropyl-5-(pyrimidin-4-yl)-1H-benzo[d]imidazol-7-yl)oxy)ethyl)pyrrolidin-2-one;
(R)-4-((R)-1-((1-cyclopropyl-5-phenyl-1H-henzo[d]imidazol-7-yl)oxy)ethyl)pyrrolidin-2-one;
(R)-4-((R)-1-((1-cyclopropyl-5-(pyrazin-2-yl)-1H-benzo[d]imidazol-7-yl)oxy)ethyl)pyrrolidin-2-one;
(R)-4-((R)-1-((1-cyclopropyl-5-(pyridin-2-yl)-1H-benzo[d]imidazol-7-yl)oxy)ethyl)pyrrolidin-2-one;
(R)-4-((R)-1-((1-cyclopropyl-5-(1-methyl-1,2,3,4-tetrahydroquinoxalin-6-yl)-1H-benzo[d]imidazol-7-yl)oxy)ethyl)pyrrolidin-2-one;

(R)-4-((R)-1-((1-cyclopropyl-5-(1-methyl-1-H-indazol-5-yl)-1H-benzo[d]imidazol-7-yl)oxy)ethyl)pyrrolidin-2-one;

(R)-4-((R)-1-((1-cyclopropyl-5-(4-(difluoromethoxy)-3-methoxyphenyl)-1H-benzo[d]imidazol-7-yl)oxy)ethyl) pyrrolidin-2-one;

(R)-4-((R)-1-((1-cyclopropyl-5-(thiazol-2-yl)-1H-benzo [d]imidazol-7-yl)oxy)ethyl)pyrrolidin-2-one;

(R)-4-((R)-1-((1-cyclopropyl-5-(2-(2-hydroxypropan-2-yl)thiazol-5-yl)-1H-benzo[d]imidazol-7-yl)oxy)ethyl) pyrrolidin-2-one;

(R)-4-((R)-1-((1-cyclopropyl-5-(2-methylthiazol-4yl)-1H-benzo[d]imidazol-7-yl)oxy)ethyl)pyrrolidin-2-one;

(R)-4-((R)-1-((1-cyclopropyl-5-(1-(tetrahydro-2H-pyran-4-yl)-1H pyrazol-5-yl)-1H-benzo[d]imidazol-7-yl)oxy) ethyl)pyrrolidin-2-one;

(R)-4-((R)-1-((1-cyclopropyl-5-(4,5-dimethylthiazol-2-yl)-1H-benzo[d]imidazol-7-yl)oxy)ethyl)pyrrolidin-2-one;

(R)-4-((R)-1-((5-(4-(tert-butyl)thiazol-2-yl)-1-cyclopropyl-1H-benzo[d]imidazol-7-yl)oxy)ethyl)pyrrolidin-2-one;

(R)-4-((R)-1-((1-cyclopropyl-5-(2-(tetrahydro-2H-pyran-4-yl)thiazol-5-yl)-1H-benzo[d]imidazol-7-yl)oxy) ethyl)pyrrolidin-2-one;

(R)-4-((R)-1-((1-cyclopropyl-5-(1,5-dimethyl-1H-pyrazol-3-yl)-1H-benzo[d]imidazol-7-yl)oxy)ethyl)pyrrolidin-2-one;

(R)-4-((R)-1-((1-cyclopropyl-5-(1,2-dimethyl-1H-imidazol-4-yl)-1H-benzo[d]imidazol-7-yl)oxy)ethyl)pyrrolidin-2-one;

(R)-4-((R)-1-((1-cyclopropyl-5-(5-methyl-1,3,4-thiadiazol-2-yl)-1H-benzo[d]imidazol-7-yl)oxy)ethyl)pyrrolidin-2-one;

(R)-4-((R)-1((5-(1-(tert-butyl)-1H-pyrazol-3yl)-1-cyclopropyl-1H-benzo[d]imidazol-7-yl)oxy)ethyl)pyrrolidin-2-one;

(R)-4-((R)-1-((1-cyclopropyl-5-(2-methyl-1H-imidazol-5-yl)-1H-benzo[d]imidazol-7-yl)oxy)ethyl)pyrrolidin-2-one;

(R)-4-((R)-1-((1-cyclopropyl-5-(5-methylthiazol-2-yl)-1H-benzo[d]imidazol-7-yl)oxy)ethyl)pyrrolidin-2-one;

(R)-4-((R)-1-((1-cyclopropyl-5-(1-methyl-1H-pyrazol-3-yl)-1H-benzo[d]imidazol-7-yl)oxy)ethyl)pyrrolidin-2-one; and (R)-4-((R)-1-((1-cyclopropyl-5-(2-methyl-2H-1,2,3,-triazol-4-yl)-1H-benzo[d]imidazol-7-yl)oxy)ethyl)pyrrolidin-2-one;

(R)-4-((R)-1-((5-(1-cyclobutyl-1H-pyrazol-4-yl)benzo[d] thiazol-7-yl)oxy)ethyl)pyrrolidin-2-one;

(R)-4-((R)-1-((5-(1-(2,2-difluoroethyl)-1H-pyrazol-4-yl) benzo[d]thiazol-7-yl)oxy)ethyl)pyrrolidin-2-one;

(R)-4-((R)-1-((-5-(1-isopropyl-1H-pyrazol-4-yl)benzo[d] thiazol-7-yl)oxy)ethyl)pyrrolidin-2-one;

(R)-4-((R)-1-((5-(1-(tert-butyl)-1H-pyrazol-4-yl)benzo [d]thiazol-7-yl)oxy)ethyl)pyrrolidin-2-one;

(R)-4-((R)-1-((5-(1-ethyl-1H-pyrazol-3-yl)benzol[d]thiazol-7-yl)oxy)ethyl)pyrrolidin-2-one;

(R)-4-((R)-1-((5-(1-(tert-butyl)-1H-pyrazol-4-yl)-2-methylbenzo[d]thiazol-7-yl)oxy)ethyl)pyrrolidin-2-one;

(R)-4-((R)-1-((5-(1-isopropyl-1H-pyrazol-3-yl)benzo[d] thiazol-7-yl)oxy)ethyl)pyrrolidin-2-one;

(R)-4-((R)-1-((5-(1-(tetrahydro-2H-pyran-4-yl)-1H-pyrazol-4-yl)benzo[d]thiazol-7-yl)oxy)ethyl)pyrrolidin-2-one;

(R)-4-((R)-1-((5-(5-morpholinopyridin-2-yl)benzo[d] thiazol-7-yl)oxy)ethyl)pyrrolidin-2-one;

tert-butyl 4-(6-(7-((R)-1-((R)-5-oxopyrrolidin-3-yl) ethoxy)benzo[d]thiazol-5-yl)pyridin-3-yl)piperazine-1-carboxylate;

(R)-4-((R)-1-((5-(5-(4-(oxetan-3-yl)piperazin-1-yl)pyridin-2-yl)benzo[d]thiazol-7-yl)oxy)ethyl)pyrrolidin-2-one;

(R)-4-((R)-1-((5-(5-(4-acetylpiperazin-1-yl)pyridin-2-yl) benzo[d]thiazol-7-yl)oxy)ethyl)pyrrolidin-2-one;

(R)-4-((R)-1-((5-(5-(4-(tetrahydro-2H-pyran-4-yl)piperazin-1-yl)pyridin-2-yl)benzo[d]thiazol-7-yl)oxy)ethyl) pyrrolidin-2-one;

(R)-4-((R)-1-((5-(5,6-dimethoxypyridin-2-yl)benzo[d] thiazol-7-yl)oxy)ethyl)pyrrolidin-2-one;

(R)-4-((R)-1-((5-(4-(4-(oxetan-3-yl)piperazin-1-yl)phenyl)benzo[d]thiazol-7-yl)oxy)ethyl)pyrrolidin-2-one;

(R)-4-((R)-1-((5-(4-morpholinophenyl)benzo[d]thiazol-7-yl)oxy)ethyl)pyrrolidin-2-one;

(R)-4-((R)-1-((5-(3,4-dimethoxyphenyl)benzo[d]thiazol-7-yl)oxy)ethyl)pyrrolidin-2-one;

(R)-4-((R)-1-((5-(3,4-dimethoxyphenyl)-2-methylbenzo [d]thiazol-7-yl)oxy)ethyl)pyrrolidin-2-one;

tert-butyl 4-(4-(7-((R)-1-((R)-5-oxopyrrolidin-3-yl) ethoxy)benzo[d]thiazol-5-yl)phenyl)piperazine-1-carboxylate;

(R)-4-((R)-1-([4,5'-bibenzo[d]thiazol]-7'-yloxy)ethyl) pyrrolidin-2-one, (S)-4-((S)-1-((5-(2-(tert-butyl)thiazol-5-yl)benzo[d]thiazol-7-yl)oxy)ethyl)pyrrolidin-2-one; and (R)-4-((R)-1-((5-(1methyl-1H-thieno[3,2-c]pyrazol-5-yl) benzo[d]thiazol-7-yl)oxy)ethyl)pyrrolidin-2-one;

(R)-4-((R)-1-(6-(benzo[d]thiazol-4-yl)-3-methyl-3H-imidazo[4,5-c]pyridin-4-yl)oxy)ethyl)pyrrolidin-2-one;

(R)-4-((R)-1-((6-(benzo[d]thiazol-5-yl)-3-methyl-3H-imidazo[4,5-c]pyridin-4-yl)oxy)ethyl)pyrrolidin-2-one; and (R)-4-((R)-1-((3-methyl-6-(2-methylbenzo[d]thiazol-5-yl)-3H-imidazo[4,5-c]pyridin-4-yl)oxy)ethyl)pyrrolidin-2-one;

or a pharmaceutically acceptable salt, ester, stereoisomer, mixture of stereoisomers or tautomer thereof.

17. A pharmaceutical composition comprising a compound of claim 1, or a pharmaceutically acceptable salt or ester thereof, and at least one pharmaceutically acceptable carrier or excipient.

18. A method for modulating spleen tyrosine kinase activity in a patient with a disorder, disease or condition, comprising administering to said patient a therapeutically effective amount of a compound of claim 1, or a pharmaceutically acceptable salt, ester, stereoisomer, mixture of stereoisomers or tautomer thereof, wherein said disorder, disease or condition is selected from the group consisting of an inflammatory disorder, an allergic disorder, an autoimmune disease and cancer.

19. The method of claim 18, wherein said disorder, disease or condition is acute lymphocytic leukemia, acute myeloid leukemia, chronic lymphocytic leukemia, small lymphocytic lymphoma, myelodysplastic syndrome, myeloproliferative disease, chronic myeloid leukemia, multiple myeloma, non-Hodgkin's lymphoma, mantle cell lymphoma, follicular lymphoma, Waldestrom's macroglobulinemia, T-cell lymphoma, B-cell lymphoma, diffuse large B-cell lymphoma, pancreatic cancer, bladder cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancer, central nervous system cancer, brain cancer, bone cancer, soft tissue sarcoma, non-small cell lung cancer, small-cell lung cancer, colon cancer, systemic lupus erythematosus, myestenia gravis, rheumatoid arthritis, acute disseminated encephalomyelitis, idiopathic thrombocytopenic purpura, multiple sclerosis, Sjoegren's syndrome, autoimmune hemolytic anemia, asthma, rheumatoid arthritis, multiple sclerosis, or lupus, psoriasis, ulcerative colitis, Crohn's disease, irritable bowel syndrome, dennatomyositis, or multiple sclerosis.

20. The method of claim 18, wherein said disorder, disease or condition is lymphoma, multiple myeloma or leukemia.

* * * * *